US012590115B2

(12) United States Patent
Kandasamy et al.

(10) Patent No.: US 12,590,115 B2
(45) Date of Patent: Mar. 31, 2026

(54) TECHNOLOGIES USEFUL FOR OLIGONUCLEOTIDE PREPARATION

(71) Applicant: WAVE LIFE SCIENCES LTD., Singapore (SG)

(72) Inventors: Pachamuthu Kandasamy, Lexington, MA (US); Mamoru Shimizu, Arlington, MA (US); David Charles Donnell Butler, Medford, MA (US); Jayakanthan Kumarasamy, Belmont, MA (US); Gopal Reddy Bommineni, Belmont, MA (US); Mohammed Rowshon Alam, Milford, MA (US); Sethumadhavan Divakaramenon, Lexington, MA (US); Bijay Tilak Bhattarai, Burlington, MA (US); Chandra Vargeese, Schwenksville, PA (US); Keith Andrew Bowman, Stow, MA (US); Stephany Michelle Standley, Wakefield, MA (US)

(73) Assignee: WAVE LIFE SCIENCES LTD., Singapore (SG)

( * ) Notice: Subject to any disclaimer, the term of this patent is extended or adjusted under 35 U.S.C. 154(b) by 1011 days.

(21) Appl. No.: 17/439,755

(22) PCT Filed: Mar. 19, 2020

(86) PCT No.: PCT/US2020/023735

§ 371 (c)(1),
(2) Date: Sep. 15, 2021

(87) PCT Pub. No.: WO2020/191252

PCT Pub. Date: Sep. 24, 2020

(65) Prior Publication Data

US 2023/0089442 A1 Mar. 23, 2023

Related U.S. Application Data

(60) Provisional application No. 62/821,423, filed on Mar. 20, 2019.

(51) Int. Cl.
*C07H 1/02* (2006.01)
*C07H 19/04* (2006.01)
*C07H 21/00* (2006.01)

(52) U.S. Cl.
CPC ............... *C07H 1/02* (2013.01); *C07H 19/04* (2013.01); *C07H 21/00* (2013.01)

(58) Field of Classification Search
None
See application file for complete search history.

(56) References Cited

U.S. PATENT DOCUMENTS

| | | | |
|---|---|---|---|
| 8,470,987 | B2 | 6/2013 | Wada et al. |
| 8,822,671 | B2 | 9/2014 | Shimizu et al. |
| 8,859,755 | B2 | 10/2014 | Wada et al. |
| 9,394,333 | B2 | 7/2016 | Wada et al. |
| 9,598,458 | B2 | 3/2017 | Shimizu et al. |
| 9,605,019 | B2 | 3/2017 | Verdine et al. |
| 9,617,547 | B2 | 4/2017 | Gemba |
| 9,695,211 | B2 | 7/2017 | Wada et al. |
| 9,744,183 | B2 | 8/2017 | Verdine et al. |
| 9,982,257 | B2 | 5/2018 | Butler et al. |
| 10,144,933 | B2 | 12/2018 | Gemba et al. |
| 10,149,905 | B2 | 12/2018 | Gemba et al. |
| 10,160,969 | B2 | 12/2018 | Meena et al. |
| 10,167,309 | B2 | 1/2019 | Shimizu et al. |
| 10,280,192 | B2 | 5/2019 | Verdine et al. |
| 10,307,434 | B2 | 6/2019 | Verdine et al. |
| 10,322,173 | B2 | 6/2019 | Gemba et al. |
| 10,329,318 | B2 | 6/2019 | Wada et al. |
| 10,428,019 | B2 | 10/2019 | Wada et al. |
| 10,450,568 | B2 | 10/2019 | Butler et al. |
| 10,479,995 | B2 | 11/2019 | Vargeese et al. |
| 10,590,413 | B2 | 3/2020 | Butler et al. |
| 10,696,711 | B2 | 6/2020 | Shimizu et al. |
| 10,724,035 | B2 | 7/2020 | Vargeese et al. |
| 10,815,482 | B2 | 10/2020 | Meena et al. |
| 11,013,757 | B2 | 5/2021 | Zhang et al. |
| 11,136,346 | B2 | 10/2021 | Shimizu et al. |
| 11,407,775 | B2 | 8/2022 | Butler et al. |
| 11,596,646 | B2 | 3/2023 | Zhang et al. |
| 11,597,927 | B2 | 3/2023 | Vargeese et al. |
| 11,603,532 | B2 | 3/2023 | Vargeese et al. |
| 11,608,355 | B2 | 3/2023 | Bowman et al. |
| 11,634,710 | B2 | 4/2023 | Frank-Kamenetsky et al. |

(Continued)

FOREIGN PATENT DOCUMENTS

| | | | |
|---|---|---|---|
| JP | 2003-238586 | A | 8/2003 |
| WO | WO-2004/007718 | A2 | 1/2004 |

(Continued)

OTHER PUBLICATIONS

U.S. Appl. No. 16/624,896, filed Dec. 19, 2019, Butler et al.

(Continued)

*Primary Examiner* — Traviss C McIntosh, III

(74) *Attorney, Agent, or Firm* — Choate, Hall & Stewart LLP; Xiaodong Li; Katherine Xie

(57) ABSTRACT

Among other things, the present disclosure provides technologies for oligonucleotide preparation, particularly chirally controlled oligonucleotide preparation, which technologies provide greatly improved crude purity and yield, and significantly reduce manufacturing costs.

22 Claims, 5 Drawing Sheets

Specification includes a Sequence Listing.

(56) References Cited

U.S. PATENT DOCUMENTS

| | | | |
|---|---|---|---|
| 11,643,657 B2 | 5/2023 | Butler et al. | |
| 11,718,638 B2 | 8/2023 | Butler et al. | |
| 11,739,325 B2 | 8/2023 | Vargeese et al. | |
| 11,873,316 B2 | 1/2024 | Butler et al. | |
| 12,391,942 B2 | 8/2025 | Zhang et al. | |
| 12,428,442 B2 | 9/2025 | Butler et al. | |
| 2006/0024330 A1 | 2/2006 | Wai et al. | |
| 2015/0211006 A1* | 7/2015 | Butler .................. | C12N 15/113 544/161 |
| 2018/0216108 A1 | 8/2018 | Vargeese et al. | |
| 2019/0077817 A1 | 3/2019 | Butler et al. | |
| 2019/0127733 A1 | 5/2019 | Butler et al. | |
| 2019/0249173 A1 | 8/2019 | Vargeese et al. | |
| 2019/0264267 A1 | 8/2019 | Yang et al. | |
| 2019/0375774 A1 | 12/2019 | Butler et al. | |
| 2020/0157545 A1 | 5/2020 | Vargeese et al. | |
| 2020/0190515 A1 | 6/2020 | Vargeese et al. | |
| 2020/0231620 A1 | 7/2020 | Bowman et al. | |
| 2020/0299692 A1 | 9/2020 | Frank-Kamenetsky et al. | |
| 2020/0362337 A1 | 11/2020 | Dodart et al. | |
| 2021/0032620 A1 | 2/2021 | Vargeese et al. | |
| 2021/0115444 A1 | 4/2021 | Meena et al. | |
| 2021/0130821 A1 | 5/2021 | Butler et al. | |
| 2021/0198305 A1 | 7/2021 | Vargeese et al. | |
| 2021/0228615 A1 | 7/2021 | Zhang et al. | |
| 2021/0254062 A1 | 8/2021 | Zhang et al. | |
| 2022/0098585 A1 | 3/2022 | Brown et al. | |
| 2022/0127301 A1 | 4/2022 | Shimizu et al. | |
| 2022/0145300 A1 | 5/2022 | Liu et al. | |
| 2022/0186217 A1 | 6/2022 | Zhang et al. | |
| 2022/0195429 A1 | 6/2022 | Vargeese et al. | |
| 2022/0306573 A1 | 9/2022 | Zhang et al. | |
| 2022/0307019 A1 | 9/2022 | Yokota et al. | |
| 2022/0401467 A1 | 12/2022 | Zhang et al. | |
| 2023/0136645 A1 | 5/2023 | Butler et al. | |
| 2023/0145795 A1 | 5/2023 | Byrne et al. | |
| 2023/0203087 A1 | 6/2023 | Kandasamy et al. | |
| 2023/0220384 A1 | 7/2023 | Monian et al. | |
| 2023/0295617 A1 | 9/2023 | Vargeese et al. | |
| 2023/0295619 A1 | 9/2023 | Maguire et al. | |
| 2023/0329201 A1 | 10/2023 | Yang et al. | |
| 2023/0348524 A1 | 11/2023 | Bowman et al. | |
| 2023/0392137 A1 | 12/2023 | Monian et al. | |
| 2024/0026358 A1 | 1/2024 | Monian et al. | |
| 2024/0109931 A1 | 4/2024 | Vargeese et al. | |
| 2024/0117347 A1 | 4/2024 | Butler et al. | |
| 2024/0132894 A1 | 4/2024 | Vargeese et al. | |
| 2024/0150756 A1 | 5/2024 | Frank-Kamenetsky et al. | |
| 2024/0174710 A1 | 5/2024 | Butler et al. | |
| 2024/0175016 A1 | 5/2024 | Liu et al. | |
| 2024/0175018 A1 | 5/2024 | Vargeese et al. | |
| 2024/0229026 A1 | 7/2024 | Butler et al. | |
| 2024/0368207 A1 | 11/2024 | Butler et al. | |
| 2025/0051778 A1 | 2/2025 | Byrne et al. | |
| 2025/0066775 A1 | 2/2025 | Vargeese et al. | |
| 2025/0154190 A1 | 5/2025 | Kandasamy et al. | |
| 2025/0262235 A1 | 8/2025 | Lu et al. | |
| 2025/0270628 A1 | 8/2025 | Yang et al. | |
| 2025/0302995 A1 | 10/2025 | Shivalila et al. | |

FOREIGN PATENT DOCUMENTS

| | | |
|---|---|---|
| WO | WO-2005/014609 A2 | 2/2005 |
| WO | WO-2005/023828 A1 | 3/2005 |
| WO | WO-2005/028494 A1 | 3/2005 |
| WO | WO-2005/070859 A1 | 8/2005 |
| WO | WO-2005/085272 A1 | 9/2005 |
| WO | WO-2005/092909 A1 | 10/2005 |
| WO | WO-2010/064146 A2 | 6/2010 |
| WO | WO-2011/005761 A1 | 1/2011 |
| WO | WO-2011/034072 A1 | 3/2011 |
| WO | WO-2011/108682 A1 | 9/2011 |
| WO | WO-2012/039448 A1 | 3/2012 |
| WO | WO-2012/073857 A1 | 6/2012 |
| WO | WO-2013/012758 A1 | 1/2013 |
| WO | WO-2014/010250 A1 | 1/2014 |
| WO | WO-2014/010718 A1 | 1/2014 |
| WO | WO-2014/012081 A2 | 1/2014 |
| WO | WO-2015/107425 A2 | 7/2015 |
| WO | WO-2015/108046 A1 | 7/2015 |
| WO | WO-2015/108047 A1 | 7/2015 |
| WO | WO-2015/108048 A1 | 7/2015 |
| WO | WO-2016/028187 A1 | 2/2016 |
| WO | WO-2017/015555 A1 | 1/2017 |
| WO | WO-2017/015575 A1 | 1/2017 |
| WO | WO-2017/062862 A2 | 4/2017 |
| WO | WO-2017/160741 A1 | 9/2017 |
| WO | WO-2017/192664 A1 | 11/2017 |
| WO | WO-2017/192679 A1 | 11/2017 |
| WO | WO-2017/210647 A1 | 12/2017 |
| WO | WO-2018/022473 A1 | 2/2018 |
| WO | WO-2018/067973 A1 | 4/2018 |
| WO | WO-2018/098264 A1 | 5/2018 |
| WO | WO-2018/177825 A1 | 10/2018 |
| WO | WO-2018/223056 A1 | 12/2018 |
| WO | WO-2018/223073 A1 | 12/2018 |
| WO | WO-2018/223081 A1 | 12/2018 |
| WO | WO-2018/237194 A1 | 12/2018 |
| WO | WO-2019/032607 A1 | 2/2019 |
| WO | WO-2019/032612 A1 | 2/2019 |
| WO | WO-2019/055951 A1 | 3/2019 |
| WO | WO-2019/075357 A1 | 4/2019 |
| WO | WO-2019/200185 A1 | 10/2019 |
| WO | WO-2019/217784 A1 | 11/2019 |
| WO | WO-2020/118246 A1 | 6/2020 |
| WO | WO-2020/160336 A1 | 8/2020 |
| WO | WO-2020/191252 A1 | 9/2020 |
| WO | WO-2020/196662 A1 | 10/2020 |
| WO | WO-2020/219981 A2 | 10/2020 |
| WO | WO-2020/219983 A2 | 10/2020 |
| WO | WO-2020/227691 A2 | 11/2020 |
| WO | WO-2021/071788 A2 | 4/2021 |
| WO | WO-2021/071858 A1 | 4/2021 |
| WO | WO-2021/178237 A2 | 9/2021 |
| WO | WO-2021/234459 A2 | 11/2021 |
| WO | WO-2021/237223 A1 | 11/2021 |
| WO | WO-2022/046667 A1 | 3/2022 |
| WO | WO-2022/046723 A1 | 3/2022 |
| WO | WO-2022/099159 A1 | 5/2022 |
| WO | WO-2023/049475 A1 | 3/2023 |
| WO | WO-2023/049477 A2 | 3/2023 |
| WO | WO-2023/075766 A1 | 5/2023 |
| WO | WO-2023/076352 A2 | 5/2023 |
| WO | WO-2023/154528 A1 | 8/2023 |
| WO | WO-2023/168014 A2 | 9/2023 |
| WO | WO-2023/201095 A2 | 10/2023 |
| WO | WO-2023/220440 A1 | 11/2023 |
| WO | WO-2024/035946 A1 | 2/2024 |
| WO | WO-2025/030155 A1 | 2/2025 |
| WO | WO-2025/160090 A1 | 7/2025 |

OTHER PUBLICATIONS

U.S. Appl. No. 16/869,126, filed May 7, 2020, Vargeese et al.
U.S. Appl. No. 17/046,752, filed Oct. 9, 2020, Zhang et al.
U.S. Appl. No. 17/177,111, filed Feb. 16, 2021, Zhang et al.
U.S. Appl. No. 17/311,285, filed Jun. 4, 2021, Zhang et al.
U.S. Appl. No. 17/375,658, filed Jul. 14, 2021, Vargeese et al.
U.S. Appl. No. 17/439,755, filed Sep. 15, 2021, Kandasamy et al.
U.S. Appl. No. 17/442,663, filed Sep. 24, 2021, Yokota et al.
U.S. Appl. No. 17/605,997, filed Oct. 22, 2021, Byrne et al.
U.S. Appl. No. 17/605,998, filed Oct. 22, 2021, Byrne et al.
U.S. Appl. No. 17/766,677, filed Apr. 5, 2022, Monlan et al.
U.S. Appl. No. 17/766,680, filed Apr. 5, 2022, Liu et al.
International Search Report for PCT/US2020/023735, 5 pages (mailed Jul. 9, 2020).
Written Opinion for PCT/US2020/023735, 11 pages (mailed Jul. 9, 2020).
U.S. Appl. No. 18/204,895, filed Jun. 1, 2023, Vargeese et al.
U.S. Appl. No. 18/695,346, filed Mar. 25, 2024, Monian et al.
U.S. Appl. No. 18/695,348, filed Mar. 25, 2024, Acker et al.

(56) References Cited

OTHER PUBLICATIONS

U.S. Appl. No. 18/704,629, filed Apr. 25, 2024, Byrne et al.
U.S. Appl. No. 18/836,993, filed Aug. 8, 2024, Kandasamy et al.
U.S. Appl. No. 18/843,171, filed Aug. 30, 2024, Hu et al.
U.S. Appl. No. 18/856,553, filed Oct. 11, 2024, Lu et al.
U.S. Appl. No. 18/864,860, filed Nov. 11, 2024, Shivalila et al.
U.S. Appl. No. 18/864,863, filed Nov. 11, 2024, Liu et al.
U.S. Appl. No. 18/942,334, filed Nov. 8, 2024, Yang et al.
U.S. Appl. No. 18/953,020, filed Nov. 19, 2024, Meena et al.
U.S. Appl. No. 19/008,522, filed Jan. 2, 2025, Vargeese et al.
U.S. Appl. No. 19/085,460, filed Mar. 20, 2025, Bowman et al.
U.S. Appl. No. 19/102,669, filed Feb. 10, 2025, Lake et al.
Anderson, B. A. et al., Towards next generation antisense oligonucleotides: mesylphosphoramidate modification improves therapeutic index and duration of effect of gapmer antisense oligonucleotides, Nucl. Acids. Res., 49(16):9026-9041 (2021).
Kupryushkin, M. S. Phosphoryl Guanidines: A New Type of Nucleic Acid Analogues, Acta Naturae, 6(4): 116-118 (2014).
Pavlova, A. S. et al., SDS-Page procedure: Application for characterization of new entirely uncharged nucleic acids analogs, Electrophor., 39:670-674 (2018).
Zhang, L. et al., The Combination of Mesyl-Phosphoramidate Inter-Nucleotide Linkages and 2'-O-Methyl in Selected Positions in the Antisense Oligonucleotide Enhances the Performance of RNaseH1 Active PS-ASOs, Nucleic Acid Ther., 32(5):401-411 (2022).
U.S. Appl. No. 19/271,472, filed Jul. 16, 2025, Zhang et al.
U.S. Appl. No. 19/276,854, filed Jul. 22, 2025, Zhang et al.
U.S. Appl. No. 19/281,441, filed Jul. 25, 2025, Butler et al.
U.S. Appl. No. 19/281,453, filed Jul. 25, 2025, Liu et al.
U.S. Appl. No. 19/284,561, filed Jul. 29, 2025, Butler et al.
U.S. Appl. No. 19/297,725, filed Aug. 12, 2025, Stetsenko et al.
Bazhenov, M. A. et al., Study of the Staudinger Reaction and Reveal of Key Factors Affecting the Efficacy of Automatic Synthesis of Phosphoryl Guanidinic Oligonucleotide Analogs, Russian J. Bioorganic Chem., 45(6):699-708 (2019).
Chubarov, A. S. et al., Allele-Specific PCR for KRAS Mutation Detection Using Phosphoryl Guanidine Modified Primers, Diagnostics, 10(872):1-14 (2020).
Dmitrienko, E. et al., Surface modification of SOI-FET sensors for label-free and specific detection of short RNA analyte, Nanomedicine (Lond), 11(16):2073-2082 (2016).
Dovydenko, I. S. et al., A convenient solid phase approach to obtain lipophilic 5'—phosphoramidate derivatives of DNA and RNA oligonucleotides, Nucleosides Nucleotides Nucleic Acids, 37(2):102-111 (2018).
Dyudeeva, E. S. et al., Physicochemical Properties of the Phosphoryl Guanidine Oligodeoxyribonucleotide Analogs, Russian J. Bioorganic Chem., 45(6):709-718 (2019).
Epanchintseva, A. et al., Non-covalent binding of nucleic acids with gold nanoparticles provides their stability and effective desorption in environment mimicking biological media, Nanotech., 29(355601):1-15 (2018).
Fokina, A. et al., Analysis of new charge-neutral DNA/RNA analogues phosphoryl guanidine oligonucleotides (PGO) by gel electrophoresis, Analytical Biochemistry, 555: 9-11 (2018).
Garafutdinov, R. R. et al., Data on multimerization efficiency for short linear DNA templates and phosphoryl guanidine primers during isothermal amplification with Bst exo-DNA polymerase, Data Brief, 2020 29(105188):1-12 (2020).
Garafutdinov, R. R. et al., Prevention of DNA multimerization using phosphoryl guanidine primers during isothermal amplification with Bst exo-DNA polymerase, Biochimie, 168:259-267 (2020).
Kupryushkin, M et al., 'Dodecyl-modified oligodeoxyribonucleotides as platform for oligonucleotide delivery into eukaryotic cells,' 13th Annual Meeting of the Oligonucleotide Therapeutics Society, (2017), abstract 057.
Kuznetsov, N. A. et al., New oligonucleotide derivatives as unreactive substrate analogues and potential inhibitors of human apurinic/apyrimidinic endonuclease APE1, Mol. Biosyst., 12(1):67-75 (2016).
Kuznetsov, N. A. et al., Pre-steady state kinetics of DNA binding and abasic site hydrolysis by tyrosyl-DNA phosphodiesterase 1, J. Biomol. Struct. Dyn., 35(11):2314-2327 (2017).
Lomzov, A. A. et al., Comparative physico chemical and biological studies of phosphorylguanidine oligonucleotide diasteriomers, Book of Abstracts, Albany 2019: The 20th Conversation, 76 (2019).
Lomzov, A. A. et al., Data for isolation and properties analysis of diastereomers of a mono-substituted phosphoryl guanidine trideoxyribonucleotide, Data Brief, 25(104148):1-25 (2019).
Lomzov, A. A. et al., Diastereomers of a mono-substituted phosphoryl guanidine trideoxyribonucleotide: Isolation and properties, Biochem. Biophys. Res. Commun., 513(4):807-811 (2019).
Lomzov, A. A. et al., Structure and hybridization properties of phosphorylguanidine oligonucleotides, Jrnl. Biomol. Struct. Dynamics, 37:83 (2019).
Markov, A. V. et al., Antiviral Activity of a New Class of Chemically Modified Antisense Oligonucleotides against Influenza A Virus, Russian J. Bioorganic Chem., 45(6):774-782 (2019).
Markov, O. V. et al., Transport Oligonucleotides-A Novel System for Intracellular Delivery of Antisense Therapeutics, Molecules, 25(3663):1-27 (2020).
Novopashina, D et al., Novel Peptide Conjugates of Modified Oligonucleotides for Inhibition of Bacterial RNase P, Front. Pharmacol., 10(813):1-21 (2019).
Pavlova A. S. et al., Amphiphilic "Like-a-Brush" Oligonucleotide Conjugates with Three Dodecyl Chains: Self-Assembly Features of Novel Scaffold Compounds for Nucleic Acids Delivery, Nanomaterials, 10(1948):1-19 (2020).
Su, Y. et al., Neutral and Negatively Charged Phosphate Modifications Altering Thermal Stability, Kinetics of Formation and Monovalent lon Dependence of DNA G-Quadruplexes, Chem. Asian J., 14(8):1212-1220 (2019).
Su, Y. et al., The Importance of Phosphates for DNA G-Quadruplex Formation: Evaluation of Zwitterionic G-Rich Oligodeoxynucleotides, ChemBioChem, 21(17):1-13 (2020).

* cited by examiner (PANEL A)

(PANEL B)

TECHNOLOGIES USEFUL FOR OLIGONUCLEOTIDE PREPARATION

CROSS-REFERENCE TO RELATED APPLICATIONS

This application is a National Stage Entry of PCT/US2020/023735, filed Mar. 19, 2020, which claims priority to U.S. Provisional Application No. 62/821,423, filed Mar. 20, 2019, the entirety of which is incorporated herein by reference.

SEQUENCE LISTING

The present application contains a Sequence Listing which has been submitted electronically in ASCII format and is hereby incorporated by reference in its entirety. Said ASCII copy, created on Jun. 6, 2022, is named Sequence-Listing.txt and is 66.5 KB in size.

BACKGROUND

Oligonucleotides may contain a variety of modifications. Certain modifications, such as phosphorothioate internucleotidic linkages, may introduce new chiral centers into oligonucleotides.

SUMMARY

Oligonucleotides are useful for many purposes. However, natural oligonucleotides have been found to suffer disadvantages, such as low stability, low activity, etc., that can reduce or negate their usefulness, e.g., as therapeutics.

Certain technologies have been developed that can improve oligonucleotide properties and usefulness. For example, certain modifications, e.g., to nucleobases, sugars, and/or internucleotidic linkages, etc., have been described that can improve oligonucleotide properties and usefulness. Moreover, technologies that permit control of stereochemistry, and/or preparation of chirally controlled oligonucleotide compositions have been demonstrated to provide particularly useful and effective oligonucleotide compositions. Certain exemplary useful technologies are described, for example, in one or more of: US 20150211006, US 20170037399, US 20180216107, US 20180216108, US 20190008986, US 20180216107, US 20180216108, US 20190008986, WO 2017/015555, WO 2017/015575, WO 2017/062862, WO 2018/067973, WO 2017/192679, WO 2017/210647, WO 2018/223056, WO 2018/237194, WO 2019/032607, etc., each of which is incorporated herein by reference.

Particularly given the demonstrated desirability and usefulness of chirally controlled oligonucleotide compositions, the present Applicant appreciated that developments of technologies that could improve or facilitate production of oligonucleotide compositions, particularly chirally controlled oligonucleotide compositions, could provide significant benefits. The present disclosure describes certain such developments, and provides technologies relating to oligonucleotide compositions, particularly to chirally controlled oligonucleotide compositions. Provided technologies may be particularly useful, for example, with respect to therapeutic oligonucleotides.

Among other things, the present disclosure encompasses the recognition that certain technologies, including conditions and/or sequences of steps, etc., that have been utilized in the preparation of oligonucleotides, particularly chirally controlled (e.g., stereopure) oligonucleotide composition PCT/US2020/023735s, can be associated with generation of certain impurities and/or use of certain reagents and/or conditions, the associated production cost of which could be further lowered, and the associated operation of which can be further improved. In some embodiments, the present disclosure thus identifies the source of a problem and/or challenge with strategies that have utilized such technologies. In some embodiments, the present disclosure provides technologies (e.g., reagents, conditions, reactions, sequences of steps, cycles, methods, etc.) that are described and demonstrated to dramatically improve crude product purity and yield, significantly increase operation efficiency and/or reduce production cost.

For example, in some embodiments, certain provided technologies utilize chiral auxiliaries that can be readily removed using bases without the utilization of HF, and/or basic conditions and/or elevated temperatures that may cause significant break of oligonucleotide chain and/or undesired transformation of certain internucleotidic linkages (e.g., formation of natural phosphate linkage from phosphorothioate internucleotidic linkages (or precursors thereof) and/or neutral internucleotidic linkage (or precursors thereof)). Such technologies can provide new chemical compatibility, and can provide high stereoselectivity, crude purity and yield as demonstrated herein. In some embodiments, a useful compound is a compound of formula I, I-a, I-a-1, I-a-2, I-b, I-c, I-d, I-e, II, II-a, II-b, III, III-a, or III-b, or a salt thereof. Among other things, such compounds may be utilized as chiral auxiliaries, e.g., for preparation of chirally controlled oligonucleotide compositions as demonstrated here.

Oligonucleotide synthesis typically utilizes highly efficient chemical transformations in its steps. However, despite the high efficiency, products of one or more steps often contain one or more reactive functional groups that can introduce significant impurities if uncapped, e.g., for coupling products, unreacted 5'-OH groups, and/or newly formed reactive groups (e.g., primary and/or secondary amino groups) when chiral auxiliaries are utilized for chirally controlled oligonucleotide synthesis. In many cases, such reactive functional groups are capped during oligonucleotide synthesis in order to reduce impurities from them. In some embodiments, the present disclosure encompasses the recognition of a source of problem that capping steps as those typically used in traditional phosphoramidite-based oligonucleotide synthesis can lead to generation of a significant amount of byproducts, particularly for many chirally controlled (stereocontrolled, stereoselective) oligonucleotide synthesis processes. Among other things, the present disclosure provides technologies that address the problems.

In some embodiments, the present disclosure provides methods comprising a post-modification capping step, e.g., after a modification step but before the next de-blocking and/or coupling step. In some embodiments, a post-modification capping step is after a modification step that provides a chirally controlled internucleotidic linkage but before the next de-blocking and/or coupling step.

In some embodiments, the present disclosure provides methods comprising capping steps of different chemistry strategies compared to a reference capping step in traditional oligonucleotide synthesis. For example, in some embodiments, the present disclosure provides methods comprising one or more capping steps, each of which selectively caps amino groups over hydroxyl groups (e.g., compared to a reference capping reagent system in traditional oligonucleotide synthesis). In some embodiments, provided capping steps are selective for amidation over esterification. In some embodiments, capping reagent systems for capping steps contain no or reduced levels (e.g., compared to a reference capping reagent system in traditional oligonucleotide synthesis) of strong nucleophiles and/or esterification catalysts (or reagents that can provide them when contacted with a composition to be capped), e.g., no or reduced levels of DMAP, NMI, etc. In some embodiments, the present disclosure provides methods comprising capping steps that can cap both amino groups and hydroxyl groups efficiently, e.g., capping steps that are comparable or identical to a reference capping step in traditional oligonucleotide synthesis.

In some embodiments, the present disclosure provides methods that comprise capping steps of the same or different chemistry strategies to achieve oligonucleotide synthesis and can provide various advantages, e.g., improved crude purity, improved yield, etc., particularly for chirally controlled (stereocontrolled, stereoselective) oligonucleotide synthesis. In some embodiments, the present disclosure provides methods of a pre-modification capping step (after a coupling step but before the next modification step) and a post-modification capping step (after a modification step but before the next de-blocking and/or coupling step). In some embodiments, a pre-modification capping step and post-modification capping step are different. In some embodiments, a pre-modification capping step and post-modification capping step have different chemistry strategies. In some embodiments, a pre-modification capping step caps amino groups selectively over hydroxyl groups (e.g., compared to a reference capping reagent system in traditional oligonucleotide synthesis). In some embodiments, a post-modification capping step can cap both amino and hydroxyl groups (e.g., compared to a reference capping reagent system in traditional oligonucleotide synthesis). In some embodiments, a pre-modification capping step caps amino groups selectively over hydroxyl groups (e.g., compared to a reference capping reagent system in traditional oligonucleotide synthesis). In some embodiments, a pre-modification capping step can cap both amino and hydroxyl groups (e.g., compared to a reference capping reagent system in traditional oligonucleotide synthesis).

In some embodiments, provided methods comprise two or more capping steps in an oligonucleotide synthesis cycle. In some embodiments, provided methods comprise two capping steps in an oligonucleotide synthesis cycle, wherein the two steps are separated by a modification step, e.g., oxidation, sulfurization, etc. In some embodiments, provided methods comprise a step in which a chiral modified internucleotidic linkage comprising a chiral linkage phosphorus is formed with a stereoselectivity of at least 80:20, 85:15, 90:10, 91:9, 92:8, 93:7, 94:6, 95:5, 96:4, 97:3, 98:2, or 99:1, favoring either the Rp or Sp configuration.

In some embodiments, the present disclosure provides a method comprising:

providing a chiral nucleoside phosphoramidite which comprises a chiral atom that is not the phosphorus atom or a sugar carbon atom; and a capping step immediately following a sulfurization or oxidation step.

In some embodiments, the present disclosure provides a method comprising:

providing a chiral nucleoside phosphoramidite which comprises a chiral atom that is not the phosphorus atom and is not an atom of the nucleoside unit; and a capping step immediately following a sulfurization or oxidation step.

In some embodiments, the present disclosure provides a method comprising:

providing an oligonucleotide intermediate comprising a chiral linkage phosphorus atom, which is bonded to a chiral unit which does not comprise a nucleoside unit or a part thereof; and a capping step immediately following a sulfurization or oxidation step.

In some embodiments, the present disclosure provides a method comprising:

providing an oligonucleotide intermediate comprising a chiral linkage phosphorus atom, which is bonded to a chiral unit which does not comprise an atom of a nucleoside unit; and a capping step immediately following a sulfurization or oxidation step.

In some embodiments, the present disclosure provides a method, e.g., for preparing an oligonucleotide, comprising:

(1) a coupling step;

(2) optionally a pre-modification capping step;

(3) a modification step;

(4) optionally a post-modification capping step; and (5) optionally a de-blocking step.

Example coupling steps, pre-modification capping steps, modification steps, post-modification capping steps, and dc-blocking steps are described herein. In some embodiments, a cycle comprises all optional steps.

In some embodiments, the present disclosure provides a method, e.g., for preparing a composition comprising a plurality of oligonucleotides comprising:

(1) a coupling step comprising:

contacting a de-blocked composition comprising a plurality of de-blocked oligonucleotides (a de-blocked oligonucleotide composition) or nucleosides, which is de-blocked in that each independently comprises a free hydroxyl group, with a coupling reagent system comprising a partner compound which comprises a nucleoside unit; and coupling a partner compound with the free hydroxyl groups of a plurality of de-blocked oligonucleotides or nucleosides;

wherein the coupling step provides a coupling product composition comprising a plurality of coupling product oligonucleotides, each of which independently comprises an internucleotidic linkage connecting a hydroxyl group of a de-blocked oligonucleotide with a nucleoside unit of a partner compound;

(2) optionally a pre-modification capping step comprising:

contacting a coupling product composition with a pre-modification capping reagent system; and capping one or more functional groups of the coupling product composition;

wherein the pre-modification capping step provides a pre-modification capping product composition comprising a plurality of pre-modification capping product oligonucleotides;

(3) a modification step comprising:

contacting a coupling product composition with a modification reagent system comprising a modification reagent, and modifying one or more internucleotidic linkages of one or more coupling product oligonucleotides; or contacting a pre-modification capping product composition with a modification reagent system and modifying one or more linkages of one or more pre-modification capping product oligonucleotides;

wherein the modification step provides a modification product composition comprising a plurality of modification product oligonucleotides;

(4) optionally a post-modification capping step comprising:

contacting a modification product composition with a post-modification capping reagent system; and capping one or more functional groups of a plurality of oligonucleotides of the modification product composition;

wherein the post-modification capping step provides a post-modification capping product composition comprising a plurality of post-modification capping product oligonucleotides;

(5) optionally a de-blocking step comprising:

contacting a modification product composition, or a post-modification capping product composition, with a de-blocking reagent system;

wherein the deblocking step provides a de-blocking product composition comprising a plurality of de-blocking product oligonucleotides, each of which independently comprises a free hydroxyl group; and (6) optionally repeating steps (1) through (5) a number of times (e.g., 1-100, 1-90, 1-80, 1-70, 1-60, 1-50, 1-40, 1-30, 1-25, 1, 2, 3, 4, 5, 6, 7, 8, 9, 10, 11, 12, 13, 14, 15, 16, 17, 18, 19, 20, 21, 22, 23, 24, or 25, etc.; or such that a desired length of an oligonucleotide has been achieved).

In some embodiments, provided methods comprise one or more pre-modification capping steps. In some embodiments, provided methods comprise one or more post-modification capping steps. In some embodiments, provided methods comprise one or more pre- and post-modification capping steps. In some embodiments, provided methods comprise one or more de-blocking steps.

In some embodiments, the present disclosure provides a method, e.g., for preparing an oligonucleotide, comprising one or more cycles, each of which independently comprises:

(1) a coupling step;

(2) optionally a pre-modification capping step;

(3) a modification step;

(4) optionally a post-modification capping step; and (5) optionally a de-blocking step.

In some embodiments, the present disclosure provides a method, e.g., for preparing a composition comprising a plurality of oligonucleotides comprising one or more cycles, each cycle independently comprising:

(1) a coupling step comprising:

contacting a de-blocked composition comprising a plurality of de-blocked oligonucleotides (a de-blocked oligonucleotide composition) or nucleosides, which is de-blocked in that each independently comprises a free hydroxyl group, with a coupling reagent system comprising a partner compound which comprises a nucleoside unit; and coupling a partner compound with the free hydroxyl groups of a plurality of de-blocked oligonucleotides or nucleosides;

wherein the coupling step provides a coupling product composition comprising a plurality of coupling product oligonucleotides, each of which independently comprises an internucleotidic linkage connecting a hydroxyl group of a de-blocked oligonucleotide with a nucleoside unit of a partner compound:

(2) optionally a pre-modification capping step comprising:

contacting a coupling product composition with a pre-modification capping reagent system; and capping one or more functional groups of the coupling product composition;

wherein the pre-modification capping step provides a pre-modification capping product composition comprising a plurality of pre-modification capping product oligonucleotides;

(3) a modification step comprising:

contacting a coupling product composition with a modification reagent system comprising a modification reagent, and modifying one or more internucleotidic linkages of one or more coupling product oligonucleotides; or contacting a pre-modification capping product composition with a modification reagent system and modifying one or more linkages of one or more pre-modification capping product oligonucleotides;

wherein the modification step provides a modification product composition comprising a plurality of modification product oligonucleotides;

(4) optionally a post-modification capping step comprising:

contacting a modification product composition with a post-modification capping reagent system; and capping one or more functional groups of a plurality of oligonucleotides of the modification product composition;

wherein the post-modification capping step provides a post-modification capping product composition comprising a plurality of post-modification capping product oligonucleotides:

(5) optionally a de-blocking step comprising:

contacting a modification product composition, or a post-modification capping product composition, with a de-blocking reagent system;

wherein the deblocking step provides a de-blocking product composition comprising a plurality of de-blocking product oligonucleotides, each of which independently comprises a free hydroxyl group.

In some embodiments, a cycle comprises one or more pre-modification capping steps. In some embodiments, a cycle comprises one or more post-modification capping steps. In some embodiments, a cycle comprises one or more pre- and post-modification capping steps. In some embodiments, a cycle comprises one or more de-blocking steps. In some embodiments, a cycle comprises a coupling step, a pre-modification capping step, a modification step, a post-modification capping step, and a de-blocking step. In some embodiments, a cycle comprises a coupling step, a pre-modification capping step, a modification step, and a de-blocking step. In some embodiments, a cycle comprises a coupling step, a modification step, a post-modification capping step and a de-blocking step. In some embodiments, comprise a coupling step, a pre-modification capping step, a modification step, a post-modification capping step, and a de-blocking step. In some embodiments, one or more cycles comprise a coupling step, a pre-modification capping step, a modification step, and a de-blocking step. In some embodiments, one or more cycles comprise a coupling step, a modification step, a post-modification capping step and a dc-blocking step.

In some embodiments, a cycle comprises one or more but not all optional steps. In some embodiments, a cycle comprises a pre-modification step. In some embodiments, a cycle does not contain a pre-modification step. In some embodiments, a cycle comprises a post-modification step. In some embodiments, a cycle does not contain a post-modification step. In some embodiments, a cycle does not contain a de-blocking step, e.g., the last cycle when a desired length of an oligonucleotide is achieved.

In some embodiments, each step in a cycle is independently selected from a coupling step, a pre-modification capping step, a modification step, a post-modification capping, and a de-blocking step. In some embodiments, a cycle may comprise two or more of the same steps (e.g., two coupling steps), each of which may utilize the same or different reagents, conditions, etc. As appreciated by those skilled in the art, in some embodiments, e.g., when a reaction of a step does not go to completion, it may be beneficial to repeat such a step, either immediately after the first such step or after one or more next steps. In many embodiments, repeat is performed before a next dc-blocking step is performed. For example, in some embodiments, a coupling step is repeated immediately after another coupling step one or more times. In some embodiments, a sequence of steps (e.g., (1)-(2), (1)-(3), (1)-(2)-(3), (1)-(3)-(4), (1)-(2)-(3)-(4)) is repeated one or more times.

As used in the present disclosure, in some embodiments, "one or more" is one. In some embodiments, "one or more" is two or two or more. In some embodiments, "one or more" is 1-200, 1-150, 1-100, 1-90, 1-80, 1-70, 1-60, 1-50, 1-40, 1-30, 1-25, 1-24, 1-23, 1-22, 1-21, 1-20, 5-200, 5-150, 5-100, 5-90, 5-80, 5-70, 5-60, 5-50, 5-40, 5-30, 5-25, 5-24, 5-23, 5-22, 5-21, 5-20, 10-200, 10-150, 10-100, 10-90, 10-80, 10-70, 10-60, 10-50, 10-40, 10-30, 10-25, 10-24, 10-23, 10-22, 10-21, 10-20, 15-200, 15-150, 15-100, 15-90, 15-80, 15-70, 15-60, 15-50, 15-40, 15-30, 15-25, 15-24, 15-23, 15-22, 15-21, 15-20, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more.

As used in the present disclosure, in some embodiments. "at least one" is one. In some embodiments, "at least one" is two or two or more. In some embodiments, "at least one" is 1-200, 1-150, 1-100, 1-90, 1-80, 1-70, 1-60, 1-50, 1-40, 1-30, 1-25, 1-24, 1-23, 1-22, 1-21, 1-20, 5-200, 5-150, 5-100, 5-90, 5-80, 5-70, 5-60, 5-50, 5-40, 5-30, 5-25, 5-24, 5-23, 5-22, 5-21, 5-20, 10-200, 10-150, 10-100, 10-90, 10-80, 10-70, 10-60, 10-50, 10-40, 10-30, 10-25, 10-24, 10-23, 10-22, 10-21, 10-20, 15-200, 15-150, 15-100, 15-90, 15-80, 15-70, 15-60, 15-50, 15-40, 15-30, 15-25, 15-24, 15-23, 15-22, 15-21, 15-20, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more.

In some embodiments, one or more cycles comprise a coupling step, a pre-modification capping step, a modification step, a post-modification capping step, and a de-blocking step, and one or more cycles comprise a coupling step, a pre-modification capping step, a modification step, and a de-blocking step. In some embodiments, one or more cycles comprise a coupling step, a pre-modification capping step, a modification step, a post-modification capping step, and a de-blocking step, and one or more cycles comprise a coupling step, a modification step, a post-modification capping step and a de-blocking step.

In some embodiments, a cycle consists of a coupling step, a pre-modification capping step, a modification step, a post-modification capping step, and a de-blocking step. In some embodiments, a cycle consists of a coupling step, a pre-modification capping step, a modification step, and a de-blocking step. In some embodiments, a cycle consists of a coupling step, a modification step, a post-modification capping step and a de-blocking step.

In some embodiments, a coupling step, e.g., in a cycle, is immediately followed by a pre-modification capping step. In some embodiments, a coupling step, e.g., in a cycle, is immediately followed by a modification step. In some embodiments, a coupling step, e.g., in a cycle, is immediately followed by a modification step which comprises an oxidation reaction converting a P(III) linkage into a P(VI) phosphate linkage (e.g., comprising installation of =O to a P(III) linkage phosphorus). In some embodiments, a pre-modification step, e.g., in a cycle, is immediately followed by a modification step. In some embodiments, a modification step comprises formation of a bond (e.g., single bond, double bond, etc.) between a linkage phosphorus and a sulfur or a nitrogen atom. In some embodiments, a modification step is immediately followed by a post-modification capping step. In some embodiments, a post-modification capping step is immediately followed by a de-blocking step.

As appreciated by those skilled in the art, one or more washes (e.g., of oligonucleotides on support) using various suitable solvents (in some embodiments, can be mixtures of chemicals) may be included in steps described herein and may be performed before and/or after reactions of such steps, e.g., those steps in various methods and/or cycles described herein. For example, as demonstrated herein in the Examples, after performing a reaction of a step, oligonucleotides on solid support are typically extensive washed (e.g., to remove excess reagents, to remove undesired products, to switch solvents, to condition for a next reaction, etc.) before performance of another reaction of the same or an immediate following step. In some embodiments, a step described herein, e.g., a coupling step, a pre-modification capping step, a modification step, a post-modification capping step, or a de-blocking step, optionally comprises one or more washes. In some embodiments, as demonstrated in the Examples, a reagent, solvent, and/or reagent system for a reaction is removed after the reaction is performed. In some embodiments, removal is performed by filtration and/or washes when product oligonucleotides are on solid support, e.g., when using solid support for oligonucleotide synthesis.

In some embodiments, the present disclosure encompasses the recognition that traditional capping conditions when used as in traditional oligonucleotide synthesis may be a significant source of various problems under certain circumstances, and may contribute to formation of one or more by-products (impurities) and significantly lower oligonucleotide crude purity and yield, particularly for stereoselective preparation of oligonucleotides comprising one or more chiral internucleotidic linkages. Among other things, the present disclosure provides technologies comprising capping strategies that can deliver unexpectedly high crude impurity and yield compared to an appropriate reference technology, for example, through designed capping strategies in combination with other steps in oligonucleotide synthesis.

In some embodiments, a reference technology uses a traditional capping condition as in traditional phosphoramidite-based oligonucleotide synthesis, which typically is or comprises an esterification condition that acrylates hydroxyl groups, e.g., by using a mixture comprising an acylating agent (e.g., acetic anhydride), a base (e.g., 2,6-lutidine), and a catalyst (e.g., N-methylimidazole, DMAP, etc.) to contact oligonucleotides to cap hydroxyl groups (e.g., unreacted 5'-OH groups). Traditional capping conditions typically use a substantial amount of acylating agent, base and catalyst for capping, generally each independently about 5%-15% volume, and/or at least 1, 2, 3, 4, 5, 6, 7, 8, 9, 10, 20, 30, 40, 50, 60, 70, 80, 90, or 100 equivalents relative to the first nucleoside incorporated into an oligonucleotide (before any cycle forming internucleotidic linkage) or oligonucleotide loading capacity of a support (e.g., loading capacity of the support used for preparing an oligonucleotide, can be calculated by multiplying unit loading capacity of a support (e.g., umol/g) by amount of support (g)). In some embodiments, as used in traditional oligonucleotide synthesis, each synthetic cycle of a reference technology contains a single capping step. In some embodiments, a reference technology comprises no more than one capping step in each of its synthetic cycle, wherein capping is performed using an esterification condition, e.g., comprising an acylating agent (e.g., acetic anhydride), a base (e.g., 2,6-lutidine), and a catalyst (e.g., N-methylimidazole (NMI), DMAP, etc.), each independently no less than about 1%, 2%, 3%, 4%, 5%, 6%, 7%, 8%, 9%, 10%, 11%, 12%, 13%, 14%, or 15% by volume of the capping reagent solution, and/or the catalyst is no less than about 0.01, 0.02, 0.05, 0.1, 0.2, 0.5, 1, 1.1, 1.2, 1.5, or 2 equivalents relative to the acylating agent and/or the base.

In some embodiments, the present disclosure provides technologies comprising one or more capping steps, e.g., pre-modification capping steps, post-modification capping steps, etc., each of which is independently comparable or identical to a reference capping step, e.g., of traditional oligonucleotide synthesis based on phosphoramidite chemistry. In some embodiments, the present disclosure reduces by-products that may be formed in such capping steps by strategically positioning their positions (or timing) in oligonucleotide synthesis methods and/or cycles. In some embodiments, such capping steps are positioned after amino groups (typically primary and secondary) are, in many instances selectively, capped (over free hydroxyl groups, particularly, 5'-OH), either as individual separate capping steps or in combination with other capping steps (e.g., capping steps capping amino groups, in many instances selectively 5'-OH).

In some embodiments, the present disclosure provides technologies comprising one or more capping steps that each independently comprise a condition that is selective or specific for amidation over esterification. In some embodiments, the present disclosure provides technologies comprising one or more capping steps that use an amidation condition which is not an efficient and/or typical esterification condition. As readily appreciated by those skilled in the art, esterification and amidation have been extensively studied, and various conditions selective or specific for amidation over esterification, and various methods for assessing selectivity and/or specificity for amidation over esterification, are widely known in the art and can be utilized in accordance with the present disclosure. For example, a typical condition selective or specific for amidation over esterification is an anhydride and a base without a catalyst (e.g., $Ac_2O$ and 2,6-lutidine), as a corresponding efficient esterification condition typically requires an anhydride, a base, and a catalyst (e.g., $Ac_2O$, 2,6-lutidine, and NMI) as traditional capping conditions. In some embodiments, the present disclosure provides technologies that comprise one or more synthetic cycles each independently comprising a coupling step, a modification step (e.g., oxidation, sulfurization, etc.), and one or more capping steps, wherein each capping step after a coupling step and before a modification step comprising an amidation condition and no esterification condition. In some embodiments, an amidation condition comprises no more than 0.01%, 0.02%, 0.05%, 0.1%, 0.2%, 0.5%, 1%, 2%, 3%, 4%, or 5% by volume of a catalyst for esterification under an appropriate corresponding condition (having the same acylating agent and base), and/or no more than about 0.01, 0.02, 0.05, 0.1, 0.2, 0.5, 1, 1.1, or 1.2 equivalents of a catalyst for esterification under an appropriate corresponding condition (having the same acylating agent and base), relative to an acylating agent and/or relative to oligonucleotide loading capacity of a support. In some embodiments, an acylating agent is an anhydride. In some embodiments, an acylating agent is $Ac_2O$. In some embodiments, a catalyst is NMI. In some embodiments, a catalyst is DMAP. In some embodiments, a catalyst is a nucleophilic nitrogen base.

Without the intention to be limited by any theory, in some embodiments, the present disclosure encompasses the recognition of a source of a problem in oligonucleotide synthesis, that an nucleophilic agent, particularly when used in a capping step that is after a coupling step and before a modification step in stereoselective oligonucleotide preparation, may contribute to generation of byproducts and lower overall preparation efficiency and/or crude purity through, e.g., degradation of oligonucleotides, lowering performance of another step, etc. Thus, in some embodiments, the present disclosure provides capping technologies comprising greatly reduced levels of or no strong nucleophiles, e.g., catalysts used in typical capping conditions such as DMAP, NMI, etc., in contrast to traditional capping conditions which can comprise a large amount of a nucleophilic catalyst (e.g., in some cases, 5%-15% NMI by volume of capping solutions). In some embodiments, each of one or more capping steps after a coupling step and before a modification step within an oligonucleotide preparation cycle independently comprises greatly reduced levels of or no strong nucleophiles. In some embodiments, a reduced level is no more than 0.01%, 0.02%, 0.05%, 0.1%, 0.2%, 0.5%, 1%, 2%, 3%, 4%, or 5% by volume of a capping reagent solution. In some embodiments, a reduced level is no more than about 0.01, 0.02, 0.05, 0.1, 0.2, 0.5, 1, 1.1, or 1.2 equivalents relative to an acylating agent. In some embodiments, a reduced level is no more than about 0.01, 0.02, 0.05, 0.1, 0.2, 0.5, 1, 1.1, or 1.2 equivalents relative to oligonucleotide loading capacity of a support.

In some embodiments, a strong nucleophile is a nucleophilic base. In some embodiments, a nucleophilic base is a nitrogen base. In some embodiments, a nucleophilic base is a nitrogen base wherein the basic nitrogen atom (e.g., =N— or —N(−)—) has no alpha substituents. In some embodiments, a nucleophilic base is a nitrogen base wherein the basic nitrogen atom (e.g., =N— or —N(−)—) has no alpha substituent that is not part of a ring. In some embodiments, a nucleophilic base is optionally substituted 5-10 membered heteroaryl compound comprising a basic nitrogen atom =N—, wherein the nitrogen atom has less than two, or no, alpha-substituents. In some embodiments, a nucleophilic base is a nucleophilic nitrogen base. In some embodiments, a nucleophilic nitrogen base is a compound of the structure of formula B-I:

$$N(R^N)_3, \qquad \text{B-I}$$

wherein each $R^N$ is independently R and the three R groups are taken together with the nitrogen atom to form an optionally substituted bicyclic or polycyclic ring as described in the present disclosure for R groups (and groups can be R), wherein the nitrogen of $\underline{N}(R^N)_3$ (underlined) is a tertiary nitrogen, and there are no substitutions at any of the positions alpha to the nitrogen atom. In some embodiments, a formed ring is saturated. In some embodiments, a nucleophilic base is DABCO (1,4-diazabicyclo[2.2.2]octane). In some embodiments, a formed ring contains one or more unsaturation.

In some embodiments, a nucleophilic nitrogen base is a base comprising =N—, wherein there are no substitutions at any of the positions alpha to the nitrogen atom. In some embodiments, a nucleophilic nitrogen base is a base comprising an aromatic moiety comprising =N—, wherein there are no substitutions at any of the positions alpha to the nitrogen atom. In some embodiments, a nucleophilic nitrogen base is a compound of the structure of formula B-II:

$$R^N—CH=N—CH=CH—R^N, \quad \text{B-II}$$

wherein each $R^N$ is independently R and the two R groups are taken together with their intervening atoms to form an optionally substituted ring as described in the present disclosure, wherein the compound comprises —CH=N—CH=. In some embodiments, a formed ring is an optionally substituted $C_{5-30}$ heteroaryl ring comprising 0-10 hetereoatoms in addition to the nitrogen atom. In some embodiments, a formed ring is an optionally substituted 5-membered heteroaryl ring. In some embodiments, a formed ring is a substituted 5-membered heteroaryl ring. In some embodiments, a formed ring is a substituted imidazolyl ring. In some embodiments, a nucleophilic base is substituted imidazole. In some embodiments, a nucleophilic nitrogen base is NMI. In some embodiments, a formed ring is an optionally substituted 6-membered heteroaryl ring. In some embodiments, a formed ring is a substituted 6-membered heteroaryl ring. In some embodiments, a formed ring is a substituted pyridinyl ring. In some embodiments, a nucleophilic base is substituted pyridine. In some embodiments, a nucleophilic nitrogen base is DMAP.

As appreciated by those skilled in the art, nucleophilicity, e.g., of basic nitrogen atoms in bases, is related to several factors, e.g., steric hindrance, electron density, etc. Technologies for assessing nucleophilicity are widely known in the art and can be utilized in accordance with the present disclosure. Additionally or alternatively, bases of various levels of nucleophilicity are well-known and can be assessed and/or utilized in accordance with the present disclosure. In some embodiments, a base that can efficiently catalyze esterification reactions, e.g., a base that can be used for efficient capping of unreacted 5'-OH together with anhydride and 2,6-lutidine in traditional oligonucleotide synthesis (e.g., DMAP, NMI, etc.) is a strong nucleophilic base and should be avoided or used at reduced levels for capping steps that comprise greatly reduced levels of or no strong nucleophiles, e.g., any capping step after a coupling step and before a modification step. In some embodiments, a strong nucleophilic base is a base that can effectively replace DMAP or NMI in esterification. In some embodiments, a strong nucleophilic base is a base that can effectively replace DMAP or NMI in a capping step of traditional oligonucleotide synthesis (which typically uses phosphoramidite chemistry and does not use chiral auxiliaries and is considered non-stereoselective/non-stereocontrolled).

In some embodiments, provided methods comprise a capping step, which capping step comprises no more than 0.1, 0.2, 0.3, 0.4, 0.5, 0.5, 0.7, 0.8, 0.9, 1, 2, 3, 4, 5, 6, 7, 8, 9, or 10 equivalents of a strong nucleophilic base relative to oligonucleotides or loading capacity of a support, or no strong nucleophilic bases. In some embodiments, such a capping step is immediately followed by a non-capping step. In some embodiments, such a capping step is immediately after a non-capping step. In some embodiments, such a capping step is immediately followed by a non-capping step, and is immediately after a non-capping step. In some embodiments, a non-capping step is a coupling step. In some embodiments, a non-coupling step is a modification step. In some embodiments, a non-capping step immediately before such a capping step is a coupling modification step.

In some embodiments, the present disclosure provides a method, e.g., for preparing an oligonucleotide, comprising one or more cycles, wherein:

each cycle independently forms an internucleotidic linkage;

each cycle independently comprising a coupling step, one or more capping steps, and a modification step, which coupling step forms an internucleotidic linkage, and which modification step modifies the internucleotidic linkage formed in the coupling step;

wherein each capping step between the coupling step and the modification step (pre-modification capping step) comprises no strong nucleophile, or if it comprises one or more strong nucleophiles, level of each of the one or more strong nucleophiles is independently reduced compared to an appropriate reference capping condition.

In some embodiments, the present disclosure provides a method, e.g., for preparing an oligonucleotide, comprising one or more cycles, wherein:

each cycle independently forms an internucleotidic linkage;

each cycle independently comprising a coupling step, one or more capping steps, and a modification step, which coupling step forms an internucleotidic linkage, and which modification step modifies the internucleotidic linkage formed in the coupling step;

wherein each capping step between the coupling step and the modification step (pre-modification capping step) comprises no strong nucleophile, or if it comprises one or more strong nucleophiles, level of each of the one or more strong nucleophiles is independently no more than no more than about 0.01, 0.02, 0.05, 0.1, 0.2, 0.5, or 1 equivalents relative to the first incorporated nucleoside of the oligonucleotide.

In some embodiments, the first incorporated nucleoside of the oligonucleotide is the first nucleoside loaded to a support before the first cycle that forms an internucleotidic linkage. In some embodiments, equivalent of the first incorporated nucleoside of an oligonucleotide to oligonucleotide loading capacity of a support used for preparing the oligonucleotide is 1.

In some embodiments, a strong nucleophile is a strong nucleophile base as described in the present disclosure. In some embodiments, a strong nucleophilic base is a compound of formula B-I. In some embodiments, a strong nucleophilic base is a compound of formula B-I and can be used for efficient capping in traditional, phosphoramidite-based oligonucleotide synthesis. In some embodiments, a strong nucleophilic base is a compound of formula B-II. In some embodiments, a strong nucleophilic base is a compound of formula B-II and can be used for efficient capping in traditional, phosphoramidite-based oligonucleotide synthesis. In some embodiments, a strong nucleophilic base is DMAP. In some embodiments, a strong nucleophilic base in NMI.

In some embodiments, the present disclosure provides a method, e.g., for preparing an oligonucleotide, comprising one or more cycles, wherein:

each cycle independently forms an internucleotidic linkage;

each cycle independently comprising a coupling step, one or more capping steps, and a modification step, which coupling step forms an internucleotidic linkage, and which modification step modifies the internucleotidic linkage formed in the coupling step;

wherein each capping step between the coupling step and the modification step (pre-modification capping step) comprises no catalyst that promotes capping of 5'-OH as in an appropriate reference capping condition, or if it comprises one or more such catalysts, level of each of the one or more such catalysts is independently reduced compared to an appropriate reference capping condition.

In some embodiments, the present disclosure provides a method, e.g., for preparing an oligonucleotide, comprising one or more cycles, wherein:

each cycle independently forms an internucleotidic linkage;

each cycle independently comprising a coupling step, one or more capping steps, and a modification step, which coupling step forms an internucleotidic linkage, and which modification step modifies the internucleotidic linkage formed in the coupling step;

wherein each capping step between the coupling step and the modification step (pre-modification capping step) comprises no catalyst that promotes capping of 5'-OH as in an appropriate reference capping condition, or if it comprises one or more such catalysts, level of each of the one or more such catalysts is independently no more than 0.01, 0.02, 0.05, 0.1, 0.2, 0.5, or 1 equivalents relative to the first incorporated nucleoside of the oligonucleotide.

In some embodiments, the present disclosure provides a method, e.g., for preparing an oligonucleotide, comprising one or more cycles, wherein:

each cycle independently forms an internucleotidic linkage;

each cycle independently comprising a coupling step, one or more capping steps, and a modification step, which coupling step forms an internucleotidic linkage, and which modification step modifies the internucleotidic linkage formed in the coupling step;

wherein each capping step between the coupling step and the modification step (pre-modification capping step) comprises no catalyst for esterification, or if it comprises one or more catalysts for esterification, level of each of the one or more such catalysts is independently reduced compared to an appropriate reference capping condition.

In some embodiments, the present disclosure provides a method, e.g., for preparing an oligonucleotide, comprising one or more cycles, wherein:

each cycle independently forms an internucleotidic linkage;

each cycle independently comprising a coupling step, one or more capping steps, and a modification step, which coupling step forms an internucleotidic linkage, and which modification step modifies the internucleotidic linkage formed in the coupling step;

wherein each capping step between the coupling step and the modification step (pre-modification capping step) comprises no catalyst for esterification, or if it comprises one or more catalysts for esterification, level of each of the one or more such catalysts is independently no more than 0.01, 0.02, 0.05, 0.1, 0.2, 0.5, or 1 equivalents relative to the first incorporated nucleoside of the oligonucleotide.

In some embodiments, a catalyst, e.g., that promotes capping of 5'-OH as in oligonucleotide synthesis, for esterification, etc., is a compound of formula B-I. In some embodiments, a catalyst is a compound of formula B-I and can be used for efficient capping in traditional, phosphoramidite-based oligonucleotide synthesis. In some embodiments, a catalyst is a compound of formula B-II. In some embodiments, a catalyst is a compound of formula B-II and can be used for efficient capping in traditional, phosphoramidite-based oligonucleotide synthesis. In some embodiments, a catalyst is DMAP. In some embodiments, a strong nucleophilic base in NMI.

In some embodiments, the present disclosure provides a method, e.g., for preparing an oligonucleotide, comprising one or more cycles, wherein:

each cycle independently forms an internucleotidic linkage;

each cycle independently comprising a coupling step, one or more capping steps, and a modification step, which coupling step forms an internucleotidic linkage, and which modification step modifies the internucleotidic linkage formed in the coupling step;

wherein each capping step between the coupling step and the modification step (pre-modification capping step) comprises a selective condition for amidation over esterification.

In some embodiments, the present disclosure provides a method, e.g., for preparing an oligonucleotide, comprising one or more cycles, wherein:

each cycle independently forms an internucleotidic linkage;

each cycle independently comprising a coupling step, one or more capping steps, and a modification step, which coupling step forms an internucleotidic linkage, and which modification step modifies the internucleotidic linkage formed in the coupling step;

wherein each capping step between the coupling step and the modification step (pre-modification capping step) comprises a selective condition for amidation over esterification, and no condition identical to or comparable to an appropriate reference condition.

In some embodiments, selective conditions for amidation over esterification comprise reduced levels of or no catalysts for esterification, e.g., no DMAP, NMI, etc. In some embodiments, a condition identical to or comparable to an appropriate reference condition can be used to replace capping conditions in traditional phosphoramidite-based oligonucleotide synthesis without significantly reducing (or with no more than 5%, 10%, 15%, 20%, 25%, 30%, 35%, 40%, 45%, or 50% of reduction of) efficiency, crude purity, and/or yield.

In some embodiments, provided methods comprise a second capping step after a modification step in one or more cycles. In some embodiments, provided methods comprise a second capping step after a modification step and before a deblocking step (which de-blocks blocked hydroxyl groups) in one or more cycles. In some embodiments, a second capping step comprises a strong nucleophile. In some embodiments, a second capping step comprises a strong nucleophile at a level comparable to a reference capping condition. In some embodiments, a second capping step comprises an esterification catalyst. In some embodiments, a second capping step comprises an esterification catalyst at a level comparable to a reference capping condition. In some embodiments, a second capping step comprises an esterification condition. In some embodiments, a second capping step comprises an esterification condition that is identical or comparable with a reference capping condition, e.g., in terms of capping unreacted 5'-OH in oligonucleotide synthesis. In some embodiments, a strong nucleophile is DMAP or NMI. In some embodiments, a strong nucleophile is DMAP. In some embodiments, a strong nucleophile is NMI. In some embodiments, an esterification catalyst is DMAP or NMI. In some embodiments, an esterification catalyst is DMAP. In some embodiments, an esterification catalyst is NMI.

In some embodiments, the present disclosure provides a method, e.g., for preparing an oligonucleotide, comprising one or more cycles each independently comprising:

(1) a coupling step;
(2) optionally a first capping step;
(3) a modification step;
(4) optionally a second capping step; and
(5) optionally a de-blocking step.

In some embodiments, a cycle comprises a first capping step. In some embodiments, a cycle comprises a second capping step. In some embodiments, a cycle comprises a first and a second capping step. In some embodiments, a cycle comprises a de-blocking step. In some embodiments, a cycle comprises a first capping step and a de-blocking step. In some embodiments, a cycle comprises a second capping and a de-blocking step.

In some embodiments, the present disclosure provides a method, e.g., for preparing an oligonucleotide, comprising one or more cycles each independently comprising:

(1) a coupling step;
(2) a first capping step;
(3) a modification step;
(4) a second capping step, and
(5) a de-blocking step.

In some embodiments, the present disclosure provides a method, e.g., for preparing an oligonucleotide, comprising one or more cycles each independently comprising:

(1) a coupling step;
(2) a pre-modification capping step;
(3) a modification step;
(4) a post-modification capping; and
(5) a de-blocking step.

In some embodiments, provided methods comprise repeating a number of steps or cycles, e.g., until a desired length (e.g., a desired length of an oligonucleotide or an intermediate) is achieved.

Some or all steps in a provided method or a cycle may be performed in certain orders. In some embodiments, an order is, or comprises (1)-(2), (1)-(3), (2)-(3), (3)-(4), (3)-(5), (4)-(5), (5)-(1), (1)-(2)-(3), (1)-(3)-(4), (1)-(2)-(3)-(4) or any combination thereof (as appreciated by those skilled in the art, each of (1)-(5) independently represents a corresponding step of a method or a cycle, e.g., (1)—a coupling step; (2)—a pre-modification capping step or a first capping step; (3)—a modification step; (4)—a post-modification capping or a second capping step: (5)—a de-blocking step). In some embodiments, an order is or comprises (1)-(2). In some embodiments, an order is or comprises (1)-(3). In some embodiments, an order is or comprises (2)-(3). In some embodiments, an order is or comprises (3)-(4). In some embodiments, an order is or comprises (3)-(5). In some embodiments, an order is or comprises (4)-(5). In some embodiments, an order is or comprises (5)-(1). In some embodiments, an order is or comprises (1)-(2)-(3). In some embodiments, an order is or comprises (1)-(3)-(4). In some embodiments, an order is or comprises (1)-(2)-(3)-(4). In some embodiments, an order is or comprises (1)-(2)-(3)-(5). In some embodiments, an order is or comprises (1)-(3)-(4)-(5). In some embodiments, an order is or comprises (1)-(2)-(3)-(4)-(5). In some embodiments, an order is or comprises (5)-(1)-(2)-(3). In some embodiments, an order is or comprises (5)-(1)-(3)-(4). In some embodiments, an order is or comprises (5)-(0)-(2)-(3)-(4).

In some embodiments, a cycle or each cycle independently consists of steps (1)-(5). In some embodiments, a cycle or each cycle independently consists of steps (1)-(5) in the order of (1)-(2)-(3)-(4)-(5). In some embodiments, a cycle or each cycle independently consists of steps (1)-(5) in the order of (5)-(1)-(2)-(3)-(4). In some embodiments, a cycle or each cycle independently consists of steps (1)-(5) in the order of (1)-(2)-(4)-(3)-(5). In some embodiments, a cycle or each cycle independently consists of steps (1)(5) in the order of (5)-(1)-(2)(4)-(3).

In some embodiments, a provided method optionally or additionally comprises one or more cycles each independently comprising steps (1), (2), (3), and (5), optionally in that order. In some embodiments, a provided method optionally or additionally comprises one or more cycles each independently consisting of steps (1), (2), (3), and (5), optionally in that order. In some embodiments, such a cycle provides a natural phosphate linkage, e.g., optionally after cleavage, deprotection, etc. of an oligonucleotide. In some embodiments, such a cycle provides a non-chirally controlled phosphorothioate internucleotidic linkage, e.g., optionally after cleavage, deprotection, etc. of an oligonucleotide. In some embodiments, each such cycle independently provides a natural phosphate linkage, e.g., optionally after cleavage, deprotection, etc. of an oligonucleotide. In some embodiments, each natural phosphate linkage in an oligonucleotide is independently formed by such a cycle optionally after cleavage, deprotection, etc. of an oligonucleotide.

In some embodiments, a provided method optionally or additionally comprises one or more cycles each independently comprising steps (1), (3), (4), and (5), optionally in that order. In some embodiments, a provided method optionally or additionally comprises one or more cycles each independently consisting of steps (1), (3), (4), and (5), optionally in that order. In some embodiments, such a cycle provides a natural phosphate linkage, e.g., optionally after cleavage, deprotection, etc. of an oligonucleotide. In some embodiments, such a cycle provides a non-chirally controlled phosphorothioate internucleotidic linkage, e.g., optionally after cleavage, deprotection, etc. of an oligonucleotide. In some embodiments, each such cycle independently provides a natural phosphate linkage, e.g., optionally after cleavage, deprotection, etc. of an oligonucleotide. In some embodiments, each natural phosphate linkage in an oligonucleotide is independently formed by such a cycle optionally after cleavage, deprotection, etc. of an oligonucleotide.

In some embodiments, a first capping comprising no strong nucleophiles, or if any, of reduced levels, as described in the present disclosure. In some embodiments, a first capping step comprises no esterification catalysts, of if any, of reduced levels. In some embodiments, a first capping step comprises a selective condition for amidation over esterification. In some embodiments, a first capping step comprises no condition identical to or comparable to an appropriate reference condition.

In some embodiments, a first capping step is a pre-modification capping step as described in the present dis closure. In some embodiments, a first capping step utilizes a capping reagent system that is a pre-modification capping reagent system. In some embodiments, a second capping step is a post-modification capping step as described in the present disclosure. In some embodiments, a second capping step utilizes a capping reagent system that is a post-modification capping reagent system.

In some embodiments, an appropriate reference capping condition is a capping condition of traditional oligonucleotide synthesis based on phosphoramidite chemistry. Example cycles for traditional phosphoramidite-based oligonucleotide synthesis are described below, wherein the illustrated modification step is an oxidation step installing P=O:

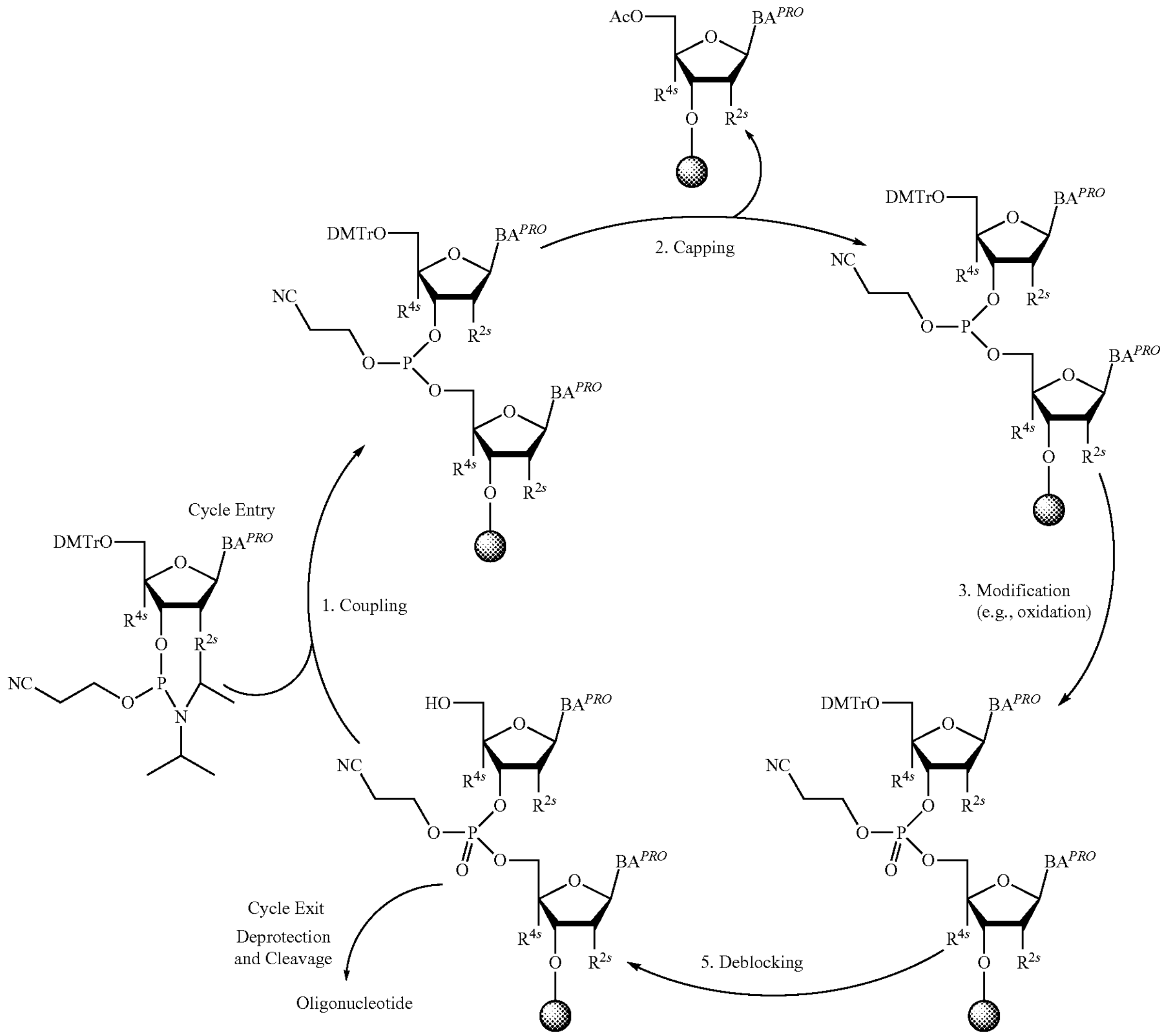

-continued
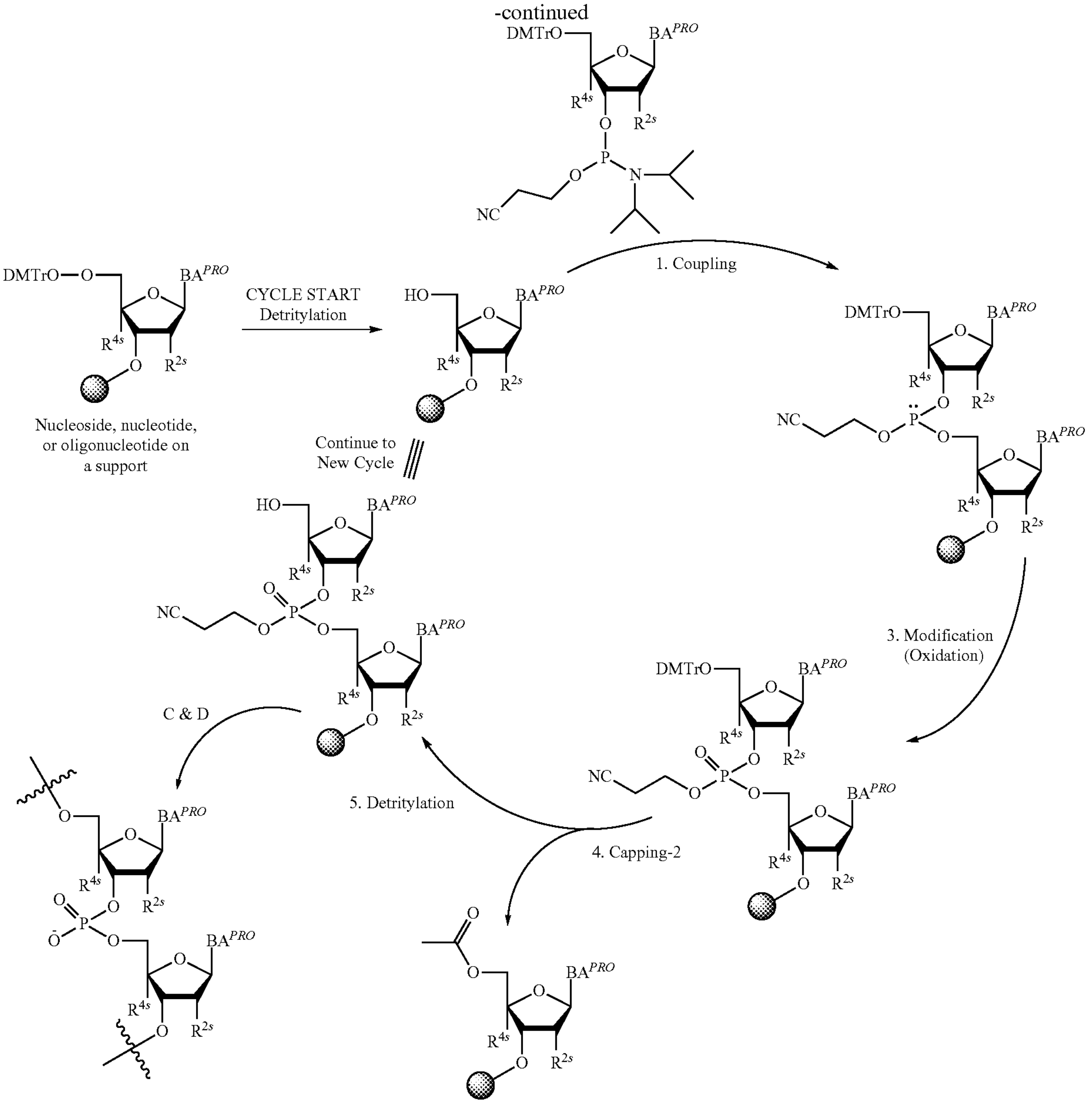
In some embodiments, a cycle of is a DPSE cycle depicted below (DPSE chiral auxiliary compounds:
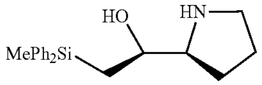
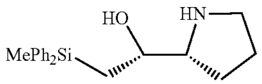

for different configurations of linkage phosphorus):
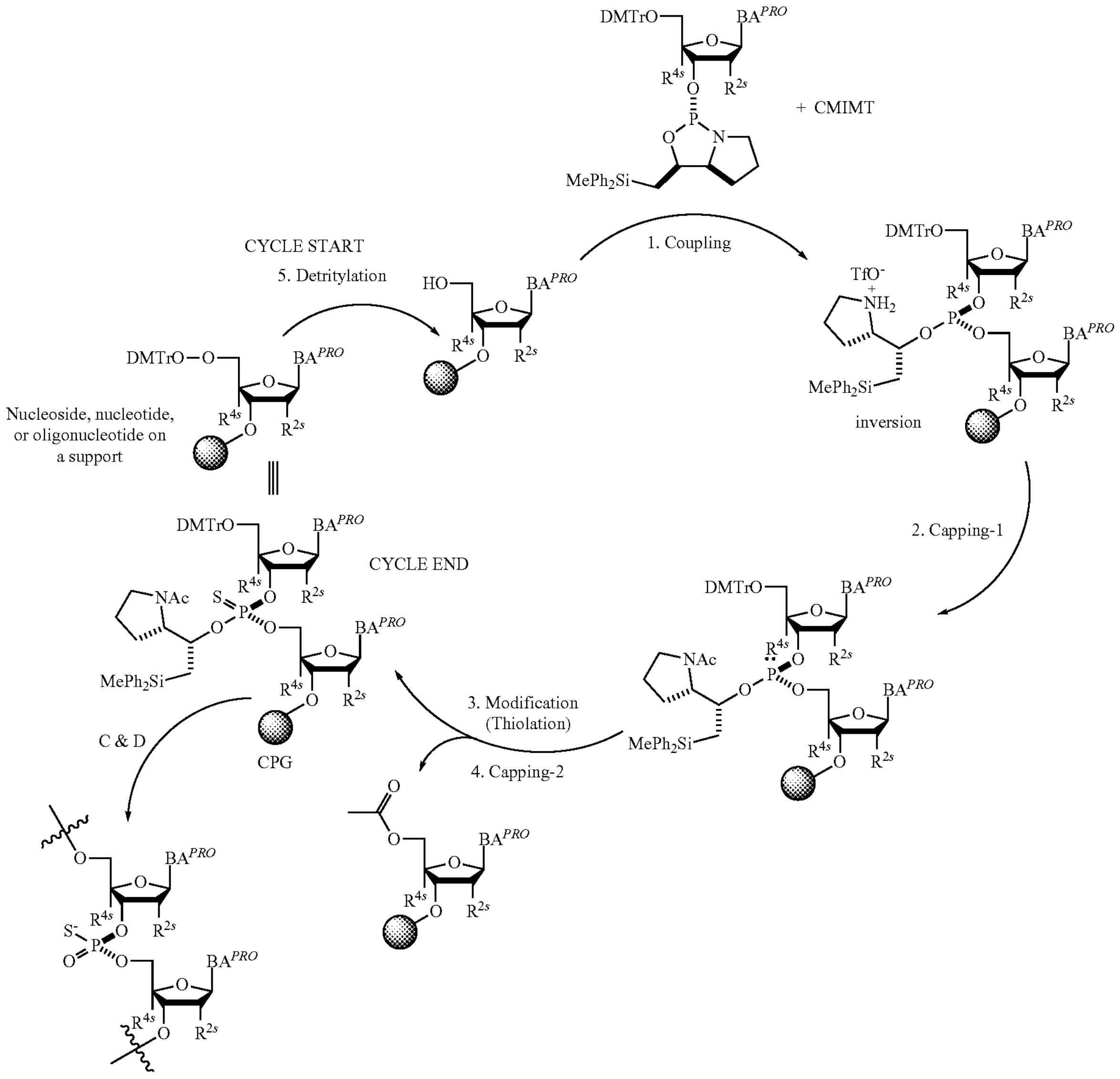
In some embodiments, a cycle of is a PSM cycle depicted below (PSM auxiliary compounds:
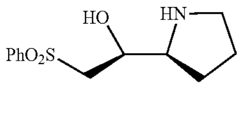
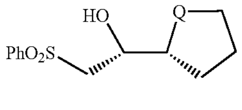

for different configurations of linkage phosphorus):
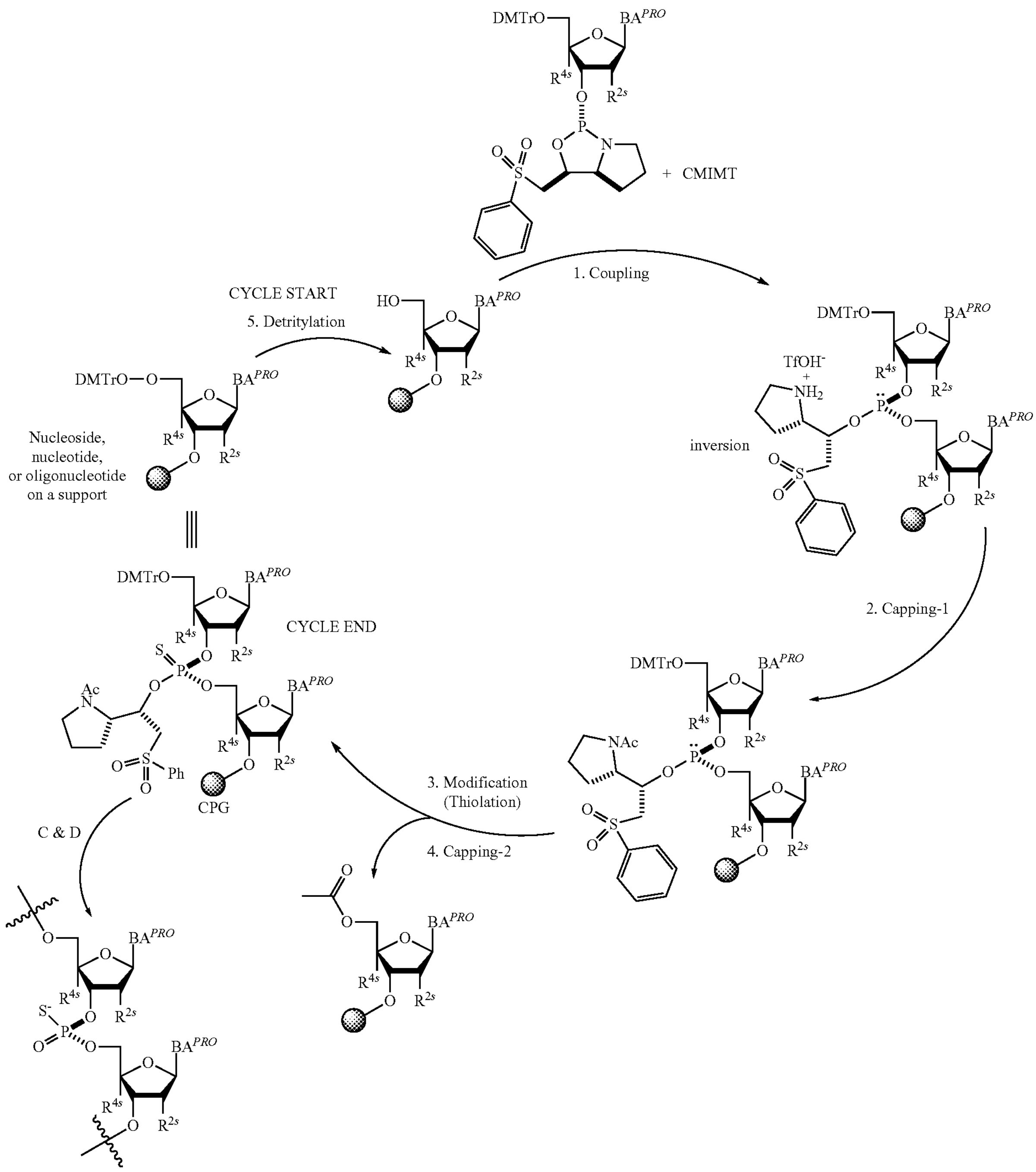

-continued

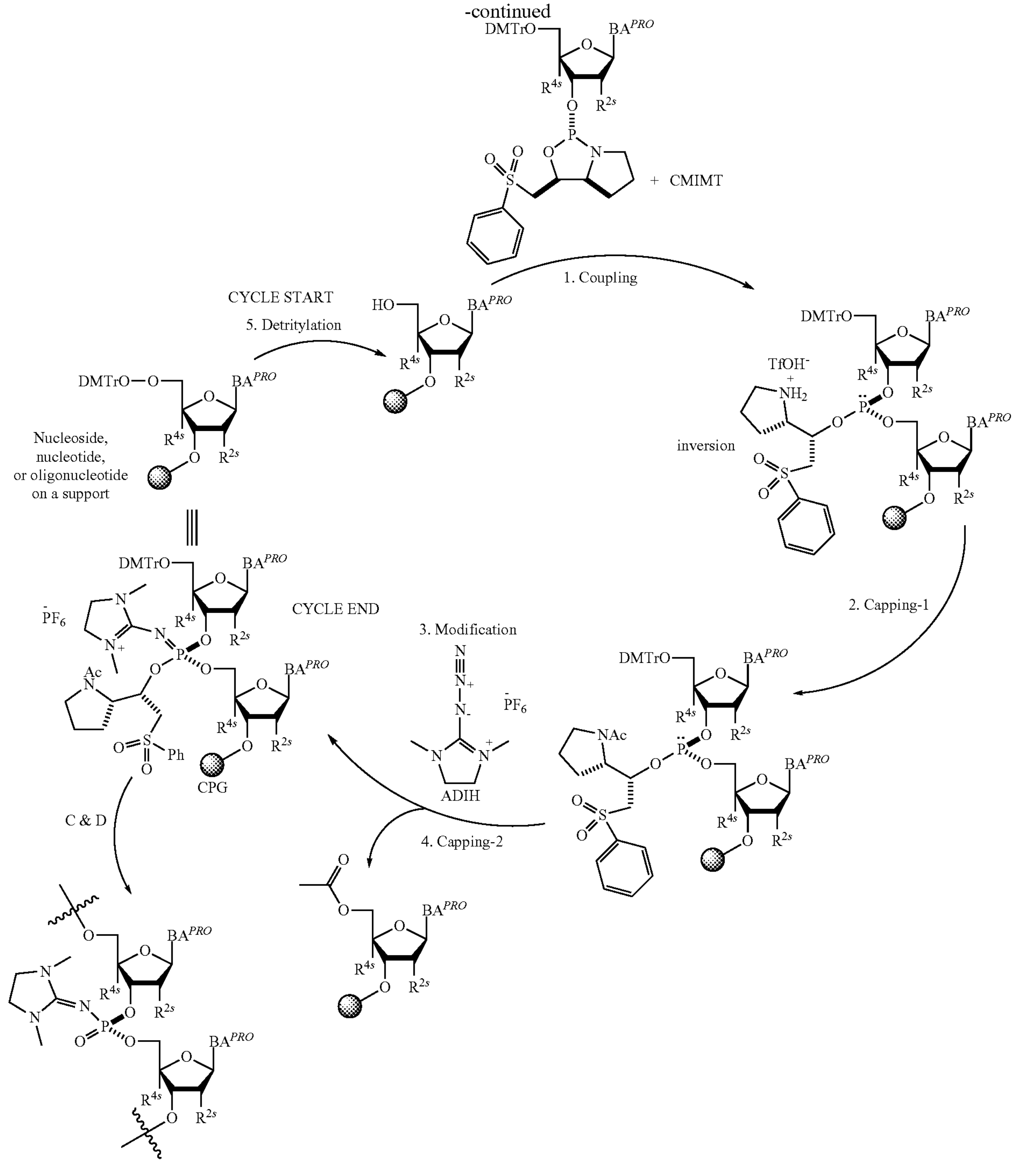

In some embodiments, Capping-1 is a pre-modification or first capping step. In some embodiments, Capping-2 is a post-modification or second capping step. In some embodiments, cycle exit is after de-blocking before the next coupling. In some embodiments, cycle exit is before de-blocking (e.g., to keep a 5'-blocking group such as DMTr on). In some embodiments,

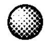

is nucleoside, nucleotide, or oligonucleotide on support (optionally linked to support via a linker). Example steps, reagents, modifications, intermediates and products, etc., are illustrated. Those skilled in the art will appreciate that other steps, reagents, modifications, intermediates and products, etc., may also be utilized in accordance with the present disclosure.

In some embodiments, a first or pre-modification capping step comprises reduced levels of a strong nucleophilic base or no strong nucleophilic base. In some embodiments, a first or pre-modification capping step comprises a reduced level of NMI. In some embodiments, a first or pre-modification capping step comprises no NMI. In some embodiments, a first or pre-modification capping step comprises a reduced level of DMAP. In some embodiments, a first or pre-modification capping step comprises no DMAP. In some embodiments, a second or post-modification capping step comprises a strong nucleophilic base. In some embodiments, a second or post-modification capping step comprises NMI. In some embodiments, a second or post-modification capping step comprises DMAP.

In some embodiments, a reduced level of the present disclosure is no more than a percentage, e.g., 0.01%, 0.02%, 0.05%, 0.1%, 0.2%, 0.5%, 1%, 2%, 3%, 4%, 5%, etc., by volume of a capping reagent solution. In some embodiments, a percentage is 0.01%. In some embodiments, a percentage is 0.02%. In some embodiments, a percentage is 0.05%. In some embodiments, a percentage is 0.1%. In some embodiments, a percentage is 0.2%. In some embodiments, a percentage is 0.5%. In some embodiments, a percentage is 1%. In some embodiments, a percentage is 2%. In some embodiments, a percentage is 3%. In some embodiments, a percentage is 4%. In some embodiments, a percentage is 5%.

In some embodiments, a reduced level is no more than about 0.01, 0.02, 0.05, 0.1, 0.2, 0.5, 1, 1.1, or 1.2 equivalents relative to a reference agent. In some embodiments, a reference agent is an acylating agent. In some embodiments, a reference agent is a support (by oligonucleotide loading capacity). In some embodiments, a reduced level is no more than about 0.01, 0.02, 0.05, 0.1, 0.2, 0.5, 1, 1.1, or 1.2 equivalents relative to an acylating agent. In some embodiments, a reduced level is no more than about 0.01, 0.02, 0.05, 0.1, 0.2, 0.5, 1, 1.1, 1.2, 1.3, 1.4, 1.5, 2, 3, 4, 5, 6, 7, 8, 9, 10, 20, 30, 40, 50, or 100 equivalents relative to oligonucleotide. In some embodiments, a reduced level is no more than about 0.01, 0.02, 0.05, 0.1, 0.2, 0.5, 1, 1.1, 1.2, 1.3, 1.4, 1.5, 2, 3, 4, 5, 6, 7, 8, 9, 10, 20, 30, 40, 50, or 100 equivalents relative to the first nucleoside incorporated to an oligonucleotide. In many instances, equivalent of the first nucleoside incorporated into an oligonucleotide to oligonucleotide loading capacity of a support used to prepare the oligonucleotide is 1. In some embodiments, a reduced level is no more than about 0.01, 0.02, 0.05, 0.1, 0.2, 0.5, 1, 1.1, 1.2, 1.3, 1.4, 1.5, 2, 3, 4, 5, 6, 7, 8, 9, 10, 20, 30, 40, 50, or 100 equivalents relative to oligonucleotide loading capacity of a support. In some embodiments, a reduced level is no more than about 0.01, 0.02, 0.05, 0.1, 0.2, 0.5, 1, 1.1, 1.2, 1.3, 1.4, 1.5, 2, 3, 4, 5, or 10 equivalents relative to oligonucleotide loading capacity of a support. In some embodiments, a reduced level is no more than about 0.01, 0.02, 0.05, 0.1, 0.2, 0.5, 1, 1.1, 1.2, 1.3, 1.4, 1.5, 2, 3, 4, or 5 equivalents relative to oligonucleotide loading capacity of a support. In some embodiments, a reduced level is no more than about 0.01, 0.02, 0.05, 0.1, 0.2, 0.5, or 1 equivalent relative to oligonucleotide loading capacity of a support. In some embodiments, a reduced level is no more than about 0.01 equivalent. In some embodiments, a reduced level is no more than about 0.02 equivalent. In some embodiments, a reduced level is no more than about 0.05 equivalent. In some embodiments, a reduced level is no more than about 0.1 equivalent. In some embodiments, a reduced level is no more than about 0.2 equivalent. In some embodiments, a reduced level is no more than about 0.5 equivalent. In some embodiments, a reduced level is no more than about 1 equivalent. In some embodiments, a reduced level is no more than about 1.1 equivalents. In some embodiments, a reduced level is no more than about 1.2 equivalents.

Among other things, provided technologies are particularly useful for preparing chirally controlled oligonucleotide compositions. In some embodiments, provided technologies comprise formation of one or more chiral internucleotidic linkages each independently comprising a chiral linkage phosphorus, wherein each of the chiral linkage phosphorus chiral center is independently formed with a stereoselectivity as described in the present disclosure, e.g., of at least 80%, 85%, 90%, 91%, 92%, 93%, 94%, 95%, 96%, 97%, 98%, or 99%.

In some embodiments, provided technologies comprise use of one or more chiral auxiliary to stereoselectively form one or more chirally controlled internucleotidic linkages. In some embodiments, provided technologies comprise providing monomeric phosphoramidites of diastereomeric purity as described in the present disclosure, e.g., of at least 60%, 65%, 70%, 75%, 80%, 85%, 90%, 91%, 92%, 93%, 94%, 95%, 96%, 97%, 98%, or 99%. In many embodiments, phosphoramidites of provided diastereomeric purity comprise a chiral auxiliary moiety. In some embodiments, phosphoramidites of traditional oligonucleotide synthesis are utilized for non-chirally controlled internucleotidic linkages, and/or non-chiral internucleotidic linkages. Suitable chiral auxiliaries and phosphoramidites for chirally controlled oligonucleotide synthesis that can be utilized in accordance with the present disclosure include those described in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784, chiral auxiliaries and phosphoramidites of each of which are independently incorporated herein by reference. In some embodiments, a chiral auxiliary is of formula I, I-a, I-a-1, I-a-2, I-b, I-c, I-d, I-e, II, II-a, II-b, III, III-a, or III-b, or a salt thereof, as described in the present disclosure. In some embodiments, a phosphoramidite has the structure of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof, as described in the present disclosure.

In some embodiments, provided technologies comprising formation of an internucleotidic linkage having the structure of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, NL-d-2, or a salt form thereof, as described in the present disclosure.

In some embodiments, provided technologies provides oligonucleotides as intermediates and/or products. In some embodiments, a provided oligonucleotide is of formula O-I or a salt thereof as described in the present disclosure. In some embodiments, an oligonucleotide, e.g., a final product, a product of a reaction, a product of a step, e.g., is one described in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784, oligonucleotides of each of which are independently incorporated herein by reference, or shares the same or comprises the base sequence, a sugar modification or patterns thereof, an internucleotidic linkage or patterns thereof, a base modification or a pattern thereof, and/or a pattern of backbone chiral centers (linkage phosphorus) of such an oligonucleotide. In some embodiments, provided intermediates and/or products are chirally controlled oligonucleotide compositions. In some embodiments, provided intermediates and/or products are chirally controlled oligonucleotide compositions of a plurality of oligonucleotides of formula O-I or salts thereof. In some embodiments, provided intermediates and/or products are chirally controlled oligonucleotide compositions of U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784, oligonucleotide compositions of each of which are independently incorporated herein by reference.

In some embodiments, the present disclosure provides a composition comprising:

a plurality of oligonucleotides of a modification product composition; and a post-modification capping reagent system;

wherein the post-modification capping reagent system is in contact with the plurality of oligonucleotides.

In some embodiments, the present disclosure provides a composition comprising:

a capping reagent system comprising a first compound having the structure of formula B-I or B-II, a plurality of oligonucleotides each comprising at least one internucleotidic linkage comprising a —C(O)—N(−)— moiety or a —P—S— moiety;

wherein the first compound is at a level of at least 0.1, 0.2, 0.5, 1, 2, 3, 4, 5, 6, 7, 8, 9, 10, 50, or 100 equivalents relative to the plurality of oligonucleotides.

In some embodiments, the present disclosure provides a composition comprising:

a capping reagent system comprising a first compound having the structure of formula B-I or B-II, a plurality of oligonucleotides, wherein each internucleotidic linkage of oligonucleotides of the plurality is independently an internucleotidic linkage comprising a —C(O)—N(−)— moiety and a linkage phosphorus that is tetravalent;

wherein the first compound is at a level of at least 0.1, 0.2, 0.5, 1, 2, 3, 4, 5, 6, 7, 8, 9, 10, 50, or 100 equivalents relative to the plurality of oligonucleotides.

In some embodiments, the plurality of oligonucleotides is a plurality of oligonucleotides of a modification product composition.

In some embodiments, in a oligonucleotide composition comprising a plurality of oligonucleotides:

oligonucleotides of the plurality share the same base sequence:

oligonucleotides of the plurality share the same pattern of backbone linkages; and oligonucleotides of the plurality comprise at least one chirally controlled internucleotidic linkage;

wherein at least $((DS)^{Nc}*100)\%$ of all oligonucleotides sharing the same base sequence in the composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

At a chirally controlled internucleotidic linkage, oligonucleotides of the plurality share the same linkage phosphorus configuration (Rp or Sp). In some embodiments, a chirally controlled internucleotidic linkage is referred to as a "stereodefined" internucleotidic linkage.

In some embodiments, a first compound is of formula B-I. In some embodiments, a first compound is of formula B-II. In some embodiments, a first compound is a strong nucleophile as described in the present disclosure. In some embodiments, a first compound is an esterification catalyst as described in the present disclosure. In some embodiments, a first compound is of formula B-I. In some embodiments, a first compound is of formula B-II. In some embodiments, a first compound is a base comprising =N—, wherein there are no substitutions at any alpha-positions relative to the nitrogen of =N—. In some embodiments, a first compound is a base comprising a heteroaryl moiety, which heteroaryl moiety comprises =N—, wherein there are no substitutions at any alpha-positions relative to the nitrogen of =N—.

In some embodiments, a first compound is NMI. In some embodiments, a first compound is DMAP.

In some embodiments, oligonucleotides of a plurality are attached to a support, e.g., a solid support used to prepare the oligonucleotides. In some embodiments, molar amount of the oligonucleotides of a plurality equals loading capacity of the solid support they are attached to. In some embodiments, oligonucleotides of a plurality are attached to a support via linkers. Various linkers are known in the art and may be utilized in accordance with the present disclosure; certain examples are described herein.

In some embodiments, a plurality of oligonucleotides share 1) a common base sequence, 2) a common pattern of backbone linkages, and 3) a common pattern of backbone phosphorus modifications, wherein the plurality of oligonucleotides share the same linkage phosphorus stereochemistry at one or more chiral internucleotidic linkages (chirally controlled or stereodefined internucleotidic linkages). In some embodiments, about 1%-100%, (e.g., 5%-100%, 10%-100%, 20%-100%, 30%-100%, 40%-100%, 50%-100%, 60%-100%, 70%-100%, 80-100%, 90-100%, 95-100%, 50%90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all internucleotidic linkages in oligonucleotides of a plurality are chirally controlled internucleotidic linkages. In some embodiments, in addition to one or more chirally controlled internucleotidic linkages, one or more internucleotidic linkages are natural phosphate linkages. In some embodiments, all chiral internucleotidic linkages which comprise chiral linkage phosphorus are chirally controlled internucleotidic linkages. In some embodiments, one or more chiral internucleotidic linkages which comprise chiral linkage phosphorus are stereorandom chiral internucleotidic linkages (not chirally controlled internucleotidic linkages, typically prepared by non-chirally controlled methods, e.g., traditional oligonucleotide synthesis without utilization of chiral auxiliaries or chiral modification (e.g., sulfurization) reagents). In some embodiments, oligonucleotides of a plurality share the same constitution. In some embodiments, oligonucleotides of a plurality share the same structure (structurally identical). In some embodiments, a plurality of oligonucleotides share the same stereochemistry at least one internucleotidic linkage comprising a —C(O)—N(–)— moiety or a —P—S— moiety. In some embodiments, about 0.1%-100% (e.g., about 1%-100%, 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition that share the common base sequence, or that share the common base sequence, the common pattern of backbone linkages, and the common pattern of backbone phosphorus modifications, or share the same constitution of oligonucleotides of the plurality, are oligonucleotides of the plurality.

In some embodiments, oligonucleotides of a plurality are each of the structure of formula O-I or a salt thereof. In some embodiments, oligonucleotides of a plurality are oligonucleotides of U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784, oligonucleotides of each of which are independently incorporated herein by reference. In some embodiments, oligonucleotides of a plurality share the same constitution. In some embodiments, oligonucleotides of a plurality are identical.

In some embodiments, a level of the present disclosure is at least 0.1 equivalent. In some embodiments, a level is at least 0.2 equivalent. In some embodiments, a level is at least 0.5 equivalent. In some embodiments, a level is at least 1 equivalent. In some embodiments, a level is at least 2 equivalents. In some embodiments, a level is at least 3 equivalents. In some embodiments, a level is at least 4 equivalents. In some embodiments, a level is at least 5 equivalents. In some embodiments, a level is at least 6 equivalents. In some embodiments, a level is at least 7 equivalents. In some embodiments, a level is at least 8 equivalents. In some embodiments, a level is at least 9 equivalents. In some embodiments, a level is at least 10 equivalents. In some embodiments, a level is at least 20 equivalents. In some embodiments, a level is at least 50 equivalents. In some embodiments, a level is at least 100 equivalents.

In some embodiments, a —C(O)—N(–)— is part of a capped amino group in a chiral auxiliary moiety bonded to a linkage phosphorus, wherein the corresponding chiral auxiliary (replacing bonding to —C(O)— of —C(O)—N(–)— with —H, and replacing bonding to the linkage phosphorus with —H) is a compound of formula I, I-a, I-a-1, I-a-2, I-b, I-c, I-d, I-e, II, II-a, II-b, III, III-a, III-b, or a salt thereof.

Among other things, the present disclosure provides oligonucleotide compositions of high crude purity. In some embodiments, the present disclosure provides a crude chirally controlled oligonucleotide composition comprising a plurality of oligonucleotides, wherein:

oligonucleotides of the plurality share the same base sequence;

oligonucleotides of the plurality share the same pattern of backbone linkages; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least $((DS)^{Nc}*100)\%$ of all oligonucleotides sharing the same base sequence in the crude composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

In some embodiments, the present disclosure provides a crude chirally controlled oligonucleotide composition comprising a plurality of oligonucleotides, wherein:

oligonucleotides of the plurality share the same constitution; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage:

wherein at least $((DS)^{Nc}*100)\%$ of all oligonucleotides sharing the same base sequence in the crude composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

In some embodiments, a provided crude chirally controlled oligonucleotide composition has a crude purity of 30%-80%, 30%-90%, 30%, 40%, 45%, 50%, 55%, 60%, 65%, 70%, or 75%, or more. In some embodiments, a crude chirally controlled oligonucleotide composition is cleaved from a support, and before any further purification. In some embodiments, crude chirally controlled oligonucleotide composition is cleaved from a support, after de-salting, and before any further purification. In some embodiments, crude chirally controlled oligonucleotide composition is before any chromatograph or gel purification. In some embodiments, a crude purity is % full-length product. In some embodiments, a crude purity is % full-length product as assessed by LC-UV monitored at UV 260 nm.

In some embodiments, DS is about 80%-100%, 85%-100%, 87%-100%, 89%-100%, 90-100%, 80%, 85%, 90%, 91%, 92%, 93%, 94%, 95%, 96%, 97%, 98% or 99% or more. In some embodiments, DS is about 85% or more. In some embodiments, DS is about 86% or more. In some embodiments, DS is about 87% or more. In some embodiments, DS is about 88% or more. In some embodiments, DS is about 89% or more. In some embodiments, DS is about 90% or more. In some embodiments, DS is about 91% or more. In some embodiments, DS is about 92% or more. In some embodiments, DS is about 93% or more. In some embodiments, DS is about 94% or more. In some embodiments, DS is about 95% or more. In some embodiments, DS is about 96% or more. In some embodiments, DS is about 97% or more. In some embodiments, DS is about 98% or more. In some embodiments, DS is about 99% or more.

In some embodiments, diastereoselectivity at, and/or diastereopurity of, chiral linkage phosphorus of a chiral internucleotidic linkage in an oligonucleotide may be measured or represented through a model reaction, e.g. formation of a dimer under essentially the same or comparable conditions wherein the dimer has the same internucleotidic linkage as the chiral internucleotidic linkage, the 5-nucleoside of the dimer is the same as the nucleoside to the 5'-end of the chiral internucleotidic linkage, and the 3'-nucleoside of the dimer is the same as the nucleoside to the 3'-end of the chiral internucleotidic linkage. For example, diastereopurity of the underlined linkage in NNNNNNNG*SGNNNNNNN can be assessed from coupling two G moieties under the same or comparable conditions, e.g., monomers, chiral auxiliaries, solvents, activators, temperatures, etc. In some embodiments, diastereopurity (and/or diastereoselectivity) of the linkage of a dimer (G*SG) is used as diastereopurity (and/or diastereoselectivity) of a corresponding linkage in an oligonucleotide (NNNNNNNG*SGNNNNNNN). In some embodiments, diastereopurity of a compound comprising multiple chiral elements is product of diastereomeric purity of all its chiral elements. In some embodiments, diastereopurity (i.e., diastereomeric purity) of a provided oligonucleotide is product of diastereomeric purity of all its chiral linkage phosphorus in its chiral internucleotidic linkages.

In some embodiments, Nc is the number of chirally controlled internucleotidic linkage and is 1-100. In some embodiments, Nc is 1-50. In some embodiments, Nc is 1-40. In some embodiments, Nc is 1-30. In some embodiments, Nc is 1-25. In some embodiments, Nc is 1-24. In some embodiments, Nc is 1-23. In some embodiments, Nc is 1-22. In some embodiments, Nc is 1-21. In some embodiments, Nc is 1-20. In some embodiments, Nc is 1-19. In some embodiments, Nc is 1-18. In some embodiments, Nc is 1-17. In some embodiments, Nc is 1-16. In some embodiments, Nc is 1-15. In some embodiments, Nc is 1-14. In some embodiments, Nc is 1-13. In some embodiments, Nc is 1-12. In some embodiments, Nc is 1-11. In some embodiments, Nc is 1-10. In some embodiments, Nc is 1-9. In some embodiments, Nc is 1-8. In some embodiments, Nc is 1-7. In some embodiments, Nc is 1-6. In some embodiments, Nc is 1-5. In some embodiments, Nc is 1. In some embodiments, Nc is 2. In some embodiments, Nc is 3. In some embodiments, Nc is 4. In some embodiments, Nc is 5. In some embodiments, Nc is 6. In some embodiments, Nc is 7. In some embodiments, Nc is 8. In some embodiments, Nc is 9. In some embodiments, Nc is 10. In some embodiments, Nc is 11. In some embodiments, Nc is 12. In some embodiments, Nc is 13. In some embodiments, Nc is 14. In some embodiments, Nc is 15. In some embodiments, Nc is 16. In some embodiments, Nc is 17. In some embodiments, Nc is 18. In some embodiments, Nc is 19. In some embodiments, Nc is 20. In some embodiments, Nc is 21. In some embodiments, Nc is 22. In some embodiments, Nc is 23. In some embodiments, Nc is 24. In some embodiments, Nc is 25.

In some embodiments, provided technologies comprising one or more modification steps that independently comprise or are sulfurization (thiolation). In some embodiments, provided intermediates and/or products comprise one or more phosphorothioate internucleotidic linkages or precursors thereof (which can be converted into phosphorothioate internucleotidic linkages upon deprotection/cleavage), optionally chirally controlled. In some embodiments, provided intermediates and/or products comprise one or more non-negatively charged internucleotidic linkages (e.g., neutral internucleotidic linkages) or precursors thereof (which can be converted into phosphorothioate internucleotidic linkages upon deprotection/cleavage), optionally chirally controlled. In some embodiments, provided technologies comprising one or more modification steps that independently comprise or are oxidation. In some embodiments, provided intermediates and/or products comprise one or more natural phosphate linkages or precursors thereof (which can be converted into natural phosphate linkages upon deprotection/cleavage). In some embodiments, provided intermediates and/or products comprise one or more natural phosphate linkages and one or more phosphorothioate internucleotidic linkages.

Various supports can be utilized in accordance with the present disclosure, e.g., those described in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784, etc. In some embodiments, a support is a polymer. In some embodiments, a support is a solid support. In some embodiments, a solid support is a polymer, e.g., polystyrene. In some embodiments, a solid support is a Primer Support (e.g., Primer Support 5G, Primer Support 200, etc.). In some embodiments, a solid support is NittoPhase support (e.g., NittoPhase HL, NittoPhase UnyLinker, etc.). In some embodiments, a solid support is controlled-pore glass (CPG). In some embodiments, volume of a solid support, e.g., certain polystyrene based solid support, changes during oligonucleotide synthesis, e.g., at different stages of synthesis and/or when contacted with different solvent systems and/or reagents. In some embodiments, volume of a solid support, e.g., many CPG support, changes less than 25%, 20%/o, 15%, 10%, or 5%, or remains substantially the same during oligonucleotide synthesis. In some embodiments, the present disclosure encompasses the recognition than volume change of solid support during synthesis may cause deviations from planned reaction conditions, e.g., solvent system, reagent concentrations, contact time, etc., and may negatively impact synthesis efficiency, crude purity and/or yield. In some embodiments, solid support that does not significantly change its volume or keep substantially the same volume during oligonucleotide synthesis may provide advantages, e.g., less deviation from planned reaction conditions, higher crude purity, higher yield, etc. A support can have a number of chemical modifications for nucleoside loading, and may have various unit loading capacities (e.g., umol/g).

In oligonucleotide synthesis using a support, typically oligonucleotides are linked to a support through a linker. A number of linkers can be utilized in accordance with the present disclosure, e.g., those described in U.S. Pat. Nos. 9,598,458, 9,744,183, 9,605,019, 9,394,333, 8,859,755, US 20130178612, U.S. Pat. Nos. 8,470,987, 8,822,671, 9,403,865, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784, etc. In some embodiments, the present disclosure provides designed linkers. Useful support and/or functionalization there are described herein.

Oligonucleotide synthesis typically comprises a deblocking step, which de-blocks a blocked hydroxyl group for a next step, e.g., a coupling step, which keeps intact capped hydroxyl groups which should not participate in a next step, e.g., a coupling step. Various conditions for de-blocking can be utilized in accordance with the present disclosure, including those described in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784. In some embodiments, de-blocking removes DMT group from DMT-protected hydroxyl (detritylation). In some embodiments, deblocking is performed by contacting oligonucleotides with an acid. In some embodiments, an acid is trichloroacetic acid or dichloroacetic acid. In some embodiments, a deblocking condition is 2% trichloroacetic acid (TCA) or 3% dichloroacetic acid (DCA), in an inert solvent (e.g., dichloromethane, toluene, etc.)

A coupling step forms an internucleotidic linkage, which adds a nucleoside unit to an existing oligonucleotide. In some embodiments, an internucleotidic linkage formed during a coupling step is a phosphite triester linkage. In some embodiments, an internucleotidic linkage can form with chirally control, e.g., as in chirally controlled oligonucleotide synthesis using diastereomerically pure phosphoramidite, typically comprising a chiral auxiliary moiety. Conditions for coupling are widely reported and many can be utilized in accordance with the present disclosure, including those described in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784. In some embodiments, a coupling reagent system comprises a nucleoside phosphoramidite and an activator. Various phosphoramidites may be used in provided technologies, including those described in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784, and those having the structure of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof, as described in the present disclosure. Example activators include those described in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, WO 2019/217784, and U.S. Pat. No. 9,403,865, activators of each of which are independently incorporated herein by reference. In some embodiments, an activator is CMPT. In some embodiments, an activator is CMIMT. In some embodiments, an activator is ETT. In some embodiments, conditions, e.g., concentrations of phosphoramidites, concentrations of activators, contact times, solvents, etc. can be optimized for each coupling to improve, e.g., crude purity, yield, etc.

In some embodiments, after a coupling step one or more capping steps are performed before a modification step. In some embodiments, each capping step after a coupling step and before a modification step is performed as described in the present disclosure, e.g., with reduced levels of or no strong nucleophiles, with reduced levels of or no catalysts for esterification, and/or under conditions selective or specific for amidation over esterification. In some embodiments, each capping step after a coupling step and before a modification step is performed to cap one or more amino groups, e.g., one or more amino groups formed after coupling in chiral auxiliaries moieties attached to linkage phosphorus atoms.

In some embodiments, after one or more capping steps as described in the present disclosure, a modification step is performed to modify a internucleotidic linkage formed after coupling, which internucleotidic linkage, in some embodiments, comprises a linkage phosphorus atom that is trivalent (e.g., as in a phosphite linkage). In some embodiments, a modification step is or comprises oxidation, e.g., converting a phosphite linkage into a tetra-coordinated phosphate triester linkage (installing an ═O to a linkage phosphorus). In some embodiments, a modification step is or comprises sulfurization. In some embodiments, sulfurization converts a phosphite linkage into a tetra-coordinated internucleotidic linkage by installing an ═S to a linkage phosphorus. In some embodiments, sulfurization converts a phosphite linkage into a tetra-coordinated internucleotidic linkage by installing ═N—, e.g., as in ═N(-L-$R^5$), $P^N$, etc., to a linkage phosphorus. In some embodiments, as described herein, $R^5$ comprises a ring comprising a nitrogen atom. In some embodiments, a nitrogen atom is in a salt form (quaternary) and is associated with a counterion (e.g., $PF_6^-$). In some embodiments, a linkage comprising ═N(-L-$R^5$) or $P^N$ is a precursor to a non-negatively charged internucleotidic linkage, e.g., a neutral internucleotidic linkage. In some embodiments, sulfurization converts a phosphite linkage into a tetra-coordinated phosphorothioate triester internucleotidic linkage (e.g., —P(═O)(S-$L^s$-$R^5$)— wherein -$L^s$-$R^5$ is not hydrogen). Example modifications and related technologies include those described in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784.

In some embodiments, provided technologies provide more flexibility with respect to modification types and/or choices of modification reagents, e.g., oxidation reagents, sulfurization reagents, reagents for installing =N—, etc. For example, reagents that tended to give inferior results in previously reported chirally controlled oligonucleotide synthesis can be utilized with technologies of the present disclosure to provide significantly improved, satisfactory results. Among other things, the present disclosure provides technologies (e.g., chiral auxiliaries, compounds, methods, etc.) that are particularly effectively for chirally controlled preparation of oligonucleotides containing certain types of modifications, e.g., non-negatively charged internucleotidic linkages (e.g., n001).

In some embodiments, after a modifying step, another capping step is performed. In some embodiments, an after-modification capping step is performed with a substantial amount of a strong nucleophile and/or an esterification catalyst (a strong nucleophile can be the same as an esterification catalyst) under an esterification condition which is comparable or identical to a capping condition in traditional oligonucleotide synthesis. In some embodiments, an after-modification capping step caps free hydroxyl groups, e.g., those residue hydroxyl groups as a result of incomplete coupling which remain intact after a modification step. After this capping step, oligonucleotides can be de-blocked to expose hydroxyl groups at sites for further chain extension, and enter another synthetic cycle.

After desired chain lengths are achieved, oligonucleotides can be fully deprotected and cleaved from support for purification and/or further uses. Various cleavage and/or deprotection technologies can be utilized in accordance with the present disclosure, including those described in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784. In some embodiments, cleavage and/or deprotection comprise removal of chiral auxiliaries. As appreciated by those skilled in the art, cleavage and/or deprotection conditions can depend on the chemistry used during oligonucleotide synthesis, e.g., properties of linkers connecting oligonucleotides to a support, properties of base and/or sugar blocking groups, properties of chiral moieties etc. In some embodiments, removal of chiral auxiliaries, e.g., DPSE-type of chiral auxiliaries, comprises use of TEA-HF. In some embodiments, the present disclosure surprisingly demonstrated that TEA-HF can be successfully utilized for oligonucleotide synthesis using CPG support.

Among other things, the present disclosure identifies that contact with water, e.g., under a basic condition optionally at an elevated temperature for a period of time (e.g., for deprotection and/or cleavage) can be a significant source of impurities/decomposition (e.g., conversion of P=S and or P=N— to P=O). In some embodiments, the present disclosure provides technologies to address such source of a problem. In some embodiments, the present disclosure provides chiral auxiliaries that can be readily removed by bases. In some embodiments, such removal does not require strong bases, elevated temperature, and/or length of time as previously reported, and can significantly improve product yield and/or purity. In some embodiments, removal of chiral auxiliaries comprises contacting oligonucleotides (e.g., a plurality of oligonucleotides) which comprise chiral auxiliaries with a base under an anhydrous condition, in some embodiments, preferably before the oligonucleotides are contacted with significant amount of water (e.g., a reagent system comprising a base, water, and optionally one or more organic solvents (e.g., one useful for deprotection of bases, cleavage of oligonucleotides from support, etc.)). In various instances, Applicant observed that remove of chiral auxiliaries using bases under anhydrous conditions before contact with conditions comprising significant amount of water (e.g., deprotection/cleavage conditions comprising $NH_3 \cdot H_2O$) can significantly improve product yield and/or purity. Additionally, removal of chiral auxiliaries using bases as described herein may simplify operation procedures and reduce manufacturing cost.

Various types of sugars and nucleobases, including non-natural, modified sugars and nucleobases, can be utilized in provided technologies in accordance with the present disclosure, e.g., those sugar and nucleobases described in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784.

In some embodiments, provided technologies are useful for large scale preparation of oligonucleotides. In some embodiments, a scale is 100 g or more. In some embodiments, a scale is 200 g or more. In some embodiments, a scale is 500 g or more. In some embodiments, a scale is at least 1000 g or more. In some embodiments, a composition comprises a large scale of an oligonucleotide (e.g., a product of a reaction, a step, a method, etc., or a final product). Among other things, the present disclosure addresses various challenges associated with large-scale preparation of oligonucleotide compositions, particularly chirally controlled oligonucleotide compositions.

In some embodiments, a composition of another step being contacted in a step is a composition of the first step preceding the step. In some embodiments, a composition of another step being contacted in each step is a composition of the first step preceding the step. For example, a de-blocked composition being contacted in a coupling step is the de-blocked composition of the first de-blocking step preceding the coupling step, a coupling product composition being contacted in a pre-modification capping step is the coupling product composition of the first coupling step preceding the pre-modification capping step, a coupling product composition being contacted in a modification step is the coupling product composition of the first coupling step preceding the modification step, a pre-modification capping product composition being contacted in a modification step is the pre-modification capping product composition of the first pre-modification capping step preceding the modification step, a modification product composition being contacted in a post-modification capping step is the modification product composition of the first modification step preceding the post-modification capping step, a modification product composition being contacted in a de-blocking step is the modification product composition of the first modification step preceding the de-blocking step, a post-modification capping product composition being contacted in a de-blocking step is the post-modification capping product composition of the first post-modification capping step preceding the de-blocking step, etc.

In some embodiments, provided technologies may be generally utilized to prepare other oligomeric compounds. In some embodiments, a method for preparing a composition comprising a plurality of oligomeric compounds comprises:

(1) a coupling step comprising:

contacting a de-blocked composition comprising a plurality of de-blocked compounds, each independently comprising a de-blocked monomeric unit, which is de-blocked in that each de-blocked monomeric unit independently comprises a free connecting group, with a coupling reagent system which comprises a partner compound comprising a monomeric unit of the oligomeric compound; and coupling a partner compound comprising a monomeric unit of the oligomeric compound with the free connecting groups of a plurality of de-blocked compounds to provide a coupling product composition comprising a plurality of coupling products, each of which independently comprises a linkage linking the connecting group of a dc-blocked monomeric unit and a monomeric unit of the partner compound;

(2) optionally a pre-modification capping step comprising:

contacting a coupling product composition with a pre-modification capping reagent system; and capping one or more functional groups of the coupling product composition to provide a pre-modification capping product composition comprising a plurality of pre-modification capping products;

(3) a modification step comprising:

contacting a coupling product composition and modifying one or more linkages of one or more coupling products to provide a modification step composition comprising a plurality of modification products; or contacting a pre-modification capping product composition and modifying one or more linkages of one or more pre-modification capping products to provide a modification product composition comprising a plurality of modification products;

(4) optionally a post-modification capping step comprising:

contacting a modification product composition with a post-modification capping reagent system; and capping one or more functional groups of one or more compounds of a modification product composition to provide a post-modification capping product composition comprising a plurality of post-modification capping products;

(5) optionally a de-blocking step comprising:

contacting a modification product composition, or a post-modification capping product composition, with a de-blocking reagent system to provide a de-blocked composition comprising a plurality of de-blocked products, each of which independently comprises a de-blocked monomeric unit comprising a free connecting group.

In some embodiments, a method optionally comprises repeating steps (1) to (5) a number of times, e.g., until a desired length is achieved. In some embodiments, a the method comprises both a pre-modification capping step and a post-modification capping step, wherein a pre-modification capping reagent system is optionally different from a post-modification reagent system, or a pre-modification capping step, wherein the pre-modification capping reagent system caps a plurality of non-connecting groups of a plurality of coupling products, and a modification step that comprises sulfurization, which sulfurization provides a modification product composition comprising a plurality of modification products, each of which independently comprises a P═S moiety, or a post-modification capping step, comprising contacting a modification product composition comprising a plurality of modification products, each of which independently comprises a linkage that comprises at least one chirally controlled chiral center in that at least 80%, 85%, 90%, 95%, 96%, 97%, 98% or 99% oligomeric compounds within the modification product composition comprising the chiral center and having the same constitution share the same stereochemical configuration at the chiral center, or a post-modification capping step, and a coupling reagent system comprising a chiral partner compound that comprises a monomeric unit of the oligomeric compound, wherein the chiral partner compound comprises a chiral atom that is not within the monomeric unit; or a coupling step which is immediately followed by a pre-modification capping step, which the pre-modification capping reagent system of the pre-modification capping step comprises no esterification catalyst or comprises no strong nucleophile.

As described in the present disclosure, in some embodiments, an oligomeric compound is an oligonucleotide. In some embodiments, a composition comprising a plurality of oligomeric compounds is an oligonucleotide composition comprising a plurality of oligonucleotides. In some embodiments, a coupling step is a coupling step as described in the present disclosure for oligonucleotide synthesis. In some embodiments, a de-blocked compound is a de-blocked oligonucleotide, e.g., an oligonucleotide after de-blocking step in an oligonucleotide synthesis cycle. In some embodiments, a de-blocked monomeric unit is a de-blocked 5'-end nucleoside unit. In some embodiments, a free connecting group is a free 5-hydroxyl group. In some embodiments, a coupling reagent system is a coupling reagent system in oligonucleotide synthesis cycles. In some embodiments, a partner compound is a phosphoramidite described herein for oligonucleotide synthesis. In some embodiments, a coupling product is an oligonucleotide formed after coupling in oligonucleotide synthesis. In some embodiments, a linkage linking the connecting group of a de-blocked monomeric unit and a monomeric unit of the partner compound is an internucleotidic linkage formed during a coupling step. In some embodiments, a pre-modification capping step is a capping step in oligonucleotide synthesis as described in the present disclosure. In some embodiments, a pre-modification capping reagent system is a pre-capping reagent system in oligonucleotide synthesis as described in the present disclosure. In some embodiments, a pre-modification capping product composition is a composition after a pre-modification capping step in oligonucleotide synthesis. In some embodiments, a pre-modification capping product is a product formed after a pre-modification capping step in oligonucleotide synthesis. In some embodiments, a modification step is a modification step as used in oligonucleotide synthesis. In some embodiments, a modification step as demonstrated in oligonucleotide synthesis described in the present disclosure modifies an internucleotidic linkage. In some embodiments, a modification product composition is an oligonucleotide composition provided after a modification step in oligonucleotide synthesis. In some embodiments, a modification product is an oligonucleotide provided after a modification step in oligonucleotide synthesis. In some embodiments, a post-modification capping step is a capping step in oligonucleotide synthesis as described in the present disclosure. In some embodiments, a post-modification capping reagent system is a post-capping reagent system in oligonucleotide synthesis as described in the present disclosure. In some embodiments, a post-modification capping product composition is a composition after a post-modification capping step in oligonucleotide synthesis. In some embodiments, a post-modification capping product is a product formed after a post-modification capping step in oligonucleotide synthesis. In some embodiments, a de-blocking step is a de-blocking step as described in the present disclosure for oligonucleotide synthesis. In some embodiments, a non-connecting group is an amino group. In some embodiments, a chirally controlled chiral center is a chirally controlled linkage phosphorus center. In some embodiments, a chiral partner compound comprising a chiral atom that is not within the monomeric unit is a phosphoramidite comprising a chiral center that is not in its nucleoside unit and is not the P. In some embodiments, a reagent system comprises no esterification catalyst comprises no DMAP and no NMI.

DETAILED DESCRIPTION OF CERTAIN EMBODIMENTS

1. Definitions

Figure 1:
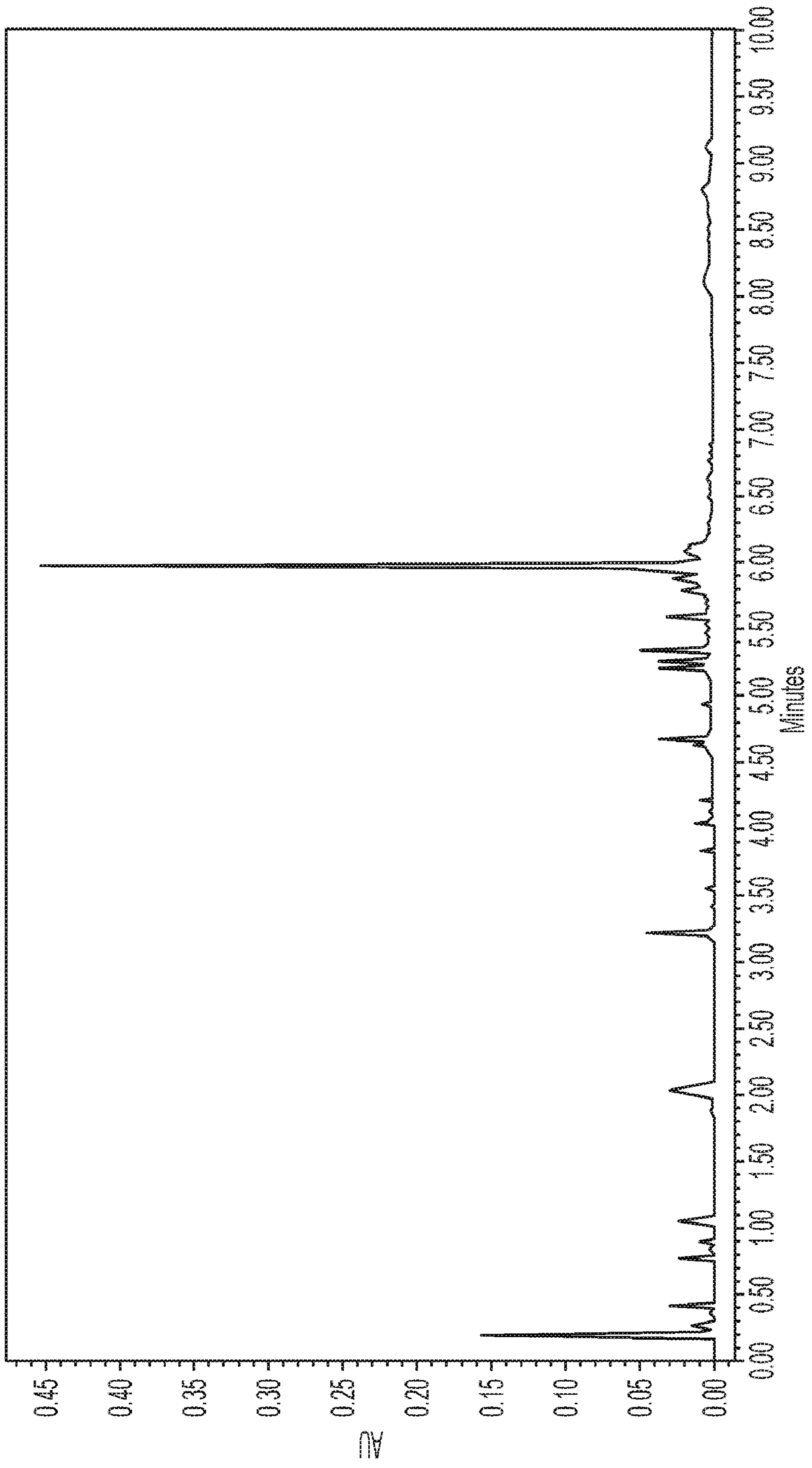
FIG. 1. Crude UPLC chromatogram for B6.

As used herein, the following definitions shall apply unless otherwise indicated. For purposes of this disclosure, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001.

As used herein in the present disclosure, unless otherwise clear from context, (i) the term "a" or "an" may be understood to mean "at least one"; (ii) the term "or" may be understood to mean "and/or"; (iii) the terms "comprising", "comprise", "including" (whether used with "not limited to" or not), and "include" (whether used with "not limited to" or not) may be understood to encompass itemized components or steps whether presented by themselves or together with one or more additional components or steps; (iv) the term "another" may be understood to mean at least an additional/second one or more; (v) the terms "about" and "approximately" may be understood to permit standard variation as would be understood by those of ordinary skill in the art; and (vi) where ranges are provided, endpoints are included.

Unless otherwise specified, description of oligonucleotides and elements thereof (e.g., base sequence, sugar modifications, internucleotidic linkages, linkage phosphorus stereochemistry, etc.) is from 5' to 3'. Unless otherwise specified, oligonucleotides described herein may be provided and/or utilized in a salt form, particularly a pharmaceutically acceptable salt form. Unless otherwise indicated, oligonucleotides include various forms of the oligonucleotides. As those skilled in the art will appreciate, in some embodiments, individual oligonucleotides within a composition may be considered to be of the same constitution and/or structure even though, within such composition (e.g., a liquid composition), particular such oligonucleotides might be in different forms (e.g., different pharmaceutically acceptable salt form(s) (and may be dissolved and the oligonucleotide chain may exist as an anion form when, e.g., in a liquid composition)) at a particular moment in time. For example, those skilled in the art will appreciate that, at a given pH, individual internucleotidic linkages along an oligonucleotide chain may be in an acid (H) form, or in one of a plurality of possible salt forms (e.g., a sodium salt, or a salt of a different cation, depending on which ions might be present in the preparation or composition), and will understand that, so long as their acid forms (e.g., replacing all cations, if any, with $H^+$) are of the same constitution and/or structure, such individual oligonucleotides may properly be considered to be of the same constitution and/or structure.

Aliphatic: As used herein, "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation (but not aromatic), or combinations thereof. In some embodiments, aliphatic groups contain 1-50 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

Alkenyl: As used herein, the term "alkenyl" refers to an aliphatic group, as defined herein, having one or more double bonds.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Alkynyl: As used herein, the term "alkynyl" refers to an aliphatic group, as defined herein, having one or more triple bonds.

Analog: The term "analog" includes any chemical moiety which differs structurally from a reference chemical moiety or class of moieties, but which is capable of performing at least one function of such a reference chemical moiety or class of moieties. As non-limiting examples, a nucleotide analog differs structurally from a nucleotide but performs at least one function of a nucleotide; a nucleobase analog differs structurally from a nucleobase but performs at least one function of a nucleobase; etc.

Aryl: The term "aryl" used alone or as part of a larger moiety as in "aralkyl," "aralkoxy," or "aryloxyalkyl," refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term "aryl" may be used interchangeably with the term "aryl ring." In certain embodiments of the present disclosure, "aryl" refers to an aromatic ring system which includes, but not limited to, phenyl, biphenyl, naphthyl, binaphthyl, anthracyl and the like, which may bear one or more substituents. In some embodiments, also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like, where a radical or point of attachment is on an aryl ring.

Chiral control: As used herein, "chiral control" refers to control of the stereochemical designation of the chiral linkage phosphorus in a chiral internucleotidic linkage within an oligonucleotide. As used herein, a chiral internucleotidic linkage is an internucleotidic linkage whose linkage phosphorus is chiral. In some embodiments, a control is achieved through a chiral element that is absent from the sugar and base moieties of an oligonucleotide, for example, in some embodiments, a control is achieved through use of one or more chiral auxiliaries during oligonucleotide preparation as described in the present disclosure, which chiral auxiliaries often are part of chiral phosphoramidites used during oligonucleotide preparation. In contrast to chiral control, a person having ordinary skill in the art appreciates that conventional oligonucleotide synthesis which does not use chiral auxiliaries cannot control stereochemistry at a chiral internucleotidic linkage if such conventional oligonucleotide synthesis is used to form the chiral internucleotidic linkage. In some embodiments, the stereochemical designation of each chiral linkage phosphorus in each chiral internucleotidic linkage within an oligonucleotide is controlled.

Chirally controlled oligonucleotide composition: The terms "chirally controlled oligonucleotide composition", "chirally controlled nucleic acid composition", and the like, as used herein, refers to a composition that comprises a plurality of oligonucleotides (or nucleic acids) which share 1) a common base sequence, 2) a common pattern of backbone linkages, and 3) a common pattern of backbone phosphorus modifications, wherein the plurality of oligonucleotides (or nucleic acids) share the same linkage phosphorus stereochemistry at one or more chiral internucleotidic linkages (chirally controlled or stereodefined internucleotidic linkages, whose chiral linkage phosphorus is Rp or Sp in the composition ("stereodefined"), not a random Rp and Sp mixture as non-chirally controlled internucleotidic linkages). Level of the plurality of oligonucleotides (or nucleic acids) in a chirally controlled oligonucleotide composition is pre-determined/controlled (e.g., through chirally controlled oligonucleotide preparation to stereoselectively form one or more chiral internucleotidic linkages). In some embodiments, about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, 99%, or 100%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition are oligonucleotides of the plurality. In some embodiments, about 1%-100%, (e.g., about 5%-100%, 10%-100%, 20%-100%, 30%-100%, 40%-100%, 50%-100%, 60%-100%, 70%100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, 99%, or 100%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition that share the common base sequence, the common pattern of backbone linkages, and the common pattern of backbone phosphorus modifications are oligonucleotides of the plurality. In some embodiments, a level is about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, 99%, or 100%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a composition, or of all oligonucleotides in a composition that share a common base sequence (e.g., of a plurality of oligonucleotide or an oligonucleotide type), or of all oligonucleotides in a composition that share a common base sequence, a common pattern of backbone linkages, and a common pattern of backbone phosphorus modifications, or of all oligonucleotides in a composition that share a common base sequence, a common patter of base modifications, a common pattern of sugar modifications, a common pattern of internucleotidic linkage types, and/or a common pattern of internucleotidic linkage modifications. In some embodiments, the plurality of oligonucleotides share the same stereochemistry at about 1-50 (e.g., about 1-10, 1-20, 5-10, 5-20, 10-15, 10-20, 10-25, 10-30, or about 1, 2, 3, 4, 5, 6, 7, 8, 9, 10, 11, 12, 13, 14, 15, 16, 17, 18, 19, or 20, or at least 1, 2, 3, 4, 5, 6, 7, 8, 9, 10, 11, 12, 13, 14, 15, 16, 17, 18, 19, or 20) chiral internucleotidic linkages. In some embodiments, the plurality of oligonucleotides share the same stereochemistry at about 1%-100% (e.g., about 5%-100%, 10%-100%, 20%-100%, 30%-100%, 40%-100%, 50%-

100%, 60%-100%, 70%-100%, 80-100%, 90-100%, 95-100%, 50%-90%, about 5%, 10%, 15%, 20%, 25%, 30%, 35%, 40%, 45%, 50%, 55%, 60%, 65%, 70%, 75%, 80%, 85%, 90%, 95%, or 100%, or at least 5%, 10%, 15%, 20%, 25%, 30%, 35%, 40%, 45%, 50%, 55%, 60%, 65%, 70%, 75%, 80%, 85%, 90%, 95%, or 99%) of chiral internucleotidic linkages. In some embodiments, oligonucleotides (or nucleic acids) of a plurality are of the same constitution. In some embodiments, level of the oligonucleotides (or nucleic acids) of the plurality is about 1%-100%. (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, 99%, or 100%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides (or nucleic acids) in a composition that share the same constitution as the oligonucleotides (or nucleic acids) of the plurality. In some embodiments, each chiral internucleotidic linkage is a chiral controlled internucleotidic linkage, and the composition is a completely chirally controlled oligonucleotide composition. In some embodiments, oligonucleotides (or nucleic acids) of a plurality are structurally identical. In some embodiments, a chirally controlled internucleotidic linkage has a diastereopurity of at least 80%, 85%, 90%, 91%, 92%, 93%, 94%, 95%, 96%, 97%, 98%, 99% or 99.5%, typically at least 90%, 91%, 92%, 93%, 94%, 95%, 96%, 97%, 98%, 99% or 99.5%. In some embodiments, a chirally controlled internucleotidic linkage has a diastereopurity of at least 95%. In some embodiments, a chirally controlled internucleotidic linkage has a diastereopurity of at least 96%. In some embodiments, a chirally controlled internucleotidic linkage has a diastereopurity of at least 97%. In some embodiments, a chirally controlled internucleotidic linkage has a diastereopurity of at least 98%. In some embodiments, a chirally controlled internucleotidic linkage has a diastereopurity of at least 99%. In some embodiments, a percentage of a level is or is at least $(DS)^{nc}$, wherein DS is a diastereopurity as described in the present disclosure (e.g., 90%, 91%, 92%, 93%, 94%, 95%, 96%, 97%, 98%, 99% or 99.5% or more) and nc is the number of chirally controlled internucleotidic linkages as described in the present disclosure (e.g., 1-50, 1-40, 1-30, 1-25, 1-20, 5-50, 5-40, 5-30, 5-25, 5-20, 1, 2, 3, 4, 5, 6, 7, 8, 9, 10, 11, 12, 13, 14, 15, 16, 17, 18, 19, 20, 21, 22, 23, 24, 25 or more). In some embodiments, a percentage of a level is or is at least $(DS)^{nc}$, wherein DS is 95%-100%. For example, when DS is 99% and nc is 10, the percentage is or is at least 90% ($(99\%)^{10}\approx0.90=90\%$). In some embodiments, level of a plurality of oligonucleotides in a composition is represented as the product of the diastereopurity of each chirally controlled internucleotidic linkage in the oligonucleotides. In some embodiments, diastereopurity of an internucleotidic linkage connecting two nucleosides in an oligonucleotide (or nucleic acid) is represented by the diastereopurity of an internucleotidic linkage of a dimer connecting the same two nucleosides, wherein the dimer is prepared using comparable conditions, in some instances, identical synthetic cycle conditions (e.g., for the linkage between Nx and Ny in an oligonucleotide . . . NxNy . . . , the dimer is NxNy). In some embodiments, not all chiral internucleotidic linkages are chiral controlled internucleotidic linkages, and the composition is a partially chirally controlled oligonucleotide composition. In some embodiments, a non-chirally controlled internucleotidic linkage has a diastereopurity of less than about 80%, 75%, 70%, 65%, 60%, 55%, or of about 50%, as typically observed in stereorandom oligonucleotide compositions (e.g., as appreciated by those skilled in the art, from traditional oligonucleotide synthesis, e.g., the phosphoramidite method). In some embodiments, oligonucleotides (or nucleic acids) of a plurality are of the same type. In some embodiments, a chirally controlled oligonucleotide composition comprises non-random or controlled levels of individual oligonucleotide or nucleic acids types. For instance, in some embodiments a chirally controlled oligonucleotide composition comprises one and no more than one oligonucleotide type. In some embodiments, a chirally controlled oligonucleotide composition comprises more than one oligonucleotide type. In some embodiments, a chirally controlled oligonucleotide composition comprises multiple oligonucleotide types. In some embodiments, a chirally controlled oligonucleotide composition is a composition of oligonucleotides of an oligonucleotide type, which composition comprises a non-random or controlled level of a plurality of oligonucleotides of the oligonucleotide type.

Comparable: The term "comparable" is used herein to describe two (or more) sets of conditions or circumstances that are sufficiently similar to one another to permit comparison of results obtained or phenomena observed. In some embodiments, comparable sets of conditions or circumstances are characterized by a plurality of substantially identical features and one or a small number of varied features. Those of ordinary skill in the art will appreciate that sets of conditions are comparable to one another when characterized by a sufficient number and type of substantially identical features to warrant a reasonable conclusion that differences in results obtained or phenomena observed under the different sets of conditions or circumstances are caused by or indicative of the variation in those features that are varied.

Cycloaliphatic: The term "cycloaliphatic," "carbocycle," "carbocyclyl," "carbocyclic radical," and "carbocyclic ring," are used interchangeably, and as used herein, refer to saturated or partially unsaturated, but non-aromatic, cyclic aliphatic monocyclic, bicyclic, or polycyclic ring systems, as described herein, having, unless otherwise specified, from 3 to 30 ring members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, a cycloaliphatic group has 3-6 carbons. In some embodiments, a cycloaliphatic group is saturated and is cycloalkyl. The term "cycloaliphatic" may also include aliphatic rings that are fused to one or more aromatic or nonaromatic rings, such as decahydronaphthyl or tetrahydronaphthyl. In some embodiments, a cycloaliphatic group is bicyclic. In some embodiments, a cycloaliphatic group is tricyclic. In some embodiments, a cycloaliphatic group is polycyclic. In some embodiments, "cycloaliphatic" refers to $C_3$-$C_6$ monocyclic hydrocarbon, or $C_8$-$C_{10}$ bicyclic or polycyclic hydrocarbon, that is completely saturated or that contains one or more units of unsaturation, but which is not aromatic, that has a single point of attachment to the rest of the molecule, or a $C_9$-$C_{16}$ polycyclic hydrocarbon that is completely saturated or that contains one or more units of unsaturation, but which is not aromatic, that has a single point of attachment to the rest of the molecule.

Halogen: The term "halogen" means F, Cl, Br, or I.

Heteroaliphatic: The term "heteroaliphatic", as used herein, is given its ordinary meaning in the art and refers to aliphatic groups as described herein in which one or more carbon atoms are independently replaced with one or more heteroatoms (e.g., oxygen, nitrogen, sulfur, silicon, phosphorus, and the like). In some embodiments, one or more units selected from C, CH, $CH_2$, and $CH_3$ are independently replaced by one or more heteroatoms (including oxidized and/or substituted forms thereof). In some embodiments, a heteroaliphatic group is heteroalkyl. In some embodiments, a heteroaliphatic group is heteroalkenyl.

Heteroalkyl: The term "heteroalkyl", as used herein, is given its ordinary meaning in the art and refers to alkyl groups as described herein in which one or more carbon atoms are independently replaced with one or more heteroatoms (e.g., oxygen, nitrogen, sulfur, silicon, phosphorus, and the like). Examples of heteroalkyl groups include, but are not limited to, alkoxy, poly(ethylene glycol)-, alkyl-substituted amino, tetrahydrofuranyl, piperidinyl, morpholinyl, etc.

Heteroaryl: The terms "heteroaryl" and "heteroar-", as used herein, used alone or as part of a larger moiety, e.g., "heteroaralkyl," or "heteroaralkoxy," refer to monocyclic, bicyclic or polycyclic ring systems having a total of five to thirty ring members, wherein at least one ring in the system is aromatic and at least one aromatic ring atom is a heteroatom. In some embodiments, a heteroaryl group is a group having 5 to 10 ring atoms (i.e., monocyclic, bicyclic or polycyclic), in some embodiments 5, 6, 9, or 10 ring atoms. In some embodiments, a heteroaryl group has 6, 10, or 14 $\pi$ electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic or polycyclic. The term "heteroaryl" may be used interchangeably with the terms "heteroaryl ring," "heteroaryl group." or "heteroaromatic," any of which terms include rings that are optionally substituted. The term "heteroaralkyl" refers to an alkyl group substituted by a heteroaryl group, wherein the alkyl and heteroaryl portions independently are optionally substituted.

Heteroatom: The term "heteroatom", as used herein, means an atom that is not carbon or hydrogen. In some embodiments, a heteroatom is boron, oxygen, sulfur, nitrogen, phosphorus, or silicon (including oxidized forms of nitrogen, sulfur, phosphorus, or silicon; charged forms of nitrogen (e.g., quaternized forms, forms as in iminium groups, etc.), phosphorus, sulfur, oxygen; etc.). In some embodiments, a heteroatom is oxygen, sulfur or nitrogen.

Heterocycle: As used herein, the terms "heterocycle," "heterocyclyl." "heterocyclic radical," and "heterocyclic ring", as used herein, are used interchangeably and refer to a monocyclic, bicyclic or polycyclic ring moiety (e.g., 3-30 membered) that is saturated or partially unsaturated and has one or more heteroatom ring atoms. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes substituted nitrogen. As an example, in a saturated or partially unsaturated ring having 0-3 heteroatoms selected from oxygen, sulfur and nitrogen, the nitrogen may be N (as in 3,4-dihydro-2H-pyrrolyl), NH (as in pyrrolidinyl), or $^{+}NR$ (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic or polycyclic. The term "heterocyclylalkyl" refers to an alkyl group substituted by a heterocyclyl, wherein the alkyl and heterocyclyl portions independently are optionally substituted.

Internucleotidic linkage: As used herein, the phrase "internucleotidic linkage" refers generally to a linkage linking nucleoside units of an oligonucleotide or a nucleic acid. In some embodiments, an internucleotidic linkage is a phosphodiester linkage, as extensively found in naturally occurring DNA and RNA molecules (natural phosphate linkage (—OP(=O)(OH)O—), which as appreciated by those skilled in the art may exist as a salt form). In some embodiments, an internucleotidic linkage is a modified internucleotidic linkage (not a natural phosphate linkage). In some embodiments, an internucleotidic linkage is a "modified internucleotidic linkage" wherein at least one oxygen atom or —OH of a phosphodiester linkage is replaced by a different organic or inorganic moiety. In some embodiments, such an organic or inorganic moiety is selected from =S, =Se, =NR', —SR', —SeR, —N(R')$_2$, B(R')$_3$, —S—, —Se—, and —N(R')—, wherein each R' is independently as defined and described in the present disclosure. In some embodiments, an internucleotidic linkage is a phosphotriester linkage, phosphorothioate linkage (or phosphorothioate diester linkage, —OP(=O)(SH)O—, which as appreciated by those skilled in the art may exist as a salt form), or phosphorothioate triester linkage. In some embodiments, a modified internucleotidic linkage is a phosphorothioate linkage. In some embodiments, an internucleotidic linkage is one of, e.g., PNA (peptide nucleic acid) or PMO (phosphorodiamidate Morpholino oligomer) linkage. In some embodiments, a modified internucleotidic linkage is a non-negatively charged internucleotidic linkage. In some embodiments, a modified internucleotidic linkage is a neutral internucleotidic linkage (e.g., n001 in certain provided oligonucleotides). It is understood by a person of ordinary skill in the art that an internucleotidic linkage may exist as an anion or cation at a given pH due to the existence of acid or base moieties in the linkage. In some embodiments, a modified internucleotidic linkages is a modified internucleotidic linkages designated as s, s1, s2, s3, s4, s5, s6, s7, s8, s9, s10, s11, s12, s13, s14, s15, s16, s17 and s18 as described in WO 2017/210647.

Linkage phosphorus: as defined herein, the phrase "linkage phosphorus" is used to indicate that the particular phosphorus atom being referred to is the phosphorus atom present in the internucleotidic linkage, which phosphorus atom corresponds to the phosphorus atom of a phosphodiester internucleotidic linkage as occurs in naturally occurring DNA and RNA. In some embodiments, a linkage phosphorus atom is in a modified internucleotidic linkage, wherein each oxygen atom of a phosphodiester linkage is optionally and independently replaced by an organic or inorganic moiety. In some embodiments, a linkage phosphorus atom is the P of, e.g., formula VII as defined herein. In some embodiments, a linkage phosphorus atom is chiral. In some embodiments, a linkage phosphorus atom is achiral (e.g., as in natural phosphate linkages).

Modified nucleobase: The terms "modified nucleobase", "modified base" and the like refer to a chemical moiety which is chemically distinct from a nucleobase, but which is capable of performing at least one function of a nucleobase. In some embodiments, a modified nucleobase is a nucleobase which comprises a modification. In some embodiments, a modified nucleobase is capable of at least one function of a nucleobase, e.g., forming a moiety in a polymer capable of base-pairing to a nucleic acid comprising an at least complementary sequence of bases. In some embodiments, a modified nucleobase is substituted A, T, C, G, or U, or a substituted tautomer of A, T, C, G, or U. In some embodiments, a modified nucleobase in the context of oligonucleotides refer to a nucleobase that is not A, T, C, G or U.

Modified nucleoside: The term "modified nucleoside" refers to a moiety derived from or chemically similar to a natural nucleoside, but which comprises a chemical modification which differentiates it from a natural nucleoside. Non-limiting examples of modified nucleosides include those which comprise a modification at the base and/or the sugar. Non-limiting examples of modified nucleosides include those with a 2' modification at a sugar. Non-limiting examples of modified nucleosides also include abasic nucleosides (which lack a nucleobase). In some embodiments, a modified nucleoside is capable of at least one function of a nucleoside, e.g., forming a moiety in a polymer capable of base-pairing to a nucleic acid comprising an at least complementary sequence of bases.

Modified nucleotide: The term "modified nucleotide" includes any chemical moiety which differs structurally from a natural nucleotide but is capable of performing at least one function of a natural nucleotide. In some embodiments, a modified nucleotide comprises a modification at a sugar, base and/or internucleotidic linkage. In some embodiments, a modified nucleotide comprises a modified sugar, modified nucleobase and/or modified internucleotidic linkage. In some embodiments, a modified nucleotide is capable of at least one function of a nucleotide, e.g., forming a subunit in a polymer capable of base-pairing to a nucleic acid comprising an at least complementary sequence of bases.

Modified sugar: The term "modified sugar" refers to a moiety that can replace a sugar. A modified sugar mimics the spatial arrangement, electronic properties, or some other physicochemical property of a sugar. In some embodiments, as described in the present disclosure, a modified sugar is substituted ribose or deoxyribose. In some embodiments, a modified sugar comprises a 2'-modification. Examples of useful 2'-modification are widely utilized in the art and described herein. In some embodiments, a 2'-modification is 2'-OR, wherein R is optionally substituted $C_{1-10}$ aliphatic. In some embodiments, a 2'-modification is 2'-OMe. In some embodiments, a 2'-modification is 2'-MOE. In some embodiments, a modified sugar is a bicyclic sugar (e.g., a sugar used in LNA, BNA, etc.). In some embodiments, in the context of oligonucleotides, a modified sugar is a sugar that is not ribose or deoxyribose as typically found in natural RNA or DNA.

Nucleobase: The term "nucleobase" refers to the parts of nucleic acids that are involved in the hydrogen-bonding that binds one nucleic acid strand to another complementary strand in a sequence specific manner. The most common naturally-occurring nucleobases are adenine (A), guanine (G), uracil (U), cytosine (C), and thymine (T). In some embodiments, a naturally-occurring nucleobases are modified adenine, guanine, uracil, cytosine, or thymine. In some embodiments, a naturally-occurring nucleobases are methylated adenine, guanine, uracil, cytosine, or thymine. In some embodiments, a nucleobase comprises a heteroaryl ring wherein a ring atom is nitrogen, and when in a nucleoside, the nitrogen is bonded to a sugar moiety. In some embodiments, a nucleobase comprises a heterocyclic ring wherein a ring atom is nitrogen, and when in a nucleoside, the nitrogen is bonded to a sugar moiety. In some embodiments, a nucleobase is a "modified nucleobase," a nucleobase other than adenine (A), guanine (G), uracil (U), cytosine (C), and thymine (T). In some embodiments, a modified nucleobase is substituted A, T, C, G or U. In some embodiments, a modified nucleobase is a substituted tautomer of A, T, C, G, or U. In some embodiments, a modified nucleobases is methylated adenine, guanine, uracil, cytosine, or thymine. In some embodiments, a modified nucleobase mimics the spatial arrangement, electronic properties, or some other physicochemical property of the nucleobase and retains the property of hydrogen-bonding that binds one nucleic acid strand to another in a sequence specific manner. In some embodiments, a modified nucleobase can pair with all of the five naturally occurring bases (uracil, thymine, adenine, cytosine, or guanine) without substantially affecting the melting behavior, recognition by intracellular enzymes or activity of the oligonucleotide duplex. As used herein, the term "nucleobase" also encompasses structural analogs used in lieu of natural or naturally-occurring nucleotides, such as modified nucleobases and nucleobase analogs. In some embodiments, a nucleobase is optionally substituted A, T, C, G, or U, or an optionally substituted tautomer of A, T, C, G, or U. In some embodiments, a "nucleobase" refers to a nucleobase unit in an oligonucleotide or a nucleic acid (e.g., A, T, C, G or U as in an oligonucleotide or a nucleic acid).

Nucleoside: The term "nucleoside" refers to a moiety wherein a nucleobase or a modified nucleobase is covalently bound to a sugar or a modified sugar. In some embodiments, a nucleoside is a natural nucleoside, e.g., adenosine, deoxyadenosine, guanosine, deoxyguanosine, thymidine, uridine, cytidine, or deoxycytidine. In some embodiments, a nucleoside is a modified nucleoside, e.g., a substituted natural nucleoside selected from adenosine, deoxyadenosine, guanosine, deoxyguanosine, thymidine, uridine, cytidine, and deoxycytidine. In some embodiments, a nucleoside is a modified nucleoside, e.g., a substituted tautomer of a natural nucleoside selected from adenosine, deoxyadenosine, guanosine, deoxyguanosine, thymidine, uridine, cytidine, and deoxycytidine. In some embodiments, a "nucleoside" refers to a nucleoside unit in an oligonucleotide or a nucleic acid.

Nucleoside analog: The term "nucleoside analog" refers to a chemical moiety which is chemically distinct from a natural nucleoside, but which is capable of performing at least one function of a nucleoside. In some embodiments, a nucleoside analog comprises an analog of a sugar and/or an analog of a nucleobase. In some embodiments, a modified nucleoside is capable of at least one function of a nucleoside, e.g., forming a moiety in a polymer capable of base-pairing to a nucleic acid comprising a complementary sequence of bases.

Nucleotide: The term "nucleotide" as used herein refers to a monomeric unit of a polynucleotide that consists of a nucleobase, a sugar, and one or more internucleotidic linkages (e.g., phosphate linkages in natural DNA and RNA). The naturally occurring bases [guanine, (G), adenine, (A), cytosine, (C), thymine, (T), and uracil (U)] are derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleotides are linked via internucleotidic linkages to form nucleic acids, or polynucleotides. Many internucleotidic linkages are known in the art (such as, though not limited to, phosphate, phosphorothioates, boranophosphates and the like). Artificial nucleic acids include PNAs (peptide nucleic acids), phosphotriesters, phosphorothionates, H-phosphonates, phosphoramidates, boranophosphates, methylphosphonates, phosphonoacetates, thiophosphonoacetates and other variants of the phosphate backbone of native nucleic acids, such as those described herein. In some embodiments, a natural nucleotide comprises a naturally occurring base, sugar and internucleotidic linkage. As used herein, the term "nucleotide" also encompasses structural analogs used in lieu of natural or naturally-occurring nucleotides, such as modified nucleotides and nucleotide analogs. In some embodiments, a "nucleotide" refers to a nucleotide unit in an oligonucleotide or a nucleic acid.

Oligonucleotide: The term "oligonucleotide" refers to a polymer or oligomer of nucleotides, and may contain any combination of natural and non-natural nucleobases, sugars, and internucleotidic linkages.

Oligonucleotides can be single-stranded or double-stranded. A single-stranded oligonucleotide can have double-stranded regions (formed by two portions of the single-stranded oligonucleotide) and a double-stranded oligonucleotide, which comprises two oligonucleotide chains, can have single-stranded regions for example, at regions where the two oligonucleotide chains are not complementary to each other. Example oligonucleotides include, but are not limited to structural genes, genes including control and termination regions, self-replicating systems such as viral or plasmid DNA, single-stranded and double-stranded RNAi agents and other RNA interference reagents (RNAi agents or iRNA agents), shRNA, antisense oligonucleotides, ribozymes, microRNAs, microRNA mimics, supermirs, aptamers, antimirs, antagomirs, Ul adaptors, triplex-forming oligonucleotides. G-quadruplex oligonucleotides, RNA activators, immuno-stimulatory oligonucleotides, and decoy oligonucleotides.

Oligonucleotides of the present disclosure can be of various lengths. In particular embodiments, oligonucleotides can range from about 2 to about 200 nucleosides in length. In various related embodiments, oligonucleotides, single-stranded, double-stranded, or triple-stranded, can range in length from about 4 to about 10 nucleosides, from about 10 to about 50 nucleosides, from about 20 to about 50 nucleosides, from about 15 to about 30 nucleosides, from about 20 to about 30 nucleosides in length. In some embodiments, the oligonucleotide is from about 9 to about 39 nucleosides in length. In some embodiments, the oligonucleotide is at least 4, 5, 6, 7, 8, 9, 10, 11, 12, 13, 14, 15, 16, 17, 18, 19, 20, 21, 22, 23, 24, or 25 nucleosides in length. In some embodiments, the oligonucleotide is at least 4 nucleosides in length. In some embodiments, the oligonucleotide is at least 5 nucleosides in length. In some embodiments, the oligonucleotide is at least 6 nucleosides in length. In some embodiments, the oligonucleotide is at least 7 nucleosides in length. In some embodiments, the oligonucleotide is at least 8 nucleosides in length. In some embodiments, the oligonucleotide is at least 9 nucleosides in length. In some embodiments, the oligonucleotide is at least 10 nucleosides in length. In some embodiments, the oligonucleotide is at least 11 nucleosides in length. In some embodiments, the oligonucleotide is at least 12 nucleosides in length. In some embodiments, the oligonucleotide is at least 15 nucleosides in length. In some embodiments, the oligonucleotide is at least 15 nucleosides in length. In some embodiments, the oligonucleotide is at least 16 nucleosides in length. In some embodiments, the oligonucleotide is at least 17 nucleosides in length. In some embodiments, the oligonucleotide is at least 18 nucleosides in length. In some embodiments, the oligonucleotide is at least 19 nucleosides in length. In some embodiments, the oligonucleotide is at least 20 nucleosides in length. In some embodiments, the oligonucleotide is at least 25 nucleosides in length. In some embodiments, the oligonucleotide is at least 30 nucleosides in length. In some embodiments, the oligonucleotide is a duplex of complementary strands of at least 18 nucleosides in length. In some embodiments, the oligonucleotide is a duplex of complementary strands of at least 21 nucleosides in length. In some embodiments, each nucleoside counted in an oligonucleotide length independently comprises A, T, C, G, or U, or optionally substituted A, T, C, G, or U, or an optionally substituted tautomer of A, T, C, G or U.

Oligonucleotide type: As used herein, the phrase "oligonucleotide type" is used to define an oligonucleotide that has a particular base sequence, pattern of backbone linkages (i.e., pattern of internucleotidic linkage types, for example, phosphate, phosphorothioate, etc.), pattern of backbone chiral centers (i.e. pattern of linkage phosphorus stereochemistry (Rp/Sp)), and pattern of backbone phosphorus modifications (e.g., pattern of "—X-$L^s$-$R^5$" groups in formula VII). In some embodiments, oligonucleotides of a common designated "type" are structurally, including stereochemically, identical to one another.

One of skill in the art will appreciate that synthetic methods of the present disclosure provide for a degree of control during the synthesis of an oligonucleotide strand such that each nucleotide unit of the oligonucleotide strand can be designed and/or selected in advance to have a particular stereochemistry at the linkage phosphorus and/or a particular modification at the linkage phosphorus, and/or a particular base, and/or a particular sugar. In some embodiments, an oligonucleotide strand is designed and/or selected in advance to have a particular combination of stereocenters at the linkage phosphorus. In some embodiments, an oligonucleotide strand is designed and/or determined to have a particular combination of modifications at the linkage phosphorus. In some embodiments, an oligonucleotide strand is designed and/or selected to have a particular combination of bases. In some embodiments, an oligonucleotide strand is designed and/or selected to have a particular combination of one or more of the above structural characteristics. In some embodiments, the present disclosure provides compositions comprising or consisting of a plurality of oligonucleotide molecules (e.g., chirally controlled oligonucleotide compositions). In some embodiments, all such molecules are of the same type (i.e., are structurally identical to one another). In some embodiments, however, provided compositions comprise a plurality of oligonucleotides of different types, typically in pre-determined relative amounts.

Optionally Substituted: As described herein, compounds, e.g., oligonucleotides, of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. In some embodiments, an optionally substituted group is unsubstituted. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. Certain substituents are described below.

Suitable monovalent substituents on a substitutable atom, e.g., a suitable carbon atom, are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}Ph$, which may be substituted with $R^\circ$; $-(CH_2)_{0-4}O(CH_2)_{0-7}$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR^\circ$, $-SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-Si(R^\circ)_3$; $-OSi(R^\circ)_3$; $-B(R^\circ)_2$; $-OB(R^\circ)_2$; $-OB(OR^\circ)_2$; $-P(R^\circ)_2$; $-P(OR^\circ)_2$; $-P(R^\circ)(OR^\circ)$; $-OP(R^\circ)_2$; $-OP(OR^\circ)_2$; $-OP(R^\circ)(OR^\circ)$; $-P(O)(R^\circ)_2$; $-P(O)(OR^\circ)_2$; $-OP(O)(R^\circ)_2$; $-OP(O)(OR^\circ)_2$; $-OP(O)(OR^\circ)(SR^\circ)$; $-SP(O)(R^\circ)_2$; $-SP(O)(OR^\circ)_2$; $-N(R^\circ)P(O)(R^\circ)_2$; $-N(R^\circ)P(O)(OR^\circ)_2$; $-P(R^\circ)_2[B(R^\circ)_3]$; $-P(OR^\circ)_2[B(R^\circ)_3]$; $-OP(R^\circ)_2[B(R^\circ)_3]$; $-OP(OR^\circ)_2[B(R^\circ)_3]$; $-(C_{1-4}$ straight or branched alkylene)O$-N(R^\circ)_2$; or $-(C_{1-4}$ straight or branched alkylene)C(O)O$-N(R^\circ)_2$, wherein each $R^\circ$ may be substituted as defined herein and is independently hydrogen, $C_{1-20}$ aliphatic, $C_{1-20}$ (heteroaliphatic having 1-5 heteroatoms independently selected from nitrogen, oxygen, sulfur, silicon and phosphorus, $-CH_2-(C_{6-14}$ aryl), $-O(CH_2)_{0-1}$ $(C_{6-14}$ aryl), $-CH_2$-(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of $R^\circ$, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)C(O)OR$^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, and a 5-6-membered saturated, partially unsaturated, or aryl ring having 0-4 heteroatoms independently selected from nitrogen, oxygen, and sulfur. Suitable divalent substituents on a saturated carbon atom of $R^\circ$ include $=O$ and $=S$.

Suitable divalent substituents, e.g., on a suitable carbon atom, are independently the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}$ S$-$, wherein each independent occurrence of $R^*$ is selected from hydrogen, $C_{1-6}$ aliphatic which may be substituted as defined below, and an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, and an unsubstituted 5-6-membered saturated, partially unsaturated, and aryl ring having 0-4 heteroatoms independently selected from nitrogen, oxygen, and sulfur.

Suitable substituents on the aliphatic group of R are independently halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic. $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur.

In some embodiments, suitable substituents on a substitutable nitrogen are independently $-R^\dagger$, $-NR^\dagger_2$, $-C(O)$ $R^\dagger$, $-C(O)OR^\dagger$, $-C(O)C(O)R^\dagger$, $-C(O)CH_2C(O)R^\dagger$, $-S(O)_2R^\dagger$, $-S(O)_2NR_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, and sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of $R^\dagger$ are independently halogen, —$R^\bullet$, -(halo$R^\bullet$), —OH, —$OR^\bullet$, —O(halo$R^\bullet$), —CN, —C(O)OH, —C(O)$OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

Partially unsaturated: As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Pharmaceutical composition: As used herein, the term "pharmaceutical composition" refers to an active agent, formulated together with one or more pharmaceutically acceptable carriers. In some embodiments, an active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salt include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, a provided compound comprises one or more acidic groups, e.g., an oligonucleotide, and a pharmaceutically acceptable salt is an alkali, alkaline earth metal, or ammonium (e.g., an ammonium salt of $N(R)_3$, wherein each R is independently defined and described in the present disclosure) salt. Representative alkali or alkaline earth metal salts include sodium, lithium, potassium, calcium, magnesium, and the like. In some embodiments, a pharmaceutically acceptable salt is a sodium salt. In some embodiments, a pharmaceutically acceptable salt is a potassium salt. In some embodiments, a pharmaceutically acceptable salt is a calcium salt. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate. In some embodiments, a provided compound comprises more than one acid groups, for example, an oligonucleotide may comprise two or more acidic groups (e.g., in natural phosphate linkages and/or modified internucleotidic linkages). In some embodiments, a pharmaceutically acceptable salt, or generally a salt, of such a compound comprises two or more cations, which can be the same or different. In some embodiments, in a pharmaceutically acceptable salt (or generally, a salt), all ionizable hydrogen (e.g., in an aqueous solution with a pKa no more than about 11, 10, 9, 8, 7, 6, 5, 4, 3, or 2; in some embodiments, no more than about 7; in some embodiments, no more than about 6; in some embodiments, no more than about 5; in some embodiments, no more than about 4; in some embodiments, no more than about 3) in the acidic groups are replaced with cations. In some embodiments, each phosphorothioate and phosphate group independently exists in its salt form (e.g., if sodium salt, —O—P(O)(SNa)—O— and —O—P(O)(ONa)—O—, respectively). In some embodiments, each phosphorothioate and phosphate internucleotidic linkage independently exists in its salt form (e.g., if sodium salt, —O—P(O)(SNa)—O— and —O—P(O)(ONa)—O—, respectively). In some embodiments, a pharmaceutically acceptable salt is a sodium salt of an oligonucleotide. In some embodiments, a pharmaceutically acceptable salt is a sodium salt of an oligonucleotide, wherein each acidic phosphate and modified phosphate group (e.g., phosphorothioate, phosphate, etc.), if any, exists as a salt form (all sodium salt).

Predetermined: By predetermined (or pre-determined) is meant deliberately selected or non-random or controlled, for example as opposed to randomly occurring, random, or achieved without control. Those of ordinary skill in the art, reading the present specification, will appreciate that the present disclosure provides technologies that permit selection of particular chemistry and/or stereochemistry features to be incorporated into oligonucleotide compositions, and further permits controlled preparation of oligonucleotide compositions having such chemistry and/or stereochemistry features. Such provided compositions are "predetermined" as described herein. Compositions that may contain certain oligonucleotides because they happen to have been generated through a process that are not controlled to intentionally generate the particular chemistry and/or stereochemistry features are not "predetermined" compositions. In some embodiments, a predetermined composition is one that can be intentionally reproduced (e.g., through repetition of a controlled process). In some embodiments, a predetermined level of a plurality of oligonucleotides in a composition means that the absolute amount, and/or the relative amount (ratio, percentage, etc.) of the plurality of oligonucleotides in the composition is controlled. In some embodiments, a predetermined level of a plurality of oligonucleotides in a composition is achieved through chirally controlled oligonucleotide preparation.

Protecting group: The term "protecting group," as used herein, is well known in the art and includes those described in detail in Protecting Groups in Organic Synthesis, T. W. Greene and P. G. M. Wuts, 3rd edition. John Wiley & Sons, 1999, the entirety of which is incorporated herein by reference. Also included are those protecting groups specially adapted for nucleoside and nucleotide chemistry described in *Current Protocols in Nucleic Acid Chemistry*, edited by Serge L. Beaucage et al. 06/2012, the entirety of Chapter 2 is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Teroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide. N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl, groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MT-HP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy) ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4',4"-bromophenacyloxyphenyl)diphenylmethyl, 4,4',4"-tris(4,5-dichlorophthalimidophenyl) methyl, 4,4',4"-tris(levulinoyloxyphenyl)methyl, 4,4',4"-tris (benzoyloxyphenyl)methyl, 3-(imidazol-1-yl)bis(4',4'-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, I-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In some embodiments, a hydroxyl protecting group is acetyl, t-butyl, tbutoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl (MMTr), 4,4'-dimethoxytrityl, (DMTr) and 4,4',4"-trimethoxytrityl (TMTr), 2-cyanoethyl (CE or Cne), 2-(trimethylsilyl)ethyl (TSE), 2-(2-nitrophenyl)ethyl, 2-(4-cyanophenyl)ethyl 2-(4-nitrophenyl)ethyl (NPE), 2-(4-nitrophenylsulfonyl)ethyl, 3,5-dichlorophenyl, 2,4-dimethylphenyl, 2-nitrophenyl, 4-nitrophenyl, 2,4,6-trimethylphenyl, 2-(2-nitrophenyl)ethyl, butylthiocarbonyl, 4,4',4"-tris(benzoyloxy)trityl, diphenylcarbamoyl, levulinyl, 2-(dibromomethyl)benzoyl (Dbmb), 2-(isopropylthiomethoxymethyl)benzoyl (Ptmt), 9-phenylxanthen-9-yl (pixyl) or 9-(p-methoxyphenyl)xanthine-9-yl (MOX). In some embodiments, each of the hydroxyl protecting groups is, independently selected from acetyl, benzyl, t-butyldimethylsilyl, t-butyldiphenylsilyl and 4,4'-dimethoxytrityl. In some embodiments, the hydroxyl protecting group is selected from the group consisting of trityl, monomethoxytrityl and 4,4'-dimethoxytrityl group. In some embodiments, a phosphorous linkage protecting group is a group attached to the phosphorous linkage (e.g., an internucleotidic linkage) throughout oligonucleotide synthesis. In some embodiments, a protecting group is attached to a sulfur atom of an phosphorothioate group. In some embodiments, a protecting group is attached to an oxygen atom of an internucleotide phosphorothioate linkage. In some embodiments, a protecting group is attached to an oxygen atom of the internucleotide phosphate linkage. In some embodiments a protecting group is 2-cyanoethyl (CE or Cne), 2-trimethylsilylethyl, 2-nitroethyl, 2-sulfonylethyl, methyl, benzyl, o-nitrobenzyl, 2-(p-nitrophenyl)ethyl (NPE or Npe), 2-phenylethyl, 3-(N-tert-butylcarboxamido)-1-propyl, 4-oxopentyl, 4-methylthio-1-butyl, 2-cyano-1,1-dimethylethyl, 4-N-methylaminobutyl, 3-(2-pyridyl)-1-propyl, 2-[N-methyl-N-(2-pyridyl)]aminoethyl, 2-(N-formyl,N-methyl)aminoethyl, or 4-[N-methyl-N(2,2,2-trifluoroacetyl) amino]butyl.

Substantially: As used herein, the term "substantially" refers to the qualitative condition of exhibiting total or near-total extent or degree of a characteristic or property of interest. A base sequence which is substantially complementary to a second sequence is not identical to the second sequence, but is mostly or nearly identical to the second sequence. In addition, one of ordinary skill in the biological and/or chemical arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Sugar: The term "sugar" refers to a monosaccharide or polysaccharide in closed and/or open form. In some embodiments, sugars are monosaccharides. In some embodiments, sugars are polysaccharides. Sugars include, but are not limited to, ribose, deoxyribose, pentofuranose, pentopyranose, and hexopyranose moieties. As used herein, the term "sugar" also encompasses structural analogs used in lieu of conventional sugar molecules, such as glycol, polymer of which forms the backbone of the nucleic acid analog, glycol nucleic acid ("GNA"), etc. As used herein, the term "sugar" also encompasses structural analogs used in lieu of natural or naturally-occurring nucleotides, such as modified sugars and nucleotide sugars. In some embodiments, a sugar is a RNA or DNA sugar (ribose or deoxyribose). In some embodiments, a sugar is a modified ribose or deoxyribose sugar, e.g., 2'-modified, 5'-modified, etc. As described herein, in some embodiments, when used in oligonucleotides and/or nucleic acids, modified sugars may provide one or more desired properties, activities, etc. In some embodiments, a sugar is optionally substituted ribose or deoxyribose. In some embodiments, a "sugar" refers to a sugar unit in an oligonucleotide or a nucleic acid.

Susceptible to: An individual who is "susceptible to" a disease, disorder and/or condition is one who has a higher risk of developing the disease, disorder and/or condition than does a member of the general public. In some embodiments, an individual who is susceptible to a disease, disorder and/or condition is predisposed to have that disease, disorder and/or condition. In some embodiments, an individual who is susceptible to a disease, disorder and/or condition may not have been diagnosed with the disease, disorder and/or condition. In some embodiments, an individual who is susceptible to a disease, disorder and/or condition may exhibit symptoms of the disease, disorder and/or condition. In some embodiments, an individual who is susceptible to a disease, disorder and/or condition may not exhibit symptoms of the disease, disorder and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutic agent: As used herein, the term "therapeutic agent" in general refers to any agent that elicits a desired effect (e.g., a desired biological, clinical, or pharmacological effect) when administered to a subject. In some embodiments, an agent is considered to be a therapeutic agent if it demonstrates a statistically significant effect across an appropriate population. In some embodiments, an appropriate population is a population of subjects suffering from and/or susceptible to a disease, disorder or condition. In some embodiments, an appropriate population is a population of model organisms. In some embodiments, an appropriate population may be defined by one or more criterion such as age group, gender, genetic background, preexisting clinical conditions, prior exposure to therapy. In some embodiments, a therapeutic agent is a substance that alleviates, ameliorates, relieves, inhibits, prevents, delays onset of, reduces severity of, and/or reduces incidence of one or more symptoms or features of a disease, disorder, and/or condition in a subject when administered to the subject in an effective amount. In some embodiments, a "therapeutic agent" is an agent that has been or is required to be approved by a government agency before it can be marketed for administration to humans. In some embodiments, a "therapeutic agent" is an agent for which a medical prescription is required for administration to humans. In some embodiments, a therapeutic agent is a provided compound, e.g., a provided oligonucleotide.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Unsaturated: The term "unsaturated" as used herein, means that a moiety has one or more units of unsaturation.

2. Detailed Description of Certain Embodiments

Among other things, the present disclosure provides technologies for preparing oligonucleotide compositions, particularly chirally controlled oligonucleotide compositions, with unexpectedly improved crude purity and yield. In some embodiments, provided technologies can dramatically reduce costs of goods, and in some embodiments, enable large production of therapeutic oligonucleotides at commercially acceptable conditions, e.g., cost, purity, yield, etc., for clinical uses and commercialization. As appreciated by those skilled in the art, provided technologies enable production of compositions of various oligonucleotides, independent of base sequences, chemical/stereochemical modifications, modes of activities, chiral auxiliaries, etc. Example embodiments of provided technologies are described herein.

Oligonucleotides and Oligonucleotide Compositions

In some embodiments, oligonucleotide compositions of provided technologies, e.g., product oligonucleotide compositions of various steps, final oligonucleotide compositions, etc., are chirally controlled oligonucleotide composition. In some embodiments, oligonucleotides of provided technologies, e.g., product oligonucleotides of various steps, final product oligonucleotides, etc., are oligonucleotides of formula O-I or salts thereof. In some embodiments, each oligonucleotide of a plurality of oligonucleotides is independently an oligonucleotide of formula O-I or a salt thereof.

In some embodiments, an oligonucleotide is of formula O-I or a salt thereof:

O-I

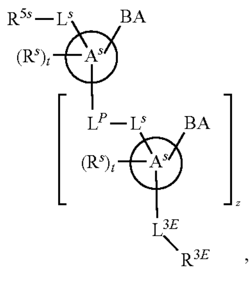

, wherein:

$R^{5s}$ is independently R' or —OR';

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_{1-6}$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each Ring $A^s$ is independently an optionally substituted 3-20 membered monocyclic, bicyclic or polycyclic ring having 0-10 heteroatoms;

each $R^s$ is independently —H, halogen, —CN, —$N_3$, —NO, —$NO_2$, -$L^s$-R', -$L^s$-Si(R')$_3$, -$L^s$-OR', -$L^s$-SR', -$L^s$-N(R')$_2$, —O-$L^s$-R', —O-$L^s$-Si(R)$_3$, —O-$L^s$-OR', —O-$L^s$-SR', or —O-$L^s$-N(R')$_2$;

each t is independently 0-20:

each BA is independently an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety:

each $L^P$ is independently an internucleotidic linkage:

z is 1-1000;

$L^{3E}$ is $-L^s-$ or $-L^s-L^s-$;

$R^{3E}$ is —R', $-L^s-R'$, —OR', or a support;

each R' is independently —R, —C(O)R, —C(O)OR, or —$S(O)_2R$;

each R is independently —H, or an optionally substituted group selected from $C_{6-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

In some embodiments, an oligonucleotide composition is a chirally controlled oligonucleotide composition.

In some embodiments, a chirally controlled oligonucleotide composition is an oligonucleotide composition comprising a plurality of oligonucleotides which share:

1) a common base sequence;
2) a common pattern of backbone linkages;
3) common stereochemistry independently at one or more, e.g., about 1-50 (e.g., about 5-50, about 10-50, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50, etc.) chiral internucleotidic linkages ("chirally controlled internucleotidic linkages");

which composition is chirally controlled in that level of the plurality of oligonucleotides in the composition is predetermined.

In some embodiments, a chirally controlled oligonucleotide composition is an oligonucleotide composition comprising a plurality of oligonucleotides, wherein oligonucleotides of the plurality are of a particular oligonucleotide type defined by:

1) base sequence:
2) pattern of backbone linkages;
3) pattern of backbone chiral centers; and
4) pattern of backbone phosphorus modifications:

which composition is chirally controlled in that level of the plurality of oligonucleotides in the composition is predetermined.

In some embodiments, a chirally controlled oligonucleotide composition is an oligonucleotide composition comprising a plurality of oligonucleotides which share:

1) a common base sequence;
2) a common pattern of backbone linkages; and
3) a common pattern of backbone chiral centers, which composition is a substantially pure preparation of a single oligonucleotide in that a predetermined level of the oligonucleotides in the composition have the common base sequence and length, the common pattern of backbone linkages, and the common pattern of backbone chiral centers.

In some embodiments, a chirally controlled oligonucleotide composition is an oligonucleotide composition comprising a plurality of oligonucleotides, wherein:

oligonucleotides of the plurality share the same base sequence;

oligonucleotides of the plurality share the same pattern of backbone linkages; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least ((DS)Nc*100)% of all oligonucleotides sharing the same base sequence in the composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

In some embodiments, a chirally controlled oligonucleotide composition is an oligonucleotide composition comprising a plurality of oligonucleotides, wherein:

oligonucleotides of the plurality share the same constitution; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage; and wherein no less than $((DS)^{Nc}*100)$% of all oligonucleotides sharing the same base sequence in the composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

In some embodiments, provided oligonucleotides comprise 1-30 non-natural internucleotidic linkages (not —O—P(O)(OH)—O— or salt forms thereof). In some embodiments, provided oligonucleotides comprise 2-30 non-natural internucleotidic linkages. In some embodiments, provided oligonucleotides comprise 5-30 non-natural internucleotidic linkages. In some embodiments, provided oligonucleotides comprise 10-30 non-natural internucleotidic linkages.

In some embodiments, provided oligonucleotides comprise 1-30 chirally controlled internucleotidic linkages. In some embodiments, provided oligonucleotides comprise 2-30 chirally controlled internucleotidic linkages. In some embodiments, provided oligonucleotides comprise 5-30 chirally controlled internucleotidic linkages. In some embodiments, provided oligonucleotides comprise 10-30 chirally controlled internucleotidic linkages. In some embodiments, provided oligonucleotides comprise 1 chirally controlled internucleotidic linkage. In some embodiments, provided oligonucleotides comprise 2 chirally controlled internucleotidic linkages. In some embodiments, provided oligonucleotides comprise 3 chirally controlled internucleotidic linkages. In some embodiments, provided oligonucleotides comprise 4 chirally controlled internucleotidic linkages. In some embodiments, provided oligonucleotides comprise 5 chirally controlled internucleotidic linkages. In some embodiments, provided oligonucleotides comprise 6 chirally controlled internucleotidic linkages. In some embodiments, provided oligonucleotides comprise 7 chirally controlled internucleotidic linkages. In some embodiments, provided oligonucleotides comprise 8 chirally controlled internucleotidic linkages. In some embodiments, provided oligonucleotides comprise 9 chirally controlled internucleotidic linkages. In some embodiments, provided oligonucleotides comprise 10 chirally controlled internucleotidic linkages. In some embodiments, provided oligonucleotides comprise 11 chirally controlled internucleotidic linkages. In some embodiments, provided oligonucleotides comprise 12 chirally controlled internucleotidic linkages. In some embodiments, provided oligonucleotides comprise 13 chirally controlled internucleotidic linkages. In some embodiments, provided oligonucleotides comprise 14 chirally controlled internucleotidic linkages. In some embodiments, provided oligonucleotides have 15 chirally controlled internucleotidic linkages. In some embodiments, provided oligonucleotides have 16 chirally controlled internucleotidic linkages. In some embodiments, provided oligonucleotides have 17 chirally controlled internucleotidic linkages. In some embodiments, provided oligonucleotides have 18 chirally controlled internucleotidic linkages. In some embodiments, provided oligonucleotides have 19 chirally controlled internucleotidic linkages. In some embodiments, provided oligonucleotides have 20 chirally controlled internucleotidic linkages. In some embodiments, about 1-100% of all internucleotidic linkages are chirally controlled internucleotidic linkages. In some embodiments, about 1-100% of all chiral internucleotidic linkages (comprising chiral linkage phosphorus) are chirally controlled internucleotidic linkages. In some embodiments, a percentage is about 5%-100%. In some embodiments, a percentage is at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments, a percentage is about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments, each chiral internucleotidic linkage is chirally controlled. In some embodiments, a portion of or all of chirally controlled internucleotidic linkages in provided oligonucleotides or one or more segments thereof (e.g., 5'-wing regions, core wings, 3'-wing regions) are consecutive. In some embodiments, all chirally controlled internucleotidic linkages in provided oligonucleotides or one or more segments thereof (e.g., 5'-wing regions, core wings, 3-wing regions) are consecutive.

In some embodiments, provided oligonucleotides comprise 1-30 natural phosphate linkages (not —O—P(O)(OH)—O— or salt forms thereof). In some embodiments, provided oligonucleotides, in addition to natural phosphate linkages, or chiral internucleotidic linkages, or chirally controlled internucleotidic linkages as described herein, further comprise 1-30 natural phosphate linkages (not —O—P(O)(OH)—O— or salt forms thereof). In some embodiments, provided oligonucleotides comprise 2-30 natural phosphate linkages. In some embodiments, provided oligonucleotides comprise 5-30 natural phosphate linkages. In some embodiments, provided oligonucleotides comprise 10-30 natural phosphate linkages. In some embodiments, provided oligonucleotides comprise 1 chirally controlled internucleotidic linkage. In some embodiments, provided oligonucleotides comprise 2 natural phosphate linkages. In some embodiments, provided oligonucleotides comprise 3 natural phosphate linkages. In some embodiments, provided oligonucleotides comprise 4 natural phosphate linkages. In some embodiments, provided oligonucleotides comprise 5 natural phosphate linkages. In some embodiments, provided oligonucleotides comprise 6 natural phosphate linkages. In some embodiments, provided oligonucleotides comprise 7 natural phosphate linkages. In some embodiments, provided oligonucleotides comprise 8 natural phosphate linkages. In some embodiments, provided oligonucleotides comprise 9 natural phosphate linkages. In some embodiments, provided oligonucleotides comprise 10 natural phosphate linkages. In some embodiments, provided oligonucleotides comprise 11 natural phosphate linkages. In some embodiments, provided oligonucleotides comprise 12 natural phosphate linkages. In some embodiments, provided oligonucleotides comprise 13 natural phosphate linkages. In some embodiments, provided oligonucleotides comprise 14 natural phosphate linkages. In some embodiments, provided oligonucleotides have 15 natural phosphate linkages. In some embodiments, provided oligonucleotides have 16 natural phosphate linkages. In some embodiments, provided oligonucleotides have 17 natural phosphate linkages. In some embodiments, provided oligonucleotides have 18 natural phosphate linkages. In some embodiments, provided oligonucleotides have 19 natural phosphate linkages. In some embodiments, provided oligonucleotides have 20 natural phosphate linkages. In some embodiments, about 1-100% of all internucleotidic linkages are natural phosphate linkages. In some embodiments, about 1-99% of all internucleotidic linkages are natural phosphate linkages, and about 1-99% of all internucleotidic linkages are non-natural internucleotidic linkages (e.g., internucleotidic linkages of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof and are non-natural internucleotidic linkages). In some embodiments, about 1-99% of all internucleotidic linkages are natural phosphate linkages, and about 1-99% of all internucleotidic linkages are chiral internucleotidic linkages (e.g., internucleotidic linkages of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof and are chiral). In some embodiments, about 1-99% of all internucleotidic linkages are natural phosphate linkages, and about 1-99% of all internucleotidic linkages are chirally controlled oligonucleotide composition internucleotidic linkages (e.g., internucleotidic linkages of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof and are chirally controlled). In some embodiments, a percentage is about 5%-100%. In some embodiments, a percentage is at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments, a percentage is about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments, each non-natural internucleotidic linkage independently has the structure of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof, wherein the structure of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof, is a non-natural internucleotidic linkage (not —O—P(O)(OH)—O— or a salt form thereof). In some embodiments, each chiral linkage independently has the structure of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof, wherein the structure of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof, is not a natural phosphate linkage (not —O—P(O)(OH)—O— or a salt form thereof). In some embodiments, each chirally controlled phosphate linkage independently has the structure of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof, wherein the structure of formula VI, VI-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or VII-e, or a salt form thereof, is not a natural phosphate linkage (not —O—P(O)(OH)—O— or a salt form thereof). In some embodiments, a portion of or all of natural phosphate linkages in provided oligonucleotides or one or more segments thereof (e.g., 5'-wing regions, core wings, 3'-wing regions) are consecutive. In some embodiments, all natural phosphate linkages in provided oligonucleotides or one or more segments thereof (e.g., 5'-wing regions, core wings, 3'-wing regions) are consecutive.

In some embodiments, a non-natural internucleotidic linkage is a phosphorothioate linkage or a salt form thereof (—O—P(O)(SH)—O— or a salt form thereof). In some embodiments, a chiral internucleotidic linkage is a phosphorothioate linkage or a salt form thereof (—O—P(O)(SH)—O— or a salt form thereof). In some embodiments, a chirally controlled internucleotidic linkage is a phosphorothioate linkage or a salt form thereof (—O—P(O)(SH)—O— or a salt form thereof).

In some embodiments, provided oligonucleotides comprise 5-200, 5-150, 5-100, 5-50, 5-40, 5-35, 5-30, 5-25, 10-200, 10-150, 10-100, 10-50, 1040, 10-35, 10-30, 10-25, 15-200, 15-150, 15-100, 15-50, 15-40, 15-35, 15-30, or 15-25 nucleobases. In some embodiments, provided oligonucleotides comprise at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 nucleobases. In some embodiments, provided oligonucleotides comprise at least 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 nucleobases. In some embodiments, provided oligonucleotides comprise at least 10, 11, 12, 13, 14, 15, 16, 17, 18, 19, 20, 21, 22, 23, 24, 25, 26, 27, 28, 29, 30, 35, 40, 45, or 50 nucleobases. In some embodiments, provided oligonucleotides comprise at least 15, 16, 17, 18, 19, 20, 21, 22, 23, 24, 25, 26, 27, 28, 29, 30, 35, 40, 45, or 50 nucleobases. In some embodiments, provided oligonucleotides comprise at least 15 nucleobases. In some embodiments, provided oligonucleotides comprise at least 16 nucleobases. In some embodiments, provided oligonucleotides comprise at least 17 nucleobases. In some embodiments, provided oligonucleotides comprise at least 18 nucleobases. In some embodiments, provided oligonucleotides comprise at least 19 nucleobases. In some embodiments, provided oligonucleotides comprise at least 20 nucleobases. In some embodiments, provided oligonucleotides comprise at least 21 nucleobases. In some embodiments, provided oligonucleotides comprise at least 22 nucleobases. In some embodiments, provided oligonucleotides comprise at least 23 nucleobases. In some embodiments, provided oligonucleotides comprise at least 24 nucleobases. In some embodiments, provided oligonucleotides comprise at least 25 nucleobases. In some embodiments, a nucleobase is optionally substituted adenine, cytosine, guanosine, thymine, or uracil, or a tautomer thereof.

In some embodiments, each chiral linkage phosphorus independently has a diastereomeric purity as described in the present disclosure. In some embodiments, a provided compound has a purity, diastereomeric purity, and/or enantiomeric purity as described in the present disclosure. In some embodiments, a provided compound has a purity as described in the present disclosure. In some embodiments, a provided compound has a diastereomeric purity as described in the present disclosure. In some embodiments, a provided compound has an enantiomeric purity as described in the present disclosure. In some embodiments, a provided compound has a diastereomeric purity and an enantiomeric purity as described in the present disclosure.

In some embodiments, provided oligonucleotides comprise or are of a 5'-wing region-core region-3'-wing region structure. In some embodiments, provided oligonucleotides comprise or are of a 5'-wing region-core region structure. In some embodiments, provided oligonucleotides comprise or are of a core region-3'-wing region structure. In some embodiments, provided oligonucleotides comprise of a 5'-wing region-core region-3'-wing region structure. In some embodiments, provided oligonucleotides comprise of a 5'-wing region-core region structure. In some embodiments, provided oligonucleotides comprise of a core region-3'-wing region structure. In some embodiments, provided oligonucleotides are of a 5'-wing region-core region-3'-wing region structure. In some embodiments, provided oligonucleotides are of a 5'-wing region-core region structure. In some embodiments, provided oligonucleotides are of a core region-3'-wing region structure. In some embodiments, a wing-core-wing (i.e., X-Y-X) motif is represented numerically as, e.g., 5-10-4, meaning 5'-wing region is 5 bases in length, the core region is 10 bases in length, and the 3'-wing region is 4-bases in length. In some embodiments, a wing-core-wing motif is any of, e.g. 2-16-2, 3-14-3, 4-124, 5-10-5, 2-9-6, 3-9-3, 3-94, 3-9-5, 4-7-4, 4-9-3, 4-94, 4-9-5, 4-10-5, 4-11-4, 4-11-5, 5-7-5, 5-8-6, 8-7-5, 7-7-6, 5-9-3, 5-9-5, 5-10-4, 5-10-5, 6-7-6, 6-8-5, and 6-9-2, etc. In certain embodiments, a wing-core-wing motif is 5-10-5. In certain embodiments, a wing-core-wing motif is 7-7-6. In certain embodiments, a wing-core-wing motif is 8-7-5. In some embodiments, a wing-core motif is 5-15, 6-14, 7-13, 8-12, 9-12, etc. In some embodiments, a core-wing motif is 5-15, 6-14, 7-13, 8-12, 9-12, etc.

In some embodiments, a wing region comprises a sugar modification absent from a core region. In some embodiments, a wing region comprises a 2'-modification. In some embodiments, each nucleotide unit of a wing region independently comprises a 2'-modification. In some embodiments, each nucleotide unit of a wing region independently comprises the same 2'-modification. In some embodiments, each nucleotide unit of a 5'-wing region independently comprises the same 2'-modification. In some embodiments, each nucleotide unit of a 3'-wing region independently comprises the same 2'-modification. In some embodiments, 2'-modifications of the 5'-wing region are the same. In some embodiments, 2'-modifications of the 5-wing region are the different. In some embodiments, a 2'-modification is 2'-OR, wherein R' is not hydrogen. In some embodiments, a 2'-modification is 2'-OR, wherein R' is optionally substituted $C_{1-6}$ aliphatic. In some embodiments, a 2'-modification is 2'-OR, wherein R' is optionally substituted $C_{1-6}$ alkyl. In some embodiments, a 2'-modification is 2'-OMe. In some embodiments, a 2'-modification is 2'-$OCH_2CH_2OMe$. In some embodiments, a wing region comprises one or more natural phosphate linkages as described in the present disclosure. Additionally or alternatively, in some embodiments, a wing region comprises one or more non-natural internucleotidic linkages, e.g., phosphorothioate internucleotidic linkages. In some embodiments, a core region comprises one or more natural phosphate linkages. In some embodiments, a core region comprises one or more consecutive natural phosphate linkages. In some embodiments, a core region comprises one or more chiral phosphate linkages. In some embodiments, a core region comprises one or more consecutive chiral phosphate linkages. In some embodiments, a chiral phosphate linkage is a phosphorothioate linkage. In some embodiments, a chiral phosphate linkage is a chirally controlled.

Oligonucleotides of the present disclosure may contain a pattern of backbone chiral centers. In some embodiments, a pattern of backbone chiral centers of oligonucleotides or segments thereof, e.g., core regions, provides increased stability. In some embodiments, a pattern of backbone chiral centers provides surprisingly increased activity. In some embodiments, a pattern of backbone chiral centers provides increased stability and activity. In some embodiments, a pattern of backbone chiral centers provides surprisingly increased binding to certain proteins. In some embodiments, a pattern of backbone chiral centers provides surprisingly enhanced delivery. In some embodiments, a pattern of backbone chiral centers comprises or is (Sp)m(Rp)n, (Rp)n(Sp)m, (Np)p(Rp)n(Sp)m, (Sp)p(Rp)n(Sp)m, (Sp)m(Op)n, (Op)n(Sp)m, (Np)p(Op)n(Sp)m, or (Sp)p(Op)n(Sp)m (unless otherwise specified, from 5' to 3'), wherein n is 1-10, and each of p and m is independently 0-50. In some embodiments, a pattern of backbone chiral centers comprises or is (Sp)m(Rp)n, (Rp)n(Sp)m, (Np)p(Rp)n(Sp)m, (Sp)p(Rp)n(Sp)m, (Sp)m(Op)n, (Op)n(Sp)m, (Np)p(Op)n(Sp)m, or (Sp)p(Op)n(Sp)m (unless otherwise specified, from 5' to 3'), wherein n is 1-10, and each of p and m is independently 1-50. In some embodiments, a pattern of backbone chiral centers comprises or is (Sp)m(Rp)n, (Rp)n(Sp)m, (Np)p(Rp)n(Sp)m, or (Sp)p(Rp)n(Sp)m (unless otherwise specified, from 5' to 3'), wherein n is 1-10, and each of p and m is independently 1-50. In some embodiments, a pattern of backbone chiral centers comprises (Sp)m(Rp)n, (Rp)n(Sp)m, (Np)p(Rp)n(Sp)m, or (Sp)p(Rp)n(Sp)m. In some embodiments, a pattern of backbone chiral centers comprises (Sp)m(Op)n, (Op)n(Sp)m, (Np)p(Op)n(Sp)m, or (Sp)p(Op)n(Sp)m. In some embodiments, a pattern of backbone chiral centers is (Sp)m(Rp)n, (Rp)n(Sp)m, (Np)p(Rp)n(Sp)m, or (Sp)p(Rp)n(Sp)m. In some embodiments, a pattern of backbone chiral centers is (Sp)m(Op)n, (Op)n(Sp)m, (Np)p(Op)n(Sp)m, or (Sp)p(Op)n(Sp)m. In some embodiments, a pattern of backbone chiral centers comprises or is a repeating pattern comprising or being of (Sp)m(Rp)n, (Rp)n(Sp)m, (Np)p(Rp)n(Sp)m, or (Sp)p(Rp)n(Sp)m. In some embodiments, a pattern of backbone chiral centers comprises or is a repeating pattern of (Sp)m(Rp)n, (Rp)n(Sp)m, (Np)p(Rp)n(Sp)m, or (Sp)p(Rp)n(Sp)m (from 5' to 3'). In some embodiments, a pattern of backbone chiral centers comprises or is a repeating pattern comprising or being of (Sp)m(Op)n, (Op)n(Sp)m, (Np)p(Op)n(Sp)m, or (Sp)p(Op)n(Sp)m. In some embodiments, a pattern of backbone chiral centers comprises or is a repeating pattern of (Sp)m(Op)n, (Op)n(Sp)m, (Np)p(Op)n(Sp)m, or (Sp)p(Op)n(Sp)m (from 5' to 3').

In some embodiments, a pattern of backbone chiral centers comprises or is (Rp)n(Sp)m, (Np)p(Rp)n(Sp)m, or (Sp)p(Rp)n(Sp)m, wherein m>2. In some embodiments, a pattern of backbone chiral centers comprises or is (Rp)n(Sp)m, (Np)p(Rp)n(Sp)m, or (Sp)p(Rp)n(Sp)m, wherein n is 1, p>1, and m>2. In some embodiments, m>3. In some embodiments, m>4. In some embodiments, a pattern of backbone chiral centers comprises or is (Op)n(Sp)m, (Np)p(Op)n(Sp)m, or (Sp)p(Op)n(Sp)m, wherein m>2. In some embodiments, a pattern of backbone chiral centers comprises or is (Op)n(Sp)m, (Np)p(Op)n(Sp)m, or (Sp)p(Op)n(Sp)m, wherein n is 1, p>1, and m>2. In some embodiments, m>3. In some embodiments, m>4. In some embodiments, a pattern of backbone chiral centers of an oligonucleotide or a region thereof comprises or is two or more units independently selected from (Rp)n(Sp)m. (Np)p(Rp)n(Sp)m, (Sp)p(Rp)n(Sp)m, (Op)n(Sp)m, (Np)p(Op)n(Sp)m, and (Sp)p(Op)n(Sp)m, wherein each variable is independently as described in the present disclosure. In some embodiments, n is 1. In some embodiments, n is 1 and m of each unit is independently 2 or greater as described in the present disclosure. In some embodiments, at least two m of two units are different. In some embodiments, a pattern of backbone chiral centers comprises 2, 3, 4, 5, 6, 7, 8, 9, or 10 such units. In some embodiments, a pattern of backbone chiral centers comprises 2 and no more than 2 such units. In some embodiments, a pattern of backbone chiral centers comprises 3 and no more than 3 such units. In some embodiments, a pattern of backbone chiral centers comprises 4 and no more than 4 such units. In some embodiments, a pattern of backbone chiral centers comprises 5 and no more than 5 such units. In some embodiments, a region of an oligonucleotide comprises such a pattern of backbone chiral centers. In some embodiments, such a region comprises no 2'-substitution at its sugar moieties (two 2'-H). In some embodiments, such a region is flanked by a 5'-region comprising a sugar modification as described in the present disclosure (e.g., a 2'-modification, e.g., 2'-OMe, 2'-MOE, 2'-F, etc., as described in the present disclosure), and/or a 5'-region comprising a sugar modification as described in the present disclosure (e.g., a 2'-modification, e.g., 2'-OMe, 2'-MOE, 2'-F, etc., as described in the present disclosure).

In some embodiments, a pattern of backbone chiral centers comprises or is (Rp)n(Sp)m, (Sp)p(Rp)n, (Np)p(Rp)n(Sp)m, (Sp)p(Sp)m or (Sp)p(Rp)n(Sp)m. In some embodiments, a pattern of backbone chiral centers comprises or is (Rp)n(Sp)m, (Sp)p(Rp)n, (Np)p(Rp)n(Sp)m, or (Sp)p(Rp)n(Sp)m, and the oligonucleotides comprise one or more 2'-modifications as described herein. In some embodiments, a pattern of backbone chiral centers comprises or is (Rp)n(Sp)m, (Sp)p(Rp)n, (Np)p(Rp)n(Sp)m, or (Sp)p(Rp)n(Sp)m, and the oligonucleotides comprise one or more 2'-F modifications as described herein. In some embodiments, a pattern of backbone chiral centers comprises or is (Rp)n(Sp)m, (Sp)p(Rp)n, (Np)p(Rp)n(Sp)m, or (Sp)p(Rp)n(Sp)m, and the oligonucleotides comprise one or more 2'-OR modifications as described herein. In some embodiments, a pattern of backbone chiral centers comprises or is (Rp)n(Sp)m, (Sp)p(Rp)n, (Np)p(Rp)n(Sp)m, or (Sp)p(Rp)n(Sp)m, and the oligonucleotides comprise one or more 2'-OR modifications, wherein R is not —H. In some embodiments, a pattern of backbone chiral centers comprises or is (Rp)n(Sp)m, (Sp)p(Rp)n, (Np)p(Rp)n(Sp)m, or (Sp)p(Rp)n(Sp)m, and each nucleoside unit between internucleotidic linkages having the pattern of (Rp)n(Sp)m, (Sp)p(Rp)n, (Np)p(Rp)n(Sp)m, or (Sp)p(Rp)n(Sp)m comprises no 2'-modifications. In some embodiments, a pattern of backbone chiral centers comprises or is (Rp)n(Sp)m, (Sp)p(Rp)n. (Np)p(Rp)n(Sp)m, or (Sp)p(Rp)n(Sp)m, and each nucleoside unit between internucleotidic linkages having the pattern of (Rp)n(Sp)m, (Sp)p(Rp)n, (Np)p(Rp)n(Sp)m, or (Sp)p(Rp)n(Sp)m comprises no 2'-substitutions (—$CH_2$— at 2'-position). In some embodiments, a pattern of backbone chiral centers comprises or is (Rp)n(Sp)m. In some embodiments, a pattern of backbone chiral centers comprises or is (Sp)p(Rp)n. In some embodiments, a pattern of backbone chiral centers comprises or is (Np)p(Rp)n(Sp)m. In some embodiments, a pattern of backbone chiral centers comprises (Rp)n(Sp)m. In some embodiments, a pattern of backbone chiral centers comprises (Sp)p(Rp)n. In some embodiments, a pattern of backbone chiral centers comprises (Np)p(Rp)n(Sp)m. In some embodiments, a pattern of backbone chiral centers is (Rp)n(Sp)m. In some embodiments, a pattern of backbone chiral centers is (Sp)p(Rp)n. In some embodiments, a pattern of backbone chiral centers is (Np)p(Rp)n(Sp)m. In some embodiments, a pattern of backbone chiral centers comprises or is (Sp)p(Sp)m, optionally with n achiral phosphate diester internucleotidic linkages and/or stereorandom (non-chirally controlled) chiral internucleotidic linkages between the section having (Sp)p and the section having (Sp)m. In some embodiments, there are n achiral phosphate diester internucleotidic linkages in between. In some embodiments, there are n stereorandom chiral internucleotidic linkages in between. In some embodiments, a pattern of backbone chiral centers comprises or is (Sp)p(Rp)n(Sp)m.

In some embodiments, a pattern of backbone chiral centers comprises or is (Op)n(Sp)m, (Sp)p(Op)n, (Np)p(Op)n(Sp)m, (Sp)p(Sp)m or (Sp)p(Op)n(Sp)m. In some embodiments, a pattern of backbone chiral centers comprises or is (Op)n(Sp)m, (Sp)p(Op)n. (Np)p(Op)n(Sp)m, or (Sp)p(Op)n(Sp)m, and the oligonucleotides comprise one or more 2'-modifications as described herein. In some embodiments, a pattern of backbone chiral centers comprises or is (Op)n(Sp)m, (Sp)p(Op)n, (Np)p(Op)n(Sp)m, or (Sp)p(Op)n(Sp)m, and the oligonucleotides comprise one or more 2'-F modifications as described herein. In some embodiments, a pattern of backbone chiral centers comprises or is (Op)n(Sp)m, (Sp)p(Op)n, (Np)p(Op)n(Sp)m, or (Sp)p(Op)n(Sp)m, and the oligonucleotides comprise one or more 2'-OR modifications as described herein. In some embodiments, a pattern of backbone chiral centers comprises or is (Op)n(Sp)m, (Sp)p(Op)n, (Np)p(Op)n(Sp)m, or (Sp)p(Op)n(Sp)m, and the oligonucleotides comprise one or more 2'-OR modifications, wherein R is not —H. In some embodiments, a pattern of backbone chiral centers comprises or is (Op)n(Sp)m, (Sp)p(Op)n, (Np)p(Op)n(Sp)m, or (Sp)p(Op)n(Sp)m, and each nucleoside unit between internucleotidic linkages having the pattern of (Op)n(Sp)m, (Sp)p(Op)n, (Np)p(Op)n(Sp)m, or (Sp)p(Op)n(Sp)m comprises no 2'-modifications. In some embodiments, a pattern of backbone chiral centers comprises or is (Op)n(Sp)m, (Sp)p(Op)n, (Np)p(Op)n(Sp)m, or (Sp)p(Op)n(Sp)m, and each nucleoside unit between internucleotidic linkages having the pattern of (Op)n(Sp)m, (Sp)p(Op)n, (Np)p(Op)n(Sp)m, or (Sp)p(Op)n(Sp)m comprises no 2'-substitutions ($—CH_2—$ at 2'-position). In some embodiments, a pattern of backbone chiral centers comprises or is (Op)n(Sp)m. In some embodiments, a pattern of backbone chiral centers comprises or is (Sp)p(Op)n. In some embodiments, a pattern of backbone chiral centers comprises or is (Np)p(Op)n(Sp)m. In some embodiments, a pattern of backbone chiral centers comprises (Op)n(Sp)m. In some embodiments, a pattern of backbone chiral centers comprises (Sp)p(Op)n. In some embodiments, a pattern of backbone chiral centers comprises (Np)p(O)p)n(Sp)m. In some embodiments, a pattern of backbone chiral centers is (Op)n(Sp)m. In some embodiments, a pattern of backbone chiral centers is (Sp)p(Op)n. In some embodiments, a pattern of backbone chiral centers is (Np)p(Op)n(Sp)m. In some embodiments, a pattern of backbone chiral centers comprises or is (Sp)p(Sp)m, optionally with n achiral phosphate diester internucleotidic linkages and/or stereorandom (non-chirally controlled) chiral internucleotidic linkages between the section having (Sp)p and the section having (Sp)m. In some embodiments, there are n achiral phosphate diester internucleotidic linkages in between. In some embodiments, there are n stereorandom chiral internucleotidic linkages in between. In some embodiments, a pattern of backbone chiral centers comprises or is (Sp)p(Op)n(Sp)m.

In some embodiments, an oligonucleotide, or a region thereof, comprises a pattern, or a repeating pattern, of backbone chiral centers of (Sp)m(Rp)n, (Rp)n(Sp)m, (Np)p(Rp)n(Sp)m, or (Sp)p(Rp)n(Sp)m (structurally starting from the first, and ending at the last, internucleotidic linkage of the internucleotidic linkages which have the pattern, or the repeating pattern, of (Sp)m(Rp)n, (Rp)n(Sp)m, (Np)p(Rp)n(Sp)m, or (Sp)p(Rp)n(Sp)m, respectively; a "(repeating) (Sp)m(Rp)n region", a "(repeating) (Rp)n(Sp)m region", a "(repeating) (Np)p(Rp)n(Sp)m region", or a "(repeating) (Sp)p(Rp)n(Sp)m region", respectively, depending on repeating or not). In some embodiments, an oligonucleotide, or a region thereof, comprises a pattern, or a repeating pattern, of backbone chiral centers of (Sp)m(Op)n, (Op)n(Sp)m, (Np)p(Op)n(Sp)m, or (Sp)p(Op)n(Sp)m (structurally starting from the first, and ending at the last, internucleotidic linkage of the internucleotidic linkages which have the pattern, or the repeating pattern, of (Sp)m(Op)n, (Op)n(Sp)m, (Np)p(Op)n(Sp)m, or (Sp)p(Op)n(Sp)m, respectively; a "(repeating) (Sp)m(Op)n region", a "(repeating) (Op)n(Sp)m region", a "(repeating) (Np)p(Op)n(Sp)m region", or a "(repeating) (Sp)p(Op)n(Sp)m region", respectively, depending on repeating or not). For example, a (Sp)p(Rp)n(Sp)m region ((Sp)7(Rp)1(Sp)3) in WV-2555: mA*SmGmCmUmU*SC*ST*ST*SG*ST*SC*SC*RA*SG*SC*SmUmUmUmA*SmU)(SEQ ID NO: 196) comprises no 2'-OR sugar modifications. In some embodiments, each sugar moieties in the region is $—CH_2—$ at the 2'-position. In some embodiments, each sugar moieties in the region is an unmodified, natural, 2'-deoxyribose moiety of DNA. In some embodiments, a region comprising a pattern, or a repeating pattern, of backbone chiral centers which comprises or is (Sp)m(Rp)n, (Rp)n(Sp)m, (Np)p(Rp)n(Sp)m, or (Sp)p(Rp)n(Sp)m is flanked by a 5'-wing region, which structurally ends with a nucleoside moiety (which nucleoside moiety, at its 3'-end, is connected to the first internucleotidic linkage of the region comprising a pattern, or a repeating pattern, of backbone chiral centers which comprises or is (Sp)m(Rp)n, (Rp)n(Sp)m, (Np)p(Rp)n(Sp)m, or (Sp)p(Rp)n(Sp)m). For example, a flanking 5'-wing region in WV-2555: mA*SmGmCmUmU*SC*ST*ST*SG*ST*SC*SC*RA*SG*SC*SmUmUmUmA*SmU) (SEQ ID NO: 196). In some embodiments, a region comprising a pattern, or a repeating pattern, of backbone chiral centers which comprises or is (Sp)m(Op)n, (Op)n(Sp)m, (Np)p(Op)n(Sp)m, or (Sp)p(Op)n(Sp)m is flanked by a 5'-wing region, which structurally ends with a nucleoside moiety (which nucleoside moiety, at its 3'-end, is connected to the first internucleotidic linkage of the region comprising a pattern, or a repeating pattern, of backbone chiral centers which comprises or is (Sp)m(Op)n, (Op)n(Sp)m, (Np)p(Op)n(Sp)m, or (Sp)p(Op)n(Sp)m). In some embodiments, a region comprising a pattern, or a repeating pattern, of backbone chiral centers which comprises or is (Sp)m(Rp)n, (Rp)n(Sp)m, (Np)p(Rp)n(Sp)m, or (Sp)p(Rp)n(Sp)m is flanked by a 3'-wing region, which structurally starts with a nucleoside moiety (which nucleoside moiety, at its 5'-end, is connected to the last internucleotidic linkage of the region comprising a pattern, or a repeating pattern, of backbone chiral centers which comprises or is (Sp)m(Rp)n, (Rp)n(Sp)m, (Np)p(Rp)n(Sp)m, or (Sp)p(Rp)n(Sp)m). For example, a flanking 3'-wing region in WV-2555: mA*SmGmCmUmU*SC*ST*ST*SG*ST*SC*SC*RA*SG*SC*SmUmUmUmA*SmU)(SEQ ID NO: 196). In some embodiments, a region comprising a pattern, or a repeating pattern, of backbone chiral centers which comprises or is (Sp)m(Op)n, (Op)n(Sp)m, (Np)p(Op)n(Sp)m, or (Sp)p(Op)n(Sp)m is flanked by a 3'-wing region, which structurally starts with a nucleoside moiety (which nucleoside moiety, at its 5'-end, is connected to the last internucleotidic linkage of the region comprising a pattern, or a repeating pattern, of backbone chiral centers which comprises or is (Sp)m(Op)n, (Op)n(Sp)m, (Np)p(Op)n(Sp)m, or (Sp)p(Op)n(Sp)m). In some embodiments, a region comprising a pattern, or a repeating pattern, of backbone chiral centers which comprises or is (Sp)m(Rp)n, (Rp)n(Sp)m, (Np)p(Rp)n(Sp)m, or (Sp)p(Rp)n(Sp)m is flanked by a 5'-end and a 3'-wing regions. In some embodiments, a region comprising a pattern, or a repeating pattern, of backbone chiral centers which comprises or is (Sp)m(Op)n, (Op)n(Sp)m, (Np)p(Op)n(Sb)m, or (Sp)p(Op)n(Sp)m is flanked by a 5'-end and a 3'-wing regions. In some embodiments, the flanking 5'-wing region and/or the 3'-wing region comprise a non-natural internucleotidic linkage. In some embodiments, the flanking 5'-wing region and/or the 3'-wing region comprise a chiral internucleotidic linkage. In some embodiments, the flanking 5'-wing region and/or the 3'-wing region comprise a chirally controlled internucleotidic linkage. In some embodiments, the flanking 5'-wing region and/or the 3'-wing region comprise a modified internucleotidic linkage comprising a Sp linkage phosphorus. In some embodiments, the flanking 5'-wing region and/or the 3'-wing region comprise a Sp phosphorothioate linkage. In some embodiments, the flanking 5'-wing region and/or the 3'-wing region comprise one or more natural phosphate linkages. In some embodiments, the flanking 5'-wing region and/or the 3'-wing region comprise one or more consecutive natural phosphate linkages. In some embodiments, the flanking 5'-end comprises only one modified internucleotidic linkage which is the 5'-end internucleotidic linkage, and one or more consecutive natural phosphate linkages (for example, in WV-2555: mA*SmGmCmUmU*SC*ST*ST*SG*ST*SC*SC*RA*SG*SC*SmUmUmUmA*SmU (SEQ ID NO: 196) (SOOOSSSSSSSRSSSOOOS)). In some embodiments, the flanking 3'-end comprises only one modified internucleotidic linkage which is the 3'-end internucleotidic linkage, and one or more consecutive natural phosphate linkages (for example, in WV-2555: mA*SmGmCmUmU*SC*ST*ST*SG*ST*SC*SC*RA*SG*SC*SmUmUmUmA*SmU (SEQ ID NO: 196) (SOOOSSSSSSSRSSSOOOS)). In some embodiments, the flanking 5'-wing region and/or the 3'-wing region comprise 2'-modified sugar units. In some embodiments, each sugar unit in the 5'-wing region and/or the 3'-wing region is independently modified. In some embodiments, each sugar unit in the 5'-wing region and/or the 3'-wing region independently comprises a 2'-modification (for example, m, 2'-OMe in WV-2555: mA*SmGmCmUmU*SC*ST*ST*SG*ST*SC*SC*RA*SG*SC*SmUmUmUmA*SmU) (SEQ ID NO: 196). In some embodiments, each sugar unit in the 5'-wing region and/or the 3'-wing region comprises the same 2'-modification. In some embodiments, a 2-modification is 2'-OR, wherein R is optionally substituted $C_1$a aliphatic. In some embodiments, a 2'-modification is 2'-OMe. In some embodiments, a 2'-modification is 2'-MOE. In some embodiments, a 2'-modification is a LNA modification (which comprises a type of C2-C4 bridge).

In some embodiments, oligonucleotides comprise 2'-F modified sugars and comprise one or more wing and one or more core (e.g., wing-core-wing, core-wing, wing-core, etc.). In some embodiments, a wing, e.g., a 5'-wing, a 3'-wing, etc., comprises one or more 2'-F modified sugar. In some embodiments, most sugars in a wing comprises a 2'-F modification. In some embodiments, each sugar in a wing comprises a 2'-F modification. In some embodiments, an internucleotidic linkages bonded to two 2'-F modified sugars is a chiral modified internucleotidic linkage. In some embodiments, each internucleotidic linkages bonded to two 2'-F modified sugars is independently a chiral modified internucleotidic linkage. In some embodiments, each chiral modified internucleotidic linkage is independently a phosphorothioate internucleotidic linkage or a non-negatively charged internucleotidic linkage. In some embodiments, each chiral modified internucleotidic linkage is independently a phosphorothioate internucleotidic linkage or a neutral internucleotidic linkage. In some embodiments, a chiral modified internucleotidic linkage is a phosphorothioate internucleotidic linkage. In some embodiments, each chiral modified internucleotidic linkage is a phosphorothioate internucleotidic linkage. In some embodiments, a chiral modified internucleotidic linkage is chirally controlled. In some embodiments, a chiral modified internucleotidic linkage is chirally controlled and is Sp at the linkage phosphorus. In some embodiments, a chiral modified internucleotidic linkage is a chirally controlled phosphorothioate internucleotidic linkage and is Sp at the linkage phosphorus. In some embodiments, a chiral modified internucleotidic linkage is a non-negatively charged internucleotidic linkage and is Rp at the linkage phosphorus. In some embodiments, each chirally controlled phosphorothioate internucleotidic linkage is Sp. In some embodiments, each chirally controlled phosphorothioate internucleotidic linkage bonded to two 2'-F modified sugars is Sp. In some embodiments, each internucleotidic linkages bonded to two 2'-F modified sugars is independently a chirally controlled phosphorothioate internucleotidic linkage and is Sp.

In some embodiments, a core comprises one or more 2'-F modified sugars and one or more 2'-OR modified sugars, wherein R is as described herein. In some embodiments, R is optionally substituted $C_{1-4}$ alkyl. In some embodiments, R is —OMe. In some embodiments, a core comprises alternating 2'-F modified sugars and 2'-OR modified sugars. In some embodiments, one or more 2'-OR modified sugars are consecutive. In some embodiments, the percentage of 2'-F modified sugar(s) in a core is lower that that for a wing or each wing. In some embodiments, a core comprises one or more natural phosphate linkages. In some embodiments, an internucleotidic linkage bonded to two 2'-OR modified sugars is a natural phosphate linkage. In some embodiments, each internucleotidic linkage bonded to two 2'-OR modified sugars is a natural phosphate linkage. In some embodiments, an internucleotidic linkage bonded to a 2'-F modified sugar and a 2'-OR modified sugar is a natural phosphate linkage. In some embodiments, an internucleotidic linkage bonded to a 2'-OR modified sugar at its 3'-position. In some embodiments, each natural phosphate linkage independently bonds to a 2'-OR modified sugar at its 3'-position. In some embodiments, an internucleotidic linkage bonded to a 2'-F modified sugar and a 2'-OR modified sugar is a modified internucleotidic linkage (e.g., a phosphorothioate internucleotidic linkage), which is optionally chirally controlled (and which is optionally Sp at its linkage phosphorus). In some embodiments, each modified internucleotidic linkage is independently a phosphorothioate internucleotidic linkage. In some embodiments, each modified internucleotidic linkage is chirally controlled. In some embodiments, each modified internucleotidic linkage is chirally controlled Sp phosphorothioate internucleotidic linkage. In some embodiments, each internucleotidic linkage in a core is independently a natural phosphate linkage or a phosphorothioate internucleotidic linkage. In some embodiments, each internucleotidic linkage in a core is independently a natural phosphate linkage or a chirally controlled phosphorothioate internucleotidic linkage. In some embodiments, each internucleotidic linkage in a core is independently a natural phosphate linkage or a chirally controlled Sp internucleotidic linkage. In some embodiments, each internucleotidic linkage in a core is independently a natural phosphate linkage or a chirally controlled Sp phosphorothioate internucleotidic linkage.

Example oligonucleotides comprising wing and core regions described herein include WV-1714, WV-2444, WV-2445, WV-2526, WV-2527, WV-2528, WV-2530, WV-2531, WV-2578, WV-2580, WV-2587, WV-3047, WV-3152, WV-3472, WV-3473, WV-3507, WV-3508, WV-3509, WV-3510, WV-3511, WV-3512, WV-3513, WV-3514, WV-3515, WV-3545, WV-3546, WV-9517, WV-12555, WV-12556, WV-12558, WV-12876, WV-12877, WV-12878, WV-12880, WV-13826, WV-13835, WV-13864, or WV-14344.

In some embodiments, n is 1-10. In some embodiments, n is 1, 2, 3, 4, 5, 6, 7 or 8. In some embodiments, n is 1. In some embodiments, n is 2, 3, 4, 5, 6, 7 or 8. In some embodiments, n is 3, 4, 5, 6, 7 or 8. In some embodiments, n is 4, 5, 6, 7 or 8. In some embodiments, n is 5, 6, 7 or 8. In some embodiments, n is 6, 7 or 8. In some embodiments, n is 7 or 8. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In some embodiments, n is 1. In some embodiments, m is at least 2, 3, 4, 5, 6, 7, 8, 9, 10, 11, 12, 13, 14, or 15. In some embodiments, m is 2, 3, 4, 5, 6, 7, 8, 9, 10, 11, 12, 13, 14, or 15. In some embodiments, p is at least 2, 3, 4, 5, 6, 7, 8, 9, 10, 11, 12, 13, 14, or 15. In some embodiments, m is at least 2. In some embodiments, p is at least 2. In some embodiments, n is 1. In some embodiments, m is at least 2, p is at least 2, n is 1. In some embodiments, p is 2, 3, 4, 5, 6, 7, 8, 9, 10, 11, 12, 13, 14, or 15. In some embodiments, each of m and p is independently at least 2, 3, 4, 5, 6, 7, 8, 9, 10, 11, 12, 13, 14, or 15. In some embodiments, each of m and p is independently 2, 3, 4, 5, 6, 7, 8, 9, 10, 11, 12, 13, 14, or 15. In some embodiments, at least one of m and p is at least 5, 6, 7, 8, 9, 10, 11, 12, 13, 14, or 15. In some embodiments, m is at least 5, 6, 7, 8, 9, 10, 11, 12, 13, 14, or 15. In some embodiments, p is at least 5, 6, 7, 8, 9, 10, 11, 12, 13, 14, or 15.

In some embodiments, p is 0-50. In some embodiments, p is 1-50. In some embodiments, p is 1. In some embodiments, p is 2-50. In some embodiments, p is 2, 3, 4, 5, 6, 7 or 8. In some embodiments, p is 3, 4, 5, 6, 7 or 8. In some embodiments, p is 4, 5, 6, 7 or 8. In some embodiments, p is 5, 6, 7 or 8. In some embodiments, p is 6, 7 or 8. In some embodiments, p is 7 or 8. In some embodiments, p is 2. In some embodiments, p is 3. In some embodiments, p is 4. In some embodiments, p is 5. In some embodiments, p is 6. In some embodiments, p is 7. In some embodiments, p is 8. In some embodiments, p is 9. In some embodiments, p is 10. In some embodiments, p is 11. In some embodiments, p is 12. In some embodiments, p is 13. In some embodiments, p is 14. In some embodiments, p is 15. In some embodiments, p is 16. In some embodiments, p is 17. In some embodiments, p is 18. In some embodiments, p is 19. In some embodiments, p is 20. In some embodiments, p is 21. In some embodiments, p is 22. In some embodiments, p is 23. In some embodiments, p is 24. In some embodiments, p is 25. In some embodiments, p is at least 2. In some embodiments, p is at least 3. In some embodiments, p is at least 4. In some embodiments, p is at least 5. In some embodiments, p is at least 6. In some embodiments, p is at least 7. In some embodiments, p is at least 8. In some embodiments, p is at least 9. In some embodiments, p is at least 10. In some embodiments, p is at least 11. In some embodiments, p is at least 12. In some embodiments, p is at least 13. In some embodiments, p is at least 14. In some embodiments, p is at least 15. In some embodiments, p is at least 16. In some embodiments, p is at least 17. In some embodiments, p is at least 18. In some embodiments, p is at least 19. In some embodiments, p is at least 20. In some embodiments, p is at least 21. In some embodiments, p is at least 22. In some embodiments, p is at least 23. In some embodiments, p is at least 24. In some embodiments, p is at least 25.

In some embodiments, m is 0-50. In some embodiments, m is 1-50. In some embodiments, m is 1. In some embodiments, m is 2-50. In some embodiments, m is 2, 3, 4, 5, 6, 7 or 8. In some embodiments, m is 3, 4, 5, 6, 7 or 8. In some embodiments, m is 4, 5, 6, 7 or 8. In some embodiments, m is 5, 6, 7 or 8. In some embodiments, m is 6, 7 or 8. In some embodiments, m is 7 or 8. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16. In some embodiments, m is 17. In some embodiments, m is 18. In some embodiments, m is 19. In some embodiments, m is 20. In some embodiments, m is 21. In some embodiments, m is 22. In some embodiments, m is 23. In some embodiments, m is 24. In some embodiments, m is 25. In some embodiments, m is at least 2. In some embodiments, m is at least 3. In some embodiments, m is at least 4. In some embodiments, m is at least 5. In some embodiments, m is at least 6. In some embodiments, m is at least 7. In some embodiments, m is at least 8. In some embodiments, m is at least 9. In some embodiments, m is at least 10. In some embodiments, m is at least 11. In some embodiments, m is at least 12. In some embodiments, m is at least 13. In some embodiments, in is at least 14. In some embodiments, in is at least 15. In some embodiments, in is at least 16. In some embodiments, m is at least 17. In some embodiments, m is at least 18. In some embodiments, m is at least 19. In some embodiments, m is at least 20. In some embodiments, m is at least 21. In some embodiments, m is at least 22. In some embodiments, m is at least 23. In some embodiments, m is at least 24. In some embodiments, m is at least 25. In some embodiments, m is at least greater than 25.

In some embodiments, at least one of m and p is greater than 2. In some embodiments, at least one of m and p is greater than 3. In some embodiments, at least one of m and p is greater than 4. In some embodiments, at least one of in and p is greater than 5. In some embodiments, at least one of in and p is greater than 6. In some embodiments, at least one of m and p is greater than 7. In some embodiments, at least one of m and p is greater than 8. In some embodiments, at least one of m and p is greater than 9. In some embodiments, at least one of m and p is greater than 10. In some embodiments, at least one of in and p is greater than 11. In some embodiments, at least one of in and p is greater than 12. In some embodiments, at least one of m and p is greater than 13. In some embodiments, at least one of in and p is greater than 14. In some embodiments, at least one of m and p is greater than 15. In some embodiments, at least one of m and p is greater than 16. In some embodiments, at least one of m and p is greater than 17. In some embodiments, at least one of m and p is greater than 18. In some embodiments, at least one of m and p is greater than 19. In some embodiments, at least one of m and p is greater than 20. In some embodiments, at least one of m and p is greater than 21. In some embodiments, at least one of m and p is greater than 22. In some embodiments, at least one of m and p is greater than 23. In some embodiments, at least one of m and p is greater than 24. In some embodiments, at least one of in and p is greater than 25.

In some embodiments, each of m and p is greater than 2. In some embodiments, each of m and p is greater than 3. In some embodiments, each of m and p is greater than 4. In some embodiments, each of m and p is greater than 5. In some embodiments, each of m and p is greater than 6. In some embodiments, each of m and p is greater than 7. In some embodiments, each of m and p is greater than 8. In some embodiments, each of in and p is greater than 9. In some embodiments, each of m and p is greater than 10. In some embodiments, each of m and p is greater than 11. In some embodiments, each of m and p is greater than 12. In some embodiments, each of m and p is greater than 13. In some embodiments, each of m and p is greater than 14. In some embodiments, each of m and p is greater than 15. In some embodiments, each of m and p is greater than 16. In some embodiments, each of m and p is greater than 17. In some embodiments, each of m and p is greater than 18. In some embodiments, each of m and p is greater than 19. In some embodiments, each of m and p is greater than 20.

In some embodiments, the sum of m and p is greater than 3. In some embodiments, the sum of m and p is greater than 4. In some embodiments, the sum of m and p is greater than 5. In some embodiments, the sum of m and p is greater than 6. In some embodiments, the sum of m and p is greater than 7. In some embodiments, the sum of m and p is greater than 8. In some embodiments, the sum of m and p is greater than 9. In some embodiments, the sum of m and p is greater than 10. In some embodiments, the sum of m and p is greater than 11. In some embodiments, the sum of m and p is greater than 12. In some embodiments, the sum of m and p is greater than 13. In some embodiments, the sum of m and p is greater than 14. In some embodiments, the sum of m and p is greater than 15. In some embodiments, the sum of m and p is greater than 16. In some embodiments, the sum of m and p is greater than 17. In some embodiments, the sum of m and p is greater than 18. In some embodiments, the sum of m and p is greater than 19. In some embodiments, the sum of m and p is greater than 20. In some embodiments, the sum of m and p is greater than 21. In some embodiments, the sum of m and p is greater than 22. In some embodiments, the sum of m and p is greater than 23. In some embodiments, the sum of m and p is greater than 24. In some embodiments, the sum of m and p is greater than 25.

In some embodiments, n is 1, and at least one of m and p is greater than 1. In some embodiments, n is 1 and each of m and p is independently greater than 1. In some embodiments, m>n and p>n. In some embodiments, (Sp)m(Rp)n (Sp)p is $(Sp)_2Rp(Sp)_2$. In some embodiments, (Sp)p(Rp)n (Sp)m is $(Sp)_2Rp(Sp)_2$. In some embodiments, (Sp)p(Rp)n (Sp)m is $SpRp(Sp)_2$. In some embodiments, (Np)p(Rp)n (Sp)m is (Np)tRp(Sp)m. In some embodiments, (Np)p(Rp) n(Sp)m is $(Np)_2Rp(Sp)m$. In some embodiments, (Np)p(Rp) n(Sp)m is $(Rp)_2Rp(Sp)m$. In some embodiments, (Np)p(Rp) n(Sp)m is $(Sp)_2Rp(Sp)m$. In some embodiments, (Np)p(Rp) n(Sp)m is RpSpRp(Sp)m. In some embodiments, (Np)p(Rp) n(Sp)m is SpRpRp(Sp)m.

In some embodiments, (Sp)p(Rp)n(Sp)m is SpRpSpSp. In some embodiments, (Sp)p(Rp)n(Sp)m is $(Sp)_2Rp(Sp)_2$. In some embodiments, (Sp)p(Rp)n(Sp)m is $(Sp)_3Rp(Sp)_3$. In some embodiments, (Sp)p(Rp)n(Sp)m is $(Sp)_4Rp(Sp)_4$. In some embodiments, (Sp)p(Rp)n(Sp)m is $(Sp)tRp(Sp)_5$. In some embodiments, (Sp)p(Rp)n(Sp)m is $SpRp(Sp)_5$. In some embodiments, (Sp)p(Rp)n(Sp)m is $(Sp)_2Rp(Sp)_5$. In some embodiments, (Sp)p(Rp)n(Sp)m is $(Sp)_3Rp(Sp)_5$. In some embodiments, (Sp)p(Rp)n(Sp)m is $(Sp)_4Rp(Sp)_5$. In some embodiments, (Sp)p(Rp)n(Sp)m is $(Sp)_5Rp(Sp)_5$.

In some embodiments, (Sp)m(Rp)n(Sp)p is $(Sp)_2Rp(Sp)_2$. In some embodiments, (Sp)m(Rp)n(Sp)p is $(Sp)_3Rp(Sp)_3$. In some embodiments, (Sp)m(Rp)n(Sp)p is $(Sp)_4Rp(Sp)_4$. In some embodiments, (Sp)m(Rp)n(Sp)p is $(Sp)mRp(Sp)_5$. In some embodiments, (Sp)m(Rp)n(Sp)p is $(Sp)_2Rp(Sp)_5$. In some embodiments, (Sp)m(Rp)n(Sp)p is $(Sp)_3Rp(Sp)_5$. In some embodiments, (Sp)m(Rp)n(Sp)p is $(Sp)_4Rp(Sp)_5$. In some embodiments, (Sp)m(Rp)n(Sp)p is $(Sp)_5Rp(Sp)_5$.

In some embodiments, provided oligonucleotides are blockmers. In some embodiments, provided oligonucleotide are altmers. In some embodiments, provided oligonucleotides are altmers comprising alternating blocks. In some embodiments, a blockmer or an altmer can be defined by chemical modifications (including presence or absence), e.g., base modifications, sugar modification, internucleotidic linkage modifications, stereochemistry, etc., or patterns thereof. Example chemical modifications, stereochemistry and patterns thereof for a block and/or an alternating unit include but are not limited to those described in this disclosure, such as those described for an oligonucleotide, etc. In some embodiments, a blockmer comprises a pattern of ..SS..RR..SS..RR.. . In some embodiments, an altmer comprises a pattern of SRSRSRSR.

In some embodiments, a provided pattern of backbone chiral centers comprises repeating (Sp)m(Rp)n, (Rp)n(Sp) m, (Np)p(Rp)n(Sp)m, or (Sp)p(Rp)n(Sp)m units. In some embodiments, a repeating unit is (Sp)m(Rp)n. In some embodiments, a repeating unit is SpRp. In some embodiments, a repeating unit is SpSpRp. In some embodiments, a repeating unit is SpRpRp. In some embodiments, a repeating unit is RpRpSp. In some embodiments, a repeating unit is (Rp)n(Sp)m. In some embodiments, a repeating unit is (Np)p(Rp)n(Sp)m. In some embodiments, a repeating unit is (Sp)p(Rp)n(Sp)m.

In some embodiments, oligonucleotides of the present disclosure comprise base sequences, base modifications, sugar modifications, pattern of backbone linkages (internucleotidic linkages), and/or pattern of backbone chiral centers (e.g., of linkage phosphorus atoms) as described in US20150211006, US20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784, each of which is independently incorporated herein by reference.

In some embodiments, provided technologies comprise labeling of oligonucleotides, e.g., using isotopes. In some embodiments, provided oligonucleotides contain increased levels of one or more isotopes. In some embodiments, provided oligonucleotides are labeled, e.g., by one or more isotopes of one or more elements, e.g., hydrogen, carbon, nitrogen, etc. In some embodiments, provided oligonucleotides in provided compositions, e.g., oligonucleotides of a first plurality, comprise one or more base modifications, sugar modifications, and/or internucleotidic linkage modifications, wherein the oligonucleotides contain an enriched level of an isotope. In some embodiments, an isotope is deuterium. In some embodiments, a hydrogen in a sugar is replaced by deuterium (e.g., at the 2' position of a 2'-deoxy). In some embodiments, a hydrogen in a base is replaced by deuterium. In some embodiments, a hydrogen in an internucleotidic linkage is replaced by deuterium. In some embodiments, provided oligonucleotides are labeled with deuterium (replacing —$^1$H with —$^2$H) at one or more positions. In some embodiments, replacement of a hydrogen with deuterium can improve the stability, activity, bioavailability, easy of use, convenience, efficacy, and/or systemic exposure of an oligonucleotide. In some embodiments, one or more $^1$H of an oligonucleotide or any moiety conjugated to the oligonucleotide (e.g., a targeting moiety, lipid, etc.) is substituted with $^2$H. Such oligonucleotides can be used in any composition or method described herein. In some embodiments, an oligonucleotide which targets HTT comprises one or more isotopes. In some embodiments, an oligonucleotide which targets dystrophin comprises one or more isotopes.

Chiral Auxiliaries

In some embodiments, provided technologies are particularly useful for preparing chirally controlled oligonucleotide composition with high (crude) purity and/or yield. In some embodiments, in chirally controlled (stereocontrolled/stereoselective) oligonucleotide synthesis, chiral auxiliaries are typically used to control stereochemistry of a formed linkage phosphorus chiral center. In some embodiments, the present disclosure provides compounds, e.g., of formula I, I-a, I-a-1, I-a-2, I-b, I-c, I-d, I-e, II, II-a, II-b, III, III-a, or III-b, or salts thereof, that may be utilized as chiral auxiliaries for oligonucleotide synthesis. In some embodiments, a chiral auxiliary is one described in U.S. Pat. Nos. 9,598,458, 9,744,183, 9,605,019, 9,394,333, 9,598,458, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784, the chiral auxiliaries of each of which is incorporated herein by reference.

In some embodiments, the present disclosure provides a compound having the structure of formula I:

I

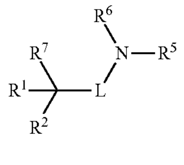

, or a salt thereof, wherein:

L is a covalent bond, or optionally substituted $C_{1-6}$ alkylene, wherein one or more methylene units are optionally and independently replaced with -L'-; or L is L';

each L' is independently a covalent bond, optionally substituted bivalent $C_{1-3}$ alkylene, —C($R^3$)($R^4$)—, —C($R^3$)($R^4$)—C($R^3$)($R^4$)—, -Cy-, or —C($R^3$)[C($R^4$)$_3$]—;

each of $R^1$, $R^2$, $R^3$, $R^4$, and $R^5$ is independently —H, -$L^s$-R', halogen, —CN, —$NO_2$, -$L^s$-Si(R')$_3$, —OR', —SR', or —N(R')$_2$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —$CO_2$R, or —$SO_2$R:

$R^6$ is -L-R';

$R^7$ is —OH or —SH;

at least one of $R^1$, $R^2$, $R^3$ and $R^4$ is not —H;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or;

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, L is a covalent bond, or optionally substituted $C_{1-6}$ alkylene, wherein one or more methylene units are optionally and independently replaced with -L'-. In some embodiments, L is a covalent bond. In some embodiments, a provided compound has the structure of

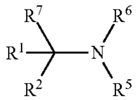

or a salt thereof. In some embodiments, $R^5$, and one or both of $R^1$ and $R^2$, are taken together with their intervening atoms to form an optionally substituted, 3-20 membered monocyclic, bicyclic or polycyclic ring having 1-5 heteroatoms. In some embodiments, one of $R^1$ and $R^2$ are taken together with $R^5$ and their intervening atoms to form an optionally substituted, 3-20 membered monocyclic, bicyclic or polycyclic ring having 1-5 heteroatoms. As extensively described in the present disclosure, a formed ring can be of various sizes, monocyclic, bicyclic or polycyclic, and contain various numbers of heteroatoms. In some embodiments, a ring is a 3-membered ring. In some embodiments, a ring is a 4-membered ring. In some embodiments, a ring is a 5-membered ring. In some embodiments, a ring is a 6-membered ring. In some embodiments, a ring is monocyclic. In some embodiments, a ring contains additional ring heteroatoms other than the intervening heteroatoms. In some embodiments, a ring is a 3-membered ring containing one ring heteroatom. In some embodiments, a ring is a 3-membered ring containing two ring heteroatoms. In some embodiments, a ring is a 3-membered ring containing one carbon, one nitrogen, and one oxygen ring atom.

In some embodiments, L is —C($R^3$)($R^4$)—. In some embodiments, a provided compound has the structure of formula I-a:

I-a

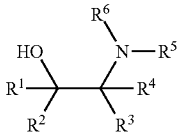

, or a salt thereof, wherein each variable is independently as described in the present disclosure. In some embodiments, a compound of formula I has the structure of formula I-a. In some embodiments, a provided compound has the structure of

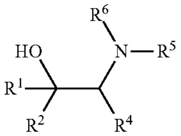

, or a salt thereof, wherein each variable is independently as described in the present disclosure, wherein $R^4$ and $R^5$ are not hydrogen.

In some embodiments, a provided compound has the structure of formula (I-a-1):

I-a-1

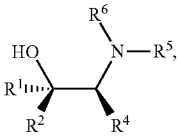

or a salt thereof, wherein each variable is independently as described in the present disclosure, and wherein $R^4$ and $R^5$ are not hydrogen, and $R^2$ has a larger size than $R^1$. In some embodiments, a compound of formula I-a has the structure of formula I-a-1.

In some embodiments, a provided compound has the structure of formula (I-a-2):

I-a-2

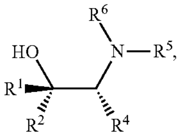

or a salt thereof, wherein each variable is independently as described in the present disclosure, and wherein $R^4$ and $R^5$ are not hydrogen, and $R^2$ has a larger size than $R^1$. In some embodiments, a compound of formula I-a has the structure of formula I-a-2.

In some embodiments, $R^5$ is —H. In some embodiments, $R^6$ is —H, and $R^4$ and $R^5$ are taken together with their intervening atoms to form an optionally substituted 3-20 membered heterocyclyl ring having 1-5 heteroatoms. In some embodiments, $R^4$ and $R^5$ are taken together with their intervening atoms to form an optionally substituted 4-10 membered heterocyclyl ring with the intervening nitrogen atom as the only ring heteroatom. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring is substituted. In some embodiments, a formed ring is unsubstituted. In some embodiments, a formed ring is monocyclic. In some embodiments, a formed ring is bicyclic. In some embodiments, a formed ring is polycyclic. In some embodiments, a formed ring is saturated. In some embodiments, a formed ring has no ring heteroatoms in addition to the nitrogen to which $R^5$ is attached.

In some embodiments, at least one of $R^1$ and $R^2$ is not hydrogen. In some embodiments, $R^1$ is hydrogen and $R^2$ is not hydrogen. In some embodiments, $R^1$ is not hydrogen and $R^2$ is hydrogen. In some embodiments, neither of $R^1$ and $R^2$ is hydrogen.

In some embodiments, one of $R^1$ and $R^2$ is —H, and the other is R, wherein R is not hydrogen. In some embodiments, one of $R^1$ and $R^2$ is —H, and the other is optionally substituted $C_{1-6}$ aliphatic. In some embodiments, one of $R^1$ and $R^2$ is —H, and the other is optionally substituted $C_{1-4}$ aliphatic. In some embodiments, one of $R^1$ and $R^2$ is —H, and the other is optionally substituted $C_{1-3}$ aliphatic. In some embodiments, one of $R^1$ and $R^2$ is —H, and the other is optionally substituted $C_{1-2}$ aliphatic. In some embodiments, one of $R^1$ and $R^2$ is —H, and the other is optionally substituted $C_{1-6}$ alkenyl. In some embodiments, one of $R^1$ and $R^2$ is —H, and the other is vinyl. In some embodiments, one of $R^1$ and $R^2$ is —H, and the other is optionally substituted $C_{1-6}$ alkynyl. In some embodiments, one of $R^1$ and $R^2$ is —H, and the other is ethynyl. In some embodiments, one of $R^1$ and $R^2$ is —H, and the other is optionally substituted benzyl. In some embodiments, one of $R^1$ and $R^2$ is —H, and the other is benzyl wherein the phenyl group of the benzyl is optionally substituted. In some embodiments, $R^1$ is —H and $R^2$ is benzyl. In some embodiments, $R^1$ is —H and $R^2$ is —R, wherein R is as described in the present disclosure and is not hydrogen. In some embodiments, $R^2$ is optionally substituted $C_{1-6}$ aliphatic. In some embodiments, $R^2$ is optionally substituted $—CH_2—CPh_2Me$. In some embodiments, $R^2$ is $—CH_2—CPh_2Me$. In some embodiments, $R^2$ is optionally substituted phenyl. In some embodiments, $R^2$ is optionally substituted benzyl. In some embodiments, a provided compound is

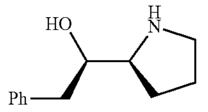 [SMILES: O[C@H](Cc1ccccc1)[C@@H]1CCCN1]

or a salt thereof.

In some embodiments, $R^1$ is not —H and $R^2$ is not —H. In some embodiments, $R^1$ and $R^2$ are independently R, wherein R is not —H. In some embodiments, $R^1$ is optionally substituted $C_{1-6}$ aliphatic, and $R^2$ is optionally substituted phenyl. In some embodiments, $R^1$ is methyl and $R^2$ is phenyl.

In some embodiments, one of $R^1$ and $R^2$ is R, wherein R comprises a ring moiety. In some embodiments, R is an optionally substituted group selected from $C_{3-20}$ cycloaliphatic, $C_{6-20}$ aryl, 5-20 membered heteroaryl having 1-5 heteroatoms, and 3-20 membered heterocyclyl having 1-5 heteroatoms. In some embodiments, R is optionally substituted $C_{3-20}$ cycloaliphatic. In some embodiments, R is optionally substituted $C_{3-10}$ cycloaliphatic. In some embodiments, R is optionally substituted $C_{3-10}$ cycloalkyl. In some embodiments, R is optionally substituted $C_{4-10}$ cycloalkyl. In some embodiments, R is optionally substituted cyclopropyl. In some embodiments, R is optionally substituted cyclobutyl. In some embodiments, R is optionally substituted cyclopentyl. In some embodiments, R is optionally substituted cyclohexyl. In some embodiments, R is optionally substituted cycloheptyl. In some embodiments, R is cyclopropyl. In some embodiments, R is cyclobutyl. In some embodiments, R is cyclopentyl. In some embodiments, R is cyclohexyl. In some embodiments, R is cycloheptyl. In some embodiments, R is optionally substituted $C_{6-20}$ aryl. In some embodiments, R is optionally substituted phenyl. In some embodiments, R is phenyl. In some embodiments, R is optionally substituted 5-20 membered heteroaryl having 1-5 heteroatoms. In some embodiments, R is optionally substituted 5-membered heteroaryl having 1-5 heteroatoms. In some embodiments, R is optionally substituted 6-membered heteroaryl having 1-5 heteroatoms. In some embodiments, R is optionally substituted 3-20 membered heterocyclyl having 1-5 heteroatoms. In some embodiments, the other of $R^1$ and $R^2$ is R wherein R is not hydrogen. In some embodiments, R is optionally substituted $C_{1-6}$ aliphatic. In some embodiments, R is optionally substituted $C_{1-6}$ alkyl. In some embodiments, R is $C_{1-6}$ alkyl. In some embodiments, R is methyl. In some embodiments, R is substituted methyl. In some embodiments, R is ethyl. In some embodiments, R is substituted ethyl. In some embodiments, one of $R^1$ and $R^2$ is R comprising a cyclic moiety as described in the present disclosure, and the other is an alkyl group as described in the present disclosure.

In some embodiments, each of $R^1$ and $R^2$ is independently R, wherein R is optionally substituted $C_{1-20}$ aliphatic. In some embodiments, R is unsubstituted $C_{1-20}$ aliphatic. In some embodiments, R is optionally substituted $C_{1-20}$alkyl. In some embodiments, R is optionally substituted $C_{1-6}$ alkyl. In some embodiments, R is linear $C_{1-6}$ alkyl. In some embodiments, one of $R^1$ and $R^2$ is optionally substituted $C_{1-6}$ alkyl, and the other is optionally substituted $C_{1-6}$ alkyl. In some embodiments, $R^1$ and $R^2$ are the same. In some embodiments, $R^1$ and $R^2$ are different.

In some embodiments, one of $R^1$ and $R^2$ is optionally substituted $C_{1-6}$ alkyl, and the other is optionally substituted $C_{1-6}$ alkenyl. In some embodiments, one of $R^1$ and $R^2$ is optionally substituted methyl or ethyl, and the other is vinyl. In some embodiments, one of $R^1$ and $R^2$ is methyl, and the other is vinyl.

In some embodiments, one of $R^1$ and $R^2$ is optionally substituted $C_{1-6}$ alkyl, and the other is optionally substituted $C_{1-6}$alkynyl. In some embodiments, one of $R^1$ and $R^2$ is optionally substituted methyl or ethyl, and the other is ethynyl. In some embodiments, one of $R^1$ and $R^2$ is methyl, and the other is ethynyl.

In some embodiments, one of $R^1$ and $R^2$ is optionally substituted $C_{1-6}$ alkyl, and the other is optionally substituted $C_{1-6}$ alkyl. In some embodiments, $R^1$ and $R^2$ are the same optionally substituted $C_{1-6}$ alkyl. In some embodiments, $R^1$ and $R^2$ are the same optionally substituted $C_{1-2}$ alkyl, and $R^1$ and $R^2$ comprise no more than two carbon atoms. In some embodiments, both $R^1$ and $R^1$ are methyl. In some embodiments, both $R^1$ and $R^1$ are ethyl. In some embodiments, both $R^1$ and $R^1$ are isopropyl. In some embodiments, one of $R^1$ and $R^2$ is optionally substituted $C_{1-3}$ linear alkyl, and the other is optionally substituted $C_{3-10}$ cycloalkyl. In some embodiments, one of $R^1$ and $R^2$ is optionally substituted $C_{1-3}$ linear alkyl, and the other is optionally substituted $C_{5-6}$ cycloalkyl. In some embodiments, $R^1$ is methyl. In some embodiments, $R^2$ is cyclopentyl. In some embodiments, $R^2$ is cyclohexyl. In some embodiments, one of $R^1$ and $R^2$ is optionally substituted $C_{1-3}$ linear alkyl, and the other is optionally substituted benzyl. In some embodiments, $R^1$ is methyl and $R^1$ is optionally substituted benzyl. In some embodiments, $R^2$ is benzyl. In some embodiments, $R^2$ is $p-CH_3O—C_6H_4—CH_2—$. In some embodiments, $R^1$ is selected from methyl, ethyl, cyclohexyl, and benzyl which is optionally substituted at the phenyl. In some embodiments, $R^2$ is selected from methyl, ethyl, cyclohexyl, and benzyl which is optionally substituted at the phenyl. In some embodiments, each of $R^1$ and $R^2$ is independently selected from methyl, ethyl, cyclohexyl, and benzyl which is optionally substituted at the phenyl. In some embodiments, a provided compound is

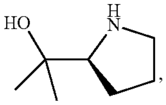,
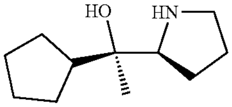,
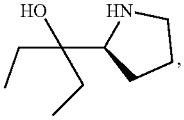,
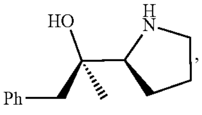,
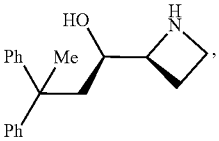,
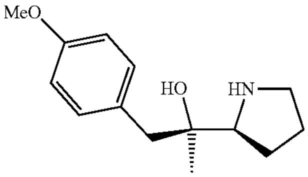,
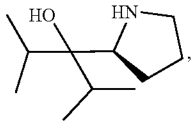, or a salt thereof. In some embodiments, a provided compound is

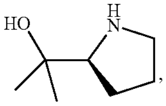,
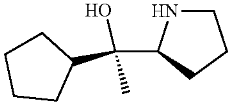,
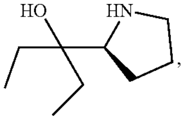,
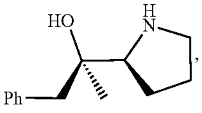,
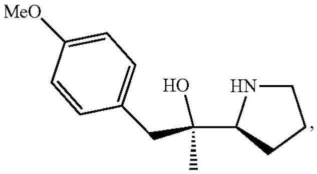, or a salt thereof. In some embodiments, a provided compound is

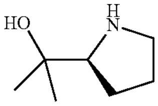

or a salt thereof. In some embodiments, a provided compound is

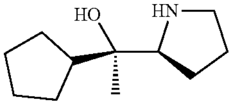

or a salt thereof. In some embodiments, a provided compound is

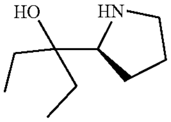

or a salt thereof. In some embodiments, a provided compound is

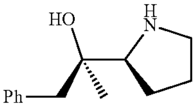

or a salt thereof. In some embodiments, a provided compound is

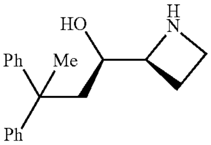 [SMILES: CC(C[C@@H](O)[C@@H]1CCN1)(c1ccccc1)c1ccccc1]

or a salt thereof. In some embodiments, a provided compound is

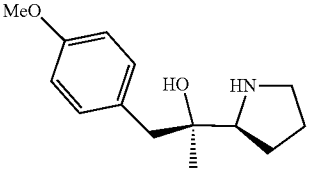 [SMILES: COc1ccc(C[C@@](C)(O)[C@@H]2CCCN2)cc1]

or a salt thereof. In some embodiments, a provided compound is

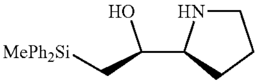

or a salt thereof. In some embodiments, a provided compound is

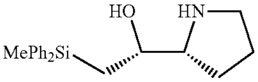

or a salt thereof. In some embodiments, a provided compound is

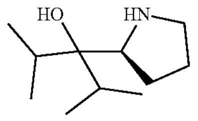

or a salt thereof.

In some embodiments, one of $R^1$ and $R^2$ is optionally substituted $C_{1-6}$ alkyl, and the other is optionally substituted phenyl. In some embodiments, $R^1$ is methyl, and $R^2$ is optionally substituted phenyl. In some embodiments, $R^1$ is methyl, and $R^2$ is phenyl. In some embodiments, $R^1$ is methyl, and $R^2$ is

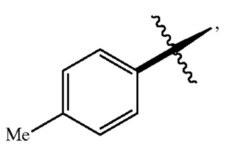

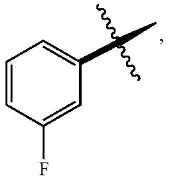

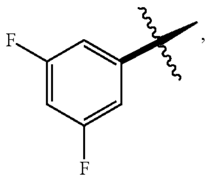

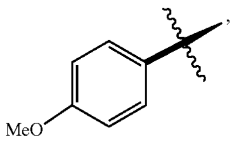

or

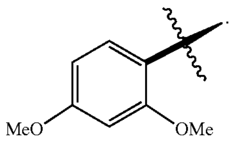

In some embodiments, a provided compound is selected from

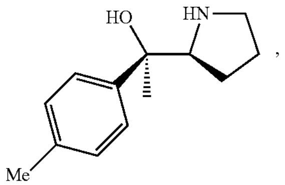

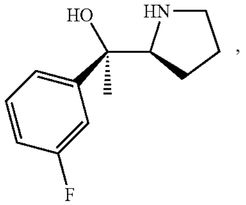

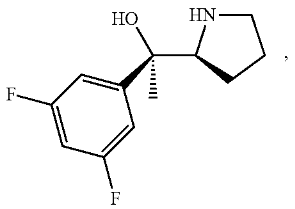

-continued

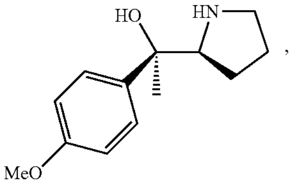

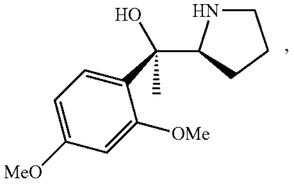

or salts thereof. In some embodiments, a provided compound is

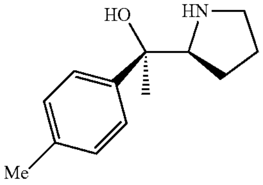

or a salt thereof. In some embodiments, a provided compound is

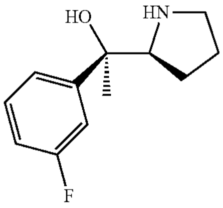

or a salt thereof. In some embodiments, a provided compound is

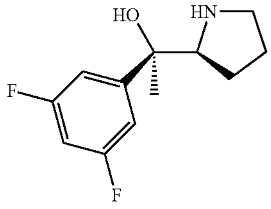 [SMILES: C[C@@](O)(c1cc(F)cc(F)c1)[C@@H]1CCCN1]

or a salt thereof. In some embodiments, a provided compound is

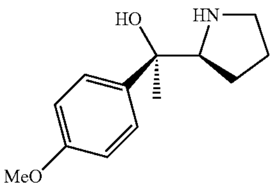 [SMILES: COc1ccc([C@@](C)(O)[C@@H]2CCCN2)cc1]

or a salt thereof. In some embodiments, a provided compound is

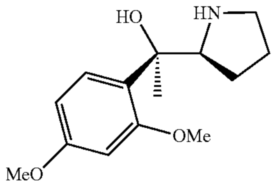 [SMILES: COc1ccc([C@@](C)(O)[C@@H]2CCCN2)c(OC)c1]

or a salt thereof.

In some embodiments, $R^1$ and $R^2$ are independently R, wherein R is an optionally substituted aryl group. In some embodiments, $R^1$ and $R^2$ are independently optionally substituted phenyl. In some embodiments, $R^1$ and $R^2$ are phenyl. In some embodiments, a provided compound is

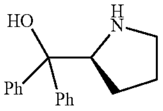 [SMILES: OC(c1ccccc1)(c1ccccc1)[C@@H]1CCCN1]

or a salt thereof.

In some embodiments, $R^1$ and $R^2$ are taken together with the carbon atom they are attached on to form an optionally substituted 3-20 membered monocyclic, bicyclic or polycyclic ring having 0-5 heteroatoms. In some embodiments, $R^1$ and $R^2$ are taken together with the carbon atom they are attached on to form an optionally substituted 3-7 membered monocyclic ring having no heteroatoms. In some embodiments, such a formed monocyclic ring is 3-membered; in some embodiments, 4-membered; in some embodiments, 5-membered; in some embodiments, 6-membered; in some embodiments 7-membered; in some embodiments, 8-membered; in some embodiments 9-membered; and in some embodiments 10-membered. In some embodiments, a formed ring is monocyclic. In some embodiments, a formed ring is bicyclic. In some embodiments, a formed ring is polycyclic. In some embodiments, a formed ring is aliphatic. In some embodiments, a formed ring comprises no unsaturation. In some embodiments, a formed ring is saturated, partially unsaturated, and/or partially aromatic, for example, a bicyclic or polycyclic ring comprising fused saturated, partially unsaturated, and/or aromatic moieties. In some embodiments, such a formed ring is substituted. In some embodiments, such a formed ring is not substituted. In some embodiments, the carbon to which $R^1$ and $R^2$ are attached is not chiral. In some embodiments, $R^1$ and $R^2$ are the same, and the carbon they are attached on is not chiral. In some embodiments, the ring formed by $R^1$ and $R^2$ taken together with the carbon atom they are attached on does not introduce asymmetry, and the carbon atom $R^1$ and $R^2$ attached on is not chiral. In some embodiments, $R^1$ and $R^2$ are different, and the carbon they are attached on is chiral. In some embodiments, the ring formed by $R^1$ and $R^2$ taken together with the carbon atom they are attached on introduces asymmetry, and the carbon atom $R^1$ and $R^2$ attached on is not chiral. In some embodiments, a provided compound is selected from

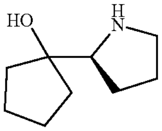,

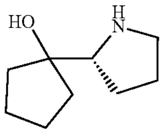

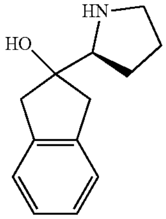,

,

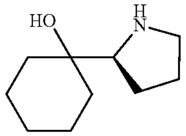,

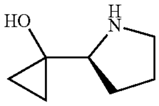, and salts thereof. In some embodiments, a provided compound is selected from

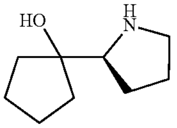 [SMILES: OC1([C@@H]2CCCN2)CCCC1],

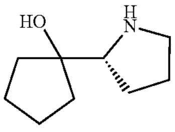 [SMILES: OC1([C@H]2CCCN2)CCCC1],

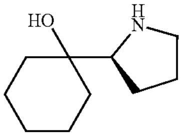 [SMILES: OC1([C@@H]2CCCN2)CCCCC1],

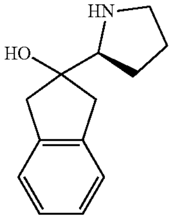 [SMILES: OC1([C@@H]2CCCN2)Cc2ccccc2C1], and salts thereof. In some embodiments, a provided compound is

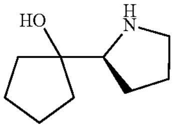

or a salt thereof. In some embodiments, a provided compound is

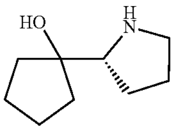

or a salt thereof. In some embodiments, a provided compound is

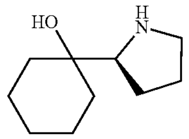

or a salt thereof. In some embodiments, a provided compound is

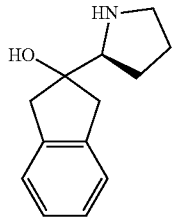

or a salt thereof.

In some embodiments, $R^4$ and $R^5$ are taken together with their intervening atoms to form an optionally substituted 3-20 membered monocyclic, bicyclic or polycyclic ring having 1-5 heteroatoms. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring is 8-membered. In some embodiments, a formed ring is 9-membered. In some embodiments, a formed ring is 10-membered. In some embodiments, $R^3$ is —H, and $R^4$ and $R^5$ are taken together with their intervening atoms to form an optionally substituted 3-20 membered monocyclic, bicyclic or polycyclic ring having 1-5 heteroatoms. In some embodiments, $R^3$ is —H, and $R^4$ and $R^5$ are taken together with their intervening atoms to form an optionally substituted 3-20 membered monocyclic, bicyclic or polycyclic ring having a nitrogen atom (the one which $R^5$ is on). In some embodiments, $R^3$ is —H, and $R^4$ and $R^5$ are taken together with their intervening atoms to form an optionally substituted 4-7 membered monocyclic ring having a nitrogen atom (the one which $R^5$ is on). In some embodiments, $R^3$ is —H, and $R^4$ and $R^5$ are taken together with their intervening atoms to form an optionally substituted 4-membered monocyclic ring having a nitrogen atom (the one which $R^5$ is on). In some embodiments, $R^3$ is —H, and $R^4$ and $R^5$ are taken together with their intervening atoms to form an optionally substituted 5-membered monocyclic ring having a nitrogen atom (the one which R is on). In some embodiments, $R^3$ is —H, and $R^4$ and $R^5$ are taken together with their intervening atoms to form an optionally substituted 6-membered monocyclic ring having a nitrogen atom (the one which $R^5$ is on). In some embodiments, $R^3$ is —H, and $R^4$ and $R^5$ are taken together with their intervening atoms to form an optionally substituted 7-membered monocyclic ring having a nitrogen atom (the one which $R^5$ is on). In some embodiments, $R^3$ is —H, and $R^4$ and $R^5$ are taken together with their intervening atoms to form an optionally substituted 8-membered monocyclic ring having a nitrogen atom (the one which $R^5$ is on). In some embodiments, $R^3$ is —H, and $R^4$ and $R^5$ are taken together with their intervening atoms to form an optionally substituted 9-membered monocyclic ring having a nitrogen atom (the one which $R^5$ is on). In some embodiments, $R^3$ is —H, and $R^4$ and $R^5$ are taken together with their intervening atoms to form an optionally substituted 10-membered monocyclic ring having a nitrogen atom (the one which $R^5$ is on). In some embodiments, a ring formed by $R^4$ and $R^5$ taken together with their intervening atoms is substituted. In some embodiments, a ring formed by $R^4$ and $R^5$ taken together with their intervening atoms is unsubstituted. In some embodiments, a ring formed by $R^4$ and $R^5$ taken together with their intervening atoms is monocyclic. In some embodiments, a ring formed by $R^4$ and $R^5$ taken together with their intervening atoms is bicyclic. In some embodiments, one of $R^1$ and $R^2$, and one of $R^3$ and $R^4$, are taken together with their intervening atoms to form an optionally substituted 3-20 membered monocyclic, bicyclic or polycyclic ring having 0-5 heteroatoms. In some embodiments, a formed ring is a 3-membered ring. In some embodiments, a formed ring is a 4-membered ring. In some embodiments, a formed ring is a 5-membered ring. In some embodiments, a formed ring is a 6-membered ring. In some embodiments, a formed ring is a 7-membered ring. In some embodiments, a formed ring is substituted. In some embodiments, a formed ring is unsubstituted. In some embodiments, a formed ring is monocyclic. In some embodiments, a formed ring is bicyclic. In some embodiments, a formed ring is polycyclic. In some embodiments, a formed ring has no additional heteroatoms in addition to an intervening atom. In some embodiments, a formed ring has additional ring heteroatoms in addition to an intervening atom. Example rings formed are extensively described in the present disclosure. In some embodiments, a provided compound is selected from

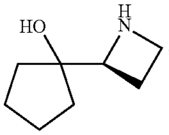
,
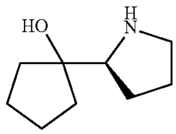
,
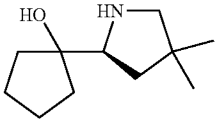
,
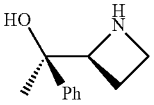
,
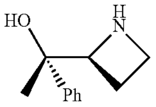
,
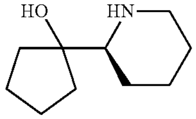
,
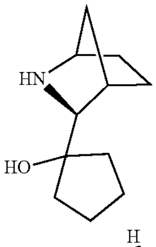
,
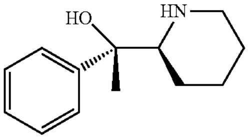
,
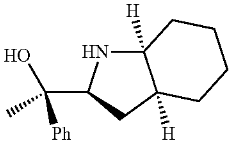
,
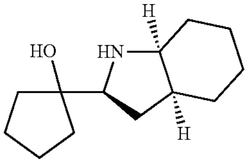
, and salts thereof. In some embodiments, a provided compound is selected from

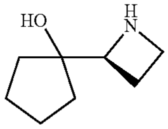
,
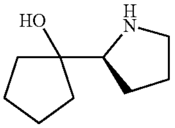
,
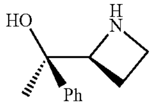
,
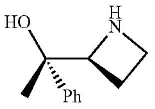
,
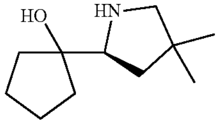
,
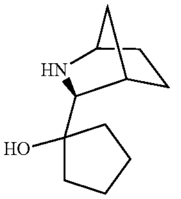
, and salts thereof. In some embodiments, a provided compound is

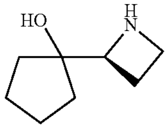

or a salt thereof. In some embodiments, a provided compound is

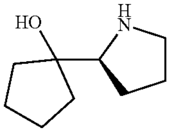 [SMILES: OC1([C@@H]2CCCN2)CCCC1]

or a salt thereof. In some embodiments, a provided compound is

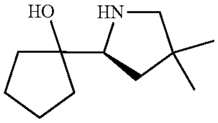

or a salt thereof. In some embodiments, a provided compound is

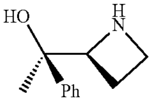

or a salt thereof. In some embodiments, a provided compound is

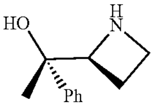

or a salt thereof. In some embodiments, a provided compound is

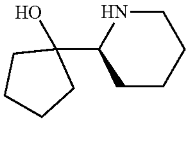 [SMILES: OC1([C@@H]2CCCCN2)CCCC1]

or a salt thereof. In some embodiments, a provided compound is

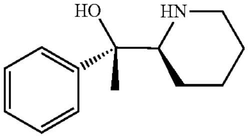

or a salt thereof. In some embodiments, a provided compound is

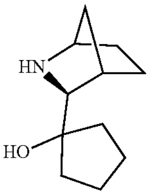 [SMILES: OC1([C@H]2NC3CCC2C3)CCCC1]

or a salt thereof. In some embodiments, a provided compound is

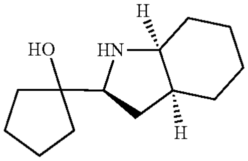 [SMILES: OC1([C@@H]2C[C@@H]3CCCC[C@@H]3N2)CCCC1]

or a salt thereof. In some embodiments, a provided compound is

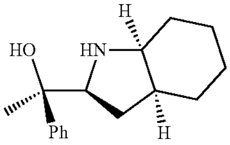 [SMILES: C[C@@](O)(c1ccccc1)[C@@H]1C[C@@H]2CCCC[C@@H]2N1]

or a salt thereof.

In some embodiments, one or two of $R^1$ and $R^2$ are taken together with one or more of $R^3$, $R^4$, and $R^5$ and the intervening atoms to form an optionally substituted 3-20 membered monocyclic, bicyclic or polycyclic ring having 0-5 heteroatoms. In some embodiments, one or two of $R^1$ and $R^2$ are taken together with one or two of $R^3$ and $R^4$ and the intervening atoms to form an optionally substituted 3-20 membered monocyclic, bicyclic or polycyclic ring having 0-5 heteroatoms. In some embodiments, one or two of $R^1$ and $R^2$ are taken together with $R^5$ and the intervening atoms to form an optionally substituted 3-20 membered monocyclic, bicyclic or polycyclic ring having 1-5 heteroatoms. In some embodiments, one or two of $R^1$ and $R^2$ are taken together with $R^5$, one or two of $R^3$ and $R^4$, and the intervening atoms to form an optionally substituted 3-20 membered monocyclic, bicyclic or polycyclic ring having 1-5 heteroatoms. In some embodiments, one or two of $R^1$ and $R^2$ are taken together with $R^5$, one or two of $R^3$ and $R^4$, and the intervening atoms to form an optionally substituted 6-20 membered bicyclic or polycyclic ring having 1-5 heteroatoms. In some embodiments, one or two of $R^1$ and $R^2$ are taken together with $R^5$, one or two of $R^3$ and $R^4$, and the intervening atoms to form an optionally substituted 8-20 membered bicyclic or polycyclic ring having 1-5 heteroatoms. In some embodiments, one of $R^1$ and $R^2$ are taken together with $R^5$, one of $R^3$ and $R^4$, and the intervening atoms to form an optionally substituted 8-20 membered bicyclic or polycyclic ring having 1-5 heteroatoms. In some embodiments, one of $R^1$ and $R^2$ are taken together with $R^5$, one of $R^3$ and $R^4$, and the intervening atoms to form an optionally substituted 8-20 membered bicyclic ring having 1-5 heteroatoms. In some embodiments, a formed ring is 8-membered. In some embodiments, a formed ring is 9-membered.

In some embodiments, $R^5$ is taken with one of $R^1$ and $R^2$ and their intervening atoms to form an optionally substituted 3-20 membered monocyclic, bicyclic or polycyclic ring having 1-5 heteroatoms. In some embodiments, $R^5$ is taken with one of $R^3$ and $R^4$ and their intervening atoms to form an optionally substituted 3-20 membered monocyclic, bicyclic or polycyclic ring having 1-5 heteroatoms. Example rings formed are extensively described in the present disclosure. In some embodiments, a formed ring is 3-membered. In some embodiments, a formed ring is 4-membered. In some embodiments, a formed ring is 5-membered. In some embodiments, a formed ring is 6-membered. In some embodiments, $R^5$ is not taken with $R^1$, $R^2$, $R^3$, or $R^4$ to form an optionally substituted ring. In some embodiments, $R^5$ is optionally substituted $C_{1-6}$ aliphatic. In some embodiments, $R^5$ is optionally substituted $C_{1-6}$ alkyl. In some embodiments, $R^5$ is unsubstituted $C_{1-6}$ alkyl. In some embodiments, $R^5$ is methyl. In some embodiments, $R^5$ is ethyl. In some embodiments, $R^5$ is isopropyl.

In some embodiments, a provided compound is

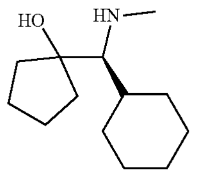

or a salt thereof. In some embodiments, a provided compound is

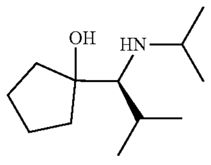

or a salt thereof. In some embodiments, a provided compound is

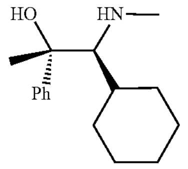 [SMILES: CN[C@@H](C1CCCCC1)[C@@](C)(O)c1ccccc1]

or a salt thereof.

In some embodiments, L is -L'-C($R^3$)($R^4$)—. In some embodiments, a provided compound has the structure of formula I-b:

I-b

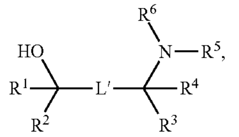

or a salt thereof, wherein each variable is independently as described in the present disclosure. In some embodiments, a compound of formula I has the structure of formula I-b.

In some embodiments, L' is a covalent bond. In some embodiments, L' is —C($R^3$)($R^4$)—. In some embodiments, a provided compound has the structure of formula I-c:

I-c

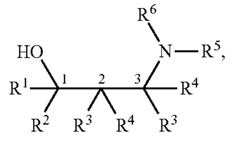

or a salt thereof, wherein each variable is independently as described in the present disclosure. In some embodiments, a compound of formula I has the structure of formula I-c.

In some embodiments, one or $R^3$ and $R^4$ on C2 are taken together with $R^5$ to form with their intervening atoms an optionally substituted 3-20 membered monocyclic, bicyclic or polycyclic ring having a nitrogen atom (the one which $R^5$ is on). In some embodiments, one or $R^3$ and $R^4$ on C3 are taken together with $R^5$ to form with their intervening atoms an optionally substituted 3-20 membered monocyclic, bicyclic or polycyclic ring having a nitrogen atom (the one which $R^5$ is on). In some embodiments, one of $R^3$ and $R^4$ on C2, and one of $R^3$ and $R^4$ on C3, are taken together with their intervening atoms to form an optionally substituted 3-20 membered monocyclic, bicyclic or polycyclic ring having 0-5 heteroatoms. In some embodiments, $R^3$ and $R^4$ on the same carbon atom are taken together with the carbon atom to form an optionally substituted 3-20 membered monocyclic, bicyclic or polycyclic ring having 0-5 heteroatoms. In some embodiments, $R^3$ and $R^4$ on C2 are taken together with C2 to form an optionally substituted 3-20 membered monocyclic, bicyclic or polycyclic ring having 0-5 heteroatoms. In some embodiments, $R^3$ and $R^4$ on C3 are taken together with C3 to form an optionally substituted 3-20 membered monocyclic, bicyclic or polycyclic ring having 0-5 heteroatoms. Example such ring moieties, e.g., formed by $R^3/R^4$ and $R^5$, by $R^3/R^4$ and $R^3/R^4$, etc., are extensively described in the present disclosure, and can be e g., 4-membered, 5-membered, 6-membered, 7-membered, monocyclic, bicyclic, polycyclic, substituted, unsubstituted, with additional ring heteroatoms (other than the intervening atom(s)), without additional ring hetereoatoms, combinations thereof, etc.

In some embodiments, $R^3$ on C2 is hydrogen. In some embodiments, $R^4$ on C2 is hydrogen. In some embodiments, $R^3$ on C3 is hydrogen. In some embodiments, $R^4$ on C3 is hydrogen. In some embodiments, both $R^3$ and $R^4$ on C2 are hydrogen. In some embodiments, both $R^3$ and $R^4$ on C3 are hydrogen. In some embodiments, both $R^3$ and $R^4$ on C2, and one of $R^3$ and $R^4$ on C3, are hydrogen. In some embodiments, both $R^3$ and $R^4$ on C3, and one of $R^3$ and $R^4$ on C2 are hydrogen.

In some embodiments, a provided compound is

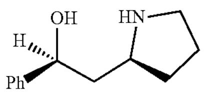 [SMILES: O[C@@H](C[C@@H]1CCCN1)c1ccccc1]

or a salt thereof.

In some embodiments, L is -Cy-. In some embodiments, a provided compound has the structure of formula I-d:

I-d

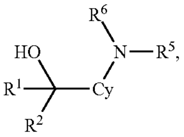

or a salt thereof, wherein each variable is independently as described in the present disclosure. In some embodiments, a compound of formula I has the structure of formula I-d. In some embodiments, -Cy- is 1,2-bivalent. In some embodiments, -Cy- is optionally substituted cycloalkylene. In some embodiments, -Cy- is optionally substituted

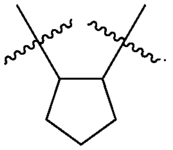 [SMILES: *C1CCCC1*]

In some embodiments, -Cy- is optionally substituted

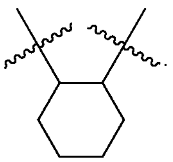 [SMILES: *C1CCCCC1*]

In some embodiments, one of $R^1$ and $R^2$, and one of $R^3$ and $R^4$, are R and are taken together with their intervening atoms to form an optionally substituted 3-20 membered ring having 1-10 heteroatoms as described in the present disclosure, e.g., Ring A as described herein. In some embodiments, a provided compound has the structure of formula I-e:

I-e

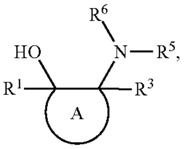

or a salt thereof, wherein each variable is independently as described in the present disclosure. In some embodiments, a compound of formula I has the structure of formula I-e.

In some embodiments, one of $R^1$ and $R^2$, and $R^4$ are taken together with their intervening atoms to form an optionally substituted 3-20 membered ring having 1-5 heteroatoms. In some embodiments, $R^3$ is —H, one of $R^1$ and $R^2$, and $R^4$ are taken together with their intervening atoms to form an optionally substituted 3-20 membered ring having 1-5 heteroatoms. In some embodiments, $R^2$ and $R^4$ are taken together with their intervening atoms to form an optionally substituted ring (e.g., formula I-e). In some embodiments, a formed ring, e.g., Ring A in formula I-e, is 3, 4, 5, 6, 7, 8, 9, or 10-membered. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring is 8-membered. In some embodiments, a formed ring is 9-membered. In some embodiments, a formed ring is 10-membered. In some embodiments, a formed ring is monocyclic. In some embodiments, a formed ring is bicyclic. In some embodiments, a formed ring is polycyclic. In some embodiments, a formed ring is saturated. In some embodiments, a formed ring is partially unsaturated. In some embodiments, a formed ring has no heteroatoms. In some embodiments, a formed ring is an optionally substituted 3-membered saturated aliphatic ring. In some embodiments, a formed ring is an optionally substituted 4-membered saturated aliphatic ring. In some embodiments, a formed ring is an optionally substituted 5-membered saturated aliphatic ring. In some embodiments, a formed ring is an optionally substituted 6-membered saturated aliphatic ring. In some embodiments, a formed ring is an optionally substituted 7-membered saturated aliphatic ring. In some embodiments, a formed ring is an optionally substituted 8-membered saturated aliphatic ring. In some embodiments, a formed ring is an optionally substituted 9-membered saturated aliphatic ring. In some embodiments, a formed ring is an optionally substituted 10-membered saturated aliphatic ring.

In some embodiments, R' is —H, $R^1$ is optionally substituted $C_{1-6}$ aliphatic or phenyl, $R^5$ is optionally substituted $C_{1-6}$ aliphatic, and $R^6$ is —H. In some embodiments, $R^3$ is —H, $R^1$ and $R^5$ are taken together with their intervening atoms to form an optionally substituted ring, and $R^6$ is —H. In some embodiments, $R^3$ is —H, $R^1$ and $R^5$ are taken together with their intervening atoms to form an optionally substituted 5- or 6-membered ring, and $R^6$ is —H. In some embodiments, $R^3$ is —H, $R^1$ and $R^5$ are taken together with their intervening atoms to form an optionally substituted 5-membered saturated ring having no heteroatom in addition to the nitrogen to which $R^5$ is attached, and $R^6$ is —H. In some embodiments, $R^3$ is —H, $R^1$ and $R^5$ are taken together with their intervening atoms to form an optionally substituted 6-membered saturated ring having no heteroatom in addition to the nitrogen to which $R^5$ is attached, and $R^6$ is —H. In some embodiments, a ring formed by $R^1$ and $R^5$ taken together are unsubstituted.

In some embodiments, —OH and —N($R^5$)($R^6$) are trans. In some embodiments, —OH and —N($R^5$)($R^6$) are cis. In some embodiments, the carbon to which $R^1$ and —OH are attached is R. In some embodiments, the carbon to which $R^1$ and —OH are attached is S. In some embodiments, $R^1$ is hydrogen. In some embodiments, $R^1$ is not hydrogen. In some embodiments, $R^1$ is optionally substituted $C_{1-6}$ aliphatic or phenyl. In some embodiments, $R^1$ is methyl. In some embodiments, $R^1$ is phenyl. In some embodiments, $R^3$ is hydrogen. In some embodiments, $R^5$ is hydrogen. In some embodiments, $R^5$ is not hydrogen. In some embodiments, $R^5$ is optionally substituted $C_{1-6}$ aliphatic or phenyl. In some embodiments, $R^5$ is methyl. In some embodiments, $R^5$ is phenyl. In some embodiments, $R^6$ is hydrogen. In some embodiments, $R^6$ is not hydrogen. In some embodiments, as demonstrated by certain example data, compounds with trans —OH and —N($R^5$)($R^6$) can provide high yields and/or diastereoselectivity. In some embodiments, as demonstrated by certain example data, compounds with trans —OH and —N($R^5$)($R^6$) can provide both high yields and diastereoselectivity.

In some embodiments, a provided compound, e.g., a compound of formula I-e, is selected from

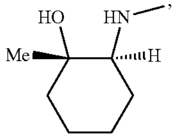,
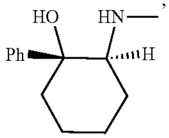,
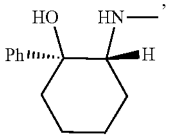,
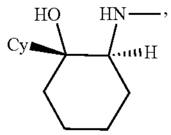,
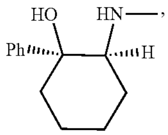,
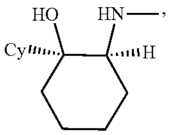,
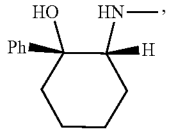, and salts thereof. In some embodiments, a provided compound is

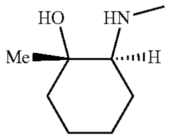

or a salt there of. In some embodiments, a provided compound is

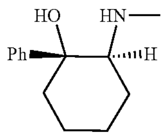

or a salt there of. In some embodiments, a provided compound is

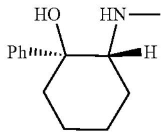

or a salt there of. In some embodiments, a provided compound is

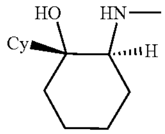

or a salt there of. In some embodiments, a provided compound is

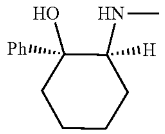

or a salt there of. In some embodiments, a provided compound is

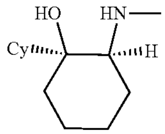

or a salt there of. In some embodiments, a provided compound is

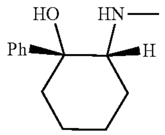

or a salt there of. In some embodiments, a provided compound is selected from

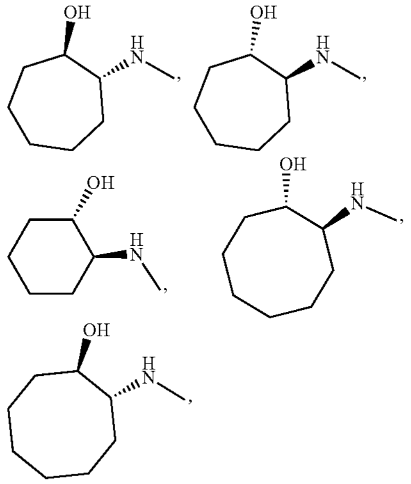

or salts thereof. In some embodiments, a provided compound is

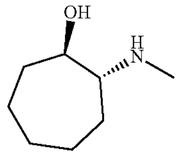

or a salt thereof. In some embodiments, a provided compound is

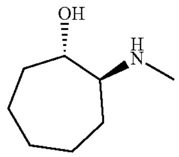

or a salt thereof. In some embodiments, a provided compound is

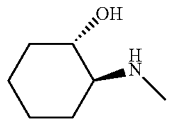

or a salt thereof. In some embodiments, a provided compound is

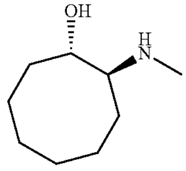

or a salt thereof. In some embodiments, a provided compound is

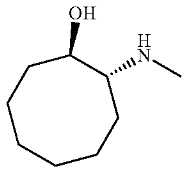

or a salt thereof.

In some embodiments, a provided compound has the structure of formula II:

II

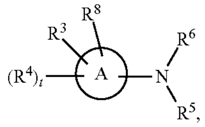

or a salt thereof, wherein:

Ring A is an optionally substituted 3-20 membered monocyclic, bicyclic or polycyclic ring having 0-10 heteroatoms independently selected from oxygen, nitrogen, sulfur, phosphorus and silicon;

each of $R^1$, $R^2$, $R^3$, $R^4$, and $R^5$ is independently —H, -$L^s$-R, halogen, —CN, —$NO_2$, -$L^s$-Si$(R)_3$, —OR, —SR, or —$N(R)_2$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N$(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B$(R')_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B$(R')_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —C(O)OR, or —$S(O)_2R$;

t is 0-20;

$R^6$ is -L-R':

$R^8$ is -L-$R^7$, -L-C($R^1$)($R^2$)—$R^7$, or -$L^s$-$R^7$;

$R^7$ is —OH or —SH;

L is a covalent bond, or optionally substituted $C_{1-6}$ alkylene, wherein one or more methylene units are optionally and independently replaced with -L'-; or L is $L^s$;

L' is a covalent bond, optionally substituted bivalent $C_{1-3}$ alkylene, —C($R^3$)($R^4$)—, —C($R^3$)($R^4$)—C($R^3$)($R^4$)—, -Cy-, or —C($R^3$)[C($R^4$)$_3$]—;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or;

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, a provided compound has the structure of formula II-a:

II-a

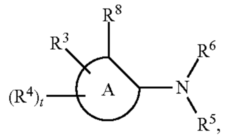

or a salt thereof, wherein each variable is independently as described in the present disclosure. In some embodiments, a compound of formula II has the structure of formula II-a.

In some embodiments, a provided compound of structure II-a, has the structure of formula II-b:

II-b

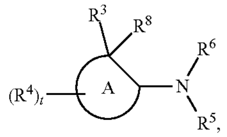

or a salt thereof, wherein each variable is independently as described in the present disclosure. In some embodiments, a compound of formula II-a has the structure of formula II-b.

In some embodiments, a provided compound of structure II-a, has the structure of formula II-c:

II-c

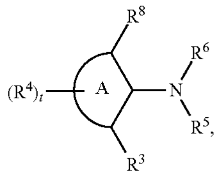

or a salt thereof, wherein each variable is independently as described in the present disclosure. In some embodiments, a compound of formula II-a has the structure of formula II-c.

In some embodiments, $R^8$ is —OH. In some embodiments, $R^6$ is —H. In some embodiments, $R^5$ is optionally substituted alkyl. In some embodiments, $R^5$ is methyl. In some embodiments, t is 0. In some embodiments, $R^3$ is optionally substituted alkyl. In some embodiments, $R^3$ is methyl. In some embodiments, $R^3$ is optionally substituted phenyl. In some embodiments, $R^3$ is phenyl. In some embodiments, $R^3$ is optionally substituted $C_{3-10}$ cycloalkyl. In some embodiments, $R^3$ is optionally substituted cyclohexyl. In some embodiments, $R^3$ is cyclohexyl.

In some embodiments, Ring A is an optionally substituted 3-20 membered monocyclic, bicyclic or polycyclic ring having 0-10 heteroatoms independently selected from oxygen, nitrogen, sulfur, phosphorus and silicon. In some embodiments, Ring A is or comprises at least one monocyclic saturated or partially unsaturated monocyclic ring moiety, optionally as part of a bicyclic or polycyclic system. In some embodiments, Ring A is monocyclic. In some embodiments, Ring A is bicyclic or polycyclic comprising at least one monocyclic saturated or partially unsaturated monocyclic ring moiety, and optionally one or more aromatic monocyclic moieties. In some embodiments, Ring A is or comprises at least one saturated monocyclic ring moiety. In some embodiments, $R^8$ is connected to a $sp^3$ ring atom of Ring A. In some embodiments, $R^8$ is connected to a $sp^3$ carbon ring atom of Ring A. In some embodiments, $R^3$ is connected to a $sp^3$ ring atom of Ring A. In some embodiments, $R^3$ is connected to a $sp^3$ carbon ring atom of Ring A. In some embodiments, —N($R^5$)($R^6$) is connected to a $sp^3$ ring atom of Ring A. In some embodiments, —N($R^5$)($R^6$) is connected to a $sp^3$ carbon ring atom of Ring A.

In some embodiments, Ring A is optionally substituted $C_{3-10}$ cycloalkyl. In some embodiments, Ring A is optionally substituted cyclohexyl. In some embodiments, Ring A is cyclohexyl. In some embodiments, $R^8$ and —N($R^5$)($R^6$) are cis. In some embodiments, $R^8$ and —N($R^5$)($R^6$) are trans. In some embodiments, a provided compound of formula II is selected from

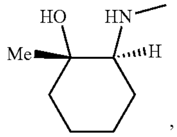,
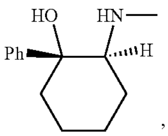,
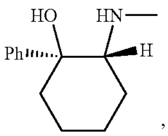,

-continued

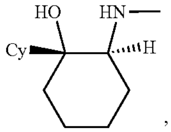, 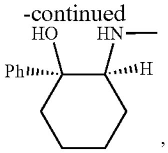, 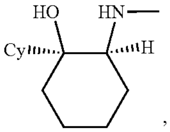, 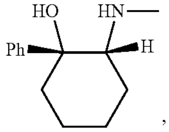, and salts thereof.

In some embodiments, a provided compound is a compound of II-c or a salt thereof. In some embodiments, $R^3$ and $R^5$ are R, and are taken together to form an optionally substituted ring as described in the present disclosure. In some embodiments, a provided compound of formula II is selected from

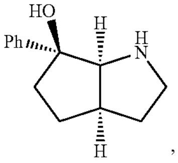, 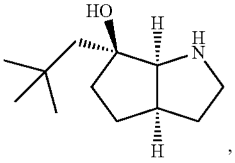, 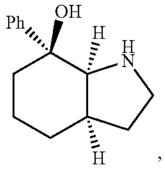, 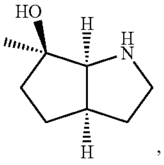, and salts thereof.

In some embodiments, a provided compound has the structure of formula III:

III

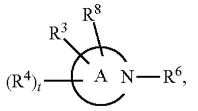

or a salt thereof, wherein:

Ring A' is an optionally substituted 3-20 membered monocyclic, bicyclic or polycyclic ring having 1-10 heteroatoms independently selected from oxygen, nitrogen, sulfur, phosphorus and silicon, wherein Ring A' comprises a —$N(R^6)$— moiety;

each of $R^1$, $R^2$, $R^3$ and $R^4$ is independently —H, -$L^s$-R, halogen, —CN, —$NO_2$, -$L^s$-$Si(R)_3$, —OR, —SR, or —$N(R)_2$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —$S(O)_2$—, —$S(O)_2N$(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[$B(R')_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[$B(R')_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —C(O)OR, or —$S(O)_2R$;

t is 0-20;

$R^6$ is -L-R':

$R^8$ is -L-$R^7$, -L-$C(R^1)(R^2)$—$R^7$, or -$L^s$-$R^7$;

$R^7$ is —OH or —SH;

L is a covalent bond, or optionally substituted $C_{1-6}$ alkylene, wherein one or more methylene units are optionally and independently replaced with -L'-; or L is $L^s$;

L' is a covalent bond, optionally substituted bivalent $C_{1-3}$ alkylene, —$C(R^3)(R^4)$—, —$C(R^3)(R^4)$—$C(R^3)(R^4)$—, -Cy-, or —$C(R^3)[C(R^4)_3]$—;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon. $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or;

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, a provided compound has the structure of formula III-a:

III-a

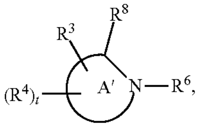

or a salt thereof, wherein each variable is independently as described in the present disclosure. In some embodiments, a compound of formula III has the structure of formula III-a.

In some embodiments, a provided compound has the structure of formula III-b:

III-b

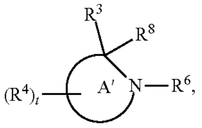

or a salt thereof, wherein each variable is independently as described in the present disclosure. In some embodiments, a compound of formula III-a has the structure of formula III-b.

In some embodiments, $R^8$ is bonded to a carbon atom ($C^2$) next to the nitrogen atom in —N($R^6$)—($N^1$) (e.g., formula III-a, formula III-b, etc.). In some embodiments, $R^8$ is bonded to a carbon atom next to $C^2$ ($C^3$). In some embodiments, $R^8$ is bonded to a carbon atom next to $C^3$ that is not $C^2$ ($C^4$). In some embodiments, $R^8$ is bonded to a carbon atom next to $C^4$ which is not $C^3$ ($C^5$). In some embodiments, $R^8$ is bonded to a carbon atom next to $C^5$ which is not $C^4$ ($C^6$).

In some embodiments, $R^8$ is —OH. In some embodiments, $R^6$ is —H. In some embodiments, $R^5$ is optionally substituted alkyl. In some embodiments, $R^5$ is methyl. In some embodiments, t is 0. In some embodiments, $R^3$ is optionally substituted alkyl. In some embodiments, $R^3$ is methyl. In some embodiments, $R^3$ is optionally substituted phenyl. In some embodiments, $R^3$ is phenyl. In some embodiments, $R^3$ is optionally substituted $C_{3-10}$ cycloalkyl. In some embodiments, $R^3$ is optionally substituted cyclohexyl. In some embodiments, $R^3$ is cyclohexyl.

In some embodiments, Ring A' is an optionally substituted 3-20 membered monocyclic, bicyclic or polycyclic ring having 1-5 heteroatoms independently selected from oxygen, nitrogen, sulfur, phosphorus and silicon, wherein Ring A' comprises a —N($R^6$)— moiety. In some embodiments, Ring A' is Ring A as described in the present disclosure, wherein Ring A comprises a nitrogen ring atom. In some embodiments, Ring A' is or comprises at least one monocyclic saturated or partially unsaturated monocyclic ring moiety, optionally as part of a bicyclic or polycyclic system. In some embodiments, Ring A' is monocyclic. In some embodiments, Ring A' is bicyclic or polycyclic comprising at least one monocyclic saturated or partially unsaturated monocyclic ring moiety, and optionally one or more aromatic monocyclic moieties. In some embodiments, Ring A' is or comprises at least one saturated monocyclic ring moiety. In some embodiments, Rx is connected to a $sp^3$ ring atom of Ring A'. In some embodiments, $R^8$ is connected to a $sp^3$ carbon ring atom of Ring A'. In some embodiments, $R^3$ is connected to a $sp^3$ ring atom of Ring A'. In some embodiments, $R^3$ is connected to a $sp^3$ carbon ring atom of Ring A'. In some embodiments, the nitrogen to which $R^6$ is attached is $sp^3$.

In some embodiments, a provided compound of formula III is selected from

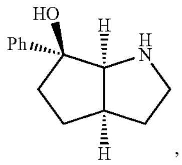 , 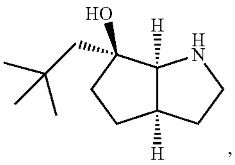 ,

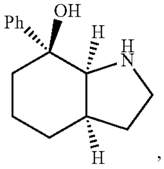 , 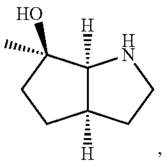 , and salts thereof. In some embodiments, In some embodiments, a provided compound of formula III is selected from compounds listed in Table 4 below and salts thereof.

In some embodiments, a compound of formula I is a compound of formula I-a. In some embodiments, a compound of formula I is a compound of formula I-a-1. In some embodiments, a compound of formula I is a compound of formula I-a-2. In some embodiments, a compound of formula I is a compound of formula I-b. In some embodiments, a compound of formula I is a compound of formula I-c In some embodiments, a compound of formula I is a compound of formula I-d In some embodiments, a compound of formula I is a compound of formula I-e In some embodiments, a compound of formula I is a compound of formula II. In some embodiments, a compound of formula I is a compound of formula II-a. In some embodiments, a compound of formula I is a compound of formula II-b. In some embodiments, a compound of formula I is a compound of formula II-c. In some embodiments, a compound of formula I is a compound of formula III. In some embodiments, a compound of formula I is a compound of formula III-a. In some embodiments, a compound of formula I is a compound of formula III-b.

TABLE 1
Example compounds.
| Compound No. | Structure | Compound No. | Structure |
| --- | --- | --- | --- |
| WV-CA-001 | 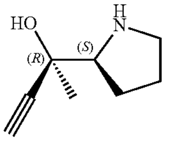 | WV-CA-012 | 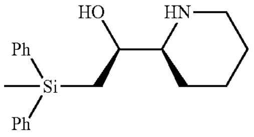 [SMILES: C[Si](C[C@@H](O)[C@@H]1CCCCN1)(c1ccccc1)c1ccccc1] |
| WV-CA-002 | 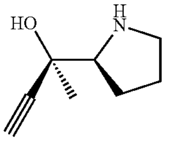 | WV-CA-012-R | 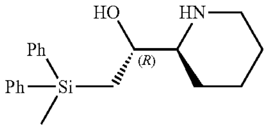 |
| WV-CA-002-S | 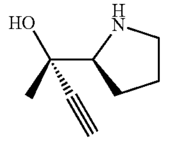 | WV-CA-013 | 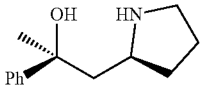 |
| WV-CA-003 | 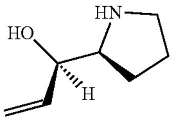 | WV-CA-014 | 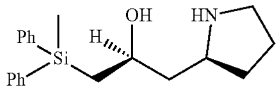 [SMILES: C[Si](C[C@@H](O)C[C@@H]1CCCN1)(c1ccccc1)c1ccccc1] |
| WV-CA-004 | 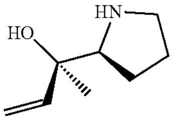 | WV-CA-014-R | 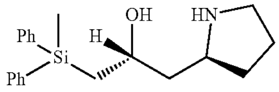 [SMILES: C[Si](C[C@H](O)C[C@@H]1CCCN1)(c1ccccc1)c1ccccc1] |
| WV-CA-005-D | 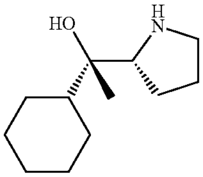 | WV-CA-015 | 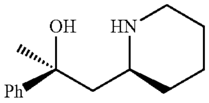 [SMILES: C[C@](O)(C[C@@H]1CCCCN1)c1ccccc1] |
| WV-CA-005-L | 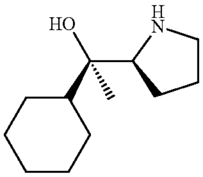 | WV-CA-016 | 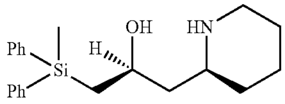 [SMILES: C[Si](C[C@@H](O)C[C@@H]1CCCCN1)(c1ccccc1)c1ccccc1] |
| WV-CA-006 | 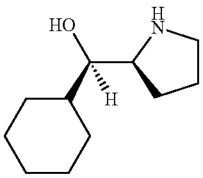 [SMILES: O[C@H](C1CCCCC1)[C@@H]1CCCN1] | WV-CA-021 | 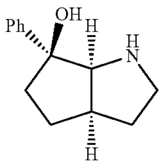 [SMILES: O[C@]1(c2ccccc2)CC[C@@H]2CCN[C@@H]21] |
| WV-CA-011 | 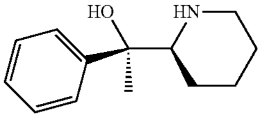 | WV-CA-022 | 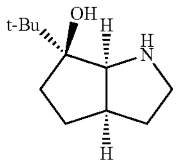 [SMILES: CC(C)(C)[C@@]1(O)CC[C@@H]2CCN[C@@H]21] |

TABLE 1-continued
| Example compounds. | | | |
|---|---|---|---|
| Compound No. | Structure | Compound No. | Structure |
| WV-CA-011-S | 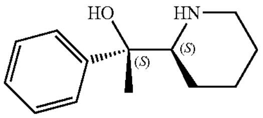 | WV-CA-023 | 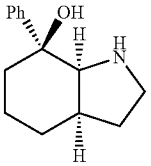 [SMILES: O[C@]1(c2ccccc2)CCC[C@@H]2CCN[C@@H]21] |
| WV-CA-040 | 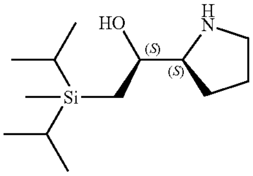 | WV-CA-050 | 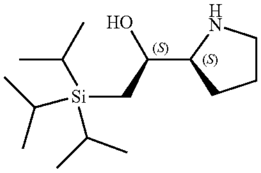 |
| WV-CA-041-D | 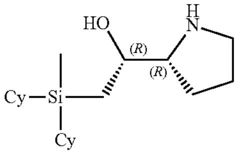 | WV-CA-051 | 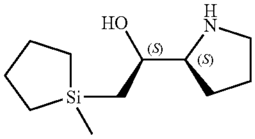 |
| WV-CA-041-L | 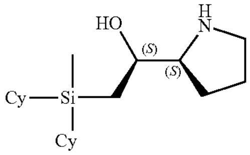 | WV-CA-052 | 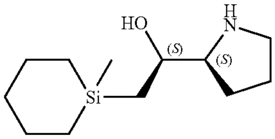 |
| WV-CA-042 | 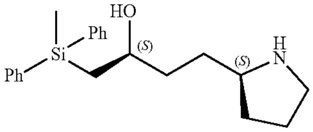 | WV-CA-053 | 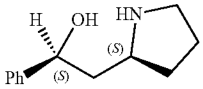 |
| WV-CA-043 | 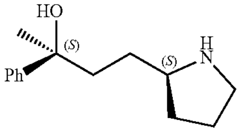 | WV-CA-054 | 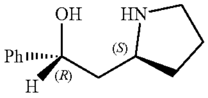 |
| WV-CA-044-R + S | 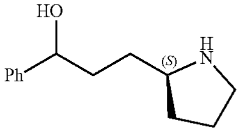 | WV-CA-056 | 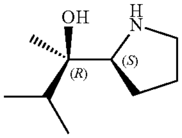 |
| WV-CA-045 | 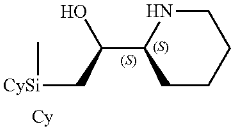 | WV-CA-056-S | 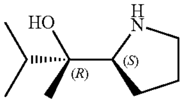 |
| WV-CA-046 | 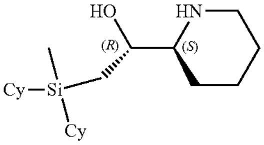 | WV-CA-057 | 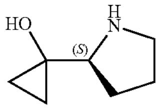 |

TABLE 1-continued
Example compounds.
| Compound No. | Structure | Compound No. | Structure |
| --- | --- | --- | --- |
| WV-CA-048 | 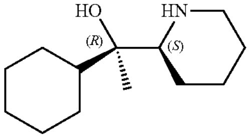 | WV-CA-058 | 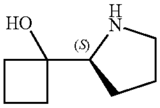 |
| WV-CA-049 | 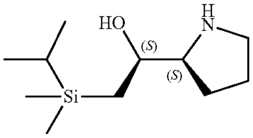 | WV-CA-059 | 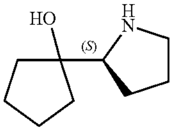 |
| WV-CA-059-R | 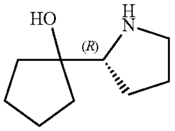 | WV-CA-073-S | 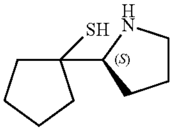 |
| WV-CA-060 | 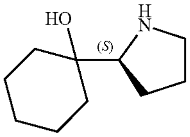 | WV-CA-074-M | 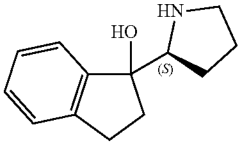 |
| WV-CA-062 | 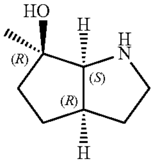 | WV-CA-074-R | 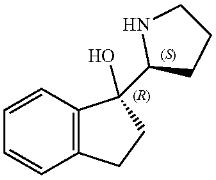 |
| WV-CA-063-S | 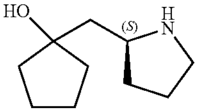 | WV-CA-074-S | 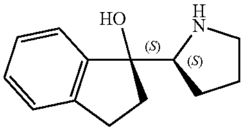 |
| WV-CA-064-S | 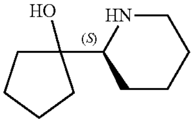 | WV-CA-076 | 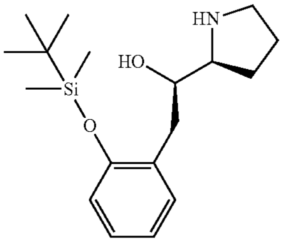 [SMILES: CC(C)(C)[Si](C)(C)Oc1ccccc1C[C@@H](O)[C@@H]1CCCN1] |
| WV-CA-065-S | 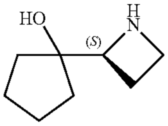 | WV-CA-077 | 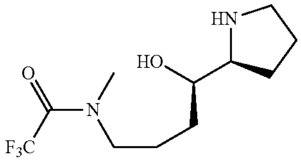 [SMILES: CN(CCC[C@@H](O)[C@@H]1CCCN1)C(=O)C(F)(F)F] |
| WV-CA-067 | 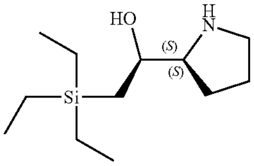 | WV-CA-078 | 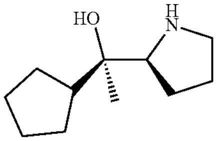 |

TABLE 1-continued
| Example compounds. | | | |
|---|---|---|---|
| Compound No. | Structure | Compound No. | Structure |
| WV-CA-068-S | 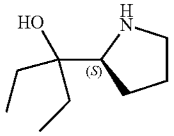 | WV-CA-079 | 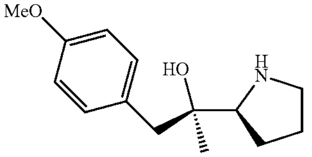 [SMILES: COc1ccc(C[C@@](C)(O)[C@@H]2CCCN2)cc1] |
| WV-CA-069-S | 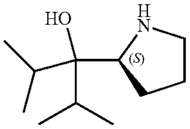 | WV-CA-080 | 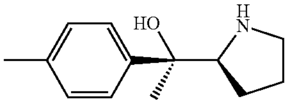 |
| WV-CA-072-S | 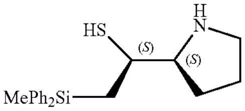 | WV-CA-081 | 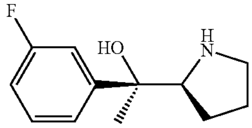 |
| WV-CA-082 | 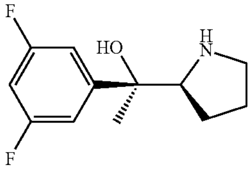 [SMILES: C[C@@](O)(c1cc(F)cc(F)c1)[C@@H]1CCCN1] | WV-CA-097 | 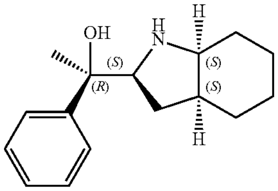 |
| WV-CA-083 | 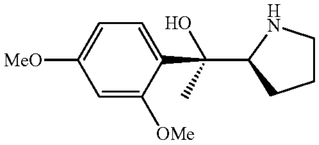 [SMILES: COc1ccc([C@@](C)(O)[C@@H]2CCCN2)c(OC)c1] | WV-CA-098 | 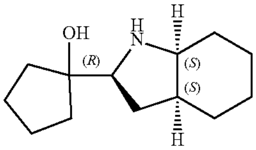 |
| WV-CA-084 | 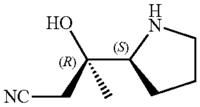 | WV-CA-099 | 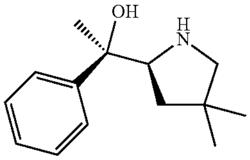 [SMILES: CC1(C)CN[C@H]([C@](C)(O)c2ccccc2)C1] |
| WV-CA-088 | 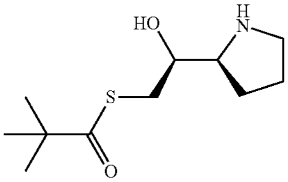 | WV-CA-100-D | 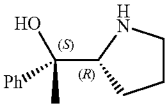 |
| WV-CA-089 | 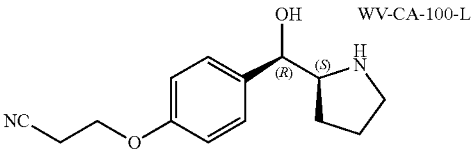 | WV-CA-100-L | 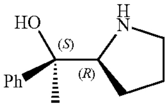 |
| WV-CA-090 | 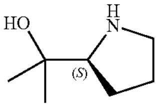 | WV-CA-101 | 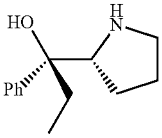 |

TABLE 1-continued
| Example compounds. | | | |
|---|---|---|---|
| Compound No. | Structure | Compound No. | Structure |
| WV-CA-091 | 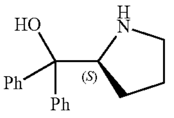 | WV-CA-102 | 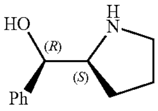 |
| WV-CA-093 | 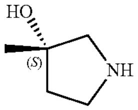 | WV-CA-103 | 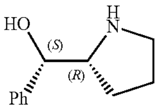 |
| WV-CA-094 | 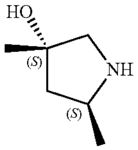 | WV-CA-104 | 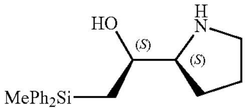 |
| WV-CA-096 | 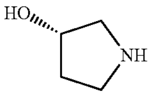 | WV-CA-105 | 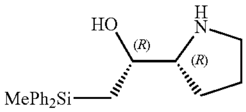 |
| WV-CA-106 | 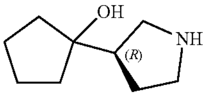 | WV-CA-117 | 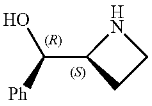 |
| WV-CA-107 | 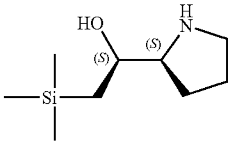 | WV-CA-118 | 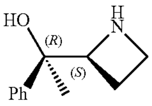 |
| WV-CA-108 | 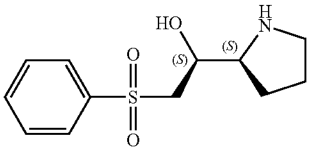 | WV-CA-118-S | 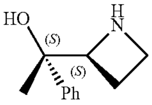 |
| WV-CA-109 | 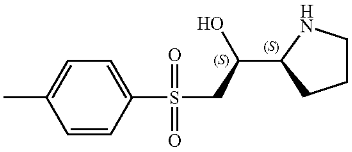 | WV-CA-119 | 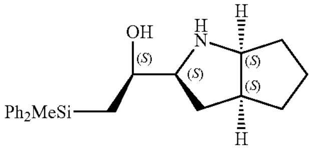 |
| WV-CA-109a | 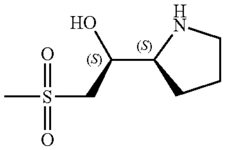 | WV-CA-120 | 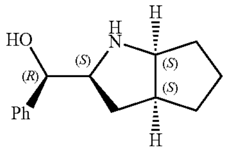 |
| WV-CA-110 | 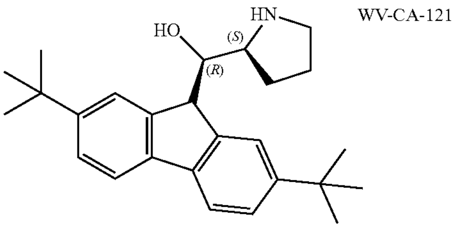 | WV-CA-121 | 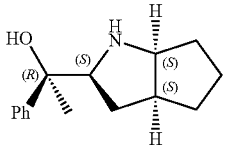 |

TABLE 1-continued
Example compounds.
| Compound No. | Structure | Compound No. | Structure |
|---|---|---|---|
| WV-CA-111 | 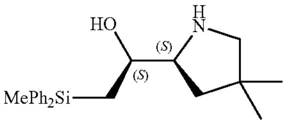 | WV-CA-122 | 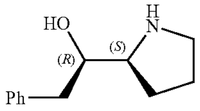 |
| WV-CA-112 | 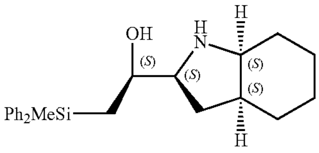 | WV-CA-123 | 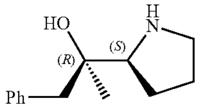 |
| WV-CA-113 | 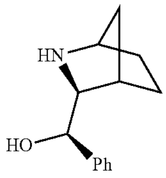 [SMILES: O[C@H](c1ccccc1)[C@H]1NC2CCC1C2] | WV-CA-124 | 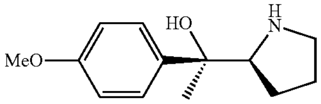 [SMILES: COc1ccc([C@@](C)(O)[C@@H]2CCCN2)cc1] |
| WV-CA-116 | 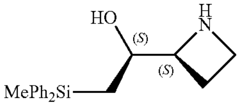 | WV-CA-125 | 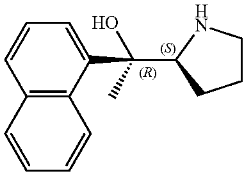 |
| WV-CA-124 | 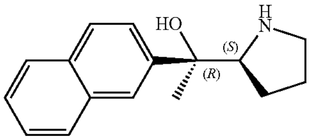 | WV-CA-146 | 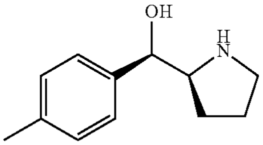 |
| WV-CA-127 | 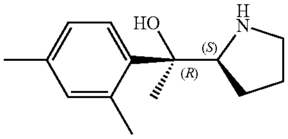 | WV-CA-147 | 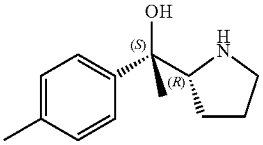 |
| WV-CA-128 | 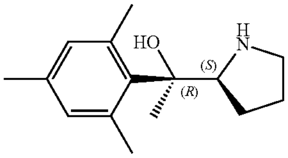 | WV-CA-148 | 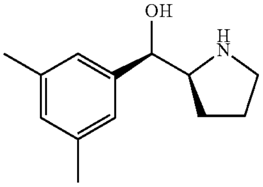 |
| WV-CA-129 | 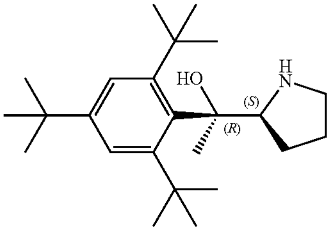 | WV-CA-149 | 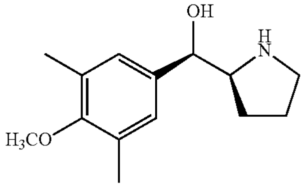 [SMILES: COc1c(C)cc([C@@H](O)[C@@H]2CCCN2)cc1C] |

TABLE 1-continued
| Example compounds. | | | |
|---|---|---|---|
| Compound No. | Structure | Compound No. | Structure |
| WV-CA-130 | 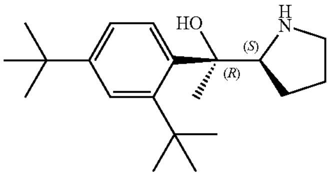 | WV-CA-150 | 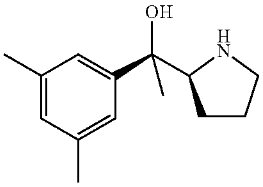 [SMILES: Cc1cc(C)cc([C@@](C)(O)[C@@H]2CCCN2)c1] |
| WV-CA-131 | 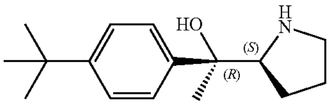 | WV-CA-151 | 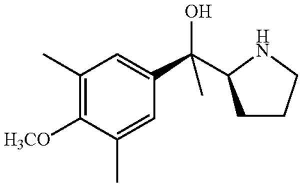 [SMILES: COc1c(C)cc([C@@](C)(O)[C@@H]2CCCN2)cc1C] |
| WV-CA-132 | 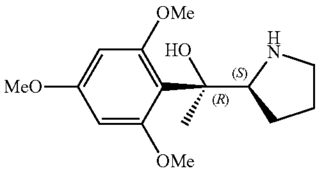 | WV-CA-152 | 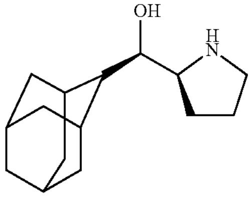 [SMILES: O[C@H](C1C2CC3CC(C2)CC1C3)[C@@H]1CCCN1] |
| WV-CA-133 | 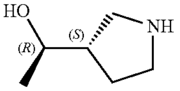 | WV-CA-153 | 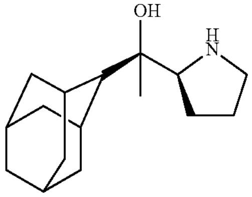 [SMILES: C[C@@](O)(C1C2CC3CC(C2)CC1C3)[C@@H]1CCCN1] |
| WV-CA-134 | 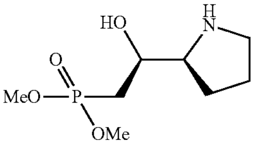 [SMILES: COP(=O)(C[C@@H](O)[C@@H]1CCCN1)OC] | WV-CA-154 | 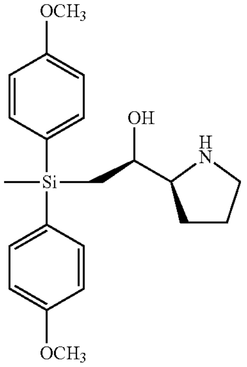 [SMILES: COc1ccc([Si](C)(C[C@@H](O)[C@@H]2CCCN2)c2ccc(OC)cc2)cc1] |
| WV-CA-145 | 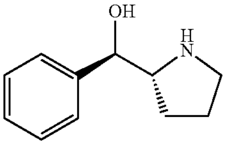 [SMILES: O[C@H](c1ccccc1)[C@H]1CCCN1] | WV-CA-155 | 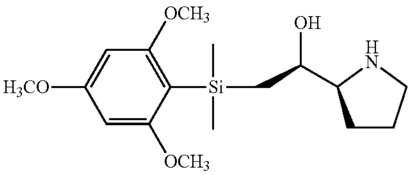 [SMILES: COc1cc(OC)c([Si](C)(C)C[C@@H](O)[C@@H]2CCCN2)c(OC)c1] |

TABLE 1-continued
| Example compounds. | | | |
|---|---|---|---|
| Compound No. | Structure | Compound No. | Structure |
| WV-CA-156 | 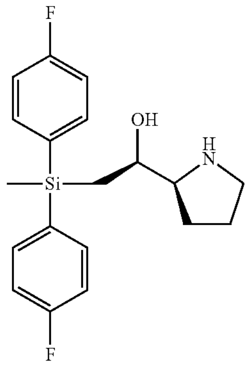 [SMILES: C[Si](C[C@@H](O)[C@@H]1CCCN1)(c1ccc(F)cc1)c1ccc(F)cc1] | WV-CA-172 | 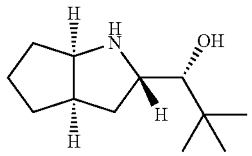 |
| WV-CA-157 | 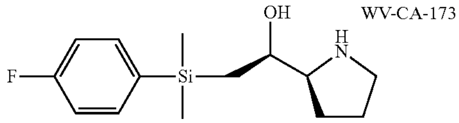 | WV-CA-173 | 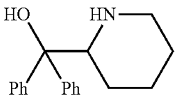 [SMILES: OC(c1ccccc1)(c1ccccc1)C1CCCCN1] |
| WV-CA-163 | 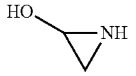 | WV-CA-174 | 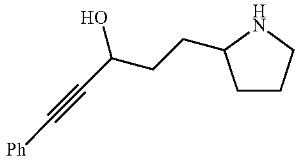 [SMILES: OC(C#Cc1ccccc1)CCC1CCCN1] |
| WV-CA-164 | 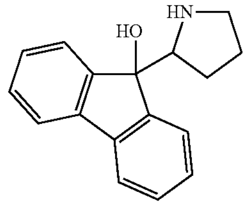 [SMILES: OC1(C2CCCN2)c2ccccc2-c2ccccc21] | WV-CA-175 | 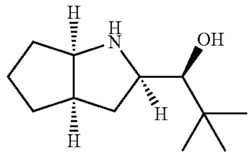 |
| WV-CA-165 | 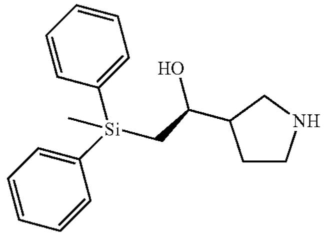 [SMILES: C[Si](C[C@@H](O)C1CCNC1)(c1ccccc1)c1ccccc1] | WV-CA-176 | 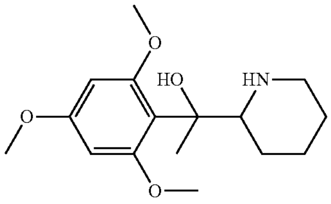 [SMILES: COc1cc(OC)c(C(C)(O)C2CCCCN2)c(OC)c1] |
| WV-CA-423 | 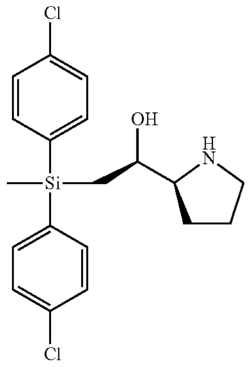 [SMILES: C[Si](C[C@@H](O)[C@@H]1CCCN1)(c1ccc(Cl)cc1)c1ccc(Cl)cc1] | WV-CA-180 | 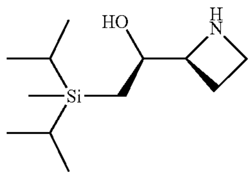 |

TABLE 1-continued
Example compounds.
| Compound No. | Structure | Compound No. | Structure |
|---|---|---|---|
| WV-CA-424 | 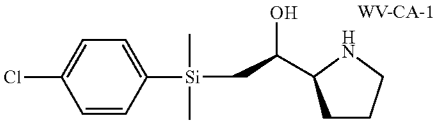 | WV-CA-181 | 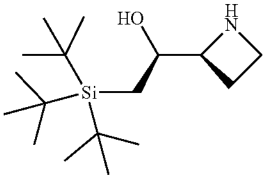 [SMILES: CC(C)(C)[Si](C[C@@H](O)[C@@H]1CCN1)(C(C)(C)C)C(C)(C)C] |
| WV-CA-165 | 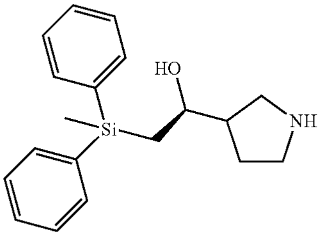 [SMILES: C[Si](C[C@@H](O)C1CCNC1)(c1ccccc1)c1ccccc1] | WV-CA-182 | 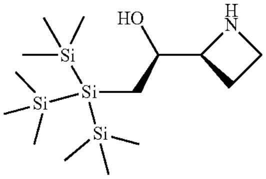 [SMILES: C[Si](C)(C)[Si](C[C@@H](O)[C@@H]1CCN1)([Si](C)(C)C)[Si](C)(C)C] |
| WV-CA-166 | 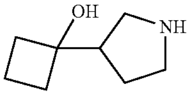 | WV-CA-183 | 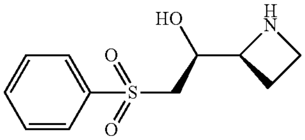 [SMILES: O=S(=O)(C[C@@H](O)[C@@H]1CCN1)c1ccccc1] |
| WV-CA-167 | 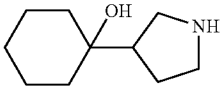 [SMILES: OC1(C2CCNC2)CCCCC1] | WV-CA-188 | 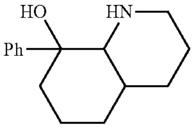 [SMILES: OC1(c2ccccc2)CCCC2CCCNC21] |
| WV-CA-201 | 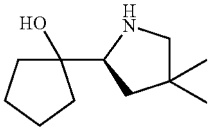 | WV-CA-229 | 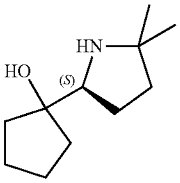 |
| WV-CA-202 | 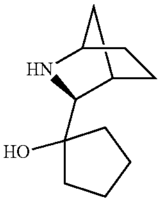 [SMILES: OC1([C@H]2NC3CCC2C3)CCCC1] | WV-CA-231 | 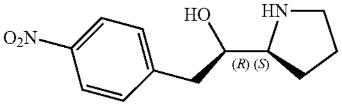 [SMILES: O=[N+]([O-])c1ccc(C[C@@H](O)[C@@H]2CCCN2)cc1] |
| WV-CA-203 | 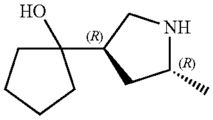 | WV-CA-233 | 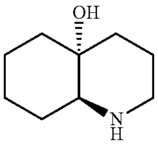 [SMILES: O[C@@]12CCCC[C@@H]1NCCC2] |
| WV-CA-204 | 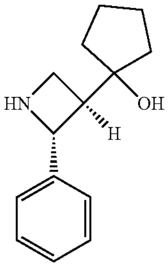 [SMILES: OC1([C@@H]2CN[C@H]2c2ccccc2)CCCC1] | WV-CA-234 | 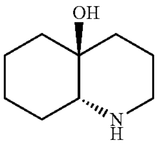 [SMILES: O[C@]12CCCC[C@H]1NCCC2] |

TABLE 1-continued
Example compounds.
| Compound No. | Structure | Compound No. | Structure |
|---|---|---|---|
| WV-CA-204a | 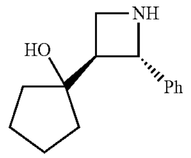 [SMILES: OC1([C@H]2CN[C@@H]2c2ccccc2)CCCC1] | WV-CA-301 | 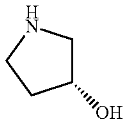 |
| WV-CA-206 | 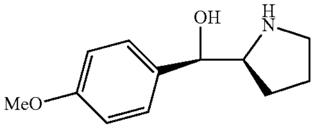 [SMILES: COc1ccc([C@@H](O)[C@@H]2CCCN2)cc1] | WV-CA-304 | 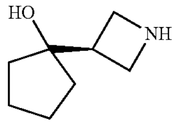 |
| WV-CA-209 | 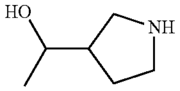 | WV-CA-306 | 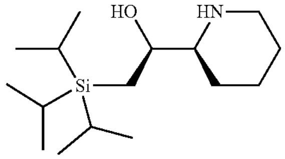 [SMILES: CC(C)[Si](C[C@@H](O)[C@@H]1CCCCN1)(C(C)C)C(C)C] |
| WV-CA-225 | 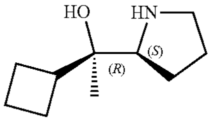 | WV-CA-307 | 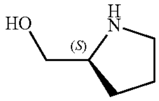 |
| WV-CA-226 | 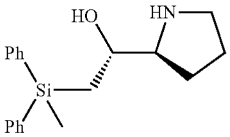 [SMILES: C[Si](C[C@H](O)[C@@H]1CCCN1)(c1ccccc1)c1ccccc1] | WV-CA-308 | 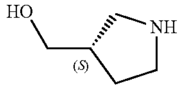 |
| WV-CA-227 | 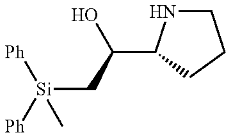 [SMILES: C[Si](C[C@@H](O)[C@H]1CCCN1)(c1ccccc1)c1ccccc1] | WV-CA-309 | 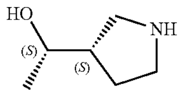 |
| WV-CA-310 | 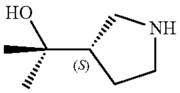 | WV-CA-320 | 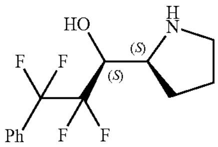 |
| WV-CA-311 | 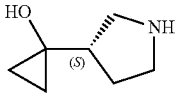 | WV-CA-321 | 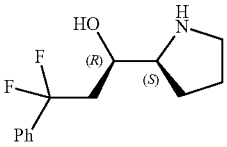 |
| WV-CA-312 | 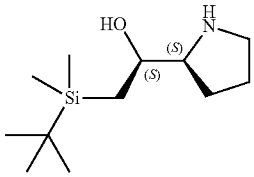 | WV-CA-322 | 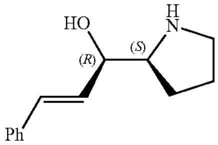 |
| WV-CA-313 | 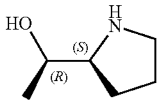 | WV-CA-323 | 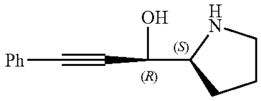 |

TABLE 1-continued
Example compounds.
| Compound No. | Structure | Compound No. | Structure |
| --- | --- | --- | --- |
| WV-CA-314 | 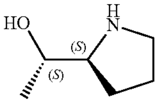 | WV-CA-324 | 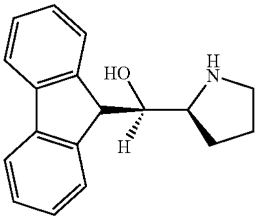 [SMILES: O[C@H](C1c2ccccc2-c2ccccc21)[C@@H]1CCCN1] |
| WV-CA-315 | 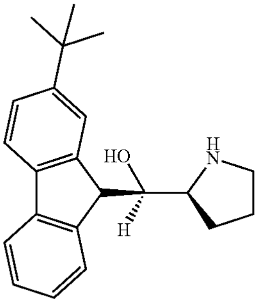 [SMILES: CC(C)(C)c1ccc2c(c1)C([C@@H](O)[C@@H]1CCCN1)c1ccccc1-2] | WV-CA-325 | 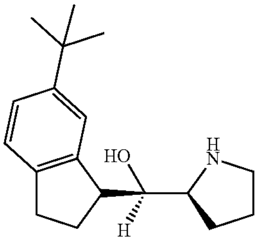 [SMILES: CC(C)(C)c1ccc2c(c1)C([C@@H](O)[C@@H]1CCCN1)CC2] |
| WV-CA-316 | 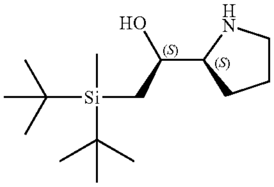 | WV-CA-326 | 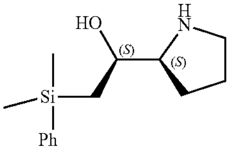 |
| WV-CA-317 | 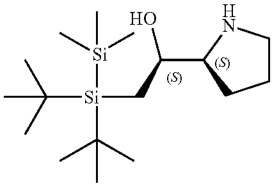 | WV-CA-327 | 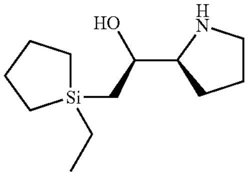 |
| WV-CA-318 | 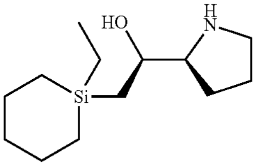 [SMILES: CC[Si]1(C[C@@H](O)[C@@H]2CCCN2)CCCCC1] | WV-CA-328 | 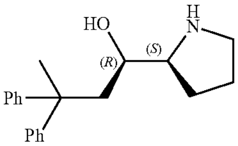 |
| WV-CA-319 | 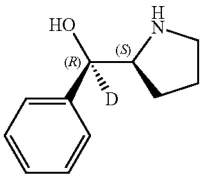 | WV-CA-329 | 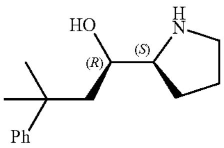 |
| WV-CA-330 | 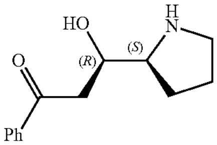 | WV-CA-340 | 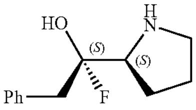 |

TABLE 1-continued
Example compounds.
| Compound No. | Structure | Compound No. | Structure |
|---|---|---|---|
| WV-CA-331 | 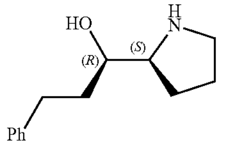 | WV-CA-341 | 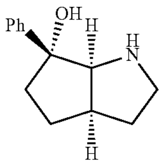 [SMILES: O[C@@]1(c2ccccc2)CC[C@@H]2CCN[C@@H]21] |
| WV-CA-332 | 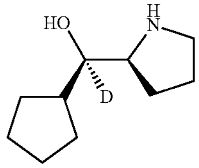 [SMILES: [2H][C@@](O)(C1CCCC1)[C@@H]1CCCN1] | WV-CA-342 | 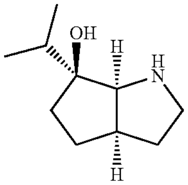 |
| WV-CA-333 | 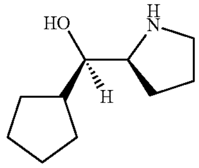 [SMILES: O[C@H](C1CCCC1)[C@@H]1CCCN1] | WV-CA-343 | 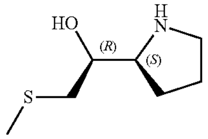 |
| WV-CA-334 | 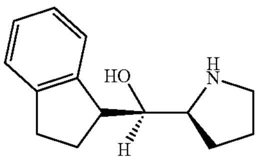 [SMILES: O[C@H](C1CCc2ccccc21)[C@@H]1CCCN1] | WV-CA-344 | 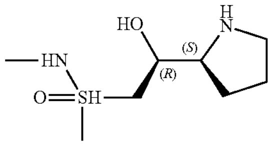 |
| WV-CA-335 | 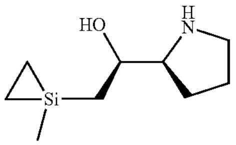 | WV-CA-344a | 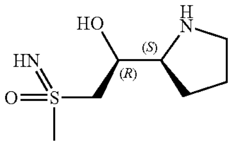 |
| WV-CA-336 | 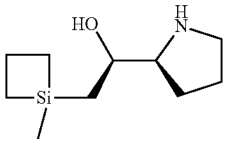 | WV-CA-345 | 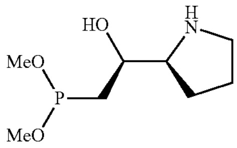 [SMILES: COP(C[C@@H](O)[C@@H]1CCCN1)OC] |
| WV-CA-337 | 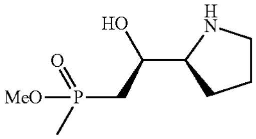 | WV-CA-346 | 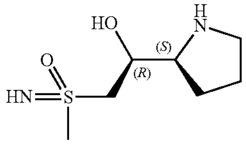 |
| WV-CA-338 | 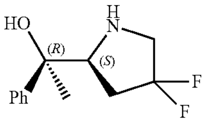 | WV-CA-347 | 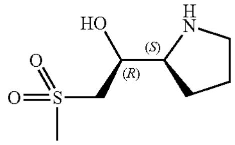 |
| WV-CA-339 | 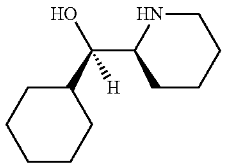 [SMILES: O[C@H](C1CCCCC1)[C@@H]1CCCCN1] | WV-CA-348 | 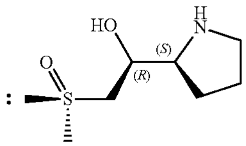 |

TABLE 1-continued
Example compounds.
| Compound No. | Structure | Compound No. | Structure |
|---|---|---|---|
| WV-CA-349 | 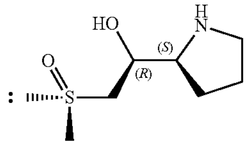 | WV-CA-358 | 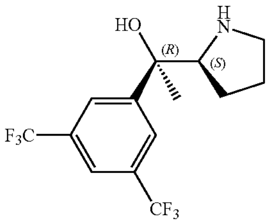 |
| WV-CA-350 | 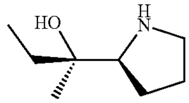 | WV-CA-359 | 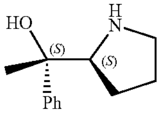 |
| WV-CA-351 | 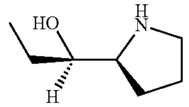 | WV-CA-360 | 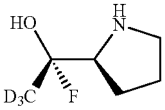 |
| WV-CA-352 | 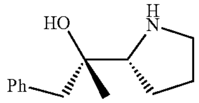 | WV-CA-361 | 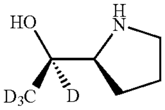 [SMILES: [2H]C([2H])([2H])[C@](O)(F)[C@@H]1CCCN1] |
| WV-CA-352a | 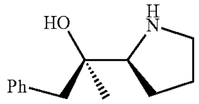 | WV-CA-363 | 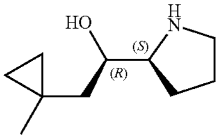 |
| WV-CA-353 | 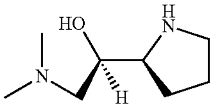 | WV-CA-364 | 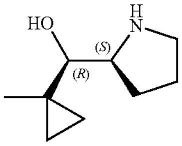 |
| WV-CA-354 | 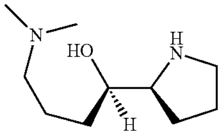 | WV-CA-365 | 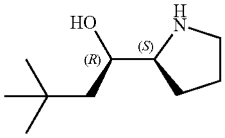 |
| WV-CA-355 | 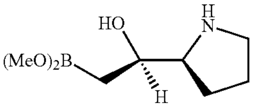 | WV-CA-366 | 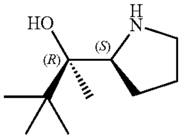 |
| WV-CA-356 | 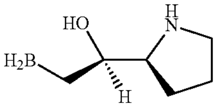 | WV-CA-367 | 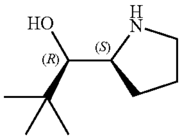 |
| WV-CA-357 | 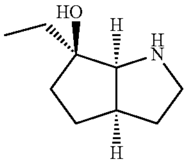 | WV-CA-368 | 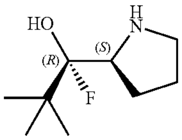 |

TABLE 1-continued
| Example compounds. | | | |
|---|---|---|---|
| Compound No. | Structure | Compound No. | Structure |
| WV-CA-369 | 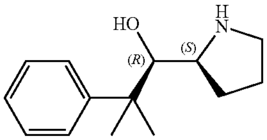 | WV-CA-369 | 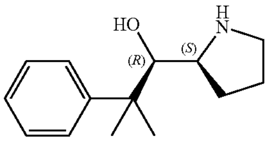 |
| WV-CA-370 | 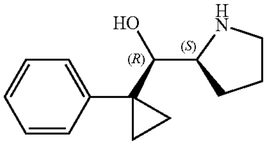 | WV-CA-370 | 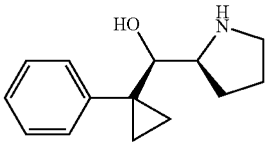 [SMILES: O[C@@H]([C@@H]1CCCN1)C1(c2ccccc2)CC1] |
| WV-CA-371 | 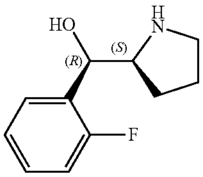 | WV-CA-371 | 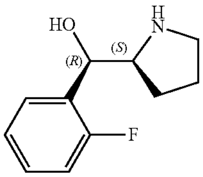 |
| WV-CA-372 | 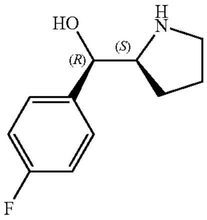 | WV-CA-372 | 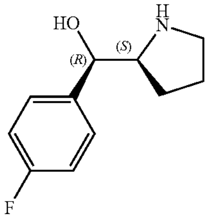 |
| WV-CA-373 | 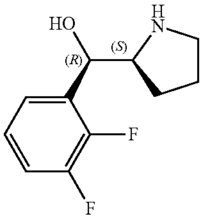 | WV-CA-373 | 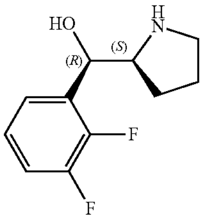 |
| WV-CA-374 | 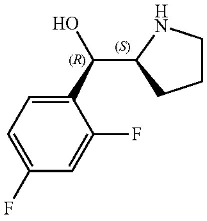 | WV-CA-374 | 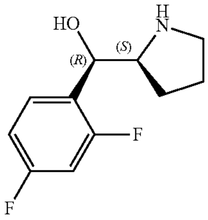 |
| WV-CA-375 | 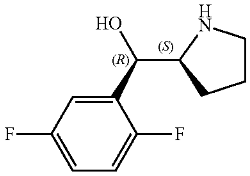 | WV-CA-375 | 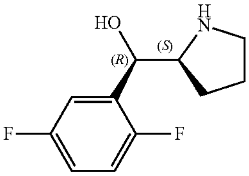 |
| WV-CA-376 | 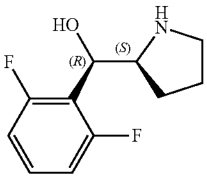 | WV-CA-376 | 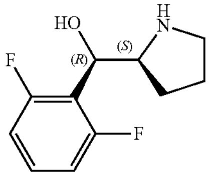 |

TABLE 1-continued
| Example compounds. | | | |
|---|---|---|---|
| Compound No. | Structure | Compound No. | Structure |
| WV-CA-377 | 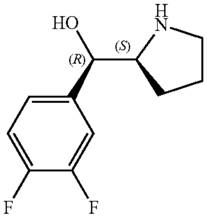 | WV-CA-377 | 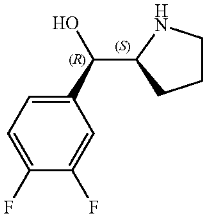 |
| WV-CA-378 | 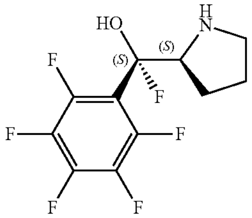 | WV-CA-378 | 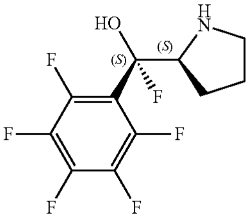 |
| WV-CA-379 | 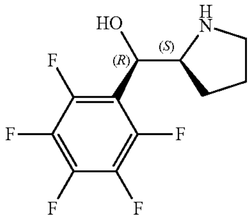 | WV-CA-395 | 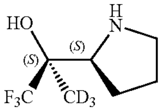 |
| WV-CA-380 | 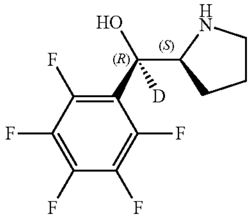 | WV-CA-396 | 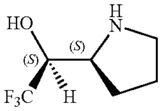 |
| WV-CA-381 | 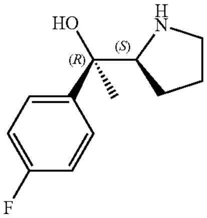 | WV-CA-397 | 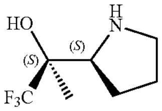 |
| WV-CA-382 | 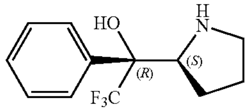 | WV-CA-398 | 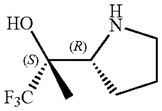 |
| WV-CA-383 | 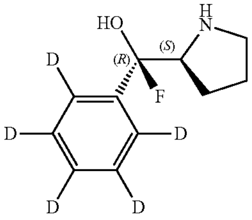 | WV-CA-398a | 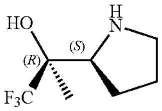 |

TABLE 1-continued

| Example compounds. | | | |
|---|---|---|---|
| Compound No. | Structure | Compound No. | Structure |
| WV-CA-384 | 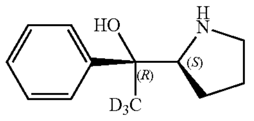 | WV-CA-399 | 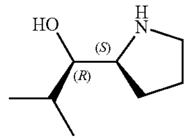 |
| WV-CA-385 | 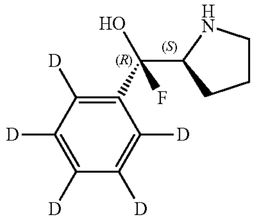 | WV-CA-400 | 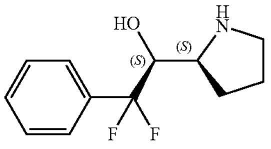 |
| WV-CA-385a | 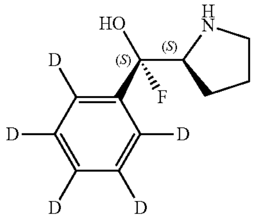 | WV-CA-408 | 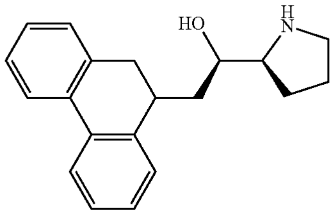 [SMILES: O[C@H](CC1Cc2ccccc2-c2ccccc21)[C@@H]1CCCN1] |
| WV-CA-386 | 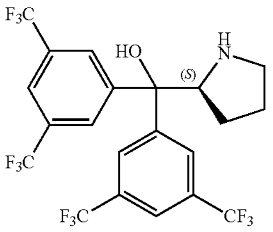 | WV-CA-409 | 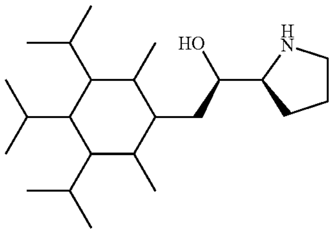 [SMILES: CC(C)C1C(C)C(C[C@@H](O)[C@@H]2CCCN2)C(C)C(C(C)C)C1C(C)C] |
| WV-CA-394 | 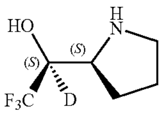 | WV-CA-410 | 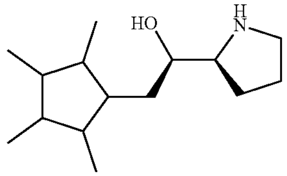 [SMILES: CC1C(C)C(C)C(C[C@@H](O)[C@@H]2CCCN2)C1C] |
| WV-CA-419 | 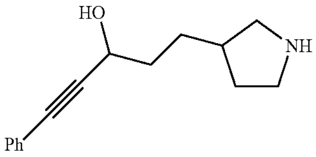 [SMILES: OC(C#Cc1ccccc1)CCC1CCNC1] | WV-CA-421 | 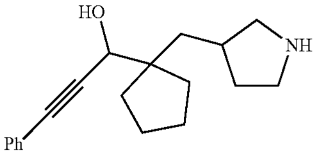 [SMILES: OC(C#Cc1ccccc1)C1(CC2CCNC2)CCCC1] |
| WV-CA-420 | 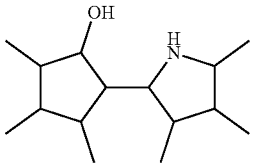 | | |

In some embodiments, a provided compound is an enantiomer of a compound selected from Table 1 or a salt thereof. In some embodiments, a provided compound is a diastereomer of a compound selected from Table 1 or a salt thereof.

TABLE 2
Example compounds.
| Compound No. | Structure | Compound No. | Structure |
|---|---|---|---|
| WV-CA-007 | 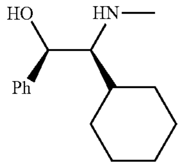 [SMILES: CN[C@@H](C1CCCCC1)[C@H](O)c1ccccc1] | WV-CA-025 | 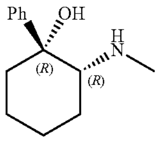 |
| WV-CA-008 | 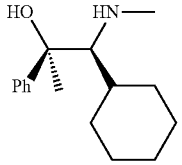 [SMILES: CN[C@@H](C1CCCCC1)[C@](C)(O)c1ccccc1] | WV-CA-026 | 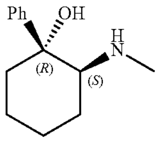 |
| WV-CA-008-S | 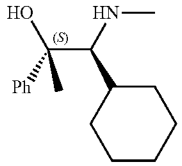 | WV-CA-027 | 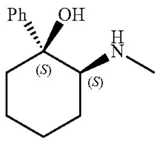 |
| WV-CA-009 | 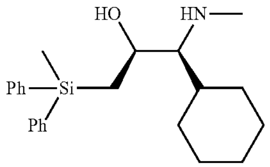 [SMILES: CN[C@@H](C1CCCCC1)[C@H](O)C[Si](C)(c1ccccc1)c1ccccc1] | WV-CA-028 | 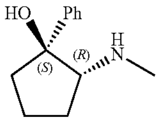 |
| WV-CA-010 | 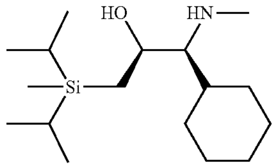 [SMILES: CN[C@@H](C1CCCCC1)[C@H](O)C[Si](C)(C(C)C)C(C)C] | WV-CA-029 | 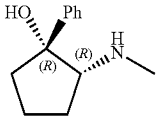 |
| WV-CA-017 | 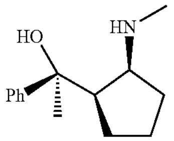 [SMILES: CN[C@H]1CCC[C@H]1[C@](C)(O)c1ccccc1] | WV-CA-030 | 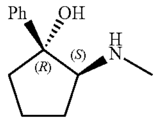 |
| WV-CA-018 | 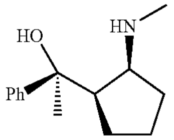 [SMILES: CN[C@H]1CCC[C@H]1[C@](C)(O)c1ccccc1] | WV-CA-031 | 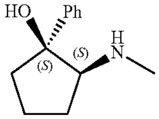 |
| WV-CA-019 | 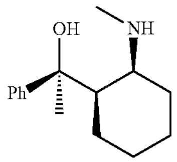 [SMILES: CN[C@H]1CCCC[C@H]1[C@](C)(O)c1ccccc1] | WV-CA-032 | 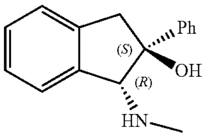 |
| WV-CA-020 | 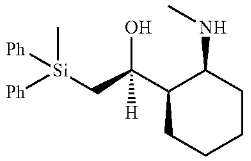 [SMILES: CN[C@H]1CCCC[C@H]1[C@H](O)C[Si](C)(c1ccccc1)c1ccccc1] | WV-CA-033 | 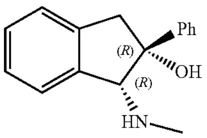 |

TABLE 2-continued
Example compounds.
| Compound No. | Structure | Compound No. | Structure |
|---|---|---|---|
| WV-CA-024 | 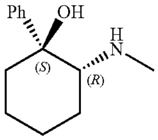 | WV-CA-034 | 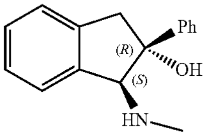 |
| WV-CA-035 | 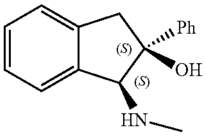 | WV-CA-070-S | 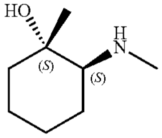 |
| WV-CA-036 | 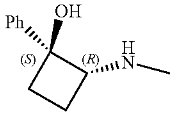 | WV-CA-071S | 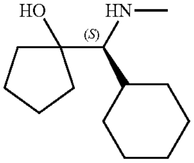 |
| WV-CA-037 | 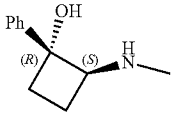 | WV-CA-075-S | 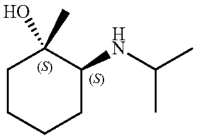 |
| WV-CA-038 | 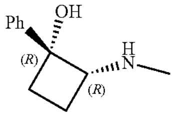 | WV-CA-092 | 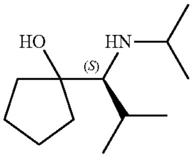 |
| WV-CA-039 | 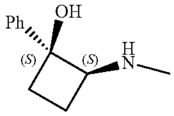 | WV-CA-114 | 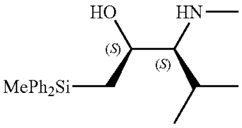 |
| WV-CA-047 | 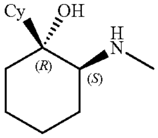 | WV-CA-115 | 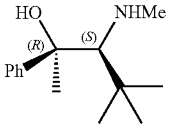 |
| WV-CA-055 | 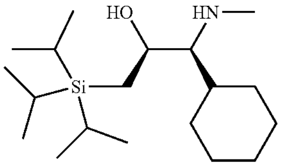 [SMILES: CN[C@@H](C1CCCCC1)[C@H](O)C[Si](C(C)C)(C(C)C)C(C)C] | WV-CA-135 | 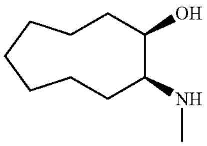 |
| WV-CA-061 | 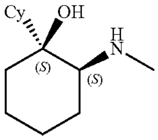 | WV-CA-136 | 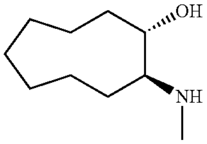 |

TABLE 2-continued
| Example compounds. | | | |
|---|---|---|---|
| Compound No. | Structure | Compound No. | Structure |
| WV-CA-066-R | 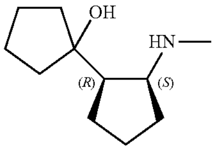 | WV-CA-137 | 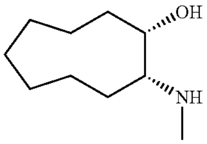 |
| WV-CA-070 | 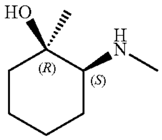 | WV-CA-138 | 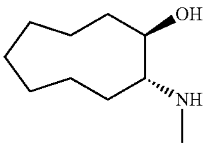 |
| WV-CA-139 | 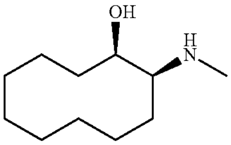 | WV-CA-169 | 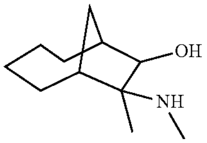 |
| WV-CA-140 | 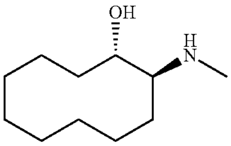 | WV-CA-170 | 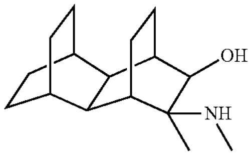 [SMILES: CNC1(C)C(O)C2CCC1C1C3CCC(CC3)C21] |
| WV-CA-141 | 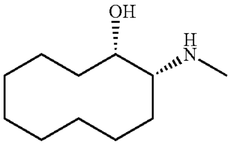 | WV-CA-171 | 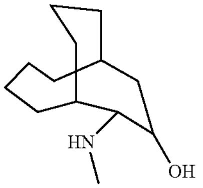 |
| WV-CA-142 | 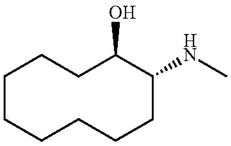 | WV-CA-205 | 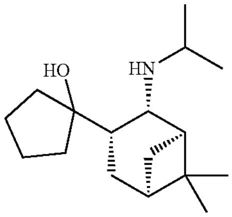 [SMILES: CC(C)N[C@H]1[C@@H](C2(O)CCCC2)C[C@H]2C[C@@H]1C2(C)C] |
| WV-CA-158 | 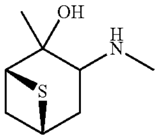 | WV-CA-207 | 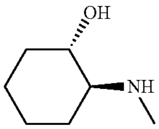 |
| WV-CA-159 | 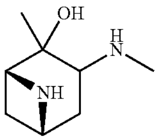 | WV-CA-208 | 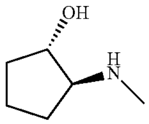 |
| WV-CA-160 | 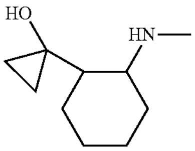 | WV-CA-210 | 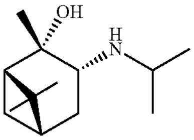 |

TABLE 2-continued
| Example compounds. | | | |
|---|---|---|---|
| Compound No. | Structure | Compound No. | Structure |
| WV-CA-161 | 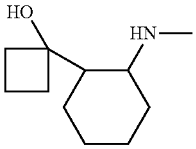 | WV-CA-211 | 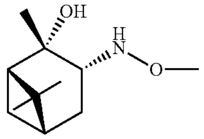 |
| WV-CA-162 | 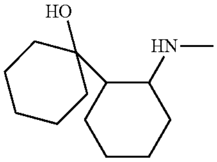 | WV-CA-216 | 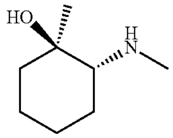 |
| WV-CA-168 | 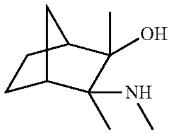 | WV-CA-217 | 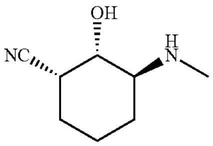 |
| WV-CA-218 | 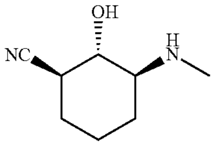 | WV-CA-302 | 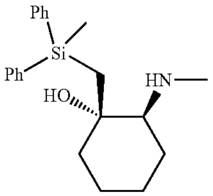 [SMILES: CN[C@H]1CCCC[C@@]1(O)C[Si](C)(c1ccccc1)c1ccccc1] |
| WV-CA-219 | 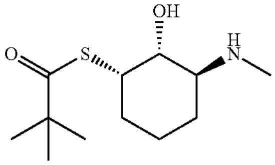 [SMILES: CN[C@H]1CCC[C@H](SC(=O)C(C)(C)C)[C@@H]1O] | WV-CA-303 | 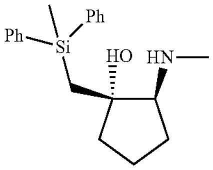 [SMILES: CN[C@H]1CCC[C@@]1(O)C[Si](C)(c1ccccc1)c1ccccc1] |
| WV-CA-220 | 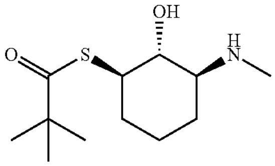 [SMILES: CN[C@H]1CCC[C@@H](SC(=O)C(C)(C)C)[C@@H]1O] | WV-CA-305 | 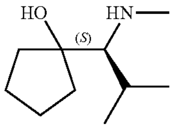 |
| WV-CA-221 | 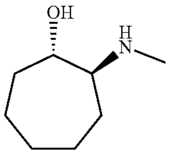 | WV-CA-362 | 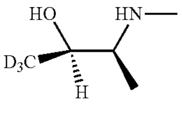 |
| WV-CA-222 | 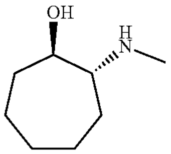 | WV-CA-387 | 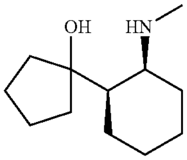 |

TABLE 2-continued
Example compounds.
| Compound No. | Structure | Compound No. | Structure |
| --- | --- | --- | --- |
| WV-CA-223 | 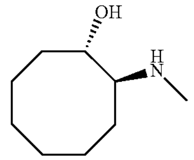 | WV-CA-388 | 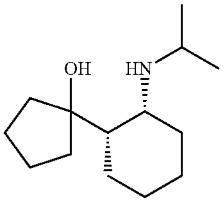 [SMILES: CC(C)N[C@@H]1CCCC[C@@H]1C1(O)CCCC1] |
| WV-CA-224 | 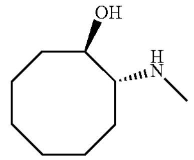 | WV-CA-389 | 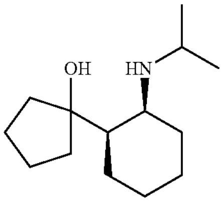 [SMILES: CC(C)N[C@H]1CCCC[C@H]1C1(O)CCCC1] |
| WV-CA-228 | 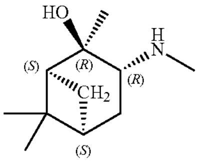 | WV-CA-390 | 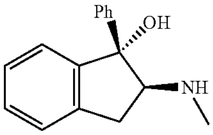 [SMILES: CN[C@H]1Cc2ccccc2[C@@]1(O)c1ccccc1] |
| WV-CA-232 | 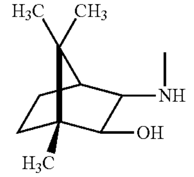 | WV-CA-391 | 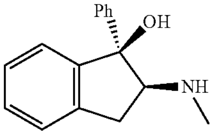 [SMILES: CN[C@H]1Cc2ccccc2[C@]1(O)c1ccccc1] |
| WV-CA-235 | 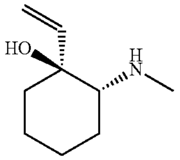 | WV-CA-392 | 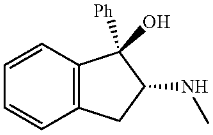 [SMILES: CN[C@@H]1Cc2ccccc2[C@]1(O)c1ccccc1] |
| WV-CA-393 | 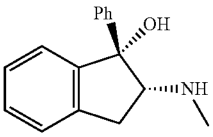 [SMILES: CN[C@@H]1Cc2ccccc2[C@@]1(O)c1ccccc1] | WV-CA-412 | 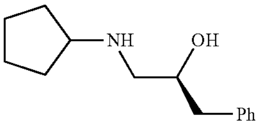 [SMILES: O[C@H](CNC1CCCC1)Cc1ccccc1] |
| WV-CA-401 | 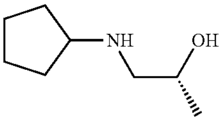 | WV-CA-413 | 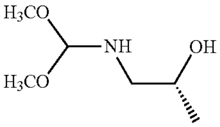 |
| WV-CA-402 | 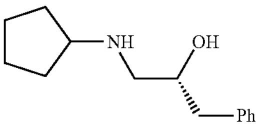 [SMILES: O[C@@H](CNC1CCCC1)Cc1ccccc1] | WV-CA-414 | 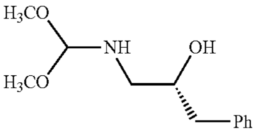 [SMILES: COC(NC[C@H](O)Cc1ccccc1)OC] |

TABLE 2-continued

| Example compounds. | | | |
|---|---|---|---|
| Compound No. | Structure | Compound No. | Structure |
| WV-CA-404 | 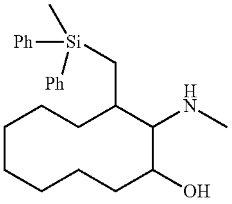 [SMILES: CNC1C(O)CCCCCCCC1C[Si](C)(c1ccccc1)c1ccccc1] | WV-CA-415 | 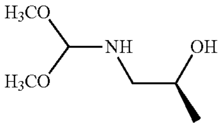 |
| WV-CA-405 | 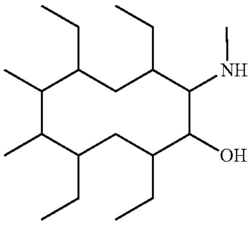 | WV-CA-416 | 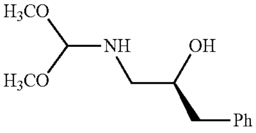 [SMILES: COC(NC[C@@H](O)Cc1ccccc1)OC] |
| WV-CA-406 | 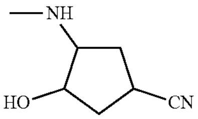 | WV-CA-417 | 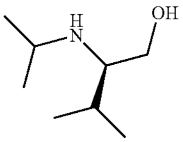 |
| WV-CA-407 | 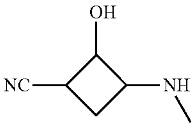 | WV-CA-418 | 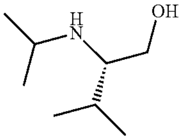 |
| WV-CA-411 | 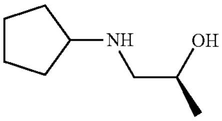 | | |

In some embodiments, a provided compound is an enantiomer of a compound selected from Table 2 or a salt thereof. In some embodiments, a provided compound is a diastereomer of a compound selected from Table 2 or a salt thereof.

TABLE 3

| Example compounds. | | | |
|---|---|---|---|
| Compound No. | Structure | Compound No. | Structure |
| WV-CA-085 | 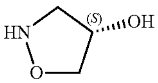 | WV-CA-179 | 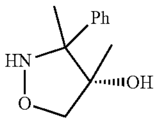 |
| WV-CA-086 | 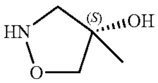 | WV-CA-184 | 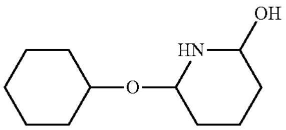 [SMILES: OC1CCCC(OC2CCCCC2)N1] |

TABLE 3-continued
Example compounds.
| Compound No. | Structure | Compound No. | Structure |
| --- | --- | --- | --- |
| WV-CA-087 | 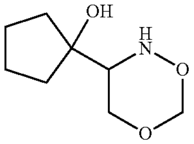 [SMILES: OC1(C2COCON2)CCCC1] | WV-CA-185 | 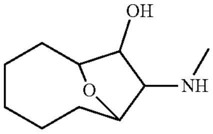 |
| WV-CA-087a | 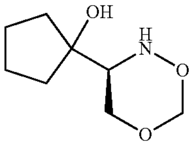 [SMILES: OC1([C@@H]2COCON2)CCCC1] | WV-CA-186 | 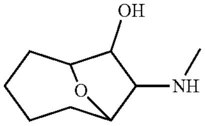 |
| WV-CA-087b | 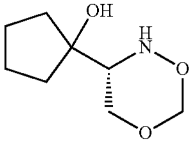 [SMILES: OC1([C@H]2COCON2)CCCC1] | WV-CA-187 | 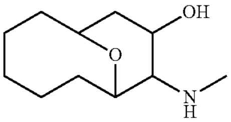 |
| WV-CA-095 | 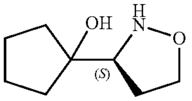 | WV-CA-189 | 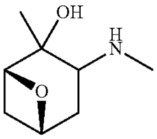 |
| WV-CA-143 | 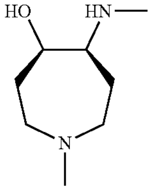 | WV-CA-190 | 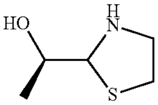 |
| WV-CA-144 | 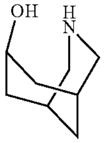 | WV-CA-191 | 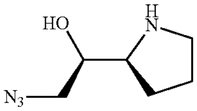 [SMILES: [N-]=[N+]=NC[C@@H](O)[C@@H]1CCCN1] |
| WV-CA-177 | 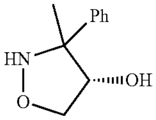 | WV-CA-192 | 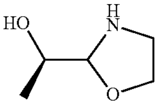 |
| WV-CA-178 | 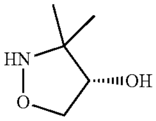 | WV-CA-193 | 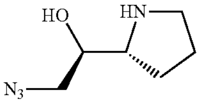 |
| WV-CA-194 | 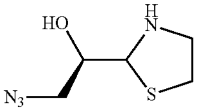 | WV-CA-212 | 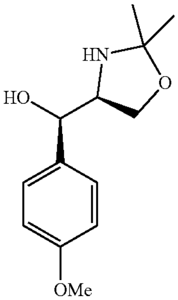 [SMILES: COc1ccc([C@@H](O)[C@@H]2COC(C)(C)N2)cc1] |

TABLE 3-continued

| Example compounds. | | | |
|---|---|---|---|
| Compound No. | Structure | Compound No. | Structure |
| WV-CA-195 | 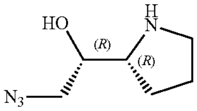 | WV-CA-213 | 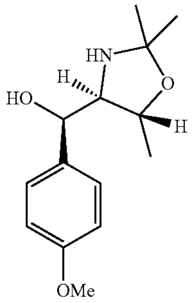 [SMILES: COc1ccc([C@@H](O)[C@H]2NC(C)(C)O[C@@H]2C)cc1] |
| WV-CA-196 | 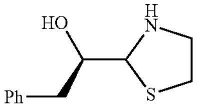 | WV-CA-214 | 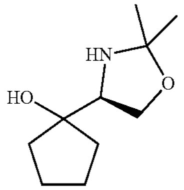 |
| WV-CA-197 | 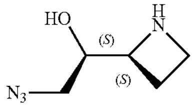 | WV-CA-215 | 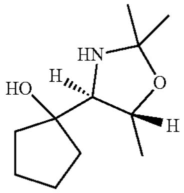 |
| WV-CA-198 | 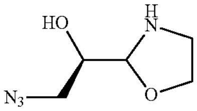 | WV-CA-403 | 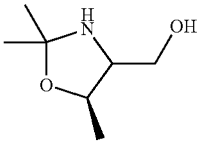 |
| WV-CA-199 | 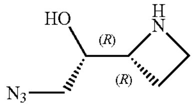 | WV-CA-422 | 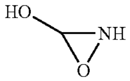 |
| WV-CA-200 | 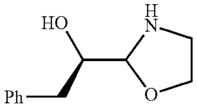 | | |

In some embodiments, a provided compound is an enantiomer of a compound selected from Table 3 or a salt thereof. In some embodiments, a provided compound is a diastereomer of a compound selected from Table 3 or a salt thereof.

TABLE 4

| Example compounds |
|---|
| 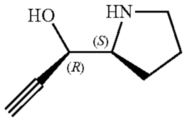 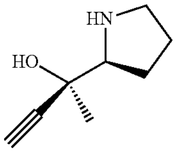 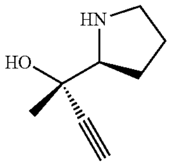 |

TABLE 4-continued
Example compounds
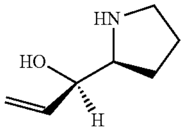 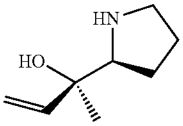
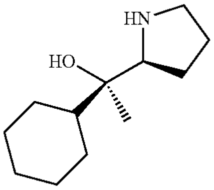 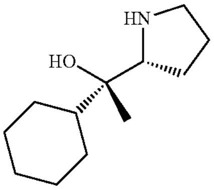
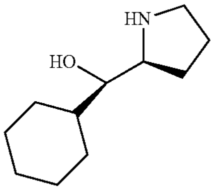 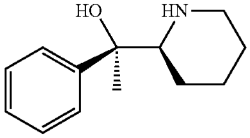
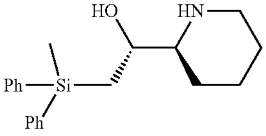 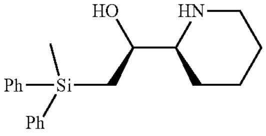
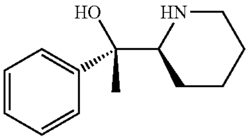 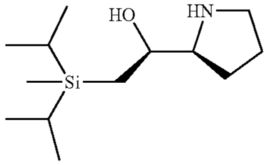
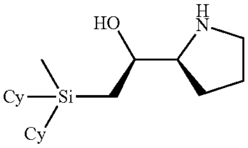 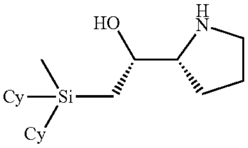
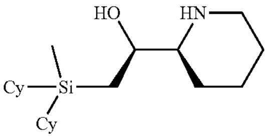 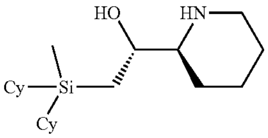
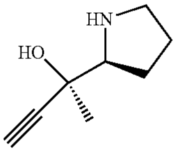 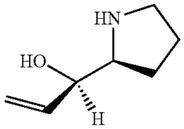
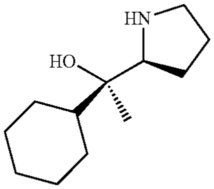 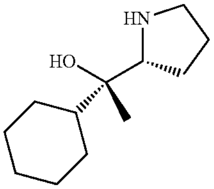 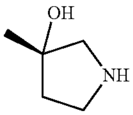
TABLE 4-continued
Example compounds
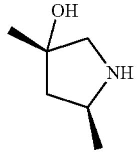 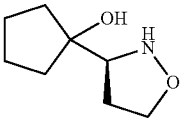 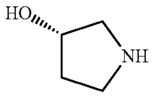
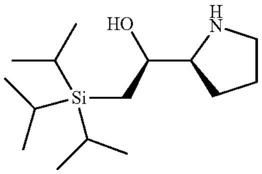 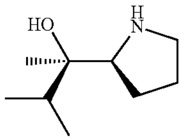
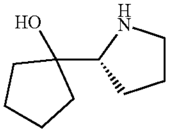 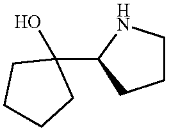 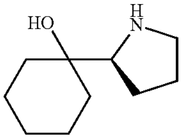
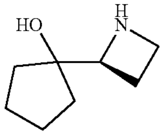 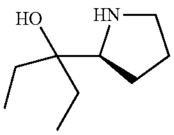 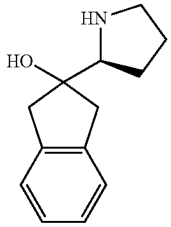
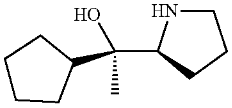 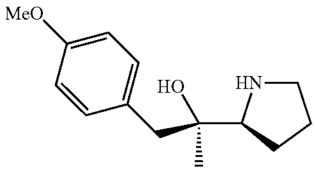
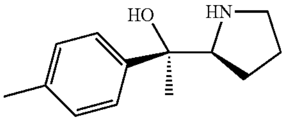 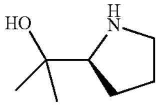
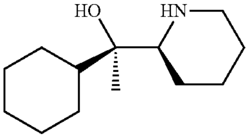 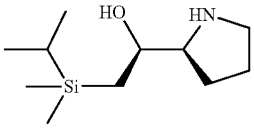
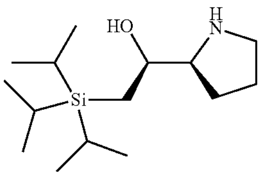 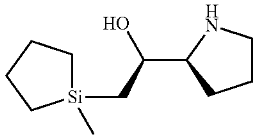
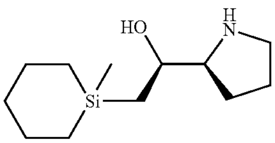 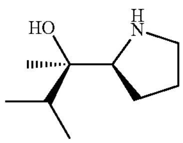

TABLE 4-continued
Example compounds
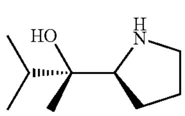
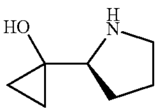
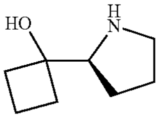
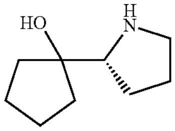
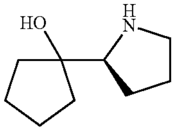
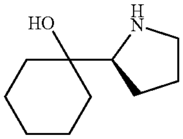
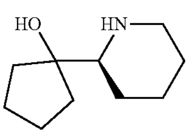
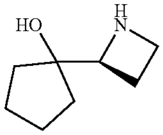
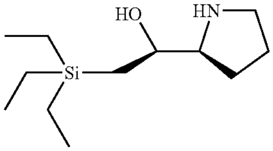
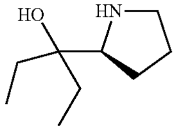
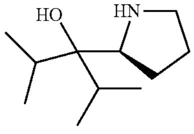
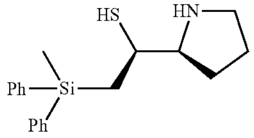
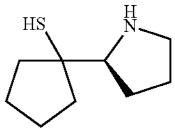
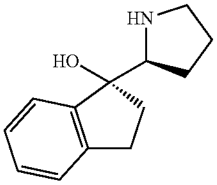
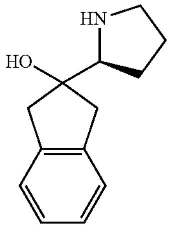
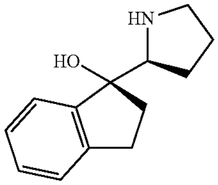
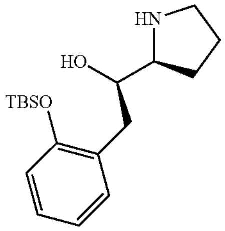
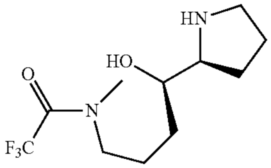
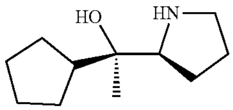
TABLE 4-continued
Example compounds
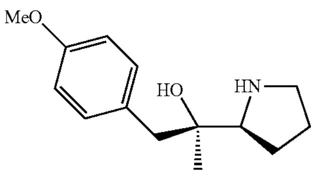
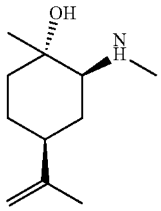
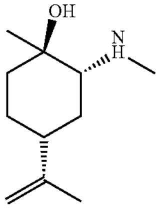
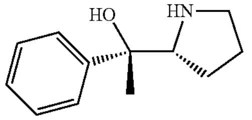
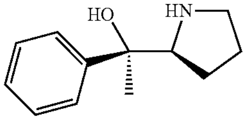
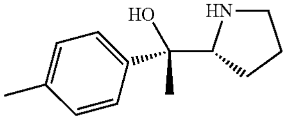
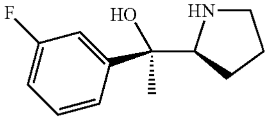
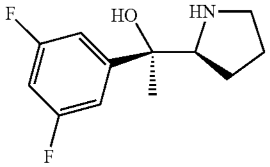
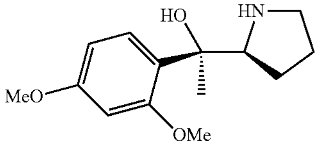
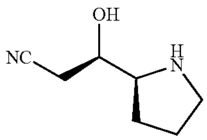
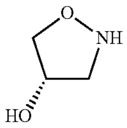
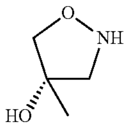
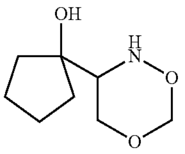
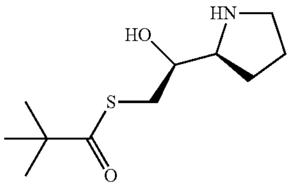
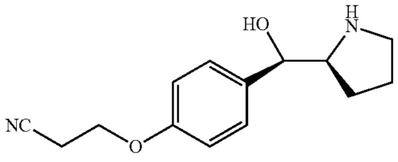
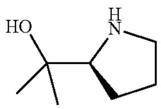
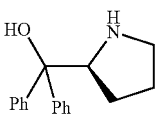
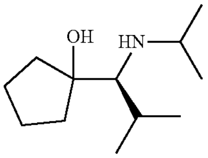
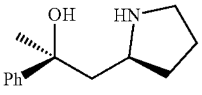

TABLE 4-continued
Example compounds
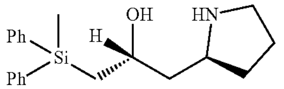
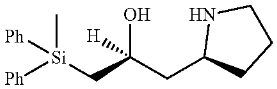
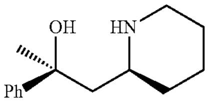
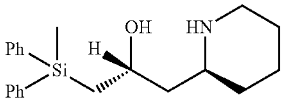
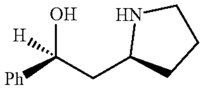
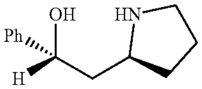
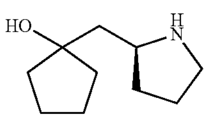
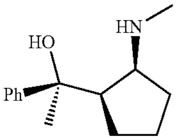
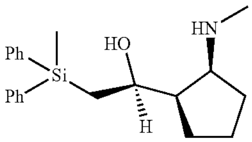
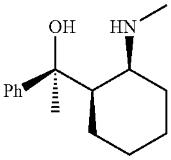
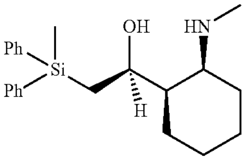
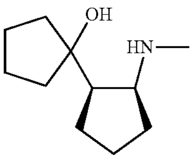
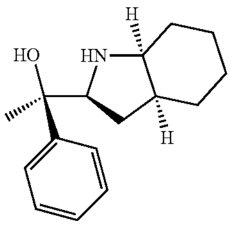
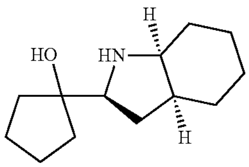
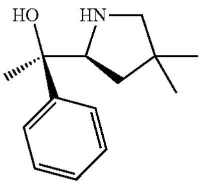
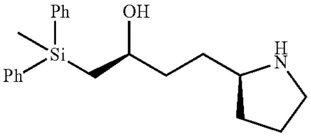
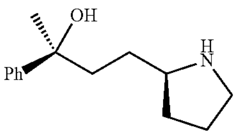
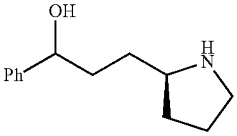
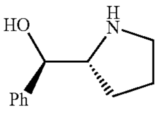
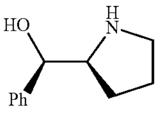
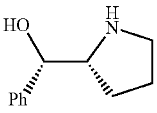
TABLE 4-continued
Example compounds
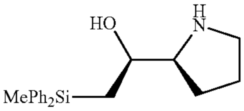
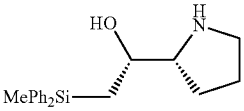
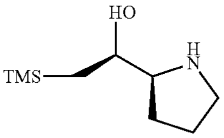
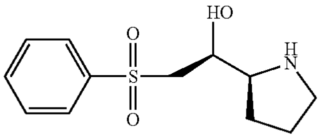
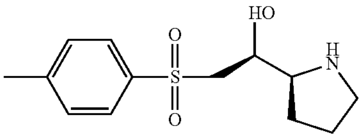 [SMILES: Cc1ccc(S(=O)(=O)C[C@@H](O)[C@@H]2CCCN2)cc1]
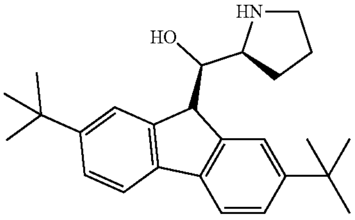 [SMILES: CC(C)(C)c1ccc2c(c1)C([C@@H](O)[C@@H]1CCCN1)c1cc(C(C)(C)C)ccc1-2]
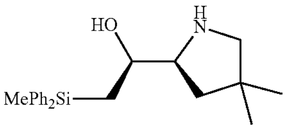
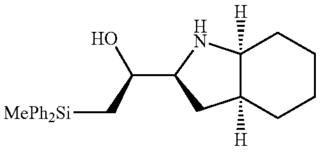
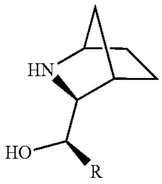
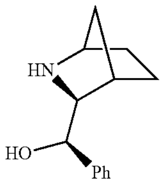
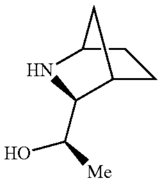
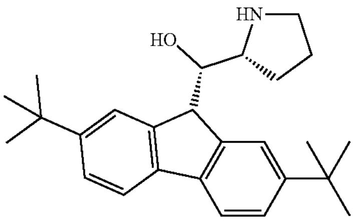 [SMILES: CC(C)(C)c1ccc2c(c1)C([C@H](O)[C@H]1CCCN1)c1cc(C(C)(C)C)ccc1-2]
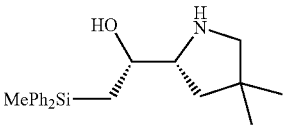

TABLE 4-continued
Example compounds
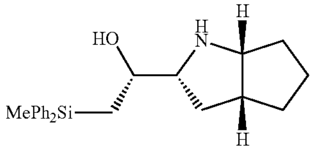
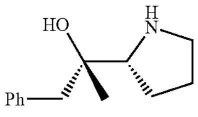
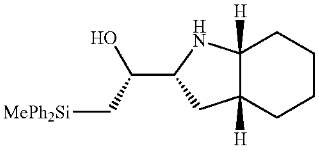
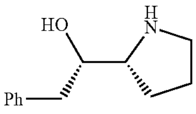
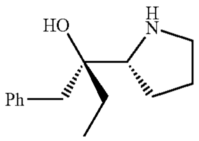
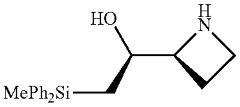
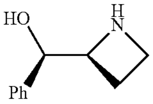
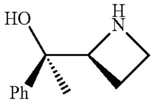
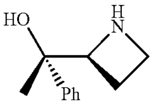
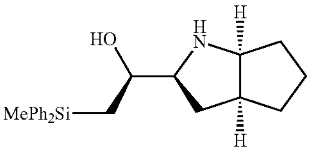
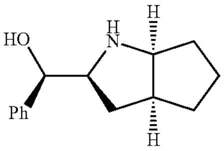
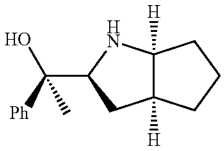
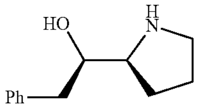
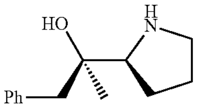
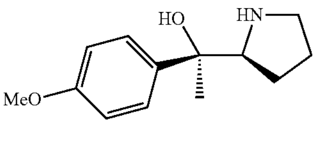
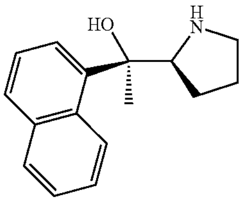
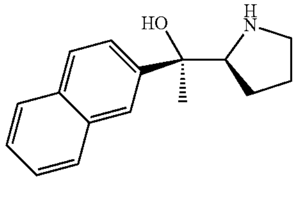
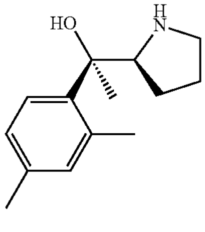
TABLE 4-continued
Example compounds
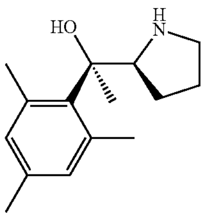
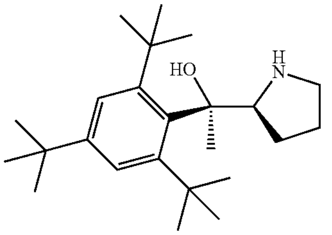
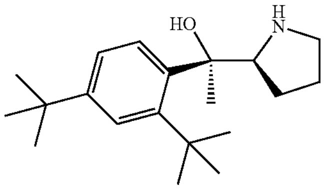
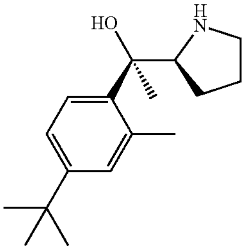
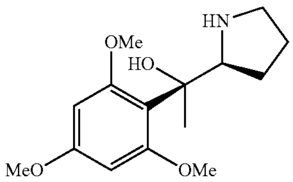
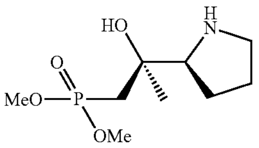
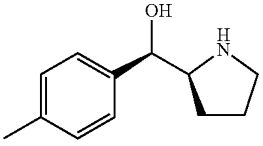
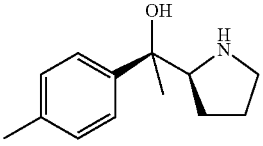
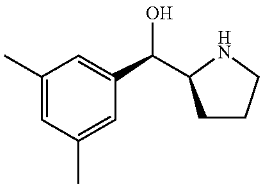
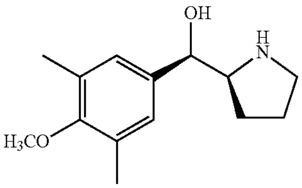
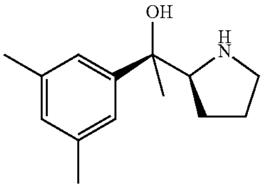
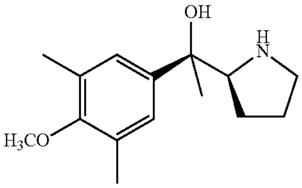
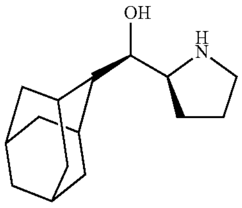
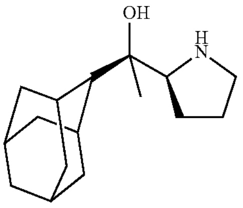

TABLE 4-continued
Example compounds
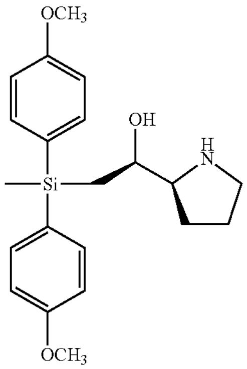
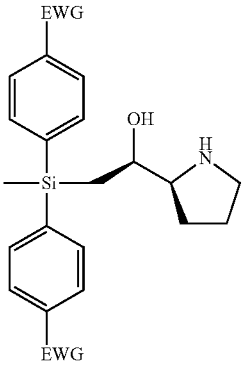
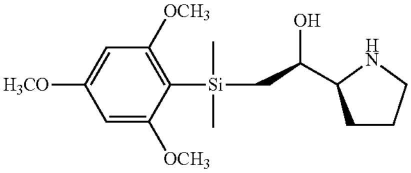 [SMILES: COc1cc(OC)c([Si](C)(C)C[C@@H](O)[C@@H]2CCCN2)c(OC)c1]
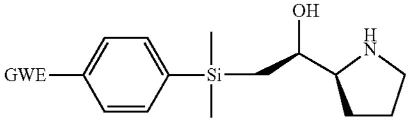
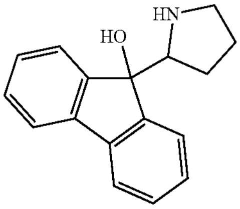
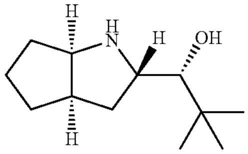
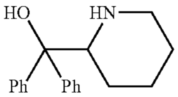
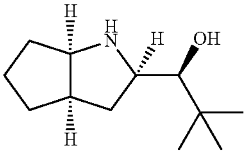
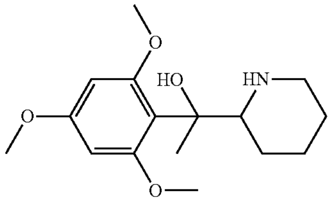 [SMILES: COc1cc(OC)c(C(C)(O)C2CCCCN2)c(OC)c1]
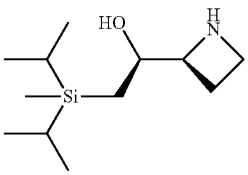
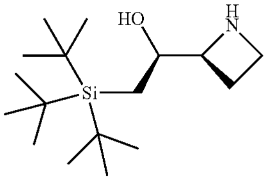
TABLE 4-continued
Example compounds
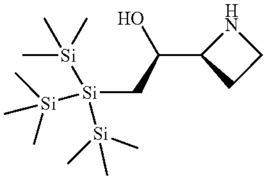
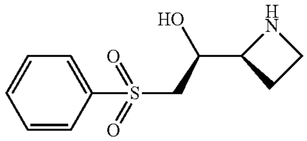
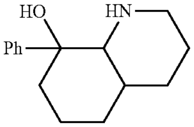
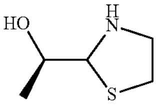
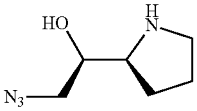
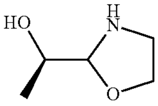
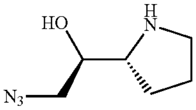
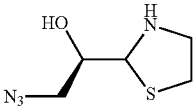
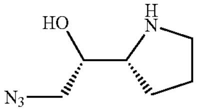
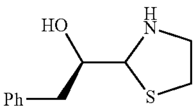
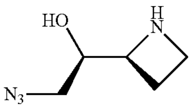
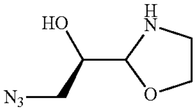
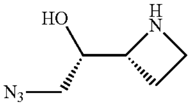
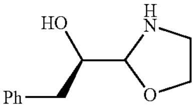
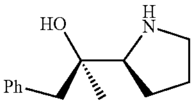
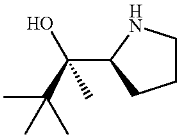
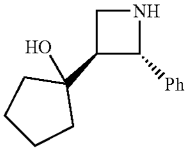
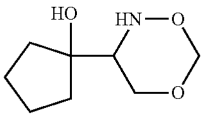
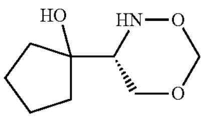
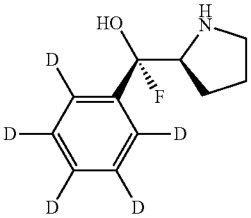

TABLE 4-continued
| Example compounds |
|---|
| 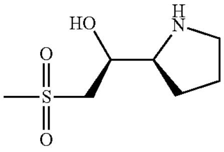 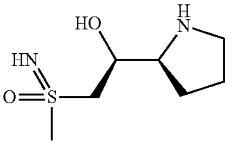 |
| 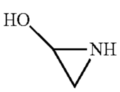 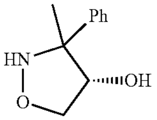 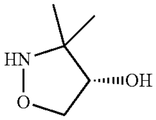 |
| 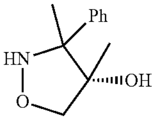 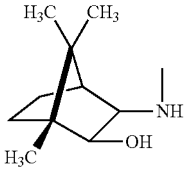 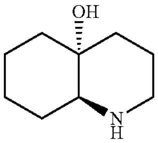 |
| 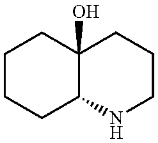 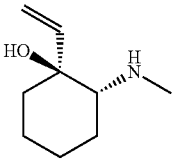 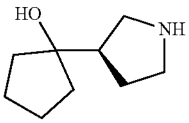 |
| 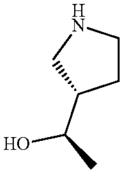 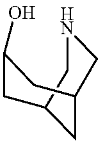 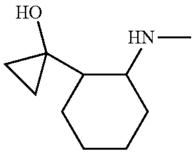 |
| 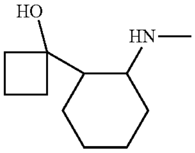 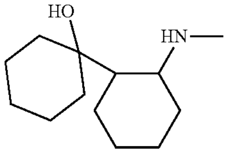 |
| 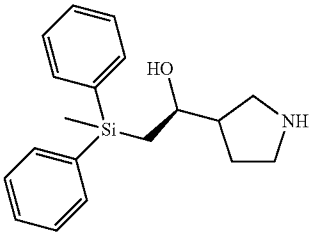 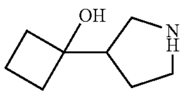 |
| 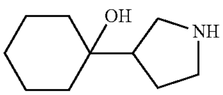 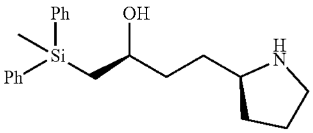 |
| 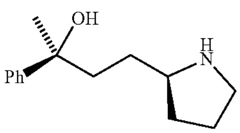 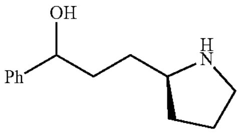 |
TABLE 4-continued
| Example compounds |
|---|
| 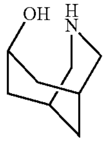 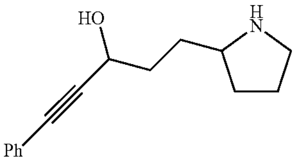 |
| 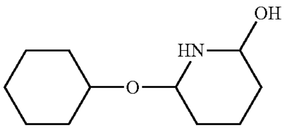 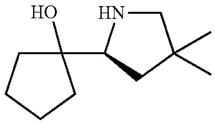 |
| 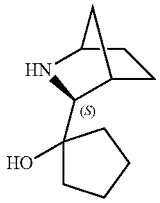 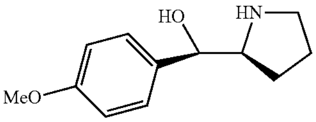 |
| 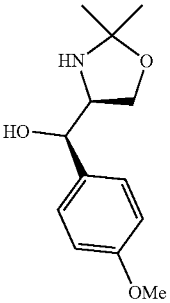 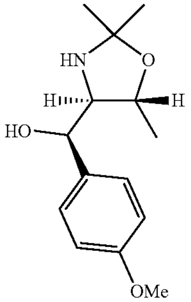 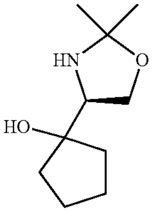 |
| 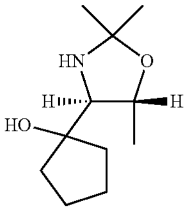 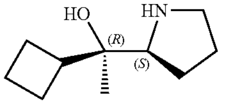 |
| 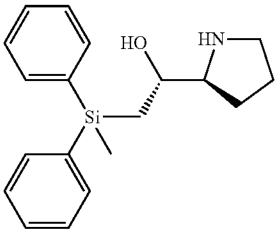 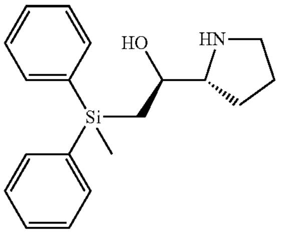 |
| 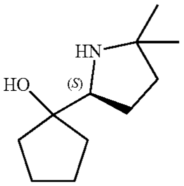 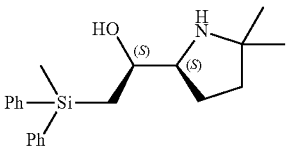 |

TABLE 4-continued
Example compounds
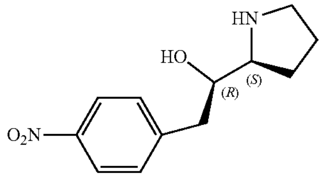
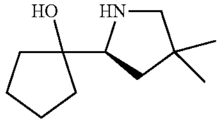
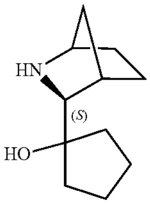
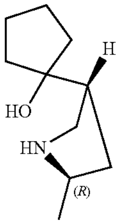
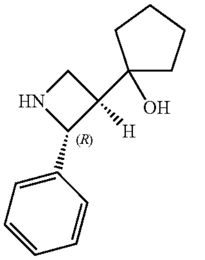
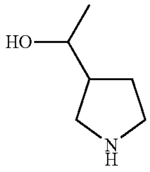
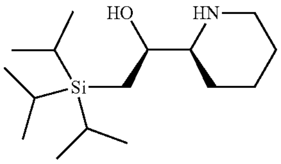
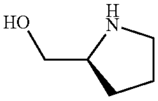
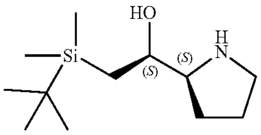
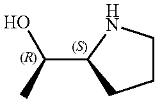
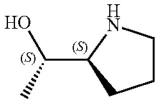
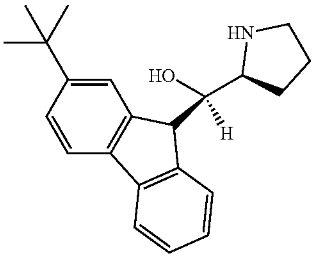 [SMILES: CC(C)(C)c1ccc2c(c1)C([C@@H](O)[C@@H]1CCCN1)c1ccccc1-2]
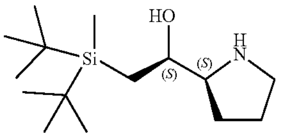
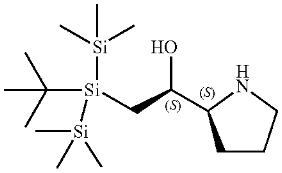
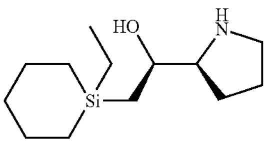
TABLE 4-continued
Example compounds
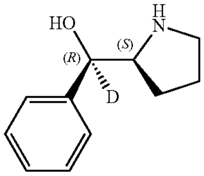
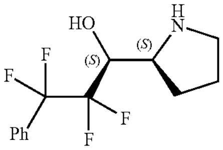
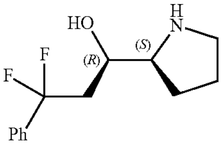
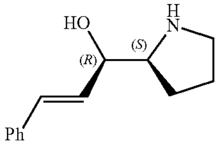
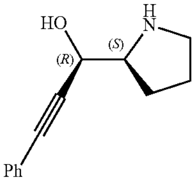
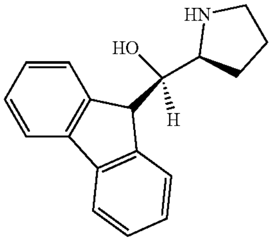
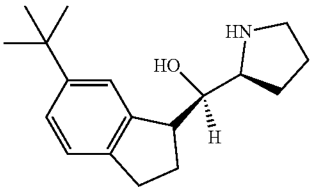
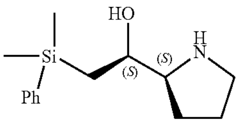
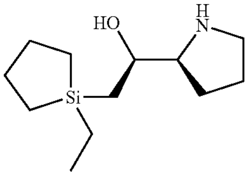
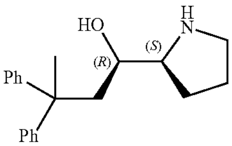
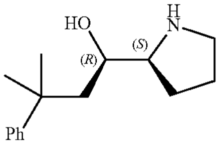
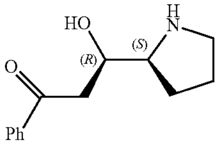
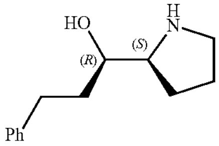
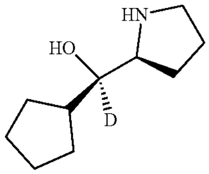
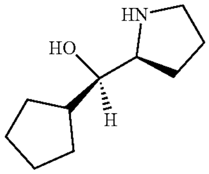
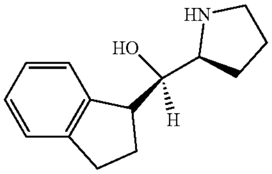

TABLE 4-continued
Example compounds
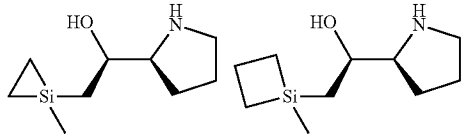
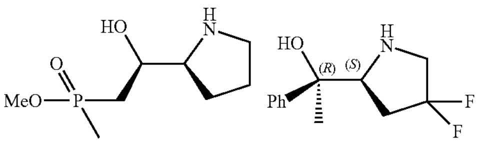
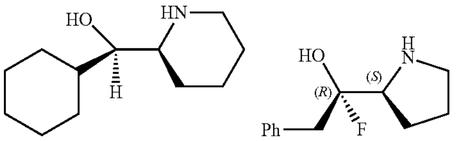
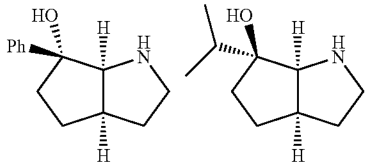
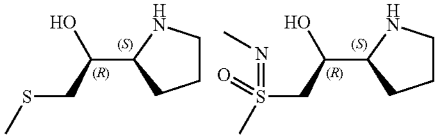
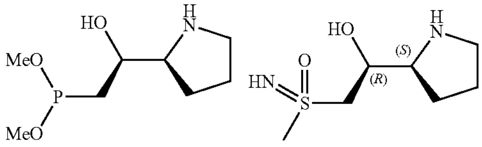
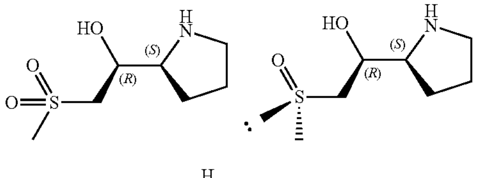
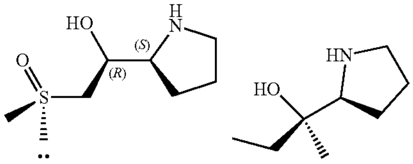
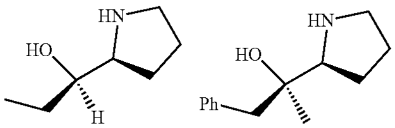
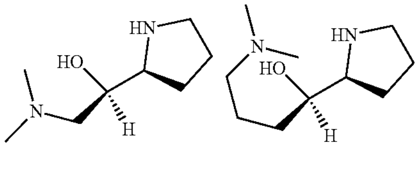
TABLE 4-continued
Example compounds
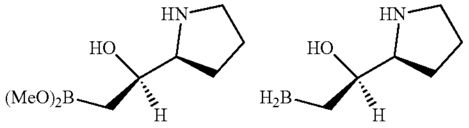
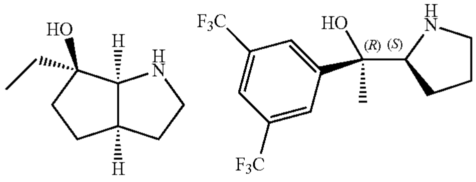
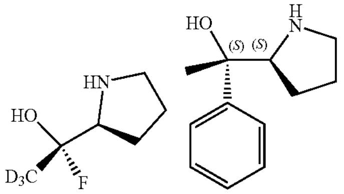
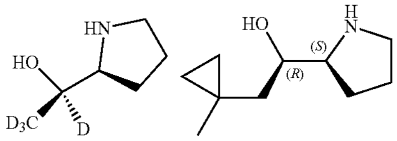
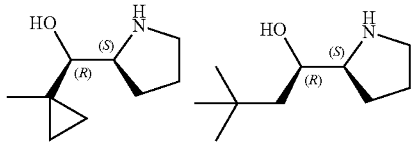
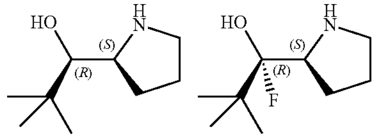
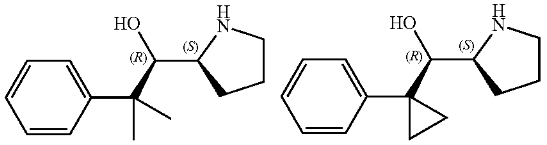
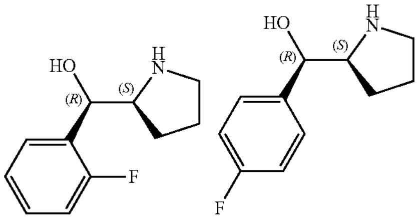
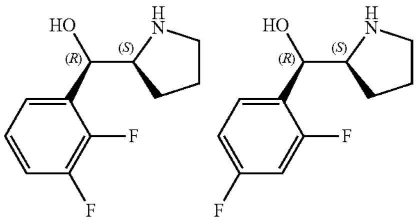

TABLE 4-continued

| Example compounds |
|---|
| 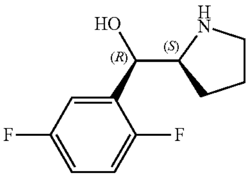 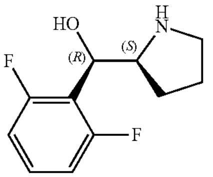 |
| 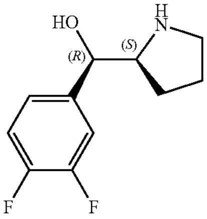 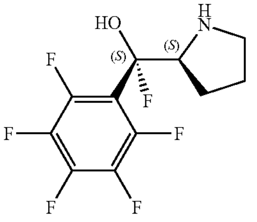 |
| 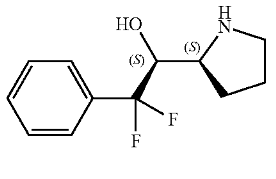 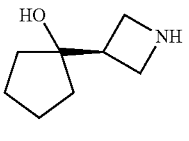 |
| 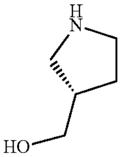 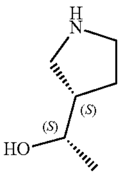 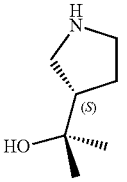 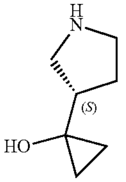 |
| 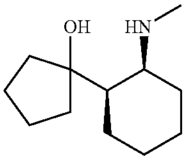 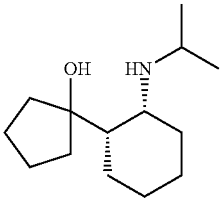 |
| 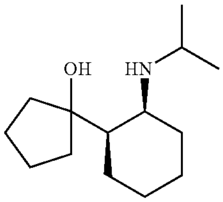 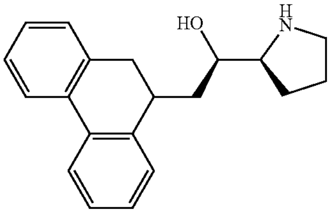 |
| 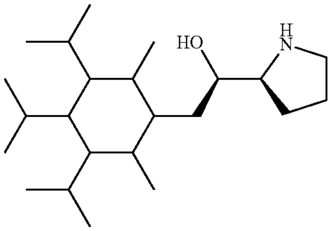 [SMILES: CC(C)C1C(C)C(C[C@@H](O)[C@@H]2CCCN2)C(C)C(C(C)C)C1C(C)C] |

TABLE 4-continued

| Example compounds |
|---|
| 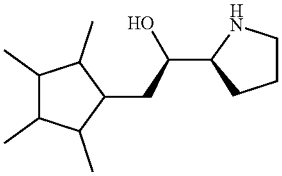 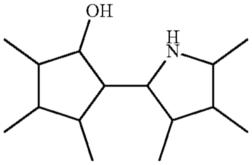 |
| 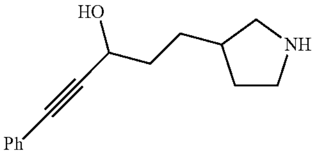 [SMILES: OC(C#Cc1ccccc1)CCC1CCNC1] |
| 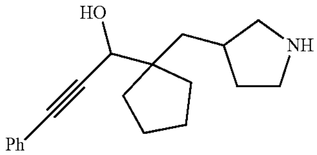 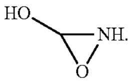 |

In some embodiments, a provided compound is an enantiomer of a compound selected from Table 4 or a salt thereof. In some embodiments, a provided compound is a diastereomer of a compound selected from Table 4 or a salt thereof.

In some embodiments, a chiral auxiliary can be readily removed by a base (base-labile, e.g., under an anhydrous condition substantially free of water; in many instances, preferably before oligonucleotides comprising internucleotidic linkages comprising such chiral auxiliaries are exposed to conditions/reagent systems comprising a substantial amount of water, particular in the presence of a base(e.g., cleavage conditions/reagent systems using $NH_4OH$)) and provides various advantages as described herein, e.g., high crude purity, high yield, high stereoselectivity, more simplified operation, fewer steps, further reduced manufacture cost, and/or more simplified downstream formulation (e.g., low amount of salt(s) after cleavage), etc. In some embodiments, such auxiliaries may provide alternative or additional chemical compatibility with other functional and/or protection groups. In some embodiments, base-labile chiral auxiliaries are particularly useful for construction of chirally controlled non-negatively charged internucleotidic linkages (e.g., neutral internucleotidic linkages such as n001); in some instances, they can provide significantly improved yield and/or crude purity with high stereoselectivity, e.g., when utilized with removal using a base under an anhydrous condition. In some embodiments, such a chiral auxiliary is bonded to a linkage phosphorus via an oxygen atom (e.g., which corresponds to a —OH group in a corresponding chiral auxiliary compound, e.g., a compound of formula I), the carbon atom in the chiral auxiliary to which the oxygen is bonded (the alpha carbon) also bonds to —H (in addition to other groups; in some embodiments, a secondary carbon), and the next carbon atom (the beta carbon) in the chiral auxiliary is boned to one or two electron-withdrawing groups. In some embodiments, $R^7$ is —OH. In some embodiments, $R^1$ is —H. In some embodiments, $R^2$ comprises one or two electron-withdrawing groups or can otherwise facilitate remove of the chiral auxiliary by a base. In some embodiments, $R^6$ is —H. In some embodiments, $R^1$ is —H, $R^2$ comprises one or two electron-withdrawing groups, $R^6$ is —H, $R^7$ is —OH. In some embodiments, $R^1$ is —H, $R^2$ comprises one or two electron-withdrawing groups, R is —H, $R^7$ is —OH, and a methylene unit of L is replaced with —$C(R^3)(R^4)$—, and one of $R^3$ and $R^4$ is taken together with $R^5$ to form with their intervening atoms a ring as described herein (e.g., an optionally substituted 3-20 membered monocyclic, bicyclic or polycyclic ring having in addition to the nitrogen atom to which $R^5$ is on, 0-5 heteroatoms (e.g., an optionally substituted 3, 4, 5, or 6-membered monocyclic saturated ring having in addition to the nitrogen atom to which $R^5$ is on no other heteroatoms)).

As appreciated by those skilled in the art, various electron-withdrawing groups are known in the art and can be utilized in accordance with the present disclosure. In some embodiments, an electronic-withdrawing group comprises and/or is connected to the carbon atom through, e.g., —S(O)—, —$S(O)_2$—, —$P(O)(R^1)$—, —$P(S)R^1$—, or —C(O)—. In some embodiments, an electron-withdrawing group is —CN, —$NO_2$, halogen, —$C(O)R^1$, —C(O)OR', —$C(O)N(R')_2$, —$S(O)R^1$, —$S(O)_2R^1$, —$P(W)(R^1)_2$, —$P(O)(R^1)_2$, —$P(O)(OR')_2$, or —$P(S)(R^1)_2$. In some embodiments, an electron-withdrawing group is aryl or heteroaryl, e.g., phenyl, substituted with one or more of —CN, —$NO_2$, halogen, —$C(O)R^1$, —C(O)OR', —$C(O)N(R')_2$, —$S(O)R^1$, —$S(O)_2R^1$, —$P(W)(R^1)_2$, —$P(O)(R^1)_2$, —$P(O)(OR')_2$, or —$P(S)(R^1)_2$.

In some embodiments, $R^2$ is -L-R'. In some embodiments, $R^2$ is -L'-L"-R', wherein L' is —$C(R)_2$— or optionally substituted —$CH_2$—, and L" is —P(O)(R')—, —P(O)(R')O—, —P(O)(OR')—, —P(O)(OR')O—, —P(O)[N(R')]—, —P(O)[N(R')]O—, —P(O)[N(R')][N(R')]—, —P(S)(R')—, —$S(O)_2$—, —$S(O)_2$—, —$S(O)_2O$—, —S(O)—, —C(O)—, —C(O)N(R')—, or —S—. In some embodiments, L' is —$C(R)_2$—. In some embodiments, L' is optionally substituted —$CH_2$—.

In some embodiments, L' is —$C(R)_2$—. In some embodiments, each R is independently hydrogen, or an optionally substituted group selected from $C_1$-$C_6$ aliphatic, carbocyclyl, aryl, heteroaryl, and heterocyclyl. In some embodiments, L' is —$CH_2$—. In some embodiments, L" is —P(O)(R')—, —P(S)(R')—, —$S(O)_2$—. In some embodiments, $R^2$ is -L'-$C(O)N(R')_2$. In some embodiments, $R^2$ is -L'-$P(O)(R')_2$. In some embodiments, $R^2$ is -L'-$P(S)(R')_2$. In some embodiments, each R' is independently optionally substituted aliphatic, heteroaliphatic, aryl, or heteroaryl as described in the present disclosure (e.g., those embodiments described for R). In some embodiments, each R' is independently optionally substituted phenyl. In some embodiments, each R' is independently optionally substituted phenyl wherein one or more substituents are independently selected from —CN, —OMe, —Cl, —Br, and —F. In some embodiments, each R' is independently substituted phenyl wherein one or more substituents are independently selected from —CN, —OMe, —Cl, —Br, and —F. In some embodiments, each R' is independently substituted phenyl wherein the substituents are independently selected from —CN, —OMe, —Cl, —Br, and —F. In some embodiments, each R' is independently mono-substituted phenyl, wherein the substituent is independently selected from —CN, —OMe, —Cl, —Br, and —F. In some embodiments, two R' are the same. In some embodiments, two $R^1$ are different. In some embodiments, $R^2$ is -L'-S(O)R'. In some embodiments, $R^2$ is -L'-$C(O)N(R')_2$. In some embodiments, $R^2$ is -L'-$S(O)_2R'$. In some embodiments, R' is optionally substituted aliphatic, heteroaliphatic, aryl, or heteroaryl as described in the present disclosure (e.g., those embodiments described for R). In some embodiments, R' is optionally substituted phenyl. In some embodiments, R' is optionally substituted phenyl wherein one or more substituents are independently selected from —CN, —OMe, —Cl, —Br, and —F. In some embodiments, R' is substituted phenyl wherein one or more substituents are independently selected from —CN, —OMe, —Cl, —Br, and —F. In some embodiments, R' is substituted phenyl wherein each substituent is independently selected from —CN, —OMe, —Cl, —Br, and —F. In some embodiments, R' is mono-substituted phenyl. In some embodiments, R' is mono-substituted phenyl, wherein the substituent is independently selected from —CN, —OMe, —Cl, —Br, and —F. In some embodiments, a substituent is an electron-withdrawing group. In some embodiments, an electron-withdrawing group is —CN, —$NO_2$, halogen. —$C(O)R^1$, —C(O)OR', —$C(O)N(R')_2$, —$S(O)R^1$, —$S(O)_2R^1$, —$P(W)(R^1)_2$, —$P(O)(R^1)_2$, —$P(O)(OR')_2$, or —$P(S)(R^1)_2$.

In some embodiments, $R^2$ is optionally substituted —$CH_2$-L"-R, wherein each of L" and R is independently as described in the present disclosure. In some embodiments, $R^2$ is optionally substituted —CH(-L"-R$)_2$, wherein each of L" and R is independently as described in the present disclosure. In some embodiments, $R^2$ is optionally substituted —CH(—S—R$)_2$. In some embodiments, $R^2$ is optionally substituted —$CH_2$—S—R. In some embodiments, the two R groups are taken together with their intervening atoms to form a ring. In some embodiments, a formed ring is an optionally substituted 5, 6, 7-membered ring having 0-2 heteroatoms in addition to the intervening heteroatoms. In some embodiments, $R^2$ is optionally substituted

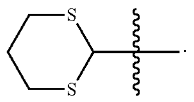

In some embodiments, $R^2$ is

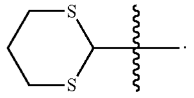

In some embodiments, —S— may be converted to —S(O)— or —$S(O)_2$—, e.g., by oxidation, e.g., to facilitate removal by a base.

In some embodiments, $R^2$ is -L'-R', wherein each variable is as described in the present disclosure. In some embodiments, $R^2$ is —CHR—R'. In some embodiments, $R^2$ is —$CH_2$—R'. In some embodiments, $R^2$ is —$CH(R')_2$. In some embodiments, $R^2$ is —$C(R')_3$. In some embodiments, R' is optionally substituted aryl or heteroaryl. In some embodiments, R' is substituted aryl or heteroaryl wherein one or more substituents are independently an electron-withdrawing group. In some embodiments, -L'- is optionally substituted —$CH_2$—, and R' is R, wherein R is optionally substituted aryl or heteroaryl. In some embodiments, R is substituted aryl or heteroaryl wherein one or more substituents are independently an electron-withdrawing group. In some embodiments, R is substituted aryl or heteroaryl wherein each substituent is independently an electron-withdrawing group. In some embodiments, R is aryl or heteroaryl substituted with two or more substituents, wherein each substituent is independently an electron-withdrawing group. In some embodiments, an electron-withdrawing group is —CN, —$NO_2$, halogen, —$C(O)R^1$, —C(O)OR', —$C(O)N(R')_2$, —$S(O)R^1$, —$S(O)_2R^1$, —$P(W)(R^1)_2$, —$P(O)(R^1)_2$, —$P(O)(OR')_2$, or —$P(S)(R^1)_2$. In some embodiments, R' is

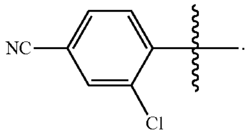 [SMILES: *c1ccc(C#N)cc1Cl]

In some embodiments, R' is p-$NO_2$Ph-. In some embodiments, R' is

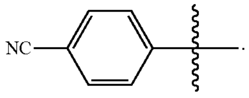

In some embodiments, R' is

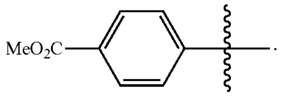

In some embodiments, R' is

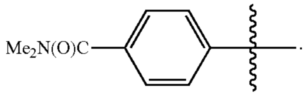

In some embodiments, R' is

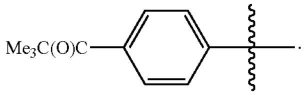

In some embodiments, R' is

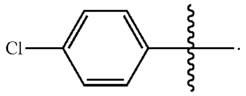 [SMILES: *c1ccc(Cl)cc1]

In some embodiments, $R^2$ is

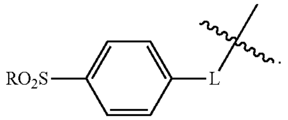

In some embodiments, R' is

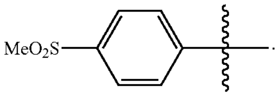

In some embodiments, R' is

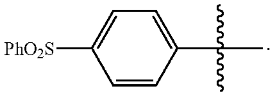

In some embodiments, R' is 2,4,6-trichlorophenyl. In some embodiments, R' is 2,4,6-trifluorophenyl. In some embodiments, $R^2$ is —CH(4-chlorophenyl)$_2$. In some embodiments, $R^2$ is —$CH(R')_2$, wherein each R' is

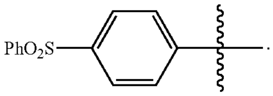

In some embodiments, $R^2$ is —$CH(R')_2$, wherein each R' is

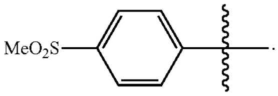 [SMILES: *c1ccc(S(C)(=O)=O)cc1]

In some embodiments, R' is —C(O)R. In some embodiments, R' is $CH_3C(O)$—.

In some embodiments, $R^2$ is -L'-$S(O)_2R'$, wherein each variable is as described in the present disclosure. In some embodiments, $R^2$ is —$CH_2$—$S(O)_2R'$. In some embodiments, $R^2$ is -L'-S(O)R', wherein each variable is as described in the present disclosure. In some embodiments, $R^2$ is —$CH_2$—S(O)R'. In some embodiments, $R^2$ is -L'-C$(O)_2R'$, wherein each variable is as described in the present disclosure. In some embodiments, $R^2$ is —$CH_2$—$C(O)_2R'$. In some embodiments, $R^2$ is -L'-C(O)R', wherein each variable is as described in the present disclosure. In some embodiments, $R^2$ is —$CH_2$—C(O)R'. In some embodiments, -L'- is optionally substituted —$CH_2$—, and R' is R. In some embodiments, R is optionally substituted aryl or heteroaryl. In some embodiments, R is optionally substituted aliphatic. In some embodiments, R is optionally substituted heteroaliphatic. In some embodiments, R is optionally substituted heteroaryl. In some embodiments, R is optionally substituted aryl. In some embodiments, R is optionally substituted phenyl. In some embodiments, R is not phenyl, or mono-, di- or tri-substituted phenyl, wherein each substituent is selected from —$NO_2$, halogen, —CN, —$C_{1-3}$ alkyl, and $C_{1-3}$ alkyloxy. In some embodiments, R is substituted aryl or heteroaryl wherein one or more substituents are independently an electron-withdrawing group. In some embodiments, R is substituted aryl or heteroaryl wherein each substituent is independently an electron-withdrawing group. In some embodiments, R is aryl or heteroaryl substituted with two or more substituents, wherein each substituent is independently an electron-withdrawing group. In some embodiments, an electron-withdrawing group is —CN, —$NO_2$, halogen, —$C(O)R^1$, —C(O)OR', —$C(O)N(R')_2$, —$S(O)R^1$, —$S(O)_2R^1$, —$P(W)(R^1)_2$, —$P(O)(R^1)_2$, —$P(O)(OR')_2$, or —$P(S)(R^1)_2$. In some embodiments, R' is phenyl. In some embodiments, R' is substituted phenyl. In some embodiments, R' is

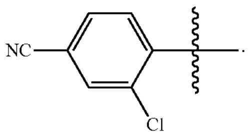 [SMILES: *c1ccc(C#N)cc1Cl]

In some embodiments, R' is

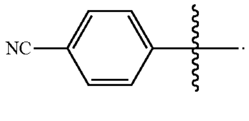

In some embodiments, R' is

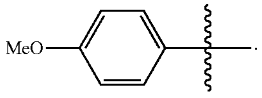 [SMILES: *c1ccc(OC)cc1]

In some embodiments, R' is optionally substituted $C_{1-6}$ aliphatic. In some embodiments, R' is t-butyl. In some embodiments, R' is isopropyl. In some embodiments, R' is methyl. In some embodiments, $R^2$ is —$CH_2C(O)OMe$. In some embodiments, $R^2$ is —$CH_2C(O)Ph$. In some embodiments, $R^2$ is —$CH_2C(O)$-tBu.

In some embodiments, $R^2$ is -L'-$NO_2$. In some embodiments, $R^2$ is —$CH_2$—$NO_2$. In some embodiments, $R^2$ is -L'-$S(O)_2N(R')_2$. In some embodiments, $R^2$ is —$CH_2$—$S(O)_2N(R')_2$. In some embodiments, $R^2$ is -L'-$S(O)_2NHR'$. In some embodiments, $R^2$ is —$CH_2$—$S(O)_2NHR'$. In some embodiments, R' is methyl. In some embodiments, $R^2$ is —$CH_2$—$S(O)_2NH(CH_3)$. In some embodiments, R' is —$CH_2Ph$. In some embodiments, $R^2$ is —$CH_2$—$S(O)_2NH(CH_2Ph)$. In some embodiments, $R^2$ is —$CH_2$—$S(O)_2N(CH_2Ph)_2$. In some embodiments, R' is phenyl. In some embodiments, $R^2$ is —$CH_2$—$S(O)_2NHPh$. In some embodiments, R' is —$CH_2$—$S(O)_2N(CH_3)Ph$. In some embodiments, $R^2$ is —$CH_2$—$S(O)_2N(CH_3)_2$. In some embodiments, $R^2$ is —$CH_2$—$S(O)_2NH(CH_2Ph)$. In some embodiments, $R^2$ is —$CH_2$—$S(O)_2NHPh$. In some embodiments, $R^2$ is —$CH_2$—$S(O)_2NH(CH_2Ph)$. In some embodiments, $R^2$ is —$CH_2$—$S(O)_2N(CH_3)_2$. In some embodiments, $R^2$ is —$CH_2$—$S(O)_2N(CH_3)Ph$. In some embodiments, $R^2$ is -L'-$S(O)_2N(R')(OR')$. In some embodiments, $R^2$ is —$CH_2$—$S(O)_2N(R')(OR')$. In some embodiments, each R' is methyl. In some embodiments, $R^2$ is —$CH_2$—$S(O)_2N(CH_3)(OCH_3)$. In some embodiments, $R^2$ is —$CH_2$—$S(O)_2N(Ph)(OCH_3)$. In some embodiments, $R^2$ is —CH—$S(O)_2N(CH_2Ph)(OCH_3)$. In some embodiments, $R^2$ is —$CH_2$—$S(O)_2N(CH_2Ph)(OCH_3)$. In some embodiments, $R^2$ is -L'-$S(O)_2OR'$. In some embodiments, $R^2$ is —$CH_2$—$S(O)_2OR'$. In some embodiments, $R^2$ is —$CH_2$—$S(O)_2OPh$. In some embodiments, $R^2$ is —$CH_2$—$S(O)_2OCH_3$. In some embodiments, $R^2$ is —$CH_2$—$S(O)_2OCH_2Ph$.

In some embodiments, $R^2$ is -L'-$P(O)(R')_2$. In some embodiments, $R^2$ is —$CH_2$—$P(O)(R')_2$. In some embodiments, $R^2$ is -L'-$P(O)[N(R')_2]_2$. In some embodiments, $R^2$ is —$CH_2$—$P(O)[N(R')_2]_2$. In some embodiments, $R^2$ is -L'-$P(O)[O(R')_2]$. In some embodiments, $R^2$ is —$CH_2$—$P(O)[O(R')_2]_2$. In some embodiments, $R^2$ is -L'-$P(O)(R')[N(R')_2]_2$. In some embodiments, $R^2$ is —CH—$P(O)(R')[N(R')_2]$. In some embodiments, $R^2$ is -L'-$P(O)(R')[O(R')]$. In some embodiments, $R^2$ is —CH—$P(O)(R')[O(R')]$. In some embodiments, $R^2$ is -L'-$P(O)(OR')[N(R')_2]$. In some embodiments, $R^2$ is —$CH_2$—$P(O)(OR')[N(R')_2]$. In some embodiments, $R^2$ is -L'-$C(O)N(R')_2$, wherein each variable is as described in the present disclosure. In some embodiments, $R^2$ is —$CH_2$—$C(O)N(R')_2$. In some embodiments, each R' is independently R. In some embodiments, one R' is optionally substituted aliphatic, and one R is optionally substituted aryl. In some embodiments, one R' is optionally substituted $C_{1-6}$ aliphatic, and one R is optionally substituted phenyl. In some embodiments, each R' is independently optionally substituted $C_{1-6}$ aliphatic. In some embodiments, $R^2$ is —$CH_2$—$P(O)(CH_3)Ph$. In some embodiments, $R^2$ is —$CH_2$—$P(O)(CH_3)_2$. In some embodiments, $R^2$ is —$CH_2$—$P(O)(Ph)_2$. In some embodiments, $R^2$ is —$CH_2$—$P(O)(OCH_3)_2$. In some embodiments, $R^2$ is —$CH_2$—$P(O)(CH_2Ph)_2$. In some embodiments, $R^2$ is —$CH_2$—$P(O)[N(CH_3)Ph]_2$. In some embodiments, $R^2$ is —$CH_2$—$P(O)[N(CH_3)_2]_2$. In some embodiments, $R^2$ is —$CH_2$—$P(O)[N(CH_2Ph)_2]_2$. In some embodiments, $R^2$ is —$CH_2$—$P(O)(OCH_3)_2$. In some embodiments, $R^2$ is —$CH_2$—$P(O)(OPh)_2$.

In some embodiments, $R^2$ is -L'-SR'. In some embodiments, $R^2$ is —$CH_2$—SR'. In some embodiments, R' is optionally substituted phenyl. In some embodiments, R' is phenyl.

In some embodiments, a provided chiral reagent has the structure of

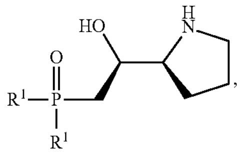

wherein each $R^1$ is independently as described in the present disclosure. In some embodiments, a provided chiral reagent has the structure of

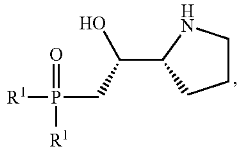

wherein each $R^1$ is independently as described in the present disclosure. In some embodiments, each $R^1$ is independently R as described in the present disclosure. In some embodiments, each $R^1$ is independently R, wherein R is optionally substituted aliphatic, aryl, heteroaliphatic, or heteroaryl as described in the present disclosure. In some embodiments, each $R^1$ is phenyl. In some embodiments, $R^1$ is -L-R'. In some embodiments, $R^1$ is -L-R', wherein L is —O—, —S—, or —N(R'). In some embodiments, a provided chiral reagent has the structure of

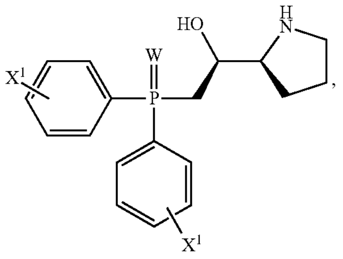

wherein each $X^1$ is independently —H, an electron-withdrawing group, $—NO_2$, —CN, —OR, —Cl, —Br, or —F, and W is O or S. In some embodiments, a provided chiral reagent has the structure of

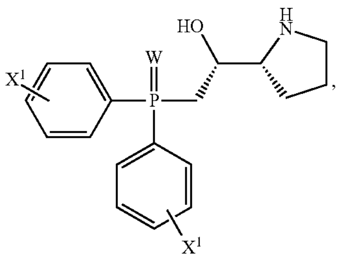

wherein each $X^1$ is independently —H, an electron-withdrawing group, $—NO_2$, —CN, —OR, —Cl, —Br, or —F, and W is O or S. In some embodiments, each $X^1$ is independently —CN, —OR, —Cl, —Br, or —F, wherein R is not —H. In some embodiments, R is optionally substituted $C_{1-6}$ aliphatic. In some embodiments, R is optionally substituted $C_{1-6}$ alkyl. In some embodiments, R is $—CH_3$. In some embodiments, one or more $X^1$ are independently electron-withdrawing groups (e.g., —CN, $—NO_2$, halogen, $—C(O)R^1$, —C(O)OR', $—C(O)N(R')_2$, $—S(O)R^1$, $—S(O)_2R^1$, $—P(W)(R^1)_2$, $—P(O)(R^1)_2$, $—P(O)(OR')_2$, $—P(S)(R^1)_2$, etc.).

In some embodiments, a provided chiral reagent has the structure of

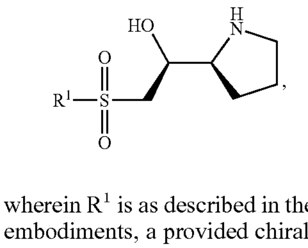

wherein $R^1$ is as described in the present disclosure. In some embodiments, a provided chiral reagent has the structure of

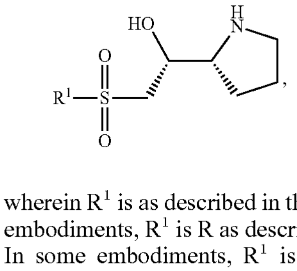

wherein $R^1$ is as described in the present disclosure. In some embodiments, $R^1$ is R as described in the present disclosure. In some embodiments, $R^1$ is R, wherein R is optionally substituted aliphatic, aryl, heteroaliphatic, or heteroaryl as described in the present disclosure. In some embodiments, $R^1$ is -L-R'. In some embodiments, $R^1$ is -L-R', wherein L is —O—, —S—, or —N(R'). In some embodiments, a provided chiral reagent has the structure of

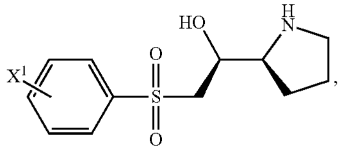

wherein $X^1$ is —H, an electron-withdrawing group, $—NO_2$, —CN, —OR, —Cl, —Br, or —F, and W is O or S. In some embodiments, a provided chiral reagent has the structure of

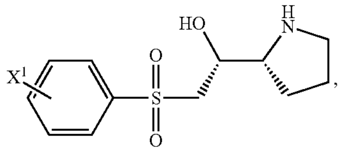

wherein $X^1$ is —H, an electron-withdrawing group, $—NO_2$, —CN, —OR, —Cl, —Br, or —F, and W is O or S. In some embodiments, $X^1$ is —CN, —OR, —Cl, —Br, or —F, wherein R is not —H. In some embodiments, R is optionally substituted $C_{1-6}$ aliphatic. In some embodiments, R is optionally substituted $C_{1-6}$ alkyl. In some embodiments, R is $—CH_3$. In some embodiments, $X^1$ is an electron-withdrawing group (e.g., —CN, $—NO_2$, halogen, $—C(O)R^1$, —C(O)OR', $—C(O)N(R')_2$, $—S(O)R^1$, $—S(O)_2R^1$, $—P(W)(R^1)_2$, $—P(O)(R^1)_2$, $—P(O)(OR')_2$, $—P(S)(R^1)_2$, etc.). In some embodiments, $X^1$ is an electron-withdrawing group that is not —CN, $—NO_2$, or halogen. In some embodiments, $X^1$ is not —H, —CN, $—NO_2$, halogen, or $C_{1-3}$ alkyloxy.

In some embodiments, $R^2$ is $—CH(R^{21})—CH(R^{22})═C(R^{23})(R^{24})$, wherein each of $R^{21}$, $R^{22}$, $R^{23}$, and $R^{24}$ is independently R. In some embodiments, $R^{22}$ and $R^{23}$ are both R, and the two R groups are taken together with their intervening atoms to form an optionally substituted aryl or heteroaryl ring as described herein. In some embodiments, one or more substituents are independently electron-withdrawing groups. In some embodiments, $R^{21}$ and $R^{24}$ are both R, and the two R groups are taken together with their intervening atoms to form an optionally substituted ring as described herein. In some embodiments, $R^{21}$ and $R^{24}$ are both R, and the two R groups are taken together with their intervening atoms to form an optionally substituted saturated or partially saturated ring as described herein. In some embodiments, $R^{22}$ and $R^{23}$ are both R, and the two R groups are taken together with their intervening atoms to form an optionally substituted aryl or heteroaryl ring as described herein, and $R^{21}$ and $R^{24}$ are both R, and the two R groups are taken together with their intervening atoms to form an optionally substituted partially saturated ring as described herein. In some embodiments, $R^{21}$ is —H. In some embodiments, $R^{24}$ is —H. In some embodiments, $R^2$ is optionally substituted

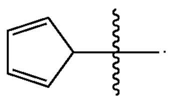

In some embodiments, $R^2$ is optionally substituted

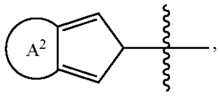,

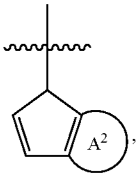, or

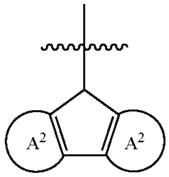, wherein each Ring $A^2$ is independently a 3-15 membered monocyclic, bicyclic or polycyclic ring as described herein. In some embodiments, Ring A is an optionally substituted 5-10 membered monocyclic aryl or heteroaryl ring having 1-5 heteroatoms as described herein. In some embodiments, Ring $A^2$ is an optionally substituted phenyl ring as described herein. In some embodiments, In some embodiments, $R^2$ is optionally substituted

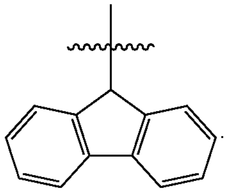 [SMILES: *C1c2ccccc2-c2ccccc21].

In some embodiments, $R^2$ is

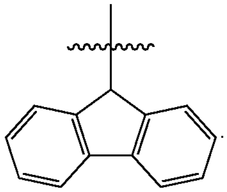 [SMILES: *C1c2ccccc2-c2ccccc21].

In some embodiments, $R^2$ is

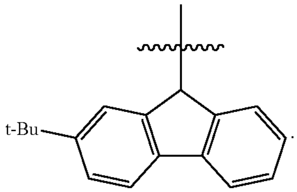 [SMILES: *C1c2ccccc2-c2ccc(C(C)(C)C)cc21].

In some embodiments, $R^2$ is

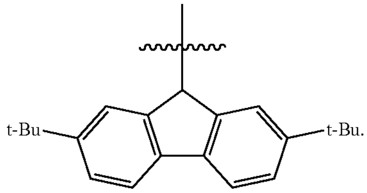 [SMILES: *C1c2cc(C(C)(C)C)ccc2-c2ccc(C(C)(C)C)cc21].

Certain useful example compounds for chiral auxiliaries are presented in, e.g., Tables 1-17. In some embodiments, a useful compound is an enantiomer of a compound in, e.g., Tables 1-17. In some embodiments, a useful compound is a diastereomer of a compound in, e.g., Tables 1-17. In some embodiments, a compound useful for chiral auxiliaries for removal under basic conditions (e.g., by a base under an anhydrous condition) is a compound of Tables 5-17, or an enantiomer or a diastereomer thereof. In some embodiments, such a compound is a compound of Table 5 or an enantiomer or a diastereomer thereof. In some embodiments, such a compound is a compound of Table 6 or an enantiomer or a diastereomer thereof. In some embodiments, such a compound is a compound of Table 7 or an enantiomer or a diastereomer thereof. In some embodiments, such a compound is a compound of Table 8 or an enantiomer or a diastereomer thereof. In some embodiments, such a compound is a compound of Table 9 or an enantiomer or a diastereomer thereof. In some embodiments, such a compound is a compound of Table 10 or an enantiomer or a diastereomer thereof. In some embodiments, such a compound is a compound of Table 11 or an enantiomer or a diastereomer thereof. In some embodiments, such a compound is a compound of Table 12 or an enantiomer or a diastereomer thereof. In some embodiments, such a compound is a compound of Table 13 or an enantiomer or a diastereomer thereof. In some embodiments, such a compound is a compound of Table 14 or an enantiomer or a diastereomer thereof. In some embodiments, such a compound is a compound of Table 15 or an enantiomer or a diastereomer thereof. In some embodiments, such a compound is a compound of Table 16 or an enantiomer or a diastereomer thereof. In some embodiments, such a compound is a compound of Table 17 or an enantiomer or a diastereomer thereof.

In some embodiments, when contacted with a base, a chiral auxiliary moiety, e.g., of an internucleotidic linkage, whose corresponding compound is a compound of formula I, I-a, I-a-1, I-a-2, I-b, I-c, I-d, I-e, II, II-a, II-b, III, III-a, or III-b may be released as an alkene, which has the same structure as a product formed by elimination of a water molecule from the corresponding compound (elimination of $R^7$=—OH and an alpha-H of $R^2$). In some embodiments, such an alkene has the structure of (electron-withdrawing group)$_2$=C($R^1$)-L-N($R^5$)($R^6$), (electron-withdrawing group)H=C($R^1$)-L-N($R^5$)($R^6$), CH(-L"-R')=C($R^1$)-L-N($R^5$)($R^6$) wherein the CH group is optionally substituted, or $C^x$=C($R^1$)-L-N($R^5$)($R^6$), wherein $C^x$ is optionally substituted

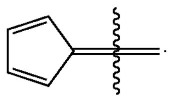 [SMILES: *=C1C=CC=C1].

and may be optionally fused with one or more optionally substituted rings, and each other variable is independently as described herein. In some embodiments, $C^x$ is optionally substituted

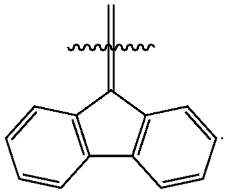 [SMILES: *=C1c2ccccc2-c2ccccc21]

In some embodiments, $C^x$ is

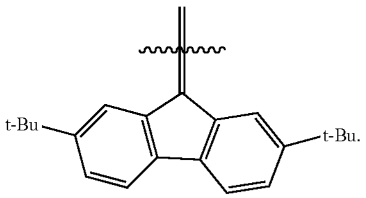 [SMILES: *=C1c2cc(C(C)(C)C)ccc2-c2ccc(C(C)(C)C)cc21]

In some embodiments, such an alkene is

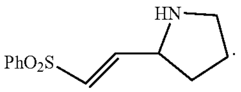

In some embodiments, such an alkene is

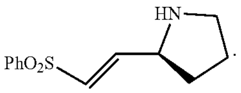

In some embodiments, such an alkene is

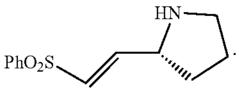

TABLE 5

Example compounds.

| | | | |
|---|---|---|---|
| WV-CA-110 | 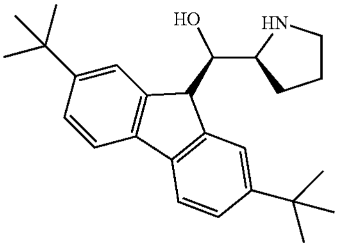 [SMILES: CC(C)(C)c1ccc2c(c1)C([C@@H](O)[C@@H]1CCCN1)c1cc(C(C)(C)C)ccc1-2] | WV-CA-241 | 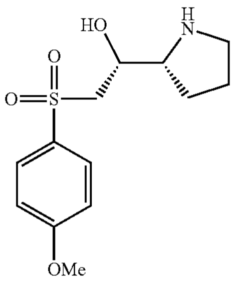 [SMILES: COc1ccc(S(=O)(=O)C[C@H](O)[C@H]2CCCN2)cc1] |
| WV-CA-110b | 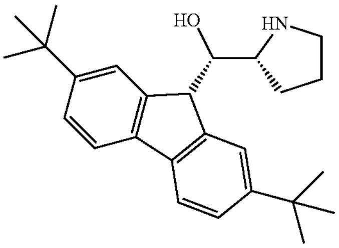 [SMILES: CC(C)(C)c1ccc2c(c1)C([C@H](O)[C@H]1CCCN1)c1cc(C(C)(C)C)ccc1-2] | WV-CA-242 | 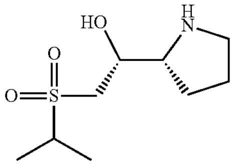 |
| WV-CA-315 | 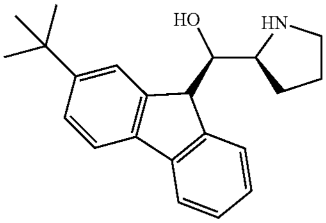 [SMILES: CC(C)(C)c1ccc2c(c1)C([C@@H](O)[C@@H]1CCCN1)c1ccccc1-2] | WV-CA-243 | 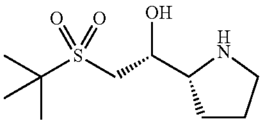 |

TABLE 5-continued
| Example compounds. | | | |
|---|---|---|---|
| WV-CA-324 | 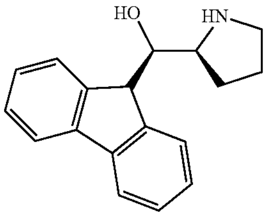 [SMILES: O[C@H](C1c2ccccc2-c2ccccc21)[C@@H]1CCCN1] | WV-CA-244 | 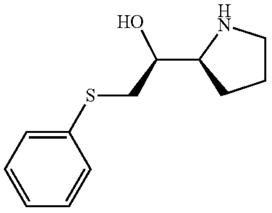 [SMILES: O[C@H](CSc1ccccc1)[C@@H]1CCCN1] |
| WV-CA-231 | 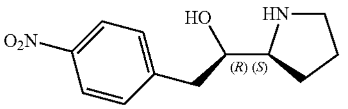 [SMILES: O=[N+]([O-])c1ccc(C[C@@H](O)[C@@H]2CCCN2)cc1] | WV-CA-245 | 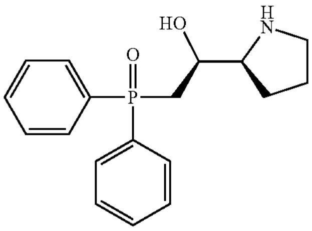 [SMILES: O=P(C[C@@H](O)[C@@H]1CCCN1)(c1ccccc1)c1ccccc1] |
| WV-CA-236 | 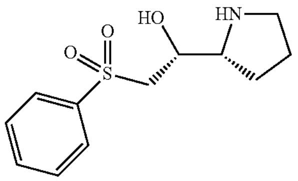 [SMILES: O=S(=O)(C[C@H](O)[C@H]1CCCN1)c1ccccc1] | WV-CA-246 | 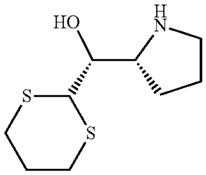 [SMILES: O[C@@H](C1SCCCS1)[C@H]1CCCN1] |
| WV-CA-237 | 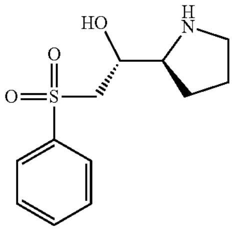 [SMILES: O=S(=O)(C[C@H](O)[C@@H]1CCCN1)c1ccccc1] | WV-CA-247 | 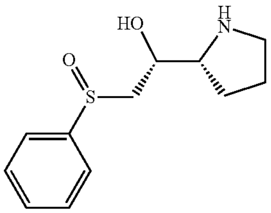 [SMILES: O=S(C[C@H](O)[C@H]1CCCN1)c1ccccc1] |
| WV-CA-238 | 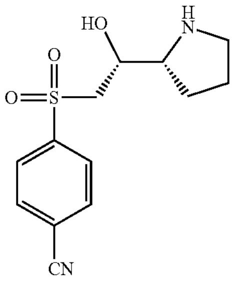 [SMILES: N#Cc1ccc(S(=O)(=O)C[C@H](O)[C@H]2CCCN2)cc1] | WV-CA-248 | 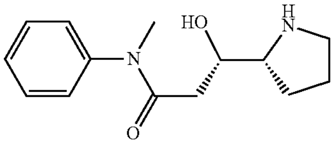 [SMILES: CN(C(=O)C[C@H](O)[C@H]1CCCN1)c1ccccc1] |
| WV-CA-239 | 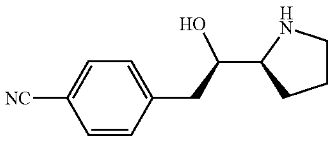 [SMILES: N#Cc1ccc(C[C@@H](O)[C@@H]2CCCN2)cc1] | WV-CA-249 | 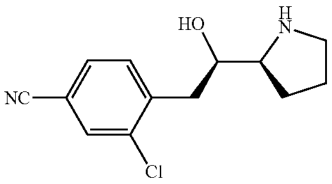 [SMILES: N#Cc1ccc(C[C@@H](O)[C@@H]2CCCN2)c(Cl)c1] |
| WV-CA-240 | 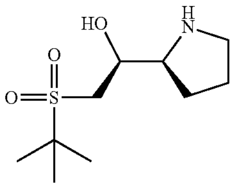 | WV-CA-250 | 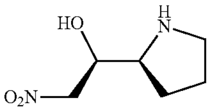 |

TABLE 5-continued
| Example compounds. | | | |
|---|---|---|---|
| WV-CA-251 | 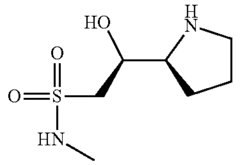 | WV-CA-261 | 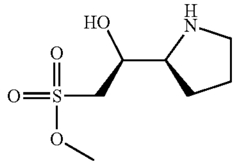 |
| WV-CA-252 | 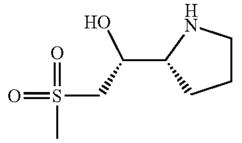 | WV-CA-262 | 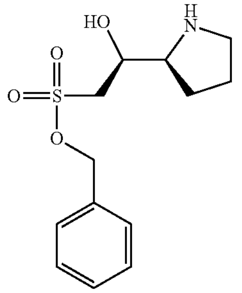 [SMILES: O=S(=O)(C[C@@H](O)[C@@H]1CCCN1)OCc1ccccc1] |
| WV-CA-253 | 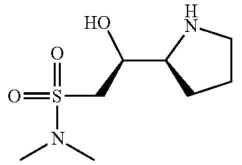 | WV-CA-263 | 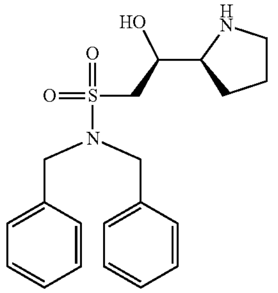 [SMILES: O=S(=O)(C[C@@H](O)[C@@H]1CCCN1)N(Cc1ccccc1)Cc1ccccc1] |
| WV-CA-254 | 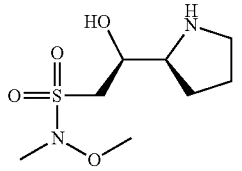 | WV-CA-264 | 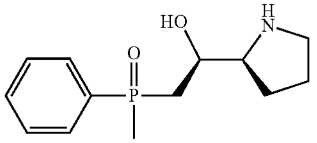 [SMILES: CP(=O)(C[C@@H](O)[C@@H]1CCCN1)c1ccccc1] |
| WV-CA-255 | 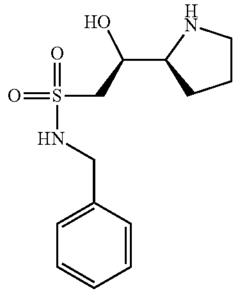 [SMILES: O=S(=O)(C[C@@H](O)[C@@H]1CCCN1)NCc1ccccc1] | WV-CA-265 | 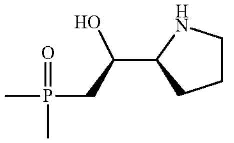 |
| WV-CA-256 | 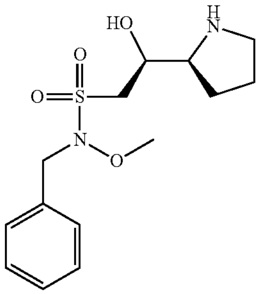 [SMILES: CON(Cc1ccccc1)S(=O)(=O)C[C@@H](O)[C@@H]1CCCN1] | WV-CA-266 | 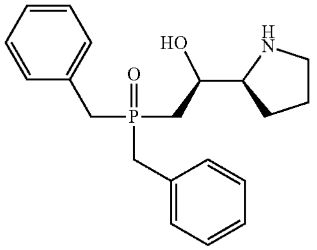 [SMILES: O=P(Cc1ccccc1)(Cc1ccccc1)C[C@@H](O)[C@@H]1CCCN1] |

TABLE 5-continued
| Example compounds. | | | |
|---|---|---|---|
| WV-CA-257 | 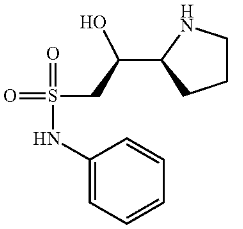 [SMILES: O=S(=O)(C[C@@H](O)[C@@H]1CCCN1)Nc1ccccc1] | WV-CA-267 | 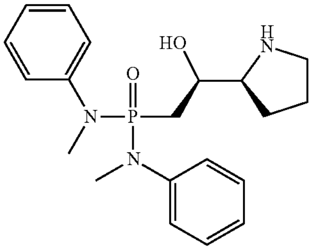 [SMILES: CN(c1ccccc1)P(=O)(C[C@@H](O)[C@@H]1CCCN1)N(C)c1ccccc1] |
| WV-CA-258 | 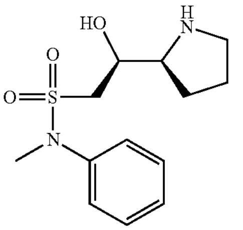 [SMILES: CN(c1ccccc1)S(=O)(=O)C[C@@H](O)[C@@H]1CCCN1] | WV-CA-268 | 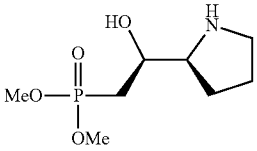 [SMILES: COP(=O)(C[C@@H](O)[C@@H]1CCCN1)OC] |
| WV-CA-259 | 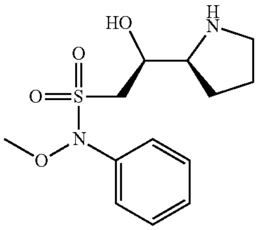 [SMILES: CON(c1ccccc1)S(=O)(=O)C[C@@H](O)[C@@H]1CCCN1] | WV-CA-269 | 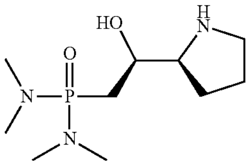 [SMILES: CN(C)P(=O)(C[C@@H](O)[C@@H]1CCCN1)N(C)C] |
| WV-CA-260 | 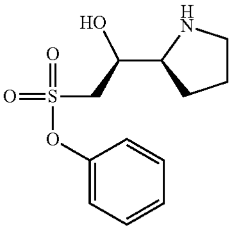 [SMILES: O=S(=O)(C[C@@H](O)[C@@H]1CCCN1)Oc1ccccc1] | WV-CA-270 | 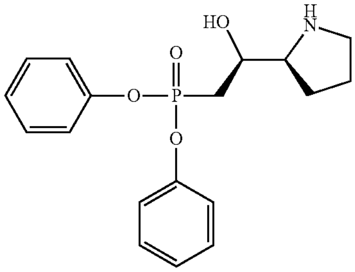 |
| WV-CA-271 | 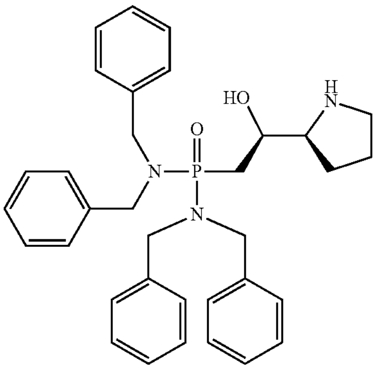 [SMILES: O=P(C[C@@H](O)[C@@H]1CCCN1)(N(Cc1ccccc1)Cc1ccccc1)N(Cc1ccccc1)Cc1ccccc1] | WV-CA-281 | 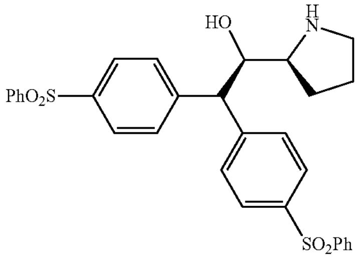 |

TABLE 5-continued
Example compounds.
WV-CA-272
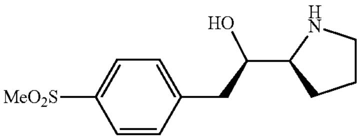 [SMILES: CS(=O)(=O)c1ccc(C[C@@H](O)[C@@H]2CCCN2)cc1]
WV-CA-282
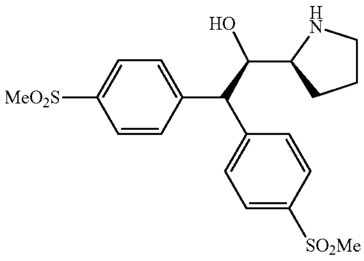 [SMILES: CS(=O)(=O)c1ccc(C(c2ccc(S(C)(=O)=O)cc2)[C@@H](O)[C@@H]2CCCN2)cc1]
WV-CA-273
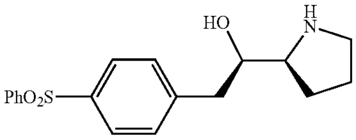
WV-CA-283
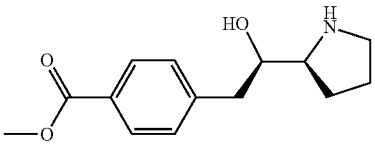 [SMILES: COC(=O)c1ccc(C[C@@H](O)[C@@H]2CCCN2)cc1]
WV-CA-274
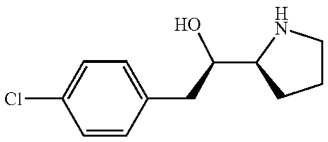 [SMILES: O[C@H](Cc1ccc(Cl)cc1)[C@@H]1CCCN1]
WV-CA-284
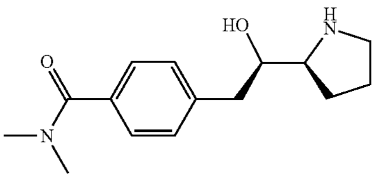 [SMILES: CN(C)C(=O)c1ccc(C[C@@H](O)[C@@H]2CCCN2)cc1]
WV-CA-275
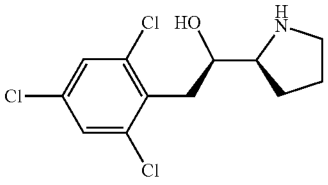 [SMILES: O[C@H](Cc1c(Cl)cc(Cl)cc1Cl)[C@@H]1CCCN1]
WV-CA-285
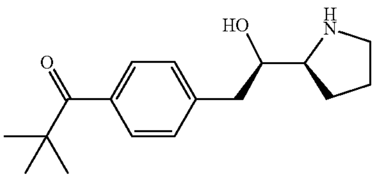 [SMILES: CC(C)(C)C(=O)c1ccc(C[C@@H](O)[C@@H]2CCCN2)cc1]
WV-CA-276
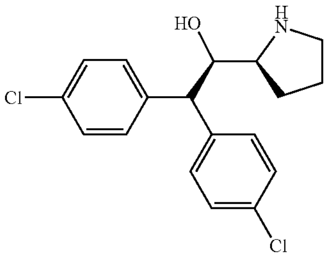 [SMILES: O[C@H](C(c1ccc(Cl)cc1)c1ccc(Cl)cc1)[C@@H]1CCCN1]
WV-CA-286
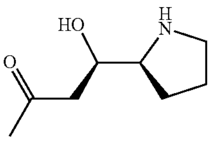
WV-CA-277
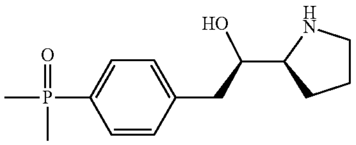 [SMILES: CP(C)(=O)c1ccc(C[C@@H](O)[C@@H]2CCCN2)cc1]
WV-CA-287
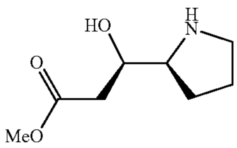 [SMILES: COC(=O)C[C@@H](O)[C@@H]1CCCN1]
WV-CA-278
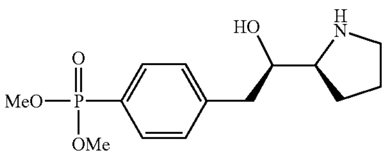 [SMILES: COP(=O)(OC)c1ccc(C[C@@H](O)[C@@H]2CCCN2)cc1]
WV-CA-288
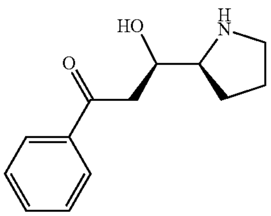 [SMILES: O=C(C[C@@H](O)[C@@H]1CCCN1)c1ccccc1]

TABLE 5-continued

| Example compounds. | | | |
|---|---|---|---|
| WV-CA-279 | 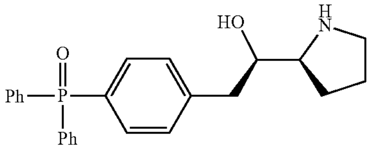 [SMILES: O=P(c1ccccc1)(c1ccccc1)c1ccc(C[C@@H](O)[C@@H]2CCCN2)cc1] | WV-CA-289 | 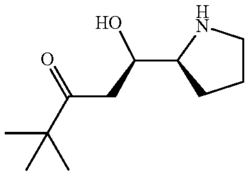 |
| WV-CA-280 | 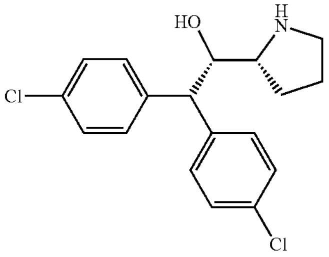 [SMILES: O[C@@H](C(c1ccc(Cl)cc1)c1ccc(Cl)cc1)[C@H]1CCCN1] | WV-CA-290 | 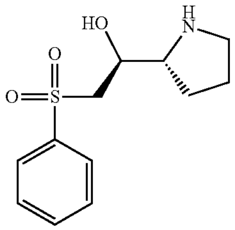 [SMILES: O=S(=O)(C[C@@H](O)[C@H]1CCCN1)c1ccccc1] |
| WV-CA-291 | 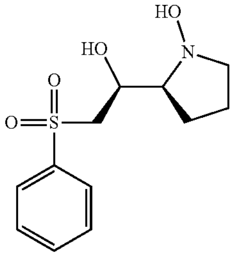 [SMILES: O=S(=O)(C[C@@H](O)[C@@H]1CCCN1O)c1ccccc1] | | |

In some embodiments, a provided compound is an enantiomer of a compound selected from Table 5 or a salt thereof. In some embodiments, a provided compound is a diastereomer of a compound selected from Table 5 or a salt thereof.

TABLE 6

| Example compounds. | |
|---|---|
| WV-CA-231 | 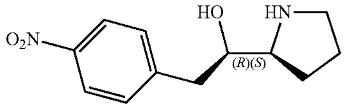 [SMILES: O=[N+]([O-])c1ccc(C[C@@H](O)[C@@H]2CCCN2)cc1] |
| WV-CA-239 | 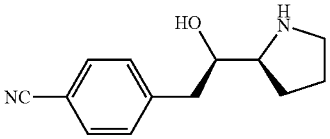 [SMILES: N#Cc1ccc(C[C@@H](O)[C@@H]2CCCN2)cc1] |
| WV-CA-249 | 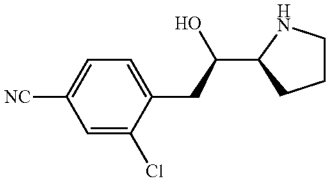 [SMILES: N#Cc1ccc(C[C@@H](O)[C@@H]2CCCN2)c(Cl)c1] |
| WV-CA-272 | 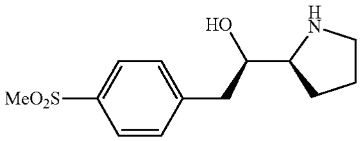 [SMILES: CS(=O)(=O)c1ccc(C[C@@H](O)[C@@H]2CCCN2)cc1] |

TABLE 6-continued

| Example compounds. | |
|---|---|
| WV-CA-273 | 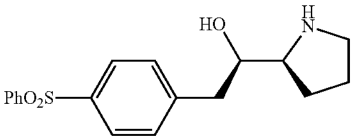 |
| WV-CA-274 | 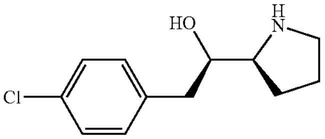 [SMILES: O[C@H](Cc1ccc(Cl)cc1)[C@@H]1CCCN1] |
| WV-CA-275 | 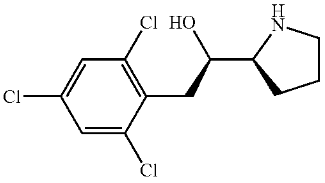 [SMILES: O[C@H](Cc1c(Cl)cc(Cl)cc1Cl)[C@@H]1CCCN1] |

TABLE 6-continued
| Example compounds. | |
|---|---|
| WV-CA-276 | 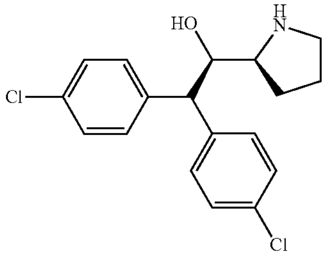 [SMILES: O[C@H](C(c1ccc(Cl)cc1)c1ccc(Cl)cc1)[C@@H]1CCCN1] |
| WV-CA-277 | 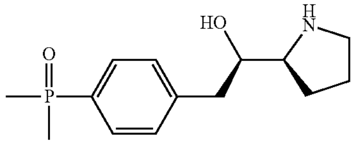 [SMILES: CP(C)(=O)c1ccc(C[C@@H](O)[C@@H]2CCCN2)cc1] |
| WV-CA-278 | 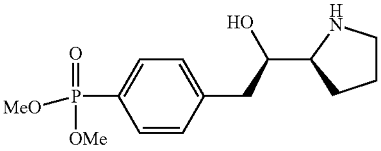 [SMILES: COP(=O)(OC)c1ccc(C[C@@H](O)[C@@H]2CCCN2)cc1] |
| WV-CA-279 | 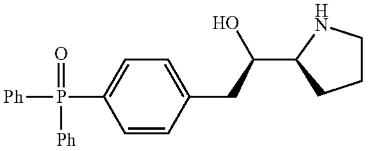 [SMILES: O=P(c1ccccc1)(c1ccccc1)c1ccc(C[C@@H](O)[C@@H]2CCCN2)cc1] |
| WV-CA-280 | 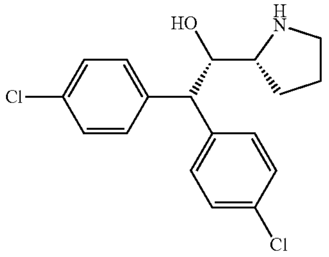 [SMILES: O[C@@H](C(c1ccc(Cl)cc1)c1ccc(Cl)cc1)[C@H]1CCCN1] |
| WV-CA-281 | 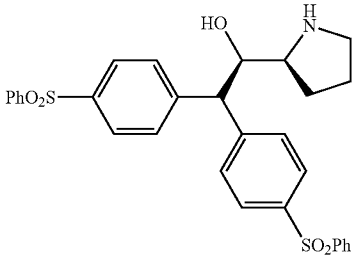 |
| WV-CA-282 | 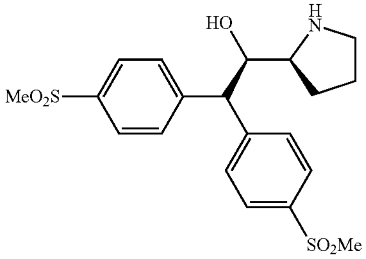 [SMILES: CS(=O)(=O)c1ccc(C(c2ccc(S(C)(=O)=O)cc2)[C@@H](O)[C@@H]2CCCN2)cc1] |
| WV-CA-283 | 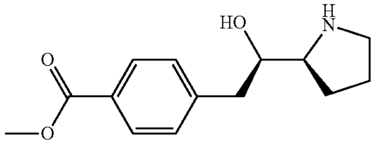 [SMILES: COC(=O)c1ccc(C[C@@H](O)[C@@H]2CCCN2)cc1] |
| WV-CA-284 | 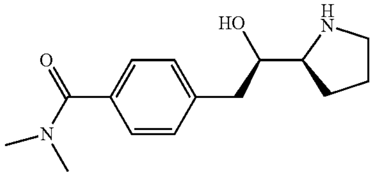 [SMILES: CN(C)C(=O)c1ccc(C[C@@H](O)[C@@H]2CCCN2)cc1] |
| WV-CA-285 | 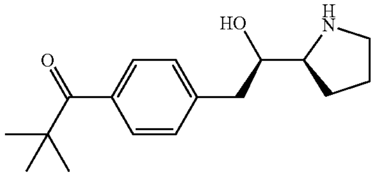 [SMILES: CC(C)(C)C(=O)c1ccc(C[C@@H](O)[C@@H]2CCCN2)cc1] |
In some embodiments, a provided compound is an enantiomer of a compound selected from Table 6 or a salt thereof. In some embodiments, a provided compound is a diastereomer of a compound selected from Table 6 or a salt thereof.
TABLE 7
| Example compounds. | |
|---|---|
| WV-CA-236 | 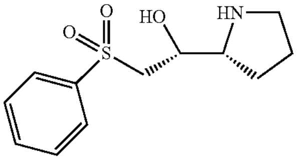 [SMILES: O=S(=O)(C[C@H](O)[C@H]1CCCN1)c1ccccc1] |
| WV-CA-237 | 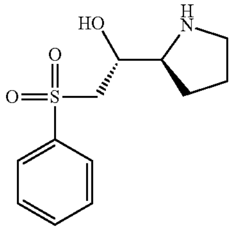 [SMILES: O=S(=O)(C[C@H](O)[C@@H]1CCCN1)c1ccccc1] |
| WV-CA-238 | 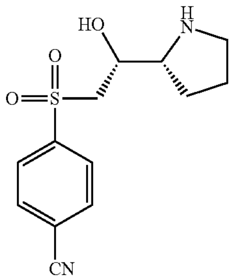 [SMILES: N#Cc1ccc(S(=O)(=O)C[C@H](O)[C@H]2CCCN2)cc1] |

TABLE 7-continued

| Example compounds. | |
|---|---|
| WV-CA-240 | 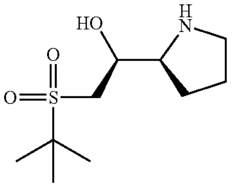 |
| WV-CA-241 | 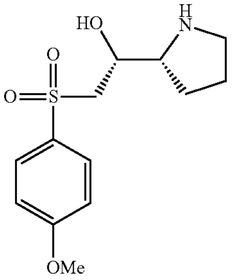 [SMILES: COc1ccc(S(=O)(=O)C[C@H](O)[C@H]2CCCN2)cc1] |
| WV-CA- 242 | 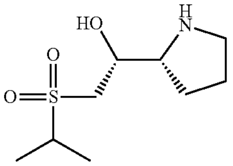 |
| WV-CA-243 | 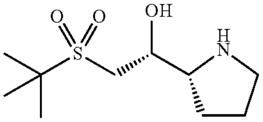 |
| WV-CA-252 | 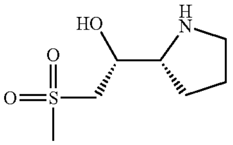 |
| WV-CA-290 | 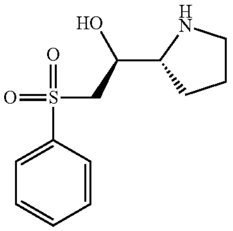 [SMILES: O=S(=O)(C[C@@H](O)[C@H]1CCCN1)c1ccccc1] |
| WV-CA-291 | 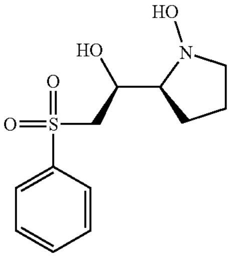 [SMILES: O=S(=O)(C[C@@H](O)[C@@H]1CCCN1O)c1ccccc1] |

TABLE 7-continued

| Example compounds. | |
|---|---|
| WV-CA-108 | 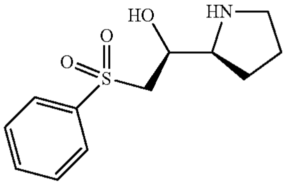 [SMILES: O=S(=O)(C[C@@H](O)[C@@H]1CCCN1)c1ccccc1] |
| WV-CA-183 | 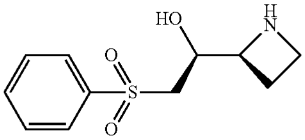 [SMILES: O=S(=O)(C[C@@H](O)[C@@H]1CCN1)c1ccccc1] |

In some embodiments, a provided compound is an enantiomer of a compound selected from Table 7 or a salt thereof. In some embodiments, a provided compound is a diastereomer of a compound selected from Table 7 or a salt thereof.

TABLE 8

| Example compounds. | |
|---|---|
| WV-CA-251 | 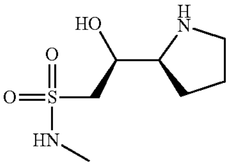 |
| WV-CA-253 | 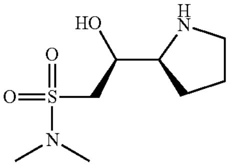 |
| WV-CA-255 | 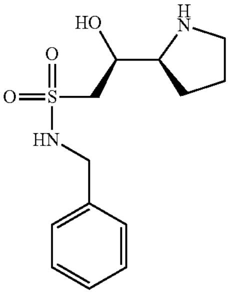 [SMILES: O=S(=O)(C[C@@H](O)[C@@H]1CCCN1)NCc1ccccc1] |
| WV-CA-257 | 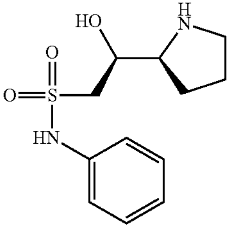 [SMILES: O=S(=O)(C[C@@H](O)[C@@H]1CCCN1)Nc1ccccc1] |

TABLE 8-continued

| Example compounds. | |
|---|---|
| WV-CA-258 | 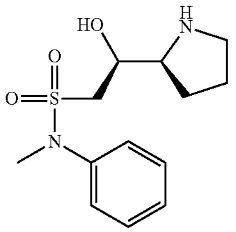 [SMILES: CN(c1ccccc1)S(=O)(=O)C[C@@H](O)[C@@H]1CCCN1] |
| WV-CA-263 | 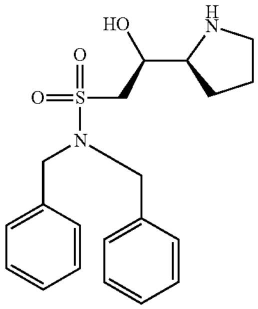 [SMILES: O=S(=O)(C[C@@H](O)[C@@H]1CCCN1)N(Cc1ccccc1)Cc1ccccc1] |

In some embodiments, a provided compound is an enantiomer of a compound selected from Table 8 or a salt thereof. In some embodiments, a provided compound is a diastereomer of a compound selected from Table 8 or a salt thereof.

TABLE 9

| Example compounds. | |
|---|---|
| WV-CA-254 | 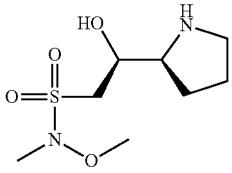 |
| WV-CA-256 | 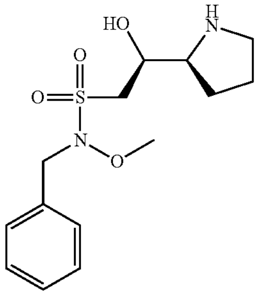 [SMILES: CON(Cc1ccccc1)S(=O)(=O)C[C@@H](O)[C@@H]1CCCN1] |
| WV-CA-259 | 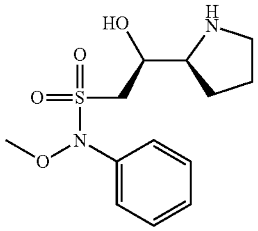 [SMILES: CON(c1ccccc1)S(=O)(=O)C[C@@H](O)[C@@H]1CCCN1] |

In some embodiments, a provided compound is an enantiomer of a compound selected from Table 9 or a salt thereof. In some embodiments, a provided compound is a diastereomer of a compound selected from Table 9 or a salt thereof.

TABLE 10

| Example compounds. | |
|---|---|
| WV-CA-260 | 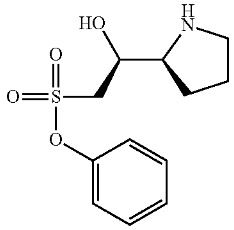 [SMILES: O=S(=O)(C[C@@H](O)[C@@H]1CCCN1)Oc1ccccc1] |
| WV-CA-261 | 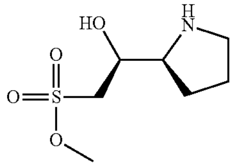 |
| WV-CA-262 | 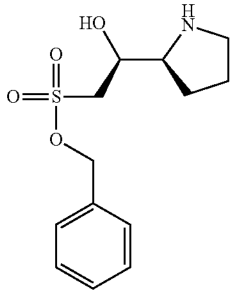 [SMILES: O=S(=O)(C[C@@H](O)[C@@H]1CCCN1)OCc1ccccc1] |

In some embodiments, a provided compound is an enantiomer of a compound selected from Table 10 or a salt thereof. In some embodiments, a provided compound is a diastereomer of a compound selected from Table 10 or a salt thereof.

TABLE 11

| Example compounds. | |
|---|---|
| WV-CA-245 | 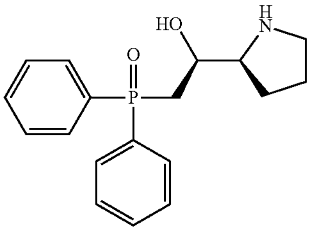 [SMILES: O=P(C[C@@H](O)[C@@H]1CCCN1)(c1ccccc1)c1ccccc1] |
| WV-CA-264 | 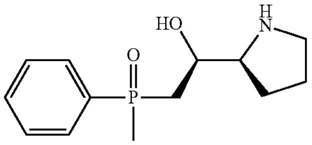 [SMILES: CP(=O)(C[C@@H](O)[C@@H]1CCCN1)c1ccccc1] |
| WV-CA-265 | 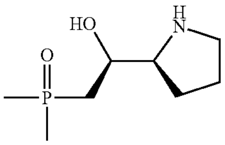 |

TABLE 11-continued

| Example compounds. | |
|---|---|
| WV-CA-266 | 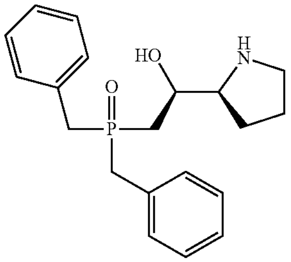 [SMILES: O=P(Cc1ccccc1)(Cc1ccccc1)C[C@@H](O)[C@@H]1CCCN1] |

In some embodiments, a provided compound is an enantiomer of a compound selected from Table 11 or a salt thereof. In some embodiments, a provided compound is a diastereomer of a compound selected from Table 11 or a salt thereof.

TABLE 12

| Example compounds. | |
|---|---|
| WV-CA-267 | 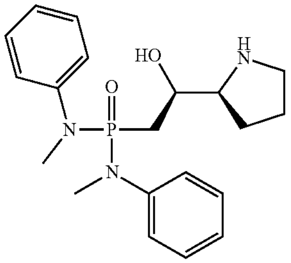 [SMILES: CN(c1ccccc1)P(=O)(C[C@@H](O)[C@@H]1CCCN1)N(C)c1ccccc1] |
| WV-CA-269 | 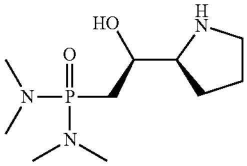 [SMILES: CN(C)P(=O)(C[C@@H](O)[C@@H]1CCCN1)N(C)C] |
| WV-CA-271 | 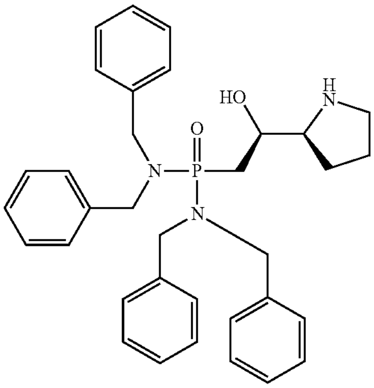 [SMILES: O=P(C[C@@H](O)[C@@H]1CCCN1)(N(Cc1ccccc1)Cc1ccccc1)N(Cc1ccccc1)Cc1ccccc1] |

In some embodiments, a provided compound is an enantiomer of a compound selected from Table 12 or a salt thereof. In some embodiments, a provided compound is a diastereomer of a compound selected from Table 12 or a salt thereof.

TABLE 13

| Example compounds. | |
|---|---|
| WV-CA-268 | 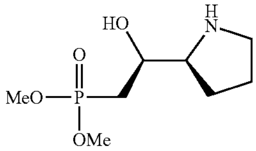 [SMILES: COP(=O)(C[C@@H](O)[C@@H]1CCCN1)OC] |
| WV-CA-270 | 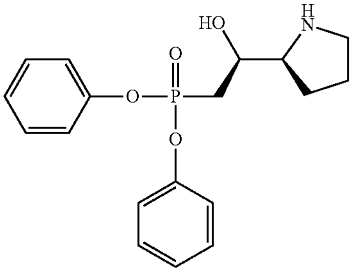 [SMILES: O=P(C[C@@H](O)[C@@H]1CCCN1)(Oc1ccccc1)Oc1ccccc1] |

In some embodiments, a provided compound is an enantiomer of a compound selected from Table 13 or a salt thereof. In some embodiments, a provided compound is a diastereomer of a compound selected from Table 13 or a salt thereof.

TABLE 14

| Example compounds. | |
|---|---|
| WV-CA-244 | 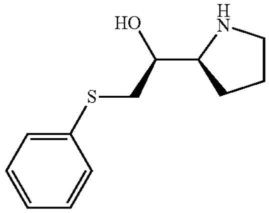 [SMILES: O[C@H](CSc1ccccc1)[C@@H]1CCCN1] |
| WV-CA-246 | 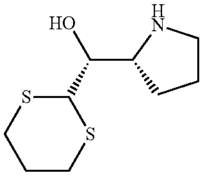 [SMILES: O[C@@H](C1SCCCS1)[C@H]1CCCN1] |

In some embodiments, a provided compound is an enantiomer of a compound selected from Table 14 or a salt thereof. In some embodiments, a provided compound is a diastereomer of a compound selected from Table 14 or a salt thereof.

TABLE 15

| Example compounds. | |
|---|---|
| WV-CA-247 | 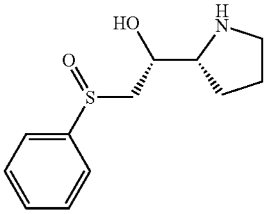 [SMILES: O=S(C[C@H](O)[C@H]1CCCN1)c1ccccc1] |

TABLE 15-continued

| Example compounds. | |
|---|---|
| WV-CA-248 | 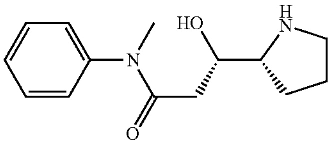 [SMILES: CN(C(=O)C[C@H](O)[C@H]1CCCN1)c1ccccc1] |

In some embodiments, a provided compound is an enantiomer of a compound selected from Table 15 or a salt thereof. In some embodiments, a provided compound is a diastereomer of a compound selected from Table 15 or a salt thereof.

TABLE 16

| Example compounds. | |
|---|---|
| WV-CA-250 | 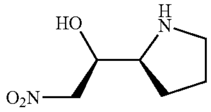 [SMILES: O=[N+]([O-])C[C@@H](O)[C@@H]1CCCN1] |
| WV-CA-286 | 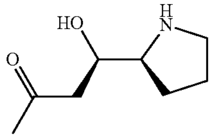 |
| WV-CA-287 | 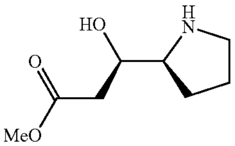 [SMILES: COC(=O)C[C@@H](O)[C@@H]1CCCN1] |
| WV-CA-288 | 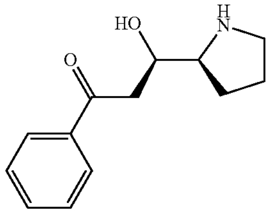 [SMILES: O=C(C[C@@H](O)[C@@H]1CCCN1)c1ccccc1] |
| WV-CA-289 | 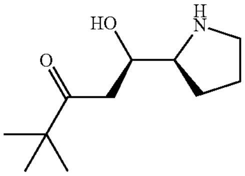 |

In some embodiments, a provided compound is an enantiomer of a compound selected from Table 16 or a salt thereof. In some embodiments, a provided compound is a diastereomer of a compound selected from 16 6 or a salt thereof.

TABLE 17

| Example compounds. | |
|---|---|
| WV-CA-110 | 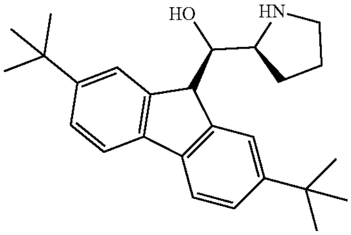 [SMILES: CC(C)(C)c1ccc2c(c1)C([C@@H](O)[C@@H]1CCCN1)c1cc(C(C)(C)C)ccc1-2] |
| WV-CA-315 | 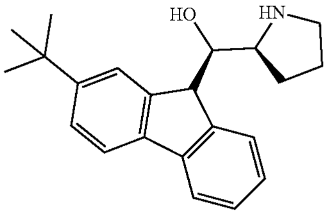 [SMILES: CC(C)(C)c1ccc2c(c1)C([C@@H](O)[C@@H]1CCCN1)c1ccccc1-2] |
| WV-CA-110b | 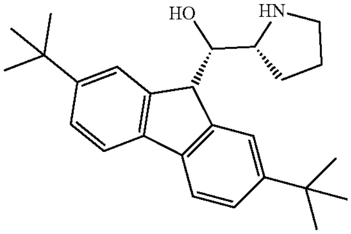 [SMILES: CC(C)(C)c1ccc2c(c1)C([C@H](O)[C@H]1CCCN1)c1cc(C(C)(C)C)ccc1-2] |
| WV-CA-324 | 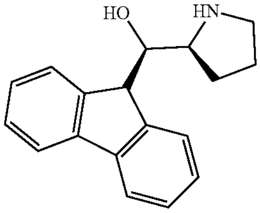 [SMILES: O[C@H](C1c2ccccc2-c2ccccc21)[C@@H]1CCCN1] |

In some embodiments, provide compound is an enantiomer of a compound selected from Table 17 or a salt thereof. In some embodiments, a provided compound is a diastereomer of a compound selected from Table 17 or a salt thereof.

As appreciated by those skilled in the art, compounds when used for chiral auxiliaries are typically stereopure or substantially stereopure, and are typically utilized as a single stereoisomer substantially free of other stereoisomers. In some embodiments, compounds of the present disclosure are stereopure or substantially stereopure.

As demonstrated herein, when used for preparing a chiral internucleotidic linkage, to obtain stereoselectivity generally stereochemically pure chiral reagents are utilized. Among other things, the present disclosure provides stereochemically pure chiral reagents, including those having structures described herein.

In some embodiments, provided compounds, e.g., compounds of formula I, I-a, I-a-1, I-a-2, I-b, I-c, I-d, I-e, II, II-a, II-b, III, III-a, or III-b, or salts thereof, comprises one or more chiral elements. In some embodiments, provided compounds of formula I, I-a, I-a-1, I-a-2, I-b, I-c, I-d, I-e, II, II-a, II-b, III, III-a, or III-b, or salts thereof, are chiral. In some embodiments, provided chiral compounds, compounds of formula I, I-a, I-a-1, I-a-2, I-b, I-c, I-d, I-e, II, II-a, II-b, III, III-a, or III-b, or salts thereof, are of a purity described in the present disclosure. In some embodiments, provided chiral compounds, compounds of formula I, I-a, I-a-1, I-a-2, I-b, I-c, I-d, I-e, II, II-a, II-b, III, III-a, or III-b, or salts thereof, are of a stereopurity described in the present disclosure. In some embodiments, provided chiral compounds, compounds of formula I, I-a, I-a-1, I-a-2, I-b, I-c, I-d, I-e, II, II-a, II-b, III, III-a, or III-b, or salts thereof, are of a diastereomeric purity described in the present disclosure. In some embodiments, provided chiral compounds, compounds of formula I, I-a, I-a-1, I-a-2, I-b, I-c, I-d, I-e, II, II-a, II-b, III, III-a, or III-b, or salts thereof, are of a enantiomeric purity described in the present disclosure. In some embodiments, provided chiral compounds, compounds of formula I, I-a, I-a-1, I-a-2, I-b, I-c, I-d, I-e, II, II-a, II-b, III, III-a, or III-b, or salts thereof, are of diastereomeric and enantiomeric purity described in the present disclosure. In some embodiments, the present disclosure provides compounds, e.g., compounds of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, VI-e, O-I, or salts thereof, that are made from compounds of formula I, I-a, I-a-1, I-a-2, I-b, I-c, I-d, I-e, II, II-a, II-b, III, III-a, or III-b, or salts thereof, and comprise chiral elements of compounds of formula I, I-a, I-a-1, I-a-2, I-b, I-c, I-d, I-e, II, II-a, II-b, III, III-a, or III-b.

In various embodiments, —X-$L^s$-$R^5$ (or —X-$L^s$-$R^1$) is of such a structure that H—X-$L^s$-$R^5$ (or H—X-$L^s$-$R^5$) is a compound of formula I, I-a, I-a-1, I-a-2, I-b, I-c, I-d, I-e, II, II-a, II-b, III, III-a, or III-b, optionally wherein $R^5$ or $R^6$ is —H or —C(O)R'. In various embodiments. —X-L-$R^5$ (or —X-$L^s$-$R^1$) is of such a structure that H—X-$L^s$-R (or H—X-$L^s$-$R^5$) is a compound of formula I, I-a, I-a-1, I-a-2, I-b, I-c, or I-d, optionally wherein $R^5$ or $R^6$ is —C(O)R'. In some embodiments, $R^6$ is —H or —C(O)R'. In some embodiments, a compound of formula I, I-a, I-a-1, I-a-2, I-b, I-c, I-d, I-e, I, II-a, I-b, II, III-a, or III-b (e.g., one corresponding to a chiral auxiliary in, e.g., a reagent, a product, a phosphoramidite, an internucleotidic linkage, an oligonucleotide, etc.) has the structure of

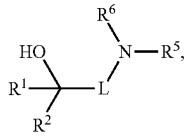
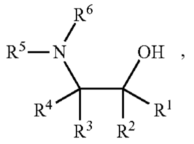
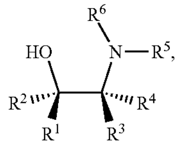
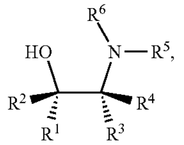
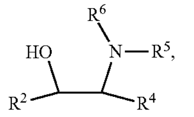
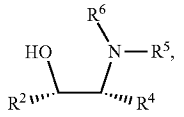
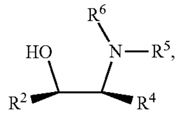
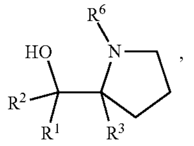
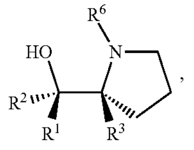
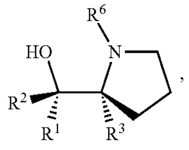

-continued

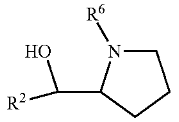
,
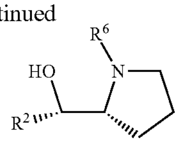
, or
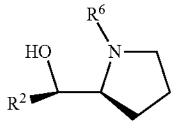
.

In some embodiments, a compound of formula I, I-a, I-a-1, I-a-2, I-b, I-c, I-d, I-e, II, II-a, II-b, III, III-a, or III-b has the structure of

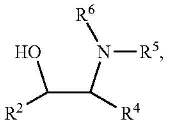
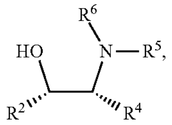
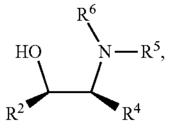
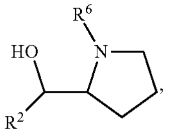
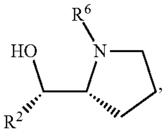
or
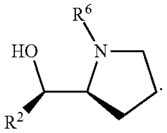

In some embodiments, a compound of formula I, I-a, I-a-1, I-a-2, I-b, I-c, I-d, I-e, II, II-a, II-b, III, III-a, or III-b has the structure of

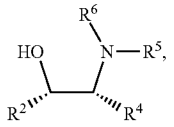
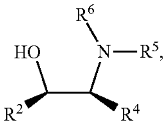
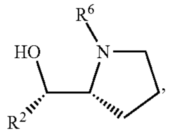
or
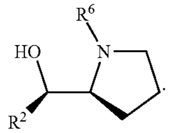

In some embodiments, a compound of formula I, I-a, I-a-1, I-a-2, I-b, I-c, I-d, I-e, II, II-a, II-b, III, III-a, or III-b is

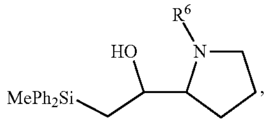
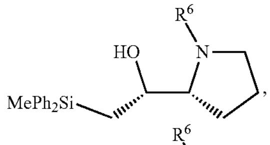
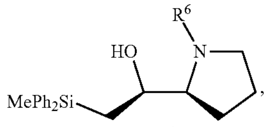
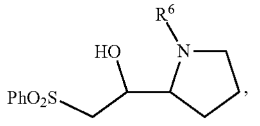

-continued
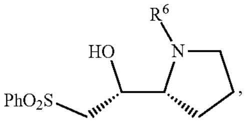
, or
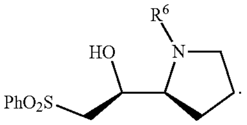
.
In some embodiments, a compound of formula I, I-a, I-a-1, I-a-2, I-b, I-c, I-d, I-e, II, II-a, II-b, III, III-a, or III-b is
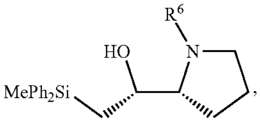
,
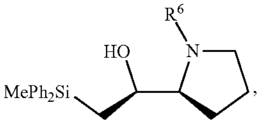
,
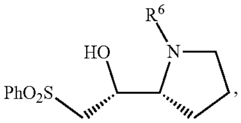
, or
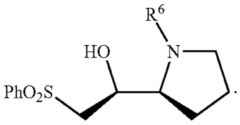
.
In some embodiments, a compound is
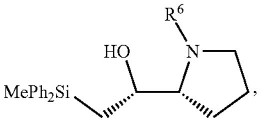
,
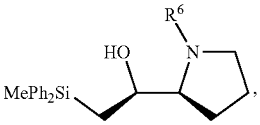
,
In some embodiments, a compound is
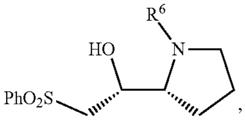
, or
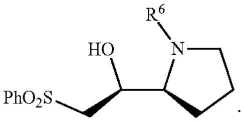
.
In some embodiments, a compound is
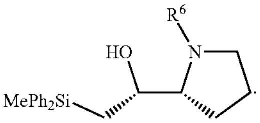
.
In some embodiments, a compound is
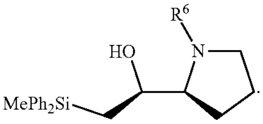
.
In some embodiments, a compound is
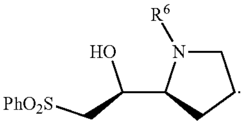
.
In some embodiments, a compound is
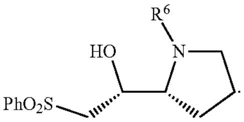
.
In some embodiments, —X-$L^s$-$R^5$ (or —X-$L^s$-$R^1$) is
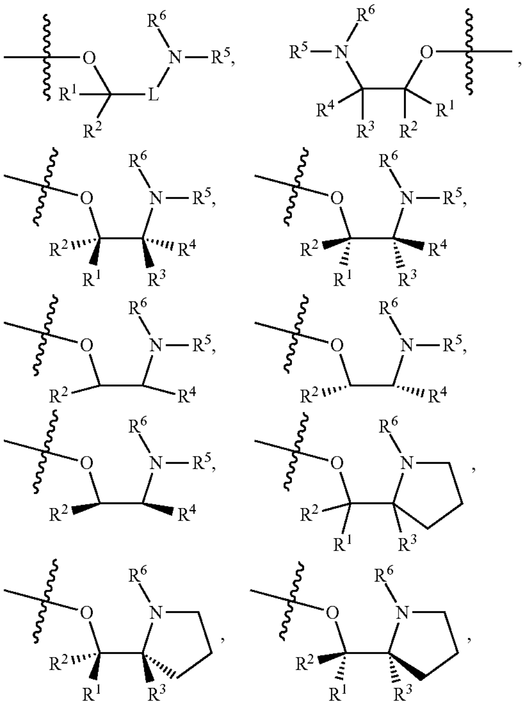

-continued
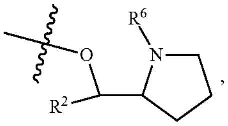,
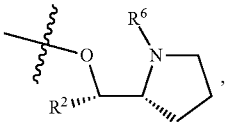,
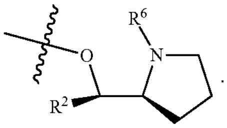.
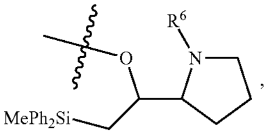,
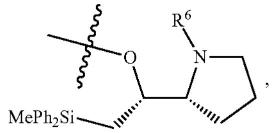,
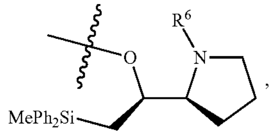,
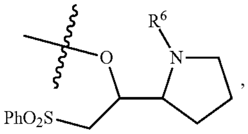,
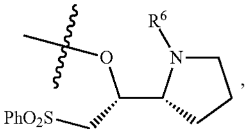, or
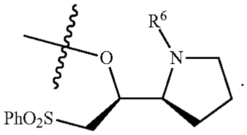.
In some embodiments, —X-$L^s$-$R^5$ (or —X-$L^s$-$R^1$) is
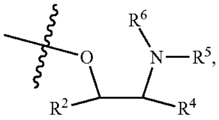
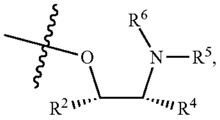
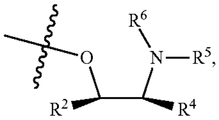
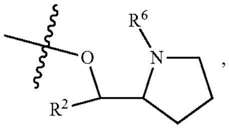,
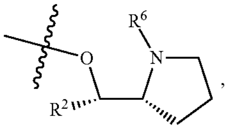,
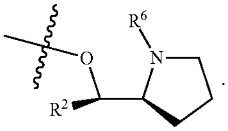.
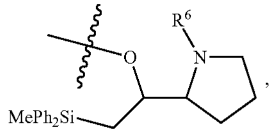,
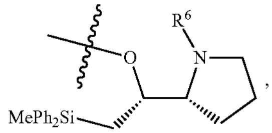,
-continued
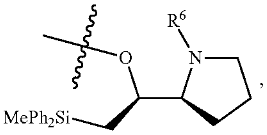,
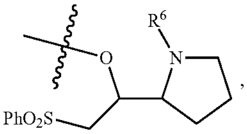,
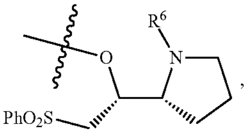, or
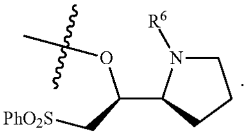.
In some embodiments, —X-$L^s$-$R^5$ (or —X-$L^s$-$R^1$) is
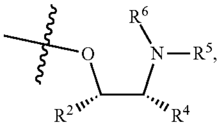
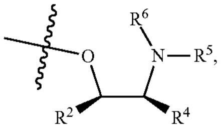
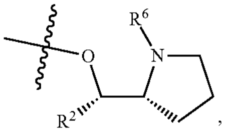,
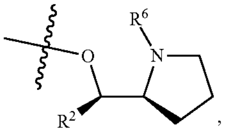,
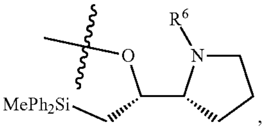,
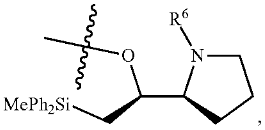,
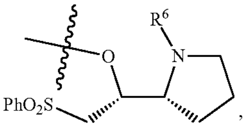, or
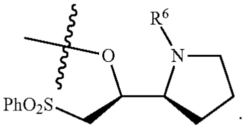.
In some embodiments, —X-$L^s$-$R^5$ (or —X-$L^s$-$R^1$) is
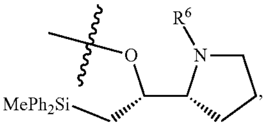,
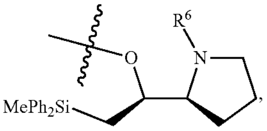, -continued

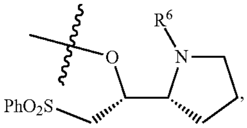

, or

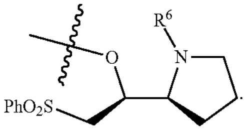

.

In some embodiments, —X-$L^s$-$R^5$ (or —X-$L^s$-$R^1$) is

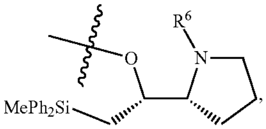

, or

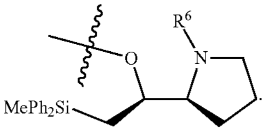

.

In some embodiments, —X-$L^s$-$R^5$ (or —X-$L^s$-$R^1$) is

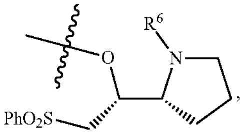

, or

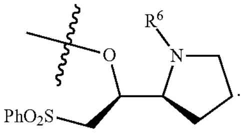

.

In some embodiments, —X-$L^s$-$R^5$ (or —X-L-$R^1$) is

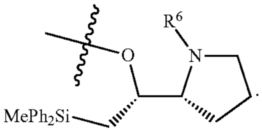

.

In some embodiments, —X-$L^s$-$R^5$ (or —X-$L^s$-$R^1$) is

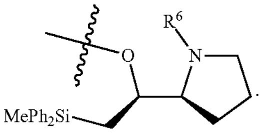

.

In some embodiments, —X-$L^s$-$R^5$ (or —X-$L^s$-$R^1$) is

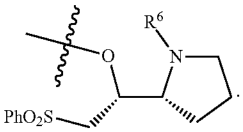

.

In some embodiments, —X-$L^s$-$R^5$ (or —X-$L^s$-$R^1$) is

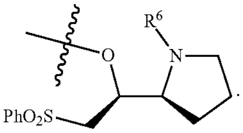

.

In some embodiments, each chirally controlled internucleotidic linkage is independently of formula VII, and each —X-$L^s$-$R^5$ is independently as described herein. In some embodiments, In some embodiments, each —X-$L^s$-$R^5$ (or —X-$L^s$-$R^1$) is independently

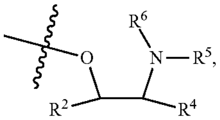

,

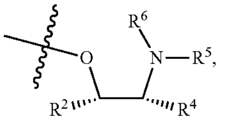

,

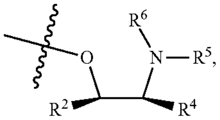

,

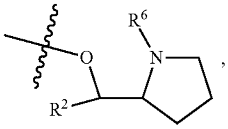

,

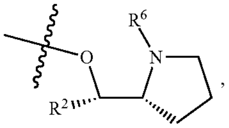

,

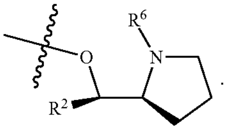

.

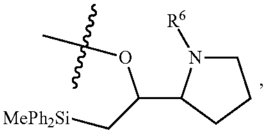

,

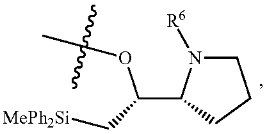

,

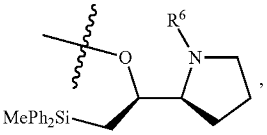

,

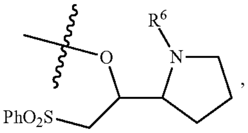

,

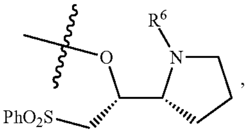

, or

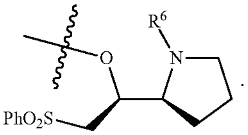

.

In some embodiments, each —X-$L^s$-$R^5$ (or —X-$L^s$-$R^1$) is independently

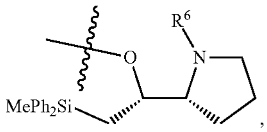,

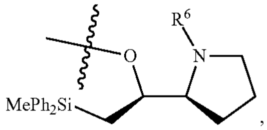,

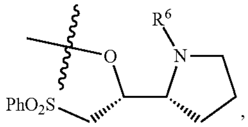, or 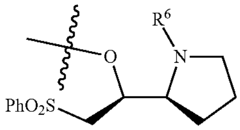.

In some embodiments, each —X-$L^s$-$R^5$ (or —X-$L^s$-$R^1$) is independently

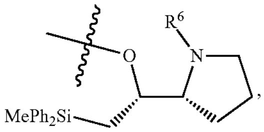, or 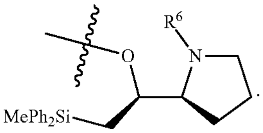.

In some embodiments, each —X-$L^s$-$R^5$ (or —X-$L^s$-$R^1$) is independently

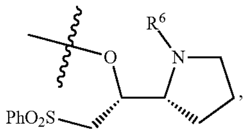, or 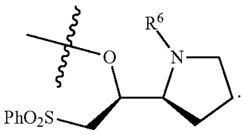.

In some embodiments, each —X-$L^s$-$R^5$ (or —X-$L^s$-$R^1$) is

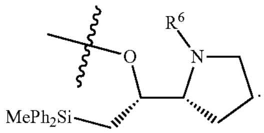.

In some embodiments, each —X-$L^s$-$R^5$ (or —X-$L^s$-$R^1$) is

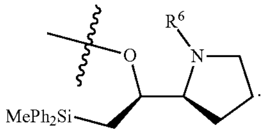.

In some embodiments, each —X-$L^s$-$R^5$ (or —X-$L^s$-$R^1$) is

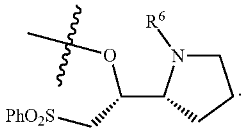.

In some embodiments, each —X-$L^s$-$R^5$ (or —X-$L^s$-$R^1$) is

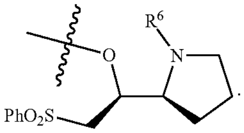.

In some embodiments, $R^6$ is —H or —C(O)R'. In some embodiments, $R^6$ is —H (e.g., in the first internucleotidic linkage of a coupling product oligonucleotide from the 5'-end). In some embodiments, $R^6$ is —C(O)R' (e.g., in a product oligonucleotide, e.g., in a product oligonucleotide of a de-blocking step, a coupling step (optionally except the first internucleotidic linkage from the 5'-end), a pre-modification capping step, a modification step, and/or a post-modification capping step). In some embodiments, $R^6$ is —$C(O)CH_3$.

Methods for preparing chiral auxiliary compounds are widely known in the art and can be utilized in accordance with the present disclosure. A large number of compounds, including many in the tables, were prepared and characterized. Many compounds described herein, when used as chiral auxiliaries, can deliver high stereoselectivity and/or purity.

Phosphoramidites

In some embodiments, the present disclosure provides useful phosphoramidites, including stereopure phosphoramidites comprising chiral auxiliaries. In some embodiments, the present disclosure provides methods utilizing such phosphoramidites. In many embodiments, chiral auxiliaries are utilized to prepare chirally pure phosphoramidites, which are used to stereoselectively form linkage phosphorus chiral centers compared to absence of chiral auxiliaries. In some embodiments, the present disclosure provides compound, e.g., of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or salts thereof, that can be utilized as phosphoramidites for oligonucleotide synthesis. In some embodiments, product oligonucleotides may contain one or more natural phosphate linkages and/or non-chirally controlled chiral internucleotidic linkages, and for such linkages, phosphoramidite for traditional oligonucleotide synthesis may be readily utilized. As understand by those skilled in the art, nucleobases may be blocked in phosphoramidite for oligonucleotide synthesis, and they can be de-blocked, e.g., after synthesis cycles. Technologies for blocking and de-blocking (protecting) nucleobases are widely known in the art and can be utilized in accordance with the present disclosure. Technologies for preparing phosphoramidites can be utilized in accordance with the present disclosure. Example technologies include those described in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, WO 2019/217784, etc. As illustrated, in some embodiments, a phosphoramidite is a DPSE-phosphoramidite comprising

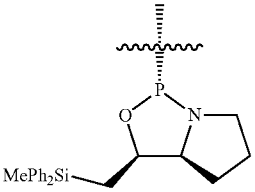
or
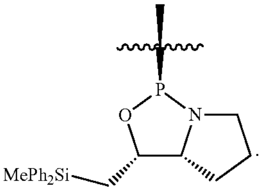

As illustrated, in some embodiments, a phosphoramidite is a PSM-phosphoramidite comprising

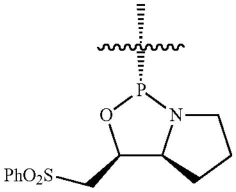
or
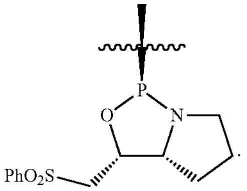

For example, in some embodiments, the present disclosure provides a compound having the structure of formula IV:

IV

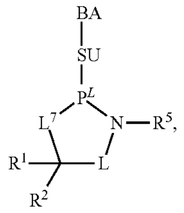

or a salt thereof, wherein:

$P^L$ is P(=W), P, or P→B(R')$_3$;

W is O, S or Se;

L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C($R^3$)($R^4$)—, —C($R^3$)($R^4$)—C($R^3$)($R^4$)—, -Cy-, or —C($R^3$)[C($R^4$)$_3$]—;

each of $R^1$, $R^2$, $R^3$, $R^4$, and $R^5$ is independently —H, -$L^s$-R, halogen, —CN, —$NO_2$, -$L^s$-Si(R)$_3$, —OR, —SR, or —N(R)$_2$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

$L^7$ is —O— or —S— or $L^s$;

at least one of $R^1$, $R^2$, $R^1$ and $R^4$ is not —H;

BA is an optionally substituted group selected from $C_{3-30}$ cycloaliphatic, $C_{6-30}$ aryl, $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus and silicon, a natural nucleobase moiety, and a modified nucleobase moiety;

SU is -$L^s$-O— or

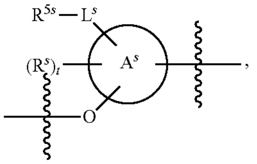

wherein SU is connected to the phosphorus atom through the oxygen atom;

each $R^5$ is independently —H, halogen, —CN, —$N_3$, —NO, —$NO_2$, -$L^s$-R', -$L^s$-Si(R)$_3$, -$L^s$-OR', -$L^s$-SR', -$L^s$-N(R')$_2$, —O-$L^s$-R', —O-$L^s$-Si(R)$_3$, —O-$L^s$-OR', —O-$L^s$-SR', or —O-$L^s$-N(R')$_2$;

t is 0-20;

Ring $A^s$ is an optionally substituted 3-20 membered monocyclic, bicyclic or polycyclic ring having 0-10 heteroatoms independently selected from oxygen, nitrogen, sulfur, phosphorus and silicon;

$R^{5s}$ is $R^s$;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or;

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, $P^L$ is P(=W). In some embodiments, $P^L$ is P. In some embodiments, $P^L$ is $P \rightarrow B(R')_3$. In some embodiments, P of $P^L$ is chiral. In some embodiments, P of $P^L$ is Rp. In some embodiments, P of $P^L$ is Sp.

In some embodiments, SU is $-L^s-O-$. In some embodiments, SU is

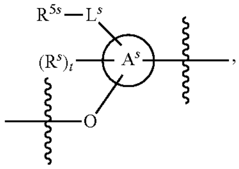

wherein each variable is independently as described in the present disclosure. In some embodiments, SU is

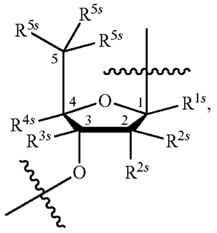

each of $R^{1s}$, $R^{2s}$, $R^{3s}$, $R^{4s}$ and $R^{5s}$ is independently $R^s$. In some embodiments, SU is

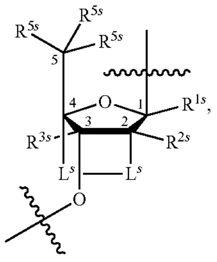

wherein each variable is independently as described in the present disclosure. In some embodiments, SU is

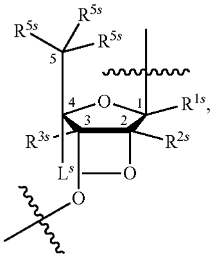

wherein each variable is independently as described in the present disclosure. In some embodiments, SU is

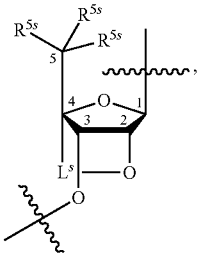

wherein each variable is independently as described in the present disclosure. In some embodiments, SU is

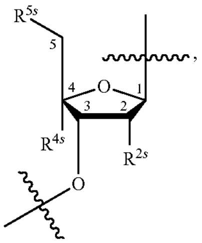

wherein each variable is independently as described in the present disclosure. In some embodiments, SU is

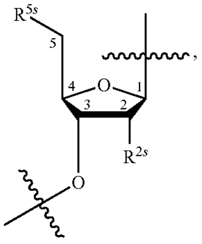

wherein each variable is independently as described in the present disclosure.

In some embodiments, a provided compound, e.g., a compound of formula IV, has the structure of formula IV-a:

IV-a

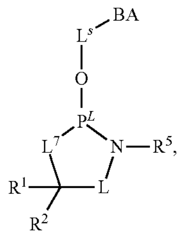

or a salt thereof, wherein each variable is independently as described in the present disclosure. In some embodiments, a provided compound of formula IV has the structure of formula IV-a. In some embodiments, $L^s$-Cy-. In some embodiments, $L^s$ is an optionally substituted monocyclic or bicyclic 3-20 membered heterocyclyl ring having 1-5 heteroatoms. In some embodiments, $L^s$ is an optionally substituted monocyclic or bicyclic 5-20 membered heterocyclyl ring having 1-5 heteroatoms, wherein at least one heteroatom is oxygen. In some embodiments, L is an optionally substituted bivalent tetrahydrofuran ring. In some embodiments, $L^s$ is an optionally substituted furanose moiety. In some embodiments, the BA in formula IV-a is bonded to C1, and the —O— in formula IV-a is bonded to C3, of the furanose moiety.

In some embodiments, a provided compound, e.g., a compound of formula IV, has the structure of formula IV-b:

IV-b

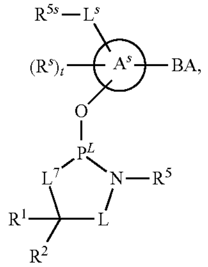

or a salt thereof, wherein each variable is independently as described in the present disclosure. In some embodiments, a provided compound of formula IV has the structure of formula IV-b.

In some embodiments, a provided compound, e.g., a compound of formula IV, has the structure of formula IV-c-1:

IV-c-1

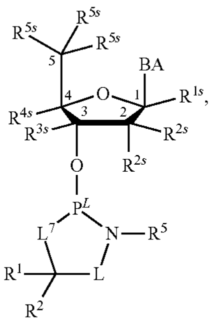

or a salt thereof, wherein each variable is independently as described in the present disclosure. In some embodiments, a provided compound of formula IV has the structure of formula IV-c-1.

In some embodiments, a provided compound, e.g., a compound of formula IV, has the structure of formula IV-c-2:

IV-c-2

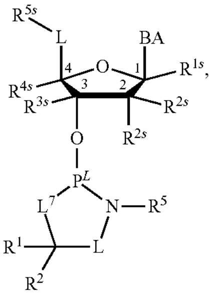

or a salt thereof, wherein each variable is independently as described in the present disclosure. In some embodiments, a provided compound of formula IV has the structure of formula IV-c-2.

In some embodiments, a provided compound, e.g., a compound of formula IV, has the structure of formula IV-d:

IV-d

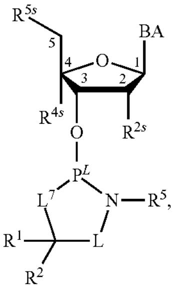

or a salt thereof, wherein each variable is independently as described in the present disclosure. In some embodiments, a provided compound of formula IV has the structure of formula IV-d.

In some embodiments, a provided compound, e.g., a compound of formula IV, has the structure of formula IV-e:

IV-e

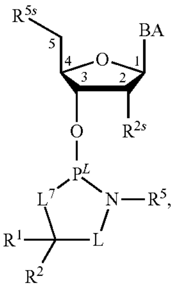

or a salt thereof, wherein each variable is independently as described in the present disclosure. In some embodiments, a provided compound of formula IV has the structure of formula IV-e.

In some embodiments, a compound of formula IV, IV-a, IV-b, IV-c-1, IV-c-2, IV-d, or IV-e, can be prepared from a compound of formula I, I-a, I-a-1, I-a-2, I-b, I-c, I-d, I-e, II, II-a, II-b, III, III-a, III-b, etc. In some embodiments,

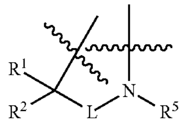

is as described for formula I, I-a, I-a-1, I-a-2, I-b, I-c, I-d, I-e, II, II-a, II-b, III, III-a, III-b, etc. In some embodiments, a compound of formula IV, IV-a, IV-b, IV-c-1, IV-c-2, IV-d, or IV-e has a structure such that

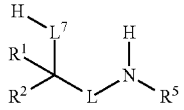

is a compound having the structure of I, I-a, I-a-1, I-a-2, I-b, I-c, I-d, or I-e, or a salt thereof.

In some embodiments, the present disclosure provides a compound having the structure of formula IVa:

IVa

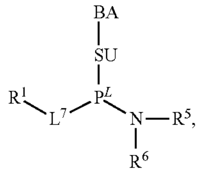

or a salt thereof, wherein each variable is independently as described in the present disclosure. In some embodiments, the present disclosure provides a compound having the structure of formula IVa-a:

IVa-a

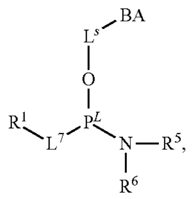

or a salt thereof, wherein each variable is independently as described in the present disclosure. In some embodiments, a compound of formula IVa is a compound of formula IVa-a. In some embodiments, the present disclosure provides a compound having the structure of formula IVa-b:

IVa-b

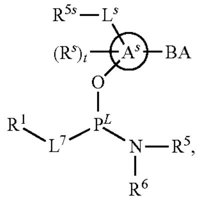

or a salt thereof, wherein each variable is independently as described in the present disclosure. In some embodiments, a compound of formula IVa is a compound of formula IVa-b. In some embodiments, the present disclosure provides a compound having the structure of formula IVa-c-1:

IVa-c-1

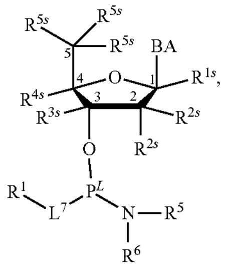

or a salt thereof, wherein each variable is independently as described in the present disclosure. In some embodiments, a compound of formula IVa is a compound of formula IVa-c-1. In some embodiments, the present disclosure provides a compound having the structure of formula IVa-c-2:

IVa-c-2

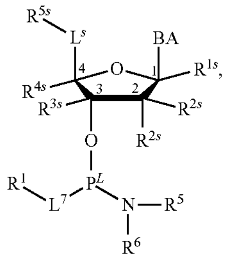

or a salt thereof, wherein each variable is independently as described in the present disclosure. In some embodiments, a compound of formula IVa is a compound of formula IVa-c-2. In some embodiments, the present disclosure provides a compound having the structure of formula IVa-d:

IVa-d

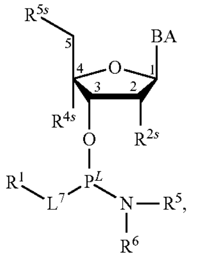

or a salt thereof, wherein each variable is independently as described in the present disclosure. In some embodiments, a compound of formula IVa is a compound of formula IVa-d. In some embodiments, the present disclosure provides a compound having the structure of formula IVa-e:

IVa-e

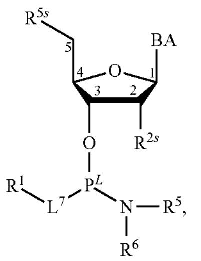

or a salt thereof, wherein each variable is independently as described in the present disclosure. In some embodiments, a compound of formula IVa is a compound of formula IVa-e. In some embodiments, $L^7$ is —O—. In some embodiments, each of $R^1$, $R^5$, and $R^6$ is independently optionally substituted $C_{1-6}$ alkyl. In some embodiments, $R^5$ and $R^6$ are the same. In some embodiments, $P^L$ is P. In some embodiments, $-L^7-R^1$ contains no chiral elements. In some embodiments, $—N(R^5)(R^6)$ contains no chiral elements. In some embodiments, $-L^7-R^1$ and $—N(R^5)(R^6)$ contains no chiral elements. In some embodiments, $-L^7-R^1$ is $—O—CH_2CH_2—CN$. In some embodiments, $—N(R^5)(R^6)$ is $—N(i\text{-}Pr)_2$. In some embodiments, a compound of formula IVa, IVa-a, IVa-b, IVa-c-1, IVa-c-2, IVa-d, or IVa-e, or a salt thereof, is a phosphoramidite for non-chirally controlled oligonucleotide synthesis, e.g., oligonucleotide synthesis using traditional phosphoramidite chemistry. In some embodiments, $R^1$ and $R^5$ are R and are taken together with their intervening atoms to form a ring as described in the present disclosure. In some embodiments, a formed ring contain a chiral element, and a compound of formula IVa, IVa-a, IVa-b, IVa-c-1, IVa-c-2, IVa-d, or IVa-e, or a salt thereof can be utilized for chirally controlled oligonucleotide synthesis.

In some embodiments, the present disclosure provides a compound having the structure of formula V:

V

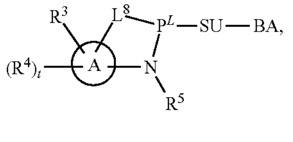

or a salt thereof, wherein:

$P^L$ is P(=W), P, or P→B(R')$_3$;

W is O, S or Se;

Ring A is an optionally substituted 3-20 membered monocyclic, bicyclic or polycyclic ring having 0-10 heteroatoms independently selected from oxygen, nitrogen, sulfur, phosphorus and silicon;

each of $R^1$, $R^2$, $R^1$, $R^4$, and $R^5$ is independently —H, $-L^s-R$, halogen, —CN, $—NO_2$, $-L^s-Si(R)_3$, —OR, —SR, or $—N(R)_2$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, $—C(R')_2—$, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, $—S(O)_2—$, $—S(O)_2N(R')—$, —C(O)S—, —C(O)O—, —P(O)(OR')—, —P(O)(SR')—, —P(O)(R')—, —P(O)(NR')—, —P(S)(OR')—. —P(S)(SR')—, —P(S)(R')—, —P(S)(NR')—, —P(R')—, —P(OR')—, —P(SR')—, —P(NR')—, $—P(OR')[B(R')_2]—$, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or $—OP(OR')[B(R')_3]O—$, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

t is 0-20;

$L^8$ is -L-O—, $-L-C(R^1)(R^2)—O—$, or $-L^s-O—$;

L is a covalent bond, or optionally substituted $C^{1-6}$ alkylene, wherein one or more methylene units are optionally and independently replaced with -L'-;

L' is a covalent bond, optionally substituted bivalent $C_{1-3}$ alkylene, $—C(R^3)(R^4)—$, $—C(R^3)(R^4)—C(R^3)(R^4)—$, -Cy-, or $—C(R^3)[C(R^4)_3]—$;

BA is an optionally substituted group selected from $C_{3-30}$ cycloaliphatic, $C_{6-30}$ aryl, $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus and silicon, a natural nucleobase moiety, and a modified nucleobase moiety;

SU is $-L^s-O—$ or

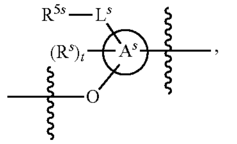

wherein SU is connected to the phosphorus atom through the oxygen atom;

$R^{5s}$ is $R^s$;

each $R^s$ is independently —H, halogen, —CN, —$N_3$, —NO, —$NO_2$, -$L^s$-R', -$L^s$-Si(R)$_3$, -$L^s$-OR', -$L^s$-SR', -$L^s$-N(R')$_2$, —O-$L^s$-R', —O-$L^s$-Si(R)$_3$, —O-$L^s$-OR', —O-$L^s$-SR', or —O-$L^s$-N(R')$_2$;

Ring $A^s$ is an optionally substituted 3-20 membered monocyclic, bicyclic or polycyclic ring having 0-10 heteroatoms independently selected from oxygen, nitrogen, sulfur, phosphorus and silicon;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{1-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or;

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, $P^L$ is P(=W). In some embodiments, $P^L$ is P. In some embodiments, $P^L$ is P→B(R')$_3$. In some embodiments, P of $P^L$ is chiral. In some embodiments, P of $P^L$ is Rp. In some embodiments, P of $P^L$ is Sp.

In some embodiments, a provided compound, e.g., a compound of formula V, has the structure of formula V-a:

V-a

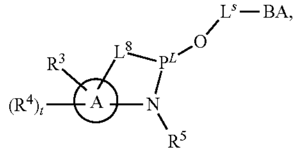

or a salt thereof, wherein each variable is independently as described in the present disclosure. In some embodiments, a provided compound of formula V has the structure of formula V-a.

In some embodiments, a provided compound, e.g., a compound of formula V, has the structure of formula V-b:

V-b

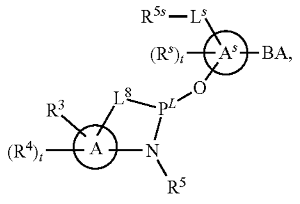

or a salt thereof, wherein each variable is independently as described in the present disclosure. In some embodiments, a provided compound of formula V has the structure of formula V-b.

In some embodiments, a provided compound, e.g., a compound of formula V, has the structure of formula V-c-1:

V-c-1

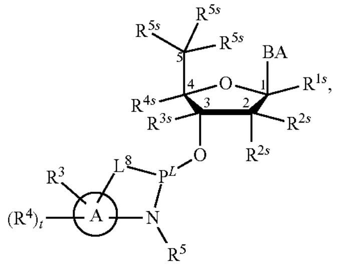

or a salt thereof, wherein each variable is independently as described in the present disclosure. In some embodiments, a provided compound of formula V has the structure of formula V-c-1.

In some embodiments, a provided compound, e.g., a compound of formula V, has the structure of formula V-c-2:

V-c-2

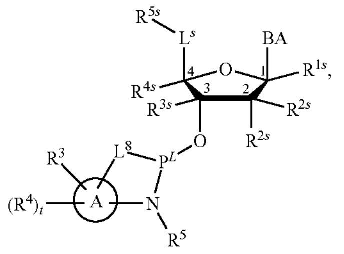

or a salt thereof, wherein each variable is independently as described in the present disclosure. In some embodiments, a provided compound of formula V has the structure of formula V-c-2.

In some embodiments, a provided compound, e.g., a compound of formula V, has the structure of formula V-d:

V-d

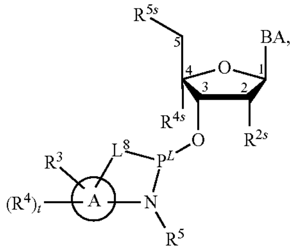

or a salt thereof, wherein each variable is independently as described in the present disclosure. In some embodiments, a provided compound of formula V has the structure of formula V-d.

In some embodiments, a provided compound, e.g., a compound of formula V, has the structure of formula V-e:

V-e

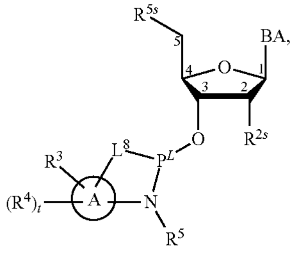

or a salt thereof, wherein each variable is independently as described in the present disclosure. In some embodiments, a provided compound of formula V has the structure of formula V-e.

In some embodiments, a compound of formula V, V-a, V-b, V-c-1, V-c-2, V-d, or V-e, can be prepared from a compound of formula I, I-a, I-a-1, I-a-2, I-b, I-c, I-d, I-e, II, II-a, II-b, III, III-a, III-b, etc. In some embodiments,

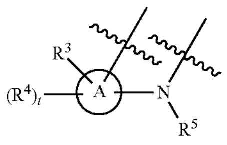

is as described for formula I, I-a, I-a-1, I-a-2, I-b, I-c, I-d, I-e, II, II-a, II-b, III, III-a, III-b, etc. In some embodiments, a compound of formula IV, IV-a, IV-b, IV-c-1, IV-c-2, IV-d, or IV-e has a structure such that

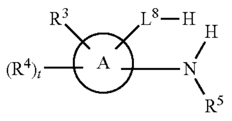

is a compound having the structure of II, II-a, or II-b.

In some embodiments, the present disclosure provides a compound having the structure of formula VI:

VI

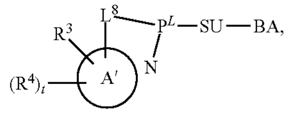

or a salt thereof, wherein each variable is independently as described in the present disclosure.

In some embodiments, a provided compound, e.g., a compound of formula VI, has the structure of formula VI-a:

VI-a

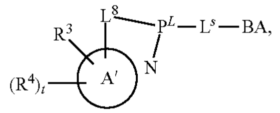

or a salt thereof, wherein Ring A' is Ring A comprising a ring nitrogen atom which is bond to P of $P^L$, and each variable is independently as described in the present disclosure. In some embodiments, a provided compound of formula VI has the structure of formula VI-a.

In some embodiments, a provided compound, e.g., a compound of formula VI, has the structure of formula VI-b:

VI-b

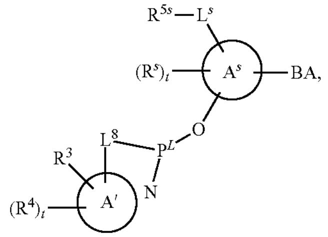

or a salt thereof, wherein each variable is independently as described in the present disclosure. In some embodiments, a provided compound of formula VI has the structure of formula VI-b.

In some embodiments, a provided compound, e.g., a compound of formula VI, has the structure of formula VI-c-1:

VI-c-1

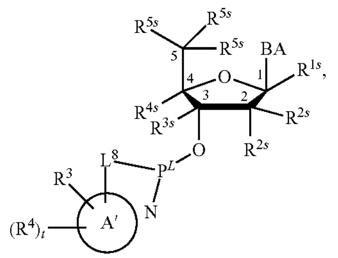

or a salt thereof, wherein each variable is independently as described in the present disclosure. In some embodiments, a provided compound of formula VI has the structure of formula VI-c-1.

In some embodiments, a provided compound, e.g., a compound of formula VI, has the structure of formula VI-c-2:

VI-c-2

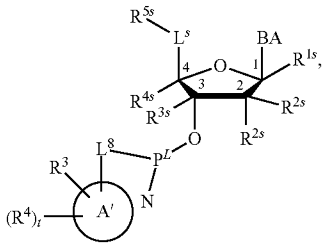

or a salt thereof, wherein each variable is independently as described in the present disclosure. In some embodiments, a provided compound of formula VI has the structure of formula VI-c-2.

In some embodiments, a provided compound, e.g., a compound of formula VI, has the structure of formula VI-d:

VI-d

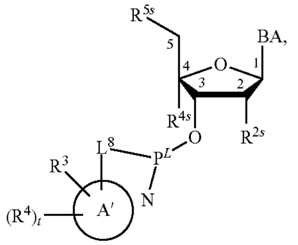

or a salt thereof, wherein each variable is independently as described in the present disclosure. In some embodiments, a provided compound of formula VI has the structure of formula VI-d.

In some embodiments, a provided compound, e.g., a compound of formula VI, has the structure of formula VI-e:

VI-e

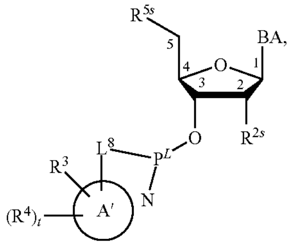

or a salt thereof, wherein each variable is independently as described in the present disclosure. In some embodiments, a provided compound of formula VI has the structure of formula VI-e.

In some embodiments, a compound of formula VI, VI-a, VI-b, VI-c-1, VI-c-2, VI-d, or VI-e, can be prepared from a compound of formula I, I-a, I-a-1, I-a-2, I-b, I-c, I-d, I-e, II, II-a, II-b, III, III-a, III-b, etc. In some embodiments,

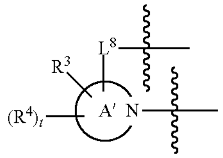

is as described for formula I, I-a, I-a-1, I-a-2, I-b, I-c, I-d, I-e, II, II-a, II-b, III, III-a, III-b, etc. In some embodiments, a compound of formula VI, VI-a, VI-b, VI-c-1, VI-c-2, VI-d, or VI-e has a structure such that

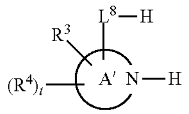

is a compound having the structure of III, III-a, or III-b.

In some embodiments, for a phosphoramidite has the structure of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof, $P^L$ is P.

In some embodiments, a phosphoramidite for non-stereocontrolled coupling is of structure

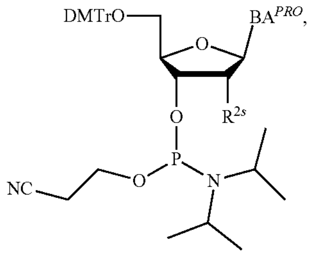

wherein each variable is independently as described in the present disclosure.

In some embodiments, a compound, e.g., a phosphoramidite, has the structure of

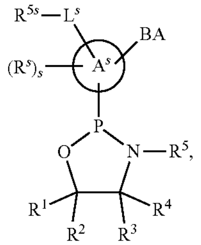

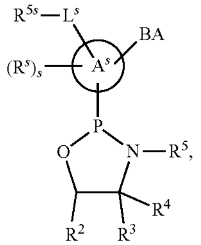

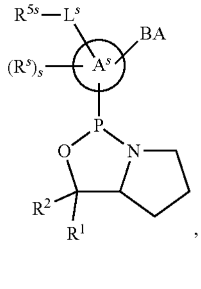

,

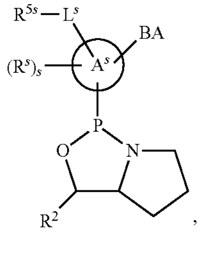

,

-continued
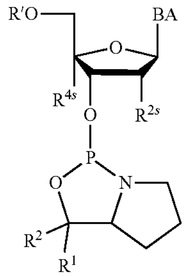,
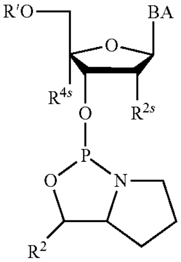,
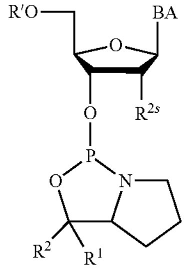, or
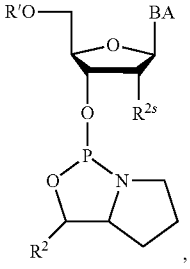,
wherein each variable is independently as described in the present disclosure. In some embodiments, a compound, e.g., a phosphoramidite, has the structure of
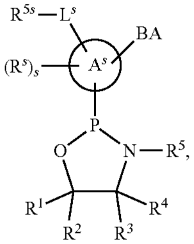
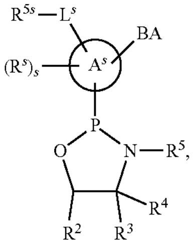
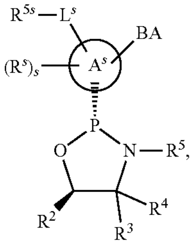
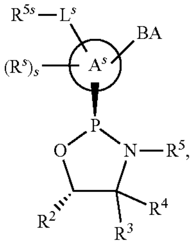
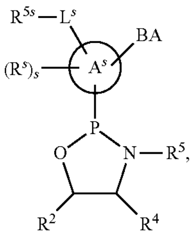
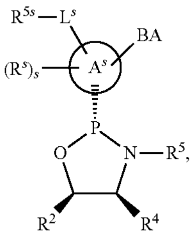
-continued
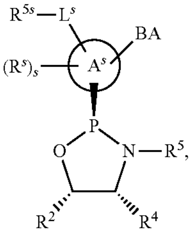
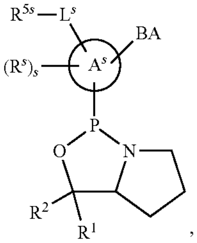,
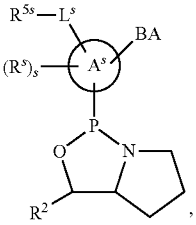,
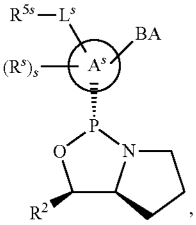,
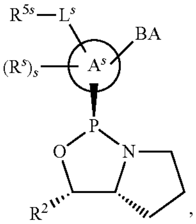,
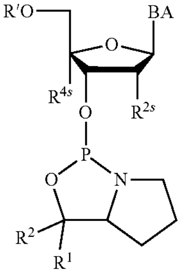,
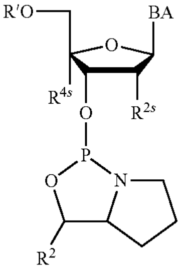,
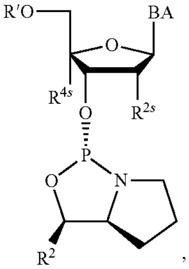,
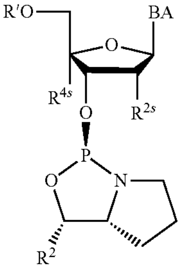,
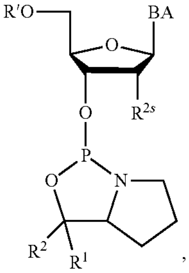,
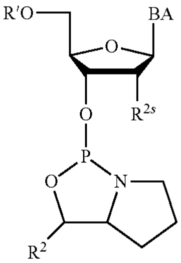,
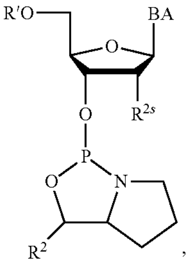, -continued

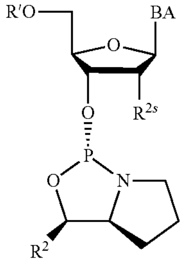
, or
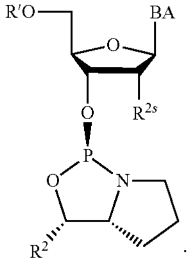
.

In some embodiments, a chiral phosphoramidite for coupling has the structure of

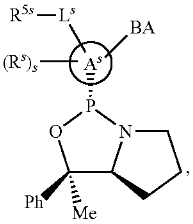
,
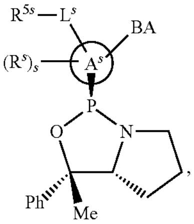
,
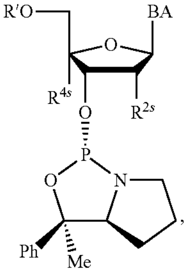
,
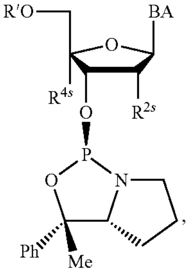
,
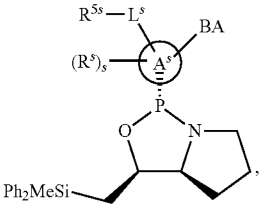
,
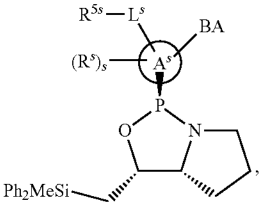
,
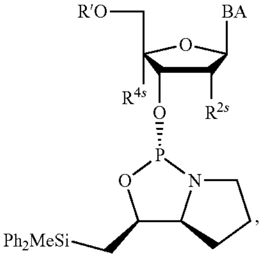
, -continued

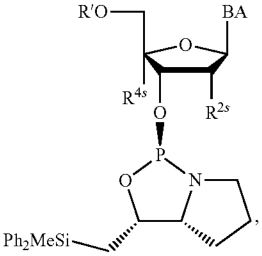
,
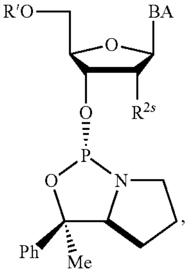
,
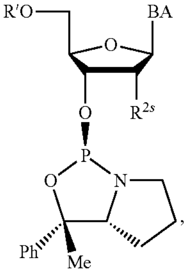
,
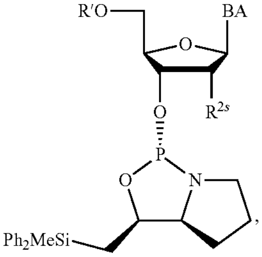
, or
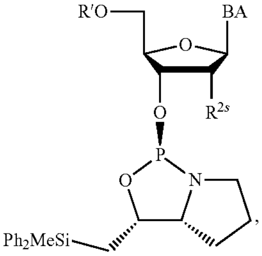
, wherein each variable is independently as described in the present disclosure. In some embodiments, $R^1$ or $R^2$ comprises an electron-withdrawing group as described in the present disclosure. In some embodiments, a chiral phosphoramidite for coupling has the structure of

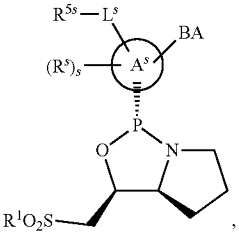
,
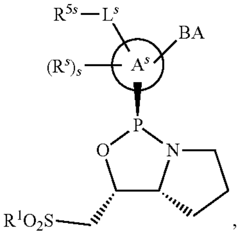
,

-continued

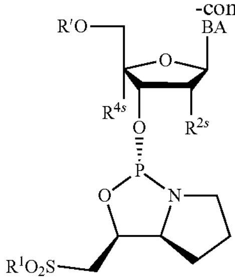

,

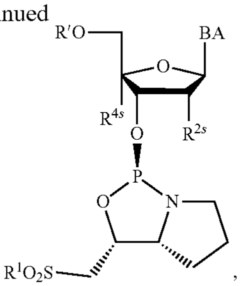

,

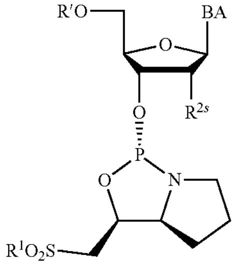

, or

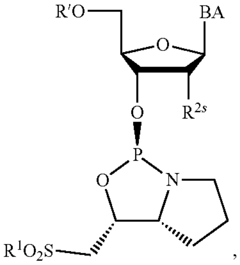

, wherein each variable is independently as described in the present disclosure. In some embodiments, $R^1$ is R' as described in the present disclosure. In some embodiments, $R^1$ is R as described in the present disclosure. In some embodiments, R is optionally substituted phenyl as described in the present disclosure. In some embodiments, R is phenyl. In some embodiments, R is optionally substituted $C_{1-6}$ aliphatic as described in the present disclosure. In some embodiments, R is optionally substituted $C_{1-6}$ alkyl as described in the present disclosure. For example, in some embodiments. R is methyl, in some embodiments, R is isopropyl; in some embodiments, R is t-butyl; etc.

In some embodiments, $R^{5s}$-$L^s$- is R'O—. In some embodiments, R'O— is DMTrO—. In some embodiments, $R^{4s}$ is —H. In some embodiments, $R^{4s}$ and $R^{2s}$ are taken together to form a bridge -L-O— as described in the present disclosure. In some embodiments, the —O— is connected to the carbon at the 2' position. In some embodiments, L is —$CH_2$—. In some embodiments, L is —CH(Me)-. In some embodiments, L is —(R)—CH(Me)-. In some embodiments, L is —(S)—CH(Me)-. In some embodiments, $R^{2s}$ is —H. In some embodiments, $R^{2s}$ is —F. In some embodiments, $R^{2s}$ is —OR'. In some embodiments, $R^{2s}$ is —OMe. In some embodiments, $R^{2s}$ is -MOE. As appreciated by those skilled in the art, BA may be suitably protected during synthesis.

Nucleobases

Various nucleobases may be utilized in accordance with the present disclosure. In some embodiments, a nucleobase, e.g., BA, is a natural nucleobase, the most commonly occurring ones being A, T, C, G and U. In some embodiments, a nucleobase is a modified nucleobase in that it is not A, T, C, G or U. In some embodiments, a nucleobase is optionally substituted A, T, C, G or U, or a substituted tautomer of A T, C, G or U. In some embodiments, a nucleobase is optionally substituted A, T, C, G or U, e.g., 5mC, 5-hydroxymethyl C, etc. In some embodiments, a nucleobase is alkyl-substituted A, T, C, G or U. In some embodiments, a nucleobase is A. In some embodiments, a nucleobase is T. In some embodiments, a nucleobase is C. In some embodiments, a nucleobase is G. In some embodiments, a nucleobase is U. In some embodiments, a nucleobase is 5mC. In some embodiments, a nucleobase is substituted A, T, C, G or U. In some embodiments, a nucleobase is a substituted tautomer of A, T, C, G or U. In some embodiments, substitution protects certain functional groups in nucleobases to minimize undesired reactions during oligonucleotide synthesis. Suitable technologies for nucleobase protection in oligonucleotide synthesis are widely known in the art and may be utilized in accordance with the present disclosure. In some embodiments, $BA^{PRO}$ is a nucleobase or protected nucleobase, e.g., suitable for oligonucleotide synthesis. In some embodiments, modified nucleobases improves properties and/or activities of oligonucleotides. For example, in many cases, 5mC may be utilized in place of C to modulate certain undesired biological effects, e.g., immune responses. In some embodiments, when determining sequence identity, a substituted nucleobase having the same hydrogen-bonding pattern is treated as the same as the unsubstituted nucleobase, e.g., 5mC may be treated the same as C [e.g., an oligonucleotide having 5mC in place of C (e.g., AT5mCG) is considered to have the same base sequence as an oligonucleotide having C at the corresponding location(s) (e.g., ATCG)].

In some embodiments, an oligonucleotide comprises one or more A, T, C, G or U. In some embodiments, an oligonucleotide comprises one or more optionally substituted A, T, C, G or U. In some embodiments, an oligonucleotide comprises one or more 5-methylcytidine, 5-hydroxymethylcytidine, 5-formylcytosine, or 5-carboxylcytosine. In some embodiments, an oligonucleotide comprises one or more 5-methylcytidine. In some embodiments, each nucleobase in an oligonucleotide is selected from the group consisting of optionally substituted A, T, C, G and U, and optionally substituted tautomers of A, T, C, G and U. In some embodiments, each nucleobase in an oligonucleotide is optionally protected A, T, C, G or U, or an optionally protected tautomer of A, T, C, G or U. In some embodiments, each nucleobase in an oligonucleotide is optionally substituted A, T, C, G or U. In some embodiments, each nucleobase in an oligonucleotide is selected from the group consisting of A, T, C, G, U, and 5mC.

In some embodiments, a nucleobase is optionally substituted 2AP or DAP. In some embodiments, a nucleobase is optionally substituted 2AP. In some embodiments, a nucleobase is optionally substituted DAP. In some embodiments, a nucleobase is 2AP. In some embodiments, a nucleobase is DAP.

As appreciated by those skilled in the art, various nucleobases are known in the art and can be utilized in accordance with the present disclosure, e.g., those described in U.S. Pat. Nos. 9,394,333, 9,744,183, 9,605,019, 9,982,257, US 20170037399, US 20180216108, US 20180216107, U.S. Pat. No. 9,598,458, WO 2017/062862, WO 2018/067973, WO 2017/160741, WO 2017/192679, WO 2017/210647, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784, the sugar, base, and internucleotidic linkage modifications of each of which are independently incorporated herein by reference. In some embodiments, nucleobases are protected and useful for oligonucleotide synthesis.

In some embodiments, a nucleobase is a natural nucleobase or a modified nucleobase derived from a natural nucleobase. Examples include uracil, thymine, adenine, cytosine, and guanine optionally having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). Certain examples of modified nucleobases are disclosed in Chiu and Rana, RNA, 2003, 9, 1034-1048, Limbach et al. Nucleic Acids Research, 1994, 22, 2183-2196 and Revankar and Rao, Comprehensive Natural Products Chemistry, vol. 7, 313. In some embodiments, a modified nucleobase is substituted uracil, thymine, adenine, cytosine, or guanine. In some embodiments, a modified nucleobase is a functional replacement, e.g., in terms of hydrogen bonding and/or base pairing, of uracil, thymine, adenine, cytosine, or guanine. In some embodiments, a nucleobase is optionally substituted uracil, thymine, adenine, cytosine, 5-methylcytosine, or guanine. In some embodiments, a nucleobase is uracil, thymine, adenine, cytosine, 5-methylcytosine, or guanine.

In some embodiments, a provided oligonucleotide comprises one or more 5-methylcytosine. In some embodiments, the present disclosure provides an oligonucleotide whose base sequence is disclosed herein, e.g., in Table 1, except that each cytosine is optionally and independently replaced with 5-methylcytosine or vice versa. As appreciated by those skilled in the art, in some embodiments, 5mC may be treated as C with respect to base sequence of an oligonucleotide— such oligonucleotide comprises a nucleobase modification at the C position (e.g., see various oligonucleotides in Table 1). In description of oligonucleotides, typically unless otherwise noted, nucleobases, sugars and internucleotidic linkages are non-modified. For example, in example oligonucleotide Aeo5mCeo *S T *R G, Aeo and m5Ceo are modified as indicated—A and C are each 2'-MOE modified, and C is also 5-methyl modified; T and G are unmodified deoxyribonucleosides comprising nucleobases T and G, respectively (e.g., as commonly occurring in natural DNA; no sugar or base modifications); and each internucleotidic linkage is independently a natural phosphate linkage (e.g., natural phosphate linkages between nucleosides Aeo and 5mCeo) unless otherwise indicated (e.g., Sp phosphorothioate internucleotidic linkage between nucleosides 5mCeo and T as indicated by *S, Rp phosphorothioate internucleotidic linkage between nucleosides T and G as indicated by *R).

In some embodiments, a modified base is optionally substituted adenine, cytosine, guanine, thymine, or uracil, or a tautomer thereof. In some embodiments, a modified nucleobase is a modified adenine, cytosine, guanine, thymine or uracil, modified by one or more modifications by which:

(1) a nucleobase is modified by one or more optionally substituted groups independently selected from acyl, halogen, amino, azide, alkyl, alkenyl, alkynyl, aryl, heteroalkyl, heteroalkenyl, heteroalkynyl, heterocyclyl, heteroaryl, carboxyl, hydroxyl, biotin, avidin, streptavidin, substituted silyl, and combinations thereof;

(2) one or more atoms of a nucleobase are independently replaced with a different atom selected from carbon, nitrogen and sulfur;

(3) one or more double bonds in a nucleobase are independently hydrogenated; or (4) one or more aryl or heteroaryl rings are independently inserted into a nucleobase.

In some embodiments, a base is optionally substituted A, T, C, G or U, wherein one or more —NH$_2$ are independently and optionally replaced with —C(-L-R$^1$)$_3$, one or more —NH— are independently and optionally replaced with —C(-L-R$^1$)$_2$—, one or more =N— are independently and optionally replaced with —C(-L-R$^1$)—, one or more =CH— are independently and optionally replaced with =N—, and one or more =O are independently and optionally replaced with =S, =N(-L-R$^1$), or =C(-L-R$^1$)$_2$, wherein two or more -L-R$^1$ are optionally taken together with their intervening atoms to form a 3-30 membered bicyclic or polycyclic ring having 0-10 heteroatom ring atoms. In some embodiments, a modified base is optionally substituted A, T, C, G or U, wherein one or more —NH$_2$ are independently and optionally replaced with —C(-L-R$^1$)$_3$, one or more —NH— are independently and optionally replaced with —C(-L-R$^1$)$_2$—, one or more =N— are independently and optionally replaced with —C(-L-R$^1$)—, one or more =CH— are independently and optionally replaced with =N—, and one or more =O are independently and optionally replaced with =S, =N(-L-R$^1$), or =C(-L-R$^1$)$_2$, wherein two or more -L-R' are optionally taken together with their intervening atoms to form a 3-30 membered bicyclic or polycyclic ring having 0-10 heteroatom ring atoms, wherein the modified base is different than the natural A, T, C, G and U. In some embodiments, a base is optionally substituted A, T, C, G or U. In some embodiments, a modified base is substituted A, T, C, G or U, wherein the modified base is different than the natural A, T, C, G and U.

In some embodiments, a modified nucleobase is a modified nucleobase known in the art, e.g., WO2017/210647. In some embodiments, modified nucleobases are expanded-size nucleobases in which one or more aryl and/or heteroaryl rings, such as phenyl rings, have been added. Certain examples of modified nucleobases, including nucleobase replacements, are described in the Glen Research catalog (Glen Research, Sterling,Virginia.); Krueger A T et al., Ace. Chem. Res., 2007, 40, 141-150; Kool, E T, Ace. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; or Hirao, I., Curr. Opin. Chem. Biol., 2006, 10, 622-627. In some embodiments, an expanded-size nucleobase is an expanded-size nucleobase described in, e.g., WO2017/210647. In some embodiments, modified nucleobases are moieties such as corrin- or porphyrin-derived rings. Certain porphyrin-derived base replacements have been described in, e.g., Morales-Rojas, H and Kool, E T. Org. Lett., 2002, 4, 4377-4380. In some embodiments, a porphyrin-derived ring is a porphyrin-derived ring described in, e.g., WO2017/219647. In some embodiments, a modified nucleobase is a modified nucleobase described in, e.g., WO2017/219647. In some embodiments, a modified nucleobase is fluorescent. Examples of such fluorescent modified nucleobases include phenanthrene, pyrene, stillbene, isoxanthine, isozanthopterin, terphenyl, terthiophene, benzoterthiophene, coumarin, lumazine, tethered stillbene, benzo-uracil, naphtho-uracil, etc., and those described in e.g., WO2017/210647. In some embodiments, a nucleobase or modified nucleobase is selected from: C5-propyne T, C5-propyne C, C5-Thiazole, phenoxazine, 2-thio-thymine, 5-triazolylphenyl-thymine, diaminopurine, and N2-aminopropylguanine.

In some embodiments, a modified nucleobase is selected from 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. In some embodiments, modified nucleobases are tricyclic pyrimidines, such as 1,3-diazaphenoxazine-2-one, 1,3-diazaphenothiazine-2-one or 9-(2-aminoethoxy)-1,3-diazaphenoxazine-2-one (G-clamp). In some embodiments, modified nucleobases are those in which the purine or pyrimidine base is replaced with other heterocycles, for example, 7-deaza-adenine, 7-deazaguanosine, 2-aminopyridine or 2-pyridone. In some embodiments, modified nucleobases are those disclosed in U.S. Pat. No. 3,687,808, The Concise Encyclopedia Of Polymer Science And Engineering, Kroschwitz, J. I., Ed., John Wiley & Sons, 1990, 858-859, Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; or in Chapters 6 and 15, Antisense Drug Technology. Crooke S. T., Ed., CRC Press, 2008, 163-166 and 442443.

In some embodiments, modified nucleobases and methods thereof are those described in US 20030158403, U.S. Pat. Nos. 3,687,808, 4,845,205, 5,130,302, 5,134,066, 5,175,273, 5,367,066, 5,432,272, 5,434,257, 5,457,187, 5,459,255, 5,484,908, 5,502,177, 5,525,711, 5,552,540, 5,587,469, 5,594,121, 5,596,091, 5,614,617, 5,645,985, 5,681,941, 5,750,692, 5,763,588, 5,830,653, or 6,005,096.

In some embodiments, a modified nucleobase is substituted. In some embodiments, a modified nucleobase is substituted such that it contains, e.g., heteroatoms, alkyl groups, or linking moieties connected to fluorescent moieties, biotin or avidin moieties, or other protein or peptides. In some embodiments, a modified nucleobase is a "universal base" that is not a nucleobase in the most classical sense, but that functions similarly to a nucleobase. One example of a universal base is 3-nitropyrrole.

In some embodiments, nucleosides that can be utilized in provided technologies comprise modified nucleobases and/or modified sugars, e.g., 4-acetylcytidine; 5-(carboxyhydroxylmethyl)uridine; 2'-O-methylcytidine; 5-carboxymethylaminomethyl-2-thiouridine; 5-carboxymethylaminomethyluridine; dihydrouridine; 2'-O-methylpseudouridine; beta,D-galactosylqueosine; 2'-O-methylguanosine; $N^6$-isopentenyladenosine; 1-methyladenosine; 1-methylpseudouridine; 1-methylguanosine; 1-methylinosine; 2,2-dimethylguanosine; 2-methyladenosine; 2-methylguanosine; $N^7$-methylguanosine; 3-methyl-cytidine; 5-methylcytidine; 5-hydroxymethylcytidine; 5-formylcytosine; 5-carboxylcytosine; $N^6$-methyladenosine; 7-methylguanosine; 5-methylaminoethyluridine; 5-methoxyaminomethyl-2-thiouridine; beta,D-mannosylqueosine; 5-methoxycarbonylmethyluridine; 5-methoxyuridine; 2-methylthio-$N^6$-isopentenyladenosine; N-((9-beta,D-ribofuranosyl-2-methylthiopurine-6-yl)carbamoyl)threonine; N-((9-beta,D-ribofuranosylpurine-6-yl)-N-methylcarbamoyl)threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'-O-methyl-5-methyluridine; and 2'-O-methyluridine.

In some embodiments, a nucleobase, e.g., a modified nucleobase comprises one or more biomolecule binding moieties such as e.g., antibodies, antibody fragments, biotin, avidin, streptavidin, receptor ligands, or chelating moieties. In other embodiments, a nucleobase is 5-bromouracil, 5-iodouracil, or 2,6-diaminopurine. In some embodiments, a nucleobase comprises substitution with a fluorescent or biomolecule binding moiety. In some embodiments, a substituent is a fluorescent moiety. In some embodiments, a substituent is biotin or avidin.

Certain examples of nucleobases and related methods are described in U.S. Pat. Nos. 3,687,808, 4,845,205, 513,030, 5,134,066, 5,175,273, 5,367,066, 5,432,272, 5,457,187, 5,457,191, 5,459,255, 5,484,908, 5,502,177, 5,525,711, 5,552,540, 5,587,469, 5,594,121, 5,596,091, 5,614,617, 5,681,941, 5,750,692, 6,015,886, 6,147,200, 6,166,197, 6,222,025, 6,235,887, 6,380,368, 6,528,640, 6,639,062, 6,617,438, 7,045,610, 7,427,672, or 7,495,088.

In some embodiments, a nucleobase, sugar, nucleoside, and/or internucleotidic linkage is described in any of: Gryaznov, S; Chen, J.-K. J. Am. Chem. Soc. 1994, 116, 3143; Hendrix et al. 1997 Chem. Eur. J. 3: 110; Hyrup et al. 1996 Bioorg. Med. Chem. 4: 5; Jepsen et al. 2004 Oligo. 14: 130-146; Jones et al. J. Org. Chem. 1993, 58, 2983; Koizumi et al. 2003 Nuc. Acids Res. 12: 3267-3273; Koshkin et al. 1998 Tetrahedron 54: 3607-3630; Kumar et al. 1998 Bioo. Med. Chem. Let. 8: 2219-2222; Lauritsen et al. 2002 Chem. Comm. 5: 530-531; Lauritsen et al. 2003 Bioo. Med. Chem. Lett. 13: 253-256; Mesmaeker et al. Angew. Chem., Int. Ed. Engl. 1994, 33, 226; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Nielsen et al. 1997 Chem. Soc. Rev. 73; Nielsen et al. 1997 J. Chem. Soc. Perkins Transl. 1: 3423-3433; Obika et al. 1997 Tetrahedron Lett. 38 (50): 8735-8; Obika et al. 1998 Tetrahedron Lett. 39: 5401-5404; Pallan et al. 2012 Chem. Comm. 48: 8195-8197; Petersen et al. 2003 TRENDS Biotech. 21: 74-81; Rajwanshi et al. 1999 Chem. Commun. 1395-1396; Schultz et al. 1996 Nucleic Acids Res. 24: 2966; Seth et al. 2009 J. Med. Chem. 52: 10-13; Seth et al. 2010 J. Med. Chem. 53: 8309-8318; Seth et al. 2010 J. Org. Chem. 75: 1569-1581; Seth et al. 2012 Bioo. Med. Chem. Lett. 22: 296-299; Seth et al. 2012 Mol. Ther-Nuc. Acids. 1, e47; Seth, Punit P; Siwkowski, Andrew; Allerson, Charles R; Vasquez, Guillemo; Lee, Sam; Prakash, Thazha P; Kinberger, Garth; Migawa, Michael T; Gaus, Hans; Bhat, Balkrishcn; et al. From Nucleic Acids Symposium Series (2008), 52(1), 553-554; Singh et al. 1998 Chem. Comm. 1247-1248; Singh et al. 1998 J. Org. Chem. 63: 10035-39; Singh et al. 1998 J. Org. Chem. 63: 6078-6079; Sorensen 2003 Chem. Comm. 2130-2131; Ts'o et al. Ann. N. Y. Acad. Sci. 1988, 507, 220; Van Aerschot et al. 1995 Angew. Chem. Int. Ed. Engl. 34: 1338; Vasseur et al. J. Am. Chem. Soc. 1992, 114, 4006: WO 2007090071; or WO 2016/079181.

In some embodiments, a modified nucleobase, nucleoside or nucleotide is described in any of: Feldman et al. 2017 J. Am. Chem. Soc. 139: 11427-11433, Feldman et al. 2017 Proc. Natl. Acad. Sci. USA 114: E6478-E6479, Hwang et al. 2009 Nucl. Acids Res. 37: 4757-4763, Hwang et al. 2008 J. Am. Chem. Soc. 130: 14872-14882, Lavergne et al. 2012 Chem. Eur. J. 18: 1231-1239, Lavergne et al. 2013 J. Am. Chem. Soc. 135: 5408-5419, Ledbetter et al. 2018 J. Am. Chem. Soc. 140: 758-765, Malyshev et al. 2009 J. Am. Chem. Soc. 131: 14620-14621, Seo et al. 2009 Chem. Bio. Chem. 10: 2394-2400, e.g., d3FB, d2Py analogs, d2Py, d3MPy, d4MPy, d5MPy, d34DMPy, d35DMPy, d45DMPy, d5FM, d5PrM, d5SICS, dFEMO, dMMO2, dNaM, dNM01, dTPT3, nucleotides with 2'-azido, 2'-chloro, 2'-amino or arabinose sugars, isocarbostiryl-, napthyl- and azaindole-nucleotides, and modifications and derivatives and functionalized versions thereof, e.g., those in which the sugar comprises a 2'-modification and/or other modification, and dMMO2 derivatives with meta-chlorine, -bromine, -iodine, -methyl, or -propinyl substituents.

In some embodiments, a nucleobase comprises at least one optionally substituted ring which comprises a heteroatom ring atom. In some embodiments, a nucleobase comprises at least one optionally substituted ring which comprises a nitrogen ring atom. In some embodiments, such a ring is aromatic. In some embodiments, a nucleobase is bonded to a sugar through a heteroatom. In some embodiments, a nucleobase is bonded to a sugar through a nitrogen atom. In some embodiments, a nucleobase is bonded to a sugar through a ring nitrogen atom.

In some embodiments, a nucleobase in a provided oligonucleotide, e.g., BA, is an optionally substituted group, which group is formed by removing a —H from

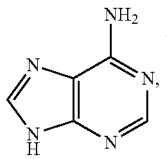
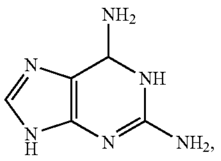
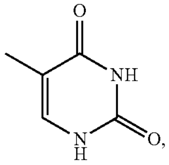
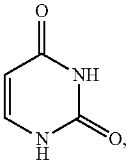
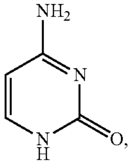
or
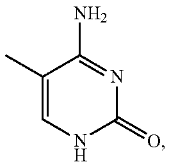

or a tautomer thereof. In some embodiments, a nucleobase in a provided oligonucleotide, e.g., BA, is an optionally substituted group, which group is formed by removing a —H from

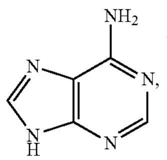
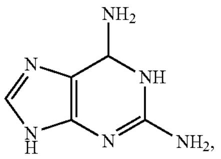
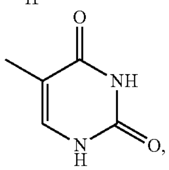
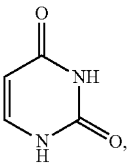
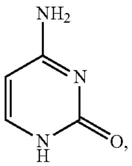
or

-continued

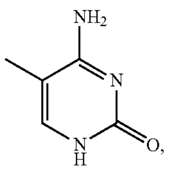

In some embodiments, a nucleobase in a provided oligonucleotide, e.g., BA, is an optionally substituted group which group is selected from

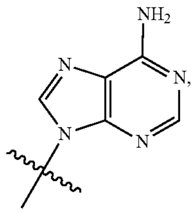
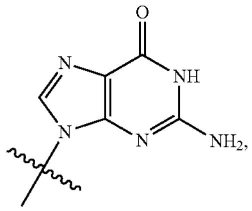
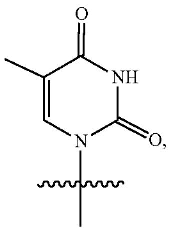
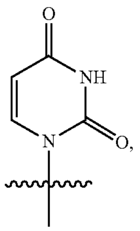
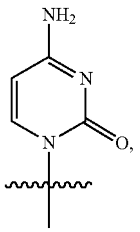
and
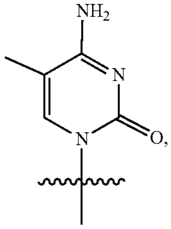

and tautomeric forms thereof. In some embodiments, a nucleobase in a provided oligonucleotide, e.g., BA, is an optionally substituted group which group is selected from

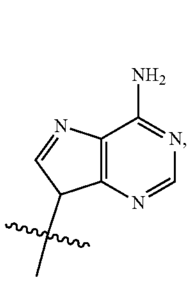
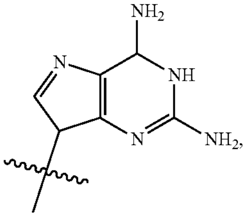
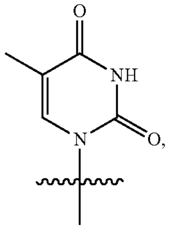
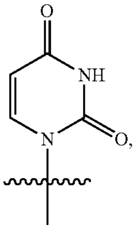
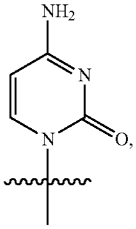
and
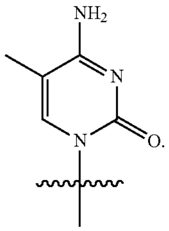

In some embodiments, a nucleobase in a provided oligonucleotide, e.g., BA, is an optionally substituted group, which group is formed by removing a —H from

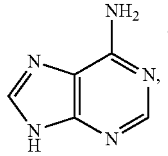
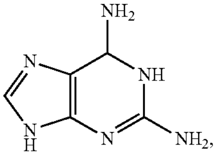
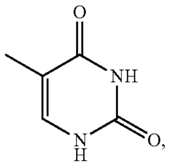
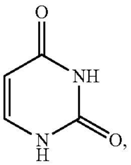
and
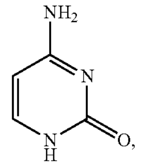

and tautomers thereof. In some embodiments, a nucleobase in a provided oligonucleotide, e.g., BA is an optionally substituted group, which group is formed by removing a —H from

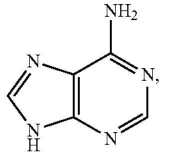
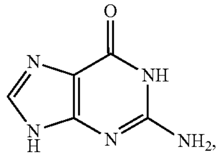
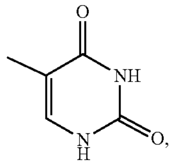
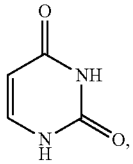
and
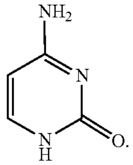

In some embodiments, a nucleobase in a provided oligonucleotide, e.g., BA, is an optionally substituted group which group is selected from

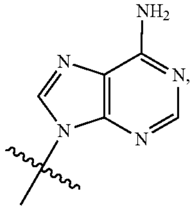
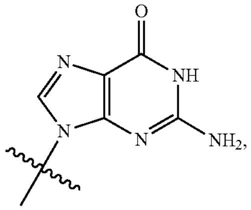
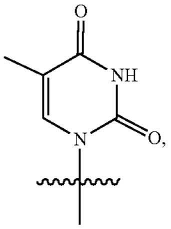

-continued

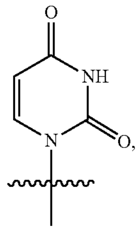

and

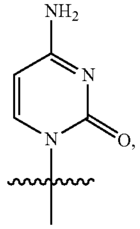

and tautomeric forms thereof. In some embodiments, a nucleobase in a provided oligonucleotide, e.g., BA, is an optionally substituted group which group is selected from

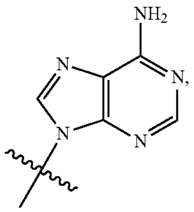

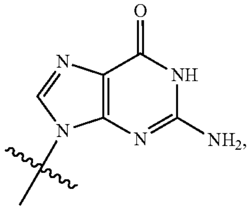

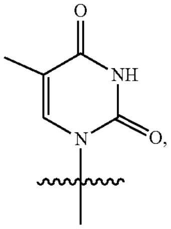

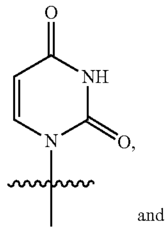

and

-continued

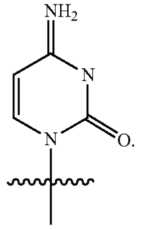

In some embodiments, a nucleobase in a provided oligonucleotide, e.g., BA is optionally substituted

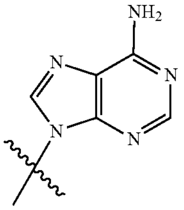

or a tautomeric form thereof. In some embodiments, a nucleobase in a provided oligonucleotide, e.g., BA is optionally substituted

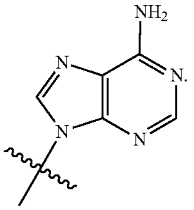

In some embodiments, a nucleobase in a provided oligonucleotide, e.g., BA is optionally substituted

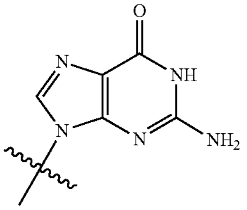

or a tautomeric form thereof. In some embodiments, a nucleobase in a provided oligonucleotide, e.g., BA is optionally substituted

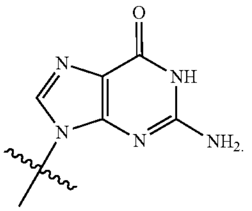

In some embodiments, a nucleobase in a provided oligonucleotide, e.g., BA is optionally substituted

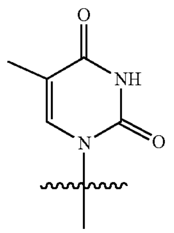

or a tautomeric form thereof. In some embodiments, a nucleobase in a provided oligonucleotide, e.g., BA is optionally substituted

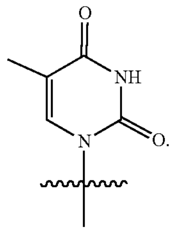

In some embodiments, a nucleobase in a provided oligonucleotide, e.g., BA is optionally substitute

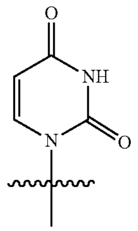

or a tautomeric form thereof. In some embodiments, a nucleobase in a provided oligonucleotide, e.g., BA is optionally substitute

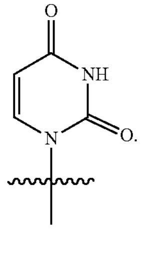 [SMILES: *n1ccc(=O)[nH]c1=O]

In some embodiments, a nucleobase in a provided oligonucleotide, e.g., BA is optionally substituted

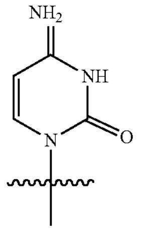 [SMILES: *n1ccc(=N)[nH]c1=O]

or a tautomeric form thereof. In some embodiments, a nucleobase in a provided oligonucleotide, e.g., BA is optionally substituted

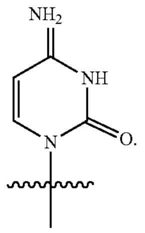 [SMILES: *n1ccc(=N)[nH]c1=O]

In some embodiments, a nucleobase in a provided oligonucleotide, e.g., BA is

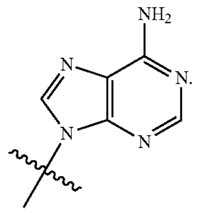 [SMILES: *n1cnc2c(N)ncnc21]

In some embodiments, a nucleobase in a provided oligonucleotide, e.g., BA is

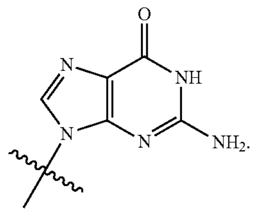 [SMILES: *n1cnc2c(=O)[nH]c(N)nc21]

In some embodiments, a nucleobase in a provided oligonucleotide, e.g., BA is

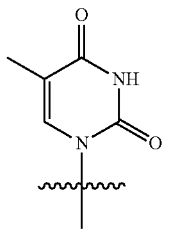 [SMILES: *n1cc(C)c(=O)[nH]c1=O]

In some embodiments, a nucleobase in a provided oligonucleotide, e.g., BA is

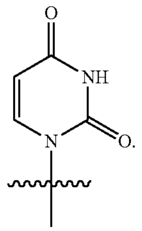 [SMILES: *n1ccc(=O)[nH]c1=O]

In some embodiments, a nucleobase in a provided oligonucleotide, e.g., BA is

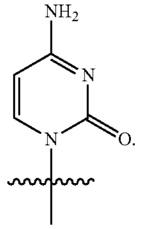 [SMILES: *n1ccc(N)nc1=O]

In some embodiments, a nucleobase of the 5'-end nucleoside unit of an oligonucleotide is an optionally substituted group, which group is formed by removing a —H from

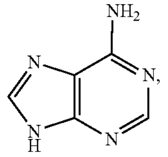

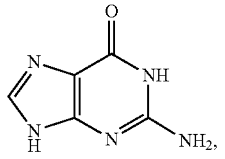

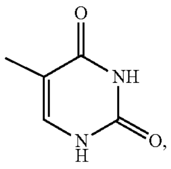

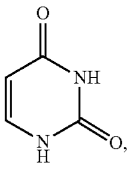

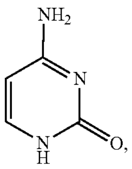

and

-continued

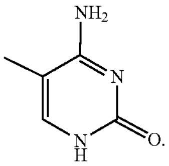

In some embodiments, a nucleobase of the 5-end nucleoside unit is an optionally substituted group which group is selected from

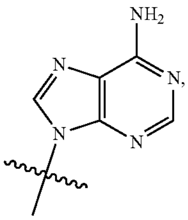

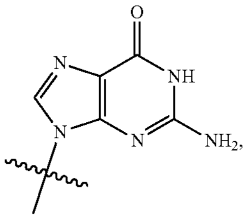

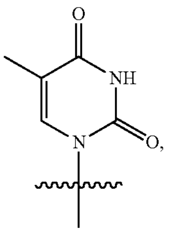

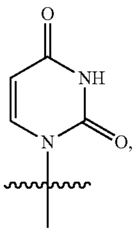

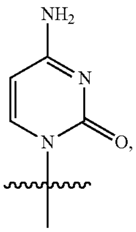

and

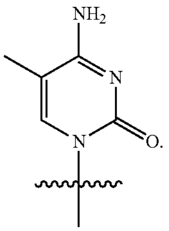

In some embodiments, a nucleobase of the 5'-end nucleoside unit is an optionally substituted group, which group is formed by removing a —H from

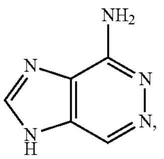

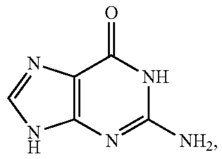

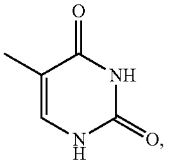

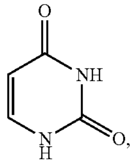

and

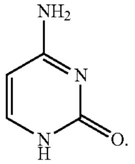

In some embodiments, a nucleobase of the 5'-end nucleoside unit is an optionally substituted group which group is selected from

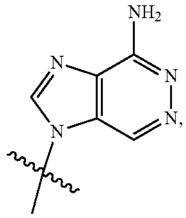
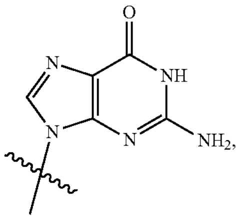

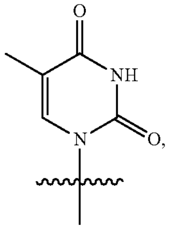
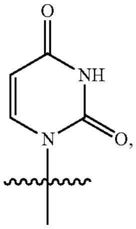
and
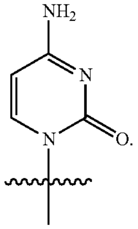

In some embodiments, a nucleobase of the 5'-end nucleoside unit is optionally substituted

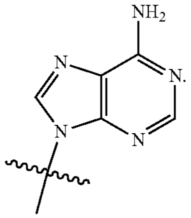 [SMILES: *n1cnc2c(N)ncnc21]

In some embodiments, a nucleobase of the 5'-end nucleoside unit is optionally substituted

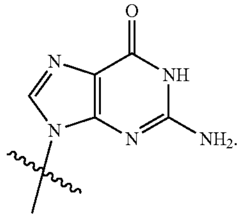 [SMILES: *n1cnc2c(=O)[nH]c(N)nc21]

In some embodiments, a nucleobase of the 5'-end nucleoside unit is optionally substituted

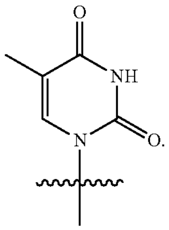 [SMILES: *n1cc(C)c(=O)[nH]c1=O]

In some embodiments, a nucleobase of the 5'-end nucleoside unit is optionally substituted

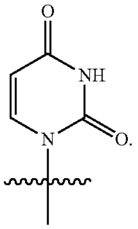 [SMILES: *n1ccc(=O)[nH]c1=O]

In some embodiments, a nucleobase of the 5'-end nucleoside unit is optionally substituted

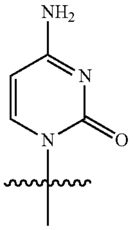 [SMILES: *n1ccc(N)nc1=O]

In some embodiments, a nucleobase of the 5'-end nucleoside unit is

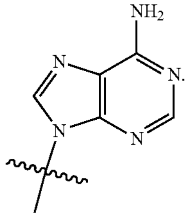

In some embodiments, a nucleobase of the 5'-end nucleoside unit is

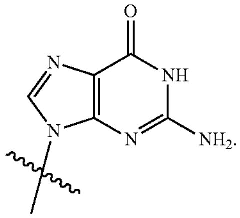 [SMILES: *n1cnc2c(=O)[nH]c(N)nc21]

In some embodiments, a nucleobase of the 5'-end nucleoside unit is

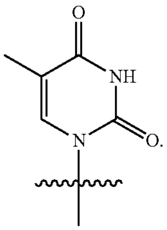 [SMILES: *n1cc(C)c(=O)[nH]c1=O]

In some embodiments, a nucleobase of the 5'-end nucleoside unit is

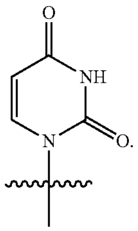 [SMILES: *n1ccc(=O)[nH]c1=O]

In some embodiments, a nucleobase of the 5'-end nucleoside unit is

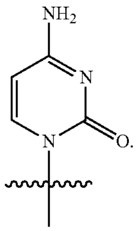 [SMILES: *n1ccc(N)nc1=O]

In some embodiments, BA is a nucleobase of the 5-end nucleoside unit described herein.

In some embodiments, a nucleobase in a provided oligonucleotide is

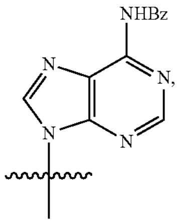

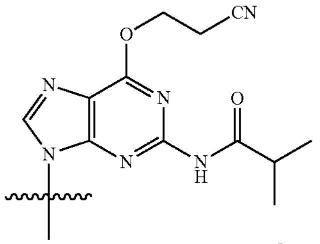
,

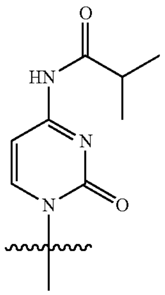
,
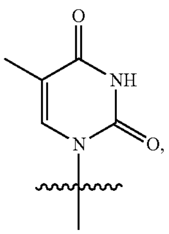

-continued

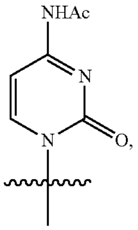
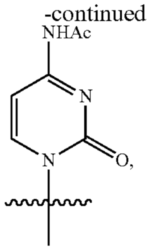
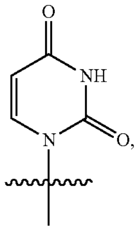
or

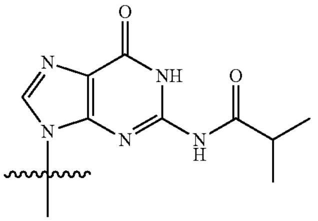
.

In some embodiments, a nucleobase in a provided oligonucleotide, e.g., BA, is

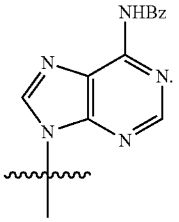

In some embodiments, a nucleobase in a provided oligonucleotide, e.g., BA, is

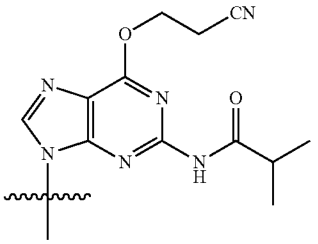
or

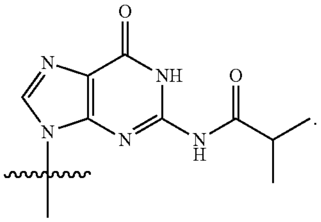

In some embodiments, a nucleobase in a provided oligonucleotide, e.g., BA, is

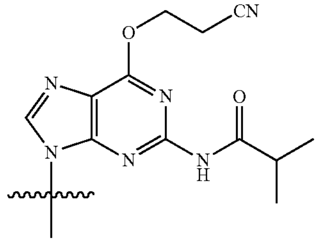 [SMILES: *n1cnc2c(OCCC#N)nc(NC(=O)C(C)C)nc21]

In some embodiments, a nucleobase in a provided oligonucleotide, e.g., BA, is

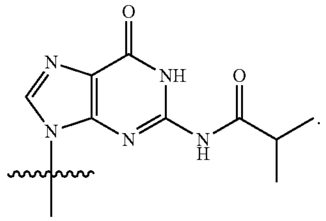 [SMILES: *n1cnc2c(=O)[nH]c(NC(=O)C(C)C)nc21]

In some embodiments, a nucleobase in a provided oligonucleotide, e.g., BA, is

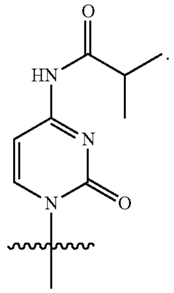 [SMILES: *n1ccc(NC(=O)C(C)C)nc1=O]

In some embodiments, a nucleobase in a provided oligonucleotide, e.g., BA, is

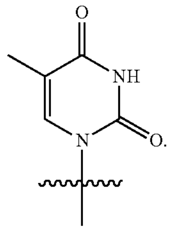 [SMILES: *n1cc(C)c(=O)[nH]c1=O]

In some embodiments, a nucleobase in a provided oligonucleotide, e.g., BA, is

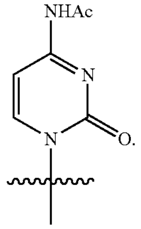 [SMILES: *n1ccc(NC(C)=O)nc1=O]

In some embodiments, a nucleobase in a provided oligonucleotide, e.g., BA, is

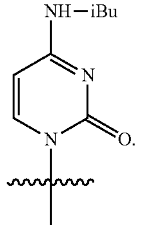

In some embodiments, a nucleobase in a provided oligonucleotide, e.g., BA, is

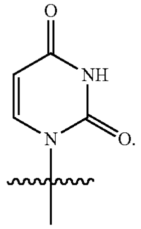 [SMILES: *n1ccc(=O)[nH]c1=O]

In some embodiments, a protection group is —Ac. In some embodiments, a protection group is -Bz. In some embodiments, a protection group is -iBu for nucleobase.

In some embodiments, a nucleobase is an optionally substituted purine base residue. In some embodiments, a nucleobase is a protected purine base residue. In some embodiments, a nucleobase is an optionally substituted adenine residue. In some embodiments, a nucleobase is a protected adenine residue. In some embodiments, a nucleobase is an optionally substituted guanine residue. In some embodiments, a nucleobase is a protected guanine residue. In some embodiments, a nucleobase is an optionally substituted cytosine residue. In some embodiments, a nucleobase is a protected cytosine residue. In some embodiments, a nucleobase is an optionally substituted thymine residue. In some embodiments, a nucleobase is a protected thymine residue. In some embodiments, a nucleobase is an optionally substituted uracil residue. In some embodiments, a nucleobase is a protected uracil residue. In some embodiments, a nucleobase is an optionally substituted 5-methylcytosine residue. In some embodiments, a nucleobase is a protected 5-methylcytosine residue.

In some embodiments, a provided oligonucleotide comprises a modified nucleobase described in, e.g., U.S. Pat. Nos. 5,552,540, 6,222,025, 6,528,640, 4,845,205, 5,681,941, 5,750,692, 6,015,886, 5,614,617, 6,147,200, 5,457,187, 6,639,062, 7,427,672, 5,459,255, 5,484,908, 7,045,610, 3,687,808, 5,502,177, 5,525,711 6,235,887, 5,175,273, 6,617,438, 5,594,121, 6,380,368, 5,367,066, 5,587,469, 6,166,197, 5,432,272, 7,495,088, 5,134,066, or 5,596,091.

Sugars

Various sugars, including modified sugars, can be utilized in accordance with the present disclosure. In some embodiments, the present disclosure includes sugar modifications and patterns thereof optionally in combination with other structural elements (e.g., internucleotidic linkage modifications and patterns thereof, pattern of backbone chiral centers thereof, etc.) that when incorporated into oligonucleotides can provide improved properties and/or activities.

The most common naturally occurring nucleosides comprise ribose sugars (e.g., in RNA) or deoxyribose sugars (e.g., in DNA) linked to the nucleobases adenosine (A), cytosine (C), guanine (G), thymine (T) or uracil (U). In some embodiments, a sugar, e.g., various sugars in many oligonucleotides (unless otherwise notes), is a natural DNA sugar (in DNA nucleic acids or oligonucleotides, having the structure of

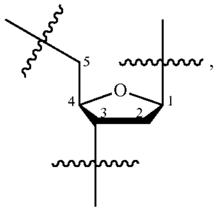

wherein a nucleobase is attached to the 1' position, and the 3' and 5' positions are connected to internucleotidic linkages (as appreciated by those skilled in the art, if at the 5'-end of an oligonucleotide, the 5' position may be connected to a 5'-end group (e.g., —OH), and if at the 3'-end of an oligonucleotide, the 3' position may be connected to a 3-end group (e.g., —OH, support (optionally via linker) during oligonucleotide synthesis, etc.)). In some embodiments, a sugar is a natural RNA sugar (in RNA nucleic acids or oligonucleotides, having the structure of

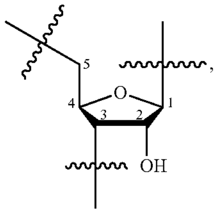

wherein a nucleobase is attached to the 1' position, and the 3' and 5' positions are connected to internucleotidic linkages (as appreciated by those skilled in the art, if at the 5'-end of an oligonucleotide, the 5' position may be connected to a 5'-end group (e.g., —OH), and if at the 3'-end of an oligonucleotide, the 3' position may be connected to a 3-end group (e.g., —OH, support (optionally via linker) during oligonucleotide synthesis, etc.)). In some embodiments, a sugar is a modified sugar in that it is not a natural DNA sugar or a natural RNA sugar. Among other things, modified sugars may provide improved stability. In some embodiments, modified sugars can be utilized to alter and/or optimize one or more hybridization characteristics. In some embodiments, modified sugars can be utilized to alter and/or optimize target recognition. In some embodiments, modified sugars can be utilized to optimize Tm. In some embodiments, modified sugars can be utilized to improve oligonucleotide activities. In some embodiments, a modified sugar comprises a 2'-modification. In some embodiments, a 2'-modification replaces 2'-OH in a natural RNA sugar. Example 2'-modifications, e.g., 2'-F, 2'-OMe, 2'-MOE, etc., are described herein.

Sugars can be bonded to internucleotidic linkages at various positions. As non-limiting examples, internucleotidic linkages can be bonded to the 2', 3', 4' or 5' positions of sugars. In some embodiments, as most commonly in natural nucleic acids, an internucleotidic linkage connects with one sugar at the 5' position, and another sugar at the 3' position.

In some embodiments, provided compounds, e.g., oligonucleotides, comprise one or more modified sugars. In some embodiments, a sugar is

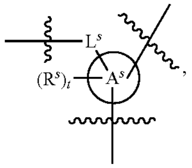

wherein each variable is independently as described in the present disclosure. In some embodiments, a sugar is

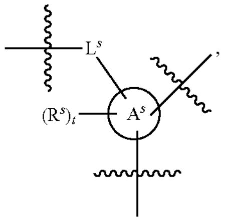

wherein $L^s$ is —$C(R^{5s})_2$—, wherein each $R^{5s}$ is independently as described in the present disclosure. In some embodiments, a sugar is an optionally substituted natural DNA or RNA sugar. In some embodiments, a sugar is optionally substituted

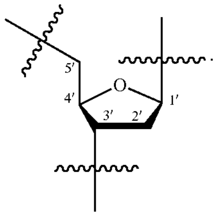 [SMILES: *C[C@H]1O[C@@H](*)C[C@H]1*]

In some embodiments, a sugar is
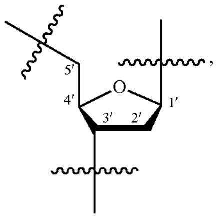 [SMILES: *C[C@H]1O[C@@H](*)C[C@H]1*]
wherein the 2' position is optionally substituted. In some embodiments, a sugar is
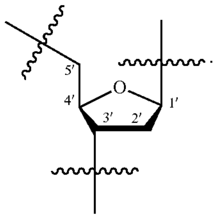 [SMILES: *C[C@H]1O[C@@H](*)C[C@H]1*]
In some embodiments, a sugar, e g.,
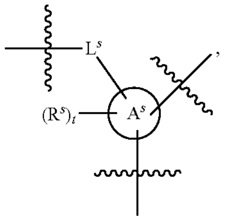
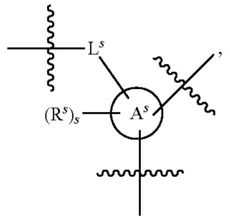
etc., has the structure of
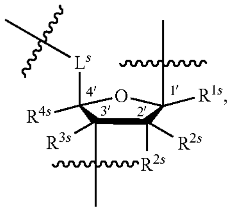
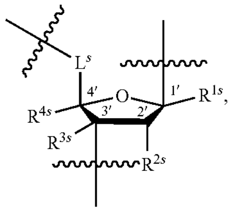
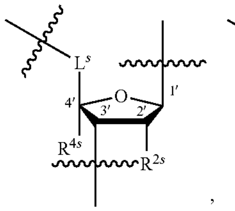
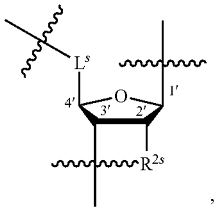
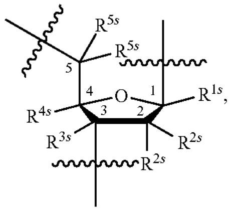
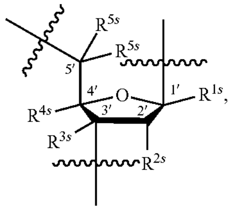
-continued
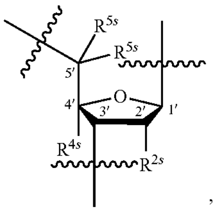
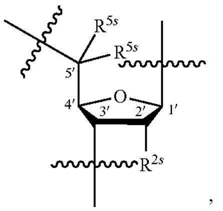
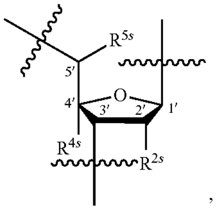
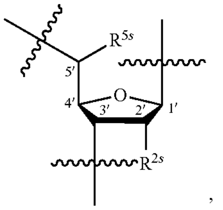
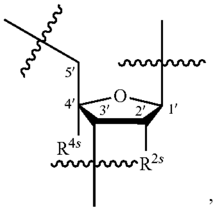
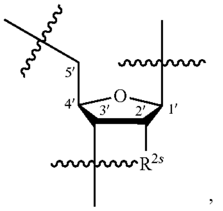
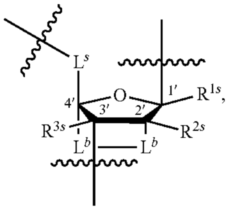
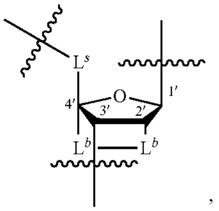
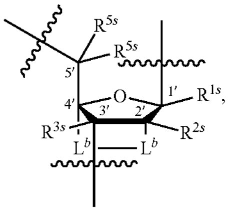
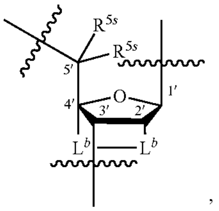
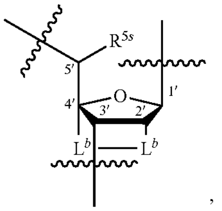
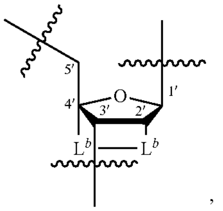

-continued

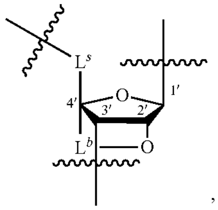

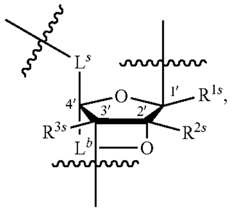

,

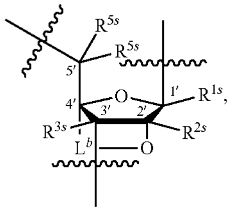

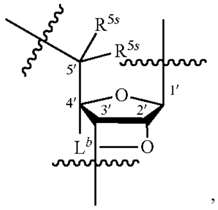

,

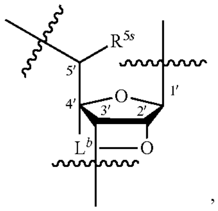

, or

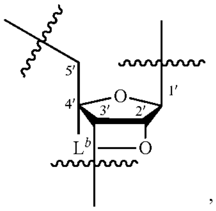

, wherein each $L^b$ is independently $L^s$, and each other variable is independently as described in the present disclosure. In some embodiments, C1 is bonded to a nucleobase, and C3 and C5 are bonded to internucleotidic linkages. In some embodiments, a sugar has the structure of

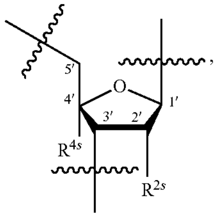

wherein each variable is independently as described in the present disclosure. In some embodiments, a sugar has the structure of

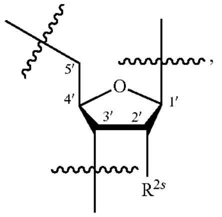

wherein each variable is independently as described in the present disclosure. In some embodiments, $R^{2s}$ is a 2'-modification as described in the present disclosure. In some embodiments, a sugar is a bicyclic sugar, e.g., sugars wherein $R^{2s}$ and $R^{4s}$ are taken to form an optionally substituted ring as described in the present disclosure, sugars whose structures comprise $L^b$, LNA sugars, BNA sugars, cEt sugars, etc. In some embodiments, two substituents on sugar carbon atom(s) are taken together to form a bicyclic sugar. In some embodiments, two substituents are on two different sugar carbon atoms, e.g., $R^{2s}$ and $R^{4s}$. In some embodiments, -$L^b$-$L^b$- is —O-$L^b$-. In some embodiments, -$L^b$-$L^b$- is 2'-O-$L^b$-4'. In some embodiments, -$L^b$-$L^b$- is —S-$L^b$-. In some embodiments, -$L^b$-$L^b$- is 2'-S-$L^b$-4'. In some embodiments, -$L^b$-$L^b$- is —NR'-$L^b$-, wherein R' is as described in the present disclosure. In some embodiments, -$L^b$-$L^b$- is 2'-NR'-$L^b$-4'. In some embodiments, R' is —H or optionally substituted $C_{1-6}$ alkyl. In some embodiments, a sugar has the structure of

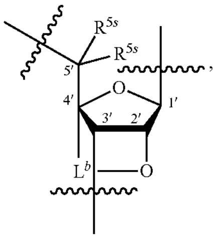

wherein each variable is independently as described in the present disclosure. In some embodiments, a sugar has the structure of

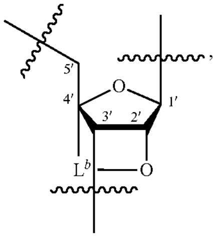

wherein each variable is independently as described in the present disclosure. In some embodiments, a sugar has the structure of

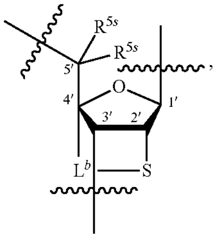

wherein each variable is independently as described in the present disclosure. In some embodiments, a sugar has the structure of

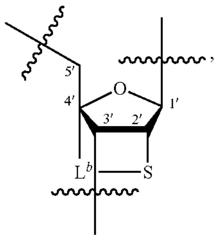, wherein each variable is independently as described in the present disclosure. In some embodiments, a sugar has the structure of

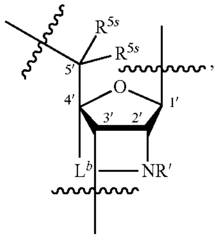, wherein each variable is independently as described in the present disclosure. In some embodiments, a sugar has the structure of

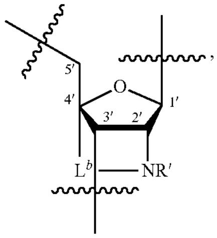, wherein each variable is independently as described in the present disclosure. In some embodiments, $L^b$ is —CH(R)—, wherein R is as described in the present disclosure. In some embodiments, R is not —H, and $L^b$ is —(R)—CH(R)—. In some embodiments, R is not —H, and $L^b$ is —(S)—CH(R)—. In some embodiments, $L^b$ is optionally substituted —$CH_2$—$CH_2$—. In some embodiments, R is —H. In some embodiments, a sugar is optionally substituted

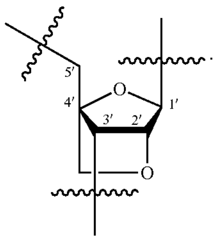 [SMILES: *C[C@@]12COC([C@H](*)O1)[C@H]2*].

In some embodiments, a sugar has the structure of

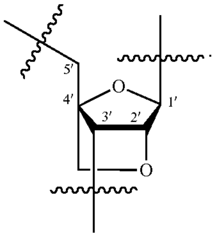 [SMILES: *C[C@@]12COC([C@H](*)O1)[C@H]2*].

In some embodiments, a sugar is optionally substituted

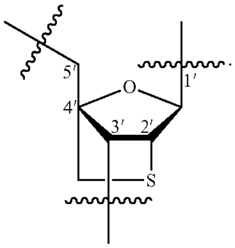 [SMILES: *C[C@@]12CSC([C@H](*)O1)[C@H]2*].

In some embodiments, a sugar has the structure of

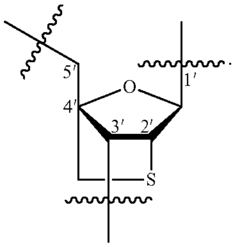 [SMILES: *C[C@@]12CSC([C@H](*)O1)[C@H]2*].

In some embodiments, a sugar is optionally substituted

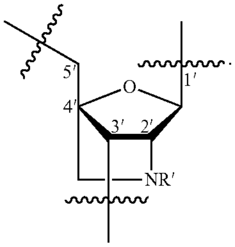.

In some embodiments, a sugar has the structure of

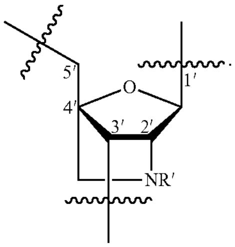.

In some embodiments, R, as described in the present disclosure, is optionally substituted $C_{1-6}$ alkyl. In some embodiments, R is methyl.

Various types of sugar modifications are known and can be utilized in accordance with the present disclosure. In some embodiments, a sugar modification is a 2'-modification. In some embodiments, a 2'-modification is 2'-F. In some embodiments, a 2'-modification is 2'-OR, wherein R is not hydrogen. In some embodiments, a 2'-modification is 2'-OR, wherein R is optionally substituted $C_{1-6}$ aliphatic. In some embodiments, a 2'-modification is 2'-OR, wherein R is optionally substituted $C_{1-6}$ alkyl. In some embodiments, a 2'-modification is 2'-OMe. In some embodiments, a 2'-modification is 2'-MOE. In some embodiments, a 2'-modification is a LNA sugar modification (C2-O—$CH_2$—C4). In some embodiments, a 2'-modification is (C2-O—$C(R)_2$—C4), wherein each R is independently as described in the present disclosure. In some embodiments, a 2'-modification is (C2-O—CHR—C4), wherein R is as described in the present disclosure. In some embodiments, a 2'-modification is (C2-O—(R)—CHR—C4), wherein R is as described in the present disclosure and is not hydrogen. In some embodiments, a 2'-modification is (C2-O—(S)—CHR—C4), wherein R is as described in the present disclosure and is not hydrogen. In some embodiments, R is optionally substituted $C_{1-6}$ aliphatic. In some embodiments, R is optionally substituted $C_{1-6}$ alkyl. In some embodiments, R is unsubstituted $C_{1-6}$ alkyl. In some embodiments, R is methyl. In some embodiments, R is ethyl. In some embodiments, a 2'-modification is (C2-O—CHR—C4), wherein R is optionally substituted $C_{1-6}$ aliphatic. In some embodiments, a 2'-modification is (C2-O—CHR—C4), wherein R is optionally substituted $C_{1-6}$ alkyl. In some embodiments, a 2'-modification is (C2-O—CHR—C4), wherein R is methyl. In some embodiments, a 2'-modification is (C2-O—CHR—C4), wherein R is ethyl. In some embodiments, a 2'-modification is (C2-O—(R)—CHR—C4), wherein R is optionally substituted $C_{1-6}$ aliphatic. In some embodiments, a 2-modification is (C2-O—(R)—CHR—C4), wherein R is optionally substituted $C_{1-6}$ alkyl. In some embodiments, a 2'-modification is (C2-O—(R)—CHR—C4), wherein R is methyl. In some embodiments, a 2'-modification is (C2-O—(R)—CHR—C4), wherein R is ethyl. In some embodiments, a 2'-modification is (C2-O—(S)—CHR—C4), wherein R is optionally substituted $C_{1-6}$ aliphatic. In some embodiments, a 2'-modification is (C2-O—(S)—CHR—C4), wherein R is optionally substituted $C_{1-6}$ alkyl. In some embodiments, a 2'-modification is (C2-O—(S)—CHR—C4), wherein R is methyl. In some embodiments, a 2'-modification is (C2-O—(S)—CHR—C4), wherein R is ethyl. In some embodiments, a 2'-modification is C2-O—(R)—$CH(CH_2CH_3)$—C4. In some embodiments, a 2'-modification is C2-O—(S)—$CH(CH_2CH_3)$—C4. In some embodiments, a sugar is a natural DNA sugar. In some embodiments, a sugar is a natural DNA sugar modified at 2' (2'-modification). In some embodiments, a sugar is an optionally substituted natural DNA sugar. In some embodiments, a sugar is an 2'-substituted natural DNA sugar.

In some embodiments, a sugar is an optionally substituted ribose or deoxyribose. In some embodiments, a sugar is an optionally modified ribose or deoxyribose, wherein one or more hydroxyl groups of the ribose or deoxyribose moiety is optionally and independently replaced by halogen, R', —$N(R')_2$, —OR', or —SR', wherein each R' is independently described in the present disclosure. In some embodiments, a sugar is an optionally substituted deoxyribose, wherein the 2' position of the deoxyribose is optionally substituted. In some embodiments, a sugar is an optionally substituted deoxyribose, wherein the 2' position of the deoxyribose is optionally substituted with halogen, R', —$N(R')_2$, —OR', or —SR', wherein each R' is independently described in the present disclosure. In some embodiments, a sugar is an optionally substituted deoxyribose, wherein the 2' position of the deoxyribose is optionally substituted with halogen. In some embodiments, a sugar is an optionally substituted deoxyribose, wherein the 2' position of the deoxyribose is optionally substituted with one or more —F. In some embodiments, a sugar is an optionally substituted deoxyribose, wherein the 2' position of the deoxyribose is optionally substituted with —OR', wherein each R' is independently described in the present disclosure. In some embodiments, a sugar is an optionally substituted deoxyribose, wherein the 2' position of the deoxyribose is optionally substituted with —OR', wherein each R' is independently optionally substituted $C_1$-$C_6$ aliphatic. In some embodiments, a sugar is an optionally substituted deoxyribose, wherein the 2' position of the deoxyribose is optionally substituted with —OR', wherein each R' is independently an optionally substituted $C_1$-$C_6$ alkyl. In some embodiments, a sugar is an optionally substituted deoxyribose, wherein the 2' position of the deoxyribose is optionally substituted with —OMe. In some embodiments, a sugar is an optionally substituted deoxyribose, wherein the 2' position of the deoxyribose is optionally substituted with —O-methoxyethyl.

In some embodiments, provided oligonucleotides comprise one or more modified sugars. In some embodiments, provided oligonucleotides comprise one or more modified sugars and one or more natural sugars.

In some embodiments, linkage phosphorus in nucleotides can be linked to various positions of a sugar or modified sugar. For example, in some embodiments, linkage phosphorus can be linked to the 2', 3, 4' or 5'hydroxyl moiety of a sugar or modified sugar. Nucleotides that incorporate modified nucleobases as described herein are also contemplated in this context. In some embodiments, nucleotides or modified nucleotides comprising an unprotected —OH moiety are used in accordance with the present disclosure.

Examples of bicyclic sugars include alpha-L-methyleneoxy (4'-$CH_2$—O-2') LNA, beta-D-methyleneoxy (4'-$CH_2$—O-2') LNA, ethyleneoxy (4'-$(CH_2)_2$—O-2') LNA, aminooxy (4'-$CH_2$—O—N(R)-2') LNA, and oxyamino (4'-$CH_2$—N(R)—O-2') LNA. In some embodiments, a bicyclic sugar, e.g., a LNA or BNA sugar, is sugar having at least one bridge between two sugar carbons. In some embodiments, a bicyclic sugar in a nucleoside may have the stereochemical configurations of alpha-L-ribofuranose or beta-D-ribofuranose. In some embodiments, a sugar is a sugar described in WO 1999014226. In some embodiments, a 4'-2' bicyclic sugar or 4' to 2' bicyclic sugar is a bicyclic sugar comprising a furanose ring which comprises a bridge connecting the 2' carbon atom and the 4' carbon atom of the sugar ring. In some embodiments, a bicyclic sugar, e.g., a LNA or BNA sugar, comprises at least one bridge between two pentofuranosyl sugar carbons. In some embodiments, a LNA or BNA sugar, comprises at least one bridge between the 4' and the 2' wo pentofuranosyl sugar carbons. In some embodiments, each bridge independently comprises or is 1 or from 2 to 4 linked groups independently selected from —$[C(R_1)(R_2)]_n$—, —$C(R_1)$=$C(R_2)$—, —$C(R_1)$=N—, —C(=$NR_1$)—, —C(=O)—, —C(=S)—, —O—, —$Si(R_1)_2$—, —$S(=O)_x$— and —$N(R_1)$—, wherein x is 0, 1, or 2, n is 1, 2, 3, or 4, and each of $R_1$ and $R_2$ is independently —H, —R, a protecting group, —OH, halogen, —$OJ_1$, —$NJ_1J_2$, —$SJ_1$, —$N_3$, —$COOJ_1$, —CN, —S(═O)$_2$-$J_1$, —S(═O)-$J_1$, a protecting group, or an optionally substituted group selected from $C_1$-$C_{12}$ alkyl, $C_2$-$C_{12}$ alkenyl, $C_2$-$C_{12}$ alkynyl, $C_5$-$C_{20}$ aryl, heterocyclyl, heteroaryl, acyl (C(═O)—H) and $C_5$-$C_7$ alicyclic, wherein each $J_1$ and $J_2$ is independently —H or an optionally substituted group selected from $C_1$-$C_{12}$ alkyl, $C_2$-$C_{12}$ alkenyl, $C_2$-$C_{12}$ alkynyl, $C_5$-$C_{20}$ aryl, acyl (C(═O)—H), heterocyclyl, heteroaryl, and $C_1$-$C_{12}$ aminoalkyl, and R is as described in the present disclosure. In some embodiments, a bridge, e.g., a 4'-2' bridge, is —[C($R_1$)($R_2$)], —[C($R_1$)($R_2$)]$_n$—O—, —C($R_1R_2$)—N($R_1$)—O— or —C($R_1R_2$)—O—N($R_1$)—. In some embodiments, a 4'-2' bridge is 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—N($R_1$)-2' or 4'-$CH_2$—N($R_1$)—O-2', wherein each of $R_1$ and $R_2$ is independently as described in the present disclosure. In some embodiments, each of $R_1$ and $R_2$ is independently —H, a protecting group or optionally substituted $C_1$-$C_{12}$ alkyl. In some embodiments, each of $R_1$ and $R_2$ is independently —H. In some embodiments, each of $R_1$ and $R_2$ is independently —R. In some embodiments, each of $R_1$ and $R_2$ is independently —H or optionally substituted $C_1$-$C_{12}$ alkyl. In some embodiments, each of $R_1$ and $R_2$ is independently —H or $C_1$-$C_6$ alkyl. In some embodiments, in LNA the 2'-hydroxyl group of the ribosyl sugar ring is connected to the 4' carbon atom of the sugar ring, thereby forming a methyleneoxy (4'-$CH_2$—O-2') bridge to form a bicyclic sugar moiety. In some embodiments, a bridge can also be a methylene (—$CH_2$—) group connecting the 2' oxygen atom and the 4' carbon atom, for which the term methyleneoxy (4'-$CH_2$—O-2') LNA is used. In some embodiments, in the case of the bicyclic sugar moiety having an ethylene bridging group in this position, the term ethylencoxy (4'-$CH_2CH_2$—O-2') LNA is used. In some embodiments, a bicyclic sugar is a sugar in alpha-L-methyleneoxy (4'-$CH_2$—O-2') LNA, an isomer of methyleneoxy (4'-$CH_2$—O-2') LNA.

In some embodiments, a bicyclic sugar may be further defined by isomeric configuration. For example, a sugar comprising a 4'-($CH_2$)—O-2' bridge may be in the alpha-L configuration or in the beta-D configuration. In some embodiments, a 4' to 2' bridge is a-L-4'-($CH_2$)—O-2', b-D-4'-$CH_2$—O-2', 4'-$(CH_2)_2$—O-2', 4'-$CH_2$—O—N(R')-2', 4'-$CH_2$—N(R')—O-2', 4'-CH(R')—O-2', 4'-CH($CH_3$)—O-2', 4'-$CH_2$—S-2', 4'-$CH_2$—N(R')—2', 4'-$CH_2$—CH(R')—2', 4'-$CH_2$—CH($CH_3$)-2', and 4'-$(CH_2)_3$-2', wherein each R' is as described in the present disclosure. In some embodiments, R' is —H, a protecting group or optionally substituted $C_1$-$C_{12}$ alkyl. In some embodiments, R' is —H or optionally substituted $C_1$-$C_{12}$ alkyl.

Certain modified sugars (e.g., bicyclic sugars that have 4' to 2' bridging groups such as 4'-$CH_2$—O-2' and 4'-$CH_2$—S-2'), their preparation and/or uses are described in Kumar et al., Bioorg. Med. Chem. Lett., 1998, 8, 2219-2222; WO 1999014226; etc. 2'-amino-BNAs, which may provide conformationally restriction and high-affinity in some cases are described in, e.g., Singh et al., J. Org. Chem., 1998, 63, 10035-10039. In addition, 2'-amino- and 2'-methylamino-BNA sugars and the thermal stability of their duplexes with complementary RNA and DNA strands have been previously reported.

In some embodiments, sugars are bicyclic sugars having a hydrocarbon bridge, e.g., a 4'-$(CH_2)_3$-2' bridge, 4'-CH═CH—$CH_2$-2' bridge, etc. (e.g., Freier et al., Nucleic Acids Research, 1997, 25(22), 4429-4443; Alback et al., J. Org. Chem., 2006, 71, 7731-7740; etc.). Example preparation of such bicyclic sugars and nucleosides along with their oligomerization and biochemical studies were reported, e.g., Srivastava et al., J. Am. Chem. Soc. 2007, 129(26), 8362-8379. In some embodiments, a modified nucleoside comprises a bridge, e.g., having the structure of -L-, formed between a nucleobase atom and a sugar atom. In some embodiments, a modified nucleoside comprises a bridge, e.g., having the structure of -L-, that is bonded to a nucleobase atom and a sugar atom, which bridge is other than the bond connecting the nucleobase to the sugar. In some embodiments, a modified nucleotide comprises a bridge (e.g., having the structure of -L-) that is bonded to a nucleobase atom and a sugar atom and is other than the bond connecting the nucleobase to the sugar, a bridge (e.g., having the structure of -L-) that is bonded to a nucleobase atom and an internucleotidic linkage, and/or a bridge (e.g., having the structure of -L-) that is bonded to a sugar atom and an internucleotidic linkage atom and is other than the bond connecting the sugar to the internucleotidic linkage.

In some embodiments, a bicyclic sugar is a sugar of alpha-L-methyleneoxy (4'-$CH_2$—O-2') BNA, beta-D-methyleneoxy (4'-$CH_2$—O-2') BNA, ethyleneoxy (4'-$(CH)_2$—O-2') BNA, aminooxy (4'-$CH_2$—O—N(R)-2') BNA, oxyamino (4'-$CH_2$—N(R)—O-2') BNA, methyl(methyleneoxy) (4'-CH($CH_3$)—O-2') BNA (also referred to as constrained ethyl or cEt), methylene-thio (4'-$CH_2$—S-2') BNA, methylene-amino (4'-$CH_2$—N(R)-2') BNA, methyl carbocyclic (4'-$CH_2$—CH($CH_3$)-2') BNA, propylene carbocyclic (4'-$(CH_2)_3$-2') BNA, or vinyl BNA.

In some embodiments, a sugar modification is a modification described in U.S. Pat. No. 9,006,198. In some embodiments, a modified sugar is described in U.S. Pat. No. 9,006,198. In some embodiments, a sugar modification is a modification described in U.S. Pat. Nos. 9,394,333, 9,744,183, 9,605,019, 9,982,257, US 20170037399, US 20180216108, US 20180216107, U.S. Pat. No. 9,598,458, WO 2017/062862, WO 2018/067973, WO 2017/160741, WO 2017/192679, WO 2017/210647, or WO 2018/098264, the sugar modifications and modified sugars of each of which are independently incorporated herein by reference.

In some embodiments, a sugar modification is 2'-OMe, 2'-MOE, 2'-LNA, 2'-F, 5'-vinyl, or S-cEt. In some embodiments, a modified sugar is a sugar of FRNA, FANA, or morpholino. In some embodiments, an oligonucleotide comprises a nucleic acid analog, e.g., GNA, LNA, PNA, TNA, F-HNA (F-THP or 3'-fluoro tetrahydropyran), MNA (mannitol nucleic acid, e.g., Leumann 2002 Bioorg. Med. Chem. 10: 841-854), ANA (anitol nucleic acid), or morpholino, or a portion thereof. In some embodiments, a sugar modification replaces a natural sugar with another cyclic or acyclic moiety. Examples of such moieties are widely known in the art, e.g., those used in morpholino, glycol nucleic acids, etc. and may be utilized in accordance with the present disclosure. As appreciated by those skilled in the art, when utilized with modified sugars, in some embodiments internucleotidic linkages may be modified, e.g., as in morpholino, PNA, etc.

In some embodiments, a sugar is a 6'-modified bicyclic sugar that have either (R) or (S)-chirality at the 6-position, e.g., those described in U.S. Pat. No. 7,399,845. In some embodiments, a sugar is a 5'-modified bicyclic sugar that has either (R) or (S)-chirality at the 5-position, e.g., those described in US 20070287831.

In some embodiments, a sugar has the structure of

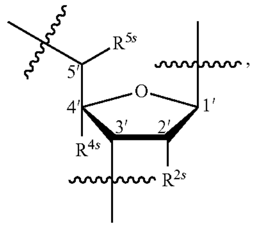

wherein each variable is independently as described in the present disclosure. In some embodiments, each sugar independently has the structure of

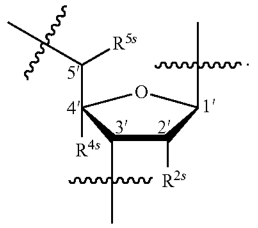

In some embodiments, a sugar has a structure of

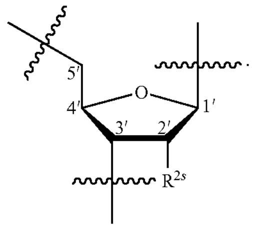

In some embodiments, each sugar independently has a structure of

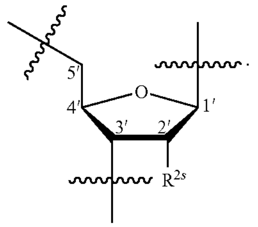

In some embodiments, $R^{2s}$ is a 2'-modification as described in the present disclosure. In some embodiments, $R^{2s}$ is —H, —OH, —F, —OMe or MOE.

In some embodiments, a modified sugar contains one or more substituents at the 2' position (typically one substituent, and often at the axial position) independently selected from —F; —$CF_3$, —CN, —$N_3$, —NO, —$NO_2$, —OR', —SR', or —$N(R')_2$, wherein each R' is independently described in the present disclosure; —O—($C_1$-$C_{10}$ alkyl), —S—($C_1$-$C_{10}$ alkyl), —NH—($C_1$-$C_{10}$ alkyl), or —N($C_1$-$C_{10}$ alkyl$)_2$; —O—($C_2$-$C_{10}$ alkenyl), —S—($C_1$-$C_{10}$ alkenyl), —NH—($C_2$-$C_{10}$ alkenyl), or —N($C_2$-$C_{10}$ alkenyl$)_2$; —O—($C_2$-$C_{10}$ alkynyl), —S—($C_2$-$C_{10}$ alkynyl), —NH—($C_2$-$C_{10}$ alkynyl), or —N($C_2$-$C_{10}$ alkynyl$)_2$; or —O—($C_1$-$C_{10}$ alkylene)-O—($C_1$-$C_{10}$ alkyl), —O—($C_1$-$C_{10}$ alkylene)-NH—($C_1$-$C_{10}$ alkyl) or —O—($C_1$-$C_{10}$ alkylene)-NH($C_1$-$C_{10}$ alkyl$)_2$, —NH—($C_1$-$C_{10}$ alkylene)-O—($C_1$-$C_{10}$ alkyl), or —N($C_1$-$C_{10}$ alkyl)-($C_1$-$C_{10}$ alkylene)-O—($C_1$-$C_{10}$ alkyl), wherein each of the alkyl, alkylene, alkenyl and alkynyl is independently and optionally substituted. In some embodiments, a substituent is —$O(CH_2)_nOCH_3$, —$O(CH_2)_nNH_2$, MOE, DMAOE, or DMAEOE, wherein n is from 1 to about 10. In some embodiments, a modified sugar is one described in WO 2001/088198; and Martin et al., Helv. Chim. Acta, 1995, 78, 486-504. In some embodiments, a modified sugar comprises one or more groups selected from a substituted silyl group, an RNA cleaving group, a reporter group, a fluorescent label, an intercalator, a group for improving the pharmacokinetic properties of a nucleic acid, a group for improving the pharmacodynamic properties of a nucleic acid, or other substituents having similar properties. In some embodiments, modifications are made at one or more of the 2', 3', 4', or 5' positions, including the 3' position of the sugar on the 3'-terminal nucleoside or in the 5' position of the 5'-terminal nucleoside.

In some embodiments, the 2'-OH of a ribose is replaced with a group selected from —H, —F; —$CF_3$, —CN, —$N_3$, —NO, —$NO_2$, —OR', —SR', or —$N(R')_2$, wherein each R' is independently described in the present disclosure; —O—($C_1$-$C_{10}$ alkyl), —S—($C_1$-$C_{10}$ alkyl), —NH—($C_1$-$C_{10}$ alkyl), or —N($C_1$-$C_{10}$ alkyl$)_2$; —O—($C_2$-$C_{10}$ alkenyl), —S—($C_2$-$C_{10}$ alkenyl), —NH—($C_2$-$C_{10}$ alkenyl), or —N($C_2$-$C_{10}$ alkenyl$)_2$; —O—($C_2$-$C_{10}$ alkynyl), —S—($C_2$-$C_{10}$ alkynyl), —NH—($C_2$-$C_{10}$ alkynyl), or —N($C_2$-$C_{10}$ alkynyl$)_2$; or —O—($C_1$-$C_{10}$ alkylene)-O—($C_1$-$C_{10}$ alkyl), —O—($C_1$-$C_{10}$ alkylene)-NH—($C_1$-$C_{10}$ alkyl) or —O—($C_1$-$C_{10}$ alkylene)-NH($C_1$-$C_{10}$ alkyl$)_2$, —NH—($C_1$-$C_{10}$ alkylene)-O—($C_1$-$C_{10}$ alkyl), or —N($C_1$-$C_{10}$ alkyl)-($C_1$-$C_{10}$ alkylene)-O—($C_1$-$C_{10}$ alkyl), wherein each of the alkyl, alkylene, alkenyl and alkynyl is independently and optionally substituted. In some embodiments, the 2'-OH is replaced with —H (deoxyribose). In some embodiments, the 2'-OH is replaced with —F. In some embodiments, the 2'-OH is replaced with —OR'. In some embodiments, the 2'-OH is replaced with —OMe. In some embodiments, the 2'-OH is replaced with —$OCH_2CH_2OMe$.

In some embodiments, a sugar modification is a 2'-modification. Commonly used 2'-modifications include but are not limited to 2'-$OR^1$, wherein $R^1$ is not hydrogen and is as described in the present disclosure. In some embodiments, a modification is 2'-OR, wherein R is optionally substituted $C_{1-6}$ aliphatic. In some embodiments, a modification is 2'-OR, wherein R is optionally substituted $C_{1-6}$ alkyl. In some embodiments, a modification is 2'-OMe. In some embodiments, a modification is 2'-MOE. In some embodiments, a 2'-modification is S-cEt. In some embodiments, a modified sugar is an LNA sugar. In some embodiments, a 2'-modification is —F. In some embodiments, a 2'-modification is FANA. In some embodiments, a 2-modification is FRNA. In some embodiments, a sugar modification is a 5'-modification, e.g., 5'-Me. In some embodiments, a sugar modification changes the size of the sugar ring. In some embodiments, a sugar modification is the sugar moiety in FHNA.

In some embodiments, a sugar modification replaces a sugar moiety with another cyclic or acyclic moiety. Examples of such moieties are widely known in the art, including but not limited to those used in morpholino (optionally with its phosphorodiamidate linkage), glycol nucleic acids, etc.

In some embodiments, 5% or more of the sugars of an oligonucleotide are modified. In some embodiments, 10% or more of the sugars of an oligonucleotide are modified. In some embodiments, 15% or more of the sugars of an oligonucleotide are modified. In some embodiments, 20% or more of the sugars of an oligonucleotide are modified. In some embodiments, 25% or more of the sugars of an oligonucleotide are modified. In some embodiments, 30% or more of the sugars of an oligonucleotide are modified. In some embodiments, 35% or more of the sugars of an oligonucleotide are modified. In some embodiments, 40% or more of the sugars of an oligonucleotide are modified. In some embodiments, 45% or more of the sugars of an oligonucleotide are modified. In some embodiments, 50% or more of the sugars of an oligonucleotide are modified. In some embodiments, 55% or more of the sugars of an oligonucleotide are modified. In some embodiments, 60% or more of the sugars of an oligonucleotide are modified. In some embodiments, 65% or more of the sugars of an oligonucleotide are modified. In some embodiments, 70% or more of the sugars of an oligonucleotide are modified. In some embodiments, 75% or more of the sugars of an oligonucleotide are modified. In some embodiments, 80% or more of the sugars of an oligonucleotide are modified. In some embodiments, 85% or more of the sugars of an oligonucleotide are modified. In some embodiments, 90% or more of the sugars of an oligonucleotide are modified. In some embodiments, 95% or more of the sugars of an oligonucleotide are modified. In some embodiments, each sugar of an oligonucleotide is independently modified. In some embodiments, a modified sugar comprises a 2'-modification. In some embodiments, each modified sugar independently comprises a 2'-modification. In some embodiments, a 2'-modification is 2'-$OR^1$. In some embodiments, a 2'-modification is a 2'-OMe. In some embodiments, a 2'-modification is a 2'-MOE. In some embodiments, a 2'-modification is an LNA sugar modification. In some embodiments, a 2'-modification is 2'-F. In some embodiments, each sugar modification is independently a 2'-modification. In some embodiments, each sugar modification is independently 2'-$OR^1$ or 2'-F. In some embodiments, each sugar modification is independently 2'-$OR^1$ or 2'-F, wherein $R^1$ is optionally substituted $C_{1-6}$ alkyl. In some embodiments, each sugar modification is independently 2'-$OR^1$ or 2'-F, wherein at least one is 2'-F. In some embodiments, each sugar modification is independently 2'-$OR^1$ or 2'-F, wherein $R^1$ is optionally substituted $C_{1-6}$ alkyl, and wherein at least one is 2'-$OR^1$. In some embodiments, each sugar modification is independently 2'-$OR^1$ or 2'-F, wherein at least one is 2'-F, and at least one is 2'-$OR^1$. In some embodiments, each sugar modification is independently 2'-$OR^1$ or 2'-F, wherein $R^1$ is optionally substituted $C_{1-6}$ alkyl, and wherein at least one is 2'-F, and at least one is 2'-$OR^1$. In some embodiments, each sugar modification is independently 2'-$OR^1$. In some embodiments, each sugar modification is independently 2'-$OR^1$, wherein $R_1$ is optionally substituted $C_{1-6}$ alkyl. In some embodiments, each sugar modification is 2'-OMe. In some embodiments, each sugar modification is 2'-MOE. In some embodiments, each sugar modification is independently 2'-OMe or 2'-MOE. In some embodiments, each sugar modification is independently 2'-OMe, 2'-MOE, or a LNA sugar.

In some embodiments, a modified sugar is an optionally substituted ENA sugar. In some embodiments, a sugar is one described in, e.g., Seth et al., J Am Chem Soc. 2010 Oct. 27; 132(42): 14942-14950. In some embodiments, a modified sugar is a sugar in XNA (xenonucleic acid), for instance, arabinose, anhydrohexitol, threose, 2'fluoroarabinose, or cyclohexene.

Modified sugars include cyclobutyl or cyclopentyl moieties in place of a pentofuranosyl sugar. Representative examples of such modified sugars include those described in U.S. Pat. Nos. 4,981,957, 5,118,800, 5,319,080, or 5,359,044. In some embodiments, the oxygen atom within the ribose ring is replaced by nitrogen, sulfur, selenium, or carbon. In some embodiments, —O— is replaced with —N(R')—, —S—, —Se— or —$C(R')_2$—. In some embodiments, a modified sugar is a modified ribose wherein the oxygen atom within the ribose ring is replaced with nitrogen, and wherein the nitrogen is optionally substituted with an alkyl group (e.g., methyl, ethyl, isopropyl, etc.).

A non-limiting example of modified sugars is glycerol, which is part of glycerol nucleic acids (GNAs), e.g., as described in Zhang, R et al., J. Am. Chem. Soc., 2008, 130, 5846-5847; Zhang L, et al., J. Am. Chem. Soc., 2005, 127, 41744175 and Tsai C H et al., PNAS, 2007, 14598-14603. In some embodiments, a nucleoside has a structure of:

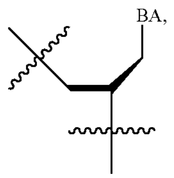

wherein BA is a nucleobase as described in the present disclosure.

A flexible nucleic acid (FNA) is based on a mixed acetal aminal of formyl glycerol, e.g., as described in Joyce G F et al., PNAS, 1987, 84, 43984402 and Heuberger B D and Switzer C, J. Am. Chem. Soc., 2008, 130, 412413. In some embodiments, a nucleoside has a structure of:

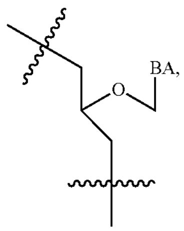

wherein BA is a nucleobase as described in the present disclosure.

In some embodiments, a sugar is a hexopyranosyl (6' to 4'), pentopyranosyl (4' to 2'), pentopyranosyl (4' to 3'), 5'-deoxy-5'-C-malonyl, squaryldiamide, or tetrofuranosyl (3' to 2') sugar. In some embodiments, an internucleotidic linkage is an internucleotidic linkage in squaryldiamide. In some embodiments, a modified nucleoside comprises a hexopyranosyl (6' to 4') sugar and has the structure of

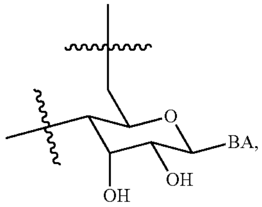

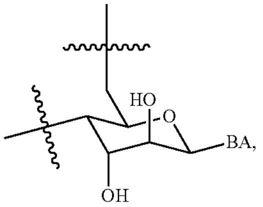

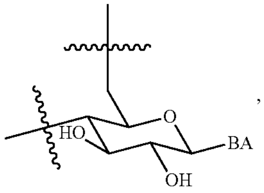

,

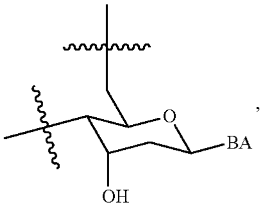

, or

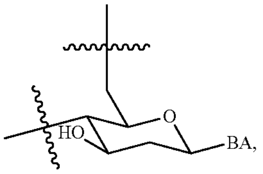

wherein BA is a nucleobase as described in the present disclosure. In some embodiments, a sugar is a sugar of such nucleoside.

In some embodiments, a modified nucleoside comprises a pentopyranosyl (4' to 2') sugar and has a structure of

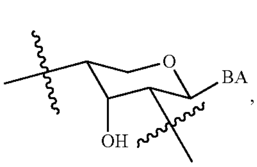

,

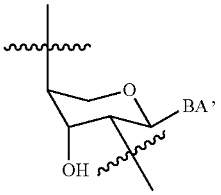

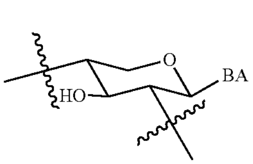

or

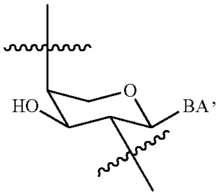

wherein BA is a nucleobase as described in the present disclosure. In some embodiments, a sugar is a sugar of such nucleoside.

In some embodiments, a modified nucleoside comprises a pentopyranosyl (4' to 3') sugar and has a structure of

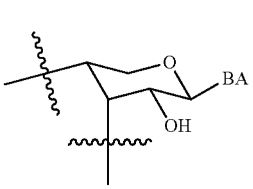

or

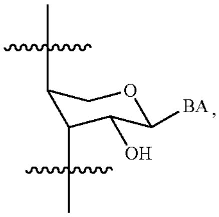

wherein BA is a nucleobase as described in the present disclosure. In some embodiments, a sugar is a sugar of such nucleoside.

In some embodiments, a modified nucleoside comprises a tetrofuranosyl (3' to 2') sugar and has the structure of

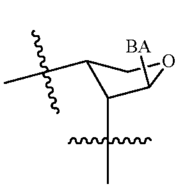

or

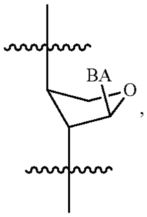

, wherein BA is a nucleobase as described in the present disclosure. In some embodiments, a sugar is a sugar of such nucleoside.

In some embodiments, a modified nucleoside comprises a modified sugar and has the structure of

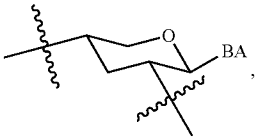

,

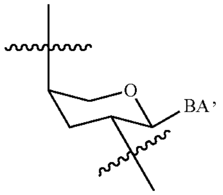

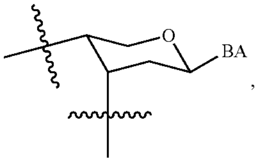

,

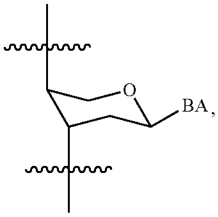

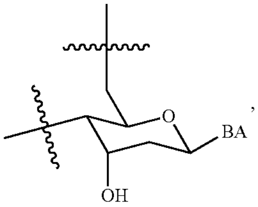

,

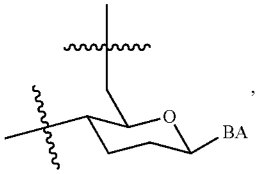

,

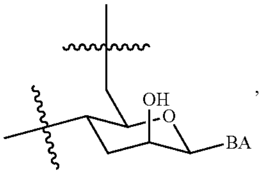

,

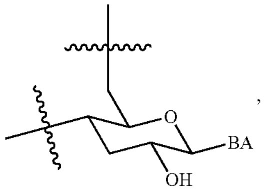

, or

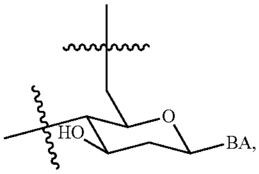

wherein BA is a nucleobase as described in the present disclosure. In some embodiments, a sugar is a sugar of such nucleoside.

In some embodiments, one or more hydroxyl group in a sugar is optionally and independently replaced with halogen, R'—N(R')$_2$, —OR', or —SR', wherein each R' is independently described in the present disclosure.

In some embodiments, a modified nucleoside is
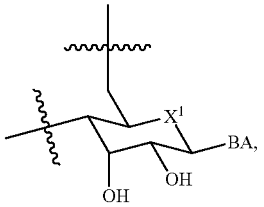
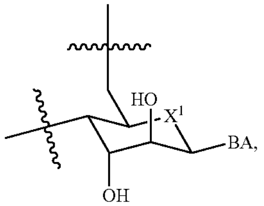
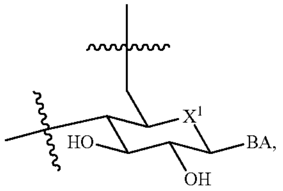
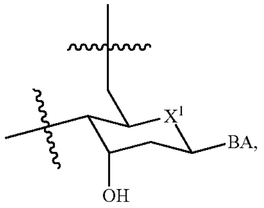
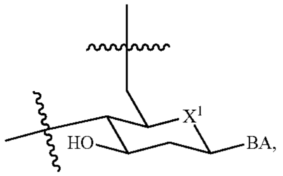
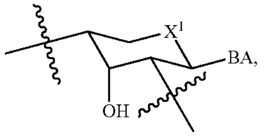
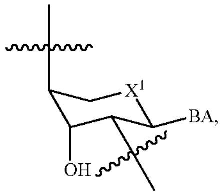
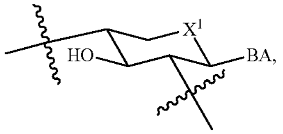
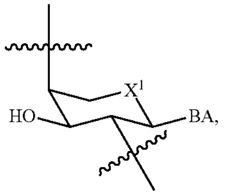
-continued
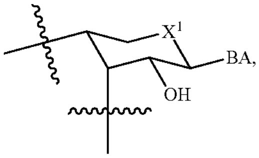
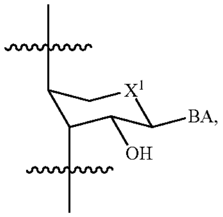
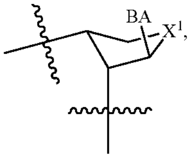
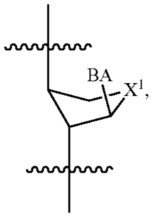
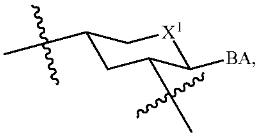
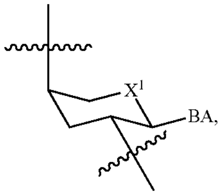
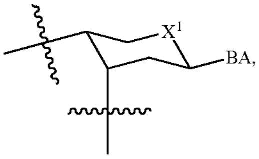
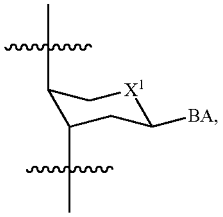
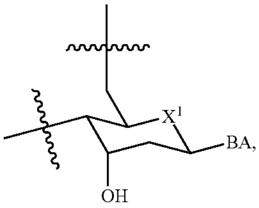
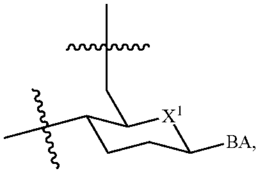
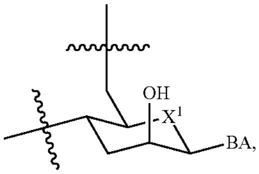
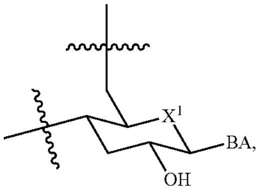 or -continued

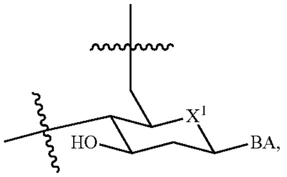

wherein BA is a nucleobase as described in the present disclosure, $X^1$ is selected from —S—, —Se—, —C(R')$_2$—, or —N(R')—, and each R' is independently as described in the present disclosure. In some embodiments, a sugar is a sugar of such nucleoside. In some embodiments, —N(R') is —NMe-, —NEt- or —NiPr—.

In some embodiments, a modified nucleoside comprises a modified sugar and has the structure

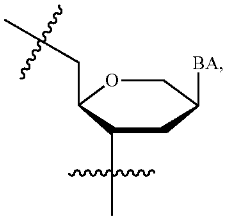

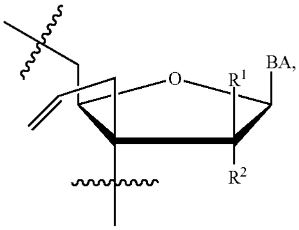

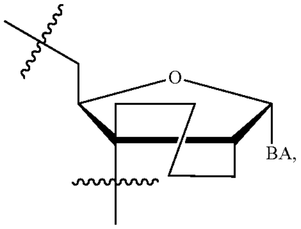

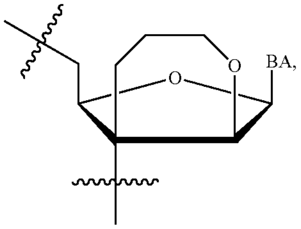

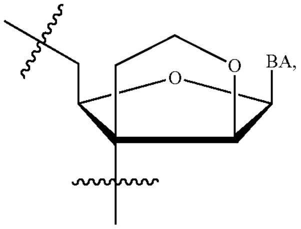

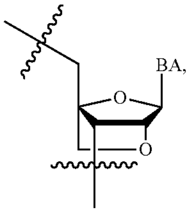

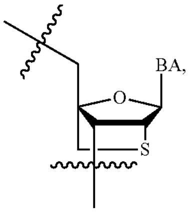

-continued

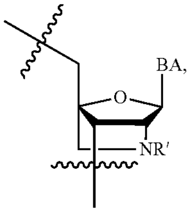

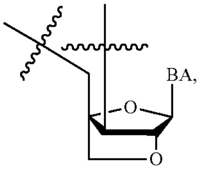

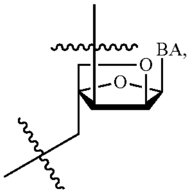

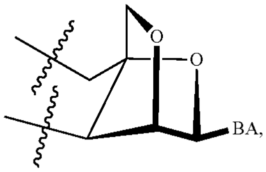

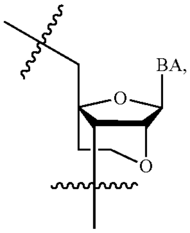

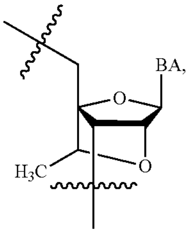

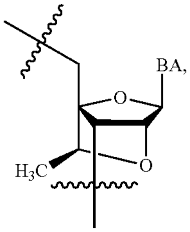

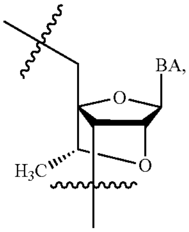

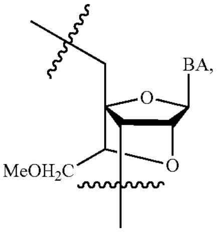

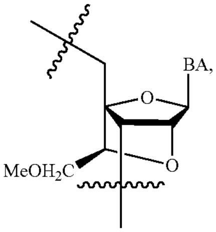

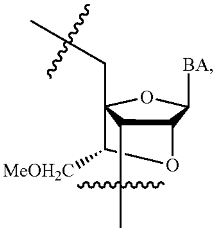

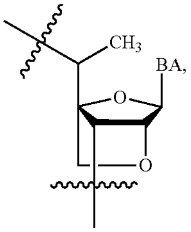

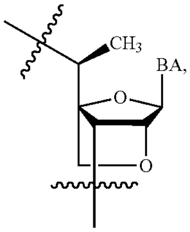

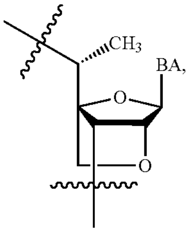

-continued

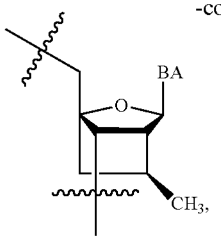

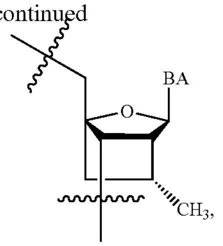

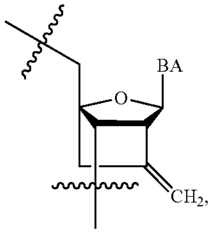

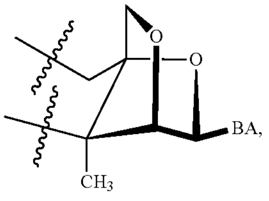

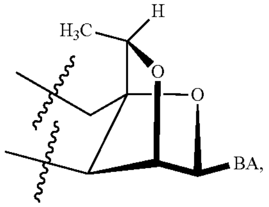

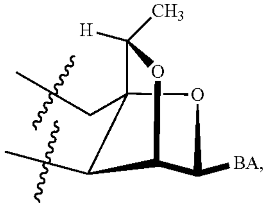

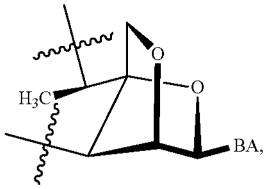

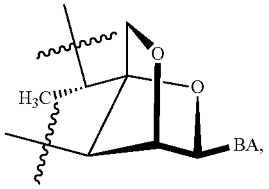

wherein each of $R^1$ and $R^2$ is independently —H, —F, —OMe, -MOE, or optionally substituted $C_{1-6}$ alkyl, R' is as described in the present disclosure, and BA is a nucleobase as described in the present disclosure. In some embodiments, a sugar is a sugar of such nucleoside. In some embodiments, a sugar is a sugar of 2'-thio-LNA, HNA, beta-D-oxy-LNA, beta-D-thio-LNA, beta-D-amino-LNA, xylo-LNA, alpha-L-LNA, ENA, beta-D-ENA, methylphosphonate-LNA, (R, S)-cEt, (R)-cEt, (S)-cEt, (R, S)-cMOE, (R)-cMOE, (S)-cMOE, (R, S)-5'-Me-LNA, (R)-5'-Me-LNA, (S)-5'-Me-LNA, (S)-Me cLNA, methylene-cLNA, 3'-methyl-alpha-L-LNA, (R)-6'-methyl-alpha-L-LNA, (S)-5'-methyl-alpha-L-LNA, or (R)-5'-Me-alpha-L-LNA. Example modified sugars are additionally described in WO 2008/101157, WO 2007/134181, WO 2016/167780 or US 20050130923.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more (e.g., 55%, 60%, 65%, 70%, 75%, 80%, 85%, 90%, 95% or more), inclusive, of the sugars in an oligonucleotide are independently modified. In some embodiments, only purine residues are modified (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the purine residues are modified). In some embodiments, only pyrimidine residues are modified (e.g., about 1%, 2%, 3%, 4%, 5%, 6%, 70, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the pyrimidine residues are modified). In some embodiments, both purine and pyrimidine residues are modified. In some embodiments, each sugar is independently modified. In some embodiments, each sugar independently comprises a 2'-modification.

Internucleotidic Linkages

Various internucleotidic linkages can be formed efficiently using provided technologies, in some embodiments, which high stereoselectivity (chiral control), if an internucleotidic linkage is a chiral internucleotidic linkage, for example, those of US20150211006, US20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784. In some embodiments, an internucleotidic linkage is a natural phosphate linkage (acid form is —O—P(O)(OH)—(O)—; can exist as various salt forms). In some embodiments, an internucleotidic linkage is a phosphorothioate linkage (acid form is —O—P(O)(SH)—(O)—; can exist as various salt forms). In some embodiments, an internucleotidic linkage is a non-negatively charged internucleotidic linkage. In some embodiments, an internucleotidic linkage is a neutral internucleotidic linkage.

In some embodiments, provided oligonucleotides comprise one or more natural phosphate linkages and one or more modified chiral internucleotidic linkages. In some embodiments, a modified chiral internucleotidic linkage is a phosphorothioate internucleotidic linkage. In some embodiments, a modified chiral internucleotidic linkage is a non-negatively charged internucleotidic linkage. In some embodiments, a modified chiral internucleotidic linkage is a neutral internucleotidic linkage. In some embodiments, provided oligonucleotides comprise one or more natural phosphate linkages and one or more phosphorothioate internucleotidic linkages. In some embodiments, provided oligonucleotides comprise one or more natural phosphate linkages and one or more non-negatively charged internucleotidic linkages. In some embodiments, one or more modified internucleotidic linkages are chiral and are each independently chirally controlled. In some embodiments, an internucleotidic linkage is a chiral internucleotidic linkage which comprises a chiral linkage phosphorus.

In some embodiments, provided oligonucleotides comprise one or more chirally controlled internucleotidic linkages. In some embodiments, provided oligonucleotides comprise 1-30, e.g., 1, 2, 3, 4, 5, 6, 7, 8, 9, 10, 11, 12, 13, 14, 15, 16, 17, 18, 19, 20, 21, 22, 23, 24, or 25, chirally controlled internucleotidic linkages. In some embodiments, provided oligonucleotides comprise at least 1, 2, 3, 4, 5, 6, 7, 8, 9, 10, 11, 12, 13, 14, 15, 16, 17, 18, 19, 20, 21, 22, 23, 24, or 25, chirally controlled internucleotidic linkages.

In some embodiments, a modified internucleotidic linkage is a phosphorothioate linkage.

In some embodiments, an linkage, e.g., an internucleotidic linkage, has the structure of formula VII:

VII

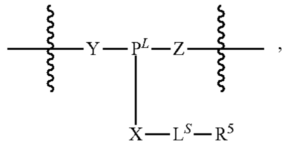

or a salt form thereof, wherein:

$P^L$ is P(=W), P, P→B(R')$_3$, or $P^N$;

$P^N$ is P(=N-L-$R^5$),

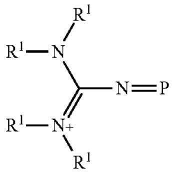 $Q^-$,

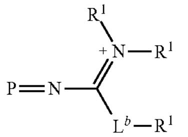 $Q^-$,

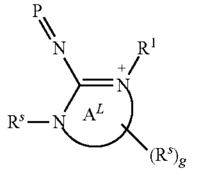 $Q^-$,

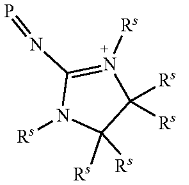 $Q^-$, or

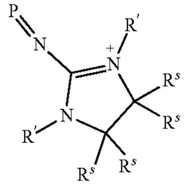 $Q^-$;

$Q^-$ is an anion;

each $R^s$ is independently —H, halogen, —CN, —$N_3$, —NO, —$NO_2$, -$L^s$-R', -$L^s$-Si(R')$_3$, -$L^s$-OR', -$L^s$-SR', -$L^s$-N(R')$_2$, —O-$L^s$-R', —O-$L^s$-Si(R)$_3$, —O-$L^s$-OR', —O-$L^s$-SR', or —O-$L^s$-N(R')$_2$;

g is 0-20;

Ring $A^L$ is Ring A as described herein;

W is O, N(-L-$R_5$), S or Se;

each of $R^1$ and $R^5$ is independently —H, -$L^s$-R', halogen, —CN, —$NO_2$, -$L^s$-Si(R')$_3$, —OR', —SR', or —N(R')$_2$;

each of X, Y and Z is independently —O—, —S—, —N(-$L^s$-$R^1$)—, or $L^s$;

each of L and $L^b$ is independently $L^s$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_{1-6}$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon; or —X-$L^s$-$R^5$ is of such a structure that H—X-$L^s$-$R^5$ has the structure of formula I, I-a, I-a-1, I-a-2, I-b, I-c, I-d, I-e, II, II-a, II-b, III, III-a, III-b, or a salt thereof as described herein.

In some embodiments, an internucleotidic linkage of formula VII is a chiral internucleotidic linkage. In some embodiments, P in $P^L$ is a chiral linkage phosphorus. In some embodiments, a chiral linkage phosphorus is Rp. In some embodiments, a chiral linkage phosphorus is Sp. In some embodiments, $P^L$ is P(═W). In some embodiments, $P^L$ is P. In some embodiments, $P^L$ is P→B(R'). In some embodiments, $P^L$ is P═N-L-$R^5$.

In some embodiments, W is O. In some embodiments, W is S. In some embodiments, W is N-L-R. In some embodiments, X is —O—. In some embodiments, Y is —O—. In some embodiments, Z is —O—. In some embodiments, X and Y are —O—. In some embodiments, X. Y and Z are —O—. In some embodiments, X and Y are —O—, and Z is —S—. In some embodiments, X. Y and Z are —O—, and W is O. In some embodiments, X, Y and Z are —O—, and W is S. In some embodiments, X, Y and Z are —O—, and W is N-L-$R^5$.

In some embodiments, an internucleotidic linkage of formula VII having the structure of formula VII-a-1:

VII-a-1

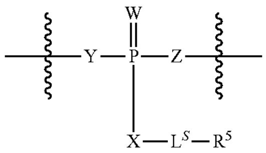
, or a salt form thereof, wherein each other variable is independently as described in the present disclosure.

In some embodiments, an internucleotidic linkage of formula VII or VII-a-1 having the structure of formula VII-a-2:

VII-a-2

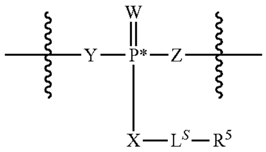
, or a salt form thereof, wherein P* is an asymmetric phosphorus atom, and each other variable is independently as described in the present disclosure.

In some embodiments, an internucleotidic linkage has the structure of formula VII-b:

VII-b

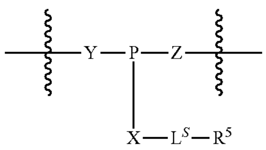
, or a salt form thereof, wherein each variable is independently as described in the present disclosure. In some embodiments, an internucleotidic linkage of formula VII has the structure of formula VII-b.

In some embodiments, an internucleotidic linkage of formula VII having the structure of formula VII-c:

VII-c

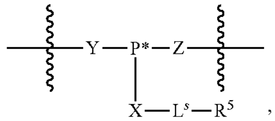
, or a salt form thereof, wherein P* is an asymmetric phosphorus atom, and each other variable is independently as described in the present disclosure.

In some embodiments, an internucleotidic linkage has the structure of formula VII-d:

VII-d

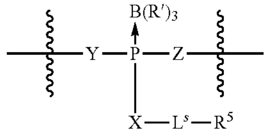
, or a salt form thereof, wherein each variable is independently as described in the present disclosure.

In some embodiments, an internucleotidic linkage of formula VII-e having the structure of:

VII-e

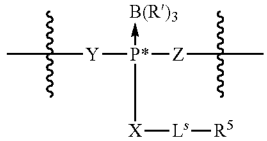
, or a salt form thereof, wherein P* is an asymmetric phosphorus atom, and each other variable is independently as described in the present disclosure.

In some embodiments, a modified internucleotidic linkage is a non-negatively charged internucleotidic linkage. In some embodiments, provided oligonucleotides comprise one or more non-negatively charged internucleotidic linkages. In some embodiments, a non-negatively charged internucleotidic linkage is a positively charged internucleotidic linkage. In some embodiments, a non-negatively charged internucleotidic linkage is a neutral internucleotidic linkage. In some embodiments, the present disclosure provides oligonucleotides comprising one or more neutral internucleotidic linkages. In some embodiments, a non-negatively charged internucleotidic linkage has the structure of formula NL-n-1, NL-n-2, NL-n-3, NL-n-4, NL, NL-a-1, NL-a-2, NL-b-1, NL-b-2, NL-c-1, NL-c-2, NL-d-1, NL-d-2, or a salt form thereof. In some embodiments, a neutral internucleotidic linkage has the structure of formula NL-n-1, NL-n-2, NL-n-3, NL-n-4, NL, NL-a-1, NL-a-2, NL-b-1, NL-b-2, NL-c-1, NL-c-2, NL-d-1, or NL-d-2. In some embodiments, a neutral internucleotidic linkage has the structure of formula NL, NL-a-1, NL-a-2, NL-b-1, NL-b-2, NL-c-1, NL-c-2, NL-d-1, or NL-d-2.

In some embodiments, a non-negatively charged internucleotidic linkage can improve the delivery and/or activity (e.g., ability to decrease the level, activity and/or expression of a target gene or a gene product thereof) of an oligonucleotide.

In some embodiments, a modified internucleotidic linkage (e.g., a non-negatively charged internucleotidic linkage) comprises optionally substituted triazolyl. In some embodiments, a modified internucleotidic linkage (e.g., a non-negatively charged internucleotidic linkage) comprises optionally substituted alkynyl. In some embodiments, a modified internucleotidic linkage comprises a triazole or alkyne moiety. In some embodiments, a triazole moiety, e.g., a triazolyl group, is optionally substituted. In some embodiments, a triazole moiety, e.g., a triazolyl group) is substituted. In some embodiments, a triazole moiety is unsubstituted. In some embodiments, a modified internucleotidic linkage comprises an optionally substituted cyclic guanidine moiety. In some embodiments, a modified internucleotidic linkage comprises an optionally substituted cyclic guanidine moiety and has the structure of:

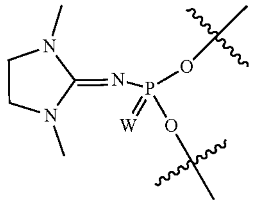
,
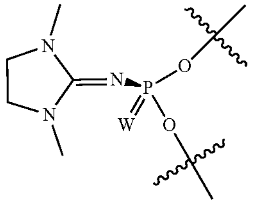
,
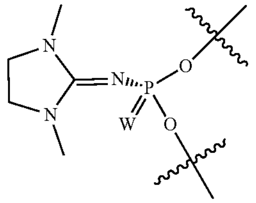
, wherein W is O or S. In some embodiments, W is O. In some embodiments, W is S. In some embodiments, a non-negatively charged internucleotidic linkage is stereochemically controlled.

In some embodiments, a non-negatively charged internucleotidic linkage or a neutral internucleotidic linkage is an internucleotidic linkage comprising a triazole moiety. In some embodiments, a non-negatively charged internucleotidic linkage or a non-negatively charged internucleotidic linkage comprises an optionally substituted triazolyl group. In some embodiments, an internucleotidic linkage comprising a triazole moiety (e.g., an optionally substituted triazolyl group) has the structure of

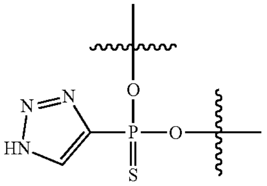
.

In some embodiments, an internucleotidic linkage comprising a triazole moiety has the structure of

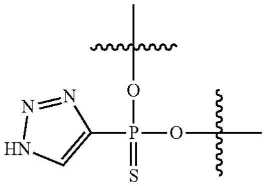
.

In some embodiments, an internucleotidic linkage comprising a triazole moiety has the formula of

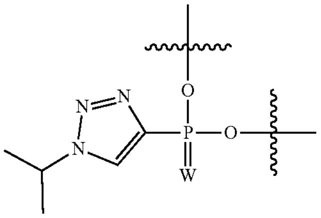
.

where W is O or S. In some embodiments, an internucleotidic linkage comprising an alkyne moiety (e.g., an optionally substituted alkynyl group) has the formula of

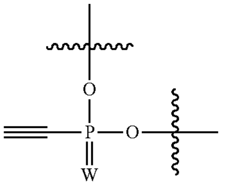
, wherein W is O or S. In some embodiments, an internucleotidic linkage, e.g., a non-negatively charged internucleotidic linkage, a neutral internucleotidic linkage, comprises a cyclic guanidine moiety. In some embodiments, an internucleotidic linkage comprising a cyclic guanidine moiety has the structure of

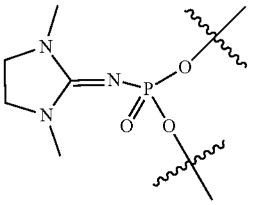
.

In some embodiments, a non-negatively charged internucleotidic linkage, or a neutral internucleotidic linkage, is or comprising a structure selected from

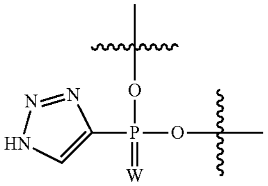
,

-continued

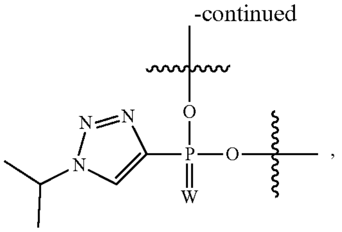

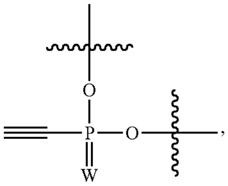

, or

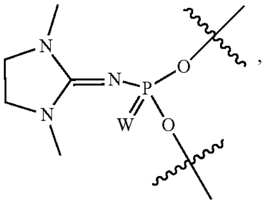

wherein W is O or S.

In some embodiments, an internucleotidic linkage comprises a Tmg group (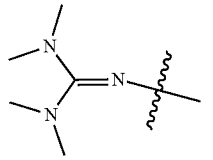).

In some embodiments, an internucleotidic linkage comprises a Tmg group and has the structure of

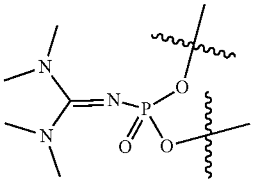 [SMILES: *OP(=O)(N=C(N(C)C)N(C)C)O*]

(the "Tmg internucleotidic linkage"). In some embodiments, neutral internucleotidic linkages include internucleotidic linkages of PNA and PMO, and an Tmg internucleotidic linkage.

In some embodiments, a non-negatively charged internucleotidic linkage has the structure of formula VII, NL-n-1, NL-n-2, NL-n-3, NL-n-4, NL, NL-a-1, NL-a-2, NL-b-1, NL-b-2, NL-c-1, NL-c-2, NL-d-1, NL-d-2, etc., or a salt form thereof. In some embodiments, a non-negatively charged internucleotidic linkage comprises an optionally substituted 3-20 membered heterocyclyl or heteroaryl group having 1-10 heteroatoms. In some embodiments, a non-negatively charged internucleotidic linkage comprises an optionally substituted 3-20 membered heterocyclyl or heteroaryl group having 1-10 heteroatoms, wherein at least one heteroatom is nitrogen. In some embodiments, such a heterocyclyl or heteroaryl group is of a 5-membered ring. In some embodiments, such a heterocyclyl or heteroaryl group is of a 6-membered ring.

In some embodiments, a non-negatively charged internucleotidic linkage comprises an optionally substituted 5-20 membered heteroaryl group having 1-10 heteroatoms. In some embodiments, a non-negatively charged internucleotidic linkage comprises an optionally substituted 5-20 membered heteroaryl group having 1-10 heteroatoms, wherein at least one heteroatom is nitrogen. In some embodiments, a non-negatively charged internucleotidic linkage comprises an optionally substituted 5-6 membered heteroaryl group having 1-4 heteroatoms, wherein at least one heteroatom is nitrogen. In some embodiments, a non-negatively charged internucleotidic linkage comprises an optionally substituted 5-membered heteroaryl group having 1-4 heteroatoms, wherein at least one heteroatom is nitrogen. In some embodiments, a heteroaryl group is directly bonded to a linkage phosphorus. In some embodiments, a non-negatively charged internucleotidic linkage comprises an optionally substituted triazolyl group. In some embodiments, a non-negatively charged internucleotidic linkage comprises an unsubstituted triazolyl group, e.g.,

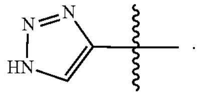

In some embodiments, a non-negatively charged internucleotidic linkage comprises a substituted triazolyl group, e.g.,

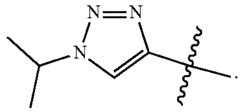 [SMILES: *c1cn(C(C)C)nn1]

In some embodiments, a non-negatively charged internucleotidic linkage comprises an optionally substituted 5-20 membered heterocyclyl group having 1-10 heteroatoms. In some embodiments, a non-negatively charged internucleotidic linkage comprises an optionally substituted 5-20 membered heterocyclyl group having 1-10 heteroatoms, wherein at least one heteroatom is nitrogen. In some embodiments, a non-negatively charged internucleotidic linkage comprises an optionally substituted 5-6 membered heterocyclyl group having 14 heteroatoms, wherein at least one heteroatom is nitrogen. In some embodiments, a non-negatively charged internucleotidic linkage comprises an optionally substituted 5-membered heterocyclyl group having 1-4 heteroatoms, wherein at least one heteroatom is nitrogen. In some embodiments, at least two heteroatoms are nitrogen. In some embodiments, a heterocyclyl group is directly bonded to a linkage phosphorus. In some embodiments, a heterocyclyl group is bonded to a linkage phosphorus through a linker, e.g., =N— when the heterocyclyl group is part of a guanidine moiety who directed bonded to a linkage phosphorus through its =N—. In some embodiments, a non-negatively charged internucleotidic linkage comprises an optionally substituted

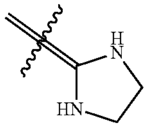 [SMILES: *=C1NCCN1]

group. In some embodiments, a non-negatively charged internucleotidic linkage comprises an substituted

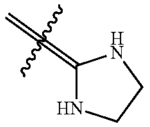 [SMILES: *=C1NCCN1]

group. In some embodiments, a non-negatively charged internucleotidic linkage comprises a

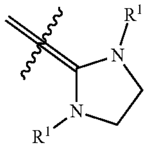

group. In some embodiments, each $R^1$ is independently optionally substituted $C_{1-6}$ alkyl. In some embodiments, each $R^1$ is independently methyl.

In some embodiments, a modified internucleotidic linkage, e.g., a non-negatively charged internucleotidic linkage, comprises a triazole or alkyne moiety, each of which is optionally substituted. In some embodiments, a modified internucleotidic linkage comprises a triazole moiety. In some embodiments, a modified internucleotidic linkage comprises a unsubstituted triazole moiety. In some embodiments, a modified internucleotidic linkage comprises a substituted triazole moiety. In some embodiments, a modified internucleotidic linkage comprises an alkyl moiety. In some embodiments, a modified internucleotidic linkage comprises an optionally substituted alkynyl group. In some embodiments, a modified internucleotidic linkage comprises an unsubstituted alkynyl group. In some embodiments, a modified internucleotidic linkage comprises a substituted alkynyl group. In some embodiments, an alkynyl group is directly bonded to a linkage phosphorus.

In some embodiments, an oligonucleotide comprises different types of internucleotidic phosphorus linkages. In some embodiments, a chirally controlled oligonucleotide comprises at least one natural phosphate linkage and at least one modified (non-natural) internucleotidic linkage. In some embodiments, an oligonucleotide comprises at least one natural phosphate linkage and at least one phosphorothioate. In some embodiments, an oligonucleotide comprises at least one non-negatively charged internucleotidic linkage. In some embodiments, an oligonucleotide comprises at least one natural phosphate linkage and at least one non-negatively charged internucleotidic linkage. In some embodiments, an oligonucleotide comprises at least one phosphorothioate internucleotidic linkage and at least one non-negatively charged internucleotidic linkage. In some embodiments, an oligonucleotide comprises at least one phosphorothioate internucleotidic linkage, at least one natural phosphate linkage, and at least one non-negatively charged internucleotidic linkage. In some embodiments, oligonucleotides comprise one or more, e.g., 1-50, 1-40, 1-30, 1-20, 1-15, 1-10, 1, 2, 3, 4, 5, 6, 7, 8, 9, 10, 11, 12, 13, 14, 15, 16, 17, 18, 19, 20 or more non-negatively charged internucleotidic linkages. In some embodiments, a non-negatively charged internucleotidic linkage is not negatively charged in that at a given pH in an aqueous solution less than 50%, 40%, 40%, 30%, 20%, 10%, 5%, or 1% of the internucleotidic linkage exists in a negatively charged salt form. In some embodiments, a pH is about pH 7.4. In some embodiments, a pH is about 4-9. In some embodiments, the percentage is less than 10%. In some embodiments, the percentage is less than 5%. In some embodiments, the percentage is less than 1%. In some embodiments, an internucleotidic linkage is a non-negatively charged internucleotidic linkage in that the neutral form of the internucleotidic linkage has no pKa that is no more than about 1, 2, 3, 4, 5, 6, or 7 in water. In some embodiments, no pKa is 7 or less. In some embodiments, no pKa is 6 or less. In some embodiments, no pKa is 5 or less. In some embodiments, no pKa is 4 or less. In some embodiments, no pKa is 3 or less. In some embodiments, no pKa is 2 or less. In some embodiments, no pKa is 1 or less. In some embodiments, pKa of the neutral form of an internucleotidic linkage can be represented by pKa of the neutral form of a compound having the structure of $CH_3$—the internucleotidic linkage—$CH_3$. For example, pKa of the neutral form of an internucleotidic linkage having the structure of formula VII may be represented by the pKa of the neutral form of a compound having the structure of

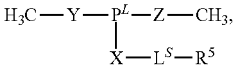

pKa of

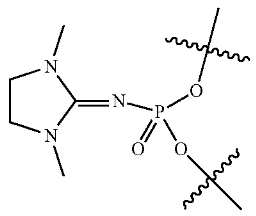 [SMILES: *OP(=O)(N=C1N(C)CCN1C)O*]

can be represented by pKa

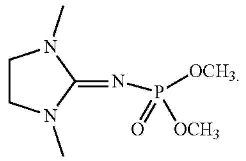

In some embodiments, a non-negatively charged internucleotidic linkage is a neutral internucleotidic linkage. In some embodiments, a non-negatively charged internucleotidic linkage is a positively-charged internucleotidic linkage. In some embodiments, a non-negatively charged internucleotidic linkage comprises a guanidine moiety. In some embodiments, a non-negatively charged internucleotidic linkage comprises a heteroaryl base moiety. In some embodiments, a non-negatively charged internucleotidic linkage comprises a triazole moiety. In some embodiments, a non-negatively charged internucleotidic linkage comprises an alkynyl moiety.

In some embodiments, a non-negatively charged internucleotidic linkage, e.g., a neutral internucleotidic linkage, comprises —$P^L$(—N═)—, wherein $P^L$ is as described in the present disclosure. In some embodiments, a non-negatively charged internucleotidic linkage, e.g., a neutral internucleotidic linkage, comprises —P(—N═)—. In some embodiments, a non-negatively charged internucleotidic linkage, e.g., a neutral internucleotidic linkage, comprises —P(═)(—N═)—. In some embodiments, a non-negatively charged internucleotidic linkage, e.g., a neutral internucleotidic linkage, comprises —P(═O)(—N═)—. In some embodiments, a non-negatively charged internucleotidic linkage, e.g., a neutral internucleotidic linkage, comprises —P(═S)(—N═)—.

In some embodiments, a non-negatively charged internucleotidic linkage, e.g., a neutral internucleotidic linkage, comprises

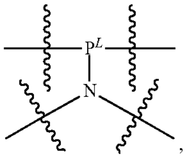
,
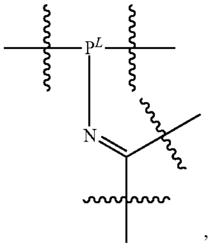
,
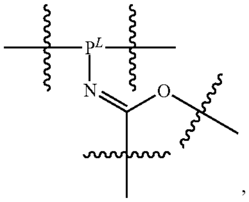
,
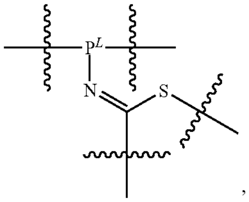
,
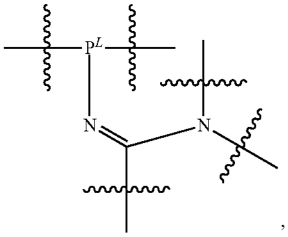
,
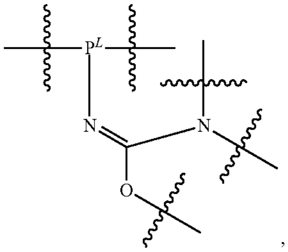
, -continued

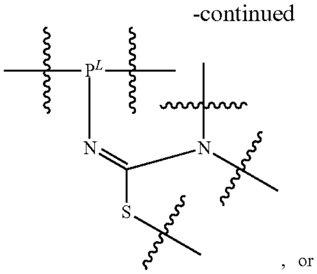
, or

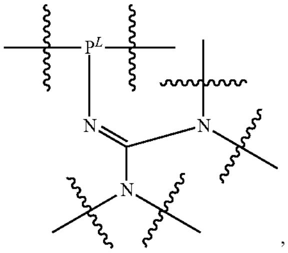
, wherein $P^L$ is as described in the present disclosure. For example, in some embodiments, $P^L$ is P; in some embodiments, $P^L$ is P(O); in some embodiments, $P^L$ is P(S); etc. In some embodiments, a non-negatively charged internucleotidic linkage, e.g., a neutral internucleotidic linkage, comprises

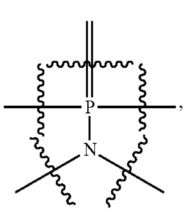
,
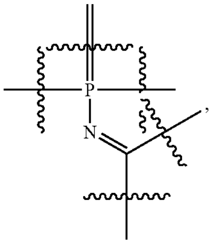
,
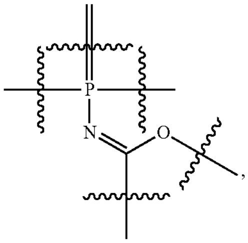
,
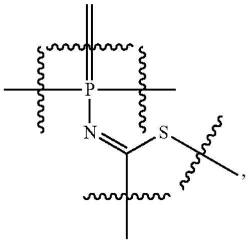
,
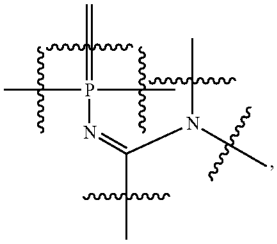
,

-continued

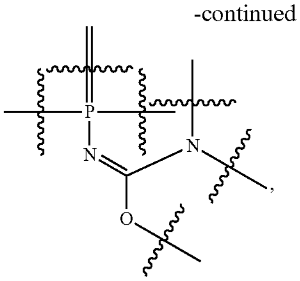

,

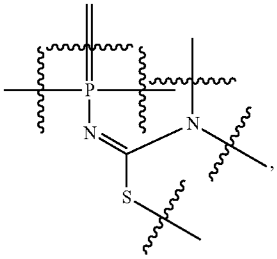

, or

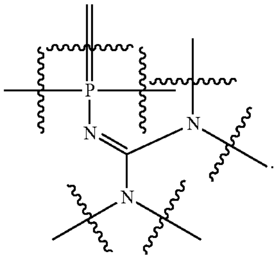

.

In some embodiments, a non-negatively charged internucleotidic linkage has the structure of formula VII, NL-n-1, NL-n-2, NL-n-3, NL-n-4, NL, NL-a-1; NL-a-2, NL-1)-1, NL-h-2, NL-c-1, NL-c-2, NL-d-1, NL-d-2, or a salt form thereof (not negatively charged). In some embodiments, a neutral internucleotidic linkage has the structure of formula VU, NL-n-1, NL-n-2, NL-n-3, NL-n-4, NL, NL-a-1, NL-a-2, NL-b-1, NL-b-2, NL-c-1, NL-c-2, NL-d-1, or NL-d-2. In some embodiments, an internucleotidic linkage having the structure of formula VII is an internucleotidic linkage having the structure of NL-n-1; NL-n-2, NL-n-3, NL-n-4, NL, NL-a-1, NL-a-2, NL-b-1, NL-b-2, NL-c-1, NL-c-2, NL-d-1, or NL-d-2 or a salt form thereof.

In some embodiments, —X-$L^s$-$R^5$ is optionally substituted alkynyl. In some embodiments, —X-$L^s$-$R^5$ is —C≡C—H. In some embodiments, an alkynyl group, e.g., —C≡C—H, can react with a number of reagents through various reactions to provide further modifications. For example, in some embodiments, an alkynyl group can react with azides through click chemistry. In some embodiments, an azide has the structure of $R^1$—$N_3$.

In some embodiments, an internucleotidic linkage, e.g., a non-negatively charged internucleotidic linkage, has the structure of formula NL-n-1 or a salt form thereof:

NL-n-1

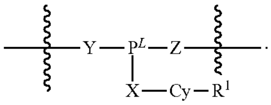

In some embodiments, a neutral internucleotidic linkage has the structure of formula NL-n-1. In some embodiments, X is a covalent bond and —X-Cy-$R^1$ is -Cy-$R^1$. In some embodiments, -Cy- is an optionally substituted bivalent group selected from a 5-20 membered heteroaryl ring having 1-10 heteroatoms, and a 3-20 membered heterocyclyl ring having 1-10 heteroatoms. In some embodiments, -Cy- is an optionally substituted bivalent 5-20 membered heteroaryl ring having 1-10 heteroatoms. In some embodiments, -Cy-$R^1$ is optionally substituted 5-20 membered heteroaryl ring having 1-10 heteroatoms, wherein at least one heteroatom is nitrogen. In some embodiments, -Cy-$R^1$ is optionally substituted 5-membered heteroaryl ring having 1-4 heteroatoms, wherein at least one heteroatom is nitrogen. In some embodiments, -Cy-$R^1$ is optionally substituted 6-membered heteroaryl ring having 1-4 heteroatoms, wherein at least one heteroatom is nitrogen. In some embodiments, -Cy-$R^1$ is optionally substituted triazolyl.

In some embodiments, an internucleotidic linkage, e.g., a non-negatively charged internucleotidic linkage, has the structure of formula NL-n-2 or a salt form thereof:

NL-n-2

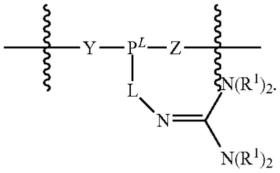

In some embodiments, a neutral internucleotidic linkage has the structure of formula NL-n-2. In some embodiments, $R^1$ is $R^1$. In some embodiments, L is a covalent bond. In some embodiments, an internucleotidic linkage, e.g., a non-negatively charged internucleotidic linkage, has the structure of formula NL-n-3 or a salt form thereof:

NL-n-3

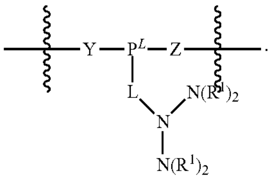

In some embodiments, a neutral internucleotidic linkage has the structure of formula NL-n-3. In some embodiments, two R' on different nitrogen atoms are taken together to form a ring as described. In some embodiments, a formed ring is 5-membered. In some embodiments, a formed ring is 6-membered. In some embodiments, a formed ring is substituted. In some embodiments, the two R' group that are not taken together to form a ring are each independently R. In some embodiments, the two R' group that are not taken together to form a ring are each independently hydrogen or an optionally substituted $C_{1-6}$ aliphatic. In some embodiments, the two R' group that are not taken together to form a ring are each independently hydrogen or an optionally substituted $C_{1-6}$ alkyl. In some embodiments, the two R' group that are not taken together to form a ring are the same. In some embodiments, the two R' group that are not taken together to form a ring are different. In some embodiments, both of them are —$CH_3$.

In some embodiments, an internucleotidic linkage, e.g., a non-negatively charged internucleotidic linkage, has the structure of formula NL-n-4 or a salt form thereof:

NL-n-4

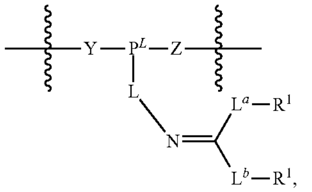

wherein each of $L^a$ and $L^b$ is independently L or —N($R^1$)—, and each other variable is independently as described in the present disclosure. In some embodiments, L is a covalent bond, and an internucleotidic linkage of formula NL-n-4 has the structure of:

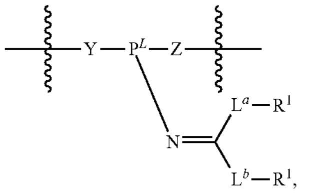

or a salt form thereof, wherein each variable is independently as described in the present disclosure.

In some embodiments, $L^a$ is —N($R^1$)—. In some embodiments, $L^a$ is L as described in the present disclosure. In some embodiments, $L^a$ is a covalent bond. In some embodiments, $L^a$ is —N(R')—. In some embodiments, $L^a$ is —N(R)—. In some embodiments, $L^a$ is —O—. In some embodiments, $L^a$ is —S—. In some embodiments, $L^a$ is —S(O)—. In some embodiments, $L^a$ is —$S(O)_2$—. In some embodiments, $L^a$ is —$S(O)_2$N(R')—. In some embodiments, $L^b$ is —N(R')—. In some embodiments, $L^b$ is L as described in the present disclosure. In some embodiments, $L^b$ is a covalent bond. In some embodiments, $L^b$ is —N(R')—. In some embodiments, $L^b$ is —N(R)—. In some embodiments, $L^b$ is —O—. In some embodiments, $L^b$ is —S—. In some embodiments, $L^b$ is —S(O)—. In some embodiments, $L^b$ is —$S(O)_2$—. In some embodiments, $L^b$ is —$S(O)_2$N(R')—. In some embodiments, $L^a$ and $L^b$ are the same. In some embodiments, $L^a$ and $L^b$ are different. In some embodiments, at least one of $L^a$ and $L^b$ is —N(R')—. In some embodiments, at least one of $L^a$ and $L^b$ is —O—. In some embodiments, at least one of $L^a$ and $L^b$ is —S—. In some embodiments, at least one of $L^a$ and $L^b$ is a covalent bond. In some embodiments, as described herein, $R^1$ is R. In some embodiments, $R^1$ is —H. In some embodiments, $R^1$ is optionally substituted $C_{1-10}$ aliphatic. In some embodiments, $R^1$ is optionally substituted $C_{1-10}$ alkyl. In some embodiments, a structure of formula NL-n-4 is a structure of formula NL-n-2. In some embodiments, a structure of formula NL-n-4 is a structure of formula NL-n-3.

In some embodiments, an internucleotidic linkage, e.g., a non-negatively charged internucleotidic linkage, has the structure of formula NL or a salt form thereof:

NL

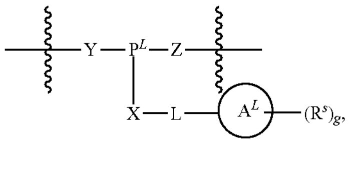

or a salt form thereof, wherein:

Ring $A^L$ is Ring A as described herein;

g is 0-20; and each other variable is independently as described herein.

In some embodiments, g is 0. In some embodiments, g is 1-20. In some embodiments, g is 1-10. In some embodiments, g is 1-5. In some embodiments, g is 2-10. In some embodiments, g is 2-5. In some embodiments, g is 1, 2, 3, 4, 5, 6, 7, 8, 9, 10, 11, 12, 13, 14, 15, 16, 17, 18, 19, 20, 21, 22, 23, 24, or 25. In some embodiments, g is 1. In some embodiments, g is 2. In some embodiments, g is 3. In some embodiments, g is 4. In some embodiments, g is 5. In some embodiments, g is 6. In some embodiments, g is 7. In some embodiments, g is 8. In some embodiments, g is 9. In some embodiments, g is 10.

In some embodiments, a neutral internucleotidic linkage has the structure of formula NL.

In some embodiments, an internucleotidic linkage, e.g., a non-negatively charged internucleotidic linkage of formula NL, has the structure of formula NL-a-1 or a salt form thereof:

NL-a-1

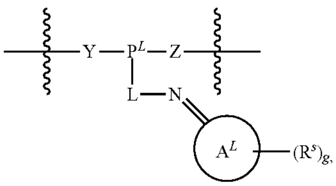

or a salt form thereof. In some embodiments, a neutral internucleotidic linkage has the structure of formula NL-a-1.

In some embodiments, an internucleotidic linkage, e.g., a non-negatively charged internucleotidic linkage of formula NL, has the structure of formula NL-a-2 or a salt form thereof:

NL-a-2

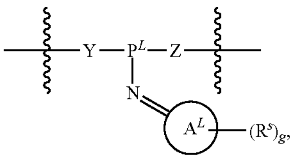

or a salt form thereof. In some embodiments, a neutral internucleotidic linkage has the structure of formula NL-a-2.

In some embodiments, $A^L$ is bonded to —N= or L through a carbon atom. In some embodiments, an internucleotidic linkage, e.g., a non-negatively charged internucleotidic linkage of formula NL or NL-a-1, NL-a-2, has the structure of formula NL-b-1 or a salt form thereof:

NL-b-1

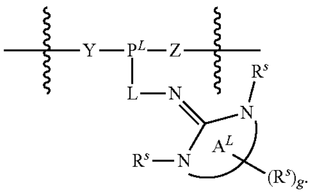

In some embodiments, a neutral internucleotidic linkage has the structure of formula NL-b-1.

In some embodiments, Ring $A^L$ is bonded to —N= or L through a carbon atom. In some embodiments, an internucleotidic linkage, e.g., a non-negatively charged internucleotidic linkage of formula NL or NL-a-1, NL-a-2, has the structure of formula NL-b-2 or a salt form thereof:

NL-b-2

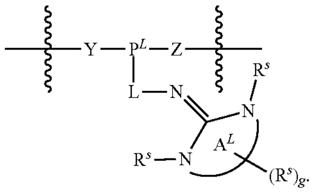

In some embodiments, a neutral internucleotidic linkage has the structure of formula NL-b-2. In some embodiments, Ring $A^L$ is an optionally substituted 3-20 membered monocyclic ring having 0-10 heteroatoms (in addition to the two nitrogen atoms for formula NL-b). In some embodiments, Ring $A^L$ is an optionally substituted 5-membered monocyclic saturated ring.

As described herein, Ring $A^L$ can be either be monovalent, bivalent or polyvalent. In some embodiments. Ring $A^L$ is monovalent (e.g., when g is 0 and no substitution). In some embodiments, Ring $A^L$ is bivalent. In some embodiments, Ring $A^L$ is polyvalent. In some embodiments, Ring $A^L$ is bivalent and is -Cy-. In some embodiments, Ring $A^L$ is an optionally substituted bivalent triazole ring. In some embodiments, Ring $A^L$ is trivalent and is $Cy^L$. In some embodiments, Ring $A^L$ is tetravalent and is $Cy^L$. In some embodiments, Ring $A^L$ is optionally substituted HN

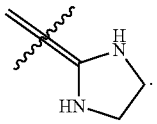 [SMILES: *=C1NCCN1]

In some embodiments, an internucleotidic linkage, e.g., a non-negatively charged internucleotidic linkage of formula NL, NL-a, or NL-b, has the structure of formula NL-c-1 or a salt form thereof:

NL-c-1

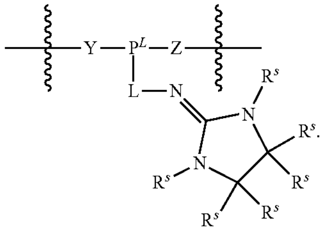

In some embodiments, a neutral internucleotidic linkage has the structure of formula NL-c-1. In some embodiments, an internucleotidic linkage, e.g., a non-negatively charged internucleotidic linkage of formula NL, NL-a, or NL-b, has the structure of formula NL-c-2 or a salt form thereof:

NL-c-2

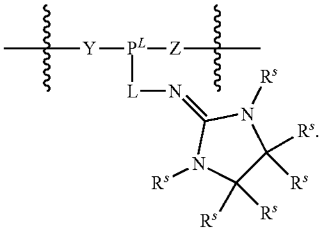

In some embodiments, a neutral internucleotidic linkage has the structure of formula NL-c-c2. In some embodiments, an internucleotidic linkage, e.g., a non-negatively charged internucleotidic linkage of formula NL, NL-a, NL-b, or NL-c has the structure of formula NL-d-1 or a salt form thereof:

NL-d-1

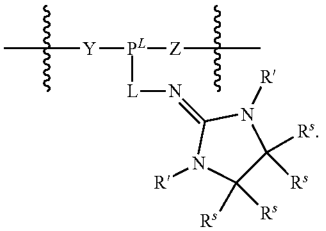

In some embodiments, a neutral internucleotidic linkage has the structure of formula NL-d-1. In some embodiments, an internucleotidic linkage, e.g., a non-negatively charged internucleotidic linkage of formula NL, NL-a, NL-b, or NL-c has the structure of formula NL-d-2 or a salt form thereof:

NL-d-2

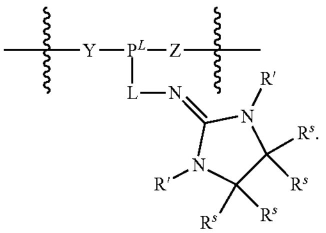

In some embodiments, a neutral internucleotidic linkage has the structure of formula NL-d-2. In some embodiments, each R' is independently optionally substituted $C_{1-6}$ aliphatic. In some embodiments, each R' is independently optionally substituted $C_{1-6}$ alkyl. In some embodiments, each R' is independently $—CH_3$. In some embodiments, each $R^5$ is —H.

In some embodiments, a non-negatively charged internucleotidic linkage has the structure of

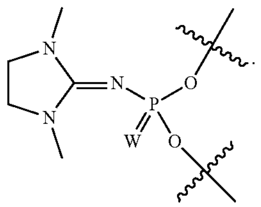

In some embodiments, a non-negatively charged internucleotidic linkage has the structure of

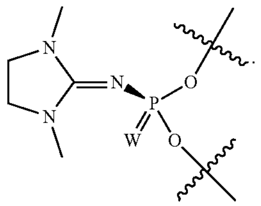

In some embodiments, a non-negatively charged internucleotidic linkage has the structure of

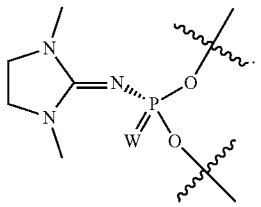

In some embodiments, a non-negatively charged internucleotidic linkage has the structure of

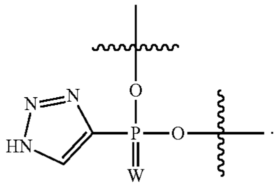

In some embodiments, a non-negatively charged internucleotidic linkage has the structure of

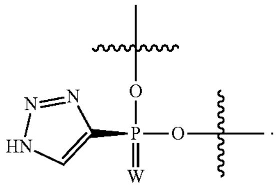

In some embodiments, a non-negatively charged internucleotidic linkage has the structure of

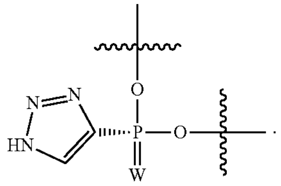

In some embodiments, a non-negatively charged internucleotidic linkage has the structure of

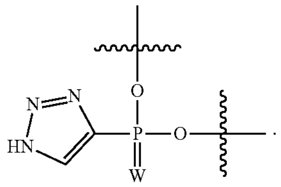

In some embodiments, a non-negatively charged internucleotidic linkage has the structure of

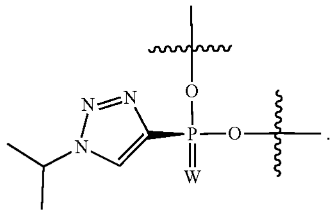

In some embodiments, a non-negatively charged internucleotidic linkage has the structure of

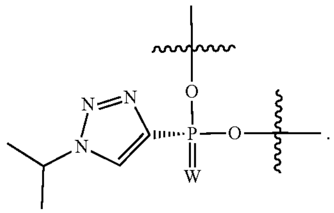

In some embodiments, a non-negatively charged internucleotidic linkage has the structure of

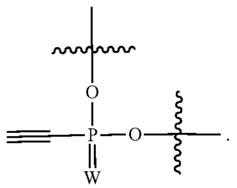

In some embodiments, a non-negatively charged internucleotidic linkage has the structure of

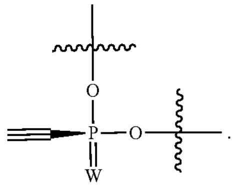

In some embodiments, a non-negatively charged internucleotidic linkage has the structure of

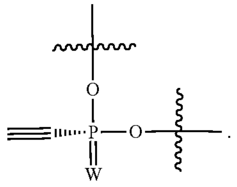

In some embodiments, W is O, In some embodiments, W is S. In some embodiments, a neutral internucleotidic linkage is a non-negatively charged internucleotidic linkage described above.

In some embodiments, provided oligonucleotides comprise 1, 2, 3, 4, 5, 6, 7, 8, 9, 10, 11, 12, 13, 14, 15, 16, 17, 18, 19, 20, 21, 22, 23, 24, or 25 or more internucleotidic linkages of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, NL-d-2, or a salt form thereof. In some embodiments, each internucleotidic linkage independently has the structure of formula VII, VII-a-1, VII-a-2, VII-b, VII-c, VII-d, VII-e, NL-n-1 NL-n-2, NL-n-3, NL-n-4, NL, NL-a-1, NL-b-2, NL-c-1, NL-e-2, NL-d-1, NL-d-2, or a salt form thereof. In some embodiments, provided oligonucleotides comprise 1, 2, 3, 4, 5, 6, 7, 8, 9, 10, 11, 12, 13, 14, 15, 16, 17, 18, 19, 20, 21, 22, 23, 24, or 25 or inure chiral internucleotidic linkages of formula VII, VII-a-1, VII-a-2, VII-b, VII-c, VII-d, VII-e, NL-n-1, NL-n-2, NL-n-4, NL, NL-a-1, NL-a-2, NL-b-1, NL-b-2, NL-c-2, NL-d-1, NL-d-2, or a salt form thereof, wherein the P is chiral. In some embodiments, provided oligonucleotides comprise 1, 2, 3, 4, 5, 6, 7, 8, 9, 10, 11, 12, 13, 14, 15, 16, 17, 18, 19, 20, 21, 22, 23, 24, or 25 or more chirally controlled chiral internucleotidic linkages of formula VII, VII-a-1, VII-a-2, VII-d, VII-e, NL-n-1, NL-n-2, NL-n-3, NL-n-4, NL, NL-a-1 NL-a-2, NL-b-2, NL-c-1 NIL-d-1, NL-d-2, or a salt form thereof, wherein the P is chiral and is chirally controlled. In some embodiments, each chiral internucleotidic linkage independently has the structure of formula VII, VII-b, NL-n-1, NL-n-2, NL-n-3, NL-n-4, NL, NL-a-1, NL-a-2, NL-b-1, NL-b-2, NL-c-1, NL-c-2, NL-d-1, NL-d-2, or a salt form thereof, wherein the P is chiral. In some embodiments, each chirally controlled internucleotidic linkage independently has the structure of formula VII, VII-a-1, VII-a-2, VII-1), VII-c, VII-d, NL-n-1, NL-n-2, NL-n-3, NL-n-4, NL, NL-a-2, NL-b-2, NL-c-1, NL-c-2, NL-d-1, NL-d-2, or a salt form thereof, wherein the P is chiral and is chirally controlled. In some embodiments, each internucleotidic linkage is selected from natural phosphate linkage, phosphorothioate internucleotidic linkage and a neutral backbone. In some embodiments, each internucleotidic linkage is selected from natural phosphate linkage, phosphorothioate internucleotidic linkage and a neutral backbone comprising a guanidine moiety.

In some embodiments, each $L^P$ independently has the structure of formula VII, VII-a-L VII-a-2, VII-b, VII-c, VII-d, VII-e, NL-n-1, NL-n-2, NL-n-3, NL-n-4, NL, NL-a-1, NL-a-2, NL-1)-1, NL-b-2, NL-c-1, NL-c-2, NL-d-1, NL-d-2, or a salt form thereof.

In some embodiments, a non-negatively charged internucleotidic linkage comprises a triazole moiety. In some embodiments, a non-negatively charged internucleotidic linkage comprises an optionally substituted triazolyl group. In some embodiments, a non-negatively charged internucleotidic linkage has the structure of

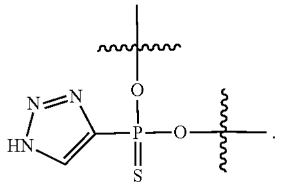 [SMILES: *OP(=S)(O*)c1c[nH]nn1]

In some embodiments, a non-negatively, charged internucleotidic linkage has the structure of

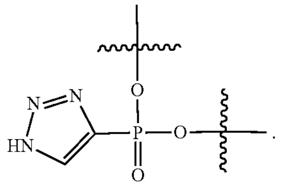 [SMILES: *OP(=O)(O*)c1c[nH]nn1]

In some embodiments, a non-negatively charged internucleotidic linkage comprises a substituted triazolyl group. In some embodiments, a non-negatively charged internucleotidic linkage has the structure of

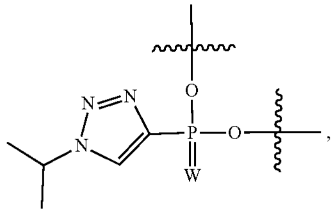

wherein W is O or S. In some embodiments, a non-negatively charged internucleotide linkage comprises an optionally substituted alkynyl group. In some embodiments, a non-negatively charged internucleotidic linkage has the structure of

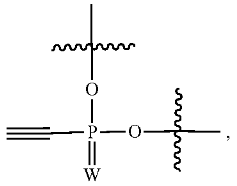

wherein W is O or S.

In some embodiments, a non-negatively charged internucleotidic linkage, or a neutral internucleotidic linkage, is or comprising a structure selected from

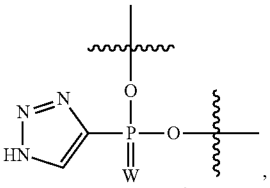

,

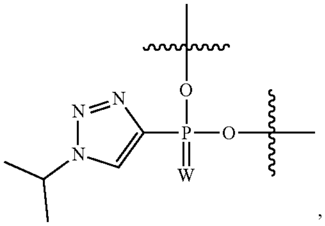

,

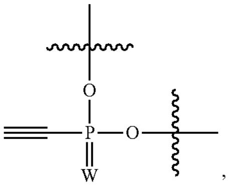

, or

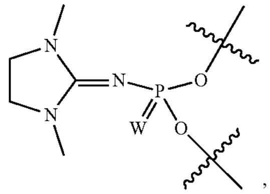

, wherein W is O or S.

In some embodiments, certain non-negatively charged internucleotidic linkages or neutral internucleotidic linkages may be prepared by reacting a P(III) phosphite triester internucleotidic linkage with azido imidazolinium salts (e.g., compounds comprising

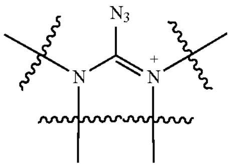

)

under suitable conditions. In some embodiments, an azido imidazolinium salt is a salt of $PF_3^-$. In some embodiments, an azido imidazolinium salt is a slat of

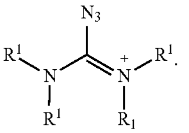

In some embodiments, an azido imidazolinium salt is 2-azido-1,3-dimethylimidazolinium hexafluorophosphate.

In some embodiments, an oligonucleotide comprises a neutral internucleotidic linkage and a chirally controlled internucleotidic linkage. In some embodiments, an oligonucleotide comprises a neutral internucleotidic linkage and a chirally controlled internucleotidic linkage which is not the neutral internucleotidic linkage. In some embodiments, an oligonucleotide comprises a neutral internucleotidic linkage and a chirally controlled phosphorothioate internucleotidic linkage. In some embodiments, the present disclosure provides an oligonucleotide comprising one or more non-negatively charged internucleotidic linkages and one or more phosphorothioate internucleotidic linkages, wherein each phosphorothioate internucleotidic linkage in the oligonucleotide is independently a chirally controlled internucleotidic linkage. In some embodiments, the present disclosure provides an oligonucleotide comprising one or more neutral internucleotidic linkages and one or more phosphorothioate internucleotidic linkage, wherein each phosphorothioate internucleotidic linkage in the oligonucleotide is independently a chirally controlled internucleotidic linkage. In some embodiments, an oligonucleotide comprises at least 5, 6, 7, 8, 9, 10, 11, 12, 13, 14, 15, 16, 17, 18, 19, 20 or more chirally controlled phosphorothioate internucleotidic linkages. In some embodiments, non-negatively charged internucleotidic linkage is chirally controlled. In some embodiments, non-negatively charged internucleotidic linkage is not chirally controlled. In some embodiments, a neutral internucleotidic linkage is chirally controlled. In some embodiments, a neutral internucleotidic linkage is not chirally controlled.

Without wishing to be bound by any particular theory, the present disclosure notes that a neutral internucleotidic linkage can be more hydrophobic than a phosphorothioate internucleotidic linkage (PS), which can be more hydrophobic than a natural phosphate linkage (PO). Typically, unlike a PS or PO, a neutral internucleotidic linkage bears less charge. Without wishing to be bound by any particular theory, the present disclosure notes that incorporation of one or more neutral internucleotidic linkages into an oligonucleotide may increase oligonucleotides' ability to be taken up by a cell and/or to escape from endosomes. Without wishing to be hound by any particular theory, the present disclosure notes that incorporation of one or more neutral internucleotidic linkages can be utilized to modulate melting temperature of duplexes formed between an oligonucleotide and its target nucleic acid.

Without wishing to be bound by any particular theory, the present disclosure notes that incorporation of one or more non-negatively charged internucleotidic linkages, e.g., neutral internucleotidic linkages, into an oligonucleotide may be able to increase the oligonucleotide's ability to mediate a function such as gene knockdown. In some embodiments, an oligonucleotide capable of mediating knockdown of level of a nucleic acid or a product encoded thereby comprises one or more non-negatively charged internucleotidic linkages. In some embodiments, an oligonucleotide capable of mediating knockdown of expression of a target gene comprises one or more non-negatively charged internucleotidic linkages. In some embodiments, an oligonucleotide capable of mediating knockdown of expression of a target gene comprises one or more neutral internucleotidic linkages.

In some embodiments, a non-negatively charged internucleotidic linkage, e.g., a neutral internucleotidic linkage is not chirally controlled. In some embodiments, a non-negatively charged internucleotidic linkage is chirally controlled. In some embodiments, a non-negatively charged internucleotidic linkage is chirally controlled and its linkage phosphorus is Rp. In some embodiments, a non-negatively charged internucleotidic linkage is chirally controlled and its linkage phosphorus is SP.

In some embodiments, an oligonucleotide comprises one or more, e.g., 1-20, 1-15, 1-10, 1-5, or 1, 2, 3, 4, 5.6, 7, 8, 9, 10, or more non-negatively charged internucleotidic linkages. In some embodiments, each of non-negatively charged internucleotidic linkage and/or neutral internucleotidic linkages is optionally and independently chirally controlled. In some embodiments, each non-negatively, charged internucleotidic linkage in an oligonucleotide is independently a chirally controlled internucleotidic linkage. In some embodiments, each neutral internucleotidic linkage in an oligonucleotide is independently a chirally controlled internucleotidic linkage. In some embodiments, at least one non-negatively charged internucleotidic linkage/neutral internucleotidic linkage has the structure of

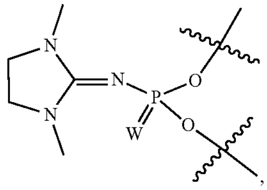
, wherein W is O or S. In some embodiments, at least one non-negatively charged internucleotidic linkage/neutral internucleotidic linkage has the structure of

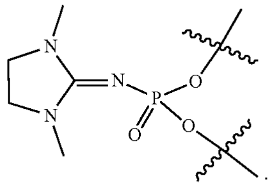 [SMILES: *OP(=O)(N=C1N(C)CCN1C)O*]
.

In some embodiments, at least one non-negatively charged internucleotidic linkage/neutral internucleotidic linkage has the structure of

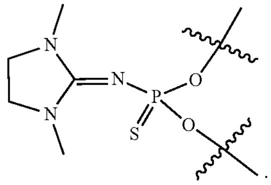 [SMILES: *OP(=S)(N=C1N(C)CCN1C)O*]
.

In some embodiments, at least one non-negatively charged internucleotidic linkage/neutral internucleotidic linkage has the structure of

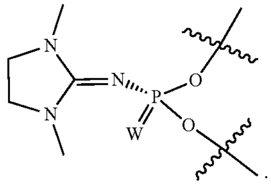
.

wherein W is O or S. In some embodiments, at least one non-negatively charged internucleotidic linkage/neutral internucleotidic linkage has the structure of

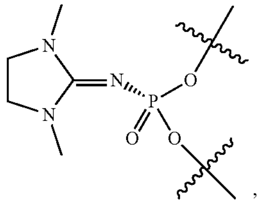
,

In some embodiments, at least one non-negatively charged internucleotidic linkage/neutral internucleotidic linkage has the structure of

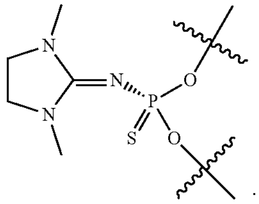
.

In some embodiments, at least one non-negatively charged internucleotidic linkage/neutral internucleotidic linkage has the structure of

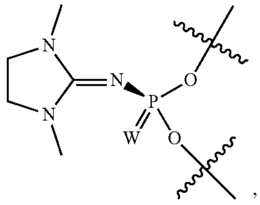
, wherein W is O or S. In some embodiments, at least one non-negatively charged internucleotidic linkage/neutral internucleotidic linkage has the structure of

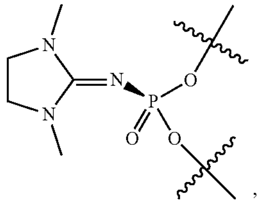
,

In some embodiments, at least one non-negatively charged internucleotidic linkage/neutral internucleotidic linkage has the structure of

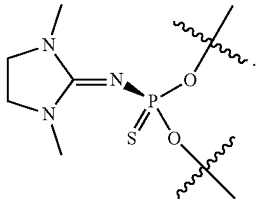
.

In some embodiments, an oligonucleotide comprises at least one non-negatively charged internucleotidic linkage wherein its linkage phosphorus is in Rp configuration, and at least one non-negatively charged internucleotidic linkage wherein its linkage phosphorus is in Sp configuration.

In some embodiments, the present disclosure provides oligonucleotides comprising one or more internucleotidic linkages having the structure of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-d-1, or NL-d-2, or a salt form thereof. In Kale embodiments, provided oligonucleotides comprise 1-100, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70 80, 90, 100 or more internucleotidic linkages having the structure of formula VII, VII-a-1, VII-a-2, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, NL-d-2, or a salt form thereof. In some embodiments, provided oligonucleotides comprise one or more such internucleotidic linkages. In some embodiments, provided oligonucleotides comprise two or more such internucleotidic linkages. In some embodiments, provided oligonucleotides comprise three or more such internucleotidic linkages. In some embodiments, provided oligonucleotides comprise four or more such internucleotidic linkages. In some embodiments, provided oligonucleotides comprise five or more such internucleotidic linkages. In some embodiments, provided oligonucleotides comprise six or more such internucleotidic linkages. In some embodiments, provided oligonucleotides comprise seven or more such internucleotidic linkages. In some embodiments, provided oligonucleotides comprise eight or more such internucleotidic linkages. In some embodiments, provided oligonucleotides comprise nine or more such internucleotidic linkages. In some embodiments, provided oligonucleotides comprise ten or more such internucleotidic linkages. In some embodiments, provided oligonucleotides comprise 11 or more such internucleotidic linkages. In some embodiments, provided oligonucleotides comprise 12 or more such internucleotidic linkages. In some embodiments, provided oligonucleotides comprise 13 or more such internucleotidic linkages. In some embodiments, provided oligonucleotides comprise 14 or more such internucleotidic linkages. In some embodiments, provided oligonucleotides comprise 15 or more such internucleotidic linkages. In some embodiments, provided oligonucleotides comprise 16 or more such internucleotidic linkages. In some embodiments, provided oligonucleotides comprise 17 or more such internucleotidic linkages. In some embodiments, provided oligonucleotides comprise 18 or more such internucleotidic linkages. In some embodiments, provided oligonucleotides comprise 19 or more such internucleotidic linkages. In some embodiments, provided oligonucleotides comprise 20 or more such internucleotidic linkages. In some embodiments, provided oligonucleotides comprise 21 or more such internucleotidic linkages. In some embodiments, provided oligonucleotides comprise 25 or more such internucleotidic linkages. In some embodiments, such an internucleotidic linkage is chiral. In some embodiments, as described in the present disclosure, each —X-$L^s$-$R^5$ is independently of such a structure that H—X-$L^s$-$R^5$ has the structure of formula I, I-a, I-a-1, I-a-2, I-b, I-c, I-d, I-e, II, II-a, II-b, III, III-a, or III-b, or a salt thereof. In some embodiments, provided oligonucleotides have the structure of formula O-I or a salt thereof.

In some embodiments, a provided oligonucleotide comprises at least two types of internucleotidic linkages, each independently having the structure of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof. In some embodiments, a provided oligonucleotide comprise at least two types of chiral internucleotidic linkages, each independently having the structure of formula VII, VII-a-1, VII-a-2, VII-b, VII-c, VII-d, VI-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof. In some embodiments, the two types may have the same or different phosphorus configuration (Rp or Sp), or one or both can be stereorandom (e.g., formed not through chirally controlled synthesis). In some embodiments, a stereorandom linkage has diastereomeric purity less than 85%, 80%, 75%, 70%, 65%, 60%, or 55%. In some embodiments, P* is not stereorandom, and is either Rp or Sp. In some embodiments, in one type W is S and in the other type W is O. In some embodiments, in one type W is S and in the other type W is O, and for both types —X-$L^s$-$R^5$ is independently of such a structure that H—X-$L^s$-$R^5$ has the structure of formula I, I-a, I-a-1, I-a-2, I-b, I-c, I-d, I-e, II, II-a, II-b, III, III-a, or III-b, or a salt thereof. In some embodiments, one type is a natural phosphate linkage (—O—P(O)(OH)—O—, which may exist as —O—P(O)($O^-$)—O—, for example, at certain pH and/or when provided as a salt), and the other is a phosphorothioate linkage (—O—P(O)(SH)—O—, which may exist as —O—P(O)(S)—O—, for example, at certain pH and/or when provided as a salt).

In some embodiments, each $L^P$ independently has the structure of VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof. In some embodiments, each $L^a$ independently has the structure of VI, VI-a-1, VI-a-2, VII-b, VII-c, VI-d, or VI-e, and in each LP, —X-$L^s$-$R^5$ independently has a structure such that H—X-$L^s$-$R^5$ is a compound of formula I, I-a, I-a-1, I-a-2, I-b, I-c, I-d, I-e, II, II-a, II-b, III, III-a, or III-b, or a salt thereof.

In some embodiments, at least one $L^P$ comprises W, wherein W is S. In some embodiments, at least 2, 3, 4, 5, 6, 7, 8, 9, 10, 11, 12, 13, 14, 15, 16, 17, 18, 19, 20 $L^P$ comprises W, wherein W is S. In some embodiments, at least one $L^P$ comprises W, wherein W is O. In some embodiments, at least 2, 3, 4, 5, 6, 7, 8, 9, 10, 11, 12, 13, 14, 15, 16, 17, 18, 19, 20 $L^P$ comprises W, wherein W is O. In some embodiments, $L^P$ independently comprises —X-$L^s$-$R^5$ wherein H—X-$L^s$-$R^5$ has the structure of formula I, I-a, I-a-1, I-a-2, I-b, I-c, I-d, I-e, II, II-a, II-b, II, III-a, or III-b, or a salt thereof.

Cycles

As those skilled in the art readily appreciates, in some embodiments, provided methods, e.g., for oligonucleotide synthesis, comprise one or more cycles. Typically, in oligonucleotide synthesis, synthetic cycles are repeated until a desired oligonucleotide length is achieved.

In some embodiments, cycles of provided methods each independently comprise:

(1) a coupling step;

(2) optionally a pre-modification capping step;

(3) a modification step;

(4) optionally a post-modification capping step; and (5) a de-blocking step.

wherein each step is independently as described in the present disclosure.

In some embodiments, a cycle comprises a pre-modification capping step. In some embodiments, a cycle comprises a post-modification capping step. In some embodiments, a cycle comprises a pre-modification capping step and a post-modification capping step. In some embodiments, steps of a cycle are performed in the order they are listed, e.g., from 1 to 5, if that given step is in the cycle. In some embodiments, a cycle starts with de-blocking, and followed by a coupling step, which is followed by an optional pre-modification capping step if it is in the cycle, which is followed by a modification step, which is followed by an optional post-modification capping step it is in the cycle. In some embodiments, a cycle ends with a modification step. In some embodiments, a cycle ends with a post-modification capping step.

In some embodiments, the present disclosure provides a method, e.g., for preparing an oligonucleotide, comprising a cycle comprising steps of:

(1) a coupling step;
(2) a first capping step;
(3) a modification step;
(4) a second capping step;
(5) a de-blocking step;

wherein the cycle comprises steps in the order of (2)-(3)-(4);

wherein the cycle is repeated until the length of the oligonucleotide is achieved.

In some embodiments, the present disclosure provides a method for preparing an oligonucleotide, comprising a cycle comprising steps of:

(1) a coupling step;
(2) a first capping step;
(3) a modification step;
(4) a second capping step;
(5) a de-blocking step;

wherein the cycle comprises steps in the order of (2)-(4)-(3);

wherein the cycle is repeated until the length of the oligonucleotide is achieved.

In some embodiments, a first capping step is a pre-modification capping step as described in the present disclosure. In some embodiments, a first capping step is a post-modification capping step, but uses a condition of a pre-modification capping step as described in the present disclosure. In some embodiments, a second capping step is a post-modification capping step as described in the present disclosure. In some embodiments, a second capping is a pre-modification capping step, but uses a condition for a post-modification capping step as described in the present disclosure.

In some embodiments, cycles of a provided method comprise different number of steps. In some embodiments, cycles of a provided method comprises the same steps, but one or more or all steps of one cycle is different than those of another cycle. Those skilled in the art appreciate that conditions may be adjusted in accordance with the present disclosure.

In some embodiments, a cycle comprises no more than one of steps listed, for example, in some embodiments, a cycle comprises no more than one coupling step, no more than one pre-modification capping step, no more than one modification step, no more than one post-modification capping step, and no more than one de-blocking step. In some embodiments, a provided step, e.g., any step described for a cycle, may independently comprise two or more contacting of a reagent system with an oligonucleotide composition comprises a plurality of oligonucleotides. For example, in some embodiments, a coupling step may comprise contacting a de-blocked composition with a coupling reagent system twice or more. In some embodiments, the coupling reagent system of each contact may independently be the same as or different from the coupling reagent system of another contact. In some embodiments, a capping step may comprises contacting a composition with a capping reagent system twice or more, wherein the coupling reagent system of each contact may independently be the same as or different from the coupling reagent system of another contact; for example, in some embodiments, the first capping reagent system is selective for amino groups over hydroxyl groups (e.g., a reagent system comprising $Ac_2O$ and 2,6-lutidine), which the second capping reagent system is less selective and caps both amino groups and hydroxyl groups efficiently (e.g., a reagent system comprising $Ac_2O$, 2,6-lutidine, and NMI.). Similarly, in some embodiments, a modification step and/or a de-blocking step may comprise contacting twice or more. Example steps of cycles are as described in the present disclosure.

Among other things, the present disclosure demonstrates that cycles using chiral auxiliaries that can be readily removed by a base under anhydrous conditions can provide oligonucleotides with various types of modified internucleotidic linkages with high efficiency, high crude purity and yield. In some embodiments, such a chiral auxiliary comprises an electron-withdrawing group. In some embodiments, such a chiral auxiliary comprises an $R^2$ which is —CH-electron-withdrawing group. In some embodiments, such a chiral auxiliary has an $R^2$ which is —CH—$SO_2R$. In some embodiments, such a chiral auxiliary is PSM (corresponding chiral auxiliary compounds

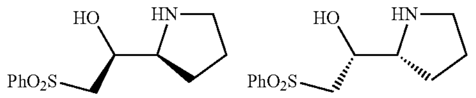

In some embodiments, such a cycle, e.g., a PSM cycle, installs =S to a P(III) linkage phosphorus, which can be converted to a chirally controlled phosphorothioate internucleotidic linkage after removal of the chiral auxiliary with high efficiency, high crude purity and high yield. In some embodiments, a cycle, e.g., a PSM cycle, installs =N(-L-$R^5$) to a P(III) linkage phosphorus or forms $P^N$ from a P(III), which can be converted to a chirally controlled neutral internucleotidic linkage (e.g., chirally controlled n001) after removal of the chiral auxiliary with high efficiency, high crude purity and high yield. In some embodiments, each chiral auxiliary group utilized in preparation of an oligonucleotide or a chirally controlled oligonucleotide composition thereof independently comprises $R^2$ comprising an electron-withdrawing group as described herein (e.g., —CH-electron-withdrawing group such as —$CH_2SO_2R'$). In some embodiments, each phosphoramidite comprising a chiral auxiliary group, or each phosphoramidite comprising a chiral carbon center that is not in its nucleoside group, independently comprises $R^2$ comprising an electron-withdrawing group as described herein (e.g., —CH-electron-withdrawing group such as —$CH_2SO_2R'$). As demonstrated herein, utilization of such chiral auxiliary groups can provide various manufacturing advantages such as high yield, high purity, single types of chiral auxiliary groups, mild conditions (e.g., for removal of chiral auxiliary groups), improved safety (e.g., reduction or removal of certain reagents such as F-containing reagents), improved compatibility (e.g., highly efficient for various types of chiral internucleotidic linkages (e.g., phosphorothioate internucleotidic linkages, non-negatively charged internucleotidic linkages, etc.) and/or sugars (natural DNA and RNA sugars, various modified sugars, etc.), simplified processes (e.g., simplified purification and/or formulation processes from reduced amount of salts), reduced cost, etc.

Coupling

In some embodiments, a coupling step comprises:

contacting a de-blocked composition comprising a plurality of de-blocked oligonucleotides (a de-blocked oligonucleotide composition) or nucleosides, which is de-blocked in that each independently comprises a free hydroxyl group, with a coupling reagent system comprising a partner compound which comprises a nucleoside unit, and coupling a partner compound with the free hydroxyl groups of a plurality of de-blocked oligonucleotides or nucleosides;

wherein the coupling step provides a coupling product composition comprising a plurality of coupling product oligonucleotides, each of which independently comprises an internucleotidic linkage connecting a hydroxyl group of a de-blocked oligonucleotide with a nucleoside unit of a partner compound.

In some embodiments, a de-blocked composition is a de-blocked oligonucleotide composition comprising a plurality of de-blocked nucleosides, each of which independently comprises a —OH group. In some embodiments, each of the nucleosides is independently the "first" nucleoside to be incorporated into an oligonucleotide. Typically, it is the first nucleoside being linked to, e.g., a solid support optionally through a linker moiety. In some embodiments, a —OH group is a 5'-OH group.

In some embodiments, a de-blocked composition is a de-blocked oligonucleotide composition comprising a plurality of de-blocked oligonucleotides, each of which independently comprises a —OH group. In some embodiments, each de-blocked oligonucleotide contains one and no more than one —OH group. In some embodiments, a —OH group is a 5'-OH group. In some embodiments, a de-blocked composition is a chirally controlled oligonucleotide composition. In some embodiments, a de-blocked composition is a chirally controlled oligonucleotide composition comprising a plurality of de-blocked oligonucleotides, each of which is independently of formula O-I or a salt thereof. In some embodiments, a de-blocked oligonucleotide is an oligonucleotide of formula O-I or a salt thereof. In some embodiments, each de-blocked oligonucleotide is independently an oligonucleotide of formula O-I or a salt thereof.

In some embodiments, for a de-blocked oligonucleotide of formula O-I or a salt thereof, $R^{5s}$ is —OH and is the only free hydroxyl. In some embodiments, $R^{5s}$ is 5'-OH. In some embodiments, an internucleotidic linkage has the structure of formula VII or a salt form thereof. In some embodiments, each $L^P$ is independently an internucleotidic linkage of formula VII or a salt form thereof. In some embodiments, for each LP, $P^L$ is not P. In some embodiments, for each LP, $P^L$ is P(═O), P(═S), P(═N(-L-$R^5$) or $P^N$. In some embodiments, —X-$L^s$-$R^5$ is -$L^s$-$R^5$, wherein $L^7$ is —O—; —S-$L^s$-$R^5$; or of such a structure that H—X-$L^s$-$R^5$ is a compound of formula I, I-a, I-a-1, I-a-2, I-b, I-c, I-d, I-e, III, II-a, II-b, III, III-a, or III-b, optionally wherein $R^5$ or $R^6$ is —C(O)R'. In some embodiments, each —X-$L^s$-$R^5$ is independently -$L^7$-$R^1$, wherein $L^7$ is —O—; —S-$L^s$-$R^5$; or of such a structure that H—X-$L^s$-$R^5$ is a compound of formula I, I-a, I-a-1, I-a-2, I-b, I-c, I-d, I-e, II-a, II-b, III, III-a, or III-b, optionally wherein $R^5$ or $R^6$ is —C(O)R'. In some embodiments, for each chirally controlled internucleotidic linkage, —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'.

In some embodiments, each internucleotidic linkage, e.g., $L^P$, is an internucleotidic linkage of formula VII or a salt form thereof, wherein:

each $P^L$ is independently P(═O), P(═S) or P(═N(-L-$R^5$), or $P^N$;

for each internucleotidic linkage whose $P^L$ is P(═O), its —X-$L^s$-$R^5$ is independently -$L^7$-$R^1$, wherein $L^7$ is —O—, or its —X-$L^s$-$R^6$ is independently —S-$L^s$-$R^5$; or its —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'; and for each internucleotidic linkage whose $P^L$ is P(═S) or P(═N(-L-R') or $P^N$, its —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'.

In some embodiments, each internucleotidic linkage, e.g., $L^P$, is an internucleotidic linkage of formula VII or a salt form thereof, wherein:

each $P^L$ is independently P(═O) or P(═S);

for each internucleotidic linkage whose $P^L$ is P(═O), its —X-$L^s$-$R^5$ is independently -$L^7$-$R^1$, wherein $L^7$ is —O—, or its —X-$L^s$-$R^5$ is independently —S-$L^s$-$R^5$; or its —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'; and for each internucleotidic linkage whose $P^L$ is P(═S), its —X-$L^s$-$R^5$ is independently of such a structure that H—X-$L^s$-$R^5$ is a compound of formula I, I-a, I-a-1, I-a-2, I-b, I-c, I-d, I-e, II, I-a, I-b, II, III-a, or III-b, optionally wherein $R^5$ or R is —C(O)R'.

In some embodiments, each internucleotidic linkage, e.g., LP, is an internucleotidic linkage of formula VII or a salt form thereof, wherein:

each $P^L$ is independently P(═O), P(═S) or P(═N(-L-$R^5$), or $P^N$;

for each internucleotidic linkage whose $P^L$ is P(═O), its —X-$L^s$-$R^5$ is independently -$L^7$-$R^1$, wherein $L^7$ is —O—, or its —X-$L^s$-$R^5$ is independently —S-$L^s$-$R^5$; or its —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'; and for each internucleotidic linkage whose $P^L$ is P(═S) or P(═N(-L-$R^5$) or $P^N$, its —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, II, III-a, or III-b, optionally wherein $R^5$ or $R^6$ is —C(O) R'; and each $L^P$ is independently a chirally controlled internucleotidic linkage when —X-$L^s$-$R^5$ is —S-$L^s$-$R^5$, or when $P^L$ is P(═S) or P(═N(-L-$R^5$) or $P^N$.

In some embodiments, $R^5$ or $R^6$ is —C(O)R'. In some embodiments, $R^6$ is —C(O)R'. In some embodiments, R' is —$CH_3$.

De-blocked oligonucleotides, except the de-blocked hydroxyl groups, are otherwise properly blocked, for example, amino groups of chiral auxiliary groups, nucleobases, etc., are properly blocked if necessary.

In some embodiments, a coupling reagent system comprises a partner compound. In some embodiments, a coupling reagent system comprises a partner compound and an activator.

In some embodiments, a partner compound is a phosphoramidite as described herein. In some embodiments, a partner compound is a nucleoside phosphoramidite having the structure of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof. In some embodiments, for chirally controlled oligonucleotide synthesis, a chirally pure partner compound comprising a chiral auxiliary moiety, e.g., a chirally pure phosphoramidite of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof is used. In some embodiments, to form an natural phosphate linkage or non-chirally controlled modified internucleotidic linkage (e.g., a stereorandom phosphorothioate linkage), non-chirally pure partner compound can be used, e.g., phosphoramidite of traditional oligonucleotide synthesis. In some embodiments, hydroxyl groups of partner compounds if any are blocked. In some embodiments, $R^{5s}$ is —ODMTr.

In some embodiments, 2'-OH of a RNA sugar is properly protected for oligonucleotide synthesis. Various suitable protection technologies are available in the art and can be utilized in accordance with the present disclosure. For example, in some embodiments, 2'-OH is protected by $—Si(R)_3$, wherein each R is independently as described herein and is not —H. In some embodiments, each R is independently an optionally substituted group selected from $C_{1-6}$ aliphatic and $C_{6-10}$ aryl. In some embodiments, each R is n optionally substituted group selected from $C_{1-6}$ aliphatic and phenyl. In some embodiments, a protecting group is TBS. In some embodiments, $R^{2s}$ is —O-PG, wherein PG is a suitable protecting group. In some embodiments, $R^{2s}$ is $—OSi(R)_3$. In some embodiments, $R^{2s}$ is —OTBS. In some embodiments, protecting groups for 2'-OH are removed during cleavage and deprotection. In some embodiments, silyl protecting groups, e.g., TBS, is removed by contact with a F source, e.g., TEA-3HF, TBAF, HF-pyridine, etc.

Various phosphoramidites can be utilized in accordance with the present disclosure, e.g., those described in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, WO 2019/217784, etc.

Various types of activators for promoting coupling of phosphoramidites and hydroxyl groups can be utilized in accordance with the present disclosure, e.g., those described in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, WO 2019/217784, etc. In some embodiments, an activator is or comprises an optionally substituted heteroaryl compound containing one or more nitrogen heteroatoms or a salt thereof. In some embodiments, the heteroaryl compound is optionally substituted tetrazole or a salt thereof.

In some embodiments, an activator is selected from:

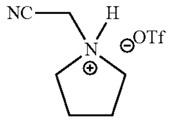

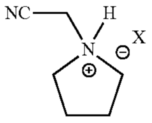

X = non nucleophilic anion

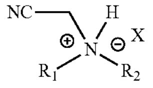

X = $^-$OTf, $BF4^-$, $PF6^-$, $TFN^-$

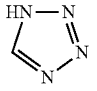

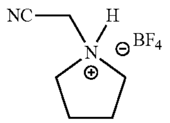

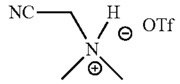

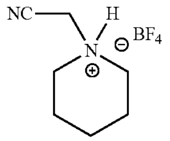

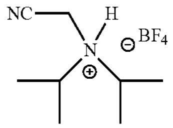

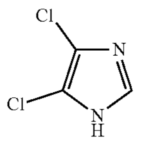

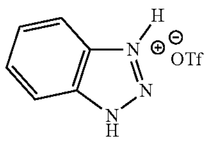

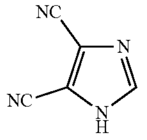

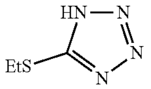

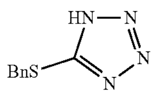

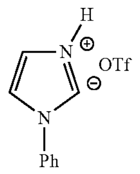

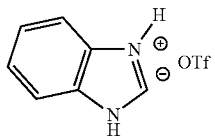

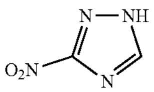

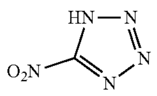

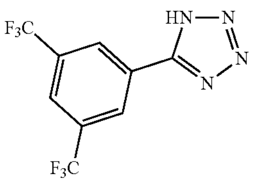

In some embodiments, an activator is selected from:

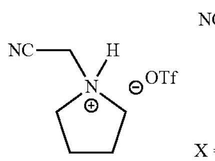
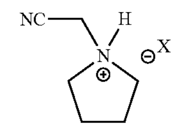

X = non nucleophilic anion

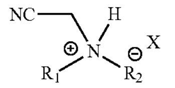

X = $^-$OTf, $BF_4^-$, $PF6^-$, $TfN^-$

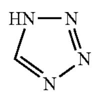
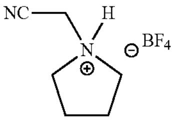
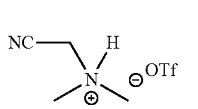
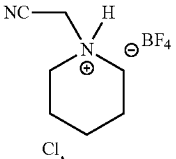
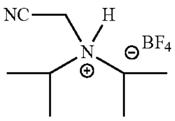
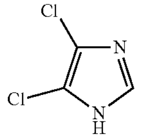
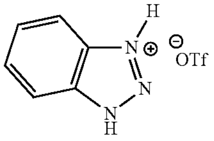
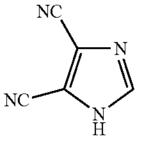
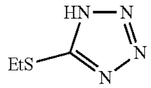
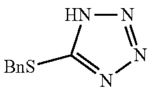
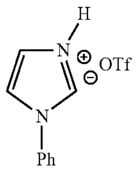
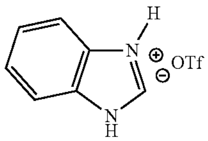
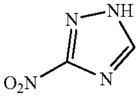
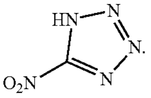

In some embodiments, an activator is selected from cyanomethyl imidazole triflate, cyanomethyl pyrrolidine triflate, ETT, phenyl(2H-tetrazol-5-yl)methanone, 2-(dimethylamino)acetonitrile/trifluorosulfonic acid(2/1), 2-(1H-imidazol-1-yl)acetonitrile/trifluorosulfonic acid(2/1), and 2-(pyrrolidin-1-yl)acetonitrile/trifluorosulfonic acid(2/1).

In some embodiments, an activator is CMIMT. In some embodiments, an activator is CMPT. In some embodiments, an activator is ETT. In some embodiments, ETT is utilized with non-chirally pure partner compounds, such as phosphoramidites of traditional oligonucleotide synthesis.

In some embodiments, each coupling product oligonucleotide is independently of formula O-I or a salt thereof. In some embodiments, a coupling product composition is a chirally controlled oligonucleotide composition. In some embodiments, an internucleotidic linkage connecting a hydroxyl group of a de-blocked oligonucleotide 5'-OH) with a nucleoside unit (e.g., 3 of a partner compound is an internucleotidic linkage of formula VII-b, or a salt form thereof. In some embodiments, each formed internucleotidic linkage is independently a chirally controlled internucleotidic linkage, wherein each chirally controlled linkage phosphorus (a linkage phosphorus of a chirally controlled internucleotidic linkage) independently has a diastereomeric purity of at least 80%, 85%, 90%, 91%, 92%, 93%, 94%, 95%, 96%, 97%, 98% or 99% within the coupling product composition.

In some embodiments, a coupling product oligonucleotide is of formula O-I or a salt thereof. In some embodiments, each coupling product oligonucleotide is independently of formula O-I or a salt thereof. In some embodiments, a coupling product composition is a chirally controlled oligonucleotide composition. In some, embodiments, a coupling product composition is a chirally controlled oligonucleotide composition comprising a plurality of oligonucleotides as described herein, wherein each oligonucleotide of the plurality is independently an oligonucleotide of formula O-I or a salt thereof.

In some embodiments, in a coupling product oligonucleotide, e.g., an oligonucleotide of formula O-I or a salt thereof, the internucleotidic linkage, e.g., $L^P$, bonded to the newly added nucleoside unit, e.g.,

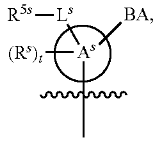

is an internucleotidic linkage whose linkage phosphorus is a P(III), e.g., an internucleotidic linkage of formula VII-b, or a salt form thereof. In some embodiments, —X-$L^s$-$R^5$ is -$L^7$-$R^1$, wherein $L^7$ is —O—. In some embodiments, its X-$L^s$-$R^5$ is independently of such a structure that H—X-$L^s$-$R^5$ is a compound of formula I, I-a, I-a-1, I-a-2, I-b, I-c, I-d, I-e, II, H-a, II-b, III, III-a, or III-b, optionally wherein $R^5$ or $R^6$ is —H. In some embodiments, $R^6$ is H. In some embodiments, each internucleotidic linkage, e.g., $L^P$, that is not bonded to the newly added nucleoside unit (e.g.,

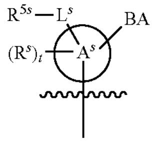

in formula O-I) is independently an internucleotidic linkage whose linkage phosphorus is P(V), e.g., an internucleotidic linkage of formula VII or a salt form thereof, wherein each $P^L$ is independently P(═O), P(═S) or P(═N(-L-$R^5$) or $P^N$. In some embodiments, each internucleotidic linkage, e.g., $L^P$, that is not bonded to the newly added nucleoside unit (e.g.,

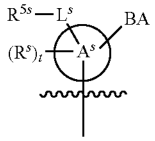

in formula O-I) is an internucleotidic linkage of formula VII or a salt form thereof, wherein each $P^L$ is independently P(═O), P(═S) or P(═N(-L-$R^5$) or $P^N$. In some embodiments, —X-$L^s$-$R^5$ is -$L^7$-$R^1$, wherein $L^7$ is —O—; —S-$L^s$-$R^5$; or of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'. In some embodiments, each —X-$L^s$-$R^5$ is independently -$L^s$-$R^5$ wherein $L^7$ is —O—; —S-$L^s$-$R^5$ or of such a structure that H—X-$L^s$-$R^5$ is a compound of formula I, I-a, I-a-1, I-a-2, I-b, I-c, I-d, I-e, II, II-a, II-b, II, II-a, or III-b, optionally wherein $R^5$ or $R^6$ is —C(O)R'. In some embodiments, for each chirally controlled internucleotidic linkage, —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'. In some embodiments, for each internucleotidic linkage whose $P^L$ is P(═O), its —X-$L^s$-$R^5$ is independently -$L^7$-$R^1$, wherein $L^7$ is —O—, or its —X-$L^s$-$R^5$ is independently —S-$L^s$-$R^5$; or its —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, II, III-a, or III-b, optionally wherein $R^5$ or $R^6$ is —C(O)R'; and for each internucleotidic linkage whose $P^L$ is P(═S) or P(═N(-L-$R^5$) or $P^N$, its —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'. In some embodiments, $R^5$ or $R^6$ is —C(O)R'. In some embodiments, $R^6$ is —C(O)R'. In some embodiments, R' is —$CH_3$.

In some embodiments, a coupling product oligonucleotide is of formula O-I or a salt thereof, wherein:

the $L^P$ bonded to

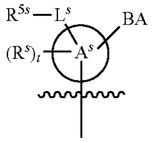

is an internucleotidic linkage of formula VII-b, or a salt form thereof;

each $L^P$ that is not bonded to

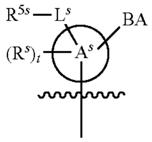

in formula O-I is independently of formula VII or a salt form thereof, wherein:

each $P^L$ is independently P(═O), P(═S) or P(═N(-L-$R^5$) or $P^N$:

for each internucleotidic linkage whose $P^L$ is P(═O), its —X-$L^s$-$R^5$ is independently -$L^7$-$R^1$, wherein $L^7$ is —O—, or its —X-$L^s$-$R^5$ is independently —S-$L^s$-$R^5$ or its —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'; and for each internucleotidic linkage whose $P^L$ is P(═S) or P(═N(-L-$R^5$) or $P^N$, its —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, II-a, or II-b, optionally wherein $R^5$ or $R^6$ is —C(O)R'.

In some embodiments, —X-$L^s$-$R^5$ of the $L^P$ bonded to

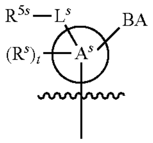

is -$L^7$-$R^1$, wherein $L^7$ is —O—, or is independently —S-$L^s$-$R^5$; or is independently of such a structure that H—X-$L^s$-$R^5$ is a compound of formula I, I-a, I-a-1, I-a-2, I-b, I-c, I-d, I-e, II-a, II-b, III, II-a, or III-b, optionally wherein $R^5$ or $R^6$ is —H. In some embodiments, —X-$L^s$-$R^5$ of the $L^P$ bonded to

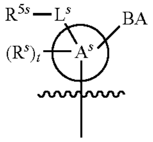

is of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —H. In some embodiments, $R^6$ is —H. In some embodiments, for each internucleotidic linkage whose $P^L$ is P(═S) or P(═N(-L-$R^5$) or $P^N$, its —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, wherein $R^5$ or $R^6$ is —C(O)R'. In some embodiments, $R^6$ is —C(O)R'. In some embodiments, R' is —$CH_3$. In some embodiments, a $L^P$ is a chirally controlled internucleotidic linkage when —X-$L^s$-$R^5$ is —S-$L^s$-$R^5$, or when $P^L$ is P(═S) or P(═N(-L-$R^5$) or $P^N$. In some embodiments, each $L^P$ is independently a chirally controlled internucleotidic linkage when —X-$L^s$-$R^5$ is —S-$L^s$-$R^5$, or when $P^L$ is P(═S) or P(═N(-L-$R^5$) or $P^N$.

In some embodiments, $R^{5s}$ of a coupling product oligonucleotide is typical blocked —OH, e.g., —ODMTr.

In some embodiments, e.g., when an phosphoramidite comprising a chiral auxiliary moiety is used, a $L^P$ bonded to

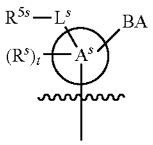

is an internucleotidic linkage of formula VII-b, or a salt form thereof, wherein —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, wherein $R^5$ or $R^6$ is —H. In some embodiments, $R^6$ is —H. Thus, such $L^P$ groups may contain primary or secondary amino groups that is, preferably, to be capped, in addition to un-coupled free hydroxyl groups of de-blocked oligonucleotide and/or nucleoside remaining in coupling product compositions. Additionally and/or alternatively, free hydroxyl group may form during coupling steps, e.g., detritylation of one or more coupling product oligonucleotide.

It is noted that when phosphoramidites of traditional oligonucleotide synthesis is used as a partner compound, typically no free amino acid group will be generated.

As appreciated by those skilled in the art, a coupling step typically adds at least one nucleoside unit to a growing oligonucleotide chain.

In some embodiments, contacting may be repeated if desired. In some embodiments, reaction conditions, such as concentrations, contact time, etc., can be adjusted in accordance with the present disclosure to improve results.

In some embodiments, a coupling step forms an internucleotidic linkage without chiral control, e.g., for a corresponding non-chirally controlled chiral modified internucleotidic linkage (e.g., a phosphorothioate internucleotidic linkage) or an internucleotidic linkage whose linkage phosphorus is achiral (e.g., a natural phosphate linkage) in a product oligonucleotide. For such a coupling step, a phosphoramidite which does not contain a chiral auxiliary group may be utilized, e.g., phosphoramidites used in traditional oligonucleotide synthesis (e.g., those comprising N,N-diisopropyl and 2-cyanoethyl groups). Alternatively or additionally, phosphoramidites containing chiral auxiliaries as described herein may be utilized, e.g., for an internucleotidic linkage whose linkage phosphorus is achiral (e.g., a natural phosphate linkage).

Pre-Modification Capping

As described in the present disclosure, in some embodiments, a coupling product composition may contain both amino groups and hydroxyl groups, preferably, to be capped. In some embodiments, a pre-modification capping step comprises contacting a coupling product composition with a pre-modification capping reagent system, which contacting selectively caps amino over hydroxyl groups of a coupling product composition. Alternatively or additionally, in some embodiments a pre-modification capping step comprises contacting a coupling product composition with a pre-modification capping reagent system, which contacting caps both amino and hydroxyl groups of a coupling product composition. In some embodiments, when there are two contacting, typical the first one is amino-selective.

Selectivity and activity of contacting events may be tuned by pre-modification capping reagent systems. In some embodiments, a pre-modification capping reagent system is selective for amidation, e.g., capping of amino groups over esterification, e.g., capping of hydroxyl groups. In some embodiments, a pre-modification capping reagent system is efficient for both amidation and esterification, and can efficiently capping both amino and hydroxyl groups, e.g., capping reagent systems of traditional oligonucleotide synthesis (although in traditional oligonucleotide synthesis, no capping of amino groups may be needed during capping step).

Conditions and reagent systems selective for amidation over esterification, and conditions and reagent systems efficient for both amidation and esterification are well known and can be utilized in accordance with the present disclosure. In some embodiments, a selective reagent system comprises no, or greatly reduced levels of esterification catalysts and/or strong nucleophiles. In some embodiments, reagent system efficient for both amidation and esterification comprises suitable levels of esterification catalysts and/or strong nucleophiles. In some embodiments, esterification catalysts and/or strong nucleophiles are those utilized in traditional capping systems to promote capping of hydroxyl groups, e.g., DMAP, NMI, etc.

In some embodiments, in a coupling product oligonucleotide, the internucleotidic linkage, e.g., $L^P$, bonded to the newly added nucleoside, e.g.,

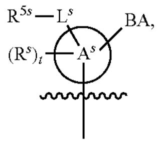

is an internucleotidic linkage comprising an amino group, e.g., an internucleotidic linkage of formula VII-b, or a salt form thereof, wherein —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, wherein $R^5$ or $R^6$ is —H. In some embodiments, a pre-modification capping step comprises capping such an amino group, e.g., by converting the $R^5$ or $R^6$ which is —H into —C(O)R'. In some embodiments, R' is —$CH_3$.

In some embodiments, a pre-modification capping reagent system comprises an acylating agent to acylate amino and/or hydroxyl groups. Various acylating agents can be utilized in accordance with the present disclosure. In some embodiments, an acylating agent is an anhydride. In some embodiments, an acylating agent is $Ac_2O$. In some embodiments, an acylating agent is a halogen-substituted acetic anhydride. In some embodiments, an acylating agent is $(Pac)_2O$. In some embodiments, a pre-modification capping reagent system further comprises a base, which among other things, may neutralize acids generated during capping. In some embodiments, for capping hydroxyl groups, an esterification catalyst, e.g., NMI, DMAP, etc. is used.

In some embodiments, a pre-modification capping reagent system comprises or is a solution of:

Pyridine/DMAP/$Ac_2O$;
2,6-Lutidine/NMI/$Ac_2O$;
2,4,6-Collidine/$Ac_2O$;
Triethylamine/$Ac_2O$;
DIEA/$Ac_2O$;
N-Methyl morpholine/$Ac_2O$;
2,6-Lutidine, then after a period of time, NMI/$Ac_2O$;
2,6-Lutidine/$Ac_2O$;
PhNCO/2,6-Lutidine;
POS;
POS then NMI/2,6-Lutidine/$Ac_2O$; or
2-(dimethylamino)acetonitrile/$Ac_2O$.

In some embodiments, a pre-modification capping reagent system comprises or is a solution of:

Pyridine (2 equiv.)/DMAP (cat.)/$Ac_2O$ (4 equiv.);
2,6-Lutidine (2 equiv.)/NMI (0.25 equiv.)/$Ac_2O$(4 equiv.);
2,4,6-Collidine/$Ac_2O$(4 equiv.);
Triethylamine/$Ac_2O$(4 equiv.);
DIEA/$Ac_2O$(4 equiv.);
N-Methyl morpholine/$Ac_2O$(4 equiv.);
2,6-Lutidine (2 equiv.) then after 5 min. NMI (1 equiv.)/$Ac_2O$(4 equiv.);
2,6-Lutidine/$Ac_2O$(4 equiv.);
PhNCO/2,6-Lutidine;
POS (both oxidation and pre-capping);
POS (both oxidation and pre-capping) then NMI/2,6-Lutidine/$Ac_2O$; or
2-(dimethylamino)acetonitrile/$Ac_2O$.

In some embodiments, a pre-modification capping product composition is a chirally controlled oligonucleotide composition. In some embodiments, a pre-modification capping product composition is a chirally controlled oligonucleotide composition comprising a plurality of oligonucleotides as described herein, wherein each oligonucleotide of the plurality is independently an oligonucleotide of formula O-I or a salt thereof. In some embodiments, a pre-modification capping product oligonucleotide is an oligonucleotide of formula O-I or a salt thereof. In some embodiments, each pre-modification capping product oligonucleotide is independently an oligonucleotide of formula O—I or a salt thereof. In some embodiments, an internucleotidic linkage in a pre-modification capping product oligonucleotide is of formula VII or a salt form thereof. In some embodiments, each internucleotidic linkage is of formula VII or a salt form thereof. In some embodiments, —X-$L^s$-$R^5$ is -$L^s$-$R^1$, wherein $L^7$ is —O—; —S-$L^s$-$R^5$; or of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'. In some embodiments, each —X-$L^s$-$R^5$ is independently -$L^7$-$R^1$, wherein $L^7$ is —O—; —S-$L^s$-$R^5$; or of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'. In some embodiments, for each chirally controlled internucleotidic linkage, —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'.

In some embodiments, in a pre-modification capping product oligonucleotide, an amino group of an internucleotidic linkage is capped by —C(O)R'.

In some embodiments, a pre-modification capping product oligonucleotide is of formula O-I or a salt thereof, wherein:

the $L^P$ bonded to

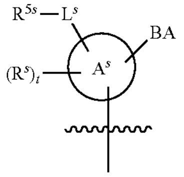

is an internucleotidic linkage of formula VII-b, or a salt form thereof, wherein —X-$L^s$-$R^5$ is of such a structure that H—X-$L^s$-$R^5$ is a compound of formula I, I-a, I-a-1, I-a-2, I-b, I-c, I-d, I-e, II, II-a, II-b, III, III-a, or III-b, wherein $R^5$ or $R^6$ is —C(O)R';

each $L^P$ that is not bonded to

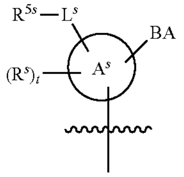

in formula O-I is independently of formula VII or a salt form thereof, wherein:

each $P^L$ is independently P(═O), P(═S) or P(═N(-L-$R^5$)) or $P^N$;

each —X-$L^s$-$R^5$ is independently -$L^7$-$R^1$, wherein $L^7$ is —O—, or its —X-$L^s$-$R^5$ is independently —S-$L^s$-$R^5$; or its —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'. In some embodiments, for each internucleotidic linkage whose $P^L$ is P(═O), its —X-$L^s$-$R^5$ is independently -$L^7$-$R^1$, wherein $L^7$ is —O—, or its —X-$L^s$-$R^5$ is independently —S-$L^s$-$R^5$; or its —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'; and for each internucleotidic linkage whose $P^L$ is P(═S) or P(═N(-L-$R^5$) or $P^N$ its —X-$L^s$-$R^5$ is independently of such a structure that H—X-$L^s$-$R^5$ is a compound of formula I, I-a, I-a-1, I-a-2, I-b, I-c, I-d, I-e, II, I-a, I-b, III, III-a, or I-b, optionally wherein $R^5$ or $R^6$ is —C(O) R'.

In some embodiments, $R^5$ or $R^6$ is —C(O)R'. In some embodiments, $R^6$ is —C(O)R'. In some embodiments, R' is —$CH_3$. In some embodiments, a $L^P$ is a chirally controlled internucleotidic linkage when —X-$L^s$-$R^5$ is —S-$L^s$-$R^5$, or when $P^L$ is P(═S) or P(═N(-L-$R^5$) or $P^N$. In some embodiments, each $L^P$ is independently a chirally controlled internucleotidic linkage when —X-$L^s$-$R^5$ is —S-$L^s$-$R^5$, or when $P^L$ is P(═S) or P(═N(-L-$R^5$) or $P^N$.

In some embodiments, a cycle does not contain a pre-modification capping step. In some embodiments, the modification step in such a cycle modifies a P(III) internucleotidic linkage (e.g., converting it into a P(V) internucleotidic linkage) without chiral control. In some embodiments, the P(III) internucleotidic linkage contains no chiral auxiliary (e.g., no chiral center except the linkage phosphorus if it is chiral). In some embodiments, the P(III) internucleotidic linkage comprises —$CH_2CH_2CN$ as in traditional oligonucleotide synthesis. In some embodiments, modification in such a cycle is oxidation which installs ═O to a P(III) internucleotidic linkage formed in the coupling step in the cycle. In some embodiments, modification in such a cycle is sulfurization (thiolation) which installs ═S to a P(III) internucleotidic linkage formed in the coupling step in the cycle without chiral control. In some embodiments, modification in such a cycle installs ═N(-L-$R^5$) to a P(III) internucleotidic linkage, or forms a $P^N$ from a P(III) linkage phosphorus of an internucleotidic linkage, formed in the coupling step in the cycle without chiral control.

Modification

In some embodiments, a modification step modifies a P(III) linkage phosphorus and convert it into a P(V) linkage phosphorus. As appreciated by those skilled in the art, a number of P-modifications can be utilized in accordance with the present disclosure, e.g., those described in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, WO 2019/217784, etc.

In some embodiments, a modification is sulfurization which installs S to P. In some embodiments, a modification is sulfurization which installs ═S to P. Many suitable reagents may be utilized in accordance with the present disclosure, e.g., those described in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, WO 2019/217784, etc.

In some embodiments, a modification step provides a non-chirally controlled chiral internucleotidic linkages or an internucleotidic linkage whose linkage phosphorus is achiral, e.g., to provide a non-chirally controlled chiral internucleotidic linkage (e.g., a non-chirally controlled phosphorothioate internucleotidic linkage, a non-chirally controlled n001 internucleotidic linkage, etc.) or an internucleotidic linkage whose linkage phosphorus is achiral (e.g., a natural phosphate linkage) in a product. In some embodiments, a coupling step utilizes a "traditional" phosphoramidite which does not contain a chiral auxiliary as described herein, e.g., a phosphoramidite comprising N,N-diisopropyl and 2-cyanoethyl groups as in traditional oligonucleotide synthesis to form a P(III) internucleotidic linkage which is modified (e.g., converted into a P(V) internucleotidic linkage during a modification step). In some embodiments, a P(III) internucleotidic linkage to be modified in a modification step is a non-chirally controlled internucleotidic linkage, or an internucleotidic linkage whose linkage phosphorus is achiral. In some embodiments, a cycle whose modification product is non-chirally controlled is a "traditional" oligonucleotide synthesis cycle. In some embodiments, a cycle has a pre-modification capping step but not a post-modification capping step when its modification is oxidation. In some embodiments, a cycle has a post-modification capping step but not a pre-modification capping step when its modification is oxidation. In some embodiments, a cycle has a pre-modification capping step and a pre-modification capping step when its modification is oxidation. As described herein, a modification step whose product is not chirally controlled can install, among others, =O, =S, =N— (e.g., as in =N(-L-$R^5$), $P^N$, etc.) to a P(III) internucleotidic linkage. In some embodiments, it installs =O. In some embodiments, it installs =S. In some embodiments, it installs =N— (e.g., as in =N(-L-$R^5$), $P^N$, etc.). Alternatively or additionally, in some embodiments phosphoramidites containing chiral auxiliaries as described herein can be utilized for internucleotidic linkages whose linkage phosphorus is achiral, e.g., natural phosphate linkages in a product. In such cases, cycles as described herein, including those comprising a pre-modification capping step before oxidation and a post-modification capping step after oxidation, may be utilized.

In some embodiments, a modification is oxidation which installs 0 to linkage phosphorus. In some embodiments, an oxidation reagent is TBHP (tert-butylhydroperoxide). In some embodiments, an oxidation reagent is $I_2$/Water/Pyridine. In some embodiments, the concentration of $I_2$ is about 0.05 M. In some embodiments, a cycle has a pre-modification capping step but not a post-modification capping step when its modification is oxidation. In some embodiments, a cycle has a post-modification capping step but not a pre-modification capping step when its modification is oxidation. In some embodiments, a cycle utilizes a "traditional" phosphoramidite which does not contain a chiral auxiliary group as described herein, e.g., a phosphoramidite comprising N,N-diisopropyl and 2-cyanoethyl groups. In some embodiments, a cycle is a "traditional" oligonucleotide synthesis cycle. Alternatively or additionally, phosphoramidites containing chiral auxiliaries as described herein can be utilized (typically with chirally controlled installation of =O) in cycles whose modification steps are oxidation which install =O to linkage phosphorus. In such cases, cycles as described herein, including those comprising a pre-modification capping step before oxidation and a post-modification capping step after oxidation, may be utilized.

In some embodiments, a modification step provides a chirally controlled oligonucleotide composition, e.g., after converting P(III) internucleotidic linkages into P(V) internucleotidic linkages.

In some embodiments, a sulfurization reagent is 3H-1,2-benzodithiol-3-one-1,1-dioxide, or the Beaucage reagent, tetraethylthiuram disulfide, phenylacetyl disulfide, dibenzoyl tetrasulfide, bis-(O,O-diisopropoxyphosphinothioyl) disulfide, benzyltriethylammonium tetrathiomolybate, bis-(p-toluenesulfonyl) disulfide, 3-ethoxy-1,2,4-dithiazoline-5-one (EDITH), 1,2,4-dithiazolidine-3,5-dionc, 3-amino-1,2,4-dithiazole-5-thione, 3-methyl-1,2,4-dithiazolin-5-one, or 3-phenyl-1,2,4-dithiazoline-5-one. In some embodiments, a sulfurization reagent is 3H-1,2,4-dithiazole-3-thiones and 3H-1,2-dithiole-3-thiones, e.g., described in Guzaev, Tetrahedron Letters 52 (2011) 434-437. In some embodiments, a sulfurization reagent is POS (3-phenyl-1,2,4-dithiazolin-5-one), DDTT (((dimethylamino-methylidene)amino)-3H-1,2,4-dithiazaoline-3-thione), DTD (dimethylthiarum disulfide), xanthene hydride (XH), S-(2-cyanoethyl) methanesulfonothioate (MTS-CNE), or phenylacetyl disulfide. In some embodiments, a sulfurization reagent is POS. In some embodiments, a sulfurization reagent is DDTT. In some embodiments, a sulfurization reagent is DTD. In some embodiments, a sulfurization reagent is xanthene hydride.

In some embodiments, a thiosulfonate reagent has a structure of formula S-I:

S-I

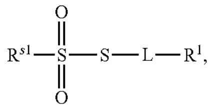

wherein: $R^{s1}$ is R; and each of R, L and $R^1$ is independently as defined and described above and herein.

In some embodiments, a sulfurization reagent is a bis (thiosulfonate) reagent. In some embodiments, the bis(thiosulfonate) reagent has the structure of formula S-II:

S-II

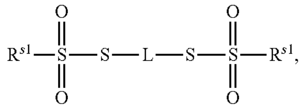

wherein each variable is independently as described in the present disclosure.

As defined generally above, $R^{s1}$ is R, wherein R is as defined and described above and herein. In some embodiments, $R^{s1}$ is optionally substituted aliphatic, aryl, heterocyclyl or heteroaryl. In some embodiments, $R^{s1}$ is optionally substituted alkyl. In some embodiments, $R^{s1}$ is optionally substituted alkyl. In some embodiments, $R^{s1}$ is methyl. In some embodiments, $R^{s1}$ is cyanomethyl. In some embodiments, $R^{s1}$ is nitromethyl. In some embodiments, $R^{s1}$ is optionally substituted aryl. In some embodiments, $R^{s1}$ is optionally substituted phenyl. In some embodiments, $R^{s1}$ is phenyl. In some embodiments, $R^{s1}$ is p-nitrophenyl. In some embodiments, $R^{s1}$ is p-methylphenyl. In some embodiments, $R^{s1}$ is p-chlorophenyl. In some embodiments, $R^{s1}$ is o-chlorophenyl. In some embodiments, $R^{s1}$ is 2,4,6-trichlorophenyl. In some embodiments, $R^{s1}$ is pentafluorophenyl. In some embodiments, $R^{s1}$ is optionally substituted heterocyclyl. In some embodiments, $R^{s1}$ is optionally substituted heteroaryl.

In some embodiments, $R^{s1}$—$S(O)_2S$— is

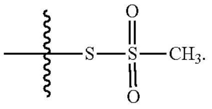

(MTS)

In some embodiments, $R^{s1}$—$S(O)_2S$— is

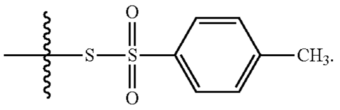

(TTS)

In some embodiments, $R^{s1}$—$S(O)_2S$— is

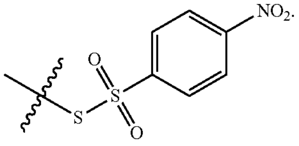

($NO_2$PheTS)

In some embodiments, $R^{s1}$—$S(O)_2S$— is

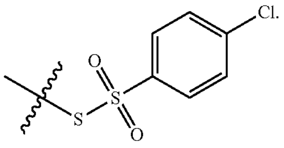

(p-ClPheTS)

In some embodiments, $R^{s1}$—$S(O)_2S$— is

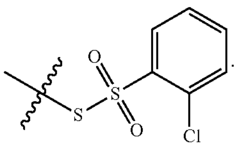

(o-ClPheTS)

In some embodiments, $R^{s1}$—$S(O)_2S$— is

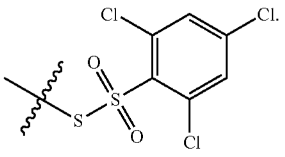

(2, 4, 6,-TriClPheTS)

In some embodiments, $R^{s1}$—$S(O)_2S$— is

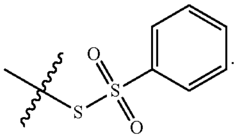

(PheTS)

In some embodiments, $R^{s1}$—$S(O)_2S$— is

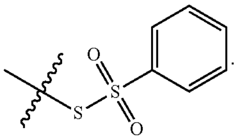

(PFPheTS)

In some embodiments, $R^{s1}$—$S(O)_2S$— is

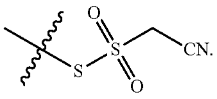

(a-CNMTS)

In some embodiments, $R^{s1}$—$S(O)_2S$— is

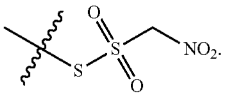

(a-$NO_2$MTS)

In some embodiments, $R^{s1}$—$S(O)_2S$— is

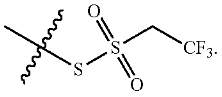

(a-$CF_3$MTS)

In some embodiments, $R^{s1}$—$S(O)_2S$— is (a-$CF_3TS$)

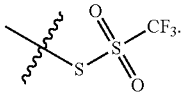

In some embodiments, $R^{s1}$—$S(O)_2S$— is (a-$CHF_2TS$)

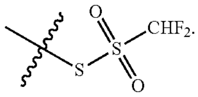

In some embodiments, $R^{s1}$—$S(O)_2S$— is (a-$CH_2FTS$)

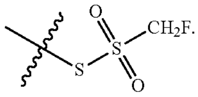

In some embodiments, a sulfurization reagent has the structure of S-I or S-II, wherein L is optionally substituted alkylene, alkenylene, arylene or heteroarylene.

In some embodiments, a sulfurization reagent is $S_8$,

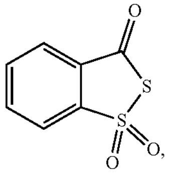

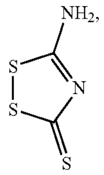

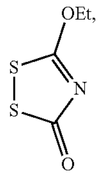

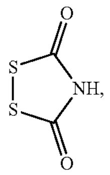

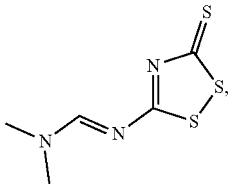

or

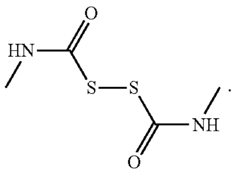

In some embodiments, a sulfurization reagent is $S_8$,

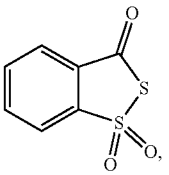

or

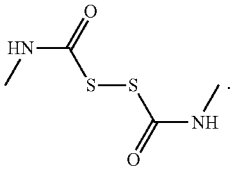

In some embodiments, a sulfurization reagent is

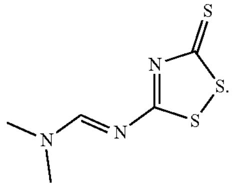

In some embodiments, a sulfurization reagent is

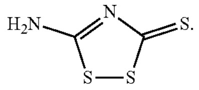

Example sulfuring reagents are depicted in below:

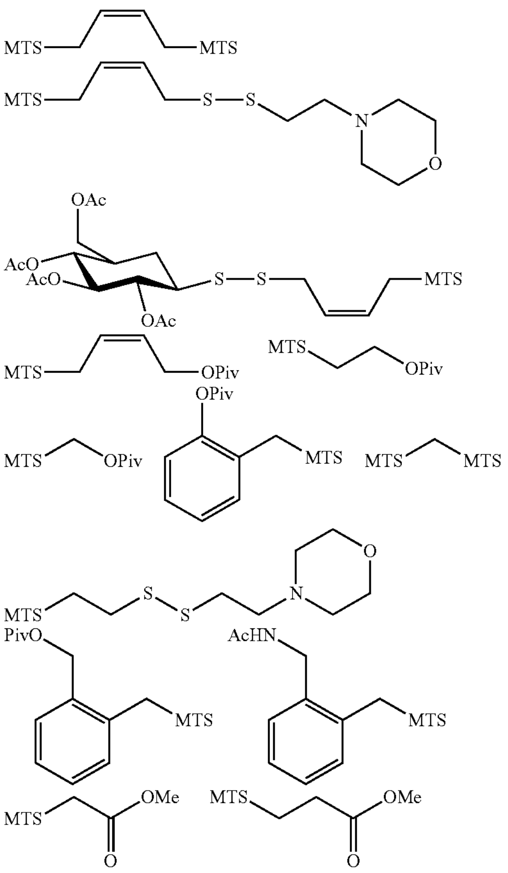

-continued
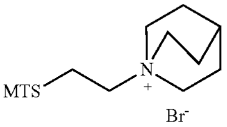
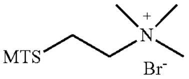
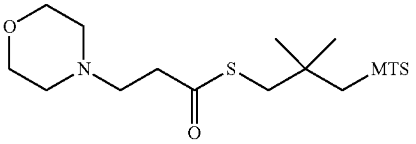
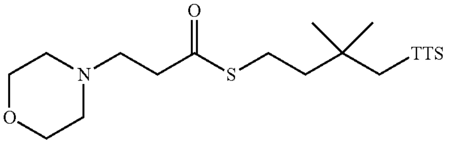
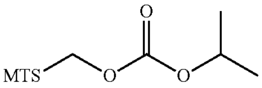
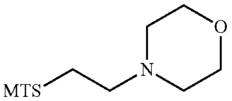
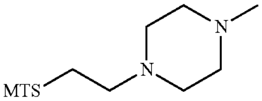
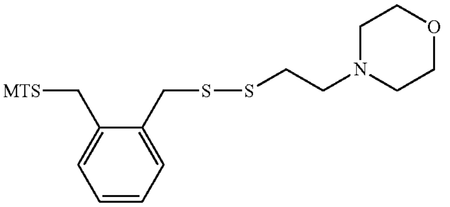
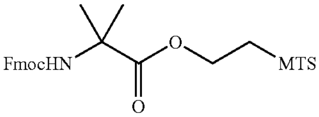
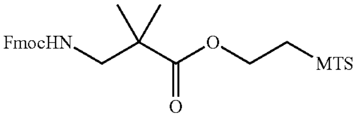
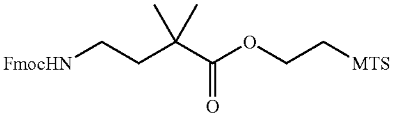
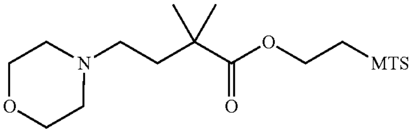
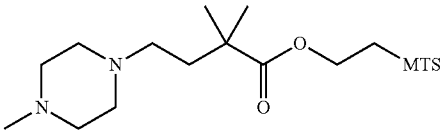
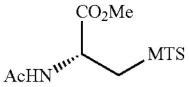
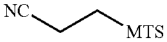
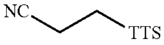
$S_8$
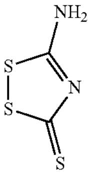
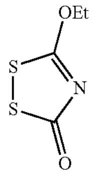
-continued
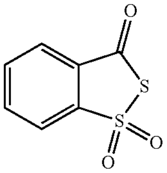
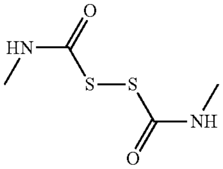
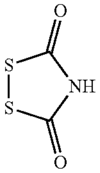
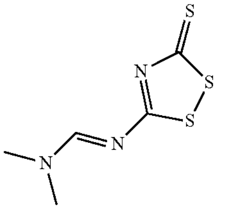
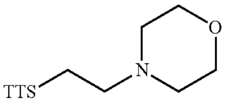
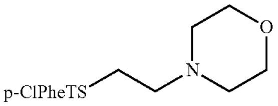
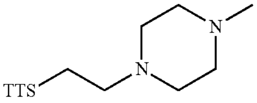
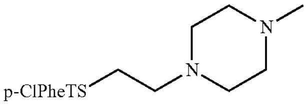
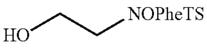
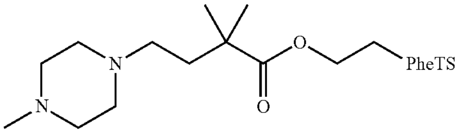
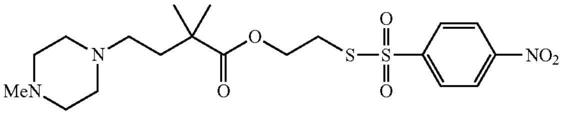
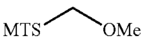
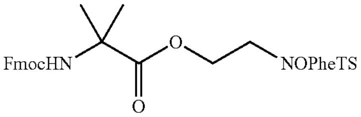
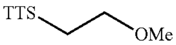
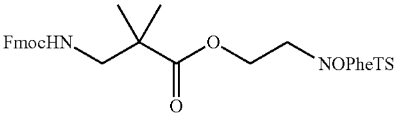
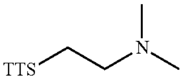
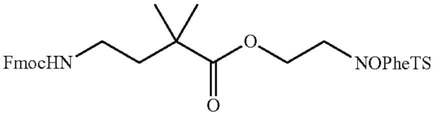
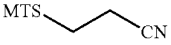
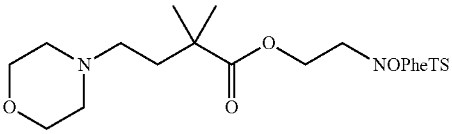
POS
In some embodiments, a selenium electrophile is used instead of a sulfurization reagent to introduce modification to the internucleotidic linkage. In some embodiments, a selenium electrophile is a compound having one of the following formulae:

$Se, R^{s2}—Se—Se—R^{s3}$, or $R^{s2}—Se—X^{s}—R^{s3}$, wherein:

each of $R^{s2}$ and $R^{s3}$ is independently an optionally substituted group selected from aliphatic, aminoalkyl, carbocyclyl, heterocyclyl, heterocycloalkyl, aryl, heteroaryl, alkyloxy, aryloxy, heteroaryloxy, acyl, amide, imide, or thiocarbonyl; or $R^{s2}$ and $R^{s3}$ are taken together with the atoms to which they are bound to form an optionally substituted heterocyclic or heteroaryl ring;

$X^{s}$ is $—S(O)_2$, —O— or —N(R')—; and

R' is as defined and described above and herein.

In other embodiments, the selenium electrophile is a compound of Se, KSeCN,

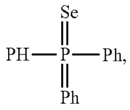

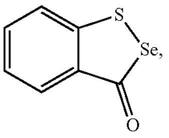

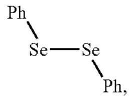

or

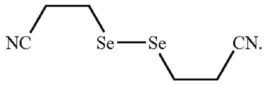

In some embodiments, the selenium electrophile is Se or

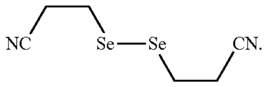

In some embodiments, a modification step is or comprises boronating of a linkage phosphorus atom. In some embodiments, a boronating reagent is a borane-amine (e.g., N,N-diisopropylethylamine ($BH_3$.DIPEA), borane-pyridine ($BH_3$.Py), borane-2-chloropyridine ($BH_3$.CPy), borane-aniline ($BH_3$.An)), a borane-ether reagent (e.g., borane-tetrahydrofuran ($BH_3$.THF)), a borane-dialkylsulfide reagent (e.g., $BH_3.Me_2S$), aniline-cyanoborane, or a triphenylphosphine-carboalkoxyborane. In some embodiments, an azide reagent is comprises an azide group capable of undergoing subsequent reduction to provide an amine group.

In some embodiments, as illustrated in the Examples, the present disclosure provides modification reagents for introducing non-negatively charged internucleotidic linkages including neutral internucleotidic linkages, e.g., those can install =N— (e.g., as in =N(-L-$R^5$), $P^N$, etc.) to a P(III) internucleotidic linkage.

In many embodiments, a modification step is typically within a cycle. In some embodiments, modification can be outside of a cycle. For example, in some embodiments, one or more modification steps can be performed after a length of oligonucleotide chain has been reached to introduce modifications simultaneously at one or more internucleotidic linkages and/or other locations.

In some embodiments, a modification step comprises use of click chemistry, e.g., wherein an alkyne group of an oligonucleotide, e.g., of an internucleotidic linkage, is reacted with an azide. Various reagents and conditions for click chemistry can be utilized in accordance with the present disclosure. In some embodiments, an azide has the structure of $R^1—N_3$, wherein $R^1$ is as described in the present disclosure. In some embodiments, $R^1$ is optionally substituted $C_{1-6}$ alkyl. In some embodiments, $R^1$ is isopropyl.

In some embodiments, a modification step installs =N—, e.g., as in =N(-L-$R^5$), $P^N$, etc., to linkage phosphorus. In some embodiments, as demonstrated in the examples, an internucleotidic linkage, e.g., a P(III) internucleotidic linkage, can be modified, e.g., converted into a non-negatively charged internucleotidic linkage in a product (optionally after other steps, e.g., removal of chiral auxiliaries etc.), by, e.g., reacting with an azide or an azido imidazolium salt (e.g., a compound comprising

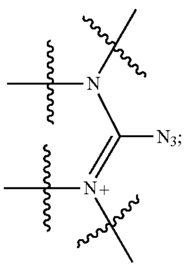

in some, embodiments, referred to as an azide reaction) under suitable conditions. In some embodiments, an azido imidazolinium salt is a salt of $PF_6^-$, In some embodiments, an azido imidazolinium salt is a salt of

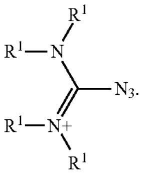

In some embodiments, a useful reagent, e.g., an azido imidazolinium salt, is a salt of

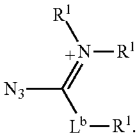

In some embodiments, a useful reagent is a salt of

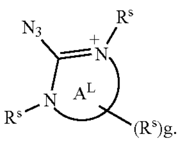

In some embodiments, a useful reagent is a salt of

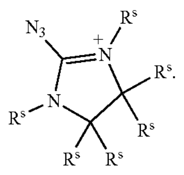

In some embodiments, a useful reagent is a salt of

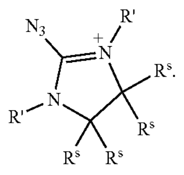

Such reagents comprising nitrogen cations also contain counter anions (e.g., $Q^-$ as described in the present disclosure), which are widely known in the art and are contained in various chemical reagents. In some embodiments, a useful reagent is $Q^+Q^-$, wherein $Q^+$ is

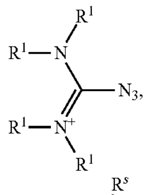
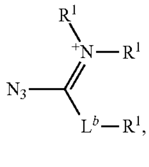
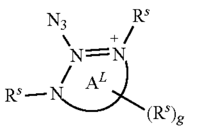
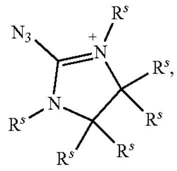
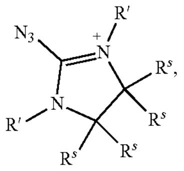

and $Q^-$ is a anion. In some embodiments, $Q^+$ is

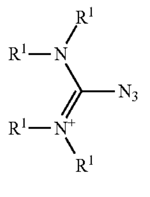

In some embodiments, $Q^+$ is

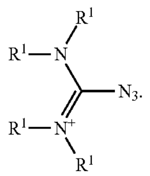

In some embodiments, $Q^+$ is

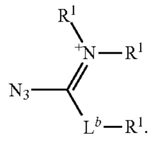

In some embodiments, $Q^+$ is

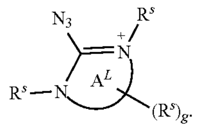

In some embodiments, $Q^+$ is

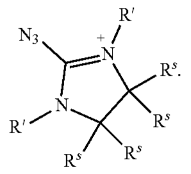

As appreciated by those skilled in the art, in a compound having the structure of $Q^+Q^-$, typically the number of positive charges in $Q^+$ equals the number of negative charges in $Q^-$. In some embodiments, $Q^+$ is a monovalent cation and $Q^-$ is a monovalent anion. In some embodiments, $Q^-$ is a non-nucleophilic anion. In some embodiments, $Q^-$ is $F^-$, $Cl^-$, $Br^-$, $BF_4^-$, $PF_6^-$, $TfO^-$, $Tf_2N^-$, $AsF_6^-$, $ClO_4^-$, or $SbF_6^-$. In some embodiments, $Q^-$ is $PF_6^-$. Those skilled in the art readily appreciate that many other types of counter anions are available and can be utilized in accordance with the present disclosure. In some embodiments, an azido imidazolinium salt is 2-azido-1,3-dimethylimidazolinium hexafluorophosphate.

In some embodiments, a P(III) linkage is reacted with an electrophile having the structure of $R\text{-}G^Z$, wherein R is as described in the present disclosure, and $G^Z$ is a leaving group, e.g., —Cl, —Br, —I, —OTf, —Oms, —OTosyl, etc. In some embodiments, R is $—CH_3$. In some embodiments, R is $—CH_2CH_3$. In some embodiments, R is $—CH_2CH_2CH_3$. In some embodiments, R is $—CH_2OCH_3$. In some embodiments, R is $CH_3CH_2OCH_2—$. In some embodiments, R is $PhCH_2OCH_2—$. In some embodiments, R is $H—C{\equiv}C—CH_2—$. In some embodiments, R is $CH_3—C{\equiv}C—CH_2—$. In some embodiments, R is $CH_2{\equiv}CHCH_2—$. In some embodiments, R is $CH_3SCH_2—$. In some embodiments, R is $—CH_2COOCH_3$. In some embodiments, R is $—CH_2COOCH_2CH_3$. In some embodiments, R is $—CH_2CONHCH_3$.

In some embodiments, after a modification step, a P(III) linkage phosphorus is converted into a P(V) internucleotidic linkage. In some embodiments, a P(III) linkage phosphorus is converted into a P(V) internucleotidic linkage, and all existing groups bounded to the linkage phosphorus remain unchanged. In some embodiments, a linkage phosphorus is converted from P into P(=O) (by installation of =O after modification). In some embodiments, a linkage phosphorus is converted from P into P(=S) (by installation of =S after modification). In some embodiments, a linkage phosphorus is converted from P into $P^N$ (e.g., $P(=N\text{-}L\text{-}R^5)$ by installation of =N(-L-$R^5$) after modification). In some embodiments, a linkage phosphorus is converted from P into

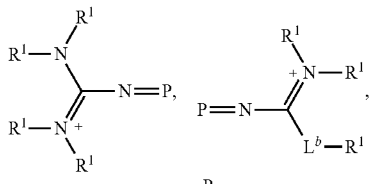

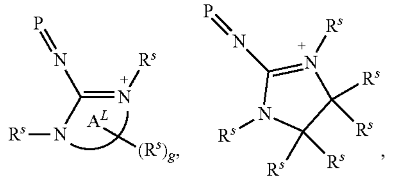

or

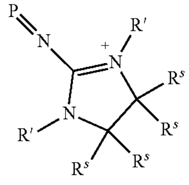

(by installation of

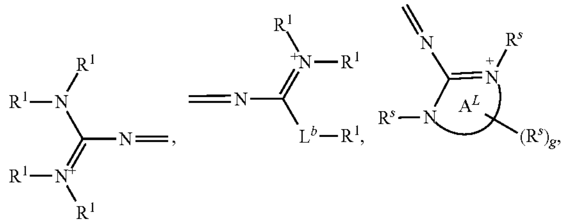

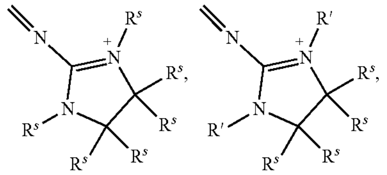

respectively) wherein each variable is independently as described in the present disclosure. In some embodiments, P is converted into

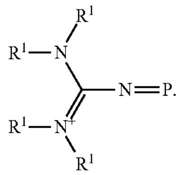

In some embodiments, P is converted into

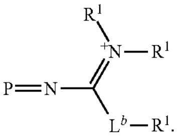

In some embodiments, P is converted into

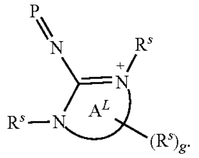

In some embodiments, P is converted into

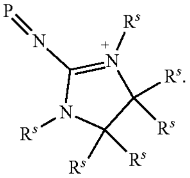

In some embodiments, P is converted into

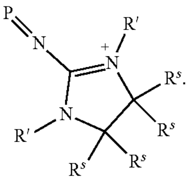

As appreciated by those skilled in the art, for each cation there typically exists a counter anion so that the total number of positive charges equals the total number of negative charges in a system (e.g., compound, composition, etc.). In some embodiments, a counter anion is $Q^-$ as described in the present disclosure (e.g., $F^-$, $Cl^-$, $Br^-$, $BF_4^-$, $PF_6^-$, $TfO^-$, $Tf_2N^-$, $AsF_6^-$, $ClO_4^-$, $SbF_6^-$, etc.). In some embodiments, a linkage phosphorus P, which is $P^L$ in an internucleotidic linkage having the structure of formula VII, VII-b, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof is converted into $P^L$ which is P(=W) or P→B(R')$_3$. In some embodiments, an internucleotidic linkage having the structure of formula VII, VII-b, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof, wherein $P^L$ is P, is converted into an internucleotidic linkage having the structure of formula VII-a-1, VII-a-2, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof, wherein $P^L$ is P(=W) or P→B(R')$_3$. In some embodiments, a linkage phosphorus P, which is $P^L$ in an internucleotidic linkage having the structure of formula VII or a salt form thereof is converted into $P^L$ which is P(=W) or P→B(R')$_3$, In some embodiments, W is O (e.g., from an oxidation reaction). In some embodiments, W is S (e.g., from a sulfurization reaction). In some embodiments, W is =N-L-$R^5$,

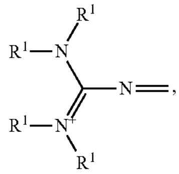

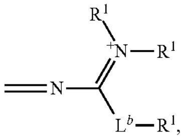

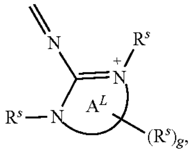

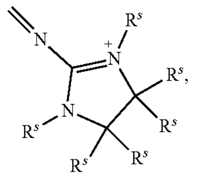

or

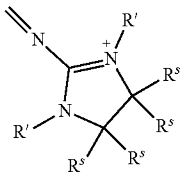

(e.g., from an azide reaction). In some embodiments, an internucleotidic linkage (e.g., an internucleotidic linkage having the structure of formula VII or a salt form thereof) has the structure of formula NL-III or a salt form thereof:

wherein:

NL-III

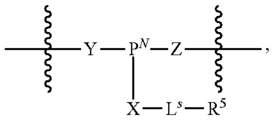

$P^N$ is $P(=N-L-R^5)$,

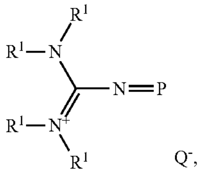

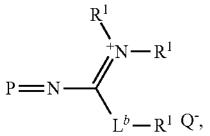

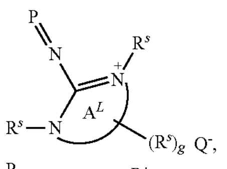

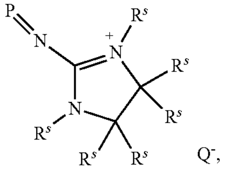

or

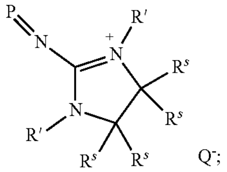

$Q^-$ is an anion; and each other variables is independently as described in the present disclosure.

In some embodiments, $P^N$ is $P(=N-L-R^5)$. In some embodiments, $P^N$ is

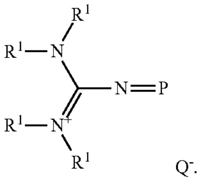

In some embodiments, $P^N$ is

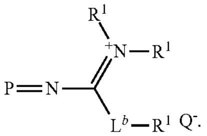

In some embodiments, $P^N$ is

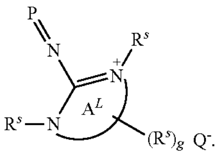

In some embodiments, $P^N$ is

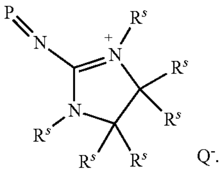

In some embodiments, $P^N$ is

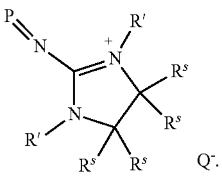

In some embodiments, internucleotidic linkages of the present disclosure may exist in a salt form. In some embodiments, internucleotidic linkages of formula NL-III may exist in a salt form. In some embodiments, in a salt form of an internucleotidic linkage of formula NL-III $P^N$ is

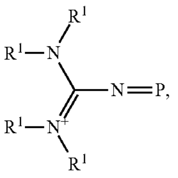

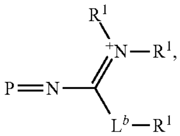

-continued

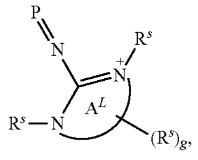

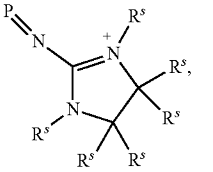

or

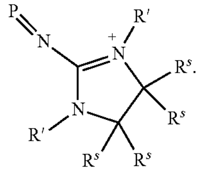

In some embodiments, in an oligonucleotide, e.g., a de-blocking product oligonucleotide, a coupling product oligonucleotide, a pre-modification capping product oligonucleotide, a modification product oligonucleotide, a post-modification capping product oligonucleotide, etc., at least one internucleotidic linkage is of formula NL-III or a salt form, thereof. In some embodiments, an internucleotidic linkage is of formula NL-III or a salt form thereof is chirally controlled. In some embodiments, each internucleotidic linkage is of formula or a salt form thereof is independently chirally controlled. In some embodiments, an internucleotidic linkage is of formula NL-III or a salt form thereof is not chirally controlled. In some embodiments, an oligonucleotide after chiral auxiliary removal (e.g., an auxiliary removal product oligonucleotide, a final product oligonucleotide, etc. j contains no internucleotidic linkage of formula NL-III or a salt form thereof. In some embodiments, an oligonucleotide after chiral auxiliary removal (e.g., an auxiliary removal product oligonucleotide, a final product oligonucleotide, etc.) contains no internucleotidic linkage of formula NL-III whose $P^N$ is

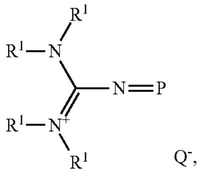

$Q^-$,

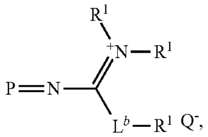

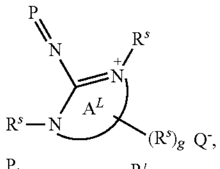

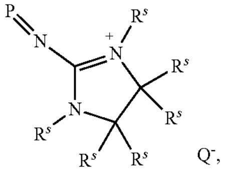

or

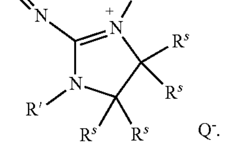

In some embodiments, an internucleotidic linkage having the structure of formula VII or a salt form thereof (e.g., wherein $P^L$ is P) is converted into an internucleotidic linkage having the structure of formula NL-III or a salt form thereof.

In some embodiments, Y, Z, and —X-$L^s$-$R^5$ (and/or Y, Z, and X-$L^s$-$R^1$) remain the same during the conversion. In some embodiments, each of X, Y and Z is independently —O—. In some embodiments, as described herein, —X-$L^s$-$R^5$ and/or —X-$L^s$-$R^1$ are independently of such structures that H—X-$L^s$-$R^5$ and/or H—X-$L^s$-$R^1$ are independently chiral reagents described herein (e.g., compounds of formula I, I-a, I-a-1, I-a-2, I-b, I-c, I-d, I-e, II, II-a, II-b, III, III-a, or III-b), or capped chiral reagents described herein wherein amino groups of the chiral reagents (e.g., N in these formulae) are capped, e.g., with —C(O)R' (replacing a hydrogen (e.g., R') with —C(O)R'; e.g., —N[—C(O)R']$R^5$—). In some embodiments, —X-$L^s$-$R^1$ and/or —X-$L^s$-$R^5$ are independently,

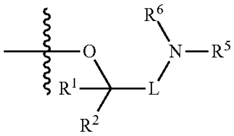

,

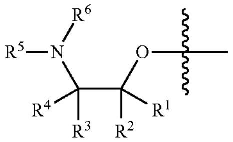

,

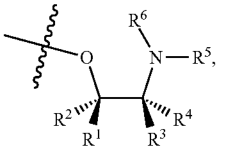

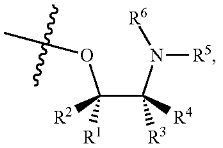

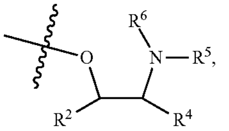

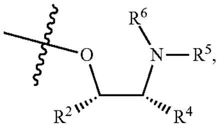

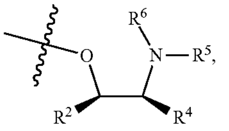

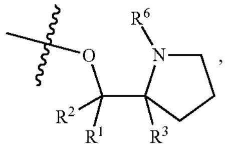

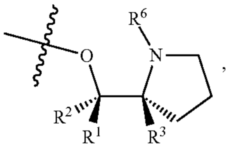

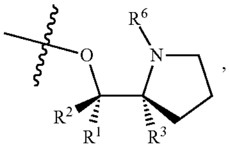

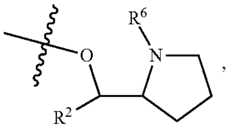

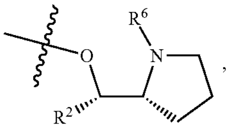

or

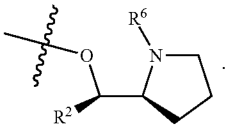

In some of embodiments, —X-$L^s$-$R^1$ and/or —X-$L^s$-$R^5$ are independently

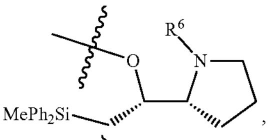

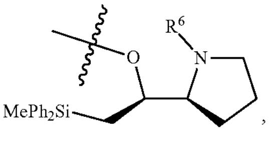

-continued

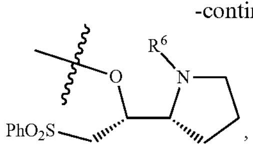

, or

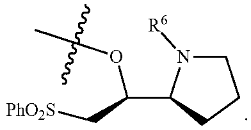

.

In some embodiments, —X-$L^s$-$R^1$ and/or —X-$L^s$-$R^5$ are independently

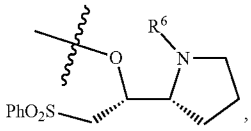

, or

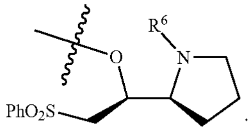

.

In some embodiments, —X-$L^s$-$R^1$ and/or —X-$L^s$-$R^5$ are independently

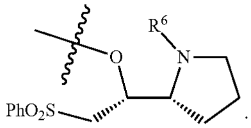

.

In some embodiments, —X-$L^s$-$R^1$ and/or —X-$L^s$-$R^5$ are independently

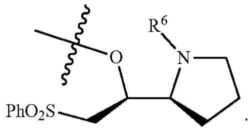

.

In some embodiments, wherein $R^6$ is —C(O)R. In some embodiments, $R^c$ is $CH_3C(O)$—.

In some embodiments, an internucleotidic linkage (e.g., a modified internucleotidic linkage, a chiral internucleotidic linkage, a chirally controlled internucleotidic linkage, etc.) has the structure of formula VII, VII-a-1, VII-a-2, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof, wherein $P^L$ is P(=N-L-$R^5$) or $P^N$ or of formula NL-III or a salt form thereof. In some embodiments, such an internucleotidic linkage is chirally controlled. In some embodiments, all such internucleotidic linkages are chirally controlled. In some embodiments, linkage phosphorus of at least one of such internucleotidic linkages is Rp. In some embodiments, linkage phosphorus of at least one of such internucleotidic linkages is Sp. In some embodiments, linkage phosphorus of at least one of such internucleotidic linkages is Rp, and linkage phosphorus of at least one of such internucleotidic linkages is Sp. In some embodiments, oligonucleotides of the present disclosure comprises one or more (e.g., 1-5, 1-10, 1-15, 1-20, 1-25, 1-30, 1-40, 1-50, 1, 2, 3, 4, 5, 6, 7, 8, 9, 10, 11, 12, 13, 14, 15, 16, 17, 18, 19, 20, 21, 22, 23, 24, 25, etc.) such internucleotidic linkages. In some embodiments, such oligonucleotide further comprise one or more other types of internucleotidic linkages, e.g., one or more natural phosphate linkages, and/or one or more phosphorothioate internucleotidic linkages (e.g., in some embodiments, one or more of which are independently chirally controlled; in some embodiments, each of which is independently chirally controlled; in some embodiments, at least one is Rp; in some embodiments, at least one is Sp; in some embodiments, at least one is Rp and at least one is Sp; etc.) In some embodiments, such oligonucleotides are stereopure (substantially free of other stereoisomers). In some embodiments, the present disclosure provides chirally controlled oligonucleotide compositions of such oligonucleotides. In some embodiments, the present disclosure provides chirally pure oligonucleotide compositions of such oligonucleotides.

In some embodiments, modification proceeds with a stereoselectivity of 80%, 85%, 90%, 91%, 92%, 93%, 94%, 95%, 96%, 97%, 98%, 99% or more. In some embodiments, the stereoselectivity is 85% or more. In some embodiments, the stereoselectivity is 85% or more. In some embodiments, the stereoselectivity is 90% or more. In some embodiments, the stereoselectivity is 91% or more. In some embodiments, the stereoselectivity is 92% or more. In some embodiments, the stereoselectivity is 93% or more. In some embodiments, the stereoselectivity is 94% or more. In some embodiments, the stereoselectivity is 95% or more. In some embodiments, the stereoselectivity is 96% or more. In some embodiments, the stereoselectivity is 97% or more. In some embodiments, the stereoselectivity is 98% or more. In some embodiments, the stereoselectivity is 99% or more. In some embodiments, modification is stereospecific.

In some embodiments, a modification product composition is a chirally controlled oligonucleotide composition. In some embodiments, a modification product composition is a chirally controlled oligonucleotide composition comprising a plurality of oligonucleotide as described herein, wherein each oligonucleotide of the plurality is independently an oligonucleotide of formula O-I or a salt thereof. In some embodiments, a modification product oligonucleotide is an oligonucleotide of formula O-I or a salt thereof. In some embodiments, each modification product oligonucleotide is independently an oligonucleotide of formula O-I or a salt thereof. In some embodiments, an internucleotidic linkage has the structure of formula VII or a salt form thereof. In some embodiments, each internucleotidic linkage independently has the structure of formula VII or a salt form thereof. In some embodiments, —X-$L^s$-$R^5$ is -$L^7$-$R^1$, wherein $L^7$ is —O—; —S-$L^s$-$R^5$; or of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'. In some embodiments, each —X-$L^s$-$R^5$ is independently -$L^7$-$R^1$, wherein $L^7$ is —O—; —S-$L^s$-$R^5$; or of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'. In some embodiments, for each chirally controlled internucleotidic linkage, —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'.

In some embodiments, each linkage phosphorus in a modification product oligonucleotide is not P(III). In some embodiments, in a modification product oligonucleotide, e.g., an oligonucleotide of formula O-I or a salt thereof:

each $L^P$ is independently of formula VII, NL or NL-III, or a salt form thereof, wherein $P^L$ is not P; and optionally each $L^P$ contains no free primary and no free secondary amino groups.

In some embodiments, each $L^P$ contains no free primary and no free secondary amino groups.

In some embodiments, in a modification product oligonucleotide, e.g., an oligonucleotide of formula O-I or a salt thereof:

each $L^P$ is independently of formula VII or a salt form thereof, wherein:

each $P^L$ is independently P(═O), P(═S) or P(═N(-L-$R^5$) or $P^N$; and each —X-$L^s$-$R^5$ is independently -$L^7$-$R^1$, wherein $L^7$ is —O—; —S-$L^s$-$R^5$; or of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'.

In some embodiments, for each $P^L$ is P(═O), each —X-$L^s$-$R^5$ is independently -$L^7$-$R^1$, wherein $L^7$ is —O—, or —X-$L^s$-$R^5$ is independently —S-$L^s$-$R^5$, or of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'; and for each $P^L$ is P(═S), each —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'.

In some embodiments, $R^5$ or $R^6$ is —C(O)R'. In some embodiments, $R^6$ is —C(O)R'. In some embodiments, R' is —$CH_3$. In some embodiments, a $L^P$ is a chirally controlled internucleotidic linkage when —X-$L^s$-$R^5$ is —S-$L^s$-$R^5$, or when $P^L$ is P(═S) or P(═N(-L-$R^5$). In some embodiments, each $L^P$ is independently a chirally controlled internucleotidic linkage when —X-$L^s$-$R^5$ is —S-$L^s$-$R^5$, or when $P^L$ is P(═S) or P(═N(-L-$R^5$).

In some embodiments, each $P^L$ is independently P(═O) or P(═S). In some embodiments, each $P^L$ is independently P(═O), P(═S), P═N(-L-$R^5$),

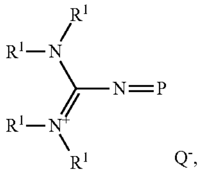

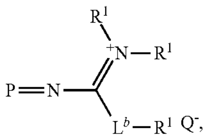

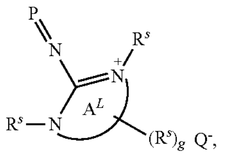

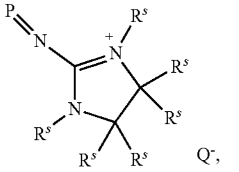

or

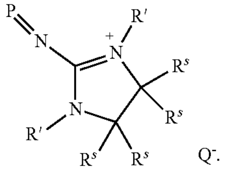

In some embodiments, each $P^L$ is independently P(═O) or P(═S),

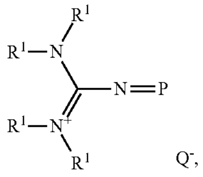

or

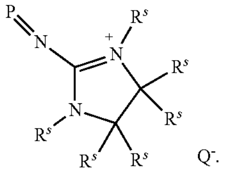

In some embodiments, each $P^L$ is independently P(═O) or P(═S), or

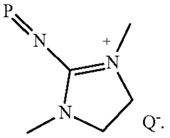

In some embodiments, internucleotidic linkages comprising $R^N$ can be converted into a non-negatively charged internucleotidic linkage, e.g., after removal of —X-$L^s$-$R^5$; for example, in some embodiments, an internucleotidic linkage of formula NL-III wherein

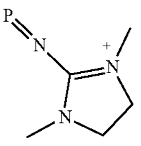

and X and Y and Z are O can be converted into n001.

In some embodiments, each —X-$L^s$-$R^5$ is independently -$L^s$-$R^1$, wherein $L^7$ is —O—; —S-$L^s$-$R^5$; or of such a structure that H—X-$L^s$-$R^5$ is a compound of formula I, I-a, I-a-1, I-a-2, I-b, I-c, I-d, I-e, II, II-a, II-b, II, III-a, or III-b, optionally wherein $R^5$ or $R^6$ is —C(O)R'. In some embodiments, -$L^7$-$R^1$ is —O—$CH_2CH_2CN$. In some embodiments, —X-$L^s$-$R^5$ is of such a structure that H—X-$L^s$-$R^5$ is compound of formula I, I-a, I-a-1, I-a-2, I-b, I-c, or I-d, or a salt thereof wherein $R^2$ is -L-Si(R')$_3$. In some embodiments, $R^2$ is —CH—Si(R')$_3$, wherein each R' is not —H. In some embodiments, a compound is

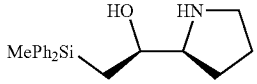

or

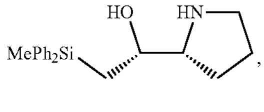

wherein the —NH— is optionally capped (e.g., with —C(O)R')). In some embodiments, —X-$L^s$-$R^5$ is of such a structure that H—X-$L^s$-$R^5$ is compound of formula I, I-a, I-a-1, I-a-2, I-b, I-c, or I-d, or a salt thereof wherein the corresponding chiral auxiliary can be readily removed under basic conditions, preferable without presence of water. In some embodiments, $R^2$ comprises an electron-withdrawing group. In some embodiments, $R^2$ is -L-$SO_2$R'. In some embodiments, $R^2$ is —$CH_2SO_2$R', wherein R' is optionally substituted $C_{1-10}$ aliphatic or aryl group. In some embodiments, —X-$L^s$-$R^5$ is of such a structure that H—X-$L^s$-$R^5$ is

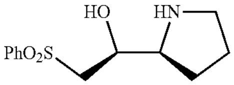

or

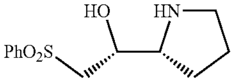

wherein the —NH— is optionally capped (e.g., with —C(O)R')). In some embodiments, each —X-$L^s$-$R^5$ is independently selected from —O—$CH_2CH_2CN$,

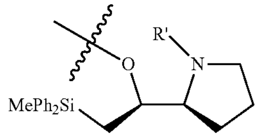

,

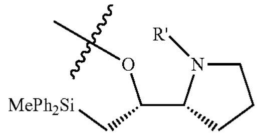

,

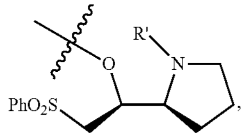

, and

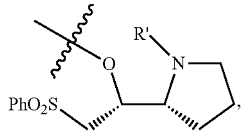

, wherein R' is —H or —C(O)R. In some embodiments, each —X-$L^s$-$R^5$ is independently selected from —O—$CH_2CH_2CN$,

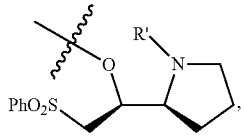

, and

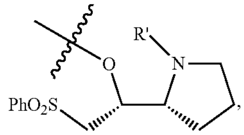

, wherein R' is —H or —C(O)R. In some embodiments, R' is —C(O)R. In some embodiments, each R' is independently —C(O)R. In some embodiments, R is —$CH_3$.

Post-Modification Capping

Various capping conditions, including those described for pre-modification capping steps, traditional capping steps, etc., can be utilized in accordance with the present disclosure, e.g., those described in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, WO 2019/217784, etc.

In some embodiments, a post-modification capping is selective for amidation over esterification. In many embodiments, a post-modification capping is efficient for both amidation and esterification, efficiently capping both amino and hydroxyl groups. In some embodiments, post-modification capping reagent systems comprise strong nucleophiles and/or esterification catalysts, e.g., DMAP, NMI, etc. at significant amount.

In some embodiments, a post-modification capping step caps various functional groups, e.g., hydroxyl groups, amino groups, that remain after, or formed during, coupling, pre-modification capping, and/or modification steps.

In some embodiments, e.g., when a modification product composition is contacted with a post-modification capping reagent system, the present disclosure provides a composition, comprising a plurality of oligonucleotides and one or more reagents of a post-modification capping reagent system, which reagents are in contact with the plurality of oligonucleotides.

In some embodiments, the present disclosure provides a composition, comprising a plurality of oligonucleotides and one or more reagents of a post-modification capping reagent system, which reagents are in contact with the plurality of oligonucleotides, wherein the plurality of oligonucleotides is a plurality of modification product oligonucleotides.

In some embodiments, the composition is a chirally controlled oligonucleotide composition. In some embodiments, a reagent is an acylating reagent, e.g., $Ac_2O$. In some embodiments, a reagent is an esterification catalyst, e.g., DMAP, NMI, etc. In some embodiments, one reagent is an anhydride, and one reagent is an esterification catalyst.

De-Blocking

In some embodiments, a step of coupling is preceded by a step of deblocking. For instance, in some embodiments, the 5' hydroxyl group of the growing oligonucleotide is blocked (i.e., protected) and is de-blocked in order to subsequently react with a nucleoside coupling partner, or before exiting the cycle.

In some embodiments, acidification is used to remove a blocking group. In some embodiments, the acid is a Brønsted acid or Lewis acid. Useful Brønsted acids are carboxylic acids, alkylsulfonic acids, arylsulfonic acids, phosphoric acid and its derivatives, phosphonic acid and its derivatives, alkylphosphonic acids and their derivatives, arylphosphonic acids and their derivatives, phosphinic acid, dialkylphosphinic acids, and diarylphosphinic acids which have a pKa (25° C. in water) value of −0.6 (trifluoroacetic acid) to 4.76 (acetic acid) in an organic solvent or water (in the case of 80% acetic acid). The concentration of the acid (1 to 80%) used in the acidification step depends on the acidity of the acid. Consideration to the acid strength must be taken into account as strong acid conditions will result in depurination/depurimidination, wherein purinyl or pyrimidinyl bases are cleaved from ribose ring and or other sugar ring. In some embodiments, an acid is selected from $R^{a1}COOH$, $R^{a1}SO_3H$, $R^{a3}SO_3H$,

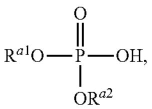

-continued

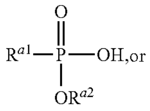

or

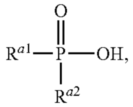

wherein each of $R^{a1}$ and $R^{a2}$ is independently hydrogen or an optionally substituted alkyl or aryl, and $R^{a3}$ is an optionally substituted alkyl or aryl.

In some embodiments, acidification is accomplished by a Lewis acid in an organic solvent. Examples of such useful Lewis acids are $Zn(X^a)_2$ wherein $X^a$ is Cl, Br, I, or $CF_3SO_3$.

In some embodiments, the step of acidifying comprises adding an amount of a Brønsted or Lewis acid effective to remove a blocking group without removing purine moieties from the condensed intermediate.

Acids that are useful in the acidifying step also include, but are not limited to 10% phosphoric acid in an organic solvent, 10% hydrochloric acid in an organic solvent, 1% trifluoroacetic acid in an organic solvent, 3% dichloroacetic acid or trichloroacetic acid in an organic solvent or 80% acetic acid in water. The concentration of any Brønsted or Lewis acid used in this step is selected such that the concentration of the acid does not exceed a concentration that causes cleavage of a nucleobase from a sugar moiety.

In some embodiments, acidification comprises adding 1% trifluoroacetic acid in an organic solvent. In some embodiments, acidification comprises adding about 0.1% to about 8% trifluoroacetic acid in an organic solvent. In some embodiments, acidification comprises adding 3% dichloroacetic acid or trichloroacetic acid in an organic solvent. In some embodiments, acidification comprises adding about 0.1% to about 10° % dichloroacetic acid or trichloroacetic acid in an organic solvent. In some embodiments, acidification comprises adding 3% trichloroacetic acid in an organic solvent. In some embodiments, acidification comprises adding about 0.1% to about 10% trichloroacetic acid in an organic solvent. In some embodiments, acidification comprises adding 80% acetic acid in water. In some embodiments, acidification comprises adding about 50% to about 90%, or about 50% to about 80%, about 50% to about 70%, about 50% to about 60%, about 70% to about 90% acetic acid in water. In some embodiments, the acidification comprises the further addition of cation scavengers to an acidic solvent. In certain embodiments, the cation scavengers can be triethylsilane or triisopropylsilane. In some embodiments, a blocking group is de-blocked by acidification, which comprises adding 1% trifluoroacetic acid in an organic solvent. In some embodiments, a blocking group is dc-blocked by acidification, which comprises adding 3% dichloroacetic acid in an organic solvent. In some embodiments, a blocking group is de-blocked by acidification, which comprises adding 3% trichloroacetic acid in an organic solvent. In some embodiments, a blocking group is de-blocked by acidification, which comprises adding 3% trichloroacetic acid in dichloromethane.

In certain embodiments, methods of the present disclosure are completed on a synthesizer and the step of deblocking the hydroxyl group of the growing oligonucleotide comprises delivering an amount solvent to the synthesizer column, which column contains a solid support to which the oligonucleotide is attached. In some embodiments, the solvent is a halogenated solvent (e.g., dichloromethane). In certain embodiments, the solvent comprises an amount of an acid. In some embodiments, the solvent comprises an amount of an organic acid such as, for instance, trichloroacetic acid. In certain embodiments, the acid is present in an amount of about 1% to about 20% w/v. In certain embodiments, the acid is present in an amount of about 1% to about 10% w/v. In certain embodiments, the acid is present in an amount of about 1% to about 5% w/v. In certain embodiments, the acid is present in an amount of about 1 to about 3% w/v. In certain embodiments, the acid is present in an amount of about 3% w/v. Methods for deblocking a hydroxyl group are described further herein. In some embodiments, the acid is present in 3% w/v is dichloromethane.

In some embodiments, a chiral auxiliary is removed before the deblocking step. In some embodiments, a chiral auxiliary is removed during the deblocking step.

In some embodiments, cycle exit is performed before a deblocking step. In some embodiments, cycle exit is preformed after a deblocking step.

Cleavage/Deprotection

After one or more cycles, e.g., when a desired length of oligonucleotide is reached, one or more reactions are performed for post-cycle modification, removal of chiral auxiliaries, deprotection of protected groups (e.g., those on sugars, nucleobases, internucleotidic linkages, etc.), cleavage of oligonucleotides from support, etc. In some embodiments, a post-cycle modification step removes one or more chiral auxiliaries.

In some embodiments, prior to, concurrently with, or subsequent to cleavage from support/deprotection, a step is performed to remove a chiral auxiliary group, if one is still attached to an internucleotidic phosphorus atom. In some embodiments, for example, one or more DPSE- and/or PSM-type chiral auxiliary groups remain attached to internucleotidic phosphorus atoms during the oligonucleotide synthesis cycle. In some embodiments, chiral auxiliary groups (capped or uncapped) may be removed during a modification step. In some embodiments, chiral auxiliary groups (capped or uncapped) may be removed under acidic conditions. In some embodiments, chiral auxiliary groups (capped or uncapped) may be removed under basic conditions. In some embodiments, chiral auxiliary groups (capped or uncapped) may be removed under $F^-$ conditions. Suitable conditions for removing remaining chiral auxiliary groups are widely known in the art and can be utilized in accordance with the present disclosure, e.g., those described in e.g., U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, WO 2019/217784, etc.

In some embodiments, a condition for removing DPSE type chiral auxiliary is TBAF or $HF\text{-}Et_3N$, e.g., 0.1M TBAF in MeCN, 0.5M $HF\text{-}Et_3N$ in THF or MeCN, etc. In some embodiments, the present disclosure recognizes that a linker may be cleaved during the process of removing a chiral auxiliary group. Additional example conditions are described in the present disclosure.

In some embodiments, certain chiral auxiliaries as described herein are removed under basic conditions. In some embodiments, oligonucleotides are contacted with a base, e.g., an amine having the structure of $N(R)_3$, to remove certain chiral auxiliaries (e.g., those comprising an electronic-withdrawing group and/or or a base-labile —H in $R^2$ as described in the present disclosure). In some embodiments, an amine is DEA. In some embodiments, an amine is TEA. In some embodiments, an amine is provided as a solution, e.g., an acetonitrile solution. In some embodiments, such contact is performed under anhydrous conditions. Those skilled in the art appreciate that various anhydrous reagents, e.g., bases, solvents, etc., are readily available, e.g., through commercial sources, common laboratory procedures, etc. In some embodiments, such a contact is performed before an oligonucleotide is exposed to a solution of a base (e.g., a primary, secondary, or tertiary $sp^3$-N amine) comprising a significant amount of water (e.g., a cleavage and/or deprotection reagent system comprising $NH_4OH$). In some embodiments, such a contact is performed immediately after desired oligonucleotide lengths are achieved (e.g., first step post synthesis cycles). In some embodiments, such a contact is performed before removal of chiral auxiliaries and/or protection groups and/or cleavage of oligonucleotides from a solid support. In some embodiments, contact with a base may remove cyanoethyl groups utilized in standard oligonucleotide synthesis, providing an natural phosphate linkage which may exist in a salt form (with the cation being, e.g., an ammonium salt).

As demonstrated herein, provided technologies can be highly efficient and effective for removal of chiral auxiliaries to provide various internucleotidic linkages, including natural phosphate linkages, phosphorothioate internucleotidic linkages, and non-negatively charged internucleotidic linkages. For example, in some embodiments, base-labile chiral auxiliaries (e.g., those with certain $R^2$ groups as described herein (e.g., PSM)) can be utilized for efficient synthesis of a variety of internucleotidic linkages, including phosphorothioate internucleotidic linkages, non-negatively charged internucleotidic linkages (e.g., n001) with high stereoselectivity, high crude purity and/or high yield. In some embodiments, provided auxiliary removal technologies can efficiently and effectively remove chiral auxiliaries without high temperature, e.g., under temperatures about or below about 80, 75, 70, 65, 60, 55, 50, 45, 40, or 35° C. In some embodiments, removal is performed at room temperature. In some embodiments, provided technologies significantly reduces removal contact time (between oligonucleotides and removal reagent systems). In some embodiments, a removal contact time is 5, 10, 15, 20, 25, 30, 35, 40, 45, 50, 55, 60, 70, 80, 90, 100, 110 or 120 minutes. In some embodiments, a removal contact time is no more than 20, 25, 30, 35, 40, 45, 50, 55, 60, 70, 80, 90, 100, 110 or 120 minutes. In some embodiments, a removal contact time is 5 min. In some embodiments, a removal contact time is 10 min. In some embodiments, a removal contact time is 15 min. In some embodiments, a removal contact time is 20 min. In some embodiments, a removal contact time is 30 min. In some embodiments, a removal contact time is 40 min. In some embodiments, a removal contact time is 50 min. In some embodiments, a removal contact time is 60 min. In some embodiments, an example removal reagent system is diethylamine (e.g., 20%) in acetonitrile. In some embodiments, an example removal condition is 20% diethylamine in acetonitrile for 20 minutes contact time. Those skilled in the art appreciate that other reagent systems and/or contact time may be utilized. Among other things, such removal technologies provide simplified manufacturing (e.g., fewer and/or shorter auxiliary removal operations), high crude purity and/or high yield, e.g., without the intention to be limited by theory, as a result of short contact times and mild conditions (e.g., reagents utilized, temperatures, etc.).

In some embodiments, contact with a base provides an internucleotidic linkage of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof. In some embodiments, contact with a base removes a chiral auxiliary from an internucleotidic linkage of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof. In some embodiments, contact with a base removes a chiral auxiliary (e.g., —X-$L^s$-$R^5$) from an internucleotidic linkage of formula VII or a salt form thereof(e.g., wherein $P^L$ is P(═N-L-$R^5$)). In some embodiments, contact with a base removes a chiral auxiliary (e.g., —X-$L^s$-$R^5$) from an internucleotidic linkage of formula NL-III or a salt form thereof. In some embodiments, In some embodiments, contact with a base converts an internucleotidic linkage of formula VII or a salt form thereof (e.g., wherein $P^L$ is P(═N-L-$R^5$)), or of formula NL-III or a salt form thereof, into an internucleotidic linkage of formula NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof, which is optionally chirally controlled. In some embodiments, contact with a base removes a chiral auxiliary from an internucleotidic linkage of formula VII or a salt form thereof (e.g., $P^L$ is P(═S)) and forms a phosphorothioate internucleotidic linkage. In some embodiments, removal of a chiral auxiliary forms a chirally controlled internucleotidic linkage. In some embodiments, each chiral internucleotidic linkage formed is independently a chirally controlled internucleotidic linkage. In some embodiments, contact with an amine removes substantially all chiral auxiliaries. In some embodiments, no additional steps are required and/or performed to remove chiral auxiliaries.

In some embodiments, chiral auxiliary removal provides an auxiliary removal product composition. In some embodiments, an auxiliary removal product composition is a chirally controlled oligonucleotide composition. In some embodiments, an auxiliary removal product composition is a chirally controlled oligonucleotide composition comprising a plurality of oligonucleotide as described herein, wherein each oligonucleotide of the plurality is independently an oligonucleotide of formula O-I or a salt thereof. In some embodiments, an auxiliary removal product oligonucleotide is an oligonucleotide of formula O-I or a salt thereof. In some embodiments, each auxiliary removal product oligonucleotide is independently an oligonucleotide of formula O-I or a salt thereof. In some embodiments, an internucleotidic linkage has the structure of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof. In some embodiments, each internucleotidic linkage independently has the structure of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof. In some embodiments, each internucleotidic linkage independently has the structure of formula VII, VII-a-1, VII-a-2, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-L or NL-d-2, or a salt form thereof. In some embodiments, a $P^L$ is P(═O) or P(═S). In some embodiments, each $P^L$ is independently P(═O) or P(═S). In some embodiments, an internucleotidic linkage is a natural phosphate linkage. In some embodiments, an internucleotidic linkage is a phosphorothioate internucleotidic linkage. In some embodiments, an internucleotidic linkage is a chirally controlled phosphorothioate internucleotidic linkage. In some embodiments, an internucleotidic linkage is a non-chirally controlled phosphorothioate internucleotidic linkage. In some embodiments, an internucleotidic linkage is a non-negatively charged internucleotidic linkage (e.g., a neutral internucleotidic linkage having the structure of NL-n-1, NL-n-2, NL-n-3, NL-n-4, NL, NL-a-1, NL-a-2, NL-b-1, NL-b-2, NL-c-1, NL-c-2, NL-d-1, or NL-d-2). In some embodiments, an internucleotidic linkage is a chirally controlled non-negatively charged internucleotidic linkage (e.g., a neutral internucleotidic linkage having the structure of NL-n-1, NL-n-2, NL-n-3, NL-n-4, NL, NL-a-1, NL-a-2, NL-b-1, NL-b-2, NL-c-1, NL-c-2, NL-d-1, or NL-d-2). In some embodiments, an internucleotidic linkage is a non-chirally controlled non-negatively charged internucleotidic linkage (e.g., a neutral internucleotidic linkage having the structure of NL-n-1, NL-n-2, NL-n-3, NL-n-4, NL, NL-a-1, NL-a-2, NL-b-1, NL-b-2, NL-c-1, NL-c-2, NL-d-1, or NL-d-2). In some embodiments, each internucleotidic linkage is independently a natural phosphate linkage, an optionally chirally controlled phosphorothioate internucleotidic linkage, or an optionally chirally controlled non-negatively charged internucleotidic linkage (e.g., a neutral internucleotidic linkage having the structure of NL-n-1, NL-n-2, NL-n-3, NL-n-4, NL, NL-a-1, NL-a-2, NL-b-1, NL-b-2, NL-c-1, NL-c-2, NL-d-1, or NL-d-2). In some embodiments, each internucleotidic linkage is independently a natural phosphate linkage, or an optionally chirally controlled phosphorothioate internucleotidic linkage. In some embodiments, a non-negatively charged internucleotidic linkage is n001. In some embodiments, each internucleotidic linkage is independently a natural phosphate linkage, an optionally chirally controlled phosphorothioate internucleotidic linkage, or an optionally chirally controlled n001. In some embodiments, each internucleotidic linkage is independently a natural phosphate linkage, a chirally controlled phosphorothioate internucleotidic linkage, or an optionally chirally controlled n001. In some embodiments, each internucleotidic linkage is independently a natural phosphate linkage, a chirally controlled phosphorothioate internucleotidic linkage, or a chirally controlled n001. In some embodiments, each internucleotidic linkage is independently a natural phosphate linkage, or an optionally chirally controlled phosphorothioate internucleotidic linkage. In some embodiments, one or more chiral internucleotidic linkages are independently chirally controlled. In some embodiments, one or more chiral internucleotidic linkages are not independently chirally controlled. In some embodiments, one or more chiral internucleotidic linkages are independently chirally controlled, and one or more chiral internucleotidic linkages are not independently chirally controlled. In some embodiments, a chirally controlled internucleotidic linkage is a phosphorothioate internucleotidic linkage. In some embodiments, a non-chirally controlled internucleotidic linkage is a phosphorothioate internucleotidic linkage. In some embodiments, a chirally controlled internucleotidic linkage is a non-negatively charged internucleotidic linkage (e.g., a neutral internucleotidic linkage such as n001). In some embodiments, a chirally controlled internucleotidic linkage is a non-negatively charged internucleotidic linkage (e.g., a neutral internucleotidic linkage such as n001). In some embodiments, each internucleotidic linkage is independently a natural phosphate linkage, or a chirally controlled phosphorothioate internucleotidic linkage. In some embodiments, one or more phosphorothioate internucleotidic linkages are not chirally controlled. In some embodiments, one or more phosphorothioate internucleotidic linkages are not chirally controlled and one or more are independently chirally controlled. In some embodiments, one or more non-negatively charged internucleotidic linkages (e.g., neutral internucleotidic linkages such as n001) are not chirally controlled. In some embodiments, one or more non-negatively charged internucleotidic linkages (e.g., neutral internucleotidic linkages such as n001) are not chirally controlled and one or more non-negatively charged internucleotidic linkages (e.g., neutral internucleotidic linkages such as n001) are chirally controlled. In some embodiments, one or more phosphorothioate internucleotidic linkages are chirally controlled and one or more non-negatively charged internucleotidic linkages (e.g., neutral internucleotidic linkages such as n001) are not chirally controlled.

In some embodiments, linkage phosphorus of a chirally controlled internucleotidic linkage has a Sp configuration. In some embodiments, linkage phosphorus of each chirally controlled internucleotidic linkage has a Sp configuration. In some embodiments, linkage phosphorus of each chirally controlled phosphorothioate internucleotidic linkage has a Sp configuration. In some embodiments, linkage phosphorus of each chirally controlled non-negatively charged internucleotidic linkage (e.g., neutral internucleotidic linkage such as n001) has a Sp configuration. In some embodiments, linkage phosphorus of a chirally controlled internucleotidic linkage has a Rp configuration. In some embodiments, linkage phosphorus of each chirally controlled internucleotidic linkage has a Rp configuration. In some embodiments, linkage phosphorus of each chirally controlled non-negatively charged internucleotidic linkage (e.g., neutral internucleotidic linkage such as n001) has a Rp configuration. In some embodiments, linkage phosphorus of one or more chirally controlled internucleotidic linkages each has a Sp configuration, and linkage phosphorus of one or more chirally controlled internucleotidic linkages each has a Rp configuration.

In some embodiments, in an auxiliary removal product oligonucleotide, e.g., an oligonucleotide of formula O-I or a salt thereof:

each $L^P$ is independently of formula VII, VII-a-1, VII-a-2, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, a salt form thereof, wherein:

each $P^L$ is independently P(═O); and each —Y— and —Z— is independently —O—.

In some embodiments, each internucleotidic linkage whose —X— is —O— is independently a natural phosphate linkage. In some embodiments, each internucleotidic linkage whose —X— is —S— is independently an optionally chirally controlled phosphorothioate internucleotidic linkage. In some embodiments, each internucleotidic linkage whose —X— is —S— is independently a chirally controlled phosphorothioate internucleotidic linkage.

Functional groups such as hydroxyl or amino moieties which are located, e.g., on nucleobases or sugar moieties, are routinely blocked with blocking (protecting) groups (moieties) during synthesis and subsequently deblocked. In general, a blocking group renders a chemical functionality of a molecule inert to specific reaction conditions and can later be removed from such functionality in a molecule without substantially damaging the remainder of the molecule (see e.g., Green and Wuts, Protective Groups in Organic Synthesis, 2nd Ed., John Wiley & Sons, New York, 1991). For example, amino groups can be blocked with nitrogen blocking groups such as phthalimido, 9-fludrenylmethoxycarbonyl (FMOC), triphenylmethylsulfenyl, t-BOC, 4,4'-dimethoxytrityl (DMTr), 4-methoxytrityl (MMTr), 9-phenylxanthin-9-yl (Pixyl), trityl (Tr), or 9-(p-methoxyphenyl)xanthin-9-yl (MOX). Carboxyl groups can be protected as acetyl groups. Hydroxy groups can be protected such as tetrahydropyranyl (THP), t-butyldimethylsilyl (TBDMS), 1-[(2-chloro-4-methyl)phenyl]-4-methoxypiperidin-4-yl (Ctmp), 1-(2-fluorophenyl)-4-methoxypiperidin-4-yl (Fpmp), 1-(2-chloroethoxy)ethyl, 3-methoxy-1,5-dicarbomethoxypentan-3-yl (MDP), bis(2-acetoxyethoxy)methyl (ACE), triisopropylsilyloxymethyl (TOM), 1-(2-cyanoethoxy)ethyl (CEE), 2-cyanoethoxymethyl (CEM), 14-(N-dichloroacetyl-N-methylamino)benzyloxylmethyl, 2-cyanoethyl (CN), pivaloyloxymethyl (PivOM), levunyloxymethyl (ALE). Other representative hydroxyl blocking groups have been described (see e.g., Beaucage et al., Tetrahedron, 1992, 46, 2223). In some embodiments, hydroxyl blocking groups are acid-labile groups, such as the trityl, monomethoxytrityl, dimethoxytrityl, trimethoxytrityl, 9-phenylxanthin-9-yl (Pixyl) and 9-(p-methoxyphenyl)xanthin-9-yl (MOX). Chemical functional groups can also be blocked by including them in a precursor form. Thus an azido group can be considered a blocked form of an amine as the azido group is easily converted to the amine. Further representative protecting groups utilized in nucleic acid synthesis are known (see e.g. Agrawal et al.. Protocols for Oligonucleotide Conjugates, Eds., Humana Press, New Jersey, 1994, Vol. 26, pp. 1-72).

Various methods are known and used for removal of blocking groups from nucleic acids. In some embodiments, all blocking groups are removed. In some embodiments, a portion of blocking groups are removed. In some embodiments, reaction conditions can be adjusted to selectively remove certain blocking groups.

In some embodiments, nucleobase blocking groups, if present, are cleavable with an acidic reagent after the assembly of a provided oligonucleotide. In some embodiment, nucleobase blocking groups, if present, are cleavable under neither acidic nor basic conditions, e.g. cleavable with fluoride salts or hydrofluoric acid complexes. In some embodiments, nucleobase blocking groups, if present, are cleavable in the presence of base or a basic solvent after the assembly of a provided oligonucleotide. In certain embodiments, one or more of the nucleobase blocking groups are characterized in that they are cleavable in the presence of base or a basic solvent after the assembly of a provided oligonucleotide but are stable to the particular conditions of one or more earlier deprotection steps occurring during the assembly of the provided oligonucleotide.

In some embodiments, blocking groups for nucleobases are not required. In some embodiments, blocking groups for nucleobases are required. In some embodiments, certain nucleobases require one or more blocking groups while other nucleobases do not require one or more blocking groups.

In some embodiments, the oligonucleotide is cleaved from the solid support after synthesis. In some embodiments, cleavage from the solid support comprises the use of propylamine. In some embodiments, cleavage from the solid support comprises the use of propylamine in pyridine. In some embodiments, cleavage from the solid support comprises the use of 20% propylamine in pyridine. In some embodiments, cleavage from the solid support comprises the use of propylamine in anhydrous pyridine. In some embodiments, cleavage from the solid support comprises the use of 20% propylamine in anhydrous pyridine. In some embodiments, cleavage from the solid support comprises use of a polar aprotic solvent such as acetonitrile, NMP, DMSO, sulfone, and/or lutidine. In some embodiments, cleavage from the solid support comprises use of solvent, e.g., a polar aprotic solvent, and one or more primary amines (e.g., a $C_{1-10}$ amine), and/or one or more of methoxylamine, hydrazine, and pure anhydrous ammonia.

In some embodiments, deprotection of oligonucleotide comprises the use of propylamine. In some embodiments, deprotection of oligonucleotide comprises the use of propylamine in pyridine. In some embodiments, deprotection of oligonucleotide comprises the use of 20% propylamine in pyridine. In some embodiments deprotection of oligonucleotide comprises the use of propylamine in anhydrous pyridine. In some embodiments, deprotection of oligonucleotide comprises the use of 20% propylamine in anhydrous pyridine.

In some embodiments, an oligonucleotide is deprotected during cleavage. In some embodiments, a useful reagent is concentrated $NH_4OH$ (e.g., 28-30%). In some embodiments, a useful temperature is about 30-40° C. In some embodiments, a useful temperature is about 37° C. In some embodiments, a useful cleavage/deprotection time is about 24 hours. In some embodiments, a cleavage/deprotection condition is concentrated $NH_4OH$ (e.g., 28-30%), about 37° C. reaction temperature, and about 24 hours reaction time.

In some embodiments, cleavage of oligonucleotide from solid support, or deprotection of oligonucleotide, is performed at about room temperature. In some embodiments, cleavage of oligonucleotide from solid support, or deprotection of oligonucleotide, is performed at elevated temperature. In some embodiments, cleavage of oligonucleotide from solid support, or deprotection of oligonucleotide, is performed at above about 30° C., 40° C., 50° C., 60° C., 70° C., 80° C. 90° C., or 100° C. In some embodiments, cleavage of oligonucleotide from solid support, or deprotection of oligonucleotide, is performed at about 30° C. 40° C., 50° C., 60° C., 70° C., 80° C. 90° C., or 100° C. In some embodiments, cleavage of oligonucleotide from solid support, or deprotection of oligonucleotide, is performed at about 40-80° C. In some embodiments, cleavage of oligonucleotide from solid support, or deprotection of oligonucleotide, is performed at about 50-70° C. In some embodiments, cleavage of oligonucleotide from solid support, or deprotection of oligonucleotide, is performed at about 60° C.

In some embodiments, cleavage of oligonucleotide from solid support, or deprotection of oligonucleotide, is performed for 0.1 hr, 1 hr, 2 hrs, 5 hrs, 10 hrs, 15 hrs, 20 hrs, 24 hrs, 30 hrs, or 40 hrs or more. In some embodiments, cleavage of oligonucleotide from solid support, or deprotection of oligonucleotide, is performed for about 0.1-5 hrs. In some embodiments, cleavage of oligonucleotide from solid support, or deprotection of oligonucleotide, is performed for about 3-10 hrs. In some embodiments, cleavage of oligonucleotide from solid support, or deprotection of oligonucleotide, is performed for about 5-15 hrs. In some embodiments, cleavage of oligonucleotide from solid support, or deprotection of oligonucleotide, is performed for about 10-20 hrs. In some embodiments, cleavage of oligonucleotide from solid support, or deprotection of oligonucleotide, is performed for about 15-25 hrs. In some embodiments, cleavage of oligonucleotide from solid support, or deprotection of oligonucleotide, is performed for about 20-40 hrs. In some embodiments, cleavage of oligonucleotide from solid support, or deprotection of oligonucleotide, is performed for about 2 hrs. In some embodiments, cleavage of oligonucleotide from solid support, or deprotection of oligonucleotide, is performed for about 5 hrs. In some embodiments, cleavage of oligonucleotide from solid support, or deprotection of oligonucleotide, is performed for about 10 hrs. In some embodiments, cleavage of oligonucleotide from solid support, or deprotection of oligonucleotide, is performed for about 15 hrs. In some embodiments, cleavage of oligonucleotide from solid support, or deprotection of oligonucleotide, is performed for about 18 hrs. In some embodiments, cleavage of oligonucleotide from solid support, or deprotection of oligonucleotide, is performed for about 24 hrs.

In some embodiments, cleavage of oligonucleotide from solid support, or deprotection of oligonucleotide, is performed at room temperature for more than 0.1 hr, 1 hr, 2 hrs, 5 hrs, 10 hrs. 15 hrs, 20 hrs, 24 hrs, 30 hrs, or 40 hrs. In some embodiments, cleavage of oligonucleotide from solid support, or deprotection of oligonucleotide, is performed at room temperature for about 5-48 hrs. In some embodiments, cleavage of oligonucleotide from solid support, or deprotection of oligonucleotide, is performed at room temperature for about 10-24 hrs. In some embodiments, cleavage of oligonucleotide from solid support, or deprotection of oligonucleotide, is performed at room temperature for about 18 hrs. In some embodiments, cleavage of oligonucleotide from solid support, or deprotection of oligonucleotide, is performed at elevated temperature for more than 0.1 hr, 1 hr, 2 hrs, 5 hrs, 10 hrs, 15 hrs, 20 hrs, 24 hrs, 30 hrs, or 40 hrs. In some embodiments, cleavage of oligonucleotide from solid support, or deprotection of oligonucleotide, is performed at elevated temperature for about 0.5-5 hrs. In some embodiments, cleavage of oligonucleotide from solid support, or deprotection of oligonucleotide, is performed at about 60° C. for about 0.5-5 hrs. In some embodiments, cleavage of oligonucleotide from solid support, or deprotection of oligonucleotide, is performed at about 60° C. for about 2 hrs.

In some embodiments, cleavage of oligonucleotide from solid support, or deprotection of oligonucleotide comprises the use of propylamine and is performed at room temperature or elevated temperature for more than 0.1 hr, 1 hr, 2 hrs, 5 hrs, 10 hrs, 15 hrs, 20 hrs, 24 hrs, 30 hrs, or 40 hrs. Example conditions are 20% propylamine in pyridine at room temperature for about 18 hrs, and 20% propylamine in pyridine at 60° C. for about 18 hrs. Additional example conditions are described in the present disclosure.

In some embodiments, a metal chelator is utilized during cleavage/deprotection. In some embodiments, a metal chelator is EDTA. In some embodiments, After cleavage/deprotection and removal of chiral auxiliaries, provided crude oligonucleotides are typically further analyzed and purified, e.g., through various analytical and purification technologies available in the art. In some embodiments, an analytical and/or purification technology is chromatography. In some embodiments, an analytical and/or purification technology is HPLC and/or UPLC. In some embodiments, oligonucleotides are processed through UF and/or DF. In some embodiments, oligonucleotides are stored and/or formulated as concentrated solutions, optionally in a pharmaceutically acceptable solvent system (e.g., as described in the Examples). In some embodiments, oligonucleotides are stored and/or formulated as solid, in some embodiments, as a pharmaceutically acceptable salt (e.g., a sodium salt). In many instances, oligonucleotides are stored at a low temperature, e.g., at or no higher than about 10, 4, 0, −5, −10, −15, −20, −30, −40, −50, −60, −70, −80, −90, −100° C.

Supports and Linkers

Various types of supports and linkers may be utilized in accordance with the present disclosure to prepare oligonucleotides, e.g., those described in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, WO 2019/217784, etc. In some embodiments, a support is a solid support. In some embodiments, a support is not a solid support.

In some embodiments, synthesis of provided oligonucleotides is performed on solid support. In some embodiments, reactive groups present on a solid support are protected. In some embodiments, reactive groups present on a solid support are unprotected. In some embodiments, during oligonucleotide synthesis a solid support is treated with various reagents in several synthesis cycles to achieve stepwise elongation of a growing oligonucleotide chain with individual nucleotide units. A nucleoside unit at the end of an oligonucleotide chain which is directly linked to a solid support is typically referred to as the first nucleoside linked to a solid support. In some embodiments, a first nucleoside linked to a solid support is bound to a solid support via a linker moiety, a diradical forming a bond at one end with a solid support. e.g., of a CPG, a polymer or other solid support, and at the other end with a nucleoside. In some embodiments, a linker stays intact during synthesis cycles performed to assemble the oligonucleotide chain and is cleaved after the chain assembly to liberate the oligonucleotide from the support.

As demonstrated herein, CPG in some embodiments provide improved crude purity. In some embodiments, a polystyrene support may provide high unit loading capacity.

In some embodiments, a solid support is a solid support whose volume does not change significantly during oligonucleotide synthesis, e.g., CPG. In some embodiments, such solid support may provide easier and more accurate control of reagent concentrations for oligonucleotide synthesis.

In some embodiments, a solid supports for solid-phase nucleic acid synthesis is a support described in, e.g., U.S. Pat. Nos. 4,659,774, 5,141,813, 4,458,066; Caruthers U.S. Pat. Nos. 4,415,732, 4,458,066, 4,500,707, 4,668,777, 4,973,679, and 5,132,418; Andrus et al. U.S. Pat. Nos. 5,047,524, 5,262,530; and Koster U.S. Pat. No. 4,725,677 (reissued as RE34,069). In some embodiments, a solid support is an organic polymer support. In some embodiments, a solid support is an inorganic polymer support. In some embodiments, an organic polymer support is polystyrene, aminomethyl polystyrene, a polyethylene glycol-polystyrene graft copolymer, polyacrylamide, polymethacrylate, polyvinylalcohol, highly cross-linked polymer (HCP), or other synthetic polymers, carbohydrates such as cellulose and starch or other polymeric carbohydrates, or other organic polymers and any copolymers, composite materials or combination of the above inorganic or organic materials. In some embodiments, an inorganic polymer support is silica, alumina, controlled pore glass (CPG), which is a silica-gel support, or aminopropyl CPG. In some embodiments, a solid support is selected from fluorous solid supports (see e.g., WO/2005/070859), and long chain alkylamine (LCAA) controlled pore glass (CPG) solid supports (see e.g., S. P. Adams, K. S. Kavka, E. J. Wykes, S. B. Holder and G. R. Galluppi, *J. Am. Chem. Soc.,* 1983, 105, 661-663; G. R. Gough, M. J. Bruden and P. T. Gilhiam, *Tetrahedron Lett.,* 1981, 22, 4177-4180). Membrane supports and polymeric membranes (see e.g. Innovation and Perspectives in Solid Phase Synthesis. Peptides, Proteins and Nucleic Acids, ch 21 pp 157-162, 1994, Ed. Roger Epton and U.S. Pat. No. 4,923,901) are also useful for the synthesis of nucleic acids. Once formed, a membrane can be chemically functionalized for use in nucleic acid synthesis. In addition to attachment of a functional group to membrane, use of a linker or spacer group attached to the membrane is also used in some embodiments to minimize steric hindrance between the membrane and the synthesized chain.

Example suitable solid supports also include those generally known in the art to be suitable for use in solid phase methodologies, including, for example, glass sold as Primer™ 200 support, controlled pore glass (CPG), oxalyl-controlled pore glass (see, e.g., Alul, et al., *Nucleic Acids Research,* 1991, 19, 1527), TENTAGEL® Suppor—an aminopolyethyleneglycol derivatized support (see, e.g., Wright, et al., *Tetrahedron Lett.,* 1993, 34, 3373), and POROS®—a copolymer of polystyrene/divinylbenzene.

Surface activated polymers have been demonstrated for use in synthesis of natural and modified nucleic acids and proteins on several solid supports mediums. In some embodiments, a solid support material is any polymer suitably uniform in porosity, having sufficient amine content, and sufficient flexibility to undergo any attendant manipulations without losing integrity. Examples of suitable selected materials include nylon, polypropylene, polyester, polytetrafluoroethylene, polystyrene, polycarbonate, and nitrocellulose. In some embodiments, other materials can serve as a solid support, depending on design in accordance with the present disclosure. In some embodiments, in consideration of some designs, for example, a coated metal, in particular gold or platinum can be selected (see e.g., US publication No. 20010055761). In some embodiments, for example, a nucleoside is anchored to a solid support which is functionalized with hydroxyl or amino residues. In some embodiments, a solid support is derivatized to provide an acid labile trialkoxytrityl group, such as a trimethoxytrityl group (TMT). Without being bound by theory, it is expected that presence of a trialkoxytrityl protecting group may permit initial detritylation under conditions commonly used on DNA synthesizers. In some embodiments, for a faster release of oligonucleotide material in solution with aqueous ammonia, a diglycoate linker is optionally introduced onto the support.

In some embodiments, a provided oligonucleotide is synthesized from 3' to 5' direction. In some embodiments, a provided oligonucleotide is synthesized from 5' to 3' direction. In some embodiments, a nucleic acid is attached to a solid support through its 5' end of the growing nucleic acid, thereby presenting its 3' group for reaction, i.e. using 5'-nucleoside phosphoramidites or in an enzymatic reaction (e.g. ligation and polymerization using nucleoside 5'-triphosphates). In some embodiments, in a 5' to 3' synthesis iterative steps of the present disclosure remain unchanged (e.g. capping and modification on the chiral phosphorus).

In some embodiments, a linking moiety or linker is optionally used to connect a solid support to a first nucleoside linked to a solid support, or a compound comprising a free nucleophilic moiety. In some embodiments, suitable linkers are known such as short moieties which serve to connect a solid support to functional groups (e.g., hydroxyl groups) of initial nucleoside molecules in solid phase synthetic techniques, and can be utilized in accordance with the present disclosure. In some embodiments, a linking moiety is a succinamic acid linker, or a succinate linker (—CO—$CH_2$—$CH_2$—CO—), or an oxalyl linker (—CO—CO—). In some embodiments, a linker is a succinamic acid linker. In some embodiments, a linker is a succinate linker. In some embodiments, a linker is an oxalyl linker. In some embodiments, a linking moiety and a nucleoside are bonded together through an ester bond. In some embodiments, a linking moiety and a nucleoside are bonded together through an amide bond. In some embodiments, a linking moiety connects a nucleoside to another nucleotide or nucleic acid. Example suitable linkers are disclosed in, for example, *Oligonucleotides And Analogues A Practical Approach,* Ekstein, F. Ed., IRL Press, N.Y., 1991, Chapter 1 and Solid-Phase Supports for Oligonucleotide Synthesis, Pon, R. T., *Curr. Prot. Nucleic Acid Chem.,* 2000, 3.1.1-3.1.28.

In some embodiments, a linking moiety is a phosphodiester linkage. In some embodiments, a linking moiety is an H-phosphonate moiety. In some embodiments, a linking moiety is a modified phosphorus linkage as described herein. In some embodiments, a universal linker (UnyLinker) is used to attach a nucleoside, nucleotide, oligonucleotide and/or nucleic acid to a solid support (Ravikumar et al., *Org. Process Res. Dev.,* 2008, 12(3), 399-410). In some embodiments, other universal linkers are used (Pon, R. T., *Curr. Prot. Nucleic Acid Chem.,* 2000, 3.1.1-3.1.28). In some embodiments, various orthogonal linkers (such as disulfide linkers) are used (Pon, R. T., *Curr. Prot. Nucleic Acid Chem.,* 2000, 3.1.1-3.1.28).

Among other things, the present disclosure recognizes that a linker can be chosen or designed to be compatible with a set of reaction conditions employed in synthesis. In some embodiments, to avoid degradation of oligonucleotides and/or to avoid decomposition of certain internucleotidic linkages (e.g. desulfurization), auxiliary groups are selectively removed before de-protection. In some embodiments, DPSE auxiliary groups can selectively be removed by $F^-$. In some embodiments, the present disclosure provides linkers that are stable under a DPSE de-protection condition, e.g., 0.1M TBAF in MeCN, 0.5M HF-$Et_3N$ in THF or MeCN, etc. In some embodiments, PSM auxiliary groups can be readily removed by a base. In some embodiments, a linker is a SP linker. In some embodiments, a linker is succinyl linker. In some embodiments, a linker is Q-linker. In some embodiments, a linker is oxalyl linker. Example use of certain linkers are depicted below. As those skilled in the art will appreciates, sugar rings may have modifications as described herein, e.g., 2'-F, 2'-MOE, 2'-OMe, or $R^{2s}$ and/or $R^{4s}$, etc. In some embodiments, BA is an optionally substituted protected nucleobase, e.g., $A^{bz}$, $C^{ac}$, $G^{ibu}$, U, or, T, etc.

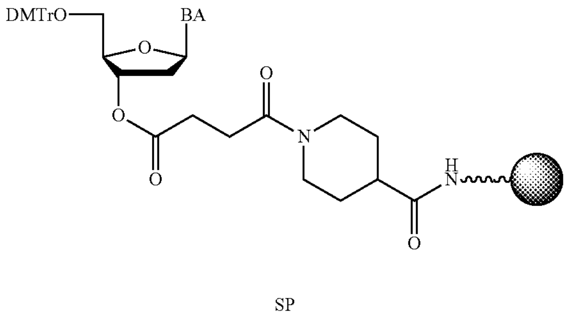

SP

-continued

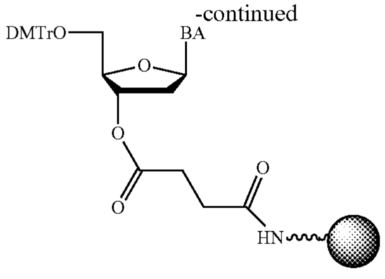

Succinyl

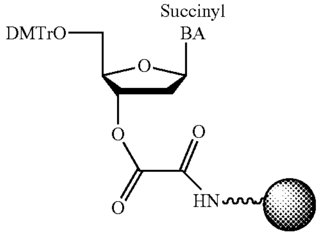

Oxalyl

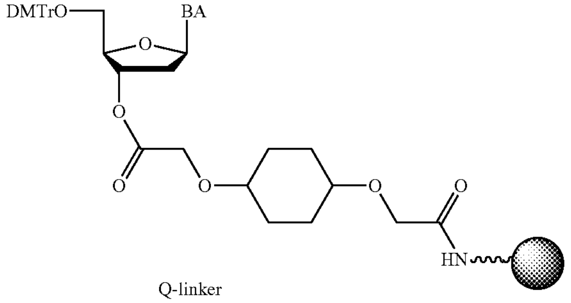

Q-linker

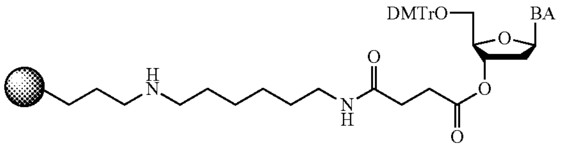

CNA linker (with succinyl linker)

In some embodiments, the present disclosure provides supports and linkers useful for oligonucleotide synthesis (in some cases, loaded with a first nucleoside for oligonucleotide synthesis). In some embodiments, a support is functionalized with amino groups. In some embodiments, a support is functionalized with $—CH_2—(CH_2)_n—CH_2—NH_2$, wherein the $—CH_2—$ end is connected to a support, e.g., CPG. In some embodiments, a first linker is $—CH_2—(CH_2)_n—CH_2—NH—$, wherein the $—CH_2—$ end is connected to a support, e.g., CPG, and the —NH— is connected to a nucleoside, e.g., 3'-OH, through a second linker, e.g., $—C(O)—CH_2—CH_2—C(O)—$, wherein n is as described in the present disclosure. In some embodiments, n is 1. In some embodiments, n is 7.

In some embodiments, a first linker is $—CH_2(CH_2)_n—CH_2—NH—C(O)—X—(CH_2)_m—NH—$, wherein each variable is independently as described in the present disclosure. In some embodiments, a first linker is $—CH_2—(CH_2)_n—CH_2NH—C(O)—X—(CH_2)_m—NH—C(O)—X—(CH_2)_p—NH—$, wherein each variable is independently as described in the present disclosure. In some embodiments, a first linker is $—CH_2—(CH_2)_n—CH_2—NH—C(O)—X—CH_2—CH_2CH_2—O—CH_2—CH_2—O—CH_2—CH_2—O—CH_2—CH_2—CH_2—NH—$, wherein each variable is independently as described in the present disclosure. In some embodiments, a first linker is $—CH_2—(CH_2)_n—CH_2—NH—C(O)—X—CH_2—CH_2—CH_2—CH_2—O—(CH_2—CH_2—O)m-CH_2—CH_2—O—CH_2—CH_2—O—CH_2—CH_2—NH—$, wherein each variable is independently as described in the present disclosure. In some embodiments, a first linker is $—CH_2—(CH_2)_n—CH_2—NH—C(O)—X—CH_2CH—CH_2—O—CH_2—CH_2—CH_2—O—(CH_2—CH_2—CH_2—O)m-CH_2—CH_2—CH_2—O—CH_2—CH_2—CH_2—NH—$, wherein each variable is independently as described in the present disclosure. In some embodiments, a first linker is $—(CH_2)_n—X—(CH_2)_m—NH—$, wherein each variable is independently as described in the present disclosure. In some embodiments, the $—CH_2—$ end is connected to a support, e.g., CPG, and the —NH— is connected to a nucleoside, e.g., 3'-OH, through a second linker, e.g., $—C(O)—CH_2—CH_2—C(O)—$. In some embodiments, a second linker is —C(O)-L-C(O)—, wherein L is as described in the present disclosure. In some embodiments, a second linker is —C(O)-L-C(O)—, wherein L is optionally substituted $C_{1-20}$ aliphatic or heteroaliphatic. In some embodiments, a second linker is —C(O)-L-C(O)—, wherein L is bivalent, optionally substituted, linear, $C_{1-20}$ aliphatic or hetereoaliphatic. In some embodiments, a second linker is —C(O)-L-C(O)—, wherein L is bivalent, unsubstituted, linear, $C_{1-20}$ aliphatic or heteroaliphatic. In some embodiments, a second linker is —C(O)-L-C(O)—, wherein L is bivalent, unsubstituted, linear, $C_{1-20}$ aliphatic or hetereoaliphatic. In some embodiments, a second linker is $—C(O)—(CH_2)n-C(O)—$. In some embodiments, a second linker is $—C(O)—(CH_2)_2—C(O)—$. In some embodiments, one —C(O)— is bonded to an amino group of a first linker, e.g. a terminal $—NH_2$ of a first linker, and the other —C(O)— is bonded to a —OH of a sugar moiety of a nucleoside, e.g., a 3'-OH group. In some embodiments, the $—CH_2—$ end is connected to a support, e.g., CPG, and the —NH— is connected to a nucleoside, e.g., 3'-OH, through a second linker, e.g., $—C(O)—CH_2—CH_2—C(O)—$.

In some embodiments, not all available amino moieties are loaded with nucleoside, e.g., through a second linker $—C(O)—CH_2—CH_2—C(O)—$. In some embodiments, some available amino moiety can be capped with an acyl group, e.g., —C(O)—R forming $—CH_2—(CH_2)_n—CH_2—NH—C(O)—R$, $—CH_2(CH_2)_n—CH_2NH—C(O)—X—(CH_2)_m—NH—C(O)—R$, $—CH_2—(CH_2)n-CH_2—NH—C(O)—X—(CH_2)m-NH—C(O)—X—(CH_2)p-NH—C(O)—R$, $—CH_2—(CH_2)_n—CH_2—NH—C(O)—X—CH_2—CH_2—CH_2—O—CH_2—CH_2—O—CH_2—CH_2—O—CH_2—CH_2—CH_2—NH—C(O)—R$, $—CH_2—(CH_2)_n—CH—NH—C(O)—X—CH_2—CH_2—O—CH_2—CH_2—(CH_2—CH_2—O)m-CH_2—CH_2—O—CH_2—CH_2—O—CH_2—CH_2—NH—C(O)—R$, $—(CH_2)_m—X—(CH_2)—NH—C(O)—R$, or $—CH_2—(CH_2)_n—CH_2—NH—C(O)—X—CH_2—CH_2—CH_2—O—CH_2—CH_2—CH_2—O—(CH_2—CH_2—CH_2—O)m-CH_2—CH_2—CH_2—O—CH_2—CH_2—CH_2—NH—C(O)—R$, wherein each variable is independently as described in the present disclosure, so that unit loading capacity of a support can be adjusted. In some embodiments, R is $—(CH_2)o-$, wherein o is 0-20.

In some embodiments, X is a covalent bond. In some embodiments, X is $—CH_2—$. In some embodiments, X is —N(R')—. In some embodiments, X is —NMe-. In some embodiments, X is —NH—. In some embodiments, X is —O—.

In some embodiments, n is 1-20. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is 11. In some embodiments, n is 12. In some embodiments, n is 13. In some embodiments, n is 14. In some embodiments, n is 15. In some embodiments, m is 1-20. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, o is 0-12. In some embodiments, o is 0. In some embodiments, o is 1. In some embodiments, o is 2. In some embodiments, o is 3. In some embodiments, o is 4. In some embodiments, o is 5. In some embodiments, o is 6. In some embodiments, o is 7. In some embodiments, o is 8. In some embodiments, o is 9. In some embodiments, o is 10. In some embodiments, o is 11. In some embodiments, o is 12. In some embodiments, o is 13. In some embodiments, o is 14. In some embodiments, o is 15.

In some embodiments, a solid support is "functionalized" for loading. In some embodiments, a solid support comprises -first linker-H. In some embodiments, a solid support is CPG-first linker-H. In some embodiments, a solid support is prepared by, e.g., reacting CPG (e.g., —Si—OH of CPG) with H-first linker-$Si(OR)_3$ (e.g., $NH_2$—$(CH_2)_6$—NH—$(CH_2)_3$—$Si(OMe)_3$) to form —Si-first linker-H (e.g., $NH_2$—$(CH_2)_6$—NH—$(CH_2)_3$—Si). In some embodiments, loading is performed by a reaction of CPG-first linker-H (e.g., $NH_2$—$(CH_2)_6$—NH—$(CH_2)_3$—CPG, the —$NH_2$ group as the reaction site (the —NH— group can be capped, e.g., by —C(O)R (e.g., —C(O)$CH_3$))) with a suitable optionally activated second linker-nucleoside reagent, e.g., HO—C(O)—$CH_2$—$CH_2$—C(O)-optionally protected nucleoside (e.g., through 3'-OH) (wherein the second linker is —C(O)—$CH_2$—$CH_2$—C(O)—).

In some embodiments, a provided support after loading of a first nucleoside having the structure of:

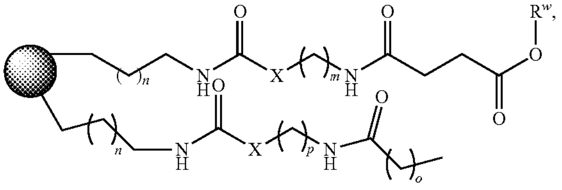

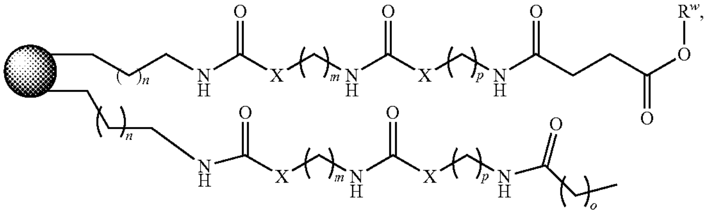

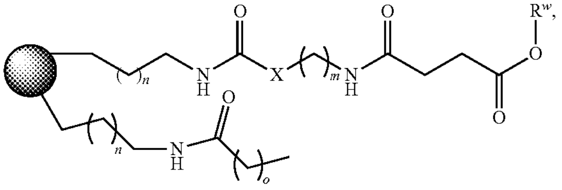

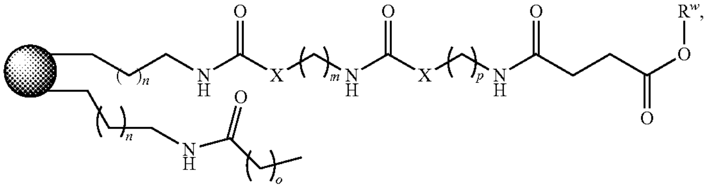

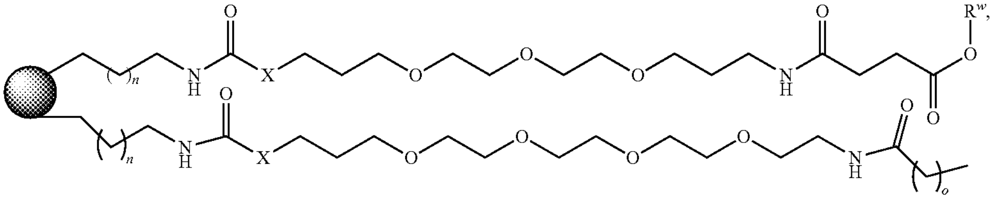

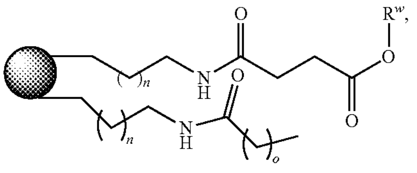

-continued

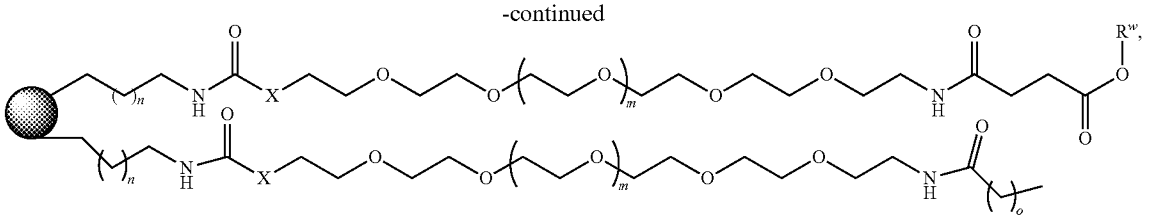

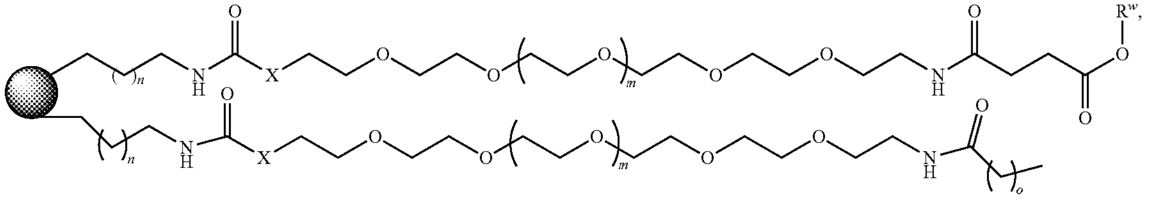

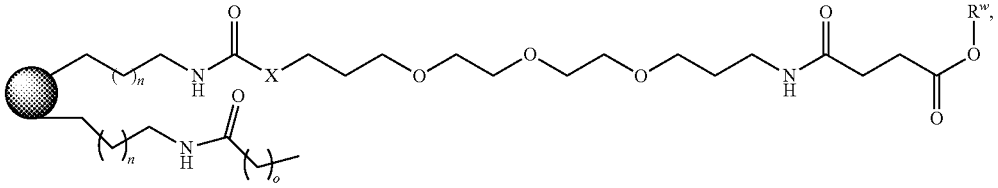

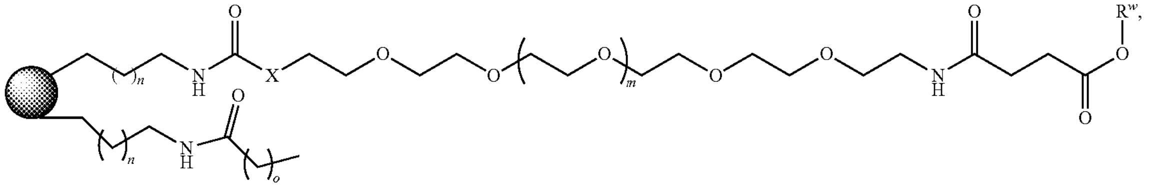

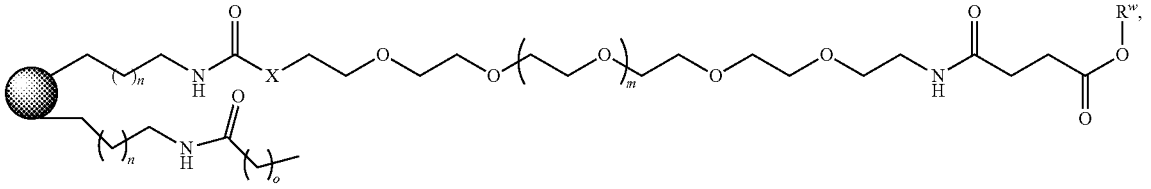

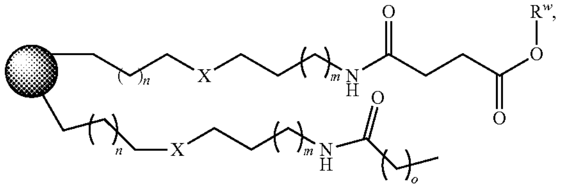

wherein —O—$R^w$ is an nucleoside moiety as described in the present disclosure.

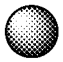

is a support as described in the present disclosure, and each other variable is independently as describe in the present disclosure. In some embodiments, In some embodiments, m is 0-10. In some embodiments, n is 1-7. In some embodiments, X is —O—, —S—, —NH—, —$CH_2$—, m is 3-15, n is 1 or 7, o is 0-12, and p is 3-15. In some embodiments, X is —O—, —S—, —NH—, —$CH_2$—, m is 0-10, n is 1 or 7, o is 0-12, and p is 3-15.

In some embodiments, —O—$R^w$ is a nucleoside moiety of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e. In some embodiments, In some embodiments, $R^W$ is

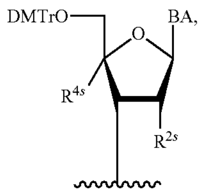

wherein each of $R^{2s}$ and $R^{4s}$ is as described in the present disclosure. In some embodiments, In some embodiments, $R^W$ is

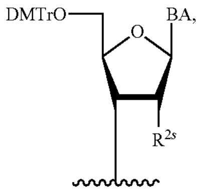

wherein $R^{2s}$ is as described in the present disclosure. In some embodiments, $R^W$ is

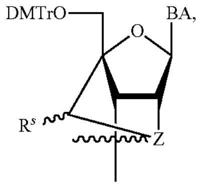

wherein each variable is independently as described in the present disclosure. In some embodiments, BA is a protected nucleobase selected from A, T, C, U, G and 5mC. In some embodiments, BA is C(N-4-Ac or Bz), 5-Me-C(N-4-Ac or Bz), U, T, A(N-6-Bz), or G(N-2-iBu), $R^{2s}$ is —OH, —H, —F, —$OCH_3$, or —$OCH_2CH_2OCH_3$, Z is —O—, —S—, —$CH_2$—, and $R^s$ is —$CH_3$, —$OCH_3$, or —$CH_2CH_3$.

In some embodiments, the present disclosure provides technologies to tune properties of support and/or linker, e.g., chemical compatibility, stability, unit loading capacities, distance to solid core, etc. for oligonucleotide synthesis.

Additional example supports and linkers are described in the Examples.

Improved Results

Provided technologies provide a number of advantages. Among other things, as demonstrated in the present disclosure, provided technologies can greatly improve oligonucleotide synthesis crude purity and yield, particularly for modified and/or chirally pure oligonucleotides that provide a number of properties and activities that are critical for therapeutic purposes. With the capability to provide unexpectedly high crude purity and yield for therapeutically important oligonucleotides, provided technologies can significantly reduce manufacturing costs (through, e.g., simplified purification, greatly improved overall yields, etc.). In some embodiments, provided technologies can be readily scaled up to produce oligonucleotides in sufficient quantities and qualities for clinical purposes. In some embodiments, provided technologies utilizes the same or the same types of chiral auxiliaries (e.g., PSM chiral auxiliaries) that can be readily removed to provide various types of chirally controlled internucleotidic linkages (e.g., phosphorothioate internucleotidic linkages, non-negatively charged internucleotidic linkages, etc.) and can significantly simplify manufacture operations, reduce cost, and/or facilitate downstream formation. In some embodiments, provided technologies with their mild conditions (e.g., removal of chiral auxiliaries under mild base conditions) are particularly useful for preparing oligonucleotides comprising sugars that comprise 2'-OH groups (e.g., RNA sugars); in some embodiments, such sugars are bonded to chiral modified internucleotidic linkages which can be prepared with chirally control.

In some embodiments, provided technologies provides improved reagents compatibility. For example, as demonstrated in the present disclosure, provided technologies provide flexibility to use different reagent systems for oxidation, sulfurization and/or azide reactions, particularly for chirally controlled oligonucleotide synthesis.

Among other things, the present disclosure provides oligonucleotide compositions of high crude purity. In some embodiments, the present disclosure provides chirally controlled oligonucleotide composition of high crude purity. In some embodiments, the present disclosure provides chirally controlled oligonucleotide of high crude purity. In some embodiments, the present disclosure provides oligonucleotide of high crude purity and/or high stereopurity.

In some embodiments, the present disclosure provides a chirally controlled oligonucleotide composition, e.g., a crude chirally controlled oligonucleotide composition, comprising a plurality of oligonucleotides which share:

1) a common base sequence;
2) a common pattern of backbone linkages;
3) common stereochemistry independently at one or more (e.g., about 1-50, about 5-50, about 10-50, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50, etc.) chiral internucleotidic linkages ("chirally controlled internucleotidic linkages");

which composition is chirally controlled in that level of the plurality of oligonucleotides in the composition is predetermined.

In some embodiments, the present disclosure provides a chirally controlled oligonucleotide composition, e.g., a crude chirally controlled oligonucleotide composition, comprising a plurality of oligonucleotides, wherein oligonucleotides of the plurality are of a particular oligonucleotide type defined by:

1) base sequence;
2) pattern of backbone linkages;
3) pattern of backbone chiral centers; and
4) pattern of backbone phosphorus modifications;

which composition is chirally controlled in that level of the plurality of oligonucleotides in the composition is predetermined.

In some embodiments, the present disclosure provides a chirally controlled oligonucleotide composition, e.g., a crude chirally controlled oligonucleotide composition, comprising a plurality of oligonucleotides which share:

1) a common base sequence;
2) a common pattern of backbone linkages; and
3) a common pattern of backbone chiral centers, which composition is a substantially pure preparation of a single oligonucleotide in that a predetermined level of the oligonucleotides in the composition have the common base sequence and length, the common pattern of backbone linkages, and the common pattern of backbone chiral centers.

In some embodiments, the present disclosure provides a chirally controlled oligonucleotide composition, e.g., a crude chirally controlled oligonucleotide composition, comprising a plurality of oligonucleotides, wherein:

oligonuclotides of the plurality share the same base sequence;

oligonucleotides of the plurality share the same pattern of backbone linkages; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least $((DS)^{Nc}*100)\%$ of all oligonucleotides sharing the same base sequence in the crude composition are oligonucleotides of the plurality, wherein DS is 80%-100%, 85%-100%, 90%-100%, or 80%, 85%, 86%, 87%, 88%, 89%, 90%, 91%, 92%, 93%, 94%, 95%, 96%, 970, 98%, 99%, or more, and Nc is the number of chirally controlled internucleotidic linkage (s) (e.g., 1-100, 5-50, 10-50, 1, 2, 3, 4, 5, 6, 7, 8, 9, 10, 11, 12, 13, 14, 15, 16, 17, 18, 19, 20, 21, 22, 23, 24, or 25, etc.).

In some embodiments, the present disclosure provides a chirally controlled oligonucleotide composition, e.g., a crude chirally controlled oligonucleotide composition, comprising a plurality of oligonucleotides, wherein:

oligonucleotides of the plurality share the same constitution; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage, wherein at least $((DS)^{Nc}*100)\%$ of all oligonucleotides sharing the same base sequence in the crude composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

In some embodiments, a provided crude chirally controlled oligonucleotide composition has a crude purity of about 35%, 40%, 45%, 50%, 55%, 60%, 65%, 70%, or 75%, or more. In some embodiments, a crude chirally controlled oligonucleotide composition is cleaved from a support, and before any further purification. In some embodiments, crude chirally controlled oligonucleotide composition is cleaved from a support, after de-salting, and before any further purification. In some embodiments, crude chirally controlled oligonucleotide composition is before any chromatograph or gel purification. In some embodiments, a crude purity is % full-length product. In some embodiments, a crude purity is % full-length product as assessed by LC-UV monitored at UV 260 nm.

In some embodiments, technologies of the present disclosure provide highly efficient oligonucleotide synthesis. In some embodiments, provided technologies are robust, versatile, and flexible (e.g., in terms of yield, purity, reaction conditions, etc.) and can be performed at various scales and/or in parallel (e.g., synthesizing multiple oligonucleotides at the same time (e.g., multiple columns, plate format, microarray, etc.) to provide highly efficient synthesis of multiple oligonucleotides, optionally with control of all structural elements of each oligonucleotide (e.g., chemical modifications of sugars, nucleobases, internucleotidic linkages, etc.; stereochemistry of linkage phosphorus, etc.). In some embodiments, the present disclosure provides technologies for highly efficient preparation of a collection of oligonucleotides, the chemistry and/or stereochemistry of each of which can be individually and independently designed and controlled at each nucleobase, sugar, and/or internucleotidic linkage (e.g., as in chirally controlled oligonucleotide compositions described in the present disclosure). As those skilled in the art appreciate, development of useful oligonucleotides, e.g., oligonucleotides for therapeutic purposes, often comprises assessment of a number of oligonucleotides. The present disclosure, among other things, provides collections of oligonucleotides, in some embodiments, chirally controlled ones, and technologies for preparing such collections. In some embodiments, oligonucleotides, e.g., those of collections of oligonucleotides, are prepared in plate formats for, e.g., storage, screening, etc. In some embodiments, the present disclosure provides technologies for preparing oligonucleotides at various scales, including scales for various formats of plates (e.g., 6, 12, 24, 48, 60, 72, 96, or 384-well plate). In some embodiments, oligonucleotides are provided on microarrays. In some embodiments, the present disclosure provides microarrays of oligonucleotides, each of which is optionally and independently chirally controlled. In some embodiments, the present disclosure provides technologies for synthesizing oligonucleotides on chips to provide oligonucleotide microarrays, with independent control of chemistry and/or stereochemistry of each oligonucleotide if desired. Various microarray technologies (e.g., chips, formats, processes, etc.) can be utilized in accordance with the present disclosure, e.g., those of Twist, Affymetrix, Agilent, etc. Among other things, chemical technologies of the present disclosure (e.g., processes, reagents, conditions, etc.) are robust, versatile, and flexible; in combination with various microarray/chip technologies they are particularly powerful for preparing microarrays of oligonucleotides, e.g., those with chemical modifications and/or stereochemistry control described in the present disclosure. In some embodiments, each oligonucleotide of a provided microarray is independently and optionally chirally controlled. In some embodiments, at least one oligonucleotide of a provided microarray comprises at least one chirally controlled internucleotidic linkage as described herein (e.g., 1, 2, 3, 4, 5, 6, 7, 8, 9, 10, 11, 12, 13, 14, 15, 16, 17, 18, 19, 20, 21, 22, 23, 24, 25 or more; or at least 5%, 10%, 15%, 20%, 25%, 30%, 35%, 40%, 45%, 50%, 55%, 60%, 65%, 70%, 75%, 80%, 85%, 90%, 95% or more of an oligonucleotide; or each chiral internucleotidic linkage is independently chirally controlled). In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5% of the oligonucleotides of a microarray independently comprise at least one chirally controlled internucleotidic linkage as described herein (e.g., 1, 2, 3, 4, 5, 6, 7, 8, 9, 10, 11, 12, 13, 14, 15, 16, 17, 18, 19, 20, 21, 22, 23, 24, 25 or more; or at least 5%, 10%, 15%, 20%, 25%, 30%, 35%, 40%, 45%, 50%, 55%, 60%, 65%, 70%, 75%, 80%, 85%, 90%, 95% or more of an oligonucleotide; or each chiral internucleotidic linkage is independently chirally controlled). In some embodiments, each oligonucleotide of a microarray independently comprises at least one chirally controlled internucleotidic linkage. Microarrays are powerful tools for many applications. Among other things, provided microarrays can be utilized in screenings against various types of agents, e.g., proteins, nucleic acids, small molecules. In some embodiments, differential binding to stereochemical motifs and/or patterns of screened agents are assessed. As appreciated by those skilled in the art, oligonucleotide compositions prepared at a certain scale can be optionally and alternatively provided in many formats as desired. In some embodiments, the present disclosure provides technologies that are particularly useful for preparing collections of oligonucleotides at scales, e.g., for various plate and/or microarray formats.

In some embodiments, technologies of the present disclosure provide highly efficient oligonucleotide synthesis. In some embodiments, provided technologies are robust, versatile, and flexible (e.g., in terms of yield, purity, reaction conditions, etc.) and can be performed at various scales and/or in parallel (e.g., synthesizing multiple oligonucleotides at the same time (e.g., multiple columns, plate format, microarray, etc.) to provide highly efficient synthesis of multiple oligonucleotides, optionally with control of all structural elements of each oligonucleotide (e.g., chemical modifications of sugars, nucleobases, internucleotidic linkages, etc.; stereochemistry of linkage phosphorus, etc.). In some embodiments, the present disclosure provides technologies for highly efficient preparation of a collection of oligonucleotides, the chemistry and/or stereochemistry of each of which can be individually and independently designed and controlled at each nucleobase, sugar, and/or internucleotidic linkage (e.g., as in chirally controlled oligonucleotide compositions described in the present disclosure). As those skilled in the art appreciate, development of useful oligonucleotides, e.g., oligonucleotides for therapeutic purposes, often comprises assessment of a number of oligonucleotides. The present disclosure, among other things, provides collections of oligonucleotides. In some embodiments, chirally controlled ones, and technologies for preparing such collections. In some embodiments, oligonucleotides, e.g., those of collections of oligonucleotides, are prepared in plate formats for, e.g., storage, screening, etc. In some embodiments, the present disclosure provides technologies for preparing oligonucleotides at various scales, including scales for various formats of plates (e.g., 6, 12, 24, 48, 60, 72, 96, or 384-well plate). In some embodiments, oligonucleotides are provided on microarrays. In some embodiments, the present disclosure provides microarrays of oligonucleotides, each of which is optionally and independently chirally controlled. In some embodiments, the present disclosure provides technologies for synthesizing oligonucleotides on chips to provide oligonucleotide microarrays, with independent control of chemistry and/or stereochemistry of each oligonucleotide if desired. Various microarray technologies (e.g., chips, formats, processes, etc.) can be utilized in accordance with the present disclosure, e.g., those of Twist, Affymetrix, Agilent, etc. Among other things, chemical technologies of the present disclosure (e.g., processes, reagents, conditions, etc.) are robust, versatile, and flexible; in combination with various microarray/chip technologies they are particularly powerful for preparing microarrays of oligonucleotides, e.g., those with chemical modifications and/or stereochemistry control described in the present disclosure. In some embodiments, each oligonucleotide of a provided microarray is independently and optionally chirally controlled. In some embodiments, at least one oligonucleotide of a provided microarray comprises at least one chirally controlled internucleotidic linkage as described herein (e.g., 1, 2, 3, 4, 5, 6, 7, 8, 9, 10, 11, 12, 13, 14, 15, 16, 17, 18, 19, 20, 21, 22, 23, 24, 25 or more; or at least 5%, 10%, 15%, 20%, 25%, 30%, 35%, 40%, 45%, 50%, 55%, 60%, 65%, 70%, 75%, 80%, 85%, 90%, 95% or more of an oligonucleotide; or each chiral internucleotidic linkage is independently chirally controlled), In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5% of the oligonucleotides of a microarray independently comprise at least one chirally controlled internucleotidic linkage as described herein (e.g., 1, 2, 3, 4, 5, 6, 7, 8, 9, 10, 11, 12, 13, 14, 15, 16, 17, 18, 19, 20, 21, 22, 23, 24, 25 or more; or at least 5%, 10%, 15%, 20%, 25%, 30%, 35%, 40%, 45%, 50%, 55%, 60%, 65%, 70%, 75%, 80%, 85%, 90%, 95% or more of an oligonucleotide; or each chiral internucleotidic linkage is independently chirally controlled). In some embodiments, each oligonucleotide of a microarray independently comprises at least one chirally controlled internucleotidic linkage. Microarrays are powerful tools for many applications. Among other things, provided microarrays can be utilized in screenings against various types of agents, e.g., proteins, nucleic acids, small molecules. In some embodiments, differential binding to stereochemical motifs and/or patterns of screened agents are assessed. As appreciated by those skilled in the art, oligonucleotide compositions prepared at a certain scale can be optionally and alternatively provided in many formats as desired. In some embodiments, the present disclosure provides technologies that are particularly useful for preparing collections of oligonucleotides at scales, e.g., for various plate and/or microarray formats.

In some embodiments, provided technologies are performed at large scale (e.g., at least about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 450, 500, mmol, etc.). In some embodiments, a scale is at least about 10 mmol. In some embodiments, a scale is at least about 20 mmol. In some embodiments, a scale is at least about 30 mmol. In some embodiments, a scale is at least about 40 mmol. In some embodiments, a scale is at least about 50 mmol. In some embodiments, a scale is at least about 75 mmol. In some embodiments, a scale is at least about 100 mmol. In some embodiments, a scale is at least about 125 mmol. In some embodiments, a scale is at least about 150 mmol. In some embodiments, a scale is at least about 200 mmol. In some embodiments, a scale is at least about 250 mmol. In some embodiments, a scale is at least about 300 mmol. In some embodiments, a scale is at least about 350 mmol. In some embodiments, a scale is at least about 400 mmol. In some embodiments, a scale is at least about 450 mmol. In some embodiments, a scale is at least about 500 mmol. In some embodiments, the present disclosure provides technologies that are particularly useful for large scale synthesis. For example, in some embodiments, the present disclosure provides technologies for performing certain procedures that are typically performed off-column in traditional oligonucleotide synthesis, e.g., chiral auxiliary removal, product cleavage, etc. on column, which can significantly simplify operation and/or lower cost.

Synthetic technologies (e.g., methods, reagents, conditions, etc.) and oligonucleotide compositions are compatible with and can be utilized in combination with various technologies for purification, formulation, enrichment, etc. Such technologies are routinely used to process (e.g., to purity, to concentrate, to dilute, to change solvent/buffer for) oligonucleotides (e.g., after cleavage/deprotection; before or after certain purification, etc.). In some embodiments, ultrafiltration is utilized to increase concentration of a product, e.g., an oligonucleotide, to a desired concentration to, e.g., at least 10, 20, 30, 40, 50, 60, 70, 80, 90, or 100 mg/mL. In some embodiments, diafiltration is utilized to remove a salt and/or change solvent for a solution, e.g., an oligonucleotide product solution. In some embodiments, diafiltration maintains product concentration (e.g., oligonucleotide concentration) of a solution subjected to diafiltration, or does not significantly change product concentration (e.g., less than 100%, 90%, 80%, 75%, 70%, 60%, 50%, 40%, 30%, 25%, 20%, 15%, 10%, 5%, 1% decrease; less than 100%, 90%, 80%, 75%, 70%, 60%, 50%, 40%, 30%, 25%, 20%, 15%, 10%, 5%, 1% increase, etc.). In some embodiments, ultrafiltration and/or diafiltration is utilized to formulate a product in its final form, e.g., after chromatography or other purification steps. In some embodiments, ultrafiltration and/or diafiltration is performed after crude product is obtained and certain purification. In some embodiments, it may be desirable to remove one or more component in a crude product (e.g., fluoride, base, etc.) to protect one or more instruments/equipment to extend life, improve results (e.g., yield, purity, etc.), save reagents, and/or lower cost.

Various purification technologies, e.g., chromatography technologies such as various types of HPLC, UPLC, etc., optionally with various of other technologies such as UV, MS, etc., can be utilized in accordance with the present disclosure. In some embodiments, provided technologies comprise one or more HPLC processes. In some embodiments, provided technologies comprise cartridge purification. Various cartridge purification technologies can be utilized in accordance with the present disclosure. For example, in some embodiments, a cartridge purification is a reverse-phase purification. In some embodiments, a cartridge is a C18 cartridge. In some embodiments, a 5'-protection group, such as DMT, is kept on when performing cartridge purification of an oligonucleotide, e.g., when using C18 cartridge purification. Among other things, the present disclosure provides synthesis technologies that are compatible with various purification technologies. For example, in some embodiments, to keep the 5'-DMT protecting group on for C18 cartridge purification, pH of cleavage conditions can be adjusted, in some cases, increased. Those skilled in the art will appreciate that one or more parameters of provided technologies (e.g., reagents, conditions, reaction times, etc.) can be adjusted to achieve desired results in accordance with the present disclosure. An example procedure for preparing oligonucleotides at a scale useful for plate formats is described in Example 5.

Provided products, e.g., various oligonucleotides as described in the present disclosure, can be formulated in various formats as described in the present disclosure. For example, in some embodiments, provided products are lyophilized (with low temperature and/or pressure) and dried. In some embodiments, products are provided as solids, e.g., of oligonucleotides or salts thereof (e.g., sodium salts or other pharmaceutically acceptable salts), as powders, tablets, etc. In some embodiments, products in solid form are dissolved with a desired solvent, e.g., water, a salt solution, a buffer, etc., before administration to a subject. In some embodiments, products are provided as high-concentration solutions, e.g., in water, a salt solution, a buffer (e.g., PBS, DPBS, etc.). As appreciated by those skilled in the art, such high-concentration solutions can be readily diluted by a suitable solvent, e.g., water, a salt solution, a buffer, etc. to a suitable concentration before administration to a subject. Typically products are stored at low temperature. For example, solutions may be frozen at low temperature for storage. In some embodiments, a form of formulation and/or storage process (e.g., ultrafiltration and/or diafiltration and high-concentration solutions) may provide better results than another form of formulation and/or storage process (e.g., lyophilization and solid forms) (e.g., higher purity, shorter time for preparation before administration, etc.).

As those skilled in the art will appreciate, various oligonucleotides may be efficiently prepared utilizing technologies of the present disclosure, including many biologically active oligonucleotides known in the art. Among other things, technologies of the present disclosure are particularly powerful in that they can effectively prepare chirally controlled oligonucleotide compositions of oligonucleotides, e.g., of a specific stereoisomer (e.g., of mipomersen, nusinersen, RG6042, BIIB067, BIIB078, BIIB080, inotersen, volanesorsen, AKCEA-ANGPTL3-$L_{RX}$, IONIS-GHR-$L_{RX}$, AKCEA-TTR-$L_{RX}$, IONIS-$PKK_{RX}$, IONIS-PKK-$L_{RX}$, IONIS-TMPRSS6-$L_{RX}$, IONIS-ENAC-$2.5_{RX}$, AKCEA-APO(a)-$L_{RX}$, AKCEA-APOCIII-$L_{RX}$, IONIS-$GCGR_{RX}$, IONIS-$FXI_{RX}$, IONIS-$DGAT2_{RX}$, IONIS-AGT-$L_{RX}$, IONIS-AZ4-2.5-$L_{RX}$, IONIS-FXI-$L_{RX}$, IONIS-AR-$2.5_{RX}$, IONIS-STAT3-$2.5_{RX}$, IONIS-$HBV_{RX}$, IONIS-HBV-$L_{RX}$, IONIS-FB-$L_{RX}$, IONIS-JBI1-$2.5_{RX}$, suvodirsen, etc.).

In some embodiments, oligonucleotides and/or compositions that can be prepared by technologies herein include those described in US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, WO 2019/217784, etc. Product oligonucleotides and compositions thereof are useful for many purposes, e.g., those described in US20150211006, US20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, WO 2019/217784, etc. In some embodiments, product oligonucleotides and compositions thereof can modulate levels and/or functions of various products of nucleic acid sequences. In some embodiments, product oligonucleotides and compositions, particularly chirally controlled oligonucleotides and compositions, are useful for treating a variety of disease. In some embodiments, the present disclosure provides pharmaceutically acceptable salts of oligonucleotides. In some embodiments, oligonucleotide compositions are pharmaceutical compositions.

In some embodiments, a final product oligonucleotide is WV-937, WV-1077, WV-1078, WV-1079, WV-1085, WV-1086, WV-1090, WV-1091, WV-1092, WV-1497, WV-1508, WV-1510, WV-2076, WV-2378, WV-2380, WV-2417, WV-2418, WV-2595, WV-2601, WV-2602, WV-2603, WV-2618, WV-2619, WV-2671, WV-887, WV-892, WV-896, WV-1714, WV-2444, WV-2445, WV-2526, WV-2527, WV-2528, WV-2530, WV-2531, WV-2578, WV-2580, WV-2587, WV-3047, WV-3152, WV-3472, WV-3473, WV-3507, WV-3508, WV-3509, WV-3510, WV-3511, WV-3512, WV-3513, WV-3514, WV-3515, WV-3545, WV-3546, WV-9517, WV-12555, WV-12556, WV-12558, WV-12876, WV-12877, WV-12878, WV-12880, WV-13826, WV-13835, WV-13864, or WV-14344. In some embodiments, a final product oligonucleotide is WV-3473. In some embodiments, a final product composition is a chirally controlled oligonucleotide composition of WV-937, WV-1077, WV-1078, WV-1079, WV-1085, WV-1086, WV-1090, WV-1091, WV-1092, WV-1508, WV-1510, WV-2378, WV-2380, WV-2417, WV-2418, WV-2595, WV-2601, WV-2602, WV-2603, WV-2671, WV-887, WV-892, WV-896, WV-2444, WV-2445, WV-2526, WV-2527, WV-2528, WV-2530, WV-2531, WV-3152, WV-3472, WV-3473, WV-3507, WV-3508, WV-3509, WV-3510, WV-3511, WV-3512, WV-3513, WV-3514, WV-3515, WV-3545, WV-3546, WV-9517, WV-12555, WV-12556, WV-12558, WV-12876, WV-12877, WV-12878, WV-12880, WV-13826, WV-13835, WV-13864, or WV-14344. In some embodiments, a final product composition is a chirally controlled oligonucleotide composition of WV-3473.

Certain oligonucleotides are presented in Table O-1 below. In some embodiments, the present disclosure provides chirally controlled oligonucleotide compositions of an oligonucleotide (or a stereoisomer thereof) of Table O-1 (SEQ ID NOS: 1-65).

TABLE O-1

Example Oligonucleotides.

| ID | SEQ ID NO | Description | Naked Base Sequence | Linkage/ Stereo-chemistry |
|---|---|---|---|---|
| WV-937 | 1 | G * SG * SC * SA * SC * SA * SA * SG * SG * SG * SC * SA * SC * RA * SG * SA * SC * ST * ST * SC | GGCACAAGGGCA CAGACTTC | SSSSS SSSSS SSRSS SSSS |
| WV-1077 | 2 | mA * SmU * SmU * SmA * SmA * SmU * SA * SA * SA * ST * ST * SG * ST * SC * RA * ST * SmA * SmC * SmC | AUUAAUAAATTGTC ATCACC | SSSSS SSSSS SSSRS SSSS |
| WV-1078 | 3 | mA * RmU * RmU * RmA * RmA * RmU * SA * SA * SA * ST * ST * SG * sT * SC * RA * ST * SmC * RmA * RmC * RmC | AUUAAUAAATTGTC ATCACC | RRRRR SSSSS SSSRS SRRR |
| WV-1079 | 4 | mA * SmU * SmU * SmA * SmA * SmU * SmA * SmA * SA * ST * ST * SG * ST * SC * RA * ST * SC * SA * SC * SC | AUUAAUAAATTGTC ATCACC | SSSSS SSSSS SSSRS SSSS |
| WV-1085 | 5 | mG * SmG* SmC * SmA * SmC * SA * SA * SG * SG * SG * SC * SA * SC * RA * SG * SmA * SmC * SmU * SmU * SmC | GGCACAAGGGCA CAGACUUC | SSSSS SSSSS SSRSS SSSS |
| WV-1086 | 6 | mG * RmG * RmC * RmA * RmC * SA * SA * SG * SG * SG * SC * SA * SC * RA * SG * SmA * RmC * RmU * RmU * RmC | GGCACAAGGGCA CAGACUUC | RRRRS SSSSS SSRSS RRRR |
| WV-1090 | 7 | mGmGmCmAmCmAmAmG * SG * SG * SC * SA * SC * RA * SG * SA * SC * ST * ST * SC | GGCACAAGGGCA CAGACTTC | OOOOO OOSSS SSRSS SSSS |
| WV-1091 | 8 | mG * RmGmCmAmC * SA * SA * SG * SG * SG * SC * SA * SC * RA * SG * SmAmCmUmU * RmC | GGCACAAGGGCA CAGACUUC | ROOOS SSSSS SSRSS OOOR |
| WV-1092 | 9 | mG * SmGmCmAmC * SA * SA * SG * SG * SG * SC * SA * SC * RA * SG * SmAmCmUmU * SmC | GGCACAAGGGCA CAGACUUC | SOOOS SSSSS SSRSS OOOS |
| WV-1497 | 10 | mG * mGmCmAmC * A * A * G * G * G * C * A * C * A * G * mAmCmUmU * mC | GGCACAAGGGCA CAGACUUC | XOOOX XXXXX XXXXX OOOX |
| WV-1508 | 11 | A * SmUmUmAmAmU * SA * SA * SA * ST * ST * SG * ST * SC * RA * ST * SmCmAmC * SC | AUUAAUAAATTGTC ATCACC | SOOOO SSSSS SSSRS SOOS |
| WV-1510 | 12 | G * SmGmCmAmC * SA * SA * SG * SG * SG* SC * SA * SC * RA * SG * SmAmCmUmU * SC | GGCACAAGGGCA CAGACUUC | SOOOS SSSSS SSRSS OOOS |
| WV-2076 | 13 | mU * mAmAmUmA * A * A * T * T * G * T * C * A * T * C * mAmCmCmA * mG | UAAUAAATTGTCAT CACCAG | XOOOX XXXXX XXXXX OOOX |
| WV-2378 | 14 | mG * SmCmAmCmA * SA * SG * SG * SG * SC * SA * SC * RA * SG * SA * SmCmUmUmC * SmC | GCACAAGGGCA CAGACUUCC | SOOOS SSSSS SRSSS OOOS |
| WV-2380 | 15 | mC * SmAmCmAmA * SG * SG * SG * SC * SA * SC * RA * SG * SA * SC * SmUmUmCmC * SmA | CACAAGGGCACAGA CUUCCA | SOOOS SSSSS RSSSS OOOS |
| WV-2417 | 16 | mA * SmUmAmAmA * ST * ST * SG * ST * SC * RA * ST * SC * SA * SC * SmCmAmGmA * SmA | AUAAATTGTCATCA CCAGAA | SOOOS SSSSR SSSSS OOOS |
| WV-2418 | 17 | mA * SmAmUmAmA * SA * ST * ST * SG * ST * SC * RA * ST * SC * SA * SmCmCmAmG * SmA | AAUAAATTGTCATC ACCAGA | SOOOS SSSSS RSSSS OOOS |
| WV-2595 | 18 | mG * SmGmGmUmC * SC * ST * SC * SC * SC * SC * SA * SC * RA * SG * SmAmGmGmG * SmA | GGGUCCTCCCCACA GAGGGA | SOOOS SSSSS SSRSS OOOS |
| WV-2601 | 19 | mG * SmCmAmCmA * SC * SA * SG * ST * SA * SG * RA * ST * SG * SA * SmGmGmGmA * SmG | GCACACAGTAGATG AGGGAG | SOOOS SSSSS RSSSS OOOS |
| WV-2602 | 20 | mU * SmGmCmAmC * SA * SC * SA * SG * ST * SA * SG * RA * ST * SG * SmAmGmGmG * SmA | UGCACACAGTAGAT GAGGGA | SOOOS SSSSS SRSSS OOOS |

TABLE O-1-continued

Example Oligonucleotides.

| ID | SEQ ID NO | Description | Naked Base Sequence | Linkage/ Stereo-chemistry |
|---|---|---|---|---|
| WV-2603 | 21 | mG * SmUmGmCmA * SC * SA * SC * SA * SG * ST * SA * SG * RA * ST * SmGmAmGmG * SmG | GUGCACACAGTAGA TGAGGG | SOOOS SSSSS SSRSS OOOS |
| WV-2618 | 22 | m-U * mGmCmAmC * A*C * A * G * T * A * G * A * T * G * mAmGmGmG * mA | UGCACACAGTAGAT GAGGGA | XOOOX XXXXX XXXXX OOOX |
| WV-2619 | 23 | mG * mUmGmCmA * C * A * C * A * G * T * A * G * A * T * mGmAmGmG * mG | GUGCACACAGTAGA TGAGGG | XOOOX XXXXX XXXXX OOOX |
| WV-2671 | 24 | mG * SmG * SmGmUmC * SC * ST * SC * SC * SC * SC * SA * SC * RA * SG * SmAmGmG * SmG * SmA | GGGUCCTCCCCACA GAGGGA | SSOOS SSSSS SSRSS OOSS |
| WV-887 | 25 | mU * SmC * SmA * SmA * RmG * RmG * RmA * RmmA * RmG * RmA * RmU * RmG * RmG * RmC * RmA * RmU * RmU * SmU * SmC * SmU | UCAAGGAAGAUGGC AUUUCU | SSSRRRRRRRRRRR RSSS |
| WV-892 | 26 | mU * SmC * RmA * RmA * RmG * RmG * RmA * RmA * RmG * RmA * RmU * RmG * RmG * RmC * RmA *RmU * RmU * RmU * RmC * SmU | UCAAGGAAGAUGGC AUUUCU | SRRRRRRRRRRRRR RRRS |
| WV-896 | 27 | mU * SmC * SmA * RmA * RmG * RmG * RmA * RmA * RmG * RmA * RmU * SmG * RmG * RmC * SmA * RmU * SmU * SmU * SmC * SmU | UCAAGGAAGAUGGC AUUUCU | SSRRRRRRRSRRSRS SSS |
| WV-1714 | 28 | fU * fC * fA * fA * fG * fG * mA * mA * mG * mA * mU * mG * mG * mC * fA * fU * fU * fU * fC * fU | UCAAGGAAGAUGGC AUUUCU | XXXXX XXXXX XXXXX XXXX |
| WV-2444 | 29 | fU * SfC * SfA * SfA * SfG * SfG * SmA * RmA * RmG * RmA * RmU * RmG * RmG * RmC * SfA * SfU * SfU * SfU * SfC * SfU | UCAAGGAAGAUGGC AUUUCU | SSSSSSRRRRRRRSSS SSS |
| WV-2445 | 30 | fU * SfC * SfA * SfA * SfG * SmG * RmA * RmA * RmG * RmA * RmU * RmG * RmG * RmC * RmA * SfU * SfU * SfU * SfC * SfU | UCAAGGAAGAUGGC AUUUCU | SSSSSRRRRRRRRRSS SSS |
| WV-2526 | 31 | fU * SfC * SfA * SfA * SfG * SfG * SfA * SfA * RmG * RmA * RmU * RmG * RmG * SfC * SfA * SfU * SfU * SfU * SfC * SfU | UCAAGGAAGAUGGC AUUUCU | SSSSSSSRRRRRSSSSS SS |
| WV-2527 | 32 | fU * SfC * SfA * SfA * SfG * SfG * sfA * SfA * SmG * RmA * RmU * RmG * SfG * SfC * SfA * SfU * SfU * SfU * SfC * SfU | UCAAGGAAGAUGGC AUUUCU | SSSSSSSSRRRSSSSSS SS |
| WV-2528 | 33 | fU * SfC * SfA * SfA * SfG * SfG * SfA * SfA * SfG * SmA * RmU * SfG * SfG * SfC * SfA * SfU * SfU * SfU * SfC * SfU | UCAAGGAAGAUGGC AUUUCU | SSSSSSSSSRSSSSSSSS S |
| WV-2530 | 34 | fU * SfC * SfA * SfA * SfG * SfG * SfA * SfA * SmG mA mU mG * SfG * SfC * SfA * SfU * SfU * SfU * SfC * SfU | UCAAGGAAGAUGGC AUUUCU | SSSSSSSSOOOSSSSSS SS |
| WV-2531 | 35 | fU * SfC * SfA * SfA * SfG * SfG * SfA * SfA * SfG * S mA mU * SfG * SfG * SfC * SfA * SfU * SfU * SfU * SfC * SfU | UCAAGGAAGAUGGC AUUUCU | SSSSSSSSSOSSSSSSS SS |
| WV-2578 | 36 | Mod013L001 * mU * mC * mA * mA * mG * mG * mA * mA * mG * mA * mU * mG * mG * mC * mA * mU * mU * mU * mC * mU | UCAAGGAAGAUGGC AUUUCU | XXXXX XXXXX XXXXX XXXXX |
| WV-2580 | 37 | Mod005L001 * mU * mC * mA * mA * mG * mG * mA * mA * mG * mA * mU * mG * mG * mC * mA * mU * mU * mU * mC * mU | UCAAGGAAGAUGGC AUUUCU | XXXXX XXXXX XXXXX XXXXX |
| WV-2587 | 38 | Mod020L001 * mU * mC * mA * mA * mG * mG * mA * mA * mG * mA * mU * mG * mG * mC * mA * mU * mU * mU * mC * mU | UCAAGGAAGAUGGC AUUUCU | XXXXX XXXXX XXXXX XXXXX |
| WV-3047 | 39 | fU * fC * fA * fA * fG * fG * mA * mA * mG * mA * fU * mG * mG * fC * fA * fU * fU * fU * fC * fU | UCAAGGAAGAUGGC AUUUCU | XXXXX XXXXX XXXXX XXXX |

TABLE O-1-continued

Example Oligonucleotides.

| ID | SEQ ID NO | Description | Naked Base Sequence | Linkage/ Stereo- chemistry |
|---|---|---|---|---|
| WV-3152 | 40 | fU * SfC * SfA * SfA * SfG * SfG * SmAfA * SmGfA * SmUfG * SmGfC * SfA * SfU * SfU * SfU * SfC * SfU | UCAAGGAAGAUGGC AUUUCU | SSSSSSOSOSOSOSSSS SS |
| WV-3472 | 41 | fU * SfC * SfA * SfA * SfG * SfG * SmAfA * SmGfA * SfU * SmG mGfC * SfA * SfU * SfU * SfU * SfC * SfU | UCAAGGAAGAUGGC AUUUCU | SSSSSSOSOSSOOSSSS SS |
| WV-3473 | 42 | fU * SfC * SfA * SfA * SfG * SfG * SmAfA * SmGmA * SfU * SmG mGfC * SfA * SfU * SfU * SfU * SfC * SfU | UCAAGGAAGAUGGC AUUUCU | SSSSSSOSOSSOOSSSS SS |
| WV-3507 | 43 | fU * SfC * SfA * SfA * SfG * SfG * SmAfA* SmGmAfU * SmGmGfC * SfA * SfU * SfU * SfU * SfC * SfU | UCAAGGAAGAUGGC AUUUCU | SSSSSSOSOOSOOSSS SSS |
| WV-3508 | 44 | fU * SfC * SfA * SfA * SfG * SfG * SmAfA * SmGfA * SfU * SmG mGfC * SfAfU * SfU * SfU * SfC * SfU | UCAAGGAAGAUGGC AUUUCU | SSSSSSOSOSSOOSOS SSS |
| WV-3509 | 45 | fU * SfC * SfA * SfA * SfG * SfG * SmAfA * SmGmA * fU * SmG mGfC * SfAfU * SfU * SfU * SfC * SfU | UCAAGGAAGAUGGC AUUUCU | SSSSSSOSOSSOOSOS SSS |
| WV-3510 | 46 | fU * SfC * SfA * SfA * SfG * SfG * SmAfA * SmGfAfU * SmGmGfC * SmA * SfU * SfU * SfU * SfC * SfU | UCAAGGAAGAUGGC AUUUCU | SSSSSSOSOOSOOSSS SSS |
| WV-3511 | 47 | fU * SfC * SfA * SfA * SfG * SfG * SmAfA * SmGmAfU * SmGmGfC * SmA * SfU * SfU * SfU * SfC * SfU | UCAAGGAAGAUGGC AUUUCU | SSSSSSOSOOSOOSSS SSS |
| WV-3512 | 48 | fU * SfC * SfA * SfA * SfG * SfG * SmAfA * SmGfAfU * SmGmGfC * SmAfU * SfU * SfU * SfC * SfU | UCAAGGAAGAUGGC AUUUCU | SSSSSSOSOOSOOSOS SSS |
| WV-3513 | 49 | fU * SfC * SfA * SfA * SfG * SfG * SmAfA * SmGmAfU * SmGmGfC * SmAfU * SfU * SfU * SfC * SfU | UCAAGGAAGAUGGC AUUUCU | SSSSSSOSOOSOOSOS SSS |
| WV-3514 | 50 | fU * SfC * SfA * SfA * SfG * SfG * SmAfA * SmGfAfU * SmGmGfC * SfAfU * SfU * SfU * SfC * SfU | UCAAGGAAGAUGGC AUUUCU | SSSSSSOSOOSOOSOS SSS |
| WV-3515 | 51 | fU * SfC * SfA * SfA * SfG * SfG * SmAfA * SmGmAfU * SmGmGfC * SfAfU * SfU * SfU * SfC * SfU | UCAAGGAAGAUGGC AUUUCU | SSSSSSOSOOSOOSOS SSS |
| WV-3545 | 52 | Mod015L001fU * SfC * SfA * SfA * SfG * SfG * SmAfA * SmGmA * SfU * SmG mGfC * SfA * SfU * SfU * SfU * SfC * SfU | UCAAGGAAGAUGGC AUUUCU | OSSSSSSOSOSSOOSS SSSS |
| WV-3546 | 53 | Mod020L001fU * SfC * SfA * SfA * SfG * SfG * SmAfA * SmGmnA * SfU * SmGmGfC * SfA * SfU * SfU * SfU * SfC * SfU | UCAAGGAAGAUGGC AUUUCU | OSSSSSSOSOSSOOSS SSSS |
| WV-9517 | 54 | fC * SfU * SfC * SfC * SfG * SfG * SfU * SfU * SmCfU * SmG * SfA * SmAmGfG * SfU * SfG * SfU * SfU * SfC | CUCCGGUUCUGAAG GUGUUC | SSSSSSSSOSSSOOSSS SS |
| WV-12555 | 55 | fC * SfU * SfC * SfC * SfG * SfG * SfU * SfU * SmCn001RfU * SmG * SfA * SmAn001RfG * SfG * SfU * SfG * SfU * SfU * SfC | CUCCGGUUCUGAAG GUGUUC | SSSSSSSSnRS SSnRSSSSSS |
| WV-12556 | 56 | fC * SfU * SfC * SfC * SfG * SfG * SfU * SfU * SmCn001RfU * SmG * SfA * SmAn001RmG * SfG * SfU * SfG * SfU * SfU * SfC | CUCCGGUUCUGAAG GUGUUC | SSSSSSSSnRS SSnRSSSSSS |

TABLE O-1-continued

Example Oligonucleotides.

| ID | SEQ ID NO | Description | Naked Base Sequence | Linkage/ Stereo-chemistry |
|---|---|---|---|---|
| WV-12558 | 57 | fC * SfU * SfC * SfC * SfG * SfG * SfU * SfU * SmCn001SFU * SmG * SfA * SmAn001SfG * SfG * SfU * SfG * SfU * SfU * SfC | CUCCGGUUCUGAAG GUGUUC | SSSSSSSSnSS SSnSSSSSSS |
| WV-12876 | 58 | fC * SfU * SfCn001fC * SfG * SfGn001fU * SfU * SmCn001fU * SmG * SfA * SmAn001mGn001fG * SfU * SfGn001fU * SfU * SfC | CUCCGGUUCUGAAG GUGUUC | SSnXSSnXSSnX SSSnXnXSSnXSS |
| WV-12877 | 59 | fC * SfU * SfCn001fC * SfG * SfGn001fU * SfU * SmCn001fU * SmG * SfA * SmAn001fG * SfG * SfU * SfGn001fU * SfU * SfC | CUCCGGUUCUGAAG GUGUUC | SSnXSSnXSSnXS SSnXSSSnXSS |
| WV-12878 | 60 | fC * SfU * SfCn001fC * SfG * SfGn001fU * SfU * SmCn001fU * SmG * SfA * SmAn001mG *SfG * SfU * SfGn001fU * SfU * SfC | CUCCGGUUCUGAAG GUGUUC | SSnXSSnXSSnXS SSnXSSSnXSS |
| WV-13826 | 61 | fU * SfC * SfC * SfG * SfG * SfU * SfU * SmCfU * SmG * SfA * SmAmGfG * SfU * SfG * SfU * SfU * SfC | UCCGGUUCUGAAGG UGUUC | SSSSSSSOSSS OOSSSSS |
| WV-12880 | 62 | fC * SfU * SfCn001fC * SfG * SfGn001fU * SfU * SmCfU * SmG * SfA * SmAfG * SfG * SfU * SfGn001fU * SfU * SfC | CUCCGGUUCUGAAG GUGUUC | SSnXSSnXSSOS SSOSSSnXSS |
| WV-14344 | 63 | fC * SfU * SfCn001RfC * SfG * SfGn001RfU * SfU * SmCfU * SmG * SfA * SmAfGfG * SfU * SfGn001RfU * SfU * SfC | CUCCGGUUCUGAAG GUGUUC | SSnRSSnRSSOS SSOOSSnRSS |
| WV-13835 | 64 | fU * SfC * SfC * SfG * SfG * SfU * SfU * SmCfU * SmG * SfA * SmAmGfG * SfU * SfG * SfU * SfU * SfC * SfU | UCCGGUUCUGAAGG UGUUCU | SSSSSSSOSSS OOSSSSSS |
| WV-13864 | 65 | fC * SfU * SfCn001RfC * SfG * SfGn001RfU * SfU * SmCfU * SmG * SfA * SmAfG * SfG * SfU * SfGn001RfU * SfU * SfC | CUCCGGUUCUGAAG GUGUUC | SSnRSSnRSSOSS SOSSSnRSS |

Spaces in Table O-1 are utilized for formatting and readability, e.g., OXXXXX XXXXX XXXXX XXXX illustrates the same stereochemistry as OXXXXXXXXXXXXXXXXXXX;
* S and *S both indicate phosphorothioate internucleotidic linkage wherein the linkage phosphorus has Sp configuration; etc.
Oligonucleotides listed in Tables A1 are single-stranded unless otherwise specified; they may be used as a single strand, or as a strand to form complexes with one or more other strands.
Some sequences, due to their length, are divided into multiple lines. As appreciated by those skilled in the art, nucleoside units are unmodified and contain unmodified nucleobases and 2'-deoxy sugars unless otherwise indicated with modifications (e.g., modified with f, m, m5, etc); linkages, unless otherwise indicated, are natural phosphate linkages; and acidic/basic groups may independently exist in their salt forms. Moieties and modifications in oligonucleotides (or other compounds, e.g., those useful for preparing provided oligonucleotides comprising these moieties or modifications):

f: 2'-F modification on the following nucleoside (e.g., fA

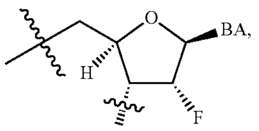

wherein BA is nucleobase A));

L001: C6 amino linker (C6, —NH—$(CH_2)_6$—) wherein —NH— is connected to Mod (e.g., through —C(O)— in Mod) or —H, and —$(CH_2)_6$— is connected to the 5'-end (or 3'-end if indicated) of oligonucleotide chain through, e.g., phosphodiester (—O—P(O)(OH)—O—. May exist as a salt form. May be illustrated in the Tables as O or PO), phosphorothioate (—O—P(O)(SH)—O—. May exist as a salt form. May be illustrated in the Tables as * if the phosphorothioate not chirally controlled, *S, S, or Sp, if chirally controlled and has an Sp configuration, and *R, R, or Rp, if chirally controlled and has an Rp configuration), or phosphorodithioate (—O—P(S)(SH)—O—. May exist as a salt form. May be illustrated in the Tables as PS2 or: or D) linkage. May also be referred to as C6 linker or C6 amine linker);

m: 2'-OMe modification on the following nucleoside (e.g., mA

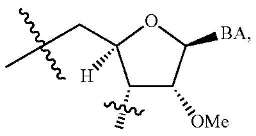

wherein BA is nucleobase A));

Mod005 (its —C(O)— may connect to, e.g., —NH— of a linker such as L001 as specified in the description of an oligonucleotide):

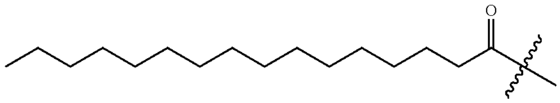
;

Mod013 (its —C(O)— may connect to, e.g., —NH— of a linker such as L001 as specified in the description of an oligonucleotide):

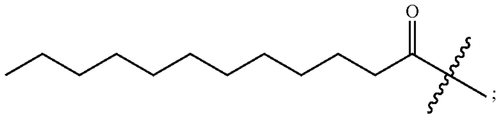 [SMILES: *C(=O)CCCCCCCCCCC]
;

Mod015 (its —C(O)— may connect to, e.g., —NH— of a linker such as L001 as specified in the description of an oligonucleotide):

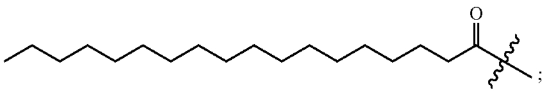 [SMILES: *C(=O)CCCCCCCCCCCCCCCCC]
;

Mod020 (its —C(O)— may connect to, e.g., —NH— of a linker such as L001 as specified in the description of an oligonucleotide):

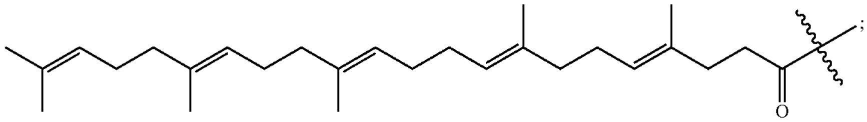 [SMILES: *C(=O)CC/C(C)=C/CC/C(C)=C/CC/C=C(\C)CC/C=C(\C)CCC=C(C)C]
;

n001; non-negatively charged linkage

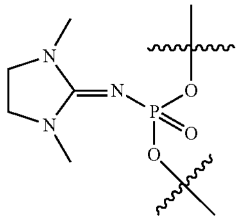 [SMILES: *OP(=O)(N=C1N(C)CCN1C)O*]

(which is stereorandom unless otherwise indicated (e.g., as n001R, or n001S));

n001R: n001 being chirally controlled and having the Rp configuration;

n001S: n001 being chirally controlled and having the Sp configuration:

nX: in Linkage/Stereochemistry, nX indicates a stereorandom n001;

nR: in Linkage/Stereochemistry, nR indicates n001 being chirally controlled and having the Rp configuration (n001R);

nS: in Linkage/Stereochemistry, nS indicates n001 being chirally controlled and having the Sp configuration (n001S):

O, PO: phosphodiester (phosphate). When no internucleotidic linkage is specified between two nucleoside units, the internucleotidic linkage is a phosphodiester linkage (natural phosphate linkage) unless otherwise specified. O may also represent a phosphodiester linkage connecting a linker, e.g., L001, and the 5'-carbon of a 5'-terminal sugar of the oligonucleotide chain (e.g., the underlined O in OSSSSSSOSOSSOOSSSSSS for WV-3545):

*, PS: phosphorothioate. * may also represent a phosphorothioate linkage connecting a linker, e.g., L001, and the 5'-carbon of a 5'-terminal sugar of the oligonucleotide chain (e.g., the underlined * in Mod013L001*mU*mC*mA*mA*mG*mG*mA*mA*mG*mA*mU*mG*mG*mC*mA*mU*mU*mU*mC*mU) (SEQ ID NO: 197):

*R, R (in Linkage/Stereochemistry). Rp: phosphorothioate in Rp conformation;

*S, S (in Linkage/Stereochemistry), Sp: phosphorothioate in Sp conformation;

X: in Linkage/Stereochemistry, X indicates stereorandom phosphorothioate.

In some embodiments, in an oligonucleotide of the present disclosure, each base is optionally protected (e.g., as commonly practiced in oligonucleotide synthesis), each internucleotidic linkage independently has the structure of formula VII or a salt form thereof, wherein:

for the internucleotidic linkage that is the first internucleotidic linkage from the 5'-end, $P^L$ is P, P(═O), P(═S) or $P^N$, and its —X-$L^s$-$R^5$ is -$L^7$-$R^1$; or its —X-$L^s$-$R^5$ is —S-$L^s$-$R^5$; or its —X-$L^s$-$R^5$ is of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —H or —C(O)R'; and for each internucleotidic linkage that is not the first internucleotidic linkage from the 5'-end, its $P^L$ is independently P(═O), P(═S) or $P^N$, and its —X-$L^s$-$R^5$ is independently -$L^7$-$R^1$; or —S-$L^s$-$R^5$; or of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'.

In some embodiments, for the internucleotidic linkage that is the first internucleotidic linkage from the 5'-end, $P^L$ is P, P(═O), P(═S) or $P^N$, and its —X-$L^s$-$R^5$ is -$L^7$-$R^1$, wherein $L^7$ is —O—; or its —X-$L^s$-$R^5$ is of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —H or —C(O)R'; and for each internucleotidic linkage that is not the first internucleotidic linkage from the 5'-end, its $P^L$ is independently P(═O), P(═S) or $P^N$, and its —X-$L^s$-$R^5$ is independently -$L^7$-$R^1$, wherein $L^7$ is —O—; or of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'.

In some embodiments, for the internucleotidic linkage that is the first internucleotidic linkage from the 5'-end, $P^L$ is P. In some embodiments, for the internucleotidic linkage that is the first internucleotidic linkage from the 5'-end, $P^L$ is P, and its —X-$L^s$-$R^5$ is -$L^7$-$R^1$, wherein $L^7$ is —O—; or its —X-$L^s$-$R^5$ is of such a structure that H—X-$L^s$-$R^5$ is a compound of formula I, I-a, I-a-1, I-a-2, I-b, I-c, I-d, I-e, II, II-a, II-b, III, III-a, or III-b, wherein $R^6$ is —H (e.g., in a coupling product oligonucleotide). In some embodiments, for the internucleotidic linkage that is the first internucleotidic linkage from the 5'-end, $P^L$ is P, and in each internucleotidic linkage, —X-$L^s$-$R^5$ is independently -$L^7$-$R^1$, wherein $L^7$ is —O—; or its —X-$L^s$-$R^5$ is of such a structure that H—X-$L^s$-$R^5$ is a compound of formula I, I-a, I-a-1, I-a-2, I-b, I-c, I-d, I-e, II, II-a, II-b, III, III-a, or III-b, wherein $R^6$ is —C(O)R'(e.g., in a pre-modification capping product oligonucleotide). In some embodiments, in each internucleotidic linkage, $P^L$ is independently P(═O), P(═S) or $P^N$, and —X-$L^s$-$R^5$ is independently -$L^7$-$R^1$; or —S-$L^s$-$R^5$; or of such a structure that H—X-$L^s$-$R^5$ is a compound of formula I, I-a, I-a-1, I-a-2, I-b, I-c, I-d, I-e, II, II-a, II-b, III, III-a, or III-b, wherein $R^6$ is —C(O)R'(e.g., in a modification product oligonucleotide, a post-modification capping product oligonucleotide, a de-blocking product oligonucleotide, etc.).

In some embodiments, as described herein, -$L^7$-$R^1$ is —O—$CH_2R^2$. In some embodiments, In some embodiments, -$L^7$-$R^1$ is —$OCH_2CH_2CN$. In some embodiments, In some embodiments, -$L^7$-$R^1$ is —$OCH_2CH_2CN$. In some embodiments, R' in $R^6$ is —$CH_3$. Those skilled in the art appreciate R' can be other group, e.g., depending on what acid (or activated derivative thereof) is utilized in a capping step.

In some embodiments, an oligonucleotide comprises one or more internucleotidic linkages each independently selected from $O^{5P}$, $O^P$, $*^P$, $*^P$S, $*^{PD}$S, $*^P$R, $*^{PD}$R, $*^N$, $*^{PD}$, $*^N$S and $*^N$R, wherein each of $O^{5P}$, $O^P$, $*^P$, $*^P$S, $*^{PD}$S, $*^P$R, $*^{PD}$R, $*^N$, $*^{PD}$, $*^N$S and $*^N$R is independently of formula VII or a salt form thereof. In some embodiments, an oligonucleotide comprises $*^P$S, $*^{PD}$S, $*^P$R, $*^{PD}$R, $*^N$S or $*^N$R In some embodiments, an oligonucleotide comprises $*^P$S, $*^P$R, $*^N$S or $*^N$R. In some embodiments, an oligonucleotide comprises $*^P$S or $*^P$R. In some embodiments, an oligonucleotide comprises $*^N$S or $*^N$R. In some embodiments, an oligonucleotide comprises an internucleotidic linkage of $*^P$S or $*^P$R, and an internucleotidic linkage of $*^N$S or $*^N$R. In some embodiments, the present disclosure provides an oligonucleotide ("a first oligonucleotide"), which has an identical structure as an oligonucleotide described in the art ("a second oligonucleotide"), e.g., US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, WO 2019/217784, etc., except that compared to the second oligonucleotide, in the first oligonucleotide:

the first internucleotidic linkage from the 5'-end is an internucleotidic linkage of $O^{5P}$; and for the rest linkages:

at each location where there is a phosphate linkage in the second oligonucleotide, there is independently a linkage of $O^P$ in the first oligonucleotide;

at each location where there is a stereorandom phosphorothioate linkages in the second oligonucleotide, there is independently a linkage of $*^P$ or $*^{PD}$ in the first oligonucleotide;

at each location where there is a Sp phosphorothioate linkage in the second oligonucleotide, there is independently a linkage of $*^P$S or $*^{PD}$S in the first oligonucleotide;

at each location there is a Rp phosphorothioate linkage in the second oligonucleotide, there is independently a linkage of $*^P$R or $*^{PD}$R in the first oligonucleotide;

at each location there is a stereorandom non-negatively charged internucleotidic linkage in the second oligonucleotide, there is independently a linkage of $*^N$ in the first oligonucleotide:

at each location there is a Sp non-negatively charged internucleotidic linkage in the second oligonucleotide, there is independently a linkage of $*^N$S in the first oligonucleotide;

at each location there is a Rp non-negatively charged internucleotidic linkage in the second oligonucleotide, there is independently a linkage of $*^N$R in the first oligonucleotide, and each nucleobase in the first oligonucleotide is optionally and independently protected (e.g., as in oligonucleotide synthesis), and each additional chemical moiety, if any, in the first oligonucleotide is optionally and independently protected (e.g., —OH in a carbohydrate moiety protected as —OAc);

wherein each of $O^{5P}$, $O^P$, $*^P$, $*^P$S, $*^{PD}$S, $*^P$R, $*^{PD}$R, $*^N$, $*^{PD}$, $*^N$S and $*^N$R is independently of formula VII or a salt form thereof.

In some embodiments, at each location where there is a phosphate linkage in the second oligonucleotide, there is independently a linkage of $O^P$ in the first oligonucleotide; at each location where there is a stereorandom phosphorothioate linkages in the second oligonucleotide, there is independently a linkage of $*^P$ or $*^{PD}$ in the first oligonucleotide; at each location where there is a Sp phosphorothioate linkage in the second oligonucleotide, there is independently a linkage of $*^P$S or $*^{PD}$S in the first oligonucleotide; at each location there is a Rp phosphorothioate linkage in the second oligonucleotide, there is independently a linkage of $*^P$R or $*^{PD}$R in the first oligonucleotide; at each location there is a stereorandom non-negatively charged internucleotidic linkage in the second oligonucleotide, there is independently a linkage of $*^N$ in the first oligonucleotide; at each location there is a Sp non-negatively charged internucleotidic linkage in the second oligonucleotide, there is independently a linkage of $*^N$S in the first oligonucleotide: at each location there is a Rp non-negatively charged internucleotidic linkage in the second oligonucleotide, there is independently a linkage of $*^N$R in the first oligonucleotide, and each nucleobase in the first oligonucleotide is optionally and independently protected (e.g., as in oligonucleotide synthesis), and each additional chemical moiety, if any, in the first oligonucleotide is optionally and independently protected (e.g., —OH in a carbohydrate moiety protected as —OAc); wherein each of $O^{5P}$, $O^P$, $*^P$, $*^P$S, $*^{PD}$S, $*^P$R, $*^{PD}$R, $*^N$, $*^N$S and $*^{N}R$ is independently of formula VII or a salt form thereof. In some embodiments, such an oligonucleotide is linked to a support optionally through a linker, e.g., a CNA linker to CPG. As appreciated by those skilled in the art, after a removal process of —X-$L^s$-$R^5$, a linkage typically becomes a linkage it replaces. In some embodiments, such oligonucleotides (e.g., WV-O-937) are useful intermediates for preparing their corresponding oligonucleotides (e.g., WV-937). In some embodiments, the present disclosure provides chirally controlled oligonucleotide composition of a provided first oligonucleotide or a stereoisomer thereof.

In some embodiments, $O^{5P}$ is of formula VII or a salt form thereof as described herein. In some embodiments, each $O^P$ is independently of formula VII or a salt form thereof as described herein wherein $P^L$ is P(═O). In some embodiments, for $O^{5P}$ or $O^P$, —X-$L^s$-$R^5$ is -$L^7$-$R^1$; —S-$L^s$-$R^5$; or of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —H or —C(O)R'. In some embodiments, for $O^{5P}$, $R^6$ is —H (e.g., as a coupling product oligonucleotide) or —C(O)R'(e.g., as a pre-modification capping product oligonucleotide). In some embodiments, for $O^P$ $R^6$ is —C(O)R'. In some embodiments, —X-$L^s$-$R^5$ is -$L^7$-$R^1$; or of such a structure that H—X-$L^s$-$R^5$ is a compound of formula I, I-a, I-a-1, I-a-2, I-b, I-c, or I-d, wherein $R^6$ is —C(O)R'. In some embodiments, —X-$L^s$-$R^5$ is -$L^7$-$R^1$, —

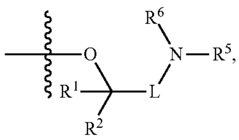 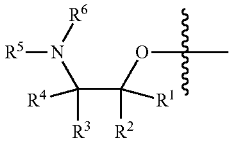,

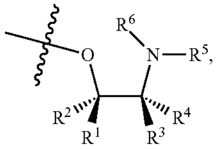 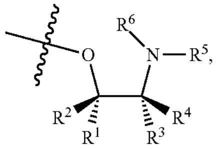

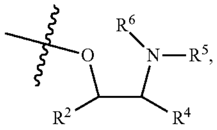 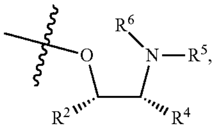

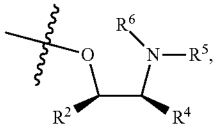 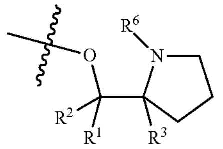,

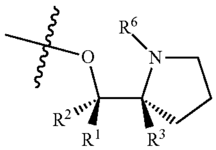, 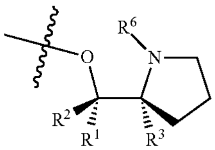,

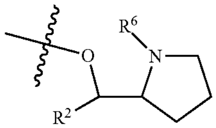, 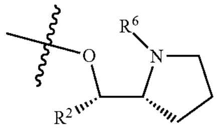,

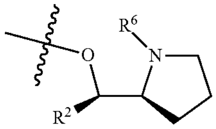, 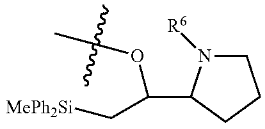,

-continued

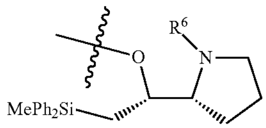,

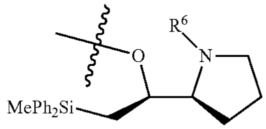,

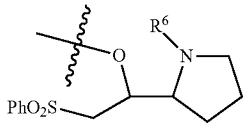,

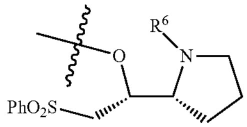, or

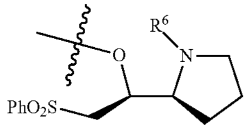.

In some embodiments, —X-$L^s$-$R^5$ is —O—$CH_2$—$R^2$, wherein $R^2$ comprises an electron-withdrawing group,

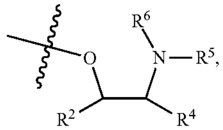 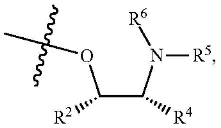

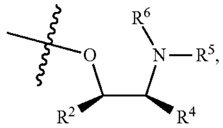 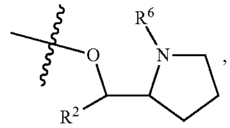,

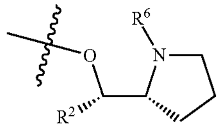, 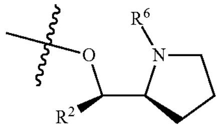,

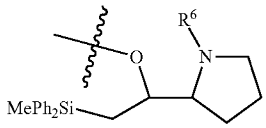,

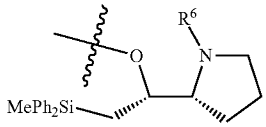,

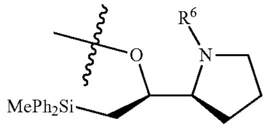,

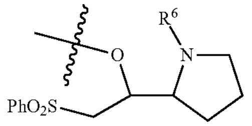,

-continued

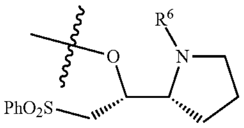, or

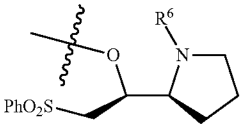.

In some embodiments, —X-$L^s$-$R^5$ is —O—$CH_2$—$R^2$, wherein $R^2$ comprises an electron-withdrawing group,

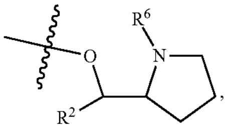, 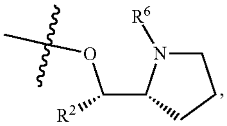,

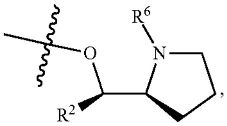, 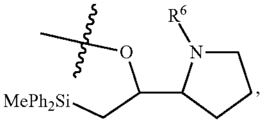,

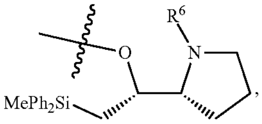, 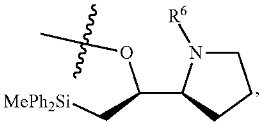,

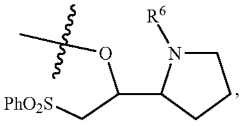, 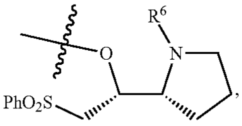, or 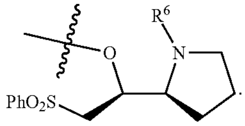.

In some embodiments, —X-$L^s$-$R^5$ is —$OCH_2CH_2CN$,

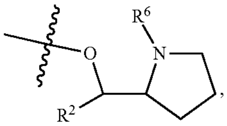, 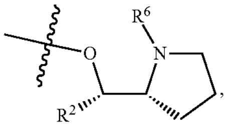,

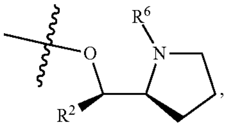, 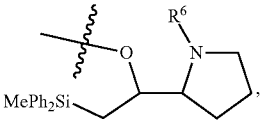,

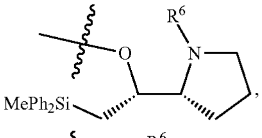, 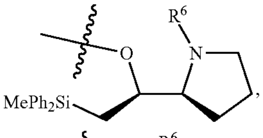,

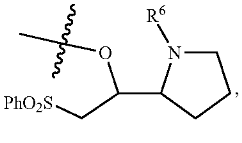, 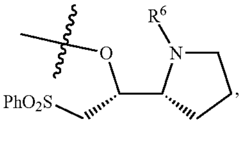,

-continued or 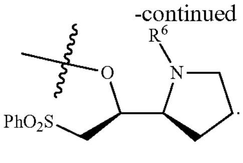.

In some embodiments, —X-$L^s$-$R^5$ is —$OCH_2CH_2CN$,

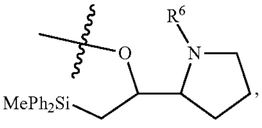, 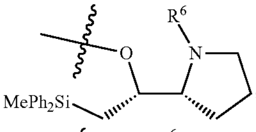,

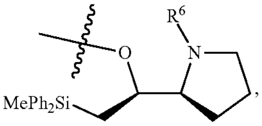, 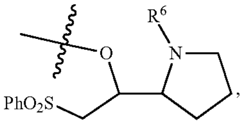,

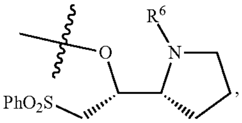, or 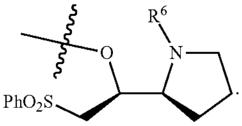.

In some embodiments, —X-$L^s$-$R^5$ is —$OCH_2CH_2CN$,

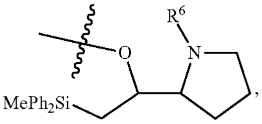, 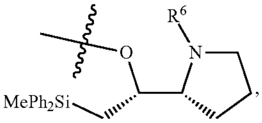, or 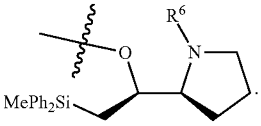.

In some embodiments, —X-$L^s$-$R^5$ is —$OCH_2CH_2CN$,

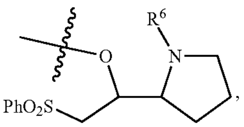, 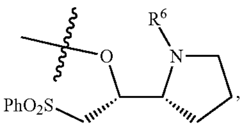, or 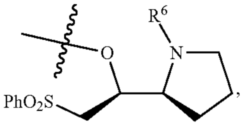,

In some embodiments, —X-$L^s$-$R^5$ is —$OCH_2CH_2CN$.

In some embodiments, each of $*^P$ and $*^{PD}$ is independently of formula VII or a salt form thereof wherein $P^L$ is P(═S), and —X-$L^s$-$R^5$ is -$L^7$-$R^1$. In some embodiments, each $*^N$ is independently of formula VII or a salt form thereof wherein $P^L$ is $P^N$, and —X-$L^s$-$R^5$ is -$L^7$-$R^1$. In some embodiments, as appreciated by those skilled in the art, $P^N$ is of such a structure that its N-moiety has the same non-hydrogen atoms and connections of non-hydrogen atoms as the N-moiety of the non-negatively charged internucleotidic linkage it replaces (without considering single, double, or triple bond etc.). For example, in some embodiments, $P^N$ in $*^N$ is

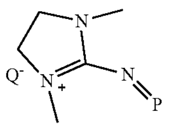

(such a $*^{N}$ is n001$^{P}$), and its corresponding non-negatively charged internucleotidic linkage is n001. In some embodiments, —X-$L^{s}$-$R^5$ is —O—$CH_2$—$R^2$, wherein $R^2$ comprises an electron-withdrawing group. In some embodiments, —X-$L^{s}$-$R^5$ is —$OCH_2CH_2CN$.

In some embodiments, each $*^{P}$S or $*^{PD}$S is independently of formula

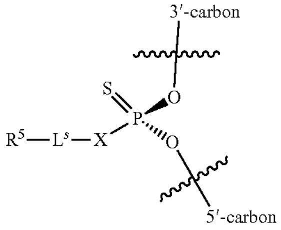

or a salt form thereof, wherein —X-$L^{s}$-$R^5$ is of such a structure that H—X-$L^{s}$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'. In some embodiments, each $*^{N}$R is of formula

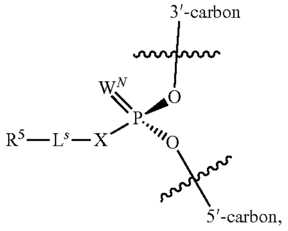

or a salt form thereof wherein P=$W^{N}$ is $P^{N}$, —X-$L^{s}$-$R^5$ is of such a structure that H—X-$L^{s}$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'. In some embodiments, as appreciated by those skilled in the art, $P^{N}$ is of such a structure that its N-moiety has the same non-hydrogen atoms and connections of non-hydrogen atoms as the N-moiety of the non-negatively charged internucleotidic linkage it replaces (without considering single, double, or triple bond etc.). For example, in some embodiments, $P^{N}$ in $*^{N}$R is

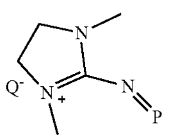

(such a $*^{N}$R is n001$^{P}$R), and its corresponding non-negatively charged internucleotidic linkage is n001R. In some embodiments, $R^6$ is —C(O)R'. In some embodiments, as appreciated by those skilled in the art, $P^{N}$ is of such a structure that its N-moiety has the same non-hydrogen atoms and connections of non-hydrogen atoms as the N-moiety of the non-negatively charged internucleotidic linkage it replaces (without considering single, double, or triple bond etc.). In some embodiments, $R^6$ is —C(O)R'. In some embodiments, —X-$L^{s}$-$R^5$ is of such a structure that H—X-$L^{s}$-$R^5$ is a compound of formula I, I-a, I-a-1, I-a-2, I-b, I-c, or I-d, wherein $R^6$ is —C(O)R'. In some embodiments, —X-$L^{s}$-$R^5$ is

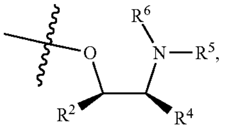,
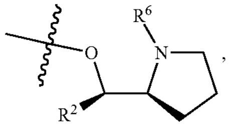,
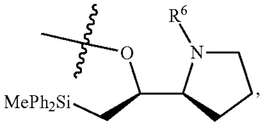, or
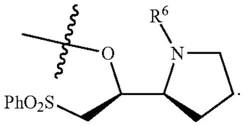.

In some embodiments, —X-$L^{s}$-$R^5$ is

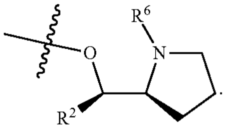.

In some embodiments, —X-$L^{s}$-$R^5$ is

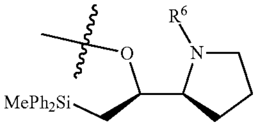 or
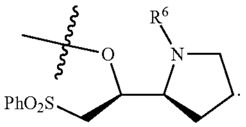.

In some embodiments, —X-$L^{s}$-$R^5$ is

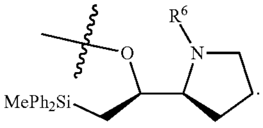.

In some embodiments, —X-$L^s$-$R^5$ is

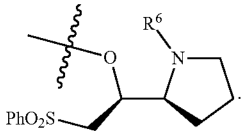

In some embodiments, for $*^{PD}S$ —X-$L^s$-$R^5$ is

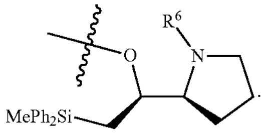

In some embodiments, for $*^{P}S$ —X-$L^s$-$R^5$ is

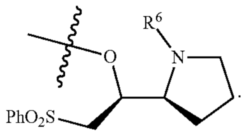

In some embodiments, for $*^{N}R$ —X-$L^s$-$R^5$ is

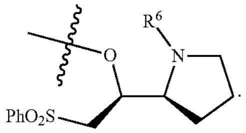

In some embodiments, $R^6$ is —C(O)R'. In some embodiments, $R^6$ is —Ac.

In some embodiments, each $*^{P}R$ or $*^{PD}R$ is independently of formula

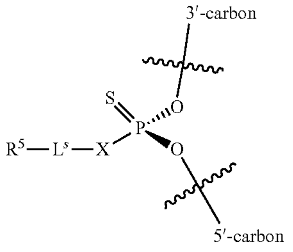

or a salt form thereof, wherein —X-$L^s$-$R^5$ is of such a structure that H—X-$L^s$-$R^5$ is a compound of formula I, I-a, I-a-1, I-a-2, I-b, I-c, I-d, I-e, II, II-a, II-b, III, II-a, or III-b, optionally wherein $R^5$ or $R^6$ is —C(O)R'. In some embodiments, each $*^{N}S$ is of formula

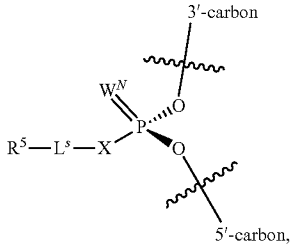

or a salt form thereof wherein P═$W^N$ is $P^N$, —X-$L^s$-$R^5$ is of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or R is —C(O)R'. In some embodiments, as appreciated by those skilled in the art, $P^N$ is of such a structure that its N-moiety has the same non-hydrogen atoms and connections of non-hydrogen atoms as the N-moiety of the non-negatively charged internucleotidic linkage it replaces (without considering single, double, or triple bond etc.). For example, in some embodiments, $P^N$ in $*^{N}S$ is

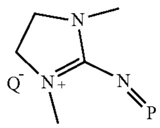

(such a $*^{N}S$ is n001$^{P}$S), and its corresponding non-negatively charged internucleotidic linkage is n001S. In some embodiments, $R^6$ is —C(O)R'. In some embodiments, —X-$L^s$-$R^5$ is of such a structure that H—X-$L^s$-$R^5$ is a compound of formula I, I-a, I-a-1, I-a-2, I-b, I-c, or I-d, wherein $R^6$ is —C(O)R'. In some embodiments, —X-$L^s$-$R^5$ is,

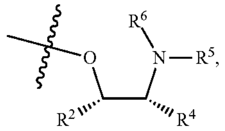

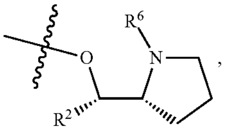

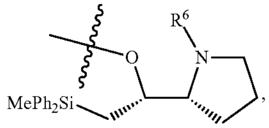

or

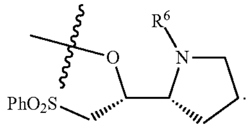

In some embodiments, —X-$L^s$-$R^5$ is

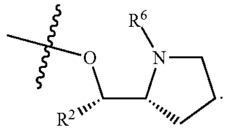

In some embodiments, —X-$L^s$-$R^5$ is

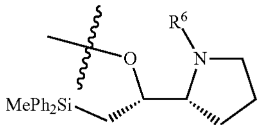

or

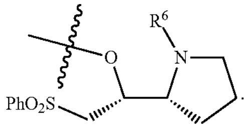

In some embodiments, —X-$L^s$-$R^5$ is

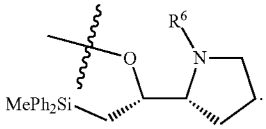

In some embodiments, —X-$L^s$-$R^5$ is

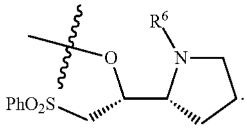

In some embodiments, for $*^{PD}$S —X-$L^s$-$R^5$ is

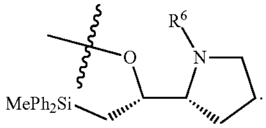

In some embodiments, for $*^{P}$S —X-$L^s$-$R^5$ is

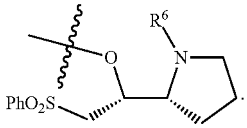

In some embodiments, for $*^{N}$R —X-$L^s$-$R^5$ is

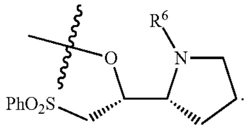

In some embodiments, $R^6$ is —C(O)R'. In some embodiments, $R^6$ is —Ac.

In some embodiments, an oligonucleotide comprises at least one of $*^{N}$, $*^{N}$S and $*^{N}$R. In some embodiments, an oligonucleotide comprises

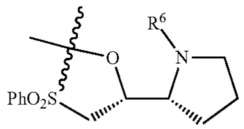

or

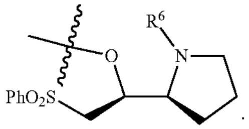

In some embodiments, an oligonucleotide comprises

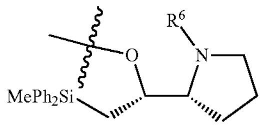

or

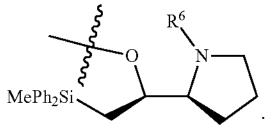

In some embodiments, an oligonucleotide comprises

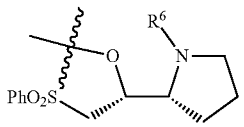

or

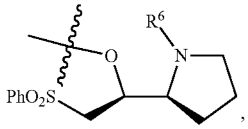

, and comprises

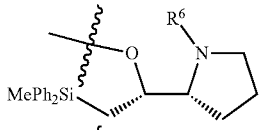

or

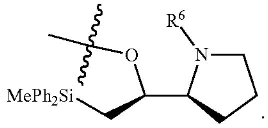

In some embodiments, the present disclosure provides an oligonucleotide comprising at least one of $*^{P}$S, $*^{PD}$S, $*^{P}$R and $*^{PD}$R. In some embodiments, an oligonucleotide comprises at least one $O^P$, and at least one of $*^{P}$S, $*^{PD}$S, $*^{P}$R and $*^{PD}$R. In some embodiments, an oligonucleotide comprises at least one $O^P$, at least one of $*^{P}$S, $*^{PD}$S, $*^{P}$R and $*^{PD}$R, and at least one of *N, $*^{N}$S and $*^{N}$R. In some embodiments, each internucleotidic linkage is independently $*^{P}$S, $*^{PD}$S, $*^{P}$R or $*^{PD}$R. In some embodiments, each internucleotidic linkage is independently $O^P$, $*^{P}$S, $*^{PD}$S, $*^{P}$R or $*^{PD}$R. In some embodiments, each internucleotidic linkage is independently $O^P$, $*^{P}$S or $*^{PD}$S. In some embodiments, each internucleotidic linkage is independently $O^P$, $*^{P}$S, $*^{PD}$S, $*^{P}$R, $*^{PD}$R, $*^{N}$, $*^{N}$S or $*^{N}$R. In some embodiments, each internucleotidic linkage is independently $O^P$, $*^{P}$S, $*^{PD}$S, $*^{P}$R, $*^{PD}$R, $*^{N}$S or $*^{N}$R. In some embodiments, each internucleotidic linkage is independently $O^P$, $*^{P}$S, $*^{PD}$S or $*^{N}$R.

As those skilled in the art appreciate, in many embodiments, internucleotidic linkages bond to 5'-sugars through 3'-carbon atoms, and 3'-sugars through 5'-carbon atoms. In some embodiments, a chirally controlled phosphorothioate internucleotidic linkage has the structure of

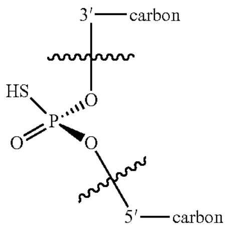

or a salt form thereof. In some embodiments, a chirally controlled phosphorothioate internucleotidic linkage has the structure of

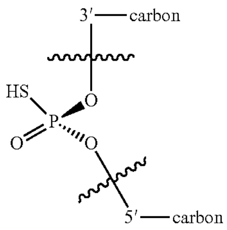

or a salt form thereof. In some embodiments, a chirally controlled non-negatively charged internucleotidic linkage or neutral internucleotidic linkage has the structure of

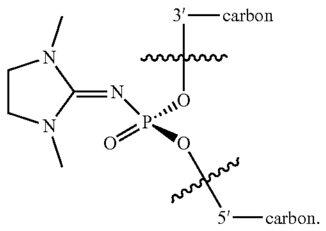

In some embodiments, a chirally controlled non-negatively charged internucleotidic linkage or neutral internucleotidic linkage has the structure of

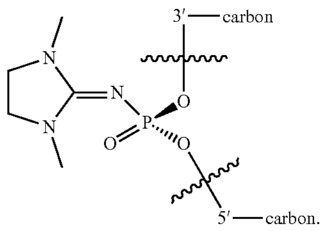

In some embodiments, A is protected with Bz. In some embodiments, C is protected with Ac. In some embodiments, G is protected with iBu. In some embodiments, U is not protected. In some embodiments, A is protected with Bz, C is protected with Ac, G is protected with iBu, and U and T are not protected. In some embodiments, protected nucleobases are

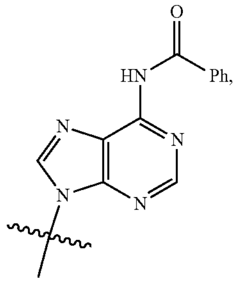

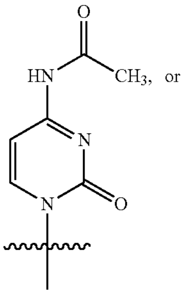
or

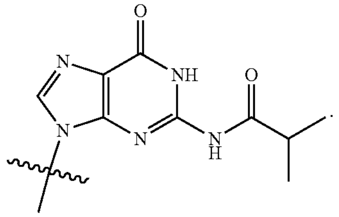

In some embodiments, an oligonucleotide is selected from Table O-2 below. In some embodiments, the present disclosure provides chirally controlled oligonucleotide compositions of an oligonucleotide (or a stereoisomer thereof) of Table O-2. In some embodiments, such oligonucleotides are linked to support (e.g., one for oligonucleotide synthesis such as CPG) optionally via a linker (e.g., a CNA linker as utilized in the Examples). In some embodiments, the present disclosure provides a chirally controlled oligonucleotide composition of an oligonucleotide or a stereoisomer thereof.

TABLE O-2

Example Oligonucleotides. (SEQ ID NOS: 66-195)

| ID | SEQ ID NO | Description | Naked Base Sequence |
|---|---|---|---|
| WV-O-937 | 66 | G *P SG *P SC *P SA *P SC *P SA *P SA *P SG *P SG *P SG *P SC *P SA *P SC *P RA *P SG *P SA *P SC *P ST *P ST *P SC | GGCACAAGGGCACAGACTTC |

TABLE O-2-continued

Example Oligonucleotides. (SEQ ID NOS: 66-195)

| ID | SEQ ID NO | Description | Naked Base Sequence |
|---|---|---|---|
| WV-O-1077 | 67 | mA *P SmU *P SmU *P SmA *P SmA *P SmU *P SA *P SA *P SA *P ST *P ST *P SG *P ST *P SC *P RA *P ST *P SmC *P SmA *P SmC *P SmC | AUUAAUAAATTGTCATCACC |
| WV-O-1078 | 68 | mA *P RmU *P RmU *P RmA *P RmA *P RmU *P SA *P SA *P SA *P ST *P ST *P SG *P ST *P SC *P RA *P ST *P SmC *P RmA *P RmC *P RmC | AUUAAUAAATTGTCATCACC |
| WV-O-1079 | 69 | mA *P SmU *P SmU *P SmA *P SmA *P SmU *P SmA *P SmA *P SA *P ST *P ST *P SG *P ST *P SC *P RA *P ST *P SC *P SA *P SC *P SC | AUUAAUAAATTGTCATCACC |
| WV-O-1085 | 70 | mG *P SmG *P SmC *P SmA *P SmC *P SA *P SA *P SG *P SG *P SG *P SC *P SA *P SC *P RA *P SG *P SmA *P SmC *P Sm *P SmU *P SmC | GGCACAAGGGCACAGACUUC |
| WV-O-1086 | 71 | mG *P RmG *P RmC *P RmA *P RmC *P SA *P SA *P SG *P SG *P SG *P SC *P SA *P SC *P RA *P SG *P SmA *P RmC *P RmU *P RmU *P RmC | GGCACAAGGGCACAGACUUC |
| WV-O-1090 | 72 | mGmGmCmAmCmAmAmG *P SG *P SG *P SC *P SA *P SC *P RA *P SG *P SA *P SC *P ST *P ST *P SC | GGCACAAGGGCACAGACTTC |
| WV-O-1091 | 73 | mG *P RmGmCmAmC *P SA *P SA *P SG *P SG *P SG *P SC *P SA *P SC *P RA *P SG *P SmAmCmUmU *P RmC | GGCACAAGGGCACAGACUUC |
| WV-O-1092 | 74 | mG *P SmGmCmAmC *P SA *P SA *P SG *P SG *P SG *P SC *P SA *P SC *P RA *P SG *P SmAmCmUmU *P SmC | GGCACAAGGGCACAGACUUC |
| WV-O-1497 | 75 | mG *P mGmCmAmC *P A *P A *P G *P G *P G *P C *P A *P C *P A *P G *P mAmCmUmU *P mC | GGCACAAGGGCACAGACUUC |
| WV-O-1508 | 76 | A *P SmUmUmAmAmU *P SA *P SA *P SA *P ST *P ST *P SG *P ST *P SC *P RA *P ST *P SmCmAmC *P SC | AUUAAUAAATTGTCATCACC |
| WV-O-1510 | 77 | G *P SmGmCmAmC *P SA *P SA *P SG *P SG *P SG *P SC *P SA *P SC *P RA *P SG *P SmAmCmUmU *P SC | GGCACAAGGGCACAGACUUC |
| WV-O-2076 | 78 | mU *P mAmAmUmA *P A *P A *P T *P T *P G *P T *P C *P A *P T *P C *P mAmCmCmA *P mG | UAAUAAATTGTCATCACCAG |
| WV-O-2378 | 79 | mG *P SmCmAmCmA *P SA *P SG *P SG *P SG *P SC *P SA *P SC *P RA *P SG *P SA *P SmCmUmUmC *P SmC | GCACAAGGGCACAGACUUCC |
| WV-O-2380 | 80 | mC *P SmAmCmAmA *P SG *P SG *P SG *P SC *P SA *P SC *P RA *P SG *P SA *P SC *P SmUmUmCmC *P SmA | CACAAGGGCACAGACUUCCA |
| WV-O-2417 | 81 | mA *P SmUmAmAmA *P ST *P ST *P SG *P ST *P SC *P RA *P ST *P SC *P SA *P SC *P SmCmAmGmA *P SmA | AUAAATTGTCATCACCAGAA |
| WV-O-2418 | 82 | mA *P SmAmUmAmA *P SA *P ST *P ST *P SG *P ST *P SC *P RA *P ST *P SC *P SA *P SmCmCmAmG *P SmA | AAUAAATTGTCATCACCAGA |
| WV-O-2595 | 83 | mG *P SmGmGmUmC *P SC *P ST *P SC *P SC *P SC *P SC *P SA *P SC *P RA *P SG *P SmAmGmGmG *P SmA | GGGUCCTCCCCACAGAGGGA |
| WV-O-2601 | 84 | mG *P SmCmAmCmA *P SC *P SA *P SG *P ST *P SA *P SG *P RA *P ST *P SG *P SA *P SmGmGmGmA *P SmG | GCACACAGTAGATGAGGGAG |
| WV-O-2602 | 85 | mU *P SmGmCmAmC *P SA *P SC *P SA *P SG *P ST *P SA *P SG *P RA *P ST *P SG *P SmAmGmGmG *P SmA | UGCACACAGTAGATGAGGGA |
| WV-O-2603 | 86 | mG *P SmUmGmCmA *P SC *P SA *P SC *P SA *P SG *P ST *P SA *P SG *P RA *P ST *P SmGmAmGmG *P SmG | GUGCACACAGTAGATGAGGG |
| WV-O-2618 | 87 | mU *P mGmCmAmC *P A *P C *P A *P G *P T *P A *P G *P A *P T *P G *P mAmGmGmG *P mA | UGCACACAGTAGATGAGGGA |
| WV-O-2619 | 88 | mG *P mUmGmCmA *P C *P A *P C *P A *P G *P T *P A *P G *P A *P T *P mGmAmGmG *P mG | GUGCACACAGTAGATGAGGG |
| WV-O-2671 | 89 | mG *P SmG *P SmGmUmC *P SC *P ST *P SC *P SC *P SC *P SC *P SA *P SC *P RA *P SG *P SmAmGmG *P SmG *P SmA | GGGUCCTCCCCACAGAGGGA |
| WV-O-887 | 90 | mU *P S mC *P S mA *P S mA *P R mG *P R mG *P R mA *P R mA *P R mG *P R mA *P R mU *P R mG *P R mG *P R mC *P R mA *P R mU *P R mU *P S mU *P S mC *P S mU | UCAAGGAAGAUGGCAUUUCU |
| WV-O-892 | 91 | mU *P S mC *P R mA *P R mA *P R mG *P R mG *P R mA *P R mA *P R mG *P R mA *P R mU *P R mG *P R mG *P R mC *P R mA *P R mU *P R mU *P R mU *P R mC *P S mU | UCAAGGAAGAUGGCAUUUCU |
| WV-O-896 | 92 | mU *P S mC *P S mA *P R mA *P R mG *P R mG *P R mA *P R mA *P R mG *P R mA *P R mU *P S mG *P R mG *P R mC *P S mA *P R mU *P S mU *P S mU *P S mC *P S mU | UCAAGGAAGAUGGCAUUUCU |
| WV-O-1714 | 93 | fU *P fC *P fA *P fA *P fG *P fG *P mA *P mA *P mG *P mA *P mU *P mG *P mG *P mC *P fA *P fU *P fU *P fU *P fC *P fU | UCAAGGAAGAUGGCAUUUCU |
| WV-O-2444 | 94 | fU *P SfC *P SfA *P SfA *P SfG *P SfG *P S mA *P R mA *P R mG *P R mA *P R mU *P R mG *P R mG *P R mC *P SfA *P SfU *P SfU *P SfU *P SfC *P SfU | UCAAGGAAGAUGGCAUUUCU |
| WV-O-2445 | 95 | fU *P SfC *P SfA *P SfA *P SfG *P S mG *P R mA *P R mA *P R mG *P R mA *P R mU *P R mG *P R mG *P R mC *P R mA *P SfU *P SfU *P SfU *P SfC *P SfU | UCAAGGAAGAUGGCAUUUCU |
| WV-O-2526 | 96 | fU *P SfC *P SfA *P SfA *P SfG *P SfG *P SfA *P SfA *P R mG *P R mA *P R mU *P R mG *P R mG *P SfC *P SfA *P SfU *P SfU *P SfU *P SfC *P SfU | UCAAGGAAGAUGGCAUUUCU |
| WV-O-2527 | 97 | fU *P SfC *P SfA *P SfA *P SfG *P SfG *P SfA *P SfA *P S mG *P R mA *P R mU *P R mG *P SfG *P SfC *P SfA *P SfU *P SfU *P SfU *P SfC *P SfU | UCAAGGAAGAUGGCAUUUCU |
| WV-O-2528 | 98 | fU *P SfC *P SfA *P SfA *P SfG *P SfG *P SfA *P SfA *P SfG *P S mA *P R mU *P SfG *P SfG *P SfC *P SfA *P SfU *P SfU *P SfU *P SfC *P SfU | UCAAGGAAGAUGGCAUUUCU |
| WV-O-2530 | 99 | fU *P SfC *P SfA *P SfA *P SfG *P SfG *P SfA *P SfA *P S mG mA mU mG *P SfG *P SfC *P SfA *P SfU *P SfU *P SfU *P SfC *P SfU | UCAAGGAAGAUGGCAUUUCU |
| WV-O-2531 | 100 | fU *P SfC *P SfA *P SfA *P SfG *P SfG *P SfA *P SfA *P SfG *P S mA mU *P SfG *P SfG *P SfC *P SfA *P SfU *P SfU *P SfU *P SfC *P SfU | UCAAGGAAGAUGGCAUUUCU |
| WV-O-2578 | 101 | Mod013L001 *P mU *P mC *P mA *P mA *P mG *P mG * mA *P mA *P mG *P mA *P mU *P mG *P mG *P mC *P mA *P mU *P mU *P mU *P mC *P mU | UCAAGGAAGAUGGCAUUUCU |

TABLE O-2-continued

Example Oligonucleotides. (SEQ ID NOS: 66-195)

| ID | SEQ ID NO | Description | Naked Base Sequence |
|---|---|---|---|
| WV-O-2580 | 102 | Mod005L001 $*^{P}$ mU $*^{P}$ mC $*^{P}$ mA $*^{P}$ mA $*^{P}$ mG $*^{P}$ mG $*^{P}$ mA $*^{P}$ mA $*^{P}$ mG $*^{P}$ mA $*^{P}$ mU $*^{P}$ mG $*^{P}$ mG $*^{P}$ mC $*^{P}$ mA $*^{P}$ mU $*^{P}$ mU $*^{P}$ mU $*^{P}$ mC $*^{P}$ mU | UCAAGGAAGAUGGC AUUUCU |
| WV-O-2587 | 103 | Mod020L001 $*^{P}$ mU $*^{P}$ mC $*^{P}$ mA $*^{P}$ mA $*^{P}$ mG $*^{P}$ mG $*^{P}$ mA $*^{P}$ mA $*^{P}$ mG $*^{P}$ mA $*^{P}$ mU $*^{P}$ mG $*^{P}$ mG $*^{P}$ mC $*^{P}$ mA $*^{P}$ mU $*^{P}$ mU $*^{P}$ mU $*^{P}$ mC $*^{P}$ mU | UCAAGGAAGAUGGC AUUUCU |
| WV-O-3047 | 104 | fU $*^{P}$ fC $*^{P}$ fA $*^{P}$ fA $*^{P}$ fG $*^{P}$ fG $*^{P}$ mA $*^{P}$ mA $*^{P}$ mG $*^{P}$ mA $*^{P}$ fU $*^{P}$ mG $*^{P}$ mG $*^{P}$ fC $*^{P}$ fA $*^{P}$ fU $*^{P}$ fU $*^{P}$ fU $*^{P}$ fC $*^{P}$ fU | UCAAGGAAGAUGGC AUUUCU |
| WV-O-3152 | 105 | fU $*^{P}$ SfC $*^{P}$ SfA $*^{P}$ SfA $*^{P}$ SfG $*^{P}$ SfG $*^{P}$ S mAfA $*^{P}$ S mGfA $*^{P}$ S mUfG $*^{P}$ S mGfC $*^{P}$ SfA $*^{P}$ SfU $*^{P}$ SfU $*^{P}$ SfU $*^{P}$ SfC $*^{P}$ SfU | UCAAGGAAGAUGGC AUUUCU |
| WV-O-3472 | 106 | fU $*^{P}$ SfC $*^{P}$ SfA $*^{P}$ SfA $*^{P}$ SfG $*^{P}$ SfG $*^{P}$ S mAfA $*^{P}$ S mGfA $*^{P}$ SfU $*^{P}$ S mG mGfC $*^{P}$ SfA $*^{P}$ SfU $*^{P}$ SfU $*^{P}$ SfU $*^{P}$ SfC $*^{P}$ SfU | UCAAGGAAGAUGGC AUUUCU |
| WV-O-3473 | 107 | fU $*^{P}$ SfC $*^{P}$ SfA $*^{P}$ SfA $*^{P}$ SfG $*^{P}$ SfG $*^{P}$ S mAfA $*^{P}$ S mG mA $*^{P}$ SfU $*^{P}$ S mG mGfC $*^{P}$ SfA $*^{P}$ SfU $*^{P}$ SfU $*^{P}$ SfU $*^{P}$ SfC $*^{P}$ SfU | UCAAGGAAGAUGGC AUUUCU |
| WV-O-3507 | 108 | fU $*^{P}$ SfC $*^{P}$ SfA $*^{P}$ SfA $*^{P}$ SfG $*^{P}$ SfG $*^{P}$ S mAfA $*^{P}$ S mG mAfU $*^{P}$ S mG mGfC $*^{P}$ SfA $*^{P}$ SfU $*^{P}$ SfU $*^{P}$ SfU $*^{P}$ SfC $*^{P}$ SfU | UCAAGGAAGAUGGC AUUUCU |
| WV-O-3508 | 109 | fU $*^{P}$ SfC $*^{P}$ SfA $*^{P}$ SfA $*^{P}$ SfG $*^{P}$ SfG $*^{P}$ S mAfA $*^{P}$ S mGfA $*^{P}$ SfU $*^{P}$ S mG mGfC $*^{P}$ SfAfU $*^{P}$ SfU $*^{P}$ SfU $*^{P}$ SfC $*^{P}$ SfU | UCAAGGAAGAUGGC AUUUCU |
| WV-O-3509 | 110 | fU $*^{P}$ SfC $*^{P}$ SfA $*^{P}$ SfA $*^{P}$ SfG $*^{P}$ SfG $*^{P}$ S mAfA $*^{P}$ S mG mA $*^{P}$ SfU $*^{P}$ S mG mGfC $*^{P}$ SfAfU $*^{P}$ SfU $*^{P}$ SfU $*^{P}$ SfC $*^{P}$ SfU | UCAAGGAAGAUGGC AUUUCU |
| WV-O-3510 | 111 | fU $*^{P}$ SfC $*^{P}$ SfA $*^{P}$ SfA $*^{P}$ SfG $*^{P}$ SfG $*^{P}$ S mAfA $*^{P}$ S mGfAfU $*^{P}$ S mG mGfC $*^{P}$ S mA $*^{P}$ SfU $*^{P}$ SfU $*^{P}$ SfU $*^{P}$ SfC $*^{P}$ SfU | UCAAGGAAGAUGGC AUUUCU |
| WV-O-3511 | 112 | fU $*^{P}$ SfC $*^{P}$ SfA $*^{P}$ SfA $*^{P}$ SfG $*^{P}$ SfG $*^{P}$ S mAfA $*^{P}$ S mG mAfU $*^{P}$ S mG mGfC $*^{P}$ S mA $*^{P}$ SfU $*^{P}$ SfU $*^{P}$ SfU $*^{P}$ SfC $*^{P}$ SfU | UCAAGGAAGAUGGC AUUUCU |
| WV-O-3512 | 113 | fU $*^{P}$ SfC $*^{P}$ SfA $*^{P}$ SfA $*^{P}$ SfG $*^{P}$ SfG $*^{P}$ S mAfA $*^{P}$ S mGfAfU $*^{P}$ S mG mGfC $*^{P}$ S mAfU $*^{P}$ SfU $*^{P}$ SfU $*^{P}$ SfC $*^{P}$ SfU | UCAAGGAAGAUGGC AUUUCU |
| WV-O-3513 | 114 | fU $*^{P}$ SfC $*^{P}$ SfA $*^{P}$ SfA $*^{P}$ SfG $*^{P}$ SfG $*^{P}$ S mAfA $*^{P}$ S mG mAfU $*^{P}$ S mG mGfC $*^{P}$ S mAfU $*^{P}$ SfU $*^{P}$ SfU $*^{P}$ SfC $*^{P}$ SfU | UCAAGGAAGAUGGC AUUUCU |
| WV-O-3514 | 115 | fU $*^{P}$ SfC $*^{P}$ SfA $*^{P}$ SfA $*^{P}$ SfG $*^{P}$ SfG $*^{P}$ S mAfA $*^{P}$ S mGfAfU $*^{P}$ S mG mGfC $*^{P}$ SfAfU $*^{P}$ SfU $*^{P}$ SfU $*^{P}$ SfC $*^{P}$ SfU | UCAAGGAAGAUGGC AUUUCU |
| WV-O-3515 | 116 | fU $*^{P}$ SfC $*^{P}$ SfA $*^{P}$ SfA $*^{P}$ SfG $*^{P}$ SfG $*^{P}$ S mAfA $*^{P}$ S mG mAfU $*^{P}$ S mG mGfC $*^{P}$ SfAfU $*^{P}$ SfU $*^{P}$ SfU $*^{P}$ SfC $*^{P}$ SfU | UCAAGGAAGAUGGC AUUUCU |
| WV-O-3545 | 117 | Mod015L001fU $*^{P}$ SfC $*^{P}$ SfA $*^{P}$ SfA $*^{P}$ SfG $*^{P}$ SfG $*^{P}$ S mAfA $*^{P}$ S mG mA $*^{P}$ SfU $*^{P}$ S mG mGfC $*^{P}$ SfA $*^{P}$ SfU $*^{P}$ SfU $*^{P}$ SfU $*^{P}$ SfC $*^{P}$ SfU | UCAAGGAAGAUGGC AUUUCU |
| WV-O-3546 | 118 | Mod020L001fU $*^{P}$ SfC $*^{P}$ SfA $*^{P}$ SfA $*^{P}$ SfG $*^{P}$ SfG $*^{P}$ S mAfA $*^{P}$ S mG mA $*^{P}$ SfU $*^{P}$ S mG mGfC $*^{P}$ SfA $*^{P}$ SfU $*^{P}$ SfU $*^{P}$ SfU $*^{P}$ SfC $*^{P}$ SfU | UCAAGGAAGAUGGC AUUUCU |
| WV-O-9517 | 119 | fC $*^{P}$ SfU $*^{P}$ SfC $*^{P}$ SfC $*^{P}$ SfG $*^{P}$ SfG $*^{P}$ SfU $*^{P}$ SfU $*^{P}$ S mCfU $*^{P}$ S mG $*^{P}$ SfA $*^{P}$ S mA mGfG $*^{P}$ SfU $*^{P}$ SfG $*^{P}$ SfU $*^{P}$ SfU $*^{P}$ SfC | CUCCGGUUCUGAAG GUGUUC |
| WV-O-12555 | 120 | fC $*^{P}$ SfU $*^{P}$ SfC $*^{P}$ SfC $*^{P}$ SfG $*^{P}$ SfG $*^{P}$ SfU $*^{P}$ SfU $*^{P}$ SmCn001$^{P}$RfU $*^{P}$ SmG $*^{P}$ SfA $*^{P}$ SmAn001$^{P}$RfG $*^{P}$ SfG $*^{P}$ SfU $*^{P}$ SfG $*^{P}$ SfU $*^{P}$ SfU $*^{P}$ SfC | CUCCGGUUCUGAAG GUGUUC |
| WV-O-12556 | 121 | fC $*^{P}$ SfU $*^{P}$ SfC $*^{P}$ SfC $*^{P}$ SfG $*^{P}$ SfG $*^{P}$ SfU $*^{P}$ SfU $*^{P}$ SmCn001$^{P}$RfU $*^{P}$ SmG $*^{P}$ SfA $*^{P}$ SmAn001$^{P}$RmG $*^{P}$ SfG $*^{P}$ SfU $*^{P}$ SfG $*^{P}$ SfU $*^{P}$ SfU $*^{P}$ SfC | CUCCGGUUCUGAAG GUGUUC |
| WV-O-12558 | 122 | fC $*^{P}$ SfU $*^{P}$ SfC $*^{P}$ SfC $*^{P}$ SfG $*^{P}$ SfG $*^{P}$ SfU $*^{P}$ SfU $*^{P}$ SmCn001$^{P}$SfU $*^{P}$ SmG $*^{P}$ SfA $*^{P}$ SmAn001$^{P}$SfG $*^{P}$ SfG $*^{P}$ SfU $*^{P}$ SfG $*^{P}$ SfU $*^{P}$ SfU $*^{P}$ SfC | CUCCGGUUCUGAAG GUGUUC |
| WV-O-12876 | 123 | fC $*^{P}$ SfU $*^{P}$ SfCn001$^{P}$fC $*^{P}$ SfG $*^{P}$ SfGn001$^{P}$fU $*^{P}$ SfU $*^{P}$ SmCn001$^{P}$fU $*^{P}$ SmG $*^{P}$ SfA $*^{P}$ SmAn001$^{P}$mGn001$^{P}$fG $*^{P}$ SfU $*^{P}$ SfGn001$^{P}$fU $*^{P}$ SfU $*^{P}$ SfC | CUCCGGUUCUGAAG GUGUUC |
| WV-O-12877 | 124 | fC $*^{P}$ SfU $*^{P}$ SfCn001$^{P}$fC $*^{P}$ SfG $*^{P}$ SfGn001$^{P}$fU $*^{P}$ SfU $*^{P}$ SmCn001$^{P}$fU $*^{P}$ SmG $*^{P}$ SfA $*^{P}$ SmAn001$^{P}$fG $*^{P}$ SfG $*^{P}$ SfU $*^{P}$ SfGn001$^{P}$fU $*^{P}$ SfU $*^{P}$ SfC | CUCCGGUUCUGAAG GUGUUC |
| WV-O-12878 | 125 | fC $*^{P}$ SfU $*^{P}$ SfCn001$^{P}$fC $*^{P}$ SfG $*^{P}$ SfGn001$^{P}$fU $*^{P}$ SfU $*^{P}$ SmCn001$^{P}$fU $*^{P}$ SmG $*^{P}$ SfA $*^{P}$ SmAn001$^{P}$mG $*^{P}$ SfG $*^{P}$ SfU $*^{P}$ SfGn001$^{P}$fU $*^{P}$ SfU $*^{P}$ SfC | CUCCGGUUCUGAAG GUGUUC |
| WV-O-13826 | 126 | fU $*^{P}$ SfC $*^{P}$ SfC $*^{P}$ SfG $*^{P}$ SAG $*^{P}$ SfIJ $*^{P}$ SfU $*^{P}$ SmCfU $*^{P}$ SmG $*^{P}$ SfA $*^{P}$ SmAmGfG $*^{P}$ SfU $*^{P}$ SfG $*^{P}$ SfU $*^{P}$ fU $*^{P}$ SfC | UCCGGUUCUGAAGG UGUUC |
| WV-O-12880 | 127 | fC $*^{P}$ SfU $*^{P}$ SfCn001$^{P}$fC $*^{P}$ SfG $*^{P}$ SfGn001$^{P}$fU $*^{P}$ SfU $*^{P}$ SmCfU $*^{P}$ SmG $*^{P}$ SfA $*^{P}$ SmAfG $*^{P}$ SfG $*^{P}$ SfU $*^{P}$ SfGn001$^{P}$fU $*^{P}$ SfU $*^{P}$ SfC | CUCCGGUUCUGAAG GUGUUC |
| WV-O-14344 | 128 | fC $*^{P}$ SfU $*^{P}$ SfCn001$^{P}$RfC $*^{P}$ SfG $*^{P}$ SfGn001$^{P}$RfU $*^{P}$ SfU $*^{P}$ SmCfU $*^{P}$ SmG $*^{P}$ SfA $*^{P}$ SmAfGfG $*^{P}$ SfU $*^{P}$ SfGn001$^{P}$RfU $*^{P}$ SfU $*^{P}$ SfC | CUCCGGUUCUGAAG GUGUUC |
| WV-O-13835 | 129 | fU $*^{P}$ SfC $*^{P}$ SfC $*^{P}$ SfG $*^{P}$ SfG $*^{P}$ SfU $*^{P}$ SfU $*^{P}$ SmCfU $*^{P}$ SmG $*^{P}$ SfA $*^{P}$ SmAmGfG $*^{P}$ SfU $*^{P}$ SfG $*^{P}$ SfU $*^{P}$ SfU $*^{P}$ SfC $*^{P}$ SfU | UCCGGUUCUGAAGG UGUUCU |
| WV-O-13864 | 130 | fC $*^{P}$ SfU $*^{P}$ SfCn001$^{P}$RfC $*^{P}$ SfG $*^{P}$ SfGn001PRfU $*^{P}$ SfU $*^{P}$ SmCfU $*^{P}$ SmG $*^{P}$ SfA $*^{P}$ SmAfG $*^{P}$ SfG $*^{P}$ SfU $*^{P}$ SfGn001$^{P}$RfU $*^{P}$ SfU $*^{P}$ SfC | CUCCGGUUCUGAAG GUGUUC |
| WV-O2-937 | 131 | G $*^{PD}$ SG $*^{PD}$ SC $*^{PD}$ SA $*^{PD}$ SC $*^{PD}$ SA $*^{PD}$ SA $*^{PD}$ SG $*^{PD}$ SG $*^{PD}$ SG $*^{PD}$ SC $*^{PD}$ SA $*^{PD}$ SC $*^{PD}$ RA $*^{PD}$ SG $*^{PD}$ SA $*^{PD}$ SC $*^{PD}$ ST $*^{PD}$ ST $*^{PD}$ SC | GGCACAAGGGCA CAGACTTC |
| WV-O2-1077 | 132 | mA $*^{PD}$ SmU $*^{PD}$ SmU $*^{PD}$ SmA $*^{PD}$ SmA $*^{PD}$ SmU $*^{PD}$ SA $*^{PD}$ SA $*^{PD}$ SA $*^{PD}$ ST $*^{PD}$ ST $*^{PD}$ SG $*^{PD}$ ST $*^{PD}$ SC $*^{PD}$ RA $*^{PD}$ ST $*^{PD}$ SmC $*^{PD}$ SmA $*^{PD}$ SmC $*^{PD}$ SmC | AUUAAUAAATTGTC ATCACC |
| WV-O2-1078 | 133 | mA $*^{PD}$ RmU $*^{PD}$ RmU $*^{PD}$ RmA $*^{PD}$ RmA $*^{PD}$ RmU $*^{PD}$ SA $*^{PD}$ SA $*^{PD}$ SA $*^{PD}$ ST $*^{PD}$ ST $*^{PD}$ SG $*^{PD}$ ST $*^{PD}$ SC $*^{PD}$ RA $*^{PD}$ ST $*^{PD}$ SmC $*^{PD}$ RmA $*^{PD}$ RmC $*^{PD}$ RmC | AUUAAUAAATTGTC ATCACC |
| WV-O2-1079 | 134 | mA $*^{PD}$ SmU $*^{PD}$ SmU $*^{PD}$ SmA $*^{PD}$ SmA $*^{PD}$ SmU $*^{PD}$ SmA $*^{PD}$ SmA $*^{PD}$ SA $*^{PD}$ ST $*^{PD}$ ST $*^{PD}$ SG $*^{PD}$ ST $*^{PD}$ SC $*^{PD}$ RA $*^{PD}$ ST $*^{PD}$ SC $*^{PD}$ SA $*^{PD}$ SC $*^{PD}$ SC | AUUAAUAAATTGTC ATCACC |
| WV-O2-1085 | 135 | mG $*^{PD}$ SmG $*^{PD}$ SmC $*^{PD}$ SmA $*^{PD}$ SmC $*^{PD}$ SA $*^{PD}$ SA $*^{PD}$ SG $*^{PD}$ SG $*^{PD}$ SG $*^{PD}$ SC $*^{PD}$ SA $*^{PD}$ SC $*^{PD}$ RA $*^{PD}$ SG $*^{PD}$ SmA $*^{PD}$ SmC $*^{PD}$ SmU $*^{PD}$ SmU $*^{PD}$ SmC | GGCACAAGGGCA CAGACUUC |
| WV-O2-1086 | 136 | mG $*^{PD}$ RmG $*^{PD}$ RmC $*^{PD}$ RmA $*^{PD}$ RmC $*^{PD}$ SA $*^{PD}$ SA $*^{PD}$ SG $*^{PD}$ SG $*^{PD}$ SG $*^{PD}$ SC $*^{PD}$ SA $*^{PD}$ SC $*^{PD}$ RA $*^{PD}$ SG $*^{PD}$ SmA $*^{PD}$ RmC $*^{PD}$ RmU $*^{PD}$ RmU $*^{PD}$ RmC | GGCACAAGGGCA CAGACUUC |
| WV-O2-1090 | 137 | mGmGmCmAmCmAmAmG $*^{PD}$ SG $*^{PD}$ SG $*^{PD}$ SC $*^{PD}$ SA $*^{PD}$ SC $*^{PD}$ RA $*^{PD}$ SG $*^{PD}$ SA $*^{PD}$ SC $*^{PD}$ ST $*^{PD}$ ST $*^{PD}$ SC | GGCACAAGGGCA CAGACTTC |

TABLE O-2-continued

Example Oligonucleotides. (SEQ ID NOS: 66-195)

| ID | SEQ ID NO | Description | Naked Base Sequence |
|---|---|---|---|
| WV-O2-1091 | 138 | mG *$^{PD}$ RmGmCmAmC *$^{PD}$ SA *$^{PD}$ SA *$^{PD}$ SG *$^{PD}$ SG *$^{PD}$ SG *$^{PD}$ SC *$^{PD}$ SA *$^{PD}$ SC *$^{PD}$ RA *$^{PD}$ SG *$^{PD}$ SmAmCmUmU *$^{PD}$ RmC | GGCACAAGGGCA CAGACUUC |
| WV-O2-1092 | 139 | mG *$^{PD}$ SmGmCmAmC *$^{PD}$ SA *$^{PD}$ SA *$^{PD}$ SG *$^{PD}$ SG *$^{PD}$ SG *$^{PD}$ SC *$^{PD}$ SA *$^{PD}$ SC *$^{PD}$ RA *$^{PD}$ SG *$^{PD}$ SmAmCmUmU *$^{PD}$ SmC | GGCACAAGGGCA CAGACUUC |
| WV-O2-1497 | 140 | mG *$^{PD}$ mGmCmAmC *$^{PD}$ A *$^{PD}$ A *$^{PD}$ G *$^{PD}$ G *$^{PD}$ G *$^{PD}$ C *$^{PD}$ A *$^{PD}$ C *$^{PD}$ A *$^{PD}$ G *$^{PD}$ mAmCmUmU *$^{PD}$ mC | GGCACAAGGGCA CAGACUUC |
| WV-O2-1508 | 141 | A *$^{PD}$ SmUmUmAmAmU *$^{PD}$ SA *$^{PD}$ SA *$^{PD}$ SA *$^{PD}$ ST *$^{PD}$ ST *$^{PD}$ SG *$^{PD}$ ST *$^{PD}$ SC *$^{PD}$ RA *$^{PD}$ ST *$^{PD}$ SmCmAmC *$^{PD}$ SC | AUUAAUAAATTGTC ATCACC |
| WV-O2-1510 | 142 | G *$^{PD}$ SmGmCmAmC *$^{PD}$ SA *$^{PD}$ SA *$^{PD}$ SG *$^{PD}$ SG *$^{PD}$ SG *$^{PD}$ SC *$^{PD}$ SA *$^{PD}$ SC *$^{PD}$ RA *$^{PD}$ SG *$^{PD}$ SmAmCmUmU *$^{PD}$ SC | GGCACAAGGGCA CAGACUUC |
| WV-O2-2076 | 143 | mU *$^{PD}$ mAmAmUmA *$^{PD}$ A *$^{PD}$ A *$^{PD}$ T $^{PD}$ T *$^{PD}$ G *$^{PD}$ T *$^{PD}$ C *$^{PD}$ A *$^{PD}$ T *$^{PD}$ C *$^{PD}$ mAmCmCmA *$^{PD}$ mG | UAAUAAATTGTCAT CACCAG |
| WV-O2-2378 | 144 | mG *$^{PD}$ SmCmAmCmA *$^{PD}$ SA *$^{PD}$ SG *$^{PD}$ SG *$^{PD}$ SG *$^{PD}$ SC *$^{PD}$ SA *$^{PD}$ SC *$^{PD}$ RA *$^{PD}$ SG *$^{PD}$ SA *$^{PD}$ SmCmUmUmC *$^{PD}$ SmC | GCACAAGGGCA CAGACUUCC |
| WV-O2-2380 | 145 | mC *$^{PD}$ SmAmCmAmA *$^{PD}$ SG *$^{PD}$ SG *$^{PD}$ SG *$^{PD}$ SC*$^{PD}$ SA *$^{PD}$ SC *$^{PD}$ RA *$^{PD}$ SG *$^{PD}$ SA *$^{PD}$ SC *$^{PD}$ SmUmUmCmC *$^{PD}$ SmA | CACAAGGGCACAGA CUUCCA |
| WV-O2-2417 | 146 | mA *$^{PD}$ SmUmAmAmA *$^{PD}$ ST *$^{PD}$ ST *$^{PD}$ SG *$^{PD}$ ST *$^{PD}$ SC *$^{PD}$ RA *$^{PD}$ ST *$^{PD}$ SC *$^{PD}$ SA *$^{PD}$ SC *$^{PD}$ SmCmAmGmA *$^{PD}$ SmA | AUAAATTGTCATCA CCAGAA |
| WV-O2-2418 | 147 | mA *$^{PD}$ SmAmUmAmA *$^{PD}$ SA *$^{PD}$ ST *$^{PD}$ ST *$^{PD}$ SG *PR ST *$^{PD}$ SC *$^{PD}$ RA *$^{PD}$ ST *$^{PD}$ SC *$^{PD}$ SA *$^{PD}$ SmCmCmAmG *$^{PD}$ SmA | AAUAAATTGTCATC ACCAGA |
| WV-O2-2595 | 148 | mG *$^{PD}$ SmGmGmUmC *$^{PD}$ SC *$^{PD}$ ST *$^{PD}$ SC *$^{PD}$ SC *$^{PD}$ SC *$^{PD}$ SC *$^{PD}$ SA *$^{PD}$ SC *$^{PD}$ RA *$^{PD}$ SG *$^{PD}$ SmAmGmGmG *$^{PD}$ SmA | GGGUCCTCCCCACA GAGGGA |
| WV-O2-2601 | 149 | mG *$^{PD}$ SmCmAmCmA *$^{PD}$ SC *$^{PD}$ SA *$^{PD}$ SG *$^{PD}$ ST *$^{PD}$ SA *$^{PD}$ SG *$^{PD}$ RA *$^{PD}$ ST *$^{PD}$ SG *$^{PD}$ SA *$^{PD}$ SmGmGmGmA *$^{PD}$ SmG | GCACACAGTAGATG AGGGAG |
| WV-O2-2602 | 150 | mU *$^{PD}$ SmGmCmAmC *$^{PD}$ SA *$^{PD}$ SC *$^{PD}$ SA *$^{PD}$ SG *$^{PD}$ ST *$^{PD}$ SA *$^{PD}$ SG *$^{PD}$ RA *$^{PD}$ ST *$^{PD}$ SG *$^{PD}$ SmAmGmGmG *$^{PD}$ SmA | UGCACACAGTAGAT GAGGGA |
| WV-O2-2603 | 151 | mG *$^{PD}$ SmUmGmCmA *$^{PD}$ SC *$^{PD}$ SA *$^{PD}$ SC *$^{PD}$ SA *$^{PD}$ SG *$^{PD}$ ST *$^{PD}$ SA *$^{PD}$ SG *$^{PD}$ RA *$^{PD}$ ST *$^{PD}$ SmGmAmGmG *$^{PD}$ SmG | GUGCACACAGTAGA TGAGGG |
| WV-O2-2618 | 152 | mU *$^{PD}$ mGmCmAmC *$^{PD}$ A *$^{PD}$ C *$^{PD}$ A *$^{PD}$ G *$^{PD}$ T *$^{PD}$ A *$^{PD}$ G *$^{PD}$ A *$^{PD}$ T *$^{PD}$ G *$^{PD}$ mAmGmGmG *$^{PD}$ mA | UGCACACAGTAGAT GAGGGA |
| WV-O2-2619 | 153 | mG *$^{PD}$ mUmGmCmA *$^{PD}$ C *$^{PD}$ A *$^{PD}$ C *$^{PD}$ A *$^{PD}$ G *$^{PD}$ T *$^{PD}$ A *$^{PD}$ G *$^{PD}$ A *$^{PD}$ T *$^{PD}$ mGmAmGmG *$^{PD}$ mG | GUGCACACAGTAGA TGAGGG |
| WV-O2-2671 | 154 | mG *$^{PD}$ SmG *$^{PD}$ SmGmUmC *$^{PD}$ SC *$^{PD}$ ST *$^{PD}$ SC *$^{PD}$ SC *$^{PD}$ SC *$^{PD}$ SC *$^{PD}$ SA *$^{PD}$ SC *$^{PD}$ RA *$^{PD}$ SG *$^{PD}$ SmAmGmG *$^{PD}$ SmG *$^{PD}$ SmA | GGGUCCTCCCCACA GAGGGA |
| WV-O2-887 | 155 | mU *$^{PD}$ S mC *$^{PD}$ S mA *$^{PD}$ S mA *$^{PD}$ R mG *$^{PD}$ R mG *$^{PD}$ R mA *$^{PD}$ R mA *$^{PD}$ R mG *$^{PD}$ R mA *$^{PD}$ R mU *$^{PD}$ R mG *$^{PD}$ R mG *$^{PD}$ R mC *$^{PD}$ R mA *$^{PD}$ R mU *$^{PD}$ R mU *$^{PD}$ S mU *$^{PD}$ S mC *$^{PD}$ S mU | UCAAGGAAGAUGGC AUUUCU |
| WV-O2-892 | 156 | mU *$^{PD}$ S mC *$^{PD}$ R mA *$^{PD}$ R mA *$^{PD}$ R mG *$^{PD}$ R mG *$^{PD}$ R mA *$^{PD}$ R mA *$^{PD}$ R mG *$^{PD}$ R mA *$^{PD}$ R mU *$^{PD}$ R mG *$^{PD}$ R mG *$^{PD}$ R mC *$^{PD}$ R mA *$^{PD}$ R mU *$^{PD}$ R mU *$^{PD}$ R mU *$^{PD}$ R mC *$^{PD}$ S mU | UCAAGGAAGAUGGC AUUUCU |
| WV-O2-896 | 157 | mU *$^{PD}$ S mC *$^{PD}$ S mA *$^{PD}$ R mA *$^{PD}$ R mG *$^{PD}$ R mG *$^{PD}$ R mA *$^{PD}$ R mA *$^{PD}$ R mG *$^{PD}$ R mA *$^{PD}$ R mU *$^{PD}$ S mG *$^{PD}$ R mG *$^{PD}$ R mC *$^{PD}$ S mA *$^{PD}$ R mU *$^{PD}$ S mU *$^{PD}$ S mU *$^{PD}$ S mC *$^{PD}$ S mU | UCAAGGAAGAUGGC AUUUCU |
| WV-O2-1714 | 158 | fU *$^{PD}$ fC *$^{PD}$ fA *$^{PD}$ fA *$^{PD}$ fG *$^{PD}$ fG *$^{PD}$ mA *$^{PD}$ mA *$^{PD}$ mG *$^{PD}$ mA *$^{PD}$ mU *$^{PD}$ mG *$^{PD}$ mG *$^{PD}$ mC *$^{PD}$ fA *$^{PD}$ fU *$^{PD}$ fU *$^{PD}$ fU *$^{PD}$ fC *$^{PD}$ fU | UCAAGGAAGAUGGC AUUUCU |
| WV-O2-2444 | 159 | fU *$^{PD}$ SfC *$^{PD}$ SfA *$^{PD}$ SfA *PK SfG *$^{PD}$ SfG *$^{PD}$ S mA *$^{PD}$ R mA *$^{PD}$ R mG *$^{PD}$ R mA *$^{PD}$ R mU *$^{PD}$ R mG *$^{PD}$ R mG *$^{PD}$ R mC *$^{PD}$ SfA *$^{PD}$ SfU *$^{PD}$ SfU *$^{PD}$ SfU *$^{PD}$ SfC *$^{PD}$ SfU | UCAAGGAAGAUGGC AUUUCU |
| WV-O2-2445 | 160 | fU *$^{PD}$ SfC *$^{PD}$ SfA*$^{PD}$ SfA *$^{PD}$ SfG *$^{PD}$ S mG *$^{PD}$ R mA *$^{PD}$ R mA *$^{PD}$ RmG *$^{PD}$ RmA *$^{PD}$ R mU *$^{PD}$ R mG *$^{PD}$ R mG *$^{PD}$ R mC *$^{PD}$ R mA *$^{PD}$ SfU *$^{PD}$ SfU *$^{PD}$ SfU *$^{PD}$ SfC *$^{PD}$ SfU | UCAAGGAAGAUGGC AUUUCU |
| WV-O2-2526 | 161 | fU *$^{PD}$ SfC *$^{PD}$ SfA *$^{PD}$ SfA *$^{PD}$ SfG *$^{PD}$ SfG *$^{PD}$ SfA *$^{PD}$ SfA *$^{PD}$ R mG *$^{PD}$ R mA *$^{PD}$ R mU *$^{PD}$ R mG *$^{PD}$ R mG *$^{PD}$ SfC *$^{PD}$ SfA *$^{PD}$ SfU *$^{PD}$ SfU *$^{PD}$ SfU *$^{PD}$ SfC *$^{PD}$ SfU | UCAAGGAAGAUGGC AUUUCU |
| WV-O2-2527 | 162 | fU *$^{PD}$ SfC *$^{PD}$ SfA *$^{PD}$ SfA *$^{PD}$ SfG *$^{PD}$ SfG *$^{PD}$ SfA *$^{PD}$ SfA *$^{PD}$ S mG *$^{PD}$ R mA *$^{PD}$ R mU *$^{PD}$ R mG *$^{PD}$ SfG *$^{PD}$ SfC *$^{PD}$ SfA *$^{PD}$ SfU *$^{PD}$ SfU *$^{PD}$ SfU *$^{PD}$ SfC *$^{PD}$ SfU | UCAAGGAAGAUGGC AUUUCU |
| WV-O2-2528 | 163 | fU *$^{PD}$ SfC *$^{PD}$ SfA *$^{PD}$ SfA *$^{PD}$ SfG *$^{PD}$ SfG *$^{PD}$ SfA *$^{PD}$ SfA *$^{PD}$ SfG *$^{PD}$ S mA *$^{PD}$ R mU *$^{PD}$ SfG *$^{PD}$ SfG *$^{PD}$ SfC *$^{PD}$ SfA *$^{PD}$ SfU *$^{PD}$ SfU *$^{PD}$ SfU *$^{PD}$ SfC *$^{PD}$ SfU | UCAAGGAAGAUGGC AUUUCU |
| WV-O2-2530 | 164 | fU *$^{PD}$ SfC *$^{PD}$ SfA *$^{PD}$ SfA *$^{PD}$ SfG *$^{PD}$ SfG *$^{PD}$ SfA *$^{PD}$ SfA *$^{PD}$ S mG mA mU mG *$^{PD}$ SfG *$^{PD}$ SfC *$^{PD}$ SfA *$^{PD}$ SfU *$^{PD}$ SfU *$^{PD}$ SfU *$^{PD}$ SfC *$^{PD}$ SfU | UCAAGGAAGAUGGC AUUUCU |
| WV-O2-2531 | 165 | fU *$^{PD}$ SfC $^{PD}$ SfA *$^{PD}$ SfA *$^{PD}$ SfG *$^{PD}$ SfG *$^{PD}$ SfA *$^{PD}$ SfA *$^{PD}$ SfG *$^{PD}$ S mA mU *$^{PD}$ SfG *$^{PD}$ SfG *$^{PD}$ SfC *$^{PD}$ SfA *$^{PD}$ SfU *$^{PD}$ SfU *$^{PD}$ SfU *$^{PD}$ SfC *$^{PD}$ SfU | UCAAGGAAGAUGGC AUUUCU |
| WV-O2-2578 | 166 | Mod013L001 *$^{PD}$ mU *$^{PD}$ mC *$^{PD}$ mA *$^{PD}$ mA *$^{PD}$ mG *$^{PD}$ mG *$^{PD}$ mA *$^{PD}$ mA *$^{PD}$ mG *$^{PD}$ mA *$^{PD}$ mU *$^{PD}$ mG *$^{PD}$ mG *$^{PD}$ mC *$^{PD}$ mA *$^{PD}$ mU *$^{PD}$ mU *$^{PD}$ mU *$^{PD}$ mC *$^{PD}$ mU | UCAAGGAAGAUGGC AUUUCU |
| WV-O2-2580 | 167 | Mod005L001 *$^{PD}$ mU *$^{PD}$ mC *$^{PD}$ mA *$^{PD}$ mA *$^{PD}$ mG *$^{PD}$ mG *$^{PD}$ mA *$^{PD}$ mA *$^{PD}$ mG *$^{PD}$ mA *$^{PD}$ mU *$^{PD}$ mG *$^{PD}$ mG *$^{PD}$ mC *$^{PD}$ mA *$^{PD}$ mU *$^{PD}$ mU *$^{PD}$ mU *$^{PD}$ mC *$^{PD}$ mU | UCAAGGAAGAUGGC AUUUCU |
| WV-O2-2587 | 168 | Mod020L001 *$^{PD}$ mU *$^{PD}$ mC *$^{PD}$ mA *$^{PD}$ mA *$^{PD}$ mG *$^{PD}$ mG *$^{PD}$ mA *$^{PD}$ mA *$^{PD}$ mG *$^{PD}$ mA *$^{PD}$ mU *$^{PD}$ mG *$^{PD}$ mG *$^{PD}$ mC *$^{PD}$ mA *$^{PD}$ mU *$^{PD}$ mU *$^{PD}$ mU *$^{PD}$ mC *$^{PD}$ mU | UCAAGGAAGAUGGC AUUUCU |
| WV-O2-3047 | 169 | fU *$^{PD}$ fC *$^{PD}$ fA *$^{PD}$ fA *$^{PD}$ fG *$^{PD}$ fG *$^{PD}$ mA *$^{PD}$ mA *$^{PD}$ mG *$^{PD}$ mA fU *$^{PD}$ mG *$^{PD}$ mG *$^{PD}$ fC *$^{PD}$ fA *$^{PD}$ fU *$^{PD}$ fU *$^{PD}$ fU *$^{PD}$ fC *$^{PD}$ fU | UCAAGGAAGAUGGC AUUUCU |
| WV-O2-3152 | 170 | fU *$^{PD}$ SfC *$^{PD}$ SfA *$^{PD}$ SfA *$^{PD}$ SfG *$^{PD}$ SfG *$^{PD}$ S mAfA *$^{PD}$ S mGfA *$^{PD}$ S mUfG *$^{PD}$ S mGfC *$^{PD}$ SfA *$^{PD}$ SfU *$^{PD}$ SfU *$^{PD}$ SfU *$^{PD}$ SfC *$^{PD}$ SfU | UCAAGGAAGAUGGC AUUUCU |

TABLE O-2-continued

| Example Oligonucleotides. (SEQ ID NOS: 66-195) | | | |
|---|---|---|---|
| ID | SEQ ID NO | Description | Naked Base Sequence |
| WV-O2-3472 | 171 | fU *$^{PD}$ SfC *$^{PD}$ SfA *$^{PD}$ SfA *$^{PD}$ SfG *$^{PD}$ SfG *$^{PD}$ S mAfA *$^{PD}$ S mGfA *$^{PD}$ SfU *$^{PD}$ S mG mGfC *$^{PD}$ SfA *$^{PD}$ SfU *$^{PD}$ SfU *$^{PD}$ SfU *$^{PD}$ SfC *$^{PD}$ SfU | UCAAGGAAGAUGGC AUUUCU |
| WV-O2-3473 | 172 | fU *$^{PD}$ SfC *$^{PD}$ SfA *$^{PD}$ SfA *$^{PD}$ SfG *$^{PD}$ SfG *$^{PD}$ S mAfA *$^{PD}$ S mG mA *$^{PD}$ SfU *$^{PD}$ S mG mGfC *$^{PD}$ SfA *$^{PD}$ SfU *$^{PD}$ SfU *$^{PD}$ SfU *$^{PD}$ SfC *$^{PD}$ SfU | UCAAGGAAGAUGGC AUUUCU |
| WV-O2-3507 | 173 | fU *$^{PD}$ SfC *$^{PD}$ SfA *$^{PD}$ SfA *$^{PD}$ SfG *$^{PD}$ SfG *$^{PD}$ S mAfA *$^{PD}$ S mG mAfU *$^{PD}$ S mG mGfC *$^{PD}$ SfA *$^{PD}$ SfU *$^{PD}$ SfU *$^{PD}$ SfU *$^{PD}$ SfC *$^{PD}$ SfU | UCAAGGAAGAUGGC AUUUCU |
| WV-O2-3508 | 174 | fU *$^{PD}$ SfC *$^{PD}$ SfA *$^{PD}$ SfA *$^{PD}$ SfG *$^{PD}$ SfG *$^{PD}$ S mAfA *$^{PD}$ S mGfA *$^{PD}$ SfU *$^{PD}$ S mG mGfC *$^{PD}$ SfAfU *$^{PD}$ SfU *$^{PD}$ SfU *$^{PD}$ SfC *$^{PD}$ SfU | UCAAGGAAGAUGGC AUUUCU |
| WV-O2-3509 | 175 | fU *$^{PD}$ SfC *$^{PD}$ SfA *$^{PD}$ SfA *$^{PD}$ SfG *$^{PD}$ SfG *$^{PD}$ S mAfA *$^{PD}$ S mG mA *$^{PD}$ SfU *$^{PD}$ S mG mGfC *$^{PD}$ SfAfU *$^{PD}$ SfU *$^{PD}$ SfU *$^{PD}$ SfC *$^{PD}$ SfU | UCAAGGAAGAUGGC AUUUCU |
| WV-O2-3510 | 176 | fU *$^{PD}$ SfC *$^{PD}$ SfA *$^{PD}$ SfA *$^{PD}$ SfG *$^{PD}$ SfG *$^{PD}$ S mAfA *$^{PD}$ S mGfAfU *$^{PD}$ S mG mGfC *$^{PD}$ S mA *$^{PD}$ SfU *$^{PD}$ SfU *$^{PD}$ SfU *$^{PD}$ SfC *$^{PD}$ SfU | UCAAGGAAGAUGGC AUUUCU |
| WV-O2-3511 | 177 | fU *$^{PD}$ SfC *$^{PD}$ SfA *$^{PD}$ SfA *$^{PD}$ SfG *$^{PD}$ SfG *$^{PD}$ S mAfA *$^{PD}$ S mG mAfU *$^{PD}$ S mG mGfC *$^{PD}$ S mA *$^{PD}$ SfU *$^{PD}$ SfU *$^{PD}$ SfU *$^{PD}$ SfC *$^{PD}$ SfU | UCAAGGAAGAUGGC AUUUCU |
| WV-O2-3512 | 178 | fU *$^{PD}$ SfC *$^{PD}$ SfA *$^{PD}$ SfA *$^{PD}$ SfG *$^{PD}$ SfG *$^{PD}$ S mAfA *$^{PD}$ S mGfAfU *$^{PD}$ S mG mGfC *$^{PD}$ S mAfU *$^{PD}$ SfU *$^{PD}$ SfU *$^{PD}$ SfC *$^{PD}$ SfU | UCAAGGAAGAUGGC AUUUCU |
| WV-O2-3513 | 179 | fU *$^{PD}$ SfC *$^{PD}$ SfA *$^{PD}$ SfA *$^{PD}$ SfG *$^{PD}$ SfG *$^{PD}$ S mAfA *$^{PD}$ S mG mAfU *$^{PD}$ S mG mGfC *$^{PD}$ S mAfU *$^{PD}$ SfU *$^{PD}$ SfU *$^{PD}$ SfC *$^{PD}$ SfU | UCAAGGAAGAUGGC AUUUCU |
| WV-O2-3514 | 180 | fU *$^{PD}$ SfC *$^{PD}$ SfA *$^{PD}$ SfA *$^{PD}$ SfG *$^{PD}$ SfG *$^{PD}$ S mAfA *$^{PD}$ S mGfAfU *$^{PD}$ S mG mGfC *$^{PD}$ SfAfU *$^{PD}$ SfU *$^{PD}$ SfU *$^{PD}$ SfC *$^{PD}$ SfU | UCAAGGAAGAUGGC AUUUCU |
| WV-O2-3515 | 181 | fU *$^{PD}$ SfC *$^{PD}$ SfA *$^{PD}$ SfA *$^{PD}$ SfG *$^{PD}$ SfG *$^{PD}$ S mAfA *$^{PD}$ S mG mAfU *$^{PD}$ S mG mGfC *$^{PD}$ SfAfU *$^{PD}$ SfU *$^{PD}$ SfU *$^{PD}$ SfC *$^{PD}$ SfU | UCAAGGAAGAUGGC AUUUCU |
| WV-O2-3545 | 182 | Mod015L001fU *$^{PD}$ SfC *$^{PD}$ SfA *$^{PD}$ SfA *$^{PD}$ SfG *$^{PD}$ SfG *$^{PD}$ S mAfA *$^{PD}$ S mG mA *$^{PD}$ SfU *$^{PD}$ S mG mGfC *$^{PD}$ SfA *$^{PD}$ SfU *$^{PD}$ SfU *$^{PD}$ SfU *$^{PD}$ SfC *$^{PD}$ SfU | UCAAGGAAGAUGGC AUUUCU |
| WV-O2-3546 | 183 | Mod020L001fU *$^{PD}$ SfC *$^{PD}$ SfA *$^{PD}$ SfA *$^{PD}$ SfG *$^{PD}$ SfG *$^{PD}$ S mAfA *$^{PD}$ S mG mA *$^{PD}$ SfU *$^{PD}$ S mG mGfC *$^{PD}$ SfA *$^{PD}$ SfU *$^{PD}$ SfU *$^{PD}$ SfU *$^{PD}$ SfC *$^{PD}$ SfU | UCAAGGAAGAUGGC AUUUCU |
| WV-O2-9517 | 184 | fC *$^{PD}$ SfU *$^{PD}$ SfC *$^{PD}$ SfC *$^{PD}$ SfG *$^{PD}$ SfG *$^{PD}$ SfU *$^{PD}$ SfU *$^{PD}$ S mCfU *$^{PD}$ S mG *$^{PD}$ SfA *$^{PD}$ S mA mGfG *$^{PD}$ SfU *$^{PD}$ SfG *$^{PD}$ SfU *$^{PD}$ SfU *$^{PD}$ SfC | CUCCGGUUCUGAAG GUGUUC |
| WV-O2-12555 | 185 | fC *$^{PD}$ SfU *$^{PD}$ SfC *$^{PD}$ SfC *$^{PD}$ SfG *$^{PD}$ SfG *$^{PD}$ SfU *$^{PD}$ SfU *$^{PD}$ SmCn001$^{P}$RfU *$^{PD}$ SmG *$^{PD}$ SfA *$^{PD}$ SmAn001$^{P}$RfG *$^{PD}$ SfG *$^{PD}$ SfU *$^{PD}$ SfG *$^{PD}$ SfU *$^{PD}$ SfU *$^{PD}$ SfC | CUCCGGUUCUGAAG GUGUUC |
| WV-O2-12556 | 186 | fC *$^{PD}$ SfU *$^{PD}$ SfC *$^{PD}$ SfC *$^{PD}$ SfG *$^{PD}$ SfG *$^{PD}$ SfU *$^{PD}$ SfU *$^{PD}$ SmCn001$^{P}$RfU *$^{PD}$ SmG *$^{PD}$ SfA *$^{PD}$ SmAn001$^{P}$RmG *$^{PD}$ SfG *$^{PD}$ SfU *$^{PD}$ SfG *$^{PD}$ SfU *$^{PD}$ SfU *$^{PD}$ SfC | CUCCGGUUCUGAAG GUGUUC |
| WV-O2-12558 | 187 | fC *$^{PD}$ SfU *$^{PD}$ SfC *$^{PD}$ SfC *$^{PD}$ SfG *$^{PD}$ SfG *$^{PD}$ SfU *$^{PD}$ SfU *$^{PD}$ SmCn001$^{P}$SfU *$^{PD}$ SmG *$^{PD}$ SfA *$^{PD}$ SmAn001$^{P}$SfG *$^{PD}$ SfG *$^{PD}$ SfU *$^{PD}$ SfG *$^{PD}$ SfU *$^{PD}$ SfU *$^{PD}$ SfC | CUCCGGUUCUGAAG GUGUUC |
| WV-O2-12876 | 188 | fC *$^{PD}$ SfU *$^{PD}$ SfCn001$^{P}$fC *$^{PD}$ SfG *$^{PD}$ SfGn001$^{P}$fU *$^{PD}$ SfU *$^{PD}$ SmCn001PfU *$^{PD}$ SmG *$^{PD}$ SfA *$^{PD}$ SmAn001PmGn001$^{P}$fG *$^{PD}$ SfU *$^{PD}$ SfGn001$^{P}$fU *$^{PD}$ SfU *$^{PD}$ SfC | CUCCGGUUCUGAAG GUGUUC |
| WV-O2-12877 | 189 | fC *$^{PD}$ SfU *$^{PD}$ SfCn001$^{P}$fC *$^{PD}$ SfG *$^{PD}$ SfGn001$^{P}$fU *$^{PD}$ SfU *$^{PD}$ SmCn001$^{P}$fU *$^{PD}$ SmG *$^{PD}$ SfA *$^{PD}$ SmAn001PfG *$^{PD}$ SfG *$^{PD}$ SfU *$^{PD}$ SfGn001$^{P}$fU *$^{PD}$ SfU *$^{PD}$ SfC | CUCCGGUUCUGAAG GUGUUC |
| WV-O2-12878 | 190 | fC *$^{PD}$ SfU *$^{PD}$ SfCn001$^{P}$fC *$^{PD}$ SfG SfGn001$^{P}$fU *$^{PD}$ SfU *$^{PD}$ SmCn001$^{P}$fU *$^{PD}$ SmG *$^{PD}$ SfA *$^{PD}$ SmAn001$^{P}$mG *$^{PD}$ SfG *$^{PD}$ SfU *$^{PD}$ SfGn001$^{P}$fU *$^{PD}$ SfU *$^{PD}$ SfC | CUCCGGUUCUGAAG GUGUUC |
| WV-O2-13826 | 191 | fU *$^{PD}$ SfC *$^{PD}$ SfC *$^{PD}$ SfG *$^{PD}$ SfG *$^{PD}$ SfU *$^{PD}$ SfU *$^{PD}$ SmCfU *$^{PD}$ SmG *$^{PD}$ SfA *$^{PD}$ SmAmGfG *$^{PD}$ SfU *$^{PD}$ SfG *$^{PD}$ SfU *$^{PD}$ SfU *$^{PD}$ SfC | UCCGGUUCUGAAGG UGUUC |
| WV-O2-12880 | 192 | fC *$^{PD}$ SfU *$^{PD}$ SfCn001$^{P}$fC *$^{PD}$ SfG *$^{PD}$ SfGn001$^{P}$fU *$^{PD}$ SfU *$^{PD}$ SmCfU *$^{PD}$ SmG *$^{PD}$ SfA *$^{PD}$ SmAfG SfG *$^{PD}$ SfU *m SfGn001$^{P}$fU *FD SfU *$^{PD}$ SfC | CUCCGGUUCUGAAG GUGUUC |
| WV-O2-14344 | 193 | fC *$^{PD}$ SfU *$^{PD}$ SfCn001$^{P}$RfC *$^{PD}$ SfG *$^{PD}$ SfGn001$^{P}$RfU *$^{PD}$ SfU *$^{PD}$ SmCfU *$^{PD}$ SmG *$^{PD}$ SfA *$^{PD}$ SmAfGfG *$^{PD}$ SfU *$^{PD}$ SfGn001$^{P}$RfU *$^{PD}$ SfU *$^{PD}$ SfC | CUCCGGUUCUGAAG GUGUUC |
| WV-O2-13835 | 194 | fU *$^{PD}$ SfC *$^{PD}$ SfC *$^{PD}$ SfG *$^{PD}$ SfG *$^{PD}$ SfU *$^{PD}$ SfU *$^{PD}$ SmCfU *$^{PD}$ SmG *$^{PD}$ SfA *$^{PD}$ SmAmGfG *$^{PD}$ SfU *$^{PD}$ SfG *$^{PD}$ SfU *$^{PD}$ SfU *$^{PD}$ SfC *$^{PD}$ SfU | UCCGGUUCUGAAGG UGUUCU |
| WV-O2-13864 | 195 | fC *$^{PD}$ SfU *$^{PD}$ SfCn001$^{P}$RfC *$^{PD}$ SfG *$^{PD}$ SfGn001$^{P}$RfU *$^{PD}$ SfU *$^{PD}$ SmCfU *$^{PD}$ SmG *$^{PD}$ SfA *$^{PD}$ SmAfG *$^{PD}$ SfG *$^{PD}$ SfU *$^{PD}$ SfGn001$^{P}$RfU *$^{PD}$ SfU *$^{PD}$ SfC | CUCCGGUUCUGAAG GUGUUC |

Spaces in Table O-2 are utilized for formatting and readability, e.g., OXXXXXX XXXXX XXXXX XXXX illustrates the same stereochemistry as OXXXXXXXXXXXXXXXXXXXX. Oligonucleotides listed in Tables A1 are single-stranded unless otherwise specified; they may be used as a single strand, or as a strand to form complexes with one or more other strands. Some sequences, due to their length, are divided into multiple lines. As appreciated by those skilled in the art, sugar units are unmodified and are 2'-deoxy sugars unless otherwise indicated with modifications (e.g., modified with f, m, m5, etc.); linkages, unless otherwise indicated, are $O^{P}$; and acidic/basic groups may independently exist in their salt forms; nucleobases are optionally protected (e.g., as typically used in oligonucleotide synthesis). Moieties and modifications in oligonucleotides (or other compounds, e.g., those useful for preparing provided oligonucleotides comprising these moieties or modifications):

f: 2'-F modification on the following nucleoside (e.g., fA (

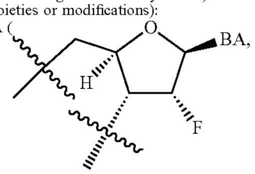

wherein BA is nucleobase A which is optionally protected));

L001: C6 amino linker (C6, —NH—$(CH_2)_6$—) wherein —NH— is connected to Mod (e.g., through —C(O)— in Mod) or —H, and —$(CH_2)_6$— is connected to the 5'-end (or 3'-end if indicated) of oligonucleotide chain through $O^{P}$ (if not indicated, it is through $O^{P}$) or *$^{P}$ or *$^{PD}$ linkage. May also be referred to as C6 linker or C6 amine linker;

TABLE O-2-continued

Example Oligonucleotides. (SEQ ID NOS: 66-195)

| ID | SEQ ID NO | Description | Naked Base Sequence |
|---|---|---|---|

m: 2'-OMe modification on the following nucleoside (e.g., mA ( 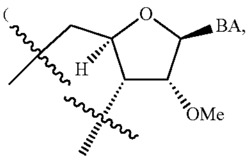

wherein BA is nucleobase A which is optionally protected));

Mod005 (its —C(O)— may connect to, e.g., —NH— of a linker such as L001 as specified in the description of an oligonucleotide):

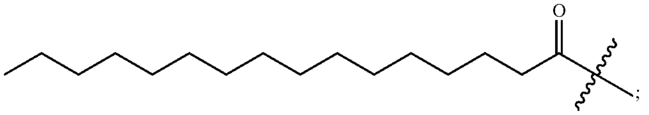 [SMILES: *C(=O)CCCCCCCCCCCCCCC]

Mod013 (its —C(O) — may connect to, e.g., —NH — of a linker such as L001 as specified in the description of an oligonucleotide):

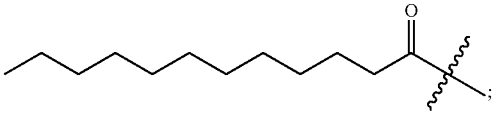 [SMILES: *C(=O)CCCCCCCCCCC]

Mod015 (its —C(O) — may connect to, e.g., —NH — of a linker such as L001 as specified in the description of an oligonucleotide):

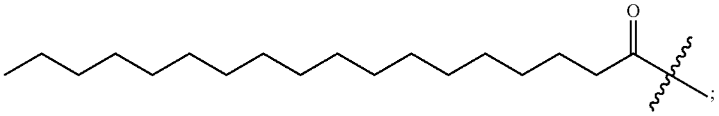 [SMILES: *C(=O)CCCCCCCCCCCCCCCCC]

Mod020 (its —C(O) — may connect to, e.g., —NH — of a linker such as L001 as specified in the description of an oligonucleotide):

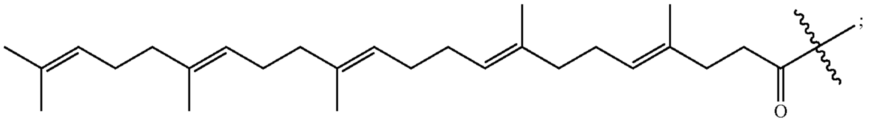 [SMILES: *C(=O)CC/C(C)=C/CC/C(C)=C/CC/C=C(\C)CC/C=C(\C)CCC=C(C)C]

and wherein in each oligonucleotide:

n001$^{P}$ is

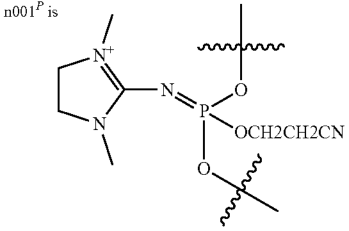

(as appreciated by those skilled in the art, it is associated with an anion (e.g., $Q^-$ such as $PF_6^-$ (which can be an anion in a modification step)));

n001$^{P}$R is

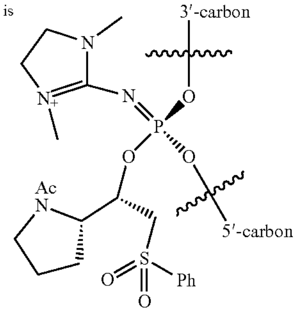

(as appreciated by those skilled in the art, it is associated with an anion (e.g., $Q^-$ such as $PF_6^-$ (which can be an anion in a modification step)));

TABLE O-2-continued

| Example Oligonucleotides. (SEQ ID NOS: 66-195) | | | |
|---|---|---|---|
| ID | SEQ ID NO | Description | Naked Base Sequence |

$n001^PS$ is

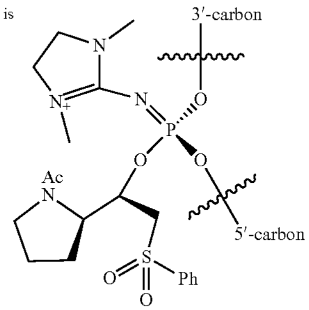

(as appreciated by those skilled in the art, it is associated with an anion (e.g., $Q^-$ such as $PF_6^-$ (which can be an anion in a modification step)));

$O^P$ is

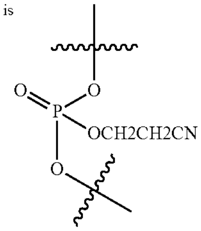

($O^P$ may also represent a linkage connecting a linker, e.g., L001, and the 5'-carbon of a 5'-terminal sugar of an oligonucleotide chain if no other linkage is specified for that linkage (e.g., between Mod015L001 and 5' fU in Mod015L001fU $*^P$ SfC $*^P$ SfA $*^P$ SfA $*^P$ SfG $*^P$ SfG $*^P$ S mAfA $*^P$ S mG mA $*^P$ SfU $*^P$ S mG mGfC $*^P$ SfA $*^P$ SfU $*^P$ SfU $*^P$ SfU $*^P$ SfC $*^P$ SfU)(SEQ ID NO: 198));

$*^P$ or $*^{PD}$ is

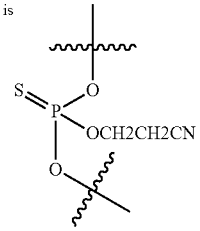

($*^P/*^{PD}$ may also represent a phosphorothioate linkage connecting a linker, e.g., L001, and the 5'-carbon of a 5'-terminal sugar of an oligonucleotide chain (e.g., the underlined $*^P$ in Mod013L001 $*^P$ mU $*^P$ mC $*^P$ mA $*^P$ mA $*^P$ mG $*^P$ mG $*^P$ mA $*^P$ mA $*^P$ mG $*^P$ mA $*^P$ mU $*^P$ mG $*^P$ mG $*^P$ mC $*^P$ mA $*^P$ mU $*^P$ mU $*^P$ mU $*^P$ mC $*^P$ mU)(SEQ ID NO: 199));

$*^PR$ is

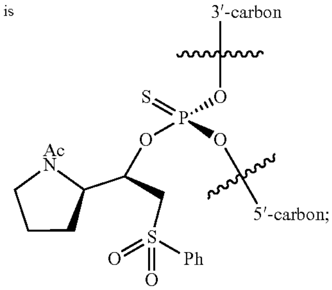

$*^PS$ is

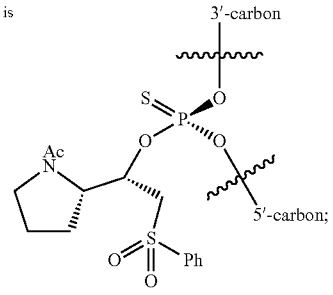

TABLE O-2-continued

Example Oligonucleotides. (SEQ ID NOS: 66-195)

| ID | SEQ ID NO | Description | Naked Base Sequence |
|---|---|---|---|

$*^{PD}R$ is

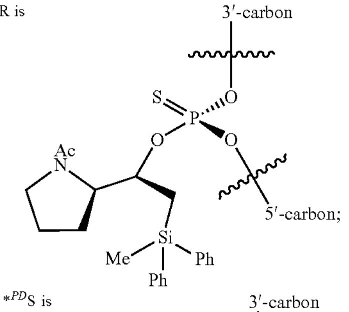

and $*^{PD}S$ is

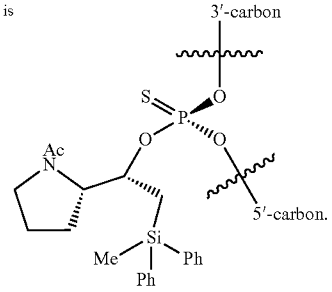

Among other things, the present disclosure contains a number of variables for, e.g., structures, formulae, etc. Unless otherwise specified, an embodiment for a variable may be optionally combined with embodiments of any other variables.

In some embodiments, $R^1$ is —H, -$L^s$-R, halogen, —CN, —$NO_2$, -$L^s$-Si$(R)_3$, —OR, —SR, or —$N(R)_2$. In some embodiments, $R^1$ is —H. In some embodiments, $R^1$ is -$L^s$-R, wherein each of $L^s$ and R is independently as described in the present disclosure. In some embodiments, $R^1$ is R, for example, an R embodiment as described in the present disclosure. In some embodiments, $R^1$ is halogen. In some embodiments, $R^1$ is —F. In some embodiments, $R^1$ is —Cl. In some embodiments, $R^1$ is —Br. In some embodiments, $R^1$ is —I. In some embodiments, $R^1$ is —CN. In some embodiments, $R^1$ is —$NO_2$. In some embodiments, $R^1$ is -$L^s$-Si$(R)_3$, wherein each of $L^s$ and R is independently as described in the present disclosure. In some embodiments, $R^1$ is —$CH_2$—Si$(R)_3$, wherein the —$CH_2$— group is optionally substituted, and each R is independently as described in the present disclosure. In some embodiments, $R^1$ is —$CH_2$—Si$(R)_3$, wherein each R is independently as described in the present disclosure. In some embodiments, each R of —Si$(R)_3$ is not —H. In some embodiments, each R of —Si$(R)_3$ is independently an optionally substituted group selected from $C_{1-6}$ alkyl and phenyl. In some embodiments, at least one R of —Si$(R)_3$ is optionally substituted $C_{1-6}$ alkyl, and at least one R of —Si$(R)_3$ is optionally substituted phenyl. In some embodiments, two R of —Si$(R)_3$ are independently optionally substituted $C_{1-6}$ alkyl, and one R of —Si$(R)_3$ is optionally substituted phenyl. In some embodiments, —Si$(R)_3$ is —Si$(Ph)_2$Me. Other non-hydrogen embodiments of R are extensively described in the present disclosure and may be used in —Si$(R)_3$. In some embodiments, $R^1$ is —OR, wherein R is as described in the present disclosure. In some embodiments, $R^1$ is —SR wherein R is as described in the present disclosure. In some embodiments, $R^1$ is —$N(R)_2$, wherein each R is independently as described in the present disclosure.

In some embodiments, $R^2$ is —H, -$L^s$-R, halogen, —CN, —$NO_2$, -$L^s$-Si$(R)_3$, —OR, —SR, or —$N(R)_2$. In some embodiments, $R^2$ is —H. In some embodiments, $R^2$ is -$L^s$-R, wherein each of $L^s$ and R is independently as described in the present disclosure. In some embodiments, $R^2$ is R, for example, an R embodiment as described in the present disclosure. In some embodiments, $R^2$ is halogen. In some embodiments, $R^2$ is —F. In some embodiments, $R^2$ is —Cl. In some embodiments, $R^2$ is —Br. In some embodiments, $R^2$ is —I. In some embodiments, $R^2$ is —CN. In some embodiments, $R^2$ is —$NO_2$. In some embodiments, $R^2$ is -$L^s$-Si$(R)_3$, wherein each of U and R is independently as described in the present disclosure. In some embodiments, $R^2$ is —$CH_2$—Si$(R)_3$, wherein the —$CH_2$— group is optionally substituted, and each R is independently as described in the present disclosure. In some embodiments, $R^2$ is —$CH_2$—Si$(R)_3$, wherein each R is independently as described in the present disclosure. In some embodiments, each R of —Si$(R)_3$ is not —H. In some embodiments, each R of —Si$(R)_3$ is independently an optionally substituted group selected from $C_{1-6}$ alkyl and phenyl. In some embodiments, —Si$(R)_3$ is —Si$(Ph)_2$Me. Other non-hydrogen embodiments of R are extensively described in the present disclosure and may be used in —Si$(R)_3$. In some embodiments, $R^2$ is —OR, wherein R is as described in the present disclosure. In some embodiments, $R^2$ is —SR wherein R is as described in the present disclosure. In some embodiments, $R^2$ is —$N(R)_2$, wherein each R is independently as described in the present disclosure. In some embodiments, $R^2$ is the same or different from $R^1$, and is a group selected from any groups described for $R^1$ in the present disclosure.

In some embodiments, at least one of $R^1$ and $R^2$ is not hydrogen. In some embodiments, $R^1$ is hydrogen and $R^2$ is not hydrogen. In some embodiments, $R^1$ is not hydrogen and $R^2$ is hydrogen. In some embodiments, neither of $R^1$ and $R^2$ is hydrogen.

In some embodiments, one of $R^1$ and $R^2$ is —H, and the other is R, wherein R is as described in the present disclosure and is not hydrogen. In some embodiments, one of $R^1$ and $R^2$ is —H, and the other is R, wherein R is optionally substituted $C_{1-6}$ aliphatic as described in the present disclosure. In some embodiments, one of $R^1$ and $R^2$ is —H, and the other is R, wherein R is optionally substituted $C_{1-4}$ aliphatic. In some embodiments, one of $R^1$ and $R^2$ is —H, and the other is R, wherein R is optionally substituted $C_{1-3}$ aliphatic. In some embodiments, one of $R^1$ and $R^2$ is —H, and the other is R, wherein R is optionally substituted $C_{1-2}$ aliphatic. In some embodiments, one of $R^1$ and $R^2$ is —H, and the other is R, wherein R is optionally substituted $C_{1-6}$ alkenyl. In some embodiments, one of $R^1$ and $R^2$ is —H, and the other R, wherein R is vinyl. In some embodiments, one of $R^1$ and $R^2$ is —H, and the other is R, wherein R is optionally substituted $C_{1-6}$ alkynyl. In some embodiments, one of $R^1$ and $R^2$ is —H, and the other is R, wherein R is ethynyl. In some embodiments, one of $R^1$ and $R^2$ is —H, and the other is R, wherein R is optionally substituted benzyl. In some embodiments, one of $R^1$ and $R^2$ is —H, and the other is R, wherein R is benzyl wherein the phenyl group of the benzyl is optionally substituted. In some embodiments, $R^1$ is —H and $R^2$ is benzyl. In some embodiments, a provided compound is

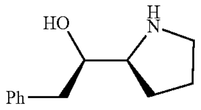

or a salt thereof. In some embodiments, a provided compound is a diastereomer of

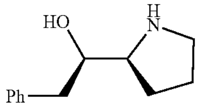

or a salt thereof. In some embodiments, a provided compound is an enantiomer of

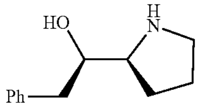 [SMILES: O[C@H](Cc1ccccc1)[C@@H]1CCCN1]

or a salt thereof.

In some embodiments, one of $R^1$ and $R^2$ is R, wherein R is as described in the present disclosure and comprises a ring moiety. In some embodiments, R is an optionally substituted group selected from $C_{3-20}$ cycloaliphatic, $C_{6-20}$ aryl, 5-20 membered heteroaryl having 1-5 heteroatoms, and 3-20 membered heterocyclyl having 1-5 heteroatoms, wherein each heteroatom is independently selected from nitrogen, oxygen, sulfur, phosphorus and silicon. In some embodiments, R is an optionally substituted group selected from $C_{3-20}$ cycloaliphatic, $C_{6-20}$ aryl, 5-20 membered heteroaryl having 1-5 heteroatoms, and 3-20 membered heterocyclyl having 1-5 heteroatoms, wherein each heteroatom is independently selected from nitrogen, oxygen, and sulfur. In some embodiments, R is optionally substituted $C_{3-20}$ cycloaliphatic. In some embodiments, R is optionally substituted $C_{3-10}$ cycloaliphatic. In some embodiments, R is optionally substituted $C_{3-10}$ cycloalkyl. In some embodiments, R is optionally substituted $C_{4-10}$ cycloalkyl. In some embodiments, R is optionally substituted cyclopropyl. In some embodiments, R is optionally substituted cyclobutyl. In some embodiments, R is optionally substituted cyclopentyl. In some embodiments, R is optionally substituted cyclohexyl. In some embodiments, R is optionally substituted cycloheptyl. In some embodiments, R is cyclopropyl. In some embodiments, R is cyclobutyl. In some embodiments, R is cyclopentyl. In some embodiments, R is cyclohexyl. In some embodiments, R is cycloheptyl. In some embodiments, R is optionally substituted $C_{6-20}$ aryl. In some embodiments, R is optionally substituted phenyl. In some embodiments, R is phenyl. In some embodiments, R is optionally substituted 5-20 membered heteroaryl having 1-5 heteroatoms. In some embodiments, R is optionally substituted 5-membered heteroaryl having 1-5 heteroatoms. In some embodiments, R is optionally substituted 6-membered heteroaryl having 1-5 heteroatoms. In some embodiments, R is optionally substituted 3-20 membered heterocyclyl having 1-5 heteroatoms. In some embodiments, the other of $R^1$ and $R^2$ is R wherein R is not hydrogen. In some embodiments, R is optionally substituted $C_{1-6}$ aliphatic. In some embodiments, R is optionally substituted $C_{1-6}$ alkyl. In some embodiments, R is $C_{1-6}$ alkyl. In some embodiments, R is methyl. In some embodiments, R is substituted methyl. In some embodiments, R is ethyl. In some embodiments, R is substituted ethyl. In some embodiments, one of $R^1$ and $R^2$ is R comprising a cyclic moiety as described in the present disclosure, and the other is an alkyl group as described in the present disclosure.

In some embodiments, one of $R^1$ and $R^2$ is R, wherein R is optionally substituted $C_{1-6}$ alkyl, and the other is R, wherein R is optionally substituted $C_{1-6}$ alkenyl. In some embodiments, one of $R^1$ and $R^2$ is optionally substituted methyl or ethyl, and the other is vinyl. In some embodiments, one of $R^1$ and $R^2$ is methyl, and the other is vinyl.

In some embodiments, one of $R^1$ and $R^2$ is R, wherein R is optionally substituted $C_{1-6}$ alkyl, and the other is R, wherein R is optionally substituted $C_{1-6}$ alkynyl. In some embodiments, one of $R^1$ and $R^2$ is optionally substituted methyl or ethyl, and the other is ethynyl. In some embodiments, one of $R^1$ and $R^2$ is methyl, and the other is ethynyl.

In some embodiments, each of $R^1$ and $R^2$ is independently R, wherein R is optionally substituted $C_{1-20}$ aliphatic. In some embodiments, R is unsubstituted $C_{1-20}$ aliphatic. In some embodiments, R is optionally substituted $C_{1-20}$ alkyl. In some embodiments, R is optionally substituted $C_{1-6}$ alkyl. In some embodiments, R is linear $C_{1-6}$ alkyl. In some embodiments, one of $R^1$ and $R^2$ is optionally substituted $C_{1-6}$ alkyl, and the other is optionally substituted $C_{1-6}$ alkyl. In some embodiments, $R^1$ and $R^2$ are the same. In some embodiments, $R^1$ and $R^2$ are different.

In some embodiments, each of $R^1$ and $R^2$ is independently R, wherein R is optionally substituted $C_{1-6}$ alkyl. In some embodiments, $R^1$ and $R^2$ are the same. Among other things, the present disclosure demonstrates that compounds with $R^1$ and $R^2$ being the same, or phosphoramidites prepared therefrom, can deliver high stereoselectivity, yields and/or purity when utilized in chirally controlled oligonucleotide preparation. In some embodiments, $R^1$ and $R^2$ are the same optionally substituted $C_{1-2}$ alkyl, and $R^1$ and $R^2$ comprise no more than two carbon atoms. In some embodiments, both $R^1$ and $R^1$ are methyl. In some embodiments, both $R^1$ and $R^1$ are ethyl. In some embodiments, both $R^1$ and $R^1$ are isopropyl. In some embodiments, one of $R^1$ and $R^2$ is optionally substituted $C_{1-3}$ linear alkyl, and the other is optionally substituted $C_{3-10}$ cycloalkyl. In some embodiments, one of $R^1$ and $R^2$ is optionally substituted $C_{1-3}$ linear alkyl, and the other is optionally substituted $C_{5-6}$ cycloalkyl. In some embodiments, $R^1$ is methyl. In some embodiments, $R^2$ is cyclopentyl. In some embodiments, $R^2$ is cyclohexyl. In some embodiments, one of $R^1$ and $R^2$ is optionally substituted $C_{1-3}$ linear alkyl, and the other is optionally substituted benzyl. In some embodiments, $R^1$ is methyl and $R^2$ is optionally substituted benzyl. In some embodiments, $R^2$ is benzyl. In some embodiments, $R^2$ is p-$CH^3O$—$C_6H_4$—$CH_2$—. In some embodiments, $R^1$ is selected from methyl, ethyl, cyclohexyl, and benzyl which is optionally substituted at the phenyl. In some embodiments, $R^2$ is selected from methyl, ethyl, cyclohexyl, and benzyl which is optionally substituted at the phenyl. In some embodiments, each of $R^1$ and $R^2$ is independently selected from methyl, ethyl, cyclohexyl, and benzyl which is optionally substituted at the phenyl.

In some embodiments, a provided compound is

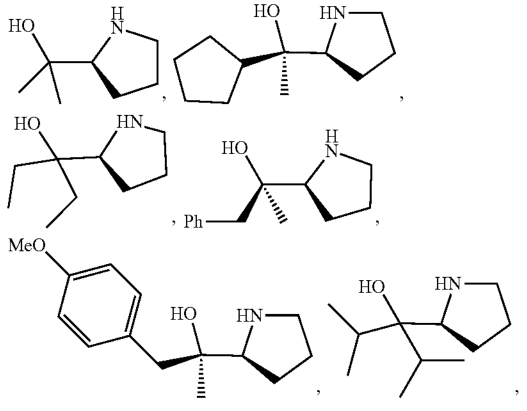

or a salt thereof. In some embodiments, a provided compound is a diastereomer of

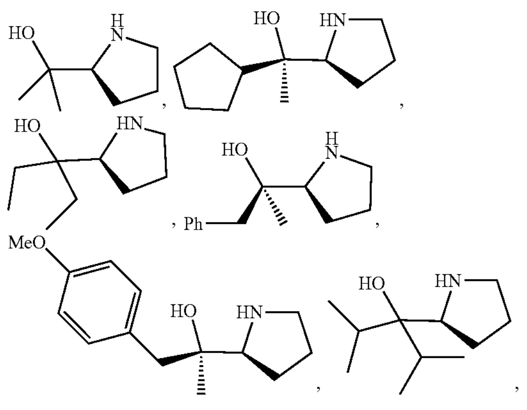

or a salt thereof. In some embodiments, a provided compound is an enantiomer of

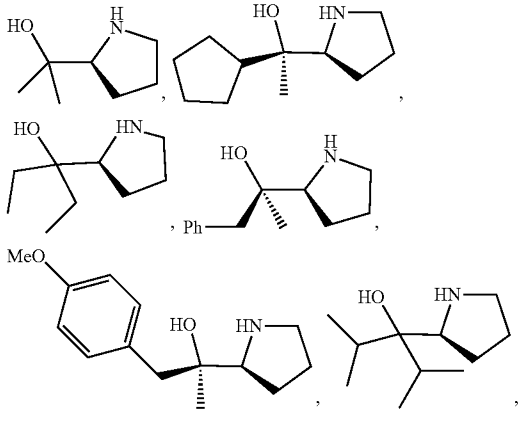

or a salt thereof. In some embodiments, a provided compound is

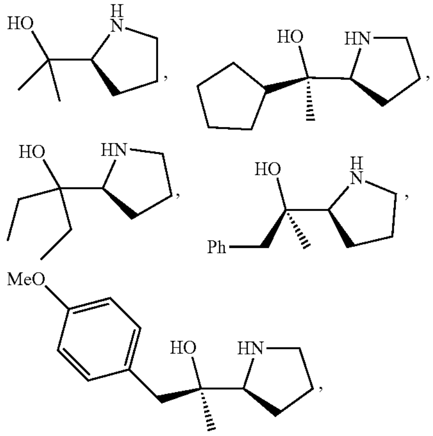

or a salt thereof. In some embodiments, a provided compound is a diastereomer of

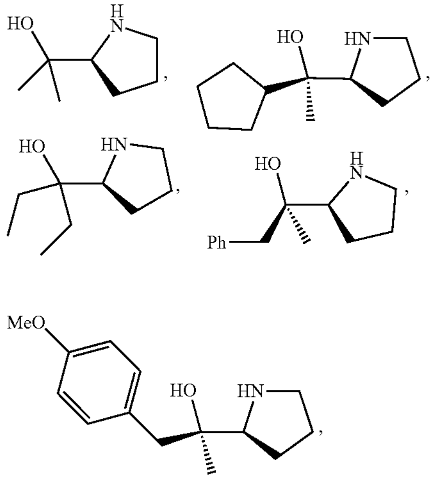

or a salt thereof. In some embodiments, a provided compound is an enantiomer of

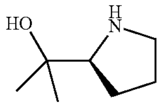,
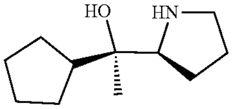,
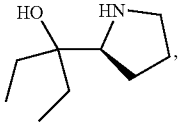,
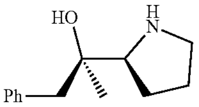,
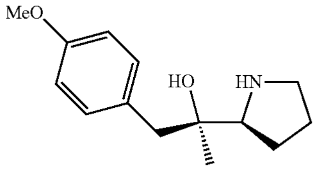, or a salt thereof. In some embodiments, a provided compound is

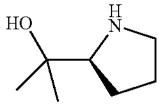

or a salt thereof. In some embodiments, a provided compound is

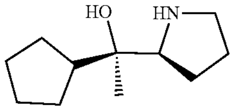

or a salt thereof. In some embodiments, a provided compound is

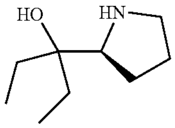

or a salt thereof. In some embodiments, a provided compound is

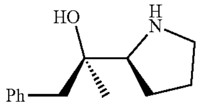

or a salt thereof. In some embodiments, a provided compound is

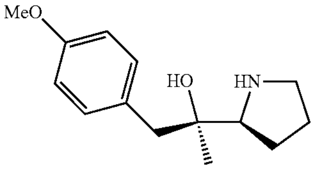 [SMILES: COc1ccc(C[C@@](C)(O)[C@@H]2CCCN2)cc1]

or a salt thereof. In some embodiments, a provided compound is

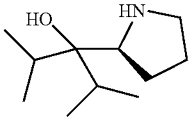

or a salt thereof. In some embodiments, a provided compound is a diastereomer of

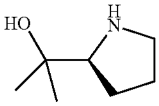

or a salt thereof. In some embodiments, a provided compound is a diastereomer of

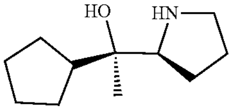

or a salt thereof. In some embodiments, a provided compound is a diastereomer of

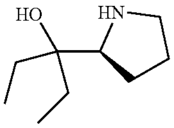

or a salt thereof. In some embodiments, a provided compound is a diastereomer of

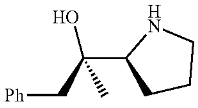

or a salt thereof. In some embodiments, a provided compound is a diastereomer of

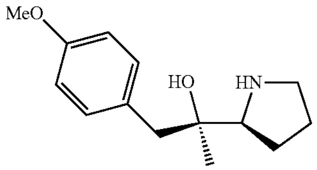 [SMILES: COc1ccc(C[C@@](C)(O)[C@@H]2CCCN2)cc1]

or a salt thereof. In some embodiments, a provided compound is a diastereomer of

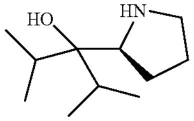

or a salt thereof. In some embodiments, a provided compound is an enantiomer of

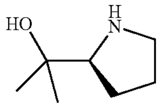

or a salt thereof. In some embodiments, a provided compound is an enantiomer of

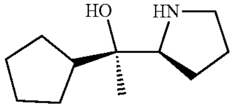

or a salt thereof. In some embodiments, a provided compound is an enantiomer of

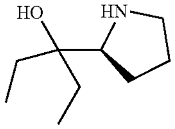

or a salt thereof. In some embodiments, a provided compound is an enantiomer of

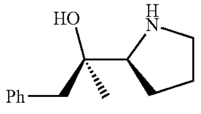

or a salt thereof. In some embodiments, a provided compound is an enantiomer of

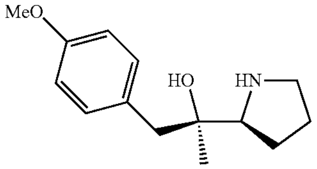 [SMILES: COc1ccc(C[C@@](C)(O)[C@@H]2CCCN2)cc1]

or a salt thereof. In some embodiments, a provided compound is an enantiomer of

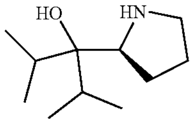

or a salt thereof.

In some embodiments, one of $R^1$ and $R^2$ is R, wherein R is optionally substituted $C_{1-6}$ alkyl, and the other is R, wherein R is an optionally substituted group selected from $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon. In some embodiments, one of $R^1$ and $R^2$ is R, wherein R is optionally substituted $C_{1-6}$ alkyl, and the other is R, wherein R is an optionally substituted group selected from $C_{3-20}$ cycloaliphatic, $C_{6-20}$ aryl, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon. In some embodiments, one of $R^1$ and $R^2$ is R, wherein R is optionally substituted $C_{1-6}$ alkyl, and the other is R, wherein R is an optionally substituted group selected from $C_{3-20}$ cycloaliphatic, $C_{6-20}$ aryl, 5-20 membered heteroaryl having 1-10 heteroatoms independently selected from oxygen, nitrogen, and sulfur, and 3-20 membered heterocyclyl having 1-10 heteroatoms independently selected from oxygen, nitrogen, and sulfur. In some embodiments, one of $R^1$ and $R^2$ is R, wherein R is optionally substituted $C_{1-6}$ alkyl, and the other is R, wherein R is an optionally substituted group selected from $C_{6-20}$ aryl, and 5-20 membered heteroaryl having 1-10 heteroatoms independently selected from oxygen, nitrogen, and sulfur. In some embodiments, one of $R^1$ and $R^2$ is R, wherein R is optionally substituted $C_{1-6}$ alkyl, and the other is R, wherein R is optionally substituted $C_{6-20}$ aryl. In some embodiments, one of $R^1$ and $R^2$ is R, wherein R is optionally substituted $C_{1-6}$ alkyl, and the other is R, wherein R is optionally substituted phenyl. In some embodiments, R as optionally substituted $C_{1-6}$ alkyl is methyl. In some embodiments, R as optionally substituted phenyl is

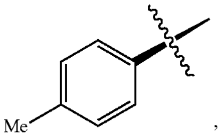
,
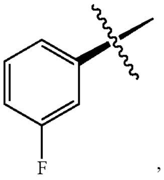
,
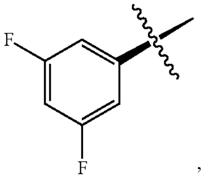
,
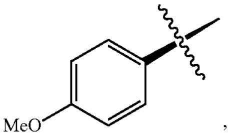
, or
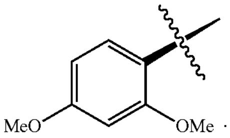
.

In some embodiments, $R^1$ is methyl, and $R^2$ is optionally substituted phenyl. In some embodiments, $R^1$ is methyl, and $R^2$ is phenyl. In some embodiments, $R^1$ is methyl, and $R^2$ is

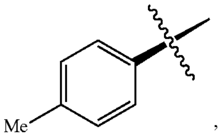
,
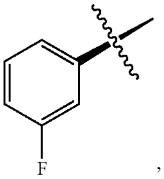
,
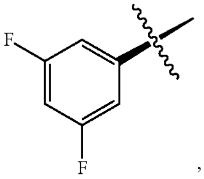
,
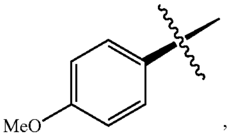
, or
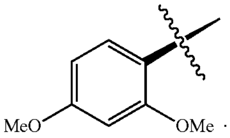
.

In some embodiments, a provided compound is selected from

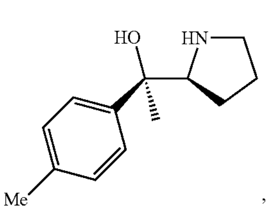
,
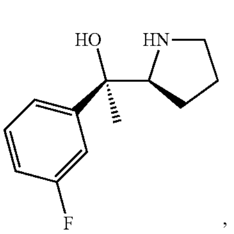
,
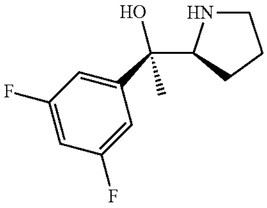
,

-continued

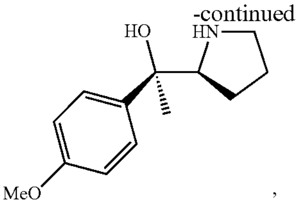
,
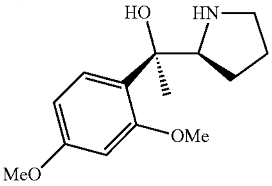
.

or salts thereof. In some embodiments, a provided compound is

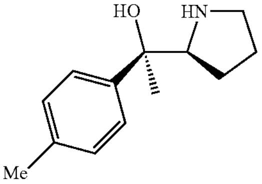

or a salt thereof. In some embodiments, a provided compound is

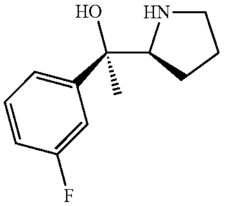

or a salt thereof. In some embodiments, a provided compound is

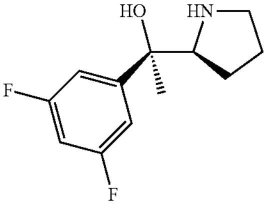 [SMILES: C[C@@](O)(c1cc(F)cc(F)c1)[C@@H]1CCCN1]

or a salt thereof. In some embodiments, a provided compound is

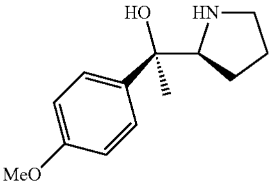 [SMILES: COc1ccc([C@@](C)(O)[C@@H]2CCCN2)cc1]

or a salt thereof. In some embodiments, a provided compound is

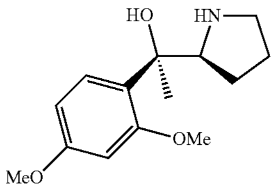 [SMILES: COc1ccc([C@@](C)(O)[C@@H]2CCCN2)c(OC)c1]

or a salt thereof. In some embodiments, a provided compound is a diastereomer of

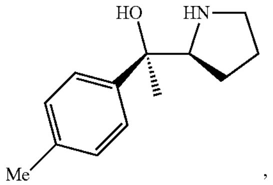
,
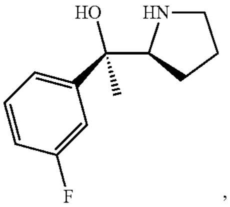
,
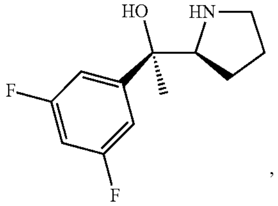
,
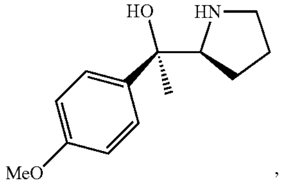
,
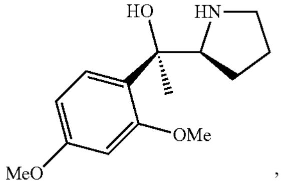
, or a salt thereof. In some embodiments, a provided compound is a diastereomer of

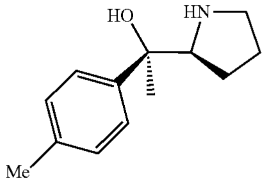

or a salt thereof. In some embodiments, a provided compound is a diastereomer of

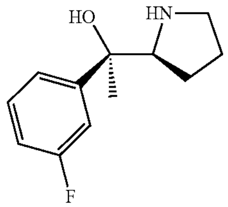

or a salt thereof. In some embodiments, a provided compound is a diastereomer of

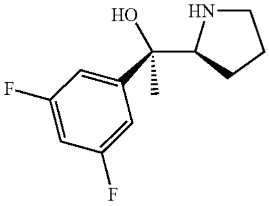 [SMILES: C[C@@](O)(c1cc(F)cc(F)c1)[C@@H]1CCCN1]

or a salt thereof. In some embodiments, a provided compound is a diastereomer of

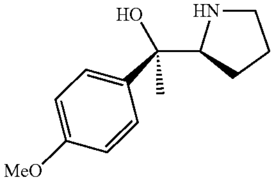 [SMILES: COc1ccc([C@@](C)(O)[C@@H]2CCCN2)cc1]

or a salt thereof. In some embodiments, a provided compound is a diastereomer of

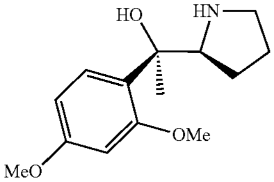 [SMILES: COc1ccc([C@@](C)(O)[C@@H]2CCCN2)c(OC)c1]

or a salt thereof. In some embodiments, a provided compound is an enantiomer of

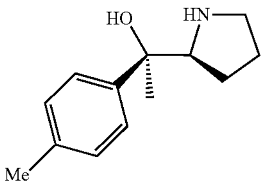
,
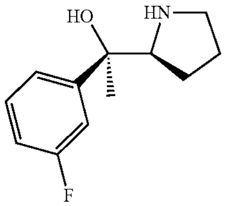
,

-continued

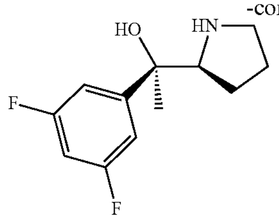

,

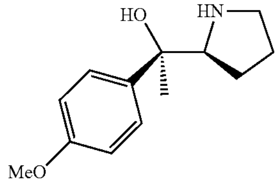

,

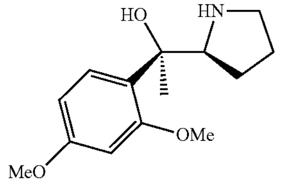

, or a salt thereof. In some embodiments, a provided compound is an enantiomer of

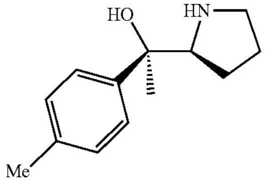

or a salt thereof. In some embodiments, a provided compound is an enantiomer of

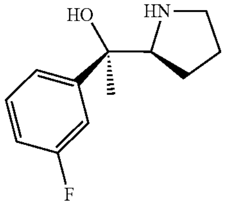

or a salt thereof. In some embodiments, a provided compound is an enantiomer of

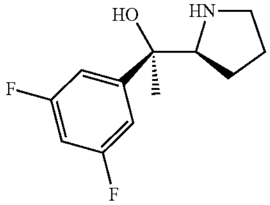 [SMILES: C[C@@](O)(c1cc(F)cc(F)c1)[C@@H]1CCCN1]

or a salt thereof. In some embodiments, a provided compound is an enantiomer of

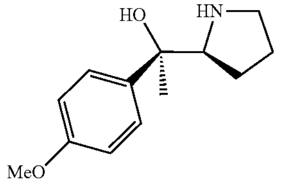 [SMILES: COc1ccc([C@@](C)(O)[C@@H]2CCCN2)cc1]

or a salt thereof. In some embodiments, a provided compound is an enantiomer of

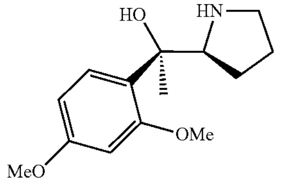 [SMILES: COc1ccc([C@@](C)(O)[C@@H]2CCCN2)c(OC)c1]

or a salt thereof.

In some embodiments, $R^1$ and $R^2$ are independently R, wherein R is as described in the present disclosure. In some embodiments, R is an optionally substituted group selected from $C_{3-20}$ cycloaliphatic, $C_{6-20}$ aryl, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon. In some embodiments, R is an optionally substituted group selected from $C_{3-20}$ cycloaliphatic, $C_{6-20}$ aryl, 5-20 membered heteroaryl having 1-10 heteroatoms independently selected from oxygen, nitrogen, and sulfur, and 3-20 membered heterocyclyl having 1-10 heteroatoms independently selected from oxygen, nitrogen, and sulfur. In some embodiments, R is an optionally substituted group selected from $C_{3-20}$ cycloaliphatic, and 3-20 membered heterocyclyl having 1-10 heteroatoms independently selected from oxygen, nitrogen, sulfur, phosphorus and silicon. In some embodiments, R is an optionally substituted group selected from $C_{6-20}$ aryl, and 5-20 membered heteroaryl having 1-10 heteroatoms independently selected from oxygen, nitrogen, sulfur, phosphorus and silicon. In some embodiments, R is an optionally substituted group selected from $C_{3-20}$ cycloaliphatic and $C_{6-20}$ aryl. In some embodiments, R is an optionally substituted group selected from 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon. In some embodiments, R is optionally substituted $C_{3-20}$ cycloaliphatic. In some embodiments, R is optionally substituted $C_{3-20}$ cycloalkyl. In some embodiments, R is optionally substituted $C_{1-20}$ heteroaliphatic having 1-10 heteroatoms independently selected from oxygen, nitrogen, sulfur, phosphorus and silicon. In some embodiments, R is optionally substituted $C_{6-2}$n aryl. In some embodiments, R is optionally substituted 5-20 membered heteroaryl having 1-10 heteroatoms independently selected from oxygen, nitrogen, sulfur, phosphorus and silicon. In some embodiments, R is optionally substituted 3-20 membered heterocyclyl having 1-10 heteroatoms independently selected from oxygen, nitrogen, sulfur, phosphorus and silicon. In some embodiments, R is optionally substituted phenyl. In some embodiments, R is phenyl. In some embodiments, $R^1$ and $R^2$ are optionally substituted phenyl. In some embodiments, $R^1$ and $R^2$ are phenyl. In some embodiments, a provided compound is

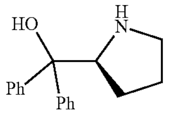 [SMILES: OC(c1ccccc1)(c1ccccc1)[C@@H]1CCCN1]

or a salt thereof. In some embodiments, a provided compound is a diastereomer of

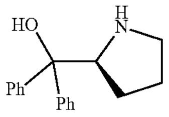 [SMILES: OC(c1ccccc1)(c1ccccc1)[C@@H]1CCCN1]

or a salt thereof. In some embodiments, a provided compound is an enantiomer of

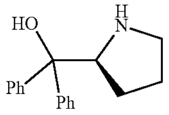 [SMILES: OC(c1ccccc1)(c1ccccc1)[C@@H]1CCCN1]

or a salt thereof.

In some embodiments, the carbon atom to which $R^1$ and $R^2$ are attached is not chiral. In some embodiments, $R^1$ and $R^2$ are the same. In some embodiments, $R^1$ and $R^2$ are the same and neither are hydrogen. In some embodiments, $R^1$ and $R^2$ are methyl. In some embodiments, $R^1$ and $R^2$ are ethyl. In some embodiments, $R^1$ and $R^2$ are optionally substituted phenyl. In some embodiments, $R^1$ and $R^2$ are phenyl. In some embodiments, $R^1$ and $R^2$ are R, wherein the two R groups are taken together to form an optionally substituted ring as described in the present disclosure. In some embodiments, a formed ring does not contain any chiral elements. In some embodiments, a formed ring is an optionally substituted 5-membered cycloaliphatic ring. In some embodiments, a formed ring is optionally substituted

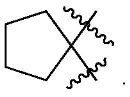

In some embodiments, a formed ring is

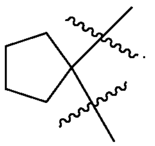 [SMILES: *C1(*)CCCC1]

In some embodiments, a formed ring is optionally substituted

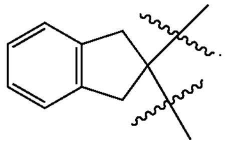 [SMILES: *C1(*)Cc2ccccc2C1]

In some embodiments, a formed ring is

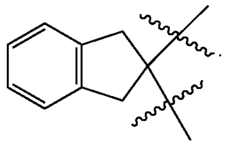 [SMILES: *C1(*)Cc2ccccc2C1]

In some embodiments, a formed ring is an optionally substituted 6-membered cycloaliphatic ring. In some embodiments, a formed ring is optionally substituted

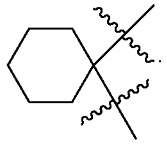 [SMILES: *C1(*)CCCCC1]

In some embodiments, a formed ring is

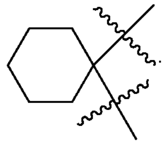 [SMILES: *C1(*)CCCCC1]

Among other things, the present disclosure demonstrated that provided compounds in which the carbon atom to which $R^1$ and $R^2$ are attached is not chiral can provide surprisingly high stereoselectivity when they are used in chirally controlled oligonucleotide synthesis. In some embodiments, such compounds provides high yields.

In some embodiments, $R^3$ is —H, $-L^s$-R, halogen, —CN, —$NO_2$, $-L^s-Si(R)_3$, —OR, —SR, or —$N(R)_2$. In some embodiments, $R^3$ is —H. In some embodiments, $R^3$ is $-L^s$-R, wherein each of $L^s$ and R is independently as described in the present disclosure. In some embodiments, $R^3$ is R, for example, an R embodiment as described in the present disclosure. In some embodiments, $R^3$ is halogen. In some embodiments, $R^3$ is —F. In some embodiments, $R^3$ is —Cl. In some embodiments, $R^3$ is —Br. In some embodiments, $R^3$ is —I. In some embodiments, $R^3$ is —CN. In some embodiments, $R^3$ is —$NO_2$. In some embodiments, $R^3$ is $-L^s-Si(R)_3$, wherein each of $L^s$ and R is independently as described in the present disclosure. In some embodiments, $R^3$ is —$CH_2$—$Si(R)_3$, wherein the —$CH_2$— group is optionally substituted, and each R is independently as described in the present disclosure. In some embodiments, $R^3$ is —$CH_2$—$Si(R)_3$, wherein each R is independently as described in the present disclosure. In some embodiments, each R of —$Si(R)_3$ is not —H. In some embodiments, each R of —$Si(R)_3$ is independently an optionally substituted group selected from $C_{1-6}$ alkyl and phenyl. In some embodiments, —$Si(R)_3$ is —$Si(Ph)_2Me$. Other non-hydrogen embodiments of R are extensively described in the present disclosure and may be used in —$Si(R)_3$. In some embodiments, $R^3$ is —OR, wherein R is as described in the present disclosure. In some embodiments, $R^3$ is —SR wherein R is as described in the present disclosure. In some embodiments, $R^3$ is —$N(R)_2$, wherein each R is independently as described in the present disclosure. In some embodiments, $R^2$ is the same or different from $R^1$, and is a group selected from any groups described for $R^1$ in the present disclosure.

In some embodiments, $R^4$ is —H, -$L^s$-R, halogen, —CN, —$NO_2$, -$L^s$-$Si(R)_3$, —OR, —SR, or —$N(R)_2$. In some embodiments, $R^4$ is —H. In some embodiments, $R^4$ is -$L^s$-R, wherein each of $L^s$ and R is independently as described in the present disclosure. In some embodiments, $R^4$ is R, for example, an R embodiment as described in the present disclosure. In some embodiments, $R^4$ is halogen. In some embodiments, $R^4$ is —F. In some embodiments, $R^4$ is —Cl. In some embodiments, $R^4$ is —Br. In some embodiments, $R^4$ is —I. In some embodiments, $R^4$ is —CN. In some embodiments, $R^4$ is —$NO_2$. In some embodiments, $R^4$ is -$L^s$-$Si(R)_3$, wherein each of $L^s$ and R is independently as described in the present disclosure. In some embodiments, $R^4$ is —$CH_2$—$Si(R)_3$, wherein the —$CH_2$— group is optionally substituted, and each R is independently as described in the present disclosure. In some embodiments, $R^4$ is —$CH_2$—$Si(R)_3$, wherein each R is independently as described in the present disclosure. In some embodiments, each R of —$Si(R)_3$ is not —H. In some embodiments, each R of —$Si(R)_3$ is independently an optionally substituted group selected from $C_{1-6}$ alkyl and phenyl. In some embodiments, —$Si(R)_3$ is —$Si(Ph)_2Me$. Other non-hydrogen embodiments of R are extensively described in the present disclosure and may be used in —$Si(R)_3$. In some embodiments, $R^4$ is —OR, wherein R is as described in the present disclosure. In some embodiments, $R^4$ is —SR wherein R is as described in the present disclosure. In some embodiments, $R^4$ is —$N(R)_2$, wherein each R is independently as described in the present disclosure. In some embodiments, $R^2$ is the same or different from $R^1$, and is a group selected from any groups described for $R^1$ in the present disclosure.

In some embodiments, at least one of $R^1$, $R^2$, $R^3$ and $R^4$ is not —H. In some embodiments, a provided compound of formula I, I-a, I-a-1, I-a-2, I-b, I-c, I-d, or I-e comprises one or more chiral elements. In some embodiments, $R^3$ and $R^4$ are not —H, and the carbon to which they are attached is a chiral center. In some embodiments, at least one of $R^1$ and $R^2$ is not hydrogen, and $R^1$ and $R^2$ are different, and the carbon to which they are attached is a chiral center. In some embodiments, at least one of $R^1$ and $R^2$ is not hydrogen, and $R^1$ and $R^2$ are the same, and the carbon to which they are attached is not a chiral center. Among other things, the present disclosure demonstrates that provided compounds, in which the carbon atoms to which $R^1$ and $R^2$ are attached are not chiral, can deliver surprisingly high stereoselectivity when used as chiral auxiliaries in oligonucleotide synthesis.

In some embodiments, $R^5$ is —H, -$L^s$-R, halogen, —CN, —$NO_2$, -$L^s$-$Si(R)_3$, —OR, —SR, or —$N(R)_2$. In some embodiments, $R^5$ is —H. In some embodiments, $R^5$ is -$L^s$-R, wherein each of $L^s$ and R is independently as described in the present disclosure. In some embodiments, $R^5$ is R, for example, an R embodiment as described in the present disclosure. In some embodiments, $R^5$ is halogen. In some embodiments, $R^5$ is —F. In some embodiments, $R^5$ is —Cl. In some embodiments, $R^5$ is —Br. In some embodiments, $R^5$ is —I. In some embodiments, $R^5$ is —CN. In some embodiments, $R^5$ is —$NO_2$. In some embodiments, $R^3$ is -$L^s$-$Si(R)_3$, wherein each of $L^s$ and R is independently as described in the present disclosure. In some embodiments, $R^5$ is —$CH_2$—$Si(R)_3$, wherein the —$CH_2$— group is optionally substituted, and each R is independently as described in the present disclosure. In some embodiments, $R^5$ is —$CH_2$—$Si(R)_3$, wherein each R is independently as described in the present disclosure. In some embodiments, each R of —$Si(R)_3$ is not —H. In some embodiments, each R of —$Si(R)_3$ is independently an optionally substituted group selected from $C_{1-6}$ alkyl and phenyl. In some embodiments, —$Si(R)_3$ is —$Si(Ph)_2Me$. Other non-hydrogen embodiments of R are extensively described in the present disclosure and may be used in —$Si(R)_3$. In some embodiments, $R^5$ is —OR, wherein R is as described in the present disclosure. In some embodiments, $R^5$ is —SR wherein R is as described in the present disclosure. In some embodiments, $R^5$ is —$N(R)_2$, wherein each R is independently as described in the present disclosure. In some embodiments, $R^2$ is the same or different from $R^1$, and is a group selected from any groups described for $R^1$ in the present disclosure.

In some embodiments, $R^5$, and one or both of $R^1$ and $R^2$, are R and are taken together with their intervening atoms to form an optionally substituted, 3-20 membered monocyclic, bicyclic or polycyclic ring having 1-5 heteroatoms. In some embodiments, $R^5$ and $R^1$ are R and are taken together with their intervening atoms to form an optionally substituted, 3-20 membered monocyclic, bicyclic or polycyclic ring having 1-5 heteroatoms. In some embodiments, one of $R^1$ and $R^2$, and $R^5$, are R and are taken together with their intervening atoms to form an optionally substituted, 3-20 membered monocyclic, bicyclic or polycyclic ring having 1-5 heteroatoms. As extensively described in the present disclosure, a formed ring by two R groups taken together can be of various sizes, monocyclic, bicyclic or polycyclic, and contain various numbers of heteroatoms. In some embodiments, a ring is a 3-membered ring. In some embodiments, a ring is a 4-membered ring. In some embodiments, a ring is a 5-membered ring. In some embodiments, a ring is a 6-membered ring. In some embodiments, a formed ring contains no ring heteroatom in addition to the nitrogen to which $R^5$ is attached. In some embodiments, a ring is a saturated ring. In some embodiments, a ring is monocyclic. In some embodiments, a ring contains additional ring heteroatoms other than the intervening heteroatoms. In some embodiments, a ring is a 3-membered ring containing one ring heteroatom. In some embodiments, a ring is a 3-membered ring containing two ring heteroatoms. In some embodiments, a ring is a 3-membered ring containing one carbon, one nitrogen, and one oxygen ring atom.

In some embodiments, two or more of $R^1$, $R^2$, $R^3$, $R^4$, and $R^5$ are independently R, and the R groups are optionally and independently taken together to form rings as described in the present disclosure. In some embodiments, $R^1$ and $R^2$ are R, and the two R groups are taken together to form an optionally substituted ring as described in the present disclosure. In some embodiments, one of $R^1$ and $R^2$, and one of $R^3$ and $R^4$, are R, and the two R groups are taken together to form an optionally substituted ring as described in the present disclosure. In some embodiments, one of $R^3$ and $R^4$, and $R^5$, are R, and the two R groups are taken together to form an optionally substituted ring as described in the present disclosure.

In some embodiments, a formed ring, e.g., by $R^1$ and $R^2$, or one of $R^1$ and $R^2$ and one of $R^3$ and $R^4$, is an optionally substituted 3-20 membered monocyclic, bicyclic or polycyclic ring having 0-5 heteroatoms. In some embodiments, a formed ring is monocyclic. In some embodiments, a formed ring is bicyclic. In some embodiments, a formed ring is polycyclic. In some embodiments, a formed ring is aliphatic. In some embodiments, a formed ring comprises no unsaturation. In some embodiments, a formed ring is partially unsaturated. In some embodiments, a formed ring comprises one or more saturated monocyclic ring moieties. In some embodiments, a formed ring comprises one or more monocyclic partially unsaturated ring moieties. In some embodiments, a formed ring comprises one or more monocyclic aromatic ring moieties. In some embodiments, a formed ring comprises one or more saturated, partially unsaturated, and/or aromatic ring moieties, for example, a bicyclic or polycyclic ring comprising fused saturated, partially unsaturated, and/or aromatic monocyclic moieties. In some embodiments, a formed ring is optionally substituted. In some embodiments, a formed ring is substituted. In some embodiments, a formed ring is not substituted. In some embodiments, a formed ring comprises no chiral elements. In some embodiments, a formed ring comprises one or more chiral elements. In some embodiments, a formed ring comprises one or more chiral elements and is chiral. In some embodiments, a chiral element is a chiral center. In some embodiments, a formed ring is an optionally substituted 3-10 membered monocyclic ring having no heteroatoms. In some embodiments, a formed monocyclic ring is 3-membered: in some embodiments, 4-membered; in some embodiments, 5-membered; in some embodiments, 6-membered; in some embodiments 7-membered; in some embodiments, 8-membered; in some embodiments 9-membered; and in some embodiments 10-membered. In some embodiments, a formed ring is a 3-membered saturated cycloaliphatic ring. In some embodiments, a formed ring is an optionally substituted 5-membered saturated cycloaliphatic ring. In some embodiments, a formed ring is an optionally substituted 5-membered saturated cycloaliphatic ring containing no chiral elements. In some embodiments, a formed ring is an unsubstituted 5-membered saturated cycloaliphatic ring containing no chiral elements. In some embodiments, a 5-membered ring described herein is fused to another optionally substituted ring, which can be saturated, partially unsaturated or aryl. In some embodiments, a 5-membered ring described herein is fused to an optionally substituted aryl ring. In some embodiments, a 5-membered ring described herein is fused to an optionally substituted phenyl ring. In some embodiments, a 5-membered ring described herein is fused to a phenyl ring. In some embodiments, fusion is at C3 and C4 (C1 being the carbon atom to which $R^1$ and $R^2$ are attached). In some embodiments, a formed ring is optionally substitute

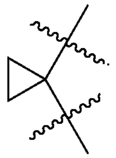 [SMILES: *C1(*)CC1]

In some embodiments, a formed ring is

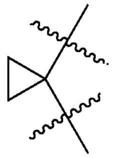 [SMILES: *C1(*)CC1]

In some embodiments, a formed ring is optionally substituted

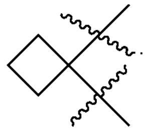 [SMILES: *C1(*)CCC1]

In some embodiments, a formed ring is

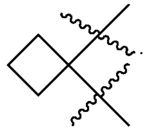 [SMILES: *C1(*)CCC1]

In some embodiments, a formed ring is optionally substituted

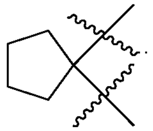 [SMILES: *C1(*)CCCC1]

In some embodiments, a formed ring is

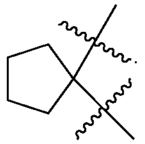

In some embodiments, a formed ring is optionally substituted

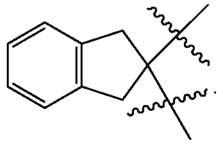 [SMILES: *C1(*)Cc2ccccc2C1]

In some embodiments, a formed ring is

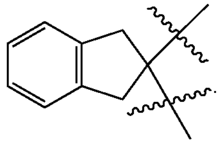 [SMILES: *C1(*)Cc2ccccc2C1]

In some embodiments, a formed ring is an optionally substituted 6-membered saturated cycloaliphatic ring. In some embodiments, a formed ring is an optionally substituted 6-membered saturated cycloaliphatic ring containing no chiral elements. In some embodiments, a formed ring is an unsubstituted 6-membered saturated cycloaliphatic ring containing no chiral elements. In some embodiments, one or more ring moieties may be fused to the 6-membered ring, for example, as described above for the 5-membered ring. Ring embodiments described herein are applicable to other variables two of which can be R and can be taken together to form an optionally substituted ring. In some embodiments, a formed ring is optionally substituted

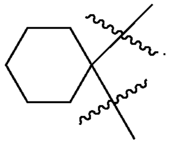 [SMILES: *C1(*)CCCCC1]

In some embodiments, a formed ring is

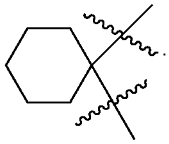 [SMILES: *C1(*)CCCCC1]

In some embodiments, a provided compound is

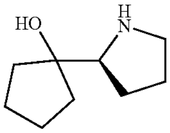 [SMILES: OC1([C@@H]2CCCN2)CCCC1],
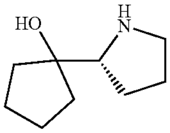,
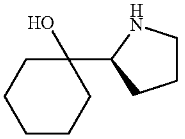,
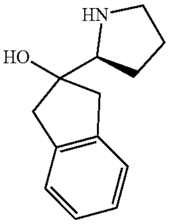,
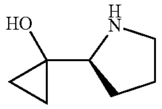, or a salt thereof. In some embodiments, a provided compound is selected from

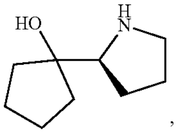,
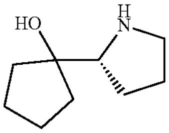 [SMILES: OC1([C@H]2CCCN2)CCCC1],
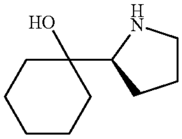,
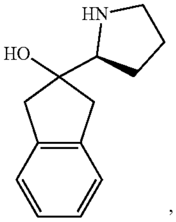, and salts thereof. In some embodiments, a provided compound is

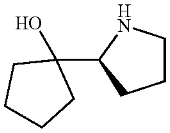

or a salt thereof. In some embodiments, a provided compound is

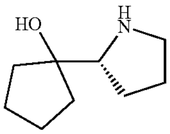

or a salt thereof. In some embodiments, a provided compound is

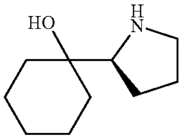 [SMILES: OC1([C@@H]2CCCN2)CCCCC1]

or a salt thereof. In some embodiments, a provided compound is

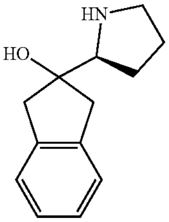 [SMILES: OC1([C@@H]2CCCN2)Cc2ccccc2C1]

or a salt thereof. In some embodiments, a provided compound is a diastereomer of

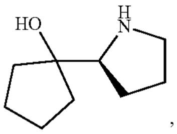,
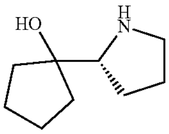,
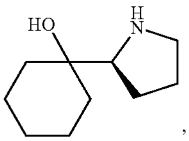,
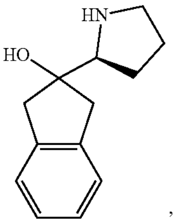,

-continued

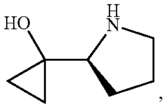, or a salt thereof. In some embodiments, a provided compound is a diastereomer of selected from

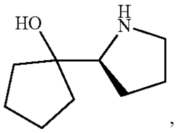, 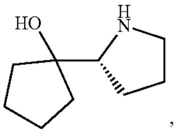,

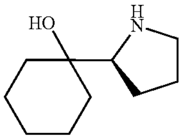, 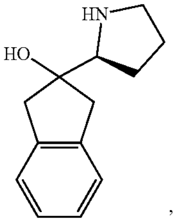, and salts thereof. In some embodiments, a provided compound is a diastereomer of

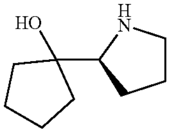 [SMILES: OC1([C@@H]2CCCN2)CCCC1]

or a salt thereof. In some embodiments, a provided compound is a diastereomer of

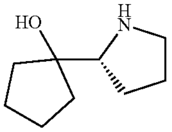 [SMILES: OC1([C@H]2CCCN2)CCCC1]

or a salt thereof. In some embodiments, a provided compound is a diastereomer of

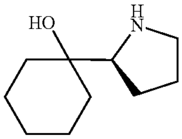 [SMILES: OC1([C@@H]2CCCN2)CCCCC1]

or a salt thereof. In some embodiments, a provided compound is a diastereomer of

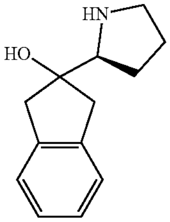 [SMILES: OC1([C@@H]2CCCN2)Cc2ccccc2C1]

or a salt thereof. In some embodiments, a provided compound is an enantiomer of

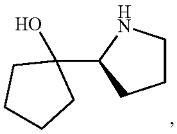, 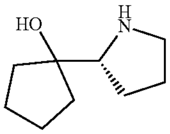,

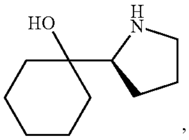, 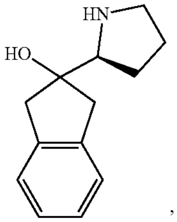,

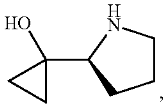, or a salt thereof. In some embodiments, a provided compound is an enantiomer of selected from

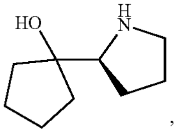, 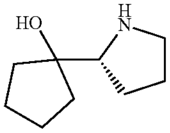,

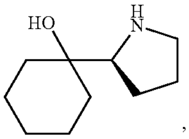, 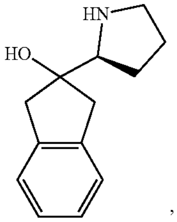, and salts thereof. In some embodiments, a provided compound is an enantiomer of

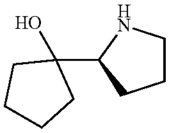 [SMILES: OC1([C@@H]2CCCN2)CCCC1]

or a salt thereof. In some embodiments, a provided compound is an enantiomer of

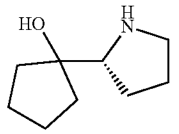 [SMILES: OC1([C@H]2CCCN2)CCCC1]

or a salt thereof. In some embodiments, a provided compound is an enantiomer of

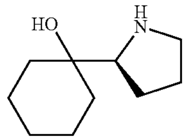 [SMILES: OC1([C@@H]2CCCN2)CCCCC1]

or a salt thereof. In some embodiments, a provided compound is an enantiomer of

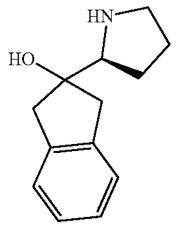 [SMILES: OC1([C@@H]2CCCN2)Cc2ccccc2C1]

or a salt thereof.

In some embodiments, one of $R^1$ and $R^2$, and one of $R^3$ and $R^4$, are R, (e.g., one of $R^1$ and $R^2$, and one of $R^3$ and $R^4$, of formula I-a) and the two R groups are taken together to form an optionally substituted ring as described in the present disclosure. In some embodiments, $R^1$ and $R^3$ are R, and the two R groups are taken together to form an optionally substituted ring as described in the present disclosure. In some embodiments, $R^3$ and $R^4$ are R, and the two R groups are taken together to form an optionally substituted ring as described in the present disclosure. In some embodiments, $R^2$ and $R^3$ are R and the two R groups are taken together to form an optionally substituted ring as described in the present disclosure. In some embodiments, $R^2$ and $R^4$ are R, and the two R groups are taken together to form an optionally substituted ring as described in the present disclosure. In some embodiments, a provided compound has the structure of formula I-e or a salt thereof. As described in the present disclosure, in some embodiments, a formed ring is an optionally substituted $C_{3-20}$ cycloaliphatic ring. In some embodiments, a formed ring is an optionally substituted $C_{3-10}$ cycloaliphatic ring. In some embodiments, a formed ring is an optionally substituted $C_{5-7}$ cycloaliphatic ring. In some embodiments, a formed ring is an optionally substituted $C_5$ cycloaliphatic ring. In some embodiments, a formed ring is an optionally substituted $C_6$ cycloaliphatic ring. In some embodiments, a formed ring is an optionally substituted $C_7$ cycloaliphatic ring. In some embodiments, a formed ring is an optionally substituted $C_8$ cycloaliphatic ring. In some embodiments, a formed ring is an optionally substituted $C_9$ cycloaliphatic ring. In some embodiments, a formed ring is an optionally substituted $C_{10}$ cycloaliphatic ring. As described in the present disclosure, in some embodiments, a formed ring can be monocyclic, bicyclic, or polycyclic, and can comprise one or more saturated, partially saturated and/or aromatic monocyclic moieties. In some embodiments, a formed ring is an optionally substituted $C_{3-20}$ saturated, monocyclic cycloaliphatic ring. In some embodiments, a formed ring is an optionally substituted $C_{3-10}$ saturated, monocyclic cycloaliphatic ring. In some embodiments, a formed ring is an optionally substituted $C_{5-7}$ saturated, monocyclic cycloaliphatic ring. In some embodiments, a formed ring is an optionally substituted $C_5$ saturated, monocyclic cycloaliphatic ring. In some embodiments, a formed ring is an optionally substituted $C_6$ saturated, monocyclic cycloaliphatic ring. In some embodiments, a formed ring is an optionally substituted $C_7$ saturated, monocyclic cycloaliphatic ring. In some embodiments, a formed ring is an optionally substituted $C_8$ saturated, monocyclic cycloaliphatic ring. In some embodiments, a formed ring is an optionally substituted $C_9$ saturated, monocyclic cycloaliphatic ring. In some embodiments, a formed ring is an optionally substituted $C_{10}$ saturated, monocyclic cycloaliphatic ring. In some embodiments, one of $R^1$ and $R^2$, and one of $R^3$ and $R^4$, are R, and the two R groups are taken together to form an optionally substituted ring as described in the present disclosure; $R^5$ is R, wherein R is an optionally substituted group selected from $C_{1-20}$ aliphatic, $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon; $R^6$ is —H; and $R^7$ is —OH. In some embodiments, one of $R^1$ and $R^2$, and one of $R^3$ and $R^4$, are R, and the two R groups are taken together to form an optionally substituted ring as described in the present disclosure; $R^5$ is R, wherein R is an optionally substituted $C_{1-20}$ aliphatic; $R^6$ is —H; and $R^7$ is —OH. In some embodiments, one of $R^1$ and $R^2$, and one of $R^3$ and $R^4$, are R, and the two R groups are taken together to form an optionally substituted ring as described in the present disclosure; $R^5$ is R, wherein R is an optionally substituted $C_{1-6}$ alkyl; $R^6$ is —H; and $R^7$ is —OH. In some embodiments, one of $R^1$ and $R^2$, and one of $R^3$ and $R^4$, are R, and the two R groups are taken together to form an optionally substituted ring as described in the present disclosure; $R^5$ is R, wherein R is methyl; $R^6$ is —H; and $R^7$ is —OH. Among other things, the present disclosure demonstrated that provided compounds, wherein the N atom to which $R^5$ and $R^6$ are attached is not within a ring, can provide surprisingly high stereoselectivity and/or yield when used in chirally controlled preparation of oligonucleotides.

In some embodiments, a provided compound, e.g., a compound of formula I-e, is

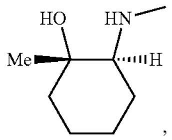

,

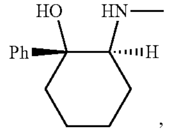

,

-continued

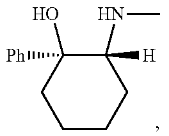

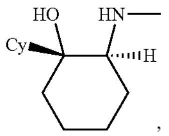

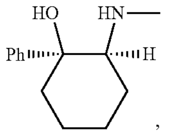

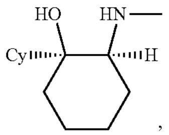

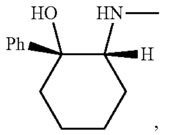

and thereof. In some embodiments, a provided compound is

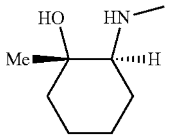

or a salt there of. In some embodiments, a provided compound is

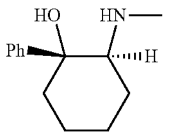

or a salt there of. In some embodiments, a provided compound is

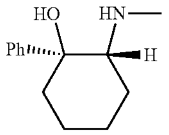

or a salt there of. In some embodiments, a provided compound is

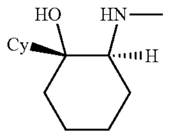

or a salt there of. In some embodiments, a provided compound is

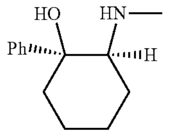

or a salt there of. In some embodiments, a provided compound is

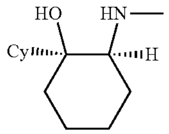

or a salt there of. In some embodiments, a provided compound is

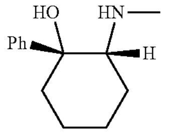

or a salt there of. In some embodiments, a provided compound is

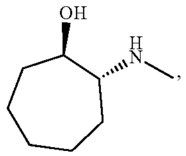

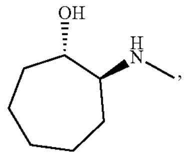

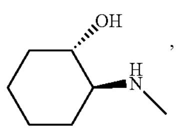

,

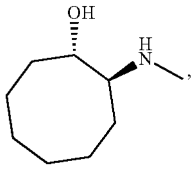

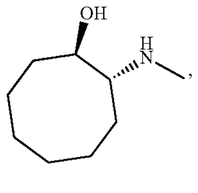

or a salt thereof. In some embodiments, a provided compound is

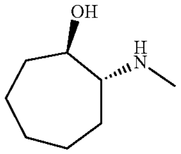

or a salt thereof. In some embodiments, a provided compound is

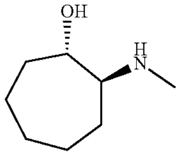

or a salt thereof. In some embodiments, a provided compound is

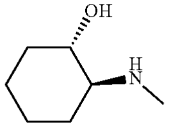

or a salt thereof. In some embodiments, a provided compound is

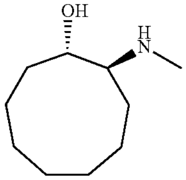

or a salt thereof. In some embodiments, a provided compound is

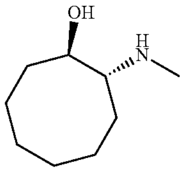

or a salt thereof.

In some embodiments, a provided compound, e.g., a compound of formula I-e, is

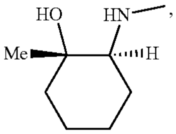

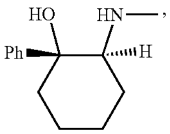

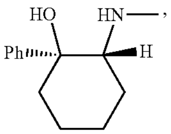

-continued

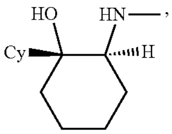

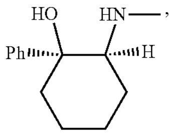

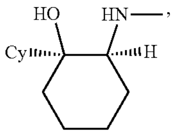

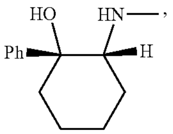

and thereof. In some embodiments, a provided compound is a diastereomer of

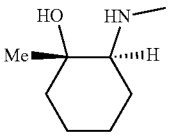

or a salt there of. In some embodiments, a provided compound is a diastereomer of

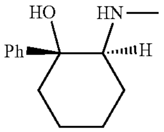

or a salt there of. In some embodiments, a provided compound is a diastereomer of

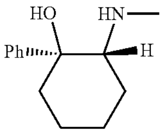

or a salt there of. In some embodiments, a provided compound is a diastereomer of

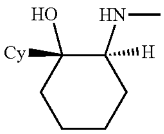

or a salt there of. In some embodiments, a provided compound is a diastereomer of

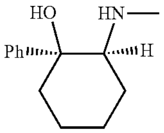

or a salt there of. In some embodiments, a provided compound is a diastereomer of

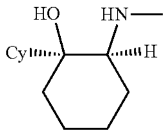

or a salt there of. In some embodiments, a provided compound is a diastereomer of

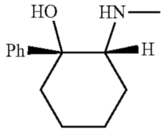

or a salt there of. In some embodiments, a provided compound is a diastereomer of

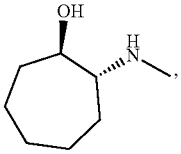,
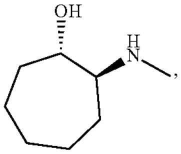,
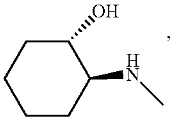,
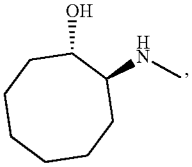,
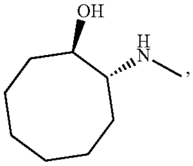, or a salt thereof. In some embodiments, a provided compound is a diastereomer of

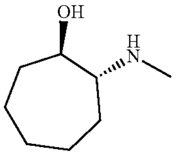

or a salt thereof. In some embodiments, a provided compound is a diastereomer of

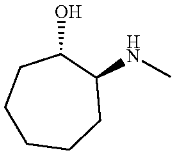

or a salt thereof. In some embodiments, a provided compound is a diastereomer of

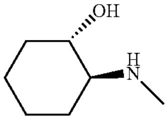

or a salt thereof. In some embodiments, a provided compound is a diastereomer of

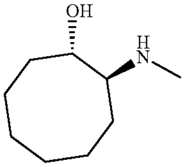

or a salt thereof. In some embodiments, a provided compound is a diastereomer of

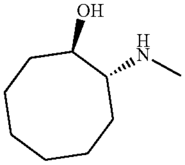

or a salt thereof.

In some embodiments, a provided compound, e.g., a compound of formula I-e, is

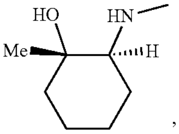,
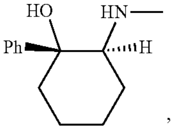,
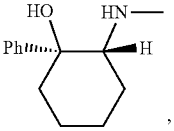,
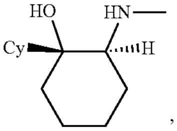,
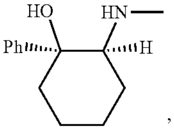,
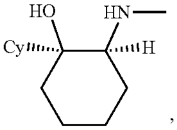,
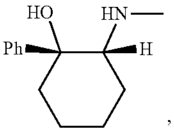, and thereof. In some embodiments, a provided compound is an enantiomer of

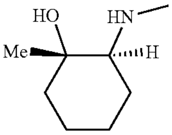

or a salt there of. In some embodiments, a provided compound is an enantiomer of

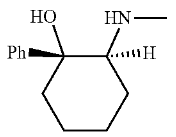

or a salt there of. In some embodiments, a provided compound is an enantiomer of

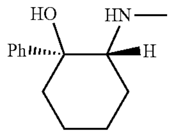

or a salt there of. In some embodiments, a provided compound is an enantiomer of

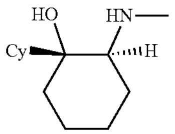

or a salt there of. In some embodiments, a provided compound is an enantiomer of

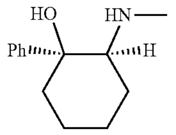

or a salt there of. In some embodiments, a provided compound is an enantiomer of

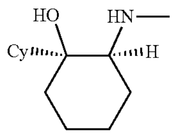

or a salt there of. In some embodiments, a provided compound is an enantiomer of

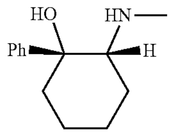

or a salt there of. In some embodiments, a provided compound is an enantiomer of

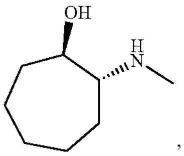,

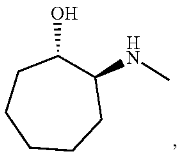,

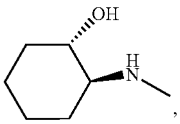,

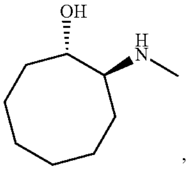,

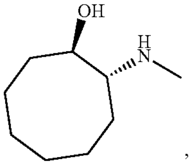, or a salt thereof. In some embodiments, a provided compound is an enantiomer of

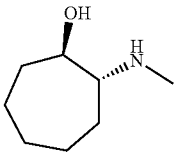

or a salt thereof. In some embodiments, a provided compound is an enantiomer of

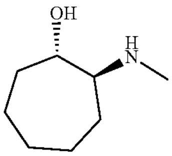

or a salt thereof. In some embodiments, a provided compound is an enantiomer of

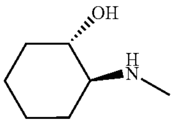

or a salt thereof. In some embodiments, a provided compound is an enantiomer of

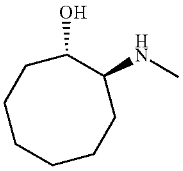

or a salt thereof. In some embodiments, a provided compound is an enantiomer of

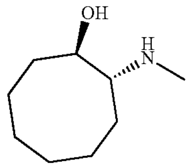

or a salt thereof.

In some embodiments, $R^3$ and $R^4$ are R, and the two R groups are taken together to form an optionally substituted ring as described in the present disclosure.

In some embodiments, $R^3$ and $R^5$ are R, and the two R groups are taken together to form an optionally substituted ring as described in the present disclosure. In some embodiments, $R^4$ and $R^5$ are R, and the two R groups are taken together to form an optionally substituted ring as described in the present disclosure. In some embodiments, $R^4$ and $R^5$ are R, and the two R groups are taken together to form an optionally substituted ring as described in the present disclosure; $R^6$ is —H; and $R^7$ is —OH.

In some embodiments, a formed ring is an optionally substituted 3-20 membered monocyclic, bicyclic or polycyclic ring having 1-5 heteroatoms. In some embodiments, a formed ring is an optionally substituted 4-6 membered monocyclic ring having no more than one heteroatom. In some embodiments, a formed ring is an optionally substituted 4-6 membered saturated monocyclic ring having only one ring heteroatom, which only ring heteroatom is the nitrogen to which $R^5$ is attached. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring is 8-membered. In some embodiments, a formed ring is 9-membered. In some embodiments, a formed ring is 10-membered. In some embodiments, $R^3$ is —H, and $R^4$ and $R^3$ are R, which are taken together with their intervening atoms to form an optionally substituted 3-20 membered monocyclic, bicyclic or polycyclic ring having 1-5 heteroatoms. In some embodiments, $R^3$ is —H, and $R^4$ and $R^5$ are R, which are taken together with their intervening atoms to form an optionally substituted 3-20 membered monocyclic, bicyclic or polycyclic ring having a nitrogen atom (the one which $R^5$ is on). In some embodiments, $R^3$ is —H, and $R^4$ and $R^5$ are R, which are taken together with their intervening atoms to form an optionally substituted 4-7 membered monocyclic ring having a nitrogen atom (the one which $R^5$ is on). In some embodiments, $R^3$ is —H, and $R^4$ and $R^5$ are R, which are taken together with their intervening atoms to form an optionally substituted 4-membered monocyclic ring having a nitrogen atom (the one which $R^5$ is on). In some embodiments, $R^3$ is —H, and $R^4$ and $R^5$ are R, which are taken together with their intervening atoms to form an optionally substituted 5-membered monocyclic ring having a nitrogen atom (the one which $R^5$ is on). In some embodiments, $R^3$ is —H, and $R^4$ and $R^5$ are R, which are taken together with their intervening atoms to form an optionally substituted 6-membered monocyclic ring having a nitrogen atom (the one which $R^5$ is on). In some embodiments, $R^3$ is —H, and $R^4$ and $R^5$ are R, which are taken together with their intervening atoms to form an optionally substituted 7-membered monocyclic ring having a nitrogen atom (the one which $R^5$ is on). In some embodiments, $R^3$ is —H, and $R^4$ and $R^5$ are R, which are taken together with their intervening atoms to form an optionally substituted 8-membered monocyclic ring having a nitrogen atom (the one which R is on). In some embodiments, $R^3$ is —H and $R^4$ and $R^5$ are R, which are taken together with their intervening atoms to form an optionally substituted 9-membered monocyclic ring having a nitrogen atom (the one which $R^5$ is on). In some embodiments, $R^3$ is —H, and $R^4$ and $R^5$ are R, which are taken together with their intervening atoms to form an optionally substituted 10-membered monocyclic ring having a nitrogen atom (the one which $R^5$ is on). In some embodiments, a formed ring is substituted. In some embodiments, a formed ring is unsubstituted. In some embodiments, formed ring is monocyclic. In some embodiments, a formed ring is bicyclic. In some embodiments, a formed ring has no additional heteroatoms in addition to an intervening atom. In some embodiments, a formed ring has additional ring heteroatoms in addition to an intervening atom. In some embodiments, a formed ring is an optionally substituted saturated, monocyclic, 4-membered ring having no more than one ring heteroatom, wherein the only ring heteroatom is nitrogen. In some embodiments, a formed ring is an optionally substituted saturated, monocyclic, 5-membered ring having no more than one ring heteroatom, wherein the only ring heteroatom is nitrogen. In some embodiments, a formed ring is an optionally substituted saturated, monocyclic, 6-membered ring having no more than one ring heteroatom, wherein the only ring heteroatom is nitrogen. In some embodiments, a formed ring is an optionally substituted saturated, monocyclic, 7-membered ring having no more than one ring heteroatom, wherein the only ring heteroatom is nitrogen. In some embodiments, a formed ring is an optionally substituted saturated, monocyclic, 8-membered ring having no more than one ring heteroatom, wherein the only ring heteroatom is nitrogen. In some embodiments, a formed ring is an optionally substituted saturated, monocyclic, 9-membered ring having no more than one ring heteroatom, wherein the only ring heteroatom is nitrogen. In some embodiments, a formed ring is an optionally substituted saturated, monocyclic, 10-membered ring having no more than one ring heteroatom, wherein the only ring heteroatom is nitrogen. In some embodiments, a formed ring is of such a structure that

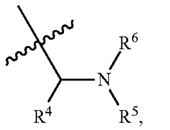

($R^6$ is—H)

is, in some embodiments,

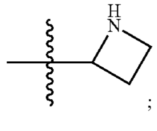

;

in some embodiments,

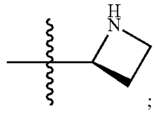 [SMILES: *[C@@H]1CCN1]

;

in some embodiments,
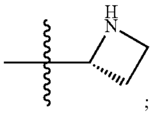
;
in some embodiments,
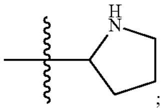
;
in some embodiments,
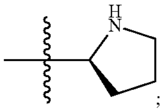 [SMILES: *[C@@H]1CCCN1]
;
in some embodiments,
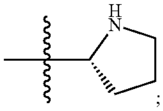 [SMILES: *[C@H]1CCCN1]
;
in some embodiments,
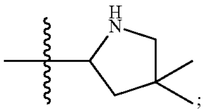 [SMILES: *C1CC(C)(C)CN1]
;
in some embodiments,
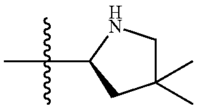
;
in some embodiments,
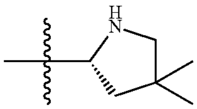
;
in some embodiments,
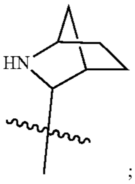 [SMILES: *C1NC2CCC1C2]
;
in some embodiments,
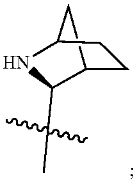 [SMILES: *[C@H]1NC2CCC1C2]
;
in some embodiments,
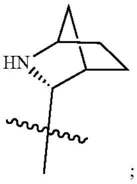 [SMILES: *[C@@H]1NC2CCC1C2]
;
in some embodiments,
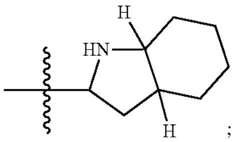 [SMILES: *C1CC2CCCCC2N1]
;
in some embodiments,
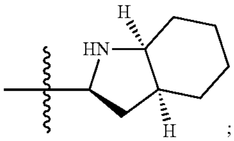 [SMILES: *[C@@H]1C[C@@H]2CCCC[C@@H]2N1]
;
in some embodiments,
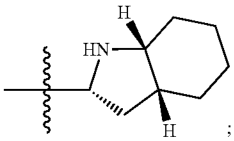 [SMILES: *[C@H]1C[C@H]2CCCC[C@H]2N1]
;

in some embodiments,

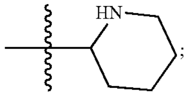 [SMILES: *C1CCCCN1];

in some embodiments,

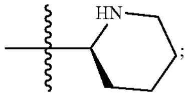 [SMILES: *[C@@H]1CCCCN1];

in some embodiments

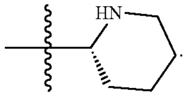.

In some embodiments, a provided compound is

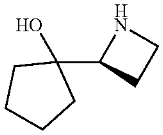, 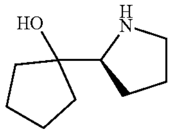, 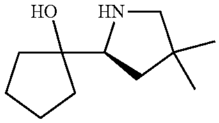, 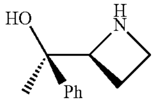, 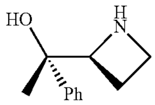, 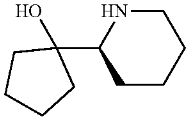, 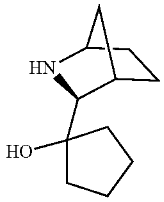, 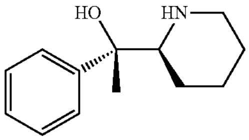, 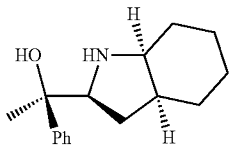, 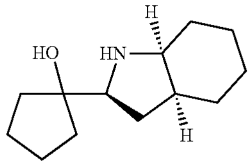, or a salt thereof. In some embodiments, a provided compound is

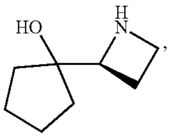, 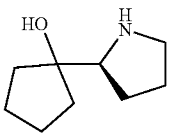, 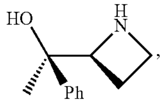,

-continued

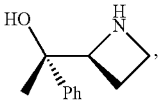, 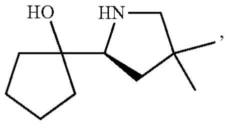, 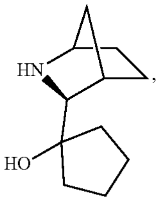, or a salt thereof. In some embodiments, a provided compound is

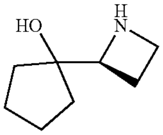

or a salt thereof. In some embodiments, a provided compound is

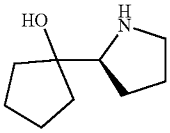 [SMILES: OC1([C@@H]2CCCN2)CCCC1]

or a salt thereof. In some embodiments, a provided compound is

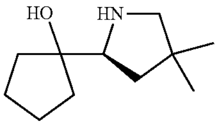

or a salt thereof. In some embodiments, a provided compound is

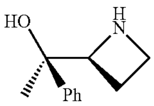

or a salt thereof. In some embodiments, a provided compound is

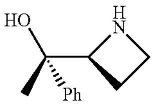

or a salt thereof. In some embodiments, a provided compound is

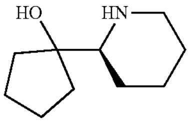 [SMILES: OC1([C@@H]2CCCCN2)CCCC1]

or a salt thereof. In some embodiments, a provided compound is

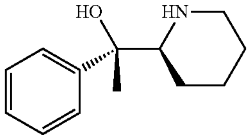

or a salt thereof. In some embodiments, a provided compound is

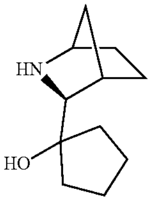 [SMILES: OC1([C@H]2NC3CCC2C3)CCCC1]

or a salt thereof. In some embodiments, a provided compound is

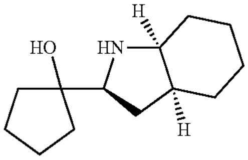 [SMILES: OC1([C@@H]2C[C@@H]3CCCC[C@@H]3N2)CCCC1]

or a salt thereof. In some embodiments, a provided compound is

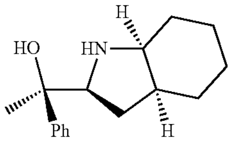

or a salt thereof.

In some embodiments, a provided compound is a diastereomer of

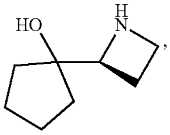,
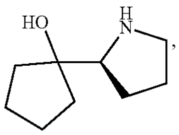,

-continued

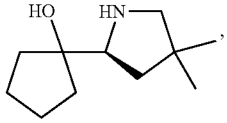,
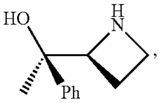,
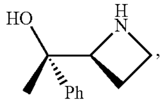,
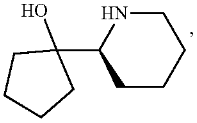,
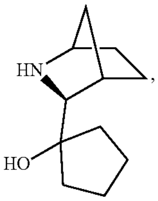,
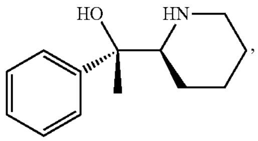,
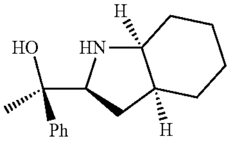 [SMILES: C[C@@](O)(c1ccccc1)[C@@H]1C[C@@H]2CCCC[C@@H]2N1],
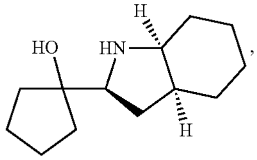, or a salt thereof. In some embodiments, a provided compound is a diastereomer of

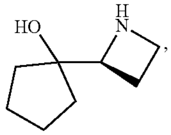,
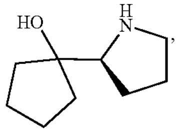,
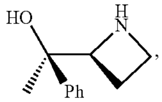,
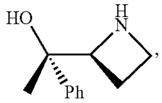,
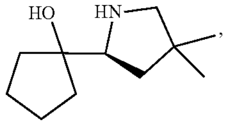,
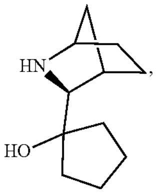, or a salt thereof. In some embodiments, a provided compound is a diastereomer of

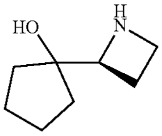

or a salt thereof. In some embodiments, a provided compound is a diastereomer of

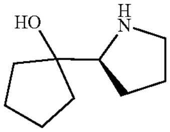 [SMILES: OC1([C@@H]2CCCN2)CCCC1]

or a salt thereof. In some embodiments, a provided compound is a diastereomer of

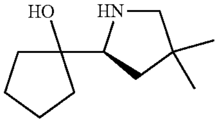

or a salt thereof. In some embodiments, a provided compound is a diastereomer of

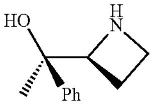

or a salt thereof. In some embodiments, a provided compound is a diastereomer of

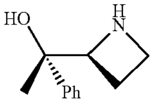

or a salt thereof. In some embodiments, a provided compound is a diastereomer of

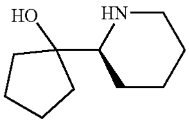 [SMILES: OC1([C@@H]2CCCCN2)CCCC1]

or a salt thereof. In some embodiments, a provided compound is a diastereomer of

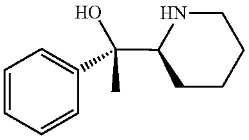

or a salt thereof. In some embodiments, a provided compound is a diastereomer of

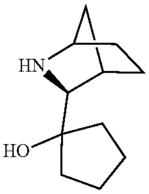 [SMILES: OC1([C@H]2NC3CCC2C3)CCCC1]

or a salt thereof. In some embodiments, a provided compound is a diastereomer of

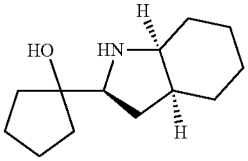 [SMILES: OC1([C@@H]2C[C@@H]3CCCC[C@@H]3N2)CCCC1]

or a salt thereof. In some embodiments, a provided compound is a diastereomer of

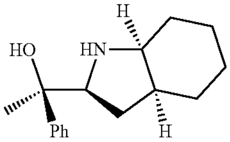 [SMILES: C[C@@](O)(c1ccccc1)[C@@H]1C[C@@H]2CCCC[C@@H]2N1]

or a salt thereof.

In some embodiments, a provided compound is an enantiomer of

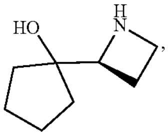

,

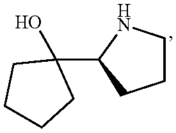

,

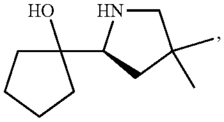

,

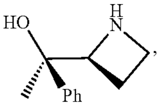

,

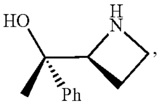

,

-continued

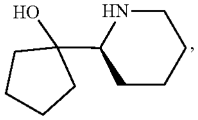

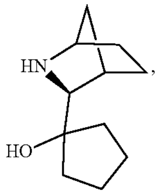

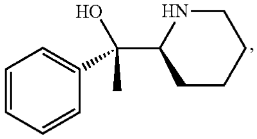

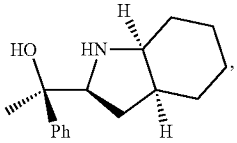

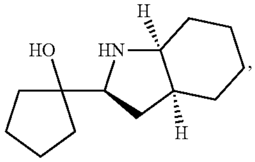

or a salt thereof. In some embodiments, a provided compound is an enantiomer of

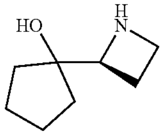
,
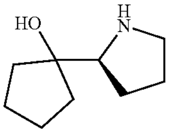
,
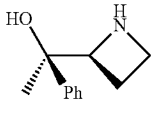
,
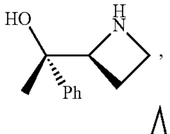
,
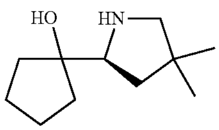
,
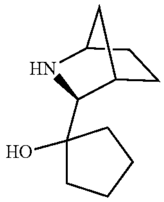
, or a salt thereof. In some embodiments, a provided compound is an enantiomer of

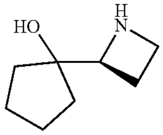

or a salt thereof. In some embodiments, a provided compound is an enantiomer of

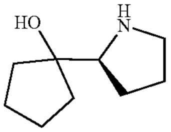 [SMILES: OC1([C@@H]2CCCN2)CCCC1]

or a salt thereof. In some embodiments, a provided compound is an enantiomer of

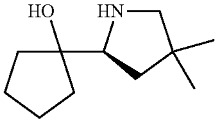

or a salt thereof. In some embodiments, a provided compound is an enantiomer of

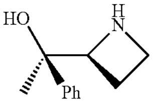

or a salt thereof. In some embodiments, a provided compound is an enantiomer of

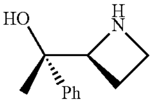

or a salt thereof. In some embodiments, a provided compound is an enantiomer of

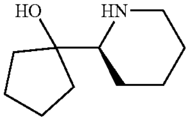 [SMILES: OC1([C@@H]2CCCCN2)CCCC1]

or a salt thereof. In some embodiments, a provided compound is an enantiomer of

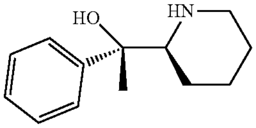

or a salt thereof. In some embodiments, a provided compound is an enantiomer of

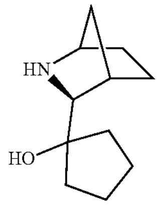 [SMILES: OC1([C@H]2NC3CCC2C3)CCCC1]

or a salt thereof. In some embodiments, a provided compound is an enantiomer of

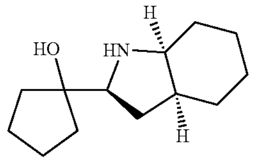 [SMILES: OC1([C@@H]2C[C@@H]3CCCC[C@@H]3N2)CCCC1]

or a salt thereof. In some embodiments, a provided compound is an enantiomer of

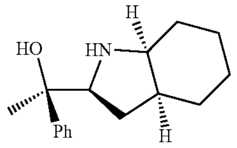 [SMILES: C[C@@](O)(c1ccccc1)[C@@H]1C[C@@H]2CCCC[C@@H]2N1]

or a salt thereof.

In some embodiments, $R^5$, and one or both of $R^1$ and $R^2$, are R, which are taken together with their intervening atoms to form an optionally substituted, 3-20 membered monocyclic, bicyclic or polycyclic ring having 1-5 heteroatoms. In some embodiments, one of $R^1$ and $R^2$, and $R^5$, are R, and the R groups are taken together with their intervening atoms to form an optionally substituted, 3-20 membered monocyclic, bicyclic or polycyclic ring having 1-5 heteroatoms. As extensively described in the present disclosure, a formed ring can be of various sizes, monocyclic, bicyclic or polycyclic, and contain various numbers and/or types of heteroatoms. In some embodiments, a ring is a 3-membered ring. In some embodiments, a ring is a 4-membered ring. In some embodiments, a ring is a 5-membered ring. In some embodiments, a ring is a 6-membered ring. In some embodiments, a ring is monocyclic. In some embodiments, a ring contains additional ring heteroatoms other than the intervening heteroatoms. In some embodiments, a ring is a 3-membered ring containing one ring heteroatom. In some embodiments, a ring is a 3-membered ring containing two ring heteroatoms. In some embodiments, a ring is a 3-membered ring containing one carbon, one nitrogen, and one oxygen ring atom.

In some embodiments, $R^6$ is R', wherein R' is as described in the present disclosure. In some embodiments, $R^6$ is —H, for example, when a provided compound has the structure of I, I-a, I-a-1, I-a-2, I-b, I-c, I-d, I-e, II, II-a, II-b, III, III-a, or III-b, or a salt thereof. In some embodiments, $R^6$ is a suitable capping group used in oligonucleotide synthesis, many of which are widely known and can be utilized in accordance with the present disclosure. In some embodiments, $R^6$ is —C(O)R, wherein R is as described in the present disclosure. In some embodiments, $R^6$ is a capping group when in a provided structure in oligonucleotide synthesis, for example, structure of formula VII, or O-I, or a salt thereof. In some embodiments, a capping group has the structure of —C(O)R, wherein R is as described in the present disclosure. In some embodiments, $R^6$ is —C(O)R, wherein R is as described in the present disclosure. In some embodiments, R is methyl. In some embodiments, R is —$CF_3$.

In some embodiments, $R^6$ is —H. In some embodiments, $R^6$ is —H, and $R^4$ and $R^5$ are R, and the R groups are taken together with their intervening atoms to form an optionally substituted 3-20 membered heterocyclyl ring having 1-5 heteroatoms as described in the present disclosure. In some embodiments, $R^6$ is —H, and $R^4$ and $R^5$ are R, and the R groups are taken together with their intervening atoms to form an optionally substituted 4-6 membered heterocyclyl ring having 1-5 heteroatoms as described in the present disclosure. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered.

In some embodiments, $R^7$ is —OH. In some embodiments, $R^7$ is —SH. In some embodiments, the present disclosure provides a compound of formula I, I-a, I-a-1, I-a-2, I-b, I-c, I-d, I-e, II, II-a, II-b, III, III-a, or III-b, or a salt thereof, wherein $R^8$ is —OH. In some embodiments, the present disclosure provides a compound of formula I, I-a, I-a-1, I-a-2, I-b, I-c, I-d, I-e, II, II-a, II-b, III, III-a, or III-b, or a salt thereof, wherein $R^7$ is —SH.

In some embodiments, $R^8$ is -L-$R^7$, -L-C($R^1$)($R^2$)—$R^7$, or -$L^s$-$R^7$, wherein each variable is independently as described in the present disclosure. In some embodiments, $R^8$ is $R^7$ as described in the present disclosure. In some embodiments, Rx is —OH. In some embodiments, $R^8$ is —SH. In some embodiments, $R^8$ is -L-$R^7$, wherein each of L and $R^7$ is independently as described in the present disclosure. In some embodiments, $R^8$ is -L-OH, wherein $L^s$ is as described in the present disclosure. In some embodiments, $R^8$ is -L-SH, wherein $L^s$ is as described in the present disclosure. In some embodiments, $R^8$ is -L-C($R^1$)($R^2$)—$R^7$, wherein each variable is independently as described in the present disclosure. In some embodiments, $R^8$ is —C($R^1$)($R^2$)—$R^7$, wherein each variable is independently as described in the present disclosure. In some embodiments, $R^8$ is —$CH_2$—$R^7$, wherein $R^7$ is as described in the present disclosure. In some embodiments, $R^8$ is —$CH_2$OH. In some embodiments, $R^8$ is —$CH_2$SH. In some embodiments, $R^8$ is -$L^s$-$R^7$, wherein each variable is independently as described in the present disclosure. In some embodiments, $R^8$ is -$L^s$-OH, wherein $L^s$ is as described in the present disclosure. In some embodiments, $R^8$ is -$L^s$-SH, wherein $L^s$ is as described in the present disclosure.

In some embodiments, $R^4$ and $R^5$ are R, which are taken together with their intervening atoms to form an optionally substituted 4-10 membered heterocyclyl ring with the intervening nitrogen atom as the only ring heteroatom. In some embodiments, $R^4$ and $R^5$ are R, which are taken together with their intervening atoms to form an optionally substituted 4-10 membered saturated monocyclic heterocyclyl ring with the intervening nitrogen atom as the only ring heteroatom. In some embodiments, $R^4$ and $R^5$ are R, which are taken together with their intervening atoms to form an optionally substituted 4-10 membered saturated bicyclic heterocyclyl ring with the intervening nitrogen atom as the only ring heteroatom. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring is an optionally substituted pyrrolidine moiety. In some embodiments, $R^7$ is —OH. In some embodiments, $R^7$ is —SH.

In some embodiments, a provided compound of formula I, I-a, I-a-1, I-a-2, I-b, I-c, I-d, I-e, II, II-a, II-b, III, III-a, or III-b comprises no more than one chiral elements. In some embodiments, a provided compound of formula I, I-a, I-a-1, I-a-2, I-b, I-c, I-d, I-e, II, II-a, II-b, III, III-a, or III-b comprises no more than one chiral elements, wherein the only one chiral element is chiral carbon atom. In some embodiments, a provided compound of formula I, I-a, I-a-1, I-a-2, I-b, I-c, I-d, I-e, II, II-a, II-b, III, III-a, or III-b comprises no more than one chiral elements, wherein the only one chiral element is chiral carbon atom to which $R^3$ and $R^4$ are attached. In some embodiments, $R^1$ and $R^2$ are the same. In some embodiments, $R^1$ and $R^2$ are the same, and are optionally substituted straight chain $C_{1-3}$ alkyl. In some embodiments, $R^1$ and $R^2$ are the same, and are optionally substituted straight chain $C_{1-3}$ alkyl wherein no substituent comprises a carbon atom. In some embodiments, $R^1$ and $R^2$ are the same, and are optionally substituted straight chain $C_{1-2}$ alkyl. In some embodiments, $R^1$ and $R^2$ are the same, and are optionally substituted straight chain $C_{1-2}$ alkyl wherein no substituent comprises a carbon atom. In some embodiments, $R^1$ and $R^2$ are methyl. In some embodiments, $R^1$ and $R^2$ are ethyl. In some embodiments, $R^1$ and $R^2$ are n-propyl. In some embodiments, $R^1$ and $R^2$ are taken together to form an optionally substituted ring as described in the present disclosure. In some embodiments, $R^1$ and $R^2$ are taken together to form an optionally substituted ring where the ring contains no chiral elements.

In some embodiments, L is a covalent bond, or optionally substituted $C_{1-6}$ alkylene, wherein one or more methylene units are optionally and independently replaced with -L'-, wherein L' is as described in the present disclosure. In some embodiments, L is a covalent bond. In some embodiments, L is optionally substituted $C_{1-6}$ alkylene, wherein one or more methylene units are optionally and independently replaced with -L'-, wherein L' is as described in the present disclosure. In some embodiments, L is optionally substituted $C_{1-6}$ alkylene, wherein one or more methylene units are independently replaced with -L'-, wherein each L' is independently as described in the present disclosure.

In some embodiments, L is a covalent bond. In some embodiments, a provided compound, e.g., a compound of formula I, has the structure of

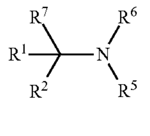

or a salt thereof.

In some embodiments, L is —C($R^3$)($R^4$)—. In some embodiments, a provided compound has the structure of formula I-a:

I-a

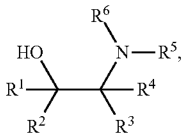

or a salt thereof, wherein each variable is independently as described in the present disclosure. In some embodiments, a compound of formula I has the structure of formula I-a. In some embodiments, a provided compound has the structure of

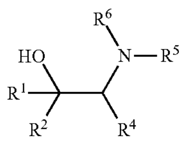

or a salt thereof, wherein each variable is independently as described in the present disclosure, and wherein $R^4$ and $R^5$ are not hydrogen. In some embodiments, a provided compound has the structure of

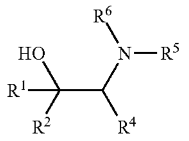

or a salt thereof, wherein each variable is independently as described in the present disclosure, and wherein $R^4$ and $R^5$ are R and are taken together to form an optionally substituted ring as described in the present disclosure. In some embodiments, $R^1$ and $R^2$ are different. In some embodiments, $R^1$ and $R^2$ are the same. In some embodiments, $R^1$ and $R^2$ are the same and are hydrogen. In some embodiments, $R^1$ and $R^2$ are the same and are not hydrogen. In some embodiments, $R^1$ and $R^2$ are the same and are optionally substituted $C_{1-6}$ aliphatic. In some embodiments, $R^1$ and $R^2$ are the same and are optionally substituted $C_{1-6}$ alkyl.

In some embodiments, a provided compound has the structure of formula (I-a-1):

I-a-1

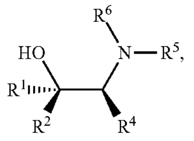

or a salt thereof, wherein each variable is independently as described in the present disclosure, and wherein $R^4$ and $R^5$ are not hydrogen, and $R^2$ has a larger size than $R^1$. In some embodiments, a compound of formula I-a has the structure of formula I-a-1. In some embodiments, $R^4$ and $R^5$ are R and are taken together to form an optionally substituted ring as described in the present disclosure. In some embodiments, $R^1$ and R are different. In some embodiments, $R^1$ and $R^2$ are the same. In some embodiments, $R^1$ and $R^2$ are the same and are hydrogen. In some embodiments, $R^1$ and $R^2$ are the same and are not hydrogen. In some embodiments, $R^1$ and $R^2$ are the same and are optionally substituted $C_{1-6}$ aliphatic. In some embodiments, $R^1$ and $R^2$ are the same and are optionally substituted $C_{1-6}$ alkyl.

In some embodiments, a provided compound has the structure of formula (I-a-2):

I-a-2

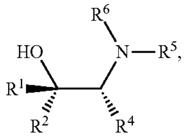

or a salt thereof, wherein each variable is independently as described in the present disclosure, and wherein $R^4$ and $R^5$ are not hydrogen, and $R^2$ has a larger size than $R^1$. In some embodiments, a compound of formula I-a has the structure of formula I-a-2. In some embodiments, $R^4$ and $R^5$ are R and are taken together to form an optionally substituted ring as described in the present disclosure. In some embodiments, $R^1$ and $R^2$ are different. In some embodiments, $R^1$ and $R^2$ are the same. In some embodiments, $R^1$ and $R^2$ are the same and are hydrogen. In some embodiments, $R^1$ and $R^2$ are the same and are not hydrogen. In some embodiments, $R^1$ and $R^2$ are the same and are optionally substituted $C_{1-6}$ aliphatic. In some embodiments, $R^1$ and $R^2$ are the same and are optionally substituted $C_{1-6}$ alkyl.

In some embodiments, L is -L'-C($R^3$)($R^4$)—, wherein each variable is independently as described in the present disclosure. In some embodiments, a provided compound has the structure of formula I-b:

I-b

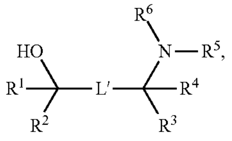

or a salt thereof, wherein each variable is independently as described in the present disclosure. In some embodiments, a compound of formula I has the structure of formula I-b.

In some embodiments, L' is a covalent bond. In some embodiments, L' is optionally substituted bivalent $C_{1-3}$ alkylene. In some embodiments, L' is —C($R^3$)($R^4$)—, wherein each of $R^3$ and $R^4$ is independently as described in the present disclosure. In some embodiments, L' is —C($R^3$)($R^4$)—C($R^3$)($R^4$)—, wherein each of $R^3$ and $R^4$ is independently as described in the present disclosure. In some embodiments, L' is -Cy- as described in the present disclosure. In some embodiments, L' is —C($R^3$)[C($R^4$)$_3$]—, wherein each of $R^3$ and $R^4$ is independently as described in the present disclosure.

In some embodiments, L' is a covalent bond. In some embodiments, L' is optionally substituted bivalent $C_{1-3}$ alkylene. In some embodiments, L' is —C($R^3$)($R^4$)—. In some embodiments, a provided compound has the structure of formula I-c:

I-c

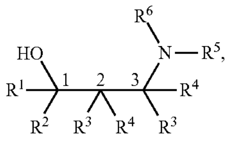

or a salt thereof, wherein each variable is independently as described in the present disclosure. In some embodiments, a compound of formula I has the structure of formula I-c, or a salt thereof. In some embodiments, a compound of formula I-b has the structure of formula I-c, or a salt thereof. In some embodiments, each of $R^1$ and $R^2$ is independently R, wherein R is as described in the present disclosure. In some embodiments, one of $R^1$ and $R^2$ is —H, and the other is R, wherein R is as described in the present disclosure and is not —H. In some embodiments, each of $R^1$ and $R^2$ is independently R, wherein R is as described in the present disclosure and is not —H. In some embodiments, each of $R^1$ and $R^2$ is independently R, wherein the two R groups are taken together to form an optionally substituted ring as described in the present disclosure. In some embodiments, one of $R^1$ and $R^2$ is —H, and the other is optionally substituted phenyl. In some embodiments, one of $R^1$ and $R^2$ is —H, and the other is phenyl. In some embodiments, each of $R^3$ and $R^4$ attached to C2 in formula I-c is independently R, wherein R is as described in the present disclosure. In some embodiments, each of $R^3$ and $R^4$ attached to C2 is —H. In some embodiments, each of $R^3$ and $R^4$ attached to C3 is independently R, wherein R is as described in the present disclosure. In some embodiments, one of $R^3$ and $R^4$ attached to C3 is hydrogen. In some embodiments, one of $R^3$ and R attached to C3 R, $R^5$ is R, and the two R groups are taken together to form an optionally substituted ring as described in the present disclosure.

In some embodiments, a formed ring is an optionally substituted heterocyclyl moiety as described in the present disclosure. In some embodiments, a formed ring is an optionally substituted, monocyclic, and saturated 4, 5, or 6-membered heterocyclyl ring having one nitrogen ring atom and no more than one heteroatom as described in the present disclosure. In some embodiments, a formed ring is an optionally substituted trivalent azetidinyl moiety as described in the present disclosure. In some embodiments, a formed ring is an optionally substituted trivalent pyrrolidinyl moiety as described in the present disclosure. In some embodiments, a formed ring is an optionally substituted trivalent piperidinyl moiety as described in the present disclosure. In some embodiments, one of $R^3$ and $R^4$ attached to C2 is R, one of $R^3$ and $R^4$ attached to C3 is R, and the two R groups are taken together to form an optionally substituted ring as described in the present disclosure. In some embodiments, a formed ring is an optionally substituted cycloaliphatic ring. In some embodiments, a formed ring an optionally substituted saturated cycloaliphatic ring. In some embodiments, a formed ring is 3, 4, 5, 6, 7, 8, 9, or 10-membered. In some embodiments, a formed ring is an optionally substituted 5-membered, saturated, monocyclic cycloaliphatic ring. In some embodiments, a provided compound is

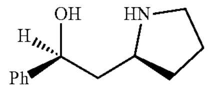 [SMILES: O[C@@H](C[C@@H]1CCCN1)c1ccccc1]

or a salt thereof. In some embodiments, a provided compound is a diastereomer of

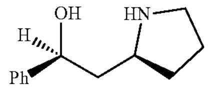 [SMILES: O[C@@H](C[C@@H]1CCCN1)c1ccccc1]

or a salt thereof. In some embodiments, a provided compound is an enantiomer of

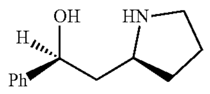 [SMILES: O[C@@H](C[C@@H]1CCCN1)c1ccccc1]

or a salt thereof. In some embodiments, a provided compound is

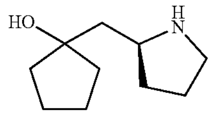

or a salt thereof. In some embodiments, a provided compound is a diastereomer of

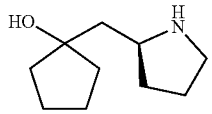 [SMILES: OC1(C[C@@H]2CCCN2)CCCC1]

or a salt thereof. In some embodiments, a provided compound is an enantiomer of

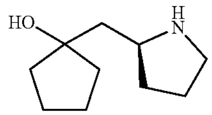 [SMILES: OC1(C[C@@H]2CCCN2)CCCC1]

or a salt thereof. In some embodiments, a provided compound is

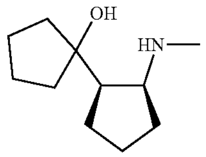

or a salt thereof. In some embodiments, a provided compound is a diastereomer of

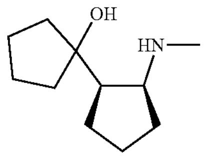

or a salt thereof. In some embodiments, a provided compound is an enantiomer of

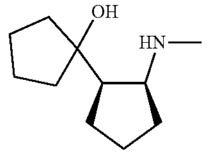

or a salt thereof.

In some embodiments, L' is —$C(R^3)(R^4)$—$C(R^3)(R^4)$—, wherein each variable is independently as described in the present disclosure. In some embodiments, L' is -Cy-. In some embodiments, L' is —$C(R^3)[C(R^4)_3]$—.

In some embodiments, each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon. In some embodiments, -Cy- is an optionally substituted ring as described in the present disclosure, for example, for R and $Cy^L$, but is bivalent.

In some embodiments, -Cy- is monocyclic. In some embodiments, -Cy- is bicyclic. In some embodiments, -Cy- is polycyclic. In some embodiments, -Cy- is saturated. In some embodiments, -Cy- is partially unsaturated. In some embodiments, -Cy- is aromatic. In some embodiments, -Cy- comprises a saturated cyclic moiety. In some embodiments, -Cy- comprises a partially unsaturated cyclic moiety. In some embodiments, -Cy- comprises an aromatic cyclic moiety. In some embodiments, -Cy- comprises a combination of a saturated, a partially unsaturated, and/or an aromatic cyclic moiety. In some embodiments, -Cy- is 3-membered. In some embodiments, -Cy- is 4-membered. In some embodiments, -Cy- is 5-membered. In some embodiments, -Cy- is 6-membered. In some embodiments, -Cy- is 7-membered. In some embodiments, -Cy- is 8-membered. In some embodiments, -Cy- is 9-membered. In some embodiments, -Cy- is 10-membered. In some embodiments, -Cy- is 11-membered. In some embodiments, -Cy- is 12-membered. In some embodiments, -Cy- is 13-membered. In some embodiments, -Cy- is 14-membered. In some embodiments, -Cy- is 15-membered. In some embodiments, -Cy- is 16-membered. In some embodiments, -Cy- is 17-membered. In some embodiments, -Cy- is 18-membered. In some embodiments, -Cy- is 19-membered. In some embodiments, -Cy- is 20-membered.

In some embodiments, -Cy- is an optionally substituted bivalent $C_{3-20}$ cycloaliphatic ring. In some embodiments, -Cy- is an optionally substituted bivalent, saturated $C_{3-20}$ cycloaliphatic ring. In some embodiments, -Cy- is an optionally substituted bivalent, partially unsaturated $C_{3-20}$ cycloaliphatic ring. In some embodiments, -Cy- comprises an aromatic moiety. In some embodiments, -Cy- is optionally substituted

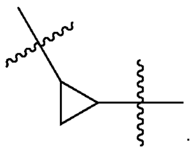 [SMILES: *C1CC1*].

In some embodiments -Cy- is optionally substituted

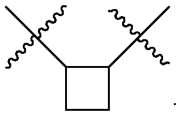 [SMILES: *C1CCC1*]

In some embodiments, -Cy- is optionally substituted

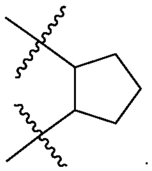 [SMILES: *C1CCCC1*]

In some embodiments, -Cy- is optionally substituted

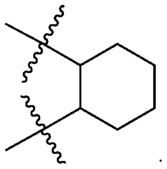 [SMILES: *C1CCCCC1*]

In some embodiments, -Cy- is optionally substituted

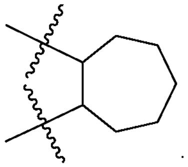 [SMILES: *C1CCCCCC1*]

In some embodiments, -Cy- is optionally substitute

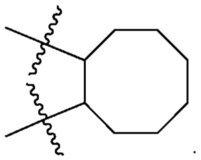 [SMILES: *C1CCCCCCC1*]

In some embodiments, -Cy-H is optionally substituted cycloaliphatic as described in the present disclosure, for example, cycloaliphatic embodiments for R.

In some embodiments, -Cy- is an optionally substituted $C_{6-20}$ aryl ring. In some embodiments, -Cy- is optionally substituted phenylene. In some embodiments, -Cy- is optionally substituted 1,2-phenylene. In some embodiments, -Cy- is optionally substituted 1,3-phenylene. In some embodiments, -Cy- is optionally substituted 1,4-phenylene. In some embodiments, -Cy- is an optionally substituted bivalent naphthalene ring. In some embodiments, -Cy-H is optionally substituted aryl as described in the present disclosure, for example, aryl embodiments for R.

In some embodiments, -Cy- is an optionally substituted bivalent 5-20 membered heteroaryl ring having 1-10 heteroatoms independently selected from oxygen, nitrogen, sulfur, phosphorus and silicon. In some embodiments, -Cy- is an optionally substituted bivalent 5-20 membered heteroaryl ring having 1-10 heteroatoms independently selected from oxygen, nitrogen, and sulfur. In some embodiments, -Cy- is an optionally substituted bivalent 5-6 membered heteroaryl ring having 1-4 heteroatoms independently selected from oxygen, nitrogen, sulfur. In some embodiments, -Cy- is an optionally substituted bivalent 5-6 membered heteroaryl ring having 1-3 heteroatoms independently selected from oxygen, nitrogen, sulfur. In some embodiments, -Cy- is an optionally substituted bivalent 5-6 membered heteroaryl ring having 1-2 heteroatoms independently selected from oxygen, nitrogen, sulfur. In some embodiments, -Cy- is an optionally substituted bivalent 5-6 membered heteroaryl ring having one heteroatom independently selected from oxygen, nitrogen, sulfur. In some embodiments, -Cy-H is optionally substituted heteroaryl as described in the present disclosure, for example, heteroaryl embodiments for R.

In some embodiments, -Cy- is an optionally substituted bivalent 3-20 membered heterocyclyl ring having 1-10 heteroatoms independently selected from oxygen, nitrogen, sulfur, phosphorus and silicon. In some embodiments, -Cy- is an optionally substituted bivalent 3-20 membered heterocyclyl ring having 1-10 heteroatoms independently selected from oxygen, nitrogen, and sulfur. In some embodiments, -Cy- is an optionally substituted bivalent 3-6 membered heterocyclyl ring having 1-4 heteroatoms independently selected from oxygen, nitrogen, sulfur. In some embodiments, -Cy- is an optionally substituted bivalent 5-6 membered heterocyclyl ring having 1-4 heteroatoms independently selected from oxygen, nitrogen, sulfur. In some embodiments, -Cy- is an optionally substituted bivalent 5-6 membered heterocyclyl ring having 1-3 heteroatoms independently selected from oxygen, nitrogen, sulfur. In some embodiments, -Cy- is an optionally substituted bivalent 5-6 membered heterocyclyl ring having 1-2 heteroatoms independently selected from oxygen, nitrogen, sulfur. In some embodiments, -Cy- is an optionally substituted bivalent 5-6 membered heterocyclyl ring having one heteroatom independently selected from oxygen, nitrogen, sulfur. In some embodiments, -Cy- is an optionally substituted saturated bivalent heterocyclyl group. In some embodiments, -Cy- is an optionally substituted partially unsaturated bivalent heterocyclyl group. In some embodiments, -Cy-H is optionally substituted heterocyclyl as described in the present disclosure, for example, heterocyclyl embodiments for R.

In some embodiments, -Cy- is an optionally substituted bivalent 3-30 membered carbocyclylene. In some embodiments, -Cy- is an optionally substituted bivalent 6-30 membered arylene. In some embodiments, -Cy- is an optionally substituted bivalent 5-30 membered heteroarylene having 1-10 heteroatoms independently selected from oxygen, nitrogen and sulfur. In some embodiments, -Cy- is an optionally substituted bivalent 3-30 membered heterocyclylene having 1-10 heteroatoms independently selected from oxygen, nitrogen, sulfur, phosphorus and silicon. In some embodiments, -Cy- is an optionally substituted bivalent 5-30 membered heteroarylene having 1-5 heteroatoms independently selected from oxygen, nitrogen and sulfur. In some embodiments, -Cy- is an optionally substituted bivalent 3-30 membered heterocyclylene having 1-5 heteroatoms independently selected from oxygen, nitrogen, sulfur, phosphorus and silicon.

In some embodiments, each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$.

In some embodiments, U is a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$. In some embodiments, U is a covalent bond, or a bivalent, optionally substituted, linear or branched $C_{1-30}$ aliphatic group, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$. In some embodiments, $L^s$ is a covalent bond, or a bivalent, optionally substituted, linear or branched $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$. In some embodiments, $L^s$ is a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—, and one or more carbon atoms are optionally and independently replaced with $Cy^L$. In some embodiments, $L^s$ is a covalent bond, or a bivalent, optionally substituted, linear or branched group selected from a $C_{1-10}$ aliphatic group and a $C_{1-10}$ heteroaliphatic group having 1-5 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, and —C(O)O—, and one or more carbon atoms are optionally and independently replaced with $Cy^L$. In some embodiments, U is a covalent bond, or a bivalent, optionally substituted, linear or branched group selected from a $C_{1-10}$ aliphatic group and a $C_{1-10}$ heteroaliphatic group having 1-5 heteroatoms independently selected from oxygen, nitrogen, sulfur, phosphorus and silicon, wherein one or more methylene units are optionally and independently replaced by an optionally substituted group selected from —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, and —C(O)O—.

In some embodiments, L is a covalent bond. In some embodiments, L is optionally substituted bivalent $C_{1-30}$ aliphatic. In some embodiments, $L^s$ is optionally substituted bivalent $C_{1-30}$ heteroaliphatic having 1-10 heteroatoms independently selected from boron, oxygen, nitrogen, sulfur, phosphorus and silicon.

In some embodiments, aliphatic moieties, e.g. those of $L^s$, R, etc., either monovalent or bivalent or multivalent, and can contain any number of carbon atoms (before any optional substitution) within its range, e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, etc. In some embodiments, heteroaliphatic moieties, e.g. those of $L^5$, R, etc., either monovalent or bivalent or multivalent, and can contain any number of carbon atoms (before any optional substitution) within its range, e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, etc.

In some embodiments, a methylene unit is replaced with -Cy-, wherein -Cy- is as described in the present disclosure. In some embodiments, one or more methylene unit is optionally and independently substituted with —O—, —S—, —N(R')—, —C(O)—, —S(O)—, $—S(O)_2—$, —P(O)(OR')—, —P(O)(SR')—, —P(S)(OR')—, or —P(S)(OR')—. In some embodiments, a methylene unit is replaced with —O—. In some embodiments, a methylene unit is replaced with —S—. In some embodiments, a methylene unit is replaced with —N(R')—. In some embodiments, a methylene unit is replaced with —C(O)—. In some embodiments, a methylene unit is replaced with —S(O)—. In some embodiments, a methylene unit is replaced with $—S(O)_2—$. In some embodiments, a methylene unit is replaced with —P(O)(OR')—. In some embodiments, a methylene unit is replaced with —P(O)(SR')—. In some embodiments, a methylene unit is replaced with —P(O)(R')—. In some embodiments, a methylene unit is replaced with —P(O)(NR')—. In some embodiments, a methylene unit is replaced with —P(S)(OR')—. In some embodiments, a methylene unit is replaced with —P(S)(SR')—. In some embodiments, a methylene unit is replaced with —P(S)(R')—. In some embodiments, a methylene unit is replaced with —P(S)(NR')—. In some embodiments, a methylene unit is replaced with —P(R')—. In some embodiments, a methylene unit is replaced with —P(OR')—. In some embodiments, a methylene unit is replaced with —P(SR')—. In some embodiments, a methylene unit is replaced with —P(NR')—. In some embodiments, a methylene unit is replaced with $—P(OR')[B(R')_3]—$. In some embodiments, one or more methylene unit is optionally and independently substituted with —O—, —S—, —N(R')—, —C(O)—, —S(O)—, $—S(O)_2—$, —P(O)(OR')—, —P(O)(SR')—, —P(S)(OR')—, or —P(S)(OR')—. In some embodiments, a methylene unit is replaced with —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or $—OP(OR')[B(R')_3]O—$, each of which may independently be an internucleotidic linkage.

In some embodiments, $L^s$, e.g., when connected to $R^5$, is $—CH_2—$. In some embodiments, $L^s$ is $—C(R)_2—$, wherein at least one R is not hydrogen. In some embodiments, $L^s$ is —CHR—. In some embodiments, R is hydrogen. In some embodiments, $L^s$ is —CHR—, wherein R is not hydrogen. In some embodiments, C of —CHR— is chiral. In some embodiments, $L^s$ is —(R)—CHR—, wherein C of —CHR— is chiral. In some embodiments, $L^s$ is —(S)—CHR—, wherein C of —CHR— is chiral. In some embodiments, R is optionally substituted $C_{1-6}$ aliphatic. In some embodiments, R is optionally substituted $C_{1-6}$ alkyl. In some embodiments, R is optionally substituted $C_{1-5}$ aliphatic. In some embodiments, R is optionally substituted $C_{1-5}$ alkyl. In some embodiments, R is optionally substituted $C_{1-4}$ aliphatic. In some embodiments, R is optionally substituted $C_{1-4}$alkyl. In some embodiments, R is optionally substituted $C_{1-3}$ aliphatic. In some embodiments, R is optionally substituted $C_{1-3}$ alkyl. In some embodiments, R is optionally substituted $C_2$ aliphatic. In some embodiments, R is optionally substituted methyl. In some embodiments, R is $C_{1-6}$ aliphatic. In some embodiments, R is $C_{1-6}$alkyl. In some embodiments, R is $C_{1-5}$ aliphatic. In some embodiments, R is $C_{1-5}$ alkyl. In some embodiments, R is $C_{1-4}$ aliphatic. In some embodiments, R is $C_{1-4}$ alkyl. In some embodiments, R is $C_{1-3}$ aliphatic. In some embodiments, R is $C_{1-3}$ alkyl. In some embodiments, R is $C_2$ aliphatic. In some embodiments, R is methyl. In some embodiments, R is $C_{1-6}$ haloaliphatic. In some embodiments, R is $C_{1-6}$ haloalkyl. In some embodiments, R is $C_{1-5}$ haloaliphatic. In some embodiments, R is $C_{1-5}$ haloalkyl. In some embodiments, R is $C_{1-4}$ haloaliphatic. In some embodiments, R is $C_{1-4}$ haloalkyl. In some embodiments, R is $C_{1-3}$ haloaliphatic. In some embodiments, R is $C_{1-3}$ haloalkyl. In some embodiments, R is $C_2$ haloaliphatic. In some embodiments, R is methyl substituted with one or more halogen. In some embodiments, R is $—CF_3$. In some embodiments, $L^s$ is optionally substituted —CH═CH—. In some embodiments, $L^s$ is optionally substituted (E) —CH═CH—. In some embodiments, $L^s$ is optionally substituted (Z)—CH═CH—. In some embodiments, $L^s$ is —C≡C—.

In some embodiments, $L^s$ comprises at least one phosphorus atom. In some embodiments, at least one methylene unit of $L^s$ is replaced with —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, $—P(OR')[B(R')_3]—$, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or $—OP(OR')[B(R')_3]O—$.

In some embodiments, $L^s$ is -Cy-. In some embodiments, -Cy- is optionally substituted monocyclic or bicyclic 3-20 membered heterocyclyl ring having 1-5 heteroatoms. In some embodiments, -Cy- is optionally substituted monocyclic or bicyclic 5-20 membered heterocyclyl ring having 1-5 heteroatoms, wherein at least one heteroatom is oxygen. In some embodiments, -Cy- is optionally substituted bivalent tetrahydrofuran ring. In some embodiments, -Cy- is an optionally substituted furanose moiety.

In some embodiments, $Cy^L$ is an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon.

In some embodiments, $Cy^L$ is monocyclic. In some embodiments, $Cy^L$ is bicyclic. In some embodiments, $Cy^L$ is polycyclic.

In some embodiments, $Cy^L$ is saturated. In some embodiments, $Cy^L$ is partially unsaturated. In some embodiments, $Cy^L$ is aromatic. In some embodiments, $Cy^L$ is or comprises a saturated ring moiety. In some embodiments, $Cy^L$ is or comprises a partially unsaturated ring moiety. In some embodiments, $Cy^L$ is or comprises an aromatic ring moiety.

In some embodiments, $Cy^L$ is an optionally substituted $C_{3-20}$ cycloaliphatic ring as described in the present disclosure (for example, those described for R but tetravalent). In some embodiments, a ring is an optionally substituted saturated $C_{3-20}$ cycloaliphatic ring. In some embodiments, a ring is an optionally substituted partially unsaturated $C_{3-20}$ cycloaliphatic ring. A cycloaliphatic ring can be of various sizes as described in the present disclosure. In some embodiments, a ring is 3, 4, 5, 6, 7, 8, 9, or 10-membered. In some embodiments, a ring is 3-membered. In some embodiments, a ring is 4-membered. In some embodiments, a ring is 5-membered. In some embodiments, a ring is 6-membered. In some embodiments, a ring is 7-membered. In some embodiments, a ring is 8-membered. In some embodiments, a ring is 9-membered. In some embodiments, a ring is 10-membered. In some embodiments, a ring is an optionally substituted cyclopropyl moiety. In some embodiments, a ring is an optionally substituted cyclobutyl moiety. In some embodiments, a ring is an optionally substituted cyclopentyl moiety. In some embodiments, a ring is an optionally substituted cyclohexyl moiety. In some embodiments, a ring is an optionally substituted cycloheptyl moiety. In some embodiments, a ring is an optionally substituted cyclooctanyl moiety. In some embodiments, a cycloaliphatic ring is a cycloalkyl ring. In some embodiments, a cycloaliphatic ring is monocyclic. In some embodiments, a cycloaliphatic ring is bicyclic. In some embodiments, a cycloaliphatic ring is polycyclic. In some embodiments, a ring is a cycloaliphatic moiety as described in the present disclosure for R with more valences.

In some embodiments, $Cy^L$ is an optionally substituted 6-20 membered aryl ring. In some embodiments, a ring is an optionally substituted tetravalent phenyl moiety. In some embodiments, a ring is a tetravalent phenyl moiety. In some embodiments, a ring is an optionally substituted naphthalene moiety. A ring can be of different size as described in the present disclosure. In some embodiments, an aryl ring is 6-membered. In some embodiments, an aryl ring is 10-membered. In some embodiments, an aryl ring is 14-membered. In some embodiments, an aryl ring is monocyclic. In some embodiments, an aryl ring is bicyclic. In some embodiments, an aryl ring is polycyclic. In some embodiments, a ring is an aryl moiety as described in the present disclosure for R with more valences.

In some embodiments, $Cy^L$ is an optionally substituted 5-20 membered heteroaryl ring having 1-10 heteroatoms independently selected from oxygen, nitrogen, sulfur, phosphorus and silicon. In some embodiments, $Cy^L$ is an optionally substituted 5-20 membered heteroaryl ring having 1-10 heteroatoms independently selected from oxygen, nitrogen, and sulfur. In some embodiments, as described in the present disclosure, heteroaryl rings can be of various sizes and contain various numbers and/or types of heteroatoms. In some embodiments, a heteroaryl ring contains no more than one heteroatom. In some embodiments, a heteroaryl ring contains more than one heteroatom. In some embodiments, a heteroaryl ring contains no more than one type of heteroatom. In some embodiments, a heteroaryl ring contains more than one type of heteroatoms. In some embodiments, a heteroaryl ring is 5-membered. In some embodiments, a heteroaryl ring is 6-membered. In some embodiments, a heteroaryl ring is 8-membered. In some embodiments, a heteroaryl ring is 9-membered. In some embodiments, a heteroaryl ring is 10-membered. In some embodiments, a heteroaryl ring is monocyclic. In some embodiments, a heteroaryl ring is bicyclic. In some embodiments, a heteroaryl ring is polycyclic. In some embodiments, a heteroaryl ring is a nucleobase moiety, e.g., A, T, C, G, U, etc. In some embodiments, a ring is a heteroaryl moiety as described in the present disclosure for R with more valences.

In some embodiments, $Cy^L$ is a 3-20 membered heterocyclyl ring having 1-10 heteroatoms independently selected from oxygen, nitrogen, sulfur, phosphorus and silicon. In some embodiments, $Cy^L$ is a 3-20 membered heterocyclyl ring having 1-10 heteroatoms independently selected from oxygen, nitrogen, and sulfur. In some embodiments, a heterocyclyl ring is saturated. In some embodiments, a heterocyclyl ring is partially unsaturated. A heterocyclyl ring can be of various sizes as described in the present disclosure. In some embodiments, a ring is 3, 4, 5, 6, 7, 8, 9, or 10-membered. In some embodiments, a ring is 3-membered. In some embodiments, a ring is 4-membered. In some embodiments, a ring is 5-membered. In some embodiments, a ring is 6-membered. In some embodiments, a ring is 7-membered. In some embodiments, a ring is 8-membered. In some embodiments, a ring is 9-membered. In some embodiments, a ring is 10-membered. Heterocyclyl rings can contain various numbers and/or types of heteroatoms. In some embodiments, a heterocyclyl ring contains no more than one heteroatom. In some embodiments, a heterocyclyl ring contains more than one heteroatom. In some embodiments, a heterocyclyl ring contains no more than one type of heteroatom. In some embodiments, a heterocyclyl ring contains more than one type of heteroatoms. In some embodiments, a heterocyclyl ring is monocyclic. In some embodiments, a heterocyclyl ring is bicyclic. In some embodiments, a heterocyclyl ring is polycyclic. In some embodiments, a ring is a heterocyclyl moiety as described in the present disclosure for R with more valences.

As readily appreciated by a person having ordinary skill in the art, many suitable ring moieties are extensively described in and can be used in accordance with the present disclosure, for example, those described for R (which may have more valences for $Cy^L$).

In some embodiments, $Cy^L$ is a sugar moiety in a nucleic acid. In some embodiments, $Cy^L$ is an optionally substituted furanose moiety. In some embodiments, $Cy^L$ is a pyranose moiety. In some embodiments, $Cy^L$ is an optionally substituted furanose moiety found in DNA. In some embodiments, $Cy^L$ is an optionally substituted furanose moiety found in RNA. In some embodiments, $Cy^L$ is an optionally substituted 2'-deoxyribofuranose moiety. In some embodiments, $Cy^L$ is an optionally substituted ribofuranose moiety. In some embodiments, substitutions provide sugar modifications as described in the present disclosure. In some embodiments, an optionally substituted 2'-deoxyribofuranose moiety and/or an optionally substituted ribofuranose moiety comprise substitution at a 2'-position. In some embodiments, a 2'-position is a 2'-modification as described in the present disclosure. In some embodiments, a 2'-modification is —F. In some embodiments, a 2'-modification is —OR, wherein R is as described in the present disclosure. In some embodiments, R is not hydrogen. In some embodiments, $Cy^L$ is a modified sugar moiety, such as a sugar moiety in LNA. In some embodiments, $Cy^L$ is a modified sugar moiety, such as a sugar moiety in ENA. In some embodiments, $Cy^L$ is a terminal sugar moiety of an oligonucleotide, connecting an internucleotidic linkage and a nucleobase. In some embodiments, $Cy^L$ is a terminal sugar moiety of an oligonucleotide, for example, when that terminus is connected to a solid support optionally through a linker. In some embodiments, $Cy^L$ is a sugar moiety connecting two internucleotidic linkages and a nucleobase. Example sugars and sugar moieties are extensively described in the present disclosure.

In some embodiments, $Cy^L$ is a nucleobase moiety. In some embodiments, a nucleobase is a natural nucleobase, such as A, T, C, G, U, etc. In some embodiments, a nucleobase is a modified nucleobase. In some embodiments, $Cy^L$ is optionally substituted nucleobase moiety selected from A, T, C, G, U, and 5 mC. Example nucleobases and nucleobase moieties are extensively described in the present disclosure.

In some embodiments, two $Cy^L$ moieties are bonded to each other, wherein one $Cy^L$ is a sugar moiety and the other is a nucleobase moiety. In some embodiments, such a sugar moiety and nucleobase moiety forms a nucleoside moiety. In some embodiments, a nucleoside moiety is natural. In some embodiments, a nucleoside moiety is modified. In some embodiments, $Cy^L$ is an optionally substituted natural nucleoside moiety selected from adenosine, 5-methyluridine, cytidine, guanosine, uridine, 5-methylcytidine, 2'-deoxyadenosine, thymidine, 2'-deoxycytidine, 2'-deoxyguanosine, 2'-deoxyuridine, and 5-methyl-2'-deoxycytidine. Example nucleosides and nucleosides moieties are extensive described in the present disclosure.

In some embodiments, for example in $L^s$, $Cy^L$ is an optionally substituted nucleoside moiety bonded to an internucleotidic linkage, for example, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, —OP(OR')[B(R')$_3$]O—, etc., which may form an optionally substituted nucleotidic unit. Example nucleotides and nucleosides moieties are extensive described in the present disclosure.

In some embodiments, R' is —R, —C(O)R, —C(O)OR, or —S(O)$_2$R, wherein R is as described in the present disclosure. In some embodiments, R' is R, wherein R is as described in the present disclosure. In some embodiments, R' is —C(O)R, wherein R is as described in the present disclosure. In some embodiments, R' is —C(O)OR, wherein R is as described in the present disclosure. In some embodiments, R' is —S(O)$_2$R, wherein R is as described in the present disclosure. In some embodiments, R' is hydrogen. In some embodiments, R' is not hydrogen. In some embodiments, R' is R, wherein R is optionally substituted $C_{1-20}$ aliphatic as described in the present disclosure. In some embodiments, R' is R, wherein R is optionally substituted $C_{1-20}$ heteroaliphatic as described in the present disclosure. In some embodiments, R' is R, wherein R is optionally substituted $C_{6-20}$ aryl as described in the present disclosure. In some embodiments, R' is R, wherein R is optionally substituted $C_{6-20}$ arylaliphatic as described in the present disclosure. In some embodiments, R' is R, wherein R is optionally substituted $C_{6-20}$ arylheteroaliphatic as described in the present disclosure. In some embodiments, R' is R, wherein R is optionally substituted 5-20 membered heteroaryl as described in the present disclosure. In some embodiments, R' is R, wherein R is optionally substituted 3-20 membered heterocyclyl as described in the present disclosure. In some embodiments, two or more R' are R, and are optionally and independently taken together to form an optionally substituted ring as described in the present disclosure.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon.

two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-20}$ aliphatic, $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-20 membered monocyclic, bicyclic or polycyclic ring having, in addition to the atom, 0-10 heteroatoms independently selected from oxygen, nitrogen, sulfur, phosphorus and silicon.

two or more R groups on two or more atoms are optionally and independently taken together with their intervening atoms to form an optionally substituted, 3-20 membered monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon.

In some embodiments, each R is independently —H, or an optionally substituted group selected from $C_{1-20}$ aliphatic, $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon.

In some embodiments, R is hydrogen. In some embodiments, R is not hydrogen. In some embodiments, R is an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

In some embodiments, R is hydrogen or an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, and sulfur, a 4-7 membered saturated or partially unsaturated heterocyclic ring having 1-3 heteroatoms independently selected from nitrogen, oxygen, and sulfur, a 7-10 membered bicyclic saturated or partially unsaturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur.

In some embodiments, R is optionally substituted $C_{1-30}$ aliphatic. In some embodiments, R is optionally substituted $C_{1-20}$ aliphatic. In some embodiments, R is optionally substituted $C_{1-15}$ aliphatic. In some embodiments, R is optionally substituted $C_{1-10}$ aliphatic. In some embodiments, R is optionally substituted $C_{1-6}$ aliphatic. In some embodiments, R is optionally substituted $C_{1-6}$ alkyl. In some embodiments, R is optionally substituted hexyl, pentyl, butyl, propyl, ethyl or methyl. In some embodiments, R is optionally substituted hexyl. In some embodiments, R is optionally substituted pentyl. In some embodiments, R is optionally substituted butyl. In some embodiments, R is optionally substituted propyl. In some embodiments, R is optionally substituted ethyl. In some embodiments, R is optionally substituted methyl. In some embodiments, R is hexyl. In some embodiments, R is pentyl. In some embodiments, R is butyl. In some embodiments, R is propyl. In some embodiments, R is ethyl. In some embodiments, R is methyl. In some embodiments, R is isopropyl. In some embodiments, R is n-propyl. In some embodiments, R is tert-butyl. In some embodiments, R is sec-butyl. In some embodiments, R is n-butyl. In some embodiments, R is $-(CH_2)_2CN$.

In some embodiments, R is optionally substituted $C_{3-30}$ cycloaliphatic. In some embodiments, R is optionally substituted $C_{3-20}$ cycloaliphatic. In some embodiments, R is optionally substituted $C_{3-10}$ cycloaliphatic. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, R is an optionally substituted 3-30 membered saturated or partially unsaturated carbocyclic ring. In some embodiments, R is an optionally substituted 3-7 membered saturated or partially unsaturated carbocyclic ring. In some embodiments, R is an optionally substituted 3-membered saturated or partially unsaturated carbocyclic ring. In some embodiments, R is an optionally substituted 4-membered saturated or partially unsaturated carbocyclic ring. In some embodiments, R is an optionally substituted 5-membered saturated or partially unsaturated carbocyclic ring. In some embodiments, R is an optionally substituted 6-membered saturated or partially unsaturated carbocyclic ring. In some embodiments, R is an optionally substituted 7-membered saturated or partially unsaturated carbocyclic ring. In some embodiments, R is optionally substituted cycloheptyl. In some embodiments, R is cycloheptyl. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, when R is or comprises a ring structure, e.g., cycloaliphatic, cycloheteroaliphatic, aryl, heteroaryl, etc., the ring structure can be monocyclic, bicyclic or polycyclic. In some embodiments, R is or comprises a monocyclic structure. In some embodiments, R is or comprises a bicyclic structure. In some embodiments, R is or comprises a polycyclic structure.

In some embodiments, R is optionally substituted $C_{1-30}$ heteroaliphatic having 1-10 heteroatoms independently selected from oxygen, nitrogen, sulfur, phosphorus and silicon. In some embodiments, R is optionally substituted $C_{1-20}$ heteroaliphatic having 1-10 heteroatoms. In some embodiments, R is optionally substituted $C_{1-20}$ heteroaliphatic having 1-10 heteroatoms independently selected from oxygen, nitrogen, sulfur, phosphorus or silicon, optionally including one or more oxidized forms of nitrogen, sulfur, phosphorus or selenium. In some embodiments, R is optionally substituted $C_{1-30}$ heteroaliphatic comprising 1-10 groups independently selected from

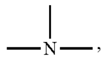,

—N═, ≡N, —S—, —S(O)—, $—S(O)_2—$, —O—, ═,

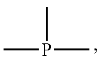, 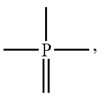, and 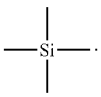.

In some embodiments, R is optionally substituted $C_{6-30}$ aryl. In some embodiments, R is optionally substituted phenyl. In some embodiments, R is phenyl. In some embodiments, R is substituted phenyl.

In some embodiments, R is an optionally substituted 8-10 membered bicyclic saturated, partially unsaturated or aryl ring. In some embodiments, R is an optionally substituted 8-10 membered bicyclic saturated ring. In some embodiments, R is an optionally substituted 8-10 membered bicyclic partially unsaturated ring. In some embodiments, R is an optionally substituted 8-10 membered bicyclic aryl ring. In some embodiments, R is optionally substituted naphthyl.

In some embodiments, R is optionally substituted 5-30 membered heteroaryl ring having 1-10 heteroatoms independently selected from oxygen, nitrogen, sulfur, phosphorus and silicon. In some embodiments, R is optionally substituted 5-30 membered heteroaryl ring having 1-10 heteroatoms independently selected from oxygen, nitrogen, and sulfur. In some embodiments, R is optionally substituted 5-30 membered heteroaryl ring having 1-5 heteroatoms independently selected from oxygen, nitrogen, sulfur, phosphorus and silicon. In some embodiments, R is optionally substituted 5-30 membered heteroaryl ring having 1-5 heteroatoms independently selected from oxygen, nitrogen, and sulfur.

In some embodiments, R is an optionally substituted 5-6 membered monocyclic heteroaryl ring having 1-4 heteroatoms independently selected from nitrogen, oxygen, and sulfur. In some embodiments, R is a substituted 5-6 membered monocyclic heteroaryl ring having 1-4 heteroatoms independently selected from nitrogen, oxygen, and sulfur. In some embodiments, R is an unsubstituted 5-6 membered monocyclic heteroaryl ring having 1-4 heteroatoms independently selected from nitrogen, oxygen, and sulfur. In some embodiments, R is an optionally substituted 5-6 membered monocyclic heteroaryl ring having 1-3 heteroatoms independently selected from nitrogen, sulfur, and oxygen. In some embodiments, R is a substituted 5-6 membered monocyclic heteroaryl ring having 1-3 heteroatoms independently selected from nitrogen, oxygen, and sulfur. In some embodiments, R is an unsubstituted 5-6 membered monocyclic heteroaryl ring having 1-3 heteroatoms independently selected from nitrogen, sulfur, and oxygen.

In some embodiments, R is an optionally substituted 5-membered monocyclic heteroaryl ring having 1-4 heteroatoms independently selected from nitrogen, oxygen or sulfur. In some embodiments, R is an optionally substituted 6-membered monocyclic heteroaryl ring having 1-4 heteroatoms independently selected from nitrogen, oxygen, and sulfur.

In some embodiments, R is an optionally substituted 5-membered monocyclic heteroaryl ring having one heteroatom selected from nitrogen, oxygen, and sulfur. In some embodiments, R is selected from optionally substituted pyrrolyl, furanyl, or thienyl.

In some embodiments, R is an optionally substituted 5-membered heteroaryl ring having two heteroatoms independently selected from nitrogen, oxygen, and sulfur. In certain embodiments, R is an optionally substituted 5-membered heteroaryl ring having one nitrogen atom, and an additional heteroatom selected from sulfur or oxygen. Example R groups include but are not limited to optionally substituted pyrazolyl, imidazolyl, thiazolyl, isothiazolyl, oxazolyl or isoxazolyl.

In some embodiments, R is an optionally substituted 5-membered heteroaryl ring having three heteroatoms independently selected from nitrogen, oxygen, and sulfur. Example R groups include but are not limited to optionally substituted triazolyl, oxadiazolyl or thiadiazolyl.

In some embodiments, R is an optionally substituted 5-membered heteroaryl ring having four heteroatoms independently selected from nitrogen, oxygen, and sulfur. Example R groups include but are not limited to optionally substituted tetrazolyl, oxatriazolyl and thiatriazolyl.

In some embodiments, R is an optionally substituted 6-membered heteroaryl ring having 1-4 nitrogen atoms. In some embodiments, R is an optionally substituted 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having four nitrogen atoms. In some embodiments, R is an optionally substituted 6-membered heteroaryl ring having three nitrogen atoms. In some embodiments, R is an optionally substituted 6-membered heteroaryl ring having two nitrogen atoms. In certain embodiments, R is an optionally substituted 6-membered heteroaryl ring having one nitrogen atom. Example R groups include but are not limited to optionally substituted pyridinyl, pyrimidinyl, pyrazinyl, pyridazinyl, triazinyl, or tetrazinyl.

In certain embodiments, R is an optionally substituted 8-10 membered bicyclic heteroaryl ring having 1-4 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In other embodiments, R is an optionally substituted 5,6-fused heteroaryl ring having 1-2 heteroatoms independently selected from nitrogen, oxygen, and sulfur. In certain embodiments, R is an optionally substituted 5,6-fused heteroaryl ring having 1 heteroatom independently selected from nitrogen, oxygen, and sulfur. In some embodiments, R is an optionally substituted indolyl. In some embodiments, R is an optionally substituted azabicyclo[3.2.1]octanyl. In certain embodiments, R is an optionally substituted 5,6-fused heteroaryl ring having 2 heteroatoms independently selected from nitrogen, oxygen, and sulfur. In some embodiments, R is an optionally substituted azaindolyl. In some embodiments, R is an optionally substituted benzimidazolyl. In some embodiments, R is an optionally substituted benzothiazolyl. In some embodiments, R is an optionally substituted benzoxazolyl. In some embodiments, R is an optionally substituted indazolyl. In certain embodiments, R is an optionally substituted 5,6-fused heteroaryl ring having 3 heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In some embodiments, R is an optionally substituted 5,6-fused heteroaryl ring having 1-3 heteroatoms independently selected from nitrogen, oxygen, and sulfur. In some embodiments, R is an optionally substituted 5,6-fused heteroaryl ring having two heteroatoms independently selected from nitrogen, oxygen, and sulfur. In some embodiments, R is an optionally substituted 5,6-fused heteroaryl ring having three heteroatoms independently selected from nitrogen, oxygen, and sulfur. In some embodiments, R is an optionally substituted 5,6-fused heteroaryl ring having four heteroatoms independently selected from nitrogen, oxygen, and sulfur. In some embodiments, R is an optionally substituted 5,6-fused heteroaryl ring having five heteroatoms independently selected from nitrogen, oxygen, and sulfur.

In certain embodiments, R is an optionally substituted 5,6-fused heteroaryl ring having one heteroatom independently selected from nitrogen, oxygen, and sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen, and sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen, and sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen, and sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen, and sulfur.

In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl.

In certain embodiments, R is an optionally substituted 6,6-fused heteroaryl ring having 1-4 heteroatoms independently selected from nitrogen, oxygen, and sulfur. In some embodiments, R is an optionally substituted 6,6-fused heteroaryl ring having 1-2 heteroatoms independently selected from nitrogen, oxygen, and sulfur. In other embodiments, R is an optionally substituted 6,6-fused heteroaryl ring having 1 heteroatom independently selected from nitrogen, oxygen, and sulfur. In some embodiments, R is an optionally substituted quinolinyl. In some embodiments, R is an optionally substituted isoquinolinyl. In some embodiments, R is an optionally substituted 6,6-fused heteroaryl ring having 2 heteroatoms independently selected from nitrogen, oxygen, and sulfur. In some embodiments, R is optionally substituted quinazoline or a quinoxaline.

In some embodiments, R is 3-30 membered heterocyclic ring having 1-10 heteroatoms independently selected from oxygen, nitrogen, sulfur, phosphorus and silicon. In some embodiments, R is 3-30 membered heterocyclic ring having 1-10 heteroatoms independently selected from oxygen, nitrogen, and sulfur. In some embodiments, R is 3-30 membered heterocyclic ring having 1-5 heteroatoms independently selected from oxygen, nitrogen, sulfur, phosphorus and silicon. In some embodiments, R is 3-30 membered heterocyclic ring having 1-5 heteroatoms independently selected from oxygen, nitrogen, and sulfur.

In some embodiments, R is an optionally substituted 3-7 membered saturated or partially unsaturated heterocyclic ring having 1-3 heteroatoms independently selected from nitrogen, oxygen, and sulfur. In some embodiments, R is a substituted 3-7 membered saturated or partially unsaturated heterocyclic ring having 1-3 heteroatoms independently selected from nitrogen, oxygen, and sulfur. In some embodiments, R is an unsubstituted 3-7 membered saturated or partially unsaturated heterocyclic ring having 1-3 heteroatoms independently selected from nitrogen, oxygen, and sulfur. In certain embodiments, R is an optionally substituted 5-7 membered partially unsaturated monocyclic ring having 1-3 heteroatoms independently selected from nitrogen, oxygen, and sulfur. In certain embodiments, R is an optionally substituted 5-6 membered partially unsaturated monocyclic ring having 1-3 heteroatoms independently selected from nitrogen, oxygen, and sulfur. In certain embodiments, R is an optionally substituted 5-membered partially unsaturated monocyclic ring having 1-3 heteroatoms independently selected from nitrogen, oxygen, and sulfur. In certain embodiments, R is an optionally substituted 6-membered partially unsaturated monocyclic ring having 1-3 heteroatoms independently selected from nitrogen, oxygen, and sulfur. In certain embodiments, R is an optionally substituted 7-membered partially unsaturated monocyclic ring having 1-3 heteroatoms independently selected from nitrogen, oxygen, and sulfur. In some embodiments, R is optionally substituted 3-membered heterocyclic ring having one heteroatom selected from nitrogen, oxygen or sulfur. In some embodiments, R is optionally substituted 4-membered heterocyclic ring having 1-3 heteroatoms independently selected from nitrogen, oxygen, and sulfur. In some embodiments, R is optionally substituted 5-membered heterocyclic ring having 1-3 heteroatoms independently selected from nitrogen, oxygen, and sulfur. In some embodiments, R is optionally substituted 6-membered heterocyclic ring having 1-3 heteroatoms independently selected from nitrogen, oxygen, and sulfur. In some embodiments, R is optionally substituted 7-membered heterocyclic ring having 1-3 heteroatoms independently selected from nitrogen, oxygen, and sulfur.

In some embodiments, R is an optionally substituted 3-membered saturated or partially unsaturated heterocyclic ring having 1-2 heteroatoms independently selected from nitrogen, oxygen, and sulfur. In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 5-membered saturated or partially unsaturated heterocyclic ring having 1-2 heteroatoms independently selected from nitrogen, oxygen, and sulfur. In some embodiments, R is an optionally substituted 6-membered saturated or partially unsaturated heterocyclic ring having 1-2 heteroatoms independently selected from nitrogen, oxygen, and sulfur. In some embodiments, R is an optionally substituted 7-membered saturated or partially unsaturated heterocyclic ring having 1-2 heteroatoms independently selected from nitrogen, oxygen, and sulfur.

In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 4-membered partially unsaturated heterocyclic ring having 2 heteroatoms independently selected from nitrogen, oxygen, and sulfur. In some embodiments, R is an optionally substituted 4-membered partially unsaturated heterocyclic ring having no more than 1 heteroatom. In some embodiments, R is an optionally substituted 4-membered partially unsaturated heterocyclic ring having no more than 1 heteroatom, wherein the heteroatom is nitrogen. In some embodiments, R is an optionally substituted 4-membered partially unsaturated heterocyclic ring having no more than 1 heteroatom, wherein the heteroatom is oxygen. In some embodiments, R is an optionally substituted 4-membered partially unsaturated heterocyclic ring having no more than 1 heteroatom, wherein the heteroatom is sulfur. In some embodiments, R is an optionally substituted 4-membered partially unsaturated heterocyclic ring having 2 oxygen atoms. In some embodiments, R is an optionally substituted 4-membered partially unsaturated heterocyclic ring having 2 nitrogen atoms. In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 4-membered partially unsaturated heterocyclic ring having 2 heteroatoms independently selected from nitrogen, oxygen, and sulfur. In some embodiments, R is an optionally substituted 4-membered partially unsaturated heterocyclic ring having no more than 1 heteroatom. In some embodiments, R is an optionally substituted 4-membered partially unsaturated heterocyclic ring having no more than 1 heteroatom, wherein the heteroatom is nitrogen. In some embodiments, R is an optionally substituted 4-membered partially unsaturated heterocyclic ring having no more than 1 heteroatom, wherein the heteroatom is oxygen. In some embodiments, R is an optionally substituted 4-membered partially unsaturated heterocyclic ring having no more than 1 heteroatom, wherein the heteroatom is sulfur. In some embodiments, R is an optionally substituted 4-membered partially unsaturated heterocyclic ring having 2 oxygen atoms. In some embodiments, R is an optionally substituted 4-membered partially unsaturated heterocyclic ring having 2 nitrogen atoms.

In some embodiments, R is an optionally substituted 5-membered saturated or partially unsaturated heterocyclic ring having 1-2 heteroatoms independently selected from nitrogen, oxygen, and sulfur. In some embodiments, R is an optionally substituted 5-membered partially unsaturated heterocyclic ring having 2 heteroatoms independently selected from nitrogen, oxygen, and sulfur. In some embodiments, R is an optionally substituted 5-membered partially unsaturated heterocyclic ring having no more than 1 heteroatom. In some embodiments, R is an optionally substituted 5-membered partially unsaturated heterocyclic ring having no more than 1 heteroatom, wherein the heteroatom is nitrogen. In some embodiments, R is an optionally substituted 5-membered partially unsaturated heterocyclic ring having no more than 1 heteroatom, wherein the heteroatom is oxygen. In some embodiments, R is an optionally substituted 5-membered partially unsaturated heterocyclic ring having no more than 1 heteroatom, wherein the heteroatom is sulfur. In some embodiments, R is an optionally substituted 5-membered partially unsaturated heterocyclic ring having 2 oxygen atoms. In some embodiments, R is an optionally substituted 5-membered partially unsaturated heterocyclic ring having 2 nitrogen atoms.

In some embodiments, R is an optionally substituted 6-membered saturated or partially unsaturated heterocyclic ring having 1-2 heteroatoms independently selected from nitrogen, oxygen, and sulfur. In some embodiments, R is an optionally substituted 6-membered partially unsaturated heterocyclic ring having 2 heteroatoms independently selected from nitrogen, oxygen, and sulfur. In some embodiments, R is an optionally substituted 6-membered partially unsaturated heterocyclic ring having no more than 1 heteroatom. In some embodiments, R is an optionally substituted 6-membered partially unsaturated heterocyclic ring having no more than 1 heteroatom, wherein the heteroatom is nitrogen. In some embodiments, R is an optionally substituted 6-membered partially unsaturated heterocyclic ring having no more than 1 heteroatom, wherein the heteroatom is oxygen. In some embodiments, R is an optionally substituted 6-membered partially unsaturated heterocyclic ring having no more than 1 heteroatom, wherein the heteroatom is sulfur. In some embodiments, R is an optionally substituted 6-membered partially unsaturated heterocyclic ring having 2 oxygen atoms. In some embodiments, R is an optionally substituted 6-membered partially unsaturated heterocyclic ring having 2 nitrogen atoms.

In certain embodiments, R is a 3-7 membered saturated or partially unsaturated heterocyclic ring having 1-2 heteroatoms independently selected from nitrogen, oxygen, and sulfur. In certain embodiments, R is optionally substituted oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl.

In certain embodiments, R is an optionally substituted 5-6 membered partially unsaturated monocyclic ring having 1-2 heteroatoms independently selected from nitrogen, oxygen, and sulfur. In certain embodiments, R is an optionally substituted tetrahydropyridinyl, dihydrothiazolyl, dihydrooxazolyl, or oxazolinyl group.

In some embodiments, R is an optionally substituted 7-10 membered bicyclic saturated or partially unsaturated heterocyclic ring having 1-5 heteroatoms independently selected from nitrogen, oxygen, and sulfur. In some embodiments, R is optionally substituted indolinyl. In some embodiments, R is optionally substituted isoindolinyl. In some embodiments, R is optionally substituted 1, 2, 3, 4-tetrahydroquinolinyl. In some embodiments, R is optionally substituted 1, 2, 3, 4-tetrahydroisoquinolinyl. In some embodiments, R is an optionally substituted azabicyclo[3.2.1]octanyl.

In some embodiments, R is an optionally substituted 8-10 membered bicyclic heteroaryl ring having 1-5 heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In some embodiments, R is an optionally substituted 5,6-fused heteroaryl ring having 1-3 heteroatoms independently selected from nitrogen, oxygen, and sulfur. In some embodiments, R is an optionally substituted 5,6-fused heteroaryl ring having two heteroatoms independently selected from nitrogen, oxygen, and sulfur. In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is an optionally substituted 5,6-fused heteroaryl ring having three heteroatoms independently selected from nitrogen, oxygen, and sulfur. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, R is an optionally substituted 5,6-fused heteroaryl ring having four heteroatoms independently selected from nitrogen, oxygen, and sulfur. In some embodiments, R is an optionally substituted 5,6-fused heteroaryl ring having five heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In other embodiments, R is an optionally substituted 5,6-fused heteroaryl ring having 1-2 heteroatoms independently selected from nitrogen, oxygen, and sulfur. In certain embodiments, R is an optionally substituted 5,6-fused heteroaryl ring having one heteroatom independently selected from nitrogen, oxygen, and sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen, and sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen, and sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen, and sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen, and sulfur.

In certain embodiments, R is an optionally substituted 6,6-fused heteroaryl ring having 1-5 heteroatoms independently selected from nitrogen, oxygen, and sulfur. In some embodiments, R is an optionally substituted 6,6-fused heteroaryl ring having 1-2 heteroatoms independently selected from nitrogen, oxygen, and sulfur. In other embodiments, R is an optionally substituted 6,6-fused heteroaryl ring having one heteroatom selected from nitrogen, oxygen, and sulfur. In some embodiments, R is optionally substituted quinolinyl. In some embodiments, R is optionally substituted isoquinolinyl. In some embodiments, R is an optionally substituted 6,6-fused heteroaryl ring having two heteroatoms independently selected from nitrogen, oxygen, and sulfur. In some embodiments, R is optionally substituted quinazolinyl, phthalazinyl, quinoxalinyl or naphthyridinyl. In some embodiments, R is an optionally substituted 6,6-fused heteroaryl ring having three heteroatoms independently selected from nitrogen, oxygen, and sulfur. In some embodiments, R is optionally substituted pyridopyrimidinyl, pyridopyridazinyl, pyridopyrazinyl, or benzotriazinyl. In some embodiments, R is an optionally substituted 6,6-fused heteroaryl ring having four heteroatoms independently selected from nitrogen, oxygen, and sulfur. In some embodiments, R is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, R is an optionally substituted 6,6-fused heteroaryl ring having five heteroatoms independently selected from nitrogen, oxygen, and sulfur.

In some embodiments, R is optionally substituted $C_{6-30}$ arylaliphatic. In some embodiments, R is optionally substituted $C_{6-20}$ arylaliphatic. In some embodiments, R is optionally substituted $C_{6-10}$ arylaliphatic. In some embodiments, an aryl moiety of the arylaliphatic has 6, 10, or 14 aryl carbon atoms. In some embodiments, an aryl moiety of the arylaliphatic has 6 aryl carbon atoms. In some embodiments, an aryl moiety of the arylaliphatic has 10 aryl carbon atoms. In some embodiments, an aryl moiety of the arylaliphatic has 14 aryl carbon atoms. In some embodiments, an aryl moiety is optionally substituted phenyl.

In some embodiments, R is optionally substituted $C_{6-30}$ arylheteroaliphatic having 1-10 heteroatoms independently selected from oxygen, nitrogen, sulfur, phosphorus and silicon. In some embodiments, R is optionally substituted $C_{6-30}$ arylheteroaliphatic having 1-10 heteroatoms independently selected from oxygen, nitrogen, and sulfur. In some embodiments, R is optionally substituted $C_{6-20}$ arylheteroaliphatic having 1-10 heteroatoms independently selected from oxygen, nitrogen, sulfur, phosphorus and silicon. In some embodiments, R is optionally substituted $C_{6-20}$ arylheteroaliphatic having 1-10 heteroatoms independently selected from oxygen, nitrogen, and sulfur. In some embodiments, R is optionally substituted $C_{6-10}$ arylheteroaliphatic having 1-5 heteroatoms independently selected from oxygen, nitrogen, sulfur, phosphorus and silicon. In some embodiments, R is optionally substituted $C_{6-10}$ arylheteroaliphatic having 1-5 heteroatoms independently selected from oxygen, nitrogen, and sulfur.

In some embodiments, two R groups are optionally and independently taken together to form a covalent bond. In some embodiments, —C≡O is formed. In some embodiments, —C≡C— is formed. In some embodiments, —C≡C— is formed.

In some embodiments, two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon. In some embodiments, two or more R groups on the same atom are optionally and independently taken together with the atom to form an optionally substituted, 3-20 membered monocyclic, bicyclic or polycyclic ring having, in addition to the atom, 0-10 heteroatoms independently selected from oxygen, nitrogen, sulfur, phosphorus and silicon. In some embodiments, two or more R groups on the same atom are optionally and independently taken together with the atom to form an optionally substituted, 3-10 membered monocyclic, bicyclic or polycyclic ring having, in addition to the atom, 0-5 heteroatoms independently selected from oxygen, nitrogen, sulfur, phosphorus and silicon. In some embodiments, two or more R groups on the same atom are optionally and independently taken together with the atom to form an optionally substituted, 3-6 membered monocyclic, bicyclic or polycyclic ring having, in addition to the atom, 0-3 heteroatoms independently selected from oxygen, nitrogen, sulfur, phosphorus and silicon. In some embodiments, two or more R groups on the same atom are optionally and independently taken together with the atom to form an optionally substituted, 3-5 membered monocyclic, bicyclic or polycyclic ring having, in addition to the atom, 0-3 heteroatoms independently selected from oxygen, nitrogen, sulfur, phosphorus and silicon.

In some embodiments, two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-20 membered monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-10 membered monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-10 membered monocyclic, bicyclic or polycyclic ring having, in addition to the intervening atoms, 0-5 heteroatoms independently selected from oxygen, nitrogen, sulfur, phosphorus and silicon. In some embodiments, two or more R groups on two or more atoms are optionally and independently taken together with their intervening atoms to form an optionally substituted, 3-6 membered monocyclic, bicyclic or polycyclic ring having, in addition to the intervening atoms, 0-3 heteroatoms independently selected from oxygen, nitrogen, sulfur, phosphorus and silicon. In some embodiments, two or more R groups on two or more atoms are optionally and independently taken together with their intervening atoms to form an optionally substituted, 3-5 membered monocyclic, bicyclic or polycyclic ring having, in addition to the intervening atoms, 0-3 heteroatoms independently selected from oxygen, nitrogen, sulfur, phosphorus and silicon.

In some embodiments, heteroatoms in R groups, or in the structures formed by two or more R groups taken together, are selected from oxygen, nitrogen, and sulfur. In some embodiments, a formed ring is 3, 4, 5, 6, 7, 8, 9, 10, 11, 12, 13, 14, 15, 16, 17, 18, 19, or 20-membered. In some embodiments, a formed ring is saturated. In some embodiments, a formed ring is partially saturated. In some embodiments, a formed ring is aromatic. In some embodiments, a formed ring comprises a saturated, partially saturated, or aromatic ring moiety. In some embodiments, a formed ring comprises 5, 6, 7, 8, 9, 10, 11, 12, 13, 14, 15, 16, 17, 18, 19, or 20 aromatic ring atoms. In some embodiments, a formed contains no more than 5, 6, 7, 8, 9, 10, 11, 12, 13, 14, 15, 16, 17, 18, 19, or 20 aromatic ring atoms. In some embodiments, aromatic ring atoms are selected from carbon, nitrogen, oxygen and sulfur.

In some embodiments, a ring formed by two or more R groups (or two or more groups selected from R and variables that can be R) taken together is a $C_{3-30}$ cycloaliphatic, $C_{6-30}$ aryl, 5-30 membered heteroaryl having 1-10 heteroatoms independently selected from oxygen, nitrogen, sulfur, phosphorus and silicon, or 3-30 membered heterocyclyl having 1-10 heteroatoms independently selected from oxygen, nitrogen, sulfur, phosphorus and silicon, ring as described for R, but bivalent or multivalent.

In some embodiments, $P^L$ is P(=W). In some embodiments, $P^L$ is P. In some embodiments, $P^L$ is $P \rightarrow B(R')_3$. In some embodiments, P of $P^L$ is chiral. In some embodiments, P of $P^L$ is Rp. In some embodiments, P of $P^L$ is Sp. In some embodiments, a linkage of formula VII is a phosphate linkage or a salt form thereof. In some embodiments, a linkage of formula VII is a phosphorothioate linkage or a salt form thereof.

In some embodiments, $L^7$ is —O— or —S—. In some embodiments, $L^7$ is —O—. In some embodiments, $L^7$ is —S—. In some embodiments, $-L^7-R^1$ is $—O—CH_2R^2$, wherein $R^2$ is as described herein and $—CH_2—$ is optionally substituted. In some embodiments, $—CH_2—$ is unsubstituted or substituted with no more than one substituent. In some embodiments, $-L^7-R^1$ is $—O—CH_2R^2$. In some embodiments, $R^2$ is of such a structure (e.g., comprising an electron-withdrawing group) that $—O-L^7-R^1$ is base labile. In some embodiments, $-L^7-R^1$ is $—O—CH_2CH$ (electron-withdrawing group)$_2$, wherein an electron-withdrawing group is as described herein. In some embodiments, $-L^7-R^1$ is $—O—CH_2CH_2$-electron-withdrawing group, wherein an electron-withdrawing group is as described herein. In some embodiments, $-L^7-R^1$ is $—O—CH_2CH_2—CN$.

In some embodiments, $L^8$ is -L-O—, $-L-C(R^1)(R^2)—O—$, or $-L^s-O—$, wherein each variable is independently as described in the present disclosure. In some embodiments, $L^8$ is -L-O, wherein L is as described in the present disclosure. In some embodiments, $L^8$ is $-L-C(R^1)(R^2)—O—$, wherein each variable is independently as described in the present disclosure. In some embodiments, $L^8$ is $-L^s-O—$, wherein $L^s$ is as described in the present disclosure.

In some embodiments, provided compounds, e.g., compounds of formula I, I-a, I-a-1, I-a-2, I-b, I-c, I-d, I-e, II, II-a, II-b, III, III-a, or III-b, or salts thereof, may be utilized to prepare other compounds which incorporate their chiral elements. In some embodiments, provided compounds of formula I, I-a, I-a-1, I-a-2, I-b, I-c, I-d, I-e, II, II-a, II-b, III, III-a, or III-b, or salts thereof, are incorporated into other compounds, e.g., compounds of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or salts thereof, as chiral auxiliaries so that such other compounds can be further utilized for stereoselective synthesis of, e.g., oligonucleotides (e.g., of formula O-I) comprising internucleotidic linkages having the structure of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof. In some embodiments, provided compounds, e.g., compounds of formula N, I-a, I-a-1, I-a-2, I-b, I-c, I-d, I-e, II, II-a, II-b, III, III-a, or III-b, or salts thereof, optionally activated, react with nucleosides or derivatives thereof to provide phosphoramidites for oligonucleotide preparation. In some embodiments, provided phosphoramidites have the structure of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or salts thereof. In some embodiments, provided phosphoramidites have the structure of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or salts thereof. In some embodiments, provided compounds, e.g., phosphoramidites of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or salts thereof have purities, diastereopurities, and/or enantiopurities as described in the present disclosure. In some embodiments, provided compounds, e.g., phosphoramidites of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or salts thereof have purities, diastereopurities, and/or enantiopurities as described in the present disclosure.

In some embodiments, BA is an optionally substituted group selected from $C_{3-30}$ cycloaliphatic, $C_{6-30}$ aryl, $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus and silicon, a natural nucleobase moiety, and a modified nucleobase moiety. In some embodiments, BA is an optionally substituted group selected from $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus and silicon, a natural nucleobase moiety, and a modified nucleobase moiety. In some embodiments, BA is an optionally substituted group selected from $C_{5-30}$ heteroaryl having 1-10 heteroatoms independently selected from oxygen, nitrogen, sulfur, phosphorus and silicon, a natural nucleobase moiety, and a modified nucleobase moiety. In some embodiments, BA is optionally substituted $C_{5-30}$ heteroaryl having 1-10 heteroatoms independently selected from oxygen, nitrogen, and sulfur. In some embodiments, BA is optionally substituted natural nucleobases and tautomers thereof. In some embodiments, BA is protected natural nucleobases and tautomers thereof. Various nucleobase protecting groups for oligonucleotide synthesis are known and can be utilized in accordance with the present disclosure. In some embodiments, BA is an optionally substituted nucleobase selected from adenine, cytosine, guanosine, thymine, and uracil, and tautomers thereof. In some embodiments, BA is an optionally protected nucleobase selected from adenine, cytosine, guanosine, thymine, and uracil, and tautomers thereof.

In some embodiments, BA is optionally substituted $C_{3-30}$ cycloaliphatic. In some embodiments, BA is optionally substituted $C_{6-30}$ aryl. In some embodiments, BA is optionally substituted $C_{3-30}$ heterocyclyl. In some embodiments, BA is optionally substituted $C_{5-30}$ heteroaryl. In some embodiments, BA is an optionally substituted natural base moiety. In some embodiments, BA is an optionally substituted modified base moiety. BA is an optionally substituted group selected from $C_{3-30}$ cycloaliphatic, $C_{6-30}$ aryl. $C_{3-30}$ heterocyclyl, and $C_{5-30}$ heteroaryl. In some embodiments, BA is an optionally substituted group selected from $C_{3-30}$ cycloaliphatic, $C_{6-30}$ aryl, $C_{3-30}$ heterocyclyl, $C_{5-30}$ heteroaryl, and a natural nucleobase moiety.

In some embodiments, BA is connected to SU through an aromatic ring. In some embodiments, BA is connected to SU through a heteroatom. In some embodiments, BA is connected to SU through a ring heteroatom of an aromatic ring. In some embodiments, BA is connected to SU through a ring nitrogen atom of an aromatic ring.

In some embodiments, BA is a natural nucleobase moiety. In some embodiments, BA is an optionally substituted natural nucleobase moiety. In some embodiments, BA is a substituted natural nucleobase moiety. In some embodiments, BA is natural nucleobase A, T, C, U, or G. In some embodiments, BA is an optionally substituted group selected from natural nucleobases A, T, C, U, and G.

In some embodiments, BA is an optionally substituted group, which group is formed by removing a —H from

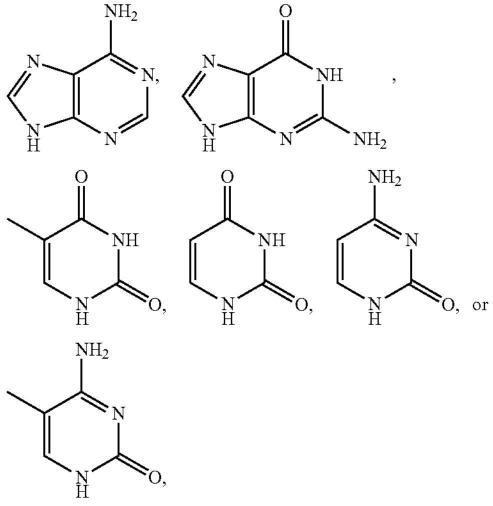

or H or a tautomer thereof. In some embodiments, BA is an optionally substituted group, which group is formed by removing a —H from

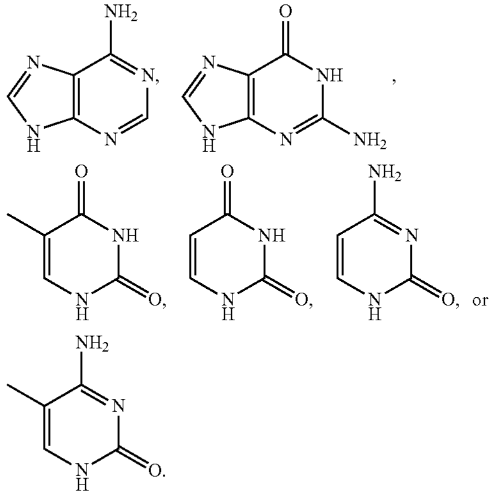

In some embodiments, BA is an optionally substituted group which group is selected from

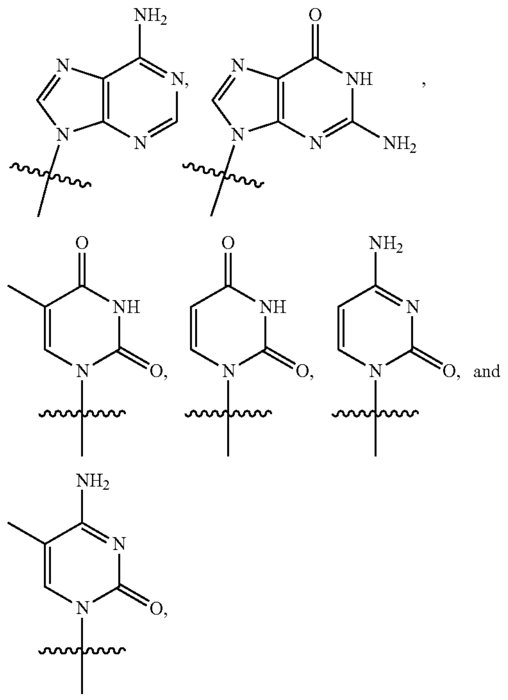

and tautomeric forms thereof. In some embodiments, BA is an optionally substituted group which group is selected from

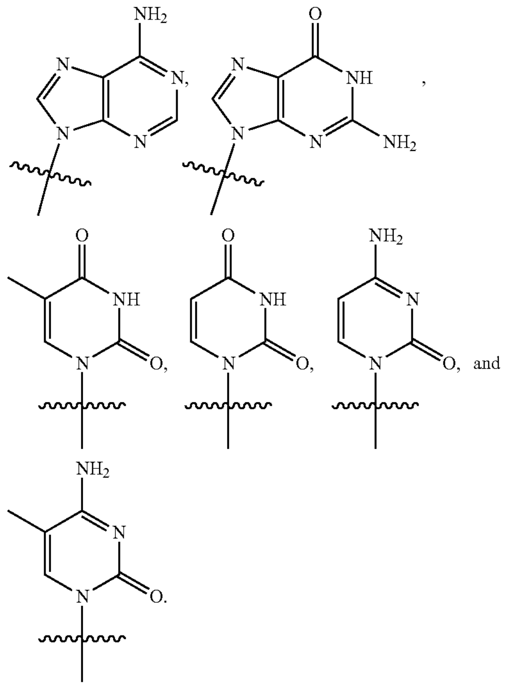

In some embodiments, BA is an optionally substituted group, which group is formed by removing a —H from

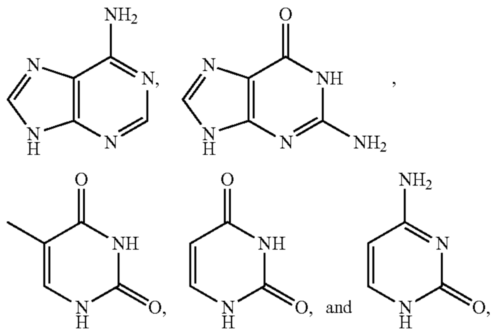

and tautomers thereof. In some embodiments, BA is an optionally substituted group, which group is formed by removing a —H from

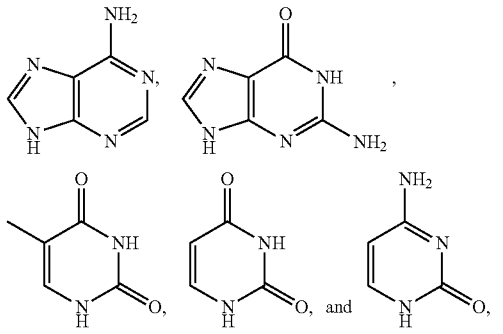

In some embodiments, BA is an optionally substituted group which group is selected from

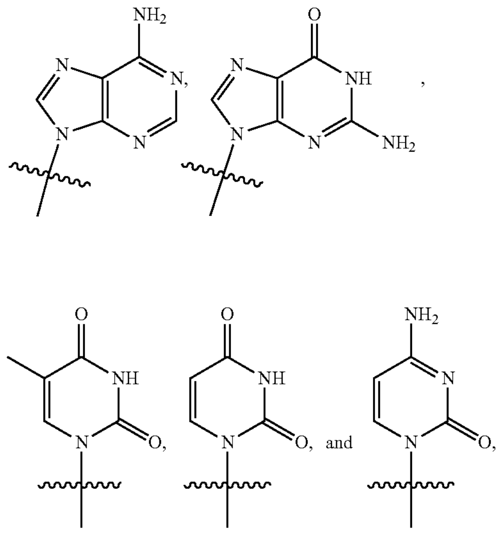

and tautomeric forms thereof. In some embodiments, BA is an optionally substituted group which group is selected from

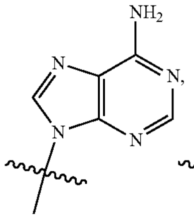
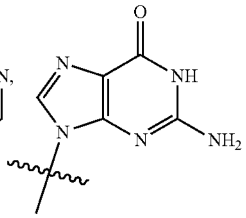
,

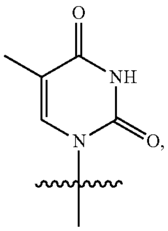
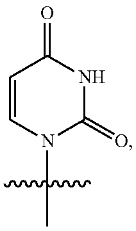
and
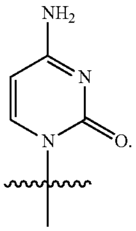

In some embodiments, BA is optionally substituted

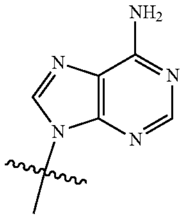 [SMILES: *n1cnc2c(N)ncnc21]

or a tautomeric form thereof. In some embodiments, BA is optionally substituted

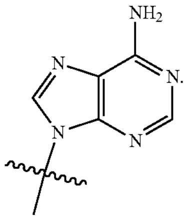 [SMILES: *n1cnc2c(N)ncnc21]

In some embodiments, BA is optionally substituted

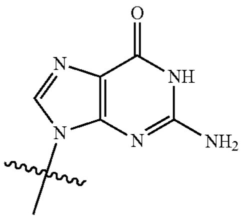 [SMILES: *n1cnc2c(=O)[nH]c(N)nc21]

or a tautomeric form thereof. In some embodiments, BA is optionally substituted

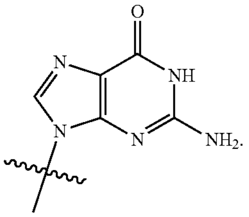 [SMILES: *n1cnc2c(=O)[nH]c(N)nc21]

In some embodiments, BA is optionally substituted

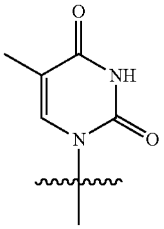 [SMILES: *n1cc(C)c(=O)[nH]c1=O]

or a tautomeric form thereof. In some embodiments, BA is optionally substituted

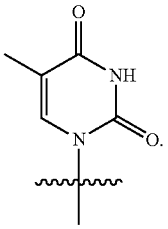 [SMILES: *n1cc(C)c(=O)[nH]c1=O]

In some embodiments, BA is optionally substituted

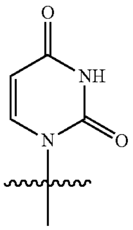 [SMILES: *n1ccc(=O)[nH]c1=O]

or a tautomeric form thereof. In some embodiments, BA is optionally substituted

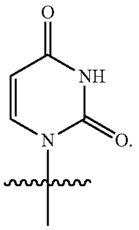 [SMILES: *n1ccc(=O)[nH]c1=O]

In some embodiments, BA is optionally substituted

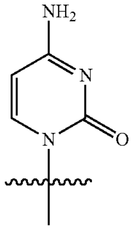 [SMILES: *n1ccc(N)nc1=O]

or a tautomeric form thereof. In some embodiments, BA is optionally substituted

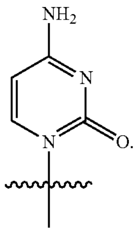

In some embodiments, BA is

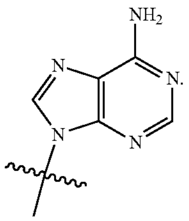

In some embodiments, BA is

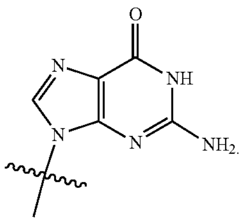

In some embodiments, BA is

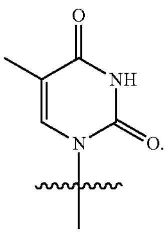 [SMILES: *n1cc(C)c(=O)[nH]c1=O]

In some embodiments, BA is

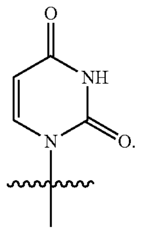 [SMILES: *n1ccc(=O)[nH]c1=O]

In some embodiments, BA is

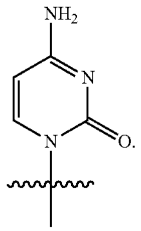 [SMILES: *n1ccc(N)nc1=O]

In some embodiments, BA of the 5'-end nucleoside unit of a provided oligonucleotide, e.g., an oligonucleotide of formula O-I, is an optionally substituted group, which group is formed by removing a —H from

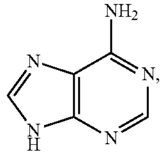,
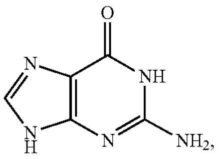,

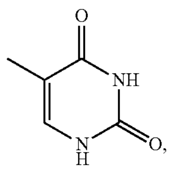,
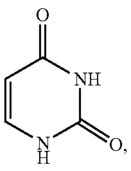,
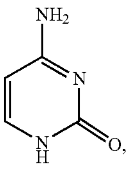, and

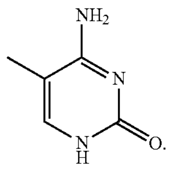

In some embodiments, BA of the 5'-end nucleoside unit is an optionally substituted group which group is selected from

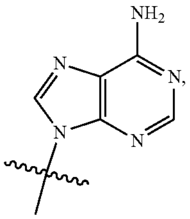
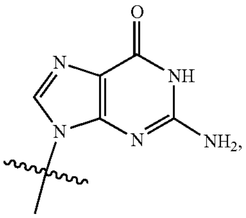

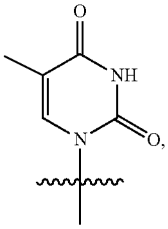
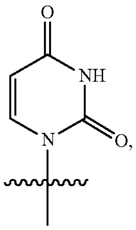

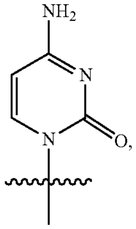 and 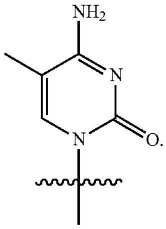

In some embodiments, BA of the 5'-end nucleoside unit is an optionally substituted group, which group is formed by removing a —H from

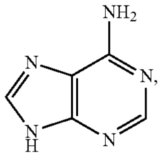
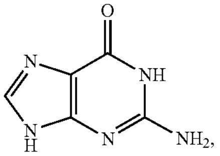

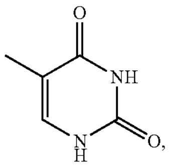
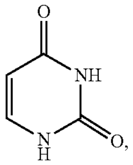 and 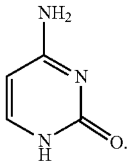

In some embodiments, BA of the 5'-end nucleoside unit is an optionally substituted group which group is selected from

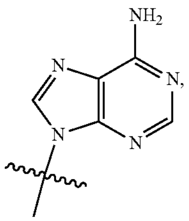

-continued

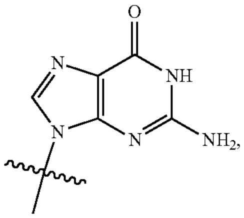

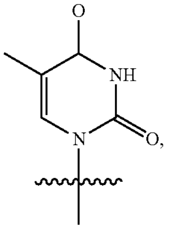

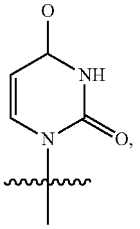 and

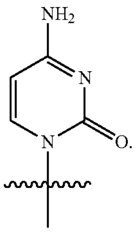

In some embodiments, BA of the 5'-end nucleoside unit is optionally substituted

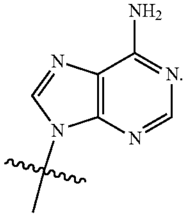

In some embodiments, BA of the 5'-end nucleoside unit is optionally substituted

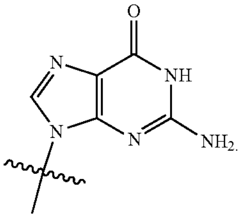

In some embodiments, BA of the 5'-end nucleoside unit is optionally substituted

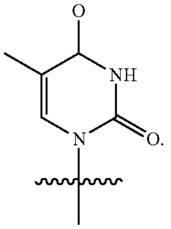 [SMILES: *N1C=C(C)C(O)NC1=O]

In some embodiments, BA of the 5'-end nucleoside unit is optionally substitute

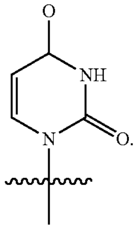 [SMILES: *N1C=CC(O)NC1=O]

In some embodiments, BA of the 5'-end nucleoside unit is optionally substituted

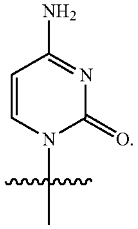 [SMILES: *n1ccc(N)nc1=O]

In some embodiments, BA of the 5'-end nucleoside unit is

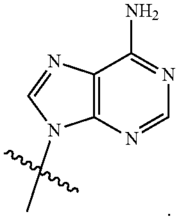 [SMILES: *n1cnc2c(N)ncnc21]

.

In some embodiments, BA of the 5'-end nucleoside unit is

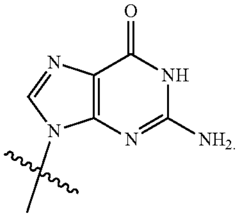 [SMILES: *n1cnc2c(=O)[nH]c(N)nc21]

In some embodiments, BA of the 5'-end nucleoside unit is

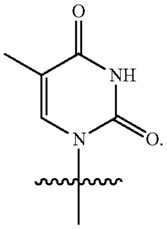 [SMILES: *n1cc(C)c(=O)[nH]c1=O]

In some embodiments, BA of the 5'-end nucleoside unit is

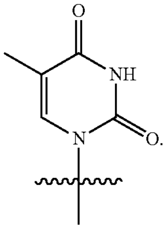 [SMILES: *n1cc(C)c(=O)[nH]c1=O]

In some embodiments, BA of the 5'-end nucleoside unit is

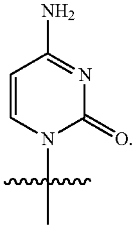 [SMILES: *n1ccc(N)nc1=O]

In some embodiments, BA is

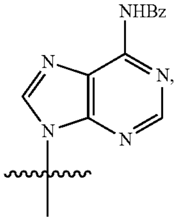

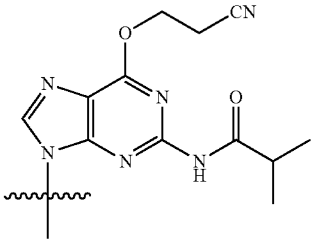

,

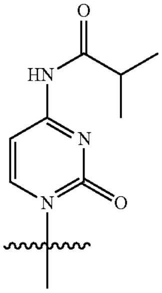

,

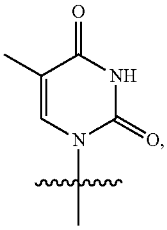

-continued
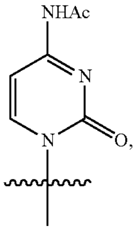, 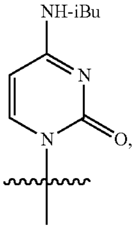, 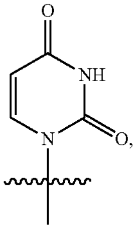, or
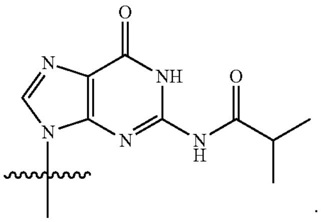.
In some embodiments, BA is
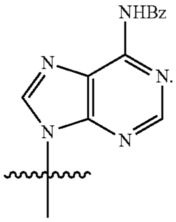.
In some embodiments, BA is
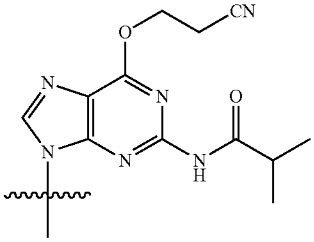 [SMILES: *n1cnc2c(OCCC#N)nc(NC(=O)C(C)C)nc21] or
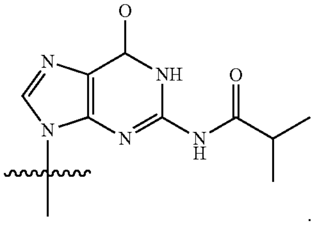 [SMILES: *n1cnc2c1N=C(NC(=O)C(C)C)NC2O].
In some embodiments, BA is
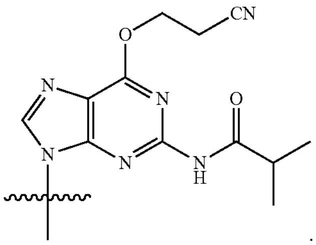.
in some embodiments, BA is
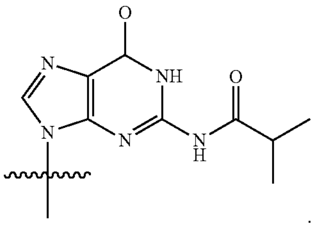.
In some embodiments, BA is
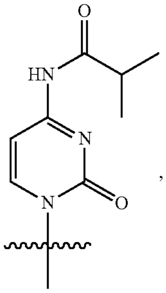 [SMILES: *n1ccc(NC(=O)C(C)C)nc1=O],
In some embodiments, BA is
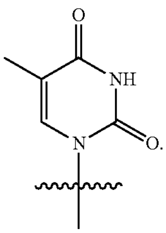 [SMILES: *n1cc(C)c(=O)[nH]c1=O].

In some embodiments, BA is

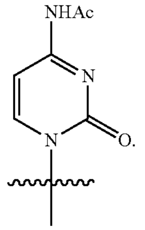 [SMILES: *n1ccc(NC(C)=O)nc1=O]

In some embodiments, BA is

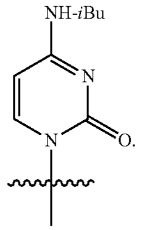

In some embodiments, BA is

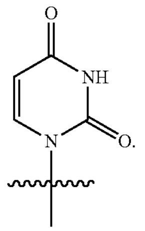 [SMILES: *n1ccc(=O)[nH]c1=O]

In some embodiments, a protection group is —Ac. In some embodiments, a protection group is -Bz. In some embodiments, a protection group is -iBu for nucleobase.

In some embodiments, BA is an optionally substituted purine base residue. In some embodiments, BA is a protected purine base residue. In some embodiments, BA is an optionally substituted adenine residue. In some embodiments, BA is a protected adenine residue. In some embodiments, BA is an optionally substituted guanine residue. In some embodiments, BA is a protected guanine residue. In some embodiments, BA is an optionally substituted cytosine residue. In some embodiments, BA is a protected cytosine residue. In some embodiments, BA is an optionally substituted thymine residue. In some embodiments, BA is a protected thymine residue. In some embodiments, BA is an optionally substituted uracil residue. In some embodiments, BA is a protected uracil residue. In some embodiments, BA is an optionally substituted 5-methylcytosine residue. In some embodiments, BA is a protected 5-methylcytosine residue.

In some embodiments, BA is a protected base residue as used in oligonucleotide preparation. In some embodiments, BA is a base residue illustrated in US 2011/0294124, US 2015/0211006, US 2015/0197540, and WO 2015/107425, each of which is incorporated herein by reference.

Those skilled in the art appreciate that a variety of modified nucleobases are suitable for use in accordance with the present disclosure in, for example, compounds of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, VI-e, or O-I, or salts thereof. Example modified bases include but are not limited to those limited in WO/2011/005761, WO/2013/012758, WO/2014/012081, WO/2015/107425, WO/2010/064146, WO/2014/010250, WO/2011/108682, WO/2012/039448, and WO/2012/073857, modified nucleobases of each of which are hereby incorporated by reference.

In some embodiments, BA is a substituted/protected nucleobase so that the phosphoramidite is properly protected with one or more protecting groups and can be used for oligonucleotide synthesis. Suitable protecting groups for nucleobases are widely known, including those useful for oligonucleotide synthesis, and can be utilized in accordance with the present disclosure. In some embodiments, a protecting group is acetyl (Ac), phenylacetyl, benzoyl (Bz), isobutyryl (iBu), phenoxyacetyl (Pac), isopropyl-Pac, tert-butyl-Pac, alkyl-Pac, dimethylformamidine (DMF), or dialkylformamidine. In some embodiments, a protecting group is phthalimido, 9-fludrenylmethoxycarbonyl (FMOC), triphenylmethylsulfenyl, t-BOC, 4,4'-dimethoxytrityl (DMTr), 4-methoxytrityl (MMTr), 9-phenylxanthin-9-yl (Pixyl), trityl (Tr), or 9-(p-methoxyphenyl)xanthin-9-yl (MOX). For additional suitable protecting groups, see Green and Wuts, Protective Groups in Organic Synthesis, 2nd Ed., John Wiley & Sons, New York, 1991, and WO/2011/005761, WO/2013/012758, WO/2014/012081, WO/2015/107425, WO/2010/064146, WO/2014/010250, WO/2011/108682, WO/2012/039448, and WO/2012/073857.

In some embodiments, SU is -$L^s$-O— or

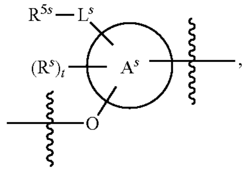

wherein SU is connected to the phosphorus atom through the oxygen atom. In some embodiments, SU is sugar moiety. In some embodiments, SU is a sugar moiety as used in oligonucleotides. In some embodiments, SU is a modified sugar moiety as used in oligonucleotides.

In some embodiments, SU is a sugar moiety or modified sugar moiety in natural or unnatural nucleosides, nucleotides, and/or oligonucleotides.

In some embodiments, SU is -$L^s$-O—, wherein SU is connected to the phosphorus atom through the oxygen atom.

In some embodiments, SU is -$L^s$-O—. In some embodiments, $L^s$ is -Cy-. In some embodiments, $L^s$ is optionally substituted 3-30 membered carbocyclylene. In some embodiments, $L^s$ is optionally substituted 6-30 membered arylene. In some embodiments, $L^s$ is optionally substituted 5-30 membered heteroarylene having 1-10 heteroatoms independently selected from oxygen, nitrogen and sulfur. In some embodiments, $L^s$ is optionally substituted 5-30 membered heteroarylene having 1-5 heteroatoms independently selected from oxygen, nitrogen and sulfur. In some embodiments, $L^s$ is optionally substituted 3-30 membered heterocyclylene having 1-10 heteroatoms independently selected from oxygen, nitrogen, sulfur, phosphorus and silicon. In some embodiments, $L^s$ is optionally substituted 3-30 membered heterocyclylene having 1-5 heteroatoms independently selected from oxygen, nitrogen, sulfur, phosphorus and silicon. In some embodiments, $L^s$ is optionally substituted 5-30 membered heterocyclylene having 1-10 heteroatoms independently selected from oxygen, nitrogen, sulfur, phosphorus and silicon. In some embodiments, $L^s$ is optionally substituted 5-30 membered heterocyclylene having 1-5 heteroatoms independently selected from oxygen, nitrogen, sulfur, phosphorus and silicon. In some embodiments, $L^s$ is optionally substituted 5-10 membered heterocyclylene having one oxygen atom. In some embodiments, $L^s$ is optionally substituted 5-membered heterocyclylene having one oxygen atom. In some embodiments, $L^s$ is optionally substituted 6-membered heterocyclylene having one oxygen atom. In some embodiments, $L^s$ is optionally substituted 5-10 membered bicyclic heterocyclylene having one or two oxygen atoms. In some embodiments, $L^s$ is optionally substituted 7-10 membered bicyclic heterocyclylene having one or two oxygen atoms. In some embodiments, $L^s$ is optionally substituted 7-10 membered bicyclic heterocyclylene having two oxygen atoms. In some embodiments, $L^s$ is optionally substituted 7-membered bicyclic heterocyclylene having two oxygen atoms.

In some embodiments, SU is a sugar moiety used in oligonucleotide synthesis. A person of ordinary skill in the art understands that phosphoramidites with a variety of sugar moieties can benefit from improved yields and/or purity when provided technologies are utilized for their preparation. In some embodiments, SU is an optionally substituted saturated monocyclic, bicyclic or polycyclic saturated aliphatic ring wherein one or more methylene units are replaced with —O—. In some embodiments, SU is a ribose or deoxyribose moiety found in natural DNA or RNA molecules.

In some embodiments, SU is

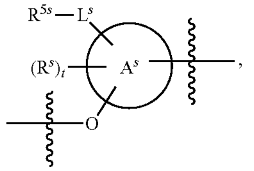

wherein each variable is independently as described in the present disclosure, and wherein SU is connected to the phosphorus atom through the oxygen atom.

In some embodiments, Ring $A^s$ is

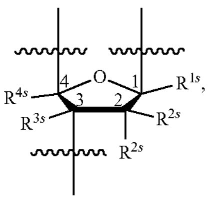

BA is connected at C1, and each of $R^{1s}$, $R^{2s}$, $R^{3s}$, $R^{4s}$ and $R^{5s}$ is independently $R^s$. In some embodiments, Ring $A^s$ is

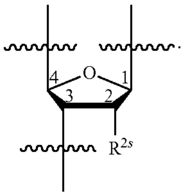

In some embodiments, Ring $A^s$ is

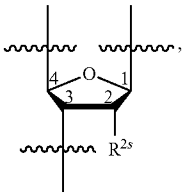

wherein $R^{2s}$ is not —OH. In some embodiments, Ring $A^s$ is

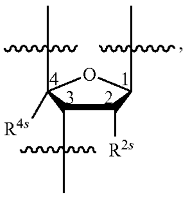

wherein $R^{2s}$ and $R^{4s}$ are R, and the two R groups are taken together with their intervening atoms to form an optionally substituted ring. In some embodiments, Ring $A^s$ is optionally substituted

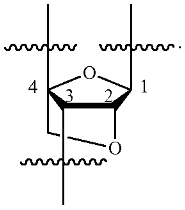 [SMILES: *C1[C@@H]2OC[C@]1(*)O[C@H]2*]

In some embodiments, Ring $A^s$ is

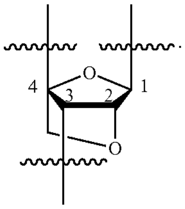 [SMILES: *C1[C@@H]2OC[C@]1(*)O[C@H]2*]

In some embodiments, Ring $A^s$ is

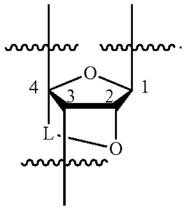

In some embodiments, SU is

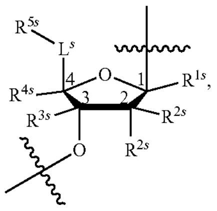

wherein each variable is independently as described in the present disclosure. In some embodiments, SU is

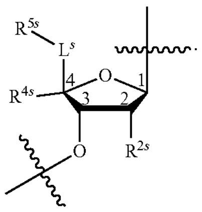

In some embodiments, SU is

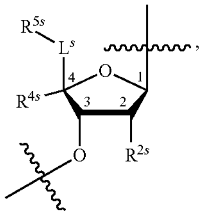

wherein $R^{4s}$ and $R^{2s}$ are taken together to form an optionally substituted ring. In some embodiments, SU is

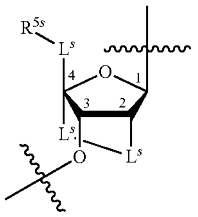

In some embodiments, SU is

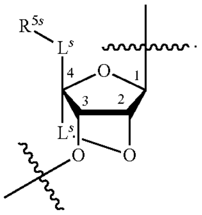

In some embodiments, SU is

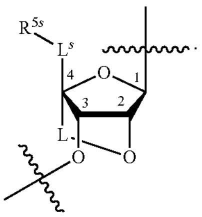

In some embodiments, SU is

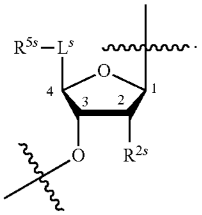

In some embodiments, $L^s$ is optionally substituted $—O—CH_2—$. In some embodiments, $L^s$ is optionally substituted $—O—CH_2—$, wherein the oxygen atom connects to $R^{5s}$. In some embodiments, $L^s$ is optionally substituted $—O—C(R)_2—$, wherein the oxygen atom connects to $R^{5s}$. In some embodiments, $L^s$ is optionally substituted $—O—CHR—$, wherein the oxygen atom connects to $R^{5s}$. In some embodiments, SU is

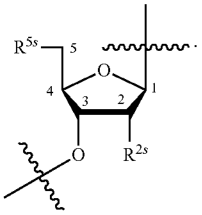

In some embodiments, SU is a modified sugar having the structure of:

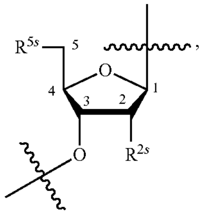

wherein $R^{5s}$ is OR', and $R^{2s}$ is —F, —CN, —$N_3$, —NO, —$NO_2$, —R', —OR', —SR', —$N(R')_2$, —O-L-OR', —O-L-SR', or —O-L-$N(R')_2$. In some embodiments, $R^{2s}$ and $R^{4s}$ are taken together to form an optionally substituted ring, and -$L^s$- connects C2 with C1, C2, C3, C4 or C5. In some embodiments, $R^{2s}$ is —H. In some embodiments, $R^{2s}$ is —F. In some embodiments, $R^{2s}$ is —OMe. In some embodiments, $R^{2s}$ is —$OCH_2CH_2OMe$.

In some embodiments, SU is

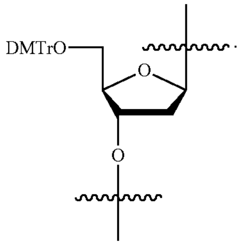

In some embodiments, SU is

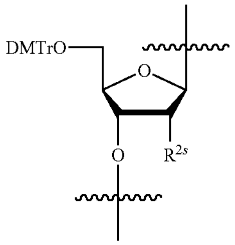

In some embodiments, SU is

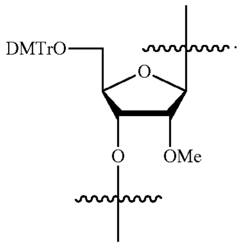

In some embodiments, SU is

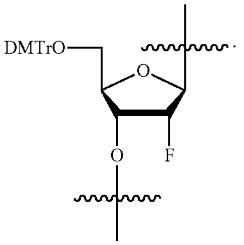

In some embodiments, SU is

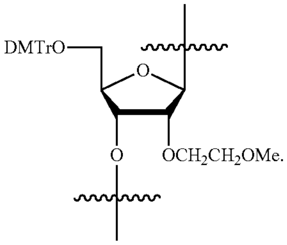

In some embodiments, SU is

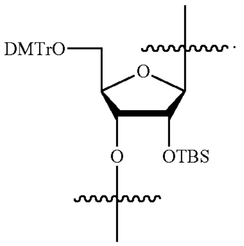

In some embodiments, a sugar moiety in a provided compound, e.g., a phosphoramidite of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or salts thereof, an oligonucleotide of formula O-I or a salt thereof, is a modified sugar moiety as described in the present disclosure.

In some embodiments, one or more hydroxyl group in a sugar moiety is optionally and independently replaced with halogen, —R'—$N(R')_2$, —OR', or —SR', wherein each R' is independently as defined above and described herein.

In some embodiments, each $R^s$ is independently —H, halogen, —CN, —$N_3$, —NO, —$NO_2$, -$L^s$-R', -$L^s$-$Si(R)_3$, -$L^s$-OR', -$L^s$-SR', -$L^s$-$N(R')^2$, —O-$L^s$-R', —O-$L^s$-$Si(R)_3$, —O-$L^s$-OR', —O-$L^s$-SR', or —O-$L^s$-$N(R')_2$.

In some embodiments, $R^s$ is R'. In some embodiments, $R^s$ is R. In some embodiments, $R^s$ is optionally substituted $C_{1-30}$ heteroaliphatic. In some embodiments, R comprises one or more silicon atoms. In some embodiments, $R^s$ is —$CH_2Si(Ph)_2CH_3$.

In some embodiments, $R^s$ is -$L^s$-R'. In some embodiments, $R^s$ is -$L^s$-R' wherein -$L^s$- is a bivalent, optionally substituted $C_{1-30}$ heteroaliphatic group. In some embodiments, $R^s$ is —$CH_2Si(Ph)^2CH_3$.

In some embodiments, $R^s$ is —F. In some embodiments, $R^s$ is —Cl. In some embodiments, $R^s$ is —Br. In some embodiments, $R^s$ is —I. In some embodiments, $R^s$ is —CN. In some embodiments, $R^s$ is —$N_3$. In some embodiments, $R^s$ is —NO. In some embodiments, $R^s$ is —$NO_2$. In some embodiments, $R^s$ is -$L^s$-Si(R)$_3$. In some embodiments, $R^s$ is —Si(R)$^3$. In some embodiments, $R^s$ is -$L^s$-R'. In some embodiments, $R^s$ is —R'. In some embodiments, $R^s$ is -$L^s$-OR'. In some embodiments, $R^s$ is —OR'. In some embodiments, $R^s$ is -L'-SR'. In some embodiments, $R^s$ is —SR'. In some embodiments, $R^s$ is -$L^s$-N(R')$_2$. In some embodiments, R' is —N(R')$_2$. In some embodiments, $R^s$ is —O-$L^s$-R'. In some embodiments, R is —O-$L^s$-Si(R)$_3$. In some embodiments, R is —O-$L^s$-OR'. In some embodiments, $R^s$ is —O-$L^s$-SR'. In some embodiments, $R^s$ is —O-$L^s$-N(R')$_2$. In some embodiments, $R^s$ is a 2'-modification as described in the present disclosure. In some embodiments, $R^s$ is —OR, wherein R is as described in the present disclosure. In some embodiments, $R^s$ is —OR, wherein R is optionally substituted $C_{1-6}$ aliphatic. In some embodiments, $R^s$ is —OMe. In some embodiments, $R^s$ is —$OCH_2CH_2OMe$.

In some embodiments, t is 0-20. In some embodiments, t is 1-20. In some embodiments, t is 1-5. In some embodiments, t is 1. In some embodiments, t is 2. In some embodiments, t is 3. In some embodiments, t is 4. In some embodiments, t is 5. In some embodiments, t is 6. In some embodiments, t is 7. In some embodiments, t is 8. In some embodiments, t is 9. In some embodiments, t is 10. In some embodiments, t is 11. In some embodiments, t is 12. In some embodiments, t is 13. In some embodiments, t is 14. In some embodiments, t is 15. In some embodiments, t is 16. In some embodiments, t is 17. In some embodiments, t is 18. In some embodiments, t is 19. In some embodiments, t is 20.

In some embodiments, each of $R^{1s}$, $R^{2s}$, $R^{3s}$, $R^{4s}$, and $R^{5s}$ is independently $R^s$, wherein $R^s$ is as described in the present disclosure.

In some embodiments, $R^{1s}$ is $R^s$ at a 1'-position (BA is at 1'-position). In some embodiments, $R^s$ at a 1'-position is —F. In some embodiments, $R^s$ at a 1'-position is —Cl. In some embodiments, $R^s$ at a 1'-position is —Br. In some embodiments, $R^s$ at a 1'-position is —I. In some embodiments, $R^s$ at a 1'-position is —CN. In some embodiments, $R^s$ at a 1'-position is —$N_3$. In some embodiments, $R^s$ at a 1'-position is —NO. In some embodiments, $R^s$ at a 1'-position is —$NO_2$. In some embodiments, $R^s$ at a 1'-position is -L-R'. In some embodiments, $R^s$ at a 1'-position is —R'. In some embodiments, $R^s$ at a 1'-position is -L-OR'. In some embodiments, $R^s$ at a 1'-position is —OR'. In some embodiments, $R^s$ at a 1'-position is -L-SR'. In some embodiments, $R^s$ at a 1'-position is —SR'. In some embodiments, $R^s$ at a 1'-position is L-L-N(R')$_2$. In some embodiments, $R^s$ at a 1'-position is —N(R')$_2$. In some embodiments, R' at a 1'-position is —OR', wherein R' is optionally substituted $C_{1-6}$ aliphatic. In some embodiments, $R^s$ at a 1'-position is —OR', wherein R' is optionally substituted $C_{1-6}$ alkyl. In some embodiments, $R^s$ at a 1'-position is —OMe. In some embodiments, $R^s$ at a 1'-position is -MOE. In some embodiments, $R^s$ at a 1'-position is hydrogen. In some embodiments, $R^s$ at one 1'-position is hydrogen, and $R^s$ at the other 1'-position is not hydrogen as described herein. In some embodiments, $R^s$ at both 1'-positions are hydrogen. In some embodiments, $R^s$ at one 1'-position is hydrogen, and the other 1'-position is connected to an internucleotidic linkage. In some embodiments, $R^{1s}$ is —F. In some embodiments, $R^{1s}$ is —Cl. In some embodiments, $R^{1s}$ is —Br. In some embodiments, $R^{1s}$ is —I. In some embodiments, $R^{1s}$ is —CN. In some embodiments, $R^{1s}$ is —$N_3$. In some embodiments, $R^{1s}$ is —NO. In some embodiments, $R^{1s}$ is —$NO_2$. In some embodiments, $R^{1s}$ is -L-R'. In some embodiments, $R^{1s}$ is —R'. In some embodiments, $R^{1s}$ is -L-OR'. In some embodiments, $R^{1s}$ is —OR'. In some embodiments, $R^{1s}$ is -L-SR'. In some embodiments, $R^{1s}$ is —SR'. In some embodiments, $R^{1s}$ is -L-N(R')$_2$. In some embodiments, $R^{1s}$ is —N(R')$_2$. In some embodiments, $R^{1s}$ is —OR', wherein R' is optionally substituted $C_{1-6}$ aliphatic. In some embodiments, $R^{1s}$ is —OR', wherein R' is optionally substituted $C_{1-6}$ alkyl. In some embodiments, $R^{1s}$ is —OH. In some embodiments, $R^{1s}$ is —OMe. In some embodiments, $R^{1s}$ is -MOE. In some embodiments, $R^{1s}$ is hydrogen. In some embodiments, one $R^{1s}$ at a 1'-position is hydrogen, and the other $R^{1s}$ at the other 1'-position is not hydrogen as described herein. In some embodiments, $R^{1s}$ at both 1'-positions are hydrogen. In some embodiments, $R^{1s}$ is —O-$L^s$-OR'. In some embodiments, $R^{1s}$ is —O-$L^s$-OR', wherein $L^s$ is optionally substituted $C_{1-6}$ alkylene, and R' is optionally substituted $C_{1-6}$ aliphatic. In some embodiments, $R^{1s}$ is —O-(optionally substituted $C_{1-6}$ alkylene)-OR'. In some embodiments, $R^{1s}$ is —O-(optionally substituted $C_{1-6}$ alkylene)-OR', wherein R' is optionally substituted $C_{1-6}$ alkyl. In some embodiments, $R^{1s}$ is —$OCH_2CH_2OMe$.

In some embodiments, $R^{2s}$ is $R^s$ at a 2'-position (BA is at 1'-position). In some embodiments, $R^s$ at a 2'-position is —F. In some embodiments, $R^s$ at a 2'-position is —Cl. In some embodiments, $R^s$ at a 2'-position is —Br. In some embodiments, $R^s$ at a 2'-position is —I. In some embodiments, $R^s$ at a 2'-position is —CN. In some embodiments, $R^s$ at a 2'-position is —$N_3$. In some embodiments, $R^s$ at a 2'-position is —NO. In some embodiments, $R^s$ at a 2'-position is —$NO_2$. In some embodiments, $R^s$ at a 2'-position is -L-R'. In some embodiments, $R^s$ at a 2'-position is —R'. In some embodiments, $R^s$ at a 2'-position is -L-OR'. In some embodiments, $R^s$ at a 2'-position is —OR'. In some embodiments, $R^s$ at a 2'-position is -L-SR'. In some embodiments, $R^s$ at a 2'-position is —SR'. In some embodiments, $R^s$ at a 2'-position is L-L-N(R')$_2$. In some embodiments, $R^s$ at a 2'-position is —N(R')$_2$. In some embodiments, $R^s$ at a 2'-position is —OR', wherein R' is optionally substituted $C_{1-6}$ aliphatic. In some embodiments, $R^s$ at a 2'-position is —OR', wherein R' is optionally substituted $C_{1-6}$ alkyl. In some embodiments, $R^s$ at a 2'-position is —OMe. In some embodiments, $R^s$ at a 2'-position is -MOE. In some embodiments, $R^s$ at a 2'-position is hydrogen. In some embodiments, $R^s$ at one 2'-position is hydrogen, and $R^s$ at the other 2'-position is not hydrogen as described herein. In some embodiments, $R^s$ at both 2'-positions are hydrogen. In some embodiments, $R^s$ at one 2'-position is hydrogen, and the other 2'-position is connected to an internucleotidic linkage. In some embodiments, $R^{2s}$ is —F. In some embodiments, $R^{2s}$ is —Cl. In some embodiments, $R^{2s}$ is —Br. In some embodiments, $R^{2s}$ is —I. In some embodiments, $R^{2s}$ is —CN. In some embodiments, $R^{2s}$ is —$N_3$. In some embodiments, $R^{2s}$ is —NO. In some embodiments, $R^{2s}$ is —$NO_2$. In some embodiments, $R^{2s}$ is -L-R'. In some embodiments, $R^{2s}$ is —R'. In some embodiments, $R^{2s}$ is -L-OR'. In some embodiments, $R^{2s}$ is —OR'. In some embodiments, $R^{2s}$ is -L-SR'. In some embodiments, $R^{2s}$ is —SR'. In some embodiments, $R^{2s}$ is -L-N(R')$_2$. In some embodiments, $R^{2s}$ is —N(R')$_2$. In some embodiments, $R^{2s}$ is —OR', wherein R' is optionally substituted $C_{1-6}$ aliphatic. In some embodiments, $R^{2s}$ is —OR', wherein R' is optionally substituted $C_{1-6}$ alkyl. In some embodiments, $R^{2s}$ is —OH. In some embodiments, $R^{2s}$ is —OMe. In some embodiments, $R^{2S}$ is -MOE. In some embodiments, $R^{2S}$ is hydrogen. In some embodiments, one $R^{2s}$ at a 2'-position is hydrogen, and the other $R^{2s}$ at the other 2'-position is not hydrogen as described herein. In some embodiments, $R^{2s}$ at both 2'-positions are hydrogen. In some embodiments, $R^{2S}$ is —O-$L^s$-OR'. In some embodiments, $R^{2s}$ is —O-$L^s$-OR', wherein $L^s$ is optionally substituted $C_{1-6}$ alkylene, and R' is optionally substituted $C_{1-6}$ aliphatic. In some embodiments, $R^{2s}$ is —O-(optionally substituted $C_{1-6}$ alkylene)-OR'. In some embodiments, $R^{2s}$ is —O-(optionally substituted $C_{1-6}$ alkylene)-OR', wherein R' is optionally substituted $C_{1-6}$ alkyl. In some embodiments, $R^{2s}$ is —$OCH_2CH_2OMe$.

In some embodiments, $R^{3s}$ is $R^s$ at a 3'-position (BA is at 1'-position). In some embodiments, $R^s$ at a 3'-position (BA is at 1'-position) is —F. In some embodiments, $R^s$ at a 3'-position is —Cl. In some embodiments, $R^s$ at a 3'-position is —Br. In some embodiments, $R^s$ at a 3'-position is —I. In some embodiments, $R^s$ at a 3'-position is —CN. In some embodiments, $R^s$ at a 3'-position is —$N_3$. In some embodiments, $R^s$ at a 3'-position is —NO. In some embodiments, $R^s$ at a 3'-position is —$NO_2$. In some embodiments, $R^s$ at a 3'-position is -L-R'. In some embodiments, $R^s$ at a 3'-position is —R'. In some embodiments, $R^s$ at a 3'-position is -L-OR'. In some embodiments, $R^s$ at a 3'-position is —OR'. In some embodiments, $R^s$ at a 3'-position is -L-SR'. In some embodiments, $R^s$ at a 3'-position is —SR'. In some embodiments, $R^s$ at a 3'-position is -L-N(R')$_2$. In some embodiments, $R^s$ at a 3'-position is —N(R')$_2$. In some embodiments, $R^s$ at a 3'-position is —OR', wherein R' is optionally substituted $C_{1-6}$ aliphatic. In some embodiments, $R^s$ at a 3'-position is —OR', wherein R' is optionally substituted $C_{1-6}$alkyl. In some embodiments, $R^s$ at a 3'-position is —OMe. In some embodiments, $R^s$ at a 3'-position is -MOE. In some embodiments, $R^s$ at a 3'-position is hydrogen. In some embodiments, $R^s$ at one 3'-position is hydrogen, and $R^s$ at the other 3'-position is not hydrogen as described herein. In some embodiments, $R^s$ at both 3'-positions are hydrogen. In some embodiments, $R^s$ at one 3'-position is hydrogen, and the other 3'-position is connected to an internucleotidic linkage. In some embodiments, $R^{3s}$ is —F. In some embodiments, $R^{3s}$ is —Cl. In some embodiments, $R^{3s}$ is —Br. In some embodiments, $R^{3s}$ is —I. In some embodiments, $R^{3s}$ is —CN. In some embodiments, $R^{3s}$ is —$N_3$. In some embodiments, $R^{3s}$ is —NO. In some embodiments, $R^{3s}$ is —$NO_2$. In some embodiments, $R^{3s}$ is -L-R'. In some embodiments, $R^{3s}$ is —R'. In some embodiments, $R^{3s}$ is -L-OR'. In some embodiments, $R^{3s}$ is —OR'. In some embodiments, $R^{3s}$ is -L-SR'. In some embodiments, $R^{3s}$ is —SR'. In some embodiments, $R^{3s}$ is L-L-N(R')$_2$. In some embodiments, $R^{3s}$ is —N(R')$_2$. In some embodiments, $R^{3s}$ is —OR', wherein R' is optionally substituted $C_{1-6}$ aliphatic. In some embodiments, $R^{3s}$ is —OR', wherein R' is optionally substituted $C_{1-6}$ alkyl. In some embodiments, $R^{3s}$ is —OH. In some embodiments, $R^{3s}$ is —OMe. In some embodiments, $R^{3s}$ is -MOE. In some embodiments, $R^{3s}$ is hydrogen.

In some embodiments, $R^{4S}$ is $R^s$ at a 4'-position (BA is at 1'-position). In some embodiments, $R^s$ at a 4'-position (BA is at 1'-position) is —F. In some embodiments, $R^s$ at a 4'-position is —Cl. In some embodiments, $R^s$ at a 4'-position is —Br. In some embodiments, $R^s$ at a 4'-position is —I. In some embodiments, $R^s$ at a 4'-position is —CN. In some embodiments, $R^s$ at a 4'-position is —$N_3$. In some embodiments, $R^s$ at a 4'-position is —NO. In some embodiments, $R^s$ at a 4'-position is —$NO_2$. In some embodiments, $R^s$ at a 4'-position is -L-R'. In some embodiments, $R^s$ at a 4'-position is —R'. In some embodiments, $R^s$ at a 4'-position is -L-OR'. In some embodiments, $R^s$ at a 4'-position is —OR'. In some embodiments, $R^s$ at a 4'-position is -L-SR'. In some embodiments, $R^s$ at a 4'-position is —SR'. In some embodiments, $R^s$ at a 4'-position is -L-N(R')$_2$. In some embodiments, $R^s$ at a 4'-position is —N(R')$_2$. In some embodiments, $R^s$ at a 4'-position is —OR', wherein R' is optionally substituted $C_{1-6}$ aliphatic. In some embodiments, $R^s$ at a 4'-position is —OR', wherein R' is optionally substituted $C_{1-6}$ alkyl. In some embodiments, $R^s$ at a 4'-position is —OMe. In some embodiments, $R^s$ at a 4'-position is -MOE. In some embodiments, $R^s$ at a 4'-position is hydrogen. In some embodiments, $R^s$ at one 4'-position is hydrogen, and $R^s$ at the other 4'-position is not hydrogen as described herein. In some embodiments, $R^s$ at both 4'-positions are hydrogen. In some embodiments, $R^s$ at one 4'-position is hydrogen, and the other 4'-position is connected to an internucleotidic linkage. In some embodiments, $R^{4s}$ is —F. In some embodiments, $R^{4s}$ is —Cl. In some embodiments, $R^{4s}$ is —Br. In some embodiments, $R^{4s}$ is —I. In some embodiments, $R^{4s}$ is —CN. In some embodiments, $R^{4s}$ is —$N_3$. In some embodiments, $R^{4s}$ is —NO. In some embodiments, $R^{4s}$ is —$NO_2$. In some embodiments, $R^{4s}$ is -L-R'. In some embodiments, $R^{4s}$ is —R'. In some embodiments, $R^{4s}$ is -L-OR'. In some embodiments, $R^{4s}$ is —OR'. In some embodiments, $R^{4s}$ is -L-SR'. In some embodiments, $R^{4s}$ is —SR'. In some embodiments, $R^{4s}$ is L-L-N(R')$_2$. In some embodiments, $R^{4s}$ is —N(R')$_2$. In some embodiments, $R^{4s}$ is —OR', wherein R' is optionally substituted $C_{1-6}$ aliphatic. In some embodiments, $R^{4s}$ is —OR', wherein R' is optionally substituted $C_{1-6}$ alkyl. In some embodiments, $R^{4s}$ is —OH. In some embodiments, $R^{4s}$ is —OMe. In some embodiments, $R^{4s}$ is -MOE. In some embodiments, $R^{4s}$ is hydrogen.

In some embodiments, $R^{5s}$ is R'. In some embodiments, $R^{5s}$ is —F. In some embodiments, $R^{5s}$ is —Cl. In some embodiments, $R^{5s}$ is —Br. In some embodiments, $R^{5s}$ is —I. In some embodiments, $R^{5s}$ is —CN. In some embodiments, $R^{5s}$ is —$N_3$. In some embodiments, $R^{5s}$ is —NO. In some embodiments, $R^{5s}$ is —$NO_2$. In some embodiments, $R^{5s}$ is -L-R'. In some embodiments, $R^{5s}$ is —R'. In some embodiments, $R^{5s}$ is -L-OR'. In some embodiments, $R^{5s}$ is —OR'. In some embodiments, $R^{5s}$ is -L-SR'. In some embodiments, $R^{5s}$ is —SR'. In some embodiments, $R^{5s}$ is L-L-N(R')$_2$. In some embodiments, $R^{5s}$ is —N(R')$_2$. In some embodiments, $R^{5s}$ is —OR', wherein R' is optionally substituted $C_{1-6}$ aliphatic. In some embodiments, $R^{5s}$ is —OR', wherein R' is optionally substituted $C_{1-6}$ alkyl. In some embodiments, $R^{5s}$ is —OH. In some embodiments, $R^{5s}$ is —OMe. In some embodiments, $R^{5s}$ is -MOE. In some embodiments, $R^{5s}$ is hydrogen.

In some embodiments, $R^{5s}$ is optionally substituted

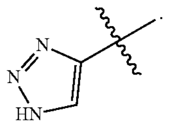 [SMILES: *c1c[nH]nn1]

In some embodiments, $R^{5s}$ is optionally substituted

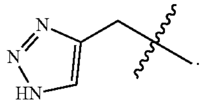 [SMILES: *Cc1c[nH]nn1]

In some embodiments, $R^{5s}$ is a protected hydroxyl group suitable for oligonucleotide synthesis. In some embodiments, $R^{5s}$, is —OR', wherein R' is optionally substituted $C_{1-6}$ aliphatic. In some embodiments, $R^{5s}$ is DMTrO—. Example protecting groups are widely known for use in accordance with the present disclosure. For additional examples, see Greene, T. W.; Wuts, P. G. M. Protective Groups in Organic Synthesis, 2nd ed.; Wiley: New York, 1991, and WO/2011/005761, WO/2013/012758, WO/2014/012081, WO/2015/107425, WO/2010/064146, WO/2014/010250, WO/2011/108682, WO/2012/039448, and WO/2012/073857, protecting groups of each of which are hereby incorporated by reference.

In some embodiments, $-L^s-R^{5s}$ is $R^E$. In some embodiments, $—C(R^{5s})_3$ is $R^E$. In some embodiments, provided oligonucleotides, e.g., oligonucleotides comprising one or more internucleotidic linkages each independently of formula VII, VII-a-1, VII-a-2, VII-b, VI-c, VI-d, VI-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof, oligonucleotides of formula O-I or salts thereof, etc. comprise $R^E$. In some embodiments, 5'-end nucleoside comprise $R^E$. In some embodiments, the present disclosure encompasses the recognition that incorporation of $R^E$ may significantly improve properties and/or activities of oligonucleotides, for example, in RNAi.

In some embodiments, $R^E$ is R. In some embodiments, $R^E$ is —H. In some embodiments, $R^E$ is —OR'. In some embodiments, $R^E$ is —OH. In some embodiments, $R^E$ is —OR', wherein R' is optionally substituted $C_{1-6}$ aliphatic. In some embodiments, $R^E$ is —OR', wherein R' is optionally substituted $C_{1-6}$ alkyl. In some embodiments, R' is methyl. In some embodiments, R' is ethyl. In some embodiments, R' is n-propyl. In some embodiments, $R^E$ is $—CH_2OCH_3$. In some embodiments, RE is $—CH_2F$. In some embodiments, RE is $—CH_2OH$.

In some embodiments, $R^E$ is $—CH_2OP(O)(OR)_2$ or a salt form thereof, wherein each R is independently as described in the present disclosure. In some embodiments, $R^E$ is $—CH_2OP(O)(OH)_2$ or a salt form thereof. In some embodiments, $R^E$ is $—CH_2OP(O)(OR)(SR)$ or a salt form thereof, wherein each R is independently as described in the present disclosure. In some embodiments, $R^E$ is $—CH_2OP(O)(SH)(OH)$ or a salt form thereof. In some embodiments, $R^E$ is $—CH═CHP(O)(OR)_2$ or a salt form thereof, wherein each R is independently as described in the present disclosure. In some embodiments, $R^E$ is $-(E)-CH═CHP(O)(OR)_2$ or a salt form thereof, wherein each R is independently as described in the present disclosure. In some embodiments, $R^E$ is $-(E)-CH═CHP(O)(OH)_2$.

In some embodiments, $R^E$ is —CH(R)—OR'. In some embodiments, $R^E$ is —(R)—CH(R)—OR'. In some embodiments, $R^E$ is —(S)—CH(R)—OR'. In some embodiments, R is not hydrogen. In some embodiments, R is optionally substituted $C_{1-6}$ aliphatic. In some embodiments, R is optionally substituted $C_{1-6}$ alkyl. In some embodiments, R is optionally substituted $C_{1-3}$ aliphatic. In some embodiments, R is optionally substituted $C_{1-3}$ alkyl. In some embodiments, R is linear. In some embodiments, R is unsubstituted. In some embodiments, R is substituted. In some embodiments, R is unsubstituted linear $C_{1-3}$ alkyl. In some embodiments, R is linear $C_{1-3}$ haloalkyl. In some embodiments, R is methyl. In some embodiments, R is ethyl. In some embodiments, R' is a hydroxyl protecting group. In some embodiments, R' is —C(O)R. In some embodiments, R' is DMTr.

In some embodiments, $R^E$ is —CH(R')—OH, wherein R' is as described in the present disclosure. In some embodiments, $R^E$ is $—CH(R')—OP(O)(R)_2$ or a salt form thereof, wherein each R' and R is independently as described in the present disclosure. In some embodiments, $R^E$ is $—CH(R')—OP(O)(OR)_2$ or a salt form thereof, wherein each R' and R is independently as described in the present disclosure. In some embodiments, $R^E$ is $—CH(R')—OP(O)(OH)_2$ or a salt form thereof. In some embodiments, $R^E$ is —CH(R')—OP(O)(OR)(SR) or a salt form thereof. In some embodiments, $R^E$ is —CH(R')—OP(O)(OH)(SH) or a salt form thereof. In some embodiments, $R^E$ is —(R)—CH(R')—OH, wherein R' is as described in the present disclosure. In some embodiments, $R^E$ is $—(R)—CH(R')—OP(O)(R)_2$ or a salt form thereof, wherein each R' and R is independently as described in the present disclosure. In some embodiments, $R^E$ is $—(R)—CH(R')—OP(O)(OR)_2$ or a salt form thereof, wherein each R' and R is independently as described in the present disclosure. In some embodiments, $R^E$ is $—(R)—CH(R')—OP(O)(OH)_2$ or a salt form thereof. In some embodiments, $R^E$ is —(R)—CH(R')—OP(O)(OR)(SR) or a salt form thereof. In some embodiments, $R^E$ is —(R)—CH(R')—OP(O)(OH)(SH) or a salt form thereof. In some embodiments, $R^E$ is —(S)—CH(R')—OH, wherein R' is as described in the present disclosure. In some embodiments, $R^E$ is $—(S)—CH(R')—OP(O)(R)_2$ or a salt form thereof, wherein each R' and R is independently as described in the present disclosure. In some embodiments, $R^E$ is $—(S)—CH(R')—OP(O)(OR)_2$ or a salt form thereof, wherein each R' and R is independently as described in the present disclosure. In some embodiments, $R^E$ is $—(S)—CH(R')—OP(O)(OH)_2$ or a salt form thereof. In some embodiments, $R^E$ is —(S)—CH(R')—OP(O)(OR)(SR) or a salt form thereof. In some embodiments, $R^E$ is —(S)—CH(R')—OP(O)(OH)(SH) or a salt form thereof. In some embodiments, R' is optionally substituted $C_1$, $C_2$, $C_3$, or $C_4$ aliphatic. In some embodiments, R' is $C_1$, $C_2$, $C_3$, or $C_4$ aliphatic or haloaliphatic. In some embodiments, R' is optionally substituted $—CH_3$. In some embodiments, R' is $—CH_3$.

In some embodiments, $R^E$ is $-L^s-P(O)(XR)_2$ or a salt form thereof, wherein each X is independently —O—, —S—, or —N(R')—. In some embodiments, $R^E$ is $-L^s-P(O)(XR)_2$ or a salt form thereof, wherein each X is independently —O—, —S—, or a covalent bond. In some embodiments, $R^E$ is $-L^s-P(O)(OR)_2$ or a salt form thereof. In some embodiments, $R^E$ is $-L^s-P(O)(OR)(SR)$ or a salt form thereof. In some embodiments, $R^E$ is $-L^s-P(O)(OR)(R)$ or a salt form thereof. In some embodiments, $L^s$ is a covalent bond, or a bivalent, optionally substituted, linear or branched $C_{1-6}$ aliphatic, wherein one or more methylene units are optionally and independently replaced with —O—, —S— or —N(R')—. In some embodiments, $R^E$ is $—X-L^s-R$. In some embodiments, $R^E$ is $—X-L^s-R^5$. In some embodiments, $R^5$ is optionally substituted 5-20 membered heteroaryl having 1-5 hetereoatoms. In some embodiments, $R^5$ is optionally substituted 5-membered heteroaryl having 1-4 hetereoatoms. In some embodiments, $R^E$ is optionally substituted

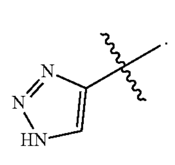 [SMILES: *c1c[nH]nn1]

In some embodiments, $R^E$ is

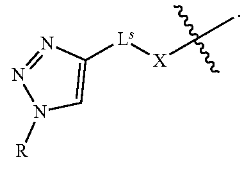

In some embodiments, $R^E$ is

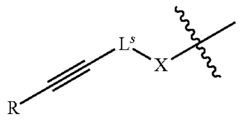

or a salt form thereof. In some embodiments, $R^E$ is

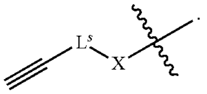

In some embodiments, X in $R^E$ is —$C(R)_2$—. In some embodiments, X is —O—. In some embodiments, X is —S—. In some embodiments, X is —N(R)—. In some embodiments, $L^s$ comprises an optionally substituted, bivalent or multivalent

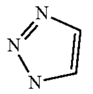

group. In some embodiments, $L^s$ comprises an optionally substituted

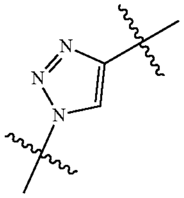 [SMILES: *c1cn(*)nn1]

group. In some embodiments, $L^s$ comprises a

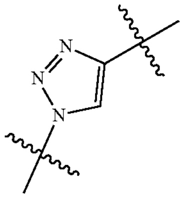 [SMILES: *c1cn(*)nn1]

group. In some embodiments, R is independently —H, or an optionally substituted group selected from $C_{1-10}$ alkyl, $C_{1-10}$ allyl, and $C_{6-14}$ aryl. In some embodiments, R is —H. In some embodiments, $R^E$ is optionally substituted

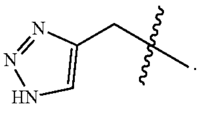

In some embodiments, $R^E$ is

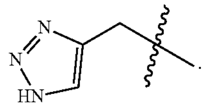 [SMILES: *Cc1c[nH]nn1]

In some embodiments, $R^E$ is —CHR—O—$R^s$, wherein R is —H or optionally substituted $C_{1-4}$ aliphatic, and $R^s$ is hydroxyl protecting group. In some embodiments, R is methyl and $R^s$ is DMTr. In some embodiments, $R^E$ is —(R)—CH(Me)-ODMTr. In some embodiments, $R^E$ is —(S)—CH(Me)-ODMTr. In some embodiments, $R^E$ is -$L^s$-$P(O)(OR)_2$. In some embodiments, $R^E$ is -$L^s$-$P(O)(OR)_2$, wherein each R is independently optionally substituted $C_{1-6}$ aliphatic. In some embodiments, -$L^s$- is -(E)-CH═CH—. In some embodiments, $R^E$ is -(E)-CH═CH—$P(O)(OR)_2$. In some embodiments, $R^E$ is -(E)-CH═CH—$P(O)(OR)_2$, wherein each R is independently optionally substituted $C_{1-6}$ aliphatic. In some embodiments, $R^E$ is -(E)-CH═CH—P(O)$(OMe)_2$.

In some embodiments, an internucleotidic linkage of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof, is a chiral internucleotidic linkage. In some embodiments, P in $P^L$ is a chiral linkage phosphorus. In some embodiments, a chiral linkage phosphorus is Rp. In some embodiments, a chiral linkage phosphorus is Sp. In some embodiments, $P^L$ is P(═W). In some embodiments, $P^L$ is P(═O). In some embodiments, $P^L$ is P(═S). In some embodiments, $P^L$ is P. In some embodiments, $P^L$ is P→B$(R')_3$.

In some embodiments, Y is —O— and Z is —O—, and X is —O— or —S—. In some embodiments, X and Y and Z are —O—. In some embodiments, X is —S—, and Y and Z are —O—.

In some embodiments, W is O. In some embodiments, W is O, and X and Y and Z are —O—. In some embodiments, W is O, X is —S—, and Y and Z are —O—. In some embodiments, W is S. In some embodiments, W is S, and X and Y and Z are —O—. In some embodiments, W is S, X is —S—, and Y and Z are —O—.

In some embodiments, as described in the present disclosure, —X-$L^s$-$R^5$ is of such structure that H—X-$L^s$-$R^5$ has the structure of formula I, I-a, I-a-1, I-a-2, I-b, I-c, I-d, I-e, II, II-a, II-b, III, III-a, III-b, or a salt thereof.

In some embodiments, —X-$L^s$-$R^5$ is —OR. In some embodiments, —X-$L^s$-$R^5$ is —OH. In some embodiments, —X-$L^s$-$R^5$ is —OR, wherein R is not hydrogen. In some embodiments, W is O and —X-$L^s$-$R^5$ is —OR. In some embodiments, W is O and —X-$L^s$-$R^5$ is —OH. In some embodiments, W is O and —X-$L^s$-$R^5$ is —OR, wherein R is not hydrogen.

In some embodiments, —X-$L^s$-$R^5$ is —SR. In some embodiments, —X-$L^s$-$R^5$ is —SH. In some embodiments, —X-$L^s$-$R^5$ is —SR, wherein R is not hydrogen. In some embodiments, W is O and —X-$L^s$-$R^5$ is —SR. In some embodiments, W is O and —X-$L^s$-$R^5$ is —SH. In some embodiments, W is O and —X-$L^s$-$R^5$ is —SR, wherein R is not hydrogen.

In some embodiments, —X-$L^s$-$R^5$ is of such a structure that H—X-$L^s$-$R^5$ has the structure of formula I, I-a, I-a-1, I-a-2, I-b, I-c, I-d, I-e, II, II-a, II-b, III, III-a, or III-b, or a salt thereof as described herein. In some embodiments, $R^7$ is —OH, and $R^6$ is —H or —R. In some embodiments, $R^6$ is —H. In some embodiments, $R^6$ is —R, wherein R is not hydrogen. In some embodiments, R is a capping group. Suitable capping groups for oligonucleotide synthesis are well known by a personal having ordinary skill in the art, for example, those described in U.S. Pat. Nos. 9,598,458, 9,744, 183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784, the capping technologies of each of which is incorporated herein by reference. In some embodiments, $R^6$ is —C(O)R'. As described in the present disclosure, in some embodiments, immediately after coupling, —X-$L^s$-$R^5$ is of such a structure that H—X-$L^s$-$R^5$ has the structure of formula I, I-a, I-a-1, I-a-2, I-b, I-c, I-d, I-e, II, II-a, II-b, III, III-a, or III-b, or a salt thereof, wherein $R^6$ is —H in formula I, I-a, I-a-1, I-a-2, I-b, I-c, I-d, I-e, II, II-a, II-b, III, III-a, or III-b, and a linkage may have the structure of formula VII, VII-a-1, VII-a-2, VII-b, VII-c, VII-d, or VII-e, or a salt form thereof. In some embodiments, after capping, —X-$L^s$-$R^5$ is of such a structure that H—X-$L^s$-$R^5$ has the structure of formula I, I-a, I-a-1, I-a-2, I-b, I-c, I-d, I-e, II, II-a, II-b, III, III-a, or III-b, or a salt thereof, wherein $R^6$ is a capping group, for example, a group having the structure of —C(O)R, and a linkage may have the structure of formula VII, VII-a-1, VII-a-2, VII-b, VII-c, VII-d, or VII-e, or a salt form thereof. In some embodiments, the nitrogen atom to which $R^5$ is attached is capped with a R—C(O)— group, forming a group of —N($R^5$)(—C(O)—R). In some embodiments, a capping group is —C(O)—$CH_3$. In some embodiments, a capping group is —C(O)—$CF_3$. In some embodiments, after additional chemical modification steps, a linkage may have the structure of formula VII, VII-a-1, VII-a-2, VII-b, VII-c, VII-d, or VII-e, or a salt form thereof.

In some embodiments, each $L^P$ is independently an internucleotidic linkage. In some embodiments, each $L^P$ independently has the structure of formula VII, VII-a-1, VII-a-2, VII-b, VI-c, VI-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof. In some embodiments, each L independently has the structure of formula VII, VII-a-1, VII-a-2, VII-b, VII-c, VII-d, or VII-e, or a salt form thereof. In some embodiments, each $L^P$ independently has the structure of formula VI, VII-a-1, VII-a-2, VI-b, VI-c, VI-d, or VI-e, or a salt form thereof, wherein each —X-$L^s$-$R^5$ is independently of a structure that H—X-$L^s$-$R^5$ is a compound of formula I, I-a, I-a-1, I-a-2, I-b, I-c, I-d, I-e, II, II-a, II-b, III, III-a, or III-b, or a salt thereof. In some embodiments, each L independently has the structure of formula VII, VII-a-1, or VII-a-2, or a salt form thereof, wherein each —X-$L^s$-$R^5$ is independently of a structure that H—X-$L^s$-$R^5$ is a compound of formula I, I-a, I-a-1, I-a-2, I-b, I-c, I-d, I-e, II, II-a, II-b, III, III-a, or III-b, or a salt thereof, and W is O or S. In some embodiments, each $L^P$ independently has the structure of formula VII, VII-a-1, or VII-a-2, or a salt form thereof, wherein each —X-$L^s$-$R^5$ is independently of a structure that H—X-$L^s$-$R^5$ is a compound of formula I, I-a, I-a-1, I-a-2, I-b, I-c, I-d, I-e, II, II-a, II-b, III, III-a, or III-b, or a salt thereof, and W is O or S, and X is O. In some embodiments, each $L^P$ independently has the structure of formula VII, VII-a-1, or VII-a-2, or a salt form thereof, wherein each —X-$L^s$-$R^5$ is independently of a structure that H—X-$L^s$-$R^5$ is a compound of formula O, I-a, I-a-1, I-a-2, I-b, I-c, I-d, I-e, II, II-a, II-b, III, III-a, or III-b, or a salt thereof, and W is O or S, and X and Y and Z are —O—. In some embodiments, $L^P$ has the structure of formula VII or a salt thereof. In some embodiments, $L^P$ has the structure of formula VII or a salt thereof, wherein W is O or S, and X and Y and Z are —O—. In some embodiments, $L^P$ has the structure of formula VII-a-1 or a salt thereof. In some embodiments, $L^P$ has the structure of formula VII-a-1 or a salt thereof, wherein W is O or S, and X and Y and Z are —O—. In some embodiments, $L^P$ has the structure of formula VII-a-2 or a salt thereof. In some embodiments, $L^P$ has the structure of formula VII-a-2 or a salt thereof, wherein W is O or S, and X and Y and Z are —O—. In some embodiments, $L^P$ has the structure of formula VII-b or a salt thereof. In some embodiments, $L^P$ has the structure of formula VII-b or a salt thereof, wherein X and Y and Z are —O—. In some embodiments, $L^P$ has the structure of formula VII-c or a salt thereof. In some embodiments, $L^P$ has the structure of formula VII-c or a salt thereof, wherein X and Y and Z are —O—. In some embodiments, L has the structure of formula VII-d or a salt thereof. In some embodiments, $L^P$ has the structure of formula VII-d or a salt thereof, wherein X and Y and Z are —O—. In some embodiments, $L^P$ has the structure of formula VII-e or a salt thereof. In some embodiments, $L^P$ has the structure of formula VII-e or a salt thereof, wherein X and Y and Z are —O—. In some embodiments, L is natural phosphate linkage. In some embodiments, L is a phosphorothioate linkage or a salt form thereof. In some embodiments, each L is independently a natural phosphate linkage or a phosphorothioate linkage, or a salt thereof. In some embodiments, one or more $L^P$ independently have the structure of formula NL-n-1, NL-n-2, NL-n-3, NL-n-4, NL, NL-a-1, NL-a-2, NL-b-1, NL-b-2, NL-c-1, NL-c-2, NL-d-1, or NL-d-2. In some embodiments, one or more $L^P$ independently have the structure of formula NL-n-1, NL-n-2, NL-n-3, NL-n-4, NL, NL-a-1, NL-a-2, NL-b-1, NL-b-2, NL-c-1, NL-c-2, NL-d-1, or NL-d-2, wherein W is O, and Y and Z are —O—. In some embodiments, one or more $L^P$ independently have the structure of formula NL, NL-a-1, NL-a-2, NL-b-1, NL-b-2, NL-c-1, NL-c-2, NL-d-1, or NL-d-2. In some embodiments, one or more $L^P$ independently have the structure of formula NL, NL-a-1, NL-a-2, NL-b-1, NL-b-2, NL-c-1, NL-c-2, NL-d-1, or NL-d-2, wherein W is O, and Y and Z are —O—. In some embodiments, one or more internucleotidic linkages are independently (n001)

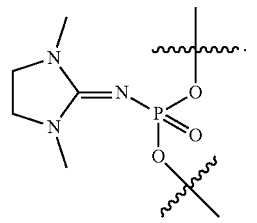

In some embodiments, one or more internucleotidic linkages are independently chirally controlled n001. In some embodiments, one or more internucleotidic linkages are independently chirally controlled n001 and have an Rp configuration. In some embodiments, one or more internucleotidic linkages are independently chirally controlled n001 and have an Sp configuration.

In some embodiments, at least one $L^P$ comprises W, wherein W is S. In some embodiments, about 1-20 $L^P$ comprises W, wherein W is S. In some embodiments, at least 2, 3, 4, 5, 6, 7, 8, 9, 10, 11, 12, 13, 14, 15, 16, 17, 18, 19, 20 $L^P$ comprises W, wherein W is S. In some embodiments, at least one $L^P$ comprises W, wherein W is O. In some embodiments, about 1-20 $L^P$ comprises W, wherein W is O. In some embodiments, at least 2, 3, 4, 5, 6, 7, 8, 9, 10, 11, 12, 13, 14, 15, 16, 17, 18, 19, 20 $L^P$ comprises W, wherein W is O.

In some embodiments, z is 1. In some embodiments, z is 2. In some embodiments, z is 3. In some embodiments, z is 4. In some embodiments, z is 5. In some embodiments, z is 6. In some embodiments, z is 7. In some embodiments, z is 8. In some embodiments, z is 9. In some embodiments, z is 10. In some embodiments, z is 11. In some embodiments, z is 12. In some embodiments, z is 13. In some embodiments, z is 14. In some embodiments, z is 15. In some embodiments, z is 16. In some embodiments, z is 17. In some embodiments, z is 18. In some embodiments, z is 19. In some embodiments, z is 20. In some embodiments, z is 21. In some embodiments, z is 22. In some embodiments, z is 23. In some embodiments, z is 24. In some embodiments, z is 25. In some embodiments, z is 26. In some embodiments, z is 27. In some embodiments, z is 28. In some embodiments, z is 29. In some embodiments, z is 30. In some embodiments, z is at least 2. In some embodiments, z is at least 3. In some embodiments, z is at least 4. In some embodiments, z is at least 5. In some embodiments, z is at least 6. In some embodiments, z is at least 7. In some embodiments, z is at least 8. In some embodiments, z is at least 9. In some embodiments, z is at least 10. In some embodiments, z is at least 11. In some embodiments, z is at least 12. In some embodiments, z is at least 13. In some embodiments, z is at least 14. In some embodiments, z is at least 15. In some embodiments, z is at least 16. In some embodiments, z is at least 17. In some embodiments, z is at least 18. In some embodiments, z is at least 19. In some embodiments, z is at least 20. In some embodiments, z is at least 21. In some embodiments, z is at least 22. In some embodiments, z is at least 23. In some embodiments, z is at least 24. In some embodiments, z is at least 25. In some embodiments, z is at least 26. In some embodiments, z is at least 27. In some embodiments, z is at least 28. In some embodiments, z is at least 29. In some embodiments, z is at least 30.

In some embodiments, $L^{3E}$ is $-L^s-$ or $-L^s-L^s-$. In some embodiments, $L^{3E}$ is $-L^s-$. In some embodiments, $L^{3E}$ is $-L^s-L^s-$. In some embodiments, $L^{3E}$ is a covalent bond. In some embodiments, $L^{3E}$ is a linker used in oligonucleotide synthesis. In some embodiments, $L^{3E}$ is a linker used in solid phase oligonucleotide synthesis. Various types of linkers are known and can be utilized in accordance with the present disclosure. In some embodiments, a linker is a succinate linker ($—O—C(O)—CH_2—CH_2—C(O)—$). In some embodiments, a linker is an oxalyl linker ($—O—C(O)—C(O)—$). In some embodiments, $L^{3E}$ is a succinyl-piperidine linker (SP) linker. In some embodiments, $L^{3E}$ is a succinyl linker. In some embodiments, $L^{3E}$ is a Q-linker.

In some embodiments, $R^{3E}$ is —R', $-L^s-R'$, —OR', or a solid support. In some embodiments, $R^{3E}$ is —R'. In some embodiments, $R^{3E}$ is $-L^s-R'$. In some embodiments, $R^{3E}$ is —OR'. In some embodiments, $R^{3E}$ is a solid support. In some embodiments, $R^{3E}$ is —H. In some embodiments, $-L^3-R^{3E}$ is —H. In some embodiments, $R^{3E}$ is —OH. In some embodiments, $-L^3-R^{3E}$ is —OH. In some embodiments, $R^{3E}$ is optionally substituted $C_{1-6}$ aliphatic. In some embodiments, $R^{3E}$ is optionally substituted $C_{1-6}$ alkyl. In some embodiments, $R^{3E}$ is —OR'. In some embodiments, $R^{3E}$ is —OH. In some embodiments, $R^{3E}$ is —OR, wherein R' is not hydrogen. In some embodiments, $R^{3E}$ is —OR', wherein R' is optionally substituted $C_{1-6}$ alkyl.

In some embodiments, $R^{3E}$ is a 3'-end cap (e.g., those used in RNAi technologies).

In some embodiments, $R^{3E}$ is a solid support. In some embodiments, $R^{3E}$ is a solid support for oligonucleotide synthesis. Various types of solid support are known and can be utilized in accordance with the present disclosure. In some embodiments, a solid support is HCP. In some embodiments, a solid support is CPG.

In some embodiments, s is 0-20. In some embodiments, s is 1-20. In some embodiments, s is 1. In some embodiments, s is 2. In some embodiments, s is 3. In some embodiments, s is 4. In some embodiments, s is 5. In some embodiments, s is 6. In some embodiments, s is 7. In some embodiments, s is 8. In some embodiments, s is 9. In some embodiments, s is 10. In some embodiments, s is 11. In some embodiments, s is 12. In some embodiments, s is 13. In some embodiments, s is 14. In some embodiments, s is 15. In some embodiments, s is 16. In some embodiments, s is 17. In some embodiments, s is 18. In some embodiments, s is 19. In some embodiments, s is 20.

In some embodiments, each Ring $A^s$ or Ring A is independently an optionally substituted 3-20 membered monocyclic, bicyclic or polycyclic ring having 0-10 heteroatoms independently selected from oxygen, nitrogen, sulfur, phosphorus and silicon. In some embodiments, Ring $A^s$ or Ring A is an optionally substituted ring, which ring is as described in the present disclosure. In some embodiments, a ring is

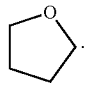

In some embodiments, a ring is

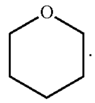

In some embodiments, Ring A' or Ring A is or comprises a ring of a sugar moiety. In some embodiments, Ring A' or Ring A is or comprises a ring of a modified sugar moiety.

In some embodiments, provided compounds comprise one or more bivalent or multivalent optionally substituted rings, e.g., Ring A, Ring $A^s$, Ring A', -Cy-, $Cy^L$, those formed by two or more R groups (R and (combinations of) variables that can be R) taken together, etc. In some embodiments, a ring is a cycloaliphatic, aryl, heteroaryl, or heterocyclyl group as described for R but bivalent or multivalent. As appreciated by those skilled in the art, ring moieties described for one variable, e.g., Ring A, can also be applicable to other variables, e.g., Ring A', -Cy-, $Cy^L$, etc., if requirements of the other variables, e.g., number of heteroatoms, valence, etc., are satisfied. Example rings are extensively described in the present disclosure.

In some embodiments, a ring, e.g., in Ring A, Ring $A^s$, R, etc. which is optionally substituted, is a 3-20 membered monocyclic, bicyclic or polycyclic ring having 0-10 heteroatoms independently selected from oxygen, nitrogen, sulfur, phosphorus and silicon. In some embodiments, a ring is a 3-20 membered monocyclic, bicyclic or polycyclic ring having 1-10 heteroatoms independently selected from oxygen, nitrogen, sulfur, phosphorus and silicon, wherein the ring comprises a —N($R^6$)— moiety.

In some embodiments, a ring can be of any size within its range, e.g., 3, 4, 5, 6, 7, 8, 9, 10, 11, 12, 13, 14, 15, 16, 17, 18, 19, or 20-membered.

In some embodiments, a ring is monocyclic. In some embodiments, a ring is saturated and monocyclic. In some embodiments, a ring is monocyclic and partially saturated. In some embodiments, a ring is monocyclic and aromatic.

In some embodiments, a ring is bicyclic. In some embodiments, a ring is polycyclic. In some embodiments, a bicyclic or polycyclic ring comprises two or more monocyclic ring moieties, each of which can be saturated, partially saturated, or aromatic, and each which can contain no or 1-10 heteroatoms. In some embodiments, a bicyclic or polycyclic ring comprises a saturated monocyclic ring. In some embodiments, a bicyclic or polycyclic ring comprises a saturated monocyclic ring containing no heteroatoms. In some embodiments, a bicyclic or polycyclic ring comprises a saturated monocyclic ring comprising one or more heteroatoms. In some embodiments, a bicyclic or polycyclic ring comprises a partially saturated monocyclic ring. In some embodiments, a bicyclic or polycyclic ring comprises a partially saturated monocyclic ring containing no heteroatoms. In some embodiments, a bicyclic or polycyclic ring comprises a partially saturated monocyclic ring comprising one or more heteroatoms. In some embodiments, a bicyclic or polycyclic ring comprises an aromatic monocyclic ring. In some embodiments, a bicyclic or polycyclic ring comprises an aromatic monocyclic ring containing no heteroatoms. In some embodiments, a bicyclic or polycyclic ring comprises an aromatic monocyclic ring comprising one or more heteroatoms. In some embodiments, a bicyclic or polycyclic ring comprises a saturated ring and a partially saturated ring, each of which independently contains one or more heteroatoms. In some embodiments, a bicyclic ring comprises a saturated ring and a partially saturated ring, each of which independently comprises no, or one or more heteroatoms. In some embodiments, a bicyclic ring comprises an aromatic ring and a partially saturated ring, each of which independently comprises no, or one or more heteroatoms. In some embodiments, a polycyclic ring comprises a saturated ring and a partially saturated ring, each of which independently comprises no, or one or more heteroatoms. In some embodiments, a polycyclic ring comprises an aromatic ring and a partially saturated ring, each of which independently comprises no, or one or more heteroatoms. In some embodiments, a polycyclic ring comprises an aromatic ring and a saturated ring, each of which independently comprises no, or one or more heteroatoms. In some embodiments, a polycyclic ring comprises an aromatic ring, a saturated ring, and a partially saturated ring, each of which independently comprises no, or one or more heteroatoms. In some embodiments, a ring comprises at least one heteroatom. In some embodiments, a ring comprises at least one nitrogen atom. In some embodiments, a ring comprises at least one oxygen atom. In some embodiments, a ring comprises at least one sulfur atom.

As appreciated by those skilled in the art in accordance with the present disclosure, a ring is typically optionally substituted. In some embodiments, a ring is unsubstituted. In some embodiments, a ring is substituted. In some embodiments, a ring is substituted on one or more of its carbon atoms. In some embodiments, a ring is substituted on one or more of its heteroatoms. In some embodiments, a ring is substituted on one or more of its carbon atoms, and one or more of its heteroatoms. In some embodiments, two or more substituents can be located on the same ring atom. In some embodiments, all available ring atoms are substituted. In some embodiments, not all available ring atoms are substituted. In some embodiments, in provided structures where rings are indicated to be connected to other structures (e.g., Ring $A^s$ in

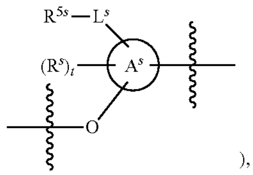

),

"optionally substituted" is to mean that, besides those structures already connected, remaining substitutable ring positions, if any, are optionally substituted (e.g., in

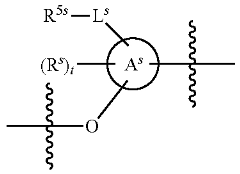

,

Ring $A^s$ may optionally have one or more substituents besides $R^{5s}$-$L^s$-, t $R^s$, —O—, and -).

In some embodiments, a ring is a bivalent or multivalent $C_{3-30}$ cycloaliphatic ring. In some embodiments, a ring is a bivalent or multivalent $C_{3-20}$ cycloaliphatic ring. In some embodiments, a ring is a bivalent or multivalent $C_{3-10}$ cycloaliphatic ring. In some embodiments, a ring is a bivalent or multivalent 3-30 membered saturated or partially unsaturated carbocyclic ring. In some embodiments, a ring is a bivalent or multivalent 3-7 membered saturated or partially unsaturated carbocyclic ring. In some embodiments, a ring is a bivalent or multivalent 3-membered saturated or partially unsaturated carbocyclic ring. In some embodiments, a ring is a bivalent or multivalent 4-membered saturated or partially unsaturated carbocyclic ring. In some embodiments, a ring is a bivalent or multivalent 5-membered saturated or partially unsaturated carbocyclic ring. In some embodiments, a ring is a bivalent or multivalent 6-membered saturated or partially unsaturated carbocyclic ring. In some embodiments, a ring is a bivalent or multivalent 7-membered saturated or partially unsaturated carbocyclic ring. In some embodiments, a ring is a bivalent or multivalent cyclohexyl ring. In some embodiments, a ring is a bivalent or multivalent cyclopentyl ring. In some embodiments, a ring is a bivalent or multivalent cyclobutyl ring. In some embodiments, a ring is a bivalent or multivalent cyclopropyl ring.

In some embodiments, a ring is a bivalent or multivalent $C_{6-30}$ aryl ring. In some embodiments, a ring is a bivalent or multivalent phenyl ring.

In some embodiments, a ring is a bivalent or multivalent 8-10 membered bicyclic saturated, partially unsaturated or aryl ring. In some embodiments, a ring is a bivalent or multivalent 8-10 membered bicyclic saturated ring. In some embodiments, a ring is a bivalent or multivalent 8-10 membered bicyclic partially unsaturated ring. In some embodiments, a ring is a bivalent or multivalent 8-10 membered bicyclic aryl ring. In some embodiments, a ring is a bivalent or multivalent naphthyl ring.

In some embodiments, a ring is a bivalent or multivalent 5-30 membered heteroaryl ring having 1-10 heteroatoms independently selected from oxygen, nitrogen, sulfur, phosphorus and silicon. In some embodiments, a ring is a bivalent or multivalent 5-30 membered heteroaryl ring having 1-10 heteroatoms independently selected from oxygen, nitrogen, and sulfur. In some embodiments, a ring is a bivalent or multivalent 5-30 membered heteroaryl ring having 1-5 heteroatoms independently selected from oxygen, nitrogen, sulfur, phosphorus and silicon. In some embodiments, a ring is a bivalent or multivalent 5-30 membered heteroaryl ring having 1-5 heteroatoms independently selected from oxygen, nitrogen, and sulfur.

In some embodiments, a ring is a bivalent or multivalent 5-6 membered monocyclic heteroaryl ring having 1-4 heteroatoms independently selected from nitrogen, oxygen, and sulfur. In some embodiments, a ring is a bivalent or multivalent 5-6 membered monocyclic heteroaryl ring having 1-3 heteroatoms independently selected from nitrogen, sulfur, and oxygen.

In some embodiments, a ring is a bivalent or multivalent 5-membered monocyclic heteroaryl ring having 1-4 heteroatoms independently selected from nitrogen, oxygen or sulfur. In some embodiments, a ring is a bivalent or multivalent 6-membered monocyclic heteroaryl ring having 1-4 heteroatoms independently selected from nitrogen, oxygen, and sulfur.

In some embodiments, a ring is a bivalent or multivalent 5-membered monocyclic heteroaryl ring having one heteroatom selected from nitrogen, oxygen, and sulfur. In some embodiments, a ring is a bivalent or multivalent pyrrolyl, furanyl, or thienyl ring.

In some embodiments, a ring is a bivalent or multivalent 5-membered heteroaryl ring having two heteroatoms independently selected from nitrogen, oxygen, and sulfur. In certain embodiments, a ring is a bivalent or multivalent 5-membered heteroaryl ring having one nitrogen atom, and an additional heteroatom selected from sulfur or oxygen. In some embodiments, a ring is a bivalent or multivalent pyrazolyl, imidazolyl, thiazolyl, isothiazolyl, oxazolyl or isoxazolyl ring.

In some embodiments, a ring is a bivalent or multivalent 5-membered heteroaryl ring having three heteroatoms independently selected from nitrogen, oxygen, and sulfur. In some embodiments, a ring is a bivalent or multivalent triazolyl, oxadiazolyl or thiadiazolyl ring.

In some embodiments, a ring is a bivalent or multivalent 5-membered heteroaryl ring having four heteroatoms independently selected from nitrogen, oxygen, and sulfur. In some embodiments, a ring is a bivalent or multivalent tetrazolyl, oxatriazolyl and thiatriazolyl ring.

In some embodiments, a ring is a bivalent or multivalent 6-membered heteroaryl ring having 1-4 nitrogen atoms. In some embodiments, a ring is a bivalent or multivalent 6-membered heteroaryl ring having 1-3 nitrogen atoms. In other embodiments, a ring is a bivalent or multivalent 6-membered heteroaryl ring having 1-2 nitrogen atoms. In some embodiments, a ring is a bivalent or multivalent 6-membered heteroaryl ring having four nitrogen atoms. In some embodiments, a ring is a bivalent or multivalent 6-membered heteroaryl ring having three nitrogen atoms. In some embodiments, a ring is a bivalent or multivalent 6-membered heteroaryl ring having two nitrogen atoms. In certain embodiments, a ring is a bivalent or multivalent 6-membered heteroaryl ring having one nitrogen atom. In some embodiments, a ring is a bivalent or multivalent pyridinyl, pyrimidinyl, pyrazinyl, pyridazinyl, triazinyl, or tetrazinyl ring.

In certain embodiments, a ring is a bivalent or multivalent 8-10 membered bicyclic heteroaryl ring having 1-4 heteroatoms independently selected from nitrogen, oxygen, and sulfur. In some embodiments, a ring is a bivalent or multivalent 5,6-fused heteroaryl ring having 1-4 heteroatoms independently selected from nitrogen, oxygen, and sulfur. In other embodiments, a ring is a bivalent or multivalent 5,6-fused heteroaryl ring having 1-2 heteroatoms independently selected from nitrogen, oxygen, and sulfur. In certain embodiments, a ring is a bivalent or multivalent 5,6-fused heteroaryl ring having 1 heteroatom independently selected from nitrogen, oxygen, and sulfur. In some embodiments, a ring is a bivalent or multivalent indolyl ring. In some embodiments, a ring is a bivalent or multivalent azabicyclo [3.2.1]octanyl ring. In certain embodiments, a ring is a bivalent or multivalent 5,6-fused heteroaryl ring having 2 heteroatoms independently selected from nitrogen, oxygen, and sulfur. In some embodiments, a ring is a bivalent or multivalent azaindolyl ring. In some embodiments, a ring is a bivalent or multivalent benzimidazolyl ring. In some embodiments, a ring is a bivalent or multivalent benzothiazolyl ring. In some embodiments, a ring is a bivalent or multivalent benzoxazolyl ring. In some embodiments, a ring is a bivalent or multivalent indazolyl ring. In certain embodiments, a ring is a bivalent or multivalent 5,6-fused heteroaryl ring having 3 heteroatoms independently selected from nitrogen, oxygen, and sulfur.

In some embodiments, a ring is a bivalent or multivalent 5,6-fused heteroaryl ring having 1-5 heteroatoms independently selected from nitrogen, oxygen, and sulfur. In some embodiments, a ring is a bivalent or multivalent 5,6-fused heteroaryl ring having 1-4 heteroatoms independently selected from nitrogen, oxygen, and sulfur. In some embodiments, a ring is a bivalent or multivalent 5,6-fused heteroaryl ring having 1-3 heteroatoms independently selected from nitrogen, oxygen, and sulfur. In some embodiments, a ring is a bivalent or multivalent 5,6-fused heteroaryl ring having two heteroatoms independently selected from nitrogen, oxygen, and sulfur. In some embodiments, a ring is a bivalent or multivalent 5,6-fused heteroaryl ring having three heteroatoms independently selected from nitrogen, oxygen, and sulfur. In some embodiments, a ring is a bivalent or multivalent 5,6-fused heteroaryl ring having four heteroatoms independently selected from nitrogen, oxygen, and sulfur. In some embodiments, a ring is a bivalent or multivalent 5,6-fused heteroaryl ring having five heteroatoms independently selected from nitrogen, oxygen, and sulfur.

In certain embodiments, a ring is a bivalent or multivalent 5,6-fused heteroaryl ring having one heteroatom independently selected from nitrogen, oxygen, and sulfur. In some embodiments, a ring is a bivalent or multivalent indolyl ring. In some embodiments, a ring is a bivalent or multivalent benzofuranyl ring. In some embodiments, a ring is a bivalent or multivalent benzo[b]thienyl ring. In certain embodiments, a ring is a bivalent or multivalent 5,6-fused heteroaryl ring having two heteroatoms independently selected from nitrogen, oxygen, and sulfur. In some embodiments, a ring is a bivalent or multivalent azaindolyl ring. In some embodiments, a ring is a bivalent or multivalent benzimidazolyl ring. In some embodiments, a ring is a bivalent or multivalent benzothiazolyl ring. In some embodiments, a ring is a bivalent or multivalent benzoxazolyl ring. In some embodiments, a ring is a bivalent or multivalent indazolyl ring. In certain embodiments, a ring is a bivalent or multivalent 5,6-fused heteroaryl ring having three heteroatoms independently selected from nitrogen, oxygen, and sulfur. In some embodiments, a ring is a bivalent or multivalent oxazolopyridiyl, thiazolopyridinyl or imidazopyridinyl ring. In certain embodiments, a ring is a bivalent or multivalent 5,6-fused heteroaryl ring having four heteroatoms independently selected from nitrogen, oxygen, and sulfur. In some embodiments, a ring is a bivalent or multivalent purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl ring. In certain embodiments, a ring is a bivalent or multivalent 5,6-fused heteroaryl ring having five heteroatoms independently selected from nitrogen, oxygen, and sulfur.

In some embodiments, a ring is a bivalent or multivalent 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl ring. In some embodiments, a ring is a bivalent or multivalent dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl ring.

In certain embodiments, a ring is a bivalent or multivalent 6,6-fused heteroaryl ring having 1-4 heteroatoms independently selected from nitrogen, oxygen, and sulfur. In some embodiments, a ring is a bivalent or multivalent 6,6-fused heteroaryl ring having 1-2 heteroatoms independently selected from nitrogen, oxygen, and sulfur. In other embodiments, a ring is a bivalent or multivalent 6,6-fused heteroaryl ring having 1 heteroatom independently selected from nitrogen, oxygen, and sulfur. In some embodiments, a ring is a bivalent or multivalent quinolinyl ring. In some embodiments, a ring is a bivalent or multivalent isoquinolinyl ring. In some embodiments, a ring is a bivalent or multivalent 6,6-fused heteroaryl ring having 2 heteroatoms independently selected from nitrogen, oxygen, and sulfur. In some embodiments, a ring is a bivalent or multivalent quinazoline or a quinoxaline.

In some embodiments, a ring is a bivalent or multivalent 3-30 membered heterocyclic ring having 1-10 heteroatoms independently selected from oxygen, nitrogen, sulfur, phosphorus and silicon. In some embodiments, a ring is a bivalent or multivalent 3-30 membered heterocyclic ring having 1-10 heteroatoms independently selected from oxygen, nitrogen, and sulfur. In some embodiments, a ring is a bivalent or multivalent 3-30 membered heterocyclic ring having 1-5 heteroatoms independently selected from oxygen, nitrogen, sulfur, phosphorus and silicon. In some embodiments, a ring is a bivalent or multivalent 3-30 membered heterocyclic ring having 1-5 heteroatoms independently selected from oxygen, nitrogen, and sulfur.

In some embodiments, a ring is a bivalent or multivalent 3-7 membered saturated or partially unsaturated heterocyclic ring having 1-3 heteroatoms independently selected from nitrogen, oxygen, and sulfur. In some embodiments, a ring is a bivalent or multivalent a substituted 3-7 membered saturated or partially unsaturated heterocyclic ring having 1-3 heteroatoms independently selected from nitrogen, oxygen, and sulfur. In some embodiments, a ring is a bivalent or multivalent an unsubstituted 3-7 membered saturated or partially unsaturated heterocyclic ring having 1-3 heteroatoms independently selected from nitrogen, oxygen, and sulfur. In certain embodiments, a ring is a bivalent or multivalent 5-7 membered partially unsaturated monocyclic ring having 1-3 heteroatoms independently selected from nitrogen, oxygen, and sulfur. In certain embodiments, a ring is a bivalent or multivalent 5-6 membered partially unsaturated monocyclic ring having 1-3 heteroatoms independently selected from nitrogen, oxygen, and sulfur. In certain embodiments, a ring is a bivalent or multivalent 5-membered partially unsaturated monocyclic ring having 1-3 heteroatoms independently selected from nitrogen, oxygen, and sulfur. In certain embodiments, a ring is a bivalent or multivalent 6-membered partially unsaturated monocyclic ring having 1-3 heteroatoms independently selected from nitrogen, oxygen, and sulfur. In certain embodiments, a ring is a bivalent or multivalent 7-membered partially unsaturated monocyclic ring having 1-3 heteroatoms independently selected from nitrogen, oxygen, and sulfur. In some embodiments, a ring is a bivalent or multivalent 3-membered heterocyclic ring having one heteroatom selected from nitrogen, oxygen or sulfur. In some embodiments, a ring is a bivalent or multivalent 4-membered heterocyclic ring having 1-3 heteroatoms independently selected from nitrogen, oxygen, and sulfur. In some embodiments, a ring is a bivalent or multivalent 5-membered heterocyclic ring having 1-3 heteroatoms independently selected from nitrogen, oxygen, and sulfur. In some embodiments, a ring is a bivalent or multivalent 6-membered heterocyclic ring having 1-3 heteroatoms independently selected from nitrogen, oxygen, and sulfur. In some embodiments, a ring is a bivalent or multivalent 7-membered heterocyclic ring having 1-3 heteroatoms independently selected from nitrogen, oxygen, and sulfur.

In some embodiments, a ring is a bivalent or multivalent 3-membered saturated or partially unsaturated heterocyclic ring having 1-2 heteroatoms independently selected from nitrogen, oxygen, and sulfur. In some embodiments, a ring is a bivalent or multivalent 4-membered saturated or partially unsaturated heterocyclic ring having 1-2 heteroatoms independently selected from nitrogen, oxygen, and sulfur. In some embodiments, a ring is a bivalent or multivalent 5-membered saturated or partially unsaturated heterocyclic ring having 1-2 heteroatoms independently selected from nitrogen, oxygen, and sulfur. In some embodiments, a ring is a bivalent or multivalent 6-membered saturated or partially unsaturated heterocyclic ring having 1-2 heteroatoms independently selected from nitrogen, oxygen, and sulfur. In some embodiments, a ring is a bivalent or multivalent 7-membered saturated or partially unsaturated heterocyclic ring having 1-2 heteroatoms independently selected from nitrogen, oxygen, and sulfur.

In some embodiments, a ring is a bivalent or multivalent 4-membered saturated or partially unsaturated heterocyclic ring having 1-2 heteroatoms independently selected from nitrogen, oxygen, and sulfur. In some embodiments, a ring is a bivalent or multivalent 4-membered partially unsaturated heterocyclic ring having 2 heteroatoms independently selected from nitrogen, oxygen, and sulfur. In some embodiments, a ring is a bivalent or multivalent 4-membered partially unsaturated heterocyclic ring having no more than 1 heteroatom. In some embodiments, a ring is a bivalent or multivalent 4-membered partially unsaturated heterocyclic ring having no more than 1 heteroatom, wherein the heteroatom is nitrogen. In some embodiments, a ring is a bivalent or multivalent 4-membered partially unsaturated heterocyclic ring having no more than 1 heteroatom, wherein the heteroatom is oxygen. In some embodiments, a ring is a bivalent or multivalent 4-membered partially unsaturated heterocyclic ring having no more than 1 heteroatom, wherein the heteroatom is sulfur. In some embodiments, a ring is a bivalent or multivalent 4-membered partially unsaturated heterocyclic ring having 2 oxygen atoms. In some embodiments, a ring is a bivalent or multivalent 4-membered partially unsaturated heterocyclic ring having 2 nitrogen atoms. In some embodiments, a ring is a bivalent or multivalent 4-membered saturated or partially unsaturated heterocyclic ring having 1-2 heteroatoms independently selected from nitrogen, oxygen, and sulfur. In some embodiments, a ring is a bivalent or multivalent 4-membered partially unsaturated heterocyclic ring having 2 heteroatoms independently selected from nitrogen, oxygen, and sulfur. In some embodiments, a ring is a bivalent or multivalent 4-membered partially unsaturated heterocyclic ring having no more than 1 heteroatom. In some embodiments, a ring is a bivalent or multivalent 4-membered partially unsaturated heterocyclic ring having no more than 1 heteroatom, wherein the heteroatom is nitrogen. In some embodiments, a ring is a bivalent or multivalent 4-membered partially unsaturated heterocyclic ring having no more than 1 heteroatom, wherein the heteroatom is oxygen. In some embodiments, a ring is a bivalent or multivalent 4-membered partially unsaturated heterocyclic ring having no more than 1 heteroatom, wherein the heteroatom is sulfur. In some embodiments, a ring is a bivalent or multivalent 4-membered partially unsaturated heterocyclic ring having 2 oxygen atoms. In some embodiments, a ring is a bivalent or multivalent 4-membered partially unsaturated heterocyclic ring having 2 nitrogen atoms.

In some embodiments, a ring is a bivalent or multivalent 5-membered saturated or partially unsaturated heterocyclic ring having 1-2 heteroatoms independently selected from nitrogen, oxygen, and sulfur. In some embodiments, a ring is a bivalent or multivalent 5-membered partially unsaturated heterocyclic ring having 2 heteroatoms independently selected from nitrogen, oxygen, and sulfur. In some embodiments, a ring is a bivalent or multivalent 5-membered partially unsaturated heterocyclic ring having no more than 1 heteroatom. In some embodiments, a ring is a bivalent or multivalent 5-membered partially unsaturated heterocyclic ring having no more than 1 heteroatom, wherein the heteroatom is nitrogen. In some embodiments, a ring is a bivalent or multivalent 5-membered partially unsaturated heterocyclic ring having no more than 1 heteroatom, wherein the heteroatom is oxygen. In some embodiments, a ring is a bivalent or multivalent 5-membered partially unsaturated heterocyclic ring having no more than 1 heteroatom, wherein the heteroatom is sulfur. In some embodiments, a ring is a bivalent or multivalent 5-membered partially unsaturated heterocyclic ring having 2 oxygen atoms. In some embodiments, a ring is a bivalent or multivalent 5-membered partially unsaturated heterocyclic ring having 2 nitrogen atoms.

In some embodiments, a ring is a bivalent or multivalent 6-membered saturated or partially unsaturated heterocyclic ring having 1-2 heteroatoms independently selected from nitrogen, oxygen, and sulfur. In some embodiments, a ring is a bivalent or multivalent 6-membered partially unsaturated heterocyclic ring having 2 heteroatoms independently selected from nitrogen, oxygen, and sulfur. In some embodiments, a ring is a bivalent or multivalent 6-membered partially unsaturated heterocyclic ring having no more than 1 heteroatom. In some embodiments, a ring is a bivalent or multivalent 6-membered partially unsaturated heterocyclic ring having no more than 1 heteroatom, wherein the heteroatom is nitrogen. In some embodiments, a ring is a bivalent or multivalent 6-membered partially unsaturated heterocyclic ring having no more than 1 heteroatom, wherein the heteroatom is oxygen. In some embodiments, a ring is a bivalent or multivalent 6-membered partially unsaturated heterocyclic ring having no more than 1 heteroatom, wherein the heteroatom is sulfur. In some embodiments, a ring is a bivalent or multivalent 6-membered partially unsaturated heterocyclic ring having 2 oxygen atoms. In some embodiments, a ring is a bivalent or multivalent 6-membered partially unsaturated heterocyclic ring having 2 nitrogen atoms.

In certain embodiments, a ring is a bivalent or multivalent a 3-7 membered saturated or partially unsaturated heterocyclic ring having 1-2 heteroatoms independently selected from nitrogen, oxygen, and sulfur. In certain embodiments, a ring is a bivalent or multivalent oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl ring.

In certain embodiments, a ring is a bivalent or multivalent 5-6 membered partially unsaturated monocyclic ring having 1-2 heteroatoms independently selected from nitrogen, oxygen, and sulfur. In certain embodiments, a ring is a bivalent or multivalent tetrahydropyridinyl, dihydrothiazolyl, dihydrooxazolyl, or oxazolinyl group.

In some embodiments, a ring is a bivalent or multivalent 7-10 membered bicyclic saturated or partially unsaturated heterocyclic ring having 1-5 heteroatoms independently selected from nitrogen, oxygen, and sulfur. In some embodiments, a ring is a bivalent or multivalent indolinyl ring. In some embodiments, a ring is a bivalent or multivalent isoindolinyl ring. In some embodiments, a ring is a bivalent or multivalent 1, 2, 3, 4-tetrahydroquinolinyl ring. In some embodiments, a ring is a bivalent or multivalent 1, 2, 3, 4-tetrahydroisoquinolinyl ring. In some embodiments, a ring is a bivalent or multivalent azabicyclo[3.2.1]octanyl ring.

In some embodiments, a ring is a bivalent or multivalent 8-10 membered bicyclic heteroaryl ring having 1-5 heteroatoms independently selected from nitrogen, oxygen, and sulfur.

In some embodiments, a ring is a bivalent or multivalent 5,6-fused heteroaryl ring having 1-5 heteroatoms independently selected from nitrogen, oxygen, and sulfur. In some embodiments, a ring is a bivalent or multivalent 5,6-fused heteroaryl ring having 1-4 heteroatoms independently selected from nitrogen, oxygen, and sulfur. In some embodiments, a ring is a bivalent or multivalent 5,6-fused heteroaryl ring having 1-3 heteroatoms independently selected from nitrogen, oxygen, and sulfur. In some embodiments, a ring is a bivalent or multivalent 5,6-fused heteroaryl ring having two heteroatoms independently selected from nitrogen, oxygen, and sulfur. In some embodiments, a ring is a bivalent or multivalent 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl ring. In some embodiments, a ring is a bivalent or multivalent 5,6-fused heteroaryl ring having three heteroatoms independently selected from nitrogen, oxygen, and sulfur. In some embodiments, a ring is a bivalent or multivalent dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl ring. In some embodiments, a ring is a bivalent or multivalent 5,6-fused heteroaryl ring having four heteroatoms independently selected from nitrogen, oxygen, and sulfur. In some embodiments, a ring is a bivalent or multivalent 5,6-fused heteroaryl ring having five heteroatoms independently selected from nitrogen, oxygen, and sulfur.

In some embodiments, a ring is a bivalent or multivalent 5,6-fused heteroaryl ring having 1-5 heteroatoms independently selected from nitrogen, oxygen, and sulfur. In other embodiments, a ring is a bivalent or multivalent 5,6-fused heteroaryl ring having 1-2 heteroatoms independently selected from nitrogen, oxygen, and sulfur. In certain embodiments, a ring is a bivalent or multivalent 5,6-fused heteroaryl ring having one heteroatom independently selected from nitrogen, oxygen, and sulfur. In some embodiments, a ring is a bivalent or multivalent indolyl ring. In some embodiments, a ring is a bivalent or multivalent benzofuranyl ring. In some embodiments, a ring is a bivalent or multivalent benzo[b]thienyl ring. In certain embodiments, a ring is a bivalent or multivalent 5,6-fused heteroaryl ring having two heteroatoms independently selected from nitrogen, oxygen, and sulfur. In some embodiments, a ring is a bivalent or multivalent azaindolyl ring. In some embodiments, a ring is a bivalent or multivalent benzimidazolyl ring. In some embodiments, a ring is a bivalent or multivalent benzothiazolyl ring. In some embodiments, a ring is a bivalent or multivalent benzoxazolyl ring. In some embodiments, a ring is a bivalent or multivalent indazolyl ring. In certain embodiments, a ring is a bivalent or multivalent 5,6-fused heteroaryl ring having three heteroatoms independently selected from nitrogen, oxygen, and sulfur. In some embodiments, a ring is a bivalent or multivalent oxazolopyridiyl, thiazolopyridinyl or imidazopyridinyl ring. In certain embodiments, a ring is a bivalent or multivalent 5,6-fused heteroaryl ring having four heteroatoms independently selected from nitrogen, oxygen, and sulfur. In some embodiments, a ring is a bivalent or multivalent purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl ring. In certain embodiments, a ring is a bivalent or multivalent 5,6-fused heteroaryl ring having five heteroatoms independently selected from nitrogen, oxygen, and sulfur.

In certain embodiments, a ring is a bivalent or multivalent 6,6-fused heteroaryl ring having 1-5 heteroatoms independently selected from nitrogen, oxygen, and sulfur. In some embodiments, a ring is a bivalent or multivalent 6,6-fused heteroaryl ring having 1-2 heteroatoms independently selected from nitrogen, oxygen, and sulfur. In other embodiments, a ring is a bivalent or multivalent 6,6-fused heteroaryl ring having one heteroatom selected from nitrogen, oxygen, and sulfur. In some embodiments, a ring is a bivalent or multivalent quinolinyl ring. In some embodiments, a ring is a bivalent or multivalent isoquinolinyl ring. In some embodiments, a ring is a bivalent or multivalent 6,6-fused heteroaryl ring having two heteroatoms independently selected from nitrogen, oxygen, and sulfur. In some embodiments, a ring is a bivalent or multivalent quinazolinyl, phthalazinyl, quinoxalinyl or naphthyridinyl ring. In some embodiments, a ring is a bivalent or multivalent 6,6-fused heteroaryl ring having three heteroatoms independently selected from nitrogen, oxygen, and sulfur. In some embodiments, a ring is a bivalent or multivalent pyridopyrimidinyl, pyridopyridazinyl, pyridopyrazinyl, or benzotriazinyl ring. In some embodiments, a ring is a bivalent or multivalent 6,6-fused heteroaryl ring having four heteroatoms independently selected from nitrogen, oxygen, and sulfur. In some embodiments, a ring is a bivalent or multivalent pyridotriazinyl, pteridinyl, pyrazinopyrazinyl, pyrazinopyridazinyl, pyridazinopyridazinyl, pyrimidopyridazinyl or pyrimidopyrimidinyl ring. In some embodiments, a ring is a bivalent or multivalent 6,6-fused heteroaryl ring having five heteroatoms independently selected from nitrogen, oxygen, and sulfur.

In some embodiments, a ring formed by two or more groups taken together, which is typically optionally substituted, is a monocyclic saturated 5-7 membered ring having no additional heteroatoms in addition to intervening heteroatoms, if any. In some embodiments, a ring formed by two or more groups taken together is a monocyclic saturated 5-membered ring having no additional heteroatoms in addition to intervening heteroatoms, if any. In some embodiments, a ring formed by two or more groups taken together is a monocyclic saturated 6-membered ring having no additional heteroatoms in addition to intervening heteroatoms, if any. In some embodiments, a ring formed by two or more groups taken together is a monocyclic saturated 7-membered ring having no additional heteroatoms in addition to intervening heteroatoms, if any.

In some embodiments, a ring formed by two or more groups taken together is a bicyclic, saturated, partially unsaturated, or aryl 5-30 membered ring having, in addition to the intervening heteroatoms, if any, 0-10 heteroatoms independently selected from oxygen, nitrogen, sulfur, phosphorus and silicon. In some embodiments, a ring formed by two or more groups taken together is a bicyclic, saturated, partially unsaturated, or aryl 5-30 membered ring having, in addition to the intervening heteroatoms, if any, 0-10 heteroatoms independently selected from oxygen, nitrogen, and sulfur. In some embodiments, a ring formed by two or more groups taken together is a bicyclic and saturated 8-10 membered bicyclic ring having no additional heteroatoms in addition to intervening heteroatoms, if any. In some embodiments, a ring formed by two or more groups taken together is a bicyclic and saturated 8-membered bicyclic ring having no additional heteroatoms in addition to intervening heteroatoms, if any. In some embodiments, a ring formed by two or more groups taken together is a bicyclic and saturated 9-membered bicyclic ring having no additional heteroatoms in addition to intervening heteroatoms, if any. In some embodiments, a ring formed by two or more groups taken together is a bicyclic and saturated 10-membered bicyclic ring having no additional heteroatoms in addition to intervening heteroatoms, if any. In some embodiments, a ring formed by two or more groups taken together is bicyclic and comprises a 5-membered ring fused to a 5-membered ring.

In some embodiments, a ring formed by two or more groups taken together is bicyclic and comprises a 5-membered ring fused to a 6-membered ring. In some embodiments, the 5-membered ring comprises one or more intervening nitrogen, phosphorus and oxygen atoms as ring atoms. In some embodiments, a ring formed by two or more groups taken together comprises a ring system having the backbone structure of

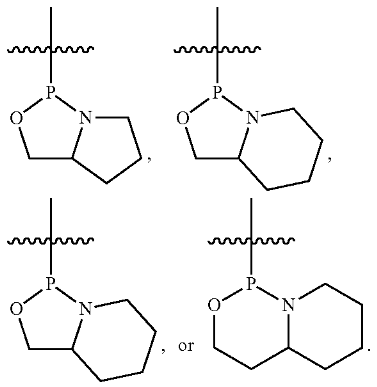

In some embodiments, a ring formed by two or more groups taken together is a polycyclic, saturated, partially unsaturated, or aryl 3-30 membered ring having, in addition to the intervening heteroatoms, if any, 0-10 heteroatoms independently selected from oxygen, nitrogen, sulfur, phosphorus and silicon. In some embodiments, a ring formed by two or more groups taken together is a polycyclic, saturated, partially unsaturated, or aryl 3-30 membered ring having, in addition to the intervening heteroatoms, if any, 0-10 heteroatoms independently selected from oxygen, nitrogen, and sulfur.

In some embodiments, a ring formed by two or more groups taken together is monocyclic, bicyclic or polycyclic and comprises a 5-10 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-9 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-8 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-7 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-6 membered monocyclic ring whose ring atoms comprise one or more intervening nitrogen, phosphorus and/or oxygen atoms.

In some embodiments, a ring formed by two or more groups taken together is monocyclic, bicyclic or polycyclic and comprises a 5-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 6-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 7-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 8-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 9-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 10-membered monocyclic ring whose ring atoms comprise one or more intervening nitrogen, phosphorus and/or oxygen atoms.

In some embodiments, a ring formed by two or more groups taken together is monocyclic, bicyclic or polycyclic and comprises a 5-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 6-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 7-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 8-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 9-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 10-membered ring whose ring atoms consist of carbon atoms and the intervening nitrogen, phosphorus and oxygen atoms.

In some embodiments, a ring formed by two or more groups taken together comprises a ring system having the backbone structure of

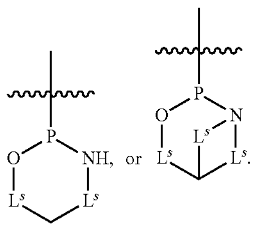

In some embodiments, rings described herein are unsubstituted. In some embodiments, rings described herein are substituted. In some embodiments, substituents are selected from those described in example compounds provided in the present disclosure.

In some embodiments, provided features, e.g., purity (e.g., overall purity, diastereomeric purity, enantiomeric purity, etc.), selectivity (e.g., overall selectivity, region-selectivity, diastereomeric selectivity, enantiomeric selectivity, etc.), levels (e.g., predetermined levels (of oligonucleotides, chiral auxiliaries, etc.), levels of activities, etc.), etc., are described as percentages or ranges of percentages. A percentage can be any percentage within provided ranges. For example, in some embodiments, depending on the ranges if any, a percentage is about 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%. In some embodiments, depending on the ranges if any, a percentage is at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%. In some embodiments, a percentage is at least 1%. In some embodiments, a percentage is at least 2%. In some embodiments, a percentage is at least 3%. In some embodiments, a percentage is at least 4%. In some embodiments, a percentage is at least 5%. In some embodiments, a percentage is at least 10%. In some embodiments, a percentage is at least 15%. In some embodiments, a percentage is at least 20%. In some embodiments, a percentage is at least 25%. In some embodiments, a percentage is at least 30%. In some embodiments, a percentage is at least 35%. In some embodiments, a percentage is at least 40%. In some embodiments, a percentage is at least 45%. In some embodiments, a percentage is at least 50%. In some embodiments, a percentage is at least 55%. In some embodiments, a percentage is at least 60%. In some embodiments, a percentage is at least 65%. In some embodiments, a percentage is at least 70%. In some embodiments, a percentage is at least 75%. In some embodiments, a percentage is at least 80%. In some embodiments, a percentage is at least 85%. In some embodiments, a percentage is at least 90%. In some embodiments, a percentage is at least 91%. In some embodiments, a percentage is at least 92%. In some embodiments, a percentage is at least 93%. In some embodiments, a percentage is at least 94%. In some embodiments, a percentage is at least 95%. In some embodiments, a percentage is at least 96%. In some embodiments, a percentage is at least 97%. In some embodiments, a percentage is at least 98%. In some embodiments, a percentage is at least 99%. In some embodiments, a percentage is about 1%. In some embodiments, a percentage is about 2%. In some embodiments, a percentage is about 3%. In some embodiments, a percentage is about 4%. In some embodiments, a percentage is about 5%. In some embodiments, a percentage is about 10%. In some embodiments, a percentage is about 15%. In some embodiments, a percentage is about 20%. In some embodiments, a percentage is about 25%. In some embodiments, a percentage is about 30%. In some embodiments, a percentage is about 35%. In some embodiments, a percentage is about 40%. In some embodiments, a percentage is about 45%. In some embodiments, a percentage is about 50%. In some embodiments, a percentage is about 55%. In some embodiments, a percentage is about 60%. In some embodiments, a percentage is about 65%. In some embodiments, a percentage is about 70%. In some embodiments, a percentage is about 75%. In some embodiments, a percentage is about 80%. In some embodiments, a percentage is about 85%. In some embodiments, a percentage is about 90%. In some embodiments, a percentage is about 91%. In some embodiments, a percentage is about 92%. In some embodiments, a percentage is about 93%. In some embodiments, a percentage is about 94%. In some embodiments, a percentage is about 95%. In some embodiments, a percentage is about 96%. In some embodiments, a percentage is about 97%. In some embodiments, a percentage is about 98%. In some embodiments, a percentage is about 99%. In some embodiments, a percentage is less than 1%. In some embodiments, a percentage is less than 2%. In some embodiments, a percentage is less than 3%. In some embodiments, a percentage is less than 4%. In some embodiments, a percentage is less than 5%. In some embodiments, a percentage is less than 10%. In some embodiments, a percentage is less than 15%. In some embodiments, a percentage is less than 20%. In some embodiments, a percentage is less than 25%. In some embodiments, a percentage is less than 30%. In some embodiments, a percentage is less than 35%. In some embodiments, a percentage is less than 40%. In some embodiments, a percentage is less than 45%. In some embodiments, a percentage is less than 50%. In some embodiments, a percentage is less than 55%. In some embodiments, a percentage is less than 60%. In some embodiments, a percentage is less than 65%. In some embodiments, a percentage is less than 70%. In some embodiments, a percentage is less than 75%. In some embodiments, a percentage is less than 80%. In some embodiments, a percentage is less than 85%. In some embodiments, a percentage is less than 90%. In some embodiments, a percentage is less than 91%. In some embodiments, a percentage is less than 92%. In some embodiments, a percentage is less than 93%. In some embodiments, a percentage is less than 94%. In some embodiments, a percentage is less than 95%. In some embodiments, a percentage is less than 96%. In some embodiments, a percentage is less than 97%. In some embodiments, a percentage is less than 98%. In some embodiments, a percentage is less than 99%.

Provided methods may comprise use of a temperature higher and/or lower than room temperature. In some embodiments, provided methods, e.g., in a reaction forming a phosphoramidite, comprise use of a lowered temperature, such as a temperature equal to or lower than about −78, −75, −70, −65, −60, −55, −50, −45, −40, −35, −30, −25, −20, −15, −10, −5, 0, 5, 10, 15, or 20° C. In some embodiments, provided methods, e.g., in a reaction forming a phosphoramidite, comprise use of an elevated temperature, such as a temperature equal to or more than about 25, 30, 35, 40, 45, 50, 55, 60, 65, 70, 75, 80, 85, 90, 95, 100, 110, 120, 130, 140 or 150° C. In some embodiments, provided methods comprise a temperature increase from a lowered temperature to another lowered temperature. In some embodiments, provided methods comprise a temperature increase from a lowered temperature to room temperature. In some embodiments, provided methods comprise a temperature increase from room temperature to an elevated temperature. In some embodiments, provided methods comprise a temperature increase from a lowered temperature to an elevated temperature. In some embodiments, provided methods comprise a temperature decrease from an elevated temperature to another elevated temperature. In some embodiments, provided methods comprise a temperature decrease from an elevated temperature to room temperature. In some embodiments, provided methods comprise a temperature decrease from room temperature to a lowered temperature. In some embodiments, provided methods comprise a temperature decrease from an elevated temperature to a lowered temperature.

Various solvents are suitable for use in provided methods. In some embodiments, reactions for forming phosphoramidites are performed in a solvent comprising ether. In some embodiments, reactions for forming phosphoramidites are performed in a solvent comprising THF. In some embodiments, reactions for forming phosphoramidites are performed in THF. Suitable solvents are widely known (e.g., those in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784, solvents of each of which are incorporated herein by reference) and can be utilized in accordance with the present disclosure.

In some embodiments, one or more steps are performed under an inert gas. In some embodiments, formation of phosphoramidites is performed under an inert gas. In some embodiments, one or more steps of oligonucleotide synthesis cycle is performed under an inert gas. In some embodiments, an inert gas is argon. In some embodiments, an inert gas is nitrogen.

In some embodiments, one or more steps are performed under increased pressure. In some embodiments, one or more steps are performed under vacuum. In some embodiments, filtration is performed under vacuum.

In some embodiments, a provided compound, e.g., a compound of formula I, I-a, I-a-1, I-a-2, I-b, I-c, I-d, I-e, II, II-a, II-b, III, III-a, or III-b, or a salt thereof, a compound of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c, VI-c-1, VI-c-2, VI-d, or VI-e, or a salt thereof, or an oligonucleotide of formula O-I or salt thereof, etc., has a purity which is about or more than 50%, 60%, 70%, 75%, 80%, 85%, 90%, 91%, 92%, 93%, 94%, 95%, 96%, 97%, 98%, or 99%. In some embodiments, a purity is about 50% or more. In some embodiments, a purity is about 55% or more. In some embodiments, a purity is about 60% or more. In some embodiments, a purity is about 65% or more. In some embodiments, a purity is about 70% or more. In some embodiments, a purity is about 75% or more. In some embodiments, a purity is about 80% or more. In some embodiments, a purity is about 85% or more. In some embodiments, a purity is about 90% or more. In some embodiments, a purity is about 91% or more. In some embodiments, a purity is about 92% or more. In some embodiments, a purity is about 93% or more. In some embodiments, a purity is about 94% or more. In some embodiments, a purity is about 95% or more. In some embodiments, a purity is about 96% or more. In some embodiments, a purity is about 97% or more. In some embodiments, a purity is about 98% or more. In some embodiments, a purity is about 99% or more. In some embodiments, a purity is about 99.5% or more.

In some embodiments, a provided compound, e.g., a chiral auxiliary, a phosphoramidite, an oligonucleotide, etc., has a diastereomeric purity of at least 60%, 65%, 70%, 75%, 80%, 85%, 90%, 91%, 92%, 93%, 94%, 95%, 96%, 97%, 98%, or 99%. In some embodiments, a provided compound has a diastereomeric purity of at least 60%. In some embodiments, a provided compound has a diastereomeric purity of at least 70%. In some embodiments, a provided compound has a diastereomeric purity of at least 80%. In some embodiments, a provided compound has a diastereomeric purity of at least 85%. In some embodiments, a provided compound has a diastereomeric purity of at least 90%. In some embodiments, a provided compound has a diastereomeric purity of at least 91%. In some embodiments, a provided compound has a diastereomeric purity of at least 92%. In some embodiments, a provided compound has a diastereomeric purity of at least 93%. In some embodiments, a provided compound has a diastereomeric purity of at least 94%. In some embodiments, a provided compound has a diastereomeric purity of at least 95%. In some embodiments, a provided compound has a diastereomeric purity of at least 96%. In some embodiments, a provided compound has a diastereomeric purity of at least 97%. In some embodiments, a provided compound has a diastereomeric purity of at least 98%. In some embodiments, a provided compound has a diastereomeric purity of at least 99%. In some embodiments, a provided compound has a diastereomeric purity of at least 99.5%.

In some embodiments, a chiral element, e.g., a chiral center (carbon, phosphorus, etc.) of a provided compound has a diastereomeric purity of 60%-100%. In some embodiments, a chiral element. e.g., a chiral center (carbon, phosphorus, etc.) of a provided compound has a diastereomeric purity of at least 60%, 65%, 70%, 75%, 80%, 85%, 90%, 91%, 92%, 93%, 94%, 95%, 96%, 97%, 98%, or 99%. In some embodiments, a chiral element is a chiral carbon. In some embodiments, a chiral element is a chiral phosphorus (e.g., a linkage phosphorus atom in a chiral internucleotidic linkage). In some embodiments, a chiral element has a diastereomeric purity of at least 60%. In some embodiments, a chiral center has a diastereomeric purity of at least 70%. In some embodiments, a chiral center has a diastereomeric purity of at least 80%. In some embodiments, a chiral center has a diastereomeric purity of at least 85%. In some embodiments, a chiral center has a diastereomeric purity of at least 90%. In some embodiments, a chiral center has a diastereomeric purity of at least 91%. In some embodiments, a chiral center has a diastereomeric purity of at least 92%. In some embodiments, a chiral center has a diastereomeric purity of at least 93%. In some embodiments, a chiral center has a diastereomeric purity of at least 94%. In some embodiments, a chiral center has a diastereomeric purity of at least 95%. In some embodiments, a chiral center has a diastereomeric purity of at least 96%. In some embodiments, a chiral center has a diastereomeric purity of at least 97%. In some embodiments, a chiral center has a diastereomeric purity of at least 98%. In some embodiments, a chiral center has a diastereomeric purity of at least 99%. In some embodiments, a chiral center has a diastereomeric purity of at least 99.5%.

In some embodiments, the present disclosure provides methods, e.g., methods for preparing chiral auxiliaries, phosphoramidites, oligonucleotides, etc., with high stereoselectivity. In some embodiments, the present disclosure provides methods with high diastereoselectivity. In some embodiments, the present disclosure provides methods with high enantioselectivity. In some embodiments, the present disclosure provides methods with both high diastereoselectivity and high enantioselectivity. In some embodiments, a selectivity is about 60%-100%. In some embodiments, a selectivity is at least 60%, 65%, 70%, 75%, 80%, 85%, 90%, 91%, 92%, 93%, 94%, 95%, 96%, 97%, 98%, or 99%. In some embodiments, a diastereoselectivity is at least 60%, 65%, 70%, 75%, 80%, 85%, 90%, 91%, 92%, 93%, 94%, 95%, 96%, 97%, 98%, or 99%. In some embodiments, a enantioselectivity is at least 60%, 65%, 70%, 75%, 80%, 85%, 90%, 91%, 92%, 93%, 94%, 95%, 96%, 97%, 98%, or 99%. In some embodiments, both a diastereoselectivity and an enantioselectivity are at least 60%, 65%, 70%, 75%, 80%, 85%, 90%, 91%, 92%, 93%, 94%, 95%, 96%, 97%, 98%, or 99%. In some embodiments, a selectivity is at least 60%. In some embodiments, a selectivity is at least 70%. In some embodiments, a selectivity is at least 80%. In some embodiments, a selectivity is at least 85%. In some embodiments, a selectivity is at least 90%. In some embodiments, a selectivity is at least 91%. In some embodiments, a selectivity is at least 92%. In some embodiments, a selectivity is at least 93%. In some embodiments, a selectivity is at least 94%. In some embodiments, a selectivity is at least 95%. In some embodiments, a selectivity is at least 96%. In some embodiments, a selectivity is at least 97%. In some embodiments, a selectivity is at least 98%. In some embodiments, a selectivity is at least 99%. In some embodiments, a selectivity is at least 99.5%.

As demonstrated herein, provided technologies can surprisingly improve yields and/or purity. In some embodiments, the absolute improvement is about 5%, 10%, 15%, 20%, 25%, 30%, 35%, 40%, 45%, 50%, 55%, 60%, 65%, 70%, 75%, 80%, 85%, 90%, 95% or more. In some embodiments, the absolute improvement is greater than about 5%, 10%, 15%, 20%, 25%, 30%, 35%, 40%, 45%, 50%, 55%, 60%, 65%, 70%, 75%, 80%, 85%, 90%, 95% or more. In some embodiments, yield from a provided technology is greater than about 80%, while yield from a corresponding technology is less than about 60% (corresponding to an absolute improvement of grater than 20%). In some embodiments, the improvement relative to a corresponding technology is greater than about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300%, 400%, 500%, 600%, 700%, 800%, 900% or more.

In some embodiments, as readily appreciated by a person having ordinary skill in the art, in provided oligonucleotide compositions oligonucleotides may exist as salts. In some embodiments, provided oligonucleotide compositions are pharmaceutical compositions. In some embodiments, provided oligonucleotides exist as pharmaceutically acceptable salts.

In some embodiments, one or more lipid moieties, one or more targeting moieties, and/or one or more carbohydrate moieties may be independently and optionally incorporated into oligonucleotides. In some embodiments, provided oligonucleotides comprise one or more lipid moieties, one or more targeting moieties, and/or one or more carbohydrate moieties. Example lipid moieties, targeting moieties, and carbohydrate moieties are widely known (e.g., those in 9598458, U.S. Pat. Nos. 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784, lipid moieties, targeting moieties, and carbohydrate moieties of each of which are incorporated herein by reference) and can be utilized in accordance with the present disclosure.

In some embodiments, the present disclosure provides multimers of provided oligonucleotides. In some embodiments, the present disclosure provides multimers of provided oligonucleotides, each of which independently has the structure of formula O-I or a salt thereof. In some embodiments, provided multimers are of oligonucleotides of the same structure. In some embodiments, provided multimers are of oligonucleotides of different structures.

Unless otherwise stated, structures depicted herein are also meant to include all isomeric (e.g., enantiomeric, diastereomeric, and geometric (or conformational)) forms of the structures. Unless otherwise stated, all tautomeric forms of compounds of the present disclosure are included. Additionally, unless otherwise stated, structures depicted herein are also meant to include compounds that differ only in the presence of one or more isotopically enriched atoms. For example, compounds having present structures except for replacement of hydrogen with deuterium and/or tritium, or replacement of carbon by $^{11}C$, $^{13}C$, and/or $^{14}C$ are included. Such compounds are useful, for example, as analytical tools or probes in biological assays. Unless otherwise specified, compounds, e.g., oligonucleotides, etc. include salts thereof.

In some embodiments, provided compounds are isotope labelled. In some embodiments, labeled compounds are useful for diagnosis, detection, modulation of one or more properties, modulation of activities, etc. In some embodiments, an isotope label is selected from $^{2}H$, $^{3}H$, $^{11}C$, $^{13}C$, $^{14}C$, $^{15}N$, $^{18}O$, $^{32}P$, $^{35}S$, etc. In some embodiments, an isotope label is selected from $^{2}H$, $^{3}H$, $^{11}C$, $^{13}C$, $^{14}C$, $^{15}N$, $^{18}O$, $^{32}P$, and $^{35}S$. In some embodiments, an isotope is a stable isotope. In some embodiments, an isotope is selected from $^{2}H$, $^{11}C$, $^{15}N$, and $^{18}O$. In some embodiments, an isotope is radioactive. In some embodiments, an isotope is selected from $^{3}H$, $^{32}P$, and $^{35}S$. In some embodiments, a provided compound comprises a $^{2}H$ label. In some embodiments, a provided compound comprises a $^{3}H$ label. In some embodiments, a provided compound comprises a $^{11}C$ label. In some embodiments, a provided compound comprises a $^{13}C$ label. In some embodiments, a provided compound comprises a $^{14}C$ label. In some embodiments, a provided compound comprises a $^{15}N$ label. In some embodiments, a provided compound comprises a $^{18}O$ label. In some embodiments, a provided compound comprises a $^{32}P$ label. In some embodiments, a provided compound comprises a $^{35}S$ label. In some embodiments, a provided compound comprises one and no more than one type of isotope label. In some embodiments, a provided compound comprises two or more types of isotope labels. In some embodiments, a provided compound comprises one or more types of isotope labels, each of which is independently enriched at least 1.5, 2, 3, 4, 5, 6, 7, 8, 9, 10, 50, 100, 1,000, 5,000, 10,000 or more folds or natural level. In some embodiments, a label is of an atom % of at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 99.5%. In some embodiments, a label is of an atom % of at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 99.5%. In some embodiments, essentially all atoms at one or more position are labelled (atom % greater than 99%).

Various methods described herein or known in the art can be utilized for confirming or identifying the stereochemistry pattern of the backbone of an oligonucleotide and/or stereochemistry of particular internucleotidic linkages, and/or determining the diastereoselectivity of one or more chiral internucleotidic linkages. Useful technologies include, as non-limiting examples: NMR (e.g., 1D (one-dimensional) and/or 2D (two-dimensional) $^{1}H$-$^{31}P$ HETCOR (heteronuclear correlation spectroscopy)), HPLC, RP-HPLC, mass spectrometry, LC-MS, and/or stereospecific nucleases. In some embodiments, stereospecific nucleases include: benzonase, micrococcal nuclease, and svPDE (snake venom phosphodiesterase), which are specific for internucleotidic linkages in the Rp configuration (e.g., a PS in the Rp configuration); and nuclease P1, mung bean nuclease, and nuclease S1, which are specific for internucleotidic linkages in the Sp configuration (e.g., a PS in the Sp configuration). Without wishing to be bound by any particular theory, the present disclosure notes that, in at least some cases, stereospecificity of a particular nuclease may be altered by a modification (e.g., 2'-modification) of a sugar, by a base sequence, or by a stereochemical context. For example, in at least some cases, benzonase and micrococcal nuclease, which are specific for Rp internucleotidic linkages, were both unable to cleave an isolated PS Rp internucleotidic linkage flanked by PS Sp internucleotidic linkages.

In some embodiments, in a compound or structure of the present disclosure, a heteroatom is boron, oxygen, sulfur, nitrogen, phosphorus, or silicon (including their oxidized forms, salt forms, etc.). In some embodiments, a heteroatom is oxygen, sulfur, nitrogen, phosphorus or silicon. In some embodiments, a heteroatom is oxygen, sulfur, nitrogen, or phosphorus. In some embodiments, a heteroatom is oxygen, sulfur, nitrogen, or silicon. In some embodiments, a heteroatom is oxygen, sulfur, or nitrogen. In some embodiments, each heteroatom is independently boron, oxygen, sulfur, nitrogen, phosphorus, or silicon (including their oxidized forms, salt forms, etc.). In some embodiments, each heteroatom is independently oxygen, sulfur, nitrogen, phosphorus or silicon. In some embodiments, each heteroatom is independently oxygen, sulfur, nitrogen, or phosphorus. In some embodiments, each heteroatom is independently oxygen, sulfur, nitrogen, or silicon. In some embodiments, each heteroatom is independently oxygen, sulfur, or nitrogen.

Among other things, the present disclosure provides the following Example Embodiments:

1. A method for preparing a composition comprising a plurality of oligonucleotides comprising:
   (1) a coupling step;
   (2) optionally a pre-modification capping step;
   (3) a modification step;
   (4) optionally a post-modification capping step; and
   (5) optionally a de-blocking step.
2. A method for preparing a composition comprising a plurality of oligonucleotides comprising:
   (1) a coupling step comprising:
      contacting a de-blocked composition comprising a plurality of de-blocked oligonucleotides (a de-blocked oligonucleotide composition) or nucleosides, which is de-blocked in that each independently comprises a free hydroxyl group, with a coupling reagent system comprising a partner compound which comprises a nucleoside unit; and
      coupling a partner compound with the free hydroxyl groups of a plurality of de-blocked oligonucleotides or nucleosides;
      wherein the coupling step provides a coupling product composition comprising a plurality of coupling product oligonucleotides, each of which independently comprises an internucleotidic linkage connecting a hydroxyl group of a de-blocked oligonucleotide with a nucleoside unit of a partner compound;
   (2) optionally a pre-modification capping step comprising:
      contacting a coupling product composition with a pre-modification capping reagent system; and
      capping one or more functional groups of the coupling product composition;
      wherein the pre-modification capping step provides a pre-modification capping product composition comprising a plurality of pre-modification capping product oligonucleotides;
   (3) a modification step comprising:
      contacting a coupling product composition with a modification reagent system comprising a modification reagent, and modifying one or more internucleotidic linkages of one or more coupling product oligonucleotides; or
      contacting a pre-modification capping product composition with a modification reagent system and modifying one or more linkages of one or more pre-modification capping product oligonucleotides;
      wherein the modification step provides a modification product composition comprising a plurality of modification product oligonucleotides:
   (4) optionally a post-modification capping step comprising:
      contacting a modification product composition with a post-modification capping reagent system; and
      capping one or more functional groups of a plurality of oligonucleotides of the modification product composition;
      wherein the post-modification capping step provides a post-modification capping product composition comprising a plurality of post-modification capping product oligonucleotides; and
   (5) optionally a de-blocking step comprising:
      contacting a modification product composition, or a post-modification capping product composition, with a de-blocking reagent system;
      wherein the deblocking step provides a de-blocking product composition comprising a plurality of de-blocking product oligonucleotides, each of which independently comprises a free hydroxyl group.
3. The method of any one of the preceding embodiments, comprising a pre-modification capping step.
4. The method of any one of the preceding embodiments, comprising a post-modification capping step.
5. The method of any one of the preceding embodiments, comprising a de-blocking step.
6. The method of any one of the preceding embodiments, comprising repeating (1) through (5) a number of times.
7. A method for preparing a composition comprising a plurality of oligonucleotides comprising one or more cycles, each cycle independently comprising:
   (1) a coupling step;
   (2) optionally a pre-modification capping step;
   (3) a modification step;
   (4) optionally a post-modification capping step; and
   (5) optionally a de-blocking step.
8. A method for preparing a composition comprising a plurality of oligonucleotides comprising one or more cycles, each cycle independently comprising:
   (1) a coupling step comprising:
      contacting a de-blocked composition comprising a plurality of de-blocked oligonucleotides (a de-blocked oligonucleotide composition) or nucleosides, which is de-blocked in that each independently comprises a free hydroxyl group, with a coupling reagent system comprising a partner compound which comprises a nucleoside unit; and coupling a partner compound with the free hydroxyl groups of a plurality of de-blocked oligonucleotides or nucleosides;

wherein the coupling step provides a coupling product composition comprising a plurality of coupling product oligonucleotides, each of which independently comprises an internucleotidic linkage connecting a hydroxyl group of a de-blocked oligonucleotide with a nucleoside unit of a partner compound;

(2) optionally a pre-modification capping step comprising:

contacting a coupling product composition with a pre-modification capping reagent system; and capping one or more functional groups of the coupling product composition;

wherein the pre-modification capping step provides a pre-modification capping product composition comprising a plurality of pre-modification capping product oligonucleotides;

(3) a modification step comprising:

contacting a coupling product composition with a modification reagent system comprising a modification reagent, and modifying one or more internucleotidic linkages of one or more coupling product oligonucleotides; or contacting a pre-modification capping product composition with a modification reagent system and modifying one or more linkages of one or more pre-modification capping product oligonucleotides;

wherein the modification step provides a modification product composition comprising a plurality of modification product oligonucleotides;

(4) optionally a post-modification capping step comprising:

contacting a modification product composition with a post-modification capping reagent system; and capping one or more functional groups of a plurality of oligonucleotides of the modification product composition;

wherein the post-modification capping step provides a post-modification capping product composition comprising a plurality of post-modification capping product oligonucleotides;

(5) optionally a de-blocking step comprising:

contacting a modification product composition, or a post-modification capping product composition, with a de-blocking reagent system;

wherein the deblocking step provides a de-blocking product composition comprising a plurality of de-blocking product oligonucleotides, each of which independently comprises a free hydroxyl group.

9. The method of any one of embodiments 7-8, comprising repeating the cycles one or more times until an oligonucleotide length is achieved.

10. The method of any one of embodiments 7-9, wherein one or more cycles comprise a pre-modification capping step.

11. The method of any one of embodiments 7-10, wherein one or more cycles comprise a post-modification capping step.

12. The method of any one of embodiments 7-11, wherein one or more cycles comprise a de-blocking step.

13. The method of any one of embodiments 7-12, wherein one or more cycles comprise no pre-modification capping step.

14. The method of any one of embodiments 7-13, wherein one or more cycles comprise no post-modification capping step.

15. The method of any one of embodiments 13-14, wherein one or more of the cycles independently comprises a coupling step which forms a non-chirally controlled internucleotidic linkage.

16. The method of embodiment 15, wherein the non-chirally controlled internucleotidic linkage is of formula VII-b or a salt form thereof, wherein —X-$L^s$-$R^5$ is -$L^7$-$R^1$.

17. The method of embodiment 16, wherein the non-chirally controlled internucleotidic linkage is of formula VII-b or a salt form thereof, wherein —X-$L^s$-$R^5$ is —$OCH_2CH_2CN$.

18. The method of any one of embodiments 13-17, wherein one or more of the cycles independently comprises a coupling step in which the coupling partner is a phosphoramidite containing no chiral elements other than those in the sugar and phosphorus.

19. The method of any one of embodiments 13-18, wherein one or more of the cycles independently comprises a coupling step in which the coupling partner is a phosphoramidite containing no chiral auxiliaries.

20. The method of any one of embodiments 13-19, wherein one or more of the cycles comprises a modification step which forms a non-chirally controlled internucleotidic linkage.

21. The method of embodiment 20, wherein the non-chirally controlled internucleotidic linkage is of formula VII or a salt form thereof, wherein —X-$L^s$-$R^5$ is -$L^7$-$R^1$.

22. The method of embodiment 21, wherein the non-chirally controlled internucleotidic linkage is of formula VII or a salt form thereof, wherein —X-$L^s$-$R^5$ is —$OCH_2CH_2CN$.

23. The method of any one of embodiments 13-22, wherein one or more of the cycles comprises a coupling step which forms a chirally controlled internucleotidic linkage.

24. The method of any one of embodiments 13-23, wherein one or more of the cycles comprises a modification step which forms a chirally controlled internucleotidic linkage.

25. The method of any one of embodiments 7-23, wherein one or more cycles comprise a pre-modification capping step and post-modification capping step.

26. The method of any one of embodiments 7-25, wherein one or more cycles comprise a pre-modification capping step which is immediately followed by a modification step which is immediately followed by a post-modification capping step.

27. The method of any one of embodiments 25-26, wherein one or more of the cycles each independently comprises a coupling step that forms a chirally controlled internucleotidic linkage.

28. The method of any one of embodiments 25-26, wherein each of the cycles independently comprises a coupling step that forms a chirally controlled internucleotidic linkage.

29. The method of embodiment 23, 27 or 28, wherein the chirally controlled internucleotidic linkage is of formula VII or NL-III, wherein $P^L$ is P, and —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein at least one of $R^5$ or $R^6$ is —H.

30. The method of embodiment 29, wherein $R^5$ is —H.

31. The method of any one of embodiments 25-30, wherein one or more of the cycles each independently comprises a modification step that forms a chirally controlled internucleotidic linkage.

32. The method of any one of embodiments 25-30, wherein each of the cycles independently comprises a modification step that forms a chirally controlled internucleotidic linkage.

33. The method of embodiment 24, 31 or 32, wherein the chirally controlled internucleotidic linkage is of formula VII or NL-III, wherein $P^L$ is P(═O), P(═S) or $P^N$, and —X-$L^s$-$R^5$ is of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein at least one of $R^5$ or $R^6$ is —C(O)R'.

34. The method of embodiment 33, wherein $R^6$ is —C(O) R'.

35. The method of embodiment 34, wherein R' is —$CH_3$.

36. The method of any one of the preceding embodiments, wherein:
   - the method comprises both a pre-modification capping step and a post-modification capping step, wherein there are no steps other than modification steps between the pre-modification capping and post-modification capping steps; or
   - the method comprises both a pre-modification capping step and a post-modification capping step, wherein there are no steps other than modification steps between the pre-modification capping and post-modification capping steps, wherein a pre-modification capping reagent system is different from a post-modification reagent system; or
   - the method comprises a pre-modification capping step and a modification step; or
   - the method comprises a post-modification capping step; or
   - the method comprises a post-modification capping step; or
   - the method comprises a coupling step, a modification step, and one or more pre-modification capping steps between the coupling step and the modification step, wherein for at least one pre-modification capping step between the coupling step and the modification step, its pre-modification capping reagent system comprises no esterification catalyst, and no agent that is converted into an esterification catalyst when the pre-modification capping reagent system contacts a plurality of oligonucleotides to be capped; or
   - the method comprises a coupling step, a modification step, and one or more pre-modification capping steps between the coupling step and the modification step, wherein for each pre-modification capping step between the coupling step and the modification step, the pre-modification capping step caps amino groups selectively over hydroxyl groups.

37. The method of any one of the preceding embodiments, wherein:
   - the method comprises both a pre-modification capping step and a post-modification capping step, wherein there are no steps other than modification steps between the pre-modification capping and post-modification capping steps, wherein a post-modification capping step comprises contacting a modification product composition comprising a plurality of modification product oligonucleotides, each of which independently comprises a linkage phosphorus bonded to an atom that is not oxygen; or
   - the method comprises both a pre-modification capping step and a post-modification capping step, wherein there are no steps other than modification steps between the pre-modification capping and post-modification capping steps, wherein a pre-modification capping reagent system is different from a post-modification reagent system; or
   - the method comprises a pre-modification capping step, wherein the pre-modification capping reagent system caps a plurality of non-hydroxyl groups of a plurality of coupling product oligonucleotides, and a modification step that comprises sulfurization, which sulfurization provides a modification product composition comprising a plurality of modification product oligonucleotides, each of which independently comprises a P═S moiety; or
   - the method comprises a post-modification capping step, comprising contacting a modification product composition comprising a plurality of modification product oligonucleotides, each of which independently comprises a linkage that comprises at least one chirally controlled chiral center in that at least 80%, 85%, 90%, 95%, 96%, 97%, 98% or 99% oligomeric compounds within the modification product composition comprising the chiral center and having the same constitution share the same stereochemical configuration at the chiral center; or
   - the method comprises a post-modification capping step, and a coupling reagent system comprising a chiral partner compound that comprises a monomeric unit of the oligomeric compound, wherein the chiral partner compound comprises a chiral atom that is not within the monomeric unit; or
   - the method comprises a coupling step, a modification step, and one or more pre-modification capping steps between the coupling step and the modification step, wherein for each pre-modification capping step between the coupling step and the modification step, its pre-modification capping reagent system comprises no esterification catalyst, and no agent that is converted into an esterification catalyst when the pre-modification capping reagent system contacts a plurality of oligonucleotides to be capped; or
   - the method comprises a coupling step, a modification step, and one or more pre-modification capping steps between the coupling step and the modification step, wherein for each pre-modification capping step between the coupling step and the modification step, the pre-modification capping step caps amino groups selectively over hydroxyl groups.

38. The method of any one of the preceding embodiments, wherein the method comprises both a pre-modification capping step and a post-modification capping step, wherein there are no steps other than modification steps between the pre-modification capping and post-modification capping steps, wherein a post-modification capping step comprises contacting a modification product composition comprising a plurality of modification product oligonucleotides, each of which independently comprises a linkage phosphorus bonded to an atom that is not oxygen.

39. The method of any one of the preceding embodiments, wherein the method comprises both a pre-modification capping step and a post-modification capping step, wherein there are no steps other than modification steps between the pre-modification capping and post-modification capping steps, wherein a pre-modification capping reagent system is different from a post-modification reagent system.

40. The method of any one of the preceding embodiments, wherein the method comprises a pre-modification capping step, wherein the pre-modification capping reagent system caps a plurality of non-hydroxyl groups of a plurality of coupling product oligonucleotides, and a modification step that comprises sulfurization, which sulfurization provides a modification product composition comprising a plurality of modification product oligonucleotides, each of which independently comprises a P═S moiety.

41. The method of any one of the preceding embodiments, wherein the method comprises a pre-modification capping step, wherein the pre-modification capping reagent system caps a plurality of non-hydroxyl groups of a plurality of coupling product oligonucleotides, and a modification step that provides a modification product composition comprising a plurality of modification product oligonucleotides, each of which independently comprises a $P^N$ moiety.

42. The method of any one of the preceding embodiments, wherein the method comprises a post-modification capping step, comprising contacting a modification product composition comprising a plurality of modification product oligonucleotide, each of which independently comprises a linkage that comprises at least one chirally controlled chiral center in that at least 80%, 85%, 90%, 95%, 96%, 97%, 98% or 99% oligomeric compounds within the modification product composition comprising the chiral center and having the same constitution share the same stereochemical configuration at the chiral center.

43. The method of any one of the preceding embodiments, wherein the method comprises a post-modification capping step, and a coupling reagent system comprising a chiral partner compound that comprises a monomeric unit of the oligomeric compound, wherein the chiral partner compound comprises a chiral atom that is not within the monomeric unit.

44. The method of any one of the preceding embodiments, wherein the method comprises a coupling step, a modification step, and one or more pre-modification capping steps between the coupling step and the modification step, wherein for each pre-modification capping step between the coupling step and the modification step, its pre-modification capping reagent system comprises no esterification catalyst, and no agent that is converted into an esterification catalyst when the pre-modification capping reagent system contacts a plurality of oligonucleotides to be capped.

45. The method of any one of the preceding embodiments, wherein the method comprises a coupling step, a modification step, and one or more pre-modification capping steps between the coupling step and the modification step, wherein for each pre-modification capping step between the coupling step and the modification step, the pre-modification capping step caps amino groups selectively over hydroxyl groups.

46. A method for preparing an oligonucleotide, comprising:

providing a chiral nucleoside phosphoramidite which comprises a chiral atom that is not the phosphorus atom or a sugar carbon atom, and a post-modification capping step after a modification step but before the next de-blocking step or the next coupling step.

47. A method for preparing an oligonucleotide, comprising one or more cycles, each of which independently comprises:

a pre-modification capping step immediately before a modification step, which comprises sulfurization or oxidation, and a post-modification capping step immediately after a modification step.

48. A method for preparing an oligonucleotide, comprising:

providing an oligonucleotide intermediate comprising a chiral linkage phosphorus atom, which is bonded to a chiral center which is not within a nucleoside unit; and a post-modification capping step after a modification step but before the next de-blocking step or the next coupling step.

49. The embodiment of any one of embodiments 46-48, wherein the post-modification capping step is a post-modification capping step of embodiment 2.

50. The embodiment of any one of embodiments 46-49, comprising a coupling step.

51. The embodiment of any one of embodiments 46-49, comprising a coupling step of embodiment 2.

52. The embodiment of any one of embodiments 46-51, comprising a pre-modification capping step.

53. The embodiment of any one of embodiments 46-51, comprising a pre-modification capping step of embodiment 2.

54. The embodiment of any one of embodiments 46-53, comprising a modification step.

55. The embodiment of any one of embodiments 46-53, comprising a modification step of embodiment 2.

56. The embodiment of any one of embodiments 46-55, comprising a de-blocking step.

57. The embodiment of any one of embodiments 46-55, comprising a de-blocking step of embodiment 2.

58. A method for preparing an oligonucleotide, comprising one or more cycles, each of which independently comprises the following steps:

(1) coupling;
(2) optionally a pre-modification capping;
(3) a modification step;
(4) optionally a post-modification capping; and
(5) de-blocking.

59. The method of embodiment 58, wherein the coupling step is a coupling step of embodiment 2.

60. The method of any one of embodiments 58-59, comprising a pre-modification capping step wherein the pre-modification capping step is a pre-modification capping step of embodiment 2.

61. The method of any one of embodiments 58-60, comprising a modification step wherein the modification step is a pre-modification capping step of embodiment 2.

62. The method of any one of embodiments 58-59, comprising a post-modification capping step wherein the post-modification capping step is a pre-modification capping step of embodiment 2.

63. The method of any one of embodiments 58-59, comprising a post-modification de-blocking step wherein the de-blocking step is a pre-modification capping step of embodiment 2.

64. A method for oligonucleotide synthesis, comprising: one or more pre-modification capping steps after a coupling step and before the next modification step, wherein the capping condition of each pre-modification capping step after a coupling step and before the next modification step is independently selective or specific for amidation over esterification.

65. A method for oligonucleotide synthesis, comprising: one or more pre-modification capping steps that are after a coupling step and before the next modification step, wherein each pre-modification capping step after a coupling step and before the next modification step independently comprises no strong nucleophile, or if it comprises one or more strong nucleophiles, the level of each of the one or more strong nucleophiles is independently reduced compared to an appropriate reference capping condition.

66. A method for oligonucleotide synthesis, comprising: one or more pre-modification capping steps after a coupling step and before the next modification step, wherein each pre-modification capping step after a coupling step and before the next modification step independently comprises no strong nucleophile, or if it comprises one or more strong nucleophiles, the level of each of the one or more strong nucleophiles is independently no more than no more than about 0.01, 0.02, 0.05, 0.1, 0.2, 0.5, or 1 equivalents relative to the first incorporated nucleoside of the oligonucleotide.

67. A method for oligonucleotide synthesis, comprising: one or more pre-modification capping steps after a coupling step and before the next modification step, wherein each pre-modification capping step after a coupling step and before the next modification step independently comprises no esterification catalyst, or if it comprises one or more esterification catalysts, the level of each of the one or more esterification catalysts is independently reduced compared to an appropriate reference capping condition.

68. A method for oligonucleotide synthesis, comprising: one or more pre-modification capping steps after a coupling step and before the next modification step, wherein each pre-modification capping step after a coupling step and before the next modification step independently comprises no esterification catalyst, or if it comprises one or more esterification catalysts, the level of each of the one or more esterification catalysts is independently no more than no more than about 0.01, 0.02, 0.05, 0.1, 0.2, 0.5, or 1 equivalents relative to the first incorporated nucleoside of the oligonucleotide.

69. The embodiment of any one of embodiments 64-68, wherein the pre-modification capping step is a pre-modification capping step of embodiment 2.

70. The embodiment of any one of embodiments 64-69, wherein the coupling step is a coupling step of embodiment 2.

71. The embodiment of any one of embodiments 64-70, wherein the modification step is a modification step of embodiment 2.

72. The embodiment of any one of embodiments 64-71, comprising a post-modification capping step.

73. The embodiment of any one of embodiments 64-72, comprising a post-modification capping step of embodiment 2.

74. The embodiment of any one of embodiments 64-73, comprising a de-blocking step.

75. The embodiment of any one of embodiments 64-74, comprising a de-blocking step of embodiment 2.

76. The method of any one of the preceding embodiments, comprising a coupling step wherein the plurality of the de-blocked oligonucleotides or nucleosides is loaded on a support.

77. The method of any one of the preceding embodiments, wherein for each coupling step, the plurality of the de-blocked oligonucleotides or nucleosides is loaded on a support.

78. The method of any one of the preceding embodiments, wherein each oligonucleotide of the plurality of the de-blocked oligonucleotides independently has the structure of formula O-I or a salt thereof.

79. The method of any one of the preceding embodiments, wherein for each coupling step, each oligonucleotide of the plurality of the de-blocked oligonucleotides independently has the structure of formula O-I.

80. The method of any one of the preceding embodiments, wherein each oligonucleotide of the plurality of the de-blocked oligonucleotides independently has the structure of formula O-I or a salt thereof, wherein each $L^P$ is independently of formula VII or a salt form thereof, wherein each $P^L$ is not P.

81. The method of any one of the preceding embodiments, wherein each oligonucleotide of the plurality of the de-blocked oligonucleotides independently has the structure of formula O-I or a salt thereof, wherein each $L^P$ is independently of formula VII or a salt form thereof, wherein each $P^L$ is independently P(═O), P(═S) or $P^N$.

82. The method of any one of the preceding embodiments, wherein each oligonucleotide of the plurality of the de-blocked oligonucleotides independently has the structure of formula O-I or a salt thereof, wherein each $L^P$ is independently of formula VII or a salt form thereof, wherein each —X-$L^s$-$R^5$ independently contains no free amino group.

83. The method of any one of the preceding embodiments, wherein each oligonucleotide of the plurality of the de-blocked oligonucleotides independently has the structure of formula O-I or a salt thereof, wherein each $L^P$ is independently of formula VII or a salt form thereof, wherein each —X-$L^s$-$R^5$ is independently -$L^7$-$R^1$, wherein $L^7$ is —O—; —S-$L^s$-$R^5$; or of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein at least one of $R^5$ or $R^6$ is —C(O)R'.

84. The method of any one of the preceding embodiments, wherein each oligonucleotide of the plurality of the de-blocked oligonucleotides independently has the structure of formula O-I or a salt thereof, wherein each $L^P$ is independently of formula VII or a salt form thereof, wherein each —X-$L^s$-$R^5$ is independently -$L^7$-$R^1$, wherein $L^7$ is —O—; or of such a structure that H—X-$L^s$-$R^5$ is a compound of formula I, I-a, I-a-1, l-a-2, I-b, I-c, I-d, I-e, II, II-a, II-b, Ill, III-a, or III-b, optionally wherein at least one of $R^5$ or $R^6$ is —C(O)R'.

85. The method of embodiment 83 or 84, wherein at least one of $R^5$ or $R^6$ is —$C(O)CH_3$.

86. The method of any one of the preceding embodiments, wherein each oligonucleotide of the plurality of the de-blocked oligonucleotides independently has the structure of formula O-I or a salt thereof, wherein each $L^P$ is independently of formula VII or a salt form thereof, wherein each X is independently —O— or —S—.
87. The method of any one of the preceding embodiments, wherein each oligonucleotide of the plurality of the de-blocked oligonucleotides independently has the structure of formula O-I or a salt thereof, wherein each $L^P$ is independently of formula VII or a salt form thereof, wherein each of Y and Z is —O—.
88. The method of any one of the preceding embodiments, wherein each oligonucleotide of the plurality of the de-blocked oligonucleotides independently has the structure of formula O-I or a salt thereof, wherein each —X-$L^s$-$R^5$ independently contains no free amino group.
89. The method of any one of the preceding embodiments, wherein each oligonucleotide of the plurality of the de-blocked oligonucleotides independently has the structure of formula O-I or a salt thereof, wherein each $R^{5s}$ is —OH.
90. The method of any one of the preceding embodiments, wherein a de-blocked oligonucleotide composition comprising a plurality of de-blocked oligonucleotides is a chirally controlled oligonucleotide composition.
91. The method of any one of the preceding embodiments, wherein a de-blocked oligonucleotide composition comprising a plurality of de-blocked oligonucleotides is a chirally controlled oligonucleotide composition, wherein:
    oligonucleotides of the plurality share the same constitution; and
    oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage; and
    wherein no less than $((DS)^{Nc}*100)\%$ of all oligonucleotides sharing the same base sequence in the de-blocked product composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.
92. The method of any one of the preceding embodiments, a free hydroxyl group of a de-blocked oligonucleotide or nucleoside is a 5'-OH.
93. The method of any one of the preceding embodiments, wherein a partner compound is a nucleoside phosphoramidite, wherein each —OH of a sugar unit is independently blocked.
94. The method of any one of the preceding embodiments, wherein a partner compound comprises a nucleoside unit having the structure of

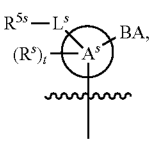

wherein $R^{5s}$ is —OR, wherein R is not —H.

95. The method of any one of the preceding embodiments, wherein a partner compound comprises a nucleoside unit having the structure of

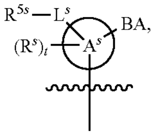

wherein $R^{5s}$ is —OR, wherein R is DMTr.

96. The method of any one of the preceding embodiments, wherein a partner compound is of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof.
97. The method of any one of the preceding embodiments, wherein a partner compound is a phosphoramidite of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof, wherein $P^L$ is P.
98. The method of any one of the preceding embodiments, wherein for each coupling step, a partner compound is a phosphoramidite of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof, wherein $P^L$ is P.
99. The method of any one of the preceding embodiments, wherein a coupling reagent system comprises a partner compound and an activator.
100. The method of any one of the preceding embodiments, wherein an activator is an optionally substituted tetrazole.
101. The method of any one of embodiments 1-97, wherein an activator is selected from cyanomethyl imidazole triflate, cyanomethyl pyrrolidine triflate, ETT, phenyl(2H-tetrazol-5-yl)methanone, 2-(dimethylamino)acetonitrile/trifluorosulfonic acid(2/1), 2-(1H-imidazol-1-yl)acetonitrile/trifluorosulfonic acid(2/1), and 2-(pyrrolidin-1-yl)acetonitrile/trifluorosulfonic acid(2/1).
102. The method of any one of the preceding embodiments, wherein an activator is CMIMT.
103. The method of any one of the preceding embodiments, comprising a coupling step in which an activator is CMIMT, and a partner is of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or a salt thereof.
104. The method of any one of the preceding embodiments, comprising a coupling step in which an activator is CMIMT, and a partner compound is diastereomerically pure.
105. The method of any one of the preceding embodiments, wherein for each coupling step in which a partner compound is diastereomerically pure, an activator is CMIMT.
106. The method of any one of the preceding embodiments, wherein an activator is CMPT.
107. The method of any one of the preceding embodiments, comprising a coupling step in which an activator is CMPT, and a partner is of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or a salt thereof.

108. The method of any one of embodiments 1-107, comprising a coupling step in which an activator is CMPT, and a partner compound is diastereomerically pure.

109. The method of any one of the preceding embodiments, wherein an activator is ETT.

110. The method of any one of the preceding embodiments, comprising a coupling step in which an activator is ETT, and a partner is of formula IV, IV-a, IV-b, IV-c-1, IV-c-2, IV-d, IV-e, V, V-a, V-b, V-c-1, V-c-2, V-d, V-c, VI, VI-a, VI-b, VI-c-2, VI-d, or VI-e, or a salt thereof.

111. The method of any one of the preceding embodiments, comprising a coupling step in which an activator is ETT, and a partner compound is of formula IVa, IVa-a, IVa-b, IVa-c-I, IVa-c-2, IVa-d, or IVa-e, or a salt thereof.

112. The method of any one of the preceding embodiments, wherein each coupling step independently forms an internucleotidic linkage of formula VII-b, or a salt form thereof.

113. The method of any one of the preceding embodiments, wherein one or more coupling steps each independently forms a chirally controlled internucleotidic linkage.

114. The method of any one of the preceding embodiments, wherein one or more coupling steps each independently forms a chirally controlled internucleotidic linkage, wherein each chirally controlled linkage phosphorus (a linkage phosphorus of a chirally controlled internucleotidic linkage) independently has a diastereomeric purity of at least 80%, 85%, 90%, 91%, 92%, 93%, 94%, 95%, 96%, 97%, 98% or 99% within the coupling product composition.

115. The method of any one of the preceding embodiments, wherein one or more coupling steps each independently forms a non-chirally controlled internucleotidic linkage.

116. The method of any one of the preceding steps, wherein a coupling step provides a coupling product composition comprising a plurality of coupling product oligonucleotides, wherein each coupling product oligonucleotide is independently an oligonucleotide of formula O-I or a salt thereof.

117. The method of any one of the preceding steps, wherein each coupling step provides a coupling product composition comprising a plurality of coupling product oligonucleotides, wherein each coupling product oligonucleotide is independently an oligonucleotide of formula O-I or a salt thereof.

118. The method of any one of embodiments 116-117, wherein for a coupling step, z of formula O-I for a coupling product oligonucleotide ($z^{CP}$) is greater than z of formula O-I for a corresponding de-blocked oligonucleotide ($z^{DB}$).

119, The method of any one of embodiments 116-117, wherein for a coupling step $z^{CP}=z^{DB}+1$.

120. The method of any one of the preceding steps, wherein a coupling product composition comprises a plurality of coupling product oligonucleotides, each of which is independently of formula O-I or a salt thereof, wherein each 12 bonded to

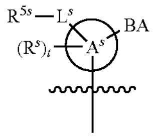

in formula O-I is independently an internucleotidic linkage of formula VII-b, or a salt form thereof.

121. The method of any one of the preceding embodiments, wherein a coupling product composition comprises a plurality of coupling product oligonucleotides, each of which is independently of formula O-I or a salt thereof, wherein each L that is not bonded to

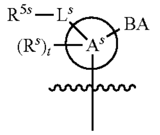

in formula O-I is independently of formula VII or a salt form thereof, wherein each $P^L$ is independently not P.

122. The method of any one of the preceding embodiments, wherein a coupling product composition comprises a plurality of coupling product oligonucleotides, each of which is independently of formula O-I or a salt thereof, wherein each $L^P$ that is not bonded to

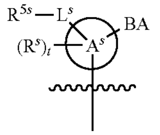

in formula O-I is independently of formula VII or a salt form thereof, wherein each $P^L$ is independently P(═O), P(═S) or $P^N$.

123. The method of any one of the preceding embodiments, wherein a coupling product composition comprises a plurality of coupling product oligonucleotides, each of which is independently of formula O-I or a salt thereof, wherein each $L^P$ that is bonded to

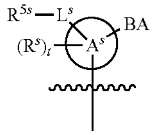

in formula O-I is independently of formula VII or a salt form thereof, wherein —X-$L^s$-$R^5$ is independently -$L^7$-$R^1$, or of such a structure that H—X-$L^s$-$R^5$ is a compound of formula I, I-a, I-a-1, I-a-2, I-b, I-d, I-c, II, II-a, II-b, III, III-a, or III-b, wherein at least one of $R^5$ or $R^6$ is —H.

124. The method of any one of the preceding embodiments, wherein for at least one coupling step, a plurality of coupling product oligonucleotides are oligonucleotide of formula O-I or a salt thereof, wherein the $L^P$ that is bonded to

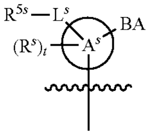

in formula O-I is independently of formula VII or a salt form thereof, wherein —X-$L^s$-$R^5$ is independently -$L^7$-$R^1$.

125. The method of any one of the preceding embodiments, wherein for at least one coupling step, a plurality of coupling product oligonucleotides are oligonucleotide of formula O-I or a salt thereof, wherein the $L^P$ that is bonded to

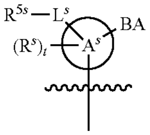

in formula O-I is independently of formula VII or a salt form thereof, wherein —X-$L^s$-$R^5$ is independently of such a structure that H—X-$L^s$-$R^5$ is a compound of formula I, I-a, I-a-1, I-a-2, I-b, I-c, I-d, II, II-a, II-b, III, III-a, or wherein at least one of $R^5$ or $R^6$ is —H.

126. The method of any, one of the preceding embodiments, wherein a coupling product composition comprises a plurality of coupling product oligonucleotides, each of which is independently of formula O-I or a salt thereof, wherein each $L^P$ that is not bonded to

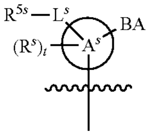

in formula O-I is independently of formula VII or a salt form thereof, wherein each —X-$L^s$-$R^5$ is independently -$L^7$-$R^1$, or of such a structure that H—X-$L^s$-$R^5$ is a compound of formula I, I-a, I-a-I, I-a-2, I-b, I-c, I-d, I-e, II, II-a, II-b, III, III-a, or III-b, wherein at least one of $R^5$ or $R^6$ is —C(O)R.

127. The method of any one of the preceding embodiments, wherein a coupling product composition comprises a plurality of coupling product oligonucleotides, each of which is independently of formula O-I or a salt thereof, wherein each $L^P$ that is not bonded to

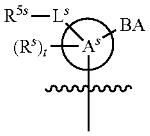

in formula O-I is independently of formula VII or a salt form thereof and contains no free primary or secondary amino groups.

128. The method of embodiment 126, wherein at least one of $R^5$ or $R^6$ is —C(O)$CH_3$.

129. The method of any one of the preceding embodiments, wherein a coupling product composition comprises a plurality of coupling product oligonucleotides, each of which is independently of formula O-I or a salt thereof, wherein each $L^P$ is independently of formula VII or a salt form thereof, wherein each X is independently —O— or —S—.

130. The method of any one of the preceding embodiments, wherein a coupling product composition comprises a plurality of coupling product oligonucleotides, each of which is independently of formula O-I or a salt thereof, wherein each $L^P$ is independently of formula VII or a salt form thereof, wherein each of Y and Z is —O—.

131, The method of any one of the preceding embodiments, comprising a coupling step wherein the coupling step provides a coupling product composition comprises a plurality of coupling product oligonucleotides, wherein each of the coupling product is independently an oligonucleotide loaded on a support.

132. The method of any one of the preceding embodiments, wherein each coupling step independently provides a coupling product composition comprises a plurality of coupling product oligonucleotides, wherein each of the coupling product is independently an oligonucleotide loaded on a support.

133. The method of any one of the preceding embodiments, wherein a coupling product composition is a chirally controlled oligonucleotide composition.

134. The method of any one of the preceding embodiments, wherein a coupling product composition comprising a plurality of coupling product oligonucleotides, and the coupling product composition comprising the plurality of oligonucleotides is a chirally controlled oligonucleotide composition wherein:

oligonucleotides of the plurality share the same constitution; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least $((DS)^{Nc}*100)\%$ of all oligonucleotides sharing the same base sequence in the coupling product composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

135. The method of any one of the preceding embodiments, wherein a coupling product composition comprises a plurality of oligonucleotides, each of which independently comprises a free —OH.

136. The method of any one of the preceding embodiments, wherein each coupling product composition comprises a plurality of oligonucleotides, each of which independently comprises a free —OH.

137. The method of any one of the preceding embodiments, wherein a coupling product composition comprises a plurality of de-blocked oligonucleotides or nucleosides, each of which independently comprises a free —OH.

138, The method of any one of the preceding embodiments, wherein each coupling product composition comprises a plurality of de-blocked oligonucleotides or nucleosides, each of which independently comprises a free —OH.

139. The method of any one of embodiments 135-138, wherein the free —OH is a free 5'-OH.
140. The method of any one of the preceding embodiments, wherein contact time of the coupling reagent system with the de-blocked composition of one coupling step is different from the other.
141. The method of any one of the preceding embodiments, wherein a coupling step comprising repeating the contacting, each time independently with the same or different coupling reagent systems.
142. The method of any one of the preceding embodiments, wherein a pre-modification capping reagent system comprises an acylating agent.
143. The method of any one of the preceding embodiments, wherein a pre-modification capping reagent system comprises an acylating agent, wherein the acylating agent is of formula R'—C(O)-$L^s$-$R^s$.
144. The method of any one of the preceding embodiments, wherein a pre-modification capping reagent system comprises an acylating agent, wherein the acylating agent is of formula R'—C(O)-$L^s$-$R^s$, wherein R'—C(O)— is bonded to a heteroatom of -$L^s$-$R^s$.
145. The method of any one of the preceding embodiments, wherein a pre-modification capping reagent system comprises an acylating agent, wherein the acylating agent is of formula R'—C(O)-$L^s$-$R^s$, wherein R'—C(O)— is bonded to an oxygen, nitrogen, halogen, or sulfur, of -$L^s$-$R^s$.
146, The method of any one of the preceding embodiments, wherein a pre-modification capping reagent system comprises an acylating agent, wherein the acylating agent is an anhydride.
147. The method of any one of the preceding embodiments, wherein a pre-modification capping reagent system comprises an acylating agent, wherein the acylating agent is R—NCO.
148. The method of any one of the preceding embodiments, wherein a pre-modification capping reagent system comprises an acylating agent, wherein the acylating agent is Ph-NCO.
149. The method of any one of the preceding embodiments, wherein a pre-modification capping reagent system comprises POS, which optionally modifies an internucleotidic linkage and caps.
150, The method of any one of the preceding embodiments, wherein a pre-modification capping reagent system comprises a base.
151. The method of embodiment 147, wherein a base is of formula N($R^3$), wherein the nitrogen atom has no alpha-substitution.
152. The method of embodiment 147, wherein a base is optionally substituted pyridine.
153. The method of embodiment 147, wherein a base is substituted pyridine, comprising substituents zit 2'- and 6'-positions.
154. The method of embodiment 147, wherein a base is pyridine.
155. The method of embodiment 147, wherein a base is 2,6-lutidine.
156. The method of embodiment 147, wherein a base is 2,6-lutidine.
157. The method of embodiment 147, wherein a base is triethylamine.
158. The method of embodiment 147, wherein a base is DIEA.
159. The method of embodiment 147, wherein a base is N-methyl morpholine.
160. The method of embodiment 147, wherein a base is 2-(dimethylamino)acetonitrile.
161. The method of any one of the preceding embodiments, wherein a pre-modification capping reagent system comprises no strong nucleophile, and no reagent that when contacted with a coupling product composition, can provide a strong nucleophile.
162. The method of any one of the preceding embodiments, wherein a pre-modification capping reagent system comprises no esterification catalyst, and no reagent that when contacted with a coupling product composition, can provide an esterification catalyst.
163. The method of any one of the preceding embodiments, wherein a strong nucleophile or an esterification catalyst is DMAP or NMI.
164. The method of any one of the preceding embodiments, wherein a strong nucleophile or an esterification catalyst is NMI.
165. The method of any one of the preceding embodiments, wherein a strong nucleophile or an esterification catalyst is DMAP.
166. The method of any one of the preceding embodiments, wherein a pre-modification capping reagent system comprises a strong nucleophile, or a reagent that when contacted with a coupling product composition, can provide a strong nucleophile.
167. The method of any, one of the preceding embodiments, wherein a pre-modification capping reagent system comprises an esterification catalyst, or a reagent that when contacted with a coupling product composition, can provide a strong nucleophile.
168. The method of any one of the preceding embodiments, wherein a strong nucleophile or an esterification catalyst is DMAP or NMI.
169, The method of any one of the preceding embodiments, wherein a strong nucleophile or an esterification catalyst is NMI.
170. The method of any one of the preceding embodiments, wherein a strong nucleophile or an esterification catalyst is DMAP.
171. The method of any one of embodiments 166-170, wherein the pre-modification capping reagent system comprises reduced level of each strong nucleophile, each reagent that when contacted with a coupling product composition can provide a strong nucleophile, each esterification catalyst, and each reagent that when contacted with a coupling product composition can provide an esterification catalyst, which reduced level is independently no more than 0.01, 0.02, 0.05, 0.1, 0.2, 0.5, 1, 1,1, 1,2, 1,5, or 2 equivalents relative to the acylating agent, the base, or the plurality of product oligonucleotides of the coupling product composition.
172. The method of embodiment 171, wherein reduced level is independently no more than 0.01, 0.02, 0.05, 0.1, 0.2, or 0.5 equivalents relative to all acylating agents of the pre-modification capping reagent system.
173. The method of embodiment 171, wherein reduced level is independently no more than 0.01, 0.02, 0.05, 0.1, 0.2, or 0.5 equivalents relative to all bases of the pre-modification capping reagent system.
174. The method of embodiment 171, wherein reduced level is independently no more than 0.01, 0.02, 0.05, 0.1, 0.2, or 0.5 equivalents relative to the plurality of product oligonucleotides of the coupling product composition.

175. The method of any one of the preceding embodiments, wherein a pre-modification capping step is selective for amidation over esterification.
176. The method of any one of the preceding embodiments, wherein a pre-modification capping step is selective for capping of primary and secondary amino groups over esterification capping of free hydroxyl groups.
177. The method of any one of the preceding embodiments, wherein a pre-modification capping step is selective for capping of primary and secondary amino groups over capping of free hydroxyl groups in that in a system comprising:
a plurality of coupling product oligonucleotides wherein each coupling product is independently art oligonucleotide comprising one or more internucleotidic linkages of formula VII, wherein —X-$L^s$-$R^5$ is of such a structure that H—X-$L^s$-$R^5$ is a compound of formula I, I-a, I-a-1, I-a-2, I-b, I-c, I-d, I-e, II, II-a, II-b, III, III-a, or III-b, wherein at least one of $R^5$ or $R^6$ is —H;
and a plurality of oligonucleotides each of which independently comprises a free 5'-OH group;
when at least 80%, 85%, 90%, 91%, 92%, 93%, 94%, 95%, 96%, 97%, 98%, or 99% —X-$L^s$-$R^5$ groups, wherein —X-$L^s$-$R^5$ is of such a structure that H—X-$L^s$-$R^5$ is a compound of formula I, I-a, I-a-1, I-b, I-c, I-d, I-e, II, II-a, II-b, III, III-a, or wherein at least one of $R^5$ or $R^6$ is —H, in internucleotidic linkages of formula VII is converted into corresponding —X-$L^s$-$R^5$ groups, wherein —X-$L^s$-$R^5$ is of such a structure that H—X-$L^s$-$R^5$ is a compound of formula I, I-a, I-a-1, I-a-2, I-b, I-c, I-d, I-e, II, II-a, II-b, III, III-a, or III-b, wherein at least one of $R^5$ or $R^6$ is —C(O)R via amidation, no more than 1%, 5%, 10%, 20%, 30%, 40%, 50%, 60%, 70%, 80%, 85%, 90%, 91%, 92%, 93%, 94%, 95%, 96%, 97%, 98%, or 99% of free hydroxyl groups is converted into —O—C(O)R.
178. The method of embodiment 177, wherein no more than 1%, 5%, 10%, 20%, 30%, 40%, or 50% of free hydroxyl groups is converted into QUA.
179, The method of any one of embodiments 1-174, wherein a pre-modification capping step caps at least 90%, 91%, 92%, 93%, 94%, 95%, 96%, 97%, 98%, or 99% of free hydroxyl groups of a coupling product composition.
180. The method of any one of embodiments 1-174, wherein a pre-modification capping step caps at least 90%, 91%, 92%, 93%, 94%, 95%, 96%, 97%, 98%, or 99% of free 5-OH of oligonucleotides of a coupling product composition.
181. The method of any one of the preceding embodiments, wherein the pre-modification capping step caps one or more amino groups.
182. The method of any one of the preceding embodiments, wherein a pre-modification capping step caps at least 90%, 91%, 92%, 93%, 94%, 95%, 96%, 97%, 98%, or 99% of free primary and secondary amino groups of a coupling product composition.
183. The method of any one of the preceding embodiments, wherein the pre-modification capping step caps one or more amino groups of a plurality of coupling product oligonucleotides, each of which is independently an oligonucleotide of a coupling product composition.
184. The method of any one of the preceding embodiments, wherein a pre-modification capping step comprises:
contacting a coupling product composition with a first pre-modification capping system; and
contacting a coupling product composition with a second pre-modification capping system.
185. The method of embodiment 184, wherein the first and second pre-modification capping systems are different.
186. The method of embodiment 184, wherein the first pre-modification capping reagent system is selective for capping of amino groups over hydroxyl groups, and the second pre-modification capping reagent system caps both amino and hydroxyl groups efficiently.
187. The method of any one of the preceding embodiments, wherein a pre-modification capping reagent system is a solution of:
Pyridine/DMAP/$Ac_2O$;
2,6-Lutidine/NMI/$Ac_2O$;
2,4,6-Collidine/$Ac_2O$;
Triethylamine/$Ac_2O$;
DIEA/$Ac_2O$;
N-Methyl morpholine/$Ac_2O$;
2,6-Lutidine, then after a period of time, NMI/$Ac_2O$;
2,6-Lutidine/$Ac_2O$;
PhNCO/2,6-Lutidine;
POS;
POS then NMI/2,6-Lutidine/$Ac_2O$; or
2-(dimethylamino)acetonitrile/$Ac_2O$.
188. The method of any one of the preceding embodiments, wherein a pre-modification capping reagent system is a solution of:
Pyridine (2 equiv.)/DMAP (cat.)/$Ac_2O$(4 equiv.);
2,6-Lutidine (2 equiv.)/NMI (0.25 equiv.)/$Ac_2O$(4 equiv.);
2,4,6-Collidine/$Ac_2O$(4 equiv.);
Triethylamine/$Ac_2O$(4 equiv.);
DIEA/$Ac_2O$(4 equiv.);
N-Methyl morpholine/$Ac_2O$(4 equiv.);
2,6-Lutidine (2 equiv.) then after 5 min. NM equiv.)/$Ac_2O$(4 equiv.);
2,6-Lutidine/$Ac_2O$(4 equiv.);
PhNCO/2,6-Lutidine;
POS (both oxidation and pre-capping);
POS (both oxidation and pre-capping) then NMI/2,6-Lutidine/$Ac_2O$; or
2-(dimethylamino)acetonitrile/$Ac_2O$.
189, The method of any one of the preceding embodiments, wherein a pre-modification capping reagent system is a solution of 2,6-Lutidine/$Ac_2O$.
190. The method of any one of embodiments 187-189, wherein a pre-modification capping reagent system is a solution in acetonitrile.
191. The method of any one of the preceding steps, wherein a pre-modification capping step provides a pre-modification capping composition comprising a plurality of pre-modification capping product oligonucleotides, wherein each pre-modification capping product is independently an oligonucleotide of formula O-I or a salt thereof.
192, The method of any one of the preceding steps, wherein each pre-modification capping step provides a pre-modification capping product composition comprising a plurality of pre-modification capping product oligonucleotides, wherein each pre-modification capping product is independently an oligonucleotide of formula O-I or a salt thereof.

193. The method of any one of embodiments 191-192, wherein for a pre-modification capping step, z of formula O-I for a pre-modification capping product oligonucleotide ($z^{PR}$) is the same as z of formula O-I for a corresponding coupling product oligonucleotide ($z^{CP}$).

194. The method of any one of the preceding steps, wherein a pre-modification capping product composition comprises a plurality of pre-modification capping product oligonucleotides, each of which is independently of formula O-I or a salt thereof, wherein each $L^P$ bonded to

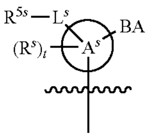

in formula O-I is independently an internucleotidic linkage of formula VII-b, or a salt form thereof.

195. The method of any one of the preceding embodiments, wherein a pre-modification capping product composition comprises a plurality of pre-modification capping product oligonucleotides, each of which is independently of formula O-I or a salt thereof wherein each $L^P$ that is not bonded to

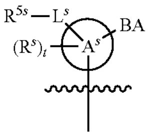

in formula O-I is independently of formula VII or a salt form thereof, wherein each $P^L$ is independently not P.

196. The method of any one of the preceding embodiments, wherein a pre-modification capping product composition comprises a plurality of pre-modification capping product oligonucleotides, each of which is independently of formula O-I or a salt thereof, wherein each $L^P$ that is not bonded to

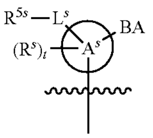

in formula O-I is independently of formula VII or a salt form thereof, wherein each $P^L$ is independently P(=O), P(=S) or $P^N$.

197. The method of any one of the preceding embodiments, wherein a pre-modification capping product composition comprises a plurality of pre-modification capping product oligonucleotides, each of which is independently of formula O-I or a salt thereof, wherein each $L^P$ that is bonded to

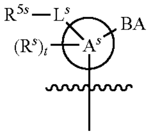

in formula O-I is independently of formula VII or a salt form thereof, wherein each $—X-L^s-R^5$ is independently $-L^7-R^1$, or of such a structure that $H—X-L^s-R^5$ is a compound of formula I, I-a, I-a-1, I-a-2, I-b, I-c, I-d, I-e, II, II-a, II-b, III, III-a, or III-b, wherein at least one of $R^5$ or $R^6$ is —C(O)R'.

198. The method of any, one of the preceding embodiments, wherein for at least one pre-modification capping step, a plurality of pre-modification capping product oligonucleotides are oligonucleotide of formula O-I or a salt thereof, wherein the $L^P$ that is bonded to

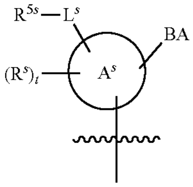

in formula O-I is independently of formula VII or a salt form thereof, wherein each $—X-L^s-R^5$ is independently $-L^7-R^1$.

199. The method of any one of the preceding embodiments, wherein for at least one pre-modification capping step, a plurality of pre-modification capping product oligonucleotides are oligonucleotide of formula O-I or a salt thereof, wherein the $L^P$ that is bonded to

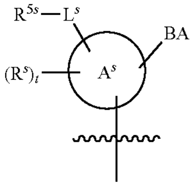

in formula O-I is independently of formula VII-b or a salt form thereof, wherein each $—X-L^s-R^5$ is independently of such a structure that $H—X-L^s-R^5$ is a compound of formula I, I-a, I-a-1, I-a-2, I-b, I-c, I-d, I-e, II, II-a, II-b, III, III-a, or III-b, wherein at least one of $R^5$ or $R^6$ is —C(O)R.

200. The method of any, one of the preceding embodiments, wherein a pre-modification capping product composition comprises a plurality of pre-modification capping product oligonucleotides, each of which is independently of formula O-I or a salt thereof, wherein each $L^P$ that is not bonded to

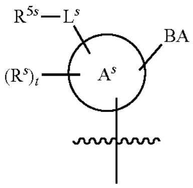

in formula O-I is independently of formula VII or a salt form thereof, wherein each —X-$L^s$-$R^5$ is independently -$L^7$-$R^1$, or of such a structure that H—X-$L^s$-$R^5$ is a compound of formula I, I-a, I-a-1, I-a-2, I-b, I-c, I-d, I-e, II, II-a, II-b, III, III-a, or III-b, wherein at least one of $R^5$ or $R^6$ is —C(O)R.

201. The method of any one of the preceding embodiments, wherein a pre-modification capping product composition comprises a plurality of pre-modification capping product oligonucleotides, each of which is independently of formula O-I or a salt thereof, wherein each $L^P$ that is not bonded to

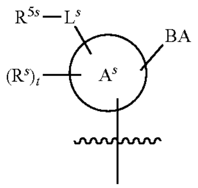

in formula O-I is independently of formula VII or a salt form thereof and contains no free primary or secondary amino groups.

2202. The method of embodiment 126, wherein at least one of $R^5$ or $R^6$ is —C(O)$CH_3$.

203. The method of any one of the preceding embodiments, wherein a pre-modification capping product composition comprises a plurality of pre-modification capping product oligonucleotides, each of which is independently of formula O-I or a salt thereof, wherein each $L^P$ is independently of formula VII or a salt form thereof, wherein each X is independently —O— or —S—.

204. The method of any one of the preceding embodiments, wherein a pre-modification capping product composition comprises a plurality of pre-modification capping product oligonucleotides, each of which is independently of formula O-I or a salt thereof, wherein each $L^P$ is independently of formula VII or a salt form thereof, wherein each of Y and Z is —O—.

205. The method of any one of the preceding embodiments, wherein the pre-modification capping step provides a pre-modification capping product composition comprises a plurality of pre-modification capping product oligonucleotides, wherein each of the pre-modification capping product is independently an oligonucleotide loaded on a support.

206. The method of any one of the preceding embodiments, wherein each pre-modification capping step independently provides a pre-modification capping product composition comprises a plurality of pre-modification capping product oligonucleotides, wherein each of the pre-modification capping product is independently an oligonucleotide loaded on a support.

207, The method of any one of the preceding embodiments, wherein a pre-modification capping product composition comprising a plurality of pre-modification capping product oligonucleotides is a chirally controlled oligonucleotide composition.

208. The method of any one of the preceding embodiments, wherein a pre-modification capping product composition comprising a plurality of pre-modification capping product oligonucleotides is a chirally controlled oligonucleotide composition wherein:

oligonucleotides of the plurality share the same constitution, and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least $((DS)^{Nc}*100)\%$ of all oligonucleotides sharing the same base sequence in the pre-modification capping product composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

209. The method of any, one of the preceding embodiments, wherein a pre-modification capping product composition comprises a plurality of oligonucleotides, each of which independently comprises a free —OH.

210. The method of any one of the preceding embodiments, wherein each pre-modification capping product composition comprises a plurality of oligonucleotides, each of which independently comprises a free —OH.

211, The method of any one of the preceding embodiments, wherein a pre-modification capping product composition comprises a plurality of de-blocked oligonucleotides or nucleosides, each of which independently comprises a free —OH.

212. The method of any one of the preceding embodiments, wherein each pre-modification capping product composition comprises a plurality of de-blocked oligonucleotides or nucleosides, each of which independently comprises a free —OH.

213. The method of any one of embodiments 209-212; wherein the free —OH is a free 5' OH.

214. The method of any one of the preceding embodiments, wherein a pre-modification capping step comprising repeating the contacting, each time independently with the same or different pre-modification capping reagent systems.

215. The method of any one of the preceding embodiments, wherein a modification step comprises contacting a coupling product composition and modifying one or more internucleotidic linkages of one or more coupling product oligonucleotides to provide a modification product composition comprising a plurality of modification product oligonucleotides.

216. The method of any one of the preceding embodiments, wherein a modification step comprises contacting a coupling product composition and modifying one or more internucleotidic linkages of one or more coupling product oligonucleotides to provide a modification product composition comprising a plurality of modification product oligonucleotides.

217, The method of any one of the preceding embodiments, wherein a modification step comprises modifying an internucleotidic linkage formed in the immediate preceding coupling step.

218. The method of any, one of the preceding embodiments, wherein a modification step comprises modifying a 5'-end internucleotidic linkage.

219. The method of any one of the preceding embodiments, wherein a modification step comprises modifying an internucleotidic linkage whose linkage phosphorus is —P(−)—.

220. The method of any one of the preceding embodiments, wherein a modification step comprises modifying an internucleotidic linkage of formula VII or a salt form thereof, wherein $P^L$ is P.

221, The method of any one of the preceding embodiments, wherein a modification step comprises modifying an internucleotidic linkage of formula VII or a salt thereof, wherein $P^L$ is P to form an internucleotidic linkage of formula VII or a salt form thereof, wherein $P^L$ is not P.

222. The method of any one of the preceding embodiments, wherein a modification step comprises modifying an internucleotidic linkage of formula VII or a salt thereof, wherein $P^L$ is P to form an internucleotidic linkage of formula VII or a salt form thereof, wherein $P^L$ is P(=O) or (P=S) $P^N$.

223. The method of any one of the preceding embodiments, wherein a modification step comprises modifying an internucleotidic linkage of formula VII or a salt thereof, wherein $P^L$ is P to form an internucleotidic linkage of formula VII or a salt form thereof, wherein $P^L$ is P(=O) or (P=S).

224, The method of any one of the preceding embodiments, wherein a modification step comprises modifying an internucleotidic linkage of formula VII or a salt form thereof in an oligonucleotide of formula O-I or a salt thereof.

225. The method of any one of the preceding embodiments, wherein a modification step comprises modifying an internucleotidic linkage of formula VII or a salt form thereof in an oligonucleotide of formula O-I or a salt thereof, wherein the internucleotidic linkage of formula VII or a salt form thereof is $L^P$ bonded to

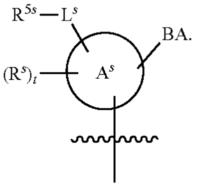

226. The method of any one of the preceding embodiments, wherein a modification step comprises:

modifying a coupling product composition comprising a plurality of coupling product oligonucleotides, or a pre-modification capping product composition comprising a plurality of pre-modification capping product oligonucleotides, each of which is independently an oligonucleotide of formula O-I or a salt thereof, wherein the $L^P$ bonded to

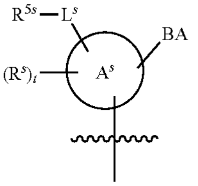

is an internucleotidic linkage of formula VII or a salt form thereof, wherein $P^L$ is P; and providing a modification product composition comprising a plurality of modification product oligonucleotides, each of which is independently an oligonucleotide of formula O-I or a salt thereof wherein the $L^P$ bonded to

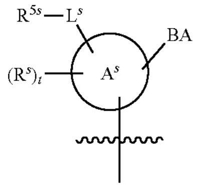

is an internucleotidic linkage of formula VII or a salt form thereof wherein $P^L$ is not P.

227. The method of any one of the preceding embodiments, wherein a modification step comprises oxidation.

228. The method of any one of the preceding embodiments, wherein a modification step comprises oxidation, which oxidation converts a —P(−)— linkage phosphorus atom into a —P(=O)(−)— linkage phosphorus atom.

229, The method of any one of the preceding embodiments, wherein a modification reagent system is an oxidation reagent system comprising one or more oxidation reagent.

230. The method of any one of the preceding embodiments, wherein a modification reagent system comprises TBHP.

231. The method of any one of the preceding embodiments, wherein a modification reagent system comprises TBHP/Decane/DCM.

232. The method of any one of the preceding embodiments, wherein a modification reagent system comprises TBHP/Decane/DCM wherein the concentration of TBHP is about 1.1 M.

233, The method of any one of the preceding embodiments, wherein a modification reagent system comprises $I_2$.

234. The method of any one of the preceding embodiments, wherein a modification reagent system comprises $I_2$/Water/Pyridine.

235. The method of any one of the preceding embodiments, wherein a modification reagent system comprises $I_2$/Water/Pyridine, wherein the concentration of $I_2$ is about 0.05 M.

236. The method of any one of the preceding embodiments, wherein a modification step comprises sulfurization, which sulfurization comprises converting a —P(−)— linkage phosphorus atom into a —P(=S)(−)— linkage phosphorus atom.

237, The method of any one of the preceding embodiments, wherein a modification step comprises sulfurization, which sulfurization comprises converting an internucleotidic linkage of formula VII-b or a salt form thereof, wherein each of X, Y, and Z is —O—, into an internucleotidic linkage of formula VII or a salt thereof, wherein $P^L$ is P(=S), and each of X, Y, and Z is —O—.

238. The method of any one of the preceding embodiments, wherein a modification step comprises sulfurization, which sulfurization comprises converting a —P(−)— linkage phosphorus atom into a —P(=O)(—X-$L^s$-$R^5$)— linkage phosphorus atom, wherein X is —S—.

239. The method of any one of the preceding embodiments, wherein a modification step comprises sulfurization, which sulfurization comprises converting an internucleotidic linkage of formula VII-b or a salt form thereof wherein each of X, Y, and Z is —O—, into an internucleotidic linkage of formula VII or a salt thereof, wherein $P^L$ is P(=O), and X is —S—, Y is —O—, and Z is —O—.

240. The method of any one of the preceding embodiments, wherein a modification step comprises sulfurization, which sulfurization comprises converting an internucleotidic linkage of formula VII-b or a salt form thereof, wherein each of X, Y, and Z is —O—, and —X-$L^s$-$R^5$ comprises a —Si(R)$_3$ group, into an internucleotidic linkage of formula VII or a salt thereof, wherein $P^L$ is P(=O), and X is —S—, Y is —O—, and Z is —O—.

241. The method of any one of the preceding embodiments, wherein a modification reagent system is a sulfurization reagent system comprising one or more sulfurization reagent.

242. The method of any one of the preceding embodiments, wherein a sulfurization reagent system comprises a sulfurization reagent selected from POS (3-phenyl-1,2,4-dithiazolin-5-one), DDTT (((dimethylamino-methylidene)amino)-3H-1,2,4-dithiazaoline-3-thione), DTD (dimethylthiarum disulfide), xanthane hydride (XH), S-(2-cyanoethyl) methanesulfonothioate (MTS-CNE), or phenylacetyl disulfide.

243. The method of embodiment 242, wherein a sulfurization reagent is POS.

244. The method of embodiment 242, wherein a sulfurization reagent is DDTT.

245. The method of embodiment 242, wherein a sulfurization reagent is DTD.

246. The method of embodiment 242, wherein a sulfurization reagent is xanthane hydride.

247. The method of any one of the preceding embodiments, wherein a modification reagent system is or comprises POS in acetonitrile.

248. The method of any one of the preceding embodiments, wherein a modification reagent system is or comprises POS in acetonitrile, wherein the concentration of POS is about 0.1 M.

249. The method of any one of the preceding embodiments, wherein a modification reagent system is or comprises xanthane hydride in pyridine.

250. The method of any one of the preceding embodiments, wherein a modification reagent system is or comprises xanthane hydride in pyridine, wherein the concentration of xanthane hydride is about 0.2 M.

251. The method of embodiment 246, wherein the concentration of xanthane hydride is about 0.05-0.5 M.

252. The method of embodiment 246, wherein the concentration of xanthane hydride is about 0.1 M.

253. The method of embodiment 246, wherein the concentration of xanthane hydride is about 0.15 M.

254. The method of embodiment 246, wherein the concentration of xanthane hydride is about 0.2 M.

255, The method of embodiment 246, wherein the concentration of xanthane hydride is about 0.25 M.

256. The method of any one of embodiments 251-255, wherein the solvent is or comprises pyridine.

257. The method of any one of embodiments 251-256, wherein the solvent is or comprises acetonitrile.

258. The method of any one of embodiments 251-257, wherein the solvent comprises pyridine and acetonitrile, and the ratio of pyridine:acetonitrile is about 5:1 to 1:5 v/v, or is about 5:1, 4:1, 3:1, 2:1, 1:1, 1:2, 1:3, 1:4, or 1:5.

259. The method of embodiment 258, wherein the ratio of pyridine:acetonitrile is about 1:1 v/v.

260, The method of any one of the preceding embodiments, wherein a modification step comprises convening a —P(−)— linkage phosphorus atom into —P(=N—)(−)— linkage phosphorus atom.

261. The method of any one of the preceding embodiments, wherein a modification step comprises converting $P^L$ which P into $P^L$ which is $P^N$.

262. The method of any one of the preceding embodiments, wherein a modification step comprises converting a $P^L$ which is P into

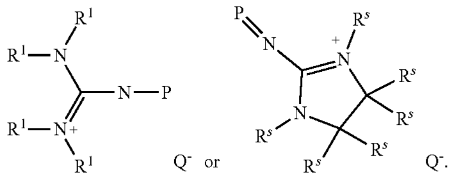

263. The method of any one of the preceding embodiments, wherein a modification step comprises converting a $P^L$ which is P into

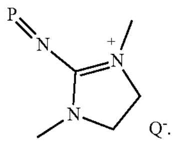

264. The method of any one of the preceding embodiments, wherein a modification step comprises converting an internucleotidic linkage of formula VII-b or a salt form thereof wherein each of X, Y, and Z is —O—, into an internucleotidic linkage of formula or a salt thereof, wherein each of X, Y, and Z is —O—.

265. The method of any one of embodiments 261-264, wherein —X-$L^s$-$R^5$ is of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein at least one of $R^5$ or $R^6$ is —C(O)R'.

266. The method of embodiment 265, wherein $R^6$ is —C(O)R'.

267. The method of embodiment 265, wherein $R^6$ is —C(O)$CH_3$.

268. The method of any one of embodiments 260-267, wherein a modification reagent system comprises an azido imidazolinium salt.

269, The method of embodiment 268, wherein the azido imidazolinium salt is 2-azido-1,3-dimethylimidazolinium hexafluorophosphate.

270. The method of any one of the preceding steps, wherein a modification step provides a modification composition comprising a plurality of modification product oligonucleotides, each of which is independently an oligonucleotide of formula O-I or a salt thereof.

271. The method of any, one of the preceding steps, wherein each modification step provides a modification product composition comprising a plurality of modification product oligonucleotides, each of which is independently an oligonucleotide of formula O-I or a salt thereof.

272. The method of any one of embodiments 255-271, wherein for a modification step, z of formula O-I for a modification product oligonucleotide ($z^{MD}$) is the same as z of formula O-I for a corresponding coupling product oligonucleotide ($z^{CP}$) or pre-modification capping product oligonucleotide ($z^{PR}$).

273, The method of any one of the preceding steps, wherein a modification product composition comprises a plurality of modification product oligonucleotides, each of which is independently of formula O-I or a salt thereof wherein each $L^P$ bonded to

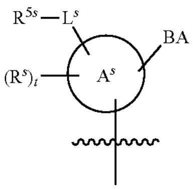

in formula O-I is independently an internucleotidic linkage of formula VII or a salt form thereof, wherein $P^L$ is not P.

274. The method of any one of the preceding steps, wherein a modification product composition comprises a plurality of modification product oligonucleotides, each of which is independently of formula O-I or a salt thereof, wherein each $L^P$ bonded to

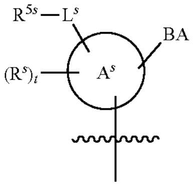

in formula O-I is independently an internucleotidic linkage of formula VII or a salt form thereof, wherein each $P^L$ is independently P(═O), P(═S) or $P^N$.

275, The method of any one of the preceding steps, wherein a modification product composition comprises a plurality of modification product oligonucleotides, each of which is independently of formula O-I or a salt thereof, wherein each $L^P$ bonded to

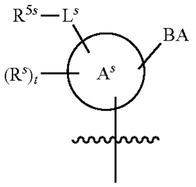

in formula O-I is independently an internucleotidic linkage of formula VII or a salt form thereof wherein each $P^L$ is independently P(═O), P(═S) $P^N$, and wherein each —X-$L^s$-$R^5$ is independently or of such a structure that H—X-$L^s$-$R^5$ is a compound of formula I, I-a, I-a-1, I-a-2, I-b, I-c, I-d, I-e, II, II-a, II-b, III, III-a, or III-b, wherein at least one of $R^5$ or $R^6$ is —C(O)R'.

276. The method of any one of the preceding steps, wherein a modification product composition comprises a plurality of modification product oligonucleotides, each of which is independently of formula O-I or a salt thereof, wherein each $L^P$ bonded to

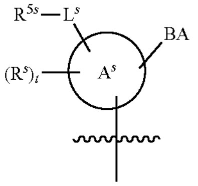

in formula O-I is independently an internucleotidic linkage of formula VII or a salt form thereof wherein each $P^L$ is independently P(═O), P(═S) or $P^N$, and wherein each —X-$L^s$-$R^5$ is of such a structure that H—X-$L^s$-$R^5$ is a compound of formula I, I-a, I-a-1, I-a-2, I-b, I-c, I-d, I-e, II, II-b, III, III-a or III-b, wherein at least one of $R^5$ or $R^6$ is —C(O)R'.

277. The method of any one of the preceding steps, wherein a modification product composition comprises a plurality of modification product oligonucleotides, each of which is independently of formula O-I or a salt thereof wherein each $L^P$ bonded to

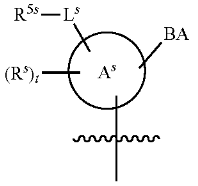

in formula O-I is independently an internucleotidic linkage of formula VII or a salt form thereof, wherein each $P^L$ is independently P(═O), and wherein each —X-$L^s$-$R^5$ is —S-$L^s$-$R^5$.

278. The method of any one of the preceding steps, wherein a modification product composition comprises a plurality of modification product oligonucleotides, each of which is independently of formula. O-I or a salt thereof wherein each $L^P$ bonded to

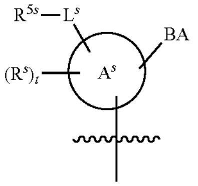

in formula O-I is independently an internucleotidic linkage of formula VII or a salt form thereof, wherein each $P^L$ is independently P(═O), and wherein each —X-$L^s$-$R^5$ is independently -$L^s$-$R^5$.

279. The method of any one of the preceding embodiments, wherein a modification product composition comprises a plurality of modification product oligonucleotides, each of which is independently of formula O-I or a salt thereof, wherein each $L^P$ is independently of formula VII or a salt form thereof and contains no free primary or secondary amino groups.

280. The method of any one of the preceding embodiments, wherein a modification product composition comprises a plurality of modification product oligonucleotides, each of which is independently of formula O-I or a salt thereof wherein each $L^P$ is independently of formula VII or a salt form thereof, wherein each of Y and Z is —O—.

281. The method of any one of the preceding embodiments, wherein the modification step provides a modification product composition comprises a plurality of modification product oligonucleotides, each of which is independently an oligonucleotide loaded on a support.

282. The method of any one of the preceding embodiments, wherein each modification step independently provides a modification product composition comprises a plurality of modification product oligonucleotides, each of which is independently an oligonucleotide loaded on a support.

283. The method of any one of the preceding embodiments, wherein a modification product composition comprising a plurality of modification product oligonucleotides is a chirally controlled oligonucleotide composition.

284. The method of any one of the preceding embodiments, wherein a modification product composition comprising a plurality of modification product oligonucleotides is a chirally controlled oligonucleotide composition wherein:

oligonucleotides of the plurality share the same constitution; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least $((DS)^{Nc}*100)\%$ of all oligonucleotides sharing the same base sequence in the modification product composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

285. The method of any one of the preceding embodiments, wherein a modification product composition comprises a plurality of oligonucleotides, each of which independently comprises a free —OH.

286. The method of any one of the preceding embodiments, wherein each modification product composition comprises a plurality of oligonucleotides, each of which independently comprises a free —OH.

287. The method of any one of the preceding embodiments, wherein a modification product composition comprises a plurality of de-blocked oligonucleotides or nucleosides, each of which independently comprises a free —OH.

288, The method of any one of the preceding embodiments, wherein each modification product composition comprises a plurality of de-blocked oligonucleotides or nucleosides, each of which independently comprises a free —OH.

289. The method of any one of embodiments 285-288, wherein the free —OH is a free 5'-OH.

290. The method of any one of the preceding embodiments, wherein a modification step comprising repeating the contacting, each time independently with the same or different modification reagent systems.

291. The method of any one of the preceding embodiments, wherein a post-modification capping step caps a plurality of hydroxyl groups.

292. The method of any one of the preceding embodiments, wherein a post-modification capping step, which caps a plurality of 5'-OH groups.

293. The method of any one of the preceding embodiments, wherein a post-modification capping reagent system comprises an acylating agent.

294. The method of any one of the preceding embodiments, wherein a post-modification capping reagent system comprises an acylating agent, wherein the acylating agent is of formula R'—C(O)-$L^s$-$R^s$.

295. The method of any one of the preceding embodiments, wherein a post-modification capping reagent system comprises an acylating agent, wherein the acylating agent is of formula R'—C(O)-$L^s$-$R^s$, wherein R'—C(O)— is bonded to a heteroatom of -$L^s$-$R^s$.

296. The method of any one of the preceding embodiments, wherein a post-modification capping reagent system comprises an acylating agent, wherein the acylating agent is of formula R'—C(O)-$L^s$-$R^s$, wherein R'—C(O)— is bonded to an oxygen, nitrogen, halogen, or sulfur, of -$L^s$-$R^s$.

297. The method of any one of the preceding embodiments, wherein a post-modification capping reagent system comprises an acylating agent, wherein the acylating agent is an anhydride.

298. The method of any one of the preceding embodiments, wherein a post-modification capping reagent system comprises an acylating agent, wherein the acylating agent is R—NCO.

299, The method of any one of the preceding embodiments, wherein a post-modification capping reagent system comprises an acylating agent, wherein the acylating agent is Ph-NCO.

300. The method of any one of the preceding embodiments, wherein a post-modification capping reagent system comprises a base.

301. The method of embodiment 300, wherein a base is of formula N(R), wherein the nitrogen atom has no alpha-substitution.

302. The method of embodiment 300, wherein a base is optionally substituted pyridine.

303. The method of embodiment 300, wherein a base is substituted pyridine, comprising substituents at 2'- and 6'-positions.

304, The method of embodiment 300, wherein a base is pyridine.

305. The method of embodiment 300, wherein a base is 2,6-lutidine.

306. The method of embodiment 300, wherein a base is 2,6-lutidine.

307. The method of embodiment 300, wherein a base is triethylamine.

308. The method of embodiment 300, wherein a base is DIEA.

309. The method of embodiment 300, wherein a base is N-methyl morpholine.

310. The method of embodiment 300, wherein a base is 2-(dimethylamino)acetonitrile.

311. The method of any one of the preceding embodiments, wherein a post-modification capping reagent system comprises a strong nucleophile, or a reagent that when contacted with a coupling product composition, can provide a strong nucleophile.

312, The method of any one of the preceding embodiments, wherein a post-modification capping reagent system comprises an esterification catalyst, or a reagent that when contacted with a coupling product composition, can provide a strong nucleophile.

313. The method of any one of the preceding embodiments, wherein a strong nucleophile or an esterification catalyst is DMAP or NMI.

314. The method of any one of the preceding embodiments, wherein a strong nucleophile or an esterification catalyst is NMI.

315, The method of any one of the preceding embodiments, wherein a strong nucleophile or an esterification catalyst is DMAP.

316. The method of any one of embodiments 166-170, wherein the post-modification capping reagent system comprises one or more reagents selected from strong nucleophiles, one or more reagents that when contacted with a coupling product composition can provide one or more strong nucleophiles, one or more esterification catalysts, and one or more reagents that when contacted with a coupling product composition can provide one or more esterification catalysts, wherein level of such one or more reagents combined are at least 0.2, 0.5, 1, 1.1, 1.2, 1.5, or 2 equivalents relative to the acylating agent, the base, or the plurality of product oligonucleotides of the modification product composition.

317, The method of embodiment 316, wherein the level is at least 0.2, 0.5, 1, 1,1, 1,2, 1,5, or 2 equivalents relative to all acylating agents of the post-modification capping reagent system.

318. The method of embodiment 316, wherein the level is at least 1, 1.1, 1.2, 1.5, or 2 equivalents relative to the plurality of product oligonucleotides of the modification product composition.

319. The method of any one of the preceding embodiments, wherein a post-modification capping step is efficient for amidation and esterification.

320. The method of any one of the preceding embodiments, wherein a post-modification capping step is efficient for capping primary and secondary amino groups and for capping of free hydroxyl groups in that the post-modification capping step caps at least 80%, 85%, 90%, 91%, 92%, 93%, 94%, 95%, 96%, 97%, 98%, or 99% primary and secondary amino groups and at least 80%, 85%, 90%, 91%, 92%, 93%, 94%, 95%, 96%, 97%, 98%, or 99% free hydroxyl groups in the modification product composition.

321. The method of any one of the preceding embodiments, wherein a post-modification capping step caps at least 90%, 91%, 92%, 93%, 94%, 95%, 96%, 97%, 98%, or 99% of free hydroxyl groups of a modification product composition.

322. The method of any one of the preceding embodiments, wherein a post-modification capping step caps at least 90%, 91%, 92%, 93%, 94%, 95%, 96%, 97%, 98%, or 99% of free 5'-OH groups of a modification product composition.

323, The method of any one of the preceding embodiments, wherein the post-modification capping step caps one or more amino groups.

324. The method of any one of the preceding embodiments, wherein a post-modification capping step caps at least 90%, 91%, 92%, 93%, 94%, 95%, 96%, 97%, 98%, or 99% of free primary and secondary amino groups of a coupling product composition.

325. The method of any one of the preceding embodiments, wherein a post-modification capping step comprises:

contacting a coupling product composition with a first post-modification capping system; and contacting a coupling product composition with a second post-modification capping system.

326. The method of embodiment 184, wherein the first and second post-modification capping systems are different.

327. The method of embodiment 326, wherein the first post-modification capping reagent system is selective for capping of amino groups over hydroxyl groups, and the second post-modification capping reagent system caps both amino and hydroxyl groups efficiently.

328. The method of any one of the preceding embodiments, wherein a post-modification capping reagent system comprises:

Pyridine/DMAP/$Ac_2O$;

2,6-Lutidine/NMI/$Ac_2O$;

2,4,6-Collidinel$Ac_2O$;

Triethylamine/$Ac_2O$;

DIEA/$Ac_2O$;

N-Methyl morpholine/$Ac_2O$;

2,6-Lutidine, then after a period of time, NMI/$Ac_2O$;

2,6-Lutidine/$Ac_2O$;

PhNCO/2,6-Lutidine; or 2-(dimethylamino)acetonitrile/$Ac_2O$.

329. The method of any one of the preceding embodiments, wherein a post-modification capping reagent system comprises:

Pyridine (2 equiv.)/DMAP (cat.)/$Ac_2O$(4 equiv.);

2,6-Lutidine (2 equiv.)/NMI (0.25 equiv.)/$Ac_2O$(4 equiv.);

2,4,6-Collidine /$Ac_2O$(4 equiv.);

Triethylamine/$Ac_2O$(4 equiv.);

DIEA/$Ac_2O$(4 equiv.);

N-Methyl morpholine/$Ac_2O$(4 equiv.);

2,6-Lutidine (2 equiv.) then after 5 min. NMI equiv.)/$Ac_2O$(4 equiv.);

2,6-Lutidine/$Ac_2O$(4 equiv.);

PhNCO/2,6-Lutidine; or 2-(dimethylamino)acetonitrile/$Ac_2O$.

330. The method of any one of the preceding embodiments, wherein a post-modification capping reagent system is a solution of 2,6-Lutidine/NMI/$Ac_2O$.

331. The method of any one of embodiments 328-330, wherein a post-modification capping reagent system is a solution in acetonitrile.

332. The method of any one of the preceding steps; wherein a post-modification capping step provides a post-modification capping composition comprising a plurality of post-modification capping product oligonucleotides, each of which is independently an oligonucleotide of formula O-I or a salt thereof.

333. The method of any one of the preceding steps, wherein each post-modification capping step provides a post-modification capping product composition comprising a plurality of post-modification capping product oligonucleotides, each of which is independently an oligonucleotide of formula O-I or a salt thereof.

334. The method of any one of embodiments 332-333, wherein for a post-modification capping step, z of formula O-I for a post-modification capping product oligonucleotide ($z^{PT}$) is the same as z of formula O-I for a corresponding modification product oligonucleotide ($z^{MD}$)).

335. The method of any one of the preceding steps, wherein a post-modification capping product composition comprises a plurality of post-modification capping product oligonucleotides, each of which is independently of formula O-I or a salt thereof, wherein each $L^P$ in formula O-I is independently an internucleotidic linkage of formula VII, or a salt form thereof, wherein $P^L$ is not P.

336. The method of any one of the preceding steps, wherein a post-modification capping product composition comprises a plurality of post-modification capping product oligonucleotides, each of which is independently of formula O-I or a salt thereof, wherein each $L^P$ in formula O-I is independently an internucleotidic linkage of formula VII, or a salt form thereof, wherein each $P^L$ is independently P(═O), P(═S) or $P^N$.

337. The method of any one of the preceding steps, wherein a post-modification capping product composition comprises a plurality of post-modification capping product oligonucleotides, each of which is independently of formula O-I or a salt thereof, wherein each $L^P$ in formula O-I is independently an internucleotidic linkage of formula VII, or a salt form thereof, wherein each $P^L$ independently P(═O) or 338. The method of any one of the preceding embodiments, wherein a post-modification capping product composition comprises a plurality of post-modification capping product oligonucleotides, each of which is independently of formula O-I or a salt thereof, wherein each LP in formula O-I is independently of formula VII or a salt form thereof, wherein each —X-$L^s$-$R^5$ is independently -$L^7$-$R^1$, or of such a structure that H—X-$L^s$-$R^5$ is a compound of formula I, I-a, I-a-1, I-a-2, I-b, I-c, I-d, I-e, II, II-a, II-b, III, III-a, or wherein at least one of $R^5$ or $R^6$ is —C(O)R'.

339. The method of any one of the preceding embodiments, wherein a post-modification capping product composition comprises a plurality of post-modification capping product oligonucleotides each of which is independently an oligonucleotide of formula O-I or a salt thereof, comprising one or more $L^P$ wherein $P^L$ is P(═O), and —X-$L^s$-$R^5$ is —S-$L^s$-$R^5$.

340. The method of any one of the preceding embodiments, wherein a post-modification capping product composition comprises a plurality of post-modification capping product oligonucleotides each of which is independently an oligonucleotide of formula O-I or a salt thereof, comprising one or more if wherein $P^L$ is P(═O), and —X-$L^s$-$R^5$ is —S-$L^s$-$R^5$.

341. The method of any one of the preceding embodiments, wherein a post-modification capping product composition comprises a plurality of post-modification capping product oligonucleotides each of which is independently an oligonucleotide of formula O-I or a salt thereof, comprising one or more LP wherein $P^L$ is P(═S), and of such a structure that H—X-$L^s$-$R^5$ is a compound of formula I, I-a, I-a-1, I-a-2, I-b, I-c, I-d, I-e, II, II-a, II-b, III, III-a, or wherein at least one of $R^5$ or $R^6$ is —C(O)R'.

342. The method of any one of the preceding embodiments, wherein a post-modification capping product composition comprises a plurality of post-modification capping product oligonucleotides each of which is independently an oligonucleotide of formula O-I or a salt thereof, comprising one or more $L^P$ wherein $P^L$ is $P^N$, and of such a structure that H—X-$L^s$-$R^5$ is a compound of formula I, I-a, I-a-1, I-a-2, I-b, I-c, i-d, I-e, II, II-a, II-b, III, III-a, or III-b, wherein at least one of $R^5$ or $R^6$ is —C(O)R'.

343. The method of any one of the preceding embodiments, wherein a post-modification capping product composition comprises a plurality of post-modification capping product oligonucleotides, each of which is independently of formula O-I or a salt thereof, wherein each $L^P$ is independently of formula VII or a salt form thereof, wherein each of Y and Z is —O—.

344. The method of any one of the preceding embodiments, wherein the post-modification capping step provides a post-modification capping product composition comprises a plurality of post-modification capping product oligonucleotides, each of which is independently an oligonucleotide loaded on a support.

345, The method of any one of the preceding embodiments, wherein each post-modification capping step independently provides a post-modification capping product composition comprises a plurality of post-modification capping product oligonucleotides, each of which is independently an oligonucleotide loaded on a support.

346. The method of any one of the preceding embodiments, wherein a post-modification capping product composition comprising a plurality of post-modification capping product oligonucleotides is a chirally controlled oligonucleotide composition.

347, The method of any one of the preceding embodiments, wherein a post-modification capping product composition comprising a plurality of post-modification capping product oligonucleotides is a chirally controlled oligonucleotide composition wherein:

oligonucleotides of the plurality share the same constitution; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least $((DS)^{NC}*100)$% of all oligonucleotides sharing the same base sequence in the post-modification capping product composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

348. The method of any one of the preceding embodiments, wherein a post-modification capping step comprising repeating the contacting, each time independently with the same or different post-modification capping reagent systems.

349. The method of any one of the preceding embodiments, wherein the strong nucleophile and/or esterification catalyst is a compound that provides at least 60%, 70%, 80%, 90%, 95%, 96%, 97%, 98%, 99%, or 99.5% completion of esterification of 5'-OH of a plurality of oligonucleotides when used in a capping reagent system at 3-10% (volume/volume for liquid compounds; weight/volume for solid compounds) concentration, together with 5-10% $Ac_2O$ (v/v), 5-15% 2,6-lutidine (v/v), in ACN or THF as solvent, and more than 10 equivalents relative to all oligonucleotides in contact with the capping reagent system for 0.1, 0.2, 0.3, 0.4, 0.5, 1, 2, 3, 4, 5, 7, 8, 9, or 10 minutes.

350. The method of any one of the preceding embodiments, wherein the post-modification capping step is comparable or identical to a capping condition of traditional oligonucleotide synthesis based on phosphoramidite chemistry with respect to efficiency of capping hydroxyl groups to be capped.

351. The method of any one of the preceding embodiments, comprising a de-blocking step, wherein a de-blocking reagent system comprises a de-blocking reagent, wherein the de-blocking reagent is an acid.

352, The method of embodiment 348, wherein the acid is DCA (dichloroacetic acid).

353, The method of embodiment 348, wherein the de-blocking reagent system is 3% DCA in toluene.

354. The method of any one of the preceding embodiments, comprising a de-blocking step, wherein:

a modification product composition being contacted comprises a plurality of modification product oligonucleotides, each of which is independently an oligonucleotide; or a post-modification capping product composition being contacted comprises a plurality of post-modification capping product oligonucleotides, each of which is independently an oligonucleotide; and the de-blocking group converts a plurality of blocked hydroxyl groups of oligonucleotides of the modification or post-modification capping plurality into a plurality of free hydroxyl groups.

355, The method of embodiment 354, wherein the de-blocking group converts a plurality of 5'-blocked hydroxyl groups of oligonucleotides of the modification or post-modification capping plurality into a plurality of 5f-free hydroxyl groups.

356. The method of embodiment 354, wherein the de-blocking step converts a plurality of DMTr-blocked 5'-blocked hydroxyl groups of oligonucleotides of the modification or post-modification capping plurality into a plurality of 5'-free hydroxyl groups.

357. The method of any one of the preceding embodiments, comprising a de-blocking step, wherein:

a modification product composition being contacted comprises a plurality of modification product oligonucleotides, each of which is independently an oligonucleotide of formula O-I or a salt thereof, wherein $R^{5s}$ is —OR where R is not —H, and each $L^P$ is an internucleotidic linkage of formula VII or a salt form thereof wherein $P^L$ is not P; or a post-modification capping product composition being contacted comprises a plurality of post-modification capping product oligonucleotides, each of which is independently an oligonucleotide of formula O-I or a salt thereof, wherein $R^{5s}$ is —OR where R is not —H, and each if is an internucleotidic linkage of formula VII or a salt form thereof, wherein $P^L$ is not P; and the de-blocking step converts $R^{5s}$ from —OR, wherein R is not —H, into —OH.

358, The method of any one of the preceding embodiments, wherein the de-blocking group only deblock a blocked hydroxyl group in a nucleoside unit that corresponds to a nucleoside unit of the coupled partner compound of the immediately preceding coupling step.

359. The method of any one of the preceding steps, wherein a de-blocking step provides a post-modification capping composition comprising a plurality of post-modification capping product oligonucleotides, each of which is independently an oligonucleotide of formula O-I or a salt thereof.

360. The method of any one of the preceding steps, wherein each deblocking step provides a deblocking product composition comprising a plurality of deblocking product oligonucleotides, each of which is independently an oligonucleotide of formula O-I or a salt thereof.

361, The method of any one of the preceding embodiments, wherein for a deblocking step, z of formula O-I for a deblocking product oligonucleotide ($z^{DB}$) is the same as z of formula O-I for a corresponding modification product oligonucleotide ($z^{MD}$) or post-modification capping product oligonucleotide ($z^{PT}$).

362. The method of any one of the preceding steps, wherein a de-blocking product composition comprises a plurality of de-blocking product oligonucleotides, each of which is independently of formula O-I or a salt thereof, wherein $R^{5s}$ is —OH.

363. The method of any one of the preceding steps, wherein a de-blocking product composition comprises a plurality of de-blocking product oligonucleotides, each of which is independently of formula O-I or a salt thereof, wherein $R^{5s}$ is 5'-OH.

364. The method of any one of the preceding steps, wherein a de-blocking product composition comprises a plurality of de-blocking product oligonucleotides, each of which is independently of formula. O-I or a salt thereof, wherein each $L^P$ in formula O-I is independently an internucleotidic linkage of formula VII, or a salt form thereof, wherein $P^L$ is not P.

365. The method of any one of the preceding steps, wherein a de-blocking product composition comprises a plurality of dc-blocking product oligonucleotides, each of which is independently of formula O-I or a salt thereof, wherein each $L^P$ in formula O-I is independently an internucleotidic linkage of formula VII, or a salt form thereof, wherein each $P^L$ is independently P(=O), P(=S) or $P^N$.

366. The method of any one of the preceding steps, wherein a de-blocking product composition comprises a plurality of de-blocking product oligonucleotides, each of which is independently of formula O-I or a salt thereof, wherein each $L^P$ in formula O-I is independently an internucleotidic linkage of formula VII, or a salt form thereof, wherein each $P^L$ independently P(=O) or P(=S).

367. The method of any one of the preceding embodiments, wherein a de-blocking product composition comprises a plurality of de-blocking product oligonucleotides, each of which is independently of formula O-I or a salt thereof, wherein each $L^P$ in formula O-I is independently of formula VII or a salt form thereof, wherein each —X-$L^s$-$R^5$ is independently -$L^7$-$R^1$, or of such a structure that H—X-$L^s$-$R^5$ is a compound of formula I, I-a, I-a-1, I-a-2, I-b, I-c, I-d, I-e, II, II-a, II-b, III, III-a, or III-b, wherein at least one of $R^5$ or $R^6$ is —C(O)R'.

368. The method of any, one of the preceding embodiments, wherein a de-blocking product composition comprises a plurality of de-blocking product oligonucleotides each of which is independently an oligonucleotide of formula O-I or a salt thereof, comprising one or more $L^P$ wherein $P^L$ is P(=O), and —X-$L^s$-$R^5$ is -$L^7$-$R^1$.

369. The method of any one of the preceding embodiments, wherein a dc-blocking product composition comprises a plurality of de-blocking product oligonucleotides each of which is independently an oligonucleotide of formula O-I or a salt thereof, comprising one or more $L^P$ wherein $P^L$ is O, and —X-$L^s$-$R^5$ is —S-$L^s$-$R^5$.

370. The method of any one of the preceding embodiments, wherein a de-blocking product composition comprises a plurality of dc-blocking product oligonucleotides each of which is independently an oligonucleotide of formula O-I or a salt thereof, comprising one or more $L^P$ wherein $P^L$ is P(=S), and of such a structure that H—X-$L^s$-$R^5$ is a compound of formula I, I-a, I-a-1, I-a-2, I-b, I-c, I-d, I-e, II, II-a, II-b, III, III-a, or III-b, wherein at least one of $R^5$ or $R^6$ is —C(O)R'.

371. The method of any one of the preceding embodiments, wherein a de-blocking product composition comprises a plurality of de-blocking product oligonucleotides each of which is independently an oligonucleotide of formula O-I or a salt thereof, comprising one or more $L^P$ wherein $P^L$ is $P^N$, and of such a structure that H—X-$L^s$-$R^5$ is a compound of formula I, I-a, I-a-1, I-a-2, I-b, I-c, I-d, I-e, II, II-a, II-b, III, III-a, or III-b, wherein at least one of $R^5$ or $R^6$ is —C(O)R'.

372. The method of any one of the preceding embodiments, wherein a de-blocking product composition comprises a plurality of de-blocking product oligonucleotides, each of which is independently of formula O-I or a salt thereof, wherein each $L^P$ is independently of formula VII or a salt form thereof, wherein each of Y and Z is —O—.

373, The method of any one of the preceding embodiments, wherein the de-blocking step provides a de-blocking product composition comprises a plurality of de-blocking product oligonucleotides, each of which is independently an oligonucleotide loaded on a support.

374. The method of any one of the preceding embodiments, wherein each de-blocking step independently provides a de-blocking product composition comprises a plurality of de-blocking product oligonucleotides, each of which is independently an oligonucleotide loaded on a support.

375. The method of any one of the preceding embodiments, wherein a de-blocking product composition comprising a plurality of de-blocking product oligonucleotides is a chirally controlled oligonucleotide composition.

376. The method of any one of the preceding embodiments, wherein a de-blocking product composition comprising a plurality of de-blocking product oligonucleotides is a chirally controlled oligonucleotide composition wherein:

oligonucleotides of the plurality share the same constitution; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least $((DS)^{Nc}*100\%$ of all oligonucleotides sharing the same base sequence in the de-blocking product composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

377. The method of any one of the preceding embodiments, wherein a de-blocking step comprising repeating the contacting, each time independently with the same or different de-blocking reagent systems.

378. The method of any one of the preceding embodiments, comprising repeating steps (1) through (5) a number of times until a desired length of a plurality of oligonucleotides is achieved to provide a post-cycle product composition comprising a plurality of post-cycle product oligonucleotides.

379. The method of embodiment 278, wherein the desired length is the common length of the plurality of oligonucleotides.

380. The method of any one of the preceding embodiments, wherein each post-cycle product oligonucleotide is independently an oligonucleotide of formula O-I or a salt thereof.

381. The method of any one of the preceding embodiments, wherein each post-cycle product oligonucleotide is independently an oligonucleotide of formula O-I or a salt thereof, wherein each is independently of formula, VII or a salt form thereof.

382. The method of any one of the preceding embodiments, wherein each post-cycle product oligonucleotide is independently an oligonucleotide of formula O-I or a salt thereof, wherein each $L^P$ is independently of formula VII or a salt form thereof, wherein $P^L$ is not P.

383, The method of any one of the preceding steps, wherein a post-cycle product composition comprises a plurality of post-cycle product oligonucleotides, each of which is independently of formula O-I or a salt thereof, wherein each $L^P$ in formula O-I is independently an internucleotidic linkage of formula VII, or a salt form thereof, wherein each $P^L$ is independently P(=O), P(=S) or $P^N$.

384. The method of any one of the preceding steps, wherein a post-cycle product composition comprises a plurality of post-cycle product oligonucleotides, each of which is independently of formula O-I or a salt thereof, wherein each $L^P$ in formula O-I is independently an internucleotidic linkage of formula VII, or a salt form thereof, wherein each $P^L$ independently P(=O) or P(=S).

385. The method of any one of the preceding embodiments, wherein a post-cycle product composition comprises a plurality of post-cycle product oligonucleotides, each of which is independently of formula O-I or a salt thereof, wherein each $L^P$ in formula O-I is independently of formula VII or a salt form thereof, wherein each —X-$L^s$-$R^5$ is independently -$L^7$-$R^1$, or of such a structure that —H—X-$L^s$-$R^5$ is a compound of formula I, I-a, I-a-1, I-a-2, I-b, 1-c, I-d, I-e, II, II-a, II-b, III, III-a, or III-b, wherein at least one of $R^5$ or $R^6$ is —C(O)R'.

386. The method of any one of the preceding embodiments, wherein a post-cycle product composition comprises a plurality of post-cycle product oligonucleotides each of which is independently an oligonucleotide of formula O-I or a salt thereof, comprising one or more $L^P$ wherein $P^L$ is P(=O), and —X-$L^s$-$R^5$ is -$L^7$-$R^1$.

387, The method of any one of the preceding embodiments, wherein a post-cycle product composition comprises a plurality of post-cycle product oligonucleotides each of which is independently an oligonucleotide of formula O-I or a salt thereof, comprising one or more $L^P$ wherein —$P^L$ is P(=S), and —X-$L^s$-$R^5$ is -$L^7$-$R^1$.

388. The method of any one of the preceding embodiments, wherein a post-cycle product composition comprises a plurality of post-cycle product oligonucleotides each of which is independently an oligonucleotide of formula O-I or a salt thereof comprising one or more $L^P$ wherein $P^L$ is $P^N$, and —X-$L^s$-$R^5$ is -$L^7$-$R^1$.

389, The method of any one of the preceding embodiments, wherein a post-cycle product composition comprises a plurality of post-cycle product oligonucleotides each of which is independently an oligonucleotide of formula O-I or a salt thereof, comprising one or more $L^P$ wherein —$P^L$ is P(═O), and —X-$L^s$-$R^5$ is —S-$L^s$-$R^5$.

390. The method of any one of the preceding embodiments, wherein a post-cycle product composition comprises a plurality of post-cycle product oligonucleotides each of which is independently an oligonucleotide of formula O-I or a salt thereof comprising one or more $L^P$ wherein $P^L$ is P(═S), and of such a structure that H—X-$L^s$-$R^5$ is a compound of formula I, I-a, I-a-1, I-a-2, I-b, I-e, I-d, I-e, II, II-a, II-b, III, III-a, or III-b, wherein at least one of $R^5$ or $R^6$ is —C(O)R'.

391, The method of any one of the preceding embodiments, wherein a post-cycle product composition comprises a plurality of post-cycle product oligonucleotides each of which is independently an oligonucleotide of formula O-I or a salt thereof, comprising one or more $L^P$ wherein —$P^L$ is $P^N$, and of such a structure that H—X-$L^s$-$R^5$ is a compound of formula I, I-a, I-a-1, I-a-2, I-b, I-c, I-d, I-e, II, II-a, II-b, III, III-a, or III-b, wherein at least one of $R^5$ or $R^6$ is —C(O)R'.

392. The method of any one of the preceding embodiments, wherein a post-cycle product composition comprises a plurality of post-cycle product oligonucleotides, each of which is independently of formula O-I or a salt thereof, wherein each $L^P$ is independently of formula VII or a salt form thereof, wherein each of Y and Z is —O—.

393. The method of any one of the preceding embodiments, wherein the post-cycle step provides a post-cycle product composition comprises a plurality of post-cycle product oligonucleotides, each of which is independently an oligonucleotide loaded on a support.

394. The method of any one of the preceding embodiments, wherein each post-cycle step independently provides a post-cycle product composition comprises a plurality of post-cycle product oligonucleotides, each of which is independently an oligonucleotide loaded on a support.

395, The method of any one of the preceding embodiments, wherein a post-cycle product composition comprising a plurality of post-cycle product oligonucleotides is a chirally controlled oligonucleotide composition.

396. The method of any one of the preceding embodiments, wherein a post-cycle product composition comprising a plurality of post-cycle product oligonucleotides is a chirally controlled oligonucleotide composition wherein:

oligonucleotides of the plurality share the same constitution; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least $((DS)^{Nc}*100)\%$ of all oligonucleotides sharing the same base sequence in the post-cycle product composition are oligonucleotides of the plurality; wherein DS is at least 80%, 85%, 90%, 91%, 92%, 93%, 94%, 95%, 96%, 97%, 98% or 99%, and Nc is the number of chirally controlled internucleotidic linkage.

397. The method of any one of the preceding embodiments, comprising further modifying a plurality of post-cycle product oligonucleotides.

398. The method of any one of the preceding embodiments, comprising conjugating a plurality of post-cycle product oligonucleotides with lipid moieties.

399. The method of any one of the preceding embodiments, comprising conjugating a plurality of post-cycle product oligonucleotides with targeting moieties.

400. The method of any one of the preceding embodiments, comprising conjugating a plurality of post-cycle product oligonucleotides with targeting moieties, which targeting moieties are cell receptor ligands.

401. The method of any one of the preceding embodiments, comprising conjugating a plurality of post-cycle product oligonucleotides with targeting moieties, which targeting moieties are carbohydrate moieties 402. The method of any one of the preceding embodiments, comprising conjugating a plurality of post-cycle product oligonucleotides with carbohydrate moieties.

403. The method of any one of the preceding embodiments, comprising a post-cycle modification step, comprising:

providing a composition comprising a plurality of oligonucleotides with a post-cycle modification reagent system;

removing one or more chiral auxiliary moieties from the plurality of oligonucleotides.

404. The method of any one of the preceding embodiments, wherein a post-cycle modification step removes one or more chiral auxiliaries.

405. The method of any one of the preceding embodiments, comprising a post-cycle modification step, wherein the post-cycle modification step comprises:

providing a composition comprising a plurality of oligonucleotides with a post-cycle modification reagent system;

converting one or more internucleotidic linkages of formula VII or a salt form thereof, wherein $P^L$ is P(═S), into phosphorothioate internucleotidic linkages (—O—P(═O)(—SH)—O— or a salt form thereof).

406. The method of any one of the preceding embodiments, comprising a post-cycle modification step, wherein the post-cycle modification step comprises:

providing a composition comprising a plurality of oligonucleotides with a post-cycle modification reagent system;

converting one or more internucleotidic linkages of formula VII or a salt form thereof, wherein $P^L$ is $P^N$, into one or more internucleotidic linkages each independently of formula NL-n-1, NL-n-2, NL-n-3, NL-n-4, NL, NL-a-1, NL-a-2, NL-b-1, NL-b-2, NL-c-1, NL-c-2, NL-d-1, or NL-d-2.

407. The method of any one of the preceding embodiments, comprising a post-cycle modification step, wherein the post-cycle modification step comprises:

providing a composition comprising a plurality of oligonucleotides with a post-cycle modification reagent system;

converting one or more internucleotidic linkages of formula VII or a salt form thereof, wherein $P^L$ is P(═S), and —X-$L^s$-$R^5$ comprises a —$Si(R)_3$ moiety, into phosphorothioate internucleotidic linkages (—O—P(═O)(—SH)—O— or a salt form thereof).

408. The method of any one of the preceding embodiments, wherein an X-$L^s$-$R^5$ comprises a —$Si(R)_3$ moiety is

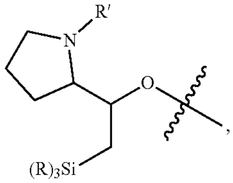
,
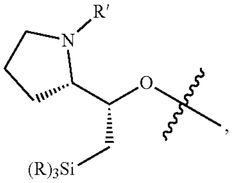
, or
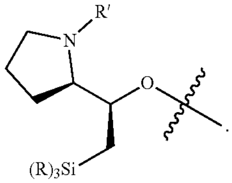
.

409. The method of embodiment 408, wherein R' is —H.

410. The method of embodiment 408, wherein R' is —C(O)R.

411, The method of embodiment 408, wherein. R' is —$C(O)CH_3$.

412, The method of any one of embodiments 408-411, wherein —$Si(R)_3$ is —$SiPh_2Me$.

413. The method of any one of the preceding embodiments, wherein the post-cycle modification reagent system comprises $F^-$.

414. The method of any one of the preceding embodiments, wherein the post-cycle modification reagent system comprises HF-Pyridine.

415. The method of any one of the preceding embodiments, wherein the post-cycle modification reagent system comprises 3HF-TEA.

416, The method of any one of the preceding embodiments, wherein the post-cycle modification reagent system comprises tetrabutylammonium fluoride.

417. The method of any one of the preceding embodiments, wherein the post-cycle modification reagent system comprises tetrabutylammonium difluorotriphenylsilicate.

418. The method of any one of the preceding embodiments, comprising a post-cycle modification step, wherein the post-cycle modification step comprises:

providing a composition comprising a plurality of oligonucleotides with a post-cycle modification reagent system;

converting one or more internucleotidic linkages of formula VII or a salt form thereof, wherein each $P^L$ is independently P(═O), P(═S) or $P^N$, and each —X-$L^s$-$R^5$ independently comprises a base-labile chiral auxiliary group, into one or more internucleotidic linkages independently selected from natural phosphate linkages, phosphorothioate internucleotidic linkages, and internucleotidic linkages of formula NL-n-1, NL-n-2, NL-n-3, NL-n-4, NL, NL-a-1, NL-a-2, NL-b-1, NL-b-2, NL-c-2, NL-d-1, or NL-d-2.

419. A method for preparing an oligonucleotide or an oligonucleotide composition, comprising a post-cycle modification step, wherein the post-cycle modification step comprises:

providing a composition comprising a plurality of oligonucleotides with a post-cycle modification reagent system;

converting one or more internucleotidic linkages of formula VII or a salt form thereof, wherein each $P^L$ is independently P(═O), P(═S) or $P^N$, and each —X-$L^s$-$R^5$ independently comprises a base-labile chiral auxiliary group, into one or more internucleotidic linkages independently selected from natural phosphate linkages, phosphorothioate internucleotidic linkages, and internucleotidic linkages of formula NL-n-1, NL-n-2, NL-n-3, NL-n-4, NL, NL-a-1, NL-a-2, NL-b-1, NL-b-2, NL-c-1, NL-c-2, NL-d-1, or NL-d-2.

420, The method of any one of embodiments 418-419, wherein the composition comprising a plurality of oligonucleotides is a post-cycle product composition of any one of embodiments 378-402.

421. The method of any one of embodiments 418-420, wherein one or more internucleotidic linkages of formula VII or a salt form thereof wherein $P^L$ is P(═O) are converted into one or more natural phosphate linkages.

422. The method of any one of embodiments 418-421, wherein one or more internucleotidic linkages of formula VII or a salt form thereof wherein $P^L$ is $P^N$ are independently converted into one or more internucleotidic linkages of formula NL-n-1, NL-n-2, NL-n-3, NL-n-4, NL, NL-a-1, NL-a-2, NL-b-1, NL-b-2, NL-c-1, NL-c-2, NL-d-1, or NL-d-2.

423, The method of any one of embodiments 418-422, wherein one or more internucleotidic linkages of formula VII or a salt form thereof wherein $P^L$ is $P^N$ are independently converted into n001.

424. The method of any one of embodiments 418-423, wherein one or more internucleotidic linkages of formula VII or a salt form thereof wherein $P^L$ is P(═S) are converted into one or more phosphorothioate internucleotidic linkages.

425. The method of any one of embodiments 418-424, wherein each —X-$L^s$-$R^5$ comprising a base-labile chiral auxiliary group is independently of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein at least one of $R^5$ or $R^6$ is —C(O)R'.

426. The method of any one of embodiments 418-425, wherein each —X-$L^s$-$R^5$ comprising a base-labile chiral auxiliary group is independently of such a structure that H—X-$L^s$-$R^5$ is a compound of formula I, I-a, I-a-1, I-a-2, I-b, I-c, or I-d, optionally wherein at least one of $R^5$ or $R^6$ is —C(O)R'.

427. The method of any one of the preceding embodiments, wherein each —X-$L^s$-$R^5$ comprising a chiral auxiliary group is independently of such a structure that H—X-$L^s$-$R^5$ is a compound of formula I, I-a, I-a-1, I-a-2, I-b, I-c, I-d, I-c, II, II-a, II-b, III, III-a, or III-b, optionally wherein at least one of $R^5$ or $R^6$ is —C(O)R'.

428, The method of any one of the preceding embodiments, wherein each —X-$L^s$-$R^5$ comprising a chiral auxiliary group is independently of such a structure that H—X-$L^s$-$R^5$ is a compound of formula I, I-a, I-a-1, I-a-2, I-b, I-c, or I-d, optionally wherein at least one of $R^5$ or $R^6$ is —C(O)R'.

429. The method of any one of embodiments 425-428, wherein $R^2$ comprises one or more electron-withdrawing groups.

430. The method of any one of embodiments 425-428, wherein $R^2$ is —$CH_2$—CH(electron-withdrawing group)$_2$ or —$CH_2$—$CH_2$ (electron-withdrawing group).

431. The method of any one of embodiments 425-428, wherein $R^2$ is -L'-L"-R'.

432. The method of any one of embodiments 425-428, wherein $R^2$ is —$CH_2SO_2R'$.

433, The method of any one of embodiments 425-428, wherein $R^2$ is —$CH_2SO_2R'$, wherein R' is optionally substituted phenyl.

434. The method of any one of embodiments 425-428, wherein $R^1$ is —$CH_2SO_2Ph$.

435. The method of any one of embodiments 425-428, wherein $R^1$ is optionally substituted

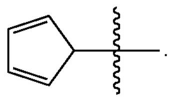

436. The method of any one of embodiments 425-428, wherein $R^2$ is optionally substituted

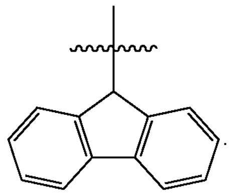 [SMILES: *C1c2ccccc2-c2ccccc21]

437. The method of any one of embodiments 425-428, wherein each —X-$L^s$-$R^5$ independently comprises a base-labile chiral auxiliary group is of such a structure that H—X-$L^s$-$R^5$ is a compound selected from Tables 5-17, or an enantiomer or a diastereomer thereof.

438. The method of any, one of embodiments 425-428, wherein each —X-$L^s$-$R^5$ is independently

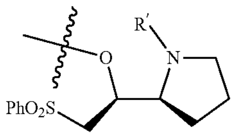

or

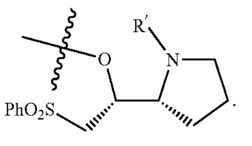

439. The method of embodiment 438, wherein R' is —H.

440. The method of embodiment 438, wherein R' is —C(O)R.

441. The method of embodiment 438, wherein R' is —C(O)$CH_3$.

442. The method of any one of embodiments 418-441; wherein the post-cycle modification reagent system comprises a base.

443. The method of embodiment 442, wherein the base has the structure of $NR_3$.

444. The method of embodiment 443, wherein the base is DEA.

445. The method of any one of embodiments 442-444, wherein the post-cycle modification reagent system comprises a base and a solvent.

446. The method of any one of embodiments 442-445, wherein the post-cycle modification reagent system comprises a base and a solvent.

447. The method of embodiment 446, wherein the solvent is acetonitrile.

448. The method of embodiment 446, wherein the post-cycle modification reagent system is 20% DEA in acetonitrile.

449. The method of any one of embodiments 418-448, wherein the post-cycle modification step is performed before contacting the post-cycle product oligonucleotides to a basic condition comprising water.

450. The method of any one of embodiments 418-449, wherein the post-cycle modification step is performed before deprotection and/or cleavage.

451. The method of any one of the preceding embodiments, comprising a cleavage/deprotection step that comprises:

contacting a plurality of oligonucleotides with one or more cleavage/deprotection reagent systems;

wherein the cleavage/deprotection step provides a final product composition comprising a plurality of final product oligonucleotides.

452. The method of any one of the preceding embodiments, comprising a cleavage/deprotection step that comprises:

contacting a plurality of oligonucleotides, each of which is independently loaded on a support, with one or more cleavage/deprotection reagent systems;

wherein the cleavage/deprotection step provides a final product composition comprising a plurality of final product oligonucleotides, each of which is cleaved from a solid support.

453. The method of any, one of the preceding embodiments, wherein a cleavage/deprotection step comprises:

contacting a plurality of oligonucleotides, each of which is independently loaded on a support, with one or more cleavage/deprotection reagent systems;

de-protecting one or more blocking groups of the oligonucleotides;

cleaving the oligonucleotides from a support; and wherein the cleavage/deprotection step provides a final product composition comprising a plurality of final product oligonucleotides.

454. The method of any one of the preceding embodiments, wherein a cleavage/deprotection reagent system comprises a base.

455. The method of any one of the preceding embodiments, wherein a cleavage/deprotection reagent system comprises concentrated $NH_4OH$.

456. The method of any one of the preceding embodiments, wherein a cleavage/deprotection reagent system comprises a metal chelator.

457, The method of any one of the preceding embodiments, wherein a cleavage/deprotection reagent system comprises mercaptoethanol, 1-dodecanthiol, dithiothreitol (DTT), thiophenol, 1,2-diaminoethane, 1,3-diaminopropane, 2,3-mercapto 1-propanesulfonic acid, 2,3-mercapto propane-1-ol, or meso 2,3-dimercapto succinic acid.

458. The method of any one of the preceding embodiments, wherein a cleavage/deprotection reagent system comprises EDTA.

459. The method of any one of the preceding embodiments, wherein a cleavage/deprotection step comprises elevated temperature.

460. The method of any one of the preceding steps, wherein a final product composition comprising a plurality of final product oligonucleotides, each of which is independently an oligonucleotide of formula O-I or a salt thereof.

461. The method of any one of the preceding steps, wherein a final product composition comprising a plurality of final product oligonucleotides, each of which is independently an oligonucleotide of formula O-I or a salt thereof, wherein each $L^P$ in formula O-I is independently an internucleotidic linkage of formula VII, NL-n-1, NL-n-2, NL-n-3, NL-n-4, NL, NL-a-1, NL-a-2, NL-h-1, NL-b-2, NL-e-1, NL-e-2, NL-d-1, or NL-d-2, or a salt form thereof, wherein $P^L$ is not P.

462, The method of any one of the preceding steps, wherein a final product composition comprising a plurality of final product oligonucleotides, each of which is independently an oligonucleotide of formula O-I or a salt thereof, wherein each $L^P$ in formula O-I is independently an internucleotidic linkage of formula VII, or a salt form thereof, wherein each $P^L$ is independently P(═O).

463. The method of any, one of the preceding steps, wherein a final product composition comprising a plurality of final product oligonucleotides, each of which is independently an oligonucleotide of formula O-I or a salt thereof, wherein each $L^P$ in formula O-I is independently an internucleotidic linkage of formula VII, or a salt form thereof, wherein each X is independently (or 464. The method of any one of the preceding steps, wherein a final product composition comprising a plurality of final product oligonucleotides, each of which is independently an oligonucleotide of formula O-I or a salt thereof, wherein each $L^P$ in formula O-I is independently an internucleotidic linkage of formula VII, or a salt form thereof, wherein each of Y and Z is —O—.

465. The method of any, one of the preceding steps, wherein a final product composition comprising a plurality of final product oligonucleotides, each of which is independently an oligonucleotide of formula O-I or a salt thereof, wherein each $L^P$ in formula O-I is independently a natural phosphate linkage (—O—P(═O)(OH)—O— or a salt form thereof), phosphorothioate linkage (—O—P(═O)(SH)—O— or a salt form thereof), or a non-negatively charged internucleotidic linkage of formula NL-n-1, NL-n-2, NL-n-3, NL-n-4, NL, NL-a-1, NL-a-2, NL-b-1, NL-b-2, NL-c-1, NL-c-2, NL-d-1, or NL-d-2.

466, The method of any one of the preceding steps, wherein a final product composition comprising a plurality of final product oligonucleotides, each of which is independently an oligonucleotide of formula O-I or a salt thereof, wherein each $L^P$ in formula O-I is independently a natural phosphate linkage (—O—P(═O)(—OH)—O— or a salt form thereof), phosphorothioate linkage (—O—P(═O)(—SH)—O— or a salt form thereof), or n001.

467. The method of any one of the preceding steps, wherein a final product composition comprising a plurality of final product oligonucleotides, each of which is independently an oligonucleotide of formula O-I or a salt thereof, wherein each $L^P$ in formula O-I is independently a natural phosphate linkage (—O—P(═O)(—OH)—O— or a salt form thereof) or phosphorothioate linkage (—O—P(═O)(—SH)—O— or a salt form thereof).

468. The method of any one of the preceding steps, wherein a final product composition comprising a plurality of final product oligonucleotides, each of which is not loaded on a support.

469. The method of any one of the preceding embodiments, wherein a final product composition comprising a plurality of final product oligonucleotides is a chirally controlled oligonucleotide composition.

470. The method of any one of the preceding embodiments, wherein a final product composition comprising a plurality of final product oligonucleotides is a chirally controlled oligonucleotide composition wherein:

oligonucleotides of the plurality share the same constitution; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least $((DS)^{Nc}*100)$% of all oligonucleotides sharing the same base sequence in the final product composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

471, The method of any one of the preceding embodiments, wherein the method provides a final product composition with at least about 30%, 35%, 40%, 45%, 50%, 55%, 60%, 65%, 70% or 75% crude purity.

472. The method of any one of the preceding embodiments, wherein the crude purity is % full-length product.

473. The method of any one of the preceding embodiments, wherein the crude purity is % full-length product as assessed by LC-LIV monitored at UV 260 nm.

474. The method of any one of the preceding embodiments, comprising purifying the final product composition using chromatography or electrophoresis.

475. The method of any one of the preceding embodiments, comprising purifying the final product composition using HPLC.

476. A crude chirally controlled oligonucleotide composition comprising a plurality of oligonucleotides, wherein:

oligonucleotides of the plurality share the same base sequence;

oligonucleotides of the plurality share the same pattern of backbone linkages; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least $((DS)^{Nc}*100)$% of all oligonucleotides sharing the same base sequence in the crude composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

477. A crude chirally controlled oligonucleotide composition comprising a plurality of oligonucleotides, wherein:
oligonucleotides of the plurality share the same constitution; and
oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;
wherein at least $((DS)^{Nc}*100)\%$ of all oligonucleotides sharing the same base sequence in the crude composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage;
wherein the crude chirally controlled oligonucleotide composition has a crude purity of at least 40%, 45%, 50%, 55%, 60%, 65%, 70%, or 75%.

478. The composition of any one of embodiments 475-477, wherein the crude chirally controlled oligonucleotide composition is cleaved from a support, and before any further purification.

479. The composition of any one of embodiments 475-477, wherein the crude chirally controlled oligonucleotide composition is cleaved from a support, after de-salting, and before any further purification.

480. The composition of any one of the preceding embodiments, wherein the crude chirally controlled oligonucleotide composition is before any chromatograph or gel purification.

481. The method or composition of any one of the preceding embodiments, wherein the crude purity is % full-length product.

482. The method or composition of any one of the preceding embodiments, wherein the crude purity is % full-length product as assessed by LC-UV monitored at UV 260 nm.

483. A composition, comprising a plurality of oligonucleotides and a reagent of a reagent system, wherein:
the plurality of oligonucleotides is a plurality of oligonucleotides of a modification product composition of any one of the preceding embodiments;
the reagent system is a pre-modification or post-modification capping reagent system of any one of the preceding embodiments; and
the post-modification capping reagent system is in contact with the plurality of oligonucleotides.

484. The composition of embodiment 483, wherein the plurality of oligonucleotides are loaded on a support.

485. The composition of any one of embodiments 483-484, wherein:
oligonucleotides of the plurality share the same base sequence;
oligonucleotides of the plurality share the same pattern of backbone linkages; and
oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;
wherein at least $((DS)^{Nc}*100)\%$ of all oligonucleotides sharing the same base sequence in the crude composition are oligonucleotides of the plurality, wherein DS is at least 80%; 85%, 90%, 91%, 92%, 93%, 94%, 95%, 96%, 97%, 98% or 99%, and Nc is the number of chirally controlled internucleotidic linkage.

486. The composition of any one of embodiments 483-484, wherein:
oligonucleotides of the plurality share the same constitution; and
oligonucleotides of the plurality comprise at least one chirally, controlled internucleotidic linkage, which internucleotidic linkage is chirally controlled in that oligonucleotides of the plurality share the same stereochemical configuration at the chiral linkage phosphorus of the internucleotidic linkage;
wherein at least $((DS)^{Nc}*100)\%$ of all oligonucleotides sharing the same base sequence in the crude composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

487. The method or composition of any one of the preceding embodiments, wherein DS is at least 85%.

488, The method or composition of any one of the preceding embodiments, wherein DS is at least 87%.

489. The method or composition of any one of the preceding embodiments, wherein DS is at least 88%.

490. The method or composition of any one of the preceding embodiments, wherein DS is at least 89%.

491. The method or composition of any one of the preceding embodiments, wherein DS is at least 90%.

492. The Method or composition of any one of the preceding embodiments wherein DS is at least 92%.

493. The method or composition of any one of the preceding embodiments, wherein DS is at least 95%.

494. The method or composition of any one of the preceding embodiments, wherein DS is at least 97%.

495. The method or composition of any one of the preceding embodiments, wherein DS is at least 98%.

496. The Method or composition of any one of the preceding embodiments wherein a support s a solid support.

497. The method or composition of any one of the preceding embodiments, wherein a support is a polystyrene support.

498. The method or composition of any one of embodiments 1-487, wherein a support is a CPG support.

499. The method or composition of any one of the preceding embodiments, wherein a support has a unit loading capacity of about 50-300 umol/g.

500. The method or composition of any one of the preceding embodiments, wherein a support has a unit loading capacity of about 50-80, 80-100, 100-120, 120-140, 140-160, 160-180, 180-210, or 210-250 umol/g.

501. The method or composition of any one of the preceding embodiments, wherein the oligonucleotides or nucleosides are connected to a solid support through a linker.

502. The method or composition of embodiment 501, wherein the linker is a CNA linker.

503. The method or composition of any one of the preceding embodiments, wherein oligonucleotides of a plurality have a length of at least 10, 11, 12, 13, 14, 15, 16, 17, 18, 19, 20, 21, 22, 23, 24, or 25 nucleobases.

504. The method or composition of any one of the preceding embodiments, wherein each nucleobase or BA is independently an optionally substituted or protected nucleobase selected from A, T, C, G, and U.

505, The method or composition of any one of the preceding embodiments, wherein oligonucleotides of a plurality independently comprise one or more modified sugar moieties.

506. The method or composition of any one of the preceding embodiments, wherein oligonucleotides of a plurality independently comprise one or more sugar moieties having the structure of

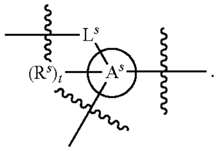

507. The method or composition of any one of the preceding embodiments, wherein oligonucleotides of a plurality independently comprise one or more sugar moieties having the structure of

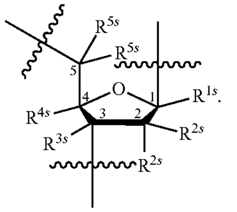

508. The method or composition of any one of the preceding embodiments, wherein oligonucleotides of a plurality independently comprise one or more sugar moieties having the structure of

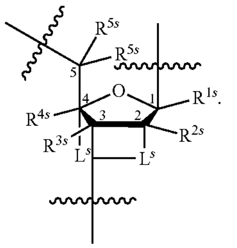

509, The method or composition of any one of the preceding embodiments, wherein oligonucleotides of a plurality independently comprise one or more sugar moieties having the structure of

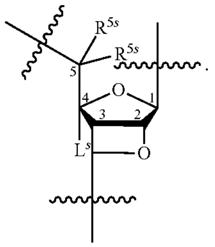

510. The method or composition of any one of the preceding embodiments, wherein oligonucleotides of a plurality independently comprise one or more sugar moieties having the structure of

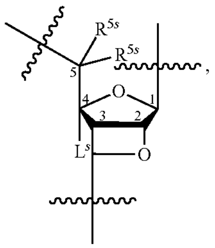

wherein $-L^S-$ is $—CH_2—$.

511. The method or composition of any one of the preceding embodiments, wherein oligonucleotides of a plurality independently comprise one or more sugar moieties having the structure of

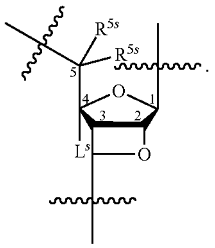

wherein $-L^S-$ is —(S)—CHR—, wherein R is not —H.

512. The method or composition of any one of the preceding embodiments, wherein oligonucleotides of a plurality independently comprise one or more sugar moieties having the structure of

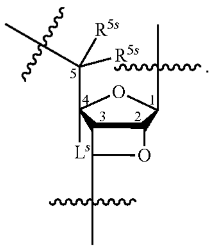

wherein $-L^S-$ is —(R)—CHR—, wherein R is not —H.

513. The method or composition of any one of the preceding embodiments, wherein oligonucleotides of a plurality independently comprise one or more sugar moieties having the structure of

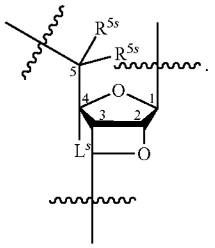

wherein $-L^{S}-$ is —CHR—.

514, The method or composition of any one of the preceding embodiments, wherein oligonucleotides of a plurality independently comprise one or more sugar moieties having the structure of

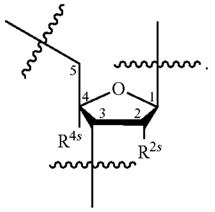

515, The method or composition of any one of the preceding embodiments, wherein oligonucleotides of a plurality independently comprise one or more sugar moieties having the structure of

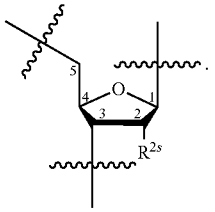

516. The method or composition of any one of the preceding embodiments, wherein $C_1$ is connected to a nucleobase or BA.

517. The method or composition of any one of the preceding embodiments, wherein for at least one sugar moiety. $R^{2s}$ is —H.

518. The method or composition of any one of the preceding embodiments, wherein for one or more, or at least 2, 3, 4, 5, 6, 7, 8, 9, 10, 11, 12, 13, 14, 15, 16, 17, 18, 19, or 20 sugar moieties, $R^{2s}$ is —H.

519. The method or composition of any one of the preceding embodiments, wherein for at least one sugar moiety, $R^{2s}$ is not —H.

520. The method or composition of any one of the preceding embodiments, wherein for one or more, or at least 2, 3, 4, 5, 6, 7, 8, 9, 10, 11, 12, 13, 14, 15, 16, 17, 18, 19, or 20 sugar moieties. $R^{2s}$ is not —H.

521, The method or composition of any one of the preceding embodiments, wherein for at least one sugar moiety, $R^{2s}$ is —F.

522. The method or composition of any one of the preceding embodiments, wherein for one or more, or at least 2, 3, 4, 5, 6, 7, 8, 9, 10, 11, 12, 13, 14, 15, 16, 17, 18, 19, or 20 sugar moieties, $R^{2s}$ is —F.

523. The method or composition of any one of the preceding embodiments, wherein for one or more, or at least 2, 3, 4, 5, 6, 7, 8, 9, 10, 11, 12, 13, 14, 15, 16, 17, 18, 19, or 20 sugar moieties, $R^{2s}$ is —OR.

524. The method or composition of any one of the preceding embodiments, wherein for at least one sugar moiety, $R^{2s}$ is —OH.

525, The method or composition of any one of the preceding embodiments, wherein for at least one sugar moiety, $R^{2s}$ is —O-PG, wherein PG is protecting group removed after the oligonucleotides have reached the desired lengths.

526. The method or composition of any one of the preceding embodiments, wherein for at least one sugar moiety, $R^{2s}$ is $—OSi(R)_3$, wherein each R is independently not H.

527. The method or composition of any one of the preceding embodiments, wherein for at least one sugar moiety, $R^{2s}$ is —OTBS.

528. The method or composition of any one of embodiments 525-527, comprising contacting an oligonucleotide comprising $R^{2s}$ with a reagent system comprises fluoride.

529. The method or composition of embodiment 528, wherein the reagent system comprises HF-Pyridine.

530. The method or composition of embodiment 528, wherein the reagent system comprises 3HF-TEA 531. The method or composition of embodiment 528, wherein the reagent system comprises tetrabutylammonium fluoride.

532. The method or composition of embodiment 528, wherein the reagent system comprises tetrabutylammonium difluorotriphenyl silicate.

533. The method or composition of any one of the preceding embodiments, wherein for one or more, or at least 2, 3, 4, 5, 6, 7, 8, 9, 10, 11, 12, 13, 14, 15, 16, 17, 18, 19, or 20 sugar moieties, $R^{2s}$ is —OMe.

534. The method or composition of any one of the preceding embodiments, wherein for one or more, or at least 2, 3, 4, 5, 6, 7, 8, 9, 10, 11, 12, 13, 14, 15, 16, 17, 18, 19, or 20 sugar moieties, $R^{2s}$ is -MOE.

535. The method or composition of any one of the preceding embodiments, wherein the one or more, or at least 2, 3, 4, 5, 6, 7, 8, 9, 10, 11, 12, 13, 14, 15, 16, 17, 18, 19, or 20 sugar moieties are consecutive.

536, The method or composition of any one of the preceding embodiments, wherein oligonucleotides of a plurality comprise 1-50, or at least 1, 2, 3, 4, 5, 6, 7, 8, 9, 10, 11, 12, 13, 14, 15, 16, 17, 18, 19, or 20 chirally controlled internucleotidic linkages (Nc is 1-50 or more, or at least 1, 2, 3, 4, 5, 6, 7, 8, 9, 10, 11, 12, 13, 14, 15, 16, 17, 18, 19, or 20).

537. The method or composition of any one of the preceding embodiments, wherein oligonucleotides of a plurality comprise 1-50, or at least 1, 2, 3, 4, 5, 6, 7, 8, 9, 10, 11, 12, 13, 14, 15, 16, 17, 18, 19, or 20 chirally controlled phosphorothioate linkages (Nc is 1-50 or more, or at least 1, 2, 3, 4, 5, 6, 7, 8, 9, 10, 11, 12, 13, 14, 15, 16, 17, 18, 19, or 20).

538. The method or composition of any one of the preceding embodiments, wherein oligonucleotides of a plurality comprise 1-50, or at least 1, 2, 3, 4, 5, 6, 7, 8, 9, 10, 11, 12, 13, 14, 15, 16, 17, 18, 19, or 20 natural phosphate linkages.

539. The method or composition of any one of the preceding embodiments, wherein at least 1, 2, 3, 4, 5, 6, 7, 8, 9, 10, 11, 12, 13, 14, 15, 16, 17, 18, 19, or 20 chirally controlled internucleotidic linkages are consecutive.

540. The method or composition of any one of the preceding embodiments, wherein at least 1, 2, 3, 4, 5, 6, 7, 8, 9, 10, 11, 12, 13, 14, 15, 16, 17, 18, 19, or 20 natural phosphate linkages are consecutive.

541. The method or composition of any one of the preceding embodiments, wherein oligonucleotides of a plurality comprise a pattern of backbone chiral centers comprising (Rp)n(Sp)p, wherein n is 1-10, and each of p and m is independently 1-50.

542, The method or composition of any one of the preceding embodiments, wherein oligonucleotides of a plurality comprise a pattern of backbone chiral centers comprising (Sp)m(Rp)n(Sp)p, wherein n is 1-10, and each of p and m is independently 1-50.

543. The method or composition of any one of the preceding embodiments, wherein oligonucleotides of a plurality comprise a pattern of backbone chiral centers comprising (Rp)n(Sp)p, wherein n is 1, m is 2-50, and p is 2-50.

544. The method or composition of any one of the preceding embodiments, wherein oligonucleotides of a plurality comprise a pattern of backbone chiral centers comprising (Sp)m(Rp)n(Sp)p, wherein n is m is 2-50, and p is 2-50.

545. The method or composition of any one of the preceding embodiments, wherein oligonucleotides of a plurality comprise a pattern of backbone chiral centers comprising (Op)n(Sp)p, wherein n is 1-10, and p is 1-50.

546. The method or composition of any one of the preceding embodiments, wherein oligonucleotides of a plurality comprise a pattern of backbone chiral centers comprising (Sp)p(Op)n, wherein n is 1-10, and p is 1-50.

547, The method or composition of any one of the preceding embodiments, wherein oligonucleotides of a plurality comprise a pattern of backbone chiral centers comprising (Sp)m(Op)n(Sp)p, wherein n is 1-10, and each of p and m is independently 1-50.

548. The method or composition of any one of the preceding embodiments, wherein oligonucleotides of a plurality comprise a pattern of backbone chiral centers comprising (Sp)m(Op)n(Sp)p, wherein n is 1, m is 2-50, and p is 2-50.

549. The method or composition of any one of the preceding embodiments, wherein oligonucleotides of a plurality comprise a pattern of backbone chiral centers comprising two or more units independently selected from (Rp)n(Sp)p or (Op)n(Sp)p, wherein n is 1 and each p is independently 2-50.

550. The method or composition of any one of the preceding embodiments, wherein oligonucleotides of a plurality comprise a pattern of backbone chiral centers comprising two or more (Rp)n(Sp)p, wherein n is 1 and each p is independently 2-50.

551. The method or composition of any one of the preceding embodiments, wherein product oligonucleotides each independently comprise a phosphorothioate internucleotidic linkage and a non-negatively charged internucleotidic linkage.

552. The method or composition of any one of the preceding embodiments, wherein product oligonucleotides each independently comprise a chirally controlled phosphorothioate internucleotidic linkage and a chirally controlled non-negatively charged internucleotidic linkage.

553, The method or composition of any one of the preceding embodiments, wherein each chiral internucleotidic linkage in product oligonucleotides is independently a phosphorothioate internucleotidic linkage or a non-negatively charged internucleotidic linkage.

554. The method or composition of any one of embodiments 551-553, wherein the non-negatively charged internucleotidic linkage is n001.

555. The method or composition of any one of the preceding embodiments, wherein each chiral internucleotidic linkage is independently chirally controlled.

556. The method or composition of any one of embodiments 541-555, wherein oligonucleotides of a plurality each comprise a region comprising the pattern of backbone chiral centers.

557, The method or composition of embodiments 556, wherein each sugar moiety of the region independently has two 2'-H.

558. The method or composition of any one of embodiments 556-557, wherein the region is flanked by a 5'-region comprising one or more sugar modifications.

559. The method or composition of embodiment 558, wherein each sugar moiety of the 5'-region independently comprises a sugar modification.

560. The method or composition of any one of embodiments 556-559, wherein the region is flanked by a 3'-region comprising one or more sugar modifications.

561, The method or composition of embodiment 560, wherein each sugar moiety of the 3'-region independently comprises a sugar modification.

562. The method or composition of any one of the preceding embodiments, wherein oligonucleotides of a plurality share a base sequence identical or complementary to a portion of a DMD sequence.

563. The method or composition of any one of the preceding embodiments, wherein oligonucleotides of a plurality share a base sequence identical or complementary to a portion of a HTT sequence.

564. The method or composition of any one of the preceding embodiments, wherein oligonucleotides of a plurality share a base sequence identical or complementary to a portion of a HTT sequence containing a SNP.

565, The method of any one of the preceding embodiments, wherein the final oligonucleotide product is a solid.

566. The method of any one of the preceding embodiments, wherein the final oligonucleotide product is an oligonucleotide solution.

567. The method or composition of any one of the preceding embodiments, wherein the base sequence shared by the oligonucleotides of a plurality or of the oligonucleotide is or comprises a base sequence of U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 20171192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784.

568. The method or composition of any one of the preceding embodiments, wherein the pattern of backbone chiral centers shared by the oligonucleotides of a plurality or of the oligonucleotide is or comprising a pattern of backbone chiral centers of U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784.

569. The method or composition of any one of the preceding embodiments, wherein the oligonucleotide is, or oligonucleotides of a plurality are the same and are, an oligonucleotide of U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO2019/075357, WO 2019/200185, or WO 2019/217784.

570. The method or composition of any one of the preceding embodiments, wherein a product oligonucleotide is, or a product composition is a chirally controlled oligonucleotide composition of an oligonucleotide of U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 201.9/075357, WO 2019/200185, or WO 2019/217784.

571. The method or composition of any one of the preceding embodiments, wherein a final product oligonucleotide is, or a final product composition is a chirally controlled oligonucleotide composition of, an oligonucleotide of U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 0.2019/055951, WO 2019/075357, WO 2019/200185, or WO 2019/217784.

572. The method or composition of any one of the preceding embodiments, wherein a final product oligonucleotide is, or a final product composition is a chirally controlled oligonucleotide composition of, an oligonucleotide of US 20180216108, US 20190008986, WO 017/01.5555, WO 2017/01.5575, WO 2017/062862, WO 2017/160741, WO 2017/192664, WO 201711.92679, WO 2017/21.0647, WO 20181022473, WO 20181067973, WO 2018/098264, WO 2018/223056, WO 2018/223073, WO 2018/223081, WO 2018/237194, WO 2019/032607, WO 2019/032612, WO 0.2019/032607, WO 2019/055951, WO 2019/075357, WO 201.9/200185, or WO 2019/217784.

573. The method of any one embodiments 1-566, wherein the final product oligonucleotide is WV-937, WV-1077, WV-1078, WV-1079, WV-1085, WV-1086, WV-1090, WV-1091, WV-1092, WV-1497, WV-1508, WV-1510, WV-2076, WV-2378, WV-2380, WV-2417, WV-2418, WV-2595, WV-2601, WV-2602, WV-2603, WV-2618, WV-2619, or WV-267.

574. The method of any one embodiments 1-566, wherein the final product composition is a chirally controlled oligonucleotide composition of WV-937, WV-1077, WV-1078, WV-1079, WV-1085, WV-1086, WV-1090, WV-1091, WV-4092, WV-1508, WV-1510, WV-2378, WV-2380, WV-2417, WV-2418, WV-2595, WV-2601, WV-2602, WV-2603, or WV-2671.

575. The method of any one embodiments 1-566, wherein the final product oligonucleotide is WV-887, WV-892, WV-896, WV-1714, WV-2444, WV-2445, WV-2526, WV-2527, WV-2528, WV-2530, WV-2531, WV-2578, WV-2580, WV-2587, WV-3047, WV-3152, WV-3472, WV-3473, WV-3507, WV-3508, WV-3509, WV-3510, WV-3511, WV-3512, WV-3513, WV-3514, WV-3515, WV-3545, or WV-3546.

576. The method of any one embodiments 1-566, wherein the final product composition is a chirally controlled oligonucleotide composition of WV-887, WV-892, WV-896, WV-2444, WV-2445, WV-2526, WV-2527, WV-2528, WV-2530, WV-2531, WV-3152, WV-3472, WV-3473, WV-3507, WV-3508, WV-3509, WV-3510, WV-3511, WV-3512, WV-351.3, WV-3514, WV-3515, WV-3545, or WV-3546.

577. The method of any one embodiments 1-566, wherein the final product oligonucleotide is WV-9517, WV-12555, WV-12556, WV-12558, WV-12876, WV-12877, WV-12878, WV-13826, WV-12880, WV-14344, WV-13835, or WV-13864.

578. The method of any one embodiments 1-566, wherein the final product composition is a chirally controlled oligonucleotide composition of WV-9517, WV-12555, WV-12556, WV-12558, WV-12876, WV-12877, WV-12878, WV-13826, WV-12880, WV-14344, WV-13835, or WV-13864.

579. The method of any one embodiments 1-566, wherein the final product oligonucleotide is WV-3473.

580. The method of any one embodiments 1-566, wherein the final product oligonucleotide composition is a chirally controlled oligonucleotide composition of WV-3472.

581. The method of any one embodiments 1-566, wherein the final product oligonucleotide composition is a chirally controlled oligonucleotide composition of WV-3473.

582. The method of any one embodiments 1-566, wherein the final product oligonucleotide composition is a chirally controlled oligonucleotide composition of WV-3545.

583. The method of any one embodiments 1-566, wherein the final product oligonucleotide composition is a chirally controlled oligonucleotide composition of WV-3546.

584. The method of any one embodiments 1-566, wherein the final product oligonucleotide composition is an oligonucleotide composition comprising mipomersen, nusinersen, RG6042, BIIB067, BIIB078, BIIB080, inotersen, volanesorsen, AKCEA-ANGPTL3-$L_{RX}$, IONIS-GHR-$L_{RX}$, AKCEA-TTR-$L_{RX}$, IONIS-$PKK_{RX}$, IONIS-PKK-$L_{RX}$, IONIS-TMPRSS6-$L_{RX}$, IONIS-ENAC-$2.5_{RX}$, AKCEA-APO(a)-$L_{RX}$, AKCEA-APOCII-$L_{RX}$, IONIS-$GCGR_{RX}$, IONIS-$FXI_{RX}$, IONIS-$DGAT2_{RX}$, IONIS-AGT-$L_{RX}$, IONIS-AZ4-2.5-$L_{RX}$, IONIS-FXI-$L_{RX}$, IONIS-AR-$2.5_{RX}$, IONIS-STAT3-$2.5_{RX}$, IONIS-$HBV_{RX}$, IONIS-HBV-$L_{RX}$, IONIS-FB-$L_{RX}$, and IONIS-JBI1-$2.5_{RX}$.

585. The method of any one embodiments 1-566, wherein the final product oligonucleotide composition is a chirally controlled oligonucleotide composition of a stereoisomer of mipomersen, nusinersen, RG6042, BIIB067, BIIB078, BIIB080, inotersen, volanesorsen, AKCEA-ANGPTL3-$L_{RX}$, IONIS-GIIR-$L_{RX}$, AKCEA-TTR-$L_{RX}$, IONIS-$PKK_{RX}$, IONIS-PKK-$L_{RX}$, IONIS-TMPRSS6-$L_{RX}$, IONIS-ENAC-$2.5_{RX}$, AKCEA-APO (a)-$L_{RX}$, AKCEA-APOCIII-$L_{RX}$, IONIS-$GCGR_{RX}$, IONIS-$FXI_{RX}$, IONIS-$DGAT2_{RX}$, IONIS-AGT-$L_{RX}$, IONIS-AZ4-2.5-$L_{RX}$, IONIS-FXI-$L_{RX}$, IONIS-AR-$2.5_{RX}$, IONIS-STAT3-$2.5_{RX}$, IONIS-$HBV_{RX}$, IONIS-HBV-$L_{RX}$, IONIS-FB-$L_{RX}$, or IONIS-JBI1-$2.5_{RX}$.

586. An oligonucleotide which a product oligonucleotide of a step in any one of the preceding embodiments.

587. An oligonucleotide composition which a product oligonucleotide composition of a step in any one of the preceding embodiments.

588. The method or composition of any one of the preceding embodiments, wherein the oligonucleotides each independently comprise an internucleotidic linkage having the structure of $*^{P}S$ or $*^{P}R$.

589. An oligonucleotide comprising comprise an internucleotidic linkage having the structure of $*^{P}S$ or $*^{P}R$.

590. The method or composition or oligonucleotide of any one of the preceding embodiments, wherein each oligonucleotide independently comprises an internucleotidic linkage having the structure of $*^{N}S$ or $*^{N}R$.

591. The method or composition or oligonucleotide of any one of the preceding embodiments, wherein each oligonucleotide independently comprises an internucleotidic linkage having the structure of $*^{P}S$ and an internucleotidic linkage having the structure of $*^{N}R$.

592, The method or composition or oligonucleotide of any one of the preceding embodiments, wherein each of $*^{P}S$, $*^{P}R$, $*^{N}S$ and $*^{N}R$ is independently chirally controlled.

593. The method or composition or oligonucleotide of any one of the preceding embodiments, wherein each independently comprises $O^{5P}$, $O^{P}$, $*^{P}$, or $*^{N}$.

594. A compound of formula I, I-a, I-a-1, I-a-2, I-b, I-d, a-e, II, II-a, II-b, III, III-a, or III-b, or salts thereof.

595. A compound of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or salts thereof.

596. The compound of embodiment 595, wherein $R^{2s}$ is —O—PG, wherein PG is a protection group suitable for oligonucleotide synthesis.

597. The compound of embodiment 595, wherein $R^{2s}$ is —O—$Si(R)_3$, wherein each R is independently not —H.

598. The compound of embodiment 595, wherein $R^{2s}$ is —OTBS.

599. The compound of embodiment 594, wherein the compound is stereopure.

600. The method of any one of the preceding embodiments, comprising providing a compound of any one of embodiments 594-599.

601, The method of any one of the preceding embodiments, wherein a partner compound is a compound of any one of embodiments 594-599.

602. A method for preparing an oligonucleotide, comprising providing a compound of any one of embodiments 594-599.

603. The method of embodiment 602, wherein the oligonucleotide is an oligonucleotide in any one of the preceding embodiments.

604. A method, comprising using a compound of any one of embodiments 594-599.

605. A method, comprising using a chiral auxiliary for a reaction, which chiral auxiliary has such a structure that H-chiral auxiliary (monovalent) or H-chiral auxiliary-H (bivalent) or (H)n-chiral auxiliary (n is the valence of the chiral auxiliary) is a compound of any one of embodiments 594-599.

606, The method of any one of embodiments 604-605 wherein the method is a method for oligonucleotide synthesis.

607. The method of any one embodiments 604-606, wherein the chiral auxiliary is removed by a base.

608. The method of any one embodiments 604-607, wherein the chiral auxiliary is removed under an anhydrous condition.

609. The method of any one embodiments 607-608, wherein the base is $N(R)_3$.

610. The method of any one embodiments 607-609, wherein the base is DEA.

611, The method of any one embodiments 607-610, wherein the removal is performed at a temperature that is lower than 40, 45, 50, 55, or 60° C.

612. The method of any one embodiments 607-611, wherein the removal is performed with a time period of no more than 15, 20, 25, 30, 35, 40, 50, or 60 minutes.

613. The method of any one of embodiments 611-612, wherein the chiral auxiliary removal is at least 85%, 90%, 95%, 96%, 97%, 98%, or 99%.

614. A compound, composition or an oligonucleotide of any one of the preceding embodiments.

615. An oligonucleotide ("a first oligonucleotide"), which has an identical structure as an existing oligonucleotide ("a second oligonucleotide"), except that compared to the second oligonucleotide, in the first oligonucleotide:

the first internucleotidic linkage from the 5'-end is an internucleotidic linkage of $O^{5P}$; and for the rest linkages:

at each location where there is a phosphate linkage in the second oligonucleotide, there is independently a linkage of $O^{P}$ in the first oligonucleotide;

at each location where there is a stereorandom phosphorothioate linkages in the second oligonucleotide, there is independently a linkage of $*^{P}$ or $*^{P}$ in the first oligonucleotide;

at each location where there is a Sp phosphorothioate linkage in the second oligonucleotide, there is independently a linkage of $*^{P}S$ or $*^{PD}S$ in the first oligonucleotide;

at each location where there is a Rp phosphorothioate linkage in the second oligonucleotide, there is independently a linkage of $*^{P}R$ or $*^{PD}R$ in the first oligonucleotide;

at each location where there is a stereorandom non-negatively charged internucleotidic linkage in the second oligonucleotide, there is independently a linkage of $*^{N}$ in the first oligonucleotide;

at each location where there is a Sp non-negatively charged internucleotidic linkage in the second oligonucleotide, there is independently a linkage of $*^{N}S$ in the first oligonucleotide;

at each location where there is a Rp non-negatively charged internucleotidic linkage in the second oligonucleotide, there is independently a linkage of $*^{N}R$ in the first oligonucleotide, and each nucleobase in the first oligonucleotide is optionally and independently protected, and each additional chemical moiety, if any, in the first oligonucleotide is optionally and independently protected;

wherein each of $O^{5P}$, $O^{P}$, $*^{P}$, $*^{P}S$, $*^{PD}S$, $*^{P}R$, $*^{PD}R$, $*^{N}$, $*^{N}S$ and $*^{N}R$ is independently of formula VII or a salt form thereof.

616. The compound, composition, method or oligonucleotide of any one of embodiments 593-615, wherein for $O^{5P}$, $P^{L}$ is P and —X-$L^{s}$-$R^5$ is -$L^7$-$R^1$; —S-$L^{s}$-$R^5$; or of such a structure that H—X-$L^{s}$-$R^5$ is a compound of formula I, I-a, I-a-1, I-a-2, I-b, I-c, I-d, I-e, II, II-a, II-b, III, III-a, or III-b, wherein $R^6$ is —H.

617, The compound, composition, method or oligonucleotide of any one of embodiments 593-615, wherein for $O^{5P}$, —X-$L^{s}$-$R^5$ is -$L^7$-$R^1$; —S-$L^{s}$-$R^5$; or of such a structure that H—X-$L^{s}$-$R^5$ is a compound of formula I, I-a, I-a-1, I-a-2, I-b, I-c, I-d, I-e, II, II-a, II-b, III, III-a, or III-b, wherein $R^6$ is —C(O)R'.

618. The compound, composition, method or oligonucleotide of any one of embodiments 593-615, wherein for $O^{P}$, $P^{L}$ is P(═O) and —X-$L^{s}$-$R^5$ is -$L^7$-$R^1$; —S-$L^{s}$-$R^5$ or of such a structure that H—X-$L^{s}$-$R^5$ is a compound of formula I, I-a, I-a-1, I-a-2, I-b, I-c, I-d, I-e, II, II-a, II-b, III, III-a, or III-b.

619. The compound, composition, method or oligonucleotide of any one of embodiments 615-618, wherein —X-$L^{s}$-$R^5$ is —O—$CH_2$—$R^2$, wherein $R^2$ comprises an electron-withdrawing group,

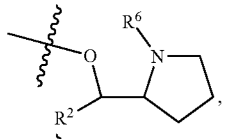,
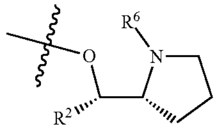 or
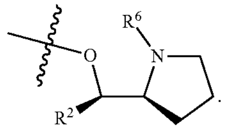.

620. The compound, composition, method or oligonucleotide of any one of embodiments 615-619, wherein —X-$L^{s}$-$R^5$ is —O—$CH_2$—$R^2$,

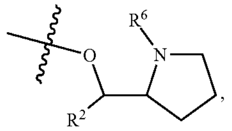,
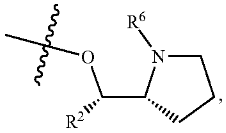, or
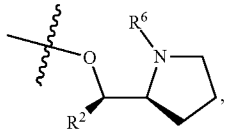, wherein each $R^2$ independently comprises an electron-withdrawing group.

621. The compound, composition, method or oligonucleotide of any one of embodiments 615-620, wherein —X-$L^{s}$-$R^5$ is —$OCH_2CH_2CN$,

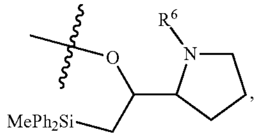,
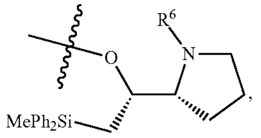,
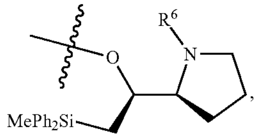,
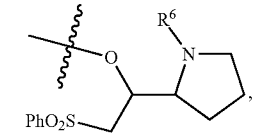,
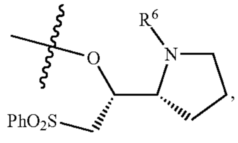, or
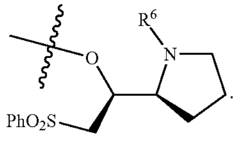.

622. The compound, composition, method or oligonucleotide of any one of embodiments 615-620, wherein —X-$L^{s}$-$R^5$ is —$OCH_2CH_2CN$,

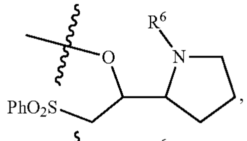,
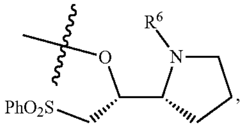, or
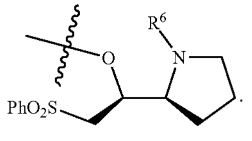.

623, The compound, composition, method or oligonucleotide of any one of embodiments 615-620, wherein —X-$L^{s}$-$R^5$ is —$OCH_2CH_2CN$.

624. The compound, composition, method or oligonucleotide of any one of embodiments 593-623, wherein each of $*^{P}$ and $*^{PD}$ is independently of formula VII or a salt form thereof wherein $P^{L}$ is P(═S), and —X-$L^{s}$-$R^5$ is -$L^7$-$R^1$.

625. The compound, composition, method or oligonucleotide of any one of embodiments 593-624, wherein each $*^N$ is independently of formula VII or a salt form thereof wherein $P^L$ is $P^N$, and —X-$L^s$-$R^5$ is -$L^7$-$R^1$.

626. The compound, composition, method or oligonucleotide of embodiment 625, wherein $*^N$ is n001$^P$.

627. The compound, composition, method or oligonucleotide of any one of embodiments 624-626, wherein —X-$L^s$-$R^5$ is —$OCH_2CH_2CN$.

628. The compound, composition, method or oligonucleotide of any one of embodiments 589-627, wherein each $*^P$S or $*^{PD}$S is independently of formula

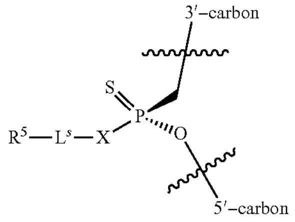

or a salt form thereof, wherein —X-$L^s$-$R^5$ is of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'.

629. The compound, composition, method or oligonucleotide of any one of embodiments 589-628, wherein each $*^N$R is of formula

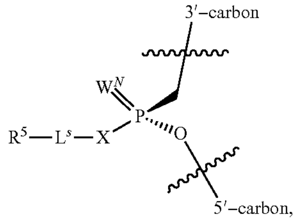

or a salt form thereof wherein P═$W^N$ is $P^N$, —X-$L^s$-$R^5$ is of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'.

630. The compound, composition, method or oligonucleotide of embodiment 629, wherein $*^N$R is n001$^P$R.

631. The compound, composition, method or oligonucleotide of any one of embodiments 589-652, wherein each $*^P$R or $*^{PD}$R is independently of formula

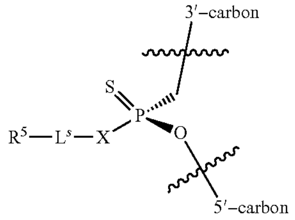

or a salt form thereof, wherein —X-$L^s$-$R^5$ is of such a structure that H—X-L-$L^s$-$R^5$ is a compound of formula I, I-a, I-a-1, I-a-2, I-b, I-c, I-d, I-e, II, H-a, II-b, III, III-a, or III-b, optionally wherein $R^5$ or $R^6$ is —C(O)R'.

632. The compound, composition, method or oligonucleotide of any one of embodiments 615-652, wherein each $*^N$S is of formula

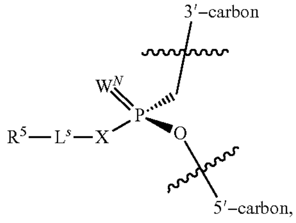

or a salt form thereof wherein P═$W^N$ is $P^N$, —X-$L^s$-$R^5$ is of such a structure that H—X-$L^s$-$R^5$ is a compound of formula I, I-a, I-a-1, I-a-2, I-b, I-c, I-d, I-e, II, II-a, II-b, III, III-a, or III-b, optionally wherein $R^5$ or $R^6$ is —C(O)R'.

633. The compound, composition, method or oligonucleotide of embodiment 632, wherein $*^N$S is n001$^P$S.

634. The compound, composition, method or oligonucleotide of any one of embodiments 628-630, wherein —X-$L^s$-$R^5$ is

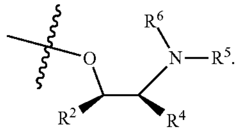

635. The compound, composition, method or oligonucleotide of any one of embodiments 594-634, wherein $R^4$ and $R^5$ are taken together with their intervening atoms to form an optionally substituted 3-20 membered monocyclic, bicyclic or polycyclic ring having 1-5 heteroatoms.

636. The compound, composition, method or oligonucleotide embodiment 635, wherein $R^4$ and $R^5$ are taken together with their intervening atoms to form an optionally substituted 3-10 membered monocyclic ring having 1-2 heteroatoms.

637. The compound, composition, method or oligonucleotide embodiment 635, wherein $R^4$ and $R^5$ are taken together with their intervening atoms to form an optionally substituted 5-membered monocyclic ring having 1 heteroatom.

638. The compound, composition, method or oligonucleotide of embodiment 635, wherein —X-$L^s$-$R^5$ is

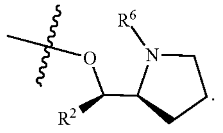

639, The compound, composition, method or oligonucleotide of any one of embodiments 631-633, wherein —X-$L^s$-$R^5$ is,

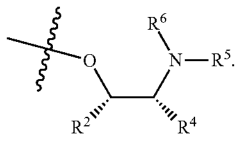

640. The compound, composition, method or oligonucleotide of embodiment 639, wherein $R^4$ and $R^5$ are taken together with their intervening atoms to form an optionally substituted 3-20 membered monocyclic, bicyclic or polycyclic ring having 1-5 heteroatoms.

641. The compound, composition, method or oligonucleotide embodiment 640, wherein $R^4$ and $R^5$ are taken together with their intervening atoms to form an optionally substituted 3-10 membered monocyclic ring having 1-2 heteroatoms.

642. The compound, composition, method or oligonucleotide embodiment 640, wherein $R^4$ and $R^5$ are taken together with their intervening atoms to form an optionally substituted 5-membered monocyclic ring having 1 heteroatom.

643. The compound, composition, method or oligonucleotide of embodiment 640, wherein —X-$L^s$-$R^5$ is

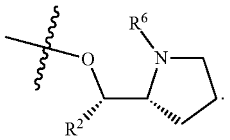

644. The compound, composition, method or oligonucleotide of any one of embodiments 594-643, wherein $R^2$ comprises an electron-withdrawing group.

645. The compound, composition, method or oligonucleotide of any one of embodiments 594-643, wherein $R^2$ is -L'-L"-R'.

646. The compound, composition, method or oligonucleotide of any one of embodiments 594-644, wherein $R^2$ is —$CH_2SO_2R'$, wherein R' is an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms.

647. The compound, composition, method or oligonucleotide of any one of embodiments 594-644, wherein $R^2$ is —$CH_2SO_2R'$, wherein R' is optionally substituted phenyl.

648. The compound, composition, method or oligonucleotide of any one of embodiments 594-644, wherein $R^2$ is —$CH_2SO_2R'$, wherein R' is optionally substituted $C_{1-6}$ aliphatic.

649. The compound, composition, method or oligonucleotide of any one of embodiments 594-644, wherein $R^2$ is —$CH_2SO_2Ph$.

650, The compound, composition, method or oligonucleotide of any one of embodiments 594-644, wherein $R^2$ is —$CH_2SO_2$(t-Bu).

651 The compound, composition, method or oligonucleotide of any one of embodiments 628-630, wherein —X-$L^s$-$R^5$ is

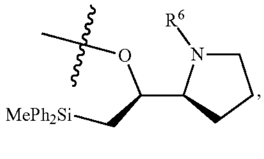

, or

-continued

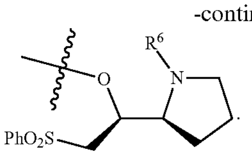

652. The compound, composition, method or oligonucleotide of any one of embodiments 628-630, wherein —X-$L^s$-$R^5$ is

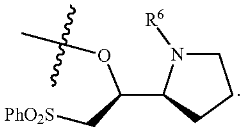

653. The compound, composition, method or oligonucleotide of any one of embodiments 631-633 wherein —X-$L^s$-$R^5$ is

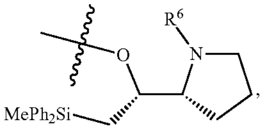

, or

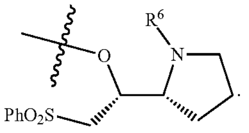

654. The compound, composition, method or oligonucleotide of any one of embodiments 631-633, wherein —X-$L^s$-$R^5$ is

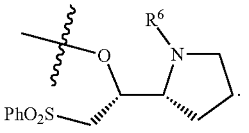

655. The compound, composition, method or oligonucleotide of any one of embodiments 615-654, wherein A is protected, optionally with Bz.

656. The compound, composition, method or oligonucleotide of any one of embodiments 615-655, wherein C is protected, optionally with Ac.

657. The compound, composition, method or oligonucleotide of any one of embodiments 615-656, wherein G is protected, optionally with iBu.

658. The compound, composition, method or oligonucleotide of any one of embodiments 615-657, wherein the oligonucleotide is linked to a support.

659. The compound, composition, method or oligonucleotide of any one of embodiments 615-658, wherein the oligonucleotide is linked to CPG through a CNA linker.

660. The oligonucleotide of any one of embodiments 615-659, wherein the second oligonucleotide is mipomersen, nusinersen, RG6042, BIIB067, BIIB078, BIIB080, inotersen, volanesorsen, AKCEA-ANGPTL3-$L_{RX}$, IONIS-GHR-$L_{RX}$, AKCEA-TTR-$L_{RX}$, IONIS-PKK$_{RX}$, IONIS-PKK-L$_{RX}$, IONIS-TMPRSS6-L$_{RX}$, IONIS-ENAC-2.5$_{RX}$, AKCEA-APO(a)-L$_{RX}$, AKCEA-APOCIII-L$_{RX}$, IONIS-GCGR$_{RX}$, IONIS-FXI$_{RX}$, IONIS-DGAT2$_{RX}$, IONIS-AFT-L$_{RX}$, IONIS-AZ4-2.5-L$_{RX}$, IONIS-FXI-L$_{RX}$, IONIS-AR-2.5$_{RX}$, IONIS-STAT3-2.5$_{RX}$, IONIS-HBV$_{RX}$, IONIS-HBV-L$_{RX}$, IONIS-FB-L$_{RX}$, IONIS-JBI1-2,5$_{RX}$, or suvodirsen.

661. The oligonucleotide of any one of embodiments 615-659, wherein the second oligonucleotide is an oligonucleotide described in or US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067971 WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, or WO 2019/217784.

662. The oligonucleotide of any one of embodiments 615-659, wherein the second oligonucleotide is WV-937, WV-1077, WV-1078, WV-1079, WV-1085, WV-1086, WV-1090, WV-1091, WV-1092, WV-1497, WV-1508, WV-1510, WV-2076, WV-2378, WV-2380, WV-2417, WV-2418, WV-2595, WV-2601, WV-2602, WV-2603, WV-2618, WV-2619, WV-2671, WV-887, WV-892, WV-896, WV-1714, WV-2444, WV-2445, WV-2526, WV-2527, WV-2528, WV-2530, WV-2531, WV-2578, WV-2580, WV-2587, WV-3047, WV-3152, WV-3472, WV-3473, WV-3507, WV-3508, WV-3509, WV-3510, WV-3511, WV-3512, WV-3513, WV-3514, WV-3515, WV-3545, WV-3546, WV-9517, WV-12555, WV-12556, WV-12558, WV-12876, WV-12877, WV-12878, WV-12880, WV-13826, WV-13835, WV-13864 or WV-14344.

663. The oligonucleotide of any one of embodiments 615-659, wherein the oligonucleotide is an oligonucleotide of Table O-2.

664, A chirally controlled oligonucleotide composition of the oligonucleotide of any one of embodiments 615-663.

665. The compound, composition, method or oligonucleotide of any one of the preceding embodiments, wherein each oligonucleotide is independently of formula O-I or a salt thereof.

EXEMPLIFICATION

Non-limiting examples were provided below. A person of ordinary skill in the art appreciates that other compounds and compositions, e.g., chiral auxiliaries of formula I-a, I-a-1, I-a-2, I-b, I-c, I-d, I-e, II, II-a, II-b, III, III-a, or III-b, or salts thereof, phosphoramidites of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-C-1, V-c-2, V-d. V-e, VI, VI-a, VI-b, VI-c, VI-c-1, VI-c-2, VI-d, or VI-e, or salts thereof, oligonucleotides of formula O-I or salts thereof, oligonucleotides comprising one or more internucleotidic linkages each independently of formula VII, VII-a-1, VII-a-2, VII-b, VII-c, VII-d, VII-e, NL-n-1, NL-n-3, NL-n-4, NL, NL-a-1, NL-a-2, NL-b-1, NL-b-2, NL-c-1, NL-c-2, NL-d-1, or NL-d-2, or a salt form thereof, compositions of provided compounds, e.g., compositions of provided oligonucleotides (including various chirally controlled compositions), etc. can be similarly prepared and utilized in accordance with the present disclosure.

Example 1. Example Reagents and/or Oligonucleotides

As appreciated by those skilled in the art, many supports, chiral auxiliaries, phosphoramidites, coupling reagents, capping reagents (both pre-modification capping and post-modification capping), modification reagents (e.g., oxidation reagents, sulfurization reagents, etc.), de-blocking reagents, post-cycle modification reagents, cleavage reagents, deprotection reagents, etc., can be utilized in accordance with the present disclosure to provide a variety of oligonucleotides and compositions thereof. Example reagents and/or product oligonucleotides and compositions thereof include those described in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 20191032607, WO 2019/055951, WO 2019/0753:37, WO 2019/20018:3, WO 2019/217784, etc. and, as demonstrated in the examples, may be utilized in technologies of the present disclosure. As readily appreciated by those skilled in the art, example conditions described herein may be adjusted in accordance with the present disclosure. In some embodiments, a step of a provided method uses a condition described herein, or a variant thereof.

Example 2. Example Support and Linkers

Many supports and/or linkers can be utilized in accordance with the present disclosure. In some embodiments, certain supports and/or linkers are commercially available from various vendors, e.g., Prime Synthese, GE, etc. Among other things, the present disclosure provides modified support and linkers for loading oligonucleotides/nucleosides onto solid support. As those skilled in the art readily appreciate, support and/or linkers described herein may be additionally and/or alternatively utilized with other support and/or linkers.

Scheme 1: Preparation of 1,3-bis(17-amino-3,6,9,12,15-pentaoxaheptadecyl)urea (3).

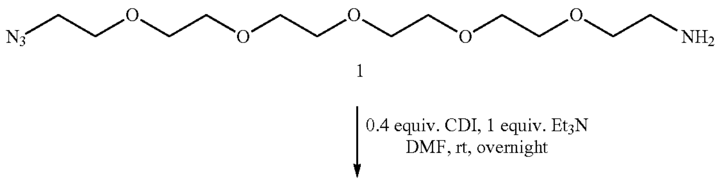

1

-continued

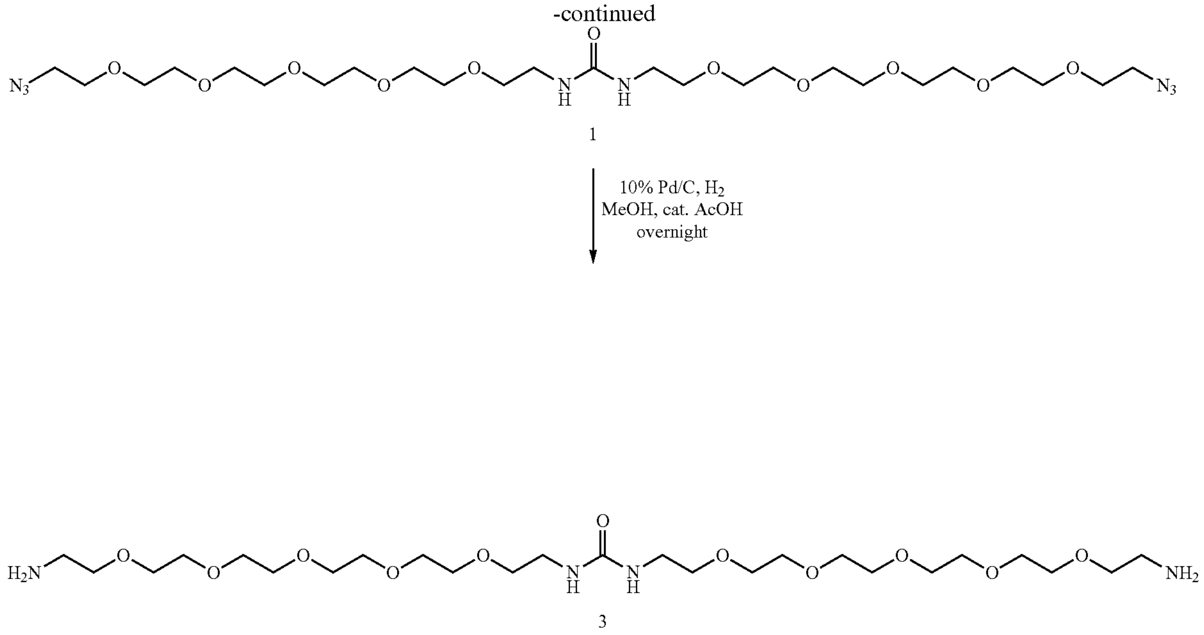

Preparation of 1,3-bis(17-azido-3,6,9,12,15-pentaoxaheptadecyl)urea (2): To a solution of 17-azido-3,6,9,12,15-pentaoxaheptadecan-1-aminium (1) (30 g, 97.73 mmol) in DMF (100 mL), triethyl amine (TEA) (9.89 g, 97.73 mmol) and 1,1-carbonyldiimidazole (7.80 g, 0.22 mmol) were added sequentially at room temperature under Argon. The reaction mixture was stirred at room temperature overnight. The solvent was evaporated under reduced pressure to give 2, as slightly yellow oil (24 g, 75% yield), which was used further without purification. MS (EST) calculated for $C_{25}H_{50}N_8O_{11}$: 638.4; found: 639.3 (M+H$^+$).

Preparation of 1,3-bis(17-azido-3,6,9,12,15-pentaoxaheptadecyl)urea (3): To a solution of 1,3-bis(17-amino-3,6,9,12,15-pentaoxaheptadecyl)urea (24 g, 37.57 mmol) in MeOH (80 mL), were added 10% wet Pd/C (2 g) and acetic acid 2 equiv.). The reaction mixture was de-gassed with help of vacuum and purged with 1 atmosphere $H_2$ gas balloon (this procedure was repeated 3 times) and stirred under $H_2$ gas overnight. TLC showed starting material was disappeared and then filtered over celite pad. Filtrate was concentrated, and co-evaporated with toluene (3×80 mL) to give 3, as yellow syrup (21.5 g, 98% yield), which was used for the next step without purification. MS (ESI) calculated for $C_{25}H_{54}N_4O_{11}$: 586.4 found: 587.3 (M+H$^+$).

Preparation of Example CPG Solid Supports.
Scheme 2: Example Aminopropyl-CPG Solid Supports.
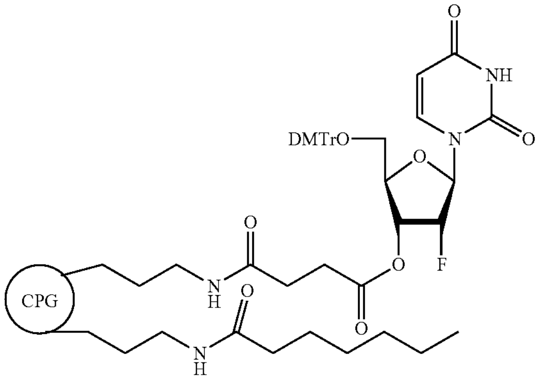
Loading: 71 μmol/g
1
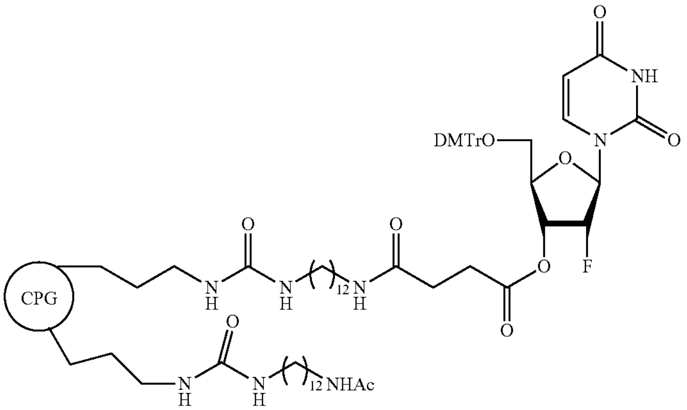
Loading: 88 and 71 μmol/g
2
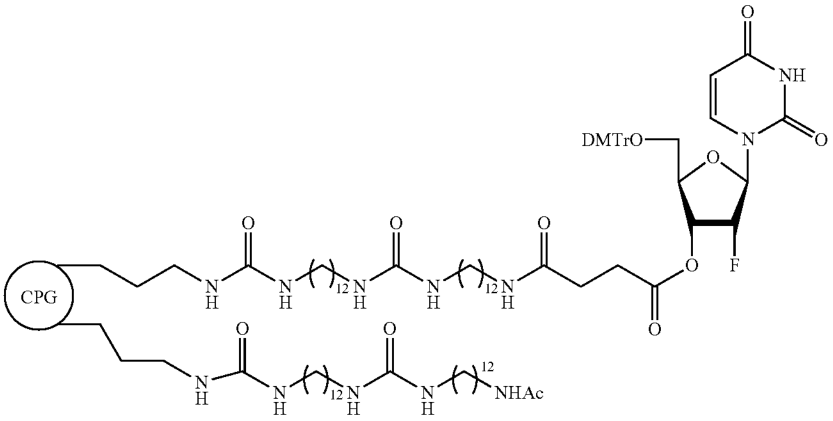
Loading: 73 μmol/g
3

-continued
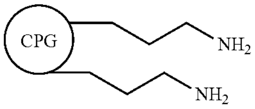
CPG aminopropyl solid support
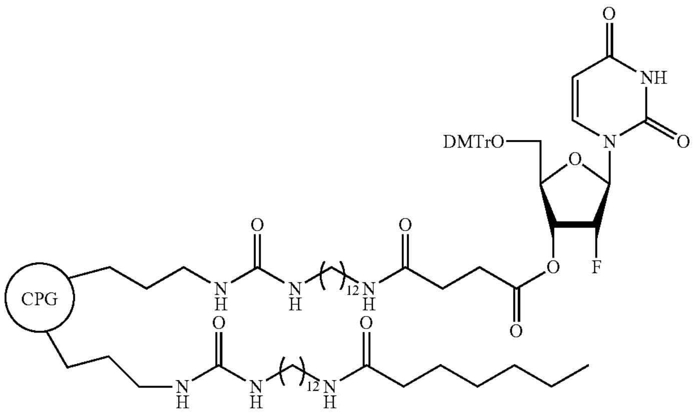
Loading: 73 μmol/g
4
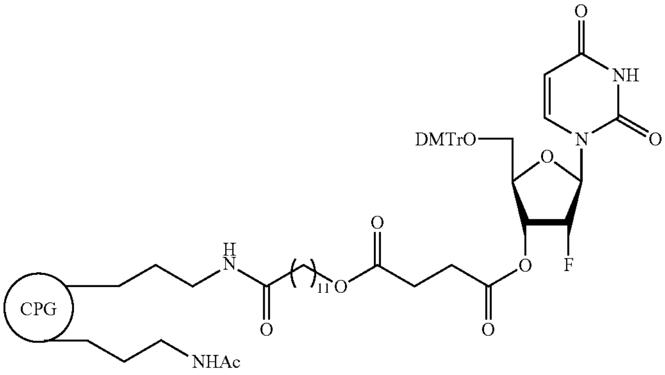
5
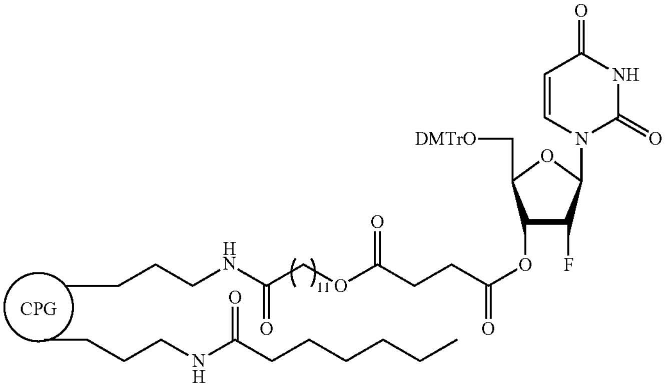
6

Scheme 3: Example Animopropyl-CPG Solid Supports.
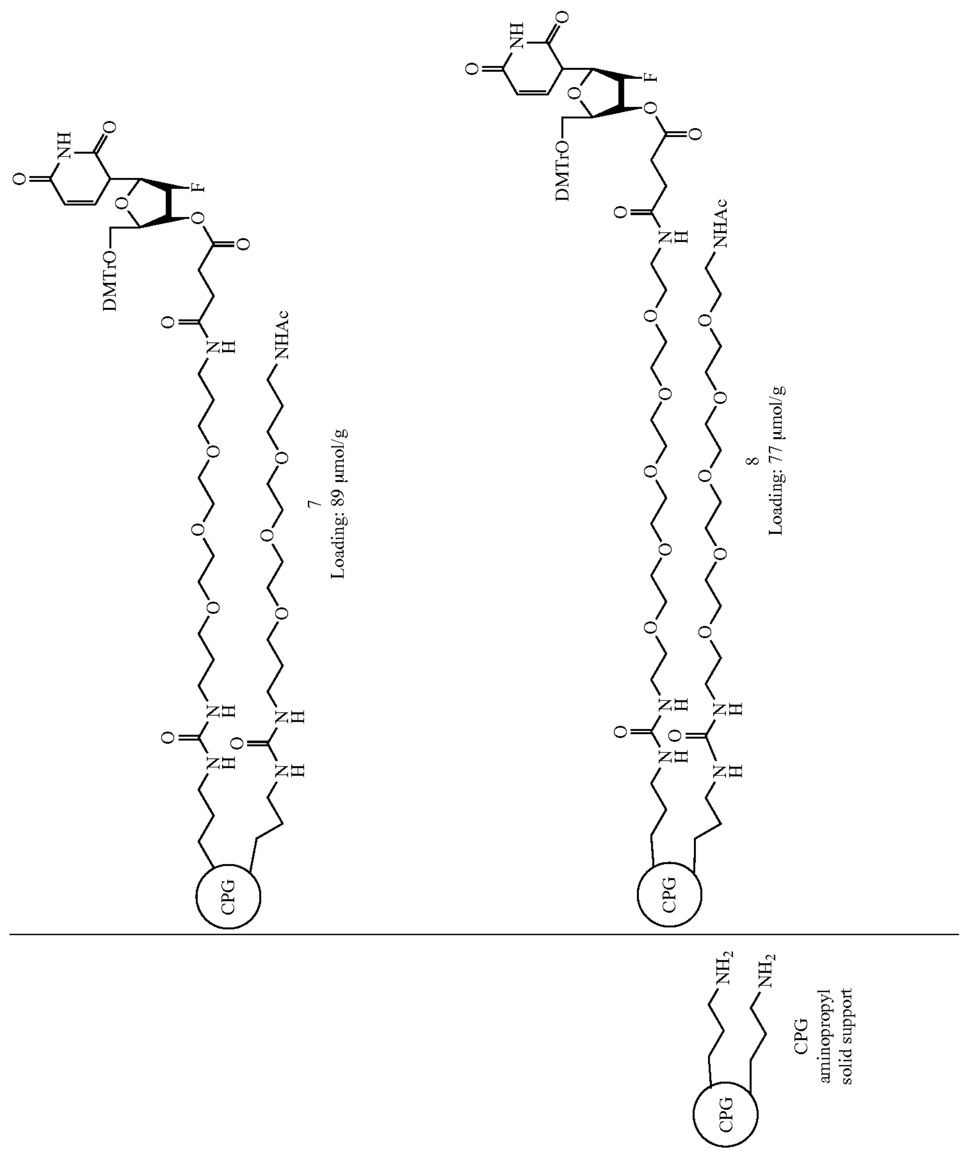
7
Loading: 89 μmol/g
8
Loading: 77 μmol/g
CPG
aminopropyl
solid support -continued
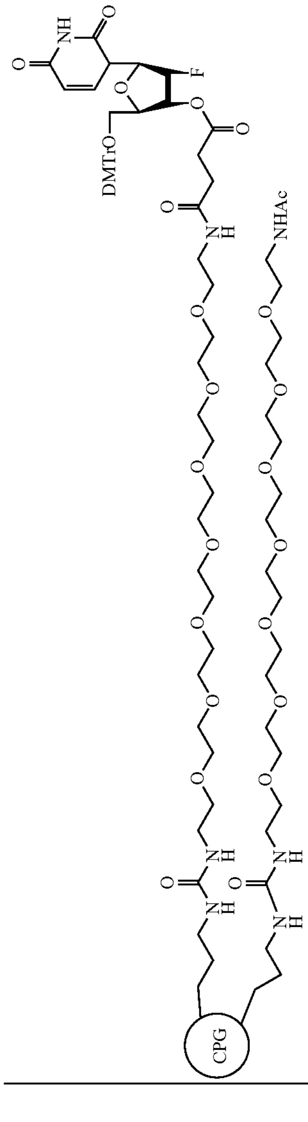
9
Loading: 66 µmol/g
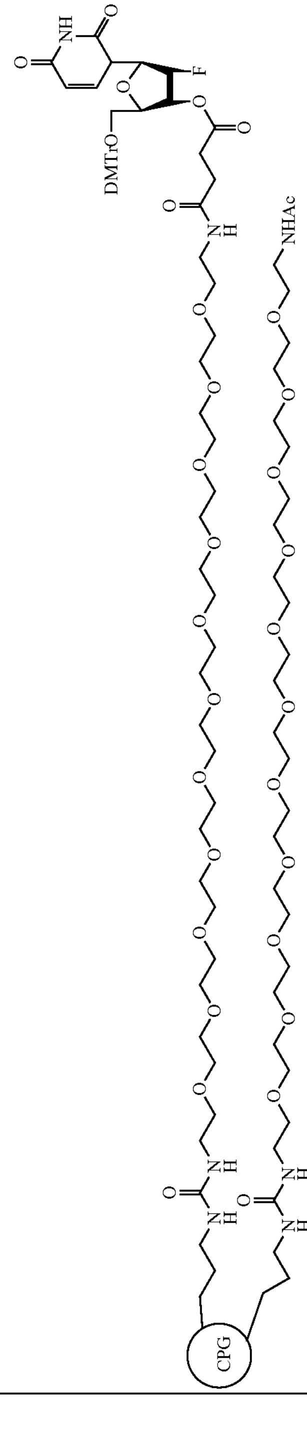
10
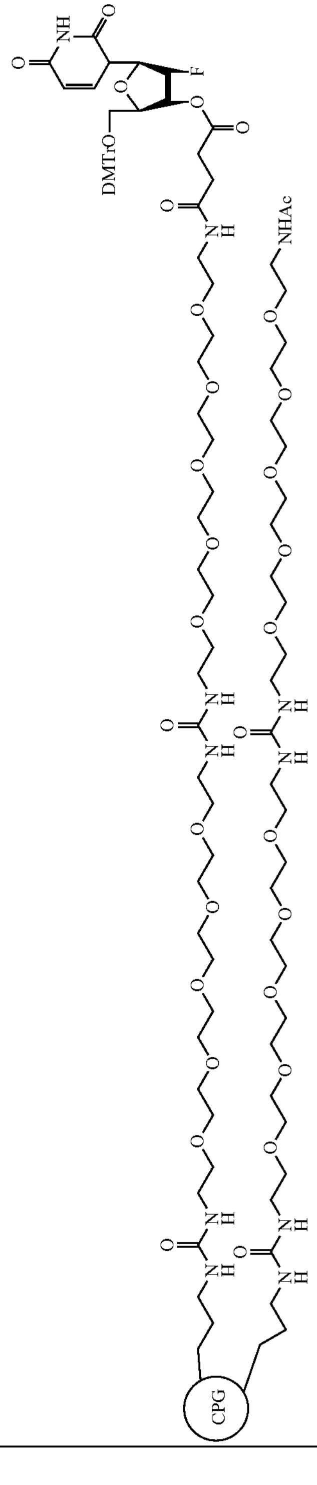
11
Loading: 45 µmol/g Scheme 4: Amino-nonyl-CPG Solid Supports.
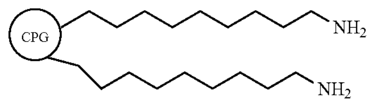
Solid support
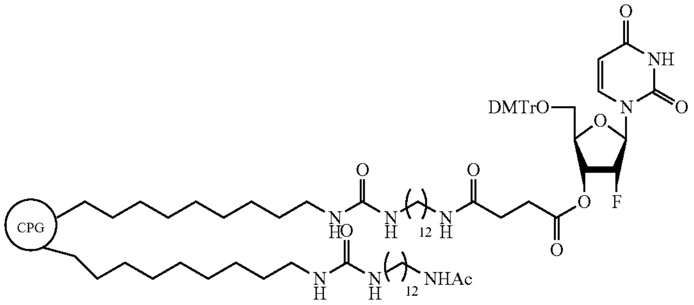
11
Loading 70 μmol/g
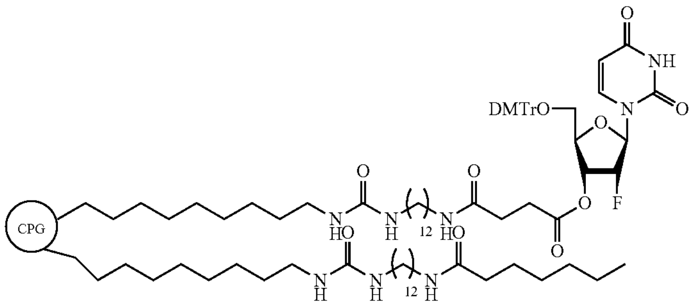
12
Loading 70 μmol/g
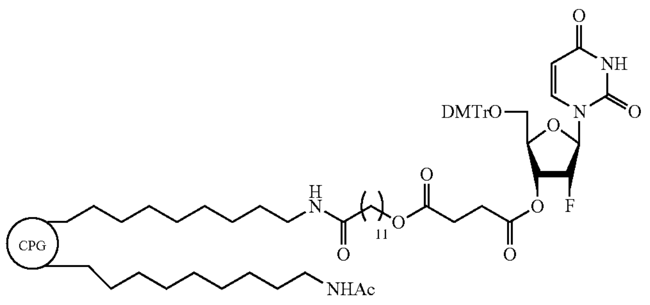
13
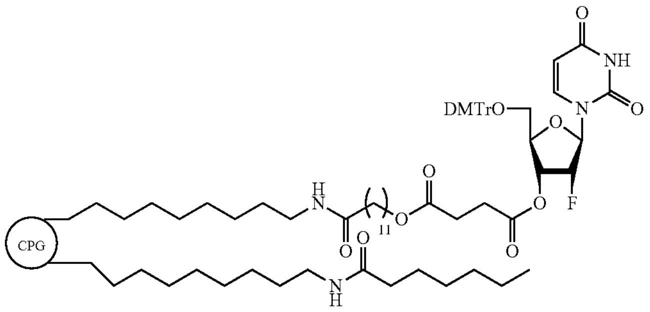
14

Scheme 5: Amino-nonyl-CPG Solid Support.

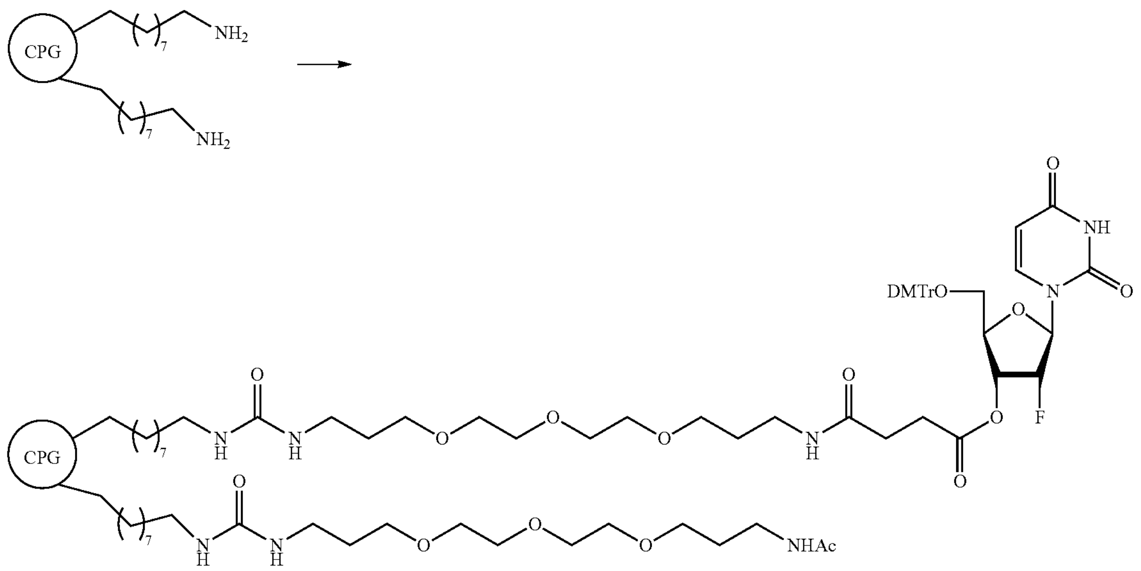

15
Loading: 57 umol/g

General procedure for CPG-p-nitrophenyl carbamate I: An dried 2 L RB flask was cooled under vacuum then filled with Argon. Then DCM (375 mL, 7.5 nit per g of CPU) and p-Nitrophenyl chloroformate (12 g, 0.24 g per g of CPU) were added under Argon and shaken the flask for 3 min, and once p-Nitrophenyl chloroformate was dissolved then pyridine (50 mL, 1 mL per g of CPG) was added, at this stage a white solid was formed with a slightly exothermic reaction. Then immediately an amino functionalized support (Aminopropyl-CPG or amino-nonyl-CNA-CPG) was added and the reaction mixture was shaken 5 min, and mechanical wrist shaker for overnight. Filtered and washed with DCM (3x350 mL) and followed by THF (3x350 mL), and solids (Aminopropyl-CPG- or CNA-p-nitrophenyl carbamate) were taken into 1 L RB flask and dried under vacuum for around 4 hr. Pyridine (200 mL) and $Ac_2O$ (50 mL) were added into the dried Aminopropyl-CPG- or CNA-p-nitrophenyl carbamate and overhead shaker for 1 h. CPG was filtered and washed with THF (350 mLx3) and $CH_3CN$ (350 mLx3) and dried under vacuum overnight to give Aminopropyl-CPG- or Amino-nonyl-CPG-p-nitrophenyl carbamate. Loading: 130-201 μmol/g.

General procedure for CPG urea derivatives II: To an over dried 1 L RB flask cooled under vacuum and plugged with Argon. $NH_2$—$(CH_2)_n$—N or $NH_2$-$(PEG)_n$-$NH_2$ (20 equiv.) was dissolved in DCM (10 mL per g of CPG), and followed by Pyridine (1 ml per g of CPG) was added. Then immediately CPG-p-nitrophenyl carbamate was added to the reaction mixture and overhead shaker for overnight. Filtered and washed with MeOH (3x300 mL), and followed by DCM (3x300 mL), and solids (CPG-$NH_2$—CO—$NH_2$—$(CH_2)_n$—$NH_2$ or CPG-$NH_2$—CO—$NH_2$-$(PEG)_n$-$NH_2$) was taken into L RB flask and dried under vacuum overnight.

General Procedure for nucleoside loading III: To an over dried 500 mL RB flask cooled under vacuum and plugged with Argon. Then 5c-DIMTr-2'-F-dU-3'-Triethylammonium-succinate (1 equiv.), and HBTU (2.5 equiv.) were added into the flask, and followed by $CH_3CN$ (10 mL per g of CPG). To this suspension, DIPEA (5.0 equiv.) was added and immediately, CPG-$NH_2$—CO—$NH_2$—$NH_2$—$(CH_2)_n$—$NH_2$ or CPG-$NH_2$—CO—$NH_2$—$(PEG)_n$-$NH_2$ or Appropriate amino-linker added and mechanical wrist shaker for overnight. At this stage, small amount of CPC; washed with DCM/MeOH and dried and checked CPG loading, it was 60-90 μm/g. Then CPG was filtered and washed with MeOH and DCM and solids were taken into 500 nit RB flask and dried under vacuum for around 4 h, and capped with Pyridine/$Ac_2O$ (3:1) or heptanoic acid/$Ac_2O$ (3:1) and followed by overhead shaker for 1-4 h. The CPG was filtered and washed with MeOH and DCM and dried under vacuum overnight to give a CPG-linker-Succinyl-Urea-2'-F-dU (Loading: 60-90 μmol/g).

Procedure for CPG solid support (3, Scheme 2): To make CPG support 3 (Scheme 2), as sequentially followed the following steps: general procedure for CPG-p-nitrophenyl carbamate 1, then general procedure for CPG urea derivatives II, and again general procedure for CPG-p-nitrophenyl carbamate 1, and general procedure for CPG urea derivatives 11 and finally general procedure for nucleoside loading III.

Procedure for CPG Solid supports (5,6,13,14): An amino functionalized support (Aminopropyl-CPG or amino-nonyl-CPG) (2 g), 12-dimethoxytritylhydroxy-dodecanoic acid (0.8 mmol), 4-dimethylaminopyridine (0.4 mmol), HBTU (2.4 mmol), triethylamine (0.4 mL), and pyridine (30 mL) were shaken at room temperature (16 h). The support was filtered off, washed, and dried. Linker loading was determined by trityl analysis. After deprotecting trityl group, nucleoside succinate was loaded following the above general procedure for nucleoside loading III Example supports and/or linkers can be utilized for preparation of compositions, including chirally controlled oligonucleotide compositions, of oligonucleotides of various, e.g., base sequences, modifications, patterns of backbone chiral centers, etc. For example, example supports and/or linkers were utilized to prepare chirally controlled oligonucleotide compositions with crude purifies of over 50%, and in many cases, over 60% or 65%.

Example 3, Example Post-Cycle Modification and Cleavage/Deprotection Conditions

In some embodiments, the present disclosure provides a variety of conditions for use in provided technologies to, e.g., to remove chiral auxiliaries, to de-protect blocked nucleobases, and to cleave oligonucleotide from support, etc. Example conditions are described herein. Those skilled in the art appreciate that other conditions may be utilized in accordance with the present disclosure.

AMA Condition (e.g., 1 μmol scale): After synthesis, the resin was treated with AMA (conc. $NH_3$-40% $MeNH_2$ (1:1, v/v)) (1 mL) for 45 min at 50° C. (if an oligonucleotide contains 2'F-nucleoside, 35° C. for 2 h can be beneficial and was typically used). Afterwards, in some embodiments, the mixture was cooled to room temperature and the resin was removed by membrane filtration (washed with $H_2O$ for 2 mL), In some embodiments, the filtrate was concentrated under reduced pressure until it becomes about 1 mL. In some embodiments, the residue was diluted with 1 mL of $H_2O$ and analyzed by RP-UPLC-MS.

TBAF Condition (e.g., SP-linker, 1 μmol scale): After synthesis, the resin was treated with 0.1 TBAF in MeCN (1 mL) for 2 h (generally, 30 min is enough) at room temperature, washed with MeCN, dried, and add conc. $NH_3$ (1 mL) for 12 h at 55° C. (which, among other things, may deprotect blocked nucleobases and cleave oligonucleotides from support). Afterwards, in some embodiments, the mixture was cooled to room temperature and the resin was removed by membrane filtration. In some embodiments, the filtrate was concentrated under reduced pressure until it becomes about 1 mL. In some embodiments, the residue was diluted with 1 mL of $H_2O$. In some embodiments, the crude product was optionally de-salted before analysis. In some embodiments, the crude product was analyzed by RP-UPLC-MS.

TEA-HF Condition (suc.-linker, 1 μmol scale): After synthesis, the resin was treated with 1 M TEA-HF in DMF-$H_2O$ (3:1, v/v; 1 mL) for 2 h at 50° C. Support, e.g., PS5G, CPG, etc., was washed with MeCN, and $H_2O$ and add AMA (conc. $NH_3$-40% $MeNH_2$ (1:1, v/v)) mL) (which, among other things, may deprotect blocked nucleobases and cleave oligonucleotides from support) for 45 min at 50° C. (if oligonucleotide contains 2'F-nucleoside, 35° C. for 2 h can be beneficial). Afterwards, in some embodiments, the mixture was cooled to room temperature and the resin was removed by membrane filtration (washed with $H_2O$ for 2 mL). In some embodiments, the filtrate was concentrated under reduced pressure until it becomes about 1 mL. In some embodiments, the residue was diluted with 1 mL of $H_2O$. In some embodiments, the crude product was optionally de-salted before analysis. In some embodiments, the crude product was analyzed by RP-UPLC-MS. In some embodiments, TEA-HF provided better yields and/or purities compared to other conditions when certain chiral auxiliaries were used.

In some embodiments, example post-cycle modification and/or cleavage/deprotection conditions are as described below:

| No. | 1$^{st}$ Treatment | 2$^{nd}$ Treatment | 3$^{rd}$ Treatment |
|---|---|---|---|
| 1 | Aq. MA, 40° C., 45 min | TEA•3HF, pH 5, 50° C., 2 h | N/A |
| 2 | Aq. MA, RT, 5 min | TEA•3HF, pH 5, 50° C., 1 h | Aq. MA, pH > 10, RT, 2 h |
| 3 | TEA•HF in DMF/$H_2O$, pH 6.7, 50° C., 1 h | a. Filtrate, AMA, pH > 10, RT, 2 h b. CPG, AMA, RT, 2 h | N/A |
| 4 | 1M KF in $H_2O$, 50° C., 1.5 h | CPG, AMA, RT, 2 h | N/A |
| 5 | Conc. NH4OH, RT, 10 min | TEA•3HF, pH 5, 50° C., 1 h | AMA, pH > 10, RT, 2.5 h, overnight |
| 6 | a. Conc. NH4OH, RT, 10 min, b. To Filtrate, Aq. MA added | TEA•3HF, pH 5, 50° C., 1 h | AMA, pH > 10, RT, 2 h, overnight |
| 7 | AMA, RT, 2 h | TEA•3HF, pH 5, 50° C., 1 h, 1.5 h | N/A |
| 8 | AMA, RT, 15 min | TEA•3HF, pH 5, 50° C., 1 h | AMA, pH > 10, RT, 2 h, overnight |
| 9 | Conc. NH4OH, RT, overnight | TEA•3HF, pH 5, 50° C., 2 h | N/A |
| 10 | AMA (Aq. NH3/MA = 9/1, v/v), RT, overnight | TEA•3HF, pH 5, 50° C., 2 h | N/A |
| 11 | AMA (Aq. NH3/MA = 3/1, v/v), RT, overnight | TEA•3HF, pH 5, 50° C., 2 h | N/A |
| 12 | Aq. NH3/EtOH = 3/1, v/v, 40° C., overnight | TEA•3HF, pH 5, 50° C., 2 h | N/A |
| 13 | Conc. NH4OH, 40° C., overnight | TEA•3HF, pH 5, 50° C., 2 h | N/A |
| 14 | 1X Conc of TEA•HF, 5 h, RT | Conc. NH4OH, 35° C., 24 h | N/A |
| 15 | 2.5X Conc of TEA•HF, 5 h, RT | Conc. NH4OH, 35° C., 24 h | N/A |
| 16 | 5X Conc of TEA•HF, 5 h, RT | Conc. NH4OH, 35° C., 24 h | N/A |
| 17 | 1X Conc of TEA•HF, 5 h, RT | AMA, RT, 3-10 h | N/A |
| 18 | 1X Conc of TEA•HF, 5 h, RT | Aq. MeNH2, RT, 3-10 h | N/A |

-continued

| No. | 1st Treatment | 2nd Treatment | 3rd Treatment |
|---|---|---|---|
| 19 | 1X Conc of TEA•HF/metal chelating agent, 5 h, RT | Conc. NH4OH, 35° C., 24 h | N/A |
| 20 | 2.5X Conc of TEA•HF/–metal chelating agent, 5 h, RT | Conc. NH4OH, 35° C., 24 h | N/A |
| 21 | 5X Conc of TEA•HF/metal chelating agent, 5 h, RT | Conc. NH4OH, 35° C., 24 h | N/A |
| 22 | 1X Conc of TEA•HF, 5 h, RT | AMA/metal chelating agent, RT, 3-10 h | N/A |
| 23 | 2.5X Conc of TEA•HF, 5 h, RT | Aq. MeNH2/metal chelating agent, RT, 2-3 h | N/A |
| 24 | 5X Conc of TEA•HF, 3-12 h, RT | Conc. NH4OH/–thiol, 9/1, v/v, 35° C., 24 h | N/A |
| 25 | 1X Conc of TEA•HF/EDTA, 5 h, RT | Conc. NH4OH, 35° C., 24 h | N/A |
| 26 | 2.5X Conc of TEA•HF/EDTA, 5 h, RT | Conc. NH4OH, 35° C., 24 h | N/A |
| 27 | 5X Conc of TEA•HF/EDTA, 5 h, RT | Conc. NH4OH, 35° C., 24 h | N/A |
| 28 | 1X Conc of TEA•HF, 5 h, RT | Conc. NH4OH/EDTA, 35° C., 24 h | N/A |
| 24 | 2.5X Conc of TEA•HF, 3-12 h, RT | Conc. NH4OH/EDTA, 35° C., 24 h | N/A |
| 25 | 5X Conc of TEA•HF, 3-5 h, RT | Conc. NH4OH/EDTA, 35° C., 24 h | N/A |
| 26 | TBAF, DMF or DMSO or ACN | Conc. NH4OH, 35° C., 24 h or AMA, RT, 3-8 h | N/A |
| 27 | Tetrabutylammonium difluorotriphenylsilicate, DMF or DMSO or ACN | Conc. NH4OH, 35° C., 24 h or AMA, RT, 3-8 h | N/A |
| 28 | Tetrabutylammonium difluorotriphenylsilicate/ Acetic acid (1/1), DMF or DMSO or ACN | Conc. NH4OH, 35° C., 24 h or AMA, RT, 3-8 h | N/A |
| 29 | Tetrabutylammonium difluorotriphenylsilicate/ Acetic acid (1/1), DMF or DMSO or ACN | Conc. NH4OH, 35° C., 24 h or AMA, RT, 3-8 h | N/A |
| 30 | Pyridine•HF, DMF or DMSO or ACN | Conc. NH4OH, 35° C., 24 h or AMA, RT, 3-8 h | N/A |
| 31 | 1M TEA•HF in DMF/Water, 50 deg C., 1-2.5 h | Conc. NH4OH, 40-55° C., 16-24 h | N/A |

In some embodiments, a metal chelating agent (metal chelator) is mercaptoethanol, 1-dodecanthiol, dithiothreitol (DTT), thiophenol, 1,2-diaminoethane, 1,3-diaminopropane, 2,3-mercapto 1-propanesulfonic acid, 2,3-mercapto propane-1-ol, or meso 2,3-dimercapto succinic acid.

In some embodiments, post-cycle modification (e.g., a TBAF or TEA-HF condition, and cleavage/deprotection steps were performed in one pot. In some embodiments, a one-pot reaction generated a large amount of salts. In some embodiments, crude products of a one-pot process were first de-salted before analysis of crude oligonucleotide purity.

In some embodiments, a post-cycle modification, and/or cleavage/deprotection condition is or comprises an AMA condition. In some embodiments, a post-cycle modification, and/or cleavage/deprotection condition is or comprises a TBAF condition. In some embodiments, a post-cycle modification, and/or cleavage/deprotection condition is or comprises a TEA-HF condition. In some embodiments, a post-cycle modification, and; or cleavage/deprotection condition is or comprises a combination of an AMA condition, a TBAF condition, and/or a TEA-HF condition. As those skilled in the art appreciates, conditions for various steps, e.g., coupling, pre-modification capping, modification, post-modification capping, de-blocking, post-cycle modification, cleavage/deprotection, etc. can be each individually optimized, including adjusting example conditions provided in the present disclosure, in accordance with the present disclosure.

Among other things, the present disclosure provides compounds with diverse properties for use as chiral auxiliaries, and various deprotection conditions which can effectively remove certain types of chiral auxiliaries according to their properties while being compatible with the overall oligonucleotide preparation schemes, thereby providing enormous flexibility and options so that oligonucleotides can be prepared with desired yield, purity, and/or selectivity.

In some embodiments, instead of using TBAF or TEA-HF, a base-labile chiral auxiliary, e.g., PSM, may be removed by base treatment, e.g., contacting with an anhydrous solution of a base. Certain examples are described Examples herein.

Example 4. Provided Technologies Deliver Greatly Improved Results

Among other things, the present disclosure provides technologies that can achieve greatly improved results, e.g., unexpectedly high crude purity and yield compared to an appropriate reference technology, e.g., one using capping steps as in traditional oligonucleotide synthesis based on phosphoramidite chemistry. Provided technologies were utilized to prepare oligonucleotide compositions, including chirally controlled oligonucleotide compositions, of oligonucleotides comprising various sequence lengths, base sequences, base modifications, sugar modifications, internucleotidic linkages (including natural phosphate linkages and modified internucleotidic linkages, including chirally controlled chiral modified internucleotidic linkages), patterns of modifications, patterns of back bone chiral centers, etc. Provided technologies can provide oligonucleotide compositions, particularly chirally controlled oligonucleotide composition, with high efficiency independently of base sequence, chemical modifications, stereochemistry, etc. The present example describes certain procedures and results from preparation of WV-3473.

Example runs using DPSE as chiral auxiliary for preparation of WV-3473, 5'-fU*SfC*SfA*SfA*SfG*SfG*SmAfA*SmGmA*SfU*SmGmGfC*SfA*SfU*Stlf*SfU*SfC*SfU-3' (SEQ ID NO: 200) (in: 2'-OMe, f: 2'-F; *: phosphorothioate linkage; *S: Sp phosphorothioate linkage; no * between bases as appreciated by those skilled in the art represents natural phosphate linkage), which has a Molecular Weight of 6732.82 (free acid), and Extinction Coefficient ($M^{-1}cm^{-1}$) of 204,500, were described below demonstrating various advantages of provided technologies, e.g., unexpectedly high crude purity and yield, increased flexibility with reaction conditions, etc.

Example Cycles for Synthesis.

| Batch | B6 | B19 | B56 | B110 |
|---|---|---|---|---|
| Process Step | Detritylation<br>Coupling<br>Pre-Cap B<br>Cap<br>Thiolation<br>N/A | Detritylation<br>Coupling<br>Pre-Cap B<br>N/A<br>Thiolation<br>Post-Thio-Cap | Detritylation<br>Coupling<br>Pre-Cap B<br>N/A<br>Thiolation<br>Post-Thio-Cap | Detritylation<br>Coupling<br>Pre-Cap B<br>N/A<br>Thiolation<br>Post-Thio-Cap |

In some embodiments, Detritylation is a de-blocking step. In some embodiments, coupling is a coupling step. In some embodiments, pre-Cap B is a pre-modification capping step, or uses conditions of a pre-modification capping step. In some embodiments, Cap is a post-modification capping step, or uses conditions of a post-modification capping step. In some embodiments, Thiolation is a modification step comprising sulfurization (thiolation). In some embodiments, Post-Thio-Cap is a post-modification capping step.

Example Conditions.

| Process Step | Parameter | B6 | B19 | B56 | B110 |
|---|---|---|---|---|---|
| Synthesis Column and Synthesizer | Scale | 0.315 mmol | 0.315 mmol | 0.430 mmol | 0.396 mmol |
| | Solid Support | PS 5G | PS 5G | NittoPhase HL | CPG |
| | Support Loading | 149 μmol/g | 149 μmol/g | 205 μmol/g | 73 μmol/g |
| | Support density | 0.11 g/mL | 0.11 g/mL | 0.109 g/mL | 0.24 g/mL |
| | Column Diameter | 3.5 cm | 3.5 cm | 3.5 cm | 2.0 cm |
| | Column Volume | 19.2 mL | 19.2 mL | 19.2 mL | 22.0 mL |
| | Column Height | 2.0 cm | 2.0 cm | 2.0 cm | 7.0 cm |
| | Synthesizer | Akta100 | Akta100 | Akta100 | Akta100 |
| | Loop Volume | 8 mL | 8 mL | 8 mL | 8 mL |
| Pre-Synthesis Wash | Pre-Synthesis Wash Solvent | Acetonitrile | Acetonitrile | Acetonitrile | Acetonitrile |
| | Pre-Synthesis Wash Flow Rate | (424 cm/hr) | (424 cm/hr) | (424 cm/hr) | (424 cm/hr) |
| | Pre-Synthesis Wash Volume | 2 CV | 2 CV | 2 CV | 2 CV |
| UV Watch Command Detritylation | Reagent | 3% DCA/toluene | 3% DCA/toluene | 3% DCA/toluene | 3% DCA/toluene |
| | Control Mode | UV Watch Command | UV Watch Command | UV Watch Command | UV Watch Command |
| | Watch Command Wavelength | 436 nm | 436 nm | 436 nm | 436 nm |
| | UV Autozero | Autozero on 3% DCA in bypass prior to the 1st detrit. | Autozero on 3% DCA in bypass prior to the 1st detrit. | Autozero on 3% DCA in bypass prior to the 1st detrit. | Autozero on 3% DCA in bypass prior to the 1st detrit. |
| | Watch Command setting | 250 mAU | 250 mAU | 250 mAU | 500 mAU |
| | Watch Command Initiation | 1.2 CV | 1.2 CV | 1.2 CV | 1.2 CV |
| | Detrit Flow Rate | 220 and 260 cm/hr | 220 and 260 cm/hr | 300 cm/hr | 424 cm/hr |
| | ACN Wash after Detrit | (212 cm/hr) 2 CV (424 cm/hr) 2 CV | (212 cm/hr) 2 CV (424 cm/hr) 2 CV | (212 cm/hr) 2 CV (424 cm/hr) 2 CV | (212 cm/hr) 2 CV (424 cm/hr) 2 CV |
| Coupling | Stereo Amidite Eq | 4 eq. | 4 eq. | 4 eq. | 2.5 eq. |
| | Diluent for Stereo DPSE Amidite | Acetonitrile for 2'-F-A-L, 2'-F-C-L, 2'-F-G-L<br>20% IBN/80% ACN for 2'-F-U-L, 2'-OMe-A-L | | | |
| | Concentration of Stereo DPSE Amidite | 0.175M | 0.2M | 0.2M | 0.2M |
| | Stereo DNA-Activator | CMIMT | | | |
| | CMIMT Concentration | 0.6M | | | |

-continued

| Process Step | Parameter | B6 | B19 | B56 | B110 |
|---|---|---|---|---|---|
| | CMIMT Solvent | Acetonitrile | | | |
| | CMIMT Eq/Support | 20.60 | 28.00 | 28.00 | 15.25 |
| | CMIMT/DPSE Amidite Molar ratio | 5.2:1 | 7.0:1 | 7.0:1 | 6.1:1 |
| | % Volume of CMIMT Activator | 60% | 70% | 70% | 67% |
| | Standard Amidite Eq | 3.5 eq. | 3.5 eq. | 3.5 eq. | 2.5 eq. |
| | Standard Amidite Solvent | Acetonitrile | | | |
| | Standard Amidite Concentration | 0.175M | 0.2M | 0.2M | 0.2M |
| | Standard amidite-Activator | ETT | | | |
| | ETT Concentration | 0.6M | | | |
| | ETT Solvent | Acetonitrile | | | |
| | ETT Eq/Support | 18.0 eq. | 15.75 | 15.75 | 11.25 |
| | ETT: Standard Amidite Molar Ratio | 5.1:1 | 4.5:1 | 4.5:1 | 4.5:1 |
| | % Volume ETT Activator | 60% | | | |
| | Push Volume | Amidite/activator port-dependent to fully deliver coupling charge to recycle loop | | | |
| | Recycle Flow Rate | 300 cm/hr | 300 cm/hr | 300 cm/hr | 212 cm/hr |
| | Stereo DPSE amidite Recycle Time | 10 min | 15 min | 15 min | 10 min |
| | Standard amidite-Recycle Time | 8 min | | | |
| | Coupling ACN Wash Flow Rate (LFlow_AB) | 424 cm/hr | 424 cm/hr | 424 cm/hr | 424 cm/hr |
| | Coupling ACN Wash Volume | 2 CV | 2 CV | 2 CV | 2 CV |
| Pre-Cap B | Mode | Flow-Through | | | |
| | Reagent | 20%:30%:50 = $Ac_2O$:2,6-Lutidine:ACN (v/v/v) | | | |
| | Charge Volume | 1 CV | 2 CV | 2 CV | 1 CV |
| | Contact Time | 1.2 min | 2 min | 2 min | 4 min |
| | ACN Wash Volume | 1.2 CV | 1.2 CV | 1 CV | 2 CV |
| | ACN Wash Flow rate (LFlow_AB) | 424 cm/hr | | | |
| Cap | Mode | Flow-Through | | | |
| | Reagent | Cap A = 20%:80% = NMI:ACN (v/v)<br>Cap B = 20%:30%:50% = $Ac_2O$:2,6-Lutidine:ACN (v/v/v) | | | |
| | Charge Volume (1:1 mix of Cap A & Cap B) | 1.2 CV | N/A | N/A | N/A |
| | Contact Time | 1.5 min | N/A | N/A | N/A |
| | ACN Push Flow Rate | Same As Capping Charge Flow Rate | N/A | N/A | N/A |
| | CV CT contactime | 1.3 CV | N/A | N/A | N/A |
| | ACN Push Flow Rate | 424 cm/hr | N/A | N/A | N/A |
| | ACN Wash Volume | 1.2 CV | N/A | N/A | N/A |
| Thiolation | Mode | Flow-Through | | | |
| | Reagent | POS in Acetonitrile | POS in Acetonitrile | POS in Acetonitrile | XH in Pyridine |
| | Concentration | 0.1M | 0.1M | 0.1M | 0.2M |
| | Eq Thio/Support | 12.2 eq. | 12.2 eq. | 12.2 eq. | 6.7 eq. |
| | Charge Volume | 2 CV | 2 CV | 2 CV | 0.6 CV |
| | Contact Time | 6 min | 6 min | 6 min | 6 min |
| | CV CT contactime | 1.3 CV | 1.3 CV | 1.3 CV | 1.3 CV |
| | ACN Wash Flow rate (LFlow_AB) | 424 cm/hr | | | 424 cm/hr |
| | ACN Wash Volume | 2.0 CV | | | 2.0 CV |
| Oxidation | Mode | Flow-Through | | | |
| | Ox Reagent | TBHP/Decane/DCM | TBHP/Decane/DCM | TBHP/Decane/DCM | Iodine/Water/Pyridine |
| | Concentration of Ox Solution | 1.1M | 1.1M | 1.1M | 0.05M |
| | Eq Ox/Support | 77 eq. | 77 eq. | 77 eq. | 3.5 eq. |
| | Contact Time | 2 min | 2 min | 2 min | 2 min |
| | ACN Push Volume | 1.3 CV | 1.3 CV | 1.3 CV | 1.3 CV |
| | ACN Wash Flow rate (LFlow_AB) | 424 cm/hr | 424 cm/hr | 424 cm/hr | 424 cm/hr |
| | ACN Wash Volume | 2.0 CV | 2.0 CV | 2.0 CV | 2.0 CV |

-continued

| Process Step | Parameter | B6 | B19 | B56 | B110 |
|---|---|---|---|---|---|
| Post Thio/Ox Cap | Mode | Flow-Through<br>Cap A = 20%: 80% = NMFACN (v/v)<br>Cap B = 20%:30%:50% = Ac2O:2,6-Lutidine:ACN (v/v/v) | | | |
| | Charge Volume (1:1 mix of Cap A & Cap B) | N/A | 0.5 CV | 0.5 CV | 0.4 CV |
| | Contact Time | N/A | 0.5 min | 0.5 min | 0.8 min |
| | ACN Push Flow Rate | N/A | Same As Capping Charge Flow Rate | Same As Capping Charge Flow Rate | Same As Capping Charge Flow Rate |
| | CV CT contactime | N/A | 1.3 CV | 1.3 CV | 1.3 CV |
| | ACN Wash Flow rate (LFlow_AB) | N/A | 424 cm/hr | 424 cm/hr | 424 cm/hr |
| | ACN Wash Volume | N/A | 1.2 CV | 1.2 CV | 1.2 CV |
| Final Column Wash with ACN | Mode | Flow Through | | | |
| | ACN Wash Volume | 2 CV | 2 CV | 2 CV | 2 CV |
| | ACN Wash Flow rate (LFlow_AB) | 424 cm/hr | 424 cm/hr | 424 cm/hr | 424 cm/hr |

Example Post-Cycle Modification. Cleavage and Deprotection Conditions. Example 2 steps cleavage and deprotection process parameters were described in this section.

| Process Step | Parameter | Examples |
|---|---|---|
| Drying Solid Support with Nitrogen | Temperature | R.T. |
| | Argon Pressure | LT 30 psi |
| | Drying Time | NLT 30 min |
| 1M TEA-HF Treatment | Reaction Vessel | High pressure rated bottle |
| | Reagents | 1.0M TEA-HF in DMF/$H_2O$, 3/1, v/v |
| | Volume | 80 ± 5 mL/mmol |
| | Reaction Temp | 50 ± 2.5° C. |
| | Reaction Time | 2.0-2.5 hrs |
| | Solid Support Wash Solvent | WFI and ACN |
| | Wash Volume | WFI: 200-250 mL/mmol<br>ACN: 200-250 mL/mmol |
| Cleavage and Deprotection | Vessel | High pressure rated bottle |
| | Reagent | Conc. $NH_4OH$ (28-30%): Ethanol = 3/1, v/v |
| | Reagent Volume | 80 ± 5 mL/mmol |
| | Reaction Time | 16-18 hrs |
| | Reaction Temperature | 55 ± 2.5° C. |
| | Filtration | Bio-automation or Nalgene Filter |
| | Support Wash Solution | WFI |
| | Support Wash Volume | 200-350 mL/mmole |

1M TEA-HE (triethylamine hydrofluoride) in DMF/water removes DPSE auxiliary group from internucleotidic linkages of stereodefined oligonucleotides (which comprises one or more stereodefined internucleotidic linkages). Crude material was released from the solid support with aqueous conc. ammonium hydroxide/ethanol under a heated condition.

For B110, which used a CPG support, a one-pot process was utilized.

Example Post-Cycle Modification, Cleavage and Deprotection Conditions.

| Process Step | Parameter | Examples |
|---|---|---|
| Drying Solid Support with Nitrogen | Temperature | R.T. |
| | Argon Pressure | LT 30 psi |
| | Drying Time | NLT 30 min |

-continued

| Process Step | Parameter | Examples |
|---|---|---|
| C&D 1 | Reaction Vessel | High pressure rated bottle |
| | Reagents | (5X) TEA-HF in DMSO/$H_2O$, 5/1, v/v |
| | Volume | 100 ± 5 mL/mmol |
| | Reaction Temp | 27 ± 2.5° C. |
| | Reaction Time | 3.0-4.0 hrs |
| | Reaction Mixture Cooling after C&D 1 | Ice Bath |
| | Cooling Time | NLT 30 min |
| C&D 2 | Vessel | High pressure rated bottle |
| | Mode | One Pot Reaction |
| | Reagent | Conc. $NH_4OH$ (28-30%) |
| | Reagent Volume | 200 ± 10 mL/mmol |
| | Reaction Time | 24 ± 0.5 hrs |
| | Reaction Temperature | 35 ± 2.5° C. |
| | Filtration | Bio-automation or Nalgene Filter, 0.2 μm |
| | Support Wash Solution | WFI |
| | Support Wash Volume | 200-350 mL/mmole |

Example Recipe for 1M TEA·HF Solution in DMF/Water, 3/1, v/v.

| Reagent | Solvents/ Reagents | Volume (mL) | Total Volume (mL) |
|---|---|---|---|
| 1M TEA•HF in DMF/Water, 3/1, v/v | DMF | 64.3 | 100 |
| | Water | 21.4 | |
| | Triethylamine (TEA) | 9.0 | |
| | Triethylamine trihydrofluoride (TEA•3HF) | 5.3 | |

Recipe for 5× Solution of TEA·HF DMSO/Water, 5/1, v/v.

| Reagent | Solvents/ Reagents | Volume (mL) | Total Volume (mL) |
|---|---|---|---|
| (5X) TEA•HF in DMSO/Water, | DMSO | 55.0 | 100 |
| | Water | 11.0 | |

-continued

| Reagent | Solvents/ Reagents | Volume (mL) | Total Volume (mL) |
|---|---|---|---|
| 5/1, v/v | Triethylamine (TEA) | 9.0 | |
| | Triethylamine trihydrofluoride (TEA•3HF) | 25.0 | |

Example Results.

| Batch# | Solid Support | Crude Purity (% FLP) |
|---|---|---|
| B6 | PS 5G | 34.0 |
| B19 | PS 5G | 47.6 |
| B56 | NittoPhaseHL | 44.3 |
| B110 | CPG | 75.2 (59.0) |

Figure 2:
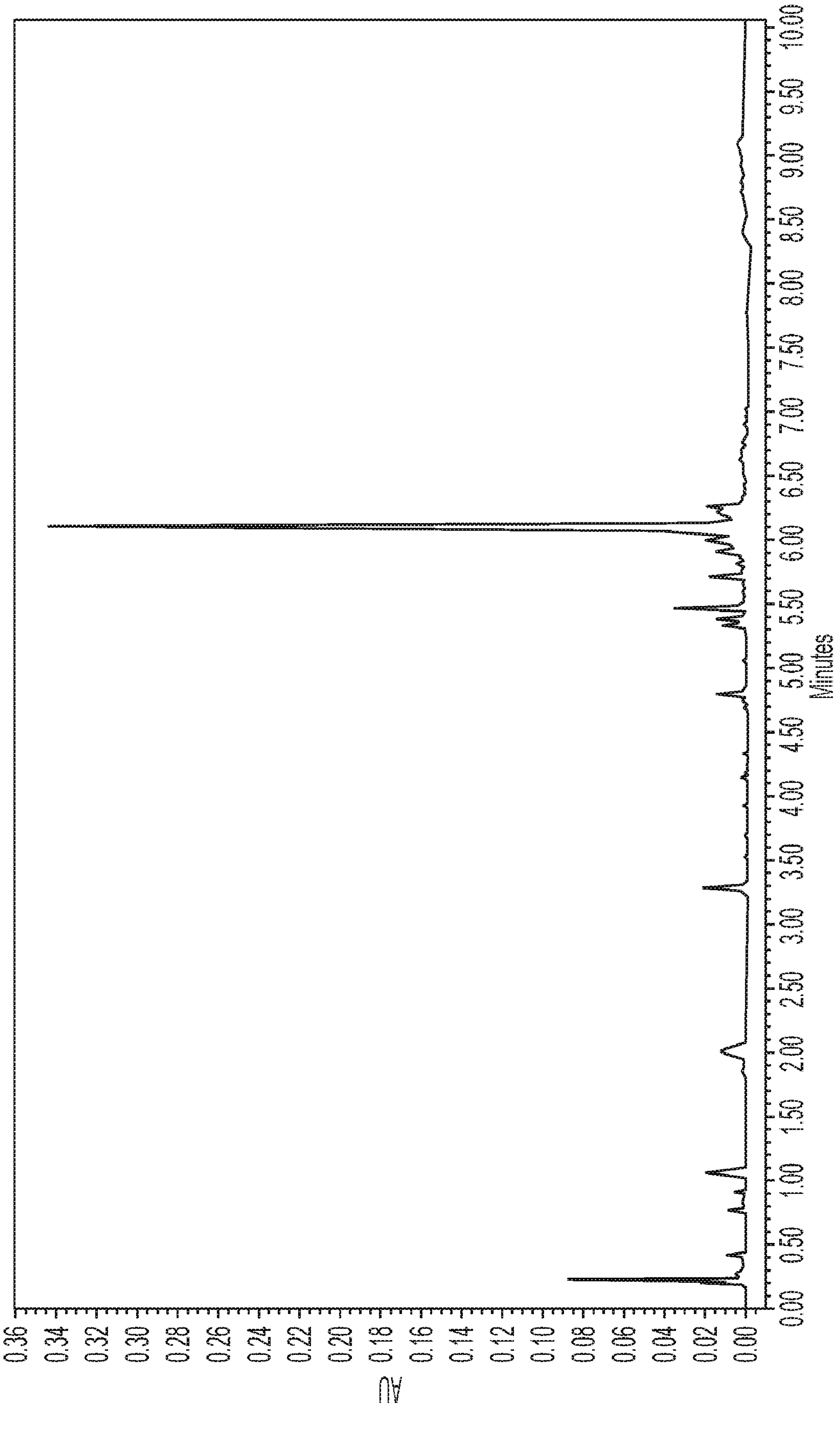
FIG. 2. Crude UPLC chromatogram for B19.
Figure 3:
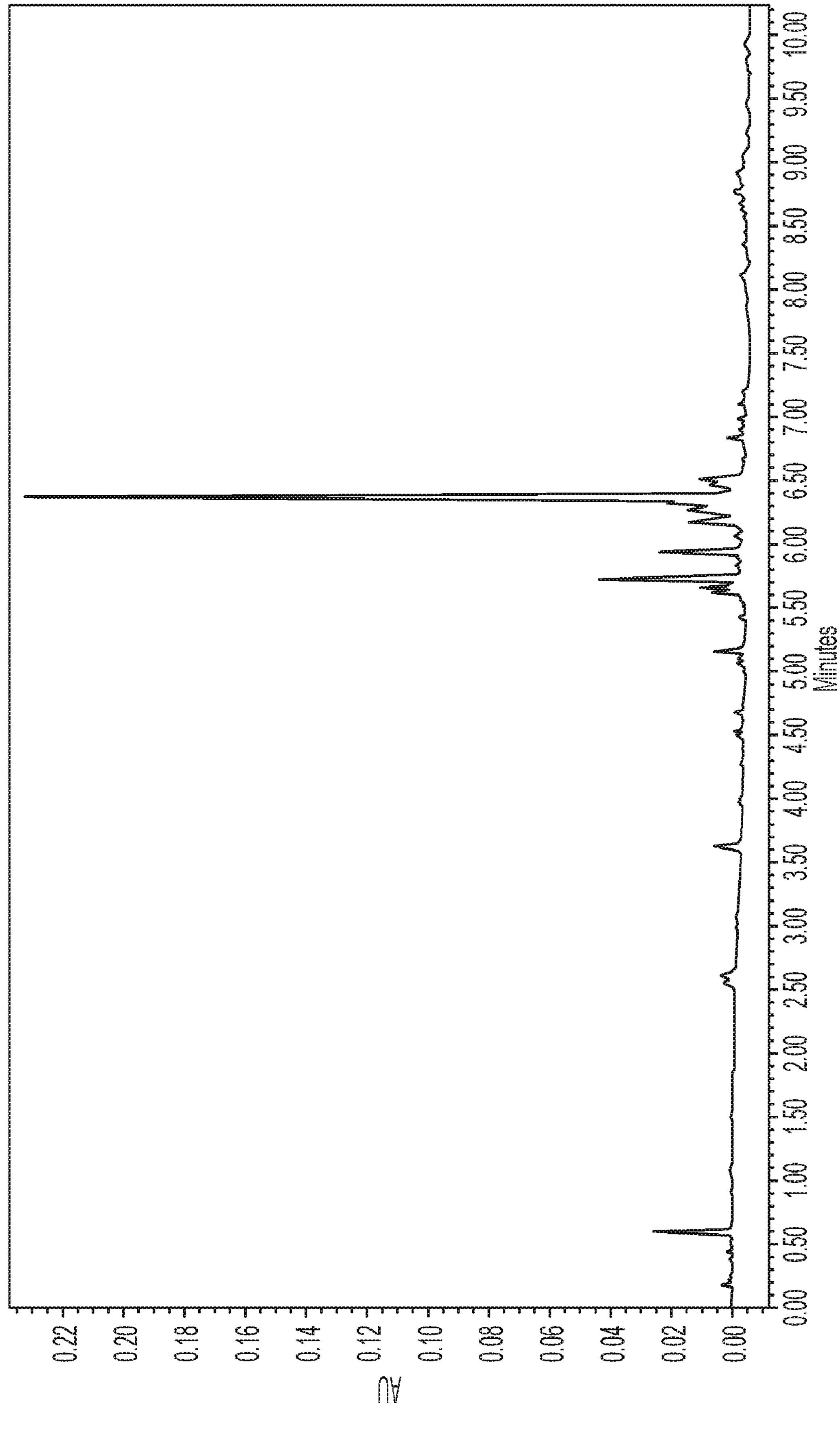
FIG. 3. Crude UPLC chromatogram for B56.
Figure 4:
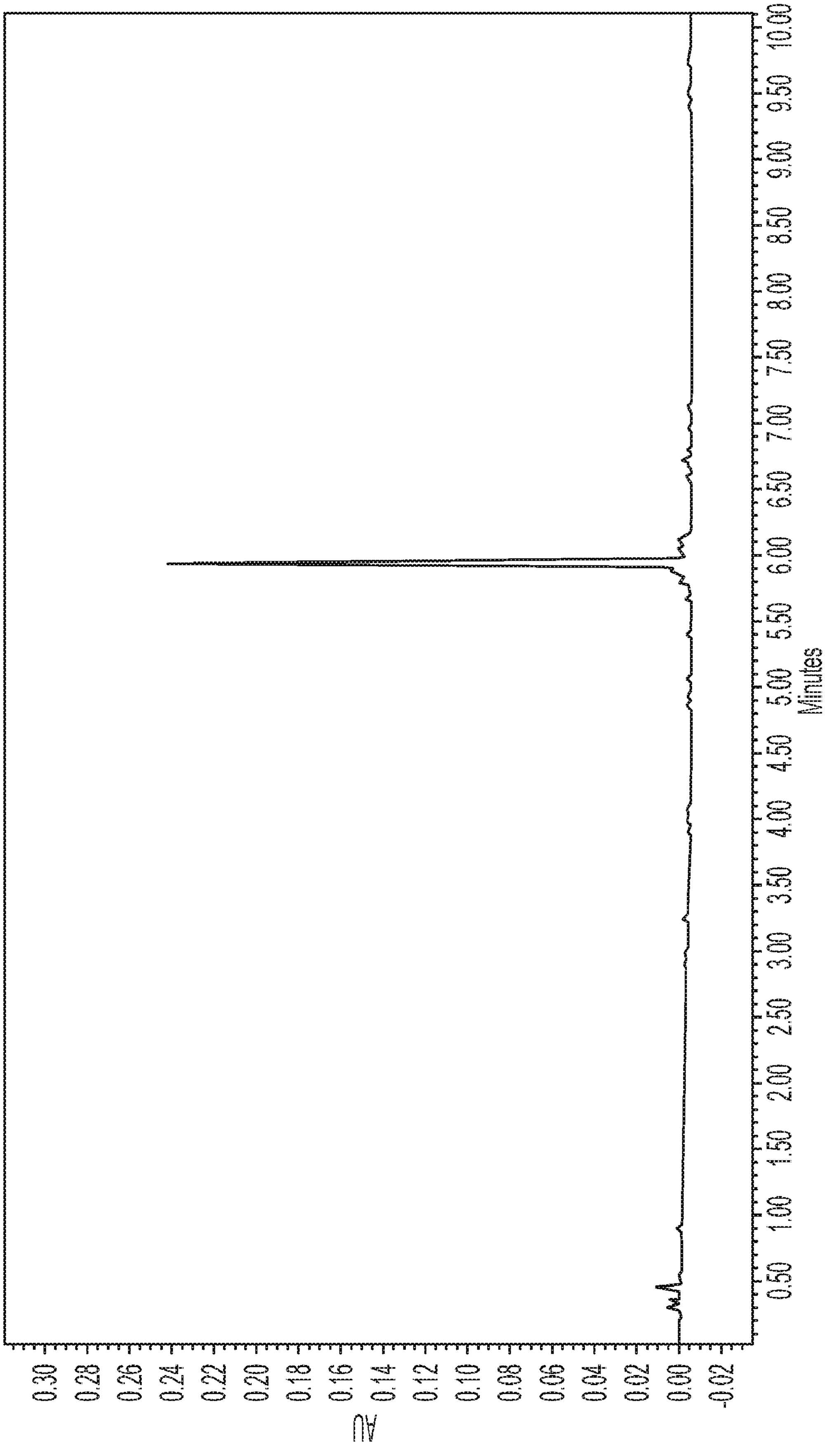
FIG. 4. (A) Crude UPLC chromatogram for B110 (after NAP). (B) Crude UPLC chromatogram for B110 (As was before NAP).
Figure 4:
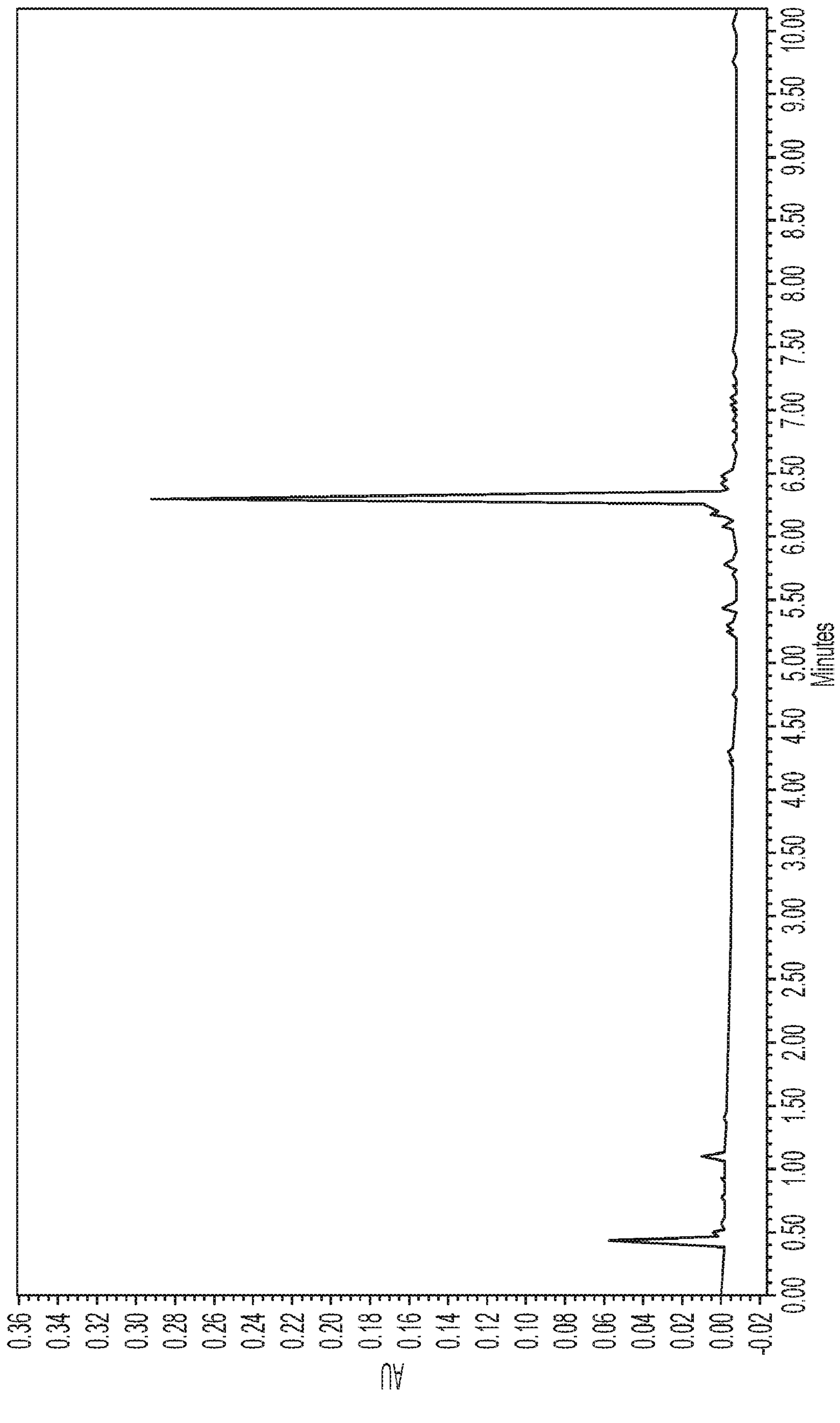

( ) indicates the purity of the crude sample as is injected into UPLC. 75.2% is after de-salting and before any other purification methods (e.g., NAP). Example results were depicted in FIGS. 1-4. An example NAP-10 used was as follows:

- Excess storage solution was allowed to flow through the column;
- Column was equilibrated with MILLIQ® water (3 mL×2);
- 25 OD in 1 mL water (~ 1 mg) was applied into the column;
- Desalted oligonucleotide was eluted from the column with 1.5 mL of water:
- Eluted oligonucleotide was injected into the UPLC to assess the crude purity.

An example UPLC analytical process was as follows. Applicant notes that retention time might shift due to running conditions, e.g., batches of buffers, gradients, sample compositions, etc.

A: 100 mM HFIP, 10 mM TEA in Water
B: 100% Acetonitrile
Flow rate: 0.8 mL/min
Temp: 55 deg C.
Column: Waters Acquity BEH C18 1.7 um 2.1×50 mm
Gradient: 3-13% in 10 min As demonstrated, provided technologies can, among other things, produce unexpectedly high crude purity and/or yield (e.g., 47.6% for B19, 44.3% for B56, and 75.2% (59%) for B110, compared to 34% for B6). Hundreds grams of therapeutic oligonucleotide agents were produced using provided technologies.

Those skilled in the art appreciate that described technologies (e.g., reagents, concentrations, conditions, solvents, etc.) may be adjusted to achieve improved results (e.g., yield, purify, etc.) For example, in some embodiments, XH may be utilized at a lower concentration than described above (e.g., less than 0.2 M). In some embodiments, XH was utilized at about 0.1 M. In some embodiments, XH was utilized at about 0.1 M in a solution comprising a base, e.g., a pyridine-acetonitrile solution (e.g., 1:1 v/v 0.2 M XH in pyridine and acetonitrile). In some embodiments, a lower concentration provides improved product yield and/or purity (e.g., in term of certain undesired product (e.g., by-product having a phosphate linkage in place of a desired phosphorothioate linkage), 1.5, 2, 3, 4, 5 or more fold of improvement). In some embodiments, a sulfurization reagent composition comprises less than or about 90%, 80%, 70%, 60%, 50%, 40%, 30%, 20%, 10% of a base, e.g., pyridine (v/v).

In some embodiments, a thiolation process is very robust; for example, no additional drying step was necessary if fresh, anhydrous acetonitrile and pyridine were used directly from new bottles. In some embodiments, the contact time was kept at the same length, e.g., 6 minutes. In some embodiments, the total amount of solution may be increased to maintain the equivalents of a reagent, e.g., XH at a lower concentration. In some embodiments, oxidation was performed using iodine in pyridine/water, which is safer and provides increased purity and/or yield. In some embodiments, solid support, e.g., CPG, may be optimized; for example, in some embodiments, CPG with loading of first base at around e.g., 50-90, 60-70, 60-80, 60-90, 70-80, 70-90 umole/g etc., and/or bulk density of e.g., 0.1-0.3, 0.1-0.15, 0.1-0.2, 0.1-0.25, 0.15-0.2, 0.15-0.25, 0.15-0.3, 0.20-0.21, 0.20-0.22, 0.20-0.23, 0.20-0.24, 0.20-0.25, 0.20-0.26, 0.20-0.27, 0.20-0.28, 0.20-0.29, 0.20-0.30, 0.22-0.23, 0.22-0.24, 0.22-0.25, 0.22-0.26, 0.22-0.27, 0.22-0.28, 0.22-0.29, 0.22-0.30, 0.25-0.26, 0.25-0.27, 0.25-0.28, 0.25-0.29, 0.25-0.30, 0.26-0.27, 0.26-0.28, 0.26-0.29, 0.27-0.28, 0.27-0.29, 0.27-0.3, 0.28-0.29, 0.28-0.3, 0.29-0.3 cc/g etc.

Crude oligonucleotides, in some cases, were purified using various chromatography technologies, e.g., those described in U.S. Pat. Nos. 9,598,458, 9,744,183, 9,605,019, 9,394,333, 8,859,755, US 20130178612, U.S. Pat. Nos. 8,470,987, 8,822,671, US 20150211006, US 20170037399, US 20180216107, US 20180216108, US 20190008986, WO 2017/015555, WO 2017/015575, WO 2017/062862, WO 2017/160741, WO 2017/192664, WO 2017/192679, WO 2017/210647, WO 2018/022473, WO 2018/067973, WO 2018/098264, WO 2018/223056, WO 2018/223073, WO 2018/223081, WO 2018/237194, WO 2019/032607, WO 2019/032612, WO 2019/032607, WO 2019/055951, WO 2019/075357, WO 2019/200185, WO 2019/217784, etc.

Example 5. Provided Technologies can Provide Oligonucleotides with High Efficiency Among other things, provided technologies are particularly useful for highly efficient synthesis of oligonucleotides with high yields and/or purity, and optionally with precise control of chemistry and stereochemistry for each oligonucleotide. In some embodiments, the present disclosure provides methods for preparing collections of oligonucleotides in plate formats. Described below is an example procedure for oligonucleotide synthesis in parallel at scales useful for plate formats. In some embodiments, the present disclosure provides technologies for high-throughput preparation of oligonucleotides optionally with independent control of chemical modifications and stereochemistry of each oligonucleotide. Those skilled in the art appreciate that exact conditions, e.g., solvents, concentrations, reaction times, etc., may be further adjusted.

DPSE (for chirally controlled internucleotidic linkages) and cyanoethyl amidites (for stereorandom or phosphate internucleotidic linkages) were prepared at 0.1 M in isobutyronitrile, acetonitrile or combinations thereof. Typically isobutyronitrile was used. In some embodiments, a combination of isobutyronitrile and acetonitrile was utilized. In some embodiments, dichloromethane or tetrahydrofuran, e.g., at about 10%, 15%, 20%, etc., was utilized for certain amidites. 1 umol standard CPG columns were used. Other supports, e.g., Nittophase (e.g., NITTOPHASE® solid support, NITTOPHASE® HL solid support, etc.), Universal support, etc., can also be utilized. In some embodiments, plates of 96 1-umol columns were used for synthesis, wherein each column can be independently and optionally utilized to prepare a designed oligonucleotide with control of its structural elements as desired. In some embodiments, the synthesis was performed as DMT-on if C18 cartridge purification was to be used for purification. Example reagents used were:

Deblocking solution -3% trichloroacetic acid in dichloromethane

Activator 1-0.25M ETT in acetonitrile

Activator 2-0.5M CMIMT in acetonitrile

Cap A—tetrahydrofuran/2,6-lutidine/acetic anhydride (80/10/10)

Oxidation -0.02M iodine in THF/pyridine/$H_2O$ (70/20/10)

Thiolation reagent—0.2M xanthane hydride in pyridine

Cap B -16% n-methylimidazole in THF

A typical cycle was as follows:

Deblock; then Double coupling; then Cap A only; then Oxidation or Thiolation; then Cap A and B (typically 1:1)

All amidites were typically double coupled. Each coupling was 9.5 equivalents of amidite to growing chain. Activator 1 was typically used with cyanoethyl amidites. Activator 2 was typically used with DPSE amidites. The activator 1/cyanoethyl amidite ratio was typically 2.9. The activator 2/DPSE amidite ratio was typically 5.8. Coupling time ranges from approximately 2 to 6 minutes depending on the amidite.

After synthesis of the oligonucleotide chain, the first step of deprotection was typically a diethylamine wash: 400 uL of 20% DEA was added to each column and allowed to drain through over 5 min, then pulled completely through. The wash was repeated twice more for a total of 1200 uL and 15 min. The oligonucleotide/solid support was then washed with 5×200 uL of acetonitrile and dried by pulling vacuum. In some embodiments, a step utilizes reagents and/or conditions that keep 5'-protection groups on; for example, in some embodiments, a second step keeps DMT on. In some embodiments, provided technologies comprise additional bases. Those skilled in the art appreciate that conditions and/or reagents may be adjusted in view of types of support, 2'-modifications, 5'-protection (e.g., DMT) on or off, etc. in accordance with the present disclosure. In some embodiments, the second deprotection step was a treatment with DMF/water/TEA/TEA·3HF followed by ammonium hydroxide: Dimethylformamide/water/triethylamine/triethylamine-trihydrofluoride solution was prepared in the ratio: TEA 0.3HF 0.5 mL; TEA 0.877 mL; DMF 7.77 mL; and Water 1.55 mL. 250 uL of this fluoride solution was added to the solid support, e.g., CPG, and incubated at room temperature for a suitable period of time, e.g., 5 h. Then 375 uL of $NH_4OH$ was added directly and incubated 24 h at 35° C. The samples were filtered using a 96 well plate filter (PTFE 0.45 uM). They were then washed with 4×250 uL of water. The products were then optionally purified through cartridge purification and/or other purification methods. In some embodiments, DMT can be removed during one or more purification processes. Alternatively, 5'-protection groups, e.g., DMT, can be removed before purification (e.g., HPLC, UPLC, etc.).

Example 6. Provided Technologies can Significantly Simplify Operations

Among other things, provided technologies can greatly improve operations particularly for large scale oligonucleotide synthesis. As those skilled in the art appreciate, transferring solid support from containers to containers for different steps can significantly lower efficiency and increase cost. In some embodiments, the present disclosure provides technologies for performing certain processes that are typically performed off-column in traditional oligonucleotide synthesis on-column, thereby improving efficiency and/or reducing cost. In some embodiments, the present disclosure provides technologies for on-column deprotection and/or cleavage. In some embodiments, provided technologies improve scalability. An example was described below.

On-Column Removal of Chiral Auxiliary.

In some embodiments, the present disclosure provides technologies for removing chiral auxiliaries on column. For example, in some embodiments, DPSE auxiliaries were removed on column. In some embodiments, a TEA-HF cocktail was charged into a reaction vessel (100 mL/mmole). The reaction vessel was connected to the column in an up flow orientation. A suitable pump was used to circulate the TEA-HF cocktail for 6+/−0.5 hours at a suitable temperature (in some embodiments, room temperature) to complete the removal of the DPSE chiral auxiliary. There can be some product cleaved from the support during this step at e.g., approximately 80%. Deprotection of the chiral auxiliary was typically complete after 6+/−0.5 hours. The TEA-HF cocktail was flushed from the column with a DMSO:Water (5:1) solution at a suitable amount, e.g., 1 cv, to remove the TEA-HF cocktail from the column, which step can prevent precipitation upon the addition of ammonium hydroxide in the next step. In some embodiments, the reaction and/or vessel were cooled, e.g., to 0° C.

On-Column Cleavage of Product from Support.

In some embodiments, the remaining product is cleaved from the support by treatment with ammonium hydroxide (200 mL/mmole) at room temperature for 30 minutes. The column is flushed with 1 cv of fresh ammonium hydroxide to complete recovery of product from the column. In some embodiments, product solution from the cleavage step were collected in a separate vessel different from the vessel containing the product solution of on-column removal of chiral auxiliaries.

Deprotection.

The ammonium hydroxide product solution was transferred with stirring to the TEA-HF product vessel. Temperature was increased and maintained at 37+/−2° C. for 24 hrs. In some embodiments, maintaining an increased temperature was crucial for complete removal of certain protecting groups, e.g., iBu on the exocyclic ring of a guanosine base. Applicant notes that the temperature cannot be too high. In some embodiments, it was observed that if the reaction temperature was high (e.g., 45° C.), the phosphate contents (instead of the desired phosphorothioate internucleotidic linkage) in the crude sample may increased.

Filtration.

The crude deprotected material was filtered with a 10 uM filter followed by a 0.45 uM filter. In some embodiments, a second filtration protects purification equipment (e.g., pumps, columns etc.) and/or facilitates a purification process.

Example Recipe for Preparation of a 1× Solution of TEA·HF (1 L)

| Solvent/Reagents | Required Volume (mL) | Total Volume of Prep (mL) |
|---|---|---|
| DMSO | 777 ± 39 | 1000 |
| Water | 155 ± 7.8 | |
| Triethylamine (TEA) | 18 ± 0.9 | |

-continued

| Solvent/Reagents | Required Volume (mL) | Total Volume of Prep (mL) |
|---|---|---|
| Triethylamine trihydrofluoride (TEA•3HF) | 50 ± 2.5 | |

Example WV-3473 Cleavage and Deprotection Parameters

| Process Step | Parameter | PD campaign |
|---|---|---|
| Drying Solid Support with Nitrogen | Temperature | R.T. |
| | Nitrogen or Argon Pressure | LT 30 psi |
| | Drying Time | NLT 30 min |
| 1X TEA-HF Treatment (1st C&D) | Reaction Vessel | Appropriate for TEA-HF solution |
| | Reagents | 1.0 X TEA-HF in DMSO/$H_2O$, 5/1, v/v |
| | Volume | 100 ± 5 mL/mmol |
| | Reaction Temp | 27 ± 2.5° C. |
| | Flow rate | 400 cm/hr |
| | Reaction Time | 6 +/− 0.5 hrs |
| | Column Flush | DMSO:Water 5:1 |
| | Column Flush Volume | 1 cv |
| Cleavage from support On-Column | Vessel | Appropriate for TEA-HF/Ammonium Hydroxide solution |
| | Reagent | Conc. $NH_4OH$ (28-30%) |
| | Reagent Volume | 200 ± 5 mL/mmol |
| | Reaction Time | 24 ± 1 hrs |
| | Reaction Temperature | 37 +/− 2° C. |
| | Column Flush | Ammonium hydroxide |
| | Column Flush Volume | 1 cv |
| Removal of Protecting groups | Vessel | Appropriate for TEA-HF/Ammonium Hydroxide solution |
| | Reagent | Conc. $NH_4OH$ (28-30%) |
| | Reagent Volume | 200 ± 5 mL/mmol |
| | Reaction Time | 24 ± 1 hrs |
| | Reaction Temperature | 37 +/− 2° C. |
| Filtration | Course Filtration | 10-40 μm filter |
| | Fine Filtration | 0.45-0.2 μm filter |
| | Support Wash Solution | WFI |

-continued

| Process Step | Parameter | PD campaign |
|---|---|---|
| | Support Wash Volume | 200-350 mL/mmole |

Example 7. Oligonucleotide Products as Solids or Solutions

The present disclosure can provide oligonucleotide products in various forms. In some embodiments, products were provided as solid. In some embodiments, products were provided as solutions, e.g., in water, a salt solution, or a buffer.

In some embodiments, for example, a product, e.g., WV-3473 from Examples above, was lyophilized and packaged in, e.g., HDPE bottles. A drug product for administration may made by reconstituting the lyophilized solid in an appropriate vehicle (e.g., water, a salt solution, a saline, etc.) to a suitable target concentration.

In some embodiments, a product, e.g., WV-3473 from Examples above, were provided as a solution, typically of a high concentration compared to the concentration used for administration to a subject. Various solvent can be utilized in accordance with the present disclosure. For example, in some embodiments, a solvent is water (e.g., injection grade water). In some embodiments, a solvent is a salt solution, e.g., a saline solution which is used in drug formulation, injection, etc. In some embodiments, a solvent is a buffer, e.g., PBS, DPBS, etc. Before administration to a subject, a product can be reconstituted using an appropriate vehicle (e.g., water, a salt solution, a saline, etc.) to a suitable target concentration. In some embodiments, liquid formulations provide certain benefits, for example, in some embodiments, elimination of a lyophilization process and related operations provide high product purity and/or yield. In some embodiments, liquid formulation (liquid drug substance) simplifies drug product vialing steps, improves efficiency, and/or lowers cost.

Described below was a procedure using DPBS as a diafiltration (DF) buffer during the final DF step. As appreciated by those skilled in the art, various other solutions, e.g., salt solutions, buffers (e.g., PBS), etc., may be utilized. The oligonucleotide was WV-3473 which were a test oligonucleotide for various process chemistry technologies.

Certain Equipment, Raw Materials and Process Aids

| Equipment/Material | Description/ Amount | Asset ID/ Lot # | Vendor |
|---|---|---|---|
| Equipment | SARTOFLOW ® Smart TFF System (crossflow filtration system) | 100368-703-TFF-001 | Sartorius |
| Cassette | 2K SARTOCON ® CELL (slice microfiltration set) | 71146123 | Sartorius |
| Sample | WV-3473 Purified Pool | PD_1821020101_Pool | N/A |
| Water for Injection (WFI) | 20 L | 1959059 | Gibco |
| DPBS 1x | 6 L | 1967621 | Gibco |
| 500 mL Corning Storage bottle | 1 | 430282 | Corning |
| 150 mL Corning Storage bottle | 3 | 431175 | Corning |
| pH/Conductivity meter | Mettler-Toledo | 100317-204-PCM-001 | Mettler-Toledo |

DPBS 1× (No Calcium, No Magnesium) Media Formulation

| Components | MW | Conc (mg/L) | mM |
|---|---|---|---|
| Potassium Chloride (KCl) | 75.0 | 200.0 | 2.6666667 |
| Potassium Phosphate monobasic ($KH_2PO_4$) | 136.0 | 200.0 | 1.4705882 |
| Sodium Chloride (NaCl) | 58.0 | 8000.0 | 137.93103 |
| Sodium Phosphate dibasic ($Na_2HPO_4$-$H_2O$) | 268.0 | 2160.0 | 8.059702 |

Example Ultrafiltration (UF)/DF Unit Operations Flow: Initial Concentration (UF) (Target 20 mg/mL), then 1st Diafiltration (DF) (Permeate cond: ≤1 mS/cm), then 2nd Diafiltration (DF) (DPBS, ≥10 DV, pH 7), then Final conc & Rinse (DPBS) (Target ≥36 mg/mL).

Initial concentration of WV-3473 (UF)

2×0.1 $M^2$ 2K SARTOCON® Slice Cellulose membranes were installed on the SARTOFLOW® Smart TFF system and the unit cleaned with 0.5 N NaOH and WFI. The pooled sample from the purification step (13.8 L, 362112 OD) in a 20 L LDPE bottle was then attached to the external peristaltic pump which was connected to the system.

Targeting a concentration of 600 OD/mL, the recirculation feed tank weight was set to 600 g (600 mL) using a WIRC2100 load cell module in the 'auto' mode. The permeate control valve was then fully opened by turning the knob counterclockwise. With a circulation pump setting of 30% and targeting a TMP of 2.5-3.0 bar, the retentate pressure control valve was carefully turned clockwise until PIR2600 recorded a value of 2.5-3.0 bar. With these settings, an initial permeate flowrate of up to 77 g/min was recorded. The initial ultrafiltration was then performed as summarized below:

Initial UF:

| Parameter | Set Point |
|---|---|
| Cassette | 2K SARTOCON ® CELL |
| Sample Amount | 362,112 OD |
| Cassette Area | 2 × $0.1M^2$ |
| Sample Volume | 13,800 mL |
| Target UF Volume | 600 mL |
| Target UF concentration | 600 OD/mL |
| Circulation Pump Setting | 30% |
| TMP | 2.5-3.0 bar |
| Initial Permeate Flux | 77 mL/min |
| Final Permeate Flux | 60 mL/min |
| Retentate pH | 9.75 |
| Initial Permeate Cond | 103.1 mS/cm |

1st Diafiltration (DF) with Water: After the sample was concentrated to 600 mL, 600 OD/mL in the feed tank, the 20 L LDPE bottle was replaced with a 20 L bag of WFI and attached to the external peristaltic pump. Using the same conditions set above, diafiltration (DF) was performed until the permeate conductivity was ≤1000 μS/cm as summarized below:

| Parameter | Set Point |
|---|---|
| Cassette | 2K SARTOCON ® CELL |
| Sample Amount | 362,112 OD |
| Cassette Area | 2 × $0.1M^2$ |
| Feed Tank Volume | 600 mL |
| Feed Tank concentration | 600 OD/mL |
| Circulation Pump Setting | 30% |
| TMP | 2.5-3.0 bar |

-continued

| Parameter | Set Point |
|---|---|
| Permeate Flux | 60-77 mL/min |
| Initial Retentate pH | 9.75 |
| Final Retentate pH | 8.65 |
| Initial Permeate Cond | 103.1 mS/cm |
| Final Permeate Cond | 866 μS/cm |

$2^{nd}$ Diafiltration (DF) with DPBS: Following DF as described above, the WFI bag was replaced with 6 L of DPBS and attached to the external peristaltic pump. Using the same conditions set above, the final diafiltration (DF) was performed using DPBS until 10 DVs had been exchanged. During this step, the pH dropped from 8.65 to 7.03. The final permeate conductivity measured was ≥13 mS/cm. An example set of parameters were summarized below:

| Parameter | Set Point |
|---|---|
| Cassette | 2K SARTOCON ® CELL |
| Sample Amount | 362,112 OD |
| Cassette Area | 2 × $0.1M^2$ |
| Feed Tank Volume | 600 mL |
| Feed Tank concentration | 600 OD/mL |
| Circulation Pump Setting | 30% |
| TMP | 2.5-3.0 bar |
| Permeate Flux | 60-77 mL/min |
| Initial Retentate pH | 8.65 |
| Final Retentate pH | 7.03 |
| Initial Permeate Cond | 866 mS/cm |
| Final Permeate Cond | 13.65 μS/cm |

Final Concentration and Rinse: After the completion of the DPBS DF step, the external peristaltic pump was stopped by setting the WIRC2100 load cell module to the "off" mode. Keeping all the other parameters as described above, the sample was concentrated until the feed tank weight was 100 g (100 mL). The 1 retentate pressure control valve was then fully opened by turning the knob counterclockwise. The 1 permeate control valve was then fully closed by turning the knob clockwise. With a circulation pump setting of 70% the product was then drained into a 500 mL sterile Corning bottle. The feed tank was rinsed with 2×50 mL of DPBS and the rinsates drained into two separate 150 mL sterile Corning bottles. The ODs of the three bottles was then measured to determine the yield and recovery. The bulk product and the two rinses were then combined to obtain a product with a concentration of 1523 OD/mL. Example results were summarized below:

| Parameter | Set Point |
|---|---|
| Cassette | 2K SARTOCON ® CELL |
| Sample Amount | 362,112 OD |
| Cassette Area | 2 × $0.1M^2$ |
| Initial Feed Tank Volume | 600 mL |
| Final Feed Tank Volume | 100 mL |
| Circulation Pump Setting | 70% |
| TMP | 0.0-3.5 bar |
| Bulk Volume | 140 mL |
| Bulk OD | 273,700 |
| Rinse 1 Volume | 50 |
| Rinse 1 OD | 55,050 |
| Rinse 2 Volume | 50 mL |
| Rinse 2 OD | 36,750 |

-continued

| Parameter | Set Point |
|---|---|
| Final Product conc. | 1523 OD/mL |
| Recovery | 365,500 |
| % Recovery | 100.9% |

Example 8. UF/DF of Crude Product

In some embodiments, provided technologies comprise removal of reagents, by-products, salts, etc. before one or more purification steps. In some embodiments, removal of such chemicals help to protect instruments, facilitate operations, improve efficiency and results, and/or lower cost. An example using UF/DF was described below.

Crude WV-3473 was filtered (0.22 uM) and stored at 2° C. In some embodiments, upon storage, precipitation occurs and the solution may turn into a turbid cloudy mixture, e.g., without the intention to be limited by any theory, due to salts, organic solvent, etc. that were in the crude solution. Typically, when a sample of the mixture was diluted with water (e.g., ×5), a clear solution was formed. The cloudy material can also be filtered (0.22 uM) resulting in a clear solution.

In one example procedure, a filtered crude material (600 mL 61,200 OD) was diluted X5 with water into a 5 L media bottle. Using a SARTOFLOW® Smart TFF system with a 0.1 $M^2$ 2K SARTOCON® Slice Cellulose membrane, example sample UF/DF parameters and data were summarized below:

| Parameter | PD Set Point |
|---|---|
| Cassette | 2K SARTOCON ® Slice Cassette Cellulose Membrane |
| Sample Amount | 61,200 OD |
| Cassette Area | 1 × 0.1 $M^2$ |
| Sample Volume | 600 mL |
| Sample Vol after Dilution | 3000 mL |
| Target UF Volume | 200 mL |
| Target UF concentration | 300 OD/mL |
| DF Volume | NLT 7 DVs |
| Circulation Pump Setting | 30% |
| TMP | 3.0 bar |
| Permeate Flux | 45 mL/min |
| Initial Retentate pH | 11.5 |
| Final Retentate pH | 9.4 |
| Initial Retentate Cond | 3.1 mS/cm |
| Final Retentate Cond | 1,037 mS/cm |
| Recovery | 58,000 OD |
| % Recovery | 95% |
| Crude Purity before UF/DF | 60.1% |
| Crude Purity after UF/DF | 62.6% |

Example 9. Example Post-Synthesis Processes

Various technologies can be utilized to purify, formulate, etc., oligonucleotides. Described below are certain example processes useful for post-synthesis processing of oligonucleotides, including purification, UF/DF, lyophilization, etc. In some embodiments, provided technologies comprise anion exchange resin purification. In some embodiments, provided technologies comprise AEX purification. In some embodiments, AEX purification is performed on TSKgel SuperQ 5PW (20 μm) targeting a loading of 20 mg/mL using LEWA purification skid. In some embodiments, anion exchange resin provides improved purification purify and yield. In some embodiments, UF/DF was performed on the SARTOFLOW® Advanced system while lyophilization was performed on the VirTis Lyo system. In some embodiments, an oligonucleotide, e.g., WV-3473, was prepared on CPG solid support at e.g., 1.26 mmol. As an example, in some embodiments, a preparation comprises solid phase synthesis (1.26 mmol), then desilylation (1× solution) (removal of DPSE auxiliary), then cleavage and deprotection (conc. $NH_4OH$), then purification (TSKgel SuperQ 5PW), then UF/DF (SARTOCON® 2K), then lyophilization (which can be optionally replaced with UF/DF if product oligonucleotides are to be provided as high concentration solutions, e.g., as described in Examples above).

Certain abbreviations:

| | |
|---|---|
| ACN | Acetonitrile |
| AEX | Anion Exchange Chromatography |
| C&D | Cleavage and Deprotection |
| cGMP | Current Good Manufacturing Practices |
| DNA | Deoxyribonucleic acid |
| DPSE | (S)-2-(methyldiphenylsilyl)-1-((S)-Pyrrolidin-2-yl)-ethan-1-ol |
| HDPE | High density polyethylene |
| LC/MS | Liquid chromatography/mass spectroscopy |
| MP | Mock Pool |
| MWCO | Molecular weight cut off |
| NA | Not applicable |
| NLT | Not less than |
| NMT | Not more than |
| OD | Optical Density |
| OP 400 | Oligo Pilot 400 Synthesizer |
| TFF | Tangential flow filtration |
| UF/DF | Ultrafiltration/Diafiltration |
| UPLC | Ultra-High Pressure Liquid Chromatography |
| UV | Ultra-violet |

Example Chromatography.

Example TSKgel SuperQ 5PW (20 μm) Column Packing Conditions

- Compression Factor: 1.20
- Target ≥10 Bar (150 psi) to pack the column
- De-fine 2-3 times prior to packing
- Slurry concentration prior to packing: 65-70%
- Packing buffer: 20% Ethanol
- Leave column under pressure (DAC mode) overnight for the bed to settle
- At 20 mg/mL loading, precipitation is observed in neutralized fractions upon storage at 2 to 8° C.

Example Column Efficiency Testing

| Process Step | Parameter | PD Set Point | MFG Set Point |
|---|---|---|---|
| Equilibration | Flow Rate | 60 cm/hr | 60 cm/hr |
| | Temperature | Ambient | Ambient |
| | Equilibration Solution | 0.4M NaCl/Water | 0.4M NaCl/Water or 0.4M NaCl/15% EtOH |

-continued

| Process Step | Parameter | PD Set Point | MFG Set Point |
|---|---|---|---|
| | Equilibration Volume | NLT 3 CV | NLT 3 CV |
| Injection | Injection Solution | 0.8M NaCl/Water | 0.8M NaCl/Water or 0.8M NaCl/15% EtOH/7% Acetone |
| | Injection Volume | 1-3% CV | 1-3% CV |
| Elution | Elution Solution | 0.4M NaCl/Water | 0.4M NaCl/Water or 0.4M NaCl/15% EtOH |
| | Elution Volume | NLT 1.5 CV | NLT 1.5 CV |
| Rinse | Rinse Volume | Water | Water |
| | Rinse Solution | NLT 2 CV | NLT 2 CV |
| Storage | Storage Solution | 20% EtOH/Water | 20% EtOH/Water |
| | Storage Volume | NLT 2 CV | NLT 2 CV |
| Acceptance Criteria | Asymmetry | 0.8-3.5 | 0.8-3.5 |

Example Chromatography Process Parameters

| Process Step | Parameter | | PD Set Point | |
|---|---|---|---|---|
| Crude Preparation | Temperature | | Ambient | Ambient |
| | Filtration | | 0.2-1.2 μm Filter unit | 0.2-1.2 μm Filter unit |
| | Crude Dilution with WFI | | Dilute to Cond ≤ 12 $mScm^{-1}$ if required | Dilute to Cond ≤ 12 $mScm^{-1}$ if required |
| Chromatography Column | Scale | | 0.4-1 mmol | 10 mmol |
| | Media | | TSKgel SuperQ 5PW | TSKgel SuperQ 5PW |
| | Diameter | | 2.5 cm | 10 cm |
| | Bed Height | | 30 ± 2 cm | 30 ± 2 cm |
| | CV | | Target 147.3 mL | Target 2.4 L |
| | Loading Range (mg/mL) | | 10 to 20 mg/mL | 10 to 20 mg/mL |
| | Loading Range (OD/mL) | | 300 to 600 OD/mL | 300 to 600 OD/mL |
| | Column Temperature | | Ambient | Ambient |
| | Mobile Phase | Eluent A | 20 mM NaOH | 20 mM NaOH |
| | | Eluent B | 20 mM NaOH + 2.5M NaCl | 20 mM NaOH + 2.5M NaCl |
| | | Eluent B Target Cond | 168 ± 5 mScm − 1 | 168 ± 5 mScm − 1 |
| | | CIP A Solution | 20 mM NaOH | 20 mM NaOH |
| | | CIP B Solution | 20 mM NaOH, 2.5M NaCl with 7% ACN | 20 mM NaOH, 2.5M NaCl with 7% ACN |
| | | SIP Solution | 0.5M NaOH | 0.5M NaOH |
| Column CIP/Sanitization | | Rinse Solution | WFI | WFI |
| | High pH Wash I (column wash) | Composition | 100% SIP Solution | 100% SIP Solution |
| | | Volume | 1 CV | 1 CV |
| | | Flow Rate | 200 cm/hr | 200 cm/hr |
| | Eluent B Equilibration (column wash) | Composition | 100% CIP B Solution | 100% CIP B Solution |
| | | Volume | 2 CV | 2 CV |
| | | Flow Rate | 200 cm/hr | 200 cm/hr |
| | Eluent A Equilibration (column wash) | Composition | 100% Eluent A | 100% Eluent A |
| | | Volume | 1 CV | 1 CV |
| | | Flow Rate | 200 cm/r | 200 cm/r |
| | A/B Gradient CIP | Flow rate | 200 cm/hr | 200 cm/hr |
| | | Composition | 100% A --> 0% A; 0% B --> 100% B | 100% A --> 0% A; 0% B --> 100% B |
| | | Volume (CV) | 0.5 | 0.5 |
| | | Composition | 0% A; 100% B (Isocratic hold) | 0% A; 100% B (Isocratic hold) |
| | | Volume (CV) | 0.4 | 0.4 |
| | | Composition | 0% A --> 100% A; 100% B --> 0% B | 0% A --> 100% A; 100% B --> 0% B |
| | | Volume (CV) | 0.1 | 0.1 |
| | | Composition | 100% A; 0% B (Isocratic hold) | 100% A: 0% B (Isocratic hold) |
| | | Volume (CV) | 0.5 | 0.5 |

-continued

| Process Step | Parameter | | PD Set Point | |
|---|---|---|---|---|
| | | Composition | 100% A --> 0% A; 0% B --> 100% B | 100% A --> 0% A; 0% B --> 100% B |
| | | Volume (CV) | 0.5 | 0.5 |
| | | Composition | 0% A; 100% B (Isocratic hold) | 0% A; 100% B (Isocratic hold) |
| | | Volume (CV) | 0.4 | 0.4 |
| | | Composition | 0% A --> 100% A; 100% B --> 0% B | 0% A --> 100% A; 100% B --> 0% B |
| | | Volume (CV) | 0.1 | 0.1 |
| | | Composition | 100% A; 0% B (Isocratic hold) | 100% A: 0% B (Isocratic hold) |
| | | Volume (CV) | 0.5 | 0.5 |
| | | Composition | 100% A --> 0% A; 0% B --> 100% B | 100% A --> 0% A; 0% B --> 100% B |
| | | Volume (CV) | 0.5 | 0.5 |
| Column CIP/Sanitization | | Composition | 0% A; 100% B (Isocratic hold) | 0% A; 100% B (Isocratic hold) |
| | | Volume (CV) | 0.4 | 0.4 |
| | | Composition | 0% A --> 100% A; 100% B --> 0% B | 0% A --> 100% A; 100% B --> 0% B |
| | | Volume (CV) | 0.1 | 0.1 |
| | | Composition | 100% A: 0% B (Isocratic hold) | 100% A; 0% B (Isocratic hold) |
| | | Volume (CV) | 0.5 | 0.5 |
| | | Composition | 100% A --> 0% A; 0% B --> 100% B | 100% A --> 0% A; 0% B --> 100% B |
| | | Volume (CV) | 0.5 | 0.5 |
| | | Composition | 0% A; 100% B (Isocratic hold) | 0% A; 100% B (Isocratic hold) |
| | | Volume (CV) | 0.4 | 0.4 |
| | High pH Wash (Column Sanitization) | Composition | 100% SIP Solution | 100% SIP Solution |
| | | Volume | 0.6 CV | 0.6 CV |
| | | Flow Rate | 115 cm/hr | 115 cm/hr |
| | High pH Wash (Column Sanitization) | Composition | 100% SIP Solution | 100% SIP Solution |
| | | Volume | 0.4 CV | 0.4 CV |
| | | Flow Rate | 200 cm/hr | 200 cm/hr |
| | High pH Wash (Column Sanitization) | Composition | 100% SIP Solution | 100% SIP Solution |
| | | Volume | 0.5 CV | 0.5 CV |
| | | Flow Rate | 2.00 cm/hr | 200 cm/hr |
| | High pH Hold | Hold time | NLT 60 min | NLT 60 min |
| | Water Wash (Column Sanitization) | Composition | 100% Water | 100% Water |
| | | Volume | NLT 4.5 CV or until pH ≤ 9 | NLT 4.5 CV or until pH ≤ 9 |
| | | Flow Rate | 200 cm/hr | 200 cm/hr |
| | Water Sampling (Column Sanitization) | Composition | 100% Water | 100% Water |
| | | Volume | 1.3 CV | 1.3 CV |
| | | Flow Rate | NLT 40 cm/hr | NLT 40 cm/hr |
| | QC Testing | Endotoxin | <0.25 EU/mL | <0.25 EU/mL |
| | | UV | <0.05 AU | <0.05 AU |
| Pre-Load/ Equilibration | A Wash 1 | Composition | 200 cm/hr | 200 cm/hr |
| | | Volume | NLT 2 CV | NLT 2 CV |
| | | Flow rate | 200 cm/hr | 200 cm/hr |
| | B Wash | Composition | N/A | N/A |
| | | Volume | N/A | N/A |
| | | Flow Rate | N/A | N/A |
| | A Wash 2 | Composition | N/A | N/A |
| | | Volume | N/A | N/A |
| | | Flow Rate | N/A | N/A |
| Loading/Post-Load Washes | Sample Loading | Composition | N/A | N/A |
| | | Temperature | Ambient | Ambient |
| | | Flow Rate | 200 cm/hr | 200 cm/hr |
| | Post Loading Wash/Re-equilibration | Composition | 100% Eluent A | 100% Eluent A |
| | | Volume | NLT 2 CV | NLT 2 CV |
| | | Flow Rate | 200 cm/hr | 200 cm/hr |
| Gradient Elution | Mixing loop Equilibration through bypass | | N/A | N/A |
| | Isocratic Step | | N/A | N/A |
| | Isocratic Step Volume | | N/A | N/A |
| | Gradient Start Point | | 0% B | 0% B |
| | Conductivity Start | | TBA | TBA |
| | Gradient 1 End Point | | 25% B | 25% B |
| | Conductivity End | | TBA | TBA |
| | Gradient 1 Duration | | 5 CV (0-25%) | 5 CV (0-25%) |
| | Isocratic Hold | | 25% B | 25% B |
| | Isocratic Hold Volume | | 1 CV | 1 CV |
| | Gradient 2 Start Point | | 25% | 25% |

-continued

| Process Step | Parameter | | PD Set Point | |
|---|---|---|---|---|
| | Conductivity Start | | TBA | TBA |
| | Gradient 2 End Point | | 90% B | 90% B |
| | Conductivity End | | TBA | TBA |
| | Gradient 2 Duration | | 15 CV (25-90%) | 15 CV (25-90%) |
| | Flow Rate | | 200 cm/hr | 200 cm/hr |
| | Fractionation UV watch 280 nm | | >1000 mAU | >1000 mAU |
| | Fraction Size | | Target 20% CV | Target 20% CV |
| | Fraction Volume | | 30 mL | 500 mL |
| | Fraction Neutralization & Storage | Reagent | 2M sodium phosphate monobasic buffer | 2M sodium phosphate monobasic buffer |
| | | Volume | NET 10 μL per 1 mL of Fraction | NLT 10 μL per 1 mL of Fraction |
| | | Target pH | 7.0-8.0 | 7.0-8.0 |
| | | Estimated Frac Concentration | N/A | |
| | | Estimated # of Fracs | N/A | |
| | | Frac Storage Conditions | 2-8° C. | 2-8° C. |
| Post-Elution Wash & Column Equilibration | Wash B Composition | | 100% Solution B | 100% Solution B |
| | Wash B Volume | | NLT 3 CV | NLT 3 CV |
| | Flow Rate | | 200 cm/hr | 200 cm/hr |
| | Wash A Composition | | 100% Solution A | 100% Solution A |
| | Wash A Volume | | NLT 3 CV | NLT 3 CV |
| Expected Recovery | FTP Recovery | | ≥80% | ≥80% |
| Expected Pool Purity | % FLP | | ≥85% | ≥85% |

Ultrafiltration (UF)/Diafiltration (DF)

UF/DF Process Parameters. In some embodiments, membranes can be re-used if they pass reuse tests.

| Process Step | Parameter | PD Set Point | MFC Set Point |
|---|---|---|---|
| Setup | Cassette | SARTOCON ® Slice Cassette Cellulose Membrane | SARTOCON ® Slice Cassette Cellulose Membrane |
| | Scale | 0.5-2.0 mmol | 10 mmol |
| | Cassette Area | 2 × 0.1 $M^2$ | 1 × 0.6 $M^2$ |
| | CIP Solution | 100% HPW or WFI | 100% HPW or WFI |
| | CIP Circulation Pump Setting | 30-70% | 30-70% |
| | CIP Solution | 100% WFI | 100% WFI |
| | CIP Volume | NET 2 L | NLT 4 |
| | SIP Solution | 0.5N NaOH | 0.5N NaOH |
| | SIP Circulation Pump Setting | 30-70% | 30-70% |
| | SIP Solution | 0.5N NaOH | 0.5N NaOH |
| | SIP Volume | NLT 2 L | NET 4 L |
| | SIP Hold Time | NET 60 min | NET 60 min |
| | Membrane Rinse Solution | 100% HPW or WFI | 100% HPW or WFI |
| | Membrane Rinse End Point | Permeate Cond. ≤ 1.0 mS/cm | Permeate Cond. ≤ 1.0 mS/cm |
| | Membrane Rinse End Point | Permeate pH 5-7 | Permeate pH 5-7 |
| Acceptance Criteria | Endotoxin | <0.25 EU/mL | <0.25 EU/mL |
| | UV | ≤0.050 AU | ≤0.050 AU |
| Membrane Conditioning | Membrane Conditioning Solution | 25 mM HCl | 25 mM HCl |
| | Membrane Conditioning End Point | Permeate pH 2-4 | Permeate pH 2-4 |
| Membrane Wash | Membrane Wash Solution | 100% HPW or WFI | 100% HPW or WFI |
| | Membrane Wash Volume | NLT 2 L | NLT 10 L |
| Pool Neutralization | Reagent | 0.1M HCl and 0.1N NaOH | 0.1M HCl and 0.1N NaOH |
| | pH | 6.7-7.3 | 6.7-7.3 |
| Initial Concentration | Target Concentration | NMT 600 OD/mL | NMT 600 OD/mL |
| | Target Volume | 200-100 mL | Calculate in MBR |
| | Circulation Pump Setting | 30-70% | 30-70% |

-continued

| Process Step | Parameter | PD Set Point | MFC Set Point |
|---|---|---|---|
| | Target TMP | Target 1.5-3.5 bar | Target 1.5-3.5 bar |
| Salt Exchange | Diafiltration Solution | | |
| | Number of Exchanges | | |
| | Permeate Conductivity Post-Diafiltration | | |
| Diafiltration | Diafiltration Solution | WFI | WFI |
| | Number of Exchanges | NLT 7 | NLT 7 |
| | Target TMP | 1.5-3.5 bar | 1.5-3.5 bar |
| | Circulation Pump Setting | 30-70% | 30-70% |
| | Target TMP | 1.5-3.5 bar | 1.5-3.5 bar |
| | Conductivity before final pH verification | NMT 1000 $\mu Scm^{-1}$ | NMT 1000 μScm − 1 |
| | Final pH Verification (Retentate) | 0.1M HCl if needed. 0.1N NaOH only if pH ≤ 6.7 | 0.1M HCl if needed. 0.1N NaOH only if pH ≤ 6.7 |
| | Post-Diafiltration Permeate Conductivity | NMT 50 μS/cm | NMT 50 μS/cm |
| Final Concentration | Target Concentration | NLT 1500 OD/mL unless limited by system capacity | NLT 1500 OD/mL unless limited by system capacity (contact managment) |
| | Target Volume | Calculate based on Yield | Calculate in MBR |
| | Final retentate pH | 6.7-7.3 | 6.7-7.3 |
| | Circulation Pump Setting | 30-70% | 30-70% |
| | Target TMP | 1.5-3.5 bar | 1.5-3.5 bar |
| Retentate Recovery | Water for Rinse | 25-30 mL | 250-500 mL |
| | Target Water Rinses 3-6 | Recirculate for 5 min each | Recirculate for 5 min each |
| Cassette Storage | Storage Wash | Purified water to NMT 0.050 OD/mL | Purified water to NMT 0.050 OD/mL |
| | Storage Wash | 0.1N NaOH | 0.1N NaOH |
| Storage Conditions | Storage Temperature | 2-8° C. | 2-8° C. |
| Expected Recovery | OD Recovery | >95% | >95% |

Freeze Drying

Example Freeze Drying Parameters

| | Operation | | PD Set Point Temp. (° C.) | Pressure (mTorr) | Time (min) |
|---|---|---|---|---|---|
| 1 | Loading | Loading shelf temp. | R.T. | atm | |
| 2 | Freezing | Shelf temp. | −40 | | 120 |
| 3 | Evacuation | Shelf temp. | −40 | 400 | 30 |
| 4 | Primary Drying | Shelf temp. | −10 | 300 | 480 |
| 5 | Primary Drying | Shelf temp. | −5 | 300 | 480 |
| 6 | Primary Drying | Shelf temp. | 0 | 300 | 480 |
| 7 | Primary Drying | Shelf temp. | 10 | 300 | 480 |
| 8 | Primary Drying | Shelf temp. | 20 | 300 | 480 |
| 9 | Primary Drying | Shelf temp. | 25 | 300 | 480 |
| 10 | Secondary Drying | Shelf temp. | 25 | 100 | 480 |
| 11 | Aeration | Gas type Dry $N_2$ | 25 | atm | — |
| 12 | Unloading | Shelf temp. | R.T. | atm | — |

Example 10. Preparation of Certain Compounds Useful for Stereoselective Synthesis Among other things, the present disclosure provides compounds, e.g., of formula I, I-a, I-a-1, I-a-2, I-b, I-c, I-d, I-e, II, II-a, II-b, III, III-a, or III-b, or a salt thereof, useful for stereoselective synthesis, e.g., to provide chiral auxiliaries for phosphoramidite and/or oligonucleotide synthesis. In some embodiments, the present disclosure provides technologies (e.g., chiral auxiliaries, phosphoramiidites, cycles, conditions, reagents, etc.) that are useful for preparing chirally controlled internucleotidic linkages. In some embodiments, provided technologies are particularly useful for preparing certain internucleotidic linkages, e.g., non-negatively charged internucleotidic linkages, neutral internucleotidic linkages, etc., comprising P—N=, wherein P is the linkage. In some embodiments, the linkage phosphorus is trivalent. In some embodiments, the linkage phosphorus is pentavalent. In some embodiments, such internucleotidic linkages have the structure of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof. Certain example technologies (chiral auxiliaries and their preparations, phosphoramidites and their preparations, cycles, conditions, reagents, etc.) are described in the Examples herein. Among other things, such chiral auxiliaries provide milder reaction conditions, higher functional group compatibility, alternative deprotection and/or cleavage conditions, higher crude and/or purified yields, higher crude purity, higher product purity, and/or higher (or substantially the same or comparable) stereoselectivity when compared to a reference chiral auxiliary (e.g., of formula O, P, Q, R or DPSE).

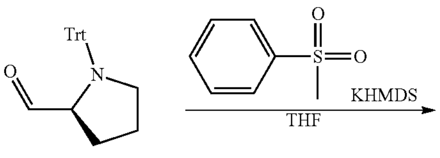

1

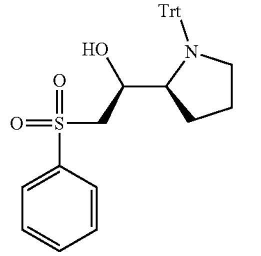

2

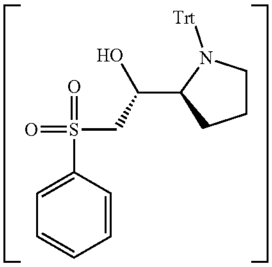

3

Two batches in parallel: To a solution of methylsulfonylbenzene (102.93 g, 658.96 mmol, 1.5 eq.) in THF (600 mL) was added KHMDS (1 M, 658.96 mL, 1.5 eq.) dropwise at −70° C., and warmed to -30° C. slowly over 30 min. The mixture was then cooled to −70° C. A solution of compound 1 (150 g, 439.31 mmol, 1 eq.) in THF (400 mL) was added dropwise at −70° C. The mixture was stirred at −70° C. for 3 hr. TLC (Petroleum ether:Ethyl acetate=3:1, Rf=0.1) indicated compound 1 was consumed completely and one major new spot with larger polarity was detected. Combined 2 batches. The reaction mixture was quenched by added to the sat. $NH_4Cl$ (aq. 1000 mL), and then extracted with EtOAc (1000 mL×3). The combined organic layers were dried over $Na_2SO_4$, filtered, and concentrated under reduced pressure to give 1000 mL solution. Then added the MeOH (600 mL), concentrated under reduced pressure to give 1000 mL solution, then filtered the residue and washed with MeOH (150 mL); the residue was dissolved with THF (1000 mL) and MeOH (600 mL), then concentrated under reduced pressure to give 1000 mL solution. Then filtered to give a residue and washed with MeOH (150 mL). And repeat one more time. Compound 2 (248 g, crude) was obtained as a white solid. And the combined mother solution was concentrated under reduced pressure to give compound 3 (200 g, crude) as yellow oil.

Compound 2: $^1H$ NMR (400 MHz, CHLOROFORM-d) δ=7.80 (d, J=7.5 Hz, 2H), 7.74-7.66 (m, 1H), 7.61-7.53 (m, 2H), 7.47 (d, J=7.5 Hz, 6H), 7.24-7.12 (m, 9H), 4.50-4.33 (m, 1H), 3.33 (s, 1H), 3.26 (ddd, J=2.9, 5.2, 8.2 Hz, 1H), 3.23-3.10 (m, 2H), 3.05-2.91 (m, 2H), 1.59-1.48 (m, 1H), 1.38-1.23 (m, 1H), 1.19-1.01 (m, 1H), 0.31-0.12 (m, 1H).

Preparation of Compound WV-CA-108.

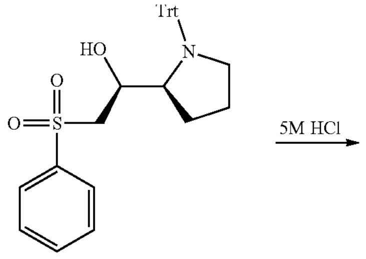

2

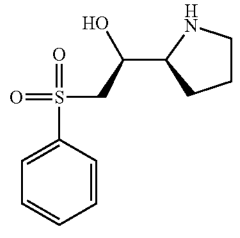

WV-CA-108

To a solution of compound 2 (248 g, 498.35 mmol, 1 eq.) in THF (1 L) was added HCl (5 M, 996.69 mL, 10 eq.). The mixture was stirred at 15° C. for 1 hr. TLC (Petroleum ether:Ethyl acetate=3:1, Rf=0.03) indicated compound 2 was consumed completely and one major new spot with larger polarity was detected. The resulting mixture was washed with MTBE (500 mL×3). The combined organic layers were back-extracted with water (100 mL). The combined aqueous layer was adjusted to pH 12 with 5M NaOH aq. and extracted with DCM (500 mL×3). The combined organic layers were dried over anhydrous $Na_2SO_4$, filtered and concentrated to afford a white solid. WV-CA-108 (122.6 g, crude) was obtained as a white solid.

$^1H$ NMR (400 MHz, CHLOROFORM-d) δ=7.95 (d, J=7.5 Hz, 2H), 7.66 (t, J=7.5 Hz, 1H), 7.57 (t, J=7.7 Hz, 2H), 4.03 (ddd, J=2.6, 5.3, 8.3 Hz, 1H), 3.37-3.23 (m, 2H), 3.20-3.14 (m, 1H), 2.91-2.75 (m, 3H), 2.69 (br s, 1H), 1.79-1.54 (m, 5H); $^{13}C$ NMR (101 MHz, CHLOROFORM-d) δ=139.58, 133.83, 129.28, 127.98, 67.90, 61.71, 59.99, 46.88, 25.98, 25.84; LCMS $[M+H]^+$: 256.1. LCMS purity: 100%. SFC 100% purity.

Among other things, the present disclosure encompasses the recognition that bases utilized in reactions (e.g., from compound 1 to compound 2) can impact stereoselectivity of such reactions. Certain example results are described below:

| S. No | Aldehyde | Nucleophile | Base | Chiral Auxiliary (Diastereo-selectivity, cis/trans) |
|---|---|---|---|---|
| 1 | 1 | 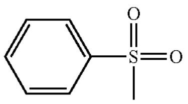 | n-BuLi | WV-CA-108 (87:13) |
| 2 | 1 | 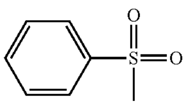 | LiHMDS | WV-CA-108 (1.85:1) |

-continued

| S. No | Aldehyde | Nucleophile | Base | Chiral Auxiliary (Diastereo-selectivity, cis/trans) |
|---|---|---|---|---|
| 3 | 1 | 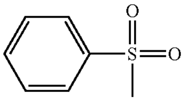 | LDA | WV-CA-108 (1.85:1) |
| 4 | 1 | 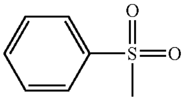 | KHMDS | WV-CA-108 (10:1) |
| 5 | 1 | 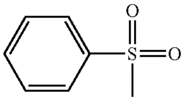 | t-BuOK | WV-CA-108 (10:1) |
| 6 | 4 | 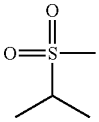 | n-BuLi | WV-CA-242 (2:1) |
| 7 | 4 | 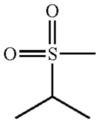 | KHMDS | WV-CA-242 (8:1) |
| 8 | 4 | 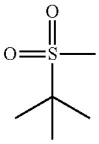 | n-BuLi | WV-CA-243 (2:1) |
| 9 | 4 | 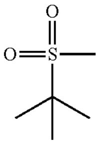 | KHMDS | WV-CA-243 (8:1) |
| 10 | 4 | 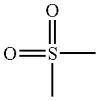 | n-BuLi | WV-CA-347 (5.5:1) |
| 11 | 4 | 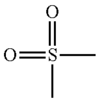 | KHMDS | WV-CA-347 (10:1) |
| 12 | 4 | 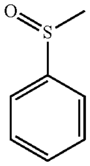 | KHMDS | WV-CA-247 (43:57) |
| 13 | 4 | 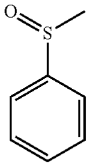 | n-BuLi | WV-CA-247 (~1:1) |

-continued

| S. No | Aldehyde | Nucleophile | Base | Chiral Auxiliary (Diastereo-selectivity, cis/trans) |
|---|---|---|---|---|
| 14 | 4 | 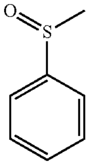 | LiHMDS | WV-CA-247 (~39:51) |
| 15 | 4 | 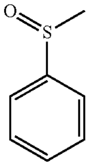 | NaHMDS | WV-CA-247 (~40:66) |

Preparation of Compound WV-CA-237.

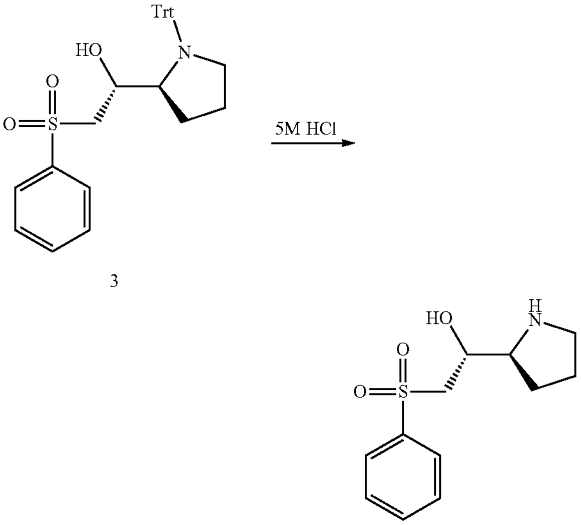

WV-CA-237

To a solution of compound 3 (400.00 g, 803.78 mmol) in THE (1.5 L) was added HCl (5 M, 1.61 L). The mixture was stirred at 15° C. for 2 hr. TLC indicated compound 3 was consumed completely and one major new spot with larger polarity was detected. The resulting mixture was washed with MTBE (500 mL×3). The combined aqueous layer was adjusted to pH 12 with 5M NaOH aq. and extracted with DCM (500 mL×1) and EtOAc (1000 mL×2). The combined organic layers were dried over anhydrous $Na_2SO_4$, filtered, and concentrated to afford as a brown solid. WV-CA-237 (100 g, crude) was obtained as a brown solid.

The residue was purified by column chromatography ($SiO_2$, Petroleum ether/Ethyl acetate=3/1 to Ethyl acetate: Methanol=1:2) to give 24 g crude. Then the 4 g residue was purified by prep-HPLC (column: Phenomenex luna C18 250×50 mm×10 um; mobile phase: [water (0.05% HCl)—ACN]; B %: 2%→20%, 15 min) to give desired compound (2.68 g, yield 65%,) as a white solid. WV-CA-237 (2.68 g) was obtained as a white solid. WV-CA-237: $^1H$ NMR (400 MHz, CHLOROFORM-d) δ=7.98-7.88 (m, 2H), 7.68-7.61

(m, 1H), 7.60-7.51 (m, 2H), 4.04 (dt, J=2.4, 5.6 Hz, 1H), 3.85 (ddd, J=3.1, 5.6, 8.4 Hz, 1H), 3.37-3.09 (m, 3H), 2.95-2.77 (m, 3H), 1.89-1.53 (m, 4H), 1.53-1.39 (m, 1H); $^{13}C$ NMR (101 MHz, CHLOROFORM-d) δ=139.89, 133.81, 133.70, 129.26, 129.16, 128.05, 127.96, 68.20, 61.77, 61.61, 61.01, 60.05, 46.67, 28.02, 26.24, 25.93; LCMS $[M+H]^+$:256.1. LCMS purity: 80.0%. SFC dr=77.3:22.7.

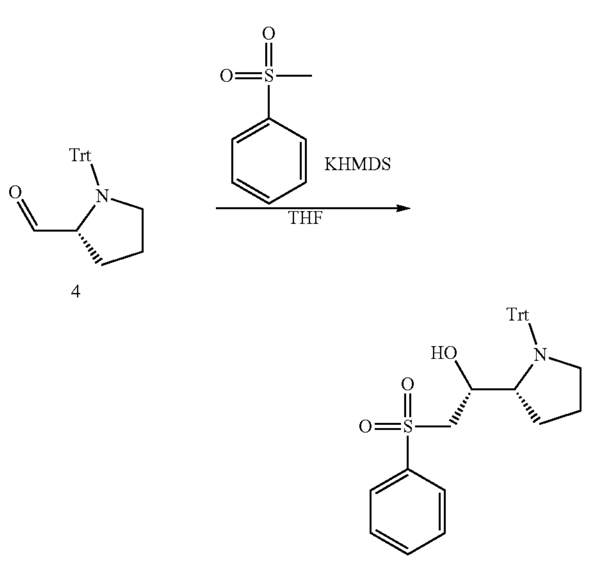

4

5

To a solution of compound 4 (140 g, 410.02 mmol) in THF (1400 mL) was added methylsulfonylbenzene (96.07 g, 615.03 mmol), then added KHMDS (1 M, 615.03 mL) in 0.5 hr. The mixture was stirred at −70~−40° C. for 3 hr. TLC indicated compound 4 was consumed and one new spot formed. The reaction mixture was quenched by addition sat. $NH_4Cl$ aq. 3000 mL at 0° C. and then diluted with EtOAc (3000 mL) and extracted with EtOAc (2000 mL×3). Dried over $Na_2SO_4$, filtered, and concentrated under reduced pressure to give a residue. To the crude was added THF (1000 mL) and MeOH (1500 mL), concentrated under reduced pressure at 45° C. until about 1000 mL residue remained, filtered the solid. Repeat 3 times. Compound 5 (590 g, 72.29% yield) was obtained as a yellow solid. $^1H$ NMR (400 MHz, CHLOROFORM-d) δ=7.81 (d, J=7.5 Hz, 2H), 7.75-7.65 (m, 1H), 7.62-7.53 (m, 2H), 7.48 (br d, J=7.2 Hz, 6H), 7.25-7.11 (m, 9H), 4.50-4.37 (m, 1H), 3.31-3.11 (m, 3H), 3.04-2.87 (m, 2H), 1.60-1.48 (m, 1H), 1.39-1.24 (m, 1H), 1.11 (dtd, J=4.5, 8.8, 12.8 Hz, 1H), 0.32-0.12 (m, 1H).

Preparation of Compound WV-CA-236.

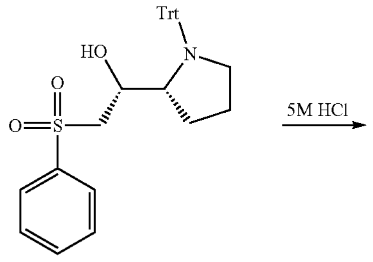

5

-continued

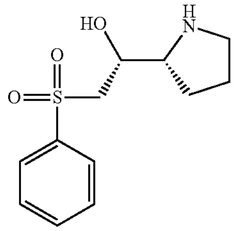

WV-CA-236

To a solution of compound 5 (283 g, 568.68 mmol) in THF (1100 mL) was added HCl (5 M, 1.14 L). The mixture was stirred at 25° C. for 2 hr. TLC indicated compound 5 was consumed and two new spots formed. The reaction mixture was washed with MTBE (1000 mL×3), then the aqueous phase was basified by addition NaOH (5M) until pH=12 at 0° C., and then extracted with DCM (1000 mL×3) to give a residue, dried over $Na_2SO_4$, filtered, and concentrated under reduced pressure to give a residue. Compound WV-CA-236 (280 g, 1.10 mol, 96.42% yield) was obtained as a yellow solid.

The crude product was added HCl/EtOAc (1400 mL, 4M) at 0° C., 2 hr later, filtered the white solid and washed the solid with MeOH (1000 mL×3). LCMS showed the solid contained another peak (MS=297). Then the white solid was added $H_2O$ (600 mL) and washed with DCM (300 mL×3). The aqueous phase was added NaOH (5 M) until pH=12. Then diluted with DCM (800 mL) and extracted with DCM (800 mL×4). The combined organic layer was dried over $Na_2SO_4$, filtered, and concentrated under reduced pressure to give the product. Compound WV-CA-236 (280 g) was obtained as a yellow solid. $^1H$ NMR (400 MHz, CHLOROFORM-d) δ=8.01-7.89 (m, 2H), 7.69-7.62 (m, 1H), 7.61-7.51 (m, 2H), 4.05 (ddd, J=2.8, 5.2, 8.4 Hz, 1H), 3.38-3.22 (m, 2H), 3.21-3.08 (m, 1H), 2.95-2.72 (m, 4H), 1.85-1.51 (m, 4H); $^{13}C$ NMR (101 MHz, CHLOROFORM-d) δ=139.75, 133.76, 129.25, 127.94, 67.57, 61.90, 60.16, 46.86, 25.86. LCMS $[M+H]^+$: 256. LCMS purity: 95.94. SFC purity: 99.86%.

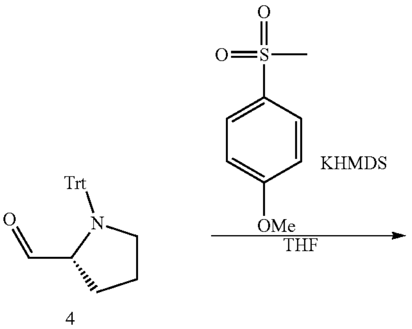

4

-continued

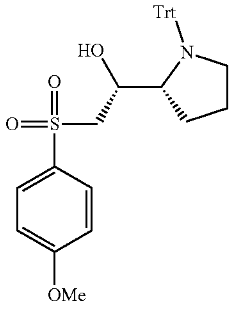

6

To a solution of 1-methoxy-4-methylsulfonyl-benzene (36.82 g, 197.69 mmol) in THF (500 mL) was added KHMDS (1 M, 197.69 mL) at −70° C., 0.5 hr later added compound 4 (45 g, 131.79 mmol) in THF (400 mL) at −70° C. The mixture was stirred at −70→−30° C. for 4 hr, and then the mixture was added with KHMDS (1M, 131.79 mL) at −70° C. The mixture was stirred at −70° C. for 1 hr. TLC indicated compound 4 was remained, and two new spots were detected. The reaction mixture was quenched by sat. $NH_4Cl$ (aq. 300 mL), and then extracted with EtOAc (500 mL×3). The combined organic layers were dried over $Na_2SO_4$, filtered, and concentrated under reduced pressure to give a residue. The residue was dissolved in THF (800 mL) and MeOH (500 mL), and then concentrated under reduced pressure until 200 mL solvent left. The mixture was added with MeOH (500 mL) and concentrated under reduced pressure to 200 mL solvent left and solid appeared. The solid was filtered to give product. Repeated the trituration 2 times. Compound 6 (49.8 g, 71.61% yield) was obtained as a brown solid. $^1$H NMR (400 MHz, CHLOROFORM-d) δ=7.73-7.66 (m, 2H), 7.46 (d, J=7.5 Hz, 6H), 7.24-7.11 (m, 9H), 7.04-6.96 (m, 2H), 4.37 (td, J=3.1, 8.3 Hz, 1H), 3.94-3.88 (m, 3H), 3.36 (s, 1H), 3.26-3.10 (m, 3H), 3.00-2.89 (m, 2H), 1.58-1.45 (m, 1H), 1.37-1.23 (m, 1H), 1.15-1.00 (m, 1H), 0.26-0.10 (m, 1H).

Preparation of Compound WV-CA-241.

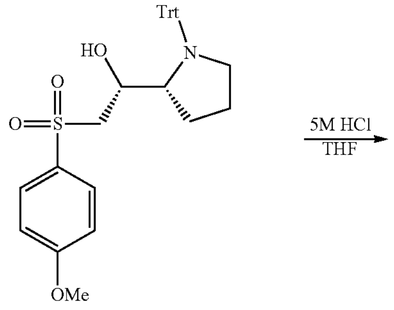

6

-continued

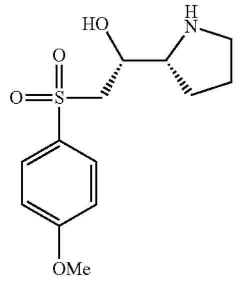

WV-CA-241

To a solution of compound 6 (50 g, 94.76 mmol) in THF (250 mL) was added HCl (5 M, 189.51 mL). The mixture was stirred at 20° C. for 3 hr. TLC indicated compound 6 was consumed and two new spots formed. The reaction mixture was extracted with MTBE (200 mL×3) and the MTBE phases were discarded. And then the water phase was added with 5 M NaOH (aq.) to pH=9 and extracted with DCM (200 mL×5). The combined organic layers were washed with brine (100 mL), dried over $Na_2SO_4$, filtered, and concentrated under reduced pressure to give the product. WV-CA-241 (27 g, 98.10% yield, LCMS purity: 98.24% purity) was obtained as a colorless oil. $^1$H NMR (400 MHz, CHLOROFORM-d) δ=7.83-7.76 (m, 2H), 6.98-6.91 (m, 2H), 4.00 (ddd, J=2.9, 5.0, 8.4 Hz, 1H), 3.81 (s, 3H), 3.33-3.07 (m, 5H), 2.87-2.75 (m, 2H), 1.74-1.49 (m, 4H); $^{13}$C NMR (101 MHz, CHLOROFORM-d δ=163.79, 131.10, 130.21, 114.44, 67.66, 61.88, 60.25, 55.69, 46.85, 25.84, 25.81. LCMS [M+H]$^+$: 286.1. LCMS purity: 98.24%. SFC: dr=0.18:99.82. LCMS purity: 99.9%; SFC purity: 99.82%.

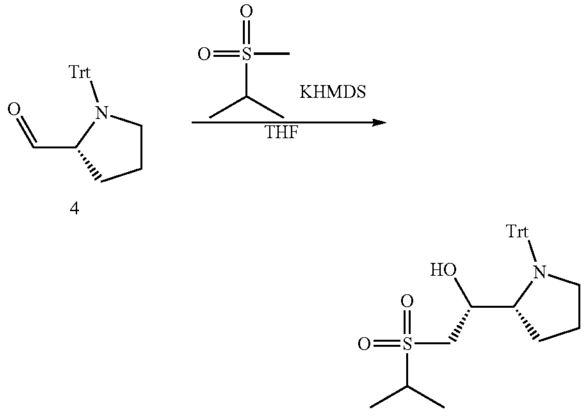

4

7

To a solution of 2-methylsulfonylpropane (32.21 g, 263.59 mmol) in THF (1200 mL) was added KHMDS (1 M, 263.59 mL) dropwise at −60° C., and warm to −30° C., slowly over 30 min. The mixture was then cooled to −70° C. A solution of compound 4 (60 g, 175.72 mmol) in THF (300 mL) was added dropwise at −70° C.→60° C., over 30 min. The mixture was stirred at −70° C.→60° C. for 2 hr. TLC showed compound 4 was consumed and new spot was detected. The reaction mixture was quenched with sat. aq. $NH_4Cl$ (800 mL), and then extracted with EtOAc (1 L×3). The combined organic layers were dried over anhydrous $Na_2SO_4$, filtered and concentrated. Compound 7 (95 g, crude) was obtained as a yellow oil.

Preparation of Compound WV-CA-242.

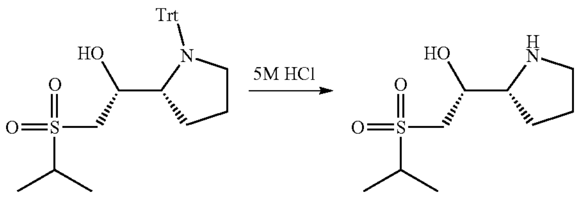

7 WV-CA-242

To a solution of compound 7 (95 g, 204.90 mmol) in THF (400 mL) was added HCl (5 M, 409.81 mL). The mixture was stirred at 0→25° C. for 2 hr. TLC indicated compound 7 was consumed and one new spot formed. The reaction mixture was washed with MTBE (300 mL×3), then the aqueous phase was basified by addition NaOH (5 M) until pH=12 at 0° C., and then extracted with DCM (300 mL×3) to give a residue dried over $Na_2SO_4$, filtered, and concentrated under reduced pressure to give a residue. Compound WV-CA-242 (45 g, 99.23% yield) was obtained as a yellow oil. LCMS $[M+H]^+$: 222.0.

Purification of Compound WV-CA-242.

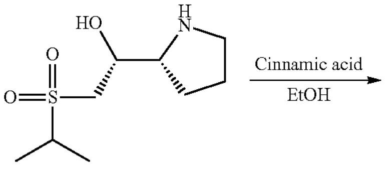

WV-CA-242

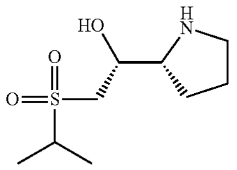

WV-CA-242

A solution of WV-CA-242 (45 g, 203.33 mmol), (E)-3-phenylprop-2-enoic acid (30.12 g, 203.33 mmol) in EtOH (450 mL) was stirred at 80° C. for 1 hr. The reaction was concentrated in vacuo. The residue was dissolved in TBME (400 mL), and then stirred at 80° C. for 15 min, and then to the mixture was added EtOH (20 mL) and MeCN (30 mL), and then the mixture was filtered, and the filtered cake was washed with TBME (30 mL×2) and then did this for 8 times. The salt (35 g, crude) was obtained as a red solid.

To a solution of salt (34 g, 92.02 mmol) in $H_2O$ (20 mL) was added aq. 5N NaOH (5 M, 36.81 mL). The mixture was stirred at 25° C. for 10 min. The reaction was extracted with DCM (100 mL×8), and then the organic phase was concentrated in vacuo. Compound WV-CA-242 (18.9 g, 91.09% yield, LCMS purity: 98.16%) was obtained as an off-white solid. $^1H$ NMR (400 MHz, CHLOROFORM-d) δ=4.13 (ddd, J=2.1, 4.6, 9.5 Hz, 1H), 3.38 (spt, J=6.9 Hz, 1H), 3.23-3.14 (m, 2H), 3.01 (dd, J=2.1, 14.4 Hz, 1H), 2.95-2.91 (m, 2H), 1.83-1.60 (m, 4H), 1.40 (dd. J=4.0, 6.8 Hz, 6H); $^{13}C$ NMR (101 MHz, CHLOROFORM-d) δ=67.45, 61.71, 53.93, 53.42, 46.80, 25.86, 5.43, 16.03, 14.17. LCMS $[M+H]^+$: 222.1. LCMS purity: 98.17%.

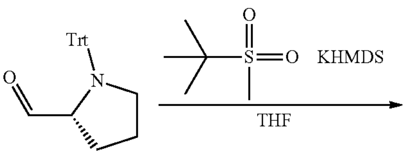

4

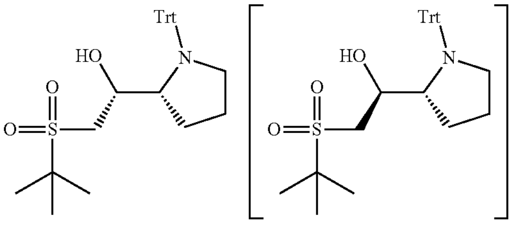

8 8A

To a solution 2-methyl-2-(methylsulfonyl)propane (14.96 g, 109.83 mmol) in THF (150 mL) was added KHMDS (1 M, 109.83 mL) dropwise at −70° C., and warm to −30° C. slowly over 30 min. The mixture was then cooled to −70° C. A solution of compound 4 (25.00 g, 73.22 mmol) in THF (100 mL) was added dropwise at −70° C. The mixture was stirred at −70° C. for 4 hr. TLC (Petroleum ether:Ethyl acetate=3:1 Rf=0.3) showed compound 4 was remained a little, and one major new spot with larger polarity was detected. The reaction mixture was quenched by added to the sat. $NH_4Cl$ (aq., 100 mL), and then extracted with EtOAc (100 mL×3). The combined organic layers were dried over $Na_2SO_4$, filtered, and concentrated under reduced pressure to give 30 mL solution. Then added MeOH (30 mL), concentrated under reduced pressure to give 30 mL solution, then filtered the residue and washed with MeOH (10 mL); the residue was dissolved with THF (30 mL) and MeOH (30 mL), and then concentrated under reduced pressure to give 30 mL solution. Then filtered to give a residue and washed with MeOH (10 mL). And repeat one more time to give 21 g white solid and 20 g brown oil. Compound 8 (21 g, crude) was obtained as a white solid, and Compound 8A (20 g, crude) as a brown oil. $^1H$ NMR (400 MHz, CHLOROFORM-d) δ=7.56 (d, J=7.5 Hz, 6H), 7.32-7.23 (m, 6H), 7.21-7.14 (m, 3H), 4.85-4.68 (m, 1H), 3.52-3.43 (m, 4H), 3.41 (td, J=3.8, 8.1 Hz, 1H), 3.28 (td, J=8.5, 11.9 Hz, 1H), 3.09-2.91 (m, 2H), 2.78 (dd, J=2.6, 13.6 Hz, 1H), 1.65-1.50 (m, 1H), 1.37 (s, 10H), 1.16-0.98 (m, 2H), 0.39-0.21 (m, 1H). LCMS $[M+H]^+$: 235.9.

Preparation of Compound WV-CA-243.

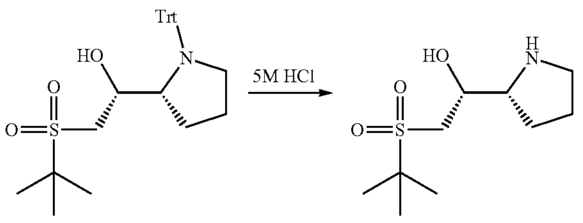

8 WV-CA-243

To a solution of compound 8 (20 g, 41.87 mmol) in THF (200 mL) was added HCl (5 M, 83.74 mL). The mixture was stirred at 15° C. for 3 hr. TLC indicated compound 8 was consumed completely and one major new spot with larger polarity was detected. The resulting mixture was washed with MTBE (100 mL×3). The combined aqueous layer was adjusted to pH 12 with 5M NaOH aq. and extracted with DCM (50 mL×3). The combined organic layers were dried over anhydrous $Na_2SO_4$, filtered and concentrated to afford a white solid. WV-CA-243 (9 g, 90.42% yield, 99% purity) was obtained as a white solid. $^1$H NMR (400 MHz, CHLOROFORM-d) δ 4.18 (ddd, J=2.8, 5.8, 8.2 Hz, 1H), 3.29-3.21 (m, 1H), 3.19 (d, J=2.6 Hz, 1H), 3.16-3.08 (m, 1H), 2.92 (t, J=6.6 Hz, 2H), 2.74 (br s, 1H), 1.92-1.81 (m, 1H), 1.81-1.61 (m, 3H), 1.42 (s, 10H); $^{13}$CNMR (101 MHz, CHLOROFORM-d) δ=68.01, 62.00, 59.73, 49.79, 46.96, 26.77, 25.80, 23.22. LCMS [M+H]$^+$: 236.1. LCMS purity: 99.46%.

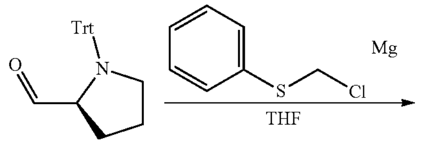

1

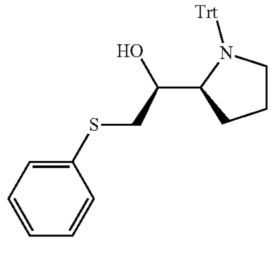

9

To a solution (chloromethyl)(phenyl)sulfane of Mg (17.08 g, 702.90 mmol, 4 eq.) and $I_2$ (0.50 g, 1.97 mmol, 396.83 uL, 1.12-2 eq.) in THF (100 mL) was added with 1,2-dibromoethane (1.25 g, 6.63 mmol, 0.5 mL, 3.77-2 eq.). Once the mixture turned to be colorless, cbloromethylsulfanylbenzene (111.51 g, 702.90 mmol, 4 eq.) in THF (100 mL) was dropwise added at 10-20° C. for 1 hr. After addition, the mixture was stirred at 10-20° C. for 1 hr, most of Mg was consumed. And then the mixture was added in the mixture of compound 1 (60 g, 175.72 mmol, 1 eq.) in THF (600 mL) at −78° C., the mixture was stirred at −78° C.-20° C. for 4 hr. TLC (Petroleum ether:Ethyl acetate=9:1, $R_f$=0.26) indicated compound 1 was remained and two new spots formed. The reaction mixture was quenched by addition water (100 mL) at 0° C., and then extracted with EtOAc (100 mL×3). The combined organic layers were dried over $Na_2SO_4$, filtered, and concentrated under reduced pressure to give a residue. The residue was purified by column chromatography ($SiO_2$, Petroleum ether/Ethyl acetate=200/1 to 10:1) 2 times. Compound 9 (80 g, 171.80 mmol, 97.77% yield) was obtained as a white solid. $^1$H NMR (400 MHz, CHLOROFORM-d) δ=7.52 (d, J=7.5 Hz, 6H), 7.31-7.09 (m, 14H), 4.24-4.14 (m, 1H), 3.54-3.44 (m, 1H), 3.30-3.18 (m, 1H), 3.08-2.96 (m, 1H), 2.91 (s, 1H), 2.80 (d, J=7.0 Hz, 2H), 1.69-1.53 (m, 1H), 1.39-1.30 (m, 1H), 1.15-1.01 (m, 1H), 0.30-0.12 (m, 1H).

Preparation of Compound WV-CA-244.

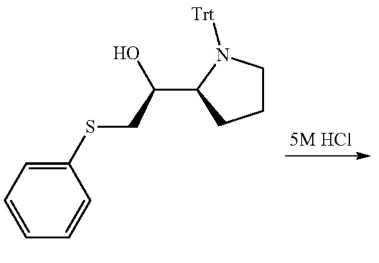

9

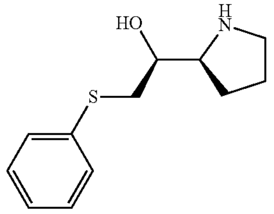

WV-CA-244

To a solution of compound 9 (80 g, 171.80 mmol, 1 eq.) in EtOAc (350 mL) was added HCl (5 M, 266.30 mL, 7.75 eq.). The mixture was stirred at 15° C. for 18 hr. TLC (Petroleum ether:Ethyl acetate=9:1, $R_f$=0.01) indicated compound 9 was consumed and new spots formed. The reaction mixture was extracted with MTBE (200 mL×3) and the MTBE phases were discarded. And then the water phase was added with 2 M NaOH (aq.) to pH=9 and extracted with EtOAc (200 mL×5). The combined organic layers were washed with brine (200 mL), dried over $Na_2SO_4$, filtered, and concentrated under reduced pressure to give the crude product. To the crude product was added EtOAc (100 mL) at 70° C. The mixture was stirred at 70° C.→20° C. for 1 hr. The reaction mixture was filtered, and the filter cake was dried to give the product. WV-CA-244 (31.9 g, 142.84 mmol, 94.66% yield) was obtained as a white solid. $^1$H NMR (400 MHz, CHLOROFORM-d) δ=7.37 (d, J=7.5 Hz, 2H), 7.26 (t, J=7.7 Hz, 2H), 7.20-7.12 (m, 1H), 3.74-3.65 (m, 1H), 3.24-3.15 (m, 1H), 3.13-3.00 (m, 2H), 3.00-2.21 (m, 4H), 1.77-1.59 (m, 4H); $^{13}$C NMR (101 MHz, CHLOROFORM-d) δ=136.04, 129.35, 128.95, 126.15, 70.75, 61.64, 46.86, 38.54, 25.86, 25.17. LCMS [M+H]$^+$: 224.1. LCMS purity: 99.57%.

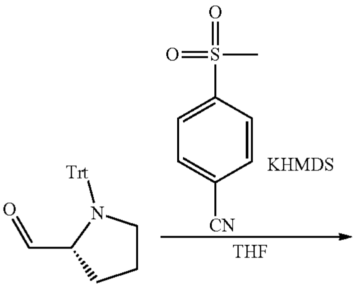

4

-continued

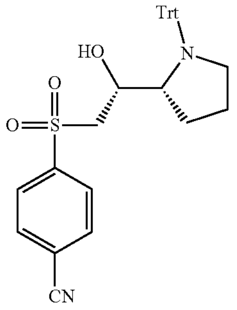

10

To a solution of 4-methylsulfonylbenzonitrile (47.76 g, 263.59 mmol, 1.5 eq.) in THF (800 mL) was added KHMDS (1 M, 263.59 mL, 1.5 eq.) at −70° C.→−40° C., 0.5 hr later, added compound 4 (60.00 g, 175.72 mmol, 1 eq.) in THF (400 mL) at −70° C. The mixture was stirred at −70° C. for 2.5 hr. TLC (Petroleum ether:Ethyl acetate=1:1, $R_f$=0.4) indicated compound 4 was consumed and one new spot formed. The reaction mixture was quenched by addition sat. $NH_4Cl$ (20 mL) at 0° C. and extracted with DCM (600 mL×3). Dried over $Na_2SO_4$, filtered, and concentrated under reduced pressure to give a residue. The residue was washed with MeOH (500 mL×5) to get compound 10 (28 g, 53.57 mmol, 30.49% yield) as a yellow solid. $^1$H NMR (400 MHz, CHLOROFORM-d) δ=7.84-7.74 (m, 2H), 7.73-7.65 (m, 2H), 7.32 (d, J=7.2 Hz, 6H), 7.15-6.99 (m, 9H), 4.20 (td, J=2.9, 5.6 Hz, 1H), 3.22 (ddd, J=3.1, 5.7, 8.3 Hz, 1H), 3.12-3.03 (m, 2H), 3.02-2.92 (m, 1H), 2.90-2.77 (m, 2H), 1.39-1.26 (m, 1H), 1.20-0.93 (m, 2H), 0.13-0.11 (m, 1H).

Preparation of Compound WV-CA-238.

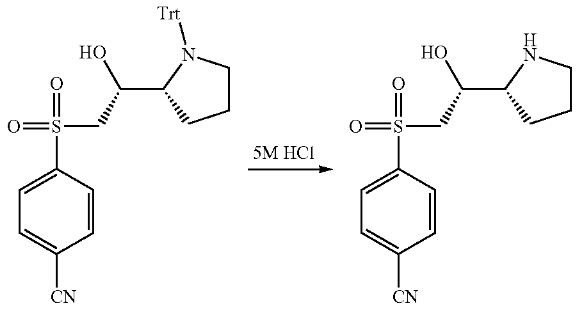

10 WV-CA-238

To a solution of compound 10 (28 g, 53.57 mmol, 1 eq.) in DCM (196 mL) was added TFA (12.22 g, 107.15 mmol, 7.93 mL, 2 eq.). The mixture was stirred at 0° C. for 3 hr. TLC and LCMS indicated compound 10 was consumed and two new spots formed. The reaction mixture was washed with MTBE (100 mL×3), then the aqueous phase was basified by addition NaOH (5 M) until pH=12 at 0° C., and then extracted with DCM (50 mL×3) to give a residue dried over $Na_2SO_4$, filtered, and concentrated under reduced pressure to give a residue. Compound WV-CA-238 (9.5 g, 33.42 mmol, 62.38% yield, 98.62% purity) was obtained as a yellow solid. $^1$H NMR (400 MHz, CHLOROFORM-d) δ=8.09 (d, J=8.4 Hz, 2H), 7.87 (d, J=8.4 Hz, 2H), 4.06 (ddd, J=2.9, 4.9, 8.3 Hz, 1H), 3.38-3.16 (m, 3H), 2.96-2.79 (m, 2H), 1.81-1.64 (m, 3H), 1.61-1.45 (m, 1H). $^{13}$C NMR (101 MHz, CHLOROFORM-d) δ=144.05, 132.88, 128.93, 117.48, 117.15, 67.63, 61.50, 60.09, 46.83, 25.88, 25.55. LCMS [M+H]$^+$: 281.1. LCMS purity: 98.62%. SFC: dr=99.75:0.25.

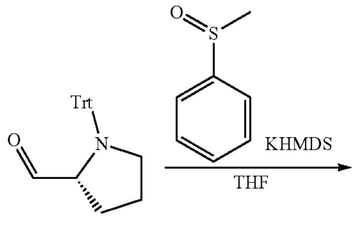

4

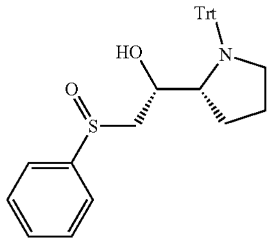

11

To a solution of methylsulfinylbenzene (25 g, 178.31 mmol, 1.5 eq.) in THF (400 mL) was added KHMDS (1 M, 178.31 mL, 1.5 eq.) dropwise at −60° C., and warm to −30° C. slowly over 30 min. The mixture was then cooled to −70° C. A solution of compound 4 (40.59 g, 118.88 mmol, 1 eq.) in THF (100 mL) was added dropwise at −70° C. The mixture was stirred at −70° C.→-50° C. for 2 hr. TLC (Petroleum ether:Ethyl acetate=3:1) showed compound 4 was remained. The reaction mixture was cooled to −70° C., additionally added KHMDS (1M, 40 mL), and stirred at −70° C.→~-40° C. for 2 hr. TLC (Petroleum ether:Ethyl acetate=3:1) showed compound 4 was little remained. The reaction mixture was quenched with sat. $NH_4Cl$ (aq. 300 mL), and the separated aqueous layer was extracted with EtOAc (200 mL×3). The combined organic layers were dried over anhydrous $Na_2SO_4$, filtered and concentrated to afford a residue as a yellow gum, which was crystallized in MeOH (100 mL), filtered and rinsed with MeOH (50 mL) to give an off-white solid (17 g), and the filtrate was concentrated to afford a yellow gum (50 g). The white solid product (17 g) was re-dissolved in THF (150 mL), and added MeOH (80 mL), and the mixture was concentrated to remove THF, filtered and dried to give an off-white solid, which was re-dissolved in THF (150 mL), and added MeOH (80 mL), and the mixture was concentrated to remove THF, filtered and dried to give the product as an off-white solid (13 g). The filtrate was concentrated to give 4 g crude. No further purification. The product compound 11 (13 g, 26.99 mmol, 22.70% yield) was obtained as an off-white solid. $^1$H NMR (400 MHz, CHLOROFORM-d) δ=7.62-7.56 (m, 2H), 7.55-7.52 (m, 3H), 7.51-7.45 (m, 6H), 7.25-7.12 (m, 9H), 4.60 (td, J=2.4, 10.1 Hz, 1H), 3.72 (s, 1H), 3.27-3.13 (m, 2H), 3.04-2.84 (m, 2H), 2.46 (dd, J=2.2, 13.5 Hz, 1H), 1.71-1.53 (m, 1H), 1.42-1.28 (m, 1H), 1.07-0.90 (m, 1H), 0.37-0.21 (m, 1H).

Preparation of Compound WV-CA-247.

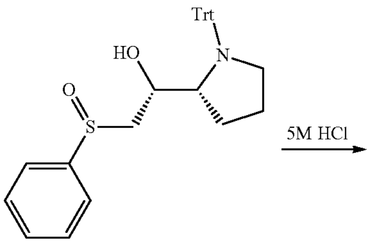

11

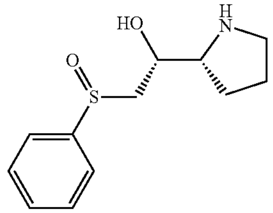

WV-CA-247

To a solution of compound 11 (13 g, 26.99 mmol, 1 eq.) in THF (45 mL) was added HCl (5 M, 52.00 mL, 9.63 eq.) aqueous. The mixture was stirred at 20° C. for 2 hr. TLC (Petroleum ether:Ethyl acetate=3:1) showed the reaction was completed. The resulting mixture was washed with MTBE (60 mL×3). The combined aqueous layer was adjusted to pH 12 with 5 M NaOH aq. and extracted with DCM (80 mL×3). The combined organic layers were dried over anhydrous $Na_2SO_4$, filtered, and concentrated to afford a white solid (5.8 g). Without further purification. The compound WV-CA-247 (5.8 g, 24.17 mmol, 89.55% yield, 99.74% purity) was obtained as a white solid. $^1$H NMR (400 MHz, CHLOROFORM-d) δ=7.67-7.60 (m, 2H), 7.55-7.42 (m, 3H), 4.17 (ddd, J=2.6, 4.2, 9.9 Hz, 1H), 3.74-3.23 (brs, 2H), 3.13 (dt, J=4.3, 7.3 Hz, 1H), 2.96-2.74 (m, 4H), 1.81-1.52 (m, 4H). $^{13}$C NMR (101 MHz, CHLOROFORM-d) δ=143.99, 130.93, 129.32, 123.92, 66.97, 62.23, 61.58, 46.86, 25.88, 25.3. LCMS $[M+H]^+$: 240. LCMS purity: 99.74%. SFC:dr=99.48:0.52.

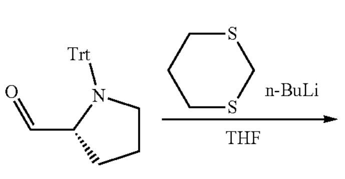

4

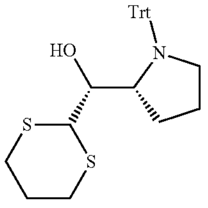

12

To a solution of 1,3-dithiane (13.21 g, 109.83 mmol) in THF (250 mL) was added n-BuLi (2.5 M, 29.29 mL) at −20° C., 0.5 hr later added compound 1 (25 g, 73.22 mmol) in THF (250 mL) at −70° C. The mixture was stirred at −70→20° C. for 16 hr. TLC indicated compound 4 was remained, and one new spot was detected. The reaction mixture was quenched by sat. $NH_4Cl$ (200 mL), and then extracted with EtOAc (200 mL×5). The combined organic layers were dried over $Na_2SO_4$, filtered and concentrated under reduced pressure to give a residue. The residue was purified by MPLC ($SiO_2$, Petroleum ether/Ethyl acetate=50/1 to 10/1, 5% TEA) 2 times. Compound 12 (16 g, 47.33% yield) was obtained as a yellow oil. $^1$H NMR (400 MHz, CHLOROFORM-d) δ=7.59 (d, J=7.0 Hz, 5H), 7.29-7.25 (m, 6H), 7.20-7.14 (m, 3H), 4.39 (dd, J=2.4, 10.3 Hz, 1H), 4.03 (ddd, J=2.4, 5.6, 8.2 Hz, 1H), 3.38 (d, J=10.1 Hz, 1H), 3.28 (ddd, J=7.0, 10.1, 12.3 Hz, 1H), 3.07-2.99 (m, 1H), 2.93-2.85 (m, 1H), 2.63-2.54 (m, 1H), 2.34-2.18 (m, 2H), 1.97-1.82 (m, 2H), 1.59-1.45 (m, 1H), 1.22-1.11 (m, 1H), 0.22-0.06 (m, 1H).

Preparation of Compound WV-CA-246.

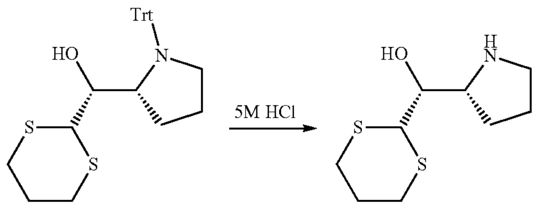

12 WV-CA-246

To a solution of compound 12 (16 g, 34.66 mmol) in EtOAc (80 mL) was added HCl (5 M, 69.31 mL). The mixture was stirred at 15° C. for 16 hr. TLC indicated compound 12 was consumed completely and new spots formed. The reaction mixture was extracted with TBME (100 mL×3) and the TBME phases were discarded. And then the water phase was added with 5 M NaOH (aq.) to pH=9 and extracted with DCM (100 mL×5). The combined organic layers were washed with brine (100 mL), dried over $Na_2SO_4$, filtered and concentrated under reduced pressure to give the crude product. The residue was purified by prep-HPLC (column: Phenomenex luna C18 250×50 mm×10 um; mobile phase: [water (0.1% TFA)—ACN]; B %: 0%-15%, 20 min and column: Phenomenex luna (2) C18 250×50×10 um; mobile phase: [water (0.1% TFA)—ACN]; B %: 0%-12%, 20 min). WV-CA-246 (4.2 g, 55.25% yield) was obtained as a white solid. $^1$H NMR (400 MHz, CHLOROFORM-d) δ=4.13 (d, J=7.2 Hz, 1H), 3.83 (dd, J=5.1, 7.2 Hz, 1H), 3.49 (dt, J=5.1, 7.3 Hz, 1H), 3.13-2.76 (m, 6H), 2.60 (br s, 2H), 2.20-2.05 (m, 1H), 2.04-1.90 (m, 1H), 1.89-1.62 (m, 4H). $^{13}$C NMR (101 MHz, CHLOROFORM-d) δ=73.76, 59.94, 50.42, 46.83, 28.95, 28.45, 25.87, 25.32. HPLC purity: 97.75%. LCMS $[M+H]^+$: 220.1. SFC:dr=0.22:99.78.

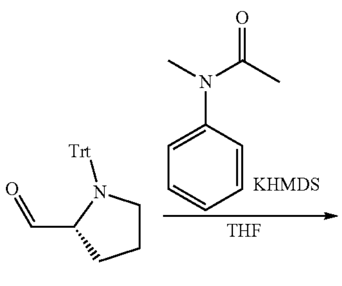

4

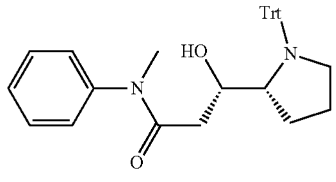

13

To a solution of N-methyl-N-phenyl-acetamide (18.5 g, 124.00 mmol) in THF (250 mL) was added KHMDS (1 M, 124.00 mL) dropwise at −70° C. and to warm to −30° C. slowly over 30 min. The mixture was then cooled to −70° C. A solution of compound 4 (28.23 g, 82.67 mmol) in THF (150 mL) was added dropwise at −70° C. The mixture was stirred at −70° C.∼−50° C. for 3 hr. TLC showed the reaction was almost completed. The reaction mixture was quenched with sat. $NH_4Cl$ (aq., 30 mL), and extracted with EtOAc (25 mL×3). The combined organic layers were dried over anhydrous $Na_2SO_4$, filtered and concentrated to afford a residue as yellow gum. The crude was purified by column chromatography on silica gel (Petroleum ether:Ethyl acetate=10:1, 3:1, 1:1, 1:2, 5% TEA). Compound 13 (38 g, 93.7% yield) was obtained as a white solid. $^1H$ NMR (400 MHz, CHLOROFORM-d) δ=7.53 (br d, J=7.5 Hz, 6H), 7.44-7.31 (m, 4H), 7.26-7.09 (m, 12H), 4.46-4.40 (m, 1H), 3.90 (br s, 1H), 3.31-3.19 (m, 4H), 3.15-3.07 (m, 1H), 3.00-2.91 (m, 1H), 1.48-1.26 (m, 2H), 0.86-0.74 (m, 1H), 0.33-0.19 (m, 1H).

Preparation of Compound WV-CA-24&

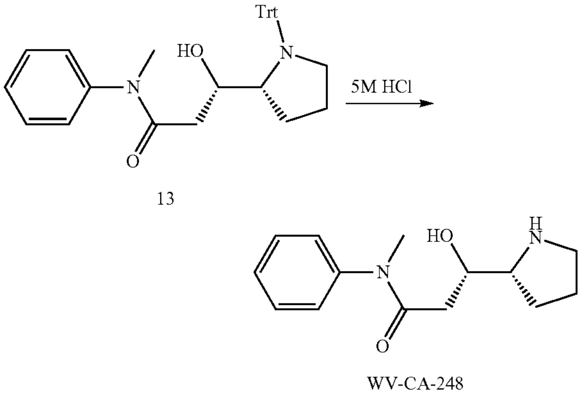

13

WV-CA-248

To a solution of compound 13 (38 g, 77.45 mmol) in THF (125 mL) was added HCl (5 M, 152.00 mL) aqueous. The mixture was stirred at 20° C. for 2 hr. TLC showed the reaction was completed. The resulting mixture was washed with MTBE (80 mL×3), EtOAc (100 mL×3), and DCM (100 mL×2) in turn. The combined aqueous layer was adjusted to pH=12 with 5M NaOH aq. and extracted with DCM (120 mL×3). The combined organic layers were dried over anhydrous $Na_2SO_4$, filtered and concentrated to afford a yellow gum. The crude of WV-CA-248 (15.2 g, 73.26% yield, 92.7% purity) appears a yellow gum. To a solution of WV-CA-248 (14.5 g, 58.39 mmol) in EtOH (150 mL) was added (E)-3-phenylprop-2-enoic acid (8.65 g, 58.39 mmol). The mixture was stirred at 80° C. for 1 hr. The mixture was concentrated in vacuo. The residue was dissolved in TBME (50 mL), and then the mixture was added MeCN (3 mL), the mixture was turned clear, then the solution was stranded, and then solid was appeared, and the mixture was filtered, and the filtered cake was washed with TMBE (10 mL×2), and the filtered cake was desired compound. The residue (6.5 g, crude) was obtained as a yellow solid. The residue was dissolved in $H_2O$ (10 mL) was added aq. NaOH (5 M, 6.56 mL, 2 eq.). The mixture was stirred at 25° C. for 10 min. The pH of the mixture was 13. The solution was extracted with DCM (40 mL×6), and the organic phase was concentrated in vacuo. Compound WV-CA-248 (4 g, 91.74% yield, 93.4% purity) was obtained as a brown oil. $^1H$ NMR (400 MHz, CHLOROFORM-d) δ=7.49-7.31 (m, 3H), 7.21 (br d, J=7.3 Hz, 2H), 4.00 (td, J=4.3, 8.6 Hz, 1H), 3.48 (br s, 2H), 3.28 (s, 3H), 3.10-2.98 (m, 1H), 2.97-2.80 (m, 2H), 2.36-2.17 (m, 2H), 1.79-1.47 (m, 3H), 1.79-1.47 (m, 1H). $^{13}C$ NMR (101 MHz, CHLOROFORM-d) δ=172.38, 143.42, 129.89, 128.04, 127.27, 69.90, 62.29, 46.77, 37.98, 37.23, 25.99, 25.65. LCMS $[M+H]^+$: 249.1. LCMS purity: 93.35%. SFC: SFC purity de=94.26%.

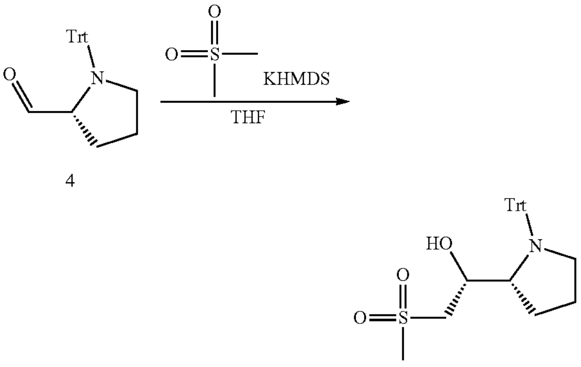

4

14

To a solution of methylsulfonylmethane (8.27 g, 87.86 mmol) in THF (150 mL) was added KHMDS (1 M, 87.86 mL) at −70° C.∼−40° C., 0.5 hr later added compound 1 (20 g, 58.57 mmol) in THF (100 mL). The mixture was stirred at −70° C. for 1.5 hr. TLC indicated compound 4 was remained a little and one new spot formed. The reaction mixture was quenched by addition sat. $NH_4Cl$ (aq. 200 mL) at 0° C., and then diluted with EtOAc (200 mL) and extracted with EtOAc (200 mL×3). Dried over $Na_2SO_4$, filtered and concentrated under reduced pressure to give a residue. The residue was purified by column chromatography ($SiO_2$, Petroleum ether/Ethyl acetate=1/0→0:1). Compound 14 (12 g, crude, HNMR showed cis/trans isomer ratio∼10:1) was obtained as a yellow oil. $^1H$ NMR (400 MHz, CHLOROFORM-d) δ=7.58-7.47 (m, 7H), 7.26-7.22 (m, 5H), 7.20-7.13 (m, 3H), 4.51-4.46 (m, 1H), 3.99-3.88 (m, 1H), 3.48-3.39 (m, 1H), 3.21-2.97 (m, 4H), 2.96-2.91 (m, 3H), 2.68 (br d, J=14.6 Hz, 1H), 1.57-1.43 (m, 1H), 1.36-1.26 (m, 1H), 1.20-1.10 (m, 1H), 0.57-0.44 (m, 1H), 0.25-0.04 (m, 1H).

Preparation of WV-CA-252.

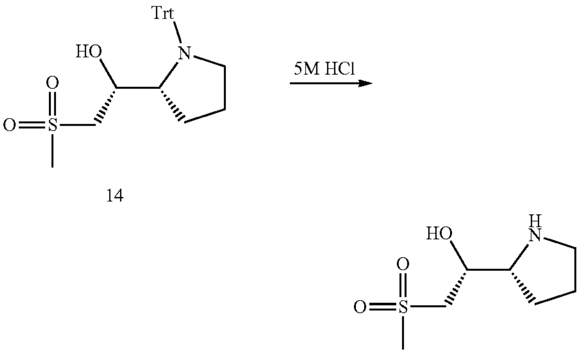

14

WV-CA-252

To a solution of compound 14 (18 g, 41.32 mmol) in THF (82 mL) was added HCl (5 M, 82.65 mL). The mixture was stirred at 25° C. for 3 hr. TLC indicated compound 14 was consumed and two new spots formed. The reaction mixture was washed with MTBE (50 mL×3), then the aqueous phase was basified by addition NaOH (5M) until pH=12 at 0° C., and then extracted with DCM (50 mL×6) to give a residue dried over $Na_2SO_4$, filtered and concentrated under reduced pressure to give a residue. The crude compound WV-CA-252 (6.5 g, 81.4% yield) was obtained as a yellow solid. $^1H$ NMR (400 MHz, CHLOROFORM-d) δ=4.13 (ddd, J=1.8, 4.0, 9.7 Hz, 1H), 3.23 (dt, J=4.2, 7.4 Hz, 1H), 3.18-3.09 (m, 1H), 3.05 (s, 4H), 3.00-2.90 (m, 3H), 1.95-1.68 (m, 4H), 1.67-1.48 (m, 1H). LCMS $[M+H]^+$: 194.0.

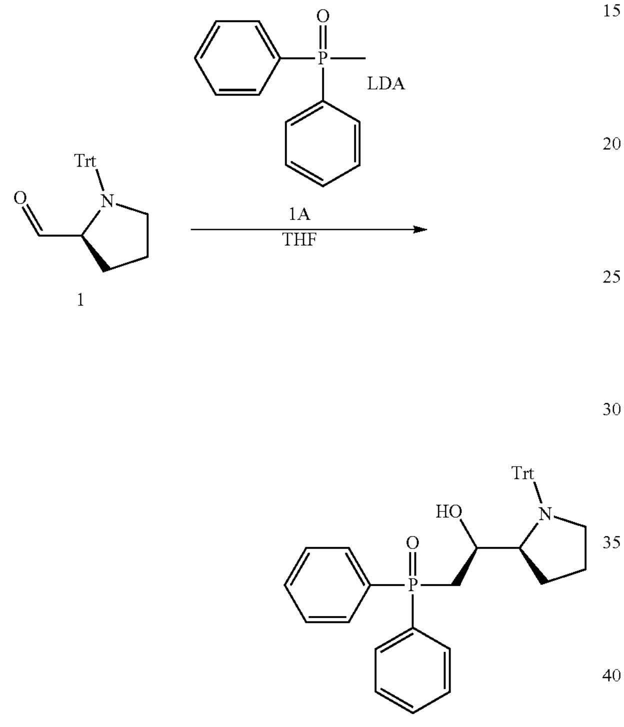

1

15

A mixture of compound 1A (52.24 g, 241.62 mmol) in THF (500 mL) was degassed and purged with $N_2$ for 3 times, and then the mixture was cooled to −70° C., and then to the mixture was added LDA (2 M, 112.76 mL). The mixture was stirred at −40° C. for 30 min, and then to the mixture was added compound 1 (55 g, 161.08 mmol) in THF (250 mL) at −70° C. The mixture was stirred at −70° C. for 2 hr under $N_2$ atmosphere. TLC indicated compound 1 was consumed completely and one new spot formed. The reaction was clean according to TLC. The reaction was quenched by sat. aq. $NH_4Cl$ (300 mL) and then extracted with EtOAc (100 mL×3). The combined organic phase was washed with brine (100 mL), dried over anhydrous $Na_2SO_4$, filtered and concentrated in vacuo. The residue was dissolved in MeOH (300 mL) and filtered; the filtered cake was the desired product. Compound 2 (53 g, crude) was obtained as a white solid.

Preparation of Compound WV-CA-245.

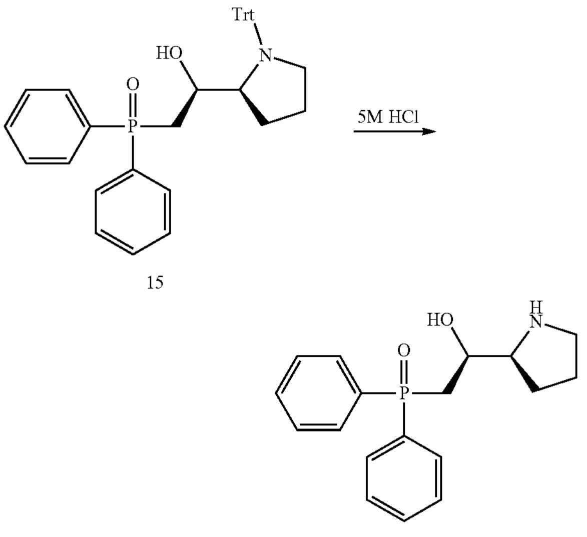

15

WV-CA-245

To a solution of compound 15 (72 g, 129.11 mmol) in THF (400 mL) was added HCl (5 M, 258.22 mL). The mixture was stirred at 25° C. for 1 hr. LC-MS showed compound 15 was consumed completely and one main peak with desired mass was detected. The reaction was extracted with TBME (100 mL×3), added aq. 5 N NaOH to pH=13, and then extracted with DCM (50 mL×3), and the combined organic phase was concentrated in vacuo. WV-CA-245 (38 g, 92.82% yield, 99.5% purity) was obtained as a white solid. $^1H$ NMR (400 MHz, CHLOROFORM-d) δ=7.81-7.71 (m, 411), 7.58-7.44 (m, 6H), 4.01-3.92 (m, 1H), 3.16-3.09 (m, 1H), 2.92-2.79 (m, 2H), 2.63-2.44 (m, 2H), 1.82-1.60 (m, 4H). $^{13}C$ NMR (101 MHz, CHLOROFORM-d) δ=133.88, 132.89, 132.86, 131.95, 131.88, 130.73, 128.74, 68.98, 68.94, 63.79, 63.67, 47.03, 34.21, 33.49, 26.37, 25.88. LCMS $[M+H]^+$: 316.1. LCMS purity: 99.45%. SFC: SFC purity de=99.5%.

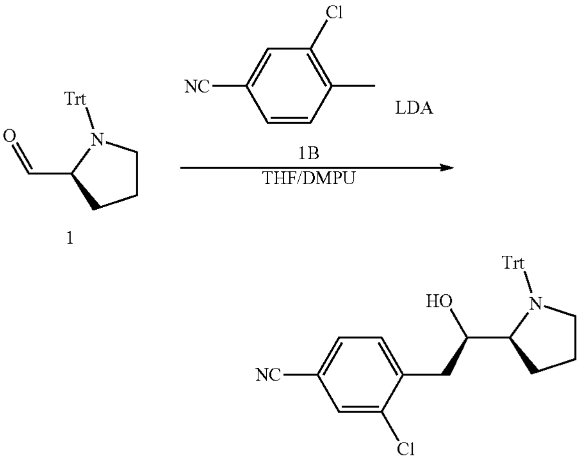

1

16

To a solution of compound 1B (13.32 g, 87.86 mmol) in THF (200 mL) was added KHMDS (1 M, 82.00 mL) at −70° C. under $N_2$, and then the mixture was stirred at −70° C. for 10 min, and then to the mixture was added compound 1 (20 g, 58.57 mmol) in THF (100 mL), the reaction was stirred at −70° C. for 30 min. TLC indicated compound 1 was consumed completely and one new spot formed. The reaction was clean according to TLC. The reaction mixture was quenched with sat. aq. $NH_4Cl$ (100 mL), and then extracted with EtOAc (50 mL×3). The combined organic layers were dried over anhydrous $Na_2SO_4$, filtered and concentrated. The residue was purified by column chromatography ($SiO_2$. Petroleum ether/Ethyl acetate=50:1, 20:1, 10:1, 1:1, 0:1). Compound 16 (12 g, crude) was obtained as a yellow solid.

Preparation of Compound WV-CA-249.

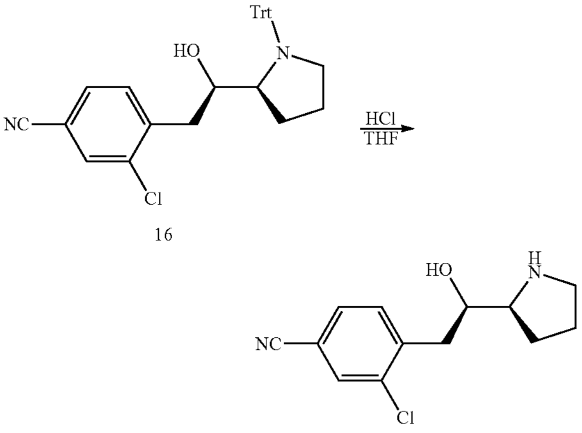

16

WV-CA-249

To a solution of compound 16 (12 g, 24.34 mmol) in THF (50 mL) was added aq. HCl (5 M, 48.68 mL). The mixture was stirred at 25° C. for 30 min. TLC indicated compound 16 was consumed completely and one new spot formed. The reaction was clean according to TLC. The reaction was extracted with TBME (100 mL×3), and then to the mixture was added 5N aq. NaOH to pH=13, extracted with DCM (100 mL×3), and then the organic phase was concentrated in vacuo. WV-CA-249 (5.36 g, 87.84% yield, 100.00% purity) was obtained as a yellow solid. $^1H$ NMR (400 MHz, CHLOROFORM-d) δ=7.64 (s, 1H), 7.49 (d, J=0.9 Hz, 2H), 3.88 (td, J=3.6, 9.4 Hz, 1H), 3.24-3.16 (m, 1H), 3.02-2.89 (m, 3H), 2.78 (dd, J=9.4, 14.0 Hz, 1H), 1.84-1.70 (m, 4H). $^{13}C$ NMR (101 MHz, CHLOROFORM-d) δ=143.11, 134.94, 132.60, 132.33, 130.12, 117.63, 111.52, 70.86, 62.02, 46.76, 37.90, 25.88, 24.21. LCMS $[M+H]^+$: 251.0. LCMS purity: 100.000%. SFC:SFC purity de=98.28%.

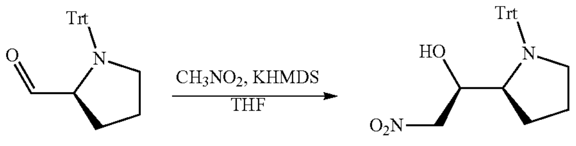

1

17

To a solution of nitromethane (30.59 g, 501.15 mmol) in THF (300 mL) was added KHMDS (1 M, 263.59 mL) at 20-25° C. and stirred for 1 hr. Compound 1 (30 g, 87.86 mmol) in THF (90 mL) was added to the mixture at 20-25° C. and stirred for 0.5 hr. TLC showed that the starting material was consumed mostly, and desired product was formed. The mixture was quenched by saturated aq. $NH_4Cl$ (300 mL) and extracted with ethyl acetate (100 mL×3). The organic phase was washed by saturated aq. NaCl (100 mL×3) and dried with anhydrous $Na_2SO_4$, then concentrated under reduced pressure to remove the solvent. The crude product was purified by MPLC ($SiO_2$, Ethyl acetate/Petroleum ether=0%→20%) to obtain compound 17 (26.55 g, 75.08% yield) as yellow solid. The product was detected by $^1H$ NMR. $^1H$ NMR (400 MHz, CHLOROFORM-d) δ=7.54-7.44 (m, 6H), 7.28-7.21 (m, 6H), 7.20-7.14 (m, 3H), 4.64 (td, J=3.0, 9.4 Hz, 1H), 4.53-4.06 (m, 3H), 3.60-3.40 (m, 1H), 3.24-2.96 (m, 3H), 1.52-1.41 (m, 1H), 1.40-1.28 (m, 1H), 1.17-0.94 (m, 1H), 0.67-0.50 (m, 1H), 0.23 (quin d, J=8.8, 11.6 Hz, 1H).

Preparation of Compound WV-CA-250.

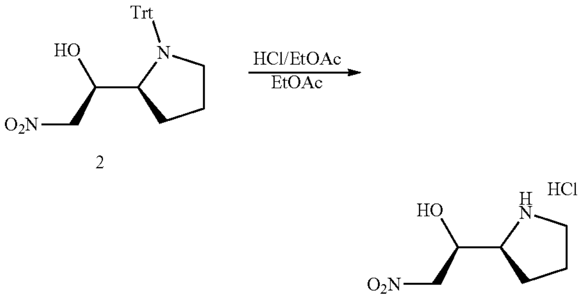

2

WV-CA-250

To a solution of compound 17 (7.5 g, 18.63 mmol) in EtOAc (35 mL) was added HCl/EtOAc (4 M, 50 mL) at 20-25° C. and stirred for 1 hr. TLC showed that the starting material was consumed completely. Poured the supernatant liquid of the mixture, the yellow gum on the bottle wall was concentrated under reduced pressure to remove the solvent. WV-CA-250 (2.10 g, 56.70% yield, 98.927% purity, HCl salt) was obtained as yellow gum. The product was detected by $^1H$ NMR, $^{13}C$ NMR and LCMS. $^1H$ NMR (400 MHz, DMSO-$d_6$) δ=9.89-9.54 (m, 1H), 9.03-8.75 (m, 1H), 8.94 (br s, 1H), 4.97-4.78 (m, 1H), 4.65-4.35 (m, 2H), 3.70-3.41 (m, 4H), 3.22-3.03 (m, 2H), 2.06-1.65 (m, 4H). $^{13}C$ NMR (101 MHz, DMSO-$d_6$) δ=79.42, 79.00, 67.89, 66.82, 61.53, 60.77, 45.44, 45.25, 26.93, 24.57, 23.95, 23.81. LCMS $[M+H]^+$: 161.1, purity: 98.92%.

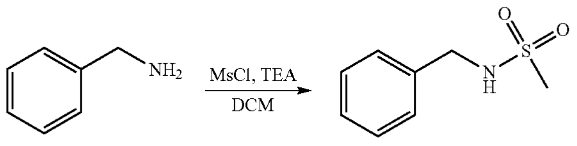

18A

To a solution of compound benzylamine (30 g, 279.97 mmol) and TEA (56.66 g, 559.95 mmol) in DCM (60 mL) was added MsCl (38.49 g, 335.97 mmol) in DCM (30 mL) at 0° C. The mixture was stirred at 0° C. for 2 hr. LC-MS showed compound 18A was consumed and many new peaks were detected. The reaction mixture was washed with HCl (1 M, 50 mL×3) and sat. $NaHCO_3$ (aq. 50 mL×3). The organic layer was washed with brine (50 mL), dried over $Na_2SO_4$, filtered and concentrated under reduced pressure to give a residue. TLC showed one main spot. The residue was purified by MPLC ($SiO_2$, Petroleum ether/Ethyl acetate=5/1 to 1:1). Compound 18A (35 g, 67.49% yield) was obtained as a light-yellow solid. $^1$H NMR (400 MHz, CHLOROFORM-d) δ=7.44-7.24 (m, 5H), 4.82 (br s, 1H), 4.31 (d, J=6.2 Hz, 2H), 2.85 (s, 3H).

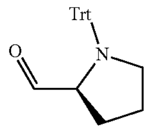

1

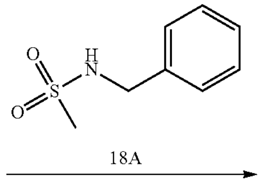

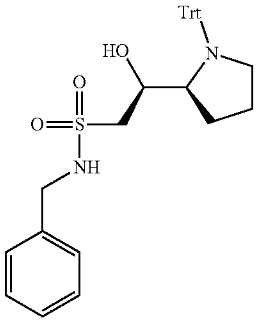

18

To a solution of compound 18A (16.28 g, 87.86 mmol) in THF (60 mL) was added with LDA (2 M, 87.86 mL) at 0° C. The mixture was stirred at 0-25° C. for 0.5 hr. And then compound 1 (15 g, 43.93 mmol) in THF (60 mL) was added to above solution at −70° C. The mixture was stirred at −70-25° C. for 4 hr. TLC indicated compound 1 was consumed completely and many new spots formed. The reaction mixture was added with sat. $NH_4Cl$ (aq. 50 mL) and extracted with EtOAc (100 mL×3). The combined organic layers were dried over $Na_2SO_4$, filtered and concentrated under reduced pressure to give a residue. The residue was purified by prep-TLC ($SiO_2$, Petroleum ether/Ethyl acetate=5/1, 2% TEA). Compound 18 (22 g, 95.08% yield) was obtained as a yellow oil.

Preparation of Compound WV-CA-255.

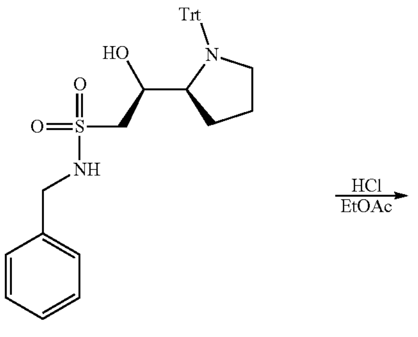

18

-continued

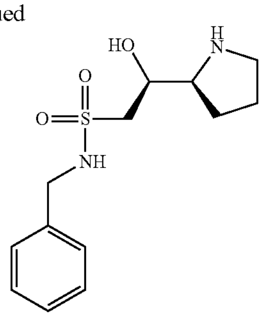

WV-CA-255

To a solution of compound 18 (22 g, 41.77 mmol) in EtOAc (15 mL) was added HCl (4 M in ethyl acetate, 31.33 mL) at 0° C. The mixture was stirred at 0-25° C. for 2 hr. And solid appeared in the reaction mixture. TLC indicated compound 18 was consumed completely and many new spots formed. The reaction mixture was filtered. The filter cake was dissolved in water (10 mL), washed with MTBE (40 mL×3). The water phase was added with $Na_2CO_3$ (powder) to pH=8~9 and extracted with DCM (50 mL×5). The combined organic layers were dried over $Na_2SO_4$, filtered and concentrated under reduced pressure to give a residue. WV-CA-255 (11 g, 92.60% yield) was obtained as a brown solid. $^1$H NMR (400 MHz, CHLOROFORM-d) δ=7.46-7.25 (m, 5H), 4.65-3.72 (m, 5H), 3.14-3.01 (m, 3H), 2.95-2.77 (m, 2H), 1.89-1.34 (m, 4H). $^{13}$C NMR (101 MHz, CHLOROFORM-d) δ=136.99, 128.71, 128.62, 128.19, 128.09, 127.85, 69.12, 67.58, 61.98, 61.70, 55.55, 55.36, 47.36, 47.30, 46.60, 46.28, 28.05, 26.16, 25.71, 24.92. LCMS $[M+H]^+$: 285.0, LCMS purity: 99.8%. SFC:dr (trans/cis)=32.36:67.64.

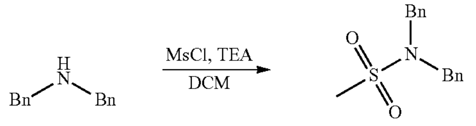

19A

To a solution of compound dibenzylamine (30 g, 152.07 mmol) in DCM (250 mL) was added TEA (15.39 g, 152.07 mmol). The mixture was cooled to 0° C., and to the mixture was added MsCl (17.42 g, 152.07 mmol) in DCM (50 mL), and then the mixture was stirred at 25° C. for 12 hours. LC-MS showed desired mass was detected. The reaction was quenched by $H_2O$ (100 mL) and the organic phase was extracted with $H_2O$ (100 mL-3), the organic phase was dried by $Na_2SO_4$, and then concentrated in vacuum. No need further purification. Compound 19A (39 g, crude) was obtained as a white solid. $^1$H NMR (400 MHz, CHLOROFORM-d) δ=7.41-7.29 (m, 9H), 4.36 (s, 4H), 2.82-2.75 (m, 3H). LCMS $[M+H]^+$: 298.0, purity: 86.6%.

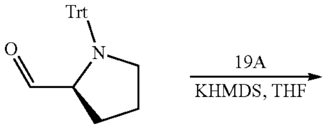

1

-continued

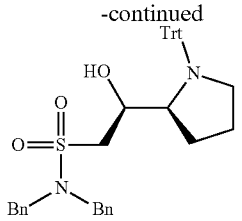

+

19

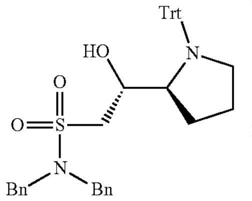

20

To a solution of compound 19A (19.36 g, 70.29 mmol) in THF (200 mL) was added KHMDS (1 M, 76.15 mL) dropwise at −78° C. to −70° C. under $N_2$. The mixture was warmed to −40° C. and stirred for 0.5 hr, then cooled to −78° C. To the mixture was added compound 1 (20 g, 58.57 mmol) in THF (100 mL) at −78° C. to −70° C. and stirred for 1 hr under $N_2$. TLC showed that the starting material was consumed completely. The mixture was quenched by saturated aq. $NH_4Cl$ (200 mL) and extracted with ethyl acetate (70 mL×3). The organic phase was washed by saturated aq. NaCl (70 mL×3) and dried with anhydrous $Na_2SO_4$, then concentrated under reduced pressure to remove the solvent to obtain the crude product as yellow gum. The crude product was re-dissolved with methanol (200 mL) and standing at 20-25° C. for 12 hours. Compound 19 (20.4 g, 99.99% yield) was crystallized from the solvent as white solid, then filtered and dried in vacuum. The filtrate was concentrated under reduced pressure to remove the solvent to give compound 20 (28.4 g, crude) as brown gum. $^1$H NMR (400 MHz, CHLOROFORM-d) 5=7.47-7.42 (m, 6H), 7.23-7.05 (m, 19H), 4.36 (td, J=3.0, 8.6 Hz, 1H), 4.23-4.12 (m, 4H), 3.29-3.19 (m, 1H), 3.29-3.19 (m, 1H), 3.11 (ddd, J=7.1, 9.5, 12.1 Hz, 1H), 2.97-2.82 (m, 2H), 2.59 (dd, J=3.1, 14.2 Hz, 1H), 1.37-1.27 (m, 1H), 1.24-1.14 (m, 1H), 1.00-0.92 (m, 1H), 0.16-0.02 (m, 1H).

Preparation of Compound WV-CA-263.

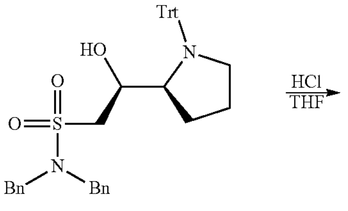

19

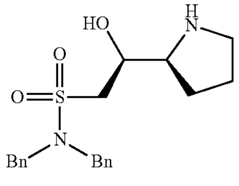

WV-CA-263

To a solution of compound 19 (20 g, 32.42 mmol) in THF (100 mL) was added HCl (5 M, 64.85 mL) at 20-25° C. and stirred for 0.5 hr. TLC showed that the starting material was consumed completely. The mixture was extracted with TBME (80 mL×3), then adjusted the pH of the mixture with aq. NaOH (65 mL, 5M) to 11-13 and extracted with DCM (100 mL×3). The organic phase was dried with anhydrous $Na_2SO_4$ and concentrated under reduced pressure to remove the solvent. The crude product was used for the next step without any purification. WV-CA-263 (10.04 g, 82.68% yield, 100% purity) was obtained as white solid. $^1$H NMR (400 MHz, CHLOROFORM-d) δ=7.38-7.28 (m, 10H), 4.38 (s, 4H), 4.01 (ddd, J=2.6, 5.6, 8.5 Hz, 1H), 3.20-3.13 (m, 2H), 3.10-3.02 (m, 1H), 2.91 (t, J=6.5 Hz, 2H), 1.89 (br d, J=8.6 Hz, 1H), 1.82-1.66 (m, 4H), 1.62-1.52 (m, 1H). $^{13}$C NMR (101 MHz, CHLOROFORM-d) δ=135.62, 128.77, 128.70, 127.98, 77.35, 76.87 (d, J=31.5 Hz, 1C), 68.84, 61.51, 57.03, 50.35, 46.96, 26.27, 25.88. LCMS $[M+H]^+$: 375.1, purity: 100.00%. SFC:dr=99.55:0.45.

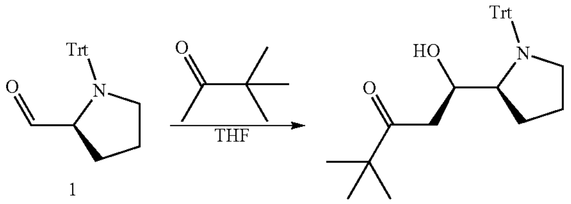

1

21

To a solution of 3,3-dimethylbutan-2-one (11.00 g, 109.83 mmol) in THF (125 mL) was added LDA (2 M, 54.91 mL) dropwise at −70° C., and it was stirred at −70° C.∼−60° C. for 1 hr. A solution of compound 1 (25 g, 73.22 mmol) in THF (125 mL) was added dropwise at −70° C.∼−60° C. The mixture was stirred at −70° C. for 1.5 hr. TLC showed compound 1 was almost consumed. The reaction mixture was quenched with sat. $NH_4Cl$ (aq., 200 mL), and the separated aqueous layer was extracted with EtOAc (150 mL×3). The combined organic layers were dried over anhydrous $Na_2SO_4$, filtered and concentrated to afford a residue as a light-yellow solid. The crude was purified by column chromatography on silica gel (Petroleum ether+5% TEA; Petroleum ether:Ethyl acetate (20:1)+5% TEA). Compound 21 (17 g, 52.6% yield) was obtained as a white solid. $^1$H NMR (400 MHz, CHLOROFORM-d) δ=7.37-7.25 (m, 6H), 7.03-6.95 (m, 6H), 6.94-6.84 (m, 3H), 4.22 (td, J=2.7, 9.2 Hz, 1H), 3.09 (td, J=4.1, 7.6 Hz, 1H), 3.04-2.92 (m, 2H), 2.75 (ddd, J=2.9, 8.5, 12.0 Hz, 1H), 2.26 (dd, J=9.3, 17.0 Hz, 1H), 2.04 (dd, J=3.4, 16.9 Hz, 1H), 1.43-1.24 (m, 2H), 1.14-1.01 (m, 1H), 0.84 (s, 9H), 0.81-0.71 (m, 1H), 0.09–0.07 (m, 1H).

Preparation of Compound WV-CA-289.

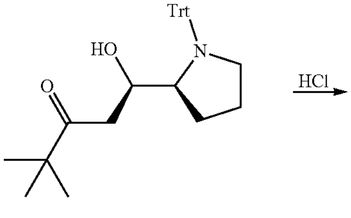

21

-continued

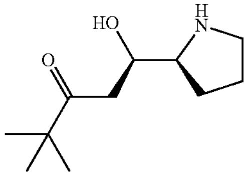

WV-CA-289

To a solution of compound 21 (16 g, 36.23 mmol) in EtOAc (25 mL) was added 4 M HCl/EtOAc (100 mL). The mixture was stirred at 25° C. for 0.5 hr. TLC showed the reaction was completed. The resulting mixture was filtered, and the solid was stirred in EtOAc (150 mL), filtered and re-triturated with EtOAc/MeOH (150 mL/5 mL), filtered and dried to afford compound WV-CA-289 (7.5 g, 87.8% yield, HCl salt) as a white solid. $^1$H NMR (400 MHz, METHANOL-$d_4$) δ=4.43 (ddd, J=3.5, 4.6, 7.8 Hz, 1H), 3.71 (dt, J=3.5, 8.0 Hz, 1H), 3.42-3.22 (m, 2H), 2.92 (dd, J=7.6, 17.7 Hz, 1H), 2.73 (dd, J=4.9, 17.7 Hz, 1H), 2.23-1.90 (m, 4H), 1.28-1.05 (m, 9H). [M+H]$^+$: 200.1, purity: 100.00%.

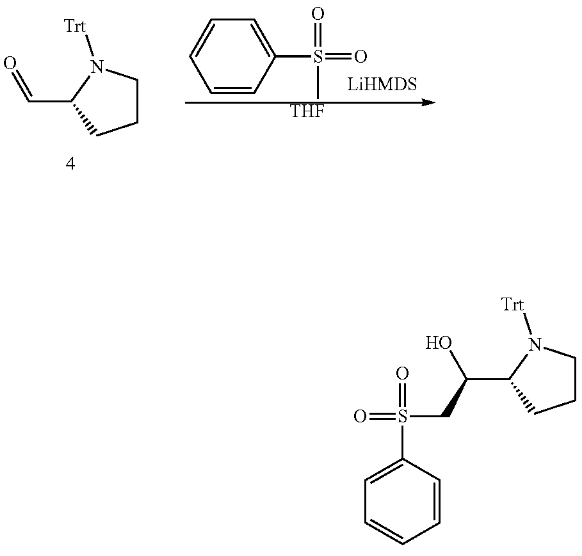

4

22

To a solution of methylsulfonylbenzene (13.72 g, 87.86 mmol) in THF (100 mL) was added LiHMDS (1 M, 87.86 mL) in 0.5 hr at −70° C.-0° C., then added compound 4 in THF (100 mL). The mixture was stirred at −70° C. in 2.5 hr. TLC indicated compound 4 was remained a little and two new spots formed. The reaction mixture was quenched by addition sat. $NH_4Cl$ aq. (300 mL) at 0° C., extracted with DCM (200 mL×3). Dried over $Na_2SO_4$, filtered and concentrated under reduced pressure to give a residue. The crude was added THF (100 mL) and MeOH (150 mL), concentrated under reduced pressure at 45° C. until about 100 mL residue remained, filtered the solid. Repeated 3 times. Got solid 20 g, the mother liquid was concentrated under reduced pressure to get compound 22 (20 g, crude) was obtained as a yellow oil. Compound (1R)-2-(benzenesulfonyl)-1-[(2R)-1-tritylpyrrolidin-2-yl]ethanol (20 g, 68.61% yield) was obtained as a white solid.

Preparation of Compound WV-CA-290.

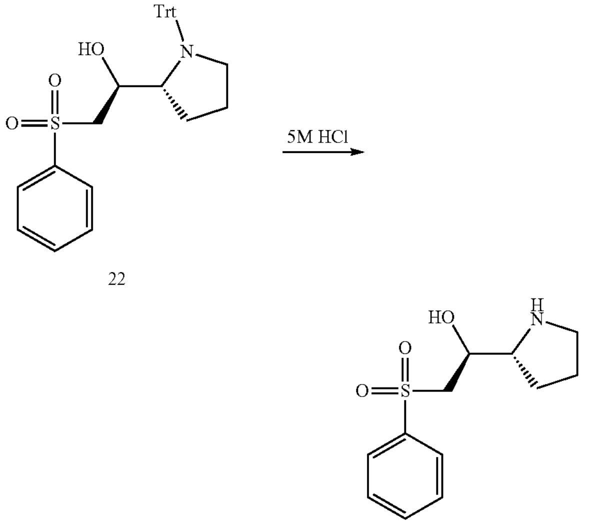

22

WV-CA-290

To a solution of compound 22 (20 g, 40.19 mmol) in THF (80 mL) was added HCl (5 M, 80.38 mL) at 0° C. The mixture was stirred at 25° C. for 2 hr. TLC showed the compound 22 was consumed and two new spots formed. The reaction mixture was washed with MTBE (50 mL×3), then the aqueous phase was basified by addition NaOH (5M) until pH=12 at 0° C., and then extracted with DCM (50 mL×3) to give a residue dried over $Na_2SO_4$, filtered and concentrated under reduced pressure to give a residue. The residue was purified by prep-HPLC (column: Phenomenex luna C18 250×50 mm×10 um; mobile phase: [water (0.1% TFA)—ACN]; B %: 0%-15%, 20 min). Compound WV-CA-290 (0.7 g, 6.78% yield, 99.39% purity) was obtained as a yellow solid. $^1$H NMR (400 MHz, CHLOROFORM-d) δ=7.95-7.85 (m, 2H), 7.64-7.56 (m, 1H), 7.55-7.46 (m, 2H), 3.79 (ddd, J=3.2, 5.4, 8.4 Hz, 1H), 3.28-3.05 (m, 3H), 2.92-2.72 (m, 2H), 1.84-1.54 (m, 3H), 1.51-1.37 (m, 1H). $^{13}$C NMR (101 MHz, CHLOROFORM-d) δ=139.81, 133.74, 129.19, 128.07, 68.15, 61.55, 60.97, 46.67, 28.03, 26.27. SFC: (AD_MeOH_IPAm_10_40_25_35_6 min), 100% purity. LCMS [M+H]$^+$: 256.1. LCMS purity: 99.39%.

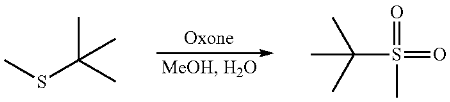

23A

Two batches in parallel: To a solution of compound tert-butyl(methyl)sulfane (25 g, 239.89 mmol) in MeOH (625 mL) was added Oxone (457.18 g, 743.67 mmol) in $H_2O$ (625 mL) at 0° C. The mixture was stirred at 15° C. for 12 hr. HNMR showed compound tert-butyl(methyl)sulfane was consumed completely and desired compound was detected. Combined two batches of the reaction mixture, filtered and concentrated under reduced pressure to evaporate the MeOH, and then extracted with EtOAc (400 mL×4). The combined organic layers were dried over $Na_2SO_4$, filtered and concentrated under reduced pressure to give a residue. Compound 23A (55 g, crude) was obtained as a colorless oil, confirmed by HNMR. $^1$HNMR (400 MHz, CHLOROFORM-d) δ=7.26 (s, 1H), 5.30 (s, 8H), 2.81 (s, 3H), 1.43 (s, 9H).

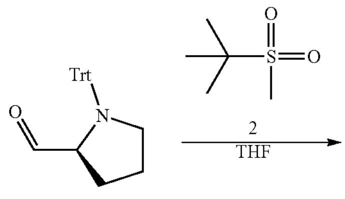

1

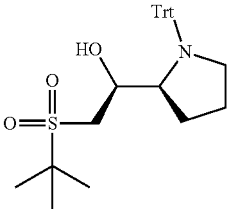

23

To a solution of compound 23A (50 g, 367.07 mmol) in THF (510 mL) was added KHMDS (1 M, 367.07 mL) dropwise at −70° C., and warm to −30° C. slowly over 30 min. The mixture was then cooled to −70° C. A solution of compound 1 (83.56 g, 244.72 mmol) in THF (340 mL) was added dropwise at −70° C. The mixture was stirred at −70° C. for 4 hr. TLC showed compound 1 was remained a little, and one major new spot with larger polarity was detected. The reaction mixture was quenched by added to the sat. $NH_4Cl$ (aq. 800 mL), and then extracted with EtOAc (500 mL×3). The combined organic layers were dried over $Na_2SO_4$, filtered and concentrated under reduced pressure to give brown oil. The crude was dissolved with THF (300 mL) then concentrated under reduced pressure (40° C.) to give 150 mL clarified solution. Then added to 300 mL MeOH and concentrated under reduced pressure to give 200 mL solution, then filtered to give a residue and washed with MeOH (10 mL). The mother solution was concentrated under reduced pressure to give 100 mL solution then filtered to give a residue and washed with MeOH (10 mL). Combined all the residue, repeated two times to give 60 g residue. Compound 23 (60 g, crude) was obtained as a white solid. $^1$HNMR (400 MHz, CHLOROFORM-d) δ=7.56 (d, J=7.5 Hz, 6H), 7.32-7.23 (m, 6H), 7.21-7.14 (m, 3H), 4.85-4.68 (m, 1H), 3.41 (td, J=3.8, 8.1 Hz, 1H), 3.28 (td, J=8.5, 11.9 Hz, 1H), 3.09-2.91 (m, 2H), 2.78 (dd, J=2.6, 13.6 Hz, 1H), 1.65-1.50 (m, 1H), 1.37 (s, 9H), 1.16-0.98 (m, 2H), 0.39-0.21 (m, 1H).

Preparation of Compound WV-CA-240.

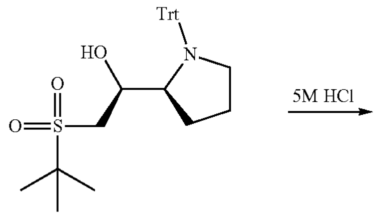

23

-continued

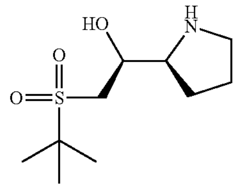

WV-CA-240

To a solution of compound 23 (59 g, 123.52 mmol) in THF (500 mL) was added HCl (5 M, 247.04 mL). The mixture was stirred at 20° C. for 3 hr. TLC indicated compound 23 was consumed completely and one major new spot with larger polarity was detected. The resulting mixture was washed with MTBE (500 mL×3). The combined aqueous layer was adjusted to pH 12 with 5 M NaOH aq. and extracted with DCM (200 mL×3). The combined organic layers were dried over anhydrous $Na_2SO_4$, filtered and concentrated to afford a white solid. WV-CA-240 (23.6 g, 81.14% yield, 99.95% purity) was obtained as a white solid. $^1$HNMR (400 MHz, CHLOROFORM-d) δ=4.18 (ddd, J=2.8, 5.8, 8.2 Hz, 1H), 3.29-3.21 (m, 1H), 3.19 (d, J=2.6 Hz, 1H), 3.16-3.08 (m, 1H), 2.92 (t, J=6.6 Hz, 2H), 2.74 (br s, 2H), 1.92-1.81 (m, 1H), 1.81-1.61 (m, 3H), 1.42 (s, 9H). $^{13}$CNMR (101 MHz, CHLOROFORM-d) δ=68.01, 62.00, 59.73, 49.79, 46.96, 26.77, 25.80, 23.22. LCMS $[M+H]^+$: 236.1. LCMS purity 99.95%.

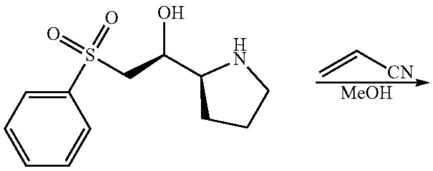

WV-CA-108

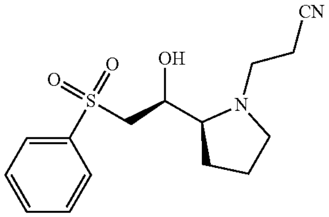

24

To a solution of WV-CA-108 (37 g, 144.91 mmol, 1 eq.) in MeOH (370 mL) was added prop-2-enenitrile (7.69 g, 144.91 mmol, 9.61 mL, 1 eq.). The mixture was stirred at 20° C. for 3 hr., (TLC, Petroleum ether:Ethyl acetate=1:3, Rf=0.31) showed WV-CA-108 was consumed completely and in LCMS one main peak with desired MS was detected. The reaction mixture was filtered and concentrated under reduced pressure to give a residue. Compound 24 (44 g, crude) was obtained as a white solid. LCMS $[M+H]^+$: 308.9.

Preparation of Compound WV-CA-291.

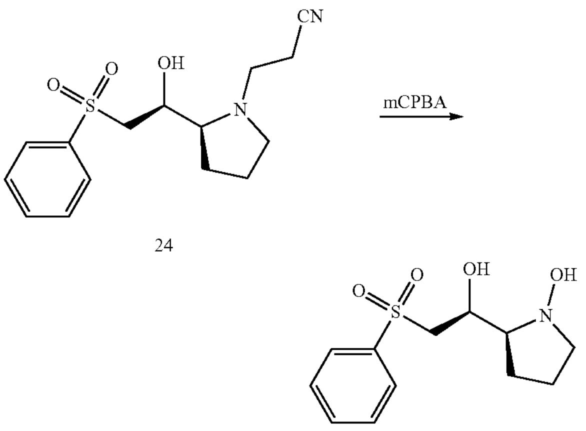

24

WV-CA-291

A solution of compound 24 (44 g, 142.67 mmol, 1 eq.) in DCM (220 mL) and MeOH (220 mL) was cooled to −78° C. Then mCPBA (36.93 g, 214.01 mmol, 1.5 eq.) and $K_2CO_3$ (29.58 g, 214.01 mmol, 1.5 eq.) was added. After addition, the mixture was stirred at −78° C. for 3 hr. And the resulting mixture was stirred at 20° C. for 12 hr. LC-MS showed compound 24 was consumed completely and one main peak with desired MS was detected. The reaction mixture was filtered and concentrated under reduced pressure to give a residue. The residue was purified by flash silica gel chromatography. The residue was purified by flash silica gel chromatography (ISCO®; 220 g SepaFlash® Silica Flash Column, Eluent of 0-30% Ethyl acetate/Petroleum ether gradient at 100 mL/min). WV-CA-291 (12 g, 42.05 mmol, 29.47% yield, 95.08% purity) was obtained as a yellow solid. $^1$H NMR (400 MHz, CHLOROFORM-d) δ=7.98-7.92 (m, 2H), 7.65 (d, J=7.5 Hz, 1H), 7.61-7.53 (m, 2H), 4.50-4.39 (m, 1H), 3.33-3.15 (m, 3H), 2.97-2.78 (m, 2H), 1.89-1.64 (m, 4H). $^{13}$CNMR (101 MHz, CHLOROFORM-d) δ=139.61, 133.90, 129.31, 128.02, 71.21, 64.96, 60.05, 58.12, 21.23, 20.29. LCMS $[M+H]^+$: 272.0. LCMS purity 95.08%.

Example 11. Example Technologies for Chirally Controlled Oligonucleotide

Preparation—Example Phosphoramidites.

Among other things, the present disclosure provides phosphoramidites useful for oligonucleotide synthesis. In some embodiments, provided phosphoramidites are particularly useful for preparation of chirally controlled internucleotidic linkages. In some embodiments, provided phosphoramidites are particularly useful for preparing chirally controlled internucleotidic linkages, e.g., non-negatively charged internucleotidic linkages or neutral internucleotidic linkages, etc., that comprise P—N═. In some embodiments, the linkage phosphorus is trivalent. In some embodiments, the linkage phosphorus is pentavalent. In some embodiments, such internucleotidic linkages have the structure of formula VII, VII-a-1, VII-a-2, VII-b, VII-c, VII-d, VII-e, NL-n-1, NL-n-2, NL-n-3, NL-n-4, NL, NL-a-1, NL-a-2, NL-b-1, NL-b-2, NL-c-1, NL-c-2, NL-d-1, or NL-d-2, or a salt form thereof.

General Procedure I for Chloroderivative: In some embodiments, in an example procedure, a chiral auxiliary (174.54 mmol) was dried by azeotropic evaporation with anhydrous toluene (80 mL×3) at 35° C. in a rota-evaporator and dried under high vacuum for overnight. A solution of this dried chiral auxiliary (174.54 mmol) and 4-methylmorpholine (366.54 mmol) dissolved in anhydrous THF (200 mL) was added to an ice-cooled (isopropyl alcohol-dry ice bath) solution of trichlorophosphine (37.07 g, 16.0 mL, 183.27 mmol) in anhydrous THF (150 mL) placed in three neck round bottomed flask through cannula under Argon (start Temp: −10.0° C., Max: temp 0° C., 28 min addition) and the reaction mixture was warmed at 15° C. for 1 hr. After that the precipitated white solid was filtered by vacuum under argon using airfree filter tube (Chemglass: Filter Tube, 24/40 Inner Joints, 80 mm OD Medium Frit, Airfree, Schlenk). The solvent was removed with rota-evaporator under argon at low temperature (25° C.) and the crude semi-solid obtained was dried under vacuum overnight (~15 h) and was used for the next step directly.

General Procedure I for Chloroderivative: In some embodiments, in an example procedure, a chiral auxiliary (174.54 mmol) was dried by azeotropic evaporation with anhydrous toluene (80 mL×3) at 35° C. in a rota-evaporator and dried under high vacuum for overnight. A solution of this dried chiral auxiliary (174.54 mmol) and 4-methylmorpholine (366.54 mmol) dissolved in anhydrous THF (200 mL) was added to an ice-cooled (isopropyl alcohol-dry ice bath) solution of trichlorophosphine (37.07 g, 16.0 mL, 183.27 mmol) in anhydrous THF (150 mL) placed in three neck round bottomed flask through cannula under Argon (start Temp: −10.0° C., Max: temp 0° C., 28 min addition) and the reaction mixture was warmed at 15° C. for 1 hr. After that the precipitated white solid was filtered by vacuum under argon using airfree filter tube (Chemglass: Filter Tube, 24/40 Inner Joints, 80 mm OD Medium Frit, Airfree, Schlenk). The solvent was removed with rota-evaporator under argon at low temperature (25° C.) and the crude semi-solid obtained was dried under vacuum overnight (~15 h) and was used for the next step directly.

General Procedure III for Coupling: In some embodiments, in an example procedure, a nucleoside (9.11 mmol) was dried by co-evaporation with 60 mL of anhydrous toluene (60 mL×2) at 35° C. and dried under high vacuum for overnight. The dried nucleoside was dissolved in dry THF (78 mL), followed by the addition of triethylamine (63.80 mmol) and then cooled to −5° C. under Argon (for 2'F-dG/2'OMe-dG case 0.95 eq of TMS-Cl used). The THF solution of the crude (made from general procedure I (or) II, 14.57 mmol), was added through cannula over 3 min then gradually warmed to room temperature. After 1 hr at room temperature, TLC indicated conversion of SM to product (total reaction time 1 h), the reaction mixture was then quenched with $H_2O$ (4.55 mmol) at 0° C. and anhydrous $MgSO_4$ (9.11 mmol) was added and stirred for 10 min. Then the reaction mixture was filtered under argon using airfree filter tube, washed with THF, and dried under rotary evaporation at 26° C. to afford white crude solid product, which was dried under high vacuum overnight. The crude product was purified by ISCO-Combiflash system (rediSep high performance silica column pre-equilibrated with Acetonitrile) using Ethyl acetate/Hexane with 1% TEA as a solvent (compound eluted at 100% EtOAc/Hexanes/1% $Et_3N$) (for 2'F-dG case Acetonitrile/Ethyl acetate with 1% TEA used). After evaporation of column fractions pooled together, the residue was dried under high vacuum to afford the product as a white solid.

Preparation of Amidites (1030-1039).

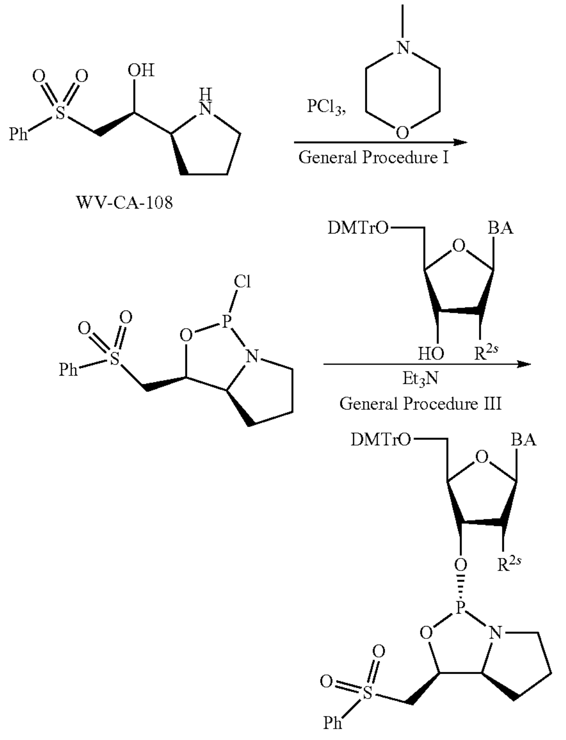

1030: $R^{2s}$ = F, BA = $G^{iBu}$
1031: $R^{2s}$ = F, BA = U
1032: $R^{2s}$ = F, BA = $C^{Ac}$
1033: $R^{2s}$ = F, BA = $A^{Bz}$
1034: $R^{2s}$ = OMe, BA = $A^{Bz}$
1035: $R^{2s}$ = MOE, BA = $A^{Bz}$
1036: $R^{2s}$ = MOE, BA = $G^{iBu}$
1037: $R^{2s}$ = MOE, BA = T
1038: $R^{2s}$ = MOE, BA = 5-Methyl-$C^{Bz}$
1039: $R^{2s}$ = H, B = $C^{Ac}$ Preparation of 1030: General Procedure I followed by General Procedure III used. Off-white foamy solid. Yield: (73%). $^{31}$P NMR (162 MHz, $CDCl_3$) δ 153.32. (ES) m/z Calculated for $C_{47}H_{50}FN_6O_{10}PS$: 940.98 $[M]^+$, Observed: 941.78 $[M+H]^+$.

Preparation of 1031: General Procedure I followed by General Procedure III used. Off-white foamy solid. Yield: (78%). $^{31}$P NMR (162 MHz, $CDCl_3$) δ 153.62. (ES) m/z Calculated for $C_{42}H_{43}FN_3O_{10}PS$: 831.85 $[M]^+$, Observed: 870.58 $[M+K]^+$.

Preparation of 1032: General Procedure I followed by General Procedure III used. Off-white foamy solid. Yield: (68%). $^{31}$P NMR (162 MHz, $CDCl_3$) δ 153.95. (ES) m/z Calculated for $C_{44}H_{46}FN_4O_{10}PS$: 872.26 $[M]^+$, Observed: 873.62 $[M+H]^+$.

Preparation of 1033: General Procedure I followed by General Procedure III used. white foamy solid. Yield: (87%). $^{31}$P NMR (162 MHz, $CDCl_3$) δ 151.70. (ES) m/z Calculated for $C_{50}H_{48}FN_6O_9PS$: 958.29 $[M]^+$, Observed: 959.79, 960.83 $[M+H]^+$.

Preparation of 1034: General Procedure I followed by General Procedure III used. Off-white foamy solid. Yield: (65%). $^{31}$P NMR (162 MHz, $CDCl_3$) δ 154.80. (ES) m/z Calculated for $C_{51}H_{51}N_6O_{10}PS$: 971.31 $[M]^+$, Observed: 971.81 $[M+H]^+$.

Preparation of 1035: General Procedure I followed by General Procedure III used. Off-white foamy solid. Yield: (76%). $^{31}$P NMR (162 MHz, $CDCl_3$) δ 156.50. (ES) m/z Calculated for $C_{53}H_{55}N_6O_{10}PS$: 1014.33 $[M]^+$, Observed: 1015.81 $[M+H]^+$.

Preparation of 1036: General Procedure I followed by General Procedure III used. Off-white foamy solid. Yield: (78%). $^{31}$P NMR (162 MHz, $CDCl_3$) δ 156.40. (ES) m-z Calculated for $C_{50}H_{57}N_6O_{12}PS$: 996.34 $[M]^+$, Observed: 997.90 $[M+H]^+$.

Preparation of 1037: General Procedure I followed by General Procedure III used. Off-white foamy solid. Yield: (73%). $^{31}$P NMR (162 MHz, $CDCl_3$) δ 154.87. (ES) m/z Calculated for $C_{46}H_{52}N_3O_{12}PS$: 901.30 $[M]^+$, Observed: 940.83 $[M+K]^+$.

Preparation of 1038: General Procedure I followed by General Procedure III used. Off-white foamy solid. Yield: (75%). $^{31}$P NMR (162 MHz, $CDCl_3$) δ 154.94. (ES) m/z Calculated for $C_{53}H_{57}N_4O_{12}PS$: 1004.34 $[M]^+$, Observed: 1005.86 $[M+H]^+$.

Preparation of 1039: General Procedure I followed by General Procedure III used. Off-white foamy solid. Yield: (80%). $^{31}$P NMR (162 MHz, $CDCl_3$) δ 153.52. (ES) m/z Calculated for $C_{44}H_{47}N_4O_{10}PS$: 854.28 $[M]^+$, Observed: 855.41 $[M+H]^+$.

Preparation of Amidites (1040-1049).

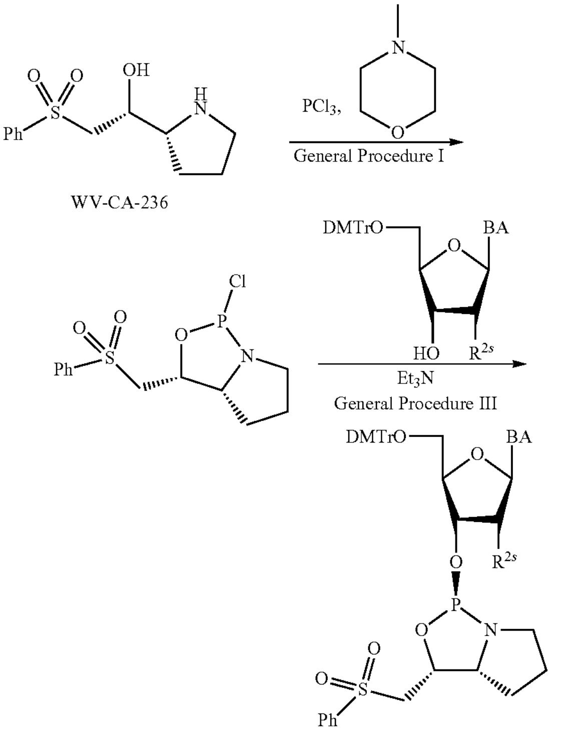

1040: $R^{2s}$ = F, BA = $G^{iBu}$
1041: $R^{2s}$ = F, BA = U
1042: $R^{2s}$ = F, BA = $C^{Ac}$
1043: $R^{2s}$ = F, BA = $A^{Bz}$
1044: $R^{2s}$ = OMe, BA = $A^{Bz}$
1045: $R^{2s}$ = MOE, BA = $A^{Bz}$
1046: $R^{2s}$ = MOE, BA = $G^{iBu}$
1047: $R^{2s}$ = MOE, BA = T
1048: $R^{2s}$ = MOE, BA = 5-Methyl-$C^{Bz}$
1049: $R^{2s}$ = H, B = $C^{Ac}$ Preparation of 1040: General Procedure I followed by General Procedure III used. Off-white foamy solid. Yield: (78%). $^{31}P$ NMR (162 MHz, $CDCl_3$) δ 157.80. (ES) m/z Calculated for $C_{47}H_{50}FN_6O_{10}PS$: 940.98 $[M]^+$, Observed: 941.68 $[M+H]^+$.

Preparation of 1041: General Procedure I followed by General Procedure III used. Off-white foamy solid. Yield: (78%). $^{31}P$ NMR (162 MHz, $CDCl_3$) δ 157.79. (ES) m/z Calculated for $C_{42}H_{43}FN_3O_{10}PS$: 831.85 $[M]^+$, Observed: 870.68 $[M+K]^+$.

Preparation of 1042: General Procedure I followed by General Procedure III used. Off-white foamy solid. Yield: (78%). $^{31}P$ NMR (162 MHz, $CDCl_3$) δ 158.07. (ES) m/z Calculated for $C_{44}H_{46}FN_4O_{10}PS$: 872.26 $[M]^+$, Observed: 873.62 $[M+H]^+$.

Preparation of 1043: General Procedure I followed by General Procedure III used. white foamy solid. Yield: (86%). $^{31}P$ NMR (162 MHz, $CDCl_3$) δ 156.48. (ES) mi Calculated for $C_{50}H_{48}FN_6O_9PS$: 958.29 $[M]^+$, Observed: 959.79, 960.83 $[M+H]^+$.

Preparation of 1044: General Procedure I followed by General Procedure III used. Off-white foamy solid. Yield: (65%). $^{31}P$ NMR (162 MHz, $CDCl_3$) δ 154.80. (ES) m/z Calculated for $C_{51}H_{51}N_6O_{10}PS$: 971.31 $[M]^+$, Observed: 971.81 $[M+H]^+$.

Preparation of 1045: General Procedure I followed by General Procedure III used. Off-white foamy solid. Yield: (77%). $^{31}P$ NMR (162 MHz, $CDCl_3$) δ 154.74. (ES) m/z Calculated for $C_{53}H_{55}N_6O_{11}PS$: 1014.33 $[M]^+$, Observed: 1015.81 $[M+H]^+$.

Preparation of 1046: General Procedure I followed by General Procedure III used. Off-white foamy solid. Yield: (76%). $^{31}P$ NMR (162 MHz, $CDCl_3$) δ 155.05. (ES) m/z Calculated for $C_{50}H_{57}N_6O_{12}PS$: 996.34 $[M]^+$, Observed: 997.90 $[M+H]^+$.

Preparation of 1047: General Procedure I followed by General Procedure III used. Off-white foamy solid. Yield: (75%). $^{31}P$ NMR (162 MHz, $CDCl_3$) δ 155.44. (ES) m/z Calculated for $C_{46}H_{52}N_3O_{12}PS$: 901.30 $[M]^+$, Observed: 940.83 $[M+K]^+$.

Preparation of 1048: General Procedure I followed by General Procedure III used. Off-white foamy solid. Yield: (73%). $^{31}P$ NMR (162 MHz, $CDCl_3$) δ 155.96. (ES) m/z Calculated for $C_{53}H_{57}N_4O_{12}PS$: 1004.34 $[M]^+$, Observed: 1005.86 $[M+H]^+$.

Preparation of 1049: General Procedure I followed by General Procedure III used. Off-white foamy solid. Yield: (80%). $^{31}P$ NMR (162 MHz, $CDCl_3$) δ 156.37. (ES) m/z Calculated for $C_{44}H_{47}N_4O_{10}PS$: 854.28 $[M]^+$, Observed: 855.31 $[M+H]^+$.

Preparation of Amidites (1051).

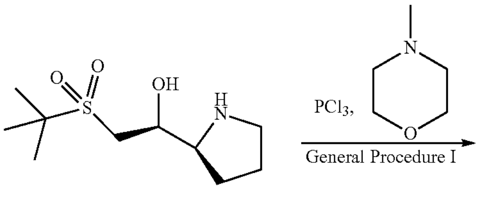

WV-CA-240

-continued

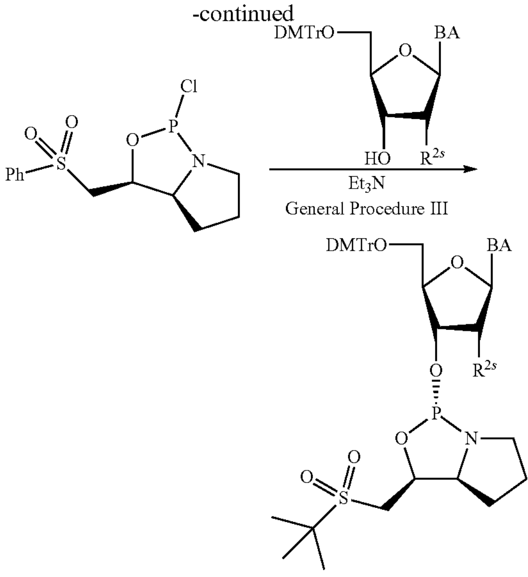

1051: $R^{2s}$ = F, BA = $C^{4c}$

Preparation of 1051: General Procedure II followed by General Procedure III used. Off-white foamy solid. Yield: (72%). $^{31}P$ NMR (162 MHz, $CDCl_3$) δ 154.26. (ES) m/z Calculated for $C_{42}H_{50}FN_4O_{10}PS$: 852.29 $[M]^+$, Observed: 853.52 $[M+H]^+$.

Preparation of Amidites (1052).

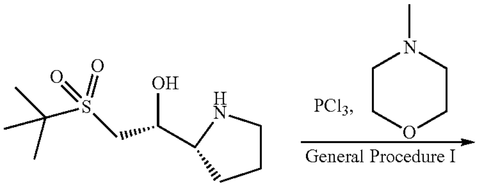

WV-CA-241

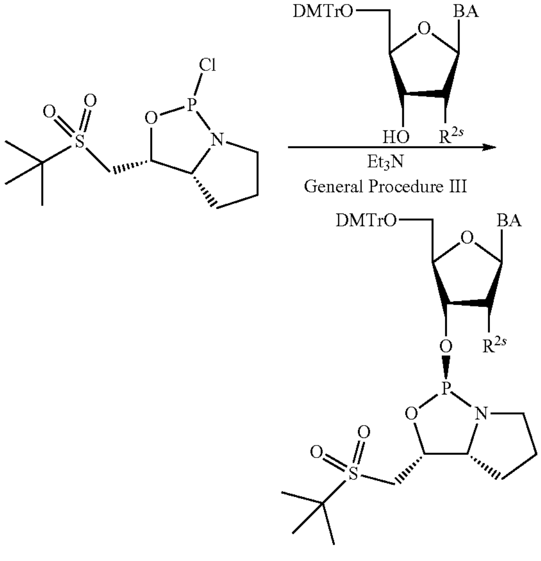

1052: $R^{2s}$ = F, BA = $C^{4c}$

Preparation of 1052: General Procedure 11 followed by General Procedure III used. Off-white foamy solid. Yield:

(76%). $^{31}P$ NMR (162 MHz, $CDCl_3$) δ 156.37. (ES) m/z Calculated for $C_{42}H_{50}FN_4O_{10}PS$: 852.29 $[M]^+$, Observed: 853.52 $[M+H]^+$.

Preparation of Amidites (1053, 1054).

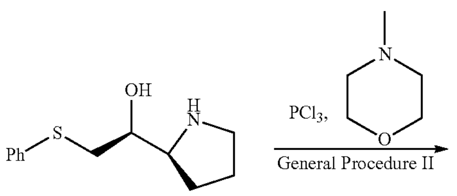

WV-CA-244

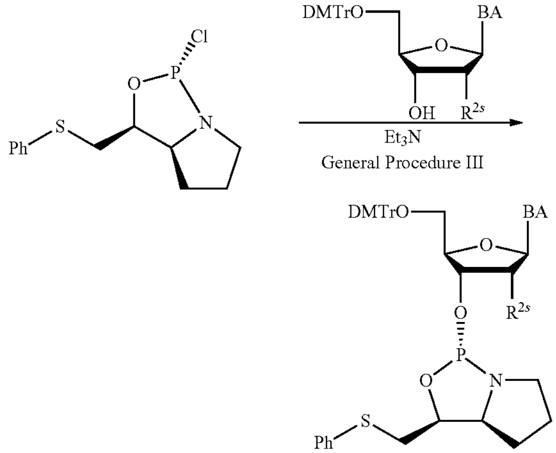

1053: $R^{2s}$ = F, BA = $G^{iBu}$
1054: $R^{2s}$ = F, BA = $C^{Ac}$

Preparation of 1053: General Procedure II followed by General Procedure III used. Off-white foamy solid. Yield: (80%). $^{31}P$ NMR (162 MHz, $CDCl_3$) δ 156.62. (ES) m/z Calculated for $C_{47}H_{50}FN_6O_8PS$: 908.98 $[M]^+$, Observed: 909.36 $[M+H]^+$.

Preparation of 1054: General Procedure 11 followed by General Procedure III used. Off-white foamy solid. Yield: (79%). $^{31}P$ NMR (162 MHz, $CDCl_3$) δ 157.62. (ES) m/z Calculated for $C_{44}H_{46}FN_4O_8PS$: 840.90 $[M]^+$, Observed: 841.67 $[M+H]^+$.

Preparation of Amidites (1055).

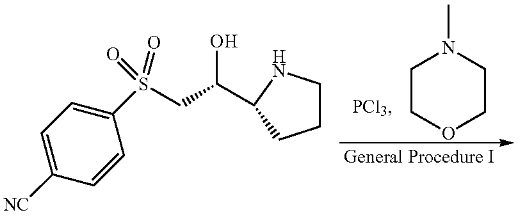

WV-CA-238

-continued

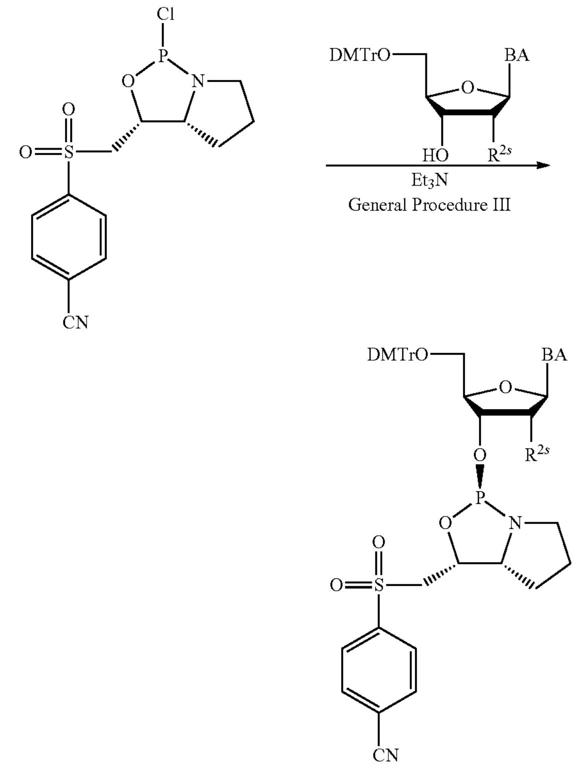

1055: $R^{2s}$ = F, BA = $C^{Ac}$

Preparation of 1055: General Procedure II followed by General Procedure III used. White foamy solid. Yield: (77%). $^{31}P$ NMR (162 MHz, $CDCl_3$) δ 160.00. (ES) m/z Calculated for $C_{45}H_{45}FN_5O_{10}PS$: 897.26 $[M]^+$, Observed: 898.74 $[M+H]^+$.

Preparation of Amidites (1056).

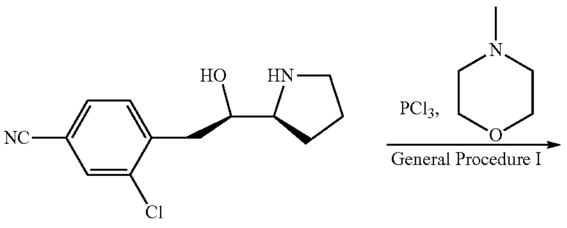

WV-CA-249

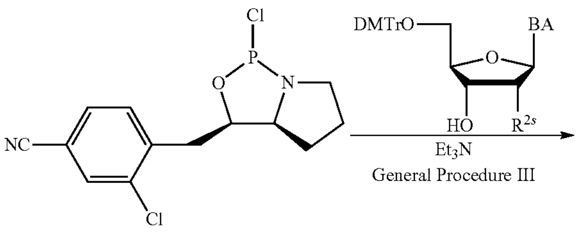

-continued

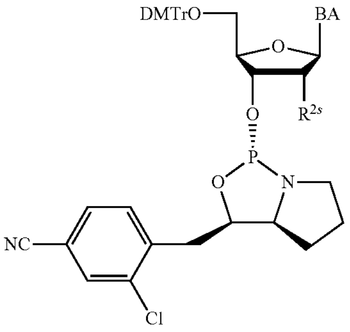

1056: $R^{2s}$ = F, BA = $C^{Ac}$

Preparation of 1056: General Procedure II followed by General Procedure III used. Off-white foamy solid. Yield: (84%). $^{31}P$ NMR (162 MHz, $CDCl_3$) δ 154.80. (ES) m/z Calculated for $C_{45}H_{44}ClFN_5O_8P$: 867.26 $[M]^+$, Observed: 868.69 $[M+H]^+$.

Preparation of Amidites (1057).

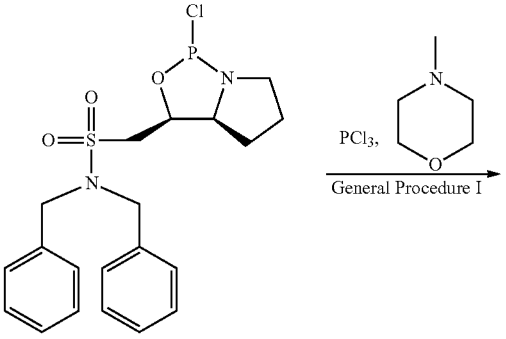

WV-CA-263

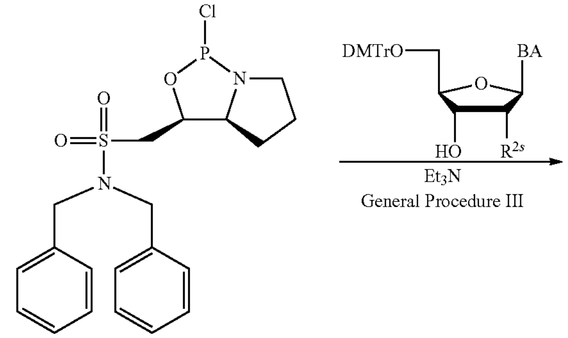

-continued

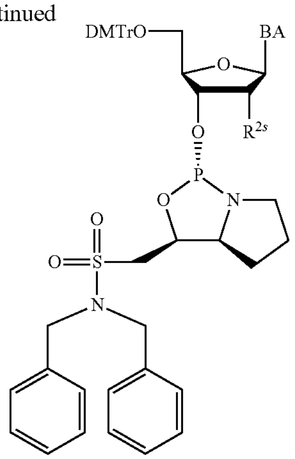

1057: $R^{2s}$ = F, BA = $C^{Ac}$

Preparation of 1057: General Procedure II followed by General Procedure III used. white foamy solid. Yield: (91%). $^{31}P$ NMR (162 MHz, $CDCl_3$) δ 154.48. (ES) m/z Calculated for $C_{52}H_{55}FN_5O_{10}PS$: 991.34 $[M]^+$, Observed: 992.87 $[M+H]^+$.

Example 12. Provided Technologies Provides High Stereoselectivity and Yields

Among other things, the present disclosure provides technologies that can deliver high stereoselectivity and yields, e.g., when used for oligonucleotide synthesis. For example, certain base-labile chiral auxiliaries, e.g., PSM auxiliaries, can deliver high stereoselectivity and yields comparable to or higher than other highly efficient and selective chiral auxiliaries, e.g., DPSE auxiliaries. Certain example results are presented herein. It is noted that to for certain assessment performed herein, "stringent" conditions were utilized—in typical oligonucleotide synthesis, provided technologies can deliver significantly better results; for example, it was routinely observed that when preparing long oligonucleotides (instead of dimers prepared under conditions described herein), coupling yields can be close to quantitative.

In some embodiments, reactions were performed starting with CPG-2'OMe-U (70 umol/g; 22.1 umol) on a nS-8II. An example synthesis condition was: 1. de-blocking: 3% TCA/DCM; 2. coupling: 0.2 M phosphoramidite (e.g., L- or D-PSM 2'-MOE/2'-F/2'-H (no 2'-substituent) amidite, etc.)/20% IBN-MeCN (4.5 eq.), 0.6 M CMIMT/MeCN (29.9 eq.), amidite (Amd): activator (Act)=1:6, 8 min: 3. pre-modification capping: Cap-B: 20% $Ac_2O$, 30% 2,6-lutidine, 50% MeCN, 2 min; 4. modification: 0.5 M ADIH/MeCN, 6 min; 5. post-modification capping: Cap-A+B, 45 sec; and 6. deprotection/removal/cleavage (for PSM): 1) 3% TCA/DCM: 2) 20% DEA/MeCN, rt, 12 min; and 3) conc. $NH_3$ (200 uL/umol), 55° C., 10 hours (for 2'-MOE dimers); or conc. $NH_3$ (fCmU sequences) or AMA (fGmU sequences) (200 uL/umol), 40° C. 2 hours.

In one run, for Aeo-n001-mU, yield was 95.6% for regular (traditional without any chiral auxiliary) Aeo amidite with $R_P$:$S_P$=68.1:31.9, yield was 91.3% for L-PSM Aeo amidite with $R_P$:$S_P$=99.8:0.2, and yield was 78.8% for D-PSM Aeo amidite with $R_P$:$S_P$=7.5:92.5.

In one run, for Geo-n001-mU, yield was 93.9% for regular Geo amidite with $R_P$:$S_P$=66.8 33.2, yield was 90.1% for L-PSM Geo amidite with $R_P$:$S_P$=99.8:0.2, and yield was 80.3% for D-PSM Geo amidite with $R_P$:$S_P$=7.7:92.3.

In one run, for Geo-PS (phosphorothioate)-mU, yield was 89.8% for regular Geo amidite with $R_P$:$S_P$=32.6:67.4, yield was 80.3% for L-PSM Geo amidite with $R_P$:$S_P$=0: >99.9, and yield was 71.7% for D-PSM Geo amidite with $R_P$:$S_P$=92.9:7.1.

In one run, for m5Ceo (5'-methyl on C and 2'-MOE on sugar)-n001-mU, yield was 86.6% for regular m5Ceo amidite with $R_P$:$S_P$=68.1:31.9, yield was 67.8% for L-PSM m5Ceo amidite with $R_P$:$S_P$=>99.9:0.1, and yield was 50.4% for D-PSM m5Ceo amidite with $R_P$:$S_P$=6.9:93.1.

In one run, for Teo-n001-mU, yield was 94.6% for regular Teo amidite with $R_P$:$S_P$=68.9:31.1, yield was 87.5% for L-PSM Teo amidite with $R_P$:$S_P$=99.9:0.1, and yield was 71.6% for D-PSM Teo amidite with $R_P$:$S_P$=10.2:89.8.

In some embodiments, it was observed D-TBTL ( 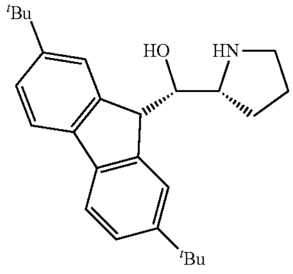 )

provided similar selectivity.

Without the intention to be limited by any theory, Applicant notes that selectivity for the D-PSM chiral auxiliary may be related to 2'-substituents; it was observed, as demonstrated below, D-PSM can deliver significantly higher selectivity for 2'-F, 2'-H (no substituent at the 2'-position), etc., which are smaller in size compared to 2'-MOE.

In one run, for fG-n001-mU, yield was 91.6% for regular fG amidite with $R_P$:$S_P$=51.2: 48.8, yield was 86.4% for L-PSM fG amidite with $R_P$:$S_P$=99.7:0.3, and yield was 84.9% for L-PSM fG amidite (2% epimer) with $R_P$:$S_P$=99.6:0.4.

In one run, for fC-n001-mU, yield was 97.3% for regular fC amidite with $R_P$:$S_P$=44.6:53.4, yield was 90.8% for L-PSM fC amidite with $R_P$:$S_P$=99.4:0.6, and yield was 91.8% for L-PSM fG amidite (1% epimer) with $R_P$:$S_P$=99.5:0.5.

In one run, for fG-PS-mU, yield was 94.3% for regular fG amidite with $R_P$:$S_P$=47.3:52.7, yield was 83.4% for L-DPSE fG amidite with $R_P$:$S_P$=0.6:99.4.

In one run, for fC-PS-mU, yield was 94.9% for regular fC amidite with $R_P$:$S_P$=52.9:47.1, yield was 80.3% for L-DPSE fC amidite with $R_P$:$S_P$=0.7:99.3.

In one run, for dC-n001-mU, yield was 94.5% for L-PSM dC amidite with $R_P$:$S_P$=1.0:99.0, and yield was 95.2% for D-PSM dC amidite with $R_P$:$S_P$=1.1:98.9.

Example 13. Provided Technologies Deliver Greatly Improved Results

Among other things, the present disclosure provides technologies which utilize base-labile chiral auxiliaries (e.g., PSM auxiliaries) that can be removed by contact with base under mild conditions. As demonstrated herein, such technologies can deliver high selectivity, high crude purity, high yield, and/or simple/alternative manufacturing processes (e.g., no use of F sources to remove chiral auxiliaries), etc. In some embodiments, technologies of the present disclosure facilitate purification and/or formulation processes by delivering crude compositions with high purity, high stereoselectivity and/or low amount of salts. An example preparation of WV-3473 utilizing PSM chiral auxiliaries based on preliminary tests is described below. In this example, preparation of WV-3473 was conducted on fU-CPG solid support using 2.0×7.0 cm stainless steel column at a scale of 396 μmol (batch 184).

Example Synthesis Process Parameters.

| Process Step | Parameter | Set Points |
|---|---|---|
| Synthesis Cycle | PSM | Detritylation<br>Coupling<br>Cap-1 (pre-modification capping step)<br>Modification - Thiolation<br>Capping (post-modification capping step) |
| | Standard | Detritylation<br>Coupling<br>Modification - Oxidation<br>Capping (Cap-2; post-modification capping step) |
| Column, Scale, Synthesizer | Column | Stainless steel |
| | Column Diameter | 2.0 cm |
| | Column Bed Height | 7.0 cm |
| | Column Volume | 22.0 mL |
| | Scale | 396 μmol |
| | Synthesizer | AKTA OligoPilot 100 |
| CPG | Solid Support | 2'-F-U Via CNA Linker CPG |
| | Support Loading | 72 μmol/g |
| | Adjusted Support Density | 0.25 g/c.c. |
| Pre-Synthesis Wash | Pre-Synthesis Wash Solvent | Acetonitrile |
| | Pre-Synthesis Wash Flow Rate | 424 cm/h |
| | Pre-Synthesis Wash Volume | 2 CV |

-continued

| Process Step | Parameter | Set Points |
|---|---|---|
| De-blocking (Detritylation) | Reagent | 3% Dichloroacetic acid (DCA) in Toluene |
| | Control Mode | UV watch command |
| | Detrit Wavelength | 436 nm |
| | Detrit UV Watch | On: 500 mAu with 1.2 CV delay<br>Off: 1000 mAu |
| | UV Autozero | Autozero on 3% DCA in bypass prior to the 1st detrit |
| | Detrit Flow Rate | 424 cm/h |
| | Post Detritylation | 4 CV |
| | ACN wash | 424 cm/h |
| Coupling (for PSM amidites) | Chiral PSM Amidite Eq./Support | 2.5 eq. |
| | Concentration and Diluent of PSM Amidite | 0.2M of 2'-F-A-(L) PSM, 2'-F-C-(L) PSM, 2'-F-G-(L) –PSM, 2'-F-U-(L) PSM and 2'-OMe-A-(L) PSM in 100% ACN |
| | Density of the PSM Amidite Solution | Non-adjusted |
| | Drying of PSM Amidite Solution | Molecular Sieves, 3 Å, 15-20% w.r.t. amidite solution, v./v<br>Drying time = NLT 4 h |
| | Activator | CMIMT |
| | Activator Concentration | 0.5M in ACN |
| | CMIMT Eq./Support | 12.69 |
| | Density of CMIMT Solution | Non-adjusted |
| | Drying of CMIMT Solution | Molecular Sieves, 3 Å, 10%, w.r.t. CMIMT solution, v/v<br>Drying time = NLT 4 h |
| | CMIMT/PSM Amidite Molar Ratio | 5.076:1 |
| | CMIMT % Volume | 67% |
| | Coupling Charge Flow Rate for all chiral amidites | 56.7 cm/h |
| | Coupling Charge Flow Rate for CMIMT | 115.1 cm/h |
| | Coupling Charge Volume (Amidite + CMIMT) | 15.0 mL |
| | Push Volume | 4.5 mL |
| | Recycle Flow Rate | 212 cm/h |
| | Recycle Times | 10 min |
| | Coupling ACN Wash Flow Rate | 424 cm/h |
| | Coupling ACN Wash Volume | 2.0 CV |
| Coupling (for standard amidites) | Standard Amidite Eq./Support | 2.5 eq. |
| | Concentration of Standard Amidite | 0.2M in ACN |
| | Density of Standard amidite Solution | Non-adjusted |
| | Drying of Standard Amidite Solution | Molecular Sieves, 3 Å, 15-20% w.r.t. amidite solution, v/v<br>Drying time = NLT 4 h |
| | Activator | ETT |
| | Activator Concentration | 0.5M in ACN |
| | Density of ETT Solution | Non-adjusted |
| | Drying of ETT Solution | Molecular sieves, 3 Å, 10% volume w.r.t. ETT solution, v/v |
| | ETT Eq./Support | 7.64 |
| | ETT/Random Amidite Molar Ratio | 3.056:1 |
| | ETT % | 55% |
| | Coupling Charge Flow Rate for standard amidites | 56.7 cm/h |
| | Coupling Charge Flow Rate for ETT | 69.3 cm/h |
| | Coupling Charge Volume (Amidite + ETT) | 11.0 mL |
| | Push Volume | 4.5 mL |
| | Recycle Flow Rate | 212 cm/h |
| | Recycle Times | 8 min |
| | Coupling ACN Wash Flow Rate | 42.4 cm/h |
| | Coupling ACN Wash Volume | 2.0 CV |

-continued

| Process Step | Parameter | Set Points |
|---|---|---|
| Cap 1 (Pre-modification capping step) | Mode | Flow Through |
| | Reagent (Cap B) | 20%:30%:50% = $Ac_2O$:2,6-Lut.:ACN (v/v/v) |
| | Column Volumn (CV) | 2 CV |
| | Contact Time (CT) | 4 min |
| | Cap B Charge Flow Rate | 11 mL/min |
| | ACN Push Volume (after Cap B charge) | 1.3 CV |
| | ACN Push Flow rate_B (after Cap B charge) | 11 mL/min |
| Modification (Thiolation) | Mode | Flow Through |
| | Reagent | 0.1M Xanthane hydride in pyridine/acetonitrile, 50/50, v/v |
| | Density of thiolation reagent | Non-adjusted |
| | Charge Volume | 1.2 CV |
| | Charge Flow Rate_B | 84.0 cm/h |
| | Contact Time | 6 min |
| | ACN Push Flow Rate B | 84.0 cm/h |
| | ACN Push Volume | 1.3 CV |
| | Post-thio ACN Wash Flow rate (Flow_AB) | 424 cm/h |
| | Post-thio ACN Wash Volume | 1.0 CV |
| Cap 2 (Post-modification capping step) | Reagent | Cap A 20% N-Methylimidazole in acetonitrile (NMI/ACN = 20/80, v/v |
| | | Cap B 20%:30%:50% = $Ac_2O$:2,6-Lut.:ACN (v/v/v) |
| | Mode | Flow Through |
| | Charge Volume | 0.4 CV |
| | Contact Time | 0.8 min |
| | Charge Flow Rate | Cap A = 105.0 cm/h<br>Cap B = 105.0 cm/h |
| | After Charge, ACNPush Plow rate_AB | ACN Pump A = 105.0 cm/h<br>ACN Pump B = 105.0 cm/h |
| | After Charge, ACN Push Volume_AB | 1.3 CV |
| | Capping Wash Volume_AB | 1.0 CV |
| | Capping Wash Plow Rate_AB | 424 cm/h |
| Modification (Oxidation) | Mode | Flow Through |
| | Reagent | 0.05M Iodine in pyridine/water, 90/10, v/v |
| | Concentration of Iodine solution | 0.05M |
| | Eq. Iodine to Solid Support | 3.5 eq. |
| | Contact Time | 2.0 min |
| | Ox Solution Charge Flow Rate | 264.0 cm/h |
| | After Charge, ACN Push Flow Rate | 264.0 cm/h |
| | After Charge, ACN Push Volume | 1.3 CV |
| | Post-Ox ACN Wash Flow rate | 424 cm/h |
| | Post-Ox ACN Wash Volume | 1.0 CV |
| Post Synthesis ACN Wash | ACN Wash Flow Rate | 424 cm/h |
| | ACN Wash Flow Volume | 2.0 CV |
| Auxiliary Removal (20% DEA Wash) | Reagent | 20% Diethylamine in acetonitrile |
| | Delivery mode | Flow through |
| | Charge Volume | 5 CV |
| | Contact time | 15 min |
| | Charge flow rate | 140 cm/h |
| | Charge ACN Push flow rate | 140 cm/h |
| | Charge ACN Push volume | 1.3 CV |
| | Post DEA ACN Wash flowrate | 424 cm/h |
| | Post DEA ACN wash volume | 3 CV |

Certain raw materials are listed below:

| Abbreviation | Name of Raw Materials |
|---|---|
| fU-CPG | 2'-fU via CNA linker CPG (600 Å LED) |
| fA-L-PSM | 5'-O-DMT-2'-F-dA (Bz)-(L)-PSM Phosphoramidite |
| fC-L-PSM | 5'-O-DMT-2'-F-dC (Ac)-(L)-PSM Phosphoramidite |
| fG-L-PSM | 5'-O-DMT-2'-F-dG (iBu)-(L)-PSM Phosphoramidite |
| fU-L-PSM | 5'-O-DMT-2'-F-dU-(L)-PSM Phosphoramidite |
| mA-L-PSM | 5'-O-DMT-2'-OMe-A (Bz)-(L)-PSM Phosphoramidite |
| mA-CE | 5'-O-DMT-2'-OMe-A (Bz)-β-Cyanoethyl Phosphoramidite |
| mG-CE | 5'-O-DMT-2'-OMe-G (iBu)-β-Cyanoethyl Phosphoramidite |
| XH | Xanthane Hydride |
| Pyr | Pyridine |
| Ox | 0.04-0.06M Iodine in pyridine/water, 90/10, v/v |
| Cap A | N-Methylimidazole in acetonitrile, 20/80, v/v |
| Cap B | Acetic anhydride/2,6-Lutidine/Acetonitrile, 20/30/50, v/v/v |
| CMIMT | 1-(Cyanomethyl)-1-H-Imidazol-3-ium-1yl-trifluoromethylsulfonate |
| ETT | 5-Ethylthio tetrazole |
| DeBlock (Detrit) | 3% Dichloroacetic acid in toluene |
| DEA | Diethylamine |
| TEA | Triethylamine |
| ACN | Acetonitrile |
| TEA•3HF | Triethylamine trihydrofluoride |
| DMSO | Dimethylsulfoxide |
| Conc. $NH_4OH$ | 28-30% Concentrated Ammonium hydroxide |
| Filter unit | Filter Device, 0.22 micron |
| — | WFI Quality Water |

Cleavage and deprotection (C&D) was conducted at a scale of 198 μmol. Certain useful cleavage & deprotection process parameters are presented below (chiral auxiliary removal processes were described above):

| Process Step | Parameter | Set Points |
|---|---|---|
| Cleavage & Deprotection | Reaction Vessel | Pressure rated reactor |
| | Scale | 198 μmol |
| | Reagent | Cold conc. $NH_4OH$ (28-30%) |
| | Reagent Volume | 200 ± 10 mL/mmol |
| | Reaction Time | 24.0 ± 1.0 h |
| | Incubator shaker rpm | 120 ± 10 rpm |
| | Reaction Temperature | 37.0 ± 2.0° C. |
| | Cooling to room temp prior to filtration | <25° C. |
| | Initial Crude Filtration Device | 0.22 micron filter, CORNING |
| | Filtration mode | Under vacuum |
| | Support Wash Solvent | Water |
| | Support Wash Volume | 250-350 mL/mmole |

UPLC analysis of crude oligonucleotide showed the purity of full length product (% FLP) was 39.3% in the crude sample before de-salting. Crude yield was estimated as 61 OD units/umol. Net FLP yield was 37 OD/umol (1.22 mg/umol). Crude storage condition was 2-8° C.; other suitable storage conditions may also be utilized. Molecular mass of the WV-3473 was confirmed by LC-MS (calculated 6732.8: observed 6730.6).

Example 14. Provided Technologies are Useful for Manufacturing Chirally Controlled Compositions of Oligonucleotides Comprising Various Types of Chiral Internucleotidic Linkages Among other things, provided technologies are highly effective for chirally controlled construction of chiral internucleotidic linkages of various types. As demonstrated and confirmed by the WV-15562 preparations as examples, provided technologies can deliver high selectivity, high crude purity, high yield, and/or simplified/alternative manufacturing processes (e.g., no use of F sources to remove chiral auxiliaries), etc. In some embodiments, technologies of the present disclosure facilitate purification and/or formulation processes by delivering crude compositions with high purity, high stereoselectivity and/or low amount of salts.

```
WV-15562:
mU*SGeon001Rm5Ceon001Rm5Ceon001RmA*SG*SG*RC*ST*SG*

RG*ST*ST*RA*ST*SmG*SmA*SmC*SmU*SmC

Base sequence.
UGCCAGGCTGGTTATGACUC (SEQ ID NO: 201)

Linkage/Steroechemistry: SnRnRnRSSRSSRSSRSSSSSS
```

An example preparation of WV-15562 utilizing PSM chiral auxiliaries based on preliminary tests is described below. In this example, preparation of WV-15562 was conducted on mC-CPG solid support using 2.0×7.0 cm stainless steel column at a scale of 401 μmol.

Abbreviation:

| Abbreviation | Name of Raw Materials |
|---|---|
| mC-CPG | 2'-OMe-C via CNA linker CPG (600 Å LBD) |
| dA-L-PSM | 5'-O-DMT-dA (Bz)-(L)-PSM Phosphoramidite |
| dC-L-PSM | 5'-O-DMT-dC (Ac)-(L)-PSM Phosphoramidite |
| dG-L-PSM | 5'-O-DMT-dG (iBu)-(L)-PSM Phosphoramidite |
| dT-L-PSM | 5'-O-DMT-dT-(L)-PSM Phosphoramidite |
| mA-L-PSM | 5'-O-DMT-2'-OMe-A (Bz)-(L)-PSM Phosphoramidite |
| mC-L-PSM | 5'-O-DMT-2'-OMe-C (Ac)-(L)-PSM Phosphoramidite |
| mG-L-PSM | 5'-O-DMT-2'-OMe-G (iBu)-(L)-PSM Phosphoramidite |
| mU-L-PSM | 5'-O-DMT-2'-OMe-U-(L)-PSM Phosphoramidite |
| m5Ceo-L-PSM | 5'-O-DMT-2'-MOE-C (Bz)-(L)-PSM Phosphoramidite |
| Geo-L-PSM | 5'-O-DMT-2'-MOE-G (iBu)-(L)-PSM Phosphoramidite |
| dG-D-PSM | 5'-O-DMT-dG (iBu)-(D)-PSM Phosphoramidite |
| dT-D-PSM | 5'-O-DMT-dT-(D)-PSM Phosphoramidite |
| ADIH | 2-Azide-1,3-dimethylimidazolium hexafluorophosphate |
| Cap A | N-Methylimidazole in acetonitrile, 20/80, v/v |
| Cap B | Acetic anhydride/2,6-Lutidine/Acetonitrile, 20/30/50, v/v/v |
| Conc. $NH_4OH$ | 28-30% Concentrated Ammonium hydroxide |
| CT | Contact time |

-continued

| Abbreviation | Name of Raw Materials |
|---|---|
| CV | Column volume |
| CMIMT | 1-(Cyanomethyl)-1-H-Imidazol-3-ium-1-yl trifluoromethanesulfonate |
| DCA | Dichloroacetic acid |
| DEA | Diethylamine |
| Deblock (Detrit) | 3% DCA in toluene |
| DMSO | Dimethylsulfoxide |
| Filter unit | Filter Device, 0.22 micron |
| IBN | Isobutyronitrile |

-continued

| Abbreviation | Name of Raw Materials |
|---|---|
| MeCN | Acetonitrile |
| MS3A | Molecular Sieves, 3 Å |
| NLT | No less than |
| TEA•3HF | Triethylamine trihydrofluoride |
| TEA | Triethylamine |
| XH | Xanthane Hydride |
| WFI | Water for injection (water) |

Synthesis Process Parameters for WV-15562 using PSM amidite and CMIMT activator.

| Process Step | Parameter | Set Points |
|---|---|---|
| Synthesis Cycle | PSM | Detritylation<br>Coupling<br>Cap-1 (pre-modification capping step)<br>Modification - Thiolation or Azide reaction<br>Cap-2 (post-modification capping step) |
| Column, Scale, Synthesizer | Column | Stainless steel |
| | Column Inner Diameter | 2.0 cm |
| | Column Bed Height | 7.0 cm |
| | Column Volume | 22.0 mL |
| | Scale | 401 μmol |
| | Synthesizer | AKTA OligoPilot 100 |
| CPG | Solid Support | mC-CPG |
| | Support Loading | 76 μmol/g |
| | Adjusted Support Density | 0.23 g/c.c. |
| Pre-Synthesis Wash | Pre-Synthesis Wash Solvent | MeCN |
| | Pre-Synthesis Wash Flow Rate | 424 cm/h |
| | Pre-Synthesis Wash Volume | 2 CV |
| Deblocking (Detritylation) | Reagent | 3% DCA in Toluene |
| | Control Mode | UV watch command |
| | Detrit Wavelength | 436 nm |
| | Detrit UV Watch | On: 500 mAu with 1.2. CV delay<br>Off: 1000 mAu |
| | UV Autozero | Autozero on Deblock in bypass prior to the 1st detritylation |
| | Detrit Flow Rate | 424 cm/h |
| | Post Detritylation | 4 CV |
| | MeCN Wash | 424 cm/h |
| Coupling (for PSM amidites) | Chiral PSM Amidite Eq./Support | 2.5 eq. |
| | Concentration and Diluent of PSM Amidite | 0.2M of dA-L-PSM, dG-L-PSM, dT-L-PSM, Geo-L-PSM, m5Ceo-L-PSM, dG-D-PSM, and dT-D-PSM in 100% MeCN |
| | Concentration and Diluent of PSM Amidite | 0.2M of dC-L-PSM, mA-L-PSM, mG-L-PSM, mC-L-PSM, and mU-L-PSM in 20% IBN-80% MeCN |
| | Density of the PSM Amidite Solution | Non-adjusted |
| | Drying of PSM Amidite Solution | Molecular Sieves, 3 Å, 15-20% w.r.t. amidite solution, v/v<br>Diving time = NLT 4 h |
| | Activator | CMIMT |
| | Activator Concentration | 0.5M in MeCN |
| | CMIMT Eq./Support | 14.58 eq. |
| | Density of CMIMT Solution | Non-adjusted |
| | Drying of CMIMT Solution | MS3A, 10%, w.r.t. CMIMT solution. v./v<br>Drying time = NLT 4 h |
| | CMIMT/PSM Amidite Molar Ratio | 5.83:1 |
| | CMIMT % Volume | 70% |
| | Coupling Charge Flow Rate for all chiral amidites | 56.7 cm/h |
| | Coupling Charge Flow Rate for CMIMT | 132.4 cm/h |
| | Coupling Charge Volume (Amidite + CMIMT) | 16.4 mL |

-continued

| Process Step | Parameter | Set Points |
|---|---|---|
| | Push Volume | 4.5 mL |
| | Recycle Flow Rate | 212 cm/h |
| | Recycle Times | 10 min |
| | Coupling MeCN Wash Flow Rate | 424 cm/h |
| | Coupling MeCN Wash Volume | 2.0 CV |
| Cap 1 (Pre-modification capping step) | Mode | Flow Through |
| | Reagent | Cap B |
| | Column Volume | 2 CV |
| | Contact Time | 4 min |
| | Cap B Charge Flow Rate | 11 mL/min |
| | MeCN Push Volume (after Cap B charge) | 1.3 CV |
| | MeCN Push Flow Rate (after Cap B charge) | 11 mL/min |
| Modification (Thiolation) | Mode | Flow Through |
| | Reagent | 0.1M XH in pyridine/MeCN, 50/50 (v/v) |
| | Density of Thiolation Reagent | Non-adjusted |
| | Charge Volume | 1.2 CV |
| | Contact Time | 6 min |
| | Charge Flow Rate | 84.0 cm/h |
| | MeCN Push Flow Rate | 84.0 cm/h |
| | MeCN Push Volume | 1.3 CV |
| | Post-thio (MeCN Wash Flow Rate | 424 cm/h |
| | Post-thio MeCN Wash Volume | 1.0 CV |
| Modification (Azide reaction) | Mode | Flow Through |
| | Reagent | 0.3M ADIH in MeCN |
| | Density of Azide Reagent | Non-adjusted |
| | Charge Volume | 1.4 CV |
| | Contact Time | 15 min |
| | Charge Flow Rate | 39.2 cm/h |
| | MeCN Push Flow Rate | 39.2 cm/h |
| | MeCN Push Volume | 1.5 CV |
| Cap 2 (Post-modification capping step) | Reagent | Cap A<br>Cap B |
| | Mode | Flow Through |
| | Charge Volume | 0.4 CV |
| | Contact Time | 0.8 min |
| | Charge Flow Rate | Cap A = 105.0 cm/h<br>Cap B = 105.0 cm/h |
| | MeCN Push Flow Rate | MeCN Pump A = 105.0 cm/h<br>MeCN Pump B = 105.0 cm/h |
| | MeCN Push Volume | 1.3 CV |
| | Capping Wash Volume | 1.0 CV |
| | Capping Wash Flow Rate | 424 cm/h |
| Post Synthesis MeCN Wash | MeCN Wash Flow Rate | 424 cm/h |
| | MeCN Wash Flow Volume | 2.0 CV |
| Auxiliary Removal (20% DEA Wash) | Reagent | 20% DEA in MeCN |
| | Delivery Mode | Flow through |
| | Charge Volume | 5 CV |
| | Contact Time | 15 min |
| | Charge Flow Rate | 140 cm/h |
| | Charge MeCN Push Flow Rate | 140 cm/h |
| | Charge MeCN Push Volume | 1.3 CV |
| | Post DEA ACN Wash flowrate | 424 cm/h |
| | Post DEA ACN wash volume | 3 CV |

Cleavage and deprotection (C&D) was conducted at a scale of 401 μmol. Certain useful cleavage & deprotection process parameters are presented below (chiral auxiliary removal processes were described above:

| Process Step | Parameter | Set Points |
|---|---|---|
| Cleavage & Deprotection | Reaction Vessel | Pressure rated reactor |
| | Scale | 401 μmol |
| | Reagent | Cold conc. $NH_4OH$ |

-continued

| Process Step | Parameter | Set Points |
|---|---|---|
| | Reagent Volume | 80 ± 4 mL/mmol |
| | Reaction Time | 16 ± 1.0 h |
| | Incubator shaker rpm | 160 ± 10 rpm |
| | Reaction Temperature | 45.0 ± 2.0° C. |
| | Cooling to room temp prior to filtration | <25° C. |
| | Initial Crude Filtration Device | Filter unit |

-continued

| Process Step | Parameter | Set Points |
|---|---|---|
| | Filtration mode | Under vacuum |
| | Support Wash Solvent | WFI |
| | Support Wash Volume | 250-350 mL/mmol |

Crude oligonucleotide UPLC analysis showed the purity of full length product (%-FLP) was 55.7% before desalting. Crude yield was estimated as 77.5 OD units/μmol. Crude storage condition was 2-8° C.; other suitable storage conditions may also be utilized. Molecular mass of the WV-15562 was confirmed by LC-MS (calculated 7098.9; observed 7099.4).

In another example preparation, PhIMT (1-(Phenyl)-1-H-Imidazol-3-ium-1-yl trifluoromethanesulfonate) was used as activator at a scale of 396 μmol (other conditions similar/identical). Crude oligonucleotide UPLC analysis showed the purity of full length product (%-FLP) was 49.8% before desalting. Crude yield was estimated as 74.0 OD units/μmol. Crude storage condition was 2-8° C.: other suitable storage conditions may also be utilized. Molecular mass of the WV-15562 was confirmed by LC-MS (calculated 7098.9; observed 7098.4). Applicant notes that PhIMT in some embodiments may provide certain benefits, as it may demonstrate higher solubility in certain desired solvents such as MeCN compared to CMIMT. In some embodiments, a higher concentration may provide better results (e.g., better purity, yield, etc.). In some embodiments, higher concentration may provide smaller reagent volumes. In some embodiments, higher concentrations may provide higher equivalents of reagents (e.g., higher phosphoramidite equivalents (e.g., 4.5 eq. compared to 2.5 eq.)).

Example 15. Provided Technologies are Useful for Manufacturing Chirally Controlled Compositions of Oligonucleotides Comprising Various Types of Sugars As described herein, provided technologies are useful for preparing oligonucleotides with various structural features. In some embodiments, as confirmed herein, provided technologies are particularly useful for chirally controlled preparation of oligonucleotides comprising 2'-OH sugars (e.g., sugars with $R^{2s}$=OH, such as sugars typically found in natural RNA). For example, in a preparation described below, a natural RNA sugar

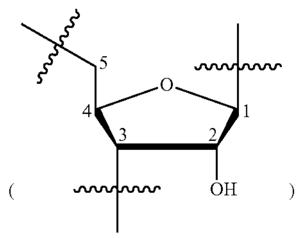

containing oligonucleotides comprising various other sugars and phosphorothioate internucleotidic linkages were prepared in high yield and purity.

Abbreviation

AEX-HPLC: anion exchange high pressure liquid chromatography

CPG: controlled pore glass

CV: column volume

DCM: dichloromethane, $CH_2Cl_2$

DMSO: dimethylsulfoxide

DMTr: 4,4'-dimethoxytrityl

HF: hydrofluoride

IBN: isobutyronitrile

LTQ: liner ion trap mass spectrometer

Melm: N-methylimidazole

PhIMT: N-phenylimidazolium triflate

RP-UPLC: reversed phased ultra performance liquid chromatography

TCA: trichloroacetic acid

TEA: triethylamine

TEAA: triethylammonium acetate

XH: xanthane hydride

A procedure for the synthesis of chirally controlled oligonucleotide compositions (25 μmol scale): An automated solid-phase synthesis of chirally controlled oligonucleotide compositions was performed according to cycles ag described below:

| step | operation | reagents and solvent | volume | waiting time |
|---|---|---|---|---|
| 1 | detritylation | 3% TCA/DCM | 10 mL | 65 s |
| 2 | coupling | 0.2M monomer/20% IBN-MeCN 0.5M PhIMT/MeCN | 0.5 mL 1.0 mL | 8 min |
| 3 | cap-1 | 20% $Ac_2O$, 30% 2,6-lutidine/MeCN | 2.0 mL | 2 min |
| 4 | sulfurization | 0.2M XH/pyridine | 2.0 mL | 6 min |
| 5 | cap-2 | 20% $Ac_2O$, 30% 2,6-lutidine/MeCN 20% MeIm/MeCN | 1.0 mL 1.0 mL | 45 s |

The cycles were performed multiple times until a desired length was achieved (e.g., 30-mer). PSM phosphoramidites were utilized for formation of chirally controlled internucleotidic linkages (for 2'-OH, protected with TBS (t-butyldimethylsilyl)).

A Procedure for C&D, purification conditions (25 μmol scale): After completion of the synthesis cycles, PSM chiral auxiliary groups were removed by DEA treatment. The CPG was treated with 40% $MeNH_2$ (5.0 mL) for 30 min at 35° C., then cooled to room temperature and the CPG was separated by membrane filtration, washed with 8.0 mL of DMSO. To the filtrate, TEA-3HF (5.0 mL) was added and stirred for 1 h at 45° C. which can remove TBS protection groups from 2'-OH. The reaction mixture was cooled to room temperature and diluted with 10 mL of 50 mM NaOAc (pH 5.2). The crude material was analyzed by LTQ and RP-UPLC. The crude materials were purified by RP-HPLC with a linear gradient of MeCN in 50 mM TEAA, desalting by $tC_{18}$ SepPak cartridge to obtain the target oligonucleotide.

A Procedure for the desalting (25 μmol scale): Material: SepPak tC18 35 cc Vac Cartridge (10 g Sorbent per Cartridge, 55-105 μm Particle Size).

1. Evaporate MeCN from samples if present.
2. Condition column with 4CV of 100% Acetonitrile (HPLC grade).
3. Rinse column with 2CV of 40% MeCN in Millipore Bio-Pak water, Endotoxin-Free.
4. Rinse column with 4CV of water (Millipore Bio-Pak, Endotoxin-Free).
5. Equilibrate column with 2CV of 50 mM TEAA in Millipore Bio-Pak water, Endotoxin-Free.
6. Load pure fractions onto equilibrated column. Loading by gravity will achieve the greatest amount of binding.

Loading slowly with vacuum will achieve decent binding. Loading quickly with vacuum will result in poor binding.
7. Wash column with 2CV of BioPak water to wash away TEAA.
8. Wash column with 2CV of 100 mM NaOAc to exchange the ammonium on the backbone of the oligo with Sodium instead.
9. Wash column with BioPak water until conductivity of eluent is <20 uS/cm.
10. Elute product with 2 column volumes of 40% MeCN in Millipore Bio-Pak water, Endotoxin-Free.
11. Place on Speed-vac overnight at 30° C. to remove acetonitrile and to concentrated.

Results from one preparation are presented below:
Synthesis scale: 25 umol
Crude ODs: 874 ODs
Crude UPLC purity: 32.17%
Crude LTQ purity: 62.45%
Final ODs: 59.8 OD
Final UPLC purity: 59.85%
Final MS purity: 74.51%
Final Observed MS: 10,064.40 (Calculated 10,063.68).

EQUIVALENTS

Having described some illustrative embodiments of the disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the disclosure. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Further, for the one or more means-plus-function limitations recited in claims, the means are not intended to be limited to the means disclosed herein for performing the recited function, but are intended to cover in scope any means, known now or later developed, for performing the recited function.

Use of ordinal terms such as “first”, “second”, “third”, etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of 1), 2), etc., a), b), etc., or i), ii), etc. does not by itself connote any priority, precedence, or order of steps in the claims. Similarly, the use of these terms in the specification does not by itself connote any required priority, precedence, or order.

The foregoing written specification is considered to be sufficient to enable one skilled in the art to practice the invention(s). The present disclosure is not to be limited in scope by examples provided, since the examples are intended as illustrations of certain aspect(s) of the invention (s) and other functionally equivalent embodiments are within the scope of the invention(s). Various modifications of the invention(s) in addition to those shown and described herein will become apparent to those skilled in the art from the foregoing description and fall within the scope of claims. The advantages and objects of an invention are not necessarily encompassed by each embodiment of the invention.

The invention claimed is:

1. A method for preparing an oligonucleotide, comprising one or more cycles, each of which independently comprises the following steps:

(1) a coupling step;

(2) optionally a pre-modification capping step;

(3) a modification step;

(4) optionally a post-modification capping step; and (5) optionally a de-blocking step, and wherein the oligonucleotide comprises a phosphorothioate internucleotidic linkage and an internucleotidic linkage having the structure of

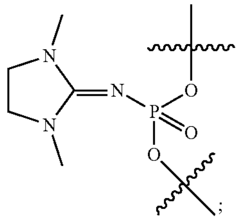 [SMILES: *OP(=O)(N=C1N(C)CCN1C)O*]

;

and wherein in at least one cycle, the coupling step independently comprises reacting a free hydroxyl group of an oligonucleotide or a nucleoside with a coupling partner compound comprising a chiral auxiliary group, and wherein each partner compound comprising a chiral auxiliary group independently has the structure of

[[,]] 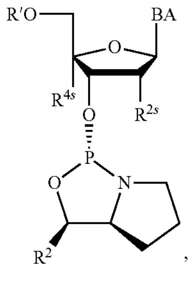 , or 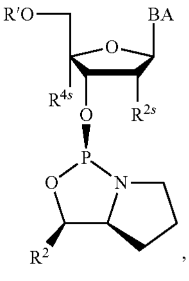 , or a salt thereof, wherein:

BA is an optionally substituted group selected from $C_{3-30}$ cycloaliphatic, $C_{6-30}$ aryl, $C_{5-30}$ heteroaryl having 1-10 heteroatoms independently selected from oxygen, nitrogen, sulfur, phosphorus and silicon, and $C_{3-30}$ heterocyclyl having 1-10 heteroatoms independently selected from oxygen, nitrogen, sulfur, phosphorus and silicon, or a nucleobase moiety;

each of $R^{2s}$ and $R^{4s}$ is independently $R^s$;

each $R^s$ is independently —H, halogen, —CN, $—N_3$, —NO, $—NO_2$, $-L^s$-R', $-L^s-Si(R)_3$, $-L^s$-OR', $-L^s$-SR', $-L^s—N(R')_2$, —O-$L^s$-R', —O-$L^s-Si(R)_3$, —O-$L^s$-OR', —O-$L^s$-SR', or —O-$L^s-N(R')_2$;

$R^2$ is $—CH_2SO_2R'$, wherein R' is an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, $—C(R')_2—$, -Cy-, —O—, —S—, —S—S—, —N(R')—, —C(O)—, —C(S)—, —C(NR')—, —C(O)N(R')—, —N(R') C(O)N(R')—, —N(R') C(O)O—, —S(O)—, $—S(O)_2$", $—S(O)_2N$(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —C(O)OR, or —S(O)$_2$R; and each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

2. The method of claim 1, wherein in a partner compound, $R^{4s}$ is —H.

3. The method of claim 1, wherein in a partner compound, $R^{2s}$ is —H, —F, or —OR, wherein R is optionally substituted $C_{1-6}$ aliphatic.

4. The method of claim 1, wherein in a partner compound, $R^{2s}$ is —$OCH_3$ or —$OCH_2CH_2OCH_3$.

5. The method of claim 1, wherein in a partner compound, $R^{2s}$ is —OR, wherein R is optionally substituted $C_{1-6}$ aliphatic.

6. The method of claim 1, wherein in a partner compound, $R^{2s}$ is —O—Si(R)$_3$, wherein each R is independently not —H.

7. The method of claim 1, wherein $R^2$ is —$CH_2SO_2R'$, wherein R' is optionally substituted phenyl.

8. The method of claim 1 wherein $R^2$ is —$CH_2SO_2R'$, wherein R' is phenyl.

9. The method of claim 1, wherein $R^2$ is —$CH_2SO_2R'$, wherein R' is tert-butyl.

10. The method of claim 1, comprising removal of a chiral auxiliary group by contacting oligonucleotides comprising a chiral auxiliary group with a base under an anhydrous condition.

11. The method of claim 10, wherein the product oligonucleotide comprises a sugar comprising 2'-OH.

12. The method of claim 10, wherein the product oligonucleotide comprises a natural phosphate linkage.

13. An oligonucleotide, wherein the oligonucleotide comprises:

an internucleotidic linkage of $^{*P}S$ or $^{*P}R$; and an internucleotidic linkage of $^{*N}S$ or $^{*N}R$;

wherein:

$^{*P}S$ is of formula

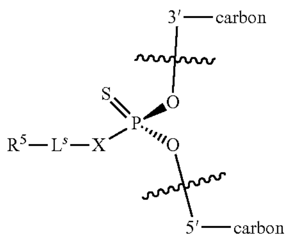

or a salt form thereof;

$^{*P}R$ is of formula

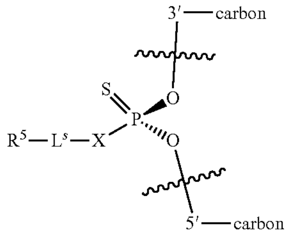

or a salt form thereof;

$^{*N}S$ is of formula

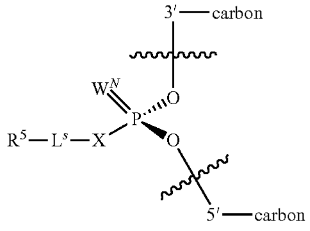

or a salt form thereof;

$^{*N}R$ is of formula

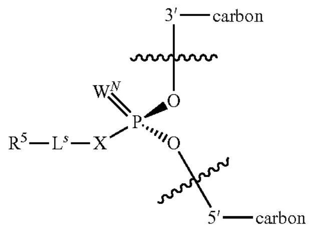

or a salt form thereof;

—X-$L^s$-$R^5$ is

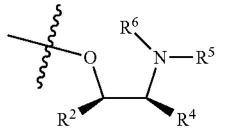

or

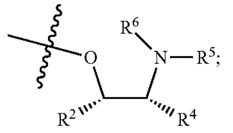

$R^4$ and $R^5$ in —X—$L^S$—$R^5$ are taken together with their intervening atoms to form an optionally substituted 3-20 membered monocyclic, bicyclic or polycyclic ring having 1-5 heteroatoms independently selected from oxygen, nitrogen, sulfur, phosphorus and silicon;

$R^6$ is —C(O)R';

$R^2$ is —$CH_2SO_2R'$, wherein R' is an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon;

P=$W^N$ is $P^N$;

$P^N$ is P(=N-L-$R^5$),

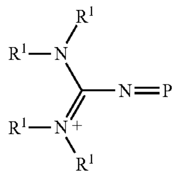

$Q^-$,

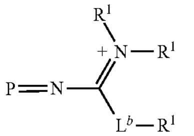

$Q^-$,

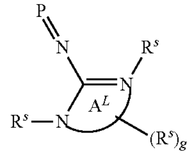

$Q^-$,

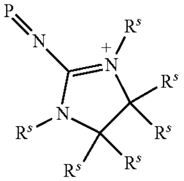

$Q^-$, or

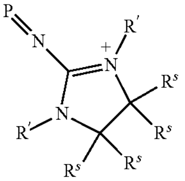

$Q^-$, $Q^-$ is an anion;

Ring $A^L$ is an optionally substituted 3-20 membered monocyclic, bicyclic or polycyclic ring having 0-10 heteroatoms independently selected from oxygen, nitrogen, sulfur, phosphorus and silicon;

each of $R^1$ and $R^5$ in $P^N$ is independently —H, -$L^s$-R', halogen, —CN, —$NO_2$, -$L^s$-Si(R')$_3$, OR', —SR', or —N(R')$_2$;

each $R^s$ is independently —H, halogen, CN, —$N_3$, —NO, —$NO_2$, -$L^s$-R', -$L^s$-Si(R')$_3$, -$L^s$-OR', -$L^s$-SR', -$L^s$—N(R')$_2$, —O-$L^s$-R', —O-$L^s$-Si(R)$_3$, —O-$L^s$-OR', —O-$L^s$-SR', or —O-$L^s$—N(R')$_2$;

g is 0-20;

each of L and $L^b$ is independently $L^S$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, C(NR')—, —C(O)N(R')—, —N(R') C(O)N(R')—, —N(R') C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, OP(O)(NR')O—, —OP(OR')O—, —OP(SR')O—, —OP(NR')O—, —OP(R')O—, or OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —C(O)OR, or —S(O)$_2$R; and each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

14. The oligonucleotide of claim 13, wherein $P{=}W^N$ in $^{*N}S$ or $^{*N}R$ is

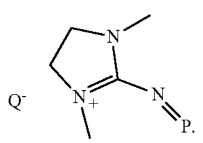

15. The oligonucleotide of claim 13, wherein $R^2$ is —$CH_2SO_2R'$, wherein R' is optionally substituted phenyl.

16. The oligonucleotide of claim 13, wherein $R^2$ is —$CH_2SO_2R'$, wherein R' is tert-butyl.

17. The oligonucleotide of claim 13, wherein $R^2$ is —$CH_2SO_2R'$, wherein R' is phenyl.

18. A method, comprising contacting an oligonucleotide with a base under an anhydrous condition, wherein the oligonucleotide comprises:

an internucleotidic linkage of $^{*P}S$ or $^{*P}R$; and an internucleotidic linkage of $^{*N}S$ or $^{*N}R$;

wherein:

$^{*P}S$ is of formula

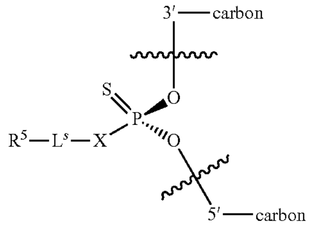

or a salt form thereof;

$^{*P}R$ is of formula

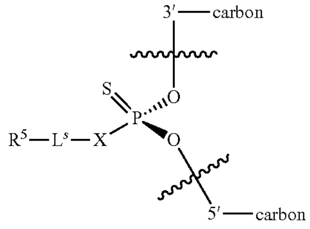

or a salt form thereof ;

$^{*N}S$ is of formula

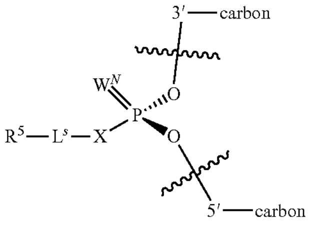

or a salt form thereof;

$^{*N}R$ is of formula

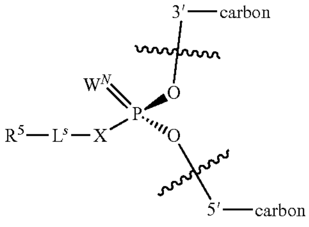

or a salt form thereof;

—$X$-$L^s$-$R^5$ is

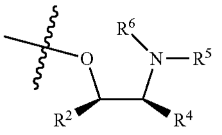 or 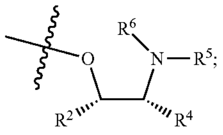

$R^4$ and $R^5$ in —X—$L^S$—$R^5$ are taken together with their intervening atoms to form an optionally substituted 3-20 membered monocyclic, bicyclic or polycyclic ring having 1-5 heteroatoms independently selected from oxygen, nitrogen, sulfur, phosphorus and silicon;

$R^6$ is —C(O)R';

$R^2$ is —$CH_2SO_2R'$, wherein R' is an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon;

$P{=}W^N$ is $P^N$;

$P^N$ is $P({=}N\text{-}L\text{-}R^5)$,

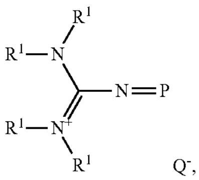, 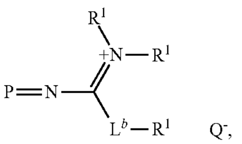,

-continued

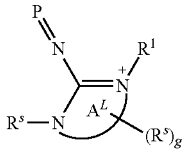

$Q^-$,

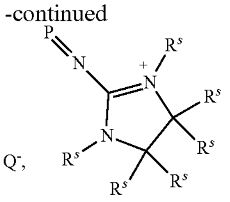

$Q^-$, or

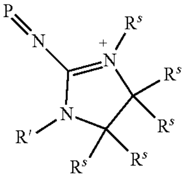

$Q^-$;

$Q^-$ is an anion;

Ring $A^L$ is an optionally substituted 3-20 membered monocyclic, bicyclic or polycyclic ring having 0-10 heteroatoms independently selected from oxygen, nitrogen, sulfur, phosphorus and silicon;

each of $R^1$ and $R^5$ in $P^N$ is independently —H, $-L^s-R'$, halogen, —CN, $—NO_2$, $-L^s-Si(R')_3$, —OR', —SR', or $—N(R')_2$;

each $R^s$ is independently —H, halogen, —CN, $—N_3$, —NO, $—NO_2$, $-L^s-R'$, $-L^s-Si(R')_3$, $-L^s-OR'$, $-L^s-SR'$, $-L^s—N(R')_2$, $—O-L^s-R'$, $—O-L^s-Si(R)_3$, $—O-L^s-OR'$, $—O-L^s-SR'$, or $—O-L^s—N(R')_2$;

g is 0-20;

each of L and $L^b$ is independently $L^S$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, $—C(R')_2—$, -Cy-, —O—, —S—, —S—S—, —N(R')—, —C(O)—, —C(S)—, C(NR')—, —C(O)N(R')—, —N(R') C(O)N(R')—, —N(R') C(O)O—, —S(O)—, $—S(0)_2—$, $—S(O)_2N(R')—$, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, $—P(OR')[B(R')_3]—$, —OP(O)(OR')O—, —OP(O)(SR')O—, —OP(O)(R')O—, OP(O)(NR')O—, —OP(OR')O—, —OP(SR')O—, —OP(NR')O—, —OP(R')O—, or $OP(OR')[B(R')_3]O—$, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —C(O)OR, or $—S(O)_2R$; and each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

19. The method of claim 18, wherein $R^2$ is $—CH_2SO_2R'$, wherein R' is optionally substituted phenyl.

20. The method of claim 18, wherein $R^2$ is $—CH_2SO_2R'$, wherein R' is phenyl.

21. The method of claim 18, wherein $R^2$ is $—CH_2SO_2R'$, wherein R' is tert-butyl.

22. The method of claim 18, wherein the base is diethylamine.

* * * * *

SEQUENCE LISTING

```
<160> NUMBER OF SEQ ID NOS: 201

<210> SEQ ID NO 1
<211> LENGTH: 20
<212> TYPE: DNA
<213> ORGANISM: Artificial Sequence
<220> FEATURE:
<223> OTHER INFORMATION: Synthetic: WV-937
<220> FEATURE:
<221> NAME/KEY: misc_feature
<223> OTHER INFORMATION: See specification as filed for detailed
      description of substitutions and preferred embodiments

<400> SEQUENCE: 1

ggcacaaggg cacagacttc                                              20


<210> SEQ ID NO 2
<211> LENGTH: 20
<212> TYPE: DNA
<213> ORGANISM: Artificial Sequence
<220> FEATURE:
<223> OTHER INFORMATION: Synthetic: WV-1077
<220> FEATURE:
<221> NAME/KEY: misc_feature
<223> OTHER INFORMATION: See specification as filed for detailed
      description of substitutions and preferred embodiments

<400> SEQUENCE: 2

auuaauaaat tgtcatcacc                                              20
```

<210> SEQ ID NO 3
<211> LENGTH: 20
<212> TYPE: DNA
<213> ORGANISM: Artificial Sequence
<220> FEATURE:
<223> OTHER INFORMATION: Synthetic: WV-1078
<220> FEATURE:
<221> NAME/KEY: misc_feature
<223> OTHER INFORMATION: See specification as filed for detailed
description of substitutions and preferred embodiments

<400> SEQUENCE: 3
auuaauaaat tgtcatcacc 20

<210> SEQ ID NO 4
<211> LENGTH: 20
<212> TYPE: DNA
<213> ORGANISM: Artificial Sequence
<220> FEATURE:
<223> OTHER INFORMATION: Synthetic: WV-1079
<220> FEATURE:
<221> NAME/KEY: misc_feature
<223> OTHER INFORMATION: See specification as filed for detailed
description of substitutions and preferred embodiments

<400> SEQUENCE: 4
auuaauaaat tgtcatcacc 20

<210> SEQ ID NO 5
<211> LENGTH: 20
<212> TYPE: RNA
<213> ORGANISM: Artificial Sequence
<220> FEATURE:
<223> OTHER INFORMATION: Synthetic: WV-1085
<220> FEATURE:
<221> NAME/KEY: misc_feature
<223> OTHER INFORMATION: See specification as filed for detailed
description of substitutions and preferred embodiments

<400> SEQUENCE: 5
ggcacaaggg cacagacuuc 20

<210> SEQ ID NO 6
<211> LENGTH: 20
<212> TYPE: RNA
<213> ORGANISM: Artificial Sequence
<220> FEATURE:
<223> OTHER INFORMATION: Synthetic: WV-1086
<220> FEATURE:
<221> NAME/KEY: misc_feature
<223> OTHER INFORMATION: See specification as filed for detailed
description of substitutions and preferred embodiments

<400> SEQUENCE: 6
ggcacaaggg cacagacuuc 20

<210> SEQ ID NO 7
<211> LENGTH: 20
<212> TYPE: DNA
<213> ORGANISM: Artificial Sequence
<220> FEATURE:
<223> OTHER INFORMATION: Synthetic: WV-1090
<220> FEATURE:
<221> NAME/KEY: misc_feature
<223> OTHER INFORMATION: See specification as filed for detailed
description of substitutions and preferred embodiments

<400> SEQUENCE: 7
ggcacaaggg cacagacttc 20

<210> SEQ ID NO 8
<211> LENGTH: 20
<212> TYPE: RNA
<213> ORGANISM: Artificial Sequence
<220> FEATURE:
<223> OTHER INFORMATION: Synthetic: WV-1091
<220> FEATURE:
<221> NAME/KEY: misc_feature
<223> OTHER INFORMATION: See specification as filed for detailed description of substitutions and preferred embodiments

<400> SEQUENCE: 8
ggcacaaggg cacagacuuc 20

<210> SEQ ID NO 9
<211> LENGTH: 20
<212> TYPE: RNA
<213> ORGANISM: Artificial Sequence
<220> FEATURE:
<223> OTHER INFORMATION: Synthetic: WV-1092
<220> FEATURE:
<221> NAME/KEY: misc_feature
<223> OTHER INFORMATION: See specification as filed for detailed description of substitutions and preferred embodiments

<400> SEQUENCE: 9
ggcacaaggg cacagacuuc 20

<210> SEQ ID NO 10
<211> LENGTH: 20
<212> TYPE: RNA
<213> ORGANISM: Artificial Sequence
<220> FEATURE:
<223> OTHER INFORMATION: Synthetic: WV-1497
<220> FEATURE:
<221> NAME/KEY: misc_feature
<223> OTHER INFORMATION: See specification as filed for detailed description of substitutions and preferred embodiments

<400> SEQUENCE: 10
ggcacaaggg cacagacuuc 20

<210> SEQ ID NO 11
<211> LENGTH: 20
<212> TYPE: DNA
<213> ORGANISM: Artificial Sequence
<220> FEATURE:
<223> OTHER INFORMATION: Synthetic: WV-1508
<220> FEATURE:
<221> NAME/KEY: misc_feature
<223> OTHER INFORMATION: See specification as filed for detailed description of substitutions and preferred embodiments

<400> SEQUENCE: 11
auuaauaaat tgtcatcacc 20

<210> SEQ ID NO 12
<211> LENGTH: 20
<212> TYPE: RNA
<213> ORGANISM: Artificial Sequence
<220> FEATURE:
<223> OTHER INFORMATION: Synthetic: WV-1510
<220> FEATURE:
<221> NAME/KEY: misc_feature
<223> OTHER INFORMATION: See specification as filed for detailed description of substitutions and preferred embodiments

<400> SEQUENCE: 12
ggcacaaggg cacagacuuc 20

<210> SEQ ID NO 13
<211> LENGTH: 20
<212> TYPE: DNA
<213> ORGANISM: Artificial Sequence
<220> FEATURE:
<223> OTHER INFORMATION: Synthetic: WV-2076
<220> FEATURE:
<221> NAME/KEY: misc_feature
<223> OTHER INFORMATION: See specification as filed for detailed description of substitutions and preferred embodiments

<400> SEQUENCE: 13
uaauaaattg tcatcaccag 20

<210> SEQ ID NO 14
<211> LENGTH: 20
<212> TYPE: RNA
<213> ORGANISM: Artificial Sequence
<220> FEATURE:
<223> OTHER INFORMATION: Synthetic: WV-2378
<220> FEATURE:
<221> NAME/KEY: misc_feature
<223> OTHER INFORMATION: See specification as filed for detailed description of substitutions and preferred embodiments

<400> SEQUENCE: 14
gcacaagggc acagacuucc 20

<210> SEQ ID NO 15
<211> LENGTH: 20
<212> TYPE: RNA
<213> ORGANISM: Artificial Sequence
<220> FEATURE:
<223> OTHER INFORMATION: Synthetic: WV-2380
<220> FEATURE:
<221> NAME/KEY: misc_feature
<223> OTHER INFORMATION: See specification as filed for detailed description of substitutions and preferred embodiments

<400> SEQUENCE: 15
cacaagggca cagacuucca 20

<210> SEQ ID NO 16
<211> LENGTH: 20
<212> TYPE: DNA
<213> ORGANISM: Artificial Sequence
<220> FEATURE:
<223> OTHER INFORMATION: Synthetic: WV-2417
<220> FEATURE:
<221> NAME/KEY: misc_feature
<223> OTHER INFORMATION: See specification as filed for detailed description of substitutions and preferred embodiments

<400> SEQUENCE: 16
auaaattgtc atcaccagaa 20

<210> SEQ ID NO 17
<211> LENGTH: 20
<212> TYPE: DNA
<213> ORGANISM: Artificial Sequence
<220> FEATURE:
<223> OTHER INFORMATION: Synthetic: WV-2418
<220> FEATURE:
<221> NAME/KEY: misc_feature
<223> OTHER INFORMATION: See specification as filed for detailed description of substitutions and preferred embodiments

<400> SEQUENCE: 17

-continued

```
aauaaattgt catcaccaga                                    20

<210> SEQ ID NO 18
<211> LENGTH: 20
<212> TYPE: DNA
<213> ORGANISM: Artificial Sequence
<220> FEATURE:
<223> OTHER INFORMATION: Synthetic: WV-2595
<220> FEATURE:
<221> NAME/KEY: misc_feature
<223> OTHER INFORMATION: See specification as filed for detailed
      description of substitutions and preferred embodiments

<400> SEQUENCE: 18

gggucctccc cacagaggga                                    20

<210> SEQ ID NO 19
<211> LENGTH: 20
<212> TYPE: DNA
<213> ORGANISM: Artificial Sequence
<220> FEATURE:
<223> OTHER INFORMATION: Synthetic: WV-2601
<220> FEATURE:
<221> NAME/KEY: misc_feature
<223> OTHER INFORMATION: See specification as filed for detailed
      description of substitutions and preferred embodiments

<400> SEQUENCE: 19

gcacacagta gatgagggag                                    20

<210> SEQ ID NO 20
<211> LENGTH: 20
<212> TYPE: DNA
<213> ORGANISM: Artificial Sequence
<220> FEATURE:
<223> OTHER INFORMATION: Synthetic: WV-2602
<220> FEATURE:
<221> NAME/KEY: misc_feature
<223> OTHER INFORMATION: See specification as filed for detailed
      description of substitutions and preferred embodiments

<400> SEQUENCE: 20

ugcacacagt agatgaggga                                    20

<210> SEQ ID NO 21
<211> LENGTH: 20
<212> TYPE: DNA
<213> ORGANISM: Artificial Sequence
<220> FEATURE:
<223> OTHER INFORMATION: Synthetic: WV-2603
<220> FEATURE:
<221> NAME/KEY: misc_feature
<223> OTHER INFORMATION: See specification as filed for detailed
      description of substitutions and preferred embodiments

<400> SEQUENCE: 21

gugcacacag tagatgaggg                                    20

<210> SEQ ID NO 22
<211> LENGTH: 20
<212> TYPE: DNA
<213> ORGANISM: Artificial Sequence
<220> FEATURE:
<223> OTHER INFORMATION: Synthetic: WV-2618
<220> FEATURE:
<221> NAME/KEY: misc_feature
<223> OTHER INFORMATION: See specification as filed for detailed
      description of substitutions and preferred embodiments
```

<400> SEQUENCE: 22
ugcacacagt agatgaggga 20

<210> SEQ ID NO 23
<211> LENGTH: 20
<212> TYPE: DNA
<213> ORGANISM: Artificial Sequence
<220> FEATURE:
<223> OTHER INFORMATION: Synthetic: WV-2619
<220> FEATURE:
<221> NAME/KEY: misc_feature
<223> OTHER INFORMATION: See specification as filed for detailed description of substitutions and preferred embodiments

<400> SEQUENCE: 23
gugcacacag tagatgaggg 20

<210> SEQ ID NO 24
<211> LENGTH: 20
<212> TYPE: DNA
<213> ORGANISM: Artificial Sequence
<220> FEATURE:
<223> OTHER INFORMATION: Synthetic: WV-2671
<220> FEATURE:
<221> NAME/KEY: misc_feature
<223> OTHER INFORMATION: See specification as filed for detailed description of substitutions and preferred embodiments

<400> SEQUENCE: 24
gggucctccc cacagaggga 20

<210> SEQ ID NO 25
<211> LENGTH: 20
<212> TYPE: RNA
<213> ORGANISM: Artificial Sequence
<220> FEATURE:
<223> OTHER INFORMATION: Synthetic: WV-887
<220> FEATURE:
<221> NAME/KEY: misc_feature
<223> OTHER INFORMATION: See specification as filed for detailed description of substitutions and preferred embodiments

<400> SEQUENCE: 25
ucaaggaaga uggcauuucu 20

<210> SEQ ID NO 26
<211> LENGTH: 20
<212> TYPE: RNA
<213> ORGANISM: Artificial Sequence
<220> FEATURE:
<223> OTHER INFORMATION: Synthetic: WV-892
<220> FEATURE:
<221> NAME/KEY: misc_feature
<223> OTHER INFORMATION: See specification as filed for detailed description of substitutions and preferred embodiments

<400> SEQUENCE: 26
ucaaggaaga uggcauuucu 20

<210> SEQ ID NO 27
<211> LENGTH: 20
<212> TYPE: RNA
<213> ORGANISM: Artificial Sequence
<220> FEATURE:
<223> OTHER INFORMATION: Synthetic: WV-896
<220> FEATURE:
<221> NAME/KEY: misc_feature
<223> OTHER INFORMATION: See specification as filed for detailed description of substitutions and preferred embodiments

<400> SEQUENCE: 27
ucaaggaaga uggcauuucu 20

<210> SEQ ID NO 28
<211> LENGTH: 20
<212> TYPE: RNA
<213> ORGANISM: Artificial Sequence
<220> FEATURE:
<223> OTHER INFORMATION: Synthetic: WV-1714
<220> FEATURE:
<221> NAME/KEY: misc_feature
<223> OTHER INFORMATION: See specification as filed for detailed description of substitutions and preferred embodiments

<400> SEQUENCE: 28
ucaaggaaga uggcauuucu 20

<210> SEQ ID NO 29
<211> LENGTH: 20
<212> TYPE: RNA
<213> ORGANISM: Artificial Sequence
<220> FEATURE:
<223> OTHER INFORMATION: Synthetic: WV-2444
<220> FEATURE:
<221> NAME/KEY: misc_feature
<223> OTHER INFORMATION: See specification as filed for detailed description of substitutions and preferred embodiments

<400> SEQUENCE: 29
ucaaggaaga uggcauuucu 20

<210> SEQ ID NO 30
<211> LENGTH: 20
<212> TYPE: RNA
<213> ORGANISM: Artificial Sequence
<220> FEATURE:
<223> OTHER INFORMATION: Synthetic: WV-2445
<220> FEATURE:
<221> NAME/KEY: misc_feature
<223> OTHER INFORMATION: See specification as filed for detailed description of substitutions and preferred embodiments

<400> SEQUENCE: 30
ucaaggaaga uggcauuucu 20

<210> SEQ ID NO 31
<211> LENGTH: 20
<212> TYPE: RNA
<213> ORGANISM: Artificial Sequence
<220> FEATURE:
<223> OTHER INFORMATION: Synthetic: WV-2526
<220> FEATURE:
<221> NAME/KEY: misc_feature
<223> OTHER INFORMATION: See specification as filed for detailed description of substitutions and preferred embodiments

<400> SEQUENCE: 31
ucaaggaaga uggcauuucu 20

<210> SEQ ID NO 32
<211> LENGTH: 20
<212> TYPE: RNA
<213> ORGANISM: Artificial Sequence
<220> FEATURE:
<223> OTHER INFORMATION: Synthetic: WV-2527
<220> FEATURE:
<221> NAME/KEY: misc_feature
<223> OTHER INFORMATION: See specification as filed for detailed description of substitutions and preferred embodiments

<400> SEQUENCE: 32
ucaaggaaga uggcauuucu 20

<210> SEQ ID NO 33
<211> LENGTH: 20
<212> TYPE: RNA
<213> ORGANISM: Artificial Sequence
<220> FEATURE:
<223> OTHER INFORMATION: Synthetic: WV-2528
<220> FEATURE:
<221> NAME/KEY: misc_feature
<223> OTHER INFORMATION: See specification as filed for detailed description of substitutions and preferred embodiments

<400> SEQUENCE: 33
ucaaggaaga uggcauuucu 20

<210> SEQ ID NO 34
<211> LENGTH: 20
<212> TYPE: RNA
<213> ORGANISM: Artificial Sequence
<220> FEATURE:
<223> OTHER INFORMATION: Synthetic: WV-2530
<220> FEATURE:
<221> NAME/KEY: misc_feature
<223> OTHER INFORMATION: See specification as filed for detailed description of substitutions and preferred embodiments

<400> SEQUENCE: 34
ucaaggaaga uggcauuucu 20

<210> SEQ ID NO 35
<211> LENGTH: 20
<212> TYPE: RNA
<213> ORGANISM: Artificial Sequence
<220> FEATURE:
<223> OTHER INFORMATION: Synthetic: WV-2531
<220> FEATURE:
<221> NAME/KEY: misc_feature
<223> OTHER INFORMATION: See specification as filed for detailed description of substitutions and preferred embodiments

<400> SEQUENCE: 35
ucaaggaaga uggcauuucu 20

<210> SEQ ID NO 36
<211> LENGTH: 20
<212> TYPE: RNA
<213> ORGANISM: Artificial Sequence
<220> FEATURE:
<223> OTHER INFORMATION: Synthetic: WV-2578
<220> FEATURE:
<221> NAME/KEY: misc_feature
<223> OTHER INFORMATION: See specification as filed for detailed description of substitutions and preferred embodiments

<400> SEQUENCE: 36
ucaaggaaga uggcauuucu 20

<210> SEQ ID NO 37
<211> LENGTH: 20
<212> TYPE: RNA
<213> ORGANISM: Artificial Sequence
<220> FEATURE:
<223> OTHER INFORMATION: Synthetic: WV-2580
<220> FEATURE:
<221> NAME/KEY: misc_feature
<223> OTHER INFORMATION: See specification as filed for detailed
      description of substitutions and preferred embodiments

<400> SEQUENCE: 37
ucaaggaaga uggcauuucu 20

<210> SEQ ID NO 38
<211> LENGTH: 20
<212> TYPE: RNA
<213> ORGANISM: Artificial Sequence
<220> FEATURE:
<223> OTHER INFORMATION: Synthetic: WV-2587
<220> FEATURE:
<221> NAME/KEY: misc_feature
<223> OTHER INFORMATION: See specification as filed for detailed
      description of substitutions and preferred embodiments

<400> SEQUENCE: 38
ucaaggaaga uggcauuucu 20

<210> SEQ ID NO 39
<211> LENGTH: 20
<212> TYPE: RNA
<213> ORGANISM: Artificial Sequence
<220> FEATURE:
<223> OTHER INFORMATION: Synthetic: WV-3047
<220> FEATURE:
<221> NAME/KEY: misc_feature
<223> OTHER INFORMATION: See specification as filed for detailed
      description of substitutions and preferred embodiments

<400> SEQUENCE: 39
ucaaggaaga uggcauuucu 20

<210> SEQ ID NO 40
<211> LENGTH: 20
<212> TYPE: RNA
<213> ORGANISM: Artificial Sequence
<220> FEATURE:
<223> OTHER INFORMATION: Synthetic: WV-3152
<220> FEATURE:
<221> NAME/KEY: misc_feature
<223> OTHER INFORMATION: See specification as filed for detailed
      description of substitutions and preferred embodiments

<400> SEQUENCE: 40
ucaaggaaga uggcauuucu 20

<210> SEQ ID NO 41
<211> LENGTH: 20
<212> TYPE: RNA
<213> ORGANISM: Artificial Sequence
<220> FEATURE:
<223> OTHER INFORMATION: Synthetic: WV-3472
<220> FEATURE:
<221> NAME/KEY: misc_feature
<223> OTHER INFORMATION: See specification as filed for detailed
      description of substitutions and preferred embodiments

<400> SEQUENCE: 41
ucaaggaaga uggcauuucu 20

<210> SEQ ID NO 42
<211> LENGTH: 20
<212> TYPE: RNA
<213> ORGANISM: Artificial Sequence
<220> FEATURE:
<223> OTHER INFORMATION: Synthetic: WV-3473
<220> FEATURE:

<221> NAME/KEY: misc_feature
<223> OTHER INFORMATION: See specification as filed for detailed
description of substitutions and preferred embodiments

<400> SEQUENCE: 42
ucaaggaaga uggcauuucu 20

<210> SEQ ID NO 43
<211> LENGTH: 20
<212> TYPE: RNA
<213> ORGANISM: Artificial Sequence
<220> FEATURE:
<223> OTHER INFORMATION: Synthetic: WV-3507
<220> FEATURE:
<221> NAME/KEY: misc_feature
<223> OTHER INFORMATION: See specification as filed for detailed
description of substitutions and preferred embodiments

<400> SEQUENCE: 43
ucaaggaaga uggcauuucu 20

<210> SEQ ID NO 44
<211> LENGTH: 20
<212> TYPE: RNA
<213> ORGANISM: Artificial Sequence
<220> FEATURE:
<223> OTHER INFORMATION: Synthetic: WV-3508
<220> FEATURE:
<221> NAME/KEY: misc_feature
<223> OTHER INFORMATION: See specification as filed for detailed
description of substitutions and preferred embodiments

<400> SEQUENCE: 44
ucaaggaaga uggcauuucu 20

<210> SEQ ID NO 45
<211> LENGTH: 20
<212> TYPE: RNA
<213> ORGANISM: Artificial Sequence
<220> FEATURE:
<223> OTHER INFORMATION: Synthetic: WV-3509
<220> FEATURE:
<221> NAME/KEY: misc_feature
<223> OTHER INFORMATION: See specification as filed for detailed
description of substitutions and preferred embodiments

<400> SEQUENCE: 45
ucaaggaaga uggcauuucu 20

<210> SEQ ID NO 46
<211> LENGTH: 20
<212> TYPE: RNA
<213> ORGANISM: Artificial Sequence
<220> FEATURE:
<223> OTHER INFORMATION: Synthetic: WV-3510
<220> FEATURE:
<221> NAME/KEY: misc_feature
<223> OTHER INFORMATION: See specification as filed for detailed
description of substitutions and preferred embodiments

<400> SEQUENCE: 46
ucaaggaaga uggcauuucu 20

<210> SEQ ID NO 47
<211> LENGTH: 20
<212> TYPE: RNA
<213> ORGANISM: Artificial Sequence
<220> FEATURE:
<223> OTHER INFORMATION: Synthetic: WV-3511

<220> FEATURE:
<221> NAME/KEY: misc_feature
<223> OTHER INFORMATION: See specification as filed for detailed
      description of substitutions and preferred embodiments

<400> SEQUENCE: 47
ucaaggaaga uggcauuucu 20

<210> SEQ ID NO 48
<211> LENGTH: 20
<212> TYPE: RNA
<213> ORGANISM: Artificial Sequence
<220> FEATURE:
<223> OTHER INFORMATION: Synthetic: WV-3512
<220> FEATURE:
<221> NAME/KEY: misc_feature
<223> OTHER INFORMATION: See specification as filed for detailed
      description of substitutions and preferred embodiments

<400> SEQUENCE: 48
ucaaggaaga uggcauuucu 20

<210> SEQ ID NO 49
<211> LENGTH: 20
<212> TYPE: RNA
<213> ORGANISM: Artificial Sequence
<220> FEATURE:
<223> OTHER INFORMATION: Synthetic: WV-3513
<220> FEATURE:
<221> NAME/KEY: misc_feature
<223> OTHER INFORMATION: See specification as filed for detailed
      description of substitutions and preferred embodiments

<400> SEQUENCE: 49
ucaaggaaga uggcauuucu 20

<210> SEQ ID NO 50
<211> LENGTH: 20
<212> TYPE: RNA
<213> ORGANISM: Artificial Sequence
<220> FEATURE:
<223> OTHER INFORMATION: Synthetic: WV-3514
<220> FEATURE:
<221> NAME/KEY: misc_feature
<223> OTHER INFORMATION: See specification as filed for detailed
      description of substitutions and preferred embodiments

<400> SEQUENCE: 50
ucaaggaaga uggcauuucu 20

<210> SEQ ID NO 51
<211> LENGTH: 20
<212> TYPE: RNA
<213> ORGANISM: Artificial Sequence
<220> FEATURE:
<223> OTHER INFORMATION: Synthetic: WV-3515
<220> FEATURE:
<221> NAME/KEY: misc_feature
<223> OTHER INFORMATION: See specification as filed for detailed
      description of substitutions and preferred embodiments

<400> SEQUENCE: 51
ucaaggaaga uggcauuucu 20

<210> SEQ ID NO 52
<211> LENGTH: 20
<212> TYPE: RNA
<213> ORGANISM: Artificial Sequence
<220> FEATURE:

-continued

```
<223> OTHER INFORMATION: Synthetic: WV-3545
<220> FEATURE:
<221> NAME/KEY: misc_feature
<223> OTHER INFORMATION: See specification as filed for detailed
      description of substitutions and preferred embodiments

<400> SEQUENCE: 52

ucaaggaaga uggcauuucu                                                    20

<210> SEQ ID NO 53
<211> LENGTH: 20
<212> TYPE: RNA
<213> ORGANISM: Artificial Sequence
<220> FEATURE:
<223> OTHER INFORMATION: Synthetic: WV-3546
<220> FEATURE:
<221> NAME/KEY: misc_feature
<223> OTHER INFORMATION: See specification as filed for detailed
      description of substitutions and preferred embodiments

<400> SEQUENCE: 53

ucaaggaaga uggcauuucu                                                    20

<210> SEQ ID NO 54
<211> LENGTH: 20
<212> TYPE: RNA
<213> ORGANISM: Artificial Sequence
<220> FEATURE:
<223> OTHER INFORMATION: Synthetic: WV-9517
<220> FEATURE:
<221> NAME/KEY: misc_feature
<223> OTHER INFORMATION: See specification as filed for detailed
      description of substitutions and preferred embodiments

<400> SEQUENCE: 54

cuccgguucu gaagguguuc                                                    20

<210> SEQ ID NO 55
<211> LENGTH: 20
<212> TYPE: RNA
<213> ORGANISM: Artificial Sequence
<220> FEATURE:
<223> OTHER INFORMATION: Synthetic: WV-12555
<220> FEATURE:
<221> NAME/KEY: misc_feature
<223> OTHER INFORMATION: See specification as filed for detailed
      description of substitutions and preferred embodiments

<400> SEQUENCE: 55

cuccgguucu gaagguguuc                                                    20

<210> SEQ ID NO 56
<211> LENGTH: 20
<212> TYPE: RNA
<213> ORGANISM: Artificial Sequence
<220> FEATURE:
<223> OTHER INFORMATION: Synthetic: WV-12556
<220> FEATURE:
<221> NAME/KEY: misc_feature
<223> OTHER INFORMATION: See specification as filed for detailed
      description of substitutions and preferred embodiments

<400> SEQUENCE: 56

cuccgguucu gaagguguuc                                                    20

<210> SEQ ID NO 57
<211> LENGTH: 20
<212> TYPE: RNA
<213> ORGANISM: Artificial Sequence
```

<220> FEATURE:
<223> OTHER INFORMATION: Synthetic: WV-12558
<220> FEATURE:
<221> NAME/KEY: misc_feature
<223> OTHER INFORMATION: See specification as filed for detailed description of substitutions and preferred embodiments

<400> SEQUENCE: 57
cuccgguucu gaagguguuc 20

<210> SEQ ID NO 58
<211> LENGTH: 20
<212> TYPE: RNA
<213> ORGANISM: Artificial Sequence
<220> FEATURE:
<223> OTHER INFORMATION: Synthetic: WV-12876
<220> FEATURE:
<221> NAME/KEY: misc_feature
<223> OTHER INFORMATION: See specification as filed for detailed description of substitutions and preferred embodiments

<400> SEQUENCE: 58
cuccgguucu gaagguguuc 20

<210> SEQ ID NO 59
<211> LENGTH: 20
<212> TYPE: RNA
<213> ORGANISM: Artificial Sequence
<220> FEATURE:
<223> OTHER INFORMATION: Synthetic: WV-12877
<220> FEATURE:
<221> NAME/KEY: misc_feature
<223> OTHER INFORMATION: See specification as filed for detailed description of substitutions and preferred embodiments

<400> SEQUENCE: 59
cuccgguucu gaagguguuc 20

<210> SEQ ID NO 60
<211> LENGTH: 20
<212> TYPE: RNA
<213> ORGANISM: Artificial Sequence
<220> FEATURE:
<223> OTHER INFORMATION: Synthetic: WV-12878
<220> FEATURE:
<221> NAME/KEY: misc_feature
<223> OTHER INFORMATION: See specification as filed for detailed description of substitutions and preferred embodiments

<400> SEQUENCE: 60
cuccgguucu gaagguguuc 20

<210> SEQ ID NO 61
<211> LENGTH: 19
<212> TYPE: RNA
<213> ORGANISM: Artificial Sequence
<220> FEATURE:
<223> OTHER INFORMATION: Synthetic: WV-13826
<220> FEATURE:
<221> NAME/KEY: misc_feature
<223> OTHER INFORMATION: See specification as filed for detailed description of substitutions and preferred embodiments

<400> SEQUENCE: 61
uccgguucug aagguguuc 19

<210> SEQ ID NO 62
<211> LENGTH: 20
<212> TYPE: RNA

<213> ORGANISM: Artificial Sequence
<220> FEATURE:
<223> OTHER INFORMATION: Synthetic: WV-12880
<220> FEATURE:
<221> NAME/KEY: misc_feature
<223> OTHER INFORMATION: See specification as filed for detailed description of substitutions and preferred embodiments

<400> SEQUENCE: 62
cuccgguucu gaagguguuc 20

<210> SEQ ID NO 63
<211> LENGTH: 20
<212> TYPE: RNA
<213> ORGANISM: Artificial Sequence
<220> FEATURE:
<223> OTHER INFORMATION: Synthetic: WV-14344
<220> FEATURE:
<221> NAME/KEY: misc_feature
<223> OTHER INFORMATION: See specification as filed for detailed description of substitutions and preferred embodiments

<400> SEQUENCE: 63
cuccgguucu gaagguguuc 20

<210> SEQ ID NO 64
<211> LENGTH: 20
<212> TYPE: RNA
<213> ORGANISM: Artificial Sequence
<220> FEATURE:
<223> OTHER INFORMATION: Synthetic: WV-13835
<220> FEATURE:
<221> NAME/KEY: misc_feature
<223> OTHER INFORMATION: See specification as filed for detailed description of substitutions and preferred embodiments

<400> SEQUENCE: 64
uccgguucug aagguguucu 20

<210> SEQ ID NO 65
<211> LENGTH: 20
<212> TYPE: RNA
<213> ORGANISM: Artificial Sequence
<220> FEATURE:
<223> OTHER INFORMATION: Synthetic: WV-13864
<220> FEATURE:
<221> NAME/KEY: misc_feature
<223> OTHER INFORMATION: See specification as filed for detailed description of substitutions and preferred embodiments

<400> SEQUENCE: 65
cuccgguucu gaagguguuc 20

<210> SEQ ID NO 66
<211> LENGTH: 20
<212> TYPE: DNA
<213> ORGANISM: Artificial Sequence
<220> FEATURE:
<223> OTHER INFORMATION: Synthetic: WV-O-937
<220> FEATURE:
<221> NAME/KEY: misc_feature
<223> OTHER INFORMATION: See specification as filed for detailed description of substitutions and preferred embodiments

<400> SEQUENCE: 66
ggcacaaggg cacagacttc 20

<210> SEQ ID NO 67
<211> LENGTH: 20

```
<212> TYPE: DNA
<213> ORGANISM: Artificial Sequence
<220> FEATURE:
<223> OTHER INFORMATION: Synthetic: WV-O-1077
<220> FEATURE:
<221> NAME/KEY: misc_feature
<223> OTHER INFORMATION: See specification as filed for detailed
      description of substitutions and preferred embodiments

<400> SEQUENCE: 67

auuaauaaat tgtcatcacc                                                20


<210> SEQ ID NO 68
<211> LENGTH: 20
<212> TYPE: DNA
<213> ORGANISM: Artificial Sequence
<220> FEATURE:
<223> OTHER INFORMATION: Synthetic: WV-O-1078
<220> FEATURE:
<221> NAME/KEY: misc_feature
<223> OTHER INFORMATION: See specification as filed for detailed
      description of substitutions and preferred embodiments

<400> SEQUENCE: 68

auuaauaaat tgtcatcacc                                                20


<210> SEQ ID NO 69
<211> LENGTH: 20
<212> TYPE: DNA
<213> ORGANISM: Artificial Sequence
<220> FEATURE:
<223> OTHER INFORMATION: Synthetic: WV-O-1079
<220> FEATURE:
<221> NAME/KEY: misc_feature
<223> OTHER INFORMATION: See specification as filed for detailed
      description of substitutions and preferred embodiments

<400> SEQUENCE: 69

auuaauaaat tgtcatcacc                                                20


<210> SEQ ID NO 70
<211> LENGTH: 20
<212> TYPE: RNA
<213> ORGANISM: Artificial Sequence
<220> FEATURE:
<223> OTHER INFORMATION: Synthetic: WV-O-1085
<220> FEATURE:
<221> NAME/KEY: misc_feature
<223> OTHER INFORMATION: See specification as filed for detailed
      description of substitutions and preferred embodiments

<400> SEQUENCE: 70

ggcacaaggg cacagacuuc                                                20


<210> SEQ ID NO 71
<211> LENGTH: 20
<212> TYPE: RNA
<213> ORGANISM: Artificial Sequence
<220> FEATURE:
<223> OTHER INFORMATION: Synthetic: WV-O-1086
<220> FEATURE:
<221> NAME/KEY: misc_feature
<223> OTHER INFORMATION: See specification as filed for detailed
      description of substitutions and preferred embodiments

<400> SEQUENCE: 71

ggcacaaggg cacagacuuc                                                20


<210> SEQ ID NO 72
```

<211> LENGTH: 20
<212> TYPE: DNA
<213> ORGANISM: Artificial Sequence
<220> FEATURE:
<223> OTHER INFORMATION: Synthetic: WV-O-1090
<220> FEATURE:
<221> NAME/KEY: misc_feature
<223> OTHER INFORMATION: See specification as filed for detailed description of substitutions and preferred embodiments

<400> SEQUENCE: 72
ggcacaaggg cacagacttc 20

<210> SEQ ID NO 73
<211> LENGTH: 20
<212> TYPE: RNA
<213> ORGANISM: Artificial Sequence
<220> FEATURE:
<223> OTHER INFORMATION: Synthetic: WV-O-1091
<220> FEATURE:
<221> NAME/KEY: misc_feature
<223> OTHER INFORMATION: See specification as filed for detailed description of substitutions and preferred embodiments

<400> SEQUENCE: 73
ggcacaaggg cacagacuuc 20

<210> SEQ ID NO 74
<211> LENGTH: 20
<212> TYPE: RNA
<213> ORGANISM: Artificial Sequence
<220> FEATURE:
<223> OTHER INFORMATION: Synthetic: WV-O-1092
<220> FEATURE:
<221> NAME/KEY: misc_feature
<223> OTHER INFORMATION: See specification as filed for detailed description of substitutions and preferred embodiments

<400> SEQUENCE: 74
ggcacaaggg cacagacuuc 20

<210> SEQ ID NO 75
<211> LENGTH: 20
<212> TYPE: RNA
<213> ORGANISM: Artificial Sequence
<220> FEATURE:
<223> OTHER INFORMATION: Synthetic: WV-O-1497
<220> FEATURE:
<221> NAME/KEY: misc_feature
<223> OTHER INFORMATION: See specification as filed for detailed description of substitutions and preferred embodiments

<400> SEQUENCE: 75
ggcacaaggg cacagacuuc 20

<210> SEQ ID NO 76
<211> LENGTH: 20
<212> TYPE: DNA
<213> ORGANISM: Artificial Sequence
<220> FEATURE:
<223> OTHER INFORMATION: Synthetic: WV-O-1508
<220> FEATURE:
<221> NAME/KEY: misc_feature
<223> OTHER INFORMATION: See specification as filed for detailed description of substitutions and preferred embodiments

<400> SEQUENCE: 76
auuaauaaat tgtcatcacc 20

<210> SEQ ID NO 77
<211> LENGTH: 20
<212> TYPE: RNA
<213> ORGANISM: Artificial Sequence
<220> FEATURE:
<223> OTHER INFORMATION: Synthetic: WV-O-1510
<220> FEATURE:
<221> NAME/KEY: misc_feature
<223> OTHER INFORMATION: See specification as filed for detailed description of substitutions and preferred embodiments

<400> SEQUENCE: 77
ggcacaaggg cacagacuuc 20

<210> SEQ ID NO 78
<211> LENGTH: 20
<212> TYPE: DNA
<213> ORGANISM: Artificial Sequence
<220> FEATURE:
<223> OTHER INFORMATION: Synthetic: WV-O-2076
<220> FEATURE:
<221> NAME/KEY: misc_feature
<223> OTHER INFORMATION: See specification as filed for detailed description of substitutions and preferred embodiments

<400> SEQUENCE: 78
uaauaaattg tcatcaccag 20

<210> SEQ ID NO 79
<211> LENGTH: 20
<212> TYPE: RNA
<213> ORGANISM: Artificial Sequence
<220> FEATURE:
<223> OTHER INFORMATION: Synthetic: WV-O-2378
<220> FEATURE:
<221> NAME/KEY: misc_feature
<223> OTHER INFORMATION: See specification as filed for detailed description of substitutions and preferred embodiments

<400> SEQUENCE: 79
gcacaagggc acagacuucc 20

<210> SEQ ID NO 80
<211> LENGTH: 20
<212> TYPE: RNA
<213> ORGANISM: Artificial Sequence
<220> FEATURE:
<223> OTHER INFORMATION: Synthetic: WV-O-2380
<220> FEATURE:
<221> NAME/KEY: misc_feature
<223> OTHER INFORMATION: See specification as filed for detailed description of substitutions and preferred embodiments

<400> SEQUENCE: 80
cacaagggca cagacuucca 20

<210> SEQ ID NO 81
<211> LENGTH: 20
<212> TYPE: DNA
<213> ORGANISM: Artificial Sequence
<220> FEATURE:
<223> OTHER INFORMATION: Synthetic: WV-O-2417
<220> FEATURE:
<221> NAME/KEY: misc_feature
<223> OTHER INFORMATION: See specification as filed for detailed description of substitutions and preferred embodiments

<400> SEQUENCE: 81
auaaattgtc atcaccagaa 20

<210> SEQ ID NO 82
<211> LENGTH: 20
<212> TYPE: DNA
<213> ORGANISM: Artificial Sequence
<220> FEATURE:
<223> OTHER INFORMATION: Synthetic: WV-O-2418
<220> FEATURE:
<221> NAME/KEY: misc_feature
<223> OTHER INFORMATION: See specification as filed for detailed description of substitutions and preferred embodiments

<400> SEQUENCE: 82
aauaaattgt catcaccaga 20

<210> SEQ ID NO 83
<211> LENGTH: 20
<212> TYPE: DNA
<213> ORGANISM: Artificial Sequence
<220> FEATURE:
<223> OTHER INFORMATION: Synthetic: WV-O-2595
<220> FEATURE:
<221> NAME/KEY: misc_feature
<223> OTHER INFORMATION: See specification as filed for detailed description of substitutions and preferred embodiments

<400> SEQUENCE: 83
gggucctccc cacagaggga 20

<210> SEQ ID NO 84
<211> LENGTH: 20
<212> TYPE: DNA
<213> ORGANISM: Artificial Sequence
<220> FEATURE:
<223> OTHER INFORMATION: Synthetic: WV-O-2601
<220> FEATURE:
<221> NAME/KEY: misc_feature
<223> OTHER INFORMATION: See specification as filed for detailed description of substitutions and preferred embodiments

<400> SEQUENCE: 84
gcacacagta gatgagggag 20

<210> SEQ ID NO 85
<211> LENGTH: 20
<212> TYPE: DNA
<213> ORGANISM: Artificial Sequence
<220> FEATURE:
<223> OTHER INFORMATION: Synthetic: WV-O-2602
<220> FEATURE:
<221> NAME/KEY: misc_feature
<223> OTHER INFORMATION: See specification as filed for detailed description of substitutions and preferred embodiments

<400> SEQUENCE: 85
ugcacacagt agatgaggga 20

<210> SEQ ID NO 86
<211> LENGTH: 20
<212> TYPE: DNA
<213> ORGANISM: Artificial Sequence
<220> FEATURE:
<223> OTHER INFORMATION: Synthetic: WV-O-2603
<220> FEATURE:
<221> NAME/KEY: misc_feature
<223> OTHER INFORMATION: See specification as filed for detailed description of substitutions and preferred embodiments

<400> SEQUENCE: 86
gugcacacag tagatgaggg 20

<210> SEQ ID NO 87
<211> LENGTH: 20
<212> TYPE: DNA
<213> ORGANISM: Artificial Sequence
<220> FEATURE:
<223> OTHER INFORMATION: Synthetic: WV-O-2618
<220> FEATURE:
<221> NAME/KEY: misc_feature
<223> OTHER INFORMATION: See specification as filed for detailed
description of substitutions and preferred embodiments

<400> SEQUENCE: 87
ugcacacagt agatgaggga 20

<210> SEQ ID NO 88
<211> LENGTH: 20
<212> TYPE: DNA
<213> ORGANISM: Artificial Sequence
<220> FEATURE:
<223> OTHER INFORMATION: Synthetic: WV-O-2619
<220> FEATURE:
<221> NAME/KEY: misc_feature
<223> OTHER INFORMATION: See specification as filed for detailed
description of substitutions and preferred embodiments

<400> SEQUENCE: 88
gugcacacag tagatgaggg 20

<210> SEQ ID NO 89
<211> LENGTH: 20
<212> TYPE: DNA
<213> ORGANISM: Artificial Sequence
<220> FEATURE:
<223> OTHER INFORMATION: Synthetic: WV-O-2671
<220> FEATURE:
<221> NAME/KEY: misc_feature
<223> OTHER INFORMATION: See specification as filed for detailed
description of substitutions and preferred embodiments

<400> SEQUENCE: 89
gggucctccc cacagaggga 20

<210> SEQ ID NO 90
<211> LENGTH: 20
<212> TYPE: RNA
<213> ORGANISM: Artificial Sequence
<220> FEATURE:
<223> OTHER INFORMATION: Synthetic: WV-O-887
<220> FEATURE:
<221> NAME/KEY: misc_feature
<223> OTHER INFORMATION: See specification as filed for detailed
description of substitutions and preferred embodiments

<400> SEQUENCE: 90
ucaaggaaga uggcauuucu 20

<210> SEQ ID NO 91
<211> LENGTH: 20
<212> TYPE: RNA
<213> ORGANISM: Artificial Sequence
<220> FEATURE:
<223> OTHER INFORMATION: Synthetic: WV-O-892
<220> FEATURE:
<221> NAME/KEY: misc_feature
<223> OTHER INFORMATION: See specification as filed for detailed
description of substitutions and preferred embodiments

<400> SEQUENCE: 91
ucaaggaaga uggcauuucu 20

<210> SEQ ID NO 92
<211> LENGTH: 20
<212> TYPE: RNA
<213> ORGANISM: Artificial Sequence
<220> FEATURE:
<223> OTHER INFORMATION: Synthetic: WV-O-896
<220> FEATURE:
<221> NAME/KEY: misc_feature
<223> OTHER INFORMATION: See specification as filed for detailed description of substitutions and preferred embodiments

<400> SEQUENCE: 92
ucaaggaaga uggcauuucu 20

<210> SEQ ID NO 93
<211> LENGTH: 20
<212> TYPE: RNA
<213> ORGANISM: Artificial Sequence
<220> FEATURE:
<223> OTHER INFORMATION: Synthetic: WV-O-1714
<220> FEATURE:
<221> NAME/KEY: misc_feature
<223> OTHER INFORMATION: See specification as filed for detailed description of substitutions and preferred embodiments

<400> SEQUENCE: 93
ucaaggaaga uggcauuucu 20

<210> SEQ ID NO 94
<211> LENGTH: 20
<212> TYPE: RNA
<213> ORGANISM: Artificial Sequence
<220> FEATURE:
<223> OTHER INFORMATION: Synthetic: WV-O-2444
<220> FEATURE:
<221> NAME/KEY: misc_feature
<223> OTHER INFORMATION: See specification as filed for detailed description of substitutions and preferred embodiments

<400> SEQUENCE: 94
ucaaggaaga uggcauuucu 20

<210> SEQ ID NO 95
<211> LENGTH: 20
<212> TYPE: RNA
<213> ORGANISM: Artificial Sequence
<220> FEATURE:
<223> OTHER INFORMATION: Synthetic: WV-O-2445
<220> FEATURE:
<221> NAME/KEY: misc_feature
<223> OTHER INFORMATION: See specification as filed for detailed description of substitutions and preferred embodiments

<400> SEQUENCE: 95
ucaaggaaga uggcauuucu 20

<210> SEQ ID NO 96
<211> LENGTH: 20
<212> TYPE: RNA
<213> ORGANISM: Artificial Sequence
<220> FEATURE:
<223> OTHER INFORMATION: Synthetic: WV-O-2526
<220> FEATURE:
<221> NAME/KEY: misc_feature
<223> OTHER INFORMATION: See specification as filed for detailed description of substitutions and preferred embodiments

<400> SEQUENCE: 96
ucaaggaaga uggcauuucu 20

<210> SEQ ID NO 97
<211> LENGTH: 20
<212> TYPE: RNA
<213> ORGANISM: Artificial Sequence
<220> FEATURE:
<223> OTHER INFORMATION: Synthetic: WV-O-2527
<220> FEATURE:
<221> NAME/KEY: misc_feature
<223> OTHER INFORMATION: See specification as filed for detailed description of substitutions and preferred embodiments

<400> SEQUENCE: 97
ucaaggaaga uggcauuucu 20

<210> SEQ ID NO 98
<211> LENGTH: 20
<212> TYPE: RNA
<213> ORGANISM: Artificial Sequence
<220> FEATURE:
<223> OTHER INFORMATION: Synthetic: WV-O-2528
<220> FEATURE:
<221> NAME/KEY: misc_feature
<223> OTHER INFORMATION: See specification as filed for detailed description of substitutions and preferred embodiments

<400> SEQUENCE: 98
ucaaggaaga uggcauuucu 20

<210> SEQ ID NO 99
<211> LENGTH: 20
<212> TYPE: RNA
<213> ORGANISM: Artificial Sequence
<220> FEATURE:
<223> OTHER INFORMATION: Synthetic: WV-O-2530
<220> FEATURE:
<221> NAME/KEY: misc_feature
<223> OTHER INFORMATION: See specification as filed for detailed description of substitutions and preferred embodiments

<400> SEQUENCE: 99
ucaaggaaga uggcauuucu 20

<210> SEQ ID NO 100
<211> LENGTH: 20
<212> TYPE: RNA
<213> ORGANISM: Artificial Sequence
<220> FEATURE:
<223> OTHER INFORMATION: Synthetic: WV-O-2531
<220> FEATURE:
<221> NAME/KEY: misc_feature
<223> OTHER INFORMATION: See specification as filed for detailed description of substitutions and preferred embodiments

<400> SEQUENCE: 100
ucaaggaaga uggcauuucu 20

<210> SEQ ID NO 101
<211> LENGTH: 20
<212> TYPE: RNA
<213> ORGANISM: Artificial Sequence
<220> FEATURE:
<223> OTHER INFORMATION: Synthetic: WV-O-2578
<220> FEATURE:
<221> NAME/KEY: misc_feature
<223> OTHER INFORMATION: See specification as filed for detailed description of substitutions and preferred embodiments

<400> SEQUENCE: 101
ucaaggaaga uggcauuucu 20

<210> SEQ ID NO 102
<211> LENGTH: 20
<212> TYPE: RNA
<213> ORGANISM: Artificial Sequence
<220> FEATURE:
<223> OTHER INFORMATION: Synthetic: WV-O-2580
<220> FEATURE:
<221> NAME/KEY: misc_feature
<223> OTHER INFORMATION: See specification as filed for detailed description of substitutions and preferred embodiments

<400> SEQUENCE: 102
ucaaggaaga uggcauuucu 20

<210> SEQ ID NO 103
<211> LENGTH: 20
<212> TYPE: RNA
<213> ORGANISM: Artificial Sequence
<220> FEATURE:
<223> OTHER INFORMATION: Synthetic: WV-O-2587
<220> FEATURE:
<221> NAME/KEY: misc_feature
<223> OTHER INFORMATION: See specification as filed for detailed description of substitutions and preferred embodiments

<400> SEQUENCE: 103
ucaaggaaga uggcauuucu 20

<210> SEQ ID NO 104
<211> LENGTH: 20
<212> TYPE: RNA
<213> ORGANISM: Artificial Sequence
<220> FEATURE:
<223> OTHER INFORMATION: Synthetic: WV-O-3047
<220> FEATURE:
<221> NAME/KEY: misc_feature
<223> OTHER INFORMATION: See specification as filed for detailed description of substitutions and preferred embodiments

<400> SEQUENCE: 104
ucaaggaaga uggcauuucu 20

<210> SEQ ID NO 105
<211> LENGTH: 20
<212> TYPE: RNA
<213> ORGANISM: Artificial Sequence
<220> FEATURE:
<223> OTHER INFORMATION: Synthetic: WV-O-3152
<220> FEATURE:
<221> NAME/KEY: misc_feature
<223> OTHER INFORMATION: See specification as filed for detailed description of substitutions and preferred embodiments

<400> SEQUENCE: 105
ucaaggaaga uggcauuucu 20

<210> SEQ ID NO 106
<211> LENGTH: 20
<212> TYPE: RNA
<213> ORGANISM: Artificial Sequence
<220> FEATURE:
<223> OTHER INFORMATION: Synthetic: WV-O-3472
<220> FEATURE:
<221> NAME/KEY: misc_feature
<223> OTHER INFORMATION: See specification as filed for detailed description of substitutions and preferred embodiments

<400> SEQUENCE: 106
ucaaggaaga uggcauuucu 20

<210> SEQ ID NO 107
<211> LENGTH: 20
<212> TYPE: RNA
<213> ORGANISM: Artificial Sequence
<220> FEATURE:
<223> OTHER INFORMATION: Synthetic: WV-O-3473
<220> FEATURE:
<221> NAME/KEY: misc_feature
<223> OTHER INFORMATION: See specification as filed for detailed description of substitutions and preferred embodiments

<400> SEQUENCE: 107
ucaaggaaga uggcauuucu 20

<210> SEQ ID NO 108
<211> LENGTH: 20
<212> TYPE: RNA
<213> ORGANISM: Artificial Sequence
<220> FEATURE:
<223> OTHER INFORMATION: Synthetic: WV-O-3507
<220> FEATURE:
<221> NAME/KEY: misc_feature
<223> OTHER INFORMATION: See specification as filed for detailed description of substitutions and preferred embodiments

<400> SEQUENCE: 108
ucaaggaaga uggcauuucu 20

<210> SEQ ID NO 109
<211> LENGTH: 20
<212> TYPE: RNA
<213> ORGANISM: Artificial Sequence
<220> FEATURE:
<223> OTHER INFORMATION: Synthetic: WV-O-3508
<220> FEATURE:
<221> NAME/KEY: misc_feature
<223> OTHER INFORMATION: See specification as filed for detailed description of substitutions and preferred embodiments

<400> SEQUENCE: 109
ucaaggaaga uggcauuucu 20

<210> SEQ ID NO 110
<211> LENGTH: 20
<212> TYPE: RNA
<213> ORGANISM: Artificial Sequence
<220> FEATURE:
<223> OTHER INFORMATION: Synthetic: WV-O-3509
<220> FEATURE:
<221> NAME/KEY: misc_feature
<223> OTHER INFORMATION: See specification as filed for detailed description of substitutions and preferred embodiments

<400> SEQUENCE: 110
ucaaggaaga uggcauuucu 20

<210> SEQ ID NO 111
<211> LENGTH: 20
<212> TYPE: RNA
<213> ORGANISM: Artificial Sequence
<220> FEATURE:
<223> OTHER INFORMATION: Synthetic: WV-O-3510
<220> FEATURE:
<221> NAME/KEY: misc_feature
<223> OTHER INFORMATION: See specification as filed for detailed description of substitutions and preferred embodiments

<400> SEQUENCE: 111
ucaaggaaga uggcauuucu 20

<210> SEQ ID NO 112
<211> LENGTH: 20
<212> TYPE: RNA
<213> ORGANISM: Artificial Sequence
<220> FEATURE:
<223> OTHER INFORMATION: Synthetic: WV-O-3511
<220> FEATURE:
<221> NAME/KEY: misc_feature
<223> OTHER INFORMATION: See specification as filed for detailed description of substitutions and preferred embodiments

<400> SEQUENCE: 112
ucaaggaaga uggcauuucu 20

<210> SEQ ID NO 113
<211> LENGTH: 20
<212> TYPE: RNA
<213> ORGANISM: Artificial Sequence
<220> FEATURE:
<223> OTHER INFORMATION: Synthetic: WV-O-3512
<220> FEATURE:
<221> NAME/KEY: misc_feature
<223> OTHER INFORMATION: See specification as filed for detailed description of substitutions and preferred embodiments

<400> SEQUENCE: 113
ucaaggaaga uggcauuucu 20

<210> SEQ ID NO 114
<211> LENGTH: 20
<212> TYPE: RNA
<213> ORGANISM: Artificial Sequence
<220> FEATURE:
<223> OTHER INFORMATION: Synthetic: WV-O-3513
<220> FEATURE:
<221> NAME/KEY: misc_feature
<223> OTHER INFORMATION: See specification as filed for detailed description of substitutions and preferred embodiments

<400> SEQUENCE: 114
ucaaggaaga uggcauuucu 20

<210> SEQ ID NO 115
<211> LENGTH: 20
<212> TYPE: RNA
<213> ORGANISM: Artificial Sequence
<220> FEATURE:
<223> OTHER INFORMATION: Synthetic: WV-O-3514
<220> FEATURE:
<221> NAME/KEY: misc_feature
<223> OTHER INFORMATION: See specification as filed for detailed description of substitutions and preferred embodiments

<400> SEQUENCE: 115
ucaaggaaga uggcauuucu 20

<210> SEQ ID NO 116
<211> LENGTH: 20
<212> TYPE: RNA
<213> ORGANISM: Artificial Sequence
<220> FEATURE:
<223> OTHER INFORMATION: Synthetic: WV-O-3515
<220> FEATURE:
<221> NAME/KEY: misc_feature
<223> OTHER INFORMATION: See specification as filed for detailed
      description of substitutions and preferred embodiments

<400> SEQUENCE: 116
ucaaggaaga uggcauuucu 20

<210> SEQ ID NO 117
<211> LENGTH: 20
<212> TYPE: RNA
<213> ORGANISM: Artificial Sequence
<220> FEATURE:
<223> OTHER INFORMATION: Synthetic: WV-O-3545
<220> FEATURE:
<221> NAME/KEY: misc_feature
<223> OTHER INFORMATION: See specification as filed for detailed
      description of substitutions and preferred embodiments

<400> SEQUENCE: 117
ucaaggaaga uggcauuucu 20

<210> SEQ ID NO 118
<211> LENGTH: 20
<212> TYPE: RNA
<213> ORGANISM: Artificial Sequence
<220> FEATURE:
<223> OTHER INFORMATION: Synthetic: WV-O-3546
<220> FEATURE:
<221> NAME/KEY: misc_feature
<223> OTHER INFORMATION: See specification as filed for detailed
      description of substitutions and preferred embodiments

<400> SEQUENCE: 118
ucaaggaaga uggcauuucu 20

<210> SEQ ID NO 119
<211> LENGTH: 20
<212> TYPE: RNA
<213> ORGANISM: Artificial Sequence
<220> FEATURE:
<223> OTHER INFORMATION: Synthetic: WV-O-9517
<220> FEATURE:
<221> NAME/KEY: misc_feature
<223> OTHER INFORMATION: See specification as filed for detailed
      description of substitutions and preferred embodiments

<400> SEQUENCE: 119
cuccgguucu gaagguguuc 20

<210> SEQ ID NO 120
<211> LENGTH: 20
<212> TYPE: RNA
<213> ORGANISM: Artificial Sequence
<220> FEATURE:
<223> OTHER INFORMATION: Synthetic: WV-O-12555
<220> FEATURE:
<221> NAME/KEY: misc_feature
<223> OTHER INFORMATION: See specification as filed for detailed
      description of substitutions and preferred embodiments

<400> SEQUENCE: 120
cuccgguucu gaagguguuc 20

<210> SEQ ID NO 121
<211> LENGTH: 20
<212> TYPE: RNA
<213> ORGANISM: Artificial Sequence
<220> FEATURE:
<223> OTHER INFORMATION: Synthetic: WV-O-12556
<220> FEATURE:

<221> NAME/KEY: misc_feature
<223> OTHER INFORMATION: See specification as filed for detailed
      description of substitutions and preferred embodiments

<400> SEQUENCE: 121
cuccgguucu gaagguguuc 20

<210> SEQ ID NO 122
<211> LENGTH: 20
<212> TYPE: RNA
<213> ORGANISM: Artificial Sequence
<220> FEATURE:
<223> OTHER INFORMATION: Synthetic: WV-O-12558
<220> FEATURE:
<221> NAME/KEY: misc_feature
<223> OTHER INFORMATION: See specification as filed for detailed
      description of substitutions and preferred embodiments

<400> SEQUENCE: 122
cuccgguucu gaagguguuc 20

<210> SEQ ID NO 123
<211> LENGTH: 20
<212> TYPE: RNA
<213> ORGANISM: Artificial Sequence
<220> FEATURE:
<223> OTHER INFORMATION: Synthetic: WV-O-12876
<220> FEATURE:
<221> NAME/KEY: misc_feature
<223> OTHER INFORMATION: See specification as filed for detailed
      description of substitutions and preferred embodiments

<400> SEQUENCE: 123
cuccgguucu gaagguguuc 20

<210> SEQ ID NO 124
<211> LENGTH: 20
<212> TYPE: RNA
<213> ORGANISM: Artificial Sequence
<220> FEATURE:
<223> OTHER INFORMATION: Synthetic: WV-O-12877
<220> FEATURE:
<221> NAME/KEY: misc_feature
<223> OTHER INFORMATION: See specification as filed for detailed
      description of substitutions and preferred embodiments

<400> SEQUENCE: 124
cuccgguucu gaagguguuc 20

<210> SEQ ID NO 125
<211> LENGTH: 20
<212> TYPE: RNA
<213> ORGANISM: Artificial Sequence
<220> FEATURE:
<223> OTHER INFORMATION: Synthetic: WV-O-12878
<220> FEATURE:
<221> NAME/KEY: misc_feature
<223> OTHER INFORMATION: See specification as filed for detailed
      description of substitutions and preferred embodiments

<400> SEQUENCE: 125
cuccgguucu gaagguguuc 20

<210> SEQ ID NO 126
<211> LENGTH: 19
<212> TYPE: RNA
<213> ORGANISM: Artificial Sequence
<220> FEATURE:
<223> OTHER INFORMATION: Synthetic: WV-O-13826

-continued

```
<220> FEATURE:
<221> NAME/KEY: misc_feature
<223> OTHER INFORMATION: See specification as filed for detailed
      description of substitutions and preferred embodiments

<400> SEQUENCE: 126

uccgguucug aagguguuc                                                   19

<210> SEQ ID NO 127
<211> LENGTH: 20
<212> TYPE: RNA
<213> ORGANISM: Artificial Sequence
<220> FEATURE:
<223> OTHER INFORMATION: Synthetic: WV-O-12880
<220> FEATURE:
<221> NAME/KEY: misc_feature
<223> OTHER INFORMATION: See specification as filed for detailed
      description of substitutions and preferred embodiments

<400> SEQUENCE: 127

cuccgguucu gaagguguuc                                                  20

<210> SEQ ID NO 128
<211> LENGTH: 20
<212> TYPE: RNA
<213> ORGANISM: Artificial Sequence
<220> FEATURE:
<223> OTHER INFORMATION: Synthetic: WV-O-14344
<220> FEATURE:
<221> NAME/KEY: misc_feature
<223> OTHER INFORMATION: See specification as filed for detailed
      description of substitutions and preferred embodiments

<400> SEQUENCE: 128

cuccgguucu gaagguguuc                                                  20

<210> SEQ ID NO 129
<211> LENGTH: 20
<212> TYPE: RNA
<213> ORGANISM: Artificial Sequence
<220> FEATURE:
<223> OTHER INFORMATION: Synthetic: WV-O-13835
<220> FEATURE:
<221> NAME/KEY: misc_feature
<223> OTHER INFORMATION: See specification as filed for detailed
      description of substitutions and preferred embodiments

<400> SEQUENCE: 129

uccgguucug aagguguucu                                                  20

<210> SEQ ID NO 130
<211> LENGTH: 20
<212> TYPE: RNA
<213> ORGANISM: Artificial Sequence
<220> FEATURE:
<223> OTHER INFORMATION: Synthetic: WV-O-13864
<220> FEATURE:
<221> NAME/KEY: misc_feature
<223> OTHER INFORMATION: See specification as filed for detailed
      description of substitutions and preferred embodiments

<400> SEQUENCE: 130

cuccgguucu gaagguguuc                                                  20

<210> SEQ ID NO 131
<211> LENGTH: 20
<212> TYPE: DNA
<213> ORGANISM: Artificial Sequence
<220> FEATURE:
```

-continued

```
<223> OTHER INFORMATION: Synthetic: WV-O2-937
<220> FEATURE:
<221> NAME/KEY: misc_feature
<223> OTHER INFORMATION: See specification as filed for detailed
      description of substitutions and preferred embodiments

<400> SEQUENCE: 131

ggcacaaggg cacagacttc                                                20

<210> SEQ ID NO 132
<211> LENGTH: 20
<212> TYPE: DNA
<213> ORGANISM: Artificial Sequence
<220> FEATURE:
<223> OTHER INFORMATION: Synthetic: WV-O2-1077
<220> FEATURE:
<221> NAME/KEY: misc_feature
<223> OTHER INFORMATION: See specification as filed for detailed
      description of substitutions and preferred embodiments

<400> SEQUENCE: 132

auuaauaaat tgtcatcacc                                                20

<210> SEQ ID NO 133
<211> LENGTH: 20
<212> TYPE: DNA
<213> ORGANISM: Artificial Sequence
<220> FEATURE:
<223> OTHER INFORMATION: Synthetic: WV-O2-1078
<220> FEATURE:
<221> NAME/KEY: misc_feature
<223> OTHER INFORMATION: See specification as filed for detailed
      description of substitutions and preferred embodiments

<400> SEQUENCE: 133

auuaauaaat tgtcatcacc                                                20

<210> SEQ ID NO 134
<211> LENGTH: 20
<212> TYPE: DNA
<213> ORGANISM: Artificial Sequence
<220> FEATURE:
<223> OTHER INFORMATION: Synthetic: WV-O2-1079
<220> FEATURE:
<221> NAME/KEY: misc_feature
<223> OTHER INFORMATION: See specification as filed for detailed
      description of substitutions and preferred embodiments

<400> SEQUENCE: 134

auuaauaaat tgtcatcacc                                                20

<210> SEQ ID NO 135
<211> LENGTH: 20
<212> TYPE: RNA
<213> ORGANISM: Artificial Sequence
<220> FEATURE:
<223> OTHER INFORMATION: Synthetic: WV-O2-1085
<220> FEATURE:
<221> NAME/KEY: misc_feature
<223> OTHER INFORMATION: See specification as filed for detailed
      description of substitutions and preferred embodiments

<400> SEQUENCE: 135

ggcacaaggg cacagacuuc                                                20

<210> SEQ ID NO 136
<211> LENGTH: 20
<212> TYPE: RNA
<213> ORGANISM: Artificial Sequence
```

<220> FEATURE:
<223> OTHER INFORMATION: Synthetic: WV-02-1086
<220> FEATURE:
<221> NAME/KEY: misc_feature
<223> OTHER INFORMATION: See specification as filed for detailed description of substitutions and preferred embodiments

<400> SEQUENCE: 136
ggcacaaggg cacagacuuc 20

<210> SEQ ID NO 137
<211> LENGTH: 20
<212> TYPE: DNA
<213> ORGANISM: Artificial Sequence
<220> FEATURE:
<223> OTHER INFORMATION: Synthetic: WV-02-1090
<220> FEATURE:
<221> NAME/KEY: misc_feature
<223> OTHER INFORMATION: See specification as filed for detailed description of substitutions and preferred embodiments

<400> SEQUENCE: 137
ggcacaaggg cacagacttc 20

<210> SEQ ID NO 138
<211> LENGTH: 20
<212> TYPE: RNA
<213> ORGANISM: Artificial Sequence
<220> FEATURE:
<223> OTHER INFORMATION: Synthetic: WV-02-1091
<220> FEATURE:
<221> NAME/KEY: misc_feature
<223> OTHER INFORMATION: See specification as filed for detailed description of substitutions and preferred embodiments

<400> SEQUENCE: 138
ggcacaaggg cacagacuuc 20

<210> SEQ ID NO 139
<211> LENGTH: 20
<212> TYPE: RNA
<213> ORGANISM: Artificial Sequence
<220> FEATURE:
<223> OTHER INFORMATION: Synthetic: WV-02-1092
<220> FEATURE:
<221> NAME/KEY: misc_feature
<223> OTHER INFORMATION: See specification as filed for detailed description of substitutions and preferred embodiments

<400> SEQUENCE: 139
ggcacaaggg cacagacuuc 20

<210> SEQ ID NO 140
<211> LENGTH: 20
<212> TYPE: RNA
<213> ORGANISM: Artificial Sequence
<220> FEATURE:
<223> OTHER INFORMATION: Synthetic: WV-02-1497
<220> FEATURE:
<221> NAME/KEY: misc_feature
<223> OTHER INFORMATION: See specification as filed for detailed description of substitutions and preferred embodiments

<400> SEQUENCE: 140
ggcacaaggg cacagacuuc 20

<210> SEQ ID NO 141
<211> LENGTH: 20
<212> TYPE: DNA

-continued

```
<213> ORGANISM: Artificial Sequence
<220> FEATURE:
<223> OTHER INFORMATION: Synthetic: WV-O2-1508
<220> FEATURE:
<221> NAME/KEY: misc_feature
<223> OTHER INFORMATION: See specification as filed for detailed
      description of substitutions and preferred embodiments

<400> SEQUENCE: 141

auuaauaaat tgtcatcacc                                                  20

<210> SEQ ID NO 142
<211> LENGTH: 20
<212> TYPE: RNA
<213> ORGANISM: Artificial Sequence
<220> FEATURE:
<223> OTHER INFORMATION: Synthetic: WV-O2-1510
<220> FEATURE:
<221> NAME/KEY: misc_feature
<223> OTHER INFORMATION: See specification as filed for detailed
      description of substitutions and preferred embodiments

<400> SEQUENCE: 142

ggcacaaggg cacagacuuc                                                  20

<210> SEQ ID NO 143
<211> LENGTH: 20
<212> TYPE: DNA
<213> ORGANISM: Artificial Sequence
<220> FEATURE:
<223> OTHER INFORMATION: Synthetic: WV-O2-2076
<220> FEATURE:
<221> NAME/KEY: misc_feature
<223> OTHER INFORMATION: See specification as filed for detailed
      description of substitutions and preferred embodiments

<400> SEQUENCE: 143

uaauaaattg tcatcaccag                                                  20

<210> SEQ ID NO 144
<211> LENGTH: 20
<212> TYPE: RNA
<213> ORGANISM: Artificial Sequence
<220> FEATURE:
<223> OTHER INFORMATION: Synthetic: WV-O2-2378
<220> FEATURE:
<221> NAME/KEY: misc_feature
<223> OTHER INFORMATION: See specification as filed for detailed
      description of substitutions and preferred embodiments

<400> SEQUENCE: 144

gcacaagggc acagacuucc                                                  20

<210> SEQ ID NO 145
<211> LENGTH: 20
<212> TYPE: RNA
<213> ORGANISM: Artificial Sequence
<220> FEATURE:
<223> OTHER INFORMATION: Synthetic: WV-O2-2380
<220> FEATURE:
<221> NAME/KEY: misc_feature
<223> OTHER INFORMATION: See specification as filed for detailed
      description of substitutions and preferred embodiments

<400> SEQUENCE: 145

cacaagggca cagacuucca                                                  20

<210> SEQ ID NO 146
<211> LENGTH: 20
```

-continued

```
<212> TYPE: DNA
<213> ORGANISM: Artificial Sequence
<220> FEATURE:
<223> OTHER INFORMATION: Synthetic: WV-O2-2417
<220> FEATURE:
<221> NAME/KEY: misc_feature
<223> OTHER INFORMATION: See specification as filed for detailed
      description of substitutions and preferred embodiments

<400> SEQUENCE: 146

auaaattgtc atcaccagaa                                                20

<210> SEQ ID NO 147
<211> LENGTH: 20
<212> TYPE: DNA
<213> ORGANISM: Artificial Sequence
<220> FEATURE:
<223> OTHER INFORMATION: Synthetic: WV-O2-2418
<220> FEATURE:
<221> NAME/KEY: misc_feature
<223> OTHER INFORMATION: See specification as filed for detailed
      description of substitutions and preferred embodiments

<400> SEQUENCE: 147

aauaaattgt catcaccaga                                                20

<210> SEQ ID NO 148
<211> LENGTH: 20
<212> TYPE: DNA
<213> ORGANISM: Artificial Sequence
<220> FEATURE:
<223> OTHER INFORMATION: Synthetic: WV-O2-2595
<220> FEATURE:
<221> NAME/KEY: misc_feature
<223> OTHER INFORMATION: See specification as filed for detailed
      description of substitutions and preferred embodiments

<400> SEQUENCE: 148

gggucctccc cacagaggga                                                20

<210> SEQ ID NO 149
<211> LENGTH: 20
<212> TYPE: DNA
<213> ORGANISM: Artificial Sequence
<220> FEATURE:
<223> OTHER INFORMATION: Synthetic: WV-O2-2601
<220> FEATURE:
<221> NAME/KEY: misc_feature
<223> OTHER INFORMATION: See specification as filed for detailed
      description of substitutions and preferred embodiments

<400> SEQUENCE: 149

gcacacagta gatgagggag                                                20

<210> SEQ ID NO 150
<211> LENGTH: 20
<212> TYPE: DNA
<213> ORGANISM: Artificial Sequence
<220> FEATURE:
<223> OTHER INFORMATION: Synthetic: WV-O2-2602
<220> FEATURE:
<221> NAME/KEY: misc_feature
<223> OTHER INFORMATION: See specification as filed for detailed
      description of substitutions and preferred embodiments

<400> SEQUENCE: 150

ugcacacagt agatgaggga                                                20

<210> SEQ ID NO 151
```

-continued

```
<211> LENGTH: 20
<212> TYPE: DNA
<213> ORGANISM: Artificial Sequence
<220> FEATURE:
<223> OTHER INFORMATION: Synthetic: WV-O2-2603
<220> FEATURE:
<221> NAME/KEY: misc_feature
<223> OTHER INFORMATION: See specification as filed for detailed
      description of substitutions and preferred embodiments

<400> SEQUENCE: 151

gugcacacag tagatgaggg                                               20

<210> SEQ ID NO 152
<211> LENGTH: 20
<212> TYPE: DNA
<213> ORGANISM: Artificial Sequence
<220> FEATURE:
<223> OTHER INFORMATION: Synthetic: WV-O2-2618
<220> FEATURE:
<221> NAME/KEY: misc_feature
<223> OTHER INFORMATION: See specification as filed for detailed
      description of substitutions and preferred embodiments

<400> SEQUENCE: 152

ugcacacagt agatgaggga                                               20

<210> SEQ ID NO 153
<211> LENGTH: 20
<212> TYPE: DNA
<213> ORGANISM: Artificial Sequence
<220> FEATURE:
<223> OTHER INFORMATION: Synthetic: WV-O2-2619
<220> FEATURE:
<221> NAME/KEY: misc_feature
<223> OTHER INFORMATION: See specification as filed for detailed
      description of substitutions and preferred embodiments

<400> SEQUENCE: 153

gugcacacag tagatgaggg                                               20

<210> SEQ ID NO 154
<211> LENGTH: 20
<212> TYPE: DNA
<213> ORGANISM: Artificial Sequence
<220> FEATURE:
<223> OTHER INFORMATION: Synthetic: WV-O2-2671
<220> FEATURE:
<221> NAME/KEY: misc_feature
<223> OTHER INFORMATION: See specification as filed for detailed
      description of substitutions and preferred embodiments

<400> SEQUENCE: 154

gggucctccc cacagaggga                                               20

<210> SEQ ID NO 155
<211> LENGTH: 20
<212> TYPE: RNA
<213> ORGANISM: Artificial Sequence
<220> FEATURE:
<223> OTHER INFORMATION: Synthetic: WV-O2-887
<220> FEATURE:
<221> NAME/KEY: misc_feature
<223> OTHER INFORMATION: See specification as filed for detailed
      description of substitutions and preferred embodiments

<400> SEQUENCE: 155

ucaaggaaga uggcauuucu                                               20
```

-continued

```
<210> SEQ ID NO 156
<211> LENGTH: 20
<212> TYPE: RNA
<213> ORGANISM: Artificial Sequence
<220> FEATURE:
<223> OTHER INFORMATION: Synthetic: WV-O2-892
<220> FEATURE:
<221> NAME/KEY: misc_feature
<223> OTHER INFORMATION: See specification as filed for detailed
      description of substitutions and preferred embodiments

<400> SEQUENCE: 156

ucaaggaaga uggcauuucu                                                    20

<210> SEQ ID NO 157
<211> LENGTH: 20
<212> TYPE: RNA
<213> ORGANISM: Artificial Sequence
<220> FEATURE:
<223> OTHER INFORMATION: Synthetic: WV-O2-896
<220> FEATURE:
<221> NAME/KEY: misc_feature
<223> OTHER INFORMATION: See specification as filed for detailed
      description of substitutions and preferred embodiments

<400> SEQUENCE: 157

ucaaggaaga uggcauuucu                                                    20

<210> SEQ ID NO 158
<211> LENGTH: 20
<212> TYPE: RNA
<213> ORGANISM: Artificial Sequence
<220> FEATURE:
<223> OTHER INFORMATION: Synthetic: WV-O2-1714
<220> FEATURE:
<221> NAME/KEY: misc_feature
<223> OTHER INFORMATION: See specification as filed for detailed
      description of substitutions and preferred embodiments

<400> SEQUENCE: 158

ucaaggaaga uggcauuucu                                                    20

<210> SEQ ID NO 159
<211> LENGTH: 20
<212> TYPE: RNA
<213> ORGANISM: Artificial Sequence
<220> FEATURE:
<223> OTHER INFORMATION: Synthetic: WV-O2-2444
<220> FEATURE:
<221> NAME/KEY: misc_feature
<223> OTHER INFORMATION: See specification as filed for detailed
      description of substitutions and preferred embodiments

<400> SEQUENCE: 159

ucaaggaaga uggcauuucu                                                    20

<210> SEQ ID NO 160
<211> LENGTH: 20
<212> TYPE: RNA
<213> ORGANISM: Artificial Sequence
<220> FEATURE:
<223> OTHER INFORMATION: Synthetic: WV-O2-2445
<220> FEATURE:
<221> NAME/KEY: misc_feature
<223> OTHER INFORMATION: See specification as filed for detailed
      description of substitutions and preferred embodiments

<400> SEQUENCE: 160

ucaaggaaga uggcauuucu                                                    20
```

US 12,590,115 B2

773

774

-continued

```
<210> SEQ ID NO 161
<211> LENGTH: 20
<212> TYPE: RNA
<213> ORGANISM: Artificial Sequence
<220> FEATURE:
<223> OTHER INFORMATION: Synthetic: WV-O2-2526
<220> FEATURE:
<221> NAME/KEY: misc_feature
<223> OTHER INFORMATION: See specification as filed for detailed
      description of substitutions and preferred embodiments

<400> SEQUENCE: 161

ucaaggaaga uggcauuucu                                             20

<210> SEQ ID NO 162
<211> LENGTH: 20
<212> TYPE: RNA
<213> ORGANISM: Artificial Sequence
<220> FEATURE:
<223> OTHER INFORMATION: Synthetic: WV-O2-2527
<220> FEATURE:
<221> NAME/KEY: misc_feature
<223> OTHER INFORMATION: See specification as filed for detailed
      description of substitutions and preferred embodiments

<400> SEQUENCE: 162

ucaaggaaga uggcauuucu                                             20

<210> SEQ ID NO 163
<211> LENGTH: 20
<212> TYPE: RNA
<213> ORGANISM: Artificial Sequence
<220> FEATURE:
<223> OTHER INFORMATION: Synthetic: WV-O2-2528
<220> FEATURE:
<221> NAME/KEY: misc_feature
<223> OTHER INFORMATION: See specification as filed for detailed
      description of substitutions and preferred embodiments

<400> SEQUENCE: 163

ucaaggaaga uggcauuucu                                             20

<210> SEQ ID NO 164
<211> LENGTH: 20
<212> TYPE: RNA
<213> ORGANISM: Artificial Sequence
<220> FEATURE:
<223> OTHER INFORMATION: Synthetic: WV-O2-2530
<220> FEATURE:
<221> NAME/KEY: misc_feature
<223> OTHER INFORMATION: See specification as filed for detailed
      description of substitutions and preferred embodiments

<400> SEQUENCE: 164

ucaaggaaga uggcauuucu                                             20

<210> SEQ ID NO 165
<211> LENGTH: 20
<212> TYPE: RNA
<213> ORGANISM: Artificial Sequence
<220> FEATURE:
<223> OTHER INFORMATION: Synthetic: WV-O2-2531
<220> FEATURE:
<221> NAME/KEY: misc_feature
<223> OTHER INFORMATION: See specification as filed for detailed
      description of substitutions and preferred embodiments

<400> SEQUENCE: 165

ucaaggaaga uggcauuucu                                             20
```

-continued

```
<210> SEQ ID NO 166
<211> LENGTH: 20
<212> TYPE: RNA
<213> ORGANISM: Artificial Sequence
<220> FEATURE:
<223> OTHER INFORMATION: Synthetic: WV-O2-2578
<220> FEATURE:
<221> NAME/KEY: misc_feature
<223> OTHER INFORMATION: See specification as filed for detailed
      description of substitutions and preferred embodiments

<400> SEQUENCE: 166

ucaaggaaga uggcauuucu                                                  20

<210> SEQ ID NO 167
<211> LENGTH: 20
<212> TYPE: RNA
<213> ORGANISM: Artificial Sequence
<220> FEATURE:
<223> OTHER INFORMATION: Synthetic: WV-O2-2580
<220> FEATURE:
<221> NAME/KEY: misc_feature
<223> OTHER INFORMATION: See specification as filed for detailed
      description of substitutions and preferred embodiments

<400> SEQUENCE: 167

ucaaggaaga uggcauuucu                                                  20

<210> SEQ ID NO 168
<211> LENGTH: 20
<212> TYPE: RNA
<213> ORGANISM: Artificial Sequence
<220> FEATURE:
<223> OTHER INFORMATION: Synthetic: WV-O2-2587
<220> FEATURE:
<221> NAME/KEY: misc_feature
<223> OTHER INFORMATION: See specification as filed for detailed
      description of substitutions and preferred embodiments

<400> SEQUENCE: 168

ucaaggaaga uggcauuucu                                                  20

<210> SEQ ID NO 169
<211> LENGTH: 20
<212> TYPE: RNA
<213> ORGANISM: Artificial Sequence
<220> FEATURE:
<223> OTHER INFORMATION: Synthetic: WV-O2-3047
<220> FEATURE:
<221> NAME/KEY: misc_feature
<223> OTHER INFORMATION: See specification as filed for detailed
      description of substitutions and preferred embodiments

<400> SEQUENCE: 169

ucaaggaaga uggcauuucu                                                  20

<210> SEQ ID NO 170
<211> LENGTH: 20
<212> TYPE: RNA
<213> ORGANISM: Artificial Sequence
<220> FEATURE:
<223> OTHER INFORMATION: Synthetic: WV-O2-3152
<220> FEATURE:
<221> NAME/KEY: misc_feature
<223> OTHER INFORMATION: See specification as filed for detailed
      description of substitutions and preferred embodiments

<400> SEQUENCE: 170
```

-continued

```
ucaaggaaga uggcauuucu                                                20


<210> SEQ ID NO 171
<211> LENGTH: 20
<212> TYPE: RNA
<213> ORGANISM: Artificial Sequence
<220> FEATURE:
<223> OTHER INFORMATION: Synthetic: WV-02-3472
<220> FEATURE:
<221> NAME/KEY: misc_feature
<223> OTHER INFORMATION: See specification as filed for detailed
      description of substitutions and preferred embodiments

<400> SEQUENCE: 171

ucaaggaaga uggcauuucu                                                20


<210> SEQ ID NO 172
<211> LENGTH: 20
<212> TYPE: RNA
<213> ORGANISM: Artificial Sequence
<220> FEATURE:
<223> OTHER INFORMATION: Synthetic: WV-02-3473
<220> FEATURE:
<221> NAME/KEY: misc_feature
<223> OTHER INFORMATION: See specification as filed for detailed
      description of substitutions and preferred embodiments

<400> SEQUENCE: 172

ucaaggaaga uggcauuucu                                                20


<210> SEQ ID NO 173
<211> LENGTH: 20
<212> TYPE: RNA
<213> ORGANISM: Artificial Sequence
<220> FEATURE:
<223> OTHER INFORMATION: Synthetic: WV-02-3507
<220> FEATURE:
<221> NAME/KEY: misc_feature
<223> OTHER INFORMATION: See specification as filed for detailed
      description of substitutions and preferred embodiments

<400> SEQUENCE: 173

ucaaggaaga uggcauuucu                                                20


<210> SEQ ID NO 174
<211> LENGTH: 20
<212> TYPE: RNA
<213> ORGANISM: Artificial Sequence
<220> FEATURE:
<223> OTHER INFORMATION: Synthetic: WV-02-3508
<220> FEATURE:
<221> NAME/KEY: misc_feature
<223> OTHER INFORMATION: See specification as filed for detailed
      description of substitutions and preferred embodiments

<400> SEQUENCE: 174

ucaaggaaga uggcauuucu                                                20


<210> SEQ ID NO 175
<211> LENGTH: 20
<212> TYPE: RNA
<213> ORGANISM: Artificial Sequence
<220> FEATURE:
<223> OTHER INFORMATION: Synthetic: WV-02-3509
<220> FEATURE:
<221> NAME/KEY: misc_feature
<223> OTHER INFORMATION: See specification as filed for detailed
      description of substitutions and preferred embodiments

<400> SEQUENCE: 175
```

-continued ucaaggaaga uggcauuucu                                               20

<210> SEQ ID NO 176
<211> LENGTH: 20
<212> TYPE: RNA
<213> ORGANISM: Artificial Sequence
<220> FEATURE:
<223> OTHER INFORMATION: Synthetic: WV-O2-3510
<220> FEATURE:
<221> NAME/KEY: misc_feature
<223> OTHER INFORMATION: See specification as filed for detailed
      description of substitutions and preferred embodiments

<400> SEQUENCE: 176
ucaaggaaga uggcauuucu                                               20

<210> SEQ ID NO 177
<211> LENGTH: 20
<212> TYPE: RNA
<213> ORGANISM: Artificial Sequence
<220> FEATURE:
<223> OTHER INFORMATION: Synthetic: WV-O2-3511
<220> FEATURE:
<221> NAME/KEY: misc_feature
<223> OTHER INFORMATION: See specification as filed for detailed
      description of substitutions and preferred embodiments

<400> SEQUENCE: 177
ucaaggaaga uggcauuucu                                               20

<210> SEQ ID NO 178
<211> LENGTH: 20
<212> TYPE: RNA
<213> ORGANISM: Artificial Sequence
<220> FEATURE:
<223> OTHER INFORMATION: Synthetic: WV-O2-3512
<220> FEATURE:
<221> NAME/KEY: misc_feature
<223> OTHER INFORMATION: See specification as filed for detailed
      description of substitutions and preferred embodiments

<400> SEQUENCE: 178
ucaaggaaga uggcauuucu                                               20

<210> SEQ ID NO 179
<211> LENGTH: 20
<212> TYPE: RNA
<213> ORGANISM: Artificial Sequence
<220> FEATURE:
<223> OTHER INFORMATION: Synthetic: WV-O2-3513
<220> FEATURE:
<221> NAME/KEY: misc_feature
<223> OTHER INFORMATION: See specification as filed for detailed
      description of substitutions and preferred embodiments

<400> SEQUENCE: 179
ucaaggaaga uggcauuucu                                               20

<210> SEQ ID NO 180
<211> LENGTH: 20
<212> TYPE: RNA
<213> ORGANISM: Artificial Sequence
<220> FEATURE:
<223> OTHER INFORMATION: Synthetic: WV-O2-3514
<220> FEATURE:
<221> NAME/KEY: misc_feature
<223> OTHER INFORMATION: See specification as filed for detailed
      description of substitutions and preferred embodiments

<400> SEQUENCE: 180
ucaaggaaga uggcauuucu 20

<210> SEQ ID NO 181
<211> LENGTH: 20
<212> TYPE: RNA
<213> ORGANISM: Artificial Sequence
<220> FEATURE:
<223> OTHER INFORMATION: Synthetic: WV-02-3515
<220> FEATURE:
<221> NAME/KEY: misc_feature
<223> OTHER INFORMATION: See specification as filed for detailed description of substitutions and preferred embodiments

<400> SEQUENCE: 181
ucaaggaaga uggcauuucu 20

<210> SEQ ID NO 182
<211> LENGTH: 20
<212> TYPE: RNA
<213> ORGANISM: Artificial Sequence
<220> FEATURE:
<223> OTHER INFORMATION: Synthetic: WV-02-3545
<220> FEATURE:
<221> NAME/KEY: misc_feature
<223> OTHER INFORMATION: See specification as filed for detailed description of substitutions and preferred embodiments

<400> SEQUENCE: 182
ucaaggaaga uggcauuucu 20

<210> SEQ ID NO 183
<211> LENGTH: 20
<212> TYPE: RNA
<213> ORGANISM: Artificial Sequence
<220> FEATURE:
<223> OTHER INFORMATION: Synthetic: WV-02-3546
<220> FEATURE:
<221> NAME/KEY: misc_feature
<223> OTHER INFORMATION: See specification as filed for detailed description of substitutions and preferred embodiments

<400> SEQUENCE: 183
ucaaggaaga uggcauuucu 20

<210> SEQ ID NO 184
<211> LENGTH: 20
<212> TYPE: RNA
<213> ORGANISM: Artificial Sequence
<220> FEATURE:
<223> OTHER INFORMATION: Synthetic: WV-02-9517
<220> FEATURE:
<221> NAME/KEY: misc_feature
<223> OTHER INFORMATION: See specification as filed for detailed description of substitutions and preferred embodiments

<400> SEQUENCE: 184
cuccgguucu gaagguguuc 20

<210> SEQ ID NO 185
<211> LENGTH: 20
<212> TYPE: RNA
<213> ORGANISM: Artificial Sequence
<220> FEATURE:
<223> OTHER INFORMATION: Synthetic: WV-02-12555
<220> FEATURE:
<221> NAME/KEY: misc_feature
<223> OTHER INFORMATION: See specification as filed for detailed description of substitutions and preferred embodiments -continued

<400> SEQUENCE: 185
cuccgguucu gaagguguuc                                                          20

<210> SEQ ID NO 186
<211> LENGTH: 20
<212> TYPE: RNA
<213> ORGANISM: Artificial Sequence
<220> FEATURE:
<223> OTHER INFORMATION: Synthetic: WV-O2-12556
<220> FEATURE:
<221> NAME/KEY: misc_feature
<223> OTHER INFORMATION: See specification as filed for detailed
      description of substitutions and preferred embodiments

<400> SEQUENCE: 186
cuccgguucu gaagguguuc                                                          20

<210> SEQ ID NO 187
<211> LENGTH: 20
<212> TYPE: RNA
<213> ORGANISM: Artificial Sequence
<220> FEATURE:
<223> OTHER INFORMATION: Synthetic: WV-O2-12558
<220> FEATURE:
<221> NAME/KEY: misc_feature
<223> OTHER INFORMATION: See specification as filed for detailed
      description of substitutions and preferred embodiments

<400> SEQUENCE: 187
cuccgguucu gaagguguuc                                                          20

<210> SEQ ID NO 188
<211> LENGTH: 20
<212> TYPE: RNA
<213> ORGANISM: Artificial Sequence
<220> FEATURE:
<223> OTHER INFORMATION: Synthetic: WV-O2-12876
<220> FEATURE:
<221> NAME/KEY: misc_feature
<223> OTHER INFORMATION: See specification as filed for detailed
      description of substitutions and preferred embodiments

<400> SEQUENCE: 188
cuccgguucu gaagguguuc                                                          20

<210> SEQ ID NO 189
<211> LENGTH: 20
<212> TYPE: RNA
<213> ORGANISM: Artificial Sequence
<220> FEATURE:
<223> OTHER INFORMATION: Synthetic: WV-O2-12877
<220> FEATURE:
<221> NAME/KEY: misc_feature
<223> OTHER INFORMATION: See specification as filed for detailed
      description of substitutions and preferred embodiments

<400> SEQUENCE: 189
cuccgguucu gaagguguuc                                                          20

<210> SEQ ID NO 190
<211> LENGTH: 20
<212> TYPE: RNA
<213> ORGANISM: Artificial Sequence
<220> FEATURE:
<223> OTHER INFORMATION: Synthetic: WV-O2-12878
<220> FEATURE:
<221> NAME/KEY: misc_feature
<223> OTHER INFORMATION: See specification as filed for detailed description of substitutions and preferred embodiments

<400> SEQUENCE: 190
cuccgguucu gaagguguuc 20

<210> SEQ ID NO 191
<211> LENGTH: 19
<212> TYPE: RNA
<213> ORGANISM: Artificial Sequence
<220> FEATURE:
<223> OTHER INFORMATION: Synthetic: WV-02-13826
<220> FEATURE:
<221> NAME/KEY: misc_feature
<223> OTHER INFORMATION: See specification as filed for detailed description of substitutions and preferred embodiments

<400> SEQUENCE: 191
uccgguucug aagguguuc 19

<210> SEQ ID NO 192
<211> LENGTH: 20
<212> TYPE: RNA
<213> ORGANISM: Artificial Sequence
<220> FEATURE:
<223> OTHER INFORMATION: Synthetic: WV-02-12880
<220> FEATURE:
<221> NAME/KEY: misc_feature
<223> OTHER INFORMATION: See specification as filed for detailed description of substitutions and preferred embodiments

<400> SEQUENCE: 192
cuccgguucu gaagguguuc 20

<210> SEQ ID NO 193
<211> LENGTH: 20
<212> TYPE: RNA
<213> ORGANISM: Artificial Sequence
<220> FEATURE:
<223> OTHER INFORMATION: Synthetic: WV-02-14344
<220> FEATURE:
<221> NAME/KEY: misc_feature
<223> OTHER INFORMATION: See specification as filed for detailed description of substitutions and preferred embodiments

<400> SEQUENCE: 193
cuccgguucu gaagguguuc 20

<210> SEQ ID NO 194
<211> LENGTH: 20
<212> TYPE: RNA
<213> ORGANISM: Artificial Sequence
<220> FEATURE:
<223> OTHER INFORMATION: Synthetic: WV-02-13835
<220> FEATURE:
<221> NAME/KEY: misc_feature
<223> OTHER INFORMATION: See specification as filed for detailed description of substitutions and preferred embodiments

<400> SEQUENCE: 194
uccgguucug aagguguucu 20

<210> SEQ ID NO 195
<211> LENGTH: 20
<212> TYPE: RNA
<213> ORGANISM: Artificial Sequence
<220> FEATURE:
<223> OTHER INFORMATION: Synthetic: WV-02-13864
<220> FEATURE:
<221> NAME/KEY: misc_feature
<223> OTHER INFORMATION: See specification as filed for detailed
      description of substitutions and preferred embodiments

<400> SEQUENCE: 195
cuccgguucu gaagguguuc                                                20

<210> SEQ ID NO 196
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: See specification as filed for detailed
      description of substitutions and preferred embodiments

<400> SEQUENCE: 196
agcuucttgt ccagcuuuau                                                20

<210> SEQ ID NO 197
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: See specification as filed for detailed
      description of substitutions and preferred embodiments

<400> SEQUENCE: 197
ucaaggaaga uggcauuucu                                                20

<210> SEQ ID NO 198
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: See specification as filed for detailed
      description of substitutions and preferred embodiments

<400> SEQUENCE: 198
ucaaggaaga uggcauuucu                                                20

<210> SEQ ID NO 199
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: See specification as filed for detailed
      description of substitutions and preferred embodiments

<400> SEQUENCE: 199
ucaaggaaga uggcauuucu                                                20

<210> SEQ ID NO 200
<211> LENGTH: 20
<212> TYPE: RNA
<213> ORGANISM: Artificial Sequence
<220> FEATURE:
<223> OTHER INFORMATION: Synthetic
<220> FEATURE:

-continued

<221> NAME/KEY: misc_feature
<223> OTHER INFORMATION: See specification as filed for detailed description of substitutions and preferred embodiments

<400> SEQUENCE: 200
ucaaggaaga uggcauuucu 20

<210> SEQ ID NO 201
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: See specification as filed for detailed description of substitutions and preferred embodiments

<400> SEQUENCE: 201
ugccaggctg gttatgacuc 20